US012110276B2

(12) United States Patent
Zbieg et al.

(10) Patent No.: US 12,110,276 B2
(45) Date of Patent: Oct. 8, 2024

(54) PYRAZOLO COMPOUNDS AND METHODS OF USE THEREOF

(71) Applicant: Genentech, Inc., South San Francisco, CA (US)

(72) Inventors: Jason Robert Zbieg, Montara, CA (US); Russell Tyler Smith, San Francisco, CA (US); Paul Powell Beroza, Belmont, CA (US); Vishal Anil Verma, San Carlos, CA (US); Bing-Yan Zhu, Palo Alto, CA (US); Ramsay Beveridge, Montreal (CA); Lisa Marie Barton, Burlingame, CA (US); Bryan Ka Ip Chan, Foster City, CA (US); Curtis Colwell, Montreal (CA); Samir Bouayad-Gervais, Montreal (CA); Anwesha Dey, Cupertino, CA (US); Marie Anne Evangelista, San Francisco, CA (US)

(73) Assignee: GENENTECH, INC., South San Francisco, CA (US)

(*) Notice: Subject to any disclaimer, the term of this patent is extended or adjusted under 35 U.S.C. 154(b) by 0 days.

(21) Appl. No.: 18/057,738

(22) Filed: Nov. 21, 2022

(65) Prior Publication Data

US 2023/0202984 A1 Jun. 29, 2023

Related U.S. Application Data

(60) Provisional application No. 63/344,025, filed on May 19, 2022, provisional application No. 63/283,138, filed on Nov. 24, 2021.

(51) Int. Cl.

| | |
|---|---|
| *C07D 231/56* | (2006.01) |
| *C07D 471/04* | (2006.01) |
| *C07F 9/09* | (2006.01) |

(52) U.S. Cl.
CPC ......... *C07D 231/56* (2013.01); *C07D 471/04* (2013.01); *C07F 9/095* (2013.01)

(58) Field of Classification Search
CPC ...... C07D 231/56; C07D 471/04; C07F 9/095
(Continued)

(56) References Cited

U.S. PATENT DOCUMENTS

| | | |
|---|---|---|
| 3,773,919 A | 11/1973 | Boswell |
| 4,485,045 A | 11/1984 | Regen |

(Continued)

FOREIGN PATENT DOCUMENTS

| | | |
|---|---|---|
| EP | 0102324 A2 | 3/1984 |
| EP | 0133988 A2 | 3/1985 |

(Continued)

OTHER PUBLICATIONS

Zhang B, Zhang Y, Zhang J, Liu P, Jiao B, Wang Z, Ren R. Focal adhesion kinase (FAK) inhibition synergizes with KRAS G12C inhibitors in treating cancer through the regulation of the FAK-YAP signaling. Advanced science. Aug. 2021;8(16):2100250. (Year: 2021).*

(Continued)

*Primary Examiner* — Jeffrey S Lundgren
*Assistant Examiner* — Heather Dahlin
(74) *Attorney, Agent, or Firm* — Morrison & Foerster LLP

(57) ABSTRACT

This disclosure relates to compounds and methods of using said compounds, as well as pharmaceutical compositions containing such compounds, for treating diseases and conditions mediated by TEAD, such as cancer.

28 Claims, 24 Drawing Sheets

Specification includes a Sequence Listing.

(58) Field of Classification Search
USPC .......................................................... 514/406
See application file for complete search history.

(56) References Cited

U.S. PATENT DOCUMENTS

| | | | | |
|---|---|---|---|---|
| 4,544,545 | A | | 10/1985 | Ryan |
| 4,670,447 | A | * | 6/1987 | Strupczewski ...... A61K 31/445 514/322 |
| 4,943,533 | A | | 7/1990 | Mendelsohn |
| 5,004,697 | A | | 4/1991 | Pardridge |
| 5,112,596 | A | | 5/1992 | Malfroy-camine |
| 5,212,290 | A | | 5/1993 | Vogelstein |
| 5,268,164 | A | | 12/1993 | Kozarich et al. |
| 5,457,105 | A | | 10/1995 | Barker |
| 5,475,001 | A | | 12/1995 | Barker |
| 5,506,206 | A | | 4/1996 | Kozarich et al. |
| 5,616,582 | A | | 4/1997 | Barker |
| 5,654,307 | A | | 8/1997 | Bridges |
| 5,679,683 | A | | 10/1997 | Bridges |
| 5,686,416 | A | | 11/1997 | Kozarich et al. |
| 5,747,498 | A | | 5/1998 | Schnur |
| 5,760,041 | A | | 6/1998 | Wissner |
| 5,770,599 | A | | 6/1998 | Gibson |
| 5,804,396 | A | | 9/1998 | Plowman |
| 5,866,572 | A | | 2/1999 | Barker |
| 5,891,996 | A | | 4/1999 | Mateo De Acosta Del Rio |
| 6,002,008 | A | | 12/1999 | Wissner |
| 6,084,095 | A | | 7/2000 | Bridges |
| 6,140,332 | A | | 10/2000 | Traxler |
| 6,235,883 | B1 | | 5/2001 | Jakobovits |
| 6,265,410 | B1 | | 7/2001 | Bridges |
| 6,344,455 | B1 | | 2/2002 | Bridges |
| 6,344,459 | B1 | | 2/2002 | Bridges |
| 6,391,874 | B1 | | 5/2002 | Cockerill |
| 6,399,602 | B1 | | 6/2002 | Barker |
| 6,455,534 | B2 | | 9/2002 | Bridges |
| 6,521,620 | B1 | | 2/2003 | Bridges |
| 6,596,726 | B1 | | 7/2003 | Bridges |
| 6,602,863 | B1 | | 8/2003 | Bridges |
| 6,713,484 | B2 | | 3/2004 | Bridges |
| 8,217,149 | B2 | | 7/2012 | Irving |
| 9,205,148 | B2 | | 12/2015 | Langermann et al. |
| 9,212,139 | B2 | | 12/2015 | Kyle et al. |
| 9,266,880 | B2 | | 2/2016 | Austin et al. |
| 2002/0025313 | A1 | | 2/2002 | Micklus et al. |
| 2002/0038086 | A1 | | 3/2002 | Hynynen et al. |
| 2002/0065259 | A1 | | 5/2002 | Schatzberg et al. |
| 2003/0073713 | A1 | | 4/2003 | Schoenhard |
| 2003/0129186 | A1 | | 7/2003 | Beliveau et al. |
| 2003/0162695 | A1 | | 8/2003 | Schatzberg et al. |
| 2004/0131692 | A1 | | 7/2004 | Kreuter et al. |
| 2004/0204354 | A1 | | 10/2004 | Nelson et al. |
| 2005/0089473 | A1 | | 4/2005 | Black et al. |
| 2005/0124533 | A1 | | 6/2005 | Schatzberg et al. |
| 2006/0223708 | A1 | | 10/2006 | Hoffmann et al. |
| 2013/0034559 | A1 | | 2/2013 | Queva |
| 2015/0210769 | A1 | | 7/2015 | Freeman et al. |
| 2016/0108123 | A1 | | 4/2016 | Freeman |
| 2016/0376367 | A1 | | 12/2016 | Yuan et al. |
| 2018/0334454 | A1 | | 11/2018 | Lanman et al. |
| 2019/0144444 | A1 | | 5/2019 | Blake et al. |
| 2020/0054653 | A1 | | 2/2020 | Lagarde et al. |
| 2020/0299285 | A1 | | 9/2020 | Fletcher et al. |
| 2021/0009688 | A1 | | 1/2021 | Chen et al. |
| 2021/0213014 | A1 | | 7/2021 | Cosmopoulos et al. |
| 2021/0230142 | A9 | | 7/2021 | Malhotra et al. |
| 2023/0203062 | A1 | | 6/2023 | Zbieg |

FOREIGN PATENT DOCUMENTS

| | | | | | |
|---|---|---|---|---|---|
| EP | 0659439 | A2 | | 6/1995 | |
| EP | 3712129 | A1 | | 9/2020 | |
| WO | 199630347 | A1 | | 10/1996 | |
| WO | 199633978 | A1 | | 10/1996 | |
| WO | 199633980 | A1 | | 10/1996 | |
| WO | 199640210 | A1 | | 12/1996 | |
| WO | 199738983 | A1 | | 10/1997 | |
| WO | 199814451 | A1 | | 4/1998 | |
| WO | 199843960 | A1 | | 10/1998 | |
| WO | 199850038 | A1 | | 11/1998 | |
| WO | 199850433 | A2 | | 11/1998 | |
| WO | 199906378 | A1 | | 2/1999 | |
| WO | 199906396 | A1 | | 2/1999 | |
| WO | 199909016 | A1 | | 2/1999 | |
| WO | 199924037 | A1 | | 5/1999 | |
| WO | 2006121168 | A1 | | 11/2006 | |
| WO | 2007005874 | A2 | | 1/2007 | |
| WO | 2009114335 | A2 | | 9/2009 | |
| WO | 2010027827 | A2 | | 3/2010 | |
| WO | 2010077634 | A1 | | 7/2010 | |
| WO | 2011066342 | A2 | | 6/2011 | |
| WO | 2011066389 | A1 | | 6/2011 | |
| WO | 2011113798 | A2 | | 9/2011 | |
| WO | 2011161699 | A2 | | 12/2011 | |
| WO | 2012145493 | A1 | | 10/2012 | |
| WO | 2012168944 | A1 | | 12/2012 | |
| WO | 2013132317 | A1 | | 9/2013 | |
| WO | 2013144704 | A1 | | 10/2013 | |
| WO | 2013181634 | A2 | | 12/2013 | |
| WO | 2014179664 | A2 | | 11/2014 | |
| WO | 2014194302 | A2 | | 12/2014 | |
| WO | 2014206107 | A1 | | 12/2014 | |
| WO | 2015033299 | A1 | | 3/2015 | |
| WO | 2015033301 | A1 | | 3/2015 | |
| WO | 2015033303 | A1 | | 3/2015 | |
| WO | 2015035606 | A1 | | 3/2015 | |
| WO | 2015036927 | A1 | | 3/2015 | |
| WO | 2015044900 | A1 | | 4/2015 | |
| WO | 2015085847 | A1 | | 6/2015 | |
| WO | 2015112800 | A1 | | 7/2015 | |
| WO | 2015112805 | A1 | | 7/2015 | |
| WO | 2015112900 | A1 | | 7/2015 | |
| WO | 2015119923 | A1 | | 8/2015 | |
| WO | 2015119930 | A1 | | 8/2015 | |
| WO | 2016000619 | A1 | | 1/2016 | |
| WO | 2016032927 | A1 | | 3/2016 | |
| WO | 2016061142 | A1 | | 4/2016 | |
| WO | 2016089873 | A1 | | 6/2016 | |
| WO | 2016106160 | A1 | | 6/2016 | |
| WO | 2020081572 | A1 | | 4/2020 | |
| WO | WO2020211563 | A1 | * | 10/2020 | ........... C07D 473/34 |
| WO | 2021081212 | A1 | | 4/2021 | |
| WO | 2021097110 | A1 | | 5/2021 | |
| WO | 2021124222 | A1 | | 6/2021 | |
| WO | 2021127333 | A1 | | 6/2021 | |
| WO | 2021204823 | A1 | | 10/2021 | |
| WO | WO2022037568 | A1 | * | 2/2022 | ........... C07D 487/00 |
| WO | 2022166469 | A1 | | 8/2022 | |
| WO | 2022204452 | A1 | | 9/2022 | |

OTHER PUBLICATIONS

WO2020211563A10, Google patents, Machine translation, retrieved 2023 (Year: 2023).*

Ahn, E.Y. et al. (Jul. 2013), "RASSF1A-Mediated Regulation of AREG Via the Hippo Pathway in Hepatocellular Carcinoma," Mol. Cancer. Res. 11(7):748-758.

Avruch, J. et al. (Mar. 15, 2012). "YAP Oncogene Overexpression Supercharges Colon Cancer Proliferation," Cell Cycle 11(6):1090-1096.

Baia, G.S. et al. (Jul. 2012). "Yes-Associated Protein 1 is Activated and Functions as an Oncogene in Meningiomas," Mol. Cancer Res. 10(7):904-913.

Bao, Y. et al. (2011). "Mammalian Hippo Pathway: From Development to Cancer and Beyond," J. Biochem. 149(4):361-379.

Bobo, R.H. et al. (Mar. 1994). "Convection-Enhanced Delivery of Macromolecules in the Brain," Proc. Natl. Acad. Sci. U.S.A. 91:2076-2080.

Bundgaard, H. (1985). "Design of Prodrugs: Bioreversible Derivatives for Various Functional Groups and Chemical Entities," in Design of Prodrugs, 3 pages.

(56) References Cited

OTHER PUBLICATIONS

Bundgaard, H. (Jan.-Feb. 1992). "(C) Means to Enhance Penetration: (1) Prodrugs as a Means to Improve the Delivery of Peptide Drugs," Advanced Drug Delivery Reviews 8(1):1-38.
CAS Registry No. 1422184-00-6 (Feb. 5, 2019). AMP-224, 7 pages.
CAS Registry No. 1859072-53-9 (Feb. 5, 2019). PDR 001, 8 pages.
CAS Registry No. 2181546-09-6 (Feb. 28, 2018), supplied by Aurora Fine Chemicals, 1 page.
CAS Registry No. 2181546-13-2 (Feb. 28, 2018), supplied by Aurora Fine Chemicals, 1 page.
CAS Registry No. 2181892-26-0 (Mar. 1, 2018), supplied by Aurora Fine Chemicals, 1 page.
CAS Registry No. 2182408-04-2 (Mar. 1, 2018), supplied by Aurora Fine Chemicals, 1 page.
CAS Registry No. 2185523-08-2 (Mar. 6, 2018), supplied by Aurora Fine Chemicals, 1 page.
CAS Registry No. 2645601-32-5 (Jun. 13, 2021), supplied by Aurora Fine Chemicals, 1 page.
CAS Registry No. 1374853-91-4 (2014). Pembrolizumab, 29 pages.
CAS Registry No. 1422185-06-5 (2023). Atezolizumab, 2 pages.
CAS Registry No. 1428935-60-7, Oct. 18, 2019, 2 pages.
CAS Registry No. 1537032-82-8, Oct. 18, 2019, 2 pages.
CAS Registry No. 946414-94-4 (2014). Nivolumab, 29 pages.
Chan, S.W. et al. (Apr. 15, 2008). "A Role for TAZ in Migration, Invasion, and Tumorigenesis of Breast Cancer Cells," Cancer Res. 68(8):2592-2598.
Database (Feb. 15, 2021). "2589189-68-2—Aurora Fine Chemicals" Acetamide, N-[[7-(4-fluorophenyl) [1,2,5] oxadiazolo [3,4-b] pyridine-5-yl] methyl]-, 1 page.
De Yebenes, J.G. et al. (1987). "Continuous Intracerebroventricular Infusion of Dopamine and Dopamine Agonists Through a Totally Implanted Drug Delivery System in Animal Models of Parkinson's Disease," Mov. Disord. 2(3):143-158.
Epstein, D.A. et al. (Jun. 1985). "Biological Activity of Lipsome-Encapsulated Murine Interferon γ is Mediated by Cell Membrane Receptor," Proc. Natl. Acad. Sci. USA 82:3688-3692.
Fleisher, D. et al. (May 22, 1996). "Improved Oral Drug Delivery: Solubility Limitations Overcome by the use of Prodrugs," Advanced Drug Delivery Reviews 19(2):115-130.
Fujii, M. et al. (2012). "TGF-β Synergizes with Defects in the Hippo Pathway to Stimulate Human Malignant Mesothelioma Growth," J. Exp. Med. 209(3):479-494.
Gasparotto, D. et al. (Dec. 22, 2011). "Overexpression of TWIST2 Correlates with Poor Prognosis in Head and Neck Squamous Cell Carcinomas," Oncotarget. 2(12):1165-1175.
Gill, S.S. et al. (May 2003, e-pub. Mar. 31, 2003). "Direct Brain Infusion of Glial Cell Line-Derived Neurotrophic Factor in Parkinson Disease," Nature Med. 9(5):589-595.
Halder, G. et al. (2011). "Hippo Signaling: Growth Control and Beyond," Development 138:9-22.
Hall, C.A. et al. (Nov. 1, 2010). "Hippo Pathway Effector Yap is an Ovarian Cancer Oncogene," Cancer Res. 70(21):8517-8525, 15 pages.
Hallin, J. et al. (Jan. 2020). "The KRASG12C Inhibitor, MRTX849, Provides Insight Toward Therapeutic Susceptibility of KRAS Mutant Cancers in Mouse Models and Patients," Cancer Discov. 10(1):54-71, 31 pages.
Harbaugh, R.E. (1987). "Intracerbroventricular Cholinergic Drug Administration in Alzheimer's Disease: Preliminary Results of a Double-Blind Study," J. Neural Transm. Suppl. 24:271-277.
Harvey, K.F. et al. (Apr. 2013, e-pub. Mar. 7, 2013). "The Hippo Pathway and Human Cancer," Nat. Rev. Cancer 13:246-257.
Hong, D.S. et al. (Sep. 24, 2020). "KRASG12C Inhibition with Sotorasib in Advanced Solid Tumors," N. Engl. J. Med. 383(13):1207-1217.
Hwang, K.J. et al. (Jul. 1980). "Hepatic Uptake and Degradation of Unilamellar Sphingomyelin/Cholesterol Liposomes: A Kinetic Study." Proc. Natl. Acad. Sci. USA 77:4030-4034.
International Search Report and Written Opinion, mailed Apr. 3, 2023, for PCT Application No. PCT/US2022/080279, filed Nov. 21, 2022, 22 pages.
International Search Report and Written Opinion, mailed Feb. 15, 2023, for PCT Application No. PCT/US2022/080281, filed Nov. 21, 2022, 7 pages.
Invitation To Pay Additional Fees, mailed Feb. 13, 2023, for PCT Application No. PCT/US2022/080279, filed Nov. 21, 2022, 16 pages.
Jie, L. et al. (2013). "The Hippo-Yes Association Protein Pathway in Liver Cancer," Gastroenterol. Res. Pract. 2013 (187070):1-7.
Jimenez-Velasco, A. et al. (2005, e-pub. Oct. 6, 2005). "Downregulation of the Large Tumor Suppressor 2 (LATS2/KPM) Gene is Associated with Poor Prognosis in Acute Lymphoblastic Leukemia," Leukemia 19:2347-2350.
Johns, F.G. et al. (Jul. 16, 2004, e-pub. Apr. 9, 2004). "Identification of the Epitope for the Epidermal Growth Factor Receptor-Specific Monoclonal Antibody 806 Reveals that it Preferentially Recognizes an Untethered Form of the Receptor," J. Biol. Chem. 279(29):30375-30374.
Kakeya, N. et al. (Feb. 1984). "Studies on Prodrugs of Cephalosporins. I. Synthesis and Biological Properties of Glycyloxybenzoyloxymethyl and Glycylaminobenzoyloxymethyl Esters of 7 beta-[2-(2-aminothiazol-4-yl)-(Z)-2-methoxyiminoacetamido]-3-methyl-3-cephem-4-carboxylic Acid," Chem. Pharm. Bull., 32(2):692-698.
Lamar, J.M. et al. (2012, e-pub Aug. 13, 2012). "The Hippo Pathway Target, YAP, Promotes Metastasis Through its TEAD-Interaction Domain," Proc. Natl. Acad. Sci, USA, pp. E2441-E2250.
Langer, R. et al. (1981). "Biocompatibility of Polymeric Delivery Systems for Marcomolecules," J. Biomed. Mater. Res. 15:267-277.
Lei, Q.-Y. et al. (Apr. 2008). "TAZ Promotes Cell Proliferation and Epithelial-Mesenchymal Transition and is Inhibited by the Hippo Pathway," Mol. Cell. Biol. 28(7):2426-2436.
Liu, A.M. et al. (2012). "An Update on Targeting Hippo-YAP Signaling in Liver Cancer," Expert. Opin. Ther. Targets 16(3):243-247.
Mizuno, T. et al. (2012, e-pub. Jan. 30, 2012). "YAP Induces Malignant Mesothelioma Cell Proliferation by Upregulating Transcription of cell Cycle-Promoting Genes," Oncogene 31:5117-5122.
Moore, A.R. et al. (Aug. 2020). "RAS-Targeted Therapies: is the Undruggable Drugged?" Nat. Rev. Drug. Discov. 19(8):533-552, 43 pages.
Nicolaou, K.C. et al. (1994). "Calicheamicin ⊖1[1]: A Rationally Designed Molecule with Extremely Potent and Selective DNA Cleaving Properties and Apoptosis Inducing Activity," Angew. Chem. Intl. Ed. Engl. 33(2):183-186.
Orr, B.A. et al. (Jul. 2011). "Yes-Associated Protein 1 Is Widely Expressed in Human Brain Tumors and Promotes Glioblastoma Growth," J. Neuropathol. Exp. Neurol. 70(7):568-577.
Papanastassiou, V. et al. (2002). "The Potential for Efficacy of the Modified (ICP 34.5-) Herpes Simplex Virus HSV1716 Following Intratumoural Injection Into Human Malignant Glioma: A Proof of Principle Study," Gene Therapy 9:398-406.
Robinson, R.P. et al. (Jan. 5, 1996). "Discovery of the Hemifumarate and (α-L-Alanyloxy)methyl Ether as Prodrugs of an Antirheumatic Oxindole: Prodrugs for the Enolic OH Group," J. Med. Chem. 39(1):10-18.
Seidel, C. et al. (2007). "Frequent Hypermethylation of MST1 and MST2 in Soft Tissue Sarcoma," Mol. Carcinogenesis 46:865-871.
Sekido Y. (2011). "Inactivation of Merlin in Malignant Mesothelioma Cells and the Hippo Signaling Cascade Dysregulation," Pathol. Int. 61:331-344.
Sidman, K.R. et al. (1983). "Controlled Release of Macromolecules and Pharmaceuticals from Synthetic Polypeptides Based on Glutamic Acid," Biopolymers 22:547-556.
Skoulidis, F. et al. (Jun. 14, 2021). "Sotorasib for Lung Cancers with KRAS p.G12C Mutation," N. Engl. J. Med. 384(25):2371-2381.
Steinhardt, A.A. et al. (Nov. 2008). "Expression of Yes-Associated Protein, YAP, in Common Solid Tumors," Hum. Pathol. 39(11):1582-1589, 15 pages.

(56) References Cited

OTHER PUBLICATIONS

Steinmann, K. et al. (2009). "Frequent Promoter Hypermethylation of Tumor-Related Genes in Head and Neck Squamous Cell Carcinoma," Oncol. Rep. 22:1519-1526.
Stragliotto, G. et al. (Apr. 1996). "Multiple Infusion of Anti-Epidermal Growth Factor Receptor (EGFR) Monoclonal Antibody (EMD 55,900) in Patient with Recurrent Malignant Gliomas," Eur. J. Cancer 32A(4):636-640.
Striedinger, K, et al. (Nov. 2008). "The Neurofibromatosis 2 Tumor Suppressor Gene Product, Merlin, Regulates Human Meningioma Cell Growth by Signaling through YAP," Neoplasia 10(11):1204-1212.
UniProtKB/Swiss-Prot Accession No. (May 3, 2023). "Q9NZQ7. 1—RecName: Full=Programmed cell death 1 ligand 1; Short=PD-L1; Short=PDCD1 ligand 1; Short=Programmed death ligand 1; Short=hPD-L1; AltName: Full=B7 homolog 1; Short=B7-H1; AltName: CD_antigen=CD274; Flags: Precursor,", 9 pages.
Vassilev, A. et al. (2001). "TEAD/TEF Transcription Factors Utilize the Activation Domain of YAP65, a Src/Yes-Associated Protein Localized in the Cytoplasm," Genes and Development 15:1229-1241.
Wang, X. et al. (2012, e-pub. Nov. 5, 2011). "Yes-Associated Protein Promotes Tumour Development in Luminal Epithelial Derived Breast Cancer," Eur. J. Cancer 48:1227-1234.
Wang, Y. et al. (2010, e-pub. Mar. 10, 2010). "Overexpression of Yes-Associated Protein Contributes to Progression and Poor Prognosis of Non-Small-Cell Lung Cancer," Cancer Sci. 101:1279-1285.
Widder, K. et al. (1985). Methods in Enzymology, vol. 42, 112:309-396, 92 pages.
Yuen, H.-F. et al. (Jan. 23, 2013). "TAZ Expression as a Prognostic Indicator in Colorectal Cancer," PLoS One 8(1):e54211, 17 pages.
Zeng, Q. et al. (Mar. 2008). "The Emerging Role of the Hippo Pathway in Cell Contact Inhibition, Organ Size Control, and Cancer Development in Mammals," Cancer Cell 13:188-192.
Zhao, B. at al. (2010). "Hippo Signaling at a Glance," J. Cell Sci. 123(23):4001-4006.
Zhao, B. et al. (2007). "Inactivation of YAP Oncoprotein by the Hippo Pathway is Involved in Cell Contact Inhibition and Tissue Growth Control," Genes Dev. 21:2747-2761.
Zhao, B. et al. (2010). "The Hippo—YAP Pathway in Organ Size Control and Tumorigenesis: An Updated Version," Genes Dev. 24:862-874.
Zhao, B. et al. (2012). "Cell Detachment Activates the Hippo Pathway Via Cytoskeleton Reorganization to Induce Anoikis," Genes Dev.26:54-68.
Zhao, B. et al. (Aug. 2011). "The Hippo Pathway in Organ Size Control, Tissue Regeneration and Stem Cell Self-Renewal," Nature Cell Biology 13(8):877-883.
Zhao, B. et al. (Feb. 1, 2009). "Both TEAD-Binding and WW Domains Are Required for the Growth Stimulation and Oncogenic Transformation Activity of Yes-Associated Protein," Cancer Res. 69(3):1089-1098.
Zhou, Z. et al. (2011, e-pub. Jan. 24, 2011). "TAZ is a Novel Oncogene in Non-Small Cell Lung Cancer," Oncogene 30:2181-2186.
Database (Jul. 20, 2017). RN-2102543-07-5-N-[[8-[4-(trifluoromethyl)phenoxy]-6-quinolinyl]methyl]-2-Propenamide, 29 pages.
Pubchem CID 14032648 (Feb. 9, 2007). "1-Acetyl-4-[1-[4-(trifluoromethyl)phenyl]-1H-indazol-3-yl]piperidine," 9 pages.
U.S. Appl. No. 18/510,227, filed Nov. 15, 2023, Dey et al. (not submitted herewith pursuant to the waiver of 37 C.F.R. §1.98(a)(2)(iii) issued by the Office on Sep. 21, 2004).

* cited by examiner

PYRAZOLO COMPOUNDS AND METHODS OF USE THEREOF

CROSS-REFERENCE TO RELATED APPLICATIONS

This application claims priority to and benefit of U.S. Provisional Patent Application No. 63/283,138, filed Nov. 24, 2021, and U.S. Provisional Patent Application No. 63/344,025, filed May 19, 2022, the disclosures of which are hereby incorporated herein by reference in their entireties.

SUBMISSION OF ELECTRONIC SEQUENCE LISTING

The content of the electronic Sequence Listing (file name: 146392054800SeqList.xml, date created: Nov. 21, 2022, size: 20,029 bytes) is herein incorporated by reference in its entirety.

FIELD OF THE DISCLOSURE

The present disclosure relates to compounds useful for therapy and/or prophylaxis in a mammal, and in particular as inhibitors of TEAD useful for treating cancer.

BRIEF DESCRIPTION

The Hippo pathway is a signaling pathway that regulates cell proliferation and cell death and determines organ size. The pathway is believed to play a role as a tumor suppressor in mammals, and disorders of the pathway are often detected in human cancers. The pathway is involved in and/or may regulate the self-renewal and differentiation of stem cells and progenitor cells. In addition, the Hippo pathway may be involved in wound healing and tissue regeneration. Furthermore, it is believed that as the Hippo pathway cross-talks with other signaling pathways such as Wnt, Notch, Hedgehog, and MAPK/ERK, it may influence a wide variety of biological events, and that its dysfunction could be involved in many human diseases in addition to cancer. For reviews, see, for example, Halder et al., 2011, Development 138:9-22; Zhao et al., 2011, Nature Cell Biology 13:877-883; Bao et al., 2011, J. Biochem. 149:361-379; Zhao at al., 2010, J. Cell Sci. 123:4001-4006.

The Hippo signaling pathway is conserved from drosophila to mammals (Vassilev et al., Genes and Development, 2001, 15, 1229-1241; Zeng and Hong, Cancer Cell, 2008, 13, 188-192). The core of the pathway consists of a cascade of kinases (Hippo-MST1-2 being upstream of Lats 1-2 and NDRI-2) leading to the phosphorylation of two transcriptional co-activators, YAP (Yes-Associated Protein) and TAZ (Transcription co-activator with PDZ binding motif or tafazzin; Zhao et al., Cancer Res., 2009, 69, 1089-1098; Lei et al., Mol. Cell. Biol., 2008, 28, 2426-2436).

Because the Hippo signaling pathway is a regulator of animal development, organ size control and stem cell regulation, it has been implicated in cancer development (Review in Harvey et al., Nat. Rev. Cancer, 2013, 13, 246-257; Zhao et al., Genes Dev. 2010, 24, 862-874). In vitro, the overexpression of YAP or TAZ in mammary epithelial cells induces cell transformation, through interaction of both proteins with the TEAD family of transcription factors. Increased YAP/TAZ transcriptional activity induces oncogenic properties such as epithelial-mesenchymal transition and was also shown to confer stem cells properties to breast cancer cells. In vivo, in mouse liver, the overexpression of YAP or the genetic knockout of its upstream regulators MST1-2 triggers the development of hepatocellular carcinomas. Furthermore, when the tumor suppressor NF2 is inactivated in the mouse liver, the development of hepatocellular carcinomas can be blocked completely by the co-inactivation of YAP.

It is believed that deregulation of the Hippo tumor suppressor pathway is a major event in the development of a wide range of malignancies, including with no limitations, lung cancer (NSCLC; Zhou et al., Oncogene, 2011, 30, 2181-2186; Wang et al., Cancer Sci., 2010, 101, 1279-1285), breast cancer (Chan et al., Cancer Res., 2008, 68, 2592-2598; Lamar et al., Proc. Natl. Acad. Sci, USA, 2012; 109, E2441-E2250; Wang et al., Eur. J. Cancer, 2012, 48, 1227-1234), head and neck cancer (Gasparotto et al., Oncotarget., 2011, 2, 1165-1175; Steinmann et al., Oncol. Rep., 2009, 22, 1519-1526), colon cancer (Angela et al., Hum. Pathol., 2008, 39, 1582-1589; Yuen et al., PLoS One, 2013, 8, e54211; Avruch et al., Cell Cycle, 2012, 11, 1090-1096), ovarian cancer (Angela et al., Hum. Pathol., 2008, 39, 1582-1589; Chad et al., Cancer Res., 2010, 70, 8517-8525; Hall et al., Cancer Res., 2010, 70, 8517-8525), liver cancer (Jie et al., Gastroenterol. Res. Pract., 2013, 2013, 187070; Ahn et al., Mol. Cancer. Res., 2013, 11, 748-758; Liu et al., Expert. Opin. Ther. Targets, 2012, 16, 243-247), brain cancer (Orr et al., J Neuropathol. Exp. Neurol. 2011, 70, 568-577; Baia et al., Mol. Cancer Res., 2012, 10, 904-913; Striedinger et al., Neoplasia, 2008, 10, 1204-1212) and prostate cancer (Zhao et al., Genes Dev., 2012, 26, 54-68; Zhao et al., Genes Dev., 2007, 21, 2747-2761), mesotheliomas (Fujii et al., J. Exp. Med., 2012, 209, 479-494; Mizuno et al., Oncogene, 2012, 31, 5117-5122; Sekido Y., Pathol. Int., 2011, 61, 331-344), sarcomas (Seidel et al., Mol. Carcinog., 2007, 46, 865-871) and leukemia (Jimenez-Velasco et al., Leukemia, 2005, 19, 2347-2350).

Two of the core components of the mammalian Hippo pathway are Lats1 and Lats2, which are nuclear Dbf2-related (NDR) family protein kinases homologous to Drosophila Warts (Wts). The Lats1/2 proteins are activated by association with the scaffold proteins Mob1A/B (Mps one binder kinase activator-like 1A and 1B), which are homologous to Drosophila Mats. Lats1/2 proteins are also activated by phosphorylation by the STE20 family protein kinases Mst1 and Mst2, which are homologous to Drosophila Hippo. Lats1/2 kinases phosphorylate the downstream effectors YAP (Yes-associated protein) and TAZ (transcriptional coactivator with PDZ-binding motif; WWTR1), which are homologous to Drosophila Yorkie. The phosphorylation of YAP and TAZ by Lats1/2 are crucial events within the Hippo signaling pathway. Lats1/2 phosphorylates YAP at multiple sites, but phosphorylation of Ser127 is critical for YAP inhibition. Phosphorylation of YAP generates a protein-binding motif for the 14-3-3 family of proteins, which upon binding of a 14-3-3 protein, leads to retention and/or sequestration of YAP in the cell cytoplasm. Likewise, Lats1/2 phosphorylates TAZ at multiple sites, but phosphorylation of Ser89 is critical for TAZ inhibition. Phosphorylation of TAZ leads to retention and/or sequestration of TAZ in the cell cytoplasm. In addition, phosphorylation of YAP and TAZ is believed to destabilize these proteins by activating phosphorylation-dependent degradation catalyzed by YAP or TAZ ubiquitination. Thus, when the Hippo pathway is "on", YAP and/or TAZ is phosphorylated, inactive, and generally sequestered in the cytoplasm; in contrast, when the Hippo pathway is "off", YAP and/or TAZ is non-phosphorylated, active, and generally found in the nucleus.

Non-phosphorylated, activated YAP is translocated into the cell nucleus where its major target transcription factors are the four proteins of the TEAD-domain-containing family (TEAD1-TEAD4, collectively "TEAD"). YAP together with TEAD (or other transcription factors such as Smad1, RUNX, ErbB4 and p73) has been shown to induce the expression of a variety of genes, including connective tissue growth factor (CTGF), Gli2, Birc5, Birc2, fibroblast growth factor 1 (FGF1), and amphiregulin (AREG). Like YAP, non-phosphorylated TAZ is translocated into the cell nucleus where it interacts with multiple DNA-binding transcription factors, such as peroxisome proliferator-activated receptor γ (PPARγ), thyroid transcription factor-1 (TTF-1), Pax3, TBX5, RUNX, TEAD1 and Smad2/3/4. Many of the genes activated by YAP/TAZ-transcription factor complexes mediate cell survival and proliferation. Therefore, under some conditions YAP and/or TAZ acts as an oncogene and the Hippo pathway acts as a tumor suppressor. Hence, pharmacological targeting of the Hippo cascade through inhibition of TEAD would be valuable approach for the treatment of cancers that harbor functional alterations of this pathway. Certain TEAD inhibitors have been shown to be associated with increased risk of adverse events such as cardiac arrhythmias due to off-target sodium channel inhibition. Thus, there is a need for TEAD inhibitors with reduced risk of adverse events.

Ras is a small GTP-binding protein that functions as a nucleotide-dependent switch for central growth signaling pathways. In response to extracellular signals, Ras is converted from a GDP-bound ($Ras^{GDP}$) to a GTP-bound ($Ras^{GTP}$) state, as catalyzed by guanine nucleotide exchange factors (GEFs), notably the SOS1 protein. Active $Ras^{GTP}$ mediates its diverse growth-stimulating functions through its direct interactions with effectors including Raf, PI3K, and Ral guanine nucleotide dissociation stimulator. The intrinsic GTPase activity of Ras then hydrolyzes GTP to GDP to terminate Ras signaling. The Ras GTPase activity can be further accelerated by its interactions with GTPase-activating proteins (GAPs), including the neurofibromin 1 tumor suppressor.

Mutant Ras has a reduced GTPase activity, which prolongs its activated conformation, thereby promoting Ras-dependent signaling and cancer cell survival or growth. Mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer. Mutations in any one of the three main isoforms of RAS (H-Ras, N-Ras, or K-Ras) genes are common events in human tumorigenesis. Among the three Ras isoforms (K, N, and H), K-Ras is most frequently mutated.

The most common K-Ras (or KRAS) mutations are found at residue G12 and G13 in the P-loop and at residue Q61. G12C is a frequent mutation of K-Ras gene (glycine-12 to cysteine). G12C is a single point mutation with a glycine-to-cysteine substitution at codon 12. This substitution favors the activated state of KRAS, amplifying signaling pathways that lead to oncogenesis (see, e.g., Hallin et al. (Cancer Discov, 2020, 10(1): 54-71), Skoulidis et al. (N. Engl. J. Med., 2021, 384(25): 2371-2381), and Hong et al. (N. Engl. J. Med., 2020, 383(13): 1207-1217)). G12D, G12V, and G13D are other frequent mutations. Mutations of Ras in cancer are associated with poor prognosis.

Inactivation of oncogenic Ras in mice results in tumor shrinkage. Thus, Ras is widely considered an oncology target of exceptional importance. However, treatment with inhibitors of Ras (for example, KRAS) can lead to resistance through bypass of KRAS/MAPK pathway dependence, and activation of the Hippo pathway.

There is, therefore, a need for therapies that improve the ability of inhibitors of Ras (for example, KRAS) and inhibitors of YAP, TAZ, TEAD, and/or the YAP:TEAD protein-protein interaction to treat a range of diseases, disorders, and conditions, including cancer.

SUMMARY OF THE DISCLOSURE

In some aspects, a compound or a stereoisomer, tautomer, or pharmaceutically acceptable salt thereof of the following formula (I-AB) is provided:

(I-AB)

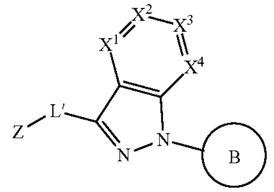

or a stereoisomer or tautomer thereof, or a pharmaceutically acceptable salt thereof, wherein:

L' is selected from the group consisting of *—N($R^1$)-L-** and

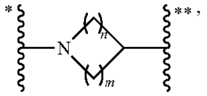

wherein * denotes the point of attachment to Z, and ** denotes the point of attachment to

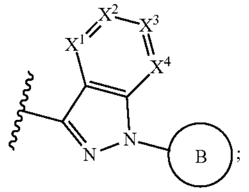

$R^1$ is H or $C_{1-6}$ alkyl;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —$OR^{f1}$, —CN, —$NR^dR^e$, and 3 to 15 membered heterocyclyl optionally substituted with one or more —OH; wherein $R^{f1}$ is —C(O)$CH_2NR^dR^e$, —C(O)$C_{1-6}$alkyl, —P(O)$(OH)_2$; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, C(O)$NH_2$, —C(O)$NR^dR^e$, —$NR^dR^e$, $C_{1-6}$alkoxyl, 3 to 6 membered heterocyclyl, $C_{3-6}$cycloalkyl, and $C_{1-6}$alkyl; wherein the $C_{1-6}$alkyl of $R^{t2}$ is optionally substituted with one or more —OH, $C_{1-6}$alkoxyl, halo, oxo, —S(O)$_2CH_3$, or —$NR^dR^e$; wherein $R^d$ and $R^e$ are each independently H, —C(O)$CH_3$, —C(O)$C_{1-6}$alkyl, or $C_{1-6}$alkyl;

$X^2$, $X^3$, and V are each independently N, CH, or CD, provided that: 1) only one of $X^1$, $X^2$, $X^3$, and $X^4$ is N; or 2) $X^1$ is N, $X^2$ is CH, $X^3$ is CH, and $X^4$ is N; or 3) $X^1$ is $CR^s$ and $X^2$, $X^3$, and $X^4$ are each independently CH or CD;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and S$(R^y)_5$, wherein each $R^y$ is halo, and wherein the $C_{1-15}$alkyl or $C_{1-6}$alkoxy of $R^t$ is optionally substituted with one or more halo;

Z is —C(O)$R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl, dihydrofuranyl, bicyclobutanyl, or cyclopentenyl; or Z is S(O)$_2R^{x1}$, wherein $R^{x1}$ is $C_{2-6}$alkenyl;

L is methylene, optionally substituted with one or more $C_{1-6}$alkyl; and n and m are each 1; or n and m are each 2.

In some aspects, a compound or a stereoisomer, tautomer, or pharmaceutically acceptable salt thereof of the following formula (AB) is provided:

(AB)

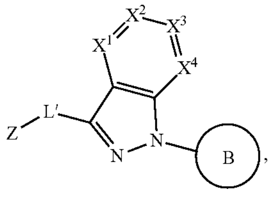

wherein:

L' is selected from the group consisting of *—N($R^1$)-L-** and

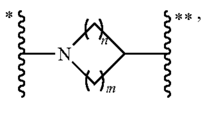

wherein * denotes the point of attachment to Z, and ** denotes the point of attachment to

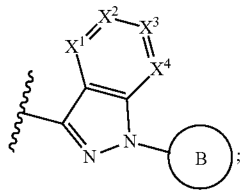

$R^1$ is H or $C_{1-6}$ alkyl;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN, —$NR^dR^e$, and 3 to 15 membered heterocyclyl optionally substituted with one or more —OH; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, C(O)$NH_2$, —C(O)$NR^dR^e$, —$NR^dR^e$, $C_{1-6}$alkoxyl, and $C_{1-6}$alkyl; wherein the $C_{1-6}$alkyl of $R^{t2}$ is optionally substituted with one or more —OH or —$NR^dR^e$; wherein $R^d$ and $R^e$ are each independently H, —C(O)$CH_3$, —C(O)$C_{1-6}$alkyl, or $C_{1-6}$alkyl;

$X^2$, $X^3$, and $X^4$ are each independently N, CH, or CD, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and S$(R^y)_5$, wherein each $R^y$ is halo, and wherein the $C_{1-15}$alkyl or $C_{1-6}$alkoxy of $R^t$ is optionally substituted with one or more halo;

Z is —C(O)$R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl;

L is methylene, optionally substituted with one or more $C_{1-6}$alkyl; and n and m are each 1; or n and m are each 2.

In some aspects, a compound or a stereoisomer, tautomer, or pharmaceutically acceptable salt thereof of the following formula (A) or (B) is provided:

(A)

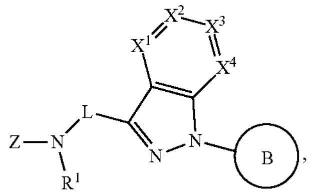

(B)

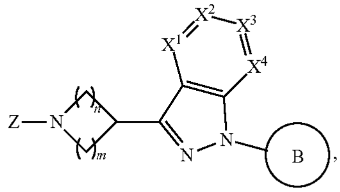

wherein:

$R^1$ is H or $C_{1-6}$ alkyl;

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo;

L is methylene, optionally substituted with one or more $C_{1-6}$alkyl; and n and m are each independently 1 or 2.

In some aspects, a compound or a stereoisomer, tautomer, or pharmaceutically acceptable salt thereof of the following formula (A') or (B') is provided:

(A')

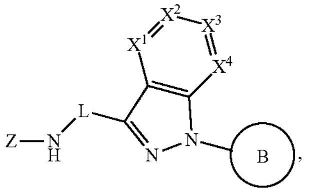

(B')

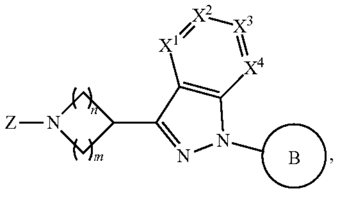

wherein:

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, $NR^dCOR^e$, —$CONR^dR^e$, —$SO_2R^d$, —$SO_2NR^dR^e$, —$NR^dSO_2R^e$, and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo;

L is methylene, optionally substituted with one or more $C_{1-6}$alkyl; and n and m are each independently 1 or 2.

In some aspects, a compound or a stereoisomer, tautomer, or pharmaceutically acceptable salt thereof of the following formula (I-A) or (I-B) is provided:

(I-A)

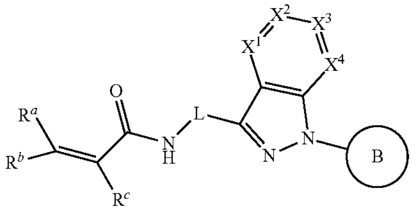

, (I-B)

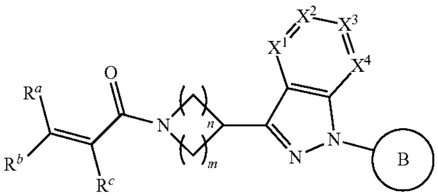

, wherein:

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, $NR^dCOR^e$, $—CONR^dR^e$, $—SO_2R^d$, $—SO_2NR^dR^e$, $—NR^dSO_2R^e$, and $—NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and $—NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

$R^a$, $R^b$, and $R^c$ are each independently H, halo, or $C_{1-5}$alkyl;

L is methylene, optionally substituted with one or more $C_{1-6}$alkyl; and n and m are each independently 1 or 2.

In some aspects, a pharmaceutical composition comprising a compound of formula (A) or a stereoisomer, tautomer, or pharmaceutically acceptable salt thereof, and a pharmaceutically acceptable carrier, diluent or excipient, is provided.

In some aspects, a pharmaceutical composition comprising a compound of formula (B) or a stereoisomer, tautomer, or pharmaceutically acceptable salt thereof, and a pharmaceutically acceptable carrier, diluent or excipient, is provided.

In some aspects, a pharmaceutical composition comprising a compound of formula (AB) or a stereoisomer, tautomer, or pharmaceutically acceptable salt thereof, and a pharmaceutically acceptable carrier, diluent or excipient, is provided.

In some aspects, a pharmaceutical composition comprising a compound of formula (I-AB) or a stereoisomer, tautomer, or pharmaceutically acceptable salt thereof, and a pharmaceutically acceptable carrier, diluent or excipient, is provided.

In some aspects, a pharmaceutical composition comprising a compound of formula (A') or a stereoisomer, tautomer, or pharmaceutically acceptable salt thereof, and a pharmaceutically acceptable carrier, diluent or excipient, is provided.

In some aspects, a pharmaceutical composition comprising a compound of formula (B') or a stereoisomer, tautomer, or pharmaceutically acceptable salt thereof, and a pharmaceutically acceptable carrier, diluent or excipient, is provided.

In some aspects, a pharmaceutical composition comprising a compound of formula (I-A) or a stereoisomer, tautomer, or pharmaceutically acceptable salt thereof, and a pharmaceutically acceptable carrier, diluent or excipient, is provided.

In some aspects, a pharmaceutical composition comprising a compound of formula (I-B) or a stereoisomer, tautomer, or pharmaceutically acceptable salt thereof, and a pharmaceutically acceptable carrier, diluent or excipient, is provided.

In some aspects, a compound of formula (A), (B), (A'), (B'), (I-A), or (I-B) or a stereoisomer, tautomer, or pharmaceutically acceptable salt thereof, is provided for use in medical therapy.

In some aspects, a compound of formula (AB) or a stereoisomer, tautomer, or pharmaceutically acceptable salt thereof, is provided for use in medical therapy.

In some aspects, a compound of formula (I-AB) or a stereoisomer, tautomer, or pharmaceutically acceptable salt thereof, is provided for use in medical therapy.

In some aspects, a compound of formula (A), (B), (A'), (B'), (I-A), or (I-B) or a stereoisomer, tautomer, or pharmaceutically acceptable salt thereof, is provided for the treatment or prophylaxis of cancer.

In some aspects, a compound of formula (AB) or a stereoisomer, tautomer, or pharmaceutically acceptable salt thereof, is provided for the treatment or prophylaxis of cancer.

In some aspects, a compound of formula (I-AB) or a stereoisomer, tautomer, or pharmaceutically acceptable salt thereof, is provided for the treatment or prophylaxis of cancer.

In some aspects, a compound of formula (A), (B), (A'), (B'), (I-A), or (I-B) or a stereoisomer, tautomer, or pharmaceutically acceptable salt thereof, is provided for the preparation of a medicament for the treatment or prophylaxis of cancer.

In some aspects, a compound of formula (AB) or a stereoisomer, tautomer, or pharmaceutically acceptable salt thereof, is provided for the preparation of a medicament for the treatment or prophylaxis of cancer.

In some aspects, a compound of formula (I-AB) or a stereoisomer, tautomer, or pharmaceutically acceptable salt thereof, is provided for the preparation of a medicament for the treatment or prophylaxis of cancer.

In some aspects, a method for treating cancer in a mammal is provided, the method comprising, administering a compound of formula (A), (B), (A'), (B'), (I-A), or (I-B) or a stereoisomer, tautomer, or pharmaceutically acceptable salt thereof, to the mammal.

In some aspects, a method for treating cancer in a mammal is provided, the method comprising, administering a compound of formula (AB) or a stereoisomer, tautomer, or pharmaceutically acceptable salt thereof, to the mammal.

In some aspects, a method for treating cancer in a mammal is provided, the method comprising, administering a compound of formula (I-AB) or a stereoisomer, tautomer, or pharmaceutically acceptable salt thereof, to the mammal.

In some aspects, a method for treating cancer in a mammal is provided, the method comprising administering a compound of formula (A), (B), (A'), (B'), (I-A), or (I-B) or a stereoisomer, tautomer, or pharmaceutically acceptable salt thereof, to the mammal in combination with a second therapeutic agent.

In some aspects, a method for treating cancer in a mammal is provided, the method comprising administering a compound of formula (AB) or a stereoisomer, tautomer, or pharmaceutically acceptable salt thereof, to the mammal in combination with a second therapeutic agent.

In some aspects, a method for treating cancer in a mammal is provided, the method comprising administering a compound of formula (I-AB) or a stereoisomer, tautomer, or pharmaceutically acceptable salt thereof, to the mammal in combination with a second therapeutic agent.

In some aspects, a compound of formula (A), (B), (A'), (B'), (I-A), or (I-B) or a stereoisomer, tautomer, or pharmaceutically acceptable salt thereof, is provided for modulating TEAD activity.

In some aspects, a compound of formula (AB) or a stereoisomer, tautomer, or pharmaceutically acceptable salt thereof, is provided for modulating TEAD activity.

In some aspects, a compound of formula (I-AB) or a stereoisomer, tautomer, or pharmaceutically acceptable salt thereof, is provided for modulating TEAD activity.

In some aspects, a compound of formula (A), (B), (A'), (B'), (I-A), or (I-B) or a stereoisomer, tautomer, or pharmaceutically acceptable salt thereof, is provided for the treatment or prophylaxis of a disease or condition mediated by TEAD activity.

In some aspects, a compound of formula (AB) or a stereoisomer, tautomer, or pharmaceutically acceptable salt thereof, is provided for the treatment or prophylaxis of a disease or condition mediated by TEAD activity.

In some aspects, a compound of formula (I-AB) or a stereoisomer, tautomer, or pharmaceutically acceptable salt thereof, is provided for the treatment or prophylaxis of a disease or condition mediated by TEAD activity.

In some aspects, a compound of formula (A), (B), (A'), (B'), (I-A), or (I-B) or a stereoisomer, tautomer, or pharmaceutically acceptable salt thereof, is provided for use for the preparation of a medicament for the treatment or prophylaxis of a disease or condition that is mediated by TEAD activity.

In some aspects, a compound of formula (AB) or a stereoisomer, tautomer, or pharmaceutically acceptable salt thereof, is provided for use for the preparation of a medicament for the treatment or prophylaxis of a disease or condition that is mediated by TEAD activity.

In some aspects, a compound of formula (I-AB) or a stereoisomer, tautomer, or pharmaceutically acceptable salt thereof, is provided for use for the preparation of a medicament for the treatment or prophylaxis of a disease or condition that is mediated by TEAD activity.

In some aspects, a method for modulating TEAD activity is provided, the method comprising contacting TEAD with a therapeutically effective amount of a compound of formula (A), (B), (A'), (B'), (I-A), or (I-B) or a stereoisomer, tautomer, or pharmaceutically acceptable salt thereof.

In some aspects, a method for modulating TEAD activity is provided, the method comprising contacting TEAD with a therapeutically effective amount of a compound of formula (AB) or a stereoisomer, tautomer, or pharmaceutically acceptable salt thereof.

In some aspects, a method for modulating TEAD activity is provided, the method comprising contacting TEAD with a therapeutically effective amount of a compound of formula (I-AB) or a stereoisomer, tautomer, or pharmaceutically acceptable salt thereof.

In some aspects, a method for treating a disease or condition mediated by TEAD activity in a mammal is provided, the method comprising administering a compound of formula (A), (B), (A'), (B'), (I-A), or (I-B) or a stereoisomer, tautomer, or pharmaceutically acceptable salt thereof, to the mammal.

In some aspects, a method for treating a disease or condition mediated by TEAD activity in a mammal is provided, the method comprising administering a compound of formula (AB) or a stereoisomer, tautomer, or pharmaceutically acceptable salt thereof, to the mammal.

In some aspects, a method for treating a disease or condition mediated by TEAD activity in a mammal is provided, the method comprising administering a compound of formula (I-AB) or a stereoisomer, tautomer, or pharmaceutically acceptable salt thereof, to the mammal.

In one aspect, the present disclosure is directed to a combination comprising: (i) one or more YAP/TAZ-TEAD inhibitors; and (ii) one or more KRAS inhibitors. In some aspects, one or more YAP/TAZ-TEAD inhibitors and one or more KRAS inhibitors are co-administered to an individual. In some aspects, the combination is administered to an individual in the same composition. In some aspects, the combination is administered to an individual in different compositions. Thus, it is understood that the one or more YAP/TAZ-TEAD inhibitors and the one or more KRAS inhibitors may be administered simultaneously or sequentially to the individual. In some aspects, provided herein are compositions comprising one or more YAP/TAZ-TEAD inhibitors and one or more KRAS inhibitors. In another aspect, the present disclosure is directed to methods of modulating or inhibiting KRAS activity in a cell, comprising administering to the cell an effective amount of such combinations. In another aspect, the present disclosure is directed to methods of treating cancer in a subject in need thereof, comprising administering to the subject an effective amount of such combinations. In another aspect, the present disclosure is directed to methods of reducing resistance of a subject to treatment comprising a KRAS inhibitor, wherein the method comprises administering to the subject a therapeutically effective amount of a TEAD inhibitor.

In one aspect, the present disclosure is directed to processes of preparing one or more TEAD inhibitors described herein.

BRIEF DESCRIPTION OF THE DRAWINGS

The following embodiments are representative of some aspects of the disclosure.

DETAILED DESCRIPTION

Definitions

Figure 1:
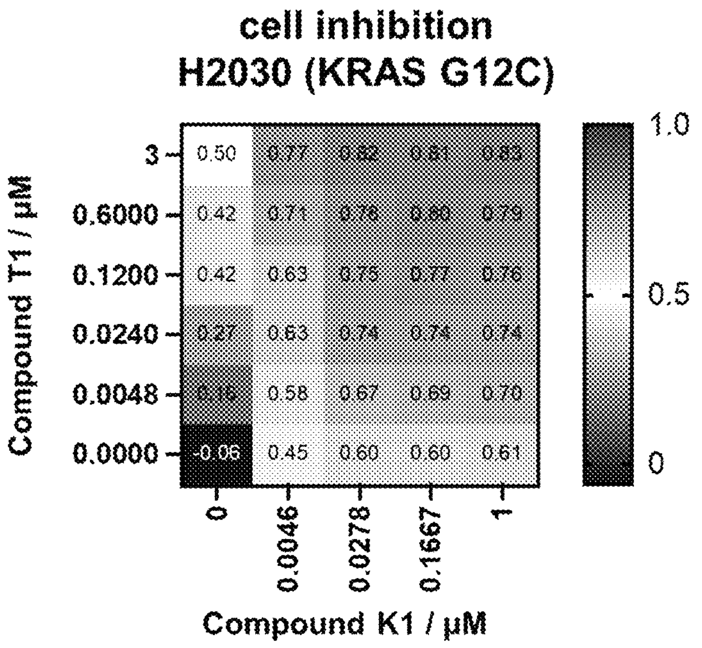
FIG. 1 depicts % inhibition of H2030 cells (KRAS G12C) following administration of a combination comprising Compound T1 (a YAP/TAZ-TEAD inhibitor) and Compound K1 (a KRAS inhibitor).

Unless otherwise indicated, the following specific terms and phrases used in the description and claims are defined as follows.

The term "moiety" refers to an atom or group of chemically bonded atoms that is attached to another atom or molecule by one or more chemical bonds thereby forming part of a molecule.

The term "substituted" refers to the fact that at least one of the hydrogen atoms of that moiety is replaced by another substituent or moiety.

The term "alkyl" refers to an aliphatic straight-chain or branched-chain saturated hydrocarbon moiety having 1 to 20 carbon atoms, such as 1 to 12 carbon atoms, or 1 to 6 carbon atoms. Alkyl groups may be optionally substituted. In some embodiments, alkyl is unsubstituted.

In some embodiments, "alkoxy" is —O-alkyl.

The term "cycloalkyl" means a saturated or partially unsaturated carbocyclic moiety having mono- or bicyclic (including bridged bicyclic) rings and 3 to 10 carbon atoms in the ring. In particular aspects, cycloalkyl may contain from 3 to 8 carbon atoms (i.e., $(C_{3-8})$cycloalkyl). In other particular aspects cycloalkyl may contain from 3 to 6 carbon atoms (i.e., $(C_3-C_6)$cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a spirocycle fashion such as spirocycloprpyl:

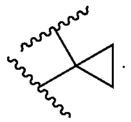 [SMILES: *C1(*)CC1]

The term "haloalkyl" refers to an alkyl group wherein one or more of the hydrogen atoms of the alkyl group has been replaced by the same or different halogen atoms, such as fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. Haloalkyl groups may be optionally substituted. In some embodiments, haloalkyl is unsubstituted.

The term "alkenyl" refers to a straight or branched chain alkyl or substituted alkyl group as defined elsewhere herein having at least one carbon-carbon double bond. Alkenyl groups may be optionally substituted. In some embodiments, alkenyl is unsubstituted.

The term "alkynyl" refers to a straight or branched chain alkyl or substituted alkyl group as defined elsewhere herein having at least one carbon-carbon triple bond. Alkynyl groups may be optionally substituted. In some embodiments, alkynyl is unsubstituted.

The terms "heterocyclyl" and "heterocycle" refer to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4) heteroatoms selected from oxygen, nitrogen and sulfur in the ring with the remaining ring atoms being carbon. When used in reference to a ring atom of a heterocycle, a nitrogen or sulfur may also be in an oxidized form, and a nitrogen may be substituted. The heterocycle can be attached to its pendant group at any heteroatom or carbon atom that results in a stable structure and any of the ring atoms can be optionally substituted. Examples of such saturated or partially unsaturated heterocycles include, without limitation, oxiranyl, oxetanyl, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazolyl, thiazepinyl, morpholinyl, and quinuclidinyl. The term heterocycle also includes groups in which a heterocycle is fused to one or more aryl, heteroaryl, or cycloalkyl rings, such as benzothiazolyl, benzofuranyl, furopyridinyl, indolinyl, 3H-indolyl, chromanyl, 2-azabicyclo[2.2.1]heptanyl, octahydroindolyl, or tetrahydroquinolinyl. Heterocyclyl groups may be optionally substituted. In some embodiments, heterocyclyl is unsubstituted.

The term "aryl" refers to a cyclic aromatic hydrocarbon moiety having a mono-, bi- or tricyclic aromatic ring of 5 to 20 carbon ring atoms. Examples of aryl moieties include, but are not limited to, phenyl, naphthyl, benzyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted. In some aspects, monocyclic aryl rings may have 5 or 6 carbon ring atoms. Aryl groups may be optionally substituted. In some embodiments, aryl is unsubstituted.

The term "heteroaryl" refers an aromatic heterocyclic mono- or bicyclic ring system of 1 to 20 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Heteroaryl groups may be optionally substituted. In some embodiments, heteroaryl is unsubstituted.

The terms "halo" and "halogen" refer fluoro, chloro, bromo and iodo. In some aspects, halo is fluoro or chloro.

The term "oxo" refers to the =O moiety.

The term "cyano" refers to the —C≡N moiety.

The terms "spirocycle" and "spirocyclyl" refer to carbogenic bicyclic ring systems comprising between 5 and 13 carbon atoms with both rings connected through a single atom. The rings can be different in size and nature, or identical in size and nature. Examples include spiropentane, spirohexane, spiroheptane, spirooctane, spirononane, or spirodecane. One or more of the carbon atoms in the spirocycle can be substituted with a heteroatom (e.g., O, N, S, or P). Spirocycle groups may be optionally substituted.

In some embodiments, the spirocycle is unsubstituted.

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The term "prodrug" refers to those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

In some prodrug aspects, prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present disclosure. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

In some other prodrug aspects, a free carboxyl group of a compound of the disclosure can be derivatized as an amide or alkyl ester. In yet other prodrug aspects, prodrugs comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl, $(C_{1-6})$alkoxy carbonyloxymethyl, N—$(C_{1-6})$alkoxy carbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present disclosure provides for metabolites of compounds of the disclosure. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., 14c or $^3H$) isotope of a compound of the disclosure, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure can exist in multiple crystalline or amorphous forms. In general, all physical forms are equivalent for the uses contemplated by the present disclosure and are intended to be within the scope of the present disclosure.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain aspects the compound is enriched by at least about 90% by weight with a single diastereomer or enantiomer. In other aspects the compound is enriched by at least about 95%, 98%, or 99% by weight with a single diastereomer or enantiomer.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure.

The compounds of the present disclosure may also exist in different tautomeric forms, and all such forms are embraced within the scope of the disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise indicated, the term "a compound of the formula" or "a compound of formula" or "compounds of the formula" or "compounds of formula" refers to any compound selected from the genus of compounds as defined by the formula. In some embodiments or aspects, the term also includes a pharmaceutically acceptable salt or ester of any such compound, a stereoisomer, or a tautomer of such compound.

The term"a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this disclosure can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

In some embodiments, the term "a therapeutically effective amount" of a compound means an amount of compound that is effective to alleviate or ameliorate symptoms of disease or prolong the survival of the subject being treated. Determination of a therapeutically effective amount is within the skill in the art. The therapeutically effective amount or dosage of a compound according to this disclosure can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

In embodiments herein, a therapeutically effective amount of a compound may be an amount of compound that is effective to alleviate or ameliorate a condition or disease, or symptoms thereof, or prolong the survival of the subject being treated.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with a compound of the disclosure, use thereof in the compositions of the disclosure is contemplated. Supplementary active compounds can also be incorporated into the compositions.

Compounds

In some aspects, a compound or a stereoisomer, tautomer, or pharmaceutically acceptable salt thereof of the following formula (I-AB) is provided:

(I-AB)

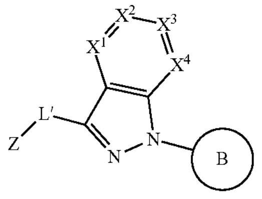

or a stereoisomer or tautomer thereof, or a pharmaceutically acceptable salt thereof, wherein:

L' is selected from the group consisting of *—N($R^1$)-L-** and

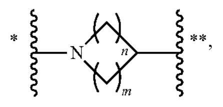

wherein * denotes the point of attachment to Z, and ** denotes the point of attachment to

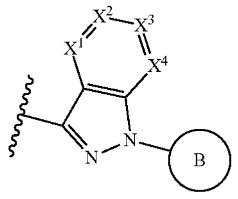

;

$R^1$ is H or $C_{1-6}$ alkyl;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —$OR^{f1}$, —CN, —$NR^dR^e$, and 3 to 15 membered heterocyclyl optionally substituted with one or more —OH; wherein $R^{f1}$ is —$C(O)CH_2NR^dR^e$, —$C(O)C_{1-6}$alkyl, —$P(O)(OH)_2$; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, 3 to 6 membered heterocyclyl, $C_{3-6}$cycloalkyl, and $C_{1-6}$alkyl; wherein the $C_{1-6}$alkyl of $R^{t2}$ is optionally substituted with one or more —OH, $C_{1-6}$alkoxyl, halo, oxo, —$S(O)_2CH_3$, or —$NR^dR^e$; wherein $R^d$ and $R^e$ are each independently H, —$C(O)CH_3$, —$C(O)C_{1-6}$alkyl, or $C_{1-6}$alkyl;

$X^2$, $X^3$, and $X^4$ are each independently N, CH, or CD, provided that: 1) only one of $X^1$, $X^2$, $X^3$, and $X^4$ is N; or 2) $X^1$ is N, $X^2$ is CH, $X^3$ is CH, and $X^4$ is N; or 3) $X^1$ is $CR^s$ and $X^2$, $X^3$, and $X^4$ are each independently CH or CD;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl, dihydrofuranyl, bicyclobutanyl, or cyclopentenyl; or Z is $S(O)_2R^{x1}$, wherein $R^{x1}$ is $C_{2-6}$alkenyl;

L is methylene, optionally substituted with one or more $C_{1-6}$alkyl; and n and m are each 1; or n and m are each 2.

Any embodiments, aspects, variations, described herein with respect to one formula, may, where applicable, be applied to any other formula listed herein. For example, any embodiments, aspects, variations, described herein with respect to any one or more of formula (AB), (A), (B), (A'), (B'), (I-A), and (I-B) apply to formula (I-AB), the same as if each and every embodiments, aspects, and variations is specifically and individually listed with respect to formula (I-AB). It is understood that such embodiments apply to structural features of compounds, as well as methods of making and using such compounds. For example, it is understood that methods of using any one or more of formula (AB), (A), (B), (A'), (B'), (I-A), and (I-B), where applicable, apply to methods of using compounds of formula (I-AB), the same as if each and every embodiments, aspects, and variations is specifically and individually listed with respect to formula (I-AB).

In some embodiments, in conjunction with embodiments above or below, L' of formula (I-AB) is *—N($R^1$)-L-**. In some embodiments, in conjunction with embodiments above or below, L' of formula (I-AB) is

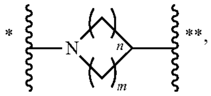

In some aspects, a compound or a stereoisomer, tautomer, or pharmaceutically acceptable salt thereof of the following formula (AB) is provided:

(AB)

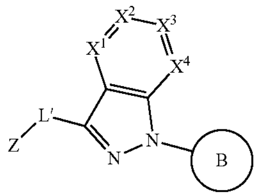

wherein:

L' is selected from the group consisting of *—N($R^1$)-L-** and

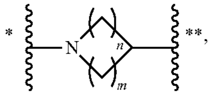

wherein * denotes the point of attachment to Z, and ** denotes the point of attachment to

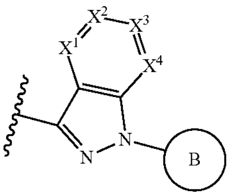

;

$R^1$ is H or $C_{1-6}$ alkyl;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN, —$NR^dR^e$, and 3 to 15 membered heterocyclyl optionally substituted with one or more —OH; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, and $C_{1-6}$alkyl; wherein the $C_{1-6}$alkyl of $R^{t2}$ is optionally substituted with one or more —OH or —$NR^dR^e$; wherein $R^d$ and $R^e$ are each independently H, —$C(O)CH_3$, —$C(O)C_{1-6}$alkyl, or $C_{1-6}$alkyl;

$X^2$, $X^3$, and $X^4$ are each independently N, CH, or CD, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl;

L is methylene, optionally substituted with one or more $C_{1-6}$alkyl; and n and m are each 1; or n and m are each 2.

In some aspects, a compound or a stereoisomer, tautomer, or pharmaceutically acceptable salt thereof of the following formula (A) or (B) is provided:

(A)

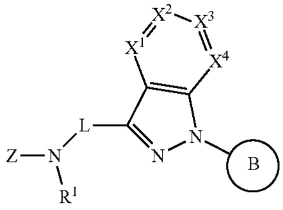

, (B)

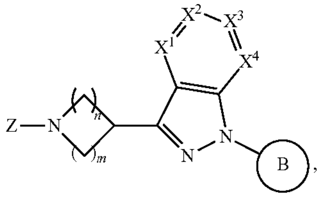

, wherein:

$R^1$ is H or $C_{1-6}$ alkyl;

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo;

L is methylene, optionally substituted with one or more $C_{1-6}$alkyl; and n and m are each independently 1 or 2.

In some aspects, a compound or a stereoisomer, tautomer, or pharmaceutically acceptable salt thereof of the following formula (A) or (B) is provided:

(A)

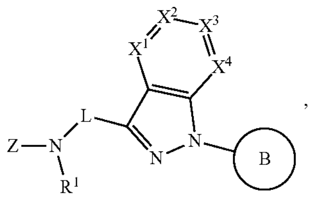

, (B)

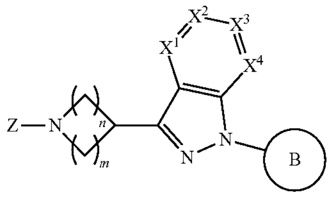

, wherein:

$R^1$ is H or $C_{1-6}$ alkyl;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN, —$NR^dR^e$, and 3 to 15 membered heterocyclyl optionally substituted with one or more —OH; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, and $C_{1-6}$alkyl; wherein the $C_{1-6}$alkyl of $R^{t2}$ is optionally substituted with one or more —OH or —$NR^dR^e$; wherein $R^d$ and $R^e$ are each independently H, —$C(O)CH_3$, —$C(O)C_{1-6}$alkyl, or $C_{1-6}$alkyl;

$X^2$, $X^3$, and $X^4$ are each independently N, CH, or CD, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl;

L is methylene, optionally substituted with one or more $C_{1-6}$alkyl; and n and m are each 1; or n and m are each 2.

In some embodiments, the compound is a compound of formula (A). In some embodiments, the compound is a compound of formula (B).

In some aspects, a compound or a stereoisomer, tautomer, or pharmaceutically acceptable salt thereof of the following formula (A') or (B') is provided:

(A')

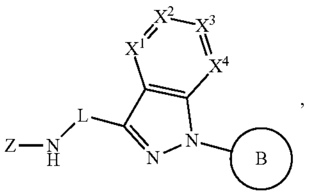

, (B')

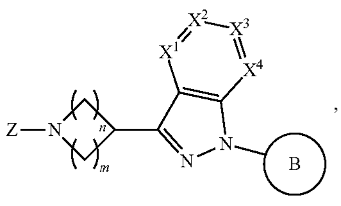

, wherein:

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo;

L is methylene, optionally substituted with one or more $C_{1-6}$alkyl; and n and m are each independently 1 or 2.

In some embodiments, provided herein is a compound of formula (AB), or a stereoisomer, tautomer, or pharmaceutically acceptable salt thereof, wherein L' is *—$N(R^1)$-L-**, wherein * denotes the point of attachment to Z, and ** denotes the point of attachment to

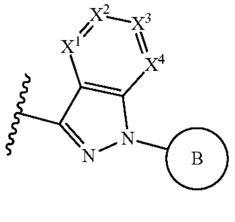

,

In some embodiments, provided herein is a compound of formula (AB), or a stereoisomer, tautomer, or pharmaceutically acceptable salt thereof, wherein L' is

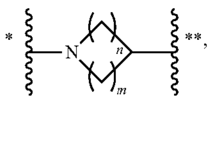

wherein * denotes the point of attachment to Z, and ** denotes the point of attachment to

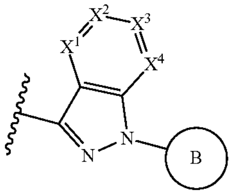

.

In some embodiments, provided herein is a compound of formula (A) or (A'), or a stereoisomer, tautomer, or pharmaceutically acceptable salt thereof, wherein $R^1$ is H. In some embodiments, $R^1$ is $C_{1-6}$ alkyl. In some embodiments, $R^1$ is methyl.

In some embodiments, provided herein is a compound of formula (A) or (A'), or a stereoisomer, tautomer, or pharmaceutically acceptable salt thereof, wherein $X^1$ is N. In some embodiments, $X^1$ is C—$CR^s$. In some embodiments, $X^1$ is C—$CR^s$, and $R^s$ is independently H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^dCOR^e$, —$CONR^dR^e$, —$SO_2R^d$, —$SO_2NR^dR^e$, —$NR^dSO_2R^e$, or —$NR^dR^e$. In other embodiments, $R^s$ is H. In other embodiments, each $R^s$ is halo. In other embodiments, $R^s$ is $C_{1-15}$alkyl. In other embodiments, $R^s$ is $C_{6-20}$aryl. In other embodiments, $R^s$ is 5 to 15 membered heteroaryl. In other embodiments, $R^s$ is $C_{3-20}$cycloalkyl. In other embodiments, $R^s$ is 3 to 15 membered heterocyclyl. In other embodiments, $R^s$ is —OH. In other embodiments, $R^s$ is —CN. In other embodiments, $R^s$ is $C_{1-15}$alkoxy. In other embodiments, $R^s$ is —$NR^dCOR^e$. In other embodiments, $R^s$ is —$CONR^dR^e$. In other embodiments, $R^s$ is —$SO_2R^d$. In other embodiments, $R^s$ is —$SO_2NR^dR^e$. In other embodiments, $R^s$ is —$NR^dSO_2R^e$. In other embodiments, $R^s$ is —$NR^dR^e$.

In some embodiments, provided herein is a compound of formula (A) or (A'), or a stereoisomer, tautomer, or pharmaceutically acceptable salt thereof, wherein $X^1$ is C—$CR^s$, and wherein $R^s$ is $C_{1-15}$alkyl or $C_{1-15}$alkoxy, the $C_{1-15}$alkyl and $C_{1-15}$alkoxy of $R^s$ are each independently optionally substituted with one or more $R^{t1}$, wherein $R^{t1}$ is independently, at each occurrence, halo, oxo, —OH, —CN, or —$NR^dR^e$. In some embodiments, $R^s$ is $C_{1-15}$alkyl substituted with one or more $R^{t1}$, wherein $R^{t1}$ is halo. In some embodiments, $R^s$ is $C_{1-15}$alkyl substituted with one or more $R^{t1}$, wherein $R^{t1}$ is oxo. In some embodiments, $R^s$ is $C_{1-15}$alkyl substituted with one or more $R^{t1}$, wherein $R^{t1}$ is —OH. In some embodiments, $R^s$ is $C_{1-15}$alkyl substituted with one or more $R^{t1}$, wherein $R^{t1}$ is —CN. In some embodiments, $R^s$ is $C_{1-15}$alkyl substituted with one or more $R^{t1}$, wherein $R^{t1}$ is —$NR^dR^e$. In some embodiments, $R^s$ is $C_{1-15}$alkoxy substituted with one or more $R^{t1}$, wherein $R^{t1}$ is halo. In some embodiments, $R^s$ is $C_{1-15}$alkoxy substituted with one or more $R^{t1}$, wherein $R^{t1}$ is oxo. In some embodiments, $R^s$ is $C_{1-15}$alkoxy substituted with one or more $R^{t1}$, wherein $R^{t1}$ is —OH. In some embodiments, $R^s$ is $C_{1-15}$alkoxy substituted with one or more $R^{t1}$, wherein $R^{t1}$ is —CN. In some embodiments, $R^s$ is $C_{1-15}$alkoxy substituted with one or more $R^{t1}$, wherein $R^{t1}$ is —$NR^dR^e$.

In some embodiments, provided herein is a compound of formula (A) or (A'), or a stereoisomer, tautomer, or pharmaceutically acceptable salt thereof, wherein $X^1$ is C—$CR^s$, and wherein $R^s$ is $C_{1-15}$alkyl or $C_{1-15}$alkoxy, the $C_{1-15}$alkyl and $C_{1-15}$alkoxy of $R^s$ are each independently optionally substituted with one or more $R^{t1}$, wherein $R^{t1}$ is independently, at each occurrence, halo, oxo, —OH, —CN, —$NR^dR^e$, or 3 to 15 membered heterocyclyl optionally substituted with —OH. In some embodiments, $R^s$ is $C_{1-15}$alkyl substituted with one or more $R^{t1}$, wherein $R^{t1}$ is halo. In some embodiments, $R^s$ is $C_{1-15}$alkyl substituted with one or more $R^{t1}$, wherein $R^{t1}$ is oxo. In some embodiments, $R^s$ is $C_{1-15}$alkyl substituted with one or more $R^{t1}$, wherein $R^{t1}$ is —OH. In some embodiments, $R^s$ is $C_{1-15}$alkyl substituted with one or more $R^{t1}$, wherein $R^{t1}$ is —CN. In some embodiments, $R^s$ is $C_{1-15}$alkyl substituted with one or more $R^{t1}$, wherein $R^{t1}$ is —$NR^dR^e$. In some embodiments, $R^s$ is $C_{1-15}$alkoxy substituted with one or more $R^{t1}$, wherein $R^{t1}$ is halo. In some embodiments, $R^s$ is $C_{1-15}$alkoxy substituted with one or more $R^{t1}$, wherein $R^{t1}$ is oxo. In some embodiments, $R^s$ is $C_{1-15}$alkoxy substituted with one or more $R^{t1}$, wherein $R^{t1}$ is —OH. In some embodiments, $R^s$ is $C_{1-15}$alkoxy substituted with one or more $R^{t1}$, wherein $R^{t1}$ is —CN. In some embodiments, $R^s$ is $C_{1-15}$alkoxy substituted with one or more $R^{t1}$, wherein $R^{t1}$ is —$NR^dR^e$. In some embodiments, $R^s$ is $C_{1-15}$alkoxy substituted with one or more $R^{t1}$, wherein $R^{t1}$ is 3 to 15 membered heterocyclyl optionally substituted with —OH.

In some embodiments, provided herein is a compound of formula (A) or (A'), or a stereoisomer, tautomer, or pharmaceutically acceptable salt thereof, wherein $X^1$ is C—$CR^s$, and wherein $R^s$ is $C_{6-20}$aryl, 5 to 15 membered heteroaryl, $C_{3-20}$cycloalkyl, or 3 to 15 membered heterocyclyl, the $C_{6-20}$aryl, 5 to 15 membered heteroaryl, $C_{3-20}$cycloalkyl, or 3 to 15 membered heterocyclyl of $R^s$ are each independently optionally substituted with one or more $R^{t2}$, wherein $R^{t2}$ is independently, at each occurrence, halo, oxo, —OH, —CN, or —$NR^dR^e$. In some embodiments, $R^s$ is $C_{6-20}$aryl substituted with one or more $R^{t2}$, wherein $R^{t2}$ is halo. In some embodiments, $R^s$ is $C_{6-20}$aryl substituted with one or more $R^{t2}$, wherein $R^{t2}$ is oxo. In some embodiments, $R^s$ is $C_{6-20}$aryl substituted with one or more $R^{t2}$, wherein $R^{t2}$ is —OH. In some embodiments, $R^s$ is $C_{6-20}$aryl substituted with one or more $R^{t2}$, wherein $R^{t2}$ is —CN. In some embodiments, $R^s$ is $C_{6-20}$aryl substituted with one or more $R^{t2}$, wherein $R^{t2}$ is —$NR^dR^e$. In some embodiments, $R^s$ is 5 to 15 membered heteroaryl substituted with one or more $R^{t2}$, wherein $R^{t2}$ is halo. In some embodiments, $R^s$ is 5 to 15 membered heteroaryl substituted with one or more $R^{t2}$, wherein $R^{t2}$ is oxo. In some embodiments, $R^s$ is 5 to 15 membered heteroaryl and $R^{t2}$ is —OH. In some embodiments, $R^s$ is 5 to 15 membered heteroaryl substituted with one or more $R^e$, wherein $R^{t2}$ is —CN. In some embodiments, $R^s$ is 5 to 15 membered heteroaryl substituted with one or more $R^{t2}$, wherein $R^{t2}$ is —$NR^dR^e$. In some embodiments, $R^s$ is $C_{3-20}$cycloalkyl substituted with one or more $R^{t2}$, wherein $R^{t2}$ is halo. In some embodiments, $R^s$ is $C_{3-20}$cycloalkyl substituted with one or more $R^{t2}$, wherein $R^{t2}$ is oxo. In some embodiments, $R^s$ is $C_{3-20}$cycloalkyl substituted with one or more $R^{t2}$, wherein $R^{t2}$ is —OH. In some embodiments, $R^s$ is $C_{3-20}$cycloalkyl substituted with one or more $R^{t2}$, wherein $R^{t2}$ is —CN. In some embodiments, $R^s$ is $C_{3-20}$cycloalkyl substituted with one or more $R^{t2}$, wherein $R^{t2}$ is —$NR^dR^e$. In some embodiments, $R^s$ is 3 to 15 membered heterocyclyl substituted with one or more $R^{t2}$, wherein $R^{t2}$ is halo. In some embodiments, $R^s$ is 3 to 15 membered heterocyclyl substituted with one or more $R^{t2}$, wherein $R^{t2}$ is oxo. In some embodiments, $R^s$ is 3 to 15 membered heterocyclyl substituted with one or more $R^{t2}$, wherein $R^{t2}$ is —OH. In some embodiments, $R^s$ is 3 to 15 membered heterocyclyl substituted with one or more $R^{t2}$, wherein $R^{t2}$ is —CN. In some embodiments, $R^s$ is 3 to 15 membered heterocyclyl substituted with one or more $R^{t1}$, wherein $R^{t1}$ is —$NR^dR^e$.

In some embodiments, provided herein is a compound of formula (A) or (A'), or a stereoisomer, tautomer, or pharmaceutically acceptable salt thereof, wherein $X^1$ is C—$CR^s$, and wherein each $R^s$ is independently further substituted by $R^{t1}$, wherein $R^{t1}$ is —$NR^dR^e$, $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $R^d$ is H. In some embodiments, $R^d$ is $C_{1-6}$alkyl. In some embodiments, $R^e$ is H. In some embodiments, $R^e$ is $C_{1-6}$alkyl. In some embodiments, wherein $R^d$ is $C_{1-6}$alkyl, the $C_{1-6}$alkyl of $R^d$ is optionally substituted with one or more halo, oxo, —OH, or —CN. In some embodiments, the $C_{1-6}$alkyl of $R^d$ is substituted with one or more halo. In some embodiments, the $C_{1-6}$alkyl of $R^d$ is substituted with one or more oxo. In some embodiments, the $C_{1-6}$alkyl of $R^d$ is substituted with one or more —OH. In some embodiments, the $C_{1-6}$alkyl of $R^d$ is substituted with one or more —CN. In some embodiments, wherein $R^e$ is $C_{1-6}$alkyl, the $C_{1-6}$alkyl of $R^e$ is optionally substituted with one or more halo, oxo, —OH, or —CN. In some embodiments, the $C_{1-6}$alkyl of $R^e$ is substituted with one or more halo. In some embodiments, the $C_{1-6}$alkyl of $R^e$ is substituted with one or more oxo. In some embodiments, the $C_{1-6}$alkyl of $R^e$ is substituted with one or more —OH. In some embodiments, the $C_{1-6}$alkyl of $R^e$ is substituted with one or more —CN.

In some embodiments, provided herein is a compound of formula (A) or (A'), or a stereoisomer, tautomer, or pharmaceutically acceptable salt thereof, wherein B is phenyl or 5 to 6 membered heteroaryl. In some embodiments, B is phenyl. In some embodiments, B is 5 to 6 membered heteroaryl. In some embodiments, the phenyl or 5 to 6 membered heteroaryl of B is each independently optionally substituted with one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, and $R^t$ is halo. In some embodiments, B is phenyl substituted by one or more $R^t$, and $R^t$ is $C_{1-15}$alkyl. In some embodiments, B is phenyl substituted by one or more $R^t$, and $R^t$ is $C_{1-6}$alkoxy. In some embodiments, B is phenyl substituted by one or more $R^t$, and $R^t$ is $S(R^y)_5$, wherein each $R^y$ is halo. In some embodiments, B is 5 to 6 membered heteroaryl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is 5 to 6 membered heteroaryl substituted by one or more $R^t$, and $R^t$ is halo. In some embodiments, B is 5 to 6 membered heteroaryl substituted by one or more $R^t$, and $R^t$ is $C_{1-15}$alkyl. In some embodiments, B is 5 to 6 membered heteroaryl substituted by one or more $R^t$, and $R^t$ is $C_{1-6}$alkoxy. In some embodiments, wherein B is phenyl or 5 to 6 membered heteroaryl substituted by one or more $R^t$, wherein $R^t$ is $C_{1-15}$alkyl, or $C_{1-6}$alkoxy, the $C_{1-15}$alkyl or $C_{1-6}$alkoxy of $R^t$ is optionally substituted with one or more halo. In some embodiments, the $C_{1-15}$alkyl of $R^t$ is substituted by one or more fluoro. In some embodiments, the $C_{1-15}$alkoxy of $R^t$ is substituted by one or more fluoro. In some embodiments, B is 5 to 6 membered heteroaryl substituted by one or more $R^t$, and $R^t$ is $S(R^y)_5$, wherein each $R^y$ is halo.

In some embodiments, provided herein is a compound of formula (A) or (A'), or a stereoisomer, tautomer, or pharmaceutically acceptable salt thereof, wherein B is phenyl. In some embodiments, B is 5 to 6 membered heteroaryl. In other embodiments, B is unsubstituted phenyl. In other embodiments, B is substituted phenyl. In other embodiments, B is phenyl substituted by one or more $R^t$. In other embodiments, $R^t$ is $C_{1-6}$ alkoxy. In other embodiments, $R^t$ is $C_{1-6}$alkoxy substituted by one or more halo. In other embodiments, $R^t$ is $C_{1-6}$alkoxy substituted by one or more fluoro. In other embodiments, B is

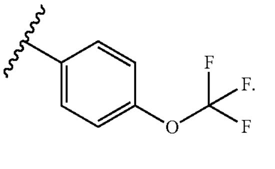 [SMILES: *c1ccc(OC(F)(F)F)cc1]

In some embodiments, provided herein is a compound of formula (A) or (A'), or a stereoisomer, tautomer, or pharmaceutically acceptable salt thereof, wherein $X^1$ is N or C—$CR^s$. In some embodiments, $X^1$ is N. In some embodiments, $X^1$ is C—$CR^s$.

In some embodiments, provided herein is a compound of formula (A) or (A'), or a stereoisomer, tautomer, or pharmaceutically acceptable salt thereof, wherein $X^1$ is C—$R^s$, $X^2$ is C—H, $X^3$ is C—H, $X^4$ is N; and $R^s$ is unsubstituted $C_{1-15}$alkyl. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$, wherein $R^{t1}$ is —OH. In other embodiments, $X^1$ is C—$R^s$, $X^2$ is C—H, $X^3$ is C—H, $X^4$ is N; and $R^s$ is

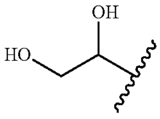
.

In some embodiments, provided herein is a compound of formula (A) or (A'), or a stereoisomer, tautomer, or pharmaceutically acceptable salt thereof, wherein L is methylene, optionally substituted with one or more $C_{1-6}$alkyl. In some embodiments, L is unsubstituted methylene. In some embodiments, L is methylene substituted with one or more $C_{1-6}$alkyl.

In some embodiments, provided herein is a compound of formula (A), or a stereoisomer, tautomer, or pharmaceutically acceptable salt thereof, wherein Z is —C(O)$R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo. In some embodiments, $R^x$ is $C_{2-6}$alkenyl, optionally substituted with one or more substituents selected from $C_{1-6}$alkyl and halo. In some embodiments, $R^x$ is unsubstituted $C_{2-6}$alkenyl. In some embodiments, $R^x$ is $C_{2-6}$alkenyl substituted with one or more $C_{1-6}$alkyl. In some embodiments, $R^x$ is $C_{2-6}$alkenyl substituted with one or more halo. In some embodiments, $R^x$ is $C_{1-6}$alkyl, optionally substituted with one or more halo. In some embodiments, $R^x$ is unsubstituted $C_{1-6}$alkyl. In some embodiments, $R^x$ is $C_{1-6}$alkyl substituted with one or more halo.

In some embodiments, provided herein is a compound of formula (A) or (A'), or a stereoisomer, tautomer, or pharmaceutically acceptable salt thereof, wherein Z is —C(O)$R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo. In some embodiments, $R^x$ is $C_{2-6}$alkenyl, optionally substituted with one or more substituents selected from $C_{1-6}$alkyl and halo. In some embodiments, $R^x$ is unsubstituted $C_{2-6}$ alkenyl. In some embodiments, $R^x$ is $C_{2-6}$alkenyl substituted with one or more $C_{1-6}$alkyl. In some embodiments, $R^x$ is $C_{2-6}$alkenyl substituted with one or more halo. In some embodiments, $R^x$ is $C_{1-6}$alkyl, optionally substituted with one or more halo. In some embodiments, $R^x$ is unsubstituted $C_{1-6}$alkyl. In some embodiments, $R^x$ is $C_{1-6}$alkyl substituted with one or more halo.

In some embodiments, provided herein is a compound of formula (A) or (A'), or a stereoisomer or tautomer thereof, or a pharmaceutically acceptable salt thereof, wherein $X^1$ is N or $CR^s$, wherein $R^s$ is selected from H, —CN and $C_{1-15}$alkyl optionally substituted with one or more $R^{t1}$, wherein $R^{t1}$ is, at each occurrence, —OH; $X^2$ and $X^3$ are each CH, and $X^4$ is N or CH; B is phenyl optionally substituted with one or more $R^t$, wherein $R^t$ is independently at each occurrence selected from $C_{1-6}$alkoxy optionally substituted with one or more halo, and $S(R^y)_5$, wherein each $R^y$ is halo; L is methylene; and Z is —C(O)$R^x$, wherein $R^x$ is $C_{2-6}$ alkenyl, or wherein $R^x$ is $C_{1-6}$alkyl substituted with halo.

In some embodiments, $X^1$ is N and $X^2$, $X^3$ and $X^4$ are each CH. In embodiments, $X^1$ is $CR^s$ and $X^2$, $X^3$ and $X^4$ are each CH. In some embodiments, $X^1$ is $CR^s$, wherein $R^s$ is H; $X^2$ and $X^3$ are each CH and $X^4$ is N. In some embodiments, $X^1$ is $CR^s$ and $R^s$ is methyl substituted with one $R^{t1}$, wherein $R^{t1}$ is —OH. In some embodiments, $X^1$ is $CR^s$ and $R^s$ is ethyl substituted with two $R^{t1}$, wherein $R^{t1}$ is, at each occurrence, —OH. In some embodiments, B is phenyl substituted with one $R^t$, wherein $R^t$ is $S(R^y)_5$, wherein each $R^y$ is fluoro. In some embodiments, B is phenyl substituted with one $R^t$, wherein $R^t$ is trifluoromethoxy. In some embodiments, Z is —C(O)$R^x$, wherein $R^x$ is ethenyl. In some embodiments, Z is —C(O)$R^x$, wherein $R^x$ is ethyl substituted with chloro.

In some embodiments, provided herein is a compound of formula (B), or a stereoisomer, tautomer, or pharmaceutically acceptable salt thereof, wherein $X^1$ is N. In some embodiments, $X^1$ is C—$CR^s$. In some embodiments, $X^1$ is C—$CR^s$ and C—$CR^s$, and $R^s$ is independently H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, —$NR^dCOR^e$, —$CONR^dR^e$, —$SO_2R^d$, —$SO_2NR^dR^e$, —$NR^dSO_2R^e$, or —$NR^dR^e$. In other embodiments, $R^s$ is H. In other embodiments, each $R^s$ is halo. In other embodiments, $R^s$ is $C_{1-15}$alkyl. In other embodiments, $R^s$ is $C_{6-20}$aryl. In other embodiments, $R^s$ is 5 to 15 membered heteroaryl. In other embodiments, $R^s$ is $C_{3-20}$cycloalkyl. In other embodiments, $R^s$ is 3 to 15 membered heterocyclyl. In other embodiments, $R^s$ is —OH. In other embodiments, $R^s$ is —CN. In other embodiments, $R^s$ is $C_{1-15}$alkoxy. In other embodiments, $R^s$ is —$NR^dCOR^e$. In other embodiments, $R^s$ is —$CONR^dR^e$. In other embodiments, $R^s$ is —$SO_2R^d$. In other embodiments, $R^s$ is —$SO_2NR^dR^e$. In other embodiments, $R^s$ is —$NR^dSO_2R^e$. In other embodiments, $R^s$ is —$NR^dR^e$.

In some embodiments, provided herein is a compound of formula (B), or a stereoisomer, tautomer, or pharmaceutically acceptable salt thereof, wherein $X^1$ is C—$CR^s$, and wherein $R^s$ is $C_{1-15}$alkyl or $C_{1-15}$alkoxy, the $C_{1-15}$alkyl and $C_{1-15}$alkoxy of $R^s$ are each independently optionally substituted with one or more $R^{t1}$, wherein $R^{t1}$ is independently, at each occurrence, halo, oxo, —OH, —CN, or —$NR^dR^e$. In some embodiments, $R^s$ is $C_{1-15}$alkyl substituted with one or more $R^{t1}$, wherein $R^{t1}$ is halo. In some embodiments, $R^s$ is $C_{1-15}$alkyl substituted with one or more $R^{t1}$, wherein $R^{t1}$ is oxo. In some embodiments, $R^s$ is $C_{1-15}$alkyl substituted with one or more $R^{t1}$, wherein $R^{t1}$ is —OH. In some embodiments, $R^s$ is $C_{1-15}$alkyl substituted with one or more $R^{t1}$, wherein $R^{t1}$ is —CN. In some embodiments, $R^s$ is $C_{1-15}$alkyl substituted with one or more $R^{t1}$, wherein $R^{t1}$ is —$NR^dR^e$. In some embodiments, $R^s$ is $C_{1-15}$alkoxy substituted with one or more $R^{t1}$, wherein $R^{t1}$ is halo. In some embodiments, $R^s$ is $C_{1-15}$alkoxy substituted with one or more $R^{t1}$, wherein $R^{t1}$ is oxo. In some embodiments, $R^s$ is $C_{1-15}$alkoxy substituted with one or more $R^{t1}$, wherein $R^{t1}$ is —OH. In some embodiments, $R^s$ is $C_{1-15}$alkoxy substituted with one or more $R^{t1}$, wherein $R^{t1}$ is —CN. In some embodiments, $R^s$ is $C_{1-15}$alkoxy substituted with one or more $R^{t1}$, wherein $R^{t1}$ is —$NR^dR^e$.

In some embodiments, provided herein is a compound of formula (B), or a stereoisomer, tautomer, or pharmaceutically acceptable salt thereof, wherein $X^1$ is C—$CR^s$, and wherein $R^s$ is $C_{6-20}$aryl, 5 to 15 membered heteroaryl, $C_{3-20}$cycloalkyl, or 3 to 15 membered heterocyclyl, the $C_{6-20}$aryl, 5 to 15 membered heteroaryl, $C_{3-20}$cycloalkyl, or 3 to 15 membered heterocyclyl of $R^s$ are each independently optionally substituted with one or more $R^{t2}$, wherein $R^{t2}$ is independently, at each occurrence, halo, oxo, —OH, —CN, or —$NR^dR^e$. In some embodiments, $R^s$ is $C_{6-20}$aryl substituted with one or more $R^{t2}$, wherein $R^{t2}$ is halo. In some embodiments, $R^s$ is $C_{6-20}$aryl substituted with one or more $R^{t2}$, wherein $R^{t2}$ is oxo. In some embodiments, $R^s$ is $C_{6-20}$aryl substituted with one or more $R^{t2}$, wherein $R^{t2}$ is —OH. In some embodiments, $R^s$ is $C_{6-20}$aryl substituted with one or more $R^{t2}$, wherein $R^{t2}$ is —CN. In some embodiments, $R^s$ is $C_{6-20}$aryl substituted with one or more $R^{t2}$ wherein $R^{t2}$ is —$NR^dR^e$. In some embodiments, $R^s$ is 5 to 15 membered heteroaryl substituted with one or more $R^{t2}$, wherein $R^{t2}$ is halo. In some embodiments, $R^s$ is 5 to 15 membered heteroaryl substituted with one or more $R^{t2}$, wherein $R^{t2}$ is oxo. In some embodiments, $R^s$ is 5 to 15 membered heteroaryl and $R^{t2}$ is —OH. In some embodiments, $R^s$ is 5 to 15 membered heteroaryl substituted with one or more $R^{t2}$, wherein $R^{t2}$ is —CN. In some embodiments, $R^s$ is 5 to 15 membered heteroaryl substituted with one or more $R^{t2}$, wherein $R^{t2}$ is —$NR^dR^e$. In some embodiments, $R^s$ is $C_{3-20}$cycloalkyl substituted with one or more $R^{t2}$, wherein $R^{t2}$ is halo. In some embodiments, $R^s$ is $C_{3-20}$cycloalkyl substituted with one or more $R^{t2}$, wherein $R^{t2}$ is oxo. In some embodiments, $R^s$ is $C_{3-20}$cycloalkyl substituted with one or more $R^{t2}$, wherein $R^{t2}$ is —OH. In some embodiments, $R^s$ is $C_{3-20}$cycloalkyl substituted with one or more $R^{t2}$, wherein $R^{t2}$ is —CN. In some embodiments, $R^s$ is $C_{3-20}$cycloalkyl substituted with one or more $R^{t2}$, wherein $R^{t2}$ is —$NR^dR^e$. In some embodiments, $R^s$ is 3 to 15 membered heterocyclyl substituted with one or more $R^{t2}$, wherein $R^{t2}$ is halo. In some embodiments, $R^s$ is 3 to 15 membered heterocyclyl substituted with one or more $R^{t2}$, wherein $R^{t2}$ is oxo. In some embodiments, $R^s$ is 3 to 15 membered heterocyclyl substituted with one or more $R^{t2}$, wherein $R^{t2}$ is —OH. In some embodiments, $R^s$ is 3 to 15 membered heterocyclyl substituted with one or more $R^{t2}$, wherein $R^{t2}$ is —CN. In some embodiments, $R^s$ is 3 to 15 membered heterocyclyl substituted with one or more $R^{t2}$, wherein $R^{t2}$ is —$NR^dR^e$.

In some embodiments, provided herein is a compound of formula (B), or a stereoisomer, tautomer, or pharmaceutically acceptable salt thereof, wherein $X^1$ is C—$CR^s$, and wherein each $R^s$ is independently further substituted by $R^{t2}$, wherein $R^{t2}$ is —$NR^dR^e$, $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $R^d$ is H. In some embodiments, $R^d$ is $C_{1-6}$alkyl. In some embodiments, $R^e$ is H. In some embodiments, $R^e$ is $C_{1-6}$alkyl. In some embodiments, wherein $R^d$ is $C_{1-6}$alkyl, the $C_{1-6}$alkyl of $R^d$ is optionally substituted with one or more halo, oxo, —OH, or —CN. In some embodiments, the $C_{1-6}$alkyl of $R^d$ is substituted with one or more halo. In some embodiments, the $C_{1-6}$alkyl of $R^d$ is substituted with one or more oxo. In some embodiments, the $C_{1-6}$alkyl of $R^d$ is substituted with one or more —OH. In some embodiments, the $C_{1-6}$alkyl of $R^d$ is substituted with one or more —CN. In some embodiments, wherein $R^e$ is $C_{1-6}$alkyl, the $C_{1-6}$alkyl of $R^e$ is optionally substituted with one or more halo, oxo, —OH, or —CN. In some embodiments, the $C_{1-6}$alkyl of $R^e$ is substituted with one or more halo. In some embodiments, the $C_{1-6}$alkyl of $R^e$ is substituted with one or more oxo. In some embodiments, the $C_{1-6}$alkyl of $R^e$ is substituted with one or more —OH. In some embodiments, the $C_{1-6}$alkyl of $R^e$ is substituted with one or more —CN.

In some embodiments, provided herein is a compound of formula (B), or a stereoisomer, tautomer, or pharmaceutically acceptable salt thereof, wherein B is phenyl or 5 to 6 membered heteroaryl. In some embodiments, B is phenyl. In some embodiments, B is 5 to 6 membered heteroaryl. In some embodiments, the phenyl or 5 to 6 membered heteroaryl of B is each independently optionally substituted with one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, and $R^t$ is halo. In some embodiments, B is phenyl substituted by one or more $R^t$, and $R^t$ is $C_{1-15}$alkyl. In some embodiments, B is phenyl substituted by one or more $R^t$, and $R^t$ is $C_{1-6}$alkoxy. In some embodiments, B is phenyl substituted by one or more $R^t$, and $R^t$ is $S(R^y)_5$, wherein each $R^y$ is halo. In some embodiments, B is 5 to 6 membered heteroaryl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is 5 to 6 membered heteroaryl substituted by one or more $R^t$, and $R^t$ is halo. In some embodiments, B is 5 to 6 membered heteroaryl substituted by one or more $R^t$, and $R^t$ is $C_{1-15}$alkyl. In some embodiments, B is 5 to 6 membered heteroaryl substituted by one or more $R^t$, and $R^t$ is $C_{1-6}$alkoxy. In some embodiments, wherein B is phenyl or 5 to 6 membered heteroaryl substituted by one or more $R^t$, wherein $R^t$ is $C_{1-15}$alkyl, or $C_{1-6}$alkoxy, the $C_{1-15}$alkyl or $C_{1-6}$alkoxy of $R^t$ is optionally substituted with one or more halo. In some embodiments, the $C_{1-15}$alkyl of $R^t$ is substituted by one or more fluoro. In some embodiments, the $C_{1-15}$alkoxy of $R^t$ is substituted by one or more fluoro. In some embodiments, B is 5 to 6 membered heteroaryl substituted by one or more $R^t$, and $R^t$ is $S(R^y)_5$, wherein each $R^y$ is halo.

In some embodiments, provided herein is a compound of formula (B), or a stereoisomer, tautomer, or pharmaceutically acceptable salt thereof, wherein B is phenyl. In some embodiments, B is 5 to 6 membered heteroaryl. In other embodiments, B is unsubstituted phenyl. In other embodiments, B is substituted phenyl. In other embodiments, B is phenyl substituted by one or more $R^t$. In other embodiments, $R^t$ is $C_{1-6}$ alkoxy. In other embodiments, $R^t$ is $C_{1-6}$alkoxy substituted by one or more halo. In other embodiments, $R^t$ is $C_{1-6}$alkoxy substituted by one or more fluoro. In other embodiments, B is

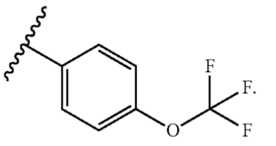 [SMILES: *c1ccc(OC(F)(F)F)cc1]

In some embodiments, provided herein is a compound of formula (B), or a stereoisomer, tautomer, or pharmaceutically acceptable salt thereof, wherein n and m are each independently 1 or 2. In some embodiments, n is 1. In some embodiments, n is 2. In some embodiments, m is 1. In some embodiments, m is 2. In some embodiments, n is 1 and m is 1. In some embodiments, n is 1 and m is 2. In some embodiments, n is 2 and m is 1. In some embodiments, n is 2 and m is 2.

In some embodiments, provided herein is a compound of formula (B), or a stereoisomer, tautomer, or pharmaceutically acceptable salt thereof, wherein $X^1$ is N or C—$CR^s$. In some embodiments, $X^1$ is N. In some embodiments, $X^1$ is C—$CR^s$.

In some embodiments, provided herein is a compound of formula (B), or a stereoisomer, tautomer, or pharmaceutically acceptable salt thereof, wherein $X^1$ is C—$R^s$, $X^2$ is C—H, $X^3$ is C—H, $X^4$ is N; and $R^s$ is unsubstituted $C_{1-15}$alkyl. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$, wherein $R^{t1}$ is —OH. In other embodiments, $X^1$ is C—$R^s$, $X^2$ is C—H, $X^3$ is C—H, $X^4$ is N; and $R^s$ is

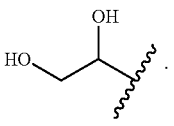 [SMILES: *C(O)CO]

In some embodiments, in conjunction with embodiments above or below, provided herein is a compound of formula (B), or a stereoisomer, tautomer, or pharmaceutically acceptable salt thereof, wherein $X^1$ is C—$R^s$, $X^2$ is C—H, $X^3$ is C—H, $X^4$ is N; and $R^s$ is

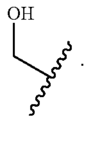

In some embodiments, provided herein is a compound of formula (B), or a stereoisomer, tautomer, or pharmaceutically acceptable salt thereof, wherein Z is —C(O)$R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo. In some embodiments, $R^x$ is $C_{2-6}$alkenyl, optionally substituted with one or more substituents selected from $C_{1-6}$alkyl and halo. In some embodiments, $R^x$ is unsubstituted $C_{2-6}$ alkenyl. In some embodiments, $R^x$ is $C_{2-6}$alkenyl substituted with one or more $C_{1-6}$alkyl. In some embodiments, $R^x$ is $C_{2-6}$alkenyl substituted with one or more halo. In some embodiments, $R^x$ is $C_{1-6}$alkyl, optionally substituted with one or more halo. In some embodiments, $R^x$ is unsubstituted $C_{1-6}$alkyl. In some embodiments, $R^x$ is $C_{1-6}$alkyl substituted with one or more halo.

In some aspects, a compound or a stereoisomer, tautomer, or pharmaceutically acceptable salt thereof of the following formula (I-A) or (I-B) is provided:

(I-A)

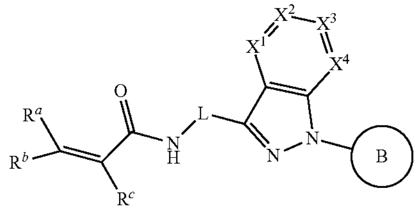

, (I-B)

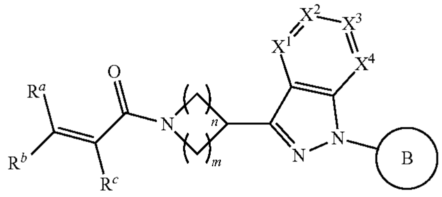

, or a stereoisomer or tautomer thereof, or a pharmaceutically acceptable salt thereof, wherein:

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

$R^a$, $R^b$, and $R^c$ are each independently H, halo, or $C_{1-5}$alkyl;

L is methylene, optionally substituted with one or more $C_{1-6}$alkyl; and n and m are each independently 1 or 2.

In some embodiments, provided herein is a compound of formula (I-A), or a stereoisomer, tautomer, or pharmaceutically acceptable salt thereof, wherein $X^1$ is N. In some embodiments, $X^1$ is C—$CR^s$. In some embodiments, $X^1$ is C—$CR^s$, and $R^s$ is independently H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, or —$NR^dR^e$. In other embodiments, $R^s$ is H. In other embodiments, each $R^s$ is halo. In other embodiments, $R^s$ is $C_{1-15}$alkyl. In other embodiments, $R^s$ is $C_{6-20}$aryl. In other embodiments, $R^s$ is 5 to 15 membered heteroaryl. In other embodiments, $R^s$ is $C_{3-20}$cycloalkyl. In other embodiments, $R^s$ is 3 to 15 membered heterocyclyl. In other embodiments, $R^s$ is —OH. In other embodiments, $R^s$ is —CN. In other embodiments, $R^s$ is $C_{1-15}$alkoxy. In other embodiments, $R^s$ is —$NR^dR^e$.

In some embodiments, provided herein is a compound of formula (I-A), or a stereoisomer, tautomer, or pharmaceutically acceptable salt thereof, wherein $X^1$ is C—$CR^s$, and wherein $R^s$ is $C_{1-15}$alkyl or $C_{1-15}$alkoxy, the $C_{1-15}$alkyl and $C_{1-15}$alkoxy of $R^s$ are each independently optionally substituted with one or more $R^{t1}$, wherein $R^{t1}$ is independently, at each occurrence, halo, oxo, —OH, —CN, or —$NR^dR^e$. In some embodiments, $R^s$ is $C_{1-15}$alkyl substituted with one or more $R^{t1}$, wherein $R^{t1}$ is halo. In some embodiments, $R^s$ is $C_{1-15}$alkyl substituted with one or more $R^{t1}$, wherein $R^{t1}$ is oxo. In some embodiments, $R^s$ is $C_{1-15}$alkyl substituted with one or more $R^{t1}$, wherein $R^{t1}$ is —OH. In some embodiments, $R^s$ is $C_{1-15}$alkyl substituted with one or more $R^{t1}$, wherein $R^{t1}$ is —CN. In some embodiments, $R^s$ is $C_{1-15}$alkyl substituted with one or more $R^{t1}$, wherein $R^{t1}$ is —$NR^dR^e$. In some embodiments, $R^s$ is $C_{1-15}$alkoxy substituted with one or more $R^{t1}$, wherein $R^{t1}$ is halo. In some embodiments, $R^s$ is $C_{1-15}$alkoxy substituted with one or more $R^{t1}$, wherein $R^{t1}$ is oxo. In some embodiments, $R^s$ is $C_{1-15}$alkoxy substituted with one or more $R^{t1}$, wherein $R^{t1}$ is —OH. In some embodiments, $R^s$ is $C_{1-15}$alkoxy substituted with one or more $R^{t1}$, wherein $R^{t1}$ is —CN. In some embodiments, $R^s$ is $C_{1-15}$alkoxy substituted with one or more $R^{t1}$, wherein $R^{t1}$ is —$NR^dR^e$.

In some embodiments, provided herein is a compound of formula (I-A), or a stereoisomer, tautomer, or pharmaceutically acceptable salt thereof, wherein $X^1$ is C—$CR^s$, and wherein $R^s$ is $C_{6-20}$aryl, 5 to 15 membered heteroaryl, $C_{3-20}$cycloalkyl, or 3 to 15 membered heterocyclyl, the $C_{6-20}$aryl, 5 to 15 membered heteroaryl, $C_{3-20}$cycloalkyl, or 3 to 15 membered heterocyclyl of $R^s$ are each independently optionally substituted with one or more $R^{t2}$, wherein $R^{t2}$ is independently, at each occurrence, halo, oxo, —OH, —CN, or —$NR^dR^e$. In some embodiments, $R^s$ is $C_{6-20}$aryl substituted with one or more $R^{t2}$, wherein $R^{t2}$ is halo. In some embodiments, $R^s$ is $C_{6-20}$aryl substituted with one or more $R^{t2}$, wherein $R^{t2}$ is oxo. In some embodiments, $R^s$ is $C_{6-20}$aryl substituted with one or more $R^{t2}$, wherein $R^{t2}$ is —OH. In some embodiments, $R^s$ is $C_{6-20}$aryl substituted with one or more $R^{t2}$, wherein $R^{t2}$ is —CN. In some embodiments, $R^s$ is $C_{6-20}$aryl substituted with one or more $R^{t2}$ wherein $R^{t2}$ is —$NR^dR^e$. In some embodiments, $R^s$ is 5 to 15 membered heteroaryl substituted with one or more $R^{t2}$, wherein $R^{t2}$ is halo. In some embodiments, $R^s$ is 5 to 15 membered heteroaryl substituted with one or more $R^{t2}$, wherein $R^{t2}$ is oxo. In some embodiments, $R^s$ is 5 to 15 membered heteroaryl and $R^{t2}$ is —OH. In some embodiments, $R^s$ is 5 to 15 membered heteroaryl substituted with one or more $R^{t2}$, wherein $R^{t2}$ is —CN. In some embodiments, $R^s$ is 5 to 15 membered heteroaryl substituted with one or more $R^{t2}$, wherein $R^{t2}$ is —$NR^dR^e$. In some embodiments, $R^s$ is $C_{3-20}$cycloalkyl substituted with one or more $R^{t2}$, wherein $R^{t2}$ is halo. In some embodiments, $R^s$ is $C_{3-20}$cycloalkyl substituted with one or more $R^{t2}$, wherein $R^{t2}$ is oxo. In some embodiments, $R^s$ is $C_{3-20}$cycloalkyl substituted with one or more $R^{t2}$, wherein $R^{t2}$ is —OH. In some embodiments, $R^s$ is $C_{3-20}$cycloalkyl substituted with one or more $R^{t2}$, wherein $R^{t2}$ is —CN. In some embodiments, $R^s$ is $C_{3-20}$cycloalkyl substituted with one or more $R^{t2}$, wherein $R^{t2}$ is —$NR^dR^e$. In some embodiments, $R^s$ is 3 to 15 membered heterocyclyl substituted with one or more $R^{t2}$, wherein $R^{t2}$ is halo. In some embodiments, $R^s$ is 3 to 15 membered heterocyclyl substituted with one or more $R^{t2}$, wherein $R^{t2}$ is oxo. In some embodiments, $R^s$ is 3 to 15 membered heterocyclyl substituted with one or more $R^{t2}$, wherein $R^{t2}$ is —OH. In some embodiments, $R^s$ is 3 to 15 membered heterocyclyl substituted with one or more $R^{t2}$, wherein $R^{t2}$ is —CN. In some embodiments, $R^s$ is 3 to 15 membered heterocyclyl substituted with one or more $R^{t2}$, wherein $R^{t2}$ is —$NR^dR^e$.

In some embodiments, provided herein is a compound of formula (I-A), or a stereoisomer, tautomer, or pharmaceutically acceptable salt thereof, wherein $X^1$ is C—$CR^s$, and wherein each $R^s$ is independently further substituted by $R^{t1}$, wherein $R^{t1}$ is —$NR^dR^e$, $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $R^d$ is H. In some embodiments, $R^d$ is $C_{1-6}$alkyl. In some embodiments, $R^e$ is H. In some embodiments, $R^e$ is $C_{1-6}$alkyl. In some embodiments, wherein $R^d$ is $C_{1-6}$alkyl, the $C_{1-6}$alkyl of $R^d$ is optionally substituted with one or more halo, oxo, —OH, or —CN. In some embodiments, the $C_{1-6}$alkyl of $R^d$ is substituted with one or more halo. In some embodiments, the $C_{1-6}$alkyl of $R^d$ is substituted with one or more oxo. In some embodiments, the $C_{1-6}$alkyl of $R^d$ is substituted with one or more —OH. In some embodiments, the $C_{1-6}$alkyl of $R^d$ is substituted with one or more —CN. In some embodiments, wherein $R^e$ is $C_{1-6}$alkyl, the $C_{1-6}$alkyl of $R^e$ is optionally substituted with one or more halo, oxo, —OH, or —CN. In some embodiments, the $C_{1-6}$alkyl of $R^e$ is substituted with one or more halo. In some embodiments, the $C_{1-6}$alkyl of $R^e$ is substituted with one or more oxo. In some embodiments, the $C_{1-6}$alkyl of $R^e$ is substituted with one or more —OH. In some embodiments, the $C_{1-6}$alkyl of $R^e$ is substituted with one or more —CN.

In some embodiments, provided herein is a compound of formula (I-A), or a stereoisomer, tautomer, or pharmaceutically acceptable salt thereof, wherein B is phenyl or 5 to 6 membered heteroaryl. In some embodiments, B is phenyl. In some embodiments, B is 5 to 6 membered heteroaryl. In some embodiments, the phenyl or 5 to 6 membered heteroaryl of B is each independently optionally substituted with one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, and $R^t$ is halo. In some embodiments, B is phenyl substituted by one or more $R^t$, and $R^t$ is $C_{1-15}$ alkyl. In some embodiments, B is phenyl substituted by one or more $R^t$, and $R^t$ is $C_{1-6}$alkoxy. In some embodiments, B is phenyl substituted by one or more $R^t$, and $R^t$ is $S(R^y)_5$, wherein each $R^y$ is halo. In some embodiments, B is 5 to 6 membered heteroaryl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is 5 to 6 membered heteroaryl substituted by one or more $R^t$, and $R^t$ is halo. In some embodiments, B is 5 to 6 membered heteroaryl substituted by one or more $R^t$, and $R^t$ is $C_{1-15}$alkyl. In some embodiments, B is 5 to 6 membered heteroaryl substituted by one or more $R^t$, and $R^t$ is $C_{1-6}$alkoxy. In some embodiments, wherein B is phenyl or 5 to 6 membered heteroaryl substituted by one or more $R^t$, wherein $R^t$ is $C_{1-15}$ alkyl, or $C_{1-6}$alkoxy, the $C_{1-15}$alkyl or $C_{1-6}$alkoxy of $R^t$ is optionally substituted with one or more halo. In some embodiments, the $C_{1-15}$alkyl of $R^t$ is substituted by one or more fluoro. In some embodiments, the $C_{1-15}$alkoxy of $R^t$ is substituted by one or more fluoro. In some embodiments, B is 5 to 6 membered heteroaryl substituted by one or more $R^t$, and $R^t$ is $S(R^y)_5$, wherein each $R^y$ is halo.

In some embodiments, provided herein is a compound of formula (I-A), or a stereoisomer, tautomer, or pharmaceutically acceptable salt thereof, wherein B is phenyl. In some embodiments, B is 5 to 6 membered heteroaryl. In other embodiments, B is unsubstituted phenyl. In other embodiments, B is substituted phenyl. In other embodiments, B is phenyl substituted by one or more $R^t$. In other embodiments, $R^t$ is $C_{1-6}$alkoxy. In other embodiments, $R^t$ is $C_{1-6}$alkoxy substituted by one or more halo. In other embodiments, $R^t$ is $C_{1-6}$alkoxy substituted by one or more fluoro. In other embodiments, B is

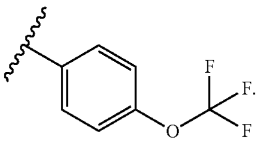 [SMILES: *c1ccc(OC(F)(F)F)cc1]

In some embodiments, provided herein is a compound of formula (I-A), or a stereoisomer, tautomer, or pharmaceutically acceptable salt thereof, wherein $R^a$, $R^b$, and $R^c$ are each independently H, halo, or $C_{1-5}$alkyl. In some embodiments, $R^a$ is H. In some embodiments, $R^a$ is halo. In some embodiments, $R^a$ is $C_{1-5}$alkyl. In some embodiments, $R^b$ is H. In some embodiments, $R^b$ is halo. In some embodiments, $R^b$ is $C_{1-5}$alkyl. In some embodiments, $R^c$ is H. In some embodiments, $R^c$ is halo. In some embodiments, $R^c$ is $C_{1-5}$alkyl. In some embodiments, provided herein is a compound of formula (I-A), or a stereoisomer, tautomer, or pharmaceutically acceptable salt thereof, wherein $R^a$, $R^b$, and $R^c$ are H.

In some embodiments, provided herein is a compound of formula (I-A), or a stereoisomer, tautomer, or pharmaceutically acceptable salt thereof, wherein $X^1$ is N or C—$CR^s$. In some embodiments, $X^1$ is N. In some embodiments, $X^1$ is C—$CR^s$.

In some embodiments, provided herein is a compound of formula (I-A), or a stereoisomer, tautomer, or pharmaceutically acceptable salt thereof, wherein $X^1$ is C—$R^s$, $X^2$ is C—H, $X^3$ is C—H, $X^4$ is N; and $R^s$ is unsubstituted $C_{1-15}$ alkyl. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$, wherein $R^{t1}$ is —OH. In other embodiments, $X^1$ is C—$R^s$, $X^2$ is C—H, $X^3$ is C—H, $X^4$ is N; and $R^s$ is

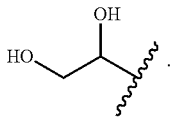 [SMILES: *C(O)CO]

In some embodiments, provided herein is a compound of formula (I-A), or a stereoisomer, tautomer, or pharmaceutically acceptable salt thereof, wherein L is methylene, optionally substituted with one or more $C_{1-6}$alkyl. In some embodiments, L is unsubstituted methylene. In some embodiments, L is methylene substituted with one or more $C_{1-6}$alkyl.

In some embodiments, provided herein is a compound of formula (I-B), or a stereoisomer, tautomer, or pharmaceutically acceptable salt thereof, wherein $X^1$ is N. In some embodiments, $X^1$ is C—$CR^s$. In some embodiments, $X^1$ is C—$CR^s$ and C—$CR^s$, and $R^s$ is independently H, halo, $C_{1-15}$alkyl, $C_{6-20}$aryl, 5 to 15 membered heteroaryl, $C_{3-20}$cycloalkyl, 3 to 15 membered heterocyclyl, —OH, —CN, $C_{1-15}$alkoxy, or —$NR^dR^e$. In other embodiments, $R^s$ is H. In other embodiments, each $R^s$ is halo. In other embodiments, $R^s$ is $C_{1-15}$alkyl. In other embodiments, $R^s$ is $C_{6-20}$aryl. In other embodiments, $R^s$ is 5 to 15 membered heteroaryl. In other embodiments, $R^s$ is $C_{3-20}$cycloalkyl. In other embodiments, $R^s$ is 3 to 15 membered heterocyclyl. In other embodiments, $R^s$ is —OH. In other embodiments, $R^s$ is —CN. In other embodiments, $R^s$ is $C_{1-15}$alkoxy. In other embodiments, $R^s$ is —$NR^dR^e$.

In some embodiments, provided herein is a compound of formula (I-B), or a stereoisomer, tautomer, or pharmaceutically acceptable salt thereof, wherein $X^1$ is C—$CR^s$, and wherein $R^s$ is $C_{1-15}$alkyl or $C_{1-15}$alkoxy, the $C_{1-15}$alkyl and $C_{1-15}$alkoxy of $R^s$ are each independently optionally substituted with one or more $R^{t1}$, wherein $R^{t1}$ is independently, at each occurrence, halo, oxo, —OH, —CN, or —$NR^dR^e$. In some embodiments, $R^s$ is $C_{1-15}$alkyl substituted with one or more $R^{t1}$, wherein $R^{t1}$ is halo. In some embodiments, $R^s$ is $C_{1-15}$alkyl substituted with one or more $R^{t1}$, wherein $R^{t1}$ is oxo. In some embodiments, $R^s$ is $C_{1-15}$alkyl substituted with one or more $R^{t1}$, wherein $R^{t1}$ is —OH. In some embodiments, $R^s$ is $C_{1-15}$alkyl substituted with one or more $R^{t1}$, wherein $R^{t1}$ is —CN. In some embodiments, $R^s$ is $C_{1-15}$alkyl substituted with one or more $R^{t1}$, wherein $R^{t1}$ is —$NR^dR^e$. In some embodiments, $R^s$ is $C_{1-15}$alkoxy substituted with one or more $R^{t1}$, wherein $R^{t1}$ is halo. In some embodiments, $R^s$ is $C_{1-15}$alkoxy substituted with one or more $R^{t1}$, wherein $R^{t1}$ is oxo. In some embodiments, $R^s$ is $C_{1-15}$alkoxy substituted with one or more $R^{t1}$, wherein $R^{t1}$ is —OH. In some embodiments, $R^s$ is $C_{1-15}$alkoxy substituted with one or more $R^{t1}$, wherein $R^{t1}$ is —CN. In some embodiments, $R^s$ is $C_{1-15}$alkoxy substituted with one or more $R^{t1}$, wherein $R^{t1}$ is —$NR^dR^e$.

In some embodiments, provided herein is a compound of formula (I-B), or a stereoisomer, tautomer, or pharmaceutically acceptable salt thereof, wherein $X^1$ is C—$CR^s$, and wherein $R^s$ is $C_{6-20}$aryl, 5 to 15 membered heteroaryl, $C_{3-20}$cycloalkyl, or 3 to 15 membered heterocyclyl, the $C_{6-20}$aryl, 5 to 15 membered heteroaryl, $C_{3-20}$cycloalkyl, or 3 to 15 membered heterocyclyl of $R^s$ are each independently optionally substituted with one or more $R^{t2}$, wherein $R^{t2}$ is independently, at each occurrence, halo, oxo, —OH, —CN, or —$NR^dR^e$. In some embodiments, $R^s$ is $C_{6-20}$aryl substituted with one or more $R^{t2}$, wherein $R^{t2}$ is halo. In some embodiments, $R^s$ is $C_{6-20}$aryl substituted with one or more $R^{t2}$, wherein $R^{t2}$ is oxo. In some embodiments, $R^s$ is $C_{6-20}$aryl substituted with one or more $R^{t2}$, wherein $R^{t2}$ is —OH. In some embodiments, $R^s$ is $C_{6-20}$aryl substituted with one or more $R^{t2}$, wherein $R^{t2}$ is —CN. In some embodiments, $R^s$ is $C_{6-20}$aryl substituted with one or more $R^{t2}$ wherein $R^{t2}$ is —$NR^dR^e$. In some embodiments, $R^s$ is 5 to 15 membered heteroaryl substituted with one or more $R^{t2}$, wherein $R^{t2}$ is halo. In some embodiments, $R^s$ is 5 to 15 membered heteroaryl substituted with one or more $R^{t2}$, wherein $R^{t2}$ is oxo. In some embodiments, $R^s$ is 5 to 15 membered heteroaryl and $R^{t2}$ is —OH. In some embodiments, $R^s$ is 5 to 15 membered heteroaryl substituted with one or more $R^{t2}$, wherein $R^{t2}$ is —CN. In some embodiments, $R^s$ is 5 to 15 membered heteroaryl substituted with one or more $R^{t2}$, wherein $R^{t2}$ is —$NR^dR^e$. In some embodiments, $R^s$ is $C_{3-20}$cycloalkyl substituted with one or more $R^{t2}$, wherein $R^{t2}$ is halo. In some embodiments, $R^s$ is $C_{3-20}$cycloalkyl substituted with one or more $R^{t2}$, wherein $R^{t2}$ is oxo. In some embodiments, $R^s$ is $C_{3-20}$cycloalkyl substituted with one or more $R^{t2}$, wherein $R^{t2}$ is —OH. In some embodiments, $R^s$ is $C_{3-20}$cycloalkyl substituted with one or more $R^{t2}$, wherein $R^{t2}$ is —CN. In some embodiments, $R^s$ is $C_{3-20}$cycloalkyl substituted with one or more $R^{t2}$, wherein $R^{t2}$ is —$NR^dR^e$. In some embodiments, $R^s$ is 3 to 15 membered heterocyclyl substituted with one or more $R^{t2}$, wherein $R^{t2}$ is halo. In some embodiments, $R^s$ is 3 to 15 membered heterocyclyl substituted with one or more $R^{t2}$, wherein $R^{t2}$ is oxo. In some embodiments, $R^s$ is 3 to 15 membered heterocyclyl substituted with one or more $R^{t2}$, wherein $R^{t2}$ is —OH. In some embodiments, $R^s$ is 3 to 15 membered heterocyclyl substituted with one or more $R^{t2}$, wherein $R^{t2}$ is —CN. In some embodiments, $R^s$ is 3 to 15 membered heterocyclyl substituted with one or more $R^{t2}$, wherein $R^{t2}$ is —$NR^dR^e$.

In some embodiments, provided herein is a compound of formula (I-B), or a stereoisomer, tautomer, or pharmaceutically acceptable salt thereof, wherein $X^1$ is C—$CR^s$, and wherein each $R^s$ is independently further substituted by $R^{t1}$, wherein $R^{t1}$ is —$NR^dR^e$, $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $R^d$ is H. In some embodiments, $R^d$ is $C_{1-6}$alkyl. In some embodiments, $R^e$ is H. In some embodiments, $R^e$ is $C_{1-6}$alkyl. In some embodiments, wherein $R^d$ is $C_{1-6}$alkyl, the $C_{1-6}$alkyl of $R^d$ is optionally substituted with one or more halo, oxo, —OH, or —CN. In some embodiments, the $C_{1-6}$alkyl of $R^d$ is substituted with one or more halo. In some embodiments, the $C_{1-6}$alkyl of $R^d$ is substituted with one or more oxo. In some embodiments, the $C_{1-6}$alkyl of $R^d$ is substituted with one or more —OH. In some embodiments, the $C_{1-6}$alkyl of $R^d$ is substituted with one or more —CN. In some embodiments, wherein $R^e$ is $C_{1-6}$alkyl, the $C_{1-6}$alkyl of $R^e$ is optionally substituted with one or more halo, oxo, —OH, or —CN. In some embodiments, the $C_{1-6}$alkyl of $R^e$ is substituted with one or more halo. In some embodiments, the $C_{1-6}$alkyl of $R^e$ is substituted with one or more oxo. In some embodiments, the $C_{1-6}$alkyl of $R^e$ is substituted with one or more —OH. In some embodiments, the $C_{1-6}$alkyl of $R^e$ is substituted with one or more —CN.

In some embodiments, provided herein is a compound of formula (I-B), or a stereoisomer, tautomer, or pharmaceutically acceptable salt thereof, wherein B is phenyl or 5 to 6 membered heteroaryl. In some embodiments, B is phenyl. In some embodiments, B is 5 to 6 membered heteroaryl. In some embodiments, the phenyl or 5 to 6 membered heteroaryl of B is each independently optionally substituted with one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, and $R^t$ is halo. In some embodiments, B is phenyl substituted by one or more $R^t$, and $R^t$ is $C_{1-15}$ alkyl. In some embodiments, B is phenyl substituted by one or more $R^t$, and $R^t$ is $C_{1-6}$alkoxy. In some embodiments, B is phenyl substituted by one or more $R^t$, and $R^t$ is $S(R^y)_5$, wherein each $R^y$ is halo. In some embodiments, B is 5 to 6 membered heteroaryl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is 5 to 6 membered heteroaryl substituted by one or more $R^t$, and $R^t$ is halo. In some embodiments, B is 5 to 6 membered heteroaryl substituted by one or more $R^t$, and $R^t$ is $C_{1-15}$alkyl. In some embodiments, B is 5 to 6 membered heteroaryl substituted by one or more $R^t$, and $R^t$ is $C_{1-6}$alkoxy. In some embodiments, wherein B is phenyl or 5 to 6 membered heteroaryl substituted by one or more $R^t$, wherein $R^t$ is $C_{1-15}$alkyl, or $C_{1-6}$alkoxy, the $C_{1-15}$alkyl or $C_{1-6}$alkoxy of $R^t$ is optionally substituted with one or more halo. In some embodiments, the $C_{1-15}$alkyl of $R^t$ is substituted by one or more fluoro. In some embodiments, the $C_{1-15}$alkoxy of $R^t$ is substituted by one or more fluoro. In some embodiments, B is 5 to 6 membered heteroaryl substituted by one or more $R^t$, and $R^t$ is $S(R^y)_5$, wherein each $R^y$ is halo.

In some embodiments, provided herein is a compound of formula (I-B), or a stereoisomer, tautomer, or pharmaceutically acceptable salt thereof, wherein B is phenyl. In some embodiments, B is 5 to 6 membered heteroaryl. In other embodiments, B is unsubstituted phenyl. In other embodiments, B is substituted phenyl. In other embodiments, B is phenyl substituted by one or more $R^t$. In other embodiments, $R^t$ is $C_{1-6}$ alkoxy. In other embodiments, $R^t$ is $C_{1-6}$alkoxy substituted by one or more halo. In other embodiments, $R^t$ is $C_{1-6}$alkoxy substituted by one or more fluoro. In other embodiments, B is

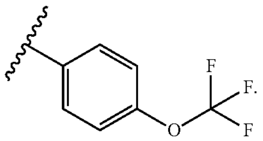 [SMILES: *c1ccc(OC(F)(F)F)cc1]

In some embodiments, provided herein is a compound of formula (I-B), or a stereoisomer, tautomer, or pharmaceutically acceptable salt thereof, wherein $R^a$, $R^b$, and $R^c$ are each independently H, halo, or $C_{1-5}$alkyl. In some embodiments, $R^a$ is H. In some embodiments, $R^a$ is halo. In some embodiments, $R^a$ is $C_{1-5}$alkyl. In some embodiments, $R^b$ is H. In some embodiments, $R^b$ is halo. In some embodiments, $R^b$ is $C_{1-5}$alkyl. In some embodiments, $R^c$ is H. In some embodiments, $R^c$ is halo. In some embodiments, $R^c$ is $C_{1-5}$alkyl. In some embodiments, provided herein is a compound of formula (I-A), or a stereoisomer, tautomer, or pharmaceutically acceptable salt thereof, wherein $R^a$, $R^b$, and $R^c$ are H.

In some embodiments, in conjunction with embodiments above or below, provided herein is a compound of formula (I-B), or a stereoisomer, tautomer, or pharmaceutically acceptable salt thereof, wherein $R^b$ and $R^c$ are each H, and $R^a$ is halo.

In some embodiments, provided herein is a compound of formula (I-B), or a stereoisomer, tautomer, or pharmaceutically acceptable salt thereof, wherein n and m are each independently 1 or 2. In some embodiments, n is 1. In some embodiments, n is 2. In some embodiments, m is 1. In some embodiments, m is 2. In some embodiments, n is 1 and m is 1. In some embodiments, n is 1 and m is 2. In some embodiments, n is 2 and m is 1. In some embodiments, n is 2 and m is 2.

In some embodiments, provided herein is a compound of formula (I-B), or a stereoisomer, tautomer, or pharmaceutically acceptable salt thereof, wherein $X^1$ is N or C—$CR^s$. In some embodiments, $X^1$ is N. In some embodiments, $X^1$ is C—$CR^s$.

In some embodiments, provided herein is a compound of formula (I-B), or a stereoisomer, tautomer, or pharmaceutically acceptable salt thereof, wherein $X^1$ is C—$R^s$, $X^2$ is C—H, $X^3$ is C—H, $X^4$ is N; and $R^s$ is unsubstituted $C_{1-15}$ alkyl. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$, wherein $R^{t1}$ is —OH. In other embodiments, $X^1$ is C—$R^s$, $X^2$ is C—H, $X^3$ is C—H, $X^4$ is N; and $R^s$ is

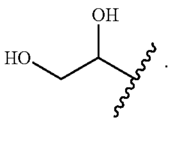 [SMILES: *C(O)CO]

In some embodiments, in conjunction with embodiments above or below, provided herein is a compound of formula (I-B), or a stereoisomer, tautomer, or pharmaceutically acceptable salt thereof, wherein $X^1$ is C—$R^s$, $X^2$ is C—H, $X^3$ is C—H, $X^4$ is N; and $R^s$ is

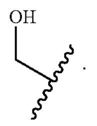

In some aspects, a compound or a stereoisomer, tautomer, or pharmaceutically acceptable salt thereof of the following formula (A') or (B') is provided:

(A')

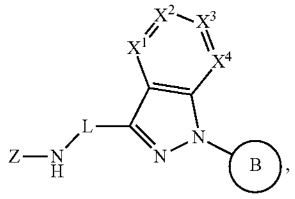

(B')

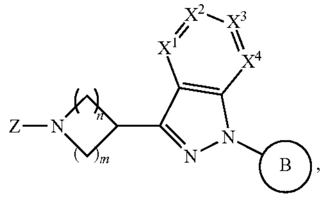

wherein:

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN, —$NR^dR^e$, and 3 to 15 membered heterocyclyl optionally substituted with one or more —OH; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, and $C_{1-6}$alkyl; wherein the $C_{1-6}$alkyl of $R^{t2}$ is optionally substituted with one or more —OH or —$NR^dR^e$; wherein $R^d$ and $R^e$ are each independently H, —$C(O)CH_3$, —$C(O)C_{1-6}$alkyl, or $C_{1-6}$alkyl;

$X^2$, $X^3$, and $X^4$ are each independently N, CH, or CD, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl;

L is methylene, optionally substituted with one or more $C_{1-6}$alkyl; and n and m are each 1; or n and m are each 2.

In some aspects, a compound or a stereoisomer, tautomer, or pharmaceutically acceptable salt thereof of the following formula (I-A) or (I-B) is provided:

(I-A)

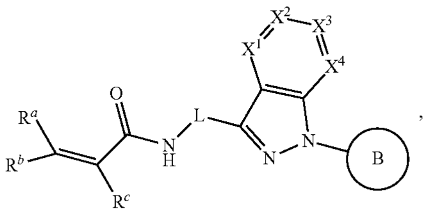

, (I-B)

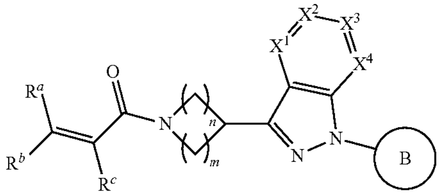

, or a stereoisomer or tautomer thereof, or a pharmaceutically acceptable salt thereof, wherein:

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN, —$NR^dR^e$, and 3 to 15 membered heterocyclyl optionally substituted with one or more —OH; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, and $C_{1-6}$alkyl; wherein the $C_{1-6}$alkyl of $R^{t2}$ is optionally substituted with one or more —OH or —$NR^dR^e$; wherein $R^d$ and $R^e$ are each independently H, —$C(O)CH_3$, —$C(O)C_{1-6}$alkyl, or $C_{1-6}$alkyl;

$X^2$, $X^3$, and $X^4$ are each independently N, CH, or CD, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

$R^a$, $R^b$, and $R^c$ are each independently H, halo, or $C_{1-5}$alkyl;

L is methylene, optionally substituted with one or more $C_{1-6}$alkyl; and n and m are each 1; or n and m are each 2.

In some embodiments, provided herein is a compound of formula (AB), (A), (A'), (I-A), (B), (B'), or (I-B), or any applicable subformulae thereof, or a stereoisomer, tautomer, or pharmaceutically acceptable salt thereof, wherein $X^1$ is N. In some embodiments, $X^1$ is $CR^s$. In some embodiments, $X^1$ is $CR^s$, and $R^s$ is independently $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$. In other embodiments, each $R^s$ is H. In other embodiments, each $R^s$ is D. In other embodiments, each $R^s$ is —CN. In other embodiments, each $R^s$ is halo. In other embodiments, each $R^s$ is $C_{1-15}$alkyl. In other embodiments, each $R^s$ is $C_{1-6}$alkynyl. In other embodiments, each $R^s$ is $C_{6-20}$aryl. In other embodiments, each $R^s$ is 5 to 15 membered heteroaryl. In other embodiments, each $R^s$ is $C_{3-20}$cycloalkyl. In other embodiments, each $R^s$ is 3 to 15 membered heterocyclyl. In other embodiments, each $R^s$ is —OH. In other embodiments, each $R^s$ is —$OR^f$. In other embodiments, each $R^s$ is $C_{1-15}$alkoxy. In other embodiments, each $R^s$ is —$NR^dCOR^e$. In other embodiments, each $R^s$ is —$CONR^dR^e$. In other embodiments, each $R^s$ is —$SO_2R^d$. In other embodiments, each $R^s$ is —$SO_2NR^dR^e$. In other embodiments, each $R^s$ is —$NR^dSO_2R^e$. In other embodiments, each $R^s$ is —$NR^dR^e$.

In some embodiments, provided herein is a compound of formula (AB), (A), (A'), (I-A), (B), (B'), or (I-B), or any applicable subformulae thereof, or a stereoisomer, tautomer, or pharmaceutically acceptable salt thereof, wherein $X^1$ is $CR^s$, and wherein $R^s$ is $C_{1-15}$alkyl or $C_{1-15}$alkoxy, $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN, —$NR^dR^e$, and 3 to 15 membered heterocyclyl optionally substituted with one or more —OH; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $R^s$ is $C_{1-15}$alkyl substituted with one or more $R^{t1}$, wherein $R^{t1}$ is halo. In some embodiments, $R^s$ is $C_{1-15}$alkyl substituted with one or more $R^{t1}$, wherein $R^{t1}$ is oxo. In some embodiments, $R^s$ is $C_{1-15}$alkyl substituted with one or more $R^{t1}$, wherein $R^{t1}$ is —OH. In some embodiments, $R^s$ is $C_{1-15}$alkyl substituted with one or more $R^{t1}$, wherein $R^{t1}$ is —CN. In some embodiments, $R^s$ is $C_{1-15}$alkyl substituted with one or more $R^{t1}$, wherein $R^{t1}$ is —$NR^dR^e$. In some embodiments, $R^s$ is $C_{1-15}$alkyl substituted with one or more $R^{t1}$, wherein $R^{t1}$ is 3 to 15 membered heterocyclyl optionally substituted with one or more —OH. In some embodiments, $R^s$ is $C_{1-15}$alkoxy substituted with one or more $R^{t1}$, wherein $R^{t1}$ is halo. In some embodiments, $R^s$ is $C_{1-15}$alkoxy substituted with one or more $R^{t1}$, wherein $R^{t1}$ is oxo. In some embodiments, $R^s$ is $C_{1-15}$alkoxy substituted with one or more $R^{t1}$, wherein $R^{t1}$ is —OH. In some embodiments, $R^s$ is $C_{1-15}$alkoxy substituted with one or more $R^{t1}$, wherein $R^{t1}$ is —CN. In some embodiments, $R^s$ is $C_{1-15}$alkoxy substituted with one or more $R^{t1}$, wherein $R^{t1}$ is —$NR^dR^e$. In some embodiments, $R^s$ is $C_{1-15}$alkoxy substituted with one or more $R^{t1}$, wherein $R^{t1}$ is 3 to 15 membered heterocyclyl optionally substituted with one or more —OH.

In some embodiments, provided herein is a compound of formula (AB), (A), (A'), (I-A), (B), (B'), or (I-B), or any applicable subformulae thereof, or a stereoisomer, tautomer, or pharmaceutically acceptable salt thereof, wherein $X^1$ is $CR^s$, and wherein $R^s$ is $C_{6-20}$aryl, 5 to 15 membered heteroaryl, $C_{3-20}$cycloalkyl, or 3 to 15 membered heterocyclyl, the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, and $C_{1-6}$alkyl; wherein the $C_{1-6}$alkyl of $R^e$ is optionally substituted with one or more —OH or —$NR^dR^e$; wherein $R^d$ and $R^e$ are each independently H, —$C(O)CH_3$, —$C(O)C_{1-6}$alkyl, or $C_{1-6}$alkyl In some embodiments, $R^s$ is $C_{6-20}$aryl substituted with one or more $R^{t2}$, wherein $R^{t2}$ is halo. In some embodiments, $R^s$ is $C_{6-20}$aryl substituted with one or more $R^{t2}$, wherein $R^{t2}$ is oxo. In some embodiments, $R^s$ is $C_{6-20}$aryl substituted with one or more $R^{t2}$, wherein $R^{t2}$ is —OH. In some embodiments, $R^s$ is $C_{6-20}$aryl substituted with one or more $R^{t2}$, wherein $R^{t2}$ is —CN. In some embodiments, $R^s$ is $C_{6-20}$aryl substituted with one or more $R^{t2}$, wherein $R^{t2}$ is $C(O)NH_2$. In some embodiments, $R^s$ is $C_{6-20}$aryl substituted with one or more $R^{t2}$, wherein $R^{t2}$ is —$C(O)NR^dR^e$. In some embodiments, $R^s$ is $C_{6-20}$aryl substituted with one or more $R^{t2}$, wherein $R^{t2}$ is —$NR^dR^e$. In some embodiments, $R^s$ is $C_{6-20}$aryl substituted with one or more $R^{t2}$, wherein $R^{t2}$ is $C_{1-6}$alkoxyl. In some embodiments, $R^s$ is $C_{6-20}$aryl substituted with one or more $R^{t2}$, wherein $R^{t2}$ is $C_{1-6}$alkyl.

In some embodiments, $R^s$ is 5 to 15 membered heteroaryl substituted with one or more $R^{t2}$, wherein $R^{t2}$ is halo. In some embodiments, $R^s$ is 5 to 15 membered heteroaryl substituted with one or more $R^{t2}$, wherein $R^{t2}$ is oxo. In some embodiments, $R^s$ is 5 to 15 membered heteroaryl substituted with one or more $R^{t2}$, wherein $R^{t2}$ is —OH. In some embodiments, $R^s$ is 5 to 15 membered heteroaryl substituted with one or more $R^{t2}$, wherein $R^{t2}$ is —CN. In some embodiments, $R^s$ is 5 to 15 membered heteroaryl substituted with one or more $R^{t2}$, wherein $R^{t2}$ is $C(O)NH_2$. In some embodiments, $R^s$ is 5 to 15 membered heteroaryl substituted with one or more $R^{t2}$, wherein $R^{t2}$ is —$C(O)NR^dR^e$. In some embodiments, $R^s$ is 5 to 15 membered heteroaryl substituted with one or more $R^{t2}$, wherein $R^{t2}$ is —$NR^dR^e$. In some embodiments, $R^s$ is 5 to 15 membered heteroaryl substituted with one or more $R^{t2}$, wherein $R^{t2}$ is $C_{1-6}$alkoxyl. In some embodiments, $R^s$ is 5 to 15 membered heteroaryl substituted with one or more $R^{t2}$, wherein $R^{t2}$ is $C_{1-6}$alkyl.

In some embodiments, $R^s$ is $C_{3-20}$cycloalkyl substituted with one or more $R^{t2}$, wherein $R^{t2}$ is halo. In some embodiments, $R^s$ is $C_{3-20}$cycloalkyl substituted with one or more $R^{t2}$, wherein $R^{t2}$ is oxo. In some embodiments, $R^s$ is $C_{3-20}$cycloalkyl substituted with one or more $R^{t2}$, wherein $R^{t2}$ is —OH. In some embodiments, $R^s$ is $C_{3-20}$cycloalkyl substituted with one or more $R^{t2}$, wherein $R^{t2}$ is —CN. In some embodiments, $R^s$ is $C_{3-20}$cycloalkyl substituted with one or more $R^{t2}$, wherein $R^{t2}$ is $C(O)NH_2$. In some embodiments, $R^s$ is $C_{3-20}$cycloalkyl substituted with one or more $R^{t2}$, wherein $R^{t2}$ is —$C(O)NR^dR^e$. In some embodiments, $R^s$ is $C_{3-20}$cycloalkyl substituted with one or more $R^{t2}$, wherein $R^{t2}$ is —$NR^dR^e$. In some embodiments, $R^s$ is $C_{3-20}$cycloalkyl substituted with one or more $R^e$, wherein $R^{t2}$ is $C_{1-6}$alkoxyl. In some embodiments, $R^s$ is $C_{3-20}$cycloalkyl substituted with one or more $R^{t2}$, wherein $R^{t2}$ is $C_{1-6}$alkyl.

In some embodiments, $R^s$ is 3 to 15 membered heterocyclyl substituted with one or more $R^{t2}$, wherein $R^{t2}$ is halo. In some embodiments, $R^s$ is 3 to 15 membered heterocyclyl substituted with one or more $R^{t2}$, wherein $R^{t2}$ is oxo. In some embodiments, $R^s$ is 3 to 15 membered heterocyclyl substituted with one or more $R^{t2}$, wherein $R^{t2}$ is —OH. In some embodiments, $R^s$ is 3 to 15 membered heterocyclyl substituted with one or more $R^{t2}$, wherein $R^{t2}$ is —CN. In some embodiments, $R^s$ is 3 to 15 membered heterocyclyl substituted with one or more $R^{t2}$, wherein $R^{t2}$ is $C(O)NH_2$. In some embodiments, $R^s$ is 3 to 15 membered heterocyclyl substituted with one or more $R^e$, wherein $R^{t2}$ is —$C(O)NR^dR^e$. In some embodiments, $R^s$ is 3 to 15 membered heterocyclyl substituted with one or more $R^{t2}$, wherein $R^{t2}$ is —$NR^dR^e$. In some embodiments, $R^s$ is 3 to 15 membered heterocyclyl substituted with one or more $R^{t2}$, wherein $R^{t2}$ is $C_{1-6}$ alkoxyl. In some embodiments, $R^s$ is 3 to 15 membered heterocyclyl substituted with one or more $R^{t2}$, wherein $R^{t2}$ is $C_{1-6}$alkyl.

In some embodiments, provided herein is a compound of formula (AB), (A), (A'), (I-A), (B), (B'), or (I-B), or any applicable subformulae thereof, or a stereoisomer, tautomer, or pharmaceutically acceptable salt thereof, wherein $X^1$ is $CR^s$, and wherein each $R^s$ is independently further substituted by $R^{t1}$, wherein $R^{t1}$ is —$NR^dR^e$, $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $R^d$ is H. In some embodiments, $R^d$ is $C_{1-6}$alkyl. In some embodiments, $R^e$ is H. In some embodiments, $R^e$ is $C_{1-6}$alkyl. In some embodiments, wherein $R^d$ is $C_{1-6}$alkyl, the $C_{1-6}$alkyl of $R^d$ is optionally substituted with one or more halo, oxo, —OH, or —CN. In some embodiments, the $C_{1-6}$alkyl of $R^d$ is substituted with one or more halo. In some embodiments, the $C_{1-6}$alkyl of $R^d$ is substituted with one or more oxo. In some embodiments, the $C_{1-6}$alkyl of $R^d$ is substituted with one or more —OH. In some embodiments, the $C_{1-6}$alkyl of $R^d$ is substituted with one or more —CN. In some embodiments, wherein $R^e$ is $C_{1-6}$alkyl, the $C_{1-6}$alkyl of $R^e$ is optionally substituted with one or more halo, oxo, —OH, or —CN. In some embodiments, the $C_{1-6}$alkyl of $R^e$ is substituted with one or more halo. In some embodiments, the $C_{1-6}$alkyl of $R^e$ is substituted with one or more oxo. In some embodiments, the $C_{1-6}$alkyl of $R^e$ is substituted with one or more —OH. In some embodiments, the $C_{1-6}$alkyl of $R^e$ is substituted with one or more —CN.

In some embodiments, provided herein is a compound of formula (AB), (A), (A'), (I-A), (B), (B'), or (I-B), or any applicable subformulae thereof, or a stereoisomer, tautomer, or pharmaceutically acceptable salt thereof, wherein B is phenyl or 5 to 6 membered heteroaryl. In some embodiments, B is phenyl. In some embodiments, B is 5 to 6 membered heteroaryl. In some embodiments, the phenyl or 5 to 6 membered heteroaryl of B is each independently optionally substituted with one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, and $R^t$ is halo. In some embodiments, B is phenyl substituted by one or more $R^t$, and $R^t$ is $C_{1-15}$alkyl. In some embodiments, B is phenyl substituted by one or more $R^t$, and $R^t$ is $C_{1-6}$alkoxy. In some embodiments, B is phenyl substituted by one or more $R^t$, and $R^t$ is $S(R^y)_5$, wherein each $R^y$ is halo. In some embodiments, B is 5 to 6 membered heteroaryl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is 5 to 6 membered heteroaryl substituted by one or more $R^t$, and $R^t$ is halo. In some embodiments, B is 5 to 6 membered heteroaryl substituted by one or more $R^t$, and $R^t$ is $C_{1-15}$alkyl. In some embodiments, B is 5 to 6 membered heteroaryl substituted by one or more $R^t$, and $R^t$ is $C_{1-6}$alkoxy. In some embodiments, wherein B is phenyl or 5 to 6 membered heteroaryl substituted by one or more $R^t$, wherein $R^t$ is $C_{1-15}$ alkyl, or $C_{1-6}$alkoxy, the $C_{1-15}$alkyl or $C_{1-6}$alkoxy of $R^t$ is optionally substituted with one or more halo. In some embodiments, the $C_{1-15}$alkyl of $R^t$ is substituted by one or more fluoro. In some embodiments, the $C_{1-15}$alkoxy of $R^t$ is substituted by one or more fluoro. In some embodiments, B is 5 to 6 membered heteroaryl substituted by one or more $R^t$, and $R^t$ is $S(R^y)_5$, wherein each $R^y$ is halo.

In some embodiments, provided herein is a compound of formula (AB), (A), (A'), (I-A), (B), (B'), or (I-B), or any applicable subformulae thereof, or a stereoisomer, tautomer, or pharmaceutically acceptable salt thereof, wherein B is phenyl. In some embodiments, B is 5 to 6 membered heteroaryl. In other embodiments, B is unsubstituted phenyl. In other embodiments, B is substituted phenyl. In other embodiments, B is phenyl substituted by one or more $R^t$. In other embodiments, $R^t$ is $C_{1-6}$ alkoxy. In other embodiments, $R^t$ is $C_{1-6}$alkoxy substituted by one or more halo. In other embodiments, $R^t$ is $C_{1-6}$alkoxy substituted by one or more fluoro. In other embodiments, B is

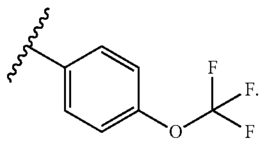 [SMILES: *c1ccc(OC(F)(F)F)cc1]

In some embodiments, provided herein is a compound of formula (AB), (A), (A'), (I-A), (B), (B'), or (I-B), or any applicable subformulae thereof, or a stereoisomer, tautomer, or pharmaceutically acceptable salt thereof, wherein $X^1$ is N or $CR^s$. In some embodiments, $X^1$ is N. In some embodiments, $X^1$ is $CR^s$.

In some embodiments, provided herein is a compound of formula (AB), (A), (A'), (I-A), (B), (B'), or (I-B), or any applicable subformulae thereof, or a stereoisomer, tautomer, or pharmaceutically acceptable salt thereof, wherein $X^1$ is C—$R^s$, $X^2$ is C—H, $X^3$ is C—H, $X^4$ is N; and $R^s$ is unsubstituted $C_{1-15}$ alkyl. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$, wherein $R^{t1}$ is —OH. In other embodiments, $X^1$ is C—$R^s$, $X^2$ is C—H, $X^3$ is C—H, $X^4$ is N; and $R^s$ is

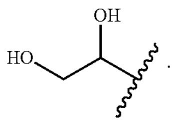

In other embodiments, $X^1$ is C—$R^s$, $X^2$ is C—H, $X^3$ is C—H, $X^4$ is N; and $R^s$ is

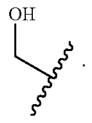

In other embodiments, $X^1$ is C—$R^s$, $X^2$ is C—H, $X^3$ is C—H, $X^4$ is N; and $R^s$ is

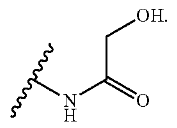 [SMILES: *NC(=O)CO]

In other embodiments, $X^1$ is C—$R^s$, $X^2$ is C—H, $X^3$ is C—H, $X^4$ is N; and $R^s$ is

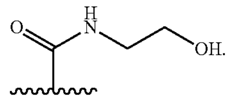 [SMILES: *C(=O)NCCO]

In other embodiments, $X^1$ is C—$R^s$, $X^2$ is C—H, $X^3$ is C—H, $X^4$ is N; and $R^s$ is

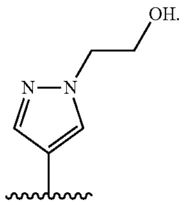 [SMILES: *c1cnn(CCO)c1]

In other embodiments, $X^1$ is C—$R^s$, $X^2$ is C—H, $X^3$ is C—H, $X^4$ is N; and $R^s$ is

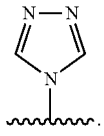

In other embodiments, $X^1$ is C—$R^s$, $X^2$ is C—H, $X^3$ is C—H, $X^4$ is N; and $R^s$ is

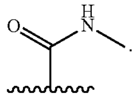

In other embodiments, $X^1$ is C—$R^s$, $X^2$ is C—H, $X^3$ is C—H, $X^4$ is N; and $R^s$ is

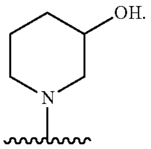 [SMILES: *N1CCCC(O)C1]

In other embodiments, $X^1$ is C—$R^s$, $X^2$ is C—H, $X^3$ is C—H, $X^4$ is N; and $R^s$ is

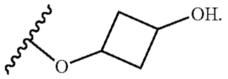 [SMILES: *OC1CC(O)C1]

In other embodiments, $X^1$ is C—$R^s$, $X^2$ is C—H, $X^3$ is C—H, $X^4$ is N; and $R^s$ is

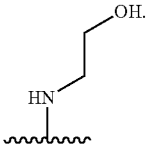 [SMILES: *NCCO]

In other embodiments, $X^1$ is C—$R^s$, $X^2$ is C—H, $X^3$ is C—H, $X^4$ is N; and $R^s$ is

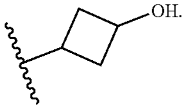 [SMILES: *C1CC(O)C1]

In other embodiments, $X^1$ is C—$R^s$, $X^2$ is C—H, $X^3$ is C—H, $X^4$ is N; and $R^s$ is

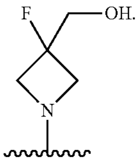 [SMILES: *N1CC(F)(CO)C1]

In other embodiments, $X^1$ is C—$R^s$, $X^2$ is C—H, $X^3$ is C—H, $X^4$ is N; and $R^s$ is

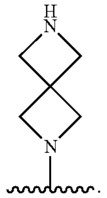 [SMILES: *N1CC2(CNC2)C1]

In other embodiments, $X^1$ is C—$R^s$, $X^2$ is C—H, $X^3$ is C—H, $X^4$ is N; and $R^s$ is

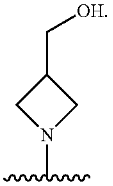 [SMILES: *N1CC(CO)C1]

In other embodiments, $X^1$ is C—$R^s$, $X^2$ is C—H, $X^3$ is C—H, $X^4$ is N; and $R^s$ is

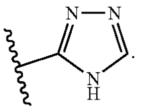 [SMILES: *c1nnc[nH]1]

In other embodiments, $X^1$ is C—$R^s$, $X^2$ is C—H, $X^3$ is C—H, $X^4$ is N; and $R^s$ is

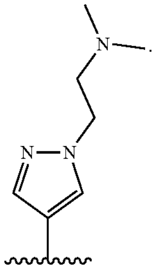 [SMILES: *c1cnn(CCN(C)C)c1]

In other embodiments, $X^1$ is C—$R^s$, $X^2$ is C—H, $X^3$ is C—H, $X^4$ is N; and $R^s$ is

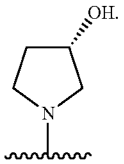

In other embodiments, $X^1$ is C—$R^s$, $X^2$ is C—H, $X^3$ is C—H, $X^4$ is N; and $R^s$ is

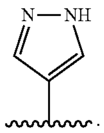

In other embodiments, $X^1$ is C—$R^s$, $X^2$ is C—H, $X^3$ is C—H, $X^4$ is N; and $R^s$ is

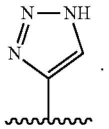

In other embodiments, $X^1$ is C—$R^s$, $X^2$ is C—H, $X^3$ is C—H, $X^4$ is N; and $R^s$ is

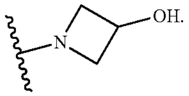 [SMILES: *N1CC(O)C1]

In other embodiments, $X^1$ is C—$R^s$, $X^2$ is C—H, $X^3$ is C—H, $X^4$ is N; and $R^s$ is

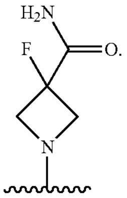 [SMILES: *N1CC(F)(C(N)=O)C1]

In other embodiments, $X^1$ is C—$R^s$, $X^2$ is C—H, $X^3$ is C—H, $X^4$ is N; and $R^s$ is

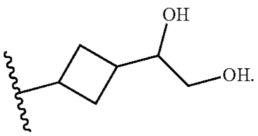 [SMILES: *C1CC(C(O)CO)C1]

In other embodiments, $X^1$ is C—$R^s$, $X^2$ is C—H, $X^3$ is C—H, $X^4$ is N; and $R^s$ is

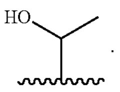

In other embodiments, $X^1$ is C—$R^s$, $X^2$ is C—H, $X^3$ is C—H, $X^4$ is N; and $R^s$ is

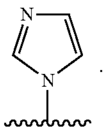 [SMILES: *n1ccnc1]

In other embodiments, $X^1$ is C—$R^s$, $X^2$ is C—H, $X^3$ is C—H, $X^4$ is N; and $R^s$ is

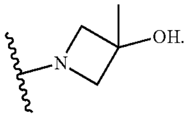 [SMILES: *N1CC(C)(O)C1]

In other embodiments, $X^1$ is C—$R^s$, $X^2$ is C—H, $X^3$ is C—H, $X^4$ is N; and $R^s$ is

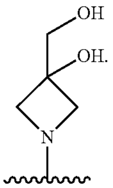 [SMILES: *N1CC(O)(CO)C1]

In other embodiments, $X^1$ is C—$R^s$, $X^2$ is C—H, $X^3$ is C—H, $X^4$ is N; and $R^s$ is

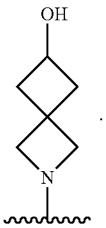 [SMILES: *N1CC2(CC(O)C2)C1]

In other embodiments, $X^1$ is C—$R^s$, $X^2$ is C—H, $X^3$ is C—H, $X^4$ is N; and $R^s$ is

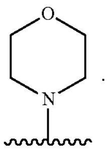 [SMILES: *N1CCOCC1]

In other embodiments, $X^1$ is C—$R^s$, $X^2$ is C—H, $X^3$ is C—H, $X^4$ is N; and $R^s$ is

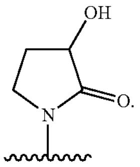 [SMILES: *N1CCC(O)C1=O]

In other embodiments, $X^1$ is C—$R^s$, $X^2$ is C—H, $X^3$ is C—H, $X^4$ is N; and $R^s$ is

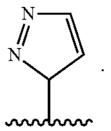

In other embodiments, $X^1$ is C—$R^s$, $X^2$ is C—H, $X^3$ is C—H, $X^4$ is N; and $R^s$ is

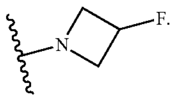 [SMILES: *N1CC(F)C1]

In other embodiments, $X^1$ is C—$R^s$, $X^2$ is C—H, $X^3$ is C—H, $X^4$ is N; and $R^s$ is

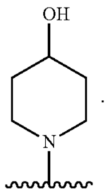 [SMILES: *N1CCC(O)CC1]

In other embodiments, $X^1$ is C—$R^s$, $X^2$ is C—H, $X^3$ is C—H, $X^4$ is N; and $R^s$ is

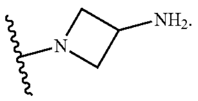 [SMILES: *N1CC(N)C1]

In other embodiments, $X^1$ is C—$R^s$, $X^2$ is C—H, $X^3$ is C—H, $X^4$ is N; and $R^s$ is methyl. In other embodiments, $X^1$ is C—$R^s$, $X^2$ is C—H, $X^3$ is C—H, $X^4$ is N; and $R^s$ is

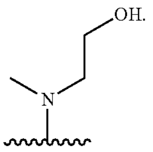 [SMILES: *N(C)CCO]

In other embodiments, $X^1$ is C—$R^s$, $X^2$ is C—H, $X^3$ is C—H, $X^4$ is N; and $R^s$ is

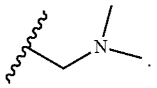 [SMILES: *CN(C)C]

In other embodiments, $X^1$ is C—$R^s$, $X^2$ is C—H, $X^3$ is C—H, $X^4$ is N; and $R^s$ is

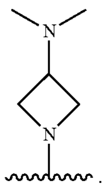

In other embodiments, $X^1$ is C—$R^s$, $X^2$ is C—H, $X^3$ is C—H, $X^4$ is N; and $R^s$ is

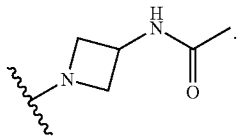 [SMILES: *N1CC(NC(C)=O)C1]

In other embodiments, $X^1$ is C—$R^s$, $X^2$ is C—H, $X^3$ is C—H, $X^4$ is N; and $R^s$ is

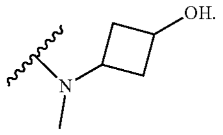 [SMILES: *N(C)C1CC(O)C1]

In other embodiments, $X^1$ is C—$R^s$, $X^2$ is C—H, $X^3$ is C—H, $X^4$ is N; and $R^s$ is

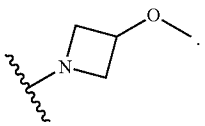 [SMILES: *N1CC(OC)C1]

In other embodiments, $X^1$ is C—$R^s$, $X^2$ is C—H, $X^3$ is C—H, $X^4$ is N; and $R^s$ is

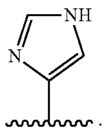

In other embodiments, $X^1$ is C—$R^s$, $X^2$ is C—H, $X^3$ is C—H, $X^4$ is N; and $R^s$ is

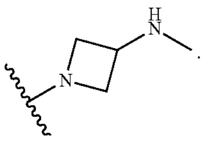 [SMILES: *N1CC(NC)C1]

In other embodiments, $X^1$ is C—$R^s$, $X^2$ is C—H, $X^3$ is C—H, $X^4$ is N; and $R^s$ is

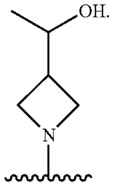 [SMILES: *N1CC(C(C)O)C1]

In other embodiments, $X^1$ is C—$R^s$, $X^2$ is C—H, $X^3$ is C—H, $X^4$ is N; and $R^s$ is

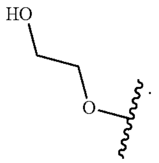 [SMILES: *OCCO]

In other embodiments, $X^1$ is C—$R^s$, $X^2$ is C—H, $X^3$ is C—H, $X^4$ is N; and $R^s$ is Cl. In other embodiments, $X^1$ is C—$R^s$, $X^2$ is C—H, $X^3$ is C—H, $X^4$ is N; and $R^s$ is

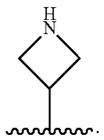 [SMILES: *C1CNC1]

In other embodiments, $X^1$ is C—$R^s$, $X^2$ is C—H, $X^3$ is C—H, $X^4$ is N; and $R^s$ is

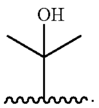 [SMILES: *C(C)(C)O]

In other embodiments, $X^1$ is C—$R^s$, $X^2$ is C—H, $X^3$ is C—H, $X^4$ is N; and $R^s$ is

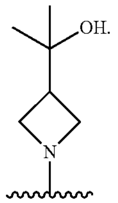 [SMILES: *N1CC(C(C)(C)O)C1]

In other embodiments, $X^1$ is C—$R^s$, $X^2$ is C—H, $X^3$ is C—H, $X^4$ is N; and $R^s$ is

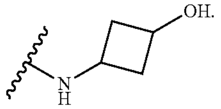 [SMILES: *NC1CC(O)C1]

In some embodiments, provided herein is a compound of formula (A) or (A'), or a stereoisomer, tautomer, or pharmaceutically acceptable salt thereof, wherein L is methylene, optionally substituted with one or more $C_{1-6}$alkyl. In some embodiments, L is unsubstituted methylene. In some embodiments, L is methylene substituted with one or more $C_{1-6}$alkyl.

In some embodiments, provided herein is a compound of formula (AB), (A), (A'), (B), or (B'), or any applicable subformulae thereof or a stereoisomer, tautomer, or pharmaceutically acceptable salt thereof, wherein Z is —C(O)$R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$ alkynyl optionally substituted with —OH; or $R^x$ is cyclobutenyl. In some embodiments, $R^x$ is $C_{2-6}$alkenyl, optionally substituted with one or more substituents selected from $C_{1-6}$alkyl, deuterium, —OH, $C_{1-6}$alkoxyl, and halo. In some embodiments, $R^x$ is unsubstituted $C_{2-6}$ alkenyl. In some embodiments, $R^x$ is $C_{2-6}$alkenyl substituted with one or more $C_{1-6}$alkyl. In some embodiments, $R^x$ is $C_{2-6}$alkenyl substituted with one or more deuterium. In some embodiments, $R^x$ is $C_{2-6}$alkenyl substituted with one or more —OH. In some embodiments, $R^x$ is $C_{2-6}$alkenyl substituted with one or more $C_{1-6}$alkoxyl. In some embodiments, $R^x$ is $C_{2-6}$alkenyl substituted with one or more halo. In some embodiments, $R^x$ is $C_{1-6}$alkyl, optionally substituted with one or more halo. In some embodiments, $R^x$ is unsubstituted $C_{1-6}$alkyl. In some embodiments, $R^x$ is $C_{1-6}$alkyl substituted with one or more halo. In some embodiments, $R^x$ is $C_{1-6}$alkynyl optionally substituted with —OH. In some embodiments, $R^x$ is unsubstituted $C_{1-6}$alkynyl. In some embodiments, $R^x$ is $C_{1-6}$alkynyl substituted with one or more —OH. In some embodiments, $R^x$ is or $R^x$ is cyclobutenyl.

In some embodiments, provided herein is a compound of formula (I-AB), or any applicable subformulae thereof, or a stereoisomer, tautomer, or pharmaceutically acceptable salt thereof, wherein $X^1$ is N. In some embodiments, $X^1$ is $CR^s$. In some embodiments, $X^1$ is $CR^s$ and $CR^s$, and $R^s$ is independently $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$. In other embodiments, each $R^s$ is H. In other embodiments, each $R^s$ is D. In other embodiments, each $R^s$ is —CN. In other embodiments, each $R^s$ is halo. In other embodiments, each $R^s$ is $C_{1-15}$alkyl. In other embodiments, each $R^s$ is $C_{1-6}$alkynyl. In other embodiments, each $R^s$ is $C_{6-20}$aryl. In other embodiments, each $R^s$ is 5 to 15 membered heteroaryl. In other embodiments, each $R^s$ is $C_{3-20}$cycloalkyl. In other embodiments, each $R^s$ is 3 to 15 membered heterocyclyl. In other embodiments, each $R^s$ is —OH. In other embodiments, each $R^s$ is —$OR^f$. In other embodiments, each $R^s$ is $C_{1-15}$alkoxy. In other embodiments, each $R^s$ is —$NR^dCOR^e$. In other embodiments, each $R^s$ is —$CONR^dR^e$. In other embodiments, each $R^s$ is —$SO_2R^d$. In other embodiments, each $R^s$ is —$SO_2NR^dR^e$. In other embodiments, each $R^s$ is —$NR^dSO_2R^e$. In other embodiments, each $R^s$ is —$NR^dR^e$.

In some embodiments, provided herein is a compound of formula (I-AB), or any applicable subformulae thereof, or a stereoisomer, tautomer, or pharmaceutically acceptable salt thereof, wherein $X^1$ is $CR^s$, and wherein $R^s$ is $C_{1-15}$alkyl or $C_{1-15}$alkoxy, $C_{1-15}$alkyl and $C_{1-15}$alkoxy of $R^s$ are each independently optionally substituted with one or $R^{t1}$, wherein $R^1$ is independently, at each occurrence, selected from halo, oxo, —OH, —$OR^{f1}$, —CN, —$NR^dR^e$, and 3 to 15 membered heterocyclyl optionally substituted with one or more —OH; wherein $R^{f1}$ is —$C(O)CH_2NR^dR^e$, —$C(O)C_{1-6}$alkyl, —$P(O)(OH)_2$; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $R^s$ is $C_{1-15}$alkyl substituted with one or more $R^{t1}$, wherein $R^{t1}$ is halo. In some embodiments, $R^s$ is $C_{1-15}$alkyl substituted with one or $R^{t1}$, wherein $R^1$ is oxo. In some embodiments, $R^s$ is $C_{1-15}$alkyl substituted with one or more $R^{t1}$, wherein $R^{t1}$ is —OH. In some embodiments, $R^s$ is $C_{1-15}$alkyl substituted with one or more $R^{t1}$, wherein $R^1$ is —$OR^{f1}$, wherein $R^{f1}$ is —$C(O)CH_2NR^dR^e$, —$C(O)C_{1-6}$alkyl, —$P(O)(OH)_2$. In some embodiments, $R^s$ is $C_{1-15}$alkyl substituted with one or more $R^{t1}$, wherein $R^{t1}$ is —CN. In some embodiments, $R^s$ is $C_{1-15}$alkyl substituted with one or more $R^{t1}$, wherein $R^{t1}$ is —$NR^dR^e$. In some embodiments, $R^s$ is $C_{1-15}$alkyl substituted with one or more $R^{t1}$, wherein $R^{t1}$ is 3 to 15 membered heterocyclyl optionally substituted with one or more —OH. In some embodiments, $R^s$ is $C_{1-15}$alkoxy substituted with one or more $R^{t1}$, wherein $R^1$ is halo. In some embodiments, $R^s$ is $C_{1-15}$alkoxy substituted with one or more $R^{t1}$, wherein $R^1$ is oxo. In some embodiments, $R^s$ is $C_{1-15}$alkoxy substituted with one or more $R^{t1}$, wherein $R^1$ is —OH. In some embodiments, $R^s$ is $C_{1-15}$alkoxy substituted with one or more $R^{t1}$, wherein $R^{t1}$ is $OR^{f1}$, wherein $R^{f1}$ is —$C(O)CH_2NR^dR^e$, —$C(O)C_{1-6}$alkyl, —$P(O)(OH)_2$. In some embodiments, $R^s$ is $C_{1-15}$alkoxy substituted with one or more $R^{t1}$, wherein $R^{t1}$ is —CN. In some embodiments, $R^s$ is $C_{1-15}$alkoxy substituted with one or more $R^{t1}$, wherein $R^1$ is —$NR^dR^e$. In some embodiments, $R^s$ is $C_{1-15}$alkoxy substituted with one or more $R^{t1}$, wherein $R^{t1}$ is 3 to 15 membered heterocyclyl optionally substituted with one or more —OH.

In some embodiments, provided herein is a compound of formula (I-AB), or any applicable subformulae thereof, or a stereoisomer, tautomer, or pharmaceutically acceptable salt thereof, wherein $X^1$ is $CR^s$, and wherein $R^s$ is $C_{6-20}$aryl, 5 to 15 membered heteroaryl, $C_{3-20}$cycloalkyl, or 3 to 15 membered heterocyclyl, the $C_{6-20}$aryl, 5 to 15 membered heteroaryl, $C_{3-20}$cycloalkyl, and 3 to 15 membered heterocyclyl of $R^s$ are each independently optionally substituted with one or more $R^e$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, 3 to 6 membered heterocyclyl, $C_{3-6}$cycloalkyl, and $C_{1-6}$alkyl; wherein the $C_{1-6}$alkyl of $R^{t2}$ is optionally substituted with one or more —OH, $C_{1-6}$alkoxyl, halo, oxo, —$S(O)_2CH_3$, or —$NR^dR^e$; wherein $R^d$ and $R^e$ are each independently H, —$C(O)CH_3$, —$C(O)C_{1-6}$alkyl, or $C_{1-6}$alkyl In some embodiments, $R^s$ is $C_{6-20}$aryl substituted with one or more $R^{t2}$, wherein $R^{t2}$ is halo. In some embodiments, $R^s$ is $C_{6-20}$aryl substituted with one or more $R^{t2}$, wherein $R^{t2}$ is oxo. In some embodiments, $R^s$ is $C_{6-20}$aryl substituted with one or more $R^{t2}$, wherein $R^{t2}$ is —OH. In some embodiments, $R^s$ is $C_{6-20}$aryl substituted with one or more $R^{t2}$, wherein $R^{t2}$ is —CN. In some embodiments, $R^s$ is $C_{6-20}$aryl substituted with one or more $R^{t2}$, wherein $R^{t2}$ is $C(O)NH_2$. In some embodiments, $R^s$ is $C_{6-20}$aryl substituted with one or more $R^{t2}$, wherein $R^{t2}$ is —$C(O)NR^dR^e$. In some embodiments, $R^s$ is $C_{6-20}$aryl substituted with one or more $R^{t2}$, wherein $R^{t2}$ is —$NR^dR^e$. In some embodiments, $R^s$ is $C_{6-20}$aryl substituted with one or more $R^{t2}$, wherein $R^{t2}$ is $C_{1-6}$alkoxyl. In some embodiments, $R^s$ is $C_{6-20}$aryl substituted with one or more $R^{t2}$, wherein $R^{t2}$ is 3 to 6 membered heterocyclyl. In some embodiments, $R^s$ is $C_{6-20}$aryl substituted with one or more $R^{t2}$, wherein $R^{t2}$ is $C_{3-6}$cycloalkyl. In some embodiments, $R^s$ is $C_{6-20}$aryl substituted with one or more $R^{t2}$, wherein $R^{t2}$ is $C_{1-6}$alkyl, wherein the $C_{1-6}$alkyl of $R^{t2}$ is optionally substituted with one or more —OH, $C_{1-6}$alkoxyl, halo, oxo, —$S(O)_2CH_3$, or —$NR^dR^e$.

In some embodiments, $R^s$ is 5 to 15 membered heteroaryl substituted with one or more $R^{t2}$, wherein $R^{t2}$ is halo. In some embodiments, $R^s$ is 5 to 15 membered heteroaryl substituted with one or more $R^{t2}$, wherein $R^{t2}$ is oxo. In some embodiments, $R^s$ is 5 to 15 membered heteroaryl substituted with one or more $R^{t2}$, wherein $R^{t2}$ is —OH. In some embodiments, $R^s$ is 5 to 15 membered heteroaryl substituted with one or more $R^{t2}$, wherein $R^{t2}$ is —CN. In some embodiments, $R^s$ is 5 to 15 membered heteroaryl substituted with one or more $R^{t2}$, wherein $R^{t2}$ is $C(O)NH_2$. In some embodiments, $R^s$ is 5 to 15 membered heteroaryl substituted with one or more $R^{t2}$, wherein $R^{t2}$ is —$C(O)NR^dR^e$. In some embodiments, $R^s$ is 5 to 15 membered heteroaryl substituted with one or more $R^{t2}$, wherein $R^{t2}$ is —$NR^dR^e$. In some embodiments, $R^s$ is 5 to 15 membered heteroaryl substituted with one or more $R^{t2}$, wherein $R^{t2}$ is $C_{1-6}$alkoxyl. In some embodiments, $R^s$ is 5 to 15 membered heteroaryl substituted with one or more $R^{t2}$, wherein $R^{t2}$ is $C_{1-6}$alkyl. In some embodiments, $R^s$ is $C_{3-20}$cycloalkyl substituted with one or more $R^{t2}$, wherein $R^{t2}$ is halo. In some embodiments, $R^s$ is $C_{3-20}$cycloalkyl substituted with one or more $R^{t2}$, wherein $R^{t2}$ is oxo. In some embodiments, $R^s$ is $C_{3-20}$cycloalkyl substituted with one or more $R^{t2}$, wherein $R^{t2}$ is —OH. In some embodiments, $R^s$ is $C_{3-20}$cycloalkyl substituted with one or more $R^{t2}$, wherein $R^{t2}$ is —CN. In some embodiments, $R^s$ is $C_{3-20}$cycloalkyl substituted with one or more $R^{t2}$, wherein $R^{t2}$ is $C(O)NH_2$. In some embodiments, $R^s$ is $C_{3-20}$cycloalkyl substituted with one or more $R^{t2}$, wherein $R^{t2}$ is —$C(O)NR^dR^e$. In some embodiments, $R^s$ is $C_{3-20}$cycloalkyl substituted with one or more $R^{t2}$, wherein $R^{t2}$ is —$NR^dR^e$. In some embodiments, $R^s$ is $C_{3-20}$cycloalkyl substituted with one or more $R^{t2}$, wherein $R^{t2}$ is $C_{1-6}$alkoxyl. In some embodiments, $R^s$ is $C_{3-20}$cycloalkyl substituted with one or more $R^{t2}$, wherein $R^{t2}$ is $C_{1-6}$ alkyl. In some embodiments, $R^s$ is 3 to 15 membered heterocyclyl substituted with one or more $R^{t2}$, wherein $R^{t2}$ is halo. In some embodiments, $R^s$ is 3 to 15 membered heterocyclyl substituted with one or more $R^{t2}$, wherein $R^{t2}$ is oxo. In some embodiments, $R^s$ is 3 to 15 membered heterocyclyl substituted with one or more $R^{t2}$, wherein $R^{t2}$ is —OH. In some embodiments, $R^s$ is 3 to 15 membered heterocyclyl substituted with one or more $R^{t2}$, wherein $R^{t2}$ is —CN. In some embodiments, $R^s$ is 3 to 15 membered heterocyclyl substituted with one or more $R^{t2}$, wherein $R^{t2}$ is $C(O)NH_2$. In some embodiments, $R^s$ is 3 to 15 membered heterocyclyl substituted with one or more $R^{t2}$ wherein $R^{t2}$ is —$C(O)NR^dR^e$. In some embodiments, $R^s$ is 3 to 15 membered heterocyclyl substituted with one or more $R^{t2}$, wherein $R^{t2}$ is —$NR^dR^e$. In some embodiments, $R^s$ is 3 to 15 membered heterocyclyl substituted with one or more $R^{t2}$, wherein $R^{t2}$ is $C_{1-6}$alkoxyl. In some embodiments, $R^s$ is 3 to 15 membered heterocyclyl substituted with one or more $R^{t2}$, wherein $R^{t2}$ is $C_{1-6}$alkyl.

In some embodiments, provided herein is a compound of formula (I-AB), or any applicable subformulae thereof, or a stereoisomer, tautomer, or pharmaceutically acceptable salt thereof, wherein $X^1$ is $CR^s$, and wherein each $R^s$ is independently further substituted by $R^{t1}$, wherein $R^{t1}$ is —$NR^dR^e$, $R^d$ and $R^e$ are each independently H or $C_{1-6}$alkyl, and the $C_{1-6}$alkyl of $R^d$ or $R^e$ is optionally substituted with one or more halo, oxo, —OH, or —CN. In some embodiments, $R^d$ is H. In some embodiments, $R^d$ is $C_{1-6}$ alkyl. In some embodiments, $R^e$ is H. In some embodiments, $R^e$ is $C_{1-6}$alkyl. In some embodiments, wherein $R^d$ is $C_{1-6}$alkyl, the $C_{1-6}$alkyl of $R^d$ is optionally substituted with one or more halo, oxo, —OH, or —CN. In some embodiments, the $C_{1-6}$alkyl of $R^d$ is substituted with one or more halo. In some embodiments, the $C_{1-6}$alkyl of $R^d$ is substituted with one or more oxo. In some embodiments, the $C_{1-6}$alkyl of $R^d$ is substituted with one or more —OH. In some embodiments, the $C_{1-6}$alkyl of $R^d$ is substituted with one or more —CN. In some embodiments, wherein $R^e$ is $C_{1-6}$alkyl, the $C_{1-6}$alkyl of $R^e$ is optionally substituted with one or more halo, oxo, —OH, or —CN. In some embodiments, the $C_{1-6}$alkyl of $R^e$ is substituted with one or more halo. In some embodiments, the $C_{1-6}$alkyl of $R^e$ is substituted with one or more oxo. In some embodiments, the $C_{1-6}$alkyl of $R^e$ is substituted with one or more —OH. In some embodiments, the $C_{1-6}$alkyl of $R^e$ is substituted with one or more —CN.

In some embodiments, provided herein is a compound of formula (I-AB), or any applicable subformulae thereof, or a stereoisomer, tautomer, or pharmaceutically acceptable salt thereof, wherein B is phenyl or 5 to 6 membered heteroaryl. In some embodiments, B is phenyl. In some embodiments, B is 5 to 6 membered heteroaryl. In some embodiments, the phenyl or 5 to 6 membered heteroaryl of B is each independently optionally substituted with one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is phenyl substituted by one or more $R^t$, and $R^t$ is halo. In some embodiments, B is phenyl substituted by one or more $R^t$, and $R^t$ is $C_{1-15}$alkyl. In some embodiments, B is phenyl substituted by one or more $R^t$, and $R^t$ is $C_{1-6}$alkoxy. In some embodiments, B is phenyl substituted by one or more $R^t$, and $R^t$ is $S(R^y)_5$, wherein each $R^y$ is halo. In some embodiments, B is 5 to 6 membered heteroaryl substituted by one or more $R^t$, wherein $R^t$ is independently at each occurrence halo, $C_{1-15}$alkyl, or $C_{1-6}$alkoxy, wherein the $C_{1-15}$alkyl or $C_{1-6}$alkoxy of $R^t$ is optionally substituted with one or more halo. In some embodiments, B is 5 to 6 membered heteroaryl substituted by one or more $R^t$, and $R^t$ is halo. In some embodiments, B is 5 to 6 membered heteroaryl substituted by one or more $R^t$, and $R^t$ is $C_{1-15}$alkyl. In some embodiments, B is 5 to 6 membered heteroaryl substituted by one or more $R^t$, and $R^t$ is $C_{1-6}$alkoxy. In some embodiments, wherein B is phenyl or 5 to 6 membered heteroaryl substituted by one or more $R^t$, wherein $R^t$ is $C_{1-15}$alkyl, or $C_{1-6}$alkoxy, the $C_{1-15}$alkyl or $C_{1-6}$alkoxy of $R^t$ is optionally substituted with one or more halo. In some embodiments, the $C_{1-15}$alkyl of $R^t$ is substituted by one or more fluoro. In some embodiments, the $C_{1-15}$alkoxy of $R^t$ is substituted by one or more fluoro. In some embodiments, B is 5 to 6 membered heteroaryl substituted by one or more $R^t$, and $R^t$ is $S(R^y)_5$, wherein each $R^y$ is halo.

In some embodiments, provided herein is a compound of formula (I-AB), or any applicable subformulae thereof, or a stereoisomer, tautomer, or pharmaceutically acceptable salt thereof, wherein B is phenyl. In some embodiments, B is 5 to 6 membered heteroaryl. In other embodiments, B is unsubstituted phenyl. In other embodiments, B is substituted phenyl. In other embodiments, B is phenyl substituted by one or more $R^t$. In other embodiments, $R^t$ is $C_{1-6}$alkoxy. In other embodiments, $R^t$ is $C_{1-6}$alkoxy substituted by one or more halo. In other embodiments, $R^t$ is $C_{1-6}$alkoxy substituted by one or more fluoro. In other embodiments, B is

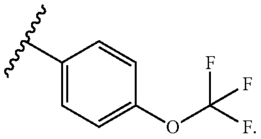 [SMILES: *c1ccc(OC(F)(F)F)cc1]

In some embodiments, provided herein is a compound of formula (I-AB), or any applicable subformulae thereof, or a stereoisomer, tautomer, or pharmaceutically acceptable salt thereof, wherein $X^1$ is N or $CR^s$, $X^2$, $X^3$, and $X^4$ are each independently N, CH, or CD, provided that: 1) only one of $X^1$, $X^2$, $X^3$, and $X^4$ is N; or 2) $X^1$ is N, $X^2$ is CH, $X^3$ is CH, and $X^4$ is N; or 3) $X^1$ is $CR^s$ and $X^2$, $X^3$, and $X^4$ are each independently CH or CD.

In some embodiments, $X^1$ is N, $X^2$, $X^3$, and $X^4$ are each independently CH or CD. In some embodiments, $X^1$ is N, $X^2$ and $X^3$ are each independently CH or CD, and $X^4$ is N. In some embodiments, $X^1$ is $CR^s$. In some embodiments, $X^1$ is $CR^s$ and $X^2$ is N. In some embodiments, $X^1$ is $CR^s$ and $X^3$ is N. In some embodiments, $X^1$ is $CR^s$ and $X^4$ is N.

In some embodiments, provided herein is a compound of formula (I-AB), or any applicable subformulae thereof, or a stereoisomer, tautomer, or pharmaceutically acceptable salt thereof, wherein $X^1$ is C—$R^s$, $X^2$ is C—H, $X^3$ is C—H, $X^4$ is N; and $R^s$ is unsubstituted $C_{1-15}$alkyl. In other embodiments, $X^1$ is C—$R^s$, $X^2$ is C—H, $X^3$ is C—H, $X^4$ is N; and $R^s$ is $C_{1-15}$alkyl substituted with one or more $R^u$. In other embodiments, $X^1$ is C—$R^s$, $X^2$ is C—H, $X^3$ is C—H, $X^4$ is N; and $R^s$ is $C_{1-15}$alkyl substituted with one or more $R^{t1}$, wherein $R^{t1}$ is —OH. In other embodiments, $X^1$ is C—$R^s$, $X^2$ is C—H, $X^3$ is C—H, $X^4$ is N; and $R^s$ is

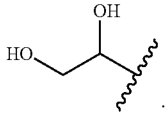
.

In other embodiments, $X^1$ is C—$R^s$, $X^2$ is C—H, $X^3$ is C—H, $X^4$ is N; and $R^s$ is
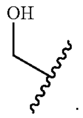.
In some embodiments, in conjunction with embodiments above or below, $R^s$ is selected from the group consisting of methyl, cyano, halo, chloro, —H, —CCH,
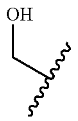, 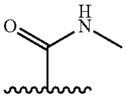, 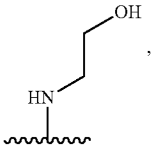,
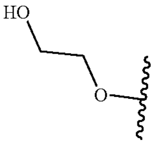, 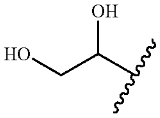, 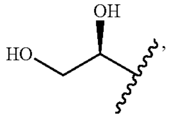,
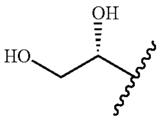, 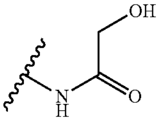,
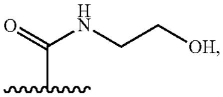 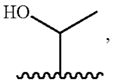, 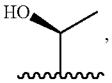,
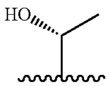, 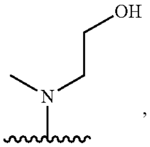, 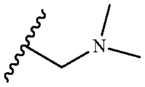,
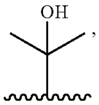, 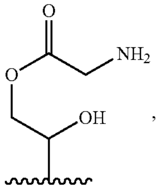, 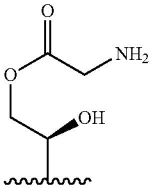,
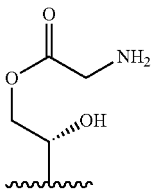, 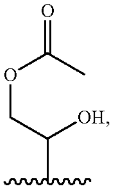 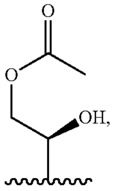
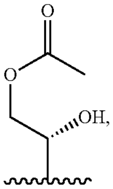 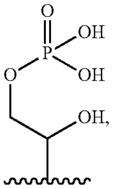 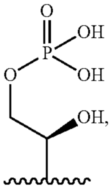 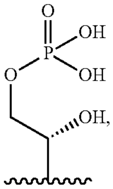
-continued
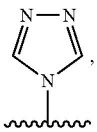, 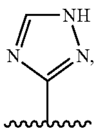 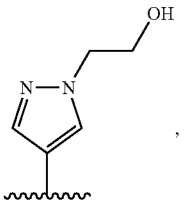,
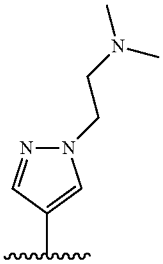, 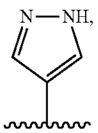 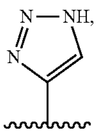
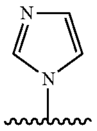, 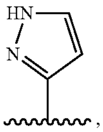, 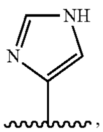, 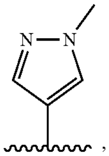,
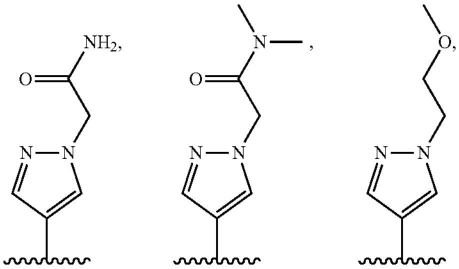
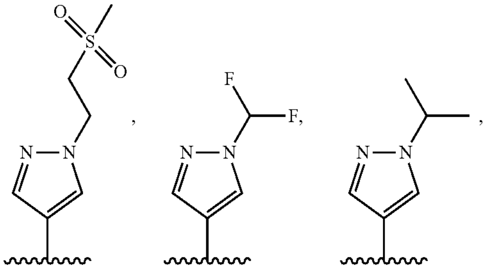
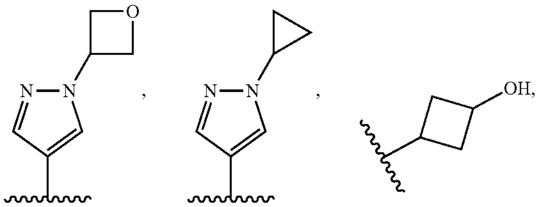
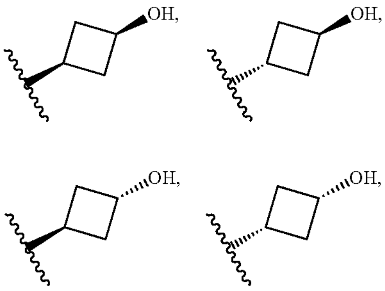

-continued
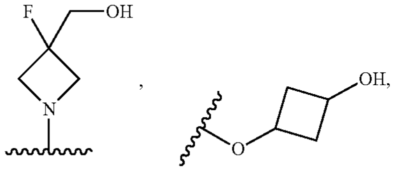
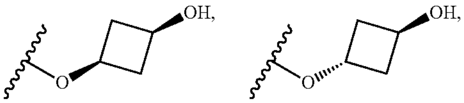
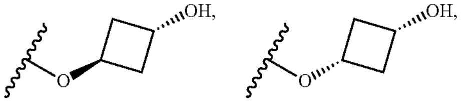
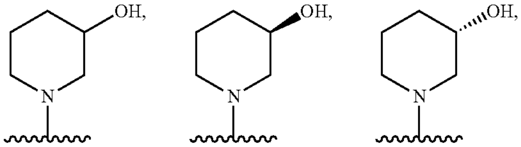
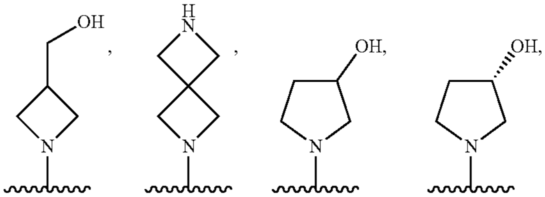
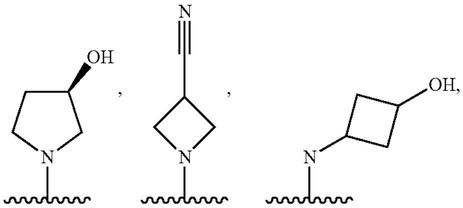
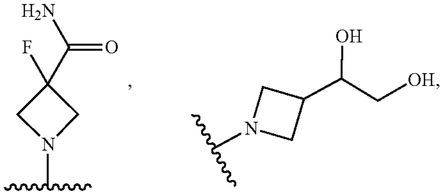
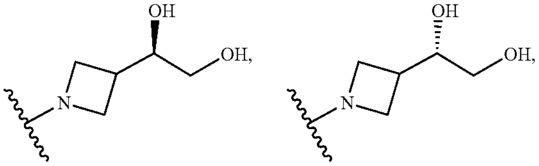
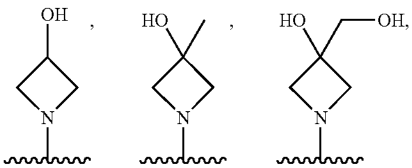
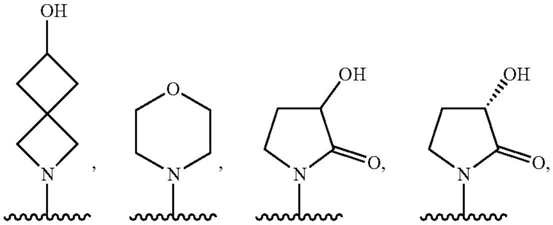
-continued
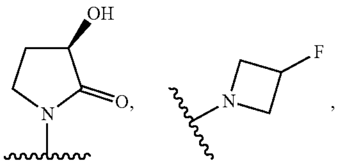
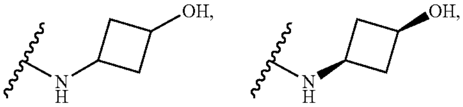
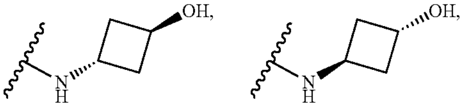
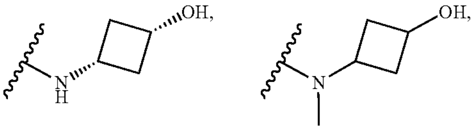
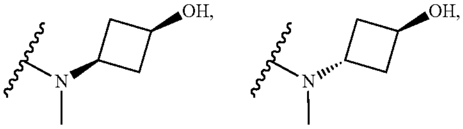
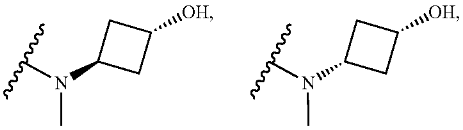
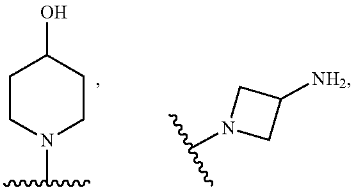
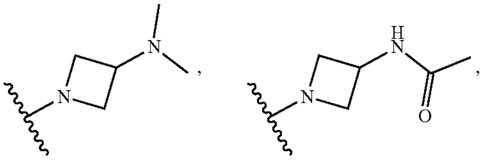
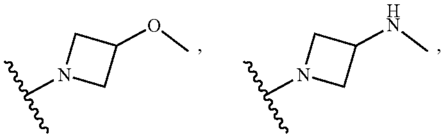
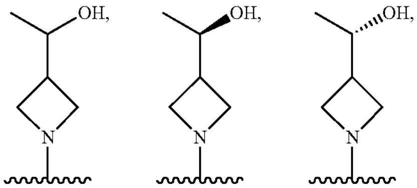
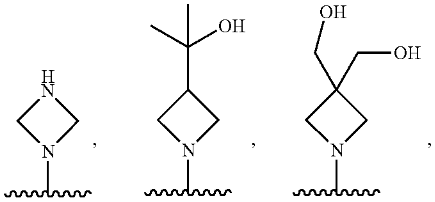

-continued

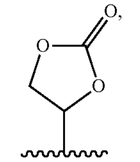 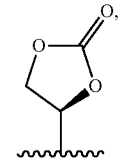 and 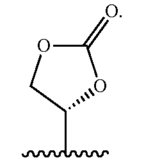

In some embodiments, provided herein is a compound of formula (I-AB) or any applicable subformulae thereof, or a stereoisomer, tautomer, or pharmaceutically acceptable salt thereof, wherein L is methylene, optionally substituted with one or more $C_{1-6}$alkyl. In some embodiments, L is unsubstituted methylene. In some embodiments, L is methylene substituted with one or more $C_{1-6}$alkyl.

In some embodiments, provided herein is a compound of formula (I-AB), or any applicable subformulae thereof, or a stereoisomer, tautomer, or pharmaceutically acceptable salt thereof, wherein Z is —C(O)$R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl, dihydrofuranyl, bicyclobutanyl, or cyclopentenyl. In some embodiments, $R^x$ is $C_{2-6}$alkenyl, optionally substituted with one or more substituents selected from $C_{1-6}$alkyl, deuterium, —OH, $C_{1-6}$alkoxyl, and halo. In some embodiments, $R^x$ is unsubstituted $C_{2-6}$ alkenyl. In some embodiments, $R^x$ is $C_{2-6}$alkenyl substituted with one or more $C_{1-6}$alkyl. In some embodiments, $R^x$ is $C_{2-6}$alkenyl substituted with one or more deuterium. In some embodiments, $R^x$ is $C_{2-6}$alkenyl substituted with one or more —OH. In some embodiments, $R^x$ is $C_{2-6}$alkenyl substituted with one or more $C_{1-6}$alkoxyl. In some embodiments, $R^x$ is $C_{2-6}$alkenyl substituted with one or more halo. In some embodiments, $R^x$ is $C_{1-6}$alkyl, optionally substituted with one or more halo. In some embodiments, $R^x$ is unsubstituted $C_{1-6}$alkyl. In some embodiments, $R^x$ is $C_{1-6}$alkyl substituted with one or more halo. In some embodiments, $R^x$ is $C_{1-6}$alkynyl optionally substituted with —OH. In some embodiments, $R^x$ is unsubstituted $C_{1-6}$alkynyl. In some embodiments, $R^x$ is $C_{1-6}$alkynyl substituted with one or more —OH. In some embodiments, $R^x$ is cyclobutenyl. In some embodiments, $R^x$ is dihydrofuranyl. In some embodiments, $R^x$ is bicyclobutanyl. In some embodiments, $R^x$ is cyclopentenyl. In some embodiments, Z is $S(O)_2R^{x1}$, wherein $R^{x1}$ is $C_{2-6}$alkenyl.

In some embodiments, a compound or a stereoisomer, tautomer, or pharmaceutically acceptable salt thereof of the following formula (AB') is provided:

(AB')

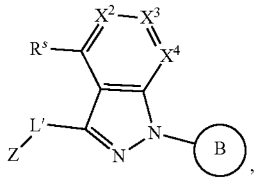

wherein $X^2$, $X^3$, $X^4$, $R^s$, B, L' and Z are as defined in formula (AB). It is understood that embodiments of $X^2$, $X^3$, $X^4$, $R^s$, B, L', and Z described for formula (AB) may, where applicable, apply in some embodiments to formula (AB'). In some embodiments, $R^s$ is not H or deuterium.

In some embodiments, $R^s$ is selected from the group consisting of methyl, cyano, halo, chloro, —H, —CCH,

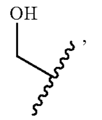, 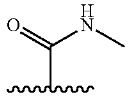, 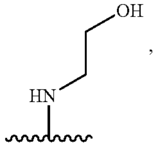,

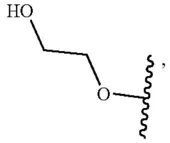, 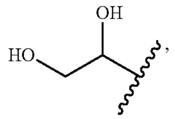, 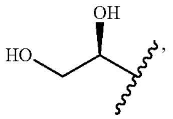,

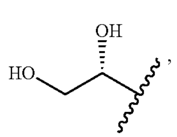, 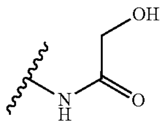,

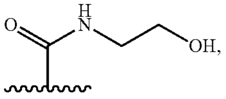, 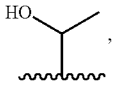, 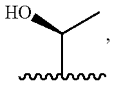,

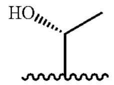, 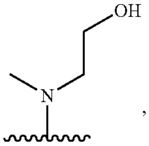, 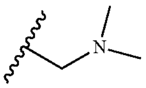,

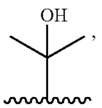, 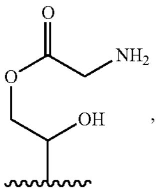, 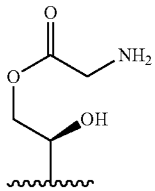,

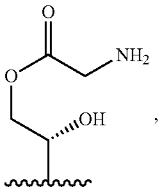, 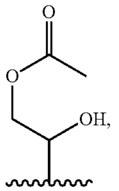, 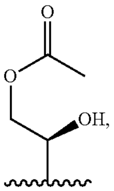

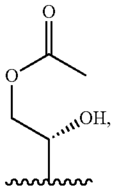 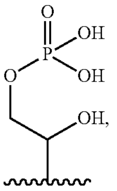 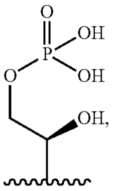 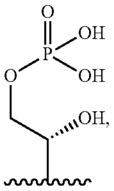

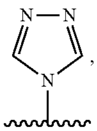, 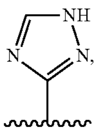, 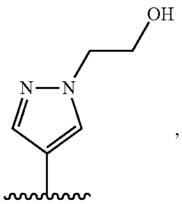,

-continued
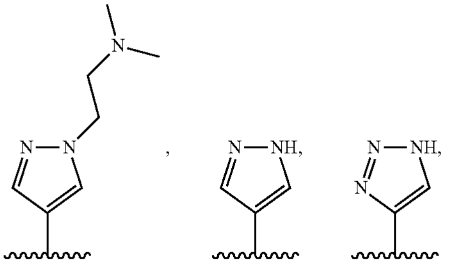
,
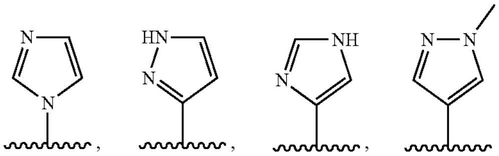
, , , ,
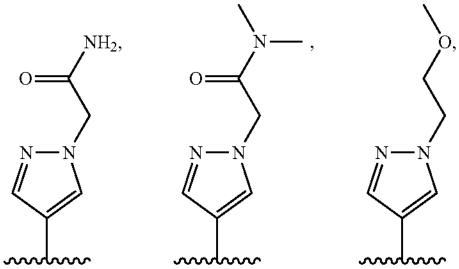
,
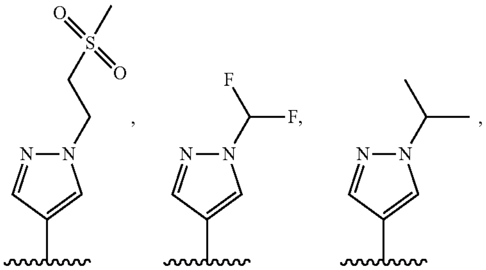
, ,
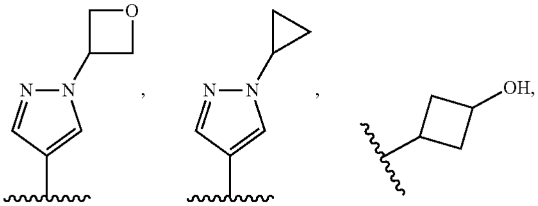
, ,
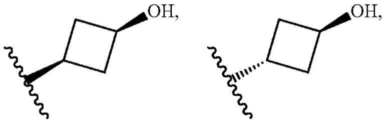
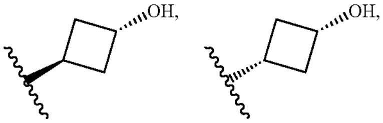
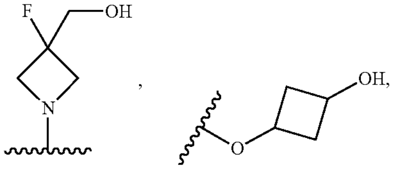
,
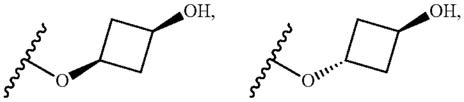
-continued
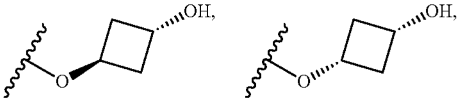
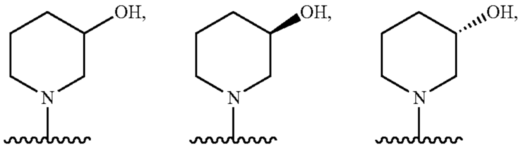
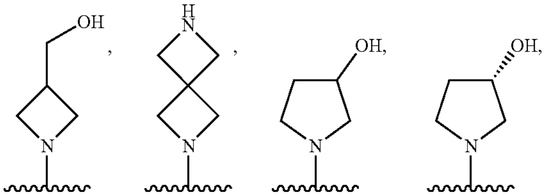
, ,
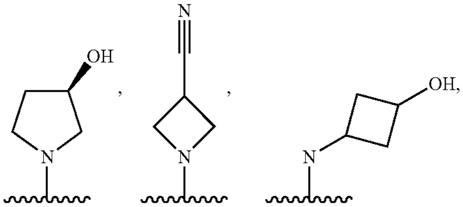
, ,
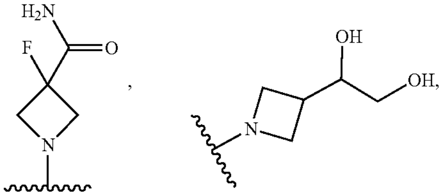
,
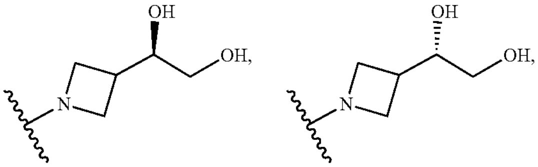
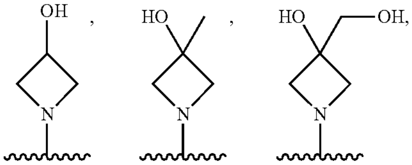
, ,
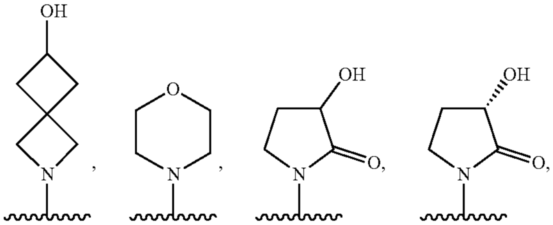
, ,
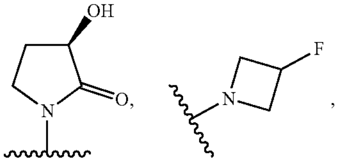
,
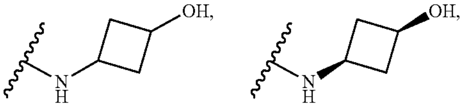

-continued

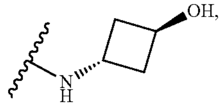 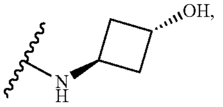

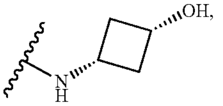 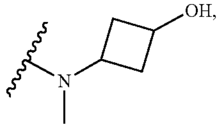

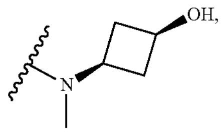 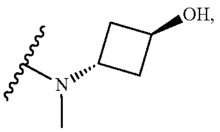

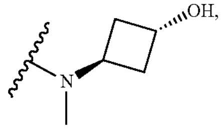 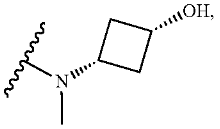

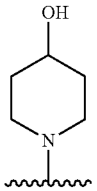 , 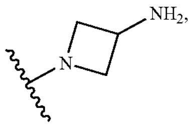

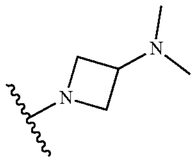 , 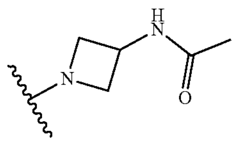 ,

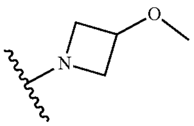 , 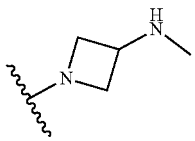 ,

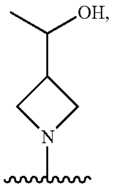 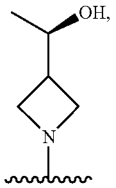 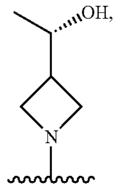

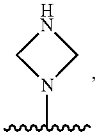 , 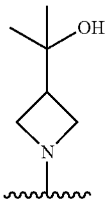 , 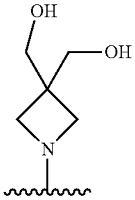 ,

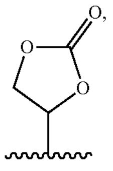 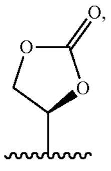 and 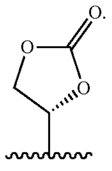

In some embodiments, $R^s$ is $C_{1-6}$ alkyl substituted with one or more —OH. In some embodiments, $R^s$ is $C_{1-3}$alkyl substituted with one or more —OH. In some embodiments, $R^s$ is

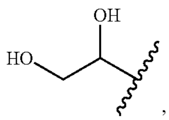 [SMILES: *C(O)CO] , or a stereoisomer thereof. In some embodiments, $R^s$ is

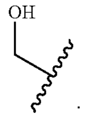 .

In some embodiments, compounds of any one of the formulae described herein, may comprise one or more of the following structural features: i) L' is *—NH—$CH_2$—**; or ii) L' is

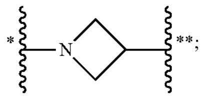 [SMILES: *C1CN(*)C1]

and/or iii) B is phenyl substituted with halo$C_{1-6}$alkoxy; and/or iv) $R^s$ is $C_{1-6}$ alkyl substituted with one or more —OH; and/or v) $X^2$ is CH; and/or vi) $X^3$ is CH; and/or vii) $X^4$ is N; and/or viii) Z is —C(O)$R^x$, wherein $R^x$ is unsubstituted $C_{2-6}$ alkenyl; and/or ix) Z is —C(O)$R^x$, wherein $R^x$ is $C_{2-6}$alkenyl optionally substituted with one or more halo. In some embodiments, compounds of any one of the formulae described herein, may comprise two of the structural features described above, such as i) and iii), i) and iv), i) and v), i) and vi), i) and vii), i) and viii), i) and (ix), ii) and iii), ii) and iv), ii) and v), ii) and vi), ii) and vii), ii) and viii), ii) and (ix), iii) and iv), iii) and v), iii) and vi), iii) and vii), iii) and viii), iii) and ix), iv) and v), iv) and vi), iv) and vii), iv) and viii), iv and ix), v) and vi), v) and vii), v) and viii), v) and ix), vi) and vii), vi) and viii), vi) and ix), vii) and viii), and vii) and ix). In some embodiments, compounds of any one of the formulae described herein, may comprise three of the structural features described above, such as i) and (iii) and iv), i) and (iii) and v), i) and iii) and vi), i) and (iii) and vii), i) and iii) and viii), i) and iii) and (ix), ii) and iii) and iv), ii) and iii) and v), ii) and iii) and vi), ii) and iii) and vii), ii) and iii) and viii), ii) and iii) and (ix), iii) and iv) and v), iii) and iv) and vi), iii) and iv) and vii), iii) and iv) and viii), iii) and iv) and ix), iv) and v) and vi), iv) and v) and vii), iv) and v) and viii), iv) and v) and ix), v) and vi) and vii), v) and vi) and viii), v) and vi) and ix), vi) and vii) and viii), and vi) and vii) and ix). In some embodiments, compounds of any one of the formulae described herein, may comprise four of the structural features described above, such as i) and iii) and iv) and v), i) and iii) and iv) and vi), i) and (iii) and iv) and vii), i) and iii) and iv) and viii), i) and iii) and iv) and (ix), ii) and iii) and iv) and v), ii) and iii) and iv) and vi), ii) and iii) and iv) and vii), ii) and iii) and iv) and viii), ii) and iii) and iv) and (ix), iii) and iv) and v) and vi), iii) and iv) and v) and vii), iii) and iv) and v) and viii), iii) and iv) and v) and ix), iv) and v) and vi) and vii), iv) and v) and vi) and viii), iv) and v) and vi) and ix), v) and vi) and vii) and viii), and v) and vi) and vii) and ix). In some embodiments, compounds of any one of the formulae described herein, may comprise five of the structural features described above, such as i) and iii) and iv) and v) and vi), i) and iii) and iv) and v) and vii), i) and iii) and iv) and v) and viii), i) and iii) and iv) and v) and ix), ii) and iii) and iv) and v) and vi), ii) and iii) and iv) and v) and vii), ii) and iii) and iv) and v) and viii), ii) and iii) and iv) and v) and ix), iii) and iv) and v) and vi) and vii), iii) and iv) and v) and viii), iii) and iv) and v) and ix), iv) and v) and vi) and vii) and viii), and iv) and v) and vi) and vii) and ix). In some embodiments, compounds of any one of the formulae described herein, may comprise six of the structural features described above, such as i) and iii) and iv) and v) and vi) and vii), i) and iii) and iv) and v) and vi) and viii), i) and iii) and iv) and v) and vi) and ix), ii) and iii) and iv) and v) and vi) and vii), ii) and iii) and iv) and v) and vi) and viii), ii) and iii) and iv) and v) and vi) and ix), iii) and iv) and v) and vi) and vii) and viii), and iii) and iv) and v) and vi) and vii) and ix). In some embodiments, compounds of any one of the formulae described herein, may comprise seven of the structural features described above, such as i) and iii) and iv) and v) and vi) and vii) and viii), i) and iii) and iv) and v) and vi) and vii) and ix), ii) and iii) and iv) and v) and vi) and vii) and viii), and ii) and iii) and iv) and v) and vi) and vii) and ix).

In some embodiments, in conjunction with embodiments above or below, reference to "one or more" may be 1 to 5, 1 to 4, 1 to 3, 1 to 2, 5, 4, 3, 2, or 1.

In some embodiments, in conjunction with embodiments above or below, reference to "one or more substituents", for example, "one or more substituents of $C_{1-6}$alkyl", may be 1 to 3 substituents, 1 to 2 substituents, 2 substituents, or 1 substituent.

In some embodiments, in conjunction with embodiments above or below, wherein when B is optionally substituted with one or more $R^t$, $R^t$ is $C_{1-15}$ alkoxy optionally substituted with 1-3 halo. In some embodiments, in conjunction with embodiments above or below, $R^t$ is $C_{1-15}$alkoxy substituted with 1-3 halo. In some embodiments, in conjunction with embodiments above or below, $R^t$ is $OCF_3$.

In some embodiments, in conjunction with embodiments above or below, wherein when $X^1$ is $CR^s$, $R^s$ is

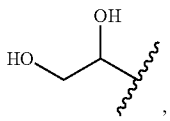

, or a stereoisomer thereof. In some embodiments, $R^s$ is

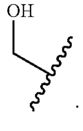

.

In some embodiments, in conjunction with embodiments above or below, n and m are each 1.

In some aspects, a compound or a stereoisomer, tautomer, or pharmaceutically acceptable salt thereof of the following formula (A-1) is provided:

(A-1)

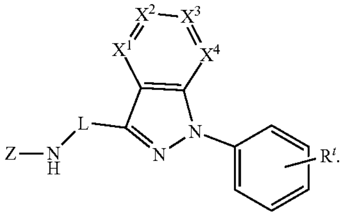

In one aspect, $X^1$, $X^2$, $X^3$, $X^4$, $R^t$, L, and Z of formula (A-1) are as defined in formula (I-AB). In one aspect, $X^1$, $X^2$, $X^3$, $X^4$, $R^t$, L, and Z of formula (A-1) are as defined in formula (AB). In one aspect, $X^1$, $X^2$, $X^3$, $X^4$, $R^t$, L, and Z of formula (A-1) are as defined in formula (A). In one aspect, $X^1$, $X^2$, $X^3$, $X^4$, $R^t$, L, and Z of formula (A-1) are as defined in formula (A'). It is understood that embodiments of $X^1$, $X^2$, $X^3$, $X^4$, $R^t$, L, and Z described for formula (I-AB), (AB), (A), or (A') may, where applicable, apply in some embodiments to formula (A-1).

In some aspects, a compound or a stereoisomer, tautomer, or pharmaceutically acceptable salt thereof of the following formula (B-1) is provided:

(B-1)

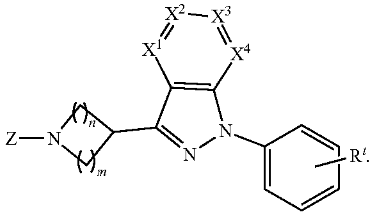

In one aspect, $X^1$, $X^2$, $X^3$, $X^4$, $R^t$, and Z of formula (B-1) are as defined in formula (I-AB). In one aspect, $X^1$, $X^2$, $X^3$, $X^4$, $R^t$, and Z of formula (B-1) are as defined in formula (AB). In one aspect, $X^1$, $X^2$, $X^3$, $X^4$, $R^t$, and Z of formula (B-1) are as defined in formula (B). In one aspect, $X^1$, $X^2$, $X^3$, $X^4$, $R^t$, and Z of formula (B-1) are as defined in formula (B'). It is understood that embodiments of $X^1$, $X^2$, $X^3$, $X^4$, $R^t$, and Z described for formula (I-AB), (AB), (B), or (B') may, where applicable, apply in some embodiments to formula (B-1).

In some aspects, a compound or a stereoisomer, tautomer, or pharmaceutically acceptable salt thereof of the following formula (I-A-1) is provided:

(I-A-1)

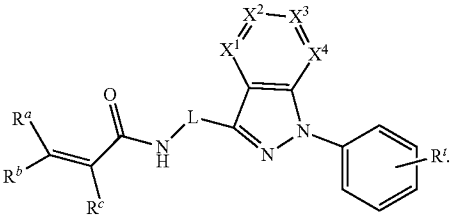

In one aspect, $X^1$, $X^2$, $X^3$, $X^4$, $R^t$, $R^a$, $R^b$, $R^c$, L, and $R^t$ of formula (I-A-1) are as defined in formula (I-AB). In one aspect, $X^1$, $X^2$, $X^3$, $X^4$, $R^t$, $R^a$, $R^b$, $R^c$, L, and $R^t$ of formula (I-A-1) are as defined in formula (AB). In one aspect, $X^1$, $X^2$, $X^3$, $X^4$, $R^t$, $R^a$, $R^b$, $R^c$, L, and $R^t$ of formula (I-A-1) are as defined in formula (A). In one aspect, $X^1$, $X^2$, $X^3$, $X^4$, $R^t$, $R^a$, $R^b$, $R^c$, L, and $R^t$ of formula (I-A-1) are as defined in formula (A'). It is understood that embodiments of $X^1$, $X^2$, $X^3$, $X^4$, $R^t$, $R^a$, $R^b$, $R^c$, L, and $R^t$ described for formula (I-AB), (AB), (A), or (A') may, where applicable, apply in some embodiments to formula (I-A-1).

In some aspects, a compound or a stereoisomer, tautomer, or pharmaceutically acceptable salt thereof of the following formula (I-A-2) is provided:

(I-A-2)

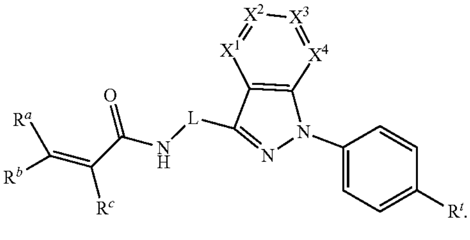

In one aspect, $X^1$, $X^2$, $X^3$, $X^4$, $R^t$, $R^a$, $R^b$, L, and $R^c$ of formula (I-A-2) are as defined in formula (I-AB). In one aspect, $X^1$, $X^2$, $X^3$, $X^4$, $R^t$, $R^a$, $R^b$, L, and $R^c$ of formula (I-A-2) are as defined in formula (AB). In one aspect, $X^1$, $X^2$, $X^3$, $X^4$, $R^t$, $R^a$, $R^b$, L, and $R^c$ of formula (I-A-2) are as defined in formula (A). In one aspect, $X^1$, $X^2$, $X^3$, $X^4$, $R^t$, $R^a$, $R^b$, L, and $R^c$ of formula (I-A-2) are as defined in formula (A'). It is understood that embodiments of $X^1$, $X^2$, $X^3$, $X^4$, $R^t$, $R^a$, $R^b$, L, and $R^c$ described for formula (I-AB), (AB), (A), or (A') may, where applicable, apply in some embodiments to formula (I-A-2).

In some aspects, a compound or a stereoisomer, tautomer, or pharmaceutically acceptable salt thereof of the following formula (I-A-3) is provided:

(I-A-3)

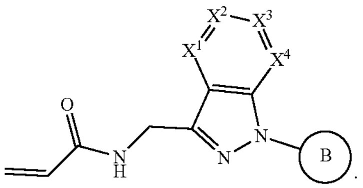

In one aspect, $X^1$, $X^2$, $X^3$, $X^4$, and B of formula (I-A-3) are as defined in formula (I-AB). In one aspect, $X^1$, $X^2$, $X^3$, $X^4$, and B of formula (I-A-3) are as defined in formula (AB). In one aspect, $X^1$, $X^2$, $X^3$, $X^4$, and B of formula (I-A-3) are as defined in formula (A). In one aspect, $X^1$, $X^2$, $X^3$, $X^4$, and B of formula (I-A-3) are as defined in formula (A'). It is understood that embodiments of $X^1$, $X^2$, $X^3$, $X^4$, and B described for formula (I-AB), (AB), (A), or (A') may, where applicable, apply in some embodiments to formula (I-A-3).

In some aspects, a compound or a stereoisomer, tautomer, or pharmaceutically acceptable salt thereof of the following formula (I-A-4) is provided:

(I-A-4)

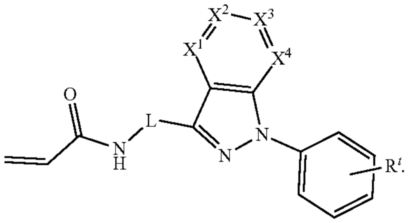

In one aspect, $X^1$, $X^2$, $X^3$, $X^4$, L, and $R^t$ of formula (I-A-4) are as defined in formula (I-AB). In one aspect, $X^1$, $X^2$, $X^3$, $X^4$, L, and $R^t$ of formula (I-A-4) are as defined in formula (AB). In one aspect, $X^1$, $X^2$, $X^3$, $X^4$, L, and $R^t$ of formula (I-A-4) are as defined in formula (A). In one aspect, $X^1$, $X^2$, $X^3$, $X^4$, L, and $R^t$ of formula (I-A-4) are as defined in formula (A'). It is understood that embodiments of $X^1$, $X^2$, $X^3$, $X^4$, L, and $R^t$ described for formula (I-AB), (AB), (A), or (A') may, where applicable, apply in some embodiments to formula (I-A-4).

In some aspects, a compound or a stereoisomer, tautomer, or pharmaceutically acceptable salt thereof of the following formula (A-1a) is provided:

(A-1a)

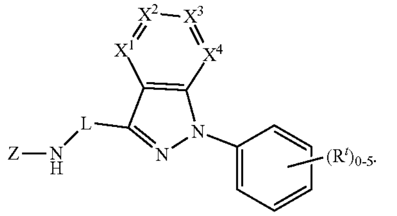

In one aspect, $X^1$, $X^2$, $X^3$, $X^4$, L, and $R^t$ of formula (A-1a) are as defined in formula (I-AB). In one aspect, $X^1$, $X^2$, $X^3$, $X^4$, L, and $R^t$ of formula (A-1a) are as defined in formula (AB). In one aspect, $X^1$, $X^2$, $X^3$, $X^4$, L, and $R^t$ of formula (A-1a) are as defined in formula (A). In one aspect, $X^1$, $X^2$, $X^3$, $X^4$, L, and $R^t$ of formula (A-1a) are as defined in formula (A'). It is understood that embodiments of $X^1$, $X^2$, $X^3$, $X^4$, L, and $R^t$ described for formula (I-AB), (AB), (A), or (A') may, where applicable, apply in some embodiments to formula (A-1a).

In some aspects, a compound or a stereoisomer, tautomer, or pharmaceutically acceptable salt thereof of the following formula (B-1a) is provided:

(B-1a)

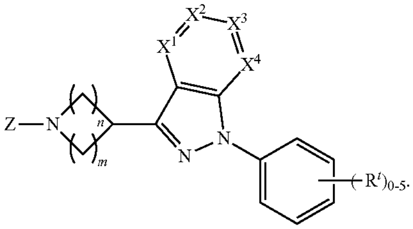

In one aspect, $X^1$, $X^2$, $X^3$, $X^4$, $R^t$, n, m, and Z of formula (B-1a) are as defined in formula (I-AB).) In one aspect, $X^1$, $X^2$, $X^3$, $X^4$, $R^t$, n, m, and Z of formula (B-1a) are as defined in formula (AB). In one aspect, $X^1$, $X^2$, $X^3$, $X^4$, $R^t$, n, m, and Z of formula (B-1a) are as defined in formula (B). In one aspect, $X^1$, $X^2$, $X^3$, $X^4$, $R^t$, n, m, and Z of formula (B-1a) are as defined in formula (B'). It is understood that embodiments of $X^1$, $X^2$, $X^3$, $X^4$, $R^t$, n, m, and Z described for formula (I-AB), (AB), (B), or (B') may, where applicable, apply in some embodiments to formula (B-1a).

In some aspects, a compound or a stereoisomer, tautomer, or pharmaceutically acceptable salt thereof of the following formula (I-A-1a) is provided:

(I-A-1a)

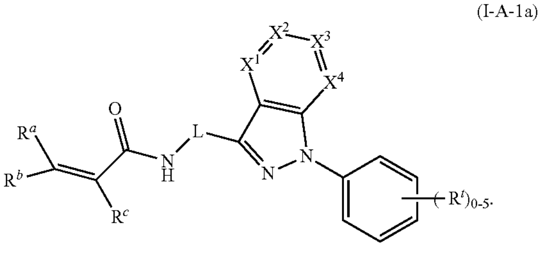

In one aspect, $X^1$, $X^2$, $X^3$, $X^4$, $R^t$, $R^a$, $R^b$, $R^c$, L, and $R^t$ of formula (I-A-1a) are as defined in formula (I-AB). In one aspect, $X^1$, $X^2$, $X^3$, $X^4$, $R^t$, $R^a$, $R^b$, $R^c$, L, and $R^t$ of formula (I-A-1a) are as defined in formula (AB). In one aspect, $X^1$, $X^2$, $X^3$, $X^4$, $R^t$, $R^a$, $R^b$, $R^c$, L, and $R^t$ of formula (I-A-1a) are as defined in formula (A). In one aspect, $X^1$, $X^2$, $X^3$, $X^4$, $R^t$, $R^a$, $R^b$, $R^c$, L, and $R^t$ of formula (I-A-1a) are as defined in formula (A'). It is understood that embodiments of $X^1$, $X^2$, $X^3$, $X^4$, $R^t$, $R^a$, $R^b$, $R^c$, L, and $R^t$ described for formula (I-AB), (AB), (A), or (A') may, where applicable, apply in some embodiments to formula (I-A-1a).

In some aspects, a compound or a stereoisomer, tautomer, or pharmaceutically acceptable salt thereof of the following formula (I-A-4a) is provided:

(I-A-4a)

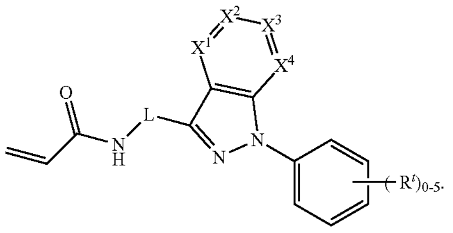

In one aspect, $X^1$, $X^2$, $X^3$, $X^4$, L, and $R^t$ of formula (I-A-4a) are as defined in formula (I-AB). In one aspect, $X^1$, $X^2$, $X^3$, $X^4$, L, and $R^t$ of formula (I-A-4a) are as defined in formula (AB). In one aspect, $X^1$, $X^2$, $X^3$, $X^4$, L, and $R^t$ of formula (I-A-4a) are as defined in formula (A). In one aspect, $X^1$, $X^2$, $X^3$, $X^4$, L, and $R^t$ of formula (I-A-4a) are as defined in formula (A'). It is understood that embodiments of $X^1$, $X^2$, $X^3$, $X^4$, L, and $R^t$ described for formula (I-AB), (AB), (A), or (A') may, where applicable, apply in some embodiments to formula (I-A-4a).

In some aspects, a compound or a stereoisomer, tautomer, or pharmaceutically acceptable salt thereof of the following formula (I-A-5) is provided:

(I-A-5)

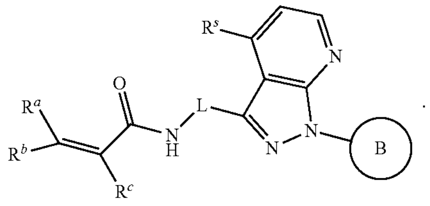

In one aspect, $R^s$, $R^a$, $R^b$, L, B, and $R^c$ of formula (I-A-5) are as defined in formula (I-AB). In one aspect, $R^s$, $R^a$, $R^b$, L, B, and $R^c$ of formula (I-A-5) are as defined in formula (AB). In one aspect, $R^s$, $R^a$, $R^b$, L, B, and $R^c$ of formula (I-A-5) are as defined in formula (AB'). In one aspect, $R^s$, $R^a$, $R^b$, L, B, and $R^c$ of formula (I-A-5) are as defined in formula (A). In one aspect, $R^s$, $R^a$, $R^b$, L, B, and $R^c$ of formula (I-A-5) are as defined in formula (A'). It is understood that embodiments of $R^s$, $R^a$, $R^b$, L, B, and $R^c$ described for formula (I-AB), (AB), (AB'), (A), or (A') may, where applicable, apply in some embodiments to formula (I-A-5).

In some aspects, a compound or a stereoisomer, tautomer, or pharmaceutically acceptable salt thereof of the following formula (I-A-6) is provided:

(I-A-6)

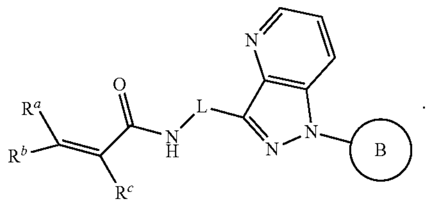

In one aspect, $R^a$, $R^b$, L, B, and $R^c$ of formula (I-A-6) are as defined in formula (I-AB). In one aspect, $R^a$, $R^b$, L, B, and $R^c$ of formula (I-A-6) are as defined in formula (AB). In one aspect, $R^a$, $R^b$, L, B, and $R^c$ of formula (I-A-6) are as defined in formula (A). In one aspect, $R^a$, $R^b$, L, B, and $R^c$ of formula (I-A-6) are as defined in formula (A'). It is understood that embodiments of $R^a$, $R^b$, L, B, and $R^c$ described for formula (I-AB), (AB), (A), or (A') may, where applicable, apply in some embodiments to formula (I-A-6).

In some aspects, a compound or a stereoisomer, tautomer, or pharmaceutically acceptable salt thereof of the following formula (I-A-7) is provided:

(I-A-7)

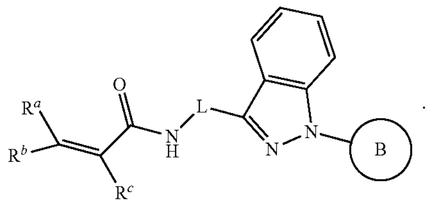

In one aspect, $R^a$, $R^b$, L, B, and $R^c$ of formula (I-A-7) are as defined in formula (I-AB). In one aspect, $R^a$, $R^b$, L, B, and $R^c$ of formula (I-A-7) are as defined in formula (AB). In one aspect, $R^a$, $R^b$, L, B, and $R^c$ of formula (I-A-7) are as defined in formula (A). In one aspect, $R^a$, $R^b$, L, B, and $R^c$ of formula (I-A-7) are as defined in formula (A'). It is understood that embodiments of $R^a$, $R^b$, L, B, and $R^c$ described for formula (I-AB), (AB), (A), or (A') may, where applicable, apply in some embodiments to formula (I-A-7).

In some aspects, a compound or a stereoisomer, tautomer, or pharmaceutically acceptable salt thereof of the following formula (I-A-8) is provided:

(I-A-8)

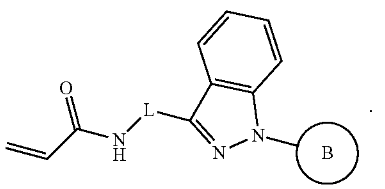

In one aspect, L and B of formula (I-A-B) are as defined in formula (I-AB). In one aspect, L and B of formula (I-A-B) are as defined in formula (AB). In one aspect, L and B of formula (I-A-B) are as defined in formula (A). In one aspect, L and B of formula (I-A-B) are as defined in formula (A'). It is understood that embodiments of L and B described for formula (I-AB), (AB), (A), or (A') may, where applicable, apply in some embodiments to formula (I-A-8).

In some aspects, a compound or a stereoisomer, tautomer, or pharmaceutically acceptable salt thereof of the following formula (I-A-9) is provided:

(I-A-9)

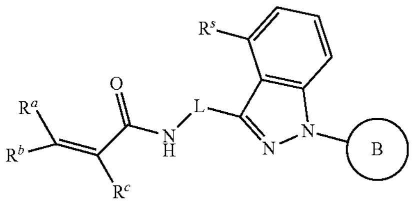

In one aspect, $R^s$, $R^a$, $R^b$, L, B, and $R^c$ of formula (I-A-9) are as defined in formula (I-AB). In one aspect, $R^s$, $R^a$, $R^b$, L, B, and $R^c$ of formula (I-A-9) are as defined in formula (AB). In one aspect, $R^s$, $R^a$, $R^b$, L, B, and $R^c$ of formula (I-A-9) are as defined in formula (AB'). In one aspect, $R^s$, $R^a$, $R^b$, L, B, and $R^c$ of formula (I-A-9) are as defined in formula (A). In one aspect, $R^s$, $R^a$, $R^b$, L, B, and $R^c$ of formula (I-A-9) are as defined in formula (A'). It is understood that embodiments of $R^s$, $R^a$, $R^b$, L, B, and $R^c$ described for formula (I-AB), (AB), (AB'), (A), or (A') may, where applicable, apply in some embodiments to formula (I-A-9).

In some aspects, a compound or a stereoisomer, tautomer, or pharmaceutically acceptable salt thereof of the following formula (I-A-10) is provided:

(I-A-10)

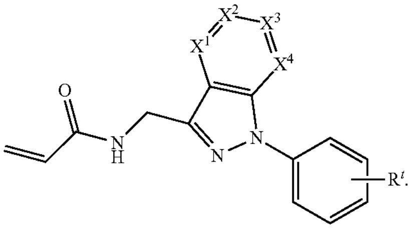

In one aspect, $X^1$, $X^2$, $X^3$, $X^4$, and $R^t$ of formula (I-A-10) are as defined in formula (I-AB). In one aspect, $X^1$, $X^2$, $X^3$, $X^4$, and $R^t$ of formula (I-A-10) are as defined in formula (AB). In one aspect, $X^1$, $X^2$, $X^3$, $X^4$, and $R^t$ of formula (I-A-10) are as defined in formula (A). In one aspect, $X^1$, $X^2$, $X^3$, $X^4$, and $R^t$ of formula (I-A-10) are as defined in formula (A'). It is understood that embodiments of $X^1$, $X^2$, $X^3$, $X^4$, and $R^t$ described for formula (I-AB), (AB), (A), or (A') may, where applicable, apply in some embodiments to formula (I-A-10).

In some aspects, a compound or a stereoisomer, tautomer, or pharmaceutically acceptable salt thereof of the following formula (I-A-11) is provided:

(I-A-11)

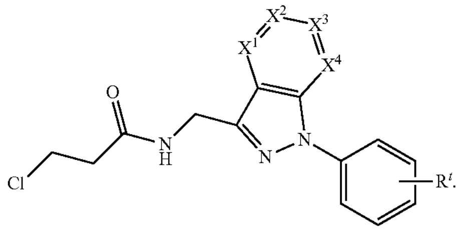

In one aspect, $X^1$, $X^2$, $X^3$, $X^4$, and $R^t$ of formula (I-A-11) are as defined in formula (I-AB). In one aspect, $X^1$, $X^2$, $X^3$, $X^4$, and $R^t$ of formula (I-A-11) are as defined in formula (AB). In one aspect, $X^1$, $X^2$, $X^3$, $X^4$, and $R^t$ of formula (I-A-11) are as defined in formula (A). In one aspect, $X^1$, $X^2$, $X^3$, $X^4$, and $R^t$ of formula (I-A-11) are as defined in formula (A'). It is understood that embodiments of $X^1$, $X^2$, $X^3$, $X^4$, and $R^t$ described for formula (I-AB), (AB), (A), or (A') may, where applicable, apply in some embodiments to formula (I-A-11).

In some aspects, a compound or a stereoisomer, tautomer, or pharmaceutically acceptable salt thereof of the following formula (I-A'-11) is provided:

(I-A'-11)

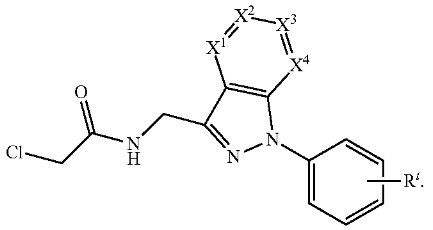

In one aspect, $X^1$, $X^2$, $X^3$, $X^4$, and $R^t$ of formula (I-A-11) or (I-A'-11) are as defined in formula (I-AB). In one aspect, $X^1$, $X^2$, $X^3$, $X^4$, and $R^t$ of formula (I-A-11) or (I-A'-11) are as defined in formula (AB). In one aspect, $X^1$, $X^2$, $X^3$, $X^4$, and $R^t$ of formula (I-A-11) or (I-A'-11) are as defined in formula (A). In one aspect, $X^1$, $X^2$, $X^3$, $X^4$, and $R^t$ of formula (I-A-11) or (I-A'-11) are as defined in formula (A'). It is understood that embodiments of $X^1$, $X^2$, $X^3$, $X^4$, and $R^t$ described for formula (I-AB), (AB), (A), or (A') may, where applicable, apply in some embodiments to formula (I-A-11) or (I-A'-11).

In some aspects, a compound or a stereoisomer, tautomer, or pharmaceutically acceptable salt thereof of the following formula (I-A-10a) is provided:

(I-A-10a)

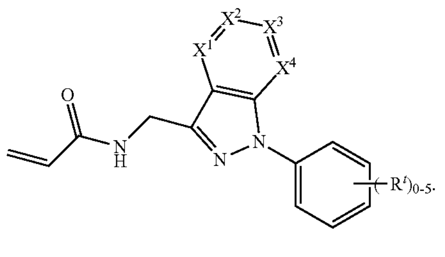

In one aspect, $X^1$, $X^2$, $X^3$, $X^4$, and $R^t$ of formula (I-A-10a) are as defined in formula (I-AB). In one aspect, $X^1$, $X^2$, $X^3$, $X^4$, and $R^t$ of formula (I-A-10a) are as defined in formula (AB). In one aspect, $X^1$, $X^2$, $X^3$, $X^4$, and $R^t$ of formula (I-A-10a) are as defined in formula (A). In one aspect, $X^1$, $X^2$, $X^3$, $X^4$, and $R^t$ of formula (I-A-10a) are as defined in formula (A'). It is understood that embodiments of $X^1$, $X^2$, $X^3$, $X^4$, and $R^t$ described for formula (I-AB), (AB), (A), or (A') may, where applicable, apply in some embodiments to formula (I-A-10a).

In some aspects, a compound or a stereoisomer, tautomer, or pharmaceutically acceptable salt thereof of the following formula (I-A-11a) is provided:

(I-A-11a)

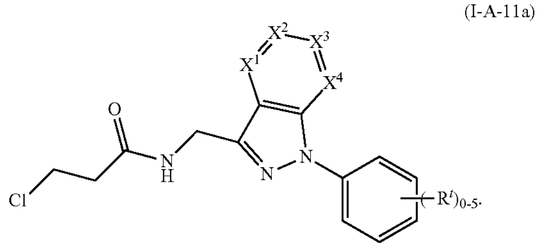

In one aspect, $X^1$, $X^2$, $X^3$, $X^4$, and $R^t$ of formula (I-A-11a) are as defined in formula (I-AB). In one aspect, $X^1$, $X^2$, $X^3$, $X^4$, and $R^t$ of formula (I-A-11a) are as defined in formula (AB). In one aspect, $X^1$, $X^2$, $X^3$, $X^4$, and $R^t$ of formula (I-A-11a) are as defined in formula (A). In one aspect, $X^1$, $X^2$, $X^3$, $X^4$, and $R^t$ of formula (I-A-11a) are as defined in formula (A'). It is understood that embodiments of $X^1$, $X^2$, $X^3$, $X^4$, and $R^t$ described for formula (I-AB), (AB), (A), or (A') may, where applicable, apply in some embodiments to formula (I-A-11a).

In some aspects, a compound or a stereoisomer, tautomer, or pharmaceutically acceptable salt thereof of the following formula (I-A-11a) is provided:

(I-A'-11a)

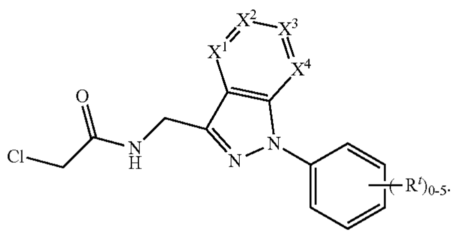

In one aspect, $X^1$, $X^2$, $X^3$, $X^4$, and $R^t$ of formula (I-A-11a) or (I-A'-11a) are as defined in formula (I-AB). In one aspect, $X^1$, $X^2$, $X^3$, $X^4$, and $R^t$ of formula (I-A-11a) or (I-A'-11a) are as defined in formula (AB). In one aspect, $X^1$, $X^2$, $X^3$, $X^4$, and $R^t$ of formula (I-A-11a) or (I-A'-11a) are as defined in formula (A). In one aspect, $X^1$, $X^2$, $X^3$, $X^4$, and $R^t$ of formula (I-A-11a) or (I-A'-11a) are as defined in formula (A'). It is understood that embodiments of $X^1$, $X^2$, $X^3$, $X^4$, and $R^t$ described for formula (I-AB), (AB), (A), or (A') may, where applicable, apply in some embodiments to formula (I-A-11a) or (I-A'-11a).

In some aspects, a compound or a stereoisomer, tautomer, or pharmaceutically acceptable salt thereof of the following formula (I-A-12) is provided:

(I-A-12)

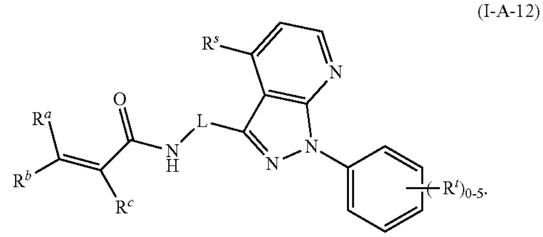

In one aspect, $R^s$, $R^a$, $R^b$, L, and $R^c$ of formula (I-A-12) are as defined in formula (I-AB). In one aspect, $R^s$, $R^a$, $R^b$, L, and $R^c$ of formula (I-A-12) are as defined in formula (AB). In one aspect, $R^s$, $R^a$, $R^b$, L, and $R^c$ of formula (I-A-12) are as defined in formula (AB'). In one aspect, $R^s$, $R^a$, $R^b$, L, and $R^c$ of formula (I-A-12) are as defined in formula (A). In one aspect, $R^s$, $R^a$, $R^b$, L, and $R^c$ of formula (I-A-12) are as defined in formula (A'). It is understood that embodiments of $R^s$, $R^a$, $R^b$, L, and $R^c$ described for formula (I-AB), (AB), (AB'), (A), or (A') may, where applicable, apply in some embodiments to formula (I-A-12).

In some aspects, a compound or a stereoisomer, tautomer, or pharmaceutically acceptable salt thereof of the following formula (I-A-13) is provided:

(I-A-13)

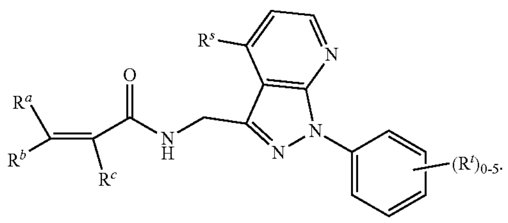

In one aspect, $R^s$, $R^t$, $R^a$, $R^b$, and $R^c$ of formula (I-A-13) are as defined in formula (I-AB). In one aspect, $R^s$, $R^t$, $R^a$, $R^b$, and $R^c$ of formula (I-A-13) are as defined in formula (AB). In one aspect, $R^s$, $R^t$, $R^a$, $R^b$, and $R^c$ of formula (I-A-13) are as defined in formula (AB'). In one aspect, $R^s$, $R^t$, $R^a$, $R^b$, and $R^c$ of formula (I-A-13) are as defined in formula (A). In one aspect, $R^s$, $R^t$, $R^a$, $R^b$, and $R^c$ of formula (I-A-13) are as defined in formula (A'). It is understood that embodiments of $R^s$, $R^t$, $R^a$, $R^b$, and $R^c$ described for formula (I-AB), (AB), (AB'), (A), or (A') may, where applicable, apply in some embodiments to formula (I-A-13).

In some aspects, a compound or a stereoisomer, tautomer, or pharmaceutically acceptable salt thereof of the following formula (I-A-14) is provided:

(I-A-14)

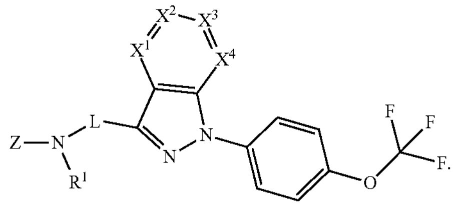

In one aspect, $X^1$, $X^2$, $X^3$, $X^4$, Z, L, and $R^1$ of formula (I-A-14) are as defined in formula (I-AB). In one aspect, $X^1$, $X^2$, $X^3$, $X^4$, Z, L, and $R^1$ of formula (I-A-14) are as defined in formula (AB). In one aspect, $X^1$, $X^2$, $X^3$, $X^4$, Z, L, and $R^1$ of formula (I-A-14) are as defined in formula (A). In one aspect, $X^1$, $X^2$, $X^3$, $X^4$, Z, L, and $R^1$ of formula (I-A-14) are as defined in formula (A'). It is understood that embodiments of $X^1$, $X^2$, $X^3$, $X^4$, Z, L, and $R^1$ described for formula (I-AB), (AB), (A), or (A') may, where applicable, apply in some embodiments to formula (I-A-14).

In some aspects, a compound or a stereoisomer, tautomer, or pharmaceutically acceptable salt thereof of the following formula (I-A-15) is provided:

(1-A-15)

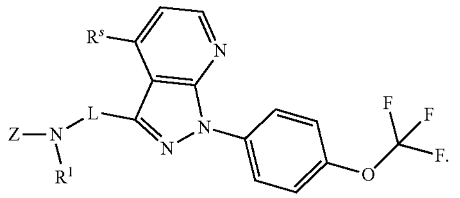

In one aspect, $R^s$, Z, L, and $R^1$ of formula (I-A-15) are as defined in formula (I-AB). In one aspect, $R^s$, Z, L, and $R^1$ of formula (I-A-15) are as defined in formula (AB). In one aspect, $R^s$, Z, L, and $R^1$ of formula (I-A-15) are as defined in formula (AB'). In one aspect, $R^s$, Z, L, and $R^1$ of formula (I-A-15) are as defined in formula (A). In one aspect, $R^s$, Z, L, and $R^1$ of formula (I-A-15) are as defined in formula (A'). It is understood that embodiments of $R^s$, Z, L, and $R^1$ described for formula (I-AB), (AB), (AB'), (A), or (A') may, where applicable, apply in some embodiments to formula (I-A-15).

In some aspects, a compound or a stereoisomer, tautomer, or pharmaceutically acceptable salt thereof of the following formula (I-A-16) is provided:

(I-A-16)

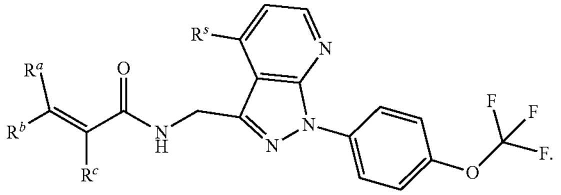

In one aspect, $R^s$, $R^a$, $R^b$, and $R^c$ of formula (I-A-16) are as defined in formula (I-AB). In one aspect, $R^s$, $R^a$, $R^b$, and $R^c$ of formula (I-A-16) are as defined in formula (AB). In one aspect, $R^s$, $R^a$, $R^b$, and $R^c$ of formula (I-A-16) are as defined in formula (AB'). In one aspect, $R^s$, $R^a$, $R^b$, and $R^c$ of formula (I-A-16) are as defined in formula (A). In one aspect, $R^s$, $R^a$, $R^b$, and $R^c$ of formula (I-A-16) are as defined in formula (A'). It is understood that embodiments of $R^s$, $R^a$, $R^b$, and $R^c$ described for formula (I-AB), (AB), (AB'), (A), or (A') may, where applicable, apply in some embodiments to formula (I-A-16).

In some aspects, a compound or a stereoisomer, tautomer, or pharmaceutically acceptable salt thereof of the following formula (I-A-17) is provided:

(1-A-17)

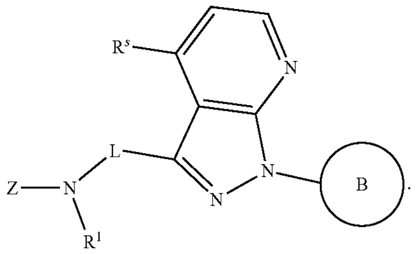

In one aspect, $R^s$, Z, L, B, and $R^1$ of formula (I-A-17) are as defined in formula (I-AB). In one aspect, $R^s$, Z, L, B, and $R^1$ of formula (I-A-17) are as defined in formula (AB). In one aspect, $R^s$, Z, L, B, and $R^1$ of formula (I-A-17) are as defined in formula (AB'). In one aspect, $R^s$, Z, L, B, and $R^1$ of formula (I-A-17) are as defined in formula (A). In one aspect, $R^s$, Z, L, B, and $R^1$ of formula (I-A-17) are as defined in formula (A'). It is understood that embodiments of $R^s$, Z, L, B, and $R^1$ described for formula (I-AB), (AB), (AB'), (A), or (A') may, where applicable, apply in some embodiments to formula (I-A-17).

In some aspects, a compound or a stereoisomer, tautomer, or pharmaceutically acceptable salt thereof of the following formula (I-A-18) is provided:

(1-A-18)

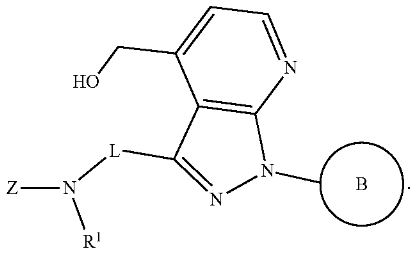

In one aspect, Z, L, B, and $R^1$ of formula (I-A-18) are as defined in formula (I-AB). In one aspect, Z, L, B, and $R^1$ of formula (I-A-18) are as defined in formula (AB). In one aspect, Z, L, B, and $R^1$ of formula (I-A-18) are as defined in formula (A). In one aspect, Z, L, B, and $R^1$ of formula (I-A-18) are as defined in formula (A'). It is understood that embodiments of Z, L, B, and $R^1$ described for formula (I-AB), (AB), (A), or (A') may, where applicable, apply in some embodiments to formula (I-A-18).

In some aspects, a compound or a stereoisomer, tautomer, or pharmaceutically acceptable salt thereof of the following formula (I-A-19) is provided:

(1-A-19)

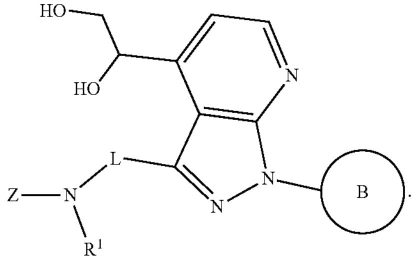

In one aspect, Z, L, B, and $R^1$ of formula (I-A-19) are as defined in formula (I-AB). In one aspect, Z, L, B, and $R^1$ of formula (I-A-19) are as defined in formula (AB). In one aspect, Z, L, B, and $R^1$ of formula (I-A-19) are as defined in formula (A). In one aspect, Z, L, B, and $R^1$ of formula (I-A-19) are as defined in formula (A'). It is understood that embodiments of Z, L, B, and $R^1$ described for formula (I-AB), (AB), (A), or (A') may, where applicable, apply in some embodiments to formula (I-A-19).

In some aspects, a compound or a stereoisomer, tautomer, or pharmaceutically acceptable salt thereof of the following formula (I-A-20) is provided:

(1-A-20)

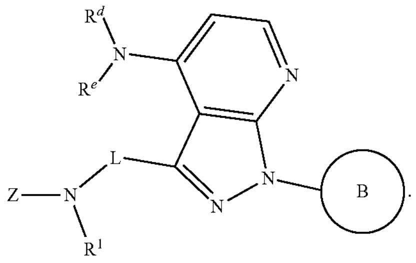

In one aspect, Z, L, B, $R^d$, $R^e$, and $R^1$ of formula (I-A-20) are as defined in formula (I-AB). In one aspect, Z, L, B, $R^d$, $R^e$, and $R^1$ of formula (I-A-20) are as defined in formula (AB). In one aspect, Z, L, B, $R^d$, $R^e$, and $R^1$ of formula (I-A-20) are as defined in formula (A). In one aspect, Z, L, B, $R^d$, $R^e$, and $R^1$ of formula (I-A-20) are as defined in formula (A'). It is understood that embodiments of Z, L, B, $R^d$, $R^e$, and $R^1$ described for formula (I-AB), (AB), (A), or (A') may, where applicable, apply in some embodiments to formula (I-A-20).

In some aspects, a compound or a stereoisomer, tautomer, or pharmaceutically acceptable salt thereof of the following formula (I-A-21) is provided:

(1-A-21)

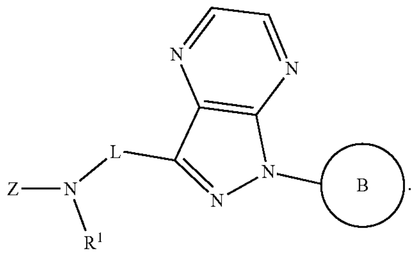

In one aspect, Z, L, B, and $R^1$ of formula (I-A-21) are as defined in formula (I-AB). In one aspect, Z, L, B, and $R^1$ of formula (I-A-21) are as defined in formula (AB). In one aspect, Z, L, B, and $R^1$ of formula (I-A-21) are as defined in formula (A). In one aspect, Z, L, B, and $R^1$ of formula (I-A-21) are as defined in formula (A'). It is understood that embodiments of Z, L, B, and $R^1$ described for formula (I-AB), (AB), (A), or (A') may, where applicable, apply in some embodiments to formula (I-A-21).

In some aspects, a compound or a stereoisomer, tautomer, or pharmaceutically acceptable salt thereof of the following formula (I-B-1) is provided:

(I-B-1)

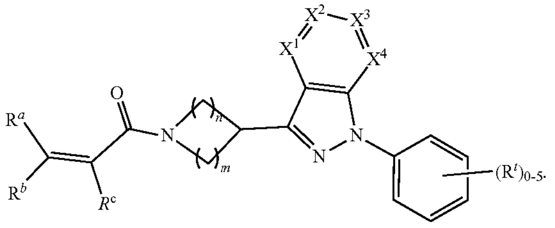

In one aspect, $X^1$, $X^2$, $X^3$, $X^4$, $R^t$, $R^a$, $R^b$, $R^c$, n, m, and $R^t$ of formula (I-B-1) are as defined in formula (I-AB). In one aspect, $X^1$, $X^2$, $X^3$, $X^4$, $R^t$, $R^a$, $R^b$, $R^c$, n, m, and $R^t$ of formula (I-B-1) are as defined in formula (AB). In one aspect, $X^1$, $X^2$, $X^3$, $X^4$, $R^t$, $R^a$, $R^b$, $R^c$, n, m, and $R^t$ of formula (I-B-1) are as defined in formula (B). In one aspect, $X^1$, $X^2$, $X^3$, $X^4$, $R^t$, $R^a$, $R^b$, $R^c$, n, m, and $R^t$ of formula (I-B-1) are as defined in formula (B'). It is understood that embodiments of $X^1$, $X^2$, $X^3$, $X^4$, $R^t$, $R^a$, $R^b$, $R^c$, n, m, and $R^t$ described for formula (I-AB), (AB), (B), or (B') may, where applicable, apply in some embodiments to formula (I-B-1).

In some aspects, a compound or a stereoisomer, tautomer, or pharmaceutically acceptable salt thereof of the following formula (I-B-2) is provided:

(I-B-2)

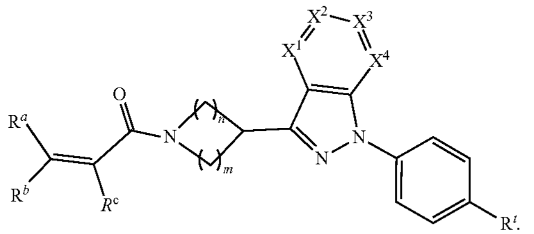

In one aspect, $X^1$, $X^2$, $X^3$, $X^4$, $R^t$, $R^a$, $R^b$, $R^c$, n, m, and $R^t$ of formula (I-B-2) are as defined in formula (I-AB). In one aspect, $X^1$, $X^2$, $X^3$, $X^4$, $R^t$, $R^a$, $R^b$, $R^c$, n, m, and $R^t$ of formula (I-B-2) are as defined in formula (AB). In one aspect, $X^1$, $X^2$, $X^3$, $X^4$, $R^t$, $R^a$, $R^b$, $R^c$, n, m, and $R^t$ of formula (I-B-2) are as defined in formula (B). In one aspect, $X^1$, $X^2$, $X^3$, $X^4$, $R^t$, $R^a$, $R^b$, $R^c$, n, m, and $R^t$ of formula (I-B-2) are as defined in formula (B'). It is understood that embodiments of $X^1$, $X^2$, $X^3$, $X^4$, $R^t$, $R^a$, $R^b$, $R^c$, n, m, and $R^t$ described for formula (I-AB), (AB), (B), or (B') may, where applicable, apply in some embodiments to formula (I-B-2).

In some aspects, a compound or a stereoisomer, tautomer, or pharmaceutically acceptable salt thereof of the following formula (I-B-2) is provided:

(I-B-3)

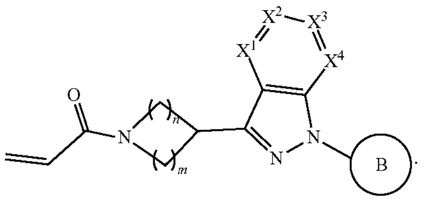

In one aspect, $X^1$, $X^2$, $X^3$, $X^4$, n, m, and B of formula (I-B-3) are as defined in formula (I-AB). In one aspect, $X^1$, $X^2$, $X^3$, $X^4$, n, m, and B of formula (I-B-3) are as defined in formula (AB). In one aspect, $X^1$, $X^2$, $X^3$, $X^4$, n, m, and B of formula (I-B-3) are as defined in formula (B). In one aspect, $X^1$, $X^2$, $X^3$, $X^4$, n, m, and B of formula (I-B-3) are as defined in formula (B'). It is understood that embodiments of $X^1$, $X^2$, $X^3$, $X^4$, n, m, and B described for formula (I-AB), (AB), (B), or (B') may, where applicable, apply in some embodiments to formula (I-B-3).

In some aspects, a compound or a stereoisomer, tautomer, or pharmaceutically acceptable salt thereof of the following formula (I-B-4) is provided:

(I-B-4)

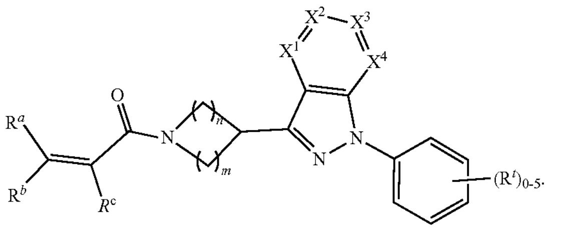

In one aspect, $X^1$, $X^2$, $X^3$, $X^4$, $R^t$, $R^a$, $R^b$, $R^c$, n, m, and $R^t$ of formula (I-B-4) are as defined in formula (I-AB). In one aspect, $X^1$, $X^2$, $X^3$, $X^4$, $R^t$, $R^a$, $R^b$, $R^c$, n, m, and $R^t$ of formula (I-B-4) are as defined in formula (AB). In one aspect, $X^1$, $X^2$, $X^3$, $X^4$, $R^t$, $R^a$, $R^b$, $R^c$, n, m, and $R^t$ of formula (I-B-4) are as defined in formula (B). In one aspect, $X^1$, $X^2$, $X^3$, $X^4$, $R^t$, $R^a$, $R^b$, $R^c$, n, m, and $R^t$ of formula (I-B-4) are as defined in (B'). It is understood that embodiments of $X^1$, $X^2$, $X^3$, $X^4$, $R^t$, $R^a$, $R^b$, $R^c$, n, m, and $R^t$ described for formula (I-AB), (AB), (B), or (B') may, where applicable, apply in some embodiments to formula (I-B-4).

In some aspects, a compound or a stereoisomer, tautomer, or pharmaceutically acceptable salt thereof of the following formula (I-B-5) is provided:

(I-B-5)

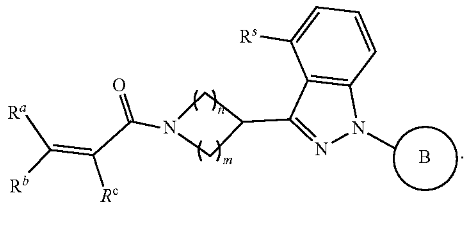

In one aspect, $R^s$, $R^a$, $R^b$, $R^c$, n, m, and B of formula (I-B-5) are as defined in formula (I-AB). In one aspect, $R^s$, $R^a$, $R^b$, $R^c$, n, m, and B of formula (I-B-5) are as defined in formula (AB). In one aspect, $R^s$, $R^a$, $R^b$, $R^c$, n, m, and B of formula (I-B-5) are as defined in formula (AB'). In one aspect, $R^s$, $R^a$, $R^b$, $R^c$, n, m, and B of formula (I-B-5) are as defined in formula (B). In one aspect, $R^s$, $R^a$, $R^b$, $R^c$, n, m, and B of formula (I-B-5) are as defined in formula (B'). It is understood that embodiments of $R^s$, $R^a$, $R^b$, $R^c$, n, m, and B described for formula (I-AB), (AB), (AB'), (B), or (B') may, where applicable, apply in some embodiments to formula (I-B-5).

In some aspects, a compound or a stereoisomer, tautomer, or pharmaceutically acceptable salt thereof of the following formula (I-B-6) is provided:

(I-B-6)

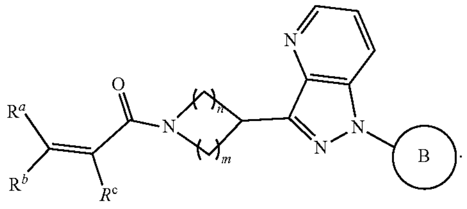

In one aspect, $R^a$, $R^b$, $R^c$, n, m, and B of formula (I-B-6) are as defined in formula (I-AB). In one aspect, $R^a$, $R^b$, $R^c$, n, m, and B of formula (I-B-6) are as defined in formula (AB). In one aspect, $R^a$, $R^b$, $R^c$, n, m, and B of formula (I-B-6) are as defined in formula (B). In one aspect, $R^a$, $R^b$, $R^c$, n, m, and B of formula (I-B-6) are as defined in formula (B'). It is understood that embodiments of $R^a$, $R^b$, $R^c$, n, m, and B described for formula (I-AB), (AB), (B), or (B') may, where applicable, apply in some embodiments to formula (I-B-6).

In some aspects, a compound or a stereoisomer, tautomer, or pharmaceutically acceptable salt thereof of the following formula (I-B-7) is provided:

(I-B-7)

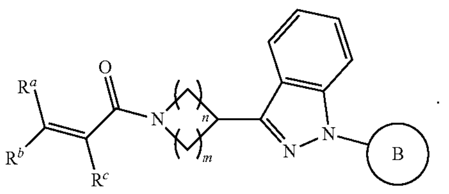

In one aspect, $R^a$, $R^b$, $R^c$, n, m, and B of formula (I-B-7) are as defined in formula (I-AB). In one aspect, $R^a$, $R^b$, $R^c$, n, m, and B of formula (I-B-7) are as defined in formula (AB). In one aspect, $R^a$, $R^b$, $R^c$, n, m, and B of formula (I-B-7) are as defined in formula (B). In one aspect, $R^a$, $R^b$, $R^c$, n, m, and B of formula (I-B-7) are as defined in formula (B'). It is understood that embodiments of $R^a$, $R^b$, $R^c$, n, m, and B described for formula (I-AB), (AB), (B), or (B') may, where applicable, apply in some embodiments to formula (I-B-7).

In some aspects, a compound or a stereoisomer, tautomer, or pharmaceutically acceptable salt thereof of the following formula (I-B-8) is provided:

(I-B-8)

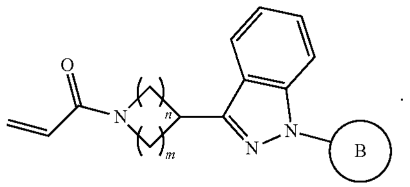

In one aspect, n, m, and B of formula (I-B-8) are as defined in formula (I-AB). In one aspect, n, m, and B of formula (I-B-8) are as defined in formula (AB). In one aspect, n, m, and B of formula (I-B-8) are as defined in formula (B). In one aspect, n, m, and B of formula (I-B-8) are as defined in formula (B'). It is understood that embodiments of n, m, and B described for formula (I-AB), (AB), (B), or (B') may, where applicable, apply in some embodiments to formula (I-B-8).

In some aspects, a compound or a stereoisomer, tautomer, or pharmaceutically acceptable salt thereof of the following formula (I-B-9) is provided:

(I-B-9)

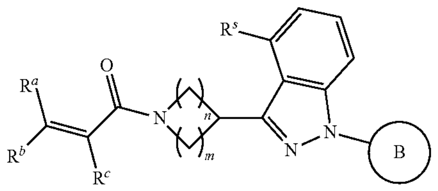

In one aspect, $R^s$, $R^a$, $R^b$, $R^c$, n, m, and B of formula (I-B-9) are as defined in formula (I-AB). In one aspect, $R^s$, $R^a$, $R^b$, $R^c$, n, m, and B of formula (I-B-9) are as defined in formula (AB). In one aspect, $R^s$, $R^a$, $R^b$, $R^c$, n, m, and B of formula (I-B-9) are as defined in formula (AB'). In one aspect, $R^s$, $R^a$, $R^b$, $R^c$, n, m, and B of formula (I-B-9) are as defined in formula (B). In one aspect, $R^s$, $R^a$, $R^b$, $R^c$, n, m, and B of formula (I-B-9) are as defined in formula (B'). It is understood that embodiments of $R^s$, $R^a$, $R^b$, $R^c$, n, m, and B described for formula (I-AB), (AB), (AB'), (B), or (B') may, where applicable, apply in some embodiments to formula (I-B-9).

In some aspects, a compound or a stereoisomer, tautomer, or pharmaceutically acceptable salt thereof of the following formula (I-B-10) is provided:

(I-B-10)

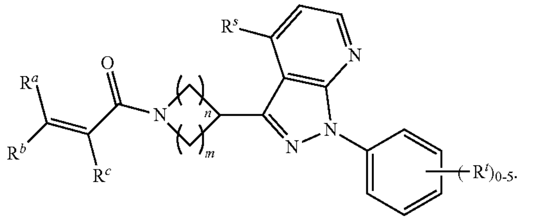

In one aspect, $R^s$, $R^a$, $R^b$, $R^c$, n, m, and $R^t$ of formula (I-B-10) are as defined in formula (I-AB). In one aspect, $R^s$, $R^a$, $R^b$, $R^c$, n, m, and $R^t$ of formula (I-B-10) are as defined in formula (AB). In one aspect, $R^s$, $R^a$, $R^b$, $R^c$, n, m, and $R^t$ of formula (I-B-10) are as defined in formula (AB'). In one aspect, $R^s$, $R^a$, $R^b$, $R^c$, n, m, and $R^t$ of formula (I-B-10) are as defined in formula (B). In one aspect, $R^s$, $R^a$, $R^b$, $R^c$, n, m, and $R^t$ of formula (I-B-10) are as defined in formula (B'). It is understood that embodiments of $R^s$, $R^a$, $R^b$, $R^c$, n, m, and $R^t$ described for formula (I-AB), (AB), (AB'), (B), or (B') may, where applicable, apply in some embodiments to formula (I-B-10).

In some aspects, a compound or a stereoisomer, tautomer, or pharmaceutically acceptable salt thereof of the following formula (I-B-11) is provided:

(I-B-11)

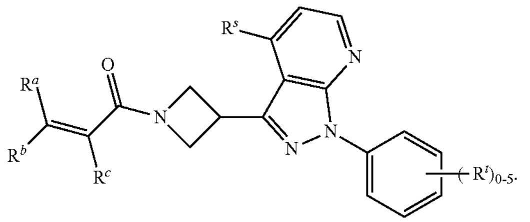

In one aspect, $R^s$, $R^a$, $R^b$, $R^c$, and $R^t$ of formula (I-B-11) are as defined in formula (I-AB). In one aspect, $R^s$, $R^a$, $R^b$, $R^c$, and $R^t$ of formula (I-B-11) are as defined in formula (AB). In one aspect, $R^s$, $R^a$, $R^b$, $R^c$, and $R^t$ of formula (I-B-11) are as defined in formula (AB'). In one aspect, $R^s$, $R^a$, $R^b$, $R^c$, and $R^t$ of formula (I-B-11) are as defined in formula (B). In one aspect, $R^s$, $R^a$, $R^b$, $R^c$, and $R^t$ of formula (I-B-11) are as defined in formula (B'). It is understood that embodiments of $R^s$, $R^a$, $R^b$, $R^c$, and $R^t$ described for formula (I-AB), (AB), (AB'), (B), or (B') may, where applicable, apply in some embodiments to formula (I-B-11).

In some aspects, a compound or a stereoisomer, tautomer, or pharmaceutically acceptable salt thereof of the following formula (I-B-12) is provided:

(I-B-12)

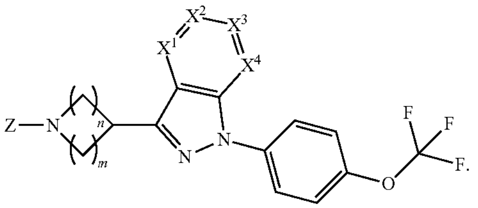

In one aspect, $X^1$, $X^2$, $X^3$, $X^4$, n, m, and Z of formula (I-B-12) are as defined in formula (I-AB). In one aspect, $X^1$, $X^2$, $X^3$, $X^4$, n, m, and Z of formula (I-B-12) are as defined in formula (AB). In one aspect, $X^1$, $X^2$, $X^3$, $X^4$, n, m, and Z of formula (I-B-12) are as defined in formula (B). In one aspect, $X^1$, $X^2$, $X^3$, $X^4$, n, m, and Z of formula (I-B-12) are as defined in formula (B'). It is understood that embodiments of $X^1$, $X^2$, $X^3$, $X^4$, n, m, and Z described for formula (I-AB), (AB), (B), or (B') may, where applicable, apply in some embodiments to formula (I-B-12).

In some aspects, a compound or a stereoisomer, tautomer, or pharmaceutically acceptable salt thereof of the following formula (I-B-13) is provided:

(I-B-13)

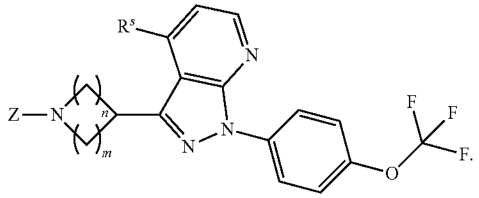

In one aspect, $R^s$, n, m, and Z of formula (I-B-13) are as defined in formula (I-AB). In one aspect, $R^s$, n, m, and Z of formula (I-B-13) are as defined in formula (AB). In one aspect, $R^s$, n, m, and Z of formula (I-B-13) are as defined in formula (AB'). In one aspect, $R^s$, n, m, and Z of formula (I-B-13) are as defined in formula (B). In one aspect, $R^s$, n, m, and Z of formula (I-B-13) are as defined in formula (B'). It is understood that embodiments of $R^s$, n, m, and Z described for formula (I-AB), (AB), (AB'), (B), or (B') may, where applicable, apply in some embodiments to formula (I-B-13).

In some aspects, a compound or a stereoisomer, tautomer, or pharmaceutically acceptable salt thereof of the following formula (I-B-14) is provided:

(I-B-14)

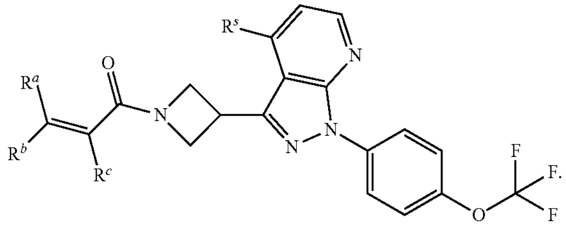

In one aspect, $R^s$, $R^a$, $R^b$, and $R^c$ of formula (I-B-14) are as defined in formula (I-AB). In one aspect, $R^s$, $R^a$, $R^b$, and $R^c$ of formula (I-B-14) are as defined in formula (AB). In one aspect, $R^s$, $R^a$, $R^b$, and $R^c$ of formula (I-B-14) are as defined in formula (AB'). In one aspect, $R^s$, $R^a$, $R^b$, and $R^c$ of formula (I-B-14) are as defined in formula (B). In one aspect, $R^s$, $R^a$, $R^b$, and $R^c$ of formula (I-B-14) are as defined in formula (B'). It is understood that embodiments of $R^s$, $R^a$, $R^b$, and $R^c$ described for formula (I-AB), (AB), (AB'), (B), or (B') may, where applicable, apply in some embodiments to formula (I-B-14).

In some aspects, a compound or a stereoisomer, tautomer, or pharmaceutically acceptable salt thereof of the following formula (I-B-15) is provided:

(I-B-15)

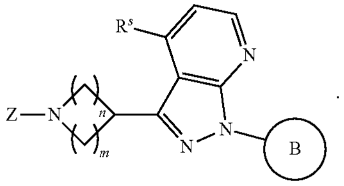

In one aspect, $R^s$, n, m, B, and Z of formula (I-B-15) are as defined in formula (I-AB). In one aspect, $R^s$, n, m, B, and Z of formula (I-B-15) are as defined in formula (AB). In one aspect, $R^s$, n, m, B, and Z of formula (I-B-15) are as defined in formula (AB'). In one aspect, $R^s$, n, m, B, and Z of formula (I-B-15) are as defined in formula (B). In one aspect, $R^s$, n, m, B, and Z of formula (I-B-15) are as defined in formula (B'). It is understood that embodiments of $R^s$, n, m, B, and Z described for formula (I-AB), (AB), (AB'), (B), or (B') may, where applicable, apply in some embodiments to formula (I-B-15).

In some aspects, a compound or a stereoisomer, tautomer, or pharmaceutically acceptable salt thereof of the following formula (I-B-16) is provided:

(I-B-16)

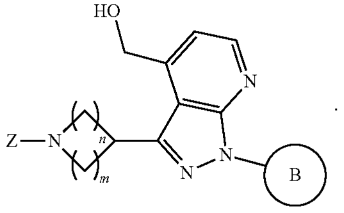

In one aspect, B, n, m, and Z of formula (I-B-16) are as defined in formula (I-AB). In one aspect, B, n, m, and Z of formula (I-B-16) are as defined in formula (AB). In one aspect, B, n, m, and Z of formula (I-B-16) are as defined in formula (B). In one aspect, B, n, m, and Z of formula (I-B-16) are as defined in formula (B'). It is understood that embodiments of B, n, m, and Z described for formula (I-AB), (AB), (B), or (B') may, where applicable, apply in some embodiments to formula (I-B-16).

In some aspects, a compound or a stereoisomer, tautomer, or pharmaceutically acceptable salt thereof of the following formula (I-B-17) is provided:

(I-B-17)

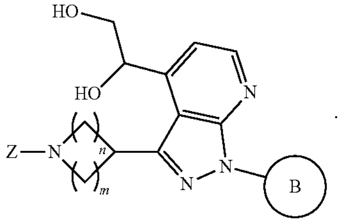

In one aspect, B, n, m, and Z of formula (I-B-17) are as defined in formula (I-AB). In one aspect, B, n, m, and Z of formula (I-B-17) are as defined in formula (AB). In one aspect, B, n, m, and Z of formula (I-B-17) are as defined in formula (B). In one aspect, B, n, m, and Z of formula (I-B-17) are as defined in formula (B'). It is understood that embodiments of B, n, m, and Z described for formula (I-AB), (AB), (B), or (B') may, where applicable, apply in some embodiments to formula (I-B-17).

In some aspects, a compound or a stereoisomer, tautomer, or pharmaceutically acceptable salt thereof of the following formula (I-B-18) is provided:

(I-B-18)

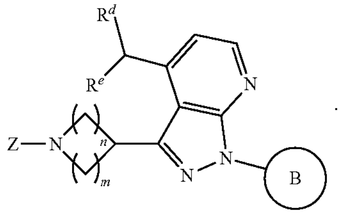

In one aspect, B, n, m, $R^d$, $R^e$, and Z of formula (I-B-18) are as defined in formula (I-AB). In one aspect, B, n, m, $R^d$, $R^e$, and Z of formula (I-B-18) are as defined in formula (AB). In one aspect, B, n, m, $R^d$, $R^e$, and Z of formula (I-B-18) are as defined in formula (B). In one aspect, B, n, m, $R^d$, $R^e$, and Z of formula (I-B-18) are as defined in formula (B'). It is understood that embodiments of B, n, m, $R^d$, $R^e$, and Z described for formula (I-AB), (AB), (B), or (B') may, where applicable, apply in some embodiments to formula (I-B-18).

In some aspects, a compound or a stereoisomer, tautomer, or pharmaceutically acceptable salt thereof of the following formula (I-B-19) is provided:

(I-B-19)

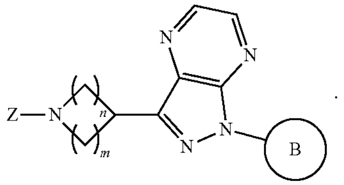

In one aspect, B, n, m, and Z of formula (I-B-19) are as defined in formula (I-AB). In one aspect, B, n, m, and Z of formula (I-B-19) are as defined in formula (AB). In one aspect, B, n, m, and Z of formula (I-B-19) are as defined in formula (B). In one aspect, B, n, m, and Z of formula (I-B-19) are as defined in formula (B'). It is understood that embodiments of B, n, m, $R^d$, $R^e$, and Z described for formula (I-AB), (AB), (B), or (B') may, where applicable, apply in some embodiments to formula (I-B-19).

Certain TEAD inhibitors described herein may exhibit reduced off-target inhibition, such as inhibition of the cardiac sodium channel (e.g., $NaV_{1.5}$). In some embodiments, the $NaV_{1.5}$ inhibition is measured by an assay described herein, such as an assay described in one or more examples.

In some aspects, compounds of formula (I-AB), (AB), (AB'), (A), (B), (A'), (B'), (I-A), or (I-B) or any variation or embodiment thereof, as appropriate, are selected from the compounds listed in Table 1 below, including racemic mixtures and resolved isomers:

TABLE 1

| Compound Number | Structure | Compound Name |
|---|---|---|
| 1 | 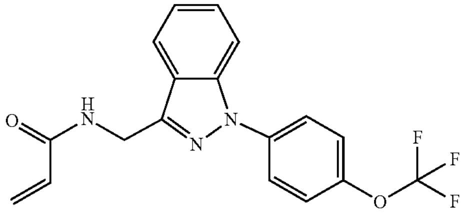 | N-((1-(4-(trifluoromethoxy)phenyl)-1H-indazol-3-yl)methyl)acrylamide |
| 2 | 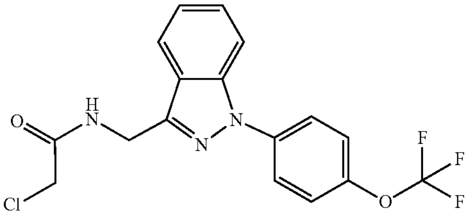 [SMILES: O=C(CCl)NCc1nn(-c2ccc(OC(F)(F)F)cc2)c2ccccc12] | 2-chloro-N-((1-(4-(trifluoromethoxy)phenyl)-1H-indazol-3-yl)methyl)acetamide |
| 3 | 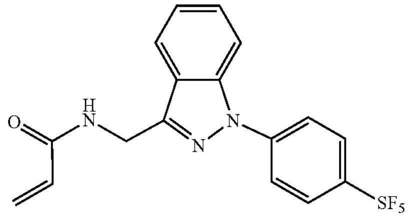 | N-((1-(4-(pentafluoro-λ6-sulfaneyl)phenyl)-1H-indazol-3-yl)methyl)acrylamide |

TABLE 1-continued

| Compound Number | Structure | Compound Name |
|---|---|---|
| 4 | 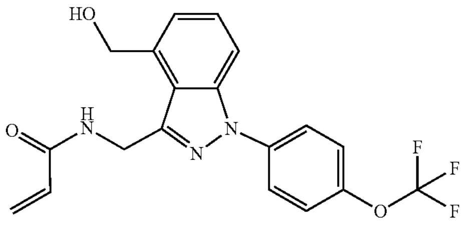 [SMILES: C=CC(=O)NCc1nn(-c2ccc(OC(F)(F)F)cc2)c2cccc(CO)c12] | N-((4-(hydroxymethyl)-1-(4-(trifluoromethoxy)phenyl)-1H-indazol-3-yl)methyl)acrylamide |
| 5 | 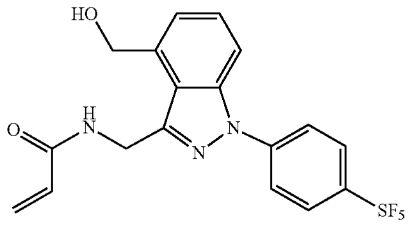 | N-((4-(hydroxymethyl)-1-(4-(pentafluoro-λ6-sulfaneyl)phenyl)-1H-indazol-3-yl)methyl)acrylamide |
| 6 | 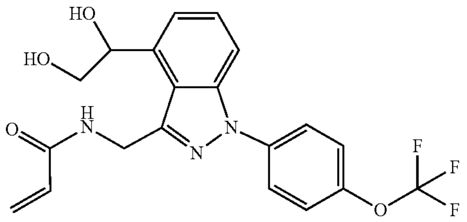 [SMILES: C=CC(=O)NCc1nn(-c2ccc(OC(F)(F)F)cc2)c2cccc(C(O)CO)c12] | N-((4-(1,2-dihydroxyethyl)-1-(4-(trifluoromethoxy)phenyl)-1H-indazol-3-yl)methyl)acrylamide |
| 7 | 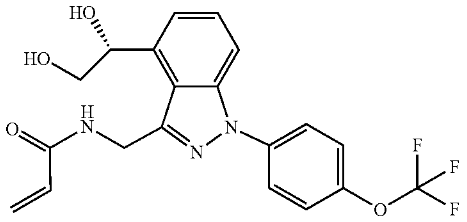 [SMILES: C=CC(=O)NCc1nn(-c2ccc(OC(F)(F)F)cc2)c2cccc([C@@H](O)CO)c12] | (R)-N-((4-(1,2-dihydroxyethyl)-1-(4-(trifluoromethoxy)phenyl)-1H-indazol-3-yl)methyl)acrylamide |
| 8 | 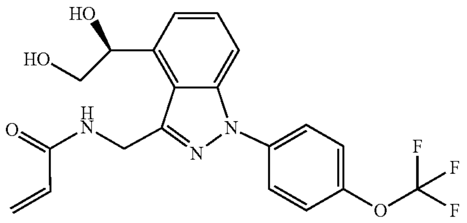 [SMILES: C=CC(=O)NCc1nn(-c2ccc(OC(F)(F)F)cc2)c2cccc([C@H](O)CO)c12] | (S)-N-((4-(1,2-dihydroxyethyl)-1-(4-(trifluoromethoxy)phenyl)-1H-indazol-3-yl)methyl)acrylamide |
| 9 | 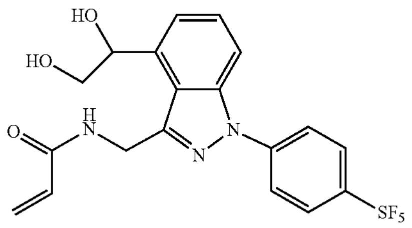 | N-((4-(1,2-dihydroxyethyl)-1-(4-(pentafluoro-λ6-sulfaneyl)phenyl)-1H-indazol-3-yl)methyl)actylamide |

TABLE 1-continued

| Compound Number | Structure | Compound Name |
| --- | --- | --- |
| 10 | 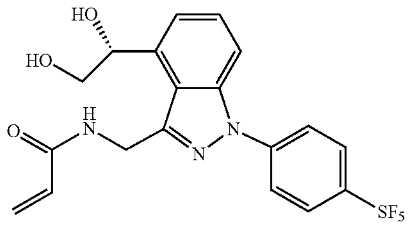 | (R)-N-((4-(1,2-dihydroxyethyl)-1-(4-(pentafluoro-λ6-sulfaneyl)phenyl)-1H-indazol-3-yl)methyl)acrylamide |
| 11 | 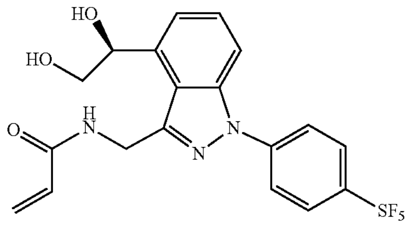 | (S)-N-((4-(1,2-dihydroxyethyl)-1-(4-(pentafluoro-λ6-sulfaneyl)phenyl)-1H-indazol-3-yl)methyl)acrylamide |
| 12 | 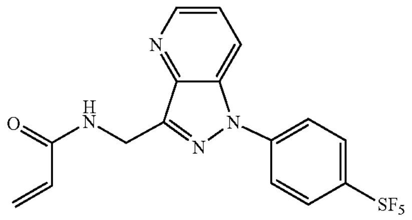 | N-((1-(4-(pentafluoro-λ6-sulfaneyl)phenyl)-1H-pyrazolo[4,3-b]pyridin-3-yl)methyl)acrylamide |
| 13 | 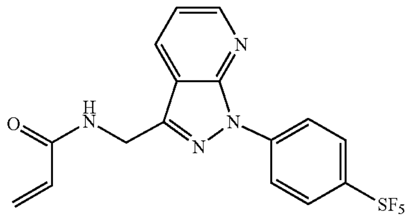 | N-((1-(4-(pentafluoro-λ6-sulfaneyl)phenyl)-1H-pyrazolo[3,4-b]pyridin-3-yl)methyl)acrylamide |
| 14 | 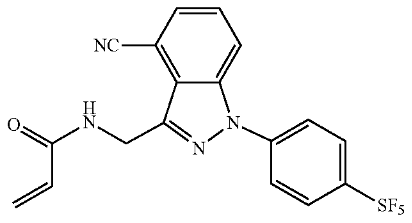 | N-((4-cyano-1-(4-(pentafluoro-λ6-sulfaneyl)phenyl)-1H-indazol-3-yl)methyl)acrylamide |
| 15 | 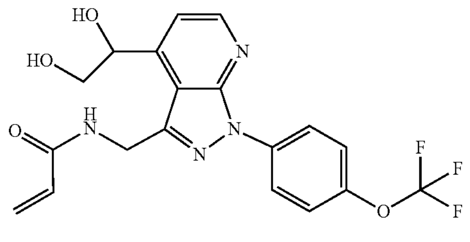 [SMILES: C=CC(=O)NCc1nn(-c2ccc(OC(F)(F)F)cc2)c2nccc(C(O)CO)c12] | N-[[4-(1,2-dihydroxyethyl)-1-(4-(trifluoromethoxy)phenyl)-1H-pyrazolo[3,4-b]pyridin-3-yl]methyl]acrylamide |

TABLE 1-continued

| Compound Number | Structure | Compound Name |
|---|---|---|
| 16 | 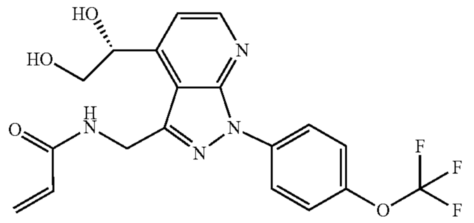 [SMILES: C=CC(=O)NCc1nn(-c2ccc(OC(F)(F)F)cc2)c2nccc([C@@H](O)CO)c12] | (R)-N-[[4-(1,2-dihydroxyethyl)-1-(4-(trifluoromethoxy)phenyl)-1H-pyrazolo[3,4-b]pyridin-3-yl]methyl]acrylamide |
| 17 | 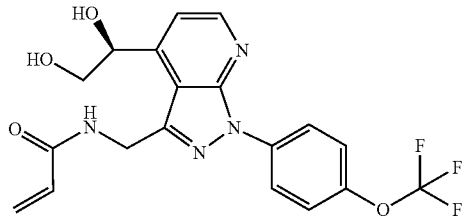 [SMILES: C=CC(=O)NCc1nn(-c2ccc(OC(F)(F)F)cc2)c2nccc([C@H](O)CO)c12] | (S)-N-[[4-(1,2-dihydroxyethyl)-1-(4-(trifluoromethoxy)phenyl)-1H-pyrazolo[3,4-b]pyridin-3-yl]methyl]acrylamide |
| 18 | 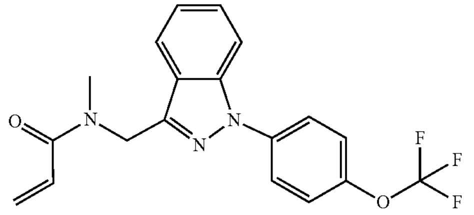 [SMILES: C=CC(=O)N(C)Cc1nn(-c2ccc(OC(F)(F)F)cc2)c2ccccc12] | N-methyl-N-((1-(4-(trifluoromethoxy)phenyl)-1H-indazol-3-yl)methyl)acrylamide |
| 19 | 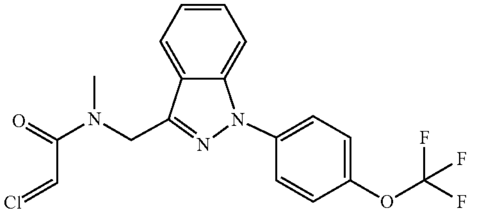 | 2-chloro-N-methyl-N-((1-(4-(trifluoromethoxy)phenyl)-1H-indazol-3-yl)methyl)acetamide |
| 20 | 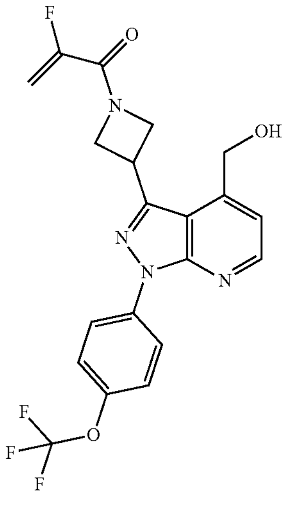 | 2-fluoro-1-[3-[4-(hydroxymethyl)-1-[4-(trifluoromethoxy)phenyl]pyrazolo[3,4-b]pyridin-3-yl]azetidin-1-yl]prop-2-en-1-one |

TABLE 1-continued
| Compound Number | Structure | Compound Name |
|---|---|---|
| 21 | 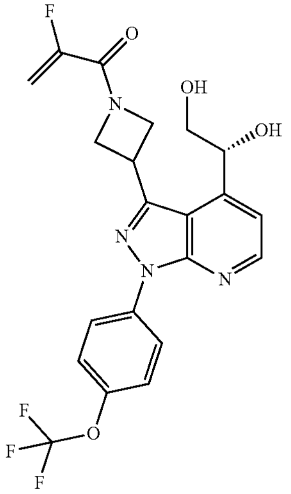 [SMILES: C=C(F)C(=O)N1CC(c2nn(-c3ccc(OC(F)(F)F)cc3)c3nccc([C@@H](O)CO)c23)C1] | 1-[3-[4-[(1R)-1,2-dihydroxyethyl]-1-[4-(trifluoromethoxy)phenyl]pyrazolo[3,4-b]pyridin-3-yl]azetidin-1-yl]-2-fluoro-prop-2-en-1-one |
| 22 | 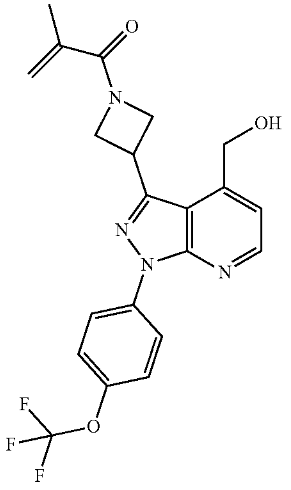 [SMILES: C=C(C)C(=O)N1CC(c2nn(-c3ccc(OC(F)(F)F)cc3)c3nccc(CO)c23)C1] | 1-[3-[4-(hydroxymethyl)-1-[4-(trifluoromethoxy)phenyl]pyrazolo[3,4-b]pyridin-3-yl]azetidin-1-yl]-2-methyl-prop-2-en-1-one |
| 23 | 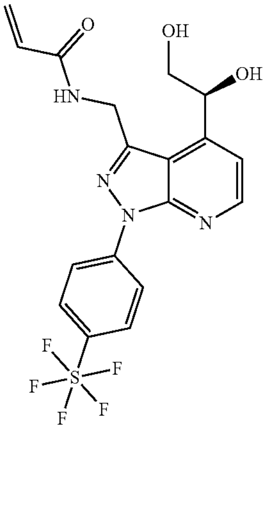 [SMILES: C=CC(=O)NCc1nn(-c2ccc(S(F)(F)(F)(F)F)cc2)c2nccc([C@H](O)CO)c12] | N-[[1-[4-(pentafluoro-lambda6-sulfanyl)phenyl]-4-[rac-(1S)-1,2-dihydroxyethyl]pyrazolo[3,4-b]pyridin-3-yl]methyl]prop-2-enamide |

TABLE 1-continued
| Compound Number | Structure | Compound Name |
|---|---|---|
| 24 | 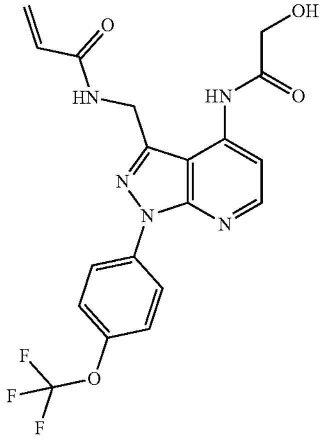 [SMILES: C=CC(=O)NCc1nn(-c2ccc(OC(F)(F)F)cc2)c2nccc(NC(=O)CO)c12] | N-[[4-[(2-hydroxyacetyl)amino]-1-[4-(trifluoromethoxy)phenyl]pyrazolo[3,4-b]pyridin-3-yl]methyl]prop-2-enamide |
| 25 | 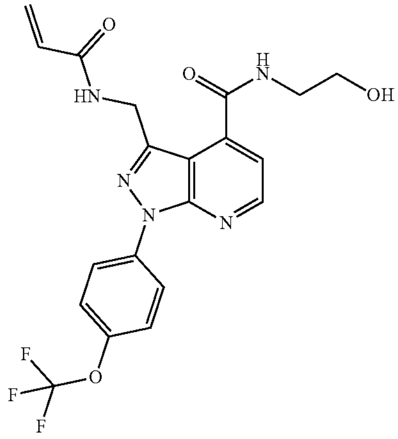 [SMILES: C=CC(=O)NCc1nn(-c2ccc(OC(F)(F)F)cc2)c2nccc(C(=O)NCCO)c12] | N-(2-hydroxyethyl)-3-[(prop-2-enoylamino)methyl]-1-[4-(trifluoromethoxy)phenyl]pyrazolo[3,4-b]pyridine-4-carboxamide |
| 26 | 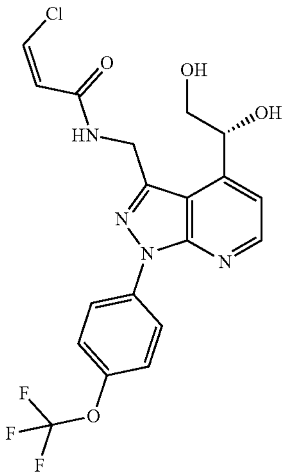 | (Z)-3-chloro-N-[[4-[(1R)-1,2-dihydroxyethyl]-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 27 | 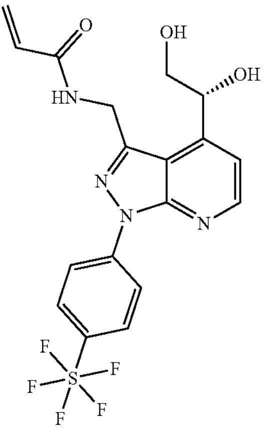 [SMILES: C=CC(=O)NCc1nn(-c2ccc(S(F)(F)(F)(F)F)cc2)c2nccc([C@@H](O)CO)c12] | N-[[1-[4-(pentafluoro-lambda6-sulfanyl)phenyl]-4-[rac-(1R)-1,2-dihydroxyethyl]pyrazolo[3,4-b]pyridin-3-yl]methyl]prop-2-enamide |
| 28 | 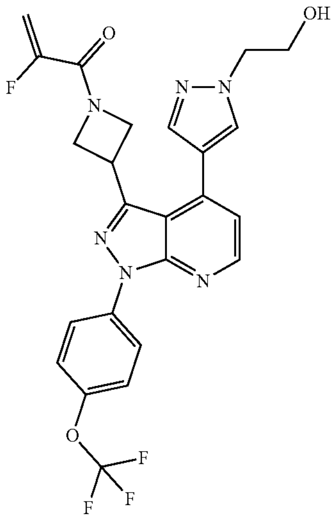 [SMILES: C=C(F)C(=O)N1CC(c2nn(-c3ccc(OC(F)(F)F)cc3)c3nccc(-c4cnn(CCO)c4)c23)C1] | 2-fluoro-1-[3-[4-[1-(2-hydroxyethyl)pyrazol-4-yl]-1-[4-(trifluoromethoxy)phenyl]pyrazolo[3,4-b]pyridin-3-yl]azetidin-1-yl]prop-2-en-1-one |
| 29 | 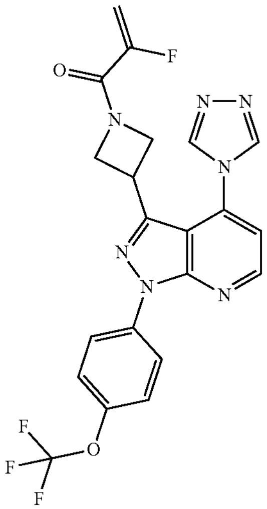 [SMILES: C=C(F)C(=O)N1CC(c2nn(-c3ccc(OC(F)(F)F)cc3)c3nccc(-n4cnnc4)c23)C1] | 2-fluoro-1-[3-[4-(1,2,4-triazol-4-yl)-1-[4-(trifluoromethoxy)phenyl]pyrazolo[3,4-b]pyridin-3-yl]azetidin-1-yl]prop-2-en-1-one |

TABLE 1-continued
| Compound Number | Structure | Compound Name |
|---|---|---|
| 30 | 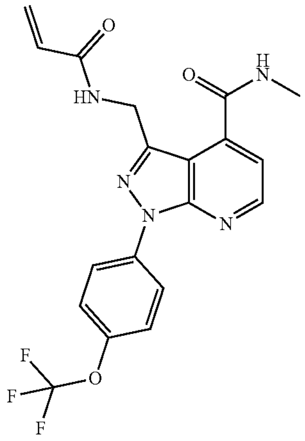 [SMILES: C=CC(=O)NCc1nn(-c2ccc(OC(F)(F)F)cc2)c2nccc(C(=O)NC)c12] | N-methyl-3-[(prop-2-enoylamino)methyl]-1-[4-(trifluoromethoxy)phenyl]pyrazolo[3,4-b]pyridine-4-carboxamide |
| 31 | 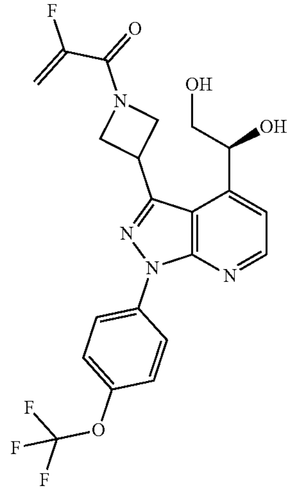 [SMILES: C=C(F)C(=O)N1CC(c2nn(-c3ccc(OC(F)(F)F)cc3)c3nccc([C@H](O)CO)c23)C1] | 1-[3-[4-[(1S)-1,2-dihydroxyethyl]-1-[4-(trifluoromethoxy)phenyl]pyrazolo[3,4-b]pyridin-3-yl]azetidin-1-yl]-2-fluoro-prop-2-en-1-one |
| 32 | 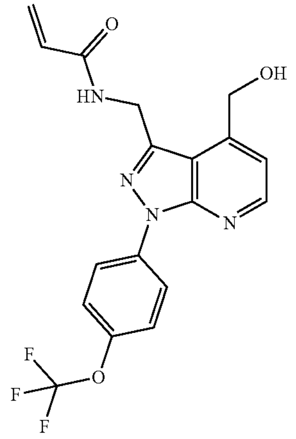 [SMILES: C=CC(=O)NCc1nn(-c2ccc(OC(F)(F)F)cc2)c2nccc(CO)c12] | N-[[4-(hydroxymethyl)-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 33 | 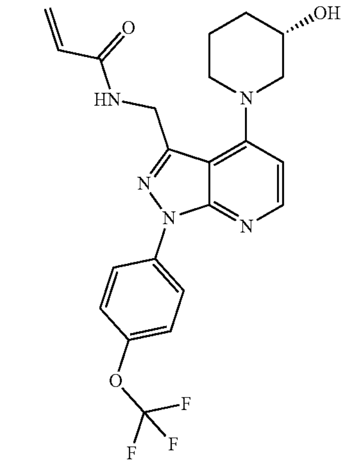 [SMILES: C=CC(=O)NCc1nn(-c2ccc(OC(F)(F)F)cc2)c2nccc(N3CCC[C@H](O)C3)c12] | N-[[4-[(3S)-3-hydroxy-1-piperidyl]-1-[4-(trifluoromethoxy)phenyl]pyrazolo[3,4-b]pyridin-3-yl]methyl]prop-2-enamide |
| 34 | 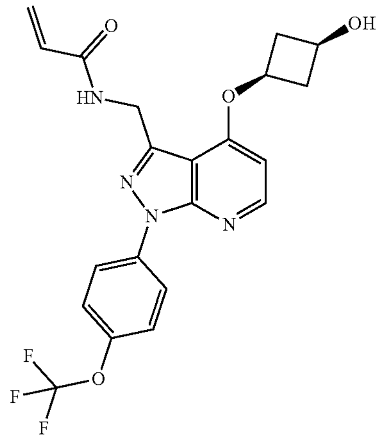 [SMILES: C=CC(=O)NCc1nn(-c2ccc(OC(F)(F)F)cc2)c2nccc(O[C@H]3C[C@@H](O)C3)c12] | N-[[4-(3-hydroxycyclobutoxy)-1-[4-(trifluoromethoxy)phenyl]pyrazolo[3,4-b]pyridin-3-yl]methyl]prop-2-enamide |
| 35 | 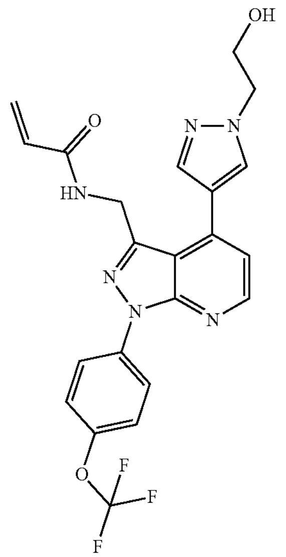 [SMILES: C=CC(=O)NCc1nn(-c2ccc(OC(F)(F)F)cc2)c2nccc(-c3cnn(CCO)c3)c12] | N-[[4-[1-(2-hydroxyethyl)pyrazol-4-yl]-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 36 | 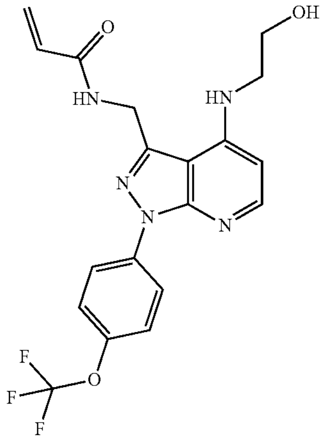 | N-[[4-(2-hydroxyethylamino)-1-[4-(trifluoromethoxy)phenyl]pyrazolo[3,4-b]pyridin-3-yl]methyl]prop-2-enamide |
| 37 | 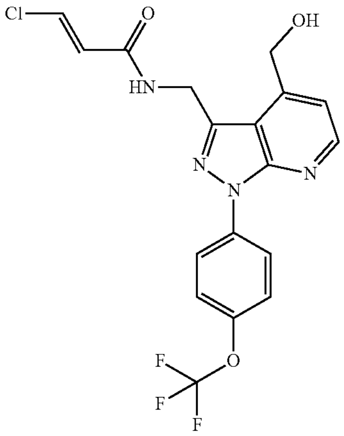 [SMILES: O=C(/C=C/Cl)NCc1nn(-c2ccc(OC(F)(F)F)cc2)c2nccc(CO)c12] | (E)-3-chloro-N-[[4-(hydroxymethyl)-1-[4-(trifluoromethoxy)phenyl]pyrazolo[3,4-b]pyridin-3-yl]methyl]prop-2-enamide |
| 38 | 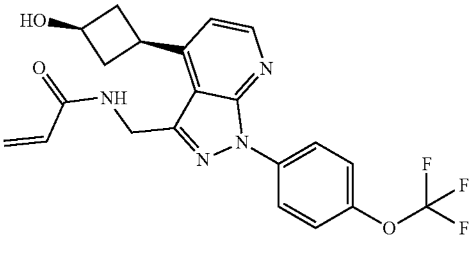 [SMILES: C=CC(=O)NCc1nn(-c2ccc(OC(F)(F)F)cc2)c2nccc([C@H]3C[C@@H](O)C3)c12] | N-[[4-(3-hydroxycyclobutyl)-1-[4-(trifluoromethoxy)phenyl]pyrazolo[3,4-b]pyridin-3-yl]methyl]prop-2-enamide |

TABLE 1-continued

| Compound Number | Structure | Compound Name |
|---|---|---|
| 39 | 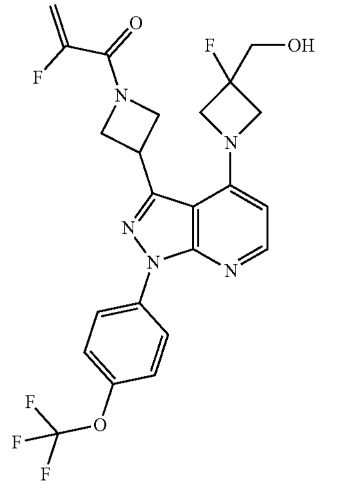 [SMILES: C=C(F)C(=O)N1CC(c2nn(-c3ccc(OC(F)(F)F)cc3)c3nccc(N4CC(F)(CO)C4)c23)C1] | 2-fluoro-1-[3-[4-[3-fluoro-3-(hydroxymethyl)azetidin-1-yl]-1-[4-(trifluoromethoxy)phenyl]pyrazolo[3,4-b]pvridin-3-yl]azetidin-1-yl]prop-2-en-1-one |
| 40 | 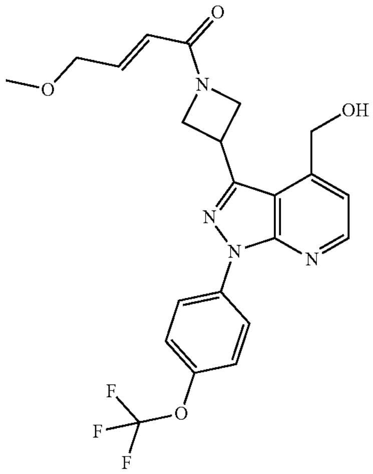 [SMILES: COC/C=C/C(=O)N1CC(c2nn(-c3ccc(OC(F)(F)F)cc3)c3nccc(CO)c23)C1] | (E)-1-[3-[4-(hydroxymethyl)-1-[4-(trifluoromethoxy)phenyl]pyrazolo[3,4-b]pyridin-3-yl]azetidin-1-yl]-4-methoxy-but-2-en-1-one |
| 41 | 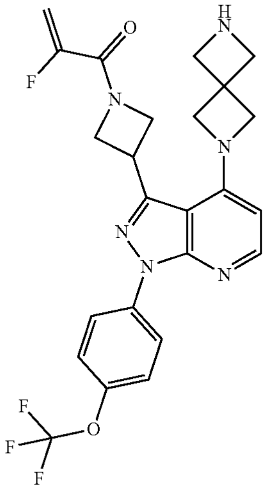 [SMILES: C=C(F)C(=O)N1CC(c2nn(-c3ccc(OC(F)(F)F)cc3)c3nccc(N4CC5(CNC5)C4)c23)C1] | 1-[3-[4-(2,6-diazaspiro[3.3]heptan-2-yl)-1-[4-(trifluoromethoxy)phenyl]pyrazolo[3,4-b]pyridin-3-yl]azetidin-1-yl]-2-fluoro-prop-2-en-1-one |

TABLE 1-continued
| Compound Number | Structure | Compound Name |
|---|---|---|
| 42 | 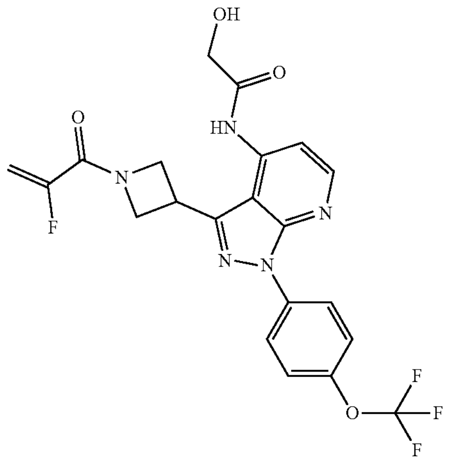 [SMILES: C=C(F)C(=O)N1CC(c2nn(-c3ccc(OC(F)(F)F)cc3)c3nccc(NC(=O)CO)c23)C1] | N-[3-[1-(2-fluoroprop-2-enoyl)azetidin-3-yl]-1-[4-(trifluoromethoxy)phenyl]pyrazolo[3,4-b]pyridin-4-yl]-2-hydroxy-acetamide |
| 43 | 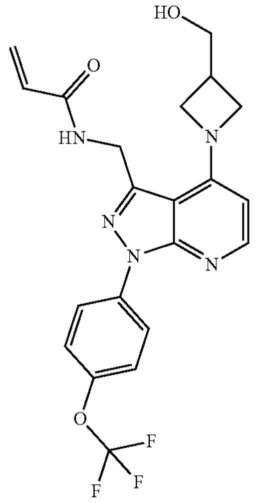 [SMILES: C=CC(=O)NCc1nn(-c2ccc(OC(F)(F)F)cc2)c2nccc(N3CC(CO)C3)c12] | N-[[4-[3-(hydroxymethyl)azetidin-1-yl]-1-[4-(trifluoromethoxy)phenyl]pyrazolo[3,4-b]pyridin-3-yl]methyl]prop-2-enamide |
| 44 | 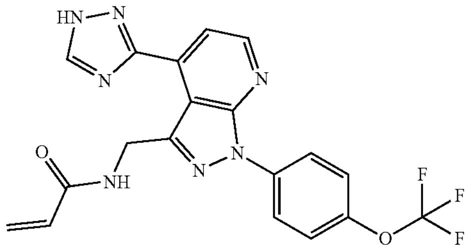 [SMILES: C=CC(=O)NCc1nn(-c2ccc(OC(F)(F)F)cc2)c2nccc(-c3nc[nH]n3)c12] | N-[[4-(1H-1,2,4-triazol-3-yl)-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 45 | 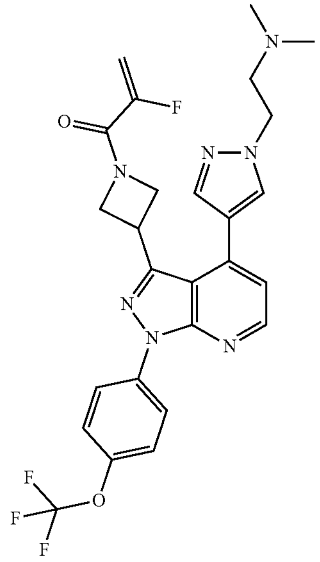 [SMILES: C=C(F)C(=O)N1CC(c2nn(-c3ccc(OC(F)(F)F)cc3)c3nccc(-c4cnn(CCN(C)C)c4)c23)C1] | 1-[3-[4-[1-[2-(dimethylamino)ethyl]pyrazol-4-yl]-1-[4-(trifluoromethoxy)phenyl]pyrazolo[3,4-b]pyridin-3-yl]azetidin-1-yl]-2-fluoro-prop-2-en-1-one |
| 46 | 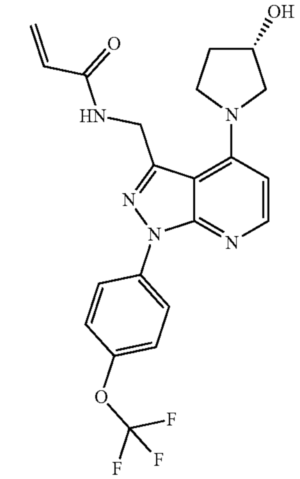 [SMILES: C=CC(=O)NCc1nn(-c2ccc(OC(F)(F)F)cc2)c2nccc(N3CC[C@H](O)C3)c12] | N-[[4-[(3S)-3-hydroxypyrrolidin-1-yl]-1-[4-(trifluoromethoxy)phenyl]pyrazolo[3,4-b]pyridin-3-yl]methyl]prop-2-enamide |
| 47 | 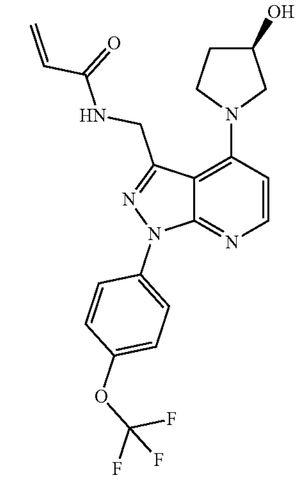 [SMILES: C=CC(=O)NCc1nn(-c2ccc(OC(F)(F)F)cc2)c2nccc(N3CC[C@@H](O)C3)c12] | N-[[4-[(3R)-3-hydroxypyrrolidin-1-yl]-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 48 | 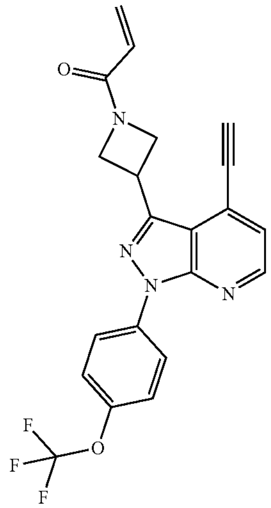 [SMILES: C#Cc1ccnc2c1c(C1CN(C(=O)C=C)C1)nn2-c1ccc(OC(F)(F)F)cc1] | 1-[3-[4-ethynyl-1-[4-(trifluoromethoxy)phenyl]pyrazolo[3,4-b]pyridin-3-yl]azetidin-1-yl]prop-2-en-1-one |
| 49 | 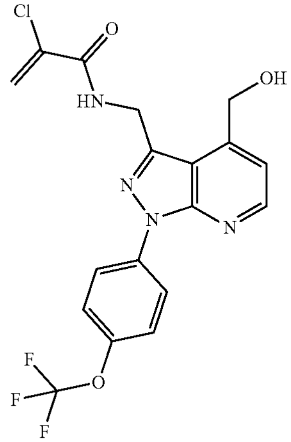 [SMILES: C=C(Cl)C(=O)NCc1nn(-c2ccc(OC(F)(F)F)cc2)c2nccc(CO)c12] | 2-chloro-N-[[4-(hydroxymethyl)-1-[4-(trifluoromethoxy)phenyl]pyrazolo[3,4-b]pyridin-3-yl]methyl]prop-2-enamide |
| 50 | 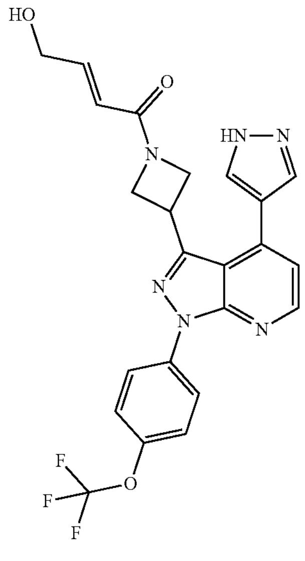 [SMILES: O=C(/C=C/CO)N1CC(c2nn(-c3ccc(OC(F)(F)F)cc3)c3nccc(-c4cn[nH]c4)c23)C1] | (E)-4-hydroxy-1-[3-[4-(1H-pyrazol-4-yl)-1-[4-(trifluoromethoxy)phenyl]pyrazolo[3,4-b]pyridin-3-yl]azetidin-1-yl]but-2-en-1-one |

TABLE 1-continued
| Compound Number | Structure | Compound Name |
|---|---|---|
| 51 | 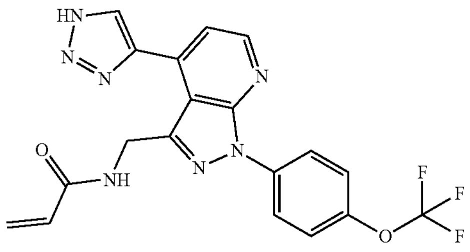 [SMILES: C=CC(=O)NCc1nn(-c2ccc(OC(F)(F)F)cc2)c2nccc(-c3c[nH]nn3)c12] | N-[[4-(1H-triazol-4-yl)-1-[4-(trifluoromethoxy)phenyl]pyrazolo[3,4-b]pyridin-3-yl]methyl]prop-2-enamide |
| 52 | 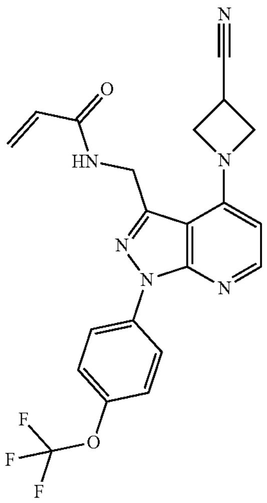 [SMILES: C=CC(=O)NCc1nn(-c2ccc(OC(F)(F)F)cc2)c2nccc(N3CC(C#N)C3)c12] | N-[[4-(3-cyanoazetidin-1-yl)-1-[4-(trifluoromethoxy)phenyl]pyrazolo[3,4-b]pyridin-3-yl]methyl]prop-2-enamide |
| 53 | 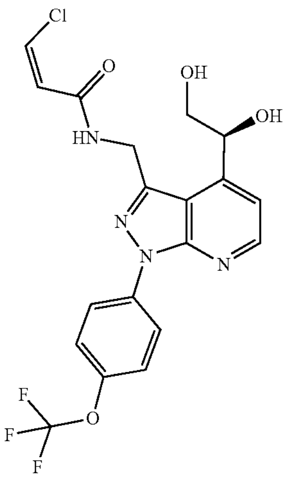 [SMILES: O=C(/C=C\Cl)NCc1nn(-c2ccc(OC(F)(F)F)cc2)c2nccc([C@H](O)CO)c12] | (Z)-3-chloro-N-[[4-[(1S)-1,2-dihydroxyethyl]-1-[4-(trifluoromethoxy)phenyl]pyrazolo[3,4-b]pyridin-3-yl]methyl]prop-2-enamide |

TABLE 1-continued
| Compound Number | Structure | Compound Name |
| --- | --- | --- |
| 54 | 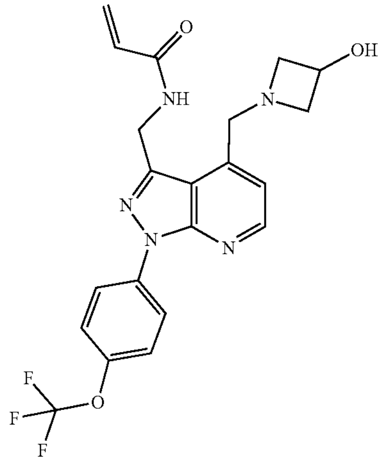 [SMILES: C=CC(=O)NCc1nn(-c2ccc(OC(F)(F)F)cc2)c2nccc(CN3CC(O)C3)c12] | N-[[4-[(3-hydroxyazetidin-1-yl)methyl]-1-[4-(trifluoromethoxy)phenyl]pyrazolo[3,4-b]pyridin-3-yl]methyl]prop-2-enamide |
| 55 | 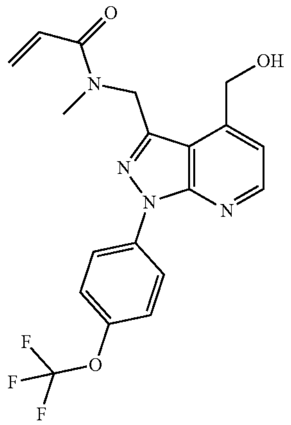 [SMILES: C=CC(=O)N(C)Cc1nn(-c2ccc(OC(F)(F)F)cc2)c2nccc(CO)c12] | N-[[4-(hydroxymethyl)-1-[4-(trifluoromethoxy)phenyl]pyrazolo[3,4-b]pyridin-3-yl]methyl]-N-methyl-prop-2-enamide |
| 56 | 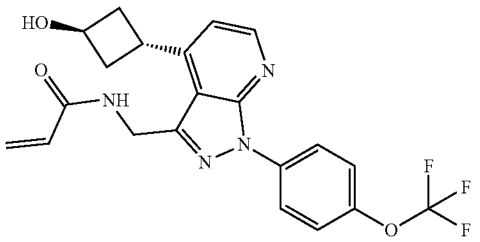 [SMILES: C=CC(=O)NCc1nn(-c2ccc(OC(F)(F)F)cc2)c2nccc([C@H]3C[C@H](O)C3)c12] | N-[[4-(3-hydroxycyclobutyl)-1-[4-(trifluoromethoxy)phenyl]pyrazolo[3,4-b]pyridin-3-yl]methyl]prop-2-enamide |

TABLE 1-continued

| Compound Number | Structure | Compound Name |
|---|---|---|
| 57 | 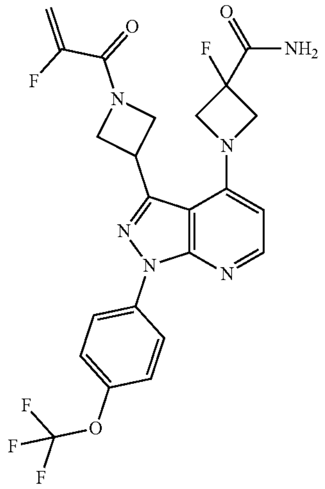 [SMILES: C=C(F)C(=O)N1CC(c2nn(-c3ccc(OC(F)(F)F)cc3)c3nccc(N4CC(F)(C(N)=O)C4)c23)C1] | 3-fluoro-1-[3-[1-(2-fluoroprop-2-enoyl)azetidin-3-yl]-1-[4-(trifluoromethoxy)phenyl]pyrazolo[3,4-b]pyridin-4-yl]azetidine-3-carboxamide |
| 58 | 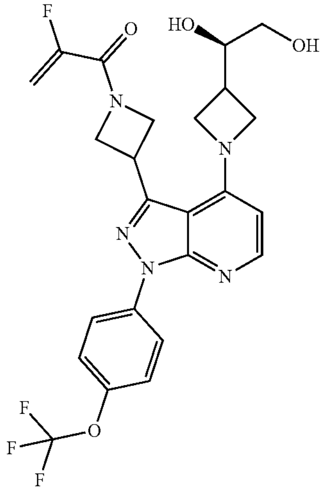 [SMILES: C=C(F)C(=O)N1CC(c2nn(-c3ccc(OC(F)(F)F)cc3)c3nccc(N4CC([C@@H](O)CO)C4)c23)C1] | 1-[3-[4-[3-[(1R)-1,2-dihydroxyethyl]azetidin-1-yl]-1-[4-(trifluoromethoxy)phenyl]pyrazolo [3,4-b]pyridin-3-yl]azetidin-1-yl]-2-fluoro-prop-2-en-1-one |
| 59 | 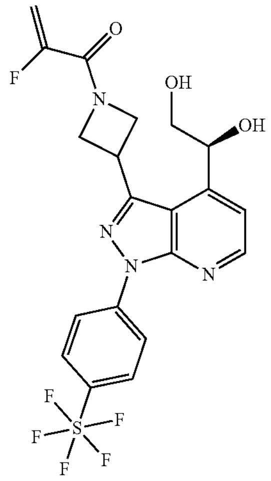 [SMILES: C=C(F)C(=O)N1CC(c2nn(-c3ccc(S(F)(F)(F)(F)F)cc3)c3nccc([C@H](O)CO)c23)C1] | 1-[3-[4-[(1S)-1,2-dihydroxyethyl]-1-[4-(pentafluoro-lambda6-sulfanyl)phenyl]pyrazolo[3,4-b]pyridin-3-yl]azetidin-1-yl]-2-fluoro-prop-2-en-1-one |

TABLE 1-continued
| Compound Number | Structure | Compound Name |
|---|---|---|
| 60 | 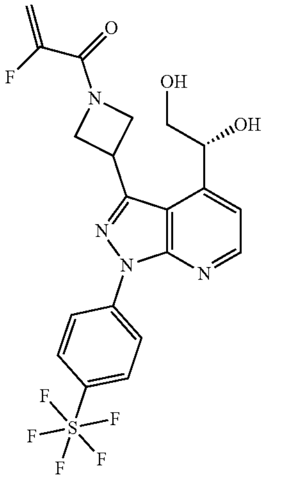 [SMILES: C=C(F)C(=O)N1CC(c2nn(-c3ccc(S(F)(F)(F)(F)F)cc3)c3nccc([C@@H](O)CO)c23)C1] | 1-[3-[4-[(1R)-1,2-dihydroxyethyl]-1-[4-(pentafluoro-lambda6-sulfanyl)phenyl]pyrazolo[3,4-b]pyridin-3-yl]azetidin-1-yl]-2-fluoro-prop-2-en-1-one |
| 61 | 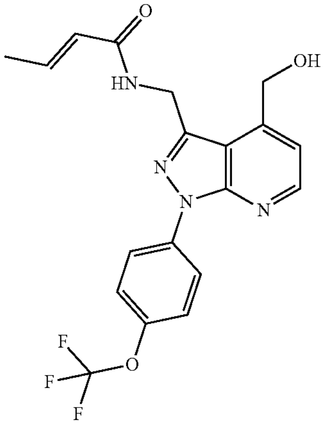 [SMILES: C/C=C/C(=O)NCc1nn(-c2ccc(OC(F)(F)F)cc2)c2nccc(CO)c12] | (E)-N-[[4-(hydroxymethyl)-1-[4-(trifluoromethoxy)phenyl]pyrazolo[3,4-b]pyridin-3-yl]methyl]but-2-enamide |
| 62 | 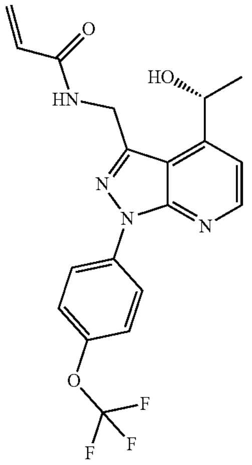 [SMILES: C=CC(=O)NCc1nn(-c2ccc(OC(F)(F)F)cc2)c2nccc([C@@H](C)O)c12] | N-[[4-[(1R)-1-hydroxyethyl]-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 63 | 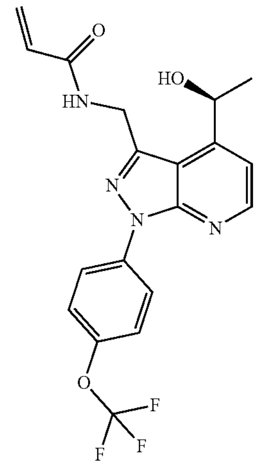 [SMILES: C=CC(=O)NCc1nn(-c2ccc(OC(F)(F)F)cc2)c2nccc([C@H](C)O)c12] | N-[[4-[(1S)-1-hydroxyethyl]-1-[4-(trifluoromethoxy)phenyl]pyrazolo[3,4-b]pyridin-3-yl]methyl]prop-2-enamide |
| 64 | 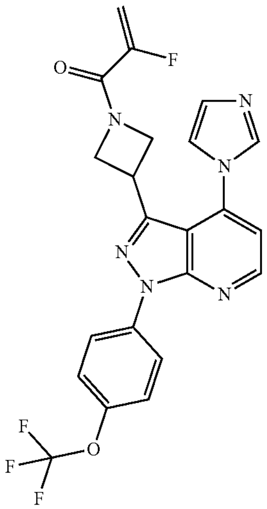 [SMILES: C=C(F)C(=O)N1CC(c2nn(-c3ccc(OC(F)(F)F)cc3)c3nccc(-n4ccnc4)c23)C1] | 2-fluoro-1-[3-[4-imidazol-1-yl-1-[4-(trifluoromethoxy)phenyl]pyrazolo[3,4-b]pyridin-3-yl]azetidin-1-yl]prop-2-en-1-one |
| 65 | 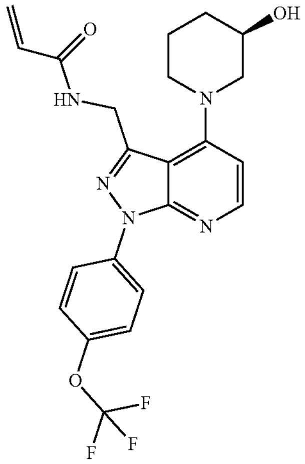 [SMILES: C=CC(=O)NCc1nn(-c2ccc(OC(F)(F)F)cc2)c2nccc(N3CCC[C@@H](O)C3)c12] | N-[[4-[(3R)-3-hydroxy-1-piperidyl]-1-[4-(trifluoromethoxy)phenyl]pyrazolo[3,4-b]pyridin-3-yl]methyl]prop-2-enamide |

TABLE 1-continued
| Compound Number | Structure | Compound Name |
| --- | --- | --- |
| 66 | 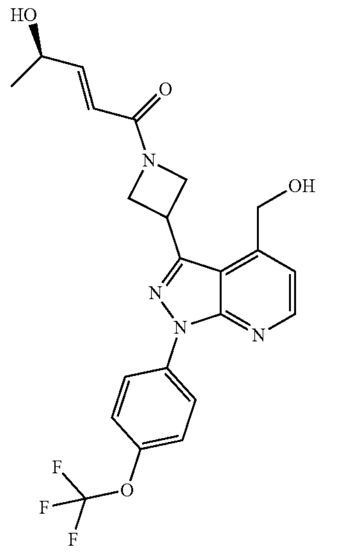 [SMILES: C[C@@H](O)/C=C/C(=O)N1CC(c2nn(-c3ccc(OC(F)(F)F)cc3)c3nccc(CO)c23)C1] | (E,4R)-4-hydroxy-1-[3-[4-(hydroxymethyl)-1-[4-(trifluoromethoxy)phenyl]pyrazolo[3,4-b]pyridin-3-yl]azetidin-1-yl]pent-2-en-1-one |
| 67 | 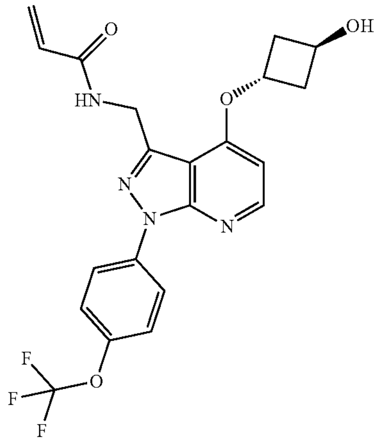 [SMILES: C=CC(=O)NCc1nn(-c2ccc(OC(F)(F)F)cc2)c2nccc(O[C@H]3C[C@H](O)C3)c12] | N-[[4-(3-hydroxycyclobutoxy)-1-[4-(trifluoromethoxy)phenyl]pyrazolo[3,4-b]pyridin-3-yl]methyl]prop-2-enamide |
| 68 | 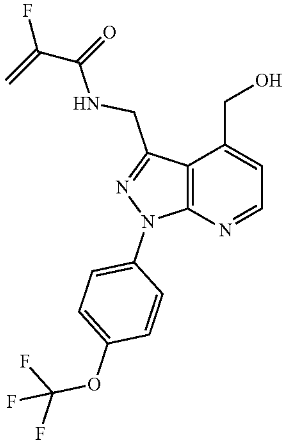 [SMILES: C=C(F)C(=O)NCc1nn(-c2ccc(OC(F)(F)F)cc2)c2nccc(CO)c12] | 2-fluoro-N-[[4-(hydroxymethyl)-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 69 | 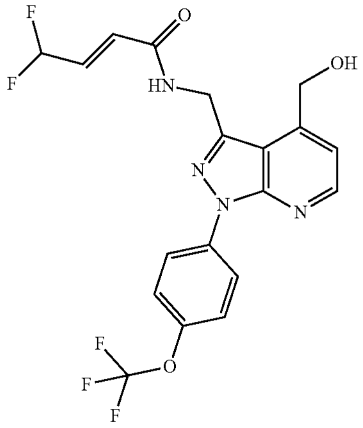 [SMILES: O=C(/C=C/C(F)F)NCc1nn(-c2ccc(OC(F)(F)F)cc2)c2nccc(CO)c12] | (E)-4,4-difluoro-N-[[4-(hydroxymethyl)-1-[4-(trifluoromethoxy)phenyl]pyrazolo[3,4-b]pyridin-3-yl]methyl]but-2-enamide |
| 70 | 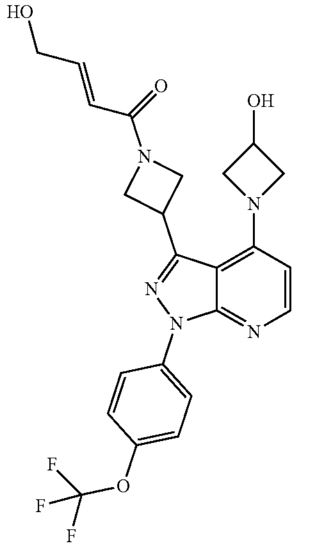 [SMILES: O=C(/C=C/CO)N1CC(c2nn(-c3ccc(OC(F)(F)F)cc3)c3nccc(N4CC(O)C4)c23)C1] | (E)-4-hydroxy-1-[3-[4-(3-hydroxyazetidin-1-yl)-1-[4-(trifluoromethoxy)phenyl]pyrazolo[3,4-b]pyridin-3-yl]azetidin-1-yl]but-2-en-1-one |
| 71 | 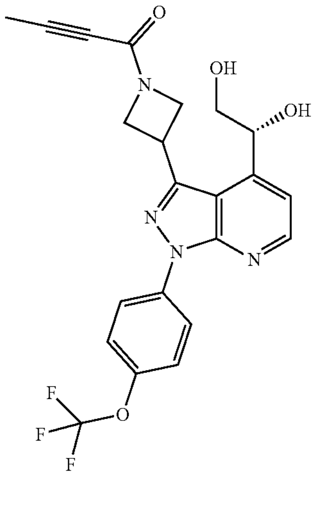 [SMILES: CC#CC(=O)N1CC(c2nn(-c3ccc(OC(F)(F)F)cc3)c3nccc([C@@H](O)CO)c23)C1] | 1-[3-[4-[(1R)-1,2-dihydroxyethyl]-1-[4-(trifluoromethoxy)phenyl]pyrazolo[3,4-b]pyridin-3-yl]azetidin-1-yl]but-2-yn-1-one |

TABLE 1-continued
| Compound Number | Structure | Compound Name |
|---|---|---|
| 72 | 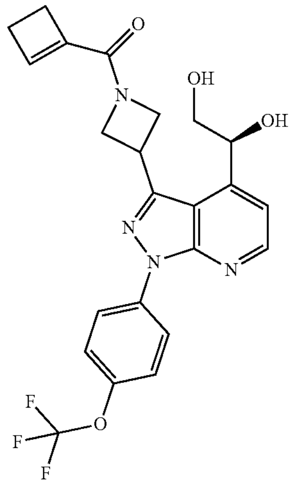 [SMILES: O=C(C1=CCC1)N1CC(c2nn(-c3ccc(OC(F)(F)F)cc3)c3nccc([C@H](O)CO)c23)C1] | cyclobuten-1-yl-[3-[4-[(1S)-1,2-dihydroxyethyl]-1-[4-(trifluoromethoxy)phenyl]pyrazolo[3,4-b]pyridin-3-yl]azetidin-1-yl]methanone |
| 73 | 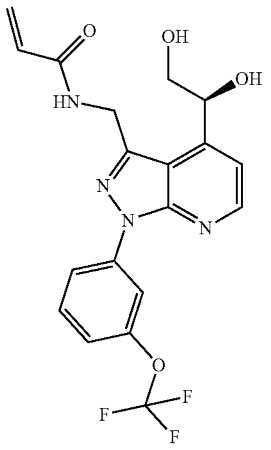 [SMILES: C=CC(=O)NCc1nn(-c2cccc(OC(F)(F)F)c2)c2nccc([C@H](O)CO)c12] | N-[[4-[rac-(1S)-1,2-dihydroxyethyl]-1-[3-(trifluoromethoxy)phenyl]pyrazolo[3,4-b]pyridin-3-yl]methyl]prop-2-enamide |
| 74 | 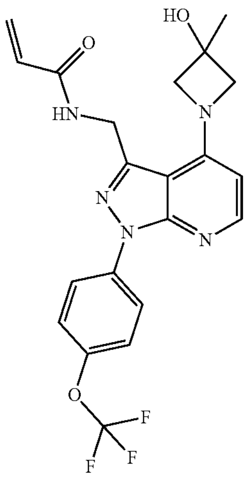 [SMILES: C=CC(=O)NCc1nn(-c2ccc(OC(F)(F)F)cc2)c2nccc(N3CC(C)(O)C3)c12] | N-[[4-(3-hydroxy-3-methyl-azetidin-1-yl)-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 75 | 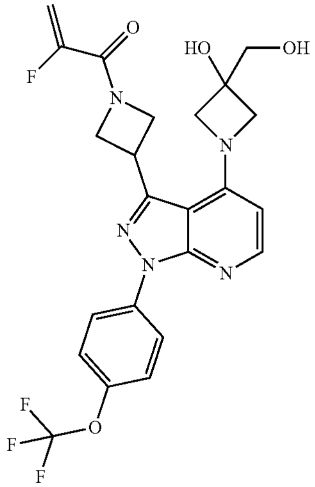 [SMILES: C=C(F)C(=O)N1CC(c2nn(-c3ccc(OC(F)(F)F)cc3)c3nccc(N4CC(O)(CO)C4)c23)C1] | 2-fluoro-1-[3-[4-[3-hydroxy-3-(hydroxymethyl)azetidin-1-yl]-1-[4-(trifluoromethoxy)phenyl]pyrazolo[3,4-b]pyridin-3-yl]azetidin-1-yl]prop-2-en-1-one |
| 76 | 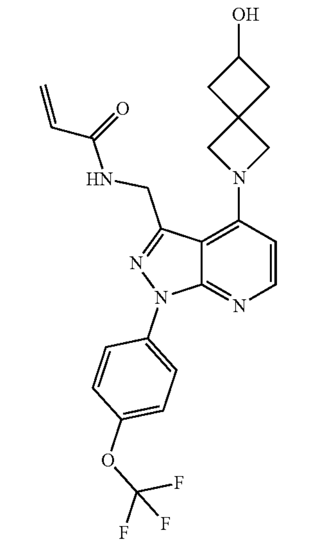 [SMILES: C=CC(=O)NCc1nn(-c2ccc(OC(F)(F)F)cc2)c2nccc(N3CC4(CC(O)C4)C3)c12] | N-[[4-(6-hydroxy-2-azaspiro[3.3]heptan-2-yl)-1-[4-(trifluoromethoxy)phenyl]pyrazolo[3,4-b]pyridin-3-yl]methyl]prop-2-enamide |
| 77 | 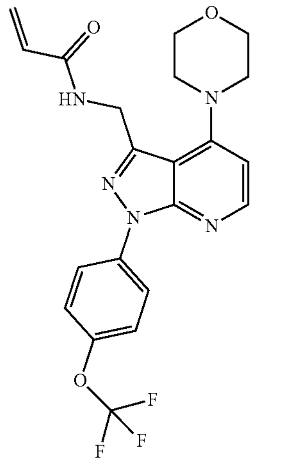 | N-[[4-morpholino-1-[4-(trifluoromethoxy)phenyl]pyrazolo[3,4-b]pyridin-3-yl]methyl]prop-2-enamide |

TABLE 1-continued
| Compound Number | Structure | Compound Name |
| --- | --- | --- |
| 78 | 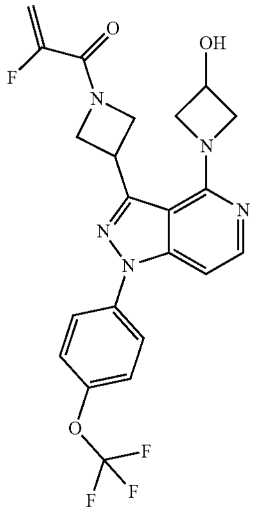 [SMILES: C=C(F)C(=O)N1CC(c2nn(-c3ccc(OC(F)(F)F)cc3)c3ccnc(N4CC(O)C4)c23)C1] | 2-fluoro-1-[3-[4-(3-hydroxyazetidin-1-yl)-1-[4-(trifluoromethoxy)phenyl]pyrazolo[4,3-c]pyridin-3-yl]azetidin-1-yl]prop-2-en-1-one |
| 79 | 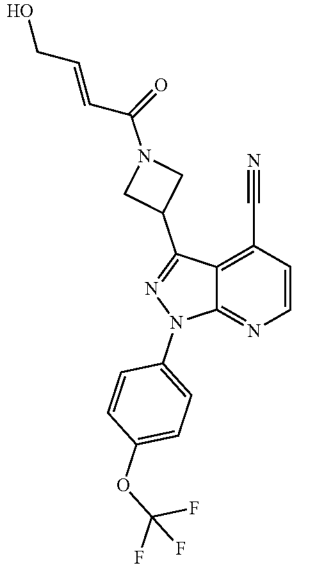 [SMILES: N#Cc1ccnc2c1c(C1CN(C(=O)/C=C/CO)C1)nn2-c1ccc(OC(F)(F)F)cc1] | 3-[1-[(E)-4-hydroxybut-2-enoyl]azetidin-3-yl]-1-[4-(trifluoromethoxy)phenyl]pyrazolo[3,4-b]pyridine-4-carbonitrile |
| 80 | 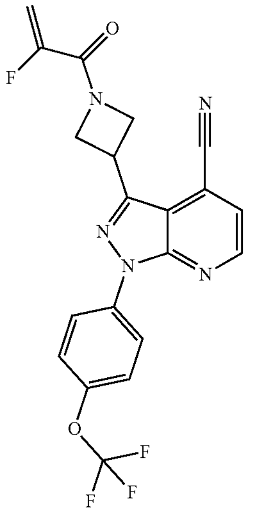 [SMILES: C=C(F)C(=O)N1CC(c2nn(-c3ccc(OC(F)(F)F)cc3)c3nccc(C#N)c23)C1] | 3-[1-(2-fluoroprop-2-enoyl)azetidin-3-yl]-1-[4-(trifluoromethoxy)phenyl]pyrazolo[3,4-b]pyridine-4-carbonitrile |

TABLE 1-continued
| Compound Number | Structure | Compound Name |
|---|---|---|
| 81 | 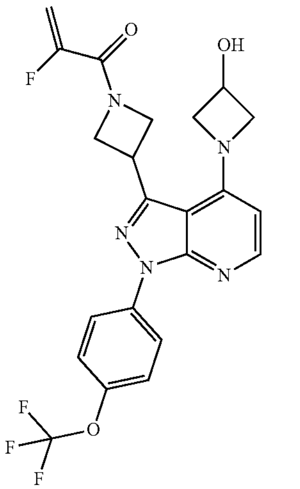 [SMILES: C=C(F)C(=O)N1CC(c2nn(-c3ccc(OC(F)(F)F)cc3)c3nccc(N4CC(O)C4)c23)C1] | 2-fluoro-1-[3-[4-(3-hydroxyazetidin-1-yl)-1-[4-(trifluoromethoxy)phenyl]pyrazolo[3,4-b]pyridin-3-yl]azetidin-1-yl]prop-2-en-1-one |
| 82 | 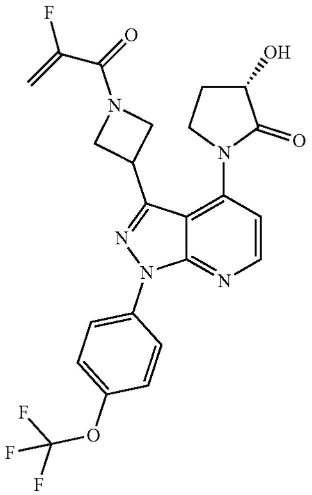 [SMILES: C=C(F)C(=O)N1CC(c2nn(-c3ccc(OC(F)(F)F)cc3)c3nccc(N4CC[C@H](O)C4=O)c23)C1] | (3S)-1-[3-[1-(2-fluoroprop-2-enoyl)azetidin-3-yl]-1-[4-(trifluoromethoxy)phenyl]pyrazolo[3,4-b]pyridin-4-yl]-3-hydroxy-pyrrolidin-2-one |
| 83 | 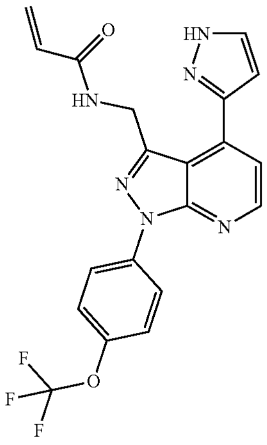 [SMILES: C=CC(=O)NCc1nn(-c2ccc(OC(F)(F)F)cc2)c2nccc(-c3cc[nH]n3)c12] | N-[[4-(1H-pyrazol-3-yl)-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 84 | 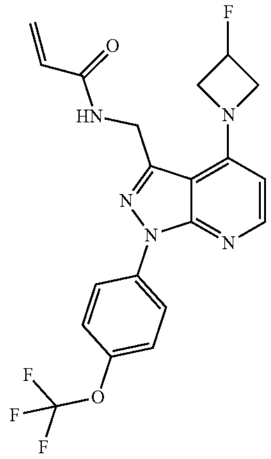 | N-[[4-(3-fluoroazetidin-1-yl)-1-[4-(trifluoromethoxy)phenyl]pyrazolo[3,4-b]pyridin-3-yl]methyl]prop-2-enamide |
| 85 | 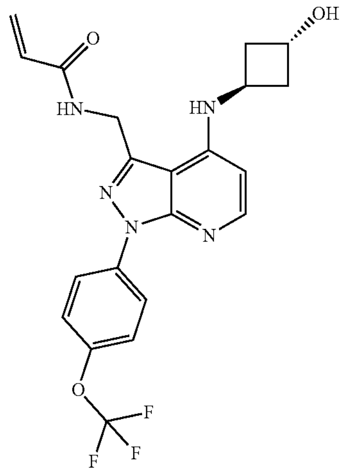 [SMILES: C=CC(=O)NCc1nn(-c2ccc(OC(F)(F)F)cc2)c2nccc(N[C@H]3C[C@H](O)C3)c12] | N-[[4-[(3-hydroxycyclobutyl)amino]-1-[4-(trifluoromethoxy)phenyl]pyrazolo[3,4-b]pyridin-3-yl]methyl]prop-2-enamide |
| 86 | 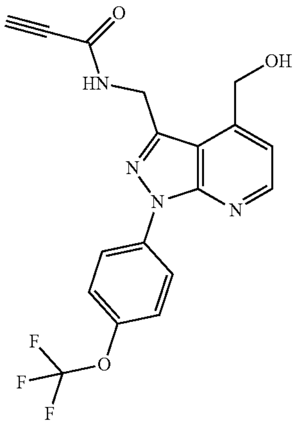 [SMILES: C#CC(=O)NCc1nn(-c2ccc(OC(F)(F)F)cc2)c2nccc(CO)c12] | N-[[4-(hydroxymethyl)-1-[4-(trifluoromethoxy)phenyl]pyrazolo[3,4-b]pyridin-3-yl]methyl]prop-2-ynamide |

TABLE 1-continued
| Compound Number | Structure | Compound Name |
| --- | --- | --- |
| 87 | 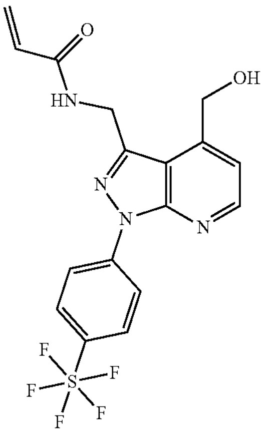 [SMILES: C=CC(=O)NCc1nn(-c2ccc(S(F)(F)(F)(F)F)cc2)c2nccc(CO)c12] | N-[[4-(hydroxymethyl)-1-[4-(pentafluoro-lambda6-sulfanyl)phenyl]pyrazolo[3,4-b]pyridin-3-yl]methyl]prop-2-enamide |
| 88 | 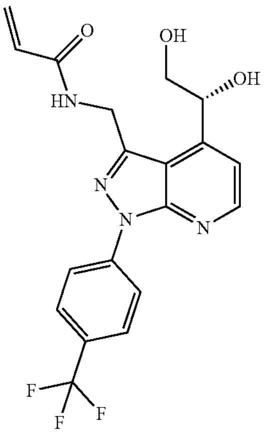 [SMILES: C=CC(=O)NCc1nn(-c2ccc(C(F)(F)F)cc2)c2nccc([C@@H](O)CO)c12] | N-[[4-[rac-(1R)-1,2-dihydroxyethyl]-1-[4-(trifluoromethyl)phenyl]pyrazolo[3,4-b]pyridin-3-yl]methyl]prop-2-enamide |
| 89 | 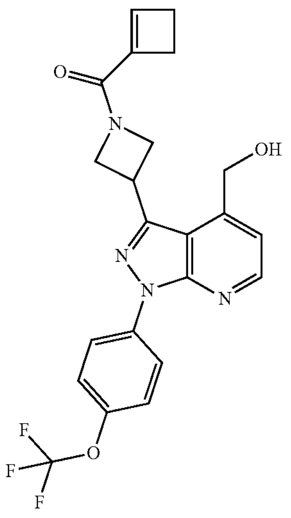 [SMILES: O=C(C1=CCC1)N1CC(c2nn(-c3ccc(OC(F)(F)F)cc3)c3nccc(CO)c23)C1] | cyclobuten-1-yl-[3-[4-(hydroxymethyl)-1-[4-(trifluoromethoxy)phenyl]pyrazolo[3,4-b]pyridin-3-yl]azetidin-1-yl]methanone |

TABLE 1-continued
| Compound Number | Structure | Compound Name |
| --- | --- | --- |
| 90 | 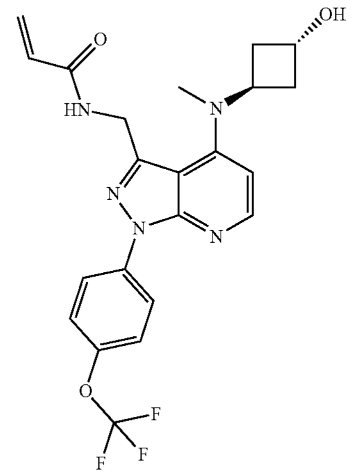 [SMILES: C=CC(=O)NCc1nn(-c2ccc(OC(F)(F)F)cc2)c2nccc(N(C)[C@H]3C[C@H](O)C3)c12] | N-[[4-[(3-hydroxycyclobutyl)-methyl-amino]-1-[4-(trifluoromethoxy)phenyl]pyrazolo[3,4-b]pyridin-3-yl]methyl]prop-2-enamide |
| 91 | 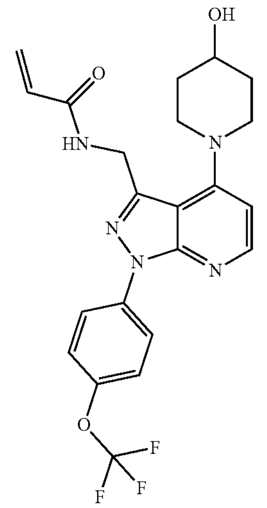 [SMILES: C=CC(=O)NCc1nn(-c2ccc(OC(F)(F)F)cc2)c2nccc(N3CCC(O)CC3)c12] | N-[[4-(4-hvdroxy-1-piperidyl)-1-[4-(trifluoromethoxy)phenyl]pyrazolo[3,4-b]pyridin-3-yl]methyl]prop-2-enamide |
| 92 | 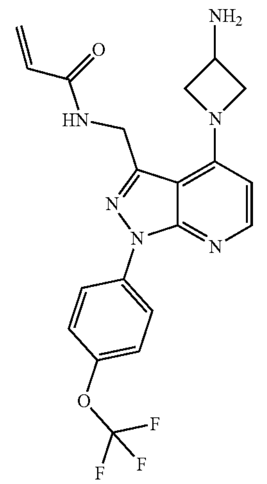 [SMILES: C=CC(=O)NCc1nn(-c2ccc(OC(F)(F)F)cc2)c2nccc(N3CC(N)C3)c12] | N-[[4-(3-aminoazetidin-1-yl)-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 93 | 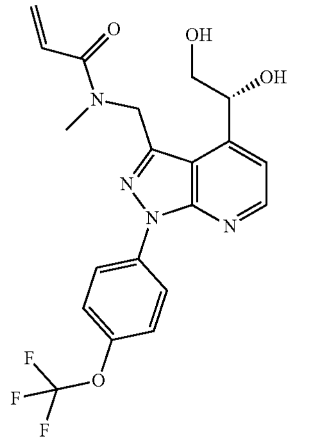 [SMILES: C=CC(=O)N(C)Cc1nn(-c2ccc(OC(F)(F)F)cc2)c2nccc([C@@H](O)CO)c12] | N-[[4-[(1R)-1,2-dihydroxyethyl]-1-[4-(trifluoromethoxy)phenyl]pyrazolo[3,4-b]pyridin-3-yl]methyl]-N-methyl-prop-2-enamide |
| 94 | 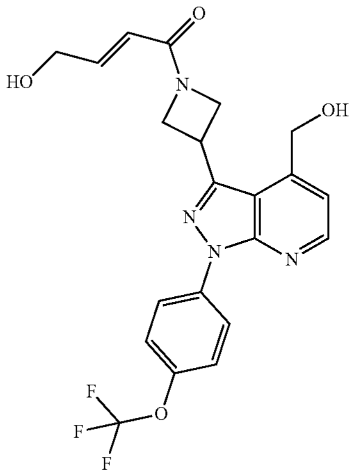 [SMILES: O=C(/C=C/CO)N1CC(c2nn(-c3ccc(OC(F)(F)F)cc3)c3nccc(CO)c23)C1] | (E)-4-hydroxy-1-[3-[4-(hydroxymethyl)-1-[4-(trifluoromethoxy)phenyl]pyrazolo[3,4-b]pyridin-3-yl]azetidin-1-yl]but-2-en-1-one |
| 95 | 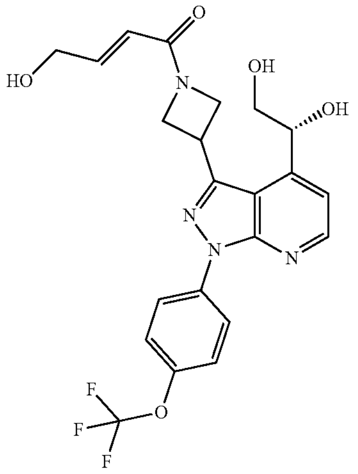 [SMILES: O=C(/C=C/CO)N1CC(c2nn(-c3ccc(OC(F)(F)F)cc3)c3nccc([C@@H](O)CO)c23)C1] | (E)-1-[3-[4-[(1R)-1,2-dihydroxyethyl]-1-[4-(trifluoromethoxy)phenyl]pyrazolo[3,4-b]pyridin-3-yl]azetidin-1-yl]-4-hydroxy-but-2-en-1-one |

TABLE 1-continued
| Compound Number | Structure | Compound Name |
| --- | --- | --- |
| 96 | 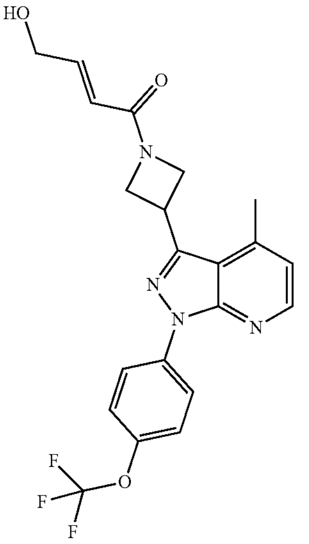 | (E)-4-hydroxy-1-[3-[4-methyl-1-[4-(trifluoromethoxy)phenyl]pyrazolo[3,4-b]pyridin-3-yl]azetidin-1-yl]but-2-en-1-one |
| 97 | 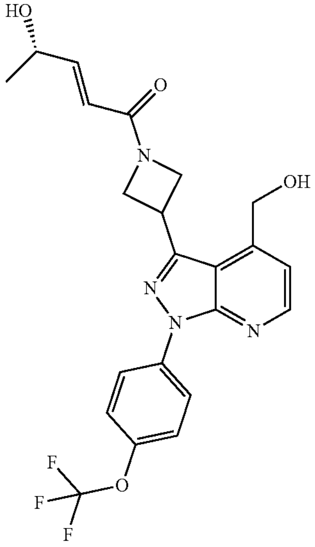 [SMILES: C[C@H](O)/C=C/C(=O)N1CC(c2nn(-c3ccc(OC(F)(F)F)cc3)c3nccc(CO)c23)C1] | (E,4S)-4-hydroxy-1-[3-[4-(hydroxymethyl)-1-[4-(trifluoromethoxy)phenyl]pyrazolo[3,4-b]pyridin-3-yl]azetidin-1-yl]pent-2-en-1-one |
| 98 | 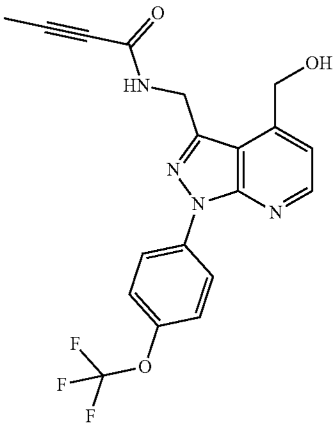 [SMILES: CC#CC(=O)NCc1nn(-c2ccc(OC(F)(F)F)cc2)c2nccc(CO)c12] | N-[[4-(hydroxymethyl)-1-[4-(trifluoromethoxy)phenyl]pyrazolo[3,4-b]pyridin-3-yl]methyl]but-2-ynamide |

TABLE 1-continued
| Compound Number | Structure | Compound Name |
| --- | --- | --- |
| 99 | 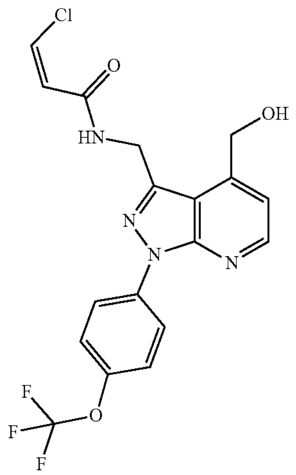 [SMILES: O=C(/C=C\Cl)NCc1nn(-c2ccc(OC(F)(F)F)cc2)c2nccc(CO)c12] | (Z)-3-chloro-N-[[4-(hydroxymethyl)-1-[4-(trifluoromethoxy)phenyl]pyrazolo[3,4-b]pyridin-3-yl]methyl]prop-2-enamide |
| 100 | 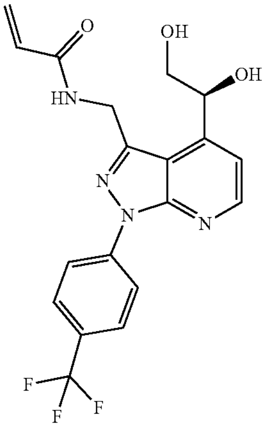 [SMILES: C=CC(=O)NCc1nn(-c2ccc(C(F)(F)F)cc2)c2nccc([C@H](O)CO)c12] | N-[[4-[rac-(1S)-1,2-dihydroxyethyl]-1-[4-(trifluoromethyl)phenyl]pyrazolo[3,4-blpyridin-3-yl]methyl]prop-2-enamide |
| 101 | 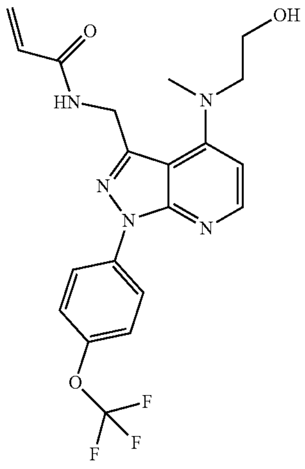 [SMILES: C=CC(=O)NCc1nn(-c2ccc(OC(F)(F)F)cc2)c2nccc(N(C)CCO)c12] | N-[[4-[2-hydroxyethyl(methyl)amino]-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 102 | 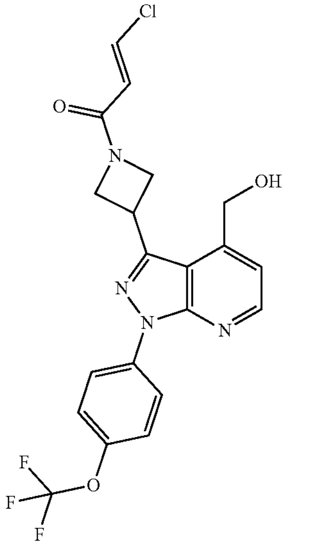 [SMILES: O=C(/C=C/Cl)N1CC(c2nn(-c3ccc(OC(F)(F)F)cc3)c3nccc(CO)c23)C1] | (E)-3-chloro-1-[3-[4-(hydroxymethyl)-1-[4-(trifluoromethoxy)phenyl]pyrazolo[3,4-b]pyridin-3-yl]azetidin-1-yl]prop-2-en-1-one |
| 103 | 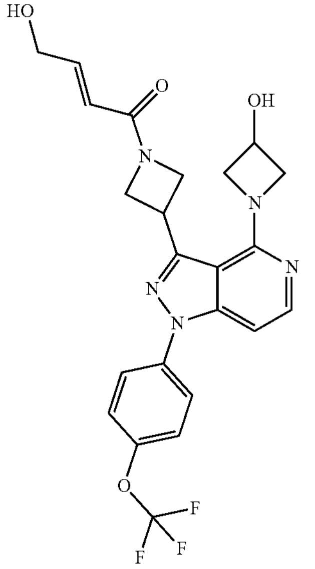 [SMILES: O=C(/C=C/CO)N1CC(c2nn(-c3ccc(OC(F)(F)F)cc3)c3ccnc(N4CC(O)C4)c23)C1] | (E)-4-hydroxy-1-[3-[4-(3-hydroxyazetidin-1-yl)-1-[4-(trifluoromethoxy)phenyl]pyrazolo[4,3-c]pyridin-3-yl]azetidin-1-yl]but-2-en-1-one |
| 104 | 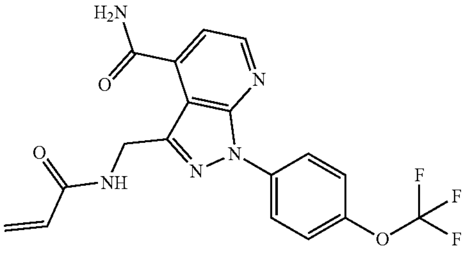 [SMILES: C=CC(=O)NCc1nn(-c2ccc(OC(F)(F)F)cc2)c2nccc(C(N)=O)c12] | 3-[(prop-2-enoylamino)methyl]-1-[4-(trifluoromethoxy)phenyl]pyrazolo[3,4-b]pyridine-4-carboxamide |

TABLE 1-continued
| Compound Number | Structure | Compound Name |
|---|---|---|
| 105 | 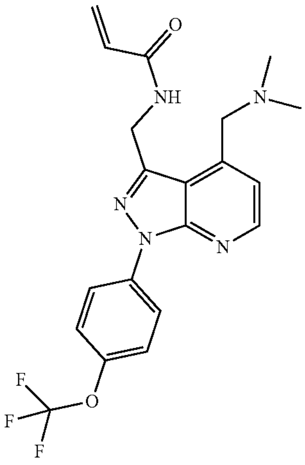 [SMILES: C=CC(=O)NCc1nn(-c2ccc(OC(F)(F)F)cc2)c2nccc(CN(C)C)c12] | N-[[4-[(dimethylamino)methyl]-1-[4-(trifluoromethoxy)phenyl]pyrazolo[3,4-b]pyridin-3-yl]methyl]prop-2-enamide |
| 106 | 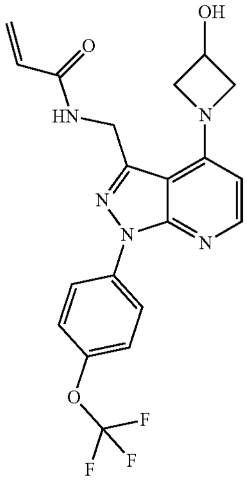 [SMILES: C=CC(=O)NCc1nn(-c2ccc(OC(F)(F)F)cc2)c2nccc(N3CC(O)C3)c12] | N-[[4-(3-hydroxyazetidin-1-yl)-1-[4-(trifluoromethoxy)phenyl]pyrazolo[3,4-b]pyridin-3-yl]methyl]prop-2-enamide |
| 107 | 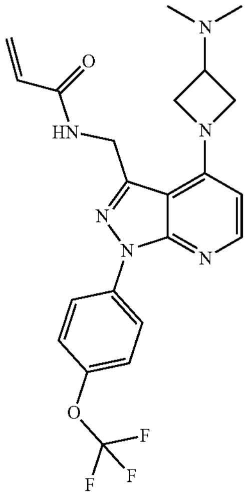 [SMILES: C=CC(=O)NCc1nn(-c2ccc(OC(F)(F)F)cc2)c2nccc(N3CC(N(C)C)C3)c12] | N-[[4-[3-(dimethylamino)azetidin-1-yl]-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 108 | 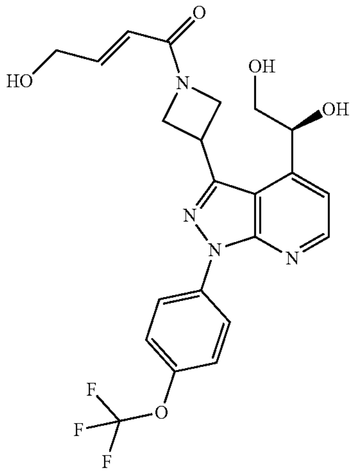 [SMILES: O=C(/C=C/CO)N1CC(c2nn(-c3ccc(OC(F)(F)F)cc3)c3nccc([C@H](O)CO)c23)C1] | (E)-1-[3-[4-[(1S)-1,2-dihydroxyethyl]-1-[4-(trifluoromethoxy)phenyl]pyrazolo[3,4-b]pyridin-3-yl]azetidin-1-yl]-4-hydroxy-but-2-en-1-one |
| 109 | 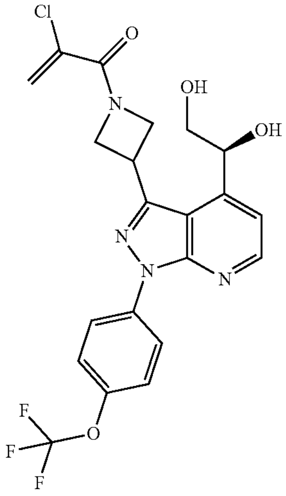 [SMILES: C=C(Cl)C(=O)N1CC(c2nn(-c3ccc(OC(F)(F)F)cc3)c3nccc([C@H](O)CO)c23)C1] | 2-chloro-1-[3-[4-[(1S)-1,2-dihydroxyethyl]-1-[4-(trifluoromethoxy)phenyl]pyrazolo[3,4-b]pyridin-3-yl]azetidin-1-yl]prop-2-en-1-one |
| 110 | 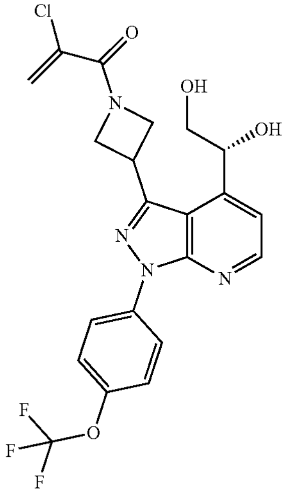 [SMILES: C=C(Cl)C(=O)N1CC(c2nn(-c3ccc(OC(F)(F)F)cc3)c3nccc([C@@H](O)CO)c23)C1] | 2-chloro-1-[3-[4-[(1R)-1,2-dihydroxyethyl]-1-[4-(trifluoromethoxy)phenyl]pyrazolo[3,4-b]pyridin-3-yl]azetidin-1-yl]prop-2-en-1-one |

TABLE 1-continued
| Compound Number | Structure | Compound Name |
|---|---|---|
| 111 | 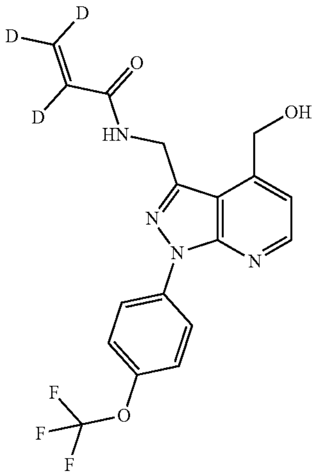 [SMILES: [2H]C([2H])=C([2H])C(=O)NCc1nn(-c2ccc(OC(F)(F)F)cc2)c2nccc(CO)c12] | 2,3,3-trideuterio-N-[[4-(hydroxymethyl)-1-[4-(trifluoromethoxy)phenyl]pyrazolo[3,4-b]pyridin-3-yl]methyl]prop-2-enamide |
| 112 | 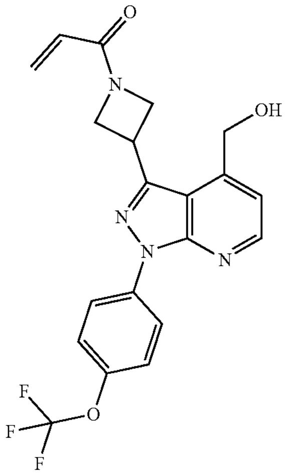 [SMILES: C=CC(=O)N1CC(c2nn(-c3ccc(OC(F)(F)F)cc3)c3nccc(CO)c23)C1] | 1-[3-[4-(hydroxymethyl)-1-[4-(trifluoromethoxy)phenyl]pyrazolo[3,4-b]pyridin-3-yl]azetidin-1-yl]prop-2-en-1-one |
| 113 | 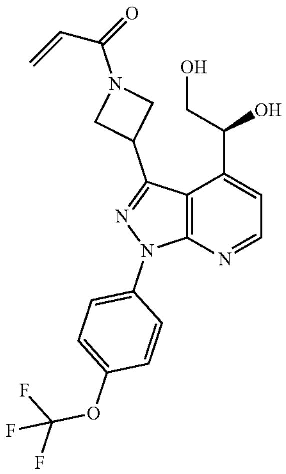 [SMILES: C=CC(=O)N1CC(c2nn(-c3ccc(OC(F)(F)F)cc3)c3nccc([C@H](O)CO)c23)C1] | 1-[3-[4-[(1S)-1,2-dihydroxyethyl]-1-[4-(trifluoromethoxy)phenyl]pyrazolo[3,4-b]pyridin-3-yl]azetidin-1-yl]prop-2-en-1-one |

TABLE 1-continued
| Compound Number | Structure | Compound Name |
|---|---|---|
| 114 | 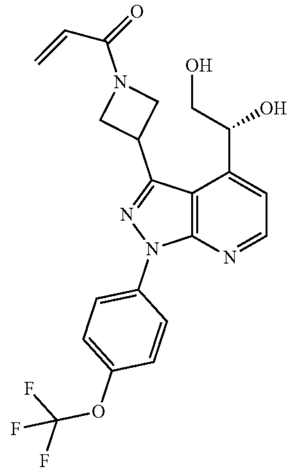 [SMILES: C=CC(=O)N1CC(c2nn(-c3ccc(OC(F)(F)F)cc3)c3nccc([C@@H](O)CO)c23)C1] | 1-[3-[4-[(1R)-1,2-dihydroxyethyl]-1-[4-(trifluoromethoxy)phenyl]pyrazolo[3,4-b]pyridin-3-yl]azetidin-1-yl]prop-2-en-1-one |
| 115 | 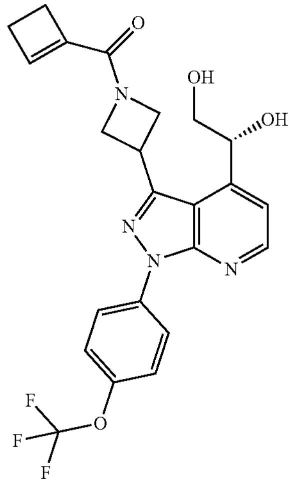 [SMILES: O=C(C1=CCC1)N1CC(c2nn(-c3ccc(OC(F)(F)F)cc3)c3nccc([C@@H](O)CO)c23)C1] | cyclobuten-1-yl-[3-[4-[(1R)-1,2-dihydroxyethyl]-1-[4-(trifluoromethoxy)phenyl]pyrazolo[3,4-b]pyridin-3-yl]azetidin-1-yl]methanone |
| 116 | 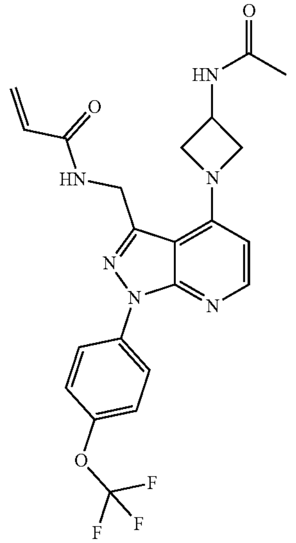 [SMILES: C=CC(=O)NCc1nn(-c2ccc(OC(F)(F)F)cc2)c2nccc(N3CC(NC(C)=O)C3)c12] | N-[[4-(3-acetamidoazetidin-1-yl)-1-[4-(trifluoromethoxy)phenyl]pyrazolo[3,4-blpyridin-3-yl]methyl]prop-2-enamide |

TABLE 1-continued
| Compound Number | Structure | Compound Name |
|---|---|---|
| 117 | 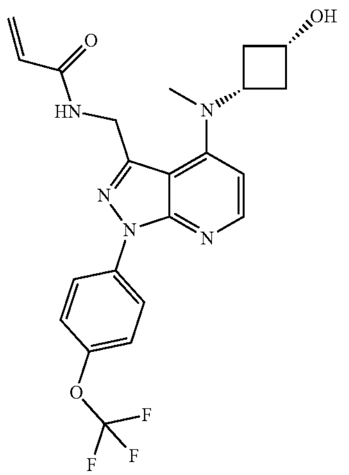 [SMILES: C=CC(=O)NCc1nn(-c2ccc(OC(F)(F)F)cc2)c2nccc(N(C)[C@H]3C[C@@H](O)C3)c12] | N-[[4-[(3-hydroxycyclobutyl)-methyl-amino]-1-[4-(trifluoromethoxy)phenyl]pyrazolo[3,4-b]pyridin-3-yl]methyl]prop-2-enamide |
| 118 | 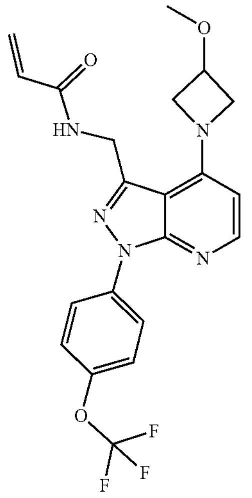 [SMILES: C=CC(=O)NCc1nn(-c2ccc(OC(F)(F)F)cc2)c2nccc(N3CC(OC)C3)c12] | N-[[4-(3-methoxyazetidin-1-yl)-1-[4-(trifluoromethoxy)phenyl]pyrazolo[3,4-b]pyridin-3-yl]methyl]prop-2-enamide |
| 119 | 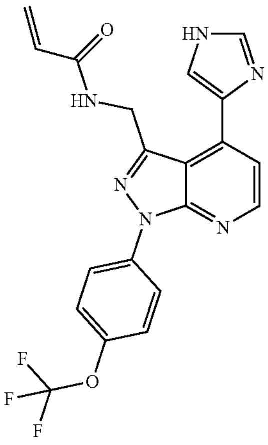 [SMILES: C=CC(=O)NCc1nn(-c2ccc(OC(F)(F)F)cc2)c2nccc(-c3c[nH]cn3)c12] | N-[[4-(1H-imidazol-4-yl)-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 120 | 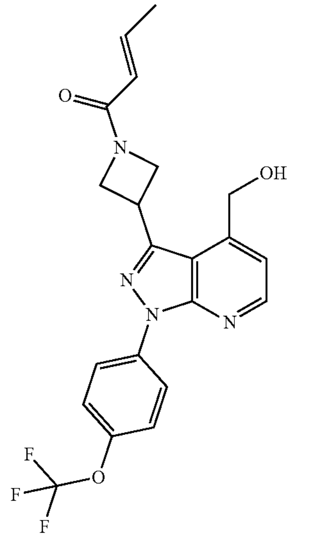 [SMILES: C/C=C/C(=O)N1CC(c2nn(-c3ccc(OC(F)(F)F)cc3)c3nccc(CO)c23)C1] | (E)-1-[3-[4-(hydroxymethyl)-1-[4-(trifluoromethoxy)phenyl]pyrazolo[3,4-b]pyridin-3-yl]azetidin-1-yl]but-2-en-1-one |
| 121 | 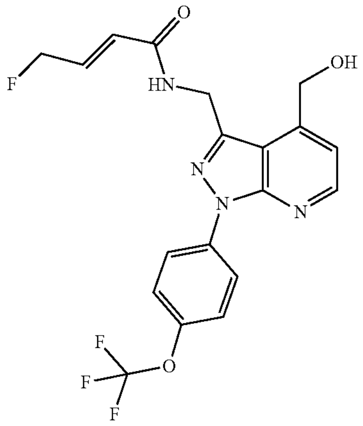 [SMILES: O=C(/C=C/CF)NCc1nn(-c2ccc(OC(F)(F)F)cc2)c2nccc(CO)c12] | (E)-4-fluoro-N-[[4-(hydroxymethyl)-1-[4-(trifluoromethoxy)phenyl]pyrazolo[3,4-b]pyridin-3-yl]methyl]but-2-enamide |
| 122 | 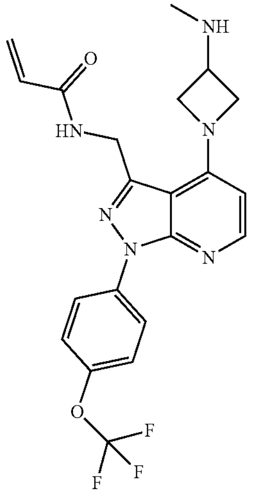 [SMILES: C=CC(=O)NCc1nn(-c2ccc(OC(F)(F)F)cc2)c2nccc(N3CC(NC)C3)c12] | N-[[4-[3-(methylamino)azetidin-1-yl]-1-[4-(trifluoromethoxy)phenyl]pyrazolo[3,4-b]pyridin-3-yl]methyl]prop-2-enamide |

TABLE 1-continued

| Compound Number | Structure | Compound Name |
|---|---|---|
| 123 | 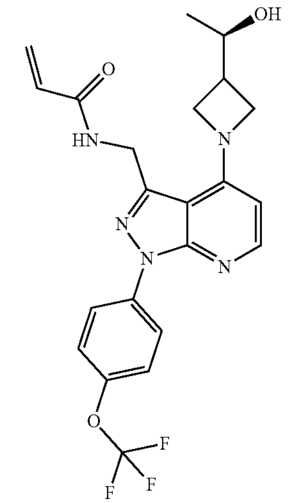 [SMILES: C=CC(=O)NCc1nn(-c2ccc(OC(F)(F)F)cc2)c2nccc(N3CC([C@@H](C)O)C3)c12] | N-[[4-[3-[(1R)-1-hydroxyethyl]azetidin-1-yl]-1-[4-(trifluoromethoxy)phenyl]pyrazolo[3,4-b]pyridin-3-yl]methyl]prop-2-enamide |
| 124 | 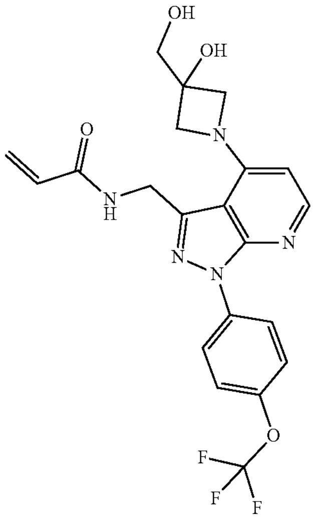 [SMILES: C=CC(=O)NCc1nn(-c2ccc(OC(F)(F)F)cc2)c2nccc(N3CC(O)(CO)C3)c12] | N-[[4-[3-hydroxy-3-(hydroxymethyl)azetidin-1-yl]-1-[4-(trifluoromethoxy)phenyl]pyrazolo[3,4-b]pyridin-3-yl]methyl]prop-2-enamide |
| 125 | 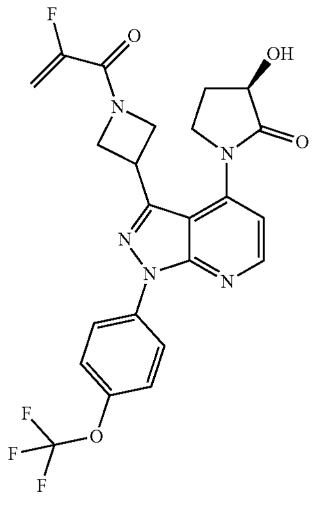 [SMILES: C=C(F)C(=O)N1CC(c2nn(-c3ccc(OC(F)(F)F)cc3)c3nccc(N4CC[C@@H](O)C4=O)c23)C1] | (3R)-1-[3-[1-(2-fluoroprop-2-enoyl)azetidin-3-yl]-1-[4-(trifluoromethoxy)phenyl]pyrazolo[3,4-b]pyridin-4-yl]-3-hydroxy-pyrrolidin-2-one |

TABLE 1-continued

| Compound Number | Structure | Compound Name |
|---|---|---|
| 126 | 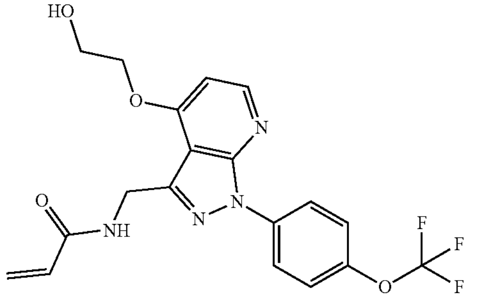 [SMILES: C=CC(=O)NCc1nn(-c2ccc(OC(F)(F)F)cc2)c2nccc(OCCO)c12] | N-[[4-(2-hydroxyethoxy)-1-[4-(trifluoromethoxy)phenyl]pyrazolo[3,4-b]pyridin-3-yl]methyl]prop-2-enamide |
| 127 | 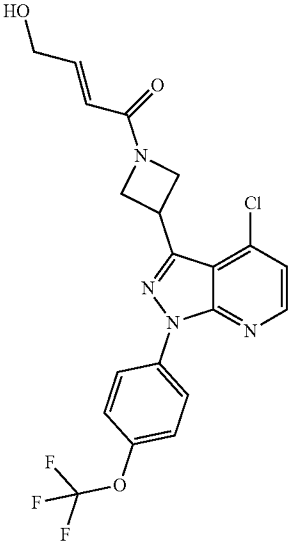 [SMILES: O=C(/C=C/CO)N1CC(c2nn(-c3ccc(OC(F)(F)F)cc3)c3nccc(Cl)c23)C1] | (E)-1-[3-[4-chloro-1-[4-(trifluoromethoxy)phenyl]pyrazolo[3,4-b]pyridin-3-yl]azetidin-1-yl]-4-hydroxy-but-2-en-1-one |
| 128 | 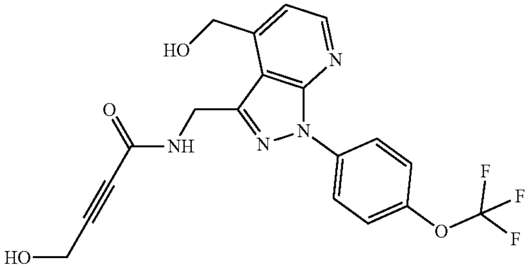 [SMILES: O=C(C#CCO)NCc1nn(-c2ccc(OC(F)(F)F)cc2)c2nccc(CO)c12] | 4-hydroxy-N-[[4-(hydroxymethyl)-1-[4-(trifluoromethoxy)phenyl]pyrazolo[3,4-b]pyridin-3-yl]methyl]but-2-ynamide |
| 129 | 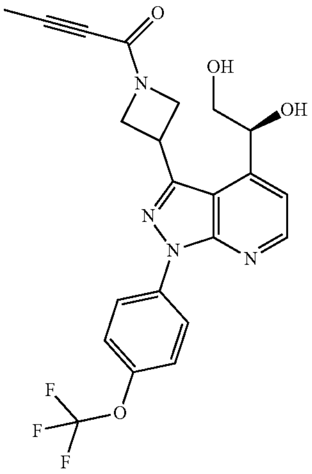 [SMILES: CC#CC(=O)N1CC(c2nn(-c3ccc(OC(F)(F)F)cc3)c3nccc([C@H](O)CO)c23)C1] | 1-[3-[4-[(1S)-1,2-dihydroxyethyl]-1-[4-(trifluoromethoxy)phenyl]pyrazolo[3,4-b]pyridin-3-yl]azetidin-1-yl]but-2-yn-1-one |

TABLE 1-continued
| Compound Number | Structure | Compound Name |
|---|---|---|
| 130 | 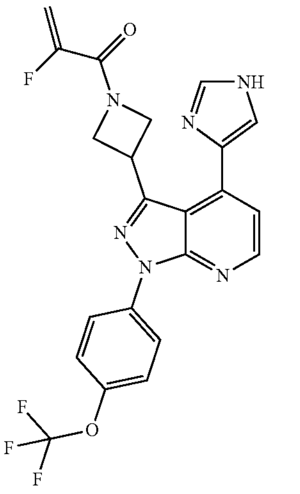 [SMILES: C=C(F)C(=O)N1CC(c2nn(-c3ccc(OC(F)(F)F)cc3)c3nccc(-c4c[nH]cn4)c23)C1] | 2-fluoro-1-[3-[4-1H-imidazol-4-yl)-1-[4-(trifluoromethoxy)phenyl]pyrazolo[3,4-b]pyridin-3-yl]azetidin-1-yl]prop-2-en-1-one |
| 131 | 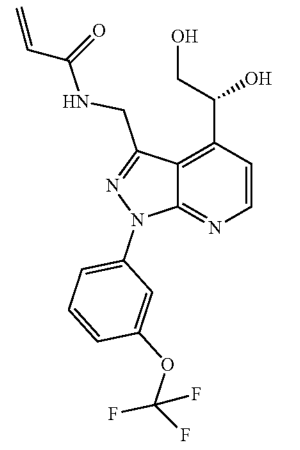 [SMILES: C=CC(=O)NCc1nn(-c2cccc(OC(F)(F)F)c2)c2nccc([C@@H](O)CO)c12] | N-[[4-[rac-(1R)-1,2-dihydroxyethyl]-1-[3-(trifluoromethoxy)phenyl]pyrazolo[3,4-b]pyridin-3-yl]methyl]prop-2-enamide |
| 132 | 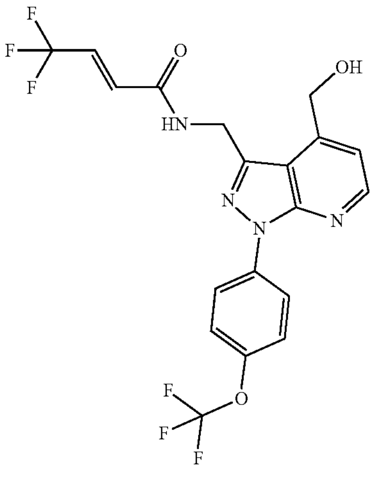 [SMILES: O=C(/C=C/C(F)(F)F)NCc1nn(-c2ccc(OC(F)(F)F)cc2)c2nccc(CO)c12] | (E)-4,4,4-trifluoro-N-[[4-(hydroxymethyl)-1-[4-(trifluoromethoxy)phenyl]pyrazolo[3,4-b]pyridin-3-yl]methyl]but-2-enamide |

TABLE 1-continued
| Compound Number | Structure | Compound Name |
|---|---|---|
| 133 | 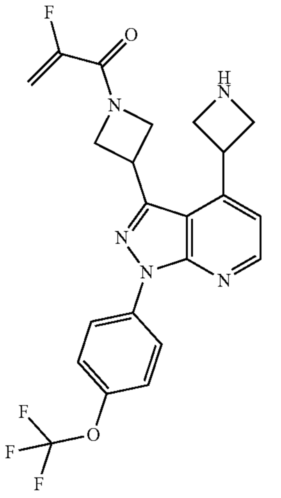 [SMILES: C=C(F)C(=O)N1CC(c2nn(-c3ccc(OC(F)(F)F)cc3)c3nccc(C4CNC4)c23)C1] | 1-[3-[4-(azetidin-3-yl)-1-[4-(trifluoromethoxy)phenyl]pyrazolo[3,4-b]pyridin-3-yl]azetidin-1-yl]-2-fluoro-prop-2-en-1-one |
| 134 | 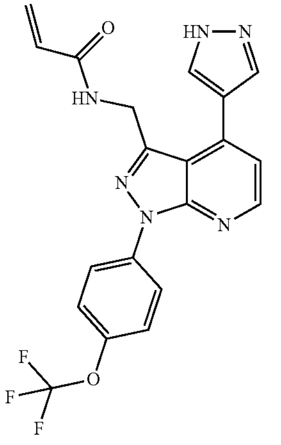 [SMILES: C=CC(=O)NCc1nn(-c2ccc(OC(F)(F)F)cc2)c2nccc(-c3cn[nH]c3)c12] | N-[[4-(1H-pyrazol-4-yl)-1-[4-(trifluoromethoxy)phenyl]pyrazolo[3,4-b]pyridin-3-yl]methyl]prop-2-enamide |
| 135 | 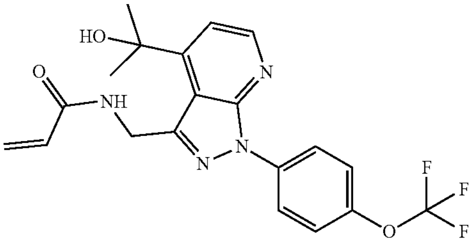 [SMILES: C=CC(=O)NCc1nn(-c2ccc(OC(F)(F)F)cc2)c2nccc(C(C)(C)O)c12] | N-[[4-(1-hydroxy-1-methyl-ethyl)-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 136 | 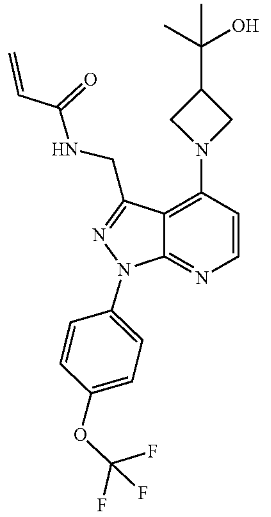 [SMILES: C=CC(=O)NCc1nn(-c2ccc(OC(F)(F)F)cc2)c2nccc(N3CC(C(C)(C)O)C3)c12] | N-[[4-[3-(1-hydroxy-1-methyl-ethyl)azetidin-1-yl]-1-[4-(trifluoromethoxy)phenyl]pyrazolo[3,4-b]pyridin-3-yl]methyl]prop-2-enamide |
| 137 | 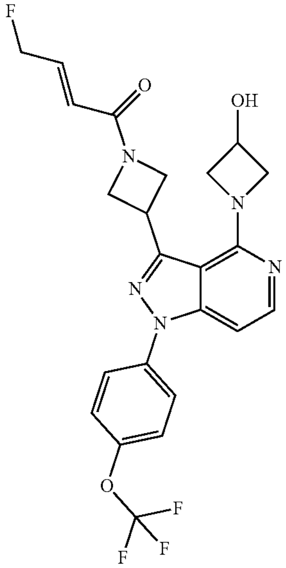 [SMILES: O=C(/C=C/CF)N1CC(c2nn(-c3ccc(OC(F)(F)F)cc3)c3ccnc(N4CC(O)C4)c23)C1] | (E)-4-fluoro-1-[3-[4-(3-hydroxyazetidin-1-yl)-1-[4-(trifluoromethoxy)phenyl]pyrazolo[4,3-c]pyridin-3-yl]azetidin-1-yl]but-2-en-1-one |
| 138 | 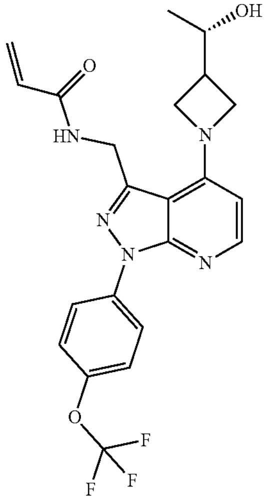 [SMILES: C=CC(=O)NCc1nn(-c2ccc(OC(F)(F)F)cc2)c2nccc(N3CC([C@H](C)O)C3)c12] | N-[[4-[3-[(lS)-1-hydroxyethyl]azetidin-1-yl]-1-[4-(trifluoromethoxy)phenyl]pyrazolo[3,4-b]pyridin-3-yl]methyl]prop-2-enamide |

TABLE 1-continued
| Compound Number | Structure | Compound Name |
|---|---|---|
| 139 | 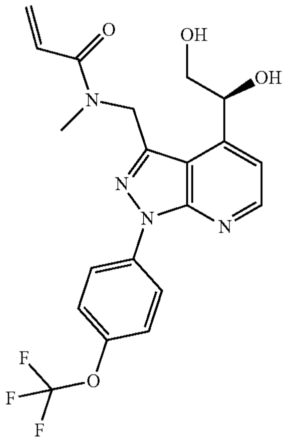 [SMILES: C=CC(=O)N(C)Cc1nn(-c2ccc(OC(F)(F)F)cc2)c2nccc([C@H](O)CO)c12] | N-[[4-[(1S)-1,2-dihydroxyethyl]-1-[4-(trifluoromethoxy)phenyl]pyrazolo[3,4-b]pyridin-3-yl]methyl]-N-methyl-prop-2-enamide |
| 140 | 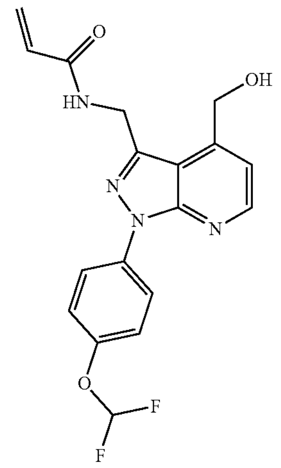 [SMILES: C=CC(=O)NCc1nn(-c2ccc(OC(F)F)cc2)c2nccc(CO)c12] | N-[[1-[4-(difluoromethoxy)phenyl]-4-(hydroxymethyl)pyrazolo[3,4-b]pyridin-3-yl]methyl]prop-2-enamide |
| 141 | 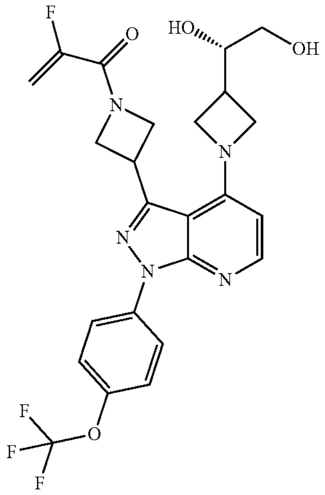 [SMILES: C=C(F)C(=O)N1CC(c2nn(-c3ccc(OC(F)(F)F)cc3)c3nccc(N4CC([C@H](O)CO)C4)c23)C1] | 1-[3-[4-[3-[(1S)-1,2-dihydroxyethyl]azetidin-1-yl]-1-[4-(trifluoromethoxy)phenyl]pyrazolo[3,4-b]pyridin-3-yl]azetidin-1-yl]-2-fluoro-prop-2-en-1-one |

TABLE 1-continued
| Compound Number | Structure | Compound Name |
|---|---|---|
| 142 | 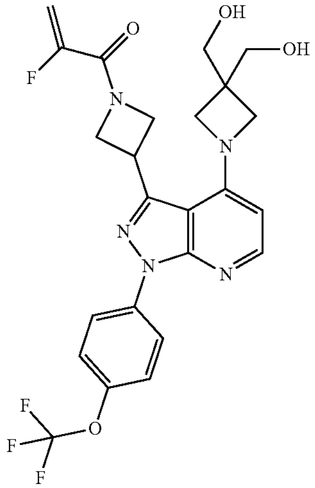 [SMILES: C=C(F)C(=O)N1CC(c2nn(-c3ccc(OC(F)(F)F)cc3)c3nccc(N4CC(CO)(CO)C4)c23)C1] | 1-[3-[4-[3,3-bis(hydroxymethyl)azetidin-1-yl]-1-[4-(trifluoromethoxy)phenyl]pyrazolo[3,4-b]pyridin-3-yl]azetidin-1-yl]-2-fluoro-prop-2-en-1-one |
| 143 | 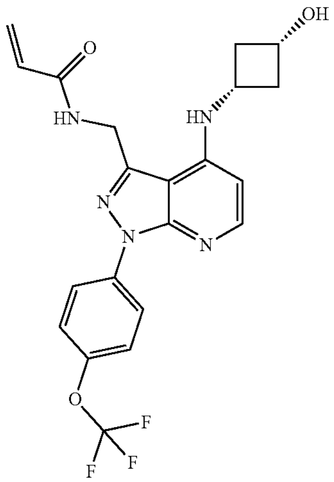 [SMILES: C=CC(=O)NCc1nn(-c2ccc(OC(F)(F)F)cc2)c2nccc(N[C@H]3C[C@@H](O)C3)c12] | N-[[4-[(3-hydroxycyclobutyl)amino]-1-[4-(trifluoromethoxy)phenyl]pyrazolo[3,4-b]pyridin-3-yl]methyl]prop-2-enamide |
| 144 | 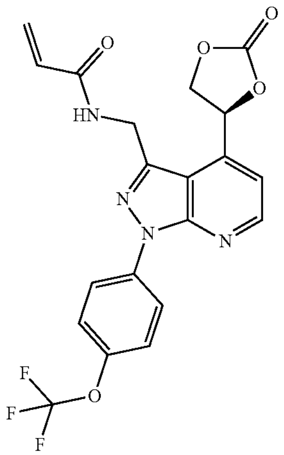 [SMILES: C=CC(=O)NCc1nn(-c2ccc(OC(F)(F)F)cc2)c2nccc([C@H]3COC(=O)O3)c12] | (S)-N-((4-(2-Oxo-1,3-dioxolan-4-yl)-1-(4-(trifluoromethoxy)phenyl)-1H-pyrazolo[3,4-b]pyridin-3-yl)methyl)acrylamide |

TABLE 1-continued

| Compound Number | Structure | Compound Name |
|---|---|---|
| 145 | 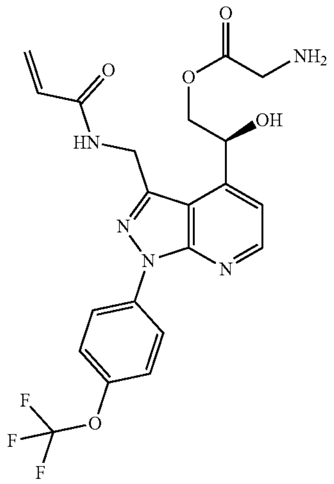 [SMILES: C=CC(=O)NCc1nn(-c2ccc(OC(F)(F)F)cc2)c2nccc([C@H](O)COC(=O)CN)c12] | (S)-2-(3-(Acrylamidomethyl)-1-(4-(trifluoromethoxy)phenyl)-1H-pyrazolo[3,4-b]pyridin-4-yl)-2-hydroxyethyl 2-aminoacetate formate |
| 146 | 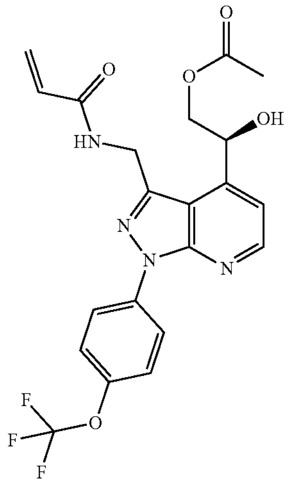 [SMILES: C=CC(=O)NCc1nn(-c2ccc(OC(F)(F)F)cc2)c2nccc([C@H](O)COC(C)=O)c12] | (S)-2-(3-(Actylamidomethyl)-1-(4-(trifluoromethoxy)phenyl)-1H-pyrazolo[3,4-b]pyridin-4-yl)-2-hydroxyethyl acetate |
| 147 | 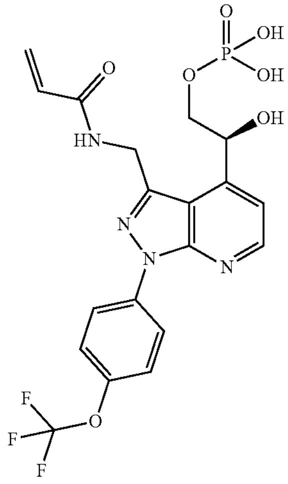 [SMILES: C=CC(=O)NCc1nn(-c2ccc(OC(F)(F)F)cc2)c2nccc([C@H](O)COP(=O)(O)O)c12] | (S)-2-(3-(Acrylamidomethyl)-1-(4-(trifluoromethoxy)phenyl)-1H-pyrazolo[3,4-b]pyridin-4-yl)-2-hydroxyethyl dihydrogen phosphate |

TABLE 1-continued

| Compound Number | Structure | Compound Name |
|---|---|---|
| 148 | 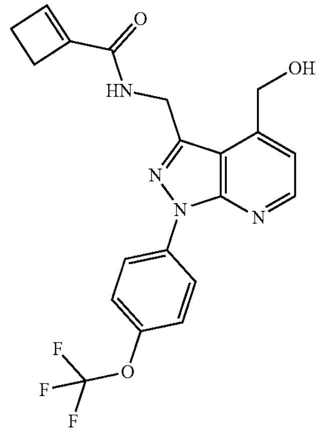 [SMILES: O=C(NCc1nn(-c2ccc(OC(F)(F)F)cc2)c2nccc(CO)c12)C1=CCC1] | N-((4-(Hydroxymethyl)-1-(4-(trifluoromethoxy)phenyl)-1H-pyrazolo[3,4-b]pyridin-3-yl)methyl)cyclobut-1-enecarboxamide |
| 149 | 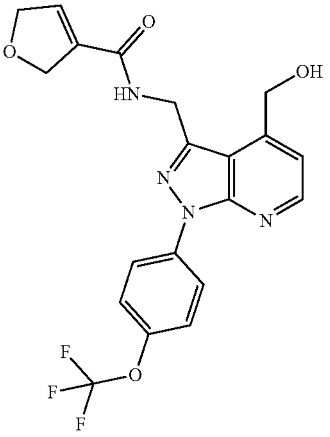 [SMILES: O=C(NCc1nn(-c2ccc(OC(F)(F)F)cc2)c2nccc(CO)c12)C1=CCOC1] | N-((4-(Hydroxymethyl)-1-(4-(trifluoromethoxy)phenyl)-1H-pyrazolo[3,4-b]pyridin-3-yl)methyl)-2,5-dihydrofuran-3-carboxamide |
| 150 | 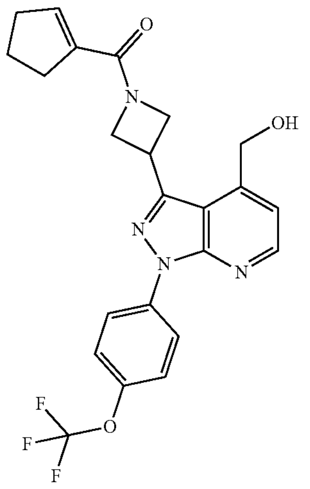 [SMILES: O=C(C1=CCCC1)N1CC(c2nn(-c3ccc(OC(F)(F)F)cc3)c3nccc(CO)c23)C1] | Cyclopent-1-en-1-yl(3-(4-(hydroxymethyl)-1-(4-(trifluoromethoxy)phenyl)-1H-pyrazolo[3,4-b]pyridin-3-yl)azetidin-1-yl)methanone |

TABLE 1-continued

| Compound Number | Structure | Compound Name |
| --- | --- | --- |
| 151 | 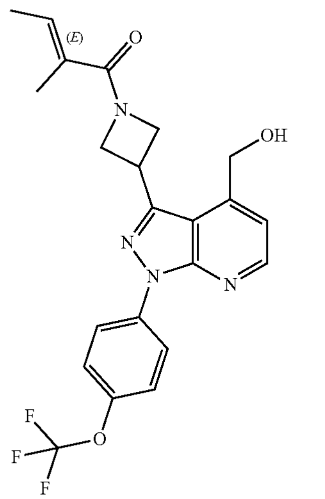 [SMILES: C/C=C(\C)C(=O)N1CC(c2nn(-c3ccc(OC(F)(F)F)cc3)c3nccc(CO)c23)C1] | (E)-1-(3-(4-(Hydroxymethyl)-1-(4-(trifluoromethoxy)phenyl)-1H-pyrazolo[3,4-b]pyridin-3-yl)azetidin-1-yl)-2-methylbut-2-en-1-one |
| 152 | 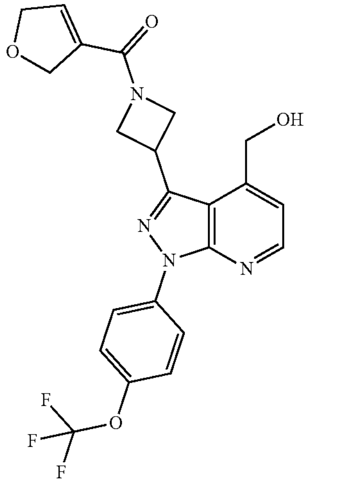 [SMILES: O=C(C1=CCOC1)N1CC(c2nn(-c3ccc(OC(F)(F)F)cc3)c3nccc(CO)c23)C1] | (2,5-Dihydrofuran-3-yl)(3-(4-(hydroxymethyl)-1-(4-(trifluoromethoxy)phenyl)-1H-pyrazolo[3,4-b]pyridin-3-yl)azetidin-1-yl)methanone |
| 153 | 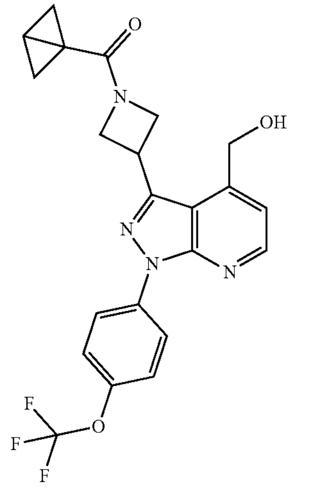 [SMILES: O=C(N1CC(c2nn(-c3ccc(OC(F)(F)F)cc3)c3nccc(CO)c23)C1)C12CC1C2] | Bicyclo[1.1.0]butan-1-yl(3-(4-(hydroxymethyl)-1-(4-(trifluoromethoxy)phenl)-1H-pyrazolo[3,4-b]pyridin-3-yl)azetidin-1-yl)methanone |

TABLE 1-continued
| Compound Number | Structure | Compound Name |
|---|---|---|
| 154 | 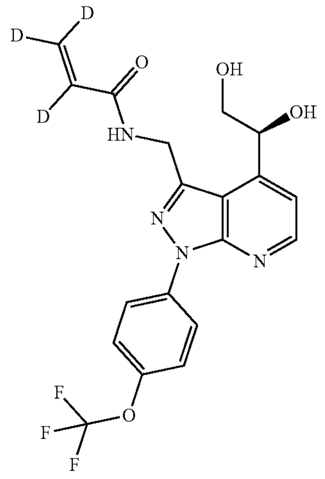 [SMILES: [2H]C([2H])=C([2H])C(=O)NCc1nn(-c2ccc(OC(F)(F)F)cc2)c2nccc([C@H](O)CO)c12] | (S)-N-((4-(1,2-Dihydroxyethyl)-1-(4-(trifluoromethoxy)phenyl)-1H-pyrazolo[3,4-b]pyridin-3-yl)methyl)acrylamide-2,3,3-d3 |
| 155 | 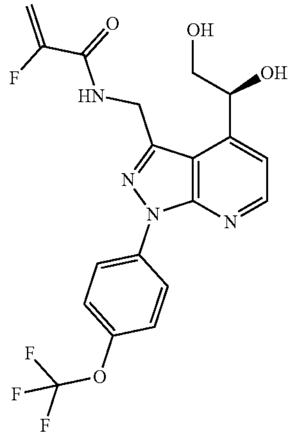 [SMILES: C=C(F)C(=O)NCc1nn(-c2ccc(OC(F)(F)F)cc2)c2nccc([C@H](O)CO)c12] | (S)-N-((4-(1,2-Dihydroxyethyl)-1-(4-(trifluoromethoxy)phenyl)-1H-pyrazolo[3,4-b]pyridin-3-yl)methyl)-2-fluoroacrylamide |
| 156 | 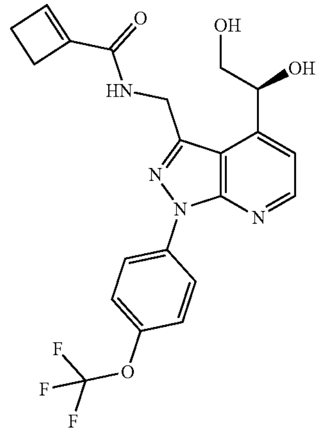 [SMILES: O=C(NCc1nn(-c2ccc(OC(F)(F)F)cc2)c2nccc([C@H](O)CO)c12)C1=CCC1] | (S)-N-((4-(1,2-Dihydroxyethyl)-1-(4-(trifluoromethoxy)phenyl)-1H-pyrazolo[3,4-b]pyridin-3-yl)methyl)cyclobut-1-enecarboxamide |

TABLE 1-continued
| Compound Number | Structure | Compound Name |
|---|---|---|
| 157 | 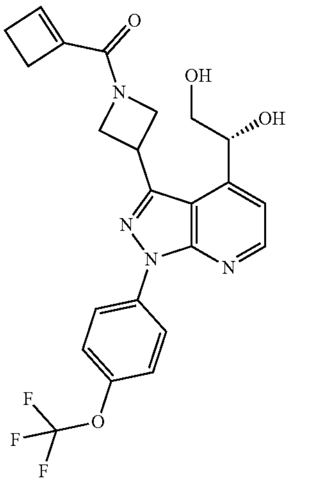 [SMILES: O=C(C1=CCC1)N1CC(c2nn(-c3ccc(OC(F)(F)F)cc3)c3nccc([C@@H](O)CO)c23)C1] | (R)-Cyclobut-1-en-1-yl(3-(4-(1,2-dihydroxyethyl)-1-(4-(trifluoromethoxy)phenyl)-1H-pyrazolo[3,4-b]pyridin-3-yl)azetidin-1-yl)methanone |
| 158 | 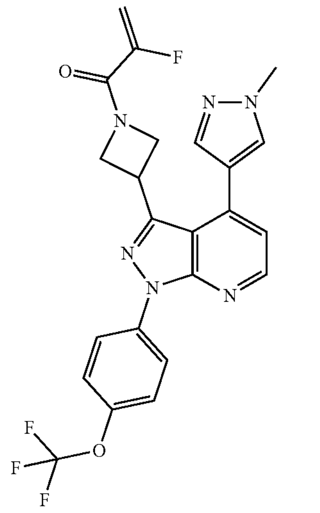 [SMILES: C=C(F)C(=O)N1CC(c2nn(-c3ccc(OC(F)(F)F)cc3)c3nccc(-c4cnn(C)c4)c23)C1] | 2-Fluoro-1-(3-(4-(1-methyl-1H-pyrazol-4-yl)-1-(4-(trifluoromethoxy)phenyl)-1H-pyrazolo[3,4-b]pyridin-3-yl)azetidin-1-yl)prop-2-en-1-one |
| 159 | 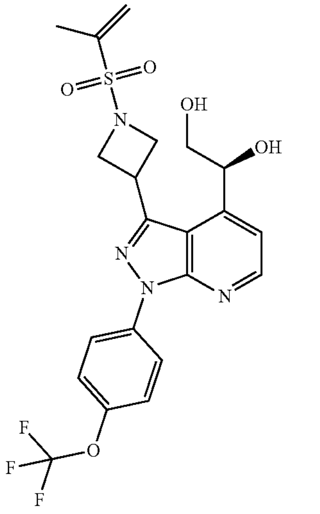 [SMILES: C=C(C)S(=O)(=O)N1CC(c2nn(-c3ccc(OC(F)(F)F)cc3)c3nccc([C@H](O)CO)c23)C1] | (S)-1-(3-(1-(Prop-1-en-2-ylsulfonyl)azetidin-3-yl)-1-(4-(trifluoromethoxy)phenyl)-1H-pyrazolo[3,4-b]pyridin-4-yl)ethane-1,2-diol |

TABLE 1-continued
| Compound Number | Structure | Compound Name |
| --- | --- | --- |
| 160 | 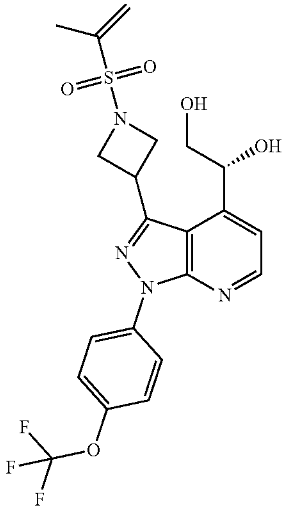 [SMILES: C=C(C)S(=O)(=O)N1CC(c2nn(-c3ccc(OC(F)(F)F)cc3)c3nccc([C@@H](O)CO)c23)C1] | (R)-1-(3-(1-(prop-1-en-2-ylsulfonyl)azetidin-3-yl)-1-(4-(trifluoromethoxy)phenyl)-1H-pyrazolo[3,4-b]pyridin-4-yl)ethane-1,2-diol |
| 161 | 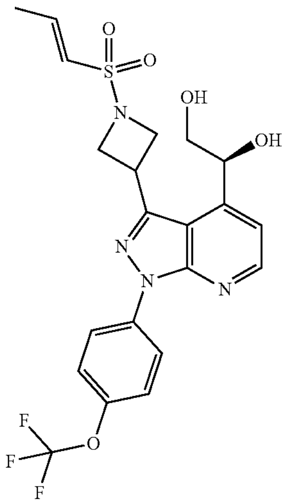 [SMILES: C/C=C/S(=O)(=O)N1CC(c2nn(-c3ccc(OC(F)(F)F)cc3)c3nccc([C@H](O)CO)c23)C1] | (S,E)-1-(3-(1-(Prop-1-en-1-ylsulfonyl)azetidin-3-yl)-1-(4-(trifluoromethoxy)phenyl)-1H-pyrazolo[3,4-b]pyridin-4-yl)ethane-1,2-diol |
| 162 | 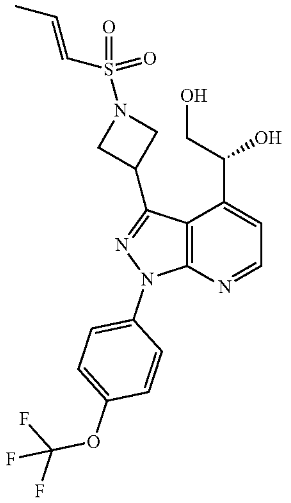 [SMILES: C/C=C/S(=O)(=O)N1CC(c2nn(-c3ccc(OC(F)(F)F)cc3)c3nccc([C@@H](O)CO)c23)C1] | (R,E)-1-(3-(1-(prop-1-en-1-ylsulfonyl)azetidin-3-yl)-1-(4-(trifluoromethoxy)phenyl)-1H-pyrazolo[3,4-b]pyridin-4-yl)ethane-1,2-diol |

TABLE 1-continued

| Compound Number | Structure | Compound Name |
| --- | --- | --- |
| 163 | 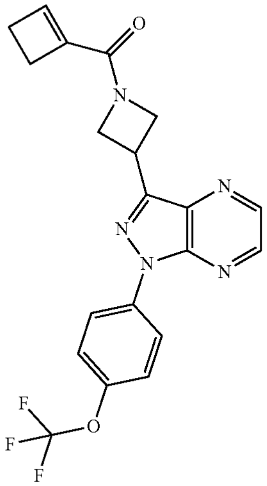 [SMILES: O=C(C1=CCC1)N1CC(c2nn(-c3ccc(OC(F)(F)F)cc3)c3nccnc23)C1] | Cyclobut-1-en-1-yl(3-(1-(4-(trifluoromethoxy)phenyl)-1H-pyrazolo[3,4-b]pyrazin-3-yl)azetidin-1-yl)methanone |
| 164 | 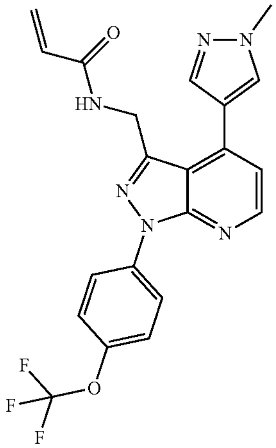 [SMILES: C=CC(=O)NCc1nn(-c2ccc(OC(F)(F)F)cc2)c2nccc(-c3cnn(C)c3)c12] | N-((4-(1-Methyl-1H-pyrazol-4-yl)-1-(4-(trifluoromethoxy)phenyl)-1H-pyrazolo[3,4-b]pyridin-3-yl)methyl)acrylamide |
| 165 | 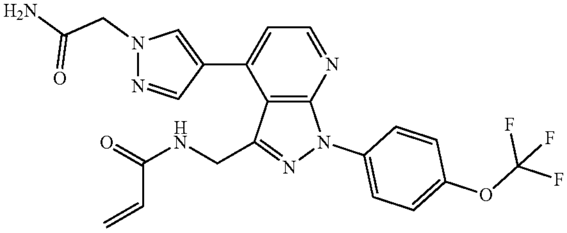 [SMILES: C=CC(=O)NCc1nn(-c2ccc(OC(F)(F)F)cc2)c2nccc(-c3cnn(CC(N)=O)c3)c12] | N-((4-(1-(2-amino-2-oxoethyl)-1H-pyrazol-4-yl)-1-(4-(trifluoromethoxy)phenyl)-1H-pyrazolo[3,4-b]pyridin-3-yl)methyl)acrylamide |
| 166 | 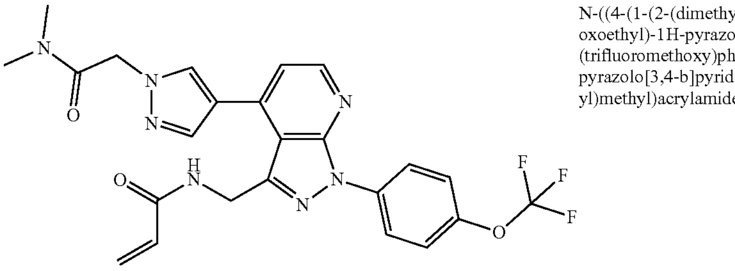 | N-((4-(1-(2-(dimethylamino)-2-oxoethyl)-1H-pyrazol-4-yl)-1-(4-(trifluoromethoxy)phenyl)-1H-pyrazolo[3,4-b]pyridin-3-yl)methyl)acrylamide |

TABLE 1-continued

| Compound Number | Structure | Compound Name |
|---|---|---|
| 167 | 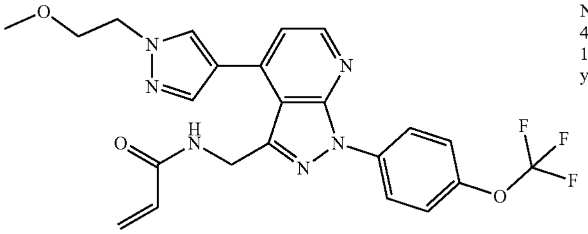 | N-((4-(1-(2-methoxyethyl)-1H-pyrazol-4-yl)-1-(4-(trifluoromethoxy)phenyl)-1H-pyrazolo[3,4-b]pyridin-3-yl)methyl)acrylamide |
| 168 | 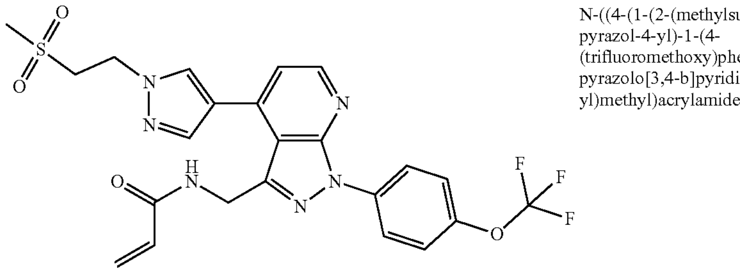 | N-((4-(1-(2-(methylsulfonyl)ethyl)-1H-pyrazol-4-yl)-1-(4-(trifluoromethoxy)phenyl)-1H-pyrazolo[3,4-b]pyridin-3-yl)methyl)acrylamide |
| 169 | 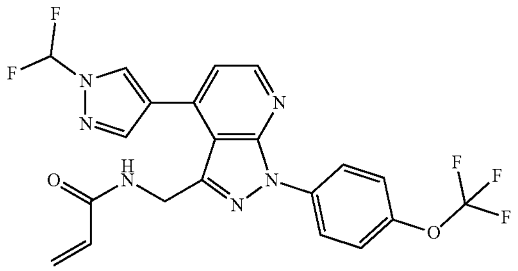 [SMILES: C=CC(=O)NCc1nn(-c2ccc(OC(F)(F)F)cc2)c2nccc(-c3cnn(C(F)F)c3)c12] | N-((4-(1-(difluoromethyl)-1H-pyrazol-4-yl)-1-(4-(trifluoromethoxy)phenyl)-1H-pyrazolo[3,4-b]pyridin-3-yl)methyl)acrylamide |
| 170 | 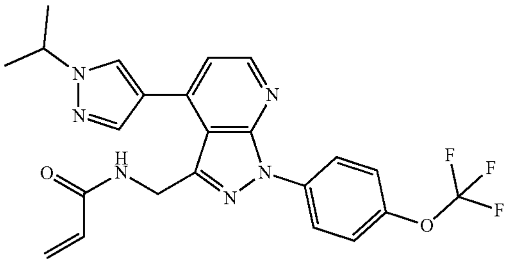 [SMILES: C=CC(=O)NCc1nn(-c2ccc(OC(F)(F)F)cc2)c2nccc(-c3cnn(C(C)C)c3)c12] | N-((4-(1-isopropyl-1H-pyrazol-4-yl)-1-(4-(trifluoromethoxy)phenyl)-1H-pyrazolo[3,4-b]pyridin-3-yl)methvl)acrylamide |
| 171 | 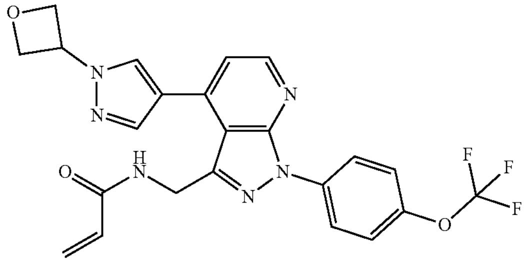 [SMILES: C=CC(=O)NCc1nn(-c2ccc(OC(F)(F)F)cc2)c2nccc(-c3cnn(C4COC4)c3)c12] | N-((4-(1-(oxetan-3-yl)-1H-pyrazol-4-yl)-1-(4-(trifluoromethoxy)phenyl)-1H-pyrazolo[3,4-b]pyridin-3-yl)methyl)acrylamide |

TABLE 1-continued

| Compound Number | Structure | Compound Name |
|---|---|---|
| 172 | 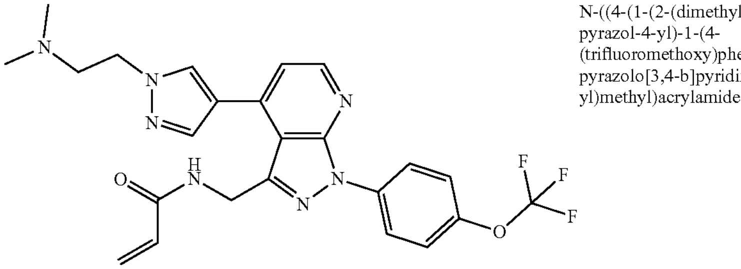 | N-((4-(1-(2-(dimethylamino)ethyl)-1H-pyrazol-4-yl)-1-(4-(trifluoromethoxy)phenyl)-1H-pyrazolo[3,4-b]pyridin-3-yl)methyl)acrylamide |
| 173 | 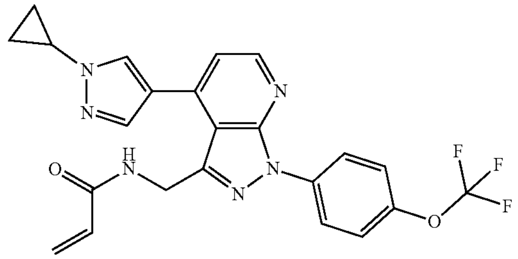 [SMILES: C=CC(=O)NCc1nn(-c2ccc(OC(F)(F)F)cc2)c2nccc(-c3cnn(C4CC4)c3)c12] | N-((4-(1-cyclopropyl-1H-pyrazol-4-yl)-1-(4-(trifluoromethoxy)phenyl)-1H-pyrazolo[3,4-b]pyridin-3-yl)methyl)acrylamide |
| 174 | 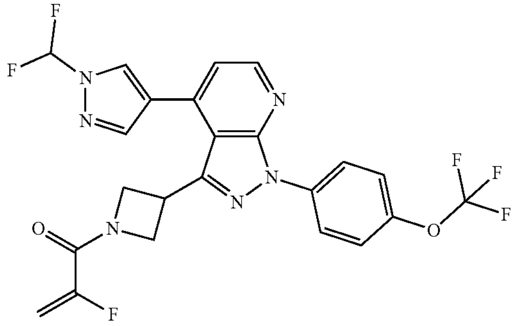 [SMILES: C=C(F)C(=O)N1CC(c2nn(-c3ccc(OC(F)(F)F)cc3)c3nccc(-c4cnn(C(F)F)c4)c23)C1] | 1-(3-(4-(1-(difluoromethyl)-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one |
| 175 | 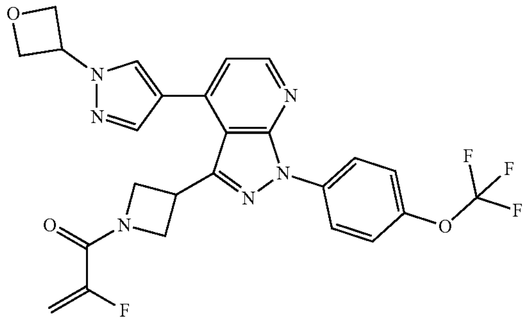 [SMILES: C=C(F)C(=O)N1CC(c2nn(-c3ccc(OC(F)(F)F)cc3)c3nccc(-c4cnn(C5COC5)c4)c23)C1] | 2-fluoro-1-(3-(4-(1-(oxetan-3-yl)-1H-pyrazol-4-yl)-1-(4-(trifluoromethoxy)phenyl)-1H-pyrazolo[3,4-b]pyridin-3-yl)azetidin-1-yl)prop-2-en-1-one |
| 176 | 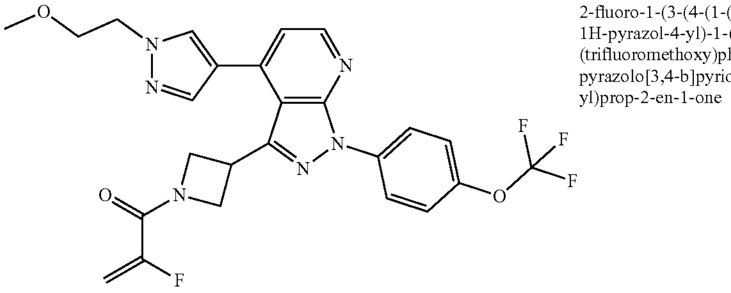 | 2-fluoro-1-(3-(4-(1-(2-methoxyethyl)-1H-pyrazol-4-yl)-1-(4-(trifluoromethoxy)phenyl)-1H-pyrazolo[3,4-b]pyridin-3-yl)azetidin-1-yl)prop-2-en-1-one |

TABLE 1-continued

| Compound Number | Structure | Compound Name |
|---|---|---|
| 177 | 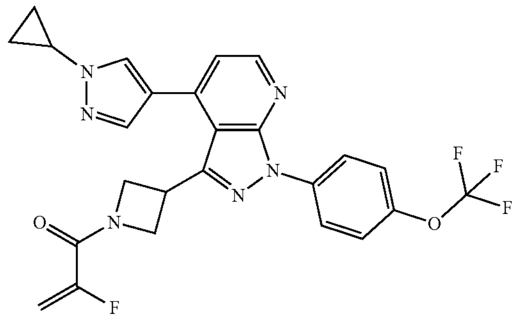 [SMILES: C=C(F)C(=O)N1CC(c2nn(-c3ccc(OC(F)(F)F)cc3)c3nccc(-c4cnn(C5CC5)c4)c23)C1] | 1-(3-(4-(1-cyclopropyl-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one |
| 178 | 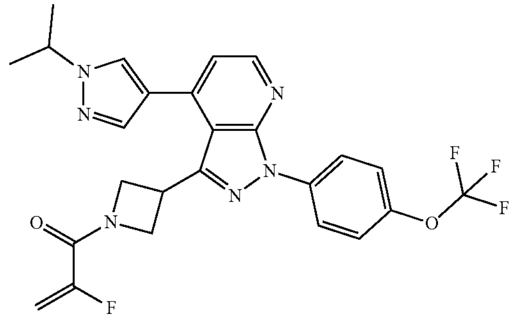 [SMILES: C=C(F)C(=O)N1CC(c2nn(-c3ccc(OC(F)(F)F)cc3)c3nccc(-c4cnn(C(C)C)c4)c23)C1] | 2-fluoro-1-(3-(4-(1-isopropyl-1H-pyrazol-4-yl)-1-(4-(trifluoromethoxy)phenyl)-1H-pyrazolo[3,4-b]pyridin-3-yl)azetidin-1-yl)prop-2-en-1-one |
| 179 | 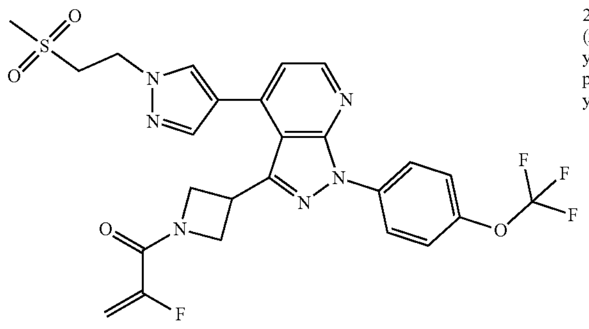 | 2-fluoro-1-(3-(4-(1-(2-(methylsulfonyl)ethyl)-1H-pyrazol-4-yl)-1-(4-(trifluoromethoxy)phenyl)-1H-pyrazolo[3,4-b]pyridin-3-yl)azetidin-1-yl)prop-2-en-1-one |
| 180 | 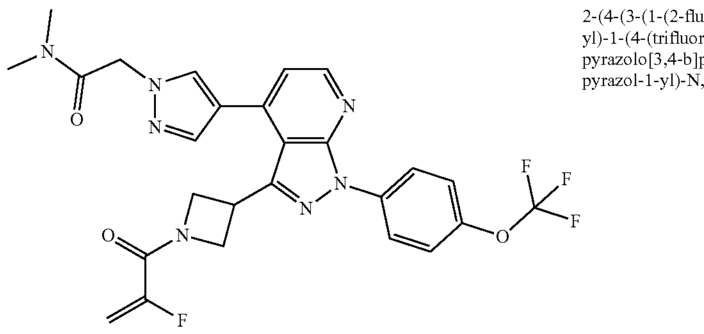 | 2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)-N,N-dimethylacetamide |

TABLE 1-continued

| Compound Number | Structure | Compound Name |
|---|---|---|
| 181 | 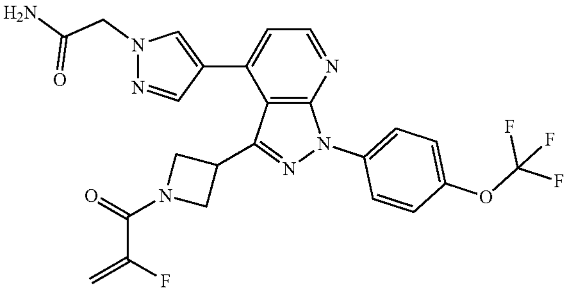 [SMILES: C=C(F)C(=O)N1CC(c2nn(-c3ccc(OC(F)(F)F)cc3)c3nccc(-c4cnn(CC(N)=O)c4)c23)C1] | 2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)acetamide |
| 182 | 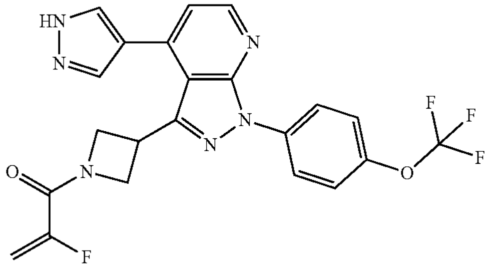 [SMILES: C=C(F)C(=O)N1CC(c2nn(-c3ccc(OC(F)(F)F)cc3)c3nccc(-c4cn[nH]c4)c23)C1] | 1-(3-(4-(1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one |
| 183 | 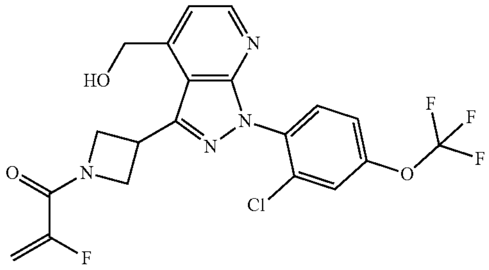 [SMILES: C=C(F)C(=O)N1CC(c2nn(-c3ccc(OC(F)(F)F)cc3Cl)c3nccc(CO)c23)C1] | 1-(3-(1-(2-chloro-4-(trifluoromethoxy)phenyl)-4-(hydroxymethyl)-1H-pyrazolo[3,4-b]pyridin-3-yl)azetidin-1-yl)-2-fluoroprop-2-en-1-one |
| 184 | 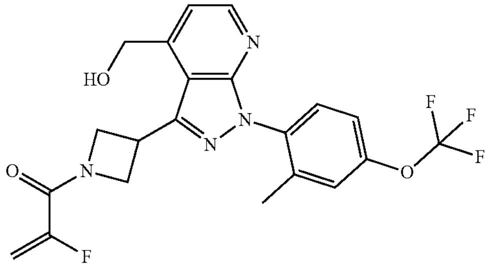 [SMILES: C=C(F)C(=O)N1CC(c2nn(-c3ccc(OC(F)(F)F)cc3C)c3nccc(CO)c23)C1] | 2-fluoro-1-(3-(4-(hydroxymethyl)-1-(2-methyl-4-(trifluoromethoxy)phenyl)-1H-pyrazolo[3,4-b]pyridin-3-yl)azetidin-1-yl)prop-2-en-1-one |
| 185 | 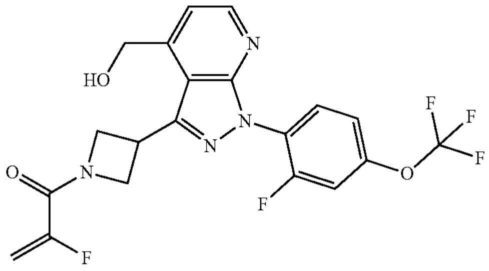 [SMILES: C=C(F)C(=O)N1CC(c2nn(-c3ccc(OC(F)(F)F)cc3F)c3nccc(CO)c23)C1] | 2-fluoro-1-(3-(1-(2-fluoro-4-(trifluoromethoxy)phenyl)-4-(hydroxymethyl)-1H-pyrazolo[3,4-b]pyridin-3-yl)azetidin-1-yl)prop-2-en-1-one |

TABLE 1-continued

| Compound Number | Structure | Compound Name |
|---|---|---|
| 186 | 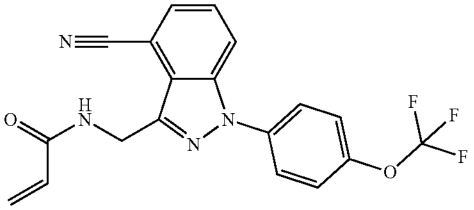 [SMILES: C=CC(=O)NCc1nn(-c2ccc(OC(F)(F)F)cc2)c2cccc(C#N)c12] | N-((4-cyano-1-(4-(trifluoromethoxy)phenyl)-1H-indazol-3-yl)methyl)acrylamide |
| 187 | 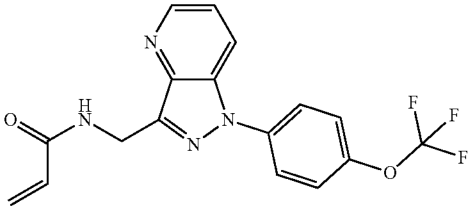 [SMILES: C=CC(=O)NCc1nn(-c2ccc(OC(F)(F)F)cc2)c2cccnc12] | N-((1-(4-(trifluoromethoxy)phenyl)-1H-pyrazolo[4,3-b]pyridin-3-yl)methyl)acrylamide |
| 188 | 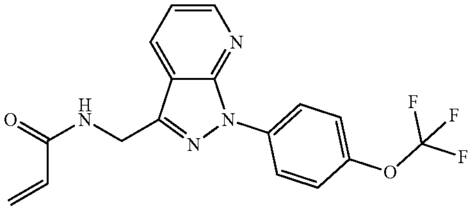 [SMILES: C=CC(=O)NCc1nn(-c2ccc(OC(F)(F)F)cc2)c2ncccc12] | N-((1-(4-(trifluoromethoxy)phenyl)-1H-pyrazolo[3,4-b]pyridin-3-yl)methyl)acrylamide |

Provided herein is a compound selected from the group consisting of:

N-((1-(4-(trifluoromethoxy)phenyl)-1H-indazol-3-yl)methyl)acrylamide, 2-chloro-N-((1-(4-(trifluoromethoxy)phenyl)-1H-indazol-3-yl)methyl)acetamide, N-((1-(4-(pentafluoro-λ6-sulfanyl)phenyl)-1H-indazol-3-yl)methyl)acrylamide, N-((4-(hydroxymethyl)-1-(4-(trifluoromethoxy)phenyl)-1H-indazol-3-yl)methyl)acrylamide, N-((4-(hydroxymethyl)-1-(4-(pentafluoro-λ6-sulfanyl)phenyl)-1H-indazol-3-yl)methyl)acrylamide, N-((4-(1,2-dihydroxyethyl)-1-(4-(trifluoromethoxy)phenyl)-1H-indazol-3-yl)methyl)acrylamide, (R)-N-((4-(1,2-dihydroxyethyl)-1-(4-(trifluoromethoxy)phenyl)-1H-indazol-3-yl)methyl)acrylamide, (S)-N-((4-(1,2-dihydroxyethyl)-1-(4-(trifluoromethoxy)phenyl)-1H-indazol-3-yl)methyl)acrylamide, N-((4-(1,2-dihydroxyethyl)-1-(4-(pentafluoro-λ6-sulfanyl)phenyl)-1H-indazol-3-yl)methyl)acrylamide, (R)-N-((4-(1,2-dihydroxyethyl)-1-(4-(pentafluoro-λ6-sulfanyl)phenyl)-1H-indazol-3-yl)methyl)acrylamide, (S)-N-((4-(1,2-dihydroxyethyl)-1-(4-(pentafluoro-λ6-sulfanyl)phenyl)-1H-indazol-3-yl)methyl)acrylamide, N-((1-(4-(pentafluoro-λ6-sulfanyl)phenyl)-1H-pyrazolo[4,3-b]pyridin-3-yl)methyl)acrylamide, N-((1-(4-(pentafluoro-λ6-sulfanyl)phenyl)-1H-pyrazolo[3,4-b]pyridin-3-yl)methyl)acrylamide, N-((4-cyano-1-(4-(pentafluoro-λ6-sulfanyl)phenyl)-1H-indazol-3-yl)methyl)acrylamide, N-[[4-(1,2-dihydroxyethyl)-1-(4-(trifluoromethoxy)phenyl)-1H-pyrazolo[3,4-b]pyridin-3-yl]methyl]acrylamide, (R)-N-[[4-(1,2-dihydroxyethyl)-1-(4-(trifluoromethoxy)phenyl)-1H-pyrazolo[3,4-b]pyridin-3-yl]methyl]acrylamide, (S)-N-[[4-(1,2-dihydroxyethyl)-1-(4-(trifluoromethoxy)phenyl)-1H-pyrazolo[3,4-b]pyridin-3-yl]methyl]acrylamide, N-methyl-N-((1-(4-(trifluoromethoxy)phenyl)-1H-indazol-3-yl)methyl)acrylamide, and 2-chloro-N-methyl-N-((1-(4-(trifluoromethoxy)phenyl)-1H-indazol-3-yl)methyl)acetamide, or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, tautomers, or mixtures thereof in any ratio, including racemic mixtures.

Provided herein is a compound selected from the group consisting of:

N-((1-(4-(trifluoromethoxy)phenyl)-1H-indazol-3-yl)methyl)acrylamide;

2-chloro-N-((1-(4-(trifluoromethoxy)phenyl)-1H-indazol-3-yl)methyl)acetamide;

N-((1-(4-(pentafluoro-λ6-sulfanyl)phenyl)-1H-indazol-3-yl)methyl)acrylamide;

N-((4-(hydroxymethyl)-1-(4-(trifluoromethoxy)phenyl)-1H-indazol-3-yl)methyl)acrylamide;

N-((4-(hydroxymethyl)-1-(4-(pentafluoro-λ6-sulfanyl)phenyl)-1H-indazol-3-yl)methyl)acrylamide;

N-((4-(1,2-dihydroxyethyl)-1-(4-(trifluoromethoxy)phenyl)-1H-indazol-3-yl)methyl)acrylamide;

(R)-N-((4-(1,2-dihydroxyethyl)-1-(4-(trifluoromethoxy)phenyl)-1H-indazol-3-yl)methyl)acrylamide;

(S)-N-((4-(1,2-dihydroxyethyl)-1-(4-(trifluoromethoxy)phenyl)-1H-indazol-3-yl)methyl)acrylamide;

N-((4-(1,2-dihydroxyethyl)-1-(4-(pentafluoro-λ6-sulfanyl)phenyl)-1H-indazol-3-yl)methyl)acrylamide;

(R)-N-((4-(1,2-dihydroxyethyl)-1-(4-(pentafluoro-λ6-sulfanyl)phenyl)-1H-indazol-3-yl)methyl)acrylamide;

(S)-N-((4-(1,2-dihydroxyethyl)-1-(4-(pentafluoro-λ6-sulfanyl)phenyl)-1H-indazol-3-yl)methyl)acrylamide;
N-((1-(4-(pentafluoro-λ6-sulfanyl)phenyl)-1H-pyrazolo[4,3-b]pyridin-3-yl)methyl)acrylamide;
N-((1-(4-(pentafluoro-λ6-sulfanyl)phenyl)-1H-pyrazolo[3,4-b]pyridin-3-yl)methyl)acrylamide;
N-((4-cyano-1-(4-(pentafluoro-λ6-sulfanyl)phenyl)-1H-indazol-3-yl)methyl)acrylamide;
N-[[4-(1,2-dihydroxyethyl)-1-(4-(trifluoromethoxy)phenyl)-1H-pyrazolo[3,4-b]pyridin-3-yl]methyl]acrylamide;
(R)-N-[[4-(1,2-dihydroxyethyl)-1-(4-(trifluoromethoxy)phenyl)-1H-pyrazolo[3,4-b]pyridin-3-yl]methyl]acrylamide;
(S)-N-[[4-(1,2-dihydroxyethyl)-1-(4-(trifluoromethoxy)phenyl)-1H-pyrazolo[3,4-b]pyridin-3-yl]methyl]acrylamide;
N-methyl-N-((1-(4-(trifluoromethoxy)phenyl)-1H-indazol-3-yl)methyl)acrylamide;
2-chloro-N-methyl-N-((1-(4-(trifluoromethoxy)phenyl)-1H-indazol-3-yl)methyl)acetamide;
2-fluoro-1-[3-[4-(hydroxymethyl)-1-[4-(trifluoromethoxy)phenyl]pyrazolo[3,4-b]pyridin-3-yl]azetidin-1-yl]prop-2-en-1-one;
1-[3-[4-[(1R)-1,2-dihydroxy ethyl]-1-[4-(trifluoromethoxy)phenyl]pyrazolo[3,4-b]pyridin-3-yl]azetidin-1-yl]-2-fluoro-prop-2-en-1-one;
1-[3-[4-(hydroxymethyl)-1-[4-(trifluoromethoxy)phenyl]pyrazolo[3,4-b]pyridin-3-yl]azetidin-1-yl]-2-methyl-prop-2-en-1-one;
N-[[1-[4-(pentafluoro-lambda6-sulfanyl)phenyl]-4-[rac-(1S)-1,2-dihydroxy ethyl]pyrazolo[3,4-b]pyridin-3-yl]methyl]prop-2-enamide;
N-[[4-[(2-hydroxyacetyl)amino]-1-[4-(trifluoromethoxy)phenyl]pyrazolo[3,4-b]pyridin-3-yl]methyl]prop-2-enamide;
N-(2-hydroxy ethyl)-3-[(prop-2-enoylamino)methyl]-1-[4-(trifluoromethoxy)phenyl]pyrazolo[3,4-b]pyridine-4-carboxamide;
(Z)-3-chloro-N-[[4-[(1R)-1,2-dihydroxy ethyl]-1-[4-(trifluoromethoxy)phenyl]pyrazolo[3,4-b]pyridin-3-yl]methyl]prop-2-enamide;
N-[[1-[4-(pentafluoro-lambda6-sulfanyl)phenyl]-4-[rac-(1R)-1,2-dihydroxy ethyl]pyrazolo[3,4-b]pyridin-3-yl]methyl]prop-2-enamide;
2-fluoro-1-[3-[4-[1-(2-hydroxyethyl)pyrazol-4-yl]-1-[4-(trifluoromethoxy)phenyl]pyrazolo[3,4-b]pyridin-3-yl]azetidin-1-yl]prop-2-en-1-one;
2-fluoro-1-[3-[4-(1,2,4-triazol-4-yl)-1-[4-(trifluoromethoxy)phenyl]pyrazolo[3,4-b]pyridin-3-yl]azetidin-1-yl]prop-2-en-1-one;
N-methyl-3-[(prop-2-enoylamino)methyl]-1-[4-(trifluoromethoxy)phenyl]pyrazolo[3,4-b]pyridine-4-carboxamide;
1-[3-[4-[(1S)-1,2-dihydroxy ethyl]-1-[4-(trifluoromethoxy)phenyl]pyrazolo[3,4-b]pyridin-3-yl]azetidin-1-yl]-2-fluoro-prop-2-en-1-one;
N-[[4-(hydroxymethyl)-1-[4-(trifluoromethoxy)phenyl]pyrazolo[3,4-b]pyridin-3-yl]methyl]prop-2-enamide;
N-[[4-[(3S)-3-hydroxy-1-piperidyl]-1-[4-(trifluoromethoxy)phenyl]pyrazolo[3,4-b]pyridin-3-yl]methyl]prop-2-enamide;
N-[[4-[(3-hydroxycyclobutoxy)-1-[4-(trifluoromethoxy)phenyl]pyrazolo[3,4-b]pyridin-3-yl]methyl]prop-2-enamide;
N-[[4-[1-(2-hydroxyethyl)pyrazol-4-yl]-1-[4-(trifluoromethoxy)phenyl]pyrazolo[3,4-b]pyridin-3-yl]methyl]prop-2-enamide;
N-[[4-(2-hydroxyethylamino)-1-[4-(trifluoromethoxy)phenyl]pyrazolo[3,4-b]pyridin-3-yl]methyl]prop-2-enamide;
(E)-3-chloro-N-[[4-(hydroxymethyl)-1-[4-(trifluoromethoxy)phenyl]pyrazolo[3,4-b]pyridin-3-yl]methyl]prop-2-enamide;
N-[[4-[(3-hydroxycyclobutyl)-1-[4-(trifluoromethoxy)phenyl]pyrazolo[3,4-b]pyridin-3-yl]methyl]prop-2-enamide;
2-fluoro-1-[3-[4-[3-fluoro-3-(hydroxymethyl)azetidin-1-yl]-1-[4-(trifluoromethoxy)phenyl]pyrazolo[3,4-b]pyridin-3-yl]azetidin-1-yl]prop-2-en-1-one;
(E)-1-[3-[4-(hydroxymethyl)-1-[4-(trifluoromethoxy)phenyl]pyrazolo[3,4-b]pyridin-3-yl]azetidin-1-yl]-4-methoxy-but-2-en-1-one;
1-[3-[4-(2,6-diazaspiro[3.3]heptan-2-yl)-1-[4-(trifluoromethoxy)phenyl]pyrazolo[3,4-b]pyridin-3-yl]azetidin-1-yl]-2-fluoro-prop-2-en-1-one;
N-[3-[1-(2-fluoroprop-2-enoyl)azetidin-3-yl]-1-[4-(trifluoromethoxy)phenyl]pyrazolo[3,4-b]pyridin-4-yl]-2-hydroxy-acetamide;
N-[[4-[3-(hydroxymethyl)azetidin-1-yl]-1-[4-(trifluoromethoxy)phenyl]pyrazolo[3,4-b]pyridin-3-yl]methyl]prop-2-enamide;
N-[[4-(1H-1,2,4-triazol-3-yl)-1-[4-(trifluoromethoxy)phenyl]pyrazolo[3,4-b]pyridin-3-yl]methyl]prop-2-enamide;
1-[3-[4-[1-[2-(dimethylamino)ethyl]pyrazol-4-yl]-1-[4-(trifluoromethoxy)phenyl]pyrazolo[3,4-b]pyridin-3-yl]azetidin-1-yl]-2-fluoro-prop-2-en-1-one;
N-[[4-[(3S)-3-hydroxypyrrolidin-1-yl]-1-[4-(trifluoromethoxy)phenyl]pyrazolo[3,4-b]pyridin-3-yl]methyl]prop-2-enamide;
N-[[4-[(3R)-3-hydroxypyrrolidin-1-yl]-1-[4-(trifluoromethoxy)phenyl]pyrazolo[3,4-b]pyridin-3-yl]methyl]prop-2-enamide;
1-[3-[4-ethynyl-1-[4-(trifluoromethoxy)phenyl]pyrazolo[3,4-b]pyridin-3-yl]azetidin-1-yl]prop-2-en-1-one;
2-chloro-N-[[4-(hydroxymethyl)-1-[4-(trifluoromethoxy)phenyl]pyrazolo[3,4-b]pyridin-3-yl]methyl]prop-2-enamide;
(E)-4-hydroxy-1-[3-[4-(1H-pyrazol-4-yl)-1-[4-(trifluoromethoxy)phenyl]pyrazolo[3,4-b]pyridin-3-yl]azetidin-1-yl]but-2-en-1-one;
N-[[4-(1H-triazol-4-yl)-1-[4-(trifluoromethoxy)phenyl]pyrazolo[3,4-b]pyridin-3-yl]methyl]prop-2-enamide;
N-[[4-[(3-cyanoazetidin-1-yl)-1-[4-(trifluoromethoxy)phenyl]pyrazolo[3,4-b]pyridin-3-yl]methyl]prop-2-enamide;
(Z)-3-chloro-N-[[4-[(1S)-1,2-dihydroxyethyl]-1-[4-(trifluoromethoxy)phenyl]pyrazolo[3,4-b]pyridin-3-yl]methyl]prop-2-enamide;
N-[[4-[(3-hydroxy azetidin-1-yl)methyl]-1-[4-(trifluoromethoxy)phenyl]pyrazolo[3,4-b]pyridin-3-yl]methyl]prop-2-enamide;
N-[[4-(hydroxymethyl)-1-[4-(trifluoromethoxy)phenyl]pyrazolo[3,4-b]pyridin-3-yl]methyl]-N-methyl-prop-2-enamide;
N-[[4-[(3-hydroxycyclobutyl)-1-[4-(trifluoromethoxy)phenyl]pyrazolo[3,4-b]pyridin-3-yl]methyl]prop-2-enamide;
3-fluoro-1-[3-[1-(2-fluoroprop-2-enoyl)azetidin-3-yl]-1-[4-(trifluoromethoxy)phenyl]pyrazolo[3,4-b]pyridin-4-yl]azetidine-3-carboxamide;
1-[3-[4-[3-[(1R)-1,2-dihydroxyethyl]azetidin-1-yl]-1-[4-(trifluoromethoxy)phenyl]pyrazolo[3,4-b]pyridin-3-yl]azetidin-1-yl]-2-fluoro-prop-2-en-1-one;
1-[3-[4-[(1S)-1,2-dihydroxyethyl]-1-[4-(pentafluoro-lambda6-sulfanyl)phenyl]pyrazolo[3,4-b]pyridin-3-yl]azetidin-1-yl]-2-fluoro-prop-2-en-1-one;

1-[3-[4-[(1R)-1,2-dihydroxyethyl]-1-[4-(pentafluoro-lambda6-sulfanyl)phenyl]pyrazolo[3,4-b]pyridin-3-yl]azetidin-1-yl]-2-fluoro-prop-2-en-1-one;

(E)-N-[[4-(hydroxymethyl)-1-[4-(trifluoromethoxy)phenyl]pyrazolo[3,4-b]pyridin-3-yl]methyl]but-2-enamide;

N-[[4-[(1R)-1-hydroxyethyl]-1-[4-(trifluoromethoxy)phenyl]pyrazolo[3,4-b]pyridin-3-yl]methyl]prop-2-enamide;

N-[[4-[(1 S)-1-hydroxyethyl]-1-[4-(trifluoromethoxy)phenyl]pyrazolo[3,4-b]pyridin-3-yl]methyl]prop-2-enamide;

2-fluoro-1-[3-[4-imidazol-1-yl-1-[4-(trifluoromethoxy)phenyl]pyrazolo[3,4-b]pyridin-3-yl]azetidin-1-yl]prop-2-en-1-one;

N-[[4-[(3R)-3-hydroxy-1-piperidyl]-[1-[4-(trifluoromethoxy)phenyl]pyrazolo[3,4-b]pyridin-3-yl]methyl]prop-2-enamide;

(E,4R)-4-hydroxy-1-[3-[4-(hydroxy methyl)-1-[4-(trifluoromethoxy)phenyl]pyrazolo[3,4-b]pyridin-3-yl]azetidin-1-yl]pent-2-en-1-one;

N-[[4-[(3-hydroxycyclobutoxy)-1-[4-(trifluoromethoxy)phenyl]pyrazolo[3,4-b]pyridin-3-yl]methyl]prop-2-enamide;

2-fluoro-N-[[4-(hydroxymethyl)-1-[4-(trifluoromethoxy)phenyl]pyrazolo[3,4-b]pyridin-3-yl]methyl]prop-2-enamide;

(E)-4,4-difluoro-N-[[4-(hydroxymethyl)-1-[4-(trifluoromethoxy)phenyl]pyrazolo[3,4-b]pyridin-3-yl]methyl]but-2-enamide;

(E)-4-hydroxy-1-[3-[4-(3-hydroxy azetidin-1-yl)-1-[4-(trifluoromethoxy)phenyl]pyrazolo[3,4-b]pyridin-3-yl]azetidin-1-yl]but-2-en-1-one;

1-[3-[4-[(1R)-1,2-dihydroxyethyl]-1-[4-(trifluoromethoxy)phenyl]pyrazolo[3,4-b]pyridin-3-yl]azetidin-1-yl]but-2-yn-1-one;

cyclobuten-1-yl-[3-[4-[(1S)-1,2-dihydroxyethyl]-1-[4-(trifluoromethoxy)phenyl]pyrazolo[3,4-b]pyridin-3-yl]azetidin-1-yl]methanone;

N-[[4-[rac-(1S)-1,2-dihydroxyethyl]-1-[3-(trifluoromethoxy)phenyl]pyrazolo[3,4-b]pyridin-3-yl]methyl]prop-2-enamide;

N-[[4-[(3-hydroxy-3-methyl-azetidin-1-yl)-1-[4-(trifluoromethoxy)phenyl]pyrazolo[3,4-b]pyridin-3-yl]methyl]prop-2-enamide;

2-fluoro-1-[3-[4-[3-hydroxy-3-(hydroxymethyl)azetidin-1-yl]-1-[4-(trifluoromethoxy)phenyl]pyrazolo[3,4-b]pyridin-3-yl]azetidin-1-yl]prop-2-en-1-one;

N-[[4-(6-hydroxy-2-azaspiro[3.3]heptan-2-yl)-1-[4-(trifluoromethoxy)phenyl]pyrazolo[3,4-b]pyridin-3-yl]methyl]prop-2-enamide;

N-[[4-morpholino-1-[4-(trifluoromethoxy)phenyl]pyrazolo[3,4-b]pyridin-3-yl]methyl]prop-2-enamide;

2-fluoro-1-[3-[4-(3-hydroxyazetidin-1-yl)-1-[4-(trifluoromethoxy)phenyl]pyrazolo[4,3-c]pyridin-3-yl]azetidin-1-yl]prop-2-en-1-one;

3-[1-[(E)-4-hydroxybut-2-enoyl]azetidin-3-yl]-1-[4-(trifluoromethoxy)phenyl]pyrazolo[3,4-b]pyridine-4-carbonitrile;

3-[1-(2-fluoroprop-2-enoyl)azetidin-3-yl]-1-[4-(trifluoromethoxy)phenyl]pyrazolo[3,4-b]pyridine-4-carbonitrile;

2-fluoro-1-[3-[4-(3-hydroxyazetidin-1-yl)-1-[4-(trifluoromethoxy)phenyl]pyrazolo[3,4-b]pyridin-3-yl]azetidin-1-yl]prop-2-en-1-one;

(3S)-1-[3-[1-(2-fluoroprop-2-enoyl)azetidin-3-yl]-1-[4-(trifluoromethoxy)phenyl]pyrazolo[3,4-b]pyridin-4-yl]-3-hydroxy-pyrrolidin-2-one;

N-[[4-(1H-pyrazol-3-yl)-1-[4-(trifluoromethoxy)phenyl]pyrazolo[3,4-b]pyridin-3-yl]methyl]prop-2-enamide;

N-[[4-[(3-fluoroazetidin-1-yl)-1-[4-(trifluoromethoxy)phenyl]pyrazolo[3,4-b]pyridin-3-yl]methyl]prop-2-enamide;

N-[[4-[(3-hydroxycyclobutyl)amino]-1-[4-(trifluoromethoxy)phenyl]pyrazolo[3,4-b]pyridin-3-yl]methyl]prop-2-enamide;

N-[[4-(hydroxymethyl)-1-[4-(trifluoromethoxy)phenyl]pyrazolo[3,4-b]pyridin-3-yl]methyl]prop-2-ynamide;

N-[[4-(hydroxymethyl)-1-[4-(pentafluoro-lambda6-sulfanyl)phenyl]pyrazolo[3,4-b]pyridin-3-yl]methyl]prop-2-enamide;

N-[[4-[rac-(1R)-1,2-dihydroxyethyl]-1-[4-(trifluoromethyl)phenyl]pyrazolo[3,4-b]pyridin-3-yl]methyl]prop-2-enamide;

cyclobuten-1-yl-[3-[4-(hydroxymethyl)-1-[4-(trifluoromethoxy)phenyl]pyrazolo[3,4-b]pyridin-3-yl]azetidin-1-yl]methanone;

N-[[4-[(3-hydroxycyclobutyl)-methyl-amino]-1-[4-(trifluoromethoxy)phenyl]pyrazolo[3,4-b]pyridin-3-yl]methyl]prop-2-enamide;

N-[[4-(4-hydroxy-1-piperidyl)-1-[4-(trifluoromethoxy)phenyl]pyrazolo[3,4-b]pyridin-3-yl]methyl]prop-2-enamide;

N-[[4-[(3-aminoazetidin-1-yl)-1-[4-(trifluoromethoxy)phenyl]pyrazolo[3,4-b]pyridin-3-yl]methyl]prop-2-enamide;

N-[[4-[(1R)-1,2-dihydroxyethyl]-1-[4-(trifluoromethoxy)phenyl]pyrazolo[3,4-b]pyridin-3-yl]methyl]-N-methyl-prop-2-enamide;

(E)-4-hydroxy-1-[3-[4-(hydroxymethyl)-1-[4-(trifluoromethoxy)phenyl]pyrazolo[3,4-b]pyridin-3-yl]azetidin-1-yl]but-2-en-1-one;

(E)-1-[3-[4-[(1R)-1,2-dihydroxyethyl]-1-[4-(trifluoromethoxy)phenyl]pyrazolo[3,4-b]pyridin-3-yl]azetidin-1-yl]-4-hydroxy-but-2-en-1-one;

(E)-4-hydroxy-1-[3-[4-methyl-1-[4-(trifluoromethoxy)phenyl]pyrazolo[3,4-b]pyridin-3-yl]azetidin-1-yl]but-2-en-1-one;

(E,4S)-4-hydroxy-1-[3-[4-(hydroxymethyl)-1-[4-(trifluoromethoxy)phenyl]pyrazolo[3,4-b]pyridin-3-yl]azetidin-1-yl]pent-2-en-1-one;

N-[[4-(hydroxymethyl)-1-[4-(trifluoromethoxy)phenyl]pyrazolo[3,4-b]pyridin-3-yl]methyl]but-2-ynamide;

(Z)-3-chloro-N-[[4-(hydroxymethyl)-1-[4-(trifluoromethoxy)phenyl]pyrazolo[3,4-b]pyridin-3-yl]methyl]prop-2-enamide;

N-[[4-[rac-(1S)-1,2-dihydroxyethyl]-1-[4-(trifluoromethyl)phenyl]pyrazolo[3,4-b]pyridin-3-yl]methyl]prop-2-enamide;

N-[[4-[2-hydroxyethyl(methyl)amino]-1-[4-(trifluoromethoxy)phenyl]pyrazolo[3,4-b]pyridin-3-yl]methyl]prop-2-enamide;

(E)-3-chloro-1-[3-[4-(hydroxymethyl)-1-[4-(trifluoromethoxy)phenyl]pyrazolo[3,4-b]pyridin-3-yl]azetidin-1-yl]prop-2-en-1-one;

(E)-4-hydroxy-1-[3-[4-(3-hydroxyazetidin-1-yl)-1-[4-(trifluoromethoxy)phenyl]pyrazolo[4,3-c]pyridin-3-yl]azetidin-1-yl]but-2-en-1-one;

3-[prop-2-enoylamino)methyl]-1-[4-(trifluoromethoxy)phenyl]pyrazolo[3,4-b]pyridine-4-carboxamide;

N-[[4-[(dimethylamino)methyl]-1-[4-(trifluoromethoxy)phenyl]pyrazolo[3,4-b]pyridin-3-yl]methyl]prop-2-enamide;

N-[[4-[(3-hydroxyazetidin-1-yl)-1-[4-(trifluoromethoxy)phenyl]pyrazolo[3,4-b]pyridin-3-yl]methyl]prop-2-enamide;

N-[[4-[(3-(dimethylamino)azetidin-1-yl]-[1-[4-(trifluoromethoxy)phenyl]pyrazolo[3,4-b]pyridin-3-yl]methyl]prop-2-enamide;

(E)-1-[3-[4-[(1S)-1,2-dihydroxy ethyl]-1-[4-(trifluoromethoxy)phenyl]pyrazolo[3,4-b]pyridin-3-yl]azetidin-1-yl]-4-hydroxy-but-2-en-1-one;
2-chloro-1-[3-[4-[(1S)-1,2-dihydroxyethyl]-1-[4-(trifluoromethoxy)phenyl]pyrazolo[3,4-b]pyridin-3-yl]azetidin-1-yl]prop-2-en-1-one;
2-chloro-1-[3-[4-[(1R)-1,2-dihydroxyethyl]-1-[4-(trifluoromethoxy)phenyl]pyrazolo[3,4-b]pyridin-3-yl]azetidin-1-yl]prop-2-en-1-one;
2,3,3-trideuterio-N-[[4-(hydroxymethyl)-1-[4-(trifluoromethoxy)phenyl]pyrazolo[3,4-b]pyridin-3-yl]methyl]prop-2-enamide;
1-[3-[4-(hydroxymethyl)-1-[4-(trifluoromethoxy)phenyl]pyrazolo[3,4-b]pyridin-3-yl]azetidin-1-yl]prop-2-en-1-one;
1-[3-[4-[(1S)-1,2-dihydroxy ethyl]-1-[4-(trifluoromethoxy)phenyl]pyrazolo[3,4-b]pyridin-3-yl]azetidin-1-yl]prop-2-en-1-one;
1-[3-[4-[(1R)-1,2-dihydroxy ethyl]-1-[4-(trifluoromethoxy)phenyl]pyrazolo[3,4-b]pyridin-3-yl]azetidin-1-yl]prop-2-en-1-one;
cyclobuten-1-yl-[3-[4-[(1R)-1,2-dihydroxyethyl]-1-[4-(trifluoromethoxy)phenyl]pyrazolo[3,4-b]pyridin-3-yl]azetidin-1-yl]methanone;
N-[[4-[(3-acetamidoazetidin-1-yl)-1-[4-(trifluoromethoxy)phenyl]pyrazolo[3,4-b]pyridin-3-yl]methyl]prop-2-enamide;
N-[[4-[(3-hydroxycyclobutyl)-methyl-amino]-1-[4-(trifluoromethoxy)phenyl]pyrazolo[3,4-b]pyridin-3-yl]methyl]prop-2-enamide;
N-[[4-[(3-methoxyazetidin-1-yl)-1-[4-(trifluoromethoxy)phenyl]pyrazolo[3,4-b]pyridin-3-yl]methyl]prop-2-enamide;
N-[[4-(1H-imidazol-4-yl)-1-[4-(trifluoromethoxy)phenyl]pyrazolo[3,4-b]pyridin-3-yl]methyl]prop-2-enamide;
(E)-1-[3-[4-(hydroxymethyl)-1-[4-(trifluoromethoxy)phenyl]pyrazolo[3,4-b]pyridin-3-yl]azetidin-1-yl]but-2-en-1-one;
(E)-4-fluoro-N-[[4-(hydroxymethyl)-1-[4-(trifluoromethoxy)phenyl]pyrazolo[3,4-b]pyridin-3-yl]methyl]but-2-enamide;
N-[[4-[3-(methylamino)azetidin-1-yl]-1-[4-(trifluoromethoxy)phenyl]pyrazolo[3,4-b]pyridin-3-yl]methyl]prop-2-enamide;
N-[[4-[3-[(1R)-1-hydroxyethyl]azetidin-1-yl]-1-[4-(trifluoromethoxy)phenyl]pyrazolo[3,4-b]pyridin-3-yl]methyl]prop-2-enamide;
N-[[4-[3-hydroxy-3-(hydroxymethyl)azetidin-1-yl]-1-[4-(trifluoromethoxy)phenyl]pyrazolo[3,4-b]pyridin-3-yl]methyl]prop-2-enamide;
(3R)-1-[3-[1-(2-fluoroprop-2-enoyl)azetidin-3-yl]-1-[4-(trifluoromethoxy)phenyl]pyrazolo[3,4-b]pyridin-4-yl]-3-hydroxy-pyrrolidin-2-one;
N-[[4-(2-hydroxy ethoxy)-1-[4-(trifluoromethoxy)phenyl]pyrazolo[3,4-b]pyridin-3-yl]methyl]prop-2-enamide;
(E)-1-[3-[4-chloro-1-[4-(trifluoromethoxy)phenyl]pyrazolo[3,4-b]pyridin-3-yl]azetidin-1-yl]-4-hydroxy-but-2-en-1-one;
4-hydroxy-N-[[4-(hydroxymethyl)-1-[4-(trifluoromethoxy)phenyl]pyrazolo[3,4-b]pyridin-3-yl]methyl]but-2-ynamide;
1-[3-[4-[(1S)-1,2-dihydroxy ethyl]-1-[4-(trifluoromethoxy)phenyl]pyrazolo[3,4-b]pyridin-3-yl]azetidin-1-yl]but-2-yn-1-one;
2-fluoro-1-[3-[4-(1H-imidazol-4-yl)-1-[4-(trifluoromethoxy)phenyl]pyrazolo[3,4-b]pyridin-3-yl]azetidin-1-yl]prop-2-en-1-one;
N-[[4-[rac-(1R)-1,2-dihydroxyethyl]-1-[3-(trifluoromethoxy)phenyl]pyrazolo[3,4-b]pyridin-3-yl]methyl]prop-2-enamide;
(E)-4,4,4-trifluoro-N-[[4-(hydroxymethyl)-1-[4-(trifluoromethoxy)phenyl]pyrazolo[3,4-b]pyridin-3-yl]methyl]but-2-enamide;
1-[3-[4-(azetidin-3-yl)-1-[4-(trifluoromethoxy)phenyl]pyrazolo[3,4-b]pyridin-3-yl]azetidin-1-yl]-2-fluoro-prop-2-en-1-one;
N-[[4-(1H-pyrazol-4-yl)-1-[4-(trifluoromethoxy)phenyl]pyrazolo[3,4-b]pyridin-3-yl]methyl]prop-2-enamide;
N-[[4-(1-hydroxy-1-methyl-ethyl)-1-[4-(trifluoromethoxy)phenyl]pyrazolo[3,4-b]pyridin-3-yl]methyl]prop-2-enamide;
N-[[4-[3-(1-hydroxy-1-methyl-ethyl)azetidin-1-yl]-1-[4-(trifluoromethoxy)phenyl]pyrazolo[3,4-b]pyridin-3-yl]methyl]prop-2-enamide;
(E)-4-fluoro-1-[3-[4-(3-hydroxy azetidin-1-yl)-1-[4-(trifluoromethoxy)phenyl]pyrazolo[4,3-c]pyridin-3-yl]azetidin-1-yl]but-2-en-1-one;
N-[[4-[3-[(1S)-1-hydroxyethyl]azetidin-1-yl]-1-[4-(trifluoromethoxy)phenyl]pyrazolo[3,4-b]pyridin-3-yl]methyl]prop-2-enamide;
N-[[4-[(1S)-1,2-dihydroxyethyl]-1-[4-(trifluoromethoxy)phenyl]pyrazolo[3,4-b]pyridin-3-yl]methyl]-N-methyl-prop-2-enamide;
N-[[1-[4-(difluoromethoxy)phenyl]-4-(hydroxymethyl)pyrazolo[3,4-b]pyridin-3-yl]methyl]prop-2-enamide;
1-[3-[4-[3-[(1S)-1,2-dihydroxy ethyl]azetidin-1-yl]-1-[4-(trifluoromethoxy)phenyl]pyrazolo[3,4-b]pyridin-3-yl]azetidin-1-yl]-2-fluoro-prop-2-en-1-one;
1-[3-[4-[3,3-bis(hydroxymethyl)azetidin-1-yl]-1-[4-(trifluoromethoxy)phenyl]pyrazolo[3,4-b]pyridin-3-yl]azetidin-1-yl]-2-fluoro-prop-2-en-1-one;
N-[[4-[(3-hydroxycyclobutyl)amino]-1-[4-(trifluoromethoxy)phenyl]pyrazolo[3,4-b]pyridin-3-yl]methyl]prop-2-enamide;
(S)-N-((4-(2-Oxo-1,3-dioxolan-4-yl)-1-(4-(trifluoromethoxy)phenyl)-1H-pyrazolo[3,4-b]pyridin-3-yl)methyl)acrylamide;
(S)-2-(3-(Acrylamidomethyl)-1-(4-(trifluoromethoxy)phenyl)-1H-pyrazolo[3,4-b]pyridin-4-yl)-2-hydroxyethyl 2-aminoacetate formate;
(S)-2-(3-(Acrylamidomethyl)-1-(4-(trifluoromethoxy)phenyl)-1H-pyrazolo[3,4-b]pyridin-4-yl)-2-hydroxy ethyl acetate;
(S)-2-(3-(Acrylamidomethyl)-1-(4-(trifluoromethoxy)phenyl)-1H-pyrazolo[3,4-b]pyridin-4-yl)-2-hydroxyethyl dihydrogen phosphate;
N-((4-(Hydroxymethyl)-1-(4-(trifluoromethoxy)phenyl)-1H-pyrazolo[3,4-b]pyridin-3-yl)methyl)cyclobut-1-enecarboxamide;
N-((4-(Hydroxymethyl)-1-(4-(trifluoromethoxy)phenyl)-1H-pyrazolo[3,4-b]pyridin-3-yl)methyl)-2,5-dihydrofuran-3-carboxamide;
Cyclopent-1-en-1-yl(3-(4-(hydroxymethyl)-1-(4-(trifluoromethoxy)phenyl)-1H-pyrazolo[3,4-b]pyridin-3-yl)azetidin-1-yl)methanone;
(E)-1-(3-(4-(Hydroxymethyl)-1-(4-(trifluoromethoxy)phenyl)-1H-pyrazolo[3,4-b]pyridin-3-yl)azetidin-1-yl)-2-methylbut-2-en-1-one;
(2,5-Dihydrofuran-3-yl)(3-(4-(hydroxy methyl)-1-(4-(trifluoromethoxy)phenyl)-1H-pyrazolo[3,4-b]pyridin-3-yl)azetidin-1-yl) methanone;
Bicyclo[1.1.0]butan-1-yl(3-(4-(hydroxymethyl)-1-(4-(trifluoromethoxy)phenyl)-1H-pyrazolo[3,4-b]pyridin-3-yl)azetidin-1-yl) methanone;

(S)-N-((4-(1,2-Dihydroxyethyl)-1-(4-(trifluoromethoxy)phenyl)-1H-pyrazolo[3,4-b]pyridin-3-yl)methyl)acrylamide-2,3,3-d3;

(S)-N-((4-(1,2-Dihydroxyethyl)-1-(4-(trifluoromethoxy)phenyl)-1H-pyrazolo[3,4-b]pyridin-3-yl)methyl)-2-fluoroacrylamide;

(S)-N-((4-(1,2-Dihydroxyethyl)-1-(4-(trifluoromethoxy)phenyl)-1H-pyrazolo[3,4-b]pyridin-3-yl)methyl)cyclobut-1-enecarboxamide;

(R)-Cyclobut-1-en-1-yl(3-(4-(1,2-dihydroxyethyl)-1-(4-(trifluoromethoxy)phenyl)-1H-pyrazolo[3,4-b]pyridin-3-yl)azetidin-1-yl)methanone;

2-Fluoro-1-(3-(4-(1-methyl-1H-pyrazol-4-yl)-1-(4-(trifluoromethoxy)phenyl)-1H-pyrazolo[3,4-b]pyridin-3-yl)azetidin-1-yl)prop-2-en-1-one;

(S)-1-(3-(1-(Prop-1-en-2-ylsulfonyl)azetidin-3-yl)-1-(4-(trifluoromethoxy)phenyl)-1H-pyrazolo[3,4-b]pyridin-4-yl)ethane-1,2-diol;

(R)-1-(3-(1-(prop-1-en-2-ylsulfonyl)azetidin-3-yl)-1-(4-(trifluoromethoxy)phenyl)-1H-pyrazolo[3,4-b]pyridin-4-yl)ethane-1,2-diol;

(S,E)-1-(3-(1-(Prop-1-en-1-ylsulfonyl)azetidin-3-yl)-1-(4-(trifluoromethoxy)phenyl)-1H-pyrazolo[3,4-b]pyridin-4-yl)ethane-1,2-diol;

(R,E)-1-(3-(1-(prop-1-en-1-ylsulfonyl)azetidin-3-yl)-1-(4-(trifluoromethoxy)phenyl)-1H-pyrazolo[3,4-b]pyridin-4-yl)ethane-1,2-diol;

Cyclobut-1-en-1-yl(3-(1-(4-(trifluoromethoxy)phenyl)-1H-pyrazolo[3,4-b]pyrazin-3-yl)azetidin-1-yl)methanone;

N-((4-(1-Methyl-1H-pyrazol-4-yl)-1-(4-(trifluoromethoxy)phenyl)-1H-pyrazolo[3,4-b]pyridin-3-yl)methyl)acrylamide;

N-((4-(1-(2-amino-2-oxoethyl)-1H-pyrazol-4-yl)-1-(4-(trifluoromethoxy)phenyl)-1H-pyrazolo[3,4-b]pyridin-3-yl)methyl)acrylamide;

N-((4-(1-(2-(dimethylamino)-2-oxoethyl)-1H-pyrazol-4-yl)-1-(4-(trifluoromethoxy)phenyl)-1H-pyrazolo[3,4-b]pyridin-3-yl)methyl)acrylamide;

N-((4-(1-(2-methoxy ethyl)-1H-pyrazol-4-yl)-1-(4-(trifluoromethoxy)phenyl)-1H-pyrazolo[3,4-b]pyridin-3-yl)methyl)acrylamide;

N-((4-(1-(2-(methylsulfonyl)ethyl)-1H-pyrazol-4-yl)-1-(4-(trifluoromethoxy)phenyl)-1H-pyrazolo[3,4-b]pyridin-3-yl)methyl)acrylamide;

N-((4-(1-(difluoromethyl)-1H-pyrazol-4-yl)-1-(4-(trifluoromethoxy)phenyl)-1H-pyrazolo[3,4-b]pyridin-3-yl)methyl)acrylamide;

N-((4-(1-isopropyl-1H-pyrazol-4-yl)-1-(4-(trifluoromethoxy)phenyl)-1H-pyrazolo[3,4-b]pyridin-3-yl)methyl)acrylamide;

N-((4-(1-(oxetan-3-yl)-1H-pyrazol-4-yl)-1-(4-(trifluoromethoxy)phenyl)-1H-pyrazolo[3,4-b]pyridin-3-yl)methyl)acrylamide;

N-((4-(1-(2-(dimethylamino)ethyl)-1H-pyrazol-4-yl)-1-(4-(trifluoromethoxy)phenyl)-1H-pyrazolo[3,4-b]pyridin-3-yl)methyl)acrylamide;

N-((4-(1-cyclopropyl-1H-pyrazol-4-yl)-1-(4-(trifluoromethoxy)phenyl)-1H-pyrazolo[3,4-b]pyridin-3-yl)methyl)acrylamide;

1-(3-(4-(1-(difluoromethyl)-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one;

2-fluoro-1-(3-(4-(1-(oxetan-3-yl)-1H-pyrazol-4-yl)-1-(4-(trifluoromethoxy)phenyl)-1H-pyrazolo[3,4-b]pyridin-3-yl)azetidin-1-yl)prop-2-en-1-one;

2-fluoro-1-(3-(4-(1-(2-methoxyethyl)-1H-pyrazol-4-yl)-1-(4-(trifluoromethoxy)phenyl)-1H-pyrazolo[3,4-b]pyridin-3-yl)azetidin-1-yl)prop-2-en-1-one;

1-(3-(4-(1-cyclopropyl-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one;

2-fluoro-1-(3-(4-(1-isopropyl-1H-pyrazol-4-yl)-1-(4-(trifluoromethoxy)phenyl)-1H-pyrazolo[3,4-b]pyridin-3-yl)azetidin-1-yl)prop-2-en-1-one;

2-fluoro-1-(3-(4-(1-(2-(methylsulfonyl)ethyl)-1H-pyrazol-4-yl)-1-(4-(trifluoromethoxy)phenyl)-1H-pyrazolo[3,4-b]pyridin-3-yl)azetidin-1-yl)prop-2-en-1-one;

2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)-N,N-dimethylacetamide;

2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)acetamide;

1-(3-(4-(1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one;

1-(3-(1-(2-chloro-4-(trifluoromethoxy)phenyl)-4-(hydroxymethyl)-1H-pyrazolo[3,4-b]pyridin-3-yl)azetidin-1-yl)-2-fluoroprop-2-en-1-one;

2-fluoro-1-(3-(4-(hydroxymethyl)-1-(2-methyl-4-(trifluoromethoxy)phenyl)-1H-pyrazolo[3,4-b]pyridin-3-yl)azetidin-1-yl)prop-2-en-1-one;

2-fluoro-1-(3-(1-(2-fluoro-4-(trifluoromethoxy)phenyl)-4-(hydroxymethyl)-1H-pyrazolo[3,4-b]pyridin-3-yl)azetidin-1-yl)prop-2-en-1-one;

N-((4-cyano-1-(4-(trifluoromethoxy)phenyl)-1H-indazol-3-yl)methyl)acrylamide;

N-((1-(4-(trifluoromethoxy)phenyl)-1H-pyrazolo[4,3-b]pyridin-3-yl)methyl)acrylamide; and N-((1-(4-(trifluoromethoxy)phenyl)-1H-pyrazolo[3,4-b]pyridin-3-yl)methyl)acrylamide, or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, tautomers, or mixtures thereof in any ratio, including racemic mixtures.

In one aspect, provided herein is a compound, or a stereoisomer, tautomer, or pharmaceutically acceptable salt thereof, of any one of the compounds as listed in Table 1.

In one aspect, provided herein is a compound, or a stereoisomer, tautomer, or pharmaceutically acceptable salt thereof, selected from the group consisting of:

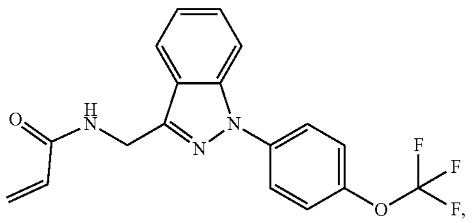

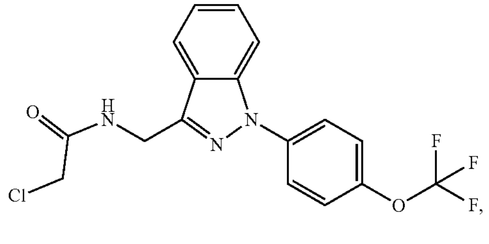

-continued
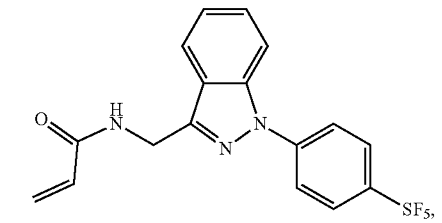
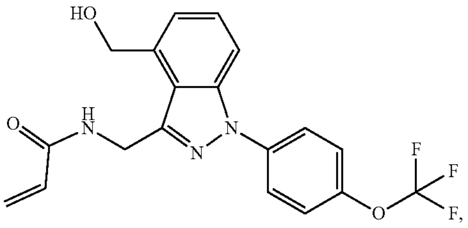
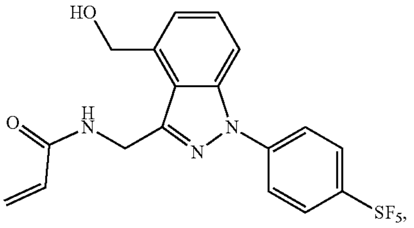
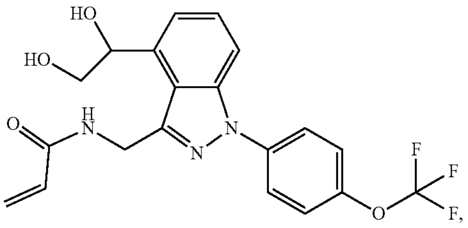
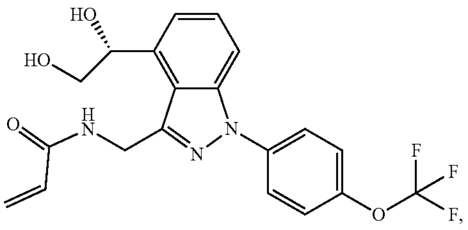
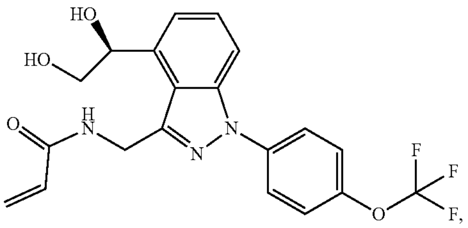
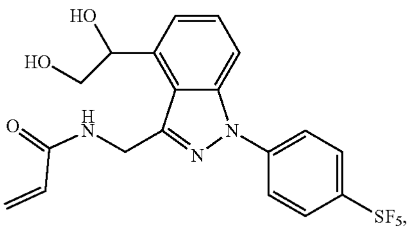
-continued
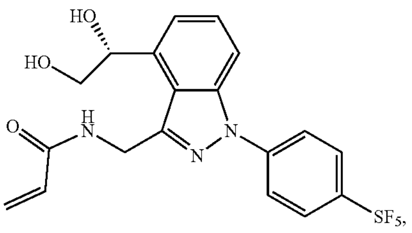
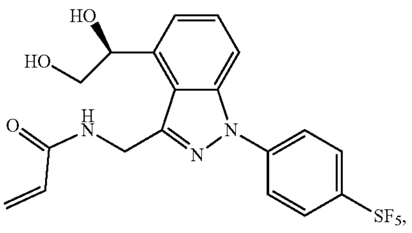
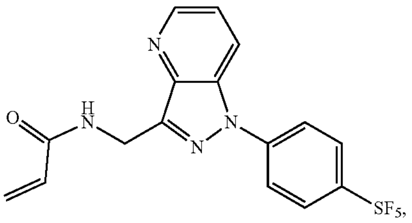
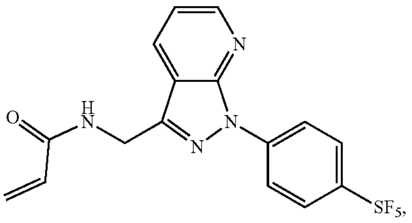
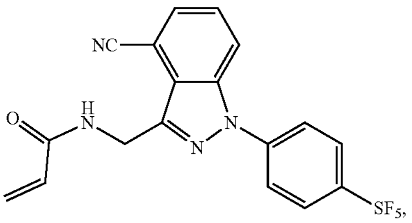
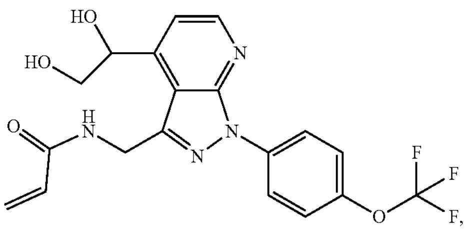
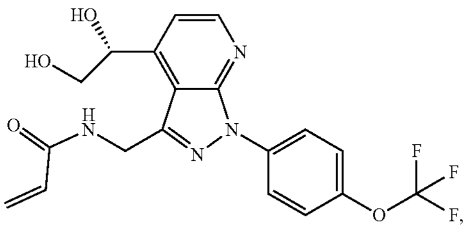

-continued

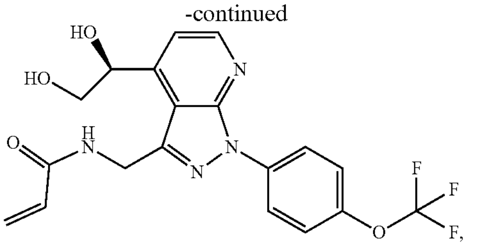

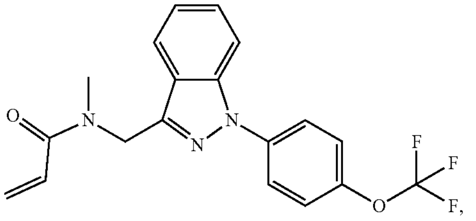

and

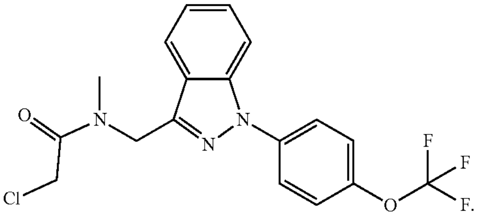 [SMILES: CN(Cc1nn(-c2ccc(OC(F)(F)F)cc2)c2ccccc12)C(=O)CCl]

In some embodiments, provided herein is a compound of formula (A) or (A'), or a stereoisomer, tautomer, or pharmaceutically acceptable salt thereof, wherein $X^1$ is N, $X^4$ is CH, $R^1$ is H, $R^t$ is $S(R^y)_5$, $R^x$ is ethenyl, and $R^y$ is fluoro.

In some embodiments, provided herein is a compound of formula (A) or (A'), or a stereoisomer, tautomer, or pharmaceutically acceptable salt thereof, wherein $X^1$ is CH, $X^4$ is N, $R^1$ is H, $R^t$ is $S(R^y)_5$, $R^x$ is ethenyl, and $R^y$ is fluoro.

In some embodiments, provided herein is a compound of formula (A) or (A'), or a stereoisomer, tautomer, or pharmaceutically acceptable salt thereof, wherein $X^1$ is $CR^s$, $X^4$ is N, $R^1$ is H, $R^s$ is CN, $R^t$ is $S(R^y)_5$, $R^x$ is ethenyl, and $R^y$ is fluoro.

In some embodiments, provided herein is a compound of formula (A) or (A'), or a stereoisomer, tautomer, or pharmaceutically acceptable salt thereof, wherein $X^1$ is $CR^s$, $X^4$ is N, $R^1$ is H, $R^s$ is ethyl substituted with two —OH, $R^t$ is methoxy substituted with three fluoro, and $R^x$ is ethenyl.

In some embodiments, provided herein is a compound of formula (A) or (A'), or a stereoisomer, tautomer, or pharmaceutically acceptable salt thereof, wherein $X^1$ is CH, $X^4$ is CH, $R^1$ is H, $R^t$ is methoxy substituted with three fluoro, and $R^x$ is ethenyl.

In some embodiments, provided herein is a compound of formula (A) or (A'), or a stereoisomer, tautomer, or pharmaceutically acceptable salt thereof, wherein $X^1$ is CH, $X^4$ is CH, $R^1$ is H, $R^t$ is methoxy substituted with three fluoro, and $R^x$ is ethanyl substituted by one chloro.

In some embodiments, provided herein is a compound of formula (A) or (A'), or a stereoisomer, tautomer, or pharmaceutically acceptable salt thereof, wherein $X^1$ is CH, $X^4$ is CH, $R^1$ is H, $R^t$ is $S(R^y)_5$, $R^x$ is ethenyl, and $R^y$ is fluoro.

In some embodiments, provided herein is a compound of formula (A) or (A'), or a stereoisomer, tautomer, or pharmaceutically acceptable salt thereof, wherein $X^1$ is $CR^s$, $X^4$ is CH, $R^1$ is H, $R^s$ is methyl substituted by one —OH, $R^t$ is methoxy substituted with three fluoro, and $R^x$ is ethenyl.

In some embodiments, provided herein is a compound of formula (A) or (A'), or a stereoisomer, tautomer, or pharmaceutically acceptable salt thereof, wherein $X^1$ is $CR^s$, $X^4$ is CH, $R^1$ is H, $R^s$ is methyl substituted by one —OH, $R^t$ is $S(R^y)_5$, $R^x$ is ethenyl, and $R^y$ is fluoro.

In some embodiments, provided herein is a compound of formula (A) or (A'), or a stereoisomer, tautomer, or pharmaceutically acceptable salt thereof, wherein $X^1$ is $CR^s$, $X^4$ is CH, $R^1$ is H, $R^s$ is ethyl substituted by two —OH, $R^t$ is methoxy substituted with three fluoro, and $R^x$ is ethenyl.

In some embodiments, provided herein is a compound of formula (A) or (A'), or a stereoisomer, tautomer, or pharmaceutically acceptable salt thereof, wherein $X^1$ is $CR^s$, $X^4$ is CH, $R^1$ is H, $R^s$ is ethyl substituted by two —OH, $R^t$ is $S(R^y)_5$, $R^x$ is ethenyl, and $R^y$ is fluoro.

In some embodiments, provided herein is a compound of formula (A) or (A'), or a stereoisomer, tautomer, or pharmaceutically acceptable salt thereof, wherein $X^1$ is CH, $X^4$ is CH, $R^t$ is methoxy substituted with three fluoro, $R^x$ is ethenyl, and $R^1$ is methyl.

In some embodiments, provided herein is a compound of formula (A) or (A'), or a stereoisomer, tautomer, or pharmaceutically acceptable salt thereof, wherein $X^1$ is CH, $X^4$ is CH, $R^t$ is methoxy substituted with three fluoro, $R^x$ is ethanyl substituted with one chloro, and $R^1$ is methyl.

In some embodiments, provided herein is a compound of formula (AB), or a stereoisomer, tautomer, or pharmaceutically acceptable salt thereof, wherein $X^1$ is N, $X^4$ is CH, $R^1$ is H, $R^t$ is $S(R^y)_5$, $R^x$ is ethenyl, and $R^y$ is fluoro.

In some embodiments, provided herein is a compound of formula (AB), or a stereoisomer, tautomer, or pharmaceutically acceptable salt thereof, wherein $X^1$ is CH, $X^4$ is N, $R^1$ is H, $R^t$ is $S(R^y)_5$, $R^x$ is ethenyl, and $R^y$ is fluoro.

In some embodiments, provided herein is a compound of formula (AB), or a stereoisomer, tautomer, or pharmaceutically acceptable salt thereof, wherein $X^1$ is $CR^s$, $X^4$ is N, $R^1$ is H, $R^s$ is CN, $R^t$ is $S(R^y)_5$, $R^x$ is ethenyl, and $R^y$ is fluoro.

In some embodiments, provided herein is a compound of formula (AB), or a stereoisomer, tautomer, or pharmaceutically acceptable salt thereof, wherein $X^1$ is $CR^s$, $X^4$ is N, $R^1$ is H, $R^s$ is ethyl substituted with two —OH, $R^t$ is methoxy substituted with three fluoro, and $R^x$ is ethenyl.

In some embodiments, provided herein is a compound of formula (AB), or a stereoisomer, tautomer, or pharmaceutically acceptable salt thereof, wherein $X^1$ is CH, $X^4$ is CH, $R^1$ is H, $R^t$ is methoxy substituted with three fluoro, and $R^x$ is ethenyl.

In some embodiments, provided herein is a compound of formula (AB), or a stereoisomer, tautomer, or pharmaceutically acceptable salt thereof, wherein $X^1$ is CH, $X^4$ is CH, $R^1$ is H, $R^t$ is methoxy substituted with three fluoro, and $R^x$ is ethanyl substituted by one chloro.

In some embodiments, $R^x$ is methyl substituted by one chloro.

In some embodiments, provided herein is a compound of formula (AB), or a stereoisomer, tautomer, or pharmaceutically acceptable salt thereof, wherein $X^1$ is CH, $X^4$ is CH, $R^1$ is H, $R^t$ is $S(R^y)_5$, $R^x$ is ethenyl, and $R^y$ is fluoro.

In some embodiments, provided herein is a compound of formula (AB), or a stereoisomer, tautomer, or pharmaceutically acceptable salt thereof, wherein $X^1$ is $CR^s$, $X^4$ is CH, $R^1$ is H, $R^s$ is methyl substituted by one —OH, $R^t$ is methoxy substituted with three fluoro, and $R^x$ is ethenyl.

In some embodiments, provided herein is a compound of formula (AB), or a stereoisomer, tautomer, or pharmaceutically acceptable salt thereof, wherein $X^1$ is $CR^s$, $X^4$ is CH, $R^1$ is H, $R^s$ is methyl substituted by one —OH, $R^t$ is $S(R^y)_5$, $R^x$ is ethenyl, and $R^y$ is fluoro.

In some embodiments, provided herein is a compound of formula (AB), or a stereoisomer, tautomer, or pharmaceutically acceptable salt thereof, wherein $X^1$ is $CR^s$, $X^4$ is CH, $R^1$ is H, $R^s$ is ethyl substituted by two —OH, $R^t$ is methoxy substituted with three fluoro, and $R^x$ is ethenyl.

In some embodiments, provided herein is a compound of formula (AB), or a stereoisomer, tautomer, or pharmaceutically acceptable salt thereof, wherein $X^1$ is $CR^s$, $X^4$ is CH, $R^1$ is H, $R^s$ is ethyl substituted by two —OH, $R^t$ is $S(R^y)_5$, $R^x$ is ethenyl, and $R^y$ is fluoro.

In some embodiments, provided herein is a compound of formula (AB), or a stereoisomer, tautomer, or pharmaceutically acceptable salt thereof, wherein $X^1$ is CH, $X^4$ is CH, $R^t$ is methoxy substituted with three fluoro, $R^x$ is ethenyl, and $R^1$ is methyl.

In some embodiments, provided herein is a compound of formula (AB), or a stereoisomer, tautomer, or pharmaceutically acceptable salt thereof, wherein $X^1$ is CH, $X^4$ is CH, $R^t$ is methoxy substituted with three fluoro, $R^x$ is ethanyl substituted with one chloro, and $R^1$ is methyl.

In some embodiments, provided herein is a compound of formula (I-AB), or a stereoisomer, tautomer, or pharmaceutically acceptable salt thereof, wherein $X^1$ is N, $X^4$ is CH, $R^1$ is H, $R^t$ is $S(R^y)_5$, $R^x$ is ethenyl, and $R^y$ is fluoro.

In some embodiments, provided herein is a compound of formula (I-AB), or a stereoisomer, tautomer, or pharmaceutically acceptable salt thereof, wherein $X^1$ is CH, $X^4$ is N, $R^1$ is H, $R^t$ is $S(R^y)_5$, $R^x$ is ethenyl, and $R^y$ is fluoro.

In some embodiments, provided herein is a compound of formula (I-AB), or a stereoisomer, tautomer, or pharmaceutically acceptable salt thereof, wherein $X^1$ is $CR^s$, $X^4$ is N, $R^1$ is H, $R^s$ is CN, $R^t$ is $S(R^y)_5$, $R^x$ is ethenyl, and $R^y$ is fluoro.

In some embodiments, provided herein is a compound of formula (I-AB), or a stereoisomer, tautomer, or pharmaceutically acceptable salt thereof, wherein $X^1$ is $CR^s$, $X^4$ is N, $R^1$ is H, $R^s$ is ethyl substituted with two —OH, $R^t$ is methoxy substituted with three fluoro, and $R^x$ is ethenyl.

In some embodiments, provided herein is a compound of formula (I-AB), or a stereoisomer, tautomer, or pharmaceutically acceptable salt thereof, wherein $X^1$ is CH, $X^4$ is CH, $R^1$ is H, $R^t$ is methoxy substituted with three fluoro, and $R^x$ is ethenyl.

In some embodiments, provided herein is a compound of formula (I-AB), or a stereoisomer, tautomer, or pharmaceutically acceptable salt thereof, wherein $X^1$ is CH, $X^4$ is CH, $R^1$ is H, $R^t$ is methoxy substituted with three fluoro, and $R^x$ is methyl substituted by one chloro.

In some embodiments, provided herein is a compound of formula (I-AB), or a stereoisomer, tautomer, or pharmaceutically acceptable salt thereof, wherein $X^1$ is CH, $X^4$ is CH, $R^1$ is H, $R^t$ is $S(R^y)_5$, $R^x$ is ethenyl, and $R^y$ is fluoro.

In some embodiments, provided herein is a compound of formula (I-AB), or a stereoisomer, tautomer, or pharmaceutically acceptable salt thereof, wherein $X^1$ is $CR^s$, $X^4$ is CH, $R^1$ is H, $R^s$ is methyl substituted by one —OH, $R^t$ is methoxy substituted with three fluoro, and $R^x$ is ethenyl.

In some embodiments, provided herein is a compound of formula (I-AB), or a stereoisomer, tautomer, or pharmaceutically acceptable salt thereof, wherein $X^1$ is $CR^s$, $X^4$ is CH, $R^1$ is H, $R^s$ is methyl substituted by one —OH, $R^t$ is $S(R^y)_5$, $R^x$ is ethenyl, and $R^y$ is fluoro.

In some embodiments, provided herein is a compound of formula (I-AB), or a stereoisomer, tautomer, or pharmaceutically acceptable salt thereof, wherein $X^1$ is $CR^s$, $X^4$ is CH, $R^1$ is H, $R^s$ is ethyl substituted by two —OH, $R^t$ is methoxy substituted with three fluoro, and $R^x$ is ethenyl.

In some embodiments, provided herein is a compound of formula (I-AB), or a stereoisomer, tautomer, or pharmaceutically acceptable salt thereof, wherein $X^1$ is $CR^s$, $X^4$ is CH, $R^1$ is H, $R^s$ is ethyl substituted by two —OH, $R^t$ is $S(R^y)_5$, $R^x$ is ethenyl, and $R^y$ is fluoro.

In some embodiments, provided herein is a compound of formula (I-AB), or a stereoisomer, tautomer, or pharmaceutically acceptable salt thereof, wherein $X^1$ is CH, $X^4$ is CH, $R^t$ is methoxy substituted with three fluoro, $R^x$ is ethenyl, and $R^1$ is methyl.

In some embodiments, provided herein is a compound of formula (I-AB), or a stereoisomer, tautomer, or pharmaceutically acceptable salt thereof, wherein $X^1$ is CH, $X^4$ is CH, $R^t$ is methoxy substituted with three fluoro, $R^x$ is ethanyl substituted with one chloro, and $R^1$ is methyl.

In some aspects, the compounds of the disclosure are isotopically labeled by having one or more atoms therein replaced by an atom having a different atomic mass or mass number. Such isotopically-labeled (i.e., radiolabeled) compounds of formula (A), (B), (A'), (B'), (I-A), or (I-B) are considered to be within the scope of this disclosure. Examples of isotopes that can be incorporated into the compounds of formula (A), (B), (A'), (B'), (I-A), or (I-B) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}F$, $^{32}F$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action, or binding affinity to TEAD. Certain isotopically-labeled compounds of formula (A), (B), (A'), (B'), (I-A), or (I-B), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (A), (B), (A'), (B'), (I-A), or (I-B) can be enriched with 1, 2, 5, 10, 25, 50, 75, 90, 95, or 99 percent of a given isotope.

In some aspects, any of the ways in which compounds of formula (A) or formula (B) may be isotopically labeled, and any of the ways in which isotopically-labeled compounds of formula (A) or formula (B) may be used (as described, e.g. in the previous paragraph) also apply to compounds of formula (AB).

In some aspects, any of the ways in which compounds of formula (A) or formula (B) may be isotopically labeled, and any of the ways in which isotopically-labeled compounds of formula (A) or formula (B) may be used (as described, e.g. in the previous paragraph) also apply to compounds of formula (I-AB).

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (A), (B), (A'), (B'), (I-A), or (I-B) can generally be prepared by conventional techniques known to those skilled in the art or by processes analogous to those described in the Examples as set out below using an appropriate isotopically-labeled reagent in place of the non-labeled reagent previously employed.

In some aspects, any of the ways in which compounds of formula (A) or formula (B) may be isotopically labeled, and any of the ways in which isotopically-labeled compounds of formula (A) or formula (B) may be used (as described, e.g. in the previous paragraph) also apply to compounds of formula (AB).

In some aspects, any of the ways in which compounds of formula (A) or formula (B) may be isotopically labeled, and any of the ways in which isotopically-labeled compounds of formula (A) or formula (B) may be used (as described, e.g. in the previous paragraph) also apply to compounds of formula (I-AB).

Also provided herein is a pharmaceutically acceptable salt or ester of any compound provided herein, as well as a stereoisomer, a geometric isomer, a tautomer, a solvate, a metabolite, an isotope or a prodrug of such compound or a pharmaceutically acceptable salt of such compound.

Process of Preparation

In one aspect, the present disclosure is directed to processes of preparing one or more TEAD inhibitors described herein. In some embodiments, a process of preparing a TEAD inhibitor is described herein in one or more examples.

In one aspect, provided herein is a process for preparing a compound of formula (I-AB):

(I-AB)

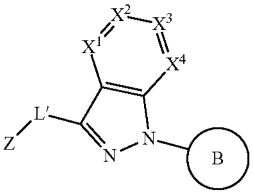

or a stereoisomer or tautomer thereof, or a pharmaceutically acceptable salt thereof, wherein the process comprises reacting a compound of formula (S1)

(S1)

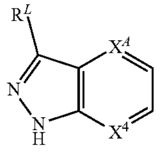

with a compound of formula (S2)

(S2)

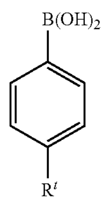

to provide a compound of formula (S3)

(S3)

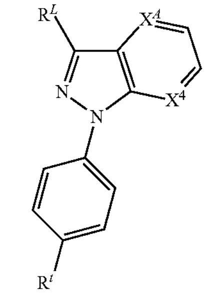

wherein:

L' is selected from the group consisting of *—N($R^1$)-L-** and

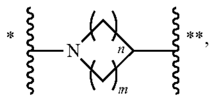

wherein * denotes the point of attachment to Z, and ** denotes the point of attachment to

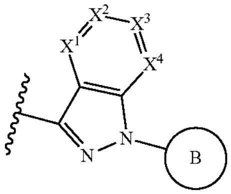

;

$R^1$ is H or $C_{1-6}$ alkyl;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —$OR^{f1}$, —CN, —$NR^dR^e$, and 3 to 15 membered heterocyclyl optionally substituted with one or more —OH; wherein $R^x$ is —C(O)$CH_2NR^dR^e$, —C(O)$C_{1-6}$alkyl, —P(O)$(OH)_2$; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, 3 to 6 membered heterocyclyl, $C_{3-6}$cycloalkyl, and $C_{1-6}$alkyl; wherein the $C_{1-6}$alkyl of $R^{t2}$ is optionally substituted with one or more —OH, $C_{1-6}$alkoxyl, halo, oxo, —$S(O)_2CH_3$, or —$NR^dR^e$; wherein $R^d$ and $R^e$ are each independently H, —$C(O)CH_3$, —$C(O)C_{1-6}$alkyl, or $C_{1-6}$alkyl;

$X^2$ and $X^3$ are each CH;

$X^4$ is independently N, CH, or CD, provided that: 1) only one of $X^1$, $X^2$, $X^3$, and $X^4$ is N; or 2) $X^1$ is N, $X^2$ is CH, $X^3$ is CH, and $X^4$ is N; or 3) $X^1$ is $CR^s$ and $X^2$, $X^3$, and $X^4$ are each independently CH or CD;

B is

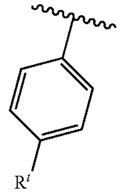

, wherein $R^t$ is independently selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl, dihydrofuranyl, bicyclobutanyl, or cyclopentenyl; or Z is $S(O)_2R^{x1}$, wherein $R^{x1}$ is $C_{2-6}$alkenyl;

L is methylene, optionally substituted with one or more $C_{1-6}$alkyl;

n and m are each 1; or n and m are each 2;

$X^A$ is N or $CR^L$; and each $R^L$ is independently selected from halo.

In one aspect, provided herein is a process for preparing a compound of formula (I-AB):

(I-AB)

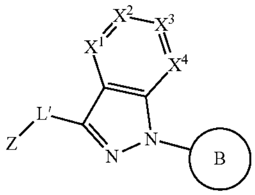

or a stereoisomer or tautomer thereof, or a pharmaceutically acceptable salt thereof, wherein the process comprises reacting a compound of formula (S4)

(S4)

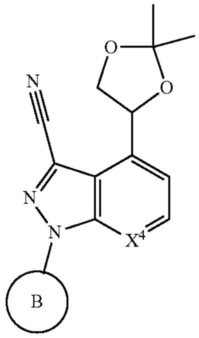

to provide a compound of formula (S5)

(S5)

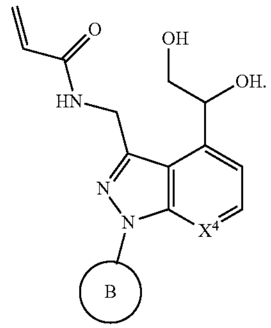

wherein:

L' is *—$N(R^1)$-L-**, wherein * denotes the point of attachment to Z, and ** denotes the point of attachment to

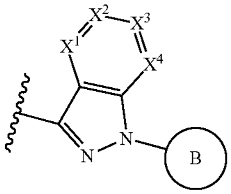

;

$R^1$ is H;

$X^1$ is $CR^s$, wherein $R^s$ is

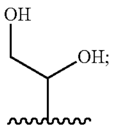 [SMILES: *C(O)CO]

$X^2$ and $X^3$ are each CH;

$X^4$ is independently N, CH, or CD, provided that: 1) only one of $X^1$, $X^2$, $X^3$, and V is N; or 2) $X^1$ is N, $X^2$ is CH, $X^3$ is CH, and $X^4$ is N; or 3) $X^1$ is $CR^s$ and $X^2$, $X^3$, and $X^4$ are each independently CH or CD;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is

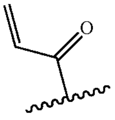

;

and

L is methylene.

In one aspect, provided herein is a process for preparing a compound of formula (I-AB):

(I-AB)

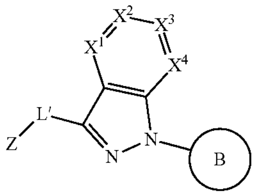

or a stereoisomer or tautomer thereof, or a pharmaceutically acceptable salt thereof, wherein the process comprises reacting a compound of formula (S6)

(S6)

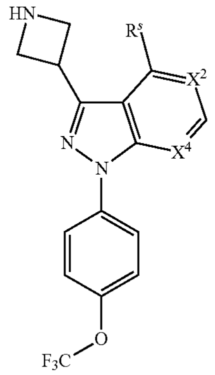

with a compound of formula (S7)

(S7)

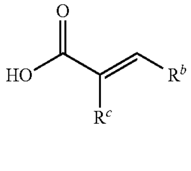

to provide a compound of formula (S8)

(S8)

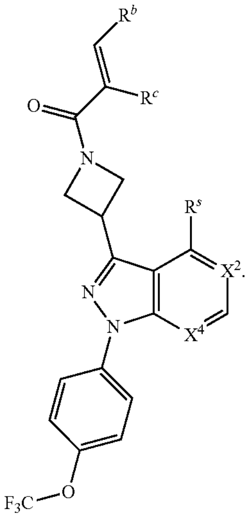

wherein:

L' is

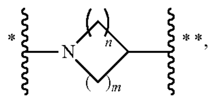

wherein * denotes the point of attachment to Z, and ** denotes the point of attachment to

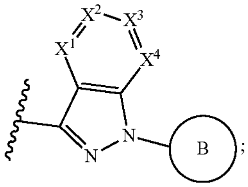

;

$R^1$ is H or $C_{1-6}$ alkyl;

$X^1$ is $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —$OR^{f1}$, —CN, —$NR^dR^e$, and 3 to 15 membered heterocyclyl optionally substituted with one or more —OH; wherein $R^{f1}$ is —$C(O)CH_2NR^dR^e$, —$C(O)C_{1-6}$alkyl, —$P(O)(OH)_2$; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, 3 to 6 membered heterocyclyl, $C_{3-6}$cycloalkyl, and $C_{1-6}$alkyl; wherein the $C_{1-6}$alkyl of $R^{t2}$ is optionally substituted with one or more —OH, $C_{1-6}$alkoxyl, halo, oxo, —$S(O)_2CH_3$, or —$NR^dR^e$; wherein $R^d$ and $R^e$ are each independently H, —C(O)$CH_3$, —C(O)$C_{1-6}$alkyl, or $C_{1-6}$alkyl;

$X^3$ is CH;

$X^2$ and $X^4$ are each independently N, CH, or CD, provided that: 1) only one of $X^1$, $X^2$, $X^3$, and $X^4$ is N; or 2) $X^1$ is N, $X^2$ is CH, $X^3$ is CH, and $X^4$ is N; or 3) $X^1$ is $CR^s$ and $X^2$, $X^3$, and $X^4$ are each independently CH or CD;

B is

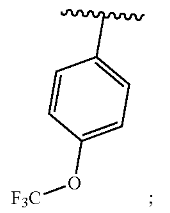 [SMILES: *c1ccc(OC(F)(F)F)cc1]

;

Z is

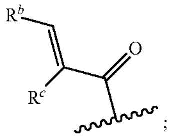

;

n and m are each 1; and $R^b$ and $R^c$ are each independently selected from the group consisting of H, $C_{1-6}$alkyl, deuterium, —OH, $C_{1-6}$alkoxyl, and halo.

In one aspect, provided herein is a process for preparing a compound of formula (I-AB):

(I-AB)

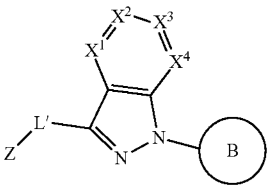

or a stereoisomer or tautomer thereof, or a pharmaceutically acceptable salt thereof, wherein the process comprises reacting a compound of formula (S9)

(S9)

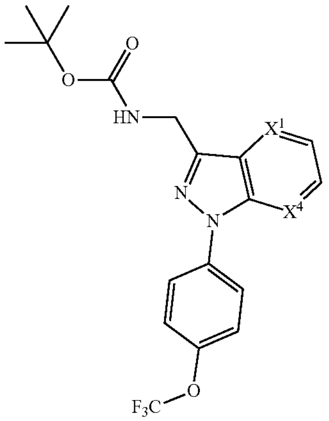

to provide a compound of formula (S10)

(S10)

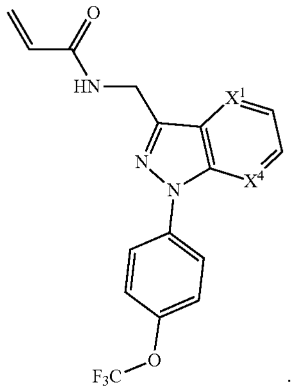

.

wherein:

L' is *—$N(R^1)$-L-**, wherein * denotes the point of attachment to Z, and ** denotes the point of attachment to

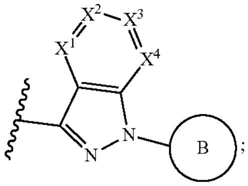

;

$R^1$ is H;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —$OR^{f1}$, —CN, —$NR^dR^e$, and 3 to 15 membered heterocyclyl optionally substituted with one or more —OH; wherein $R^x$ is —$C(O)CH_2NR^dR^e$, —$C(O)C_{1-6}$alkyl, —$P(O)(OH)_2$; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, 3 to 6 membered heterocyclyl, $C_{3-6}$cycloalkyl, and $C_{1-6}$alkyl; wherein the $C_{1-6}$alkyl of $R^{t2}$ is optionally substituted with one or more —OH, $C_{1-6}$alkoxyl, halo, oxo, —$S(O)_2CH_3$, or —$NR^dR^e$; wherein $R^d$ and $R^e$ are each independently H, —$C(O)CH_3$, —$C(O)C_{1-6}$alkyl, or $C_{1-6}$alkyl;

$X^2$ and $X^3$ are each CH;

$X^4$ is independently N, CH, or CD, provided that: 1) only one of $X^1$, $X^2$, $X^3$, and $X^4$ is N; or 2) $X^1$ is N, $X^2$ is CH, $X^3$ is CH, and $X^4$ is N; or 3) $X^1$ is $CR^s$ and $X^2$, $X^3$, and $X^4$ are each independently CH or CD;

B is

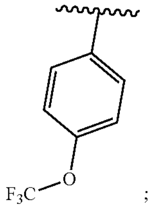 [SMILES: *c1ccc(OC(F)(F)F)cc1]

;

Z is

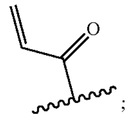 [SMILES: *C(=O)C=C]

;

and

L is methylene.

Pharmaceutical Compositions and Administration

In addition to one or more of the compounds provided above (including stereoisomers, geometric isomers, tautomers, solvates, metabolites, isotopes, pharmaceutically acceptable salts, or prodrugs thereof), the disclosure also provides for compositions and medicaments comprising a compound of the present disclosure or an embodiment or aspect thereof and at least one pharmaceutically acceptable carrier. The compositions of the disclosure can be used to selectively inhibit TEAD in patients (e.g., humans).

In one aspect, the disclosure provides for pharmaceutical compositions or medicaments comprising a compound of the disclosure (or embodiments and aspects thereof including stereoisomers, geometric isomers, tautomers, solvates, metabolites, isotopes, pharmaceutically acceptable salts, and prodrugs) and a pharmaceutically acceptable carrier, diluent or excipient. In another aspect, the disclosure provides for preparing compositions (or medicaments) comprising compounds of the disclosure. In another aspect, the disclosure provides for administering compounds of the disclosure and compositions comprising compounds of the disclosure to a patient (e.g., a human patient) in need thereof.

The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of a compound of the disclosure which are prepared by dissolving solid compounds of the disclosure in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of a compound of the disclosure together with a suitable carrier so as to prepare the proper dosage form for proper administration to the recipient.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TEAD activity as required to prevent or treat the undesired disease or disorder, such as for example, pain. For example, such amount may be below the amount that is toxic to normal cells, or the mammal as a whole.

In one example, the therapeutically effective amount of the compound of the disclosure administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain aspects, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present disclosure may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compositions comprising compounds of the disclosure (or embodiments or aspects thereof including stereoisomers, geometric isomers, tautomers, solvates, metabolites, isotopes, pharmaceutically acceptable salts, and prodrugs thereof) are normally formulated in accordance with standard pharmaceutical practice as a pharmaceutical composition. A typical formulation is prepared by mixing a compound of the present disclosure and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present disclosure or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). An active pharmaceutical ingredient of the disclosure (e.g., a compound of formula (I), or an embodiment or aspect thereof) can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, PA The particular carrier, diluent or excipient used will depend upon the means and purpose for which a compound of the present disclosure is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

Sustained-release preparations of a compound of the disclosure (e.g., compound of formula (A), (B), (A'), (B'), (I-A), or (I-B) or an embodiment or aspect thereof) can be prepared. Suitable examples of sustained-release preparations include semipermeable matrices of solid hydrophobic polymers containing a compound of formula (A), (B), (A'), (B'), (I-A), or (I-B) or an embodiment or aspect thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamellar type in which the lipid content is greater than about 30 mol % cholesterol, the selected proportion being adjusted for the optimal therapy.

Sustained-release preparations of a compound of formula (AB) may be prepared in the same way as sustained-release preparations of a compound of formula (A) or formula (B) (as described, e.g. in the preceding paragraph).

Sustained-release preparations of a compound of formula (I-AB) may be prepared in the same way as sustained-release preparations of a compound of formula (A) or formula (B) (as described, e.g. in the preceding paragraph).

In one example, compounds of the disclosure or an embodiment or aspect thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of the disclosure (or an embodiment or aspect thereof) is formulated in an acetate buffer, at pH 5. In another aspect, the compounds of the disclosure or an embodiment thereof are sterile. The compound may be stored, for example, as a solid or amorphous composition, as a lyophilized formulation or as an aqueous solution Formulations of a compound of the disclosure suitable for oral administration can be prepared as discrete units such as pills, capsules, cachets or tablets each containing a predetermined amount of a compound of the disclosure.

Compressed tablets can be prepared by compressing in a suitable machine a compound of the disclosure in a free-flowing form such as a powder or granules, optionally mixed with a binder, lubricant, inert diluent, preservative, surface active or dispersing agent. Molded tablets can be made by molding in a suitable machine a mixture of a powdered compound of the disclosure moistened with an inert liquid diluent. The tablets can optionally be coated or scored and optionally are formulated so as to provide slow or controlled release of a compound of the disclosure therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the disclosure intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing a compound of the disclosure in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 0.1 mg, about 1 mg, about 5 mg, about 10 mg, about 25 mg, about 30 mg, about 50 mg, about 80 mg, about 100 mg, about 150 mg, about 250 mg, about 300 mg and about 500 mg of the compounds (or an embodiment or aspect thereof) of the disclosure compounded with a filler (e.g., lactose, such as about 90-30 mg anhydrous lactose), a disintegrant (e.g, croscarellose, such as about 5-40 mg sodium croscarmellose), a polymer (e.g. polyvinylpyrrolidone (PVP), a cellulose (e.g., hydroxypropylmethyl cellulose (HPMC), and/or copovidone, such as about 5-30 mg PVP, HPMC or copovidone), and a lubricant (e.g., magnesium stearate, such as about 1-10 mg). Wet granulation, dry granulation or dry blending may be used. In one wet granulation aspect, powdered ingredients are first mixed together and then mixed with a solution or suspension of the polymer (e.g., PVP). The resulting composition can be dried, granulated, mixed with lubricant and compressed to tablet form using conventional equipment. An example of an aerosol formulation can be prepared by dissolving the compound, for example 5-400 mg, of the disclosure in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the compounds of the disclosure in an amount of, for example, 0.075 to 20% w/w. When formulated in an ointment, the compounds of the disclosure can be employed with either a paraffinic or a water-miscible ointment base. Alternatively, the compounds of the disclosure can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of a compound of the disclosure through the skin or other affected areas. Examples of such dermal penetration enhancers include dimethyl sulfoxide and related analogs.

For topical formulations, it is desired to administer an effective amount of a pharmaceutical composition according to the disclosure to target area, e.g., skin surfaces, mucous membranes, and the like, which are adjacent to peripheral neurons which are to be treated. This amount will generally range from about 0.0001 mg to about 1 g of a compound of the disclosure (or an embodiment or aspect thereof) per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of a compound of the disclosure is used per cc of ointment base. The pharmaceutical composition can be formulated as transdermal compositions or transdermal delivery devices ("patches"). Such compositions include, for example, a backing, compound of the disclosure reservoir, a control membrane, liner and contact adhesive. Such transdermal patches may be used to provide continuous pulsatile, or on demand delivery of the compounds of the present disclosure as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of a compound of the disclosure.

When the binding target is located in the brain, certain aspects of the disclosure provide for a compound of the disclosure (or an embodiment or aspect thereof) to traverse the blood-brain barrier. Certain neurodegenerative diseases are associated with an increase in permeability of the blood-brain barrier, such that a compound of the disclosure (or an embodiment or aspect thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of the disclosure (or an embodiment or aspect thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford Pharmaceutical).

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula of the disclosure (or an embodiment or aspect thereof) across the blood-brain barrier include, but are not limited to, encapsulating the a compound of the disclosure (or an embodiment or aspect thereof) in liposomes that are coupled to antibody binding fragments that bind to receptors on the vascular endothelium of the blood-brain barrier (see, e.g., U.S. Patent Application Publication No. 2002/0025313), and coating a compound of the disclosure (or an embodiment or aspect thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of the disclosure (or an embodiment or aspect thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of the disclosure (or an embodiment or aspect thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain aspects, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic mini pumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the disclosure have been shown to modulate TEAD activity.

In some embodiments, a compound that modulates TEAD activity is a compound of formula (A), or a stereoisomer, tautomer, or pharmaceutically acceptable salt thereof:

(A)

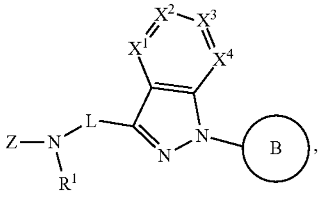

wherein:

$R^1$ is H or $C_{1-6}$ alkyl;

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo; and L is methylene, optionally substituted with one or more $C_{1-6}$alkyl.

In some embodiments, a compound that modulates TEAD activity is a compound of formula (B), or a stereoisomer, tautomer, or pharmaceutically acceptable salt thereof:

(B)

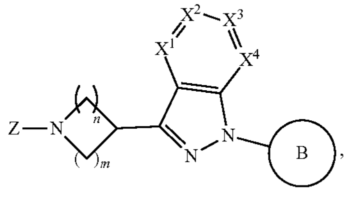

wherein:

$R^1$ is H or $C_{1-6}$ alkyl;

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —C(O)$R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo; and n and m are each independently 1 or 2.

In some embodiments, a compound that modulates TEAD activity is a compound of formula (A'), or a stereoisomer, tautomer, or pharmaceutically acceptable salt thereof:

(A')

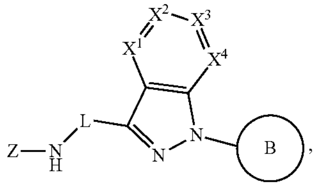

wherein:

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —C(O)$R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo; and L is methylene, optionally substituted with one or more $C_{1-6}$alkyl.

In some embodiments, a compound that modulates TEAD activity is a compound of formula (B'), or a stereoisomer, tautomer, or pharmaceutically acceptable salt thereof:

(B')

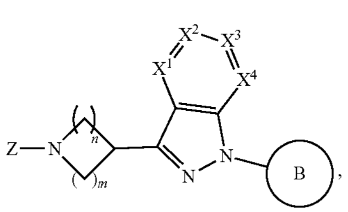

wherein:

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —C(O)$R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo; and n and m are each independently 1 or 2.

In some embodiments, a compound that modulates TEAD activity is a compound of formula (I-A), or a stereoisomer, tautomer, or pharmaceutically acceptable salt thereof:

(I-A)

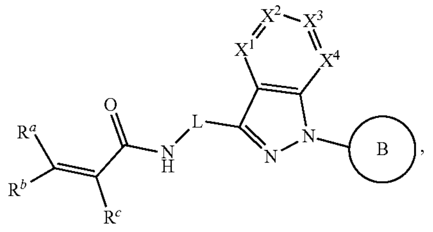

wherein:

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, $—NR^dCOR^e$, $—CONR^dR^e$, $—SO_2R^d$, $—SO_2NR^dR^e$, $—NR^dSO_2R^e$, and $—NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and $—NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

$R^a$, $R^b$, and $R^c$ are each independently H, halo, or $C_{1-5}$alkyl; and

L is methylene, optionally substituted with one or more $C_{1-6}$alkyl.

In some embodiments, a compound that modulates TEAD activity is a compound of formula (I-B), or a stereoisomer, tautomer, or pharmaceutically acceptable salt thereof:

(I-B)

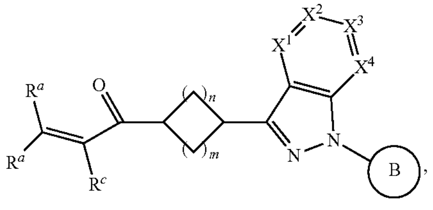

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, $—NR^dCOR^e$, $—CONR^dR^e$, $—SO_2R^d$, $—SO_2NR^dR^e$, $—NR^dSO_2R^e$, and $—NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN and $—NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

$R^a$, $R^b$, and $R^c$ are each independently H, halo, or $C_{1-5}$alkyl; and n and m are each independently 1 or 2.

In some embodiments, a compound that modulates TEAD activity is a compound of formula (A) or (B):

(A)

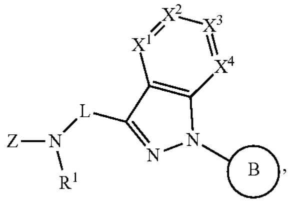

(B)

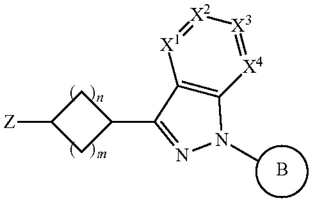

or a stereoisomer or tautomer thereof, or a pharmaceutically acceptable salt thereof, wherein:

$R^1$ is H or $C_{1-6}$ alkyl;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, $—OR^f$, $C_{1-15}$alkoxy, $—NR^dCOR^e$, $—CONR^dR^e$, $—SO_2R^d$, $—SO_2NR^dR^e$, $—NR^dSO_2R^e$, and $—NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN, —$NR^dR^e$, and 3 to 15 membered heterocyclyl optionally substituted with one or more —OH; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, and $C_{1-6}$alkyl; wherein the $C_{1-6}$alkyl of $R^{t2}$ is optionally substituted with one or more —OH or —$NR^dR^e$; wherein $R^d$ and $R^e$ are each independently H, —$C(O)CH_3$, —$C(O)C_{1-6}$alkyl, or $C_{1-6}$alkyl;

$X^2$, $X^3$, and $X^4$ are each independently N, CH, or CD, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl;

L is methylene, optionally substituted with one or more $C_{1-6}$alkyl; and n and m are each 1; or n and m are each 2.

In some embodiments, the compound that modulates TEAD activity is selected from any of the formulae described herein. In some embodiments, the compound that modulates TEAD activity is a compound of any one of formulae (AB), (A), (A'), (I-A), (B), (B'), (I-B), or any subformulae described herein.

In some embodiments, the compound that modulates TEAD activity is selected from any of the formulae described herein. In some embodiments, the compound that modulates TEAD activity is a compound of any one of formulae (I-AB) or any subformulae described herein.

The compounds of the disclosure (or any embodiment or aspect thereof) are useful as a medical therapy for treating diseases and conditions mediated by TEAD activity. Such diseases and conditions include but are not limited to proliferative disorders such as cancer including acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In a specific embodiment, compounds of the disclosure (or any embodiment or aspect thereof) can be administered as a medical therapy to treat proliferative disorders such as cancer.

In one specific aspect, compounds of the disclosure (or any embodiment or aspect thereof) are administered as a medical therapy to treat proliferative disorders such as cancer.

In another aspect, the disclosure provides for a method for treating proliferative disorders such as cancer, comprising the step of administering a therapeutically effective amount of a compound according to formula (A), (B), (A'), (B'), (I-A), or (I-B) (or an embodiment or aspect thereof) as described elsewhere herein to a subject in need thereof.

In another aspect, the disclosure provides for a method for treating any of the indications enumerated herein, comprising the step of administering a therapeutically effective amount of a compound according to formula (AB) (or an embodiment or aspect thereof) as described elsewhere herein to a subject in need thereof.

In another aspect, the disclosure provides for a method for treating any of the indications enumerated herein, comprising the step of administering a therapeutically effective amount of a compound according to formula (I-AB) (or an embodiment or aspect thereof) as described elsewhere herein to a subject in need thereof.

In another aspect, the disclosure provides for a compound of formula (A), (B), (A'), (B'), (I-A), or (I-B) as described elsewhere herein (or any embodiment or aspect thereof) for modulating TEAD activity. In some embodiments, the disclosure provides for a pharmaceutically acceptable salt of a compound of formula (A), (B), (A'), (B'), (I-A), or (I-B) for modulating TEAD activity.

In another aspect, the disclosure provides for a compound of formula (AB) as described elsewhere herein (or any embodiment or aspect thereof) for modulating TEAD activity. In some embodiments, the disclosure provides for a pharmaceutically acceptable salt of a compound of formula (AB) for modulating TEAD activity.

In another aspect, the disclosure provides for a compound of formula (AB) as described elsewhere herein (or any embodiment or aspect thereof) for modulating TEAD activity. In some embodiments, the disclosure provides for a pharmaceutically acceptable salt of a compound of formula (I-AB) for modulating TEAD activity.

In another aspect, the disclosure provides for a compound of formula (A), (B), (A'), (B'), (I-A), or (I-B) as described elsewhere herein, or an embodiment or aspect thereof, such as a pharmaceutically acceptable salt thereof, for use in medical therapy.

In another aspect, the disclosure provides for a compound of formula (AB) as described elsewhere herein, or an embodiment or aspect thereof, such as a pharmaceutically acceptable salt thereof, for use in medical therapy.

In another aspect, the disclosure provides for a compound of formula (I-AB) as described elsewhere herein, or an embodiment or aspect thereof, such as a pharmaceutically acceptable salt thereof, for use in medical therapy.

In another aspect, the disclosure provides for a method for treatment or prophylaxis of proliferative disorders such as cancer, comprising the step of administering a therapeutically effective amount of a compound according to formula (A), (B), (A'), (B'), (I-A), or (I-B) (or an embodiment or aspect thereof) as described elsewhere herein, to a subject in need thereof.

In another aspect, the disclosure provides for a method for treatment or prophylaxis of any of the indications enumerated herein, comprising the step of administering a therapeutically effective amount of a compound according to formula (AB) (or an embodiment or aspect thereof) as described elsewhere herein, to a subject in need thereof.

In another aspect, the disclosure provides for a method for treatment or prophylaxis of any of the indications enumerated herein, comprising the step of administering a therapeutically effective amount of a compound according to formula (I-AB) (or an embodiment or aspect thereof) as described elsewhere herein, to a subject in need thereof.

In another aspect, the disclosure provides for a compound of formula (A), (B), (A'), (B'), (I-A), or (I-B) as described elsewhere herein, or an embodiment or aspect thereof, such as a pharmaceutically acceptable salt thereof, for the treatment or prophylaxis of proliferative disorders such as cancer.

In another aspect, the disclosure provides for a compound of formula (AB), as described elsewhere herein, or an embodiment or aspect thereof, such as a pharmaceutically acceptable salt thereof, for the treatment or prophylaxis of any of the indications enumerated herein.

In another aspect, the disclosure provides for a compound of formula (I-AB), as described elsewhere herein, or an embodiment or aspect thereof, such as a pharmaceutically acceptable salt thereof, for the treatment or prophylaxis of any of the indications enumerated herein.

In another aspect, the disclosure provides for the use of a compound of formula (A), (B), (A'), (B'), (I-A), or (I-B) as described elsewhere herein, or an embodiment or aspect thereof, such as a pharmaceutically acceptable salt thereof, for the preparation of a medicament for the treatment or prophylaxis of proliferative disorders such as cancer.

In another aspect, the disclosure provides for the use of a compound of formula (AB), as described elsewhere herein, or an embodiment or aspect thereof, such as a pharmaceutically acceptable salt thereof, for the preparation of a medicament for the treatment or prophylaxis of any of the indications enumerated herein.

In another aspect, the disclosure provides for the use of a compound of formula (I-AB), as described elsewhere herein, or an embodiment or aspect thereof, such as a pharmaceutically acceptable salt thereof, for the preparation of a medicament for the treatment or prophylaxis of any of the indications enumerated herein.

In another aspect, the disclosure provides for a method for treating proliferative disorders such as cancer in a mammal (e.g., a human) comprising administering a compound of formula (A), (B), (A'), (B'), (I-A), or (I-B) as described elsewhere herein or an embodiment or aspect thereof such as a pharmaceutically acceptable salt thereof to the mammal.

In another aspect, the disclosure provides for a method for treating any of the indications enumerated herein, comprising administering a compound of formula (AB) as described elsewhere herein or an embodiment or aspect thereof such as a pharmaceutically acceptable salt thereof to the mammal.

In another aspect, the disclosure provides for a method for treating any of the indications enumerated herein, comprising administering a compound of formula (I-AB) as described elsewhere herein or an embodiment or aspect thereof such as a pharmaceutically acceptable salt thereof to the mammal.

In another aspect, the disclosure provides for a method for modulating TEAD activity, comprising contacting TEAD with a compound of formula (A), (B), (A'), (B'), (I-A), or (I-B) as described elsewhere herein, or an embodiment or aspect thereof, such as a pharmaceutically acceptable salt thereof.

In another aspect, the disclosure provides for a method for modulating TEAD activity, comprising contacting TEAD with a compound of formula (AB), as described elsewhere herein, or an embodiment or aspect thereof, such as a pharmaceutically acceptable salt thereof.

In another aspect, the disclosure provides for a method for modulating TEAD activity, comprising contacting TEAD with a compound of formula (I-AB), as described elsewhere herein, or an embodiment or aspect thereof, such as a pharmaceutically acceptable salt thereof.

It is understood that, in some embodiments, in conjunction with embodiments above or below, a compound of formula (I-AB), (AB), (A), (B), (A'), (B'), (I-A), or (I-B) as described elsewhere herein, or an embodiment or aspect thereof, such as a pharmaceutically acceptable salt thereof, may be used in a therapeutically effective amount.

In another aspect, the disclosure provides for a compound of formula (A), (B), (A'), (B'), (I-A), or (I-B) as described elsewhere herein, or an embodiment or aspect thereof, such as a pharmaceutically acceptable salt thereof, for the treatment or prophylaxis of a disease or condition mediated by TEAD activity.

In another aspect, the disclosure provides for a compound of formula (AB), as described elsewhere herein, or an embodiment or aspect thereof, such as a pharmaceutically acceptable salt thereof, for the treatment or prophylaxis of a disease or condition mediated by TEAD activity. Within aspects of this embodiment, the disease or condition is any of the indications enumerated herein.

In another aspect, the disclosure provides for a compound of formula (I-AB), as described elsewhere herein, or an embodiment or aspect thereof, such as a pharmaceutically acceptable salt thereof, for the treatment or prophylaxis of a disease or condition mediated by TEAD activity. Within aspects of this embodiment, the disease or condition is any of the indications enumerated herein.

In another aspect, the disclosure provides for the use of a compound of formula (A), (B), (A'), (B'), (I-A), or (I-B) as described elsewhere herein, or an embodiment or aspect thereof, such as a pharmaceutically acceptable salt thereof for the preparation of a medicament for the treatment or prophylaxis of a disease or condition that is mediated by TEAD activity. Within aspects of this embodiment, the disease or condition is proliferative disorders such as cancer.

In another aspect, the disclosure provides for the use of a compound of formula (AB), as described elsewhere herein, or an embodiment or aspect thereof, such as a pharmaceutically acceptable salt thereof for the preparation of a medicament for the treatment or prophylaxis of a disease or condition that is mediated by TEAD activity. Within aspects of this embodiment, the disease or condition is any of the diseases enumerated herein.

In another aspect, the disclosure provides for the use of a compound of formula (I-AB), as described elsewhere herein, or an embodiment or aspect thereof, such as a pharmaceutically acceptable salt thereof for the preparation of a medicament for the treatment or prophylaxis of a disease or condition that is mediated by TEAD activity. Within aspects of this embodiment, the disease or condition is any of the diseases enumerated herein.

In one aspect, compounds of the disclosure demonstrate higher potency as compared to other analogues.

Combination Therapy

The compounds of formula (A), (B), (A'), (B'), (I-A), or (I-B) or stereoisomers, tautomers, or pharmaceutically acceptable salts thereof, may be employed alone or in combination with other agents for treatment. For example, the second agent of the pharmaceutical combination formulation or dosing regimen may have complementary activities to the compound of formula (A), (B), (A'), (B'), (I-A), or (I-B) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (A), (B), (A'), (B'), (I-A), or (I-B) or stereoisomers, tautomers, or pharmaceutically acceptable salts thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Any of the methods of using a compound of formula (A) or (B) described in the preceeding paragraphs may also be applied to a compound of formula (AB).

Any of the methods of using a compound of formula (A) or (B) described in the preceeding paragraphs may also be applied to a compound of formula (I-AB).

Those additional agents may be administered separately from a composition comprising a disclosed compound, as part of a multiple dosage regimen. Alternatively, those agents may be part of a single dosage form, mixed together with a disclosed compound in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this disclosure. For example, a compound of the present disclosure may be administered with another therapeutic agent simultaneously or sequentially in separate unit dosage forms or together in a single unit dosage form. Accordingly, the present disclosure provides a single unit dosage form comprising a compound of formula I or formula II, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of a disclosed compound can be administered.

Typically, any agent that has activity against a disease or condition being treated may be co-administered. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (A), (B), (A'), (B'), (I-A), or (I-B) or stereoisomers, tautomers, or pharmaceutically acceptable salts thereof, and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Any of the treatment methods involving a compound of formula (A) or (B) or stereoisomers, tautomers, or pharmaceutically acceptable salts thereof, also apply to a compound or stereoisomers, tautomers, or pharmaceutically acceptable salts thereof, of formula (AB).

Any of the treatment methods involving a compound of formula (A) or (B) or stereoisomers, tautomers, or pharmaceutically acceptable salts thereof, also apply to a compound or stereoisomers, tautomers, or pharmaceutically acceptable salts thereof, of formula (I-AB).

Exemplary cytotoxic agents can be selected from antimicrotubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4 (5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pas colizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc.); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PM-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[44 (3-chloro-4-fluorophenyl)aminol-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3-fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PM 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE0); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc.); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), *vinca* alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

In another embodiment, provided are methods of using a compound of formula (A), (B), (A'), (B'), (I-A), or (I-B) or a stereoisomer, tautomer, or pharmaceutically acceptable salt thereof, as described elsewhere herein, or an embodiment or aspect thereof, to treat cancer in combination with a PD-1 axis binding antagonist.

In another embodiment, provided are methods of using a compound of formula (AB) or a stereoisomer, tautomer, or pharmaceutically acceptable salt thereof, as described elsewhere herein, or an embodiment or aspect thereof, to treat cancer in combination with a PD-1 axis binding antagonist.

In another embodiment, provided are methods of using a compound of formula (I-AB) or a stereoisomer, tautomer, or pharmaceutically acceptable salt thereof, as described elsewhere herein, or an embodiment or aspect thereof, to treat cancer in combination with a PD-1 axis binding antagonist.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. Specific examples of PD-1 binding antagonists are provided infra.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. Specific examples of PD-L1 binding antagonists are provided infra.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

PD-1 Axis Binding Antagonists

Provided herein are methods for treating cancer in an individual comprising administering to the individual an effective amount of a PD-1 axis binding antagonist and a compound of formula (A), (B), (A'), (B'), (I-A), or (I-B) or a stereoisomer, tautomer, or pharmaceutically acceptable salt thereof, as described elsewhere herein. Also provided herein are methods of enhancing immune function or response in an individual (e.g., an individual having cancer) comprising administering to the individual an effective amount of a PD-1 axis binding antagonist and a compound of formula (A), (B), (A'), (B'), (I-A), or (I-B) or a stereoisomer, tautomer, or pharmaceutically acceptable salt thereof, as described elsewhere herein.

Provided herein are methods for treating cancer in an individual comprising administering to the individual an effective amount of a PD-1 axis binding antagonist and a compound of formula (AB) or a stereoisomer, tautomer, or pharmaceutically acceptable salt thereof, as described elsewhere herein. Also provided herein are methods of enhancing immune function or response in an individual (e.g., an individual having cancer) comprising administering to the individual an effective amount of a PD-1 axis binding antagonist and a compound of formula (AB) or a stereoisomer, tautomer, or pharmaceutically acceptable salt thereof, as described elsewhere herein.

Provided herein are methods for treating cancer in an individual comprising administering to the individual an effective amount of a PD-1 axis binding antagonist and a compound of formula (I-AB) or a stereoisomer, tautomer, or pharmaceutically acceptable salt thereof, as described elsewhere herein. Also provided herein are methods of enhancing immune function or response in an individual (e.g., an individual having cancer) comprising administering to the individual an effective amount of a PD-1 axis binding antagonist and a compound of formula (I-AB) or a stereoisomer, tautomer, or pharmaceutically acceptable salt thereof, as described elsewhere herein.

In such methods, the PD-1 axis binding antagonist includes a PD-1 binding antagonist, a PDL1 binding antagonist, and/or a PDL2 binding antagonist. Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 binding antagonist is a molecule that inhibits the binding of PD-1 to its ligand binding partner(s). In a specific aspect the PD-1 ligand binding partners are PDL1 and/or PDL2. In another embodiment, a PDL1 binding antagonist is a molecule that inhibits the binding of PDLL to its binding partner(s). In a specific aspect, PDLL binding partner(s) are PD-1 and/or B7-1. In another embodiment, the PDL2 binding antagonist is a molecule that inhibits the binding of PDL2 to its binding partner(s). In a specific aspect, a PDL2 binding partner is PD-1. The antagonist may be an antibody, an antigen binding fragment thereof, an immunoadhesin, a fusion protein, an oligopeptide or a small molecule. If the antagonist is an antibody, in some embodiments the antibody comprises a human constant region selected from the group consisting of IgG1, IgG2, IgG3 and IgG4

Anti-PD-1 Antibodies

In some embodiments, the PD-1 binding antagonist is an anti-PD-1 antibody. A variety of anti-PDL1 antibodies can be utilized in the methods disclosed herein. In any of the embodiments herein, the PD-1 antibody can bind to a human PD-1 or a variant thereof. In some embodiments the anti-PD-1 antibody is a monoclonal antibody. In some embodiments, the anti-PD-1 antibody is an antibody fragment selected from the group consisting of Fab, Fab', Fab'-SH, Fv, scFv, and $(Fab')_2$ fragments. In some embodiments, the anti-PD-1 antibody is a chimeric or humanized antibody. In other embodiments, the anti-PD-1 antibody is a human antibody.

In some embodiments, the anti-PD-1 antibody is nivolumab (CAS Registry Number: 946414-94-4). Nivolumab (Bristol-Myers Squibb/Ono), also known as MDX-1106-04, MDX-1106, ONO-4538, BMS-936558, and OPDIVO®, is an anti-PD-1 antibody described in WO2006/121168. Nivolumab comprises a heavy chain and a light chain sequence, wherein:

(a) the heavy chain comprises the amino acid sequence. QVQLVESGGGVVQPGRSLRLDCK-ASGITFSNSGMHWVRQAPGKGLEWVAVIW Y DGSKRYYADSVKGRFTISRDNSKNTLFLQMNSL-RAEDTAVYYCATNDDYWGQGTLV TVSSAS-TKGPSVFPLAPCSRSTSESTAALGCLVKDYF-PEPVTVSWNSGALTSGVHTFPAV LQSSGLYS-LSSVVTVPSSSLGTKTYTCNVDHKPSNTK VDKRVESKYGPPCPPCPAPEFLG GPSVFLFPPKPKDTLM ISRTPEVTCVVVDVSQEDPE-VQFNWYVDGVEVHNAKTKPREEQ FNSTYRVVSVLTVLHQDWLNGKEYKCKV SNKGLPSSIEKTISKAKGQPREPQVYTLPPS QEEMTKNQVSLTCLVKGFYPSDIAVEWESNGQ-PENNYKTTPPVLDSDGSFFLYSRLTVD KSRWQEGNVFSCSVMHEALHN-HYTQKSLSLSLGK (SEQ ID NO:1), and (b) the light chain comprises the amino acid sequence:

```
                                          (SEQ ID NO: 2)
EIVLTQSPATLSLSPGERATLSCRASQSVSSYLAWYQQKPGQAPRLLIY

DASNRAT GIPARFSGSGSGTDFTLTISSLEPEDFAVYYCQQSSNWPRT

FGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC.
```

In some embodiments, the anti-PD-1 antibody comprises the six HVR sequences from SEQ ID NO:1 and SEQ ID NO:2 (e.g., the three heavy chain HVRs from SEQ ID NO:1 and the three light chain HVRs from SEQ ID NO:2). In some embodiments, the anti-PD-1 antibody comprises the heavy chain variable domain from SEQ ID NO:1 and the light chain variable domain from SEQ ID NO:2.

In some embodiments, the anti-PD-1 antibody is pembrolizumab (CAS Registry Number: 1374853-91-4). Pembrolizumab (Merck), also known as MK-3475, Merck 3475, lambrolizumab, SCH-900475, and KEYTRUDA® is an anti-PD-1 antibody described in WO2009/114335. Pembrolizumab comprises a heavy chain and a light chain sequence, wherein:

(a) the heavy chain comprises the amino acid sequence: QVQLVQSGVEVKKPGASVKVSCKASGYTFTNYY-MYWVRQAPGQGLEWMGGI NPSNGGTNFNEKFKNRVTLTTDSSTT-TAYMELKSLQFDDTAVYYCARRDYRFDMGFDY W GQGTTVTVSSASTKGPSVFPLAPCSRSTSES-TAALGCLVKDYFPEPVTVSWNSGALTS GV HTFPAVLQSSGLYS-LSSVVTVPSSSLGTKTYTCNVDHKPSNTK VDKRVESKYGPPCP PCP APE-FLGGPSVFLFPPKPKDTLMISRTPE-VTCVVVDVSQEDPEVQFNWYVDGVEVHN AKTK PREEQFN-STYRVVSVLTVLHQDWLNGKEYKCKVSNK GLPSSIEKTISKAK GQPR EPQVYTLPPSQEEMT- KNQVSLTCLVKGFYPSDIAVEWESNGQPENN YKTTPPVLDSDGS FFLYSRLTVDKSRWQEGNVFSCSVMHEALHNHYTQKSLSLSLGK (SEQ ID NO:3), and (b) the light chain comprises the amino acid sequence:

```
                                          (SEQ ID NO: 4)
EIVLTQSPATLSLSPGERATLSCRASKGVSTSGYSYLHWYQQKPGQAPR

LLIYLASYLES GVPARFSGSGSGTDFTLTISSLEPEDFAVYYCQHSRD

LPLTFGGGTKVEIKRTVAAPSVF IFPPSDEQLKSGTASVVCLLNNFYP

REAKVQWKVDNALQSGNSQESVTEQ DSKDSTYSLSSTLTLSKADYEKH

KVYACEVTHQGLSSPVTKSFNRGEC.
```

In some embodiments, the anti-PD-1 antibody comprises the six HVR sequences from SEQ ID NO:3 and SEQ ID NO:4 (e.g., the three heavy chain HVRs from SEQ ID NO:3 and the three light chain HVRs from SEQ ID NO:4). In some embodiments, the anti-PD-1 antibody comprises the heavy chain variable domain from SEQ ID NO:3 and the light chain variable domain from SEQ ID NO:4.

In some embodiments, the anti-PD-1 antibody is MEDI-0680 (AMP-514; AstraZeneca). MEDI-0680 is a humanized IgG4 anti-PD-1 antibody.

In some embodiments, the anti-PD-1 antibody is PDR001 (CAS Registry No. 1859072-53-9; Novartis). PDR001 is a humanized IgG4 anti-PD1 antibody that blocks the binding of PDL1 and PDL2 to PD-1.

In some embodiments, the anti-PD-1 antibody is REGN2810 (Regeneron). REGN2810 is a human anti-PD1 antibody.

In some embodiments, the anti-PD-1 antibody is BGB-108 (BeiGene). In some embodiments, the anti-PD-1 antibody is BGB-A317 (BeiGene).

In some embodiments, the anti-PD-1 antibody is JS-001 (Shanghai Junshi). JS-001 is a humanized anti-PD1 antibody.

In some embodiments, the anti-PD-1 antibody is STI-A1110 (Sorrento). STI-A1110 is a human anti-PD1 antibody.

In some embodiments, the anti-PD-1 antibody is INCSHR-1210 (Incyte). INCSHR-1210 is a human IgG4 anti-PD1 antibody.

In some embodiments, the anti-PD-1 antibody is PF-06801591 (Pfizer).

In some embodiments, the anti-PD-1 antibody is TSR-042 (also known as ANB011; Tesaro/AnaptysBio).

In some embodiments, the anti-PD-1 antibody is AM0001 (ARMO Biosciences).

In some embodiments, the anti-PD-1 antibody is ENUM 244C8 (Enumeral Biomedical Holdings). ENUM 244C8 is an anti-PD1 antibody that inhibits PD-1 function without blocking binding of PDL1 to PD-1.

In some embodiments, the anti-PD-1 antibody is ENUM 388D4 (Enumeral Biomedical Holdings). ENUM 388D4 is an anti-PD1 antibody that competitively inhibits binding of PDL1 to PD-1.

In some embodiments, the PD-1 antibody comprises the six HVR sequences (e.g., the three heavy chain HVRs and the three light chain HVRs) and/or the heavy chain variable domain and light chain variable domain from a PD-1 antibody described in WO2015/112800 (Applicant: Regeneron), WO2015/112805 (Applicant: Regeneron), WO2015/112900 (Applicant: Novartis), US20150210769 (Assigned to Novartis), WO2016/089873 (Applicant: Celgene), WO2015/035606 (Applicant: Beigene), WO2015/085847 (Applicants: Shanghai Hengrui Pharmaceutical/Jiangsu Hengrui Medicine), WO2014/206107 (Applicants: Shanghai Junshi Biosciences/Junmeng Biosciences), WO2012/145493 (Applicant: Amplimmune), U.S. Pat. No. 9,205,148 (Assigned to MedImmune), WO2015/119930 (Applicants: Pfizer/Merck), WO2015/119923 (Applicants: Pfizer/Merck), WO2016/032927 (Applicants: Pfizer/Merck), WO2014/179664 (Applicant: AnaptysBio), WO2016/106160 (Applicant: Enumeral), and WO2014/194302 (Applicant: Sorrento).

Anti-PDL1 Antibodies

In some embodiments, the PD-1 axis binding antagonist is an anti-PDL1 antibody. A variety of anti-PDL1 antibodies are contemplated and described herein. In any of the embodiments herein, the isolated anti-PDL1 antibody can bind to a human PDL1, for example a human PDL1 as shown in UniProtKB/Swiss-Prot Accession No. Q9NZQ7.1, or a variant thereof. In some embodiments, the anti-PDL1 antibody is capable of inhibiting binding between PDL1 and PD-1 and/or between PDL1 and B7-1. In some embodiments, the anti-PDL1 antibody is a monoclonal antibody. In some embodiments, the anti-PDL1 antibody is an antibody fragment selected from the group consisting of Fab, Fab'-SH, Fv, scFv, and $(Fab')_2$ fragments. In some embodiments, the anti-PDL1 antibody is a chimeric or humanized antibody. In some embodiments, the anti-PDL1 antibody is a human antibody. Examples of anti-PDL1 antibodies useful in the methods of this invention and methods of making them are described in PCT patent application WO 2010/077634 and U.S. Pat. No. 8,217,149, both of which are incorporated herein.

In some embodiments, the anti-PDL1 antibody is atezolizumab (CAS Registry Number: 1422185-06-5). Atezolizumab (Genentech), also known as MPDL3280A, is an anti-PDL1 antibody.

Atezolizumab Comprises:

(a) an HVR-H1, HVR-H2, and HVR-H3 sequence of GFTFSDSWIH (SEQ ID NO:5), AWISPYGGSTYYADSVKG (SEQ ID NO:6) and RHWPGGFDY (SEQ ID NO:7), respectively, and (b) an HVR-L1, HVR-L2, and HVR-L3 sequence of RASQDVSTAVA (SEQ ID NO:8), SASFLYS (SEQ ID NO:9) and QQYLYHPAT (SEQ ID NO:10), respectively.

Atezolizumab comprises a heavy chain and a light chain sequence, wherein:

(a) the heavy chain variable region sequence comprises the amino acid sequence: EVQLVESGGGLVQPGGSLRLSCAASGFTFSDSWIHWVRQAPGKGLEWVAWISPY GGSTYYADSVKGRFTISADTSKNTAYLQMNSLRAE DTAVYYCARRHWPGGFDYWGQG TLVTVSS (SEQ ID NO:11, and (b) the light chain variable region sequence comprises the amino acid sequence:

```
                                          (SEQ ID NO: 12)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKR.
```

Atezolizumab comprises a heavy chain and a light chain sequence, wherein:

(a) the heavy chain comprises the amino acid sequence: EVQLVESGGGLVQPGGSLRLSCAASGFTFSD-SWIHWVRQAPGKGLEWVAWISPY GGSTYY-ADSVKGRFTISADTSKNTAYLQMNSLRAED-TAVYYCARRHWPGGFDYWGQG TLVTVSSASTKGPSVFPLAPSSKSTSGGTAAL-GCLVKDYFPEPVTVSWNSGALTSGVHTF PAVLQSSGLYSLSSVVTVPSSSLGTQTYICNV NHKPSNTKVDKKVEPKSCDKTHTCPPCP APELLGGPSVFLFPPKPKDTLMISRTPE-VTCVVVDVSHEDPEVKFNVVYVDGVEVHNAKT KPRE-EQYASTYRVVSVLTVLHQDWLNGKEYKCK VSNKALPAPIEKTISKAKGQPREPQ VYTLPPS-REEMTKNQVSLTCLVKGFYPSDIAVEWESNGQ-PENNYKTTPPVLDSDGSFFL YSK-LTVDKSRWQQGNVFSCSVMHEALHNHY TQKSLSLSPG (SEQ ID NO:13), and (b) the light chain comprises the amino acid sequence:

(SEQ ID NO: 14)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

In some embodiments, the anti-PDL1 antibody is avelumab (CAS Registry Number: 1537032-82-8). Avelumab, also known as MSB0010718C, is a human monoclonal IgG1 anti-PDL1 antibody (Merck KGaA, Pfizer). Avelumab comprises a heavy chain and a light chain sequence, wherein:

(a) the heavy chain comprises the amino acid sequence: EVQLLESGGGLVQPGGSLRLSCAASGFTFSSY-IMMWVRQAPGKGLEWVSSIYPS GGITFY-ADTVKGRFTISRDNSKNTLYLQMNSLRAED-TAVYYCARIKLGTVTTVDYWGQ GTLVTVSSASTKGPSVFPLAPSSKSTSGGTAAL-GCLVKDYFPEPVTVSWNSGALTSGVHT FPAVLQSSGLYS-LSSVVTVPSSSLGTQTYICNVNHKPSNTK VDKKVEPKSCDKTHTCPPC PAPELLGGPSVFLFPPKPKDTLMISRTPE-VTCVVVDVSHEDPEVKFNWYVDGVEVHNAK TKPREEQYN-STYRVVSVLTVLHQDWLNGKEYKCKVSNKAL-PAPIEKTISKAKGQPREPQ VYTLPPSRDELT-KNQVSLTCLVKGFYPSDIAVEWESNGQ PENNYKTTPPVLDSDGSFFLY SKLTVDKSRWQQGNVFSCSVMHEALHN-HYTQKSLSLSPG (SEQ ID NO:15), and (b) the light chain comprises the amino acid sequence:

(SEQ ID NO: 16)
QSALTQPASVSGSPGQSITISCTGTSSDVGGYNYVSWYQQHPGKAPKLM

IYDVSNRPSGVSNRFSGSKSGNTASLTISGLQAEDEADYYCSSYTSSST

RVFGTGTKVTVLGQPKANPTVTLFPPSSEELQANKATLVCLISDFYPGA

-continued

VTVAWKADGSPVKAGVETTKPSKQSNNKYAASSYLSLTPEQWKSHRSYS

CQVTHEGSTVEKTVAPTECS.

In some embodiments, the anti-PDL1 antibody comprises the six HVR sequences from SEQ ID NO:15 and SEQ ID NO:16 (e.g., the three heavy chain HVRs from SEQ ID NO:15 and the three light chain HVRs from SEQ ID NO:16). In some embodiments, the anti-PDL1 antibody comprises the heavy chain variable domain from SEQ ID NO:15 and the light chain variable domain from SEQ ID NO:16.

In some embodiments, the anti-PDL1 antibody is durvalumab (CAS Registry Number: 1428935-60-7). Durvalumab, also known as MEDI4736, is an Fc-optimized human monoclonal IgG1 kappa anti-PDL1 antibody (MedImmune, AstraZeneca) described in WO2011/066389 and US2013/034559. Durvalumab comprises a heavy chain and a light chain sequence, wherein:

(a) the heavy chain comprises the amino acid sequence: EVQLVESGGGLVQPGGSLRLS-CAASGFTFSRYWMSWVRQAPGKGLEWVANIKQ DGSEKYYVDSVKGRFTISRDNAKNS-LYLQMNSLRAEDTAVYYCAREGGWFGELAFDY WGQGTLVTVSSASTKGPSVFPLAPSSKST-SGGTAALGCLVKDYFPEPVTVSWNSGALTS GVHTFPAVLQSSGLYS-LSSVVTVPSSSLGTQTYICNVNHKPSNT KVDKRVEPKSCDKTHT CPPCPAPE-FEGGPSVFLFPPKPKDTLMISRTPE-VTCVVVDVSHEDPEVKFNWYVDGVEV HNAKTKPREEQYN-STYRVVSVLTVLHQDWLNGKEYKCKVSNKAL-PASIEKTISKAKGQ PREPQVYTLPPSREEMT-KNQVSLTCLVKGFYPSDIAVEWESNGQPE NNYKTTPPVLDSD GSFFLYSK-LTVDKSRWQQGNVFSCSVMHEALHN-HYTQKSLSLSPG (SEQ ID NO:17), and (b) the light chain comprises the amino acid sequence:

(SEQ ID NO: 18)
EIVLTQSPGTLSLSPGERATLSCRASQRVSSSYLAWYQQKPGQAPRLLI

YDASSRATGIPDRFSGSGSGTDFTLTISRLEPEDFAVYYCQQYGSLPWT

FGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC.

In some embodiments, the anti-PDL1 antibody comprises the six HVR sequences from SEQ ID NO:17 and SEQ ID NO:18 (e.g., the three heavy chain HVRs from SEQ ID NO:17 and the three light chain HVRs from SEQ ID NO:18). In some embodiments, the anti-PDL1 antibody comprises the heavy chain variable domain from SEQ ID NO:17 and the light chain variable domain from SEQ ID NO:18.

In some embodiments, the anti-PDL1 antibody is MDX-1105 (Bristol Myers Squibb). MDX-1105, also known as BMS-936559, is an anti-PDL1 antibody described in WO2007/005874.

In some embodiments, the anti-PDL1 antibody is LY3300054 (Eli Lilly).

In some embodiments, the anti-PDL1 antibody is STI-A1014 (Sorrento). STI-A1014 is a human anti-PDL1 antibody.

In some embodiments, the anti-PDL1 antibody is KN035 (Suzhou Alphamab). KN035 is single-domain antibody (dAB) generated from a camel phage display library.

In some embodiments, the anti-PDL1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some embodiments, the anti-PDL1 antibody is CX-072 (CytomX Therapeutics).

In some embodiments, the PDL1 antibody comprises the six HVR sequences (e.g., the three heavy chain HVRs and the three light chain HVRs) and/or the heavy chain variable domain and light chain variable domain from a PDL1 antibody described in US20160108123 (Assigned to Novartis), WO2016/000619 (Applicant: Beigene), WO2012/145493 (Applicant: Amplimmune), U.S. Pat. No. 9,205,148 (Assigned to MedImmune), WO2013/181634 (Applicant: Sorrento), and WO2016/061142 (Applicant: Novartis).

In a still further specific aspect, the PD-1 or PDL1 antibody has reduced or minimal effector function. In a still further specific aspect the minimal effector function results from an "effector-less Fc mutation" or aglycosylation mutation. In still a further embodiment, the effector-less Fc mutation is an N297A or D265A/N297A substitution in the constant region. In some embodiments, the isolated anti-PDL1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

Other PD-1 Antagonists

In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. AMP-224 (CAS Registry No. 1422184-00-6; GlaxoSmithKline/MedImmune), also known as B7-DCIg, is a PDL2-Fc fusion soluble receptor described in WO2010/027827 and WO2011/066342.

In some embodiments, the PD-1 binding antagonist is a peptide or small molecule compound. In some embodiments, the PD-1 binding antagonist is AUNP-12 (PierreFabre/Aurigene). See, e.g., WO2012/168944, WO2015/036927, WO2015/044900, WO2015/033303, WO2013/144704, WO2013/132317, and WO2011/161699.

In some embodiments, the PDL1 binding antagonist is a small molecule that inhibits PD-1. In some embodiments, the PDL1 binding antagonist is a small molecule that inhibits PDL1. In some embodiments, the PDL1 binding antagonist is a small molecule that inhibits PDL1 and VISTA. In some embodiments, the PDL1 binding antagonist is CA-170 (also known as AUPM-170). In some embodiments, the PDL1 binding antagonist is a small molecule that inhibits PDL1 and TIM3. In some embodiments, the small molecule is a compound described in WO2015/033301 and WO2015/033299.

In some embodiments, the treatment method includes the co-administration of a compound of formula (A), (B), (A'), (B'), (I-A), or (I-B) or stereoisomers or tautomers thereof, or pharmaceutically acceptable salts of any of the foregoing, and at least one mitogen-activated protein kinase (MAPK) inhibitor. In some embodiments, the treatment method includes the co-administration of a compound of formula (A), (B), (A'), (B'), (I-A), or (I-B) or stereoisomers or tautomers thereof, or pharmaceutically acceptable salts of any of the foregoing, and at least one inhibitor of the RAS/MAPK pathway. In some embodiments, the treatment method includes the co-administration of a compound of formula (A), (B), (A'), (B'), (I-A), or (I-B) or stereoisomers or tautomers thereof, or pharmaceutically acceptable salts of any of the foregoing, and at least one epidermal growth factor receptor (EGFR) inhibitor. In some embodiments, the inhibitor of the RAS/MAPK pathway is a KRAS inhibitor, a RAF inhibitor, such as a BRAF monomer or RAF dimer inhibitor, a MEK inhibitor, an ERK inhibitor, an EGFR inhibitor, or a MAPK inhibitor, or any combination thereof. In certain embodiments, the inhibitor of the RAS/MAPK pathway is an EGFR inhibitor or a MAPK inhibitor, or a combination thereof. Examples of EGFR inhibitors, MAPK inhibitors, and/or RAS/MAPK pathway inhibitors are disclosed in Moore, A. R., Rosenberg, S. C., McCormick, F. et al. RAS-targeted therapies: is the undruggable drugged?. *Nat Rev Drug Discov* (2020), incorporated herein by reference and include, but are not limited to: sotorasib (AMG 510 from Amgen), MRTX849 (from Mirati Therapeutics), JNJ-74699157/ARS-3248 (from J&J Wellspring Biosciences), LY3499446 (from Eli Lilly), GDCBI 1701963 (from Boehringer Ingelheim), mRNA-5671 (from Moderna Therapeutics), G12D inhibitor (from Mirati Therapeutics), RAS(ON) inhibitors (from Revolution Medicines), BBP-454 (from BridgeBio Pharma), SP600125, PLX4032, GW5074, AZD6244, PD98059, simvastatin, alisertib, teriflunomide, NSC95397, PD325901, PD98059, lovastatin, sorafenib (NEXAVAR®, Bayer Labs), vermurafenib (ZELBORAF®, Hoffman La Roche Inc.), dabrafenib (TAFLINAR®, Novartis Pharmaceuticals Corportation), selumetinib (KOSELUGO™, AstraZeneca Pharmaceuticals LP), trametinib (MEKINIST®, Novartis Pharmaceuticals Corporation), ulixertinib, silimarin, sirolimus (RAPAMUNE®, PV Prism CV), lapatinib (TYKERB®/TYVERB®, GlaxoSmithKline), crizotinib (XALKORI®, PF Prism CV), taselisib (Roche), PF-0491502, PF502, enterolactone, PLX4720, PD0325901, PD184352, SC-514, alisterib (MLN8237), SB415286, PLX4720, obtaoclax (GX15-070), pimasterib, venetoclax (ABT-199/VENCLEXTA®/VENCLYXTO®), eprenetapopt (APR-246), gemcitabine (GEMZAR®), birinapant (TL32711), pexmetinib (ARRY-614), afuresertib, ralimetinib (LY2228820, Eli Lilly), cobimetinib (COTELLIC®, Exelixis/Genentech), prexasertib (LY2606368), erlotinib (TARCEVA®, OSI Pharmaceuticals), bevacizumab (AVASTIN®, Genentech), belvarafenib (Hanmi Pharm./Genentech, Inc.), and binimetinib (MEKTOVI®, Array Biopharma Inc.).

In some embodiments, the any of the treatment methods using compounds of formula (A) or formula (B), or stereoisomers or tautomers thereof, or pharmaceutically acceptable salts of any of the foregoing, also apply to a compound of formula (AB), or stereoisomers or tautomers thereof, or pharmaceutically acceptable salts of any of the foregoing.

In some embodiments, the any of the treatment methods using compounds of formula (A) or formula (B), or stereoisomers or tautomers thereof, or pharmaceutically acceptable salts of any of the foregoing, also apply to a compound of formula (I-AB), or stereoisomers or tautomers thereof, or pharmaceutically acceptable salts of any of the foregoing.

As used herein "combination" refers to any mixture or permutation of one or more compounds of the disclosure (or an embodiment or aspect thereof) and one or more other compounds of the disclosure or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the disclosure with another therapeutic agent. Unless the context makes clear otherwise, "combination" may include routes of administration of a compound of the disclosure with another therapeutic agent. Unless the context makes clear otherwise, "combination" may include formulations of a compound of the disclosure with another therapeutic agent. Dosage forms, routes of administration and pharmaceutical compositions include, but are not limited to, those described herein.

In some embodiments, provided herein are compositions, methods, and kits, comprising: (i) one or more TEAD inhibitors (e.g., any one of the TEAD inhibitors described herein, including but not limited to, any one of compounds of formula (I-AB), (AB), (AB'), (A), (I-A), (A-1), (I-A-1), (B), (I-B), (B-1), or (I-B-1), or any variations or embodiments thereof), or a pharmaceutically acceptable salt thereof and (ii) one or more KRAS inhibitors (e.g., any one of compounds of formula (K-I), (K-II), or (K-III), or any variations or embodiments thereof), or a pharmaceutically acceptable salt thereof. TEAD inhibitors may, in some embodiments, be referred to as YAP/TAZ-TEAD inhibitors. In some embodiments, the one or more KRAS inhibitor is a G12C KRAS inhibitor.

In some embodiments, provided herein are methods of reducing resistance of a subject to treatment with a KRAS inhibitor, wherein the method comprises administering to a subject in need thereof one or more TEAD inhibitors, such as a TEAD inhibitor provided herein, or a pharmaceutically acceptable salt thereof. In some embodiments, the TEAD inhibitor is co-administered to the subject with the KRAS inhibitor. Also provided herein are kits comprising one or more TEAD inhibitors, or a pharmaceutically acceptable salt thereof, and optionally one or more KRAS inhibitors, or a pharmaceutically acceptable salt thereof, and instructions for use in reducing resistance of a subject to treatment with a KRAS inhibitor. In some embodiments, the reduction in resistance is sufficient for the subject to overcome resistance to treatment with a KRAS inhibitor. In some embodiments, the subject has experienced resistance to treatment with a KRAS inhibitor. In some embodiments, treatment with a KRAS inhibitor and a TEAD inhibitor decreases the likelihood of a subject receiving treatment with a KRAS inhibitor to develop resistance to such KRAS inhibitor.

In some embodiments, in conjunction with embodiments above or below, the one or more KRAS inhibitors comprise a compound of formula (K-I):

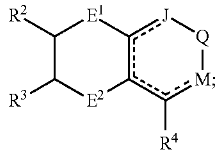

(K-I)

wherein E1 and E2 are each independently Nor $CR^1$; J is N, $NR^{10}$, or $CR^{10}$; M is N, $NR^{13}$, or $CR^{13}$; $\overline{---}$ is a single or double bond as necessary to give every atom its normal valence; $R^1$ is independently H, hydroxy, $C_{1-4}$alkyl, $C_{1-4}$haloalkyl, $C_{1-4}$alkoxy, $NHC_{1-4}$alkyl, $N(C_{1-4}alkyl)_2$, cyano, or halo; $R^2$ is halo, $C_{1-6}$alkyl, $C_{1-6}$ haloalkyl, OR', $N(R')_2$, $C_{2-3}$ alkenyl, $C_{2-3}$ alkynyl, $C_{0-3}$alkylene-$C_{3-8}$cycloalkyl, $C_{0-3}$alkylene-$C_{2-7}$heterocycloalkyl, $C_{0-3}$alkylenearyl, or $C_{0-3}$alkyleneheteroaryl, and each $R^x$ is independently H, $C_{1-6}$alkyl, $C_{1-6}$haloalkyl, $C_{3-4}$cycloalkyl, $C_{2-3}$alkenyl, $C_{2-3}$alkynyl, aryl, or heteroaryl, or two R' substituents, together with the nitrogen atom to which they are attached, form a 3-7-membered ring; $R^3$ is halo, $C_{1-3}$alkyl, $C_{1-2}$haloalkyl, $C_{1-3}$alkoxy, $C_{3-4}$cycloalkyl, $C_{2-3}$alkenyl, $C_{2-3}$alkynyl, aryl, or heteroaryl; $R^4$ is

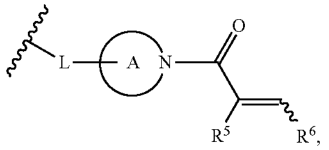

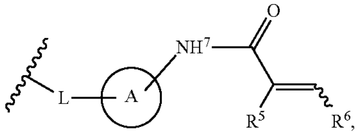

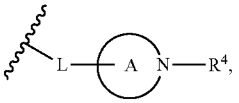

or

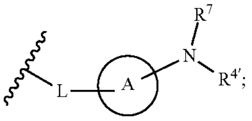

ring A is a monocyclic 4-7 membered ring or a bicyclic, bridged, fused, or spiro 6-11 membered ring; L is a bond, $C_{1-6}$alkylene, —O—$C_{0-5}$alkylene, —S—$C_{0-5}$alkylene, or —NH—$C_{0-5}$alkylene, and for $C_{2-6}$alkylene, —O—$C_{2-5}$alkylene, —S—$C_{2-5}$alkylene, and NH —$C_{2-5}$alkylene, one carbon atom of the alkylene group can optionally be replaced with O, S, or NH; $R^{4'}$ is H, $C_{1-8}$alkyl, $C_{2-8}$alkynyl, $C_{1-6}$alkylene-O—$C_{1-4}$alkyl, $C_{1-6}$alkylene-OH, $C_{1-6}$haloalkyl, $C_{0-3}$alkylene-$C_{3-8}$cycloalkyl, $C_{0-3}$alkylene-$C_{2-7}$heterocycloalkyl, $C_{0-3}$alkylenearyl, or selected from

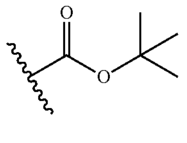

,

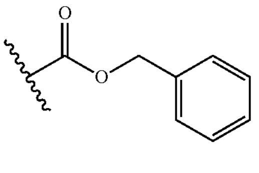

,

-continued

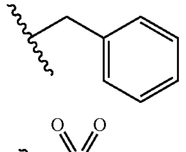,
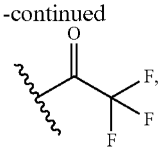
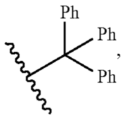

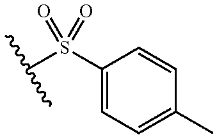,
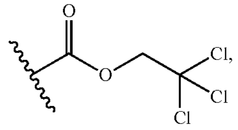

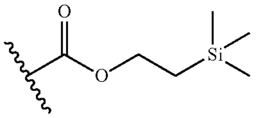,
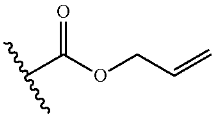, or

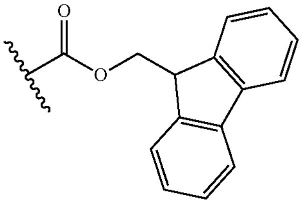;

$R^5$ and $R^6$ are each independently H, halo, $C_{1-8}$alkyl, $C_{2-8}$alkynyl, $C_{1-6}$alkylene-O—$C_{1-4}$alkyl, $C_{1-6}$alkylene-OH, $C_{1-6}$ haloalkyl, $C_{1-6}$alkyleneamine, $C_{0-6}$alkyleneamide, $C_{0-3}$alkylene-C(O)OH, $C_{0-3}$alkylene-C(O)O$C_{1-4}$alkyl, $C_{1-6}$alkylene-O-aryl, $C_{0-3}$alkylene-C(O)$C_{1-4}$alkylene-OH, $C_{0-3}$alkylene-$C_{3-8}$cycloalkyl, $C_{0-3}$alkylene-$C_{2-7}$heterocycloalkyl, $C_{0-3}$alkylenearyl, or cyano, or $R^5$ and $R^6$, together with the atoms to which they are attached, form a 4-6 membered ring; $R^7$ is H or $C_{1-3}$alkyl, or $R^7$ and $R^5$, together with the atoms to which they are attached, form a 4-6 membered ring; Q is $CR^8R^9$, C═$CR^8R^9$, C═O, C═S, or C═$NR^8$; $R^8$ and $R^9$ are each independently H, $C_{1-3}$alkyl, hydroxy, $C_{1-3}$alkoxy, cyano, nitro, or $C_{3-6}$cycloalkyl, or $R^8$ and $R^9$, taken together with the carbon atom to which they are attached, can form a 3-6 membered ring; $R^{10}$ is $C_{1-8}$alkyl, $C_{0-3}$alkylenearyl, $C_{0-3}$alkyleneheteroaryl, $C_{0-3}$alkylene-$C_{3-8}$cycloalkyl, $C_{0-3}$alkylene-$C_{2-7}$heterocycloalkyl, $C_{1-6}$alkoxy, O—$C_{0-3}$alkylenearyl, O—$C_{0-3}$alkyleneheteroaryl, O—$C_{0-3}$alkylene-$C_{3-8}$ cycloalkyl, O—$C_{0-3}$alkylenearyl, O—$C_{0-3}$alkylene-$C_{2-7}$heterocycloalkyl, NH—$C_{1-8}$alkyl, N($C_{1-8}$alkyl$)_2$, NH—$C_{0-3}$alkylenearyl, NH—$C_{0-3}$alkyleneheteroaryl, NH—$C_{0-3}$alkylene-$C_{3-8}$cycloalkyl, NH—$C_{0-3}$alkylene-$C_{2-7}$heterocycloalkyl, halo, cyano, or $C_{1-6}$alkyleneamine; and $R^{13}$ is $C_{1-4}$alkyl, $C_{1-3}$haloalkyl, $C_{1-3}$alkyleneamine, and $C_{3-5}$cycloalkyl, or a stereoisomer or tautomer thereof, or a pharmaceutically acceptable salt or any of the foregoing, with the proviso that (1) when J is $NR^{10}$, M is Nor $CR^{13}$; (2) when M is $NR^{13}$, J is N or $CR^{10}$; (3) when J is $CR^{10}$, M is N or $NR^{13}$; and (4) when M is $CR^{13}$, J is N or $NR^{10}$.

Description of formula (K-I) can be found in US2018/0334454A1, the entirety of which is incorporated herein by reference. Formula (K-I) is described as formula (II) in US2018/0334454A1 (see, e.g., paragraphs [0033]-[0053], which paragraphs and description of formula (II) and methods of making compounds of formula (II) are hereby incorporated herein by reference. Moieties of formula (K-I), such as J, Q, M, $E^1$, $E^2$, $R^2$, $R^3$, and $R^4$ are as defined in US2018/0334454A1, including any variations or embodiments thereof.

In some embodiments, in conjunction with embodiments above or below, the one or more KRAS inhibitors comprise a compound of formula (K-I-A):

(K-I-A)

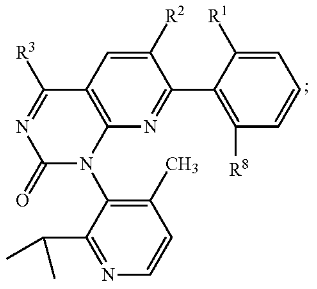;

wherein $R^1$ is H, halo, or —$CH_3$;

$R^2$ is H, halo, or —$CH_3$;

$R^3$ is

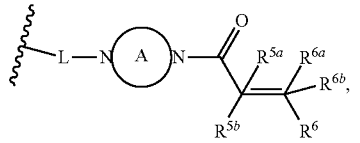,

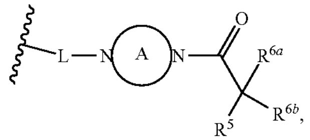,

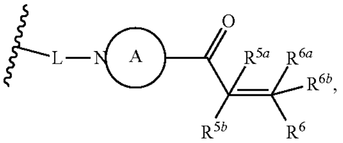,

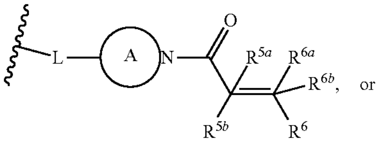, or

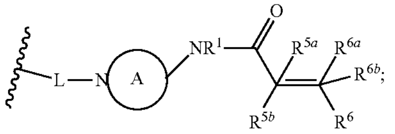;

b is optionally a single or a double bond;

ring A is a monocyclic 4-7 membered ring or a bicyclic, bridged, fused, or spiro 6-11 membered ring;

L is a bond or $NR^4$;

$R^4$ is H, —$C_{1-6}$alkyl, —$C_{2-6}$alkynyl, $C_{1-6}$alkylene-O—$C_{1-4}$alkyl, $C_{1-6}$alkylene-OH, $C_{1-6}$haloalkyl, —$C_{1-6}$alkyleneamine, —$C_{0-6}$alkylene-amide, —C(O)OH, —C(O)O$C_{1-4}$alkyl, —$C_{1-6}$alkylene-O-aryl, —N═N, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl;

$R^5$ is H, halo, an —$C_{1-6}$alkyl, —$C_{2-6}$alkynyl, —$C_{0-6}$alkylene-O—$C_{1-6}$alkyl, —$C_{1-6}$alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —C(O)OH, —C(O)O$C_{1-4}$alkyl, —$C_{0-6}$alkylene-O—$C_{6-14}$aryl, —$C_{0-3}$alkylene-C(O)$C_{1-4}$alkylene-OH, cyclocalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$-alkylene-$C_{6-14}$aryl, —$C_{0-3}$alkylene-$C_{2-14}$heteroaryl, or cyano;

$R^{5a}$ is selected from H, —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —C(O)OH, —C(O)O$C_{1-4}$alkyl, —$C_{0-6}$alkylene-O—$C_{6-14}$aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl;

$R^{5b}$ is selected from H, —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —C(O)OH, —C(O)O$C_{1-4}$alkyl, —$C_{0-6}$alkylene-O—$C_{6-14}$aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl;

or $R^{5a}$ and $R^{5b}$ together, may represent an ═O or ═N═N;

$R^6$ is H, halo, —$C_{1-6}$alkyl, —$C_{2-6}$alkynyl, —$C_{1-6}$alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —C(O)OH, —C(O)O$C_{1-4}$alkyl, —$C_{0-6}$alkylene-O—$C_{6-14}$aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl;

$R^{5a}$ and $R^{6a}$, together with the atoms to which they are attached, may form a 3-6 membered ring that optionally includes one or two heteroatoms selected from O, S or N; or $R^{5a}$ and $R^{6a}$ are absent when b is a double bond;

$R^{6a}$ is H, or —$C_{1-6}$alkyl;

$R^{6b}$ is H, —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —C(O)OH, —C(O)O$C_{1-4}$alkyl, —$C_{0-6}$alkylene-O—$C_{6-14}$aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, —$C_{0-3}$alkylene-$C_{2-14}$heteroaryl, or cyano;

or $R^{6a}$ and $R^{6b}$ together, may represent an ═O;

$R^7$ is H or $C_{1-8}$alkyl;

$R^8$ is H, OH, $NR^aR^b$;

wherein $R^a$ and $R^b$ are each independently H, halo, —$C_{1-6}$alkyl, —$C_{2-6}$alkynyl;

wherein the ring A or the —$C_{1-6}$alkyl, —$C_{2-6}$alkynyl, —$C_{1-6}$ alkylene-O—$C_{1-4}$alkyl, —$C_{1-6}$alkylene-OH, —$C_{1-6}$haloalkyl, —$C_{1-6}$alkyleneamine, —$C_{0-6}$alkylene-amide, —C(O)O$C_{1-4}$alkyl, —$C_{1-6}$ alkylene-O-aryl, —$C_{0-3}$alkylene-C(O)$C_{1-4}$alkylene-OH, cycloalkyl, heterocycloalkyl, aryl, heteroaryl, —$C_{0-3}$alkylene-$C_{3-14}$cycloalkyl, —$C_{0-3}$alkylene-$C_{2-14}$heterocycloalkyl, —$C_{0-3}$alkylene-$C_{6-14}$aryl, or —$C_{0-3}$alkylene-$C_{2-14}$heteroaryl groups of any of the $R^4$, $R^5$, $R^{5a}$, $R^{5b}$, $R^6$, $R^{6a}$, $R^{6b}$, $R^7$ and $R^8$ may be unsubstituted or substituted with 1, 2, 3, or 4 substituents, as allowed, independently selected from halo, —$C_{1-6}$alkyl, —O—$C_{1-6}$alkyl, —OH, or —$C_{1-6}$alkyl-CN; or a stereoisomer or tautomer thereof, or a pharmaceutically acceptable salt of any of the foregoing.

Description of formula (K-I-A) can be found in WO2021/081212A1, the entirety of which is incorporated herein by reference. Formula (K-I-A) is described as formula (I) in WO2021/081212A1 (see, e.g., Embodiment 1, paragraph [0037]), which paragraphs and description of formula (I) and methods of making compounds of formula (I) are hereby incorporated herein by reference. Moieties of formula (K-I-A), such as $R^1$, $R^2$, $R^3$, and $R^8$ are as defined in WO2021/081212A1, including any variations or embodiments thereof.

In some embodiments, in conjunction with embodiments above or below, a compound of formula (K-I) or (K-I-A) is sotorasib (Compound K1), or a stereoisomer or tautomer thereof, or a pharmaceutically acceptable salt of any of the foregoing. Sotorasib is chemically described as 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2 (1H)-one, having the structure below:

(Sotorasib or Compound K1)

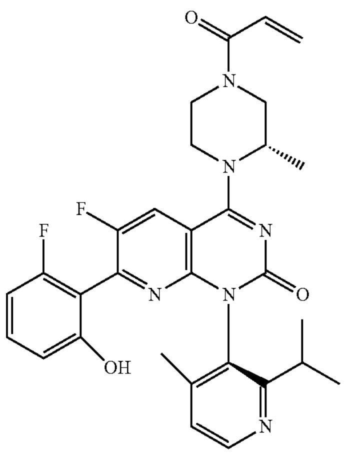

Description of sotorasib (Compound K1) and methods of making sotorasib can be found in US2018/0334454A1, the entirety of which is incorporated herein by reference. Description of sotorasib (Compound K1) and methods of making sotorasib can be found in, e.g., Example 41, pages 210-212 of US2018/0334454A1.

In some embodiments, in conjunction with embodiments above or below, the one or more KRAS inhibitors comprise a compound of formula (K-II):

(K-II)

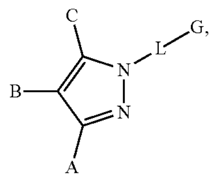

wherein,

A is selected from the group consisting of:

(a) $C_5$-$C_7$ cycloalkylene which is unsubstituted or substituted with one or more, preferably 1, 2 or 3, substituents independently selected from fluoro and $C_1$-$C_4$ alkyl;

(b) a 5-7 membered unsaturated heterocyclyl containing one carbon-carbon double bond and one oxygen atom as ring member, wherein said heterocyclyl is unsubstituted or substituted with one or more, preferably 1, 2 or 3, substituents, independently selected from fluoro and $C_1$-$C_4$ alkyl, preferably 1, 2 or 3, $C_1$-$C_4$ alkyl;

(c) $C_6$-$C_{10}$ aryl which is unsubstituted or substituted with 1, 2 or 3 $R^{A2}$;

(d) a 5-6 membered heteroaryl ring containing 1, 2 or 3 heteroatoms independently selected from N, O and S as ring members, wherein said heteroaryl ring is unsubstituted or substituted on one or more (e.g., 1, 2 or 3) carbon atoms with $R^{A3}$, and wherein a nitrogen atom, when present in the heteroaryl ring, is unsubstituted or substituted with a substituent selected from the group consisting of: $C_1$-$C_4$ alkyl, —$(CH_2)_{1-2}$—$C_{3-4}$-cycloalkyl, $C_3$-$C_6$ cycloalkyl, hydroxy-$C_1$-$C_4$ alkyl, fluoro-$C_1$-$C_4$ alkyl, $C_1$-$C_4$ alkoxy-$C_1$-$C_4$ alkyl, $N(R^9)(R^{10})$—$C_1$-$C_4$ alkyl, —$SO_2$—$C_1$-$C_4$ alkyl, —$SO_2$—$C_3$-$C_4$ cycloalkyl, —$(CH_2)_p$-$Het^{py}$, and —$(CH_2)_p$—$N(R^9)(R^{10})$;

(e) an 8-10 membered heteroaryl ring containing 1 to 3 heteroatoms independently selected from nitrogen, oxygen and sulfur, or an 8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 $S(=O)_2$ group in the hetero-bicyclic ring, wherein said heteroaryl ring or hetero-bicyclic ring is unsubstituted or substituted on a carbon atom with 1, 2, 3, 4, or 5 $R^{A4}$, and wherein the hetero-bicyclic ring is further optionally substituted on a carbon atom by oxo and wherein a nitrogen atom, when present, is unsubstituted or substituted with a substituent which is —(CO)—$C_1$-$C_4$ alkyl or $C_1$-$C_4$ alkyl, and wherein said $C_1$-$C_4$ alkyl is optionally substituted with 1 or 2 substituents independently selected from cyano, hydroxy, oxo, fluoro, $C_1$-$C_4$ alkoxy, $C_1$-$C_4$ alkoxy-$C_1$-$C_4$ alkyloxy, $Het^b$ and $NR^9R^{10}$; and wherein $Het^b$ is a 4- or 5- or 6-membered heterocyclic ring comprising 1 or 2 heteroatoms or groups independently selected from N, O, S, SO and $SO_2$, wherein said heterocyclic ring $Het^b$ is unsubstituted or substituted on a carbon atom with one or two substituents independently selected from $C_1$-$C_4$ alkyl, hydroxy, cyano, fluoro, $C_1$-$C_4$ alkoxy-hydroxy-$C_1$-$C_4$ alkyl, hydroxy-$C_1$-$C_4$ alkyl, $C_1$-$C_4$ alkoxy, fluoro-$C_1$-$C_4$ alkoxy and fluoro $C_1$-$C_4$ alkyl, and wherein said heterocyclic ring $Het^b$ is further optionally substituted on a carbon atom by oxo, and wherein the nitrogen atom when present in $Het^b$ is optionally further substituted with $C_1$-$C_4$ alkyl which is optionally substituted with 1 to 3 substituents independently selected from fluoro, hydroxy and $C_1$-$C_4$ alkoxy;

wherein A is attached to the rest of the compound of Formula (I) by a carbon atom on A which is $sp^2$ hybridized;

wherein

B is selected from the group consisting of $B^1$ and $B^2$;

wherein $B^1$ is $C_{6-10}$ aryl which is unsubstituted or substituted with 1, 2, 3 or 4 $R^{Ba}$;

$B^2$ is a 6-13 membered heteroaryl which comprises 1, 2 or 3 nitrogen atoms, wherein $B^2$ is unsubstituted or substituted with 1, 2, 3 or 4 $R^{Bb}$;

C is selected from the group consisting of hydrogen, $C_1$-$C_3$ alkyl, $C_3$-$C_5$ cycloalkyl, fluoro-$C_1$-$C_3$ alkyl, cyano, —$CH_2$—CN, —CH(CN)—$CH_3$, —$CH_2$—OH, —CH(OH)—$CH_3$ and halo;

L is selected from the group consisting of:

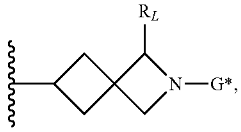,

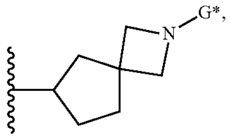,

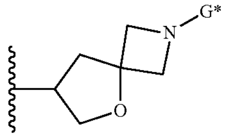

and

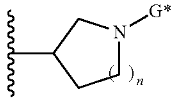

wherein n is 1, 2 or 3, $R_L$ is selected from hydrogen, methyl, ethyl, —$CH_2$—CN and —$CH_2$—OH, where G* represents the point of attachment to G;

G is selected from the group consisting of

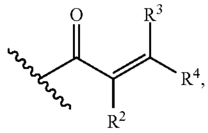,

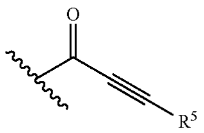

and

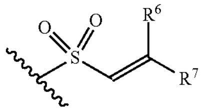

wherein $R^2$ is selected from hydrogen, $C_1$-$C_3$ alkyl, —C(O)—$C_1$-$C_3$ alkyl, and fluoro;

$R^3$ is hydrogen;

$R^4$ is selected from hydrogen, methyl, —$CH_2F$, —$CH_2$—$OCH_3$ and —$CH_2$—$N(CH_3)_2$;

$R^5$ is selected from hydrogen and methyl;

$R^6$ is hydrogen;

$R^7$ is selected from hydrogen and methyl;

wherein $R^{A2}$ is independently selected from the group consisting of: $NR^9R^{10}$, cyano, —$(CH_2)_p$—CN, halo, OH, hydroxy-$C_1$-$C_4$ alkyl, —(COOH), —$(CH_2)_p$—COOH, $C_1$-$C_4$ alkyl, fluoro-$C_1$-$C_4$ alkyl, $C_1$-$C_4$ alkoxy, $C_1$-$C_4$ alkoxy-$C_1$-$C_4$ alkyl, $N(R^9)(R^{10})$—$C_1$-$C_4$alkyl, $N(R^9)(R^{10})$—$C_1$-$C_4$ alkyl-oxy, $N(R^9)(R^{10})$—$C_1$-$C_4$ alkoxy, $C_1$-$C_4$ alkyl-carbonyl-oxy-$C_1$-$C_4$ alkyl-oxy, hydroxy-$C_1$-$C_4$ alkyl-oxy, $C_1$-$C_4$ alkoxy-$C_1$-$C_4$ alkyl-oxy, $C_1$-$C_4$ alkoxy-$C_1$-$C_4$ alkyl-oxy-$C_1$-$C_4$ alkyl, —$SO_2$—$C_1$-$C_4$ alkyl, —$SO_2$—$C_3$-$C_4$ cycloalkyl, —$(CH_2)_{1-2}$—$C_3$-$C_4$ cycloalkyl, $Het^{py}$, —$(CH_2)_p$-$Het^{py}$, —C(=O)-$NR^9R^{10}$, —$(CH_2)_p$—C(=O)$NR^9R^{10}$;

wherein $R^{A3}$ is independently selected from the group consisting of oxo, $NR^9R^{10}$, cyano, —$(CH_2)_p$—CN, halo, OH, hydroxy-$C_1$-$C_4$ alkyl, —(COOH), —$(CH_2)_p$—COOH, $C_1$-$C_4$alkyl, fluoro-$C_1$-$C_4$ alkyl, $C_1$-$C_4$ alkoxy, $C_1$-$C_4$ alkoxy-$C_1$-$C_4$ alkyl, $N(R^9)(R^{10})$—$C_1$-$C_4$ alkyl, $N(R^9)(R^{10})$—$C_1$-$C_4$ alkyl-oxy, $N(R^9)(R^{10})$—$C_1$-$C_4$ alkoxy, $C_1$-$C_4$ alkyl-carbonyl-oxy-$C_1$-$C_4$ alkyl-oxy, hydroxy-$C_1$-$C_4$ alkyl-oxy, $C_1$-$C_4$ alkoxy-$C_1$-$C_4$ alkyl-oxy, $C_1$-$C_4$ alkoxy-$C_1$-$C_4$ alkyl-oxy-$C_1$-$C_4$ alkyl, $-SO_2-C_1-C_4$ alkyl, $-SO_2-C_3-C_4$ cycloalkyl, $-(CH_2)_{1-2}-C_3-C_4$ cycloalkyl, $Het^{py}$, $-(CH_2)_p-Het^{py}$, $-C(=O)-NR^9R^{10}$, $-(CH_2)_p-C(=O)NR^9R^{10}$, $(CH_2)_p-NR^9R^{10}$;

wherein $R^{A4}$ is independently selected from the group consisting of cyano, $CO_2H$, halo, $C_1-C_4$ alkyl, fluoro-$C_1-C_4$ alkyl, hydroxy, hydroxy-$C_1-C_4$ alkyl, hydroxy-$C_1-C_4$ alkyl-oxy, $C_1-C_4$ alkoxy, $C_1-C_4$ alkoxy-$C_1-C_4$ alkyl, $C_1-C_4$ alkoxy-$C_1-C_4$ alkyl-oxy, $NR^9R^{10}$, $N(R^9)(R^{10})-C_1-C_4$ alkyl, $N(R^9)(R^{10})-C_1-C_4$ alkyl-oxy, $-(CO)-C_1-C_4$ alkyl, and $R^9R^{10}N-C_1-C_4$ alkyl-oxy-$(CO)-C_1-C_4$ alkyl;

wherein p is 1 or 2 or 3;

$R^9$ is selected from hydrogen and $C_1-C_4$ alkyl;

$R^{10}$ is selected from the group consisting of hydrogen, $C_1-C_4$ alkyl, hydroxyl-$C_1-C_4$ alkyl, $C_1-C_4$ alkoxy-$C_1-C_4$ alkyl and di-$C_1-C_4$ alkyl-amino-$C_1-C_4$ alkyl;

$Het^{py}$ is a 4-, 5-, 6- or 7-membered saturated heterocyclic ring comprising one or two heteroatoms independently selected from O, N and S, or comprising an S-oxide (SO) or S-dioxide ($SO_2$) group, and wherein said heterocyclic ring is optionally substituted with oxo on one carbon atom, and wherein said heterocyclic ring is optionally further substituted on one or more carbon atoms with 1, 2 or 3 substituents independently selected from $C_1-C_4$ alkoxy, halo, $C_1-C_4$ alkyl, hydroxy-$C_1-C_4$ alkyl, and fluoro-$C_1-C_4$ alkyl, and wherein the nitrogen atom, if present in said heterocycle, is optionally further substituted with $R^{10}$;

or $Het^{py}$ is a 5- or 6-membered heteroaryl ring, comprising 1, 2 or 3 nitrogen atoms and wherein said heteroaryl ring is optionally substituted with one or more (e.g., 1, 2 3) substituents independently selected from $NR^9R^{10}$, $-C(=O)-NR^9R^{10}$, halo, $C_1-C_4$ alkyl, hydroxy-$C_1-C_4$ alkyl, fluoro-$C_1-C_4$ alkyl, cyano, OH, and $C_1-C_4$ alkoxy;

each $R^{Ba}$ is independently selected from the group consisting of hydroxy, $NH_2$, $C_1-C_4$ alkyl and halo;

each $R^{Bb}$ is independently selected from the group consisting of $C_1-C_4$ alkyl, cyclopropyl, fluoro-$C_1-C_3$ alkyl, cyano, halo, $NH_2$, and $C_1-C_3$ alkoxy, or a stereoisomer or tautomer thereof, or a pharmaceutically acceptable salt of any of the foregoing.

Description of formula (K-II) can be found in WO2021/124222A1, the entirety of which is incorporated herein by reference. Formula (K-II) is described as Formula (I) in WO2021/124222A1 (see, e.g., pages 5-13 and Embodiment 1 pages 29-32), which paragraphs and description of Formula (I) and methods of making compounds of Formula (I) are hereby incorporated herein by reference. Moieties of formula (K-II), such as A, B, C, L, and G are as defined in WO2021/124222A1, including any variations or embodiments thereof.

In some embodiments, in conjunction with embodiments above or below, the one or more KRAS inhibitors comprise a compound of formula (K-II-A):

(K-II-A)

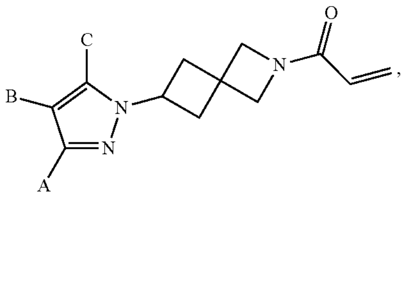

or a stereoisomer or tautomer thereof, or a pharmaceutically acceptable salt of any of the foregoing, wherein A, B, and C are as defined in formula (K-II). It is understood that A, B, and C of such embodiments of compounds of Formula (K-II-A) may include A, B, and C as described for Formula (K-II). Formula (K-II-A) is described as formula (Ia) in, e.g., Embodiment 21, of WO2021/124222A1, which paragraphs and description of formula (Ia) and methods of making compounds of formula (Ia) are hereby incorporated herein by reference. Moieties of formula (K-II-A), such as A, B, and C are as defined in WO2021/124222A1, including any variations or embodiments thereof.

In some embodiments, in conjunction with embodiments above or below, the one or more KRAS inhibitors comprise a compound of formula (K-II-B) or (K-II-C):

(K-II-B)

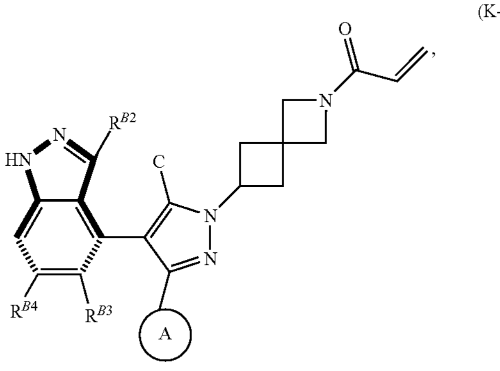

(K-II-C)

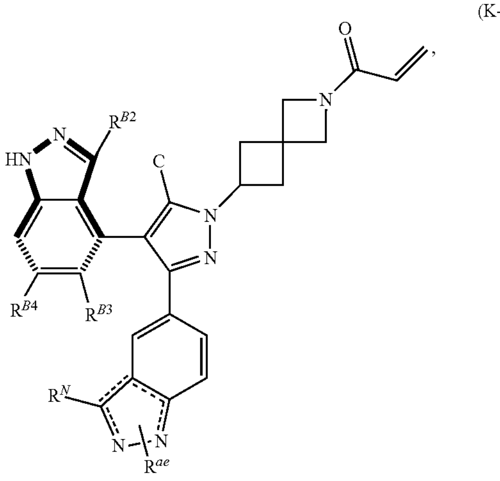

wherein, $R^{B2}$ is independently selected from hydrogen, halo, $C_1-C_4$-alkyl, cyclopropyl and $NH_2$;

$R^{B3}$ is independently selected from hydrogen, halo, cyclopropyl and $C_1-C_4$-alkyl;

$R^{B4}$ is independently selected from hydrogen, halo and $C_1-C_4$-alkyl, or $R^{B3}$ and $R^{B4}$ together with the atoms to which they are attached, form a 4-6 membered ring fused to the aromatic ring to which $R^{B3}$ and $R^{B4}$ are attached;

$R^N$ is hydrogen, halo, $C_{1-4}$alkyl, or halo or fluoro-$C_{1-4}$alkyl;

$R^{ae}$ is selected from the group consisting of hydrogen and $C_{1-4}$alkyl, wherein said alkyl is optionally substituted with 1 or 2 substituents selected from cyano, hydroxyl, fluoro, $C_{1-4}$alkoxy, $C_{1-4}$alkoxy-$C_{1-4}$alkyl-oxy, $Het^b$ and $NR^9R^{10}$;

$R^9$ is selected from hydrogen and $C_{1-4}$alkyl;

$R^{10}$ is selected from hydrogen, $C_{1-4}$alkyl, hydroxy-$C_{1-4}$alkyl, $C_{1-4}$alkoxy-$C_{1-4}$alkyl and di-$C_{1-4}$alkyl-amino-$C_{1-4}$alkyl;

wherein $Het^b$ is a 4- or 5- or 6-membered heterocyclic ring comprising 1 or 2 heteroatoms or groups independently selected from N, O, S, SO and $SO_2$, wherein said heterocyclic ring $Het^b$ is unsubstituted or substituted on a carbon atom with one or two substituents independently selected from $C_{1-4}$alkyl, hydroxy, cyano, fluoro, hydroxy-$C_{1-4}$alkyl, $C_{1-4}$alkoxy and fluoro-$C_{1-4}$alkyl, and wherein said heterocyclic ring $Het^b$ is further optionally substituted on a carbon atom by oxo, and wherein the nitrogen atom when present in $Het^b$ is optionally further substituted with $C_{1-4}$alkyl which is optionally substituted with 1 to 3 substituents independently selected from fluoro, hydroxy and $C_{1-4}$alkoxy;

or a stereoisomer or tautomer thereof, or a pharmaceutically acceptable salt of any of the foregoing, wherein A and C are as defined in Formula (K-II). It is understood that A and C of such embodiments of compounds of Formulae (K-II-B) and (K-II-C) may include A and C as described for Formula (K-II).

Formulae (K-II-B) and (K-II-C) are described as formula (Ib*) and (Id*), respectively in, e.g., Embodiment 39 and 41, of WO2021/124222A1, which paragraphs and description of formula (Ib*) or (Id*) and methods of making compounds of formula (Ib*) or (Id*) are hereby incorporated herein by reference. Moieties of formula (K-II-B) or (K-II-C), such as A, C, $R^{B2}$, $R^{B3}$, $R^{B4}$, $R^N$, and $R^{ae}$ are as defined in WO2021/124222A1, including any variations or embodiments thereof.

In some embodiments, in conjunction with embodiments above or below, a compound of formula (K-II), (K-II-A), (K-II-B), or (K-II-C) is Compound K2, or a stereoisomer or tautomer thereof, or a pharmaceutically acceptable salt of any of the foregoing. Compound K2 is chemically described as 1-[6-[4-(5-chloro-6-methyl-1H-indazol-4-yl)-5-methyl-3-(1-methylindazol-5-yl)pyrazol-1-yl]-2-azaspiro[3.3]heptan-2-yl]prop-2-en-1-one, having the structure below:

(Compound K2)

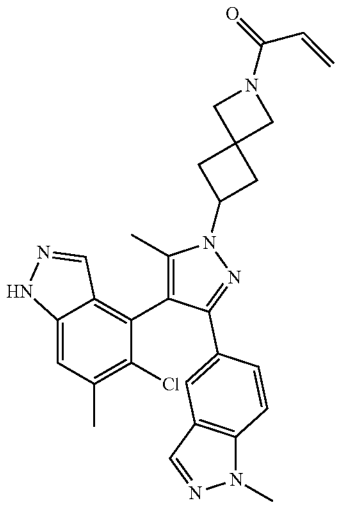

Description of Compound K2 and methods of making Compound K2 can be found in, e.g., Method 1-Synthetic Scheme on pages 111 to 114 of WO2021/124222A1.

In some embodiments, in conjunction with embodiments above or below, the one or more KRAS inhibitors comprise a compound of formula (K-III):

(K-III)

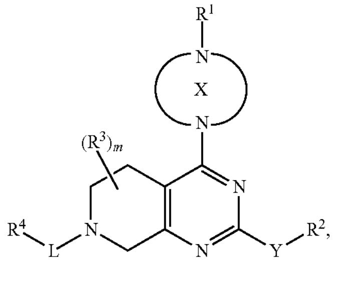

wherein:

X is a 4-12 membered saturated or partially saturated monocyclic, bridged or spirocyclic ring, wherein the saturated or partially saturated monocyclic ring is optionally substituted with one or more $R^8$;

Y is a bond, O, S or $NR^5$;

$R^1$ is $—C(O)C(R^A)\equiv C(R^B)_p$ or $—SO_2C(R^A)\equiv C(R^B)_p$;

$R^2$ is hydrogen, alkyl, hydroxyalkyl, dihydroxyalkyl, alkylaminylalkyl, dialkylaminylalkyl, —Z—$NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;

each Z is C1-C4 alkylene;

each $R^3$ is independently C1-C3 alkyl, oxo, haloalkyl, hydroxyl or halogen;

L is a bond, —C(O)—, or C1-C3 alkylene;

$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$, $R^7$ or $R^8$;

each $R^5$ is independently hydrogen or C1-C3 alkyl;

$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;

each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;

$R^8$ is oxo, C1-C3 alkyl, C2-C4 alkynyl, heteroalkyl, cyano, —$C(O)OR^5$, —$C(O)N(R^5)_2$, —$N(R^5)_2$, wherein the C1-C3 alkyl may be optionally substituted with cyano, halogen, —$OR^5$, —$N(R^5)_2$, or heteroaryl;

each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl;

each $R^{10}$ is independently hydrogen, acyl, C1-C3 alkyl, heteroalkyl or hydroxyalkyl;

$R^{11}$ is haloalkyl;

$R^A$ is absent, hydrogen, deuterium, cyano, halogen, C1-C3 alkyl, haloalkyl, heteroalkyl, —$C(O)N(R^5)_2$, or hydroxyalkyl;

each $R^B$ is independently hydrogen, deuterium, cyano, C1-C3 alkyl, hydroxyalkyl, heteroalkyl, C1-C3 alkoxy, halogen, haloalkyl, —$ZNR^5R^{11}$, —$C(O)N(R^5)_2$, —NHC(O)C1-C3 alkyl, —$CH_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$;

or when $\equiv$ is a double bond and p is two, one $R^B$ is hydrogen and $R^A$ and one $R^B$ and the carbon atoms to which they are attached form a 4-8 membered partially saturated cycloalkyl substituted with oxo;

m is zero or an integer between 1 and 2;

p is one or two; and wherein, when $\equiv$ is a triple bond then $R^A$ is absent, p equals one and $R^B$ is hydroxyalkyl, or when $\equiv$ is a double bond then $R^A$ is present, $R^B$ is present and p equals two, wherein when $R^A$ is hydrogen or C1-C3 alkyl, at least one $R_B$ is deuterium, cyano, halogen, haloalkyl, hydroxyalkyl, heteroalkyl, heteroaryl, heteroarylalkyl, —$ZNR^5R^{11}$, —$C(O)N(R^5)_2$, —NHC(O)C1-C3 alkyl, —$CH_2$NHC(O)C1-C3 alkyl or heterocyclylalkyl, wherein the heterocyclyl portion is substituted with one or more substituents independently selected from halogen, hydroxyl, alkoxy and C1-C3 alkyl; or when each $R^B$ is hydrogen, then $R^A$ is deuterium, cyano, halogen, haloalkyl, —$C(O)N(R^5)_2$, hydroxyalkyl or heteroalkyl;

or a stereoisomer or tautomer thereof, or a pharmaceutically acceptable salt of any of the foregoing.

Description of formula (K-III) can be found in US2019/0144444A1, the entirety of which is incorporated herein by reference. Formula (K-III) is described as Formula (II) in US2019/0144444A1 (see, e.g., paragraphs [0169]40193D, which paragraphs and description of Formula (II) and methods of making compounds of Formula (II) are hereby incorporated herein by reference. Moieties of formula (K-III), such as X, Y, L, m, $R^1$, $R^2$, $R^3$, and $R^4$ are as defined in US2019/0144444A1, including any variations or embodiments thereof.

In some embodiments, in conjunction with embodiments above or below, the one or more KRAS inhibitors comprise a compound of formula (K-III-A):

(K-III-A)

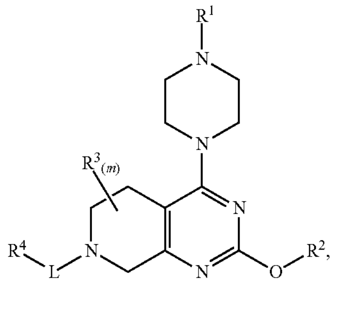

where the piperazinyl ring is optionally substituted with $R^8$; or a stereoisomer or tautomer thereof, or a pharmaceutically acceptable salt of any of the foregoing, wherein $R^1$, $R^3$, $R^4$, $R^8$, L, and m are as defined in Formula (K-III). It is understood that $R^1$, $R^3$, $R^4$, $R^8$, L, and m of such embodiments of compounds of Formula (K-III-A) may include $R^1$, $R^3$, $R^4$, $R^8$, L, and m as described for Formula (K-III). Formula (K-III-A) is described as Formula (II-B) in, e.g., paragraphs [0231]-[0241] of US2019/0144444A1, which paragraphs and description of Formula (II-B) and methods of making compounds of Formula (II-B) are hereby incorporated herein by reference. Moieties of formula (K-III-A), such as L, m, $R^1$, $R^2$, $R^3$, and $R^4$ are as defined in US2019/0144444A1, including any variations or embodiments thereof.

In some embodiments, in conjunction with embodiments above or below, a compound of formula (K-III) or (K-III-A) is adagrasib (Compound K3), or a stereoisomer or tautomer thereof, or a pharmaceutically acceptable salt of any of the foregoing. Adagrasib is chemically described as 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile, having the structure below:

(Adagrasib or Compound K3)

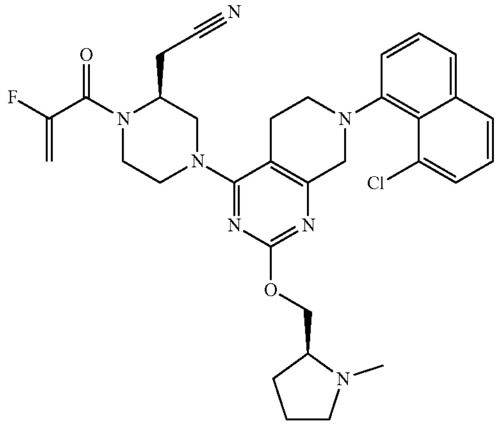

Description of adagrasib (Compound K3) and methods of making adagrasib can be found in, e.g., Example 478 on pages 668-669 of US2019/0144444A1.

In some embodiments, in conjunction with embodiments above or below, the one or more KRAS inhibitors comprise a compound of formula (K-IV):

(K-IV)

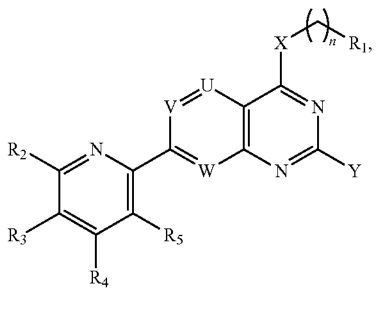

wherein, $R_1$ is an electrophilic moiety capable of forming a covalent bond with a cysteine residue at position 12 of a K-Ras G12C mutant protein;

$R_2$ is selected from a group consisting of H, OH, $NH_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkenyl)NH($CH_3$)—($C_{1-6}$ alkylenyl)N($CH_3$)$_2$, and —($C_{1-3}$ alkylenyl)(3-7 membered-heterocyclyl);

$R_3$ and $R_4$ are each independently selected from the group consisting of H, $NH_2$, halo, $C_{1-6}$ alkyl, $C_{1-6}$ haloakyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;

$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl, Wherein at least one of $R_2$, $R_3$, $R_4$, and $R_5$ is other than H; or $R_2$ and $R_3$, $R_3$ and $R_4$, or $R_4$ and $R^5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy;

X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

Y is selected from the group consisting of -L-$Y_1$ or $Y_1$;

$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ haloalkoxy, $C_{1-6}$ haloalkyl, 5- to 10-membered heteroaryl, 4- to 10-membered heterocyclyl, a 4- to 10-membered heterocyclyl substituted with methyl, hydroxyl, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$alkoxy $C_{1-6}$alkyl, $C_{1-6}$ haloalkyl, oxo, hydroxyl, $NH_2$, cyano, $C_{1-6}$ carboxyalkyl, $C_{1-6}$ cyanoalkyl, $C_{1-6}$ hydroxyalkyl, and $C_{1-6}$ haloalkoxy;

L is selected from the group consisting of a bond, O, S, and N($L^a$);

$L^a$ is selected from the group consisting of hydrogen and $C_{1-3}$ alkyl;

U is C($R_{6a}$);

V is C($R_{6b}$);

$R^e$ is C($R_{6c}$) or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and n is selected from the group consisting of 0, 1, and 2;

or a stereoisomer or tautomer thereof, or a pharmaceutically acceptable salt of any of the foregoing.

Description of formula (K-IV) can be found in US2021/0230142A9, the entirety of which is incorporated herein by reference. Formula (K-IV) is described as Formula (I) in US2021/0230142A9 (see, e.g., paragraphs [0113]40132D, which paragraphs and description of Formula (I) and methods of making compounds of Formula (I) are hereby incorporated herein by reference. Moieties of formula (K-IV), such as U, V, W, X, Y, $R^1$, $R^2$, $R^3$, $R^4$ and $R^5$ are as defined in US2021/0230142A9, including any variations or embodiments thereof.

In some embodiments, in conjunction with embodiments above or below, the one or more KRAS inhibitors comprise a compound of formula (K-IV-A):

(II) (K-IV-A)

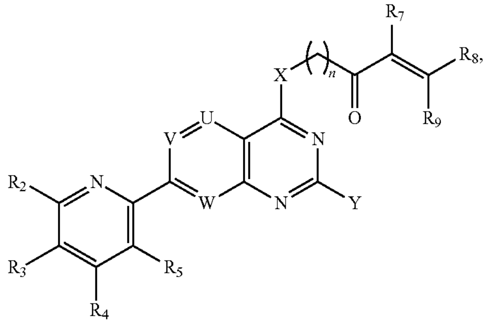

wherein, $R_2$ is selected from the group consisting of H, OH, $NH_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)NH($CH_3$)—($C_{1-6}$ alkylenyl) N($CH_3$)$_2$, and —($C_{1-3}$ alkylenyl)(3-7 membered-heterocyclyl);

$R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;

$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl, wherein at least one of $R_2$, $R_3$, $R_4$, and $R_5$ is other than H; or $R_2$ and $R_3$, $R_3$ and $R_4$, or $R_4$ and $R^5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy;

$R_7$ is selected from the group consisting of H, cyano, and halo; and $R_8$ and $R_9$ are each independently selected from the group consisting of H, $C_{1-6}$ alkyl, $C_{1-6}$ haloalkyl, $C_{1-6}$ hydroxyalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

or $R_7$ and $R_8$ together form a triple bond between the carbons to which they are attached, or $R_7$ and $R_8$ together with the carbons to which they are each bonded form a $C_{3-7}$ cycloalkenyl optionally substituted with one or two halo substituents; and $R_9$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

Y is selected from the group consisting of $-L-Y_1$ or $Y_1$;

$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, 4- to 10-membered heterocyclyl substituted with methyl, hydroxy, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy;

L is selected from the group consisting of a bond, O, S, and $N(L^a)$;

$L^a$ is selected from the group consisting of hydrogen and $C_{1-3}$ alkyl;

U is $C(R_{6a})$;

V is $C(R_{6b})$;

$R^e$ is $C(R_{6c})$ or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and n is selected from the group consisting of 0, 1, and 2;

or a stereoisomer or tautomer thereof, or a pharmaceutically acceptable salt of any of the foregoing.

Formula (K-IV-A) is described as Formula (II) in, e.g., paragraph [0137] of US2021/0230142A9, which paragraphs and description of Formula (II) and methods of making compounds of Formula (II) are hereby incorporated herein by reference. Moieties of formula (K-IV-A), such as U, V, W, X, Y, $R^1$, $R^2$, $R^3$, $R^4$, $R^5$, $R^7$, $R^8$, and $R^9$ are as defined in US2021/0230142A9, including any variations or embodiments thereof.

In some embodiments, in conjunction with embodiments above or below, the one or more KRAS inhibitors comprise a compound of formula (K-IV-B) or (K-IV-C):

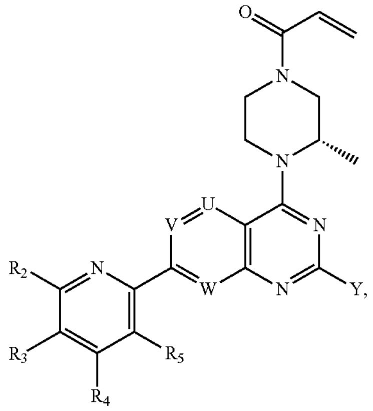

(K-IV-B)

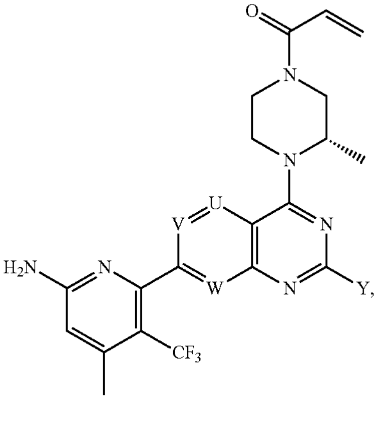

(K-IV-C)

or a stereoisomer or tautomer thereof, or a pharmaceutically acceptable salt of any of the foregoing, wherein U, V, W, Y, $R_2$, $R_3$, $R_4$, and $R_5$ are as defined in Formula (K-IV). It is understood that U, V, W, Y, $R_2$, $R_3$, $R_4$, and $R_5$ of such embodiments of compounds of Formulae (K-IV-B) and (K-IV-C) may include U, V, W, Y, $R_2$, $R_3$, $R_4$, and $R_5$ as described for Formula (K-IV). Formulae (K-IV-B) and (K-IV-C) are described as Formulae (Ib) and (IVb), respectively, in, e.g., paragraphs [0277] and [0285] of US2021/0230142A9, which paragraphs and description of Formula (Ib) or (IVb) and methods of making compounds of Formula (Ib) or (IVb) are hereby incorporated herein by reference. Moieties of formulae (K-IV-B) and (K-IV-C), such as U, V, W, Y, $R^2$, $R^3$, $R^4$, and $R^5$ are as defined in US2021/0230142A9, including any variations or embodiments thereof.

In some embodiments, in conjunction with embodiments above or below, a compound of formula (K-IV), (K-IV-A), (K-IV-B), or (K-IV-C) is Compound K4, or a stereoisomer or tautomer thereof, or a pharmaceutically acceptable salt of any of the foregoing. Compound K2 is chemically described as 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one, having the structure below:

(Compound K4)

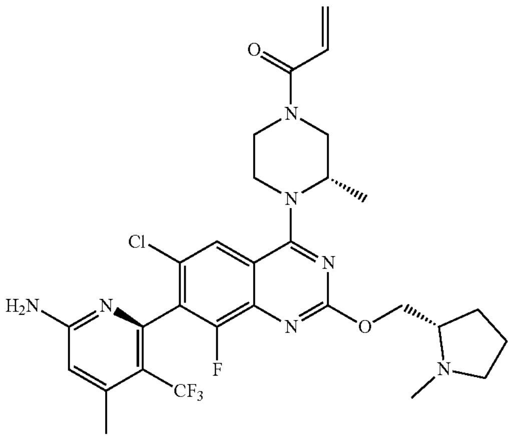

Description of Compound K4 and methods of making Compound K4 can be found in, e.g., Example 17a & 17b on pages 130 to 135 of US2021/0230142A9.

In some embodiments, in conjunction with embodiments above or below, the one or more KRAS inhibitors comprise a G12C KRAS inhibitor (e.g., any one of Compound K1, Compound K2, Compound K3, and Compound K4). G12C KRAS inhibitors are described in, for example, Hallin et al. (Cancer Discov, 2020, 10(1): 54-71), Skoulidis et al. (N. Engl. J. Med., 2021, 384(25): 2371-2381), and Hong et al. (N. Engl. J. Med., 2020, 383(13): 1207-1217), each of which is incorporated herein by reference in its entirety and specifically with respect to G12C KRAS inhibitors described therein.

In some embodiments, in conjunction with embodiments above or below, the one or more TEAD inhibitors are selected from the group consisting of compounds T1, T2, and T3 as listed in Table 2, or a stereoisomer or tautomer thereof, or a pharmaceutically acceptable salt of any of the foregoing. In some embodiments, in conjunction with embodiments above or below, the one or more TEAD inhibitors are selected from the group consisting of the compounds listed in Table 1, or a stereoisomer or tautomer thereof, or a pharmaceutically acceptable salt of any of the foregoing. In some embodiments, in conjunction with embodiments above or below, the one or more KRAS inhibitors are selected from the group consisting of compounds K1, K2, K3, and K4 as listed in Table 2, or a stereoisomer or tautomer thereof, or a pharmaceutically acceptable salt of any of the foregoing.

TABLE 2

| Compound Number | Structure | Chemical name |
|---|---|---|
| T1 (also referred to as Compound 17) | 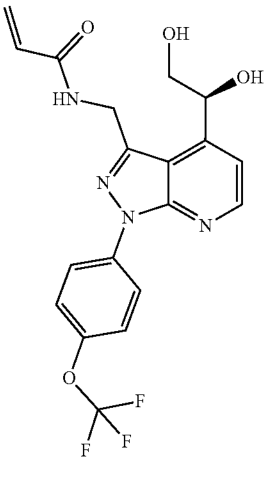 [SMILES: C=CC(=O)NCc1nn(-c2ccc(OC(F)(F)F)cc2)c2nccc([C@H](O)CO)c12] | N-[[4-[(1S)-1,2-dihydroxyethyl]-1-[4-(trifluoromethoxy)phenyl]pyrazolo[3,4-b]pyridin-3-yl]methyl]prop-2-enamide |

TABLE 2-continued

| Compound Number | Structure | Chemical name |
|---|---|---|
| T2 (also referred to as Compound 20) | 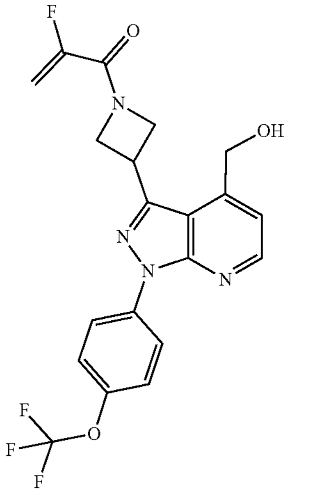 [SMILES: C=C(F)C(=O)N1CC(c2nn(-c3ccc(OC(F)(F)F)cc3)c3nccc(CO)c23)C1] | 2-fluoro-1-[3-[4-(hydroxymethyl)-1-[4-(trifluoromethoxy)phenyl]pyrazolo[3,4-b]pyridin-3-yl]azetidin-1-yl]prop-2-en-1-one |
| T3 (also referred to as Compound 21) | 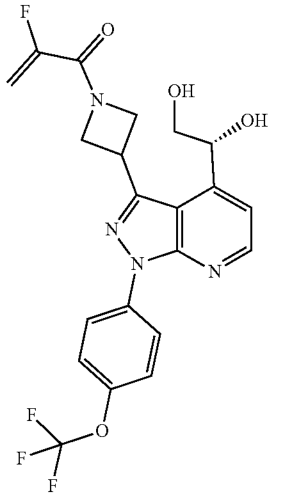 [SMILES: C=C(F)C(=O)N1CC(c2nn(-c3ccc(OC(F)(F)F)cc3)c3nccc([C@@H](O)CO)c23)C1] | 1-[3-[4-[(1R)-1,2-dihydroxyethyl]-1-[4-(trifluoromethoxy)phenyl]pyrazolo[3,4-b]pyridin-3-yl]azetidin-1-yl]-2-fluoro-prop-2-en-1-one |
| K1 | 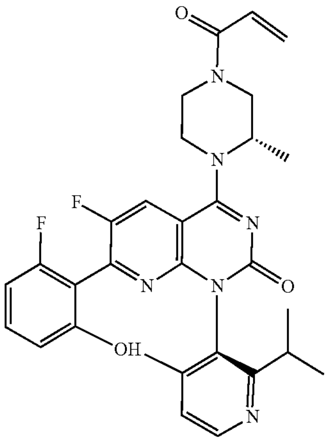 | 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one |

TABLE 2-continued

| Compound Number | Structure | Chemical name |
|---|---|---|
| K2 | 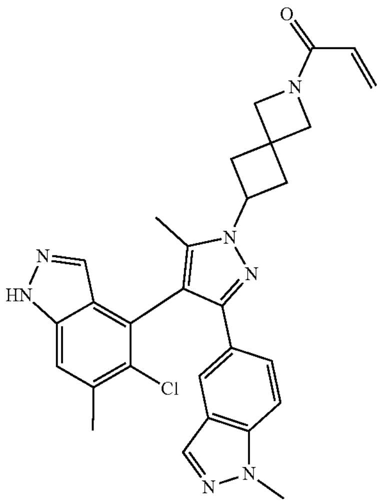 [SMILES: C=CC(=O)N1CC2(CC(n3nc(-c4ccc5c(cnn5C)c4)c(-c4c(Cl)c(C)cc5[nH]ncc45)c3C)C2)C1] | 1-[6-[4-(5-chloro-6-methyl-1H-indazol-4-yl)-5-methyl-3-(1-methylindazol-5-yl)pyrazol-1-yl]-2-azaspiro[3.3]heptan-2-yl]prop-2-en-1-one |
| K3 | 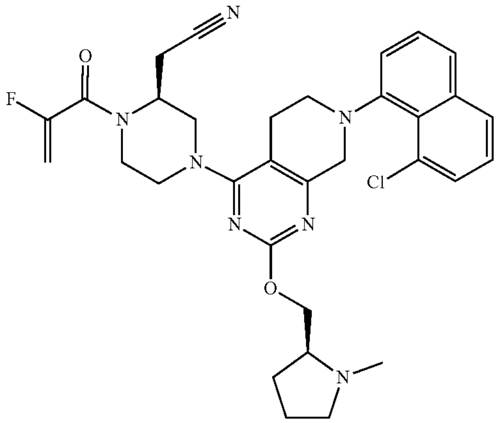 [SMILES: C=C(F)C(=O)N1CCN(c2nc(OC[C@@H]3CCCN3C)nc3c2CCN(c2cccc4cccc(Cl)c24)C3)C[C@@H]1CC#N] | 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile |
| K4 | 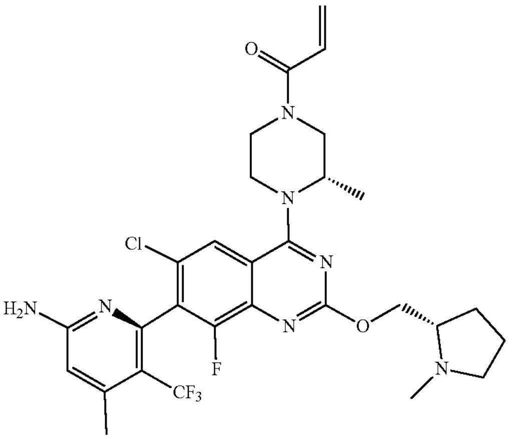 | 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one |

In some embodiments, in conjunction with embodiments above or below, the YAP/TAZ-TEAD inhibitors are selected from the group consisting of:

N-((4-(1,2-dihydroxyethyl)-1-(4-(trifluoromethoxy)phenyl)-1H-pyrazolo[3,4-b]pyridin-3-yl)methyl)acrylamide;

2-fluoro-1-[3-[4-(hydroxymethyl)-1-[4-(trifluoromethoxy) phenyl]pyrazolo[3,4-b]pyridin-3-yl]azetidin-1-yl]prop-2-en-1-one; and 1-(3-(4-(1,2-dihydroxyethyl)-1-(4-(trifluoromethoxy)phenyl)-1H-pyrazolo[3,4-b]pyridin-3-yl)azetidin-1-yl)-2-fluoroprop-2-en-1-one, or a stereoisomer or tautomer thereof, or a pharmaceutically acceptable salt of any of the foregoing.

In some embodiments, in conjunction with embodiments above or below, the one or more KRAS inhibitors are selected from the group consisting of:

4-(4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2 (1H)-one;

1-[6-[4-(5-chloro-6-methyl-1H-indazol-4-yl)-5-methyl-3-(1-methylindazol-5-yl)pyrazol-1-yl]-2-azaspiro[3.3]heptan-2-yl]prop-2-en-1-one;

2-(4-(7-(8-chloronaphthalen-1-yl)-2-((l-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile; and 1-(4-(7-(6-amino-4-methyl-3-(trifluoromethyl)pyridin-2-yl)-6-chloro-8-fluoro-2-((l-methylpyrrolidin-2-yl)methoxy)quinazolin-4-yl)-3-methylpiperazin-1-yl)prop-2-en-1-one, or a stereoisomer or tautomer thereof, or a pharmaceutically acceptable salt of any of the foregoing.

In some embodiments, the compositions, methods, or kits, comprise one or more TEAD inhibitors (e.g., any one of the TEAD inhibitors described herein, including but not limited to, any one of compounds of formula (I-AB), (AB), (AB'), (A), (I-A), (A-1), (I-A-1), (B), (I-B), (B-1), or (I-B-1), or any variations or embodiments thereof) and one or more KRAS inhibitors (e.g., any one of compounds of formula (K-I), (K-I-A), (K-II), (K-II-A), (K-II-B), (K-II-C), (K-III), (K-III-A), (K-IV), (K-IV-A), (K-IV-B), or (K-IV-C), or any variations or embodiments thereof). TEAD inhibitors may, in some embodiments, be referred to as YAP/TAZ-TEAD inhibitors. In some embodiments, in conjunction with embodiments above or below, the one or more KRAS inhibitors may be a G12C KRAS inhibitor (e.g., Compound K1, Compound K2, Compound K3, or Compound K4). Each and every combination of TEAD inhibitor and KRAS inhibitor is intended the same as if each and every combination is specifically and individually listed. Thus, for example, it is intended that any combination of: (1) a compound of formula (I-AB), (AB), (AB'), (A), (I-A), (A-1), (I-A-1), (B), (I-B), (B-1), or (I-B-1), or any variation or embodiment thereof; and (2) a compound of formula (K-I), (K-I-A), (K-II), (K-II-A), (K-II-B), (K-II-C), (K-III), (K-III-A), (K-IV), (K-IV-A), (K-IV-B), or (K-IV-C), or any variation or embodiment thereof, is provided herein.

In some embodiments, the one or more TEAD inhibitors comprise a compound of formula (I-AB) or (AB) (e.g., Compound T1, Compound T2, or Compound T3) and the one or more KRAS inhibitors comprise a compound of formula (K-I) (e.g., Compound K1). In some embodiments, the one or more TEAD inhibitors comprise a compound of formula (AB) (e.g., Compound T1, Compound T2, or Compound T3) and the one or more KRAS inhibitors comprise a compound of formula (K-II) (e.g., Compound K2). In some embodiments, the one or more TEAD inhibitors comprise a compound of formula (AB) (e.g., Compound T1, Compound T2, or Compound T3) and the one or more KRAS inhibitors comprise a compound of formula (K-III) (e.g., Compound K3). In some embodiments, the one or more TEAD inhibitors comprise a compound of formula (AB) (e.g., Compound T1, Compound T2, or Compound T3) and the one or more KRAS inhibitors comprise a compound of formula (K-IV) (e.g., Compound K4).

In some embodiments, the one or more TEAD inhibitors comprise a compound of formula (A) (e.g., Compound T1) and the one or more KRAS inhibitors comprise a compound of formula (K-I) (e.g., Compound K1). In some embodiments, the one or more TEAD inhibitors comprise a compound of formula (A) (e.g., Compound T1) and the one or more KRAS inhibitors comprise a compound of formula (K-II) (e.g., Compound K2). In some embodiments, the one or more TEAD inhibitors comprise a compound of formula (A) (e.g., Compound T1) and the one or more KRAS inhibitors comprise a compound of formula (K-III) (e.g., Compound K3). In some embodiments, the one or more TEAD inhibitors comprise a compound of formula (A) (e.g., Compound T1) and the one or more KRAS inhibitors comprise a compound of formula (K-IV) (e.g., Compound K4).

In some embodiments, the one or more TEAD inhibitors comprise a compound of formula (B) (e.g., Compound T2 or Compound T3) and the one or more KRAS inhibitors comprise a compound of formula (K-I) (e.g., Compound K1). In some embodiments, the one or more TEAD inhibitors comprise a compound of formula (B) (e.g., Compound T2 or Compound T3) and the one or more KRAS inhibitors comprise a compound of formula (K-II) (e.g., Compound K2). In some embodiments, the one or more TEAD inhibitors comprise a compound of formula (B) (e.g., Compound T2 or Compound T3) and the one or more KRAS inhibitors comprise a compound of formula (K-III) (e.g., Compound K3). In some embodiments, the one or more TEAD inhibitors comprise a compound of formula (B) (e.g., Compound T2 or Compound T3) and the one or more KRAS inhibitors comprise a compound of formula (K-IV) (e.g., Compound K4).

In some embodiments, the one or more TEAD inhibitors are selected from compounds of formula (I-AB), (AB), (AB'), (A), (A'), (B), or (B'), and the one or more KRAS inhibitors are selected from compounds of formula (K-IV), (K-IV-A), (K-IV-B), or (K-IV-C). In some embodiments, in conjunction with the embodiments above or below, the one or more KRAS inhibitors comprise Compound K4. In some embodiments, in conjunction with the embodiments above or below, the one or more TEAD inhibitors comprise Compound T1. In some embodiments, in conjunction with the embodiments above or below, the one or more TEAD inhibitors comprise Compound T2. In some embodiments, in conjunction with the embodiments above or below, the one or more TEAD inhibitors comprise Compound T3.

In some embodiments, the one or more TEAD inhibitors are selected from compounds of formula (I-AB), (AB), (AB'), (A), (A'), (B), or (B'), and the one or more KRAS inhibitors are selected from compounds of formula (K-III) or (K-III-A). In some embodiments, in conjunction with the embodiments above or below, the one or more KRAS inhibitors comprise Compound K3. In some embodiments, in conjunction with the embodiments above or below, the one or more TEAD inhibitors comprise Compound T1. In some embodiments, in conjunction with the embodiments above or below, the one or more TEAD inhibitors comprise Compound T2. In some embodiments, in conjunction with the embodiments above or below, the one or more TEAD inhibitors comprise Compound T3.

In some embodiments, the one or more TEAD inhibitors are selected from compounds of formula (I-AB), (AB), (AB'), (A), (A'), (B), or (B'), and the one or more KRAS inhibitors are selected from compounds of formula (K-II), (K-II-A), (K-II-B), or (K-III-C). In some embodiments, in conjunction with the embodiments above or below, the one or more KRAS inhibitors comprise Compound K2. In some embodiments, in conjunction with the embodiments above or below, the one or more TEAD inhibitors comprise Compound T1. In some embodiments, in conjunction with the embodiments above or below, the one or more TEAD inhibitors comprise Compound T2. In some embodiments, in conjunction with the embodiments above or below, the one or more TEAD inhibitors comprise Compound T3.

In some embodiments, the one or more TEAD inhibitors are selected from compounds of formula (I-AB), (AB), (AB'), (A), (A'), (B), or (B'), and the one or more KRAS inhibitors are selected from compounds of formula (K-I) or (K-I-A). In some embodiments, in conjunction with the embodiments above or below, the one or more KRAS inhibitors comprise Compound K1. In some embodiments, in conjunction with the embodiments above or below, the one or more TEAD inhibitors comprise Compound T1. In some embodiments, in conjunction with the embodiments above or below, the one or more TEAD inhibitors comprise Compound T2. In some embodiments, in conjunction with the embodiments above or below, the one or more TEAD inhibitors comprise Compound T3.

In some embodiments, the one or more TEAD inhibitors are selected from compounds of Table 1, and the one or more KRAS inhibitors are selected from compounds of formula (K-IV), (K-IV-A), (K-IV-B), or (K-IV-C). In some embodiments, the one or more KRAS inhibitors comprise Compound K4. In some embodiments, the one or more TEAD inhibitors are selected from compounds of Table 1, and the one or more KRAS inhibitors are selected from compounds of formula (K-III) or (K-III-A). In some embodiments, the one or more KRAS inhibitors comprise Compound K3. In some embodiments, the one or more TEAD inhibitors are selected from compounds of Table 1, and the one or more KRAS inhibitors are selected from compounds of formula (K-II), (K-II-A), (K-II-B), or (K-II-C). In some embodiments, the one or more KRAS inhibitors comprise Compound K2. In some embodiments, the one or more TEAD inhibitors are selected from compounds of Table 1, and the one or more KRAS inhibitors are selected from compounds of formula (K-I) or (K-I-A). In some embodiments, the one or more KRAS inhibitors comprise Compound K1.

In some embodiments, the one or more TEAD inhibitors comprise Compound T1, and the one or more KRAS inhibitors are selected from compounds of formula (K-IV), (K-IV-A), (K-IV-B), or (K-IV-C). In some embodiments, the one or more TEAD inhibitors comprise Compound T1, and the one or more KRAS inhibitors are selected from compounds of formula (K-III) or (K-III-A). In some embodiments, the one or more TEAD inhibitors comprise Compound T1, and the one or more KRAS inhibitors are selected from compounds of formula (K-II), (K-II-A), (K-II-B), or (K-II-C). In some embodiments, the one or more TEAD inhibitors comprise Compound T1, and the one or more KRAS inhibitors are selected from compounds of formula (K-I) or (K-I-A). In some embodiments, the one or more TEAD inhibitors comprise Compound T1, and the one or more KRAS inhibitors comprise Compound K4. In some embodiments, the one or more TEAD inhibitors comprise Compound T1, and the one or more KRAS inhibitors comprise Compound K3. In some embodiments, the one or more TEAD inhibitors comprise Compound T1, and the one or more KRAS inhibitors comprise Compound K2. In some embodiments, the one or more TEAD inhibitors comprise Compound T1, and the one or more KRAS inhibitors comprise Compound K1.

In some embodiments, the one or more TEAD inhibitors comprise Compound T2, and the one or more KRAS inhibitors are selected from compounds of formula (K-IV), (K-IV-A), (K-IV-B), or (K-IV-C). In some embodiments, the one or more TEAD inhibitors comprise Compound T2, and the one or more KRAS inhibitors are selected from compounds of formula (K-III) or (K-III-A). In some embodiments, the one or more TEAD inhibitors comprise Compound T2, and the one or more KRAS inhibitors are selected from compounds of formula (K-II), (K-II-A), (K-II-B), or (K-II-C). In some embodiments, the one or more TEAD inhibitors comprise Compound T2, and the one or more KRAS inhibitors are selected from compounds of formula (K-I) or (K-I-A). In some embodiments, the one or more TEAD inhibitors comprise Compound T2, and the one or more KRAS inhibitors comprise Compound K4. In some embodiments, the one or more TEAD inhibitors comprise Compound T2, and the one or more KRAS inhibitors comprise Compound K3. In some embodiments, the one or more TEAD inhibitors comprise Compound T2, and the one or more KRAS inhibitors comprise Compound K2. In some embodiments, the one or more TEAD inhibitors comprise Compound T2, and the one or more KRAS inhibitors comprise Compound K1.

In some embodiments, the one or more TEAD inhibitors comprise Compound T3, and the one or more KRAS inhibitors are selected from compounds of formula (K-IV), (K-IV-A), (K-IV-B), or (K-IV-C). In some embodiments, the one or more TEAD inhibitors comprise Compound T3, and the one or more KRAS inhibitors are selected from compounds of formula (K-III) or (K-III-A). In some embodiments, the one or more TEAD inhibitors comprise Compound T3, and the one or more KRAS inhibitors are selected from compounds of formula (K-II), (K-II-A), (K-II-B), or (K-II-C). In some embodiments, the one or more TEAD inhibitors comprise Compound T3, and the one or more KRAS inhibitors are selected from compounds of formula (K-I) or (K-I-A). In some embodiments, the one or more TEAD inhibitors comprise Compound T3, and the one or more KRAS inhibitors comprise Compound K4. In some embodiments, the one or more TEAD inhibitors comprise Compound T3, and the one or more KRAS inhibitors comprise Compound K3. In some embodiments, the one or more TEAD inhibitors comprise Compound T3, and the one or more KRAS inhibitors comprise Compound K2. In some embodiments, the one or more TEAD inhibitors comprise Compound T3, and the one or more KRAS inhibitors comprise Compound K1.

In some embodiments, the one or more TEAD inhibitors are selected from the group consisting of:

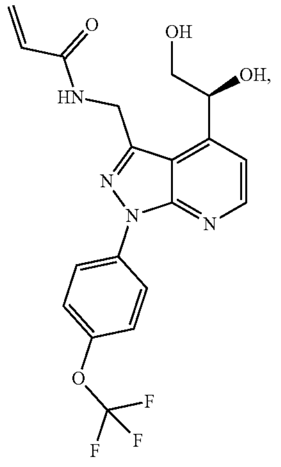

-continued

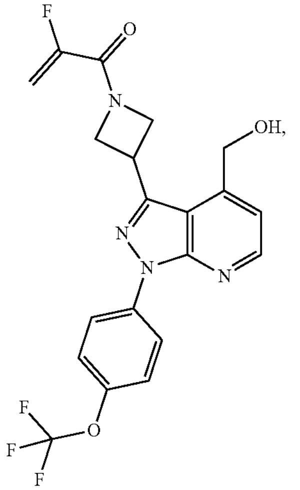

and

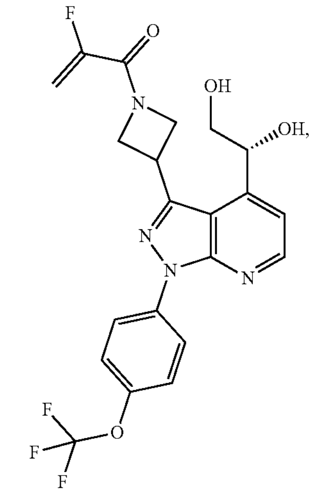

or a stereoisomer or tautomer thereof, or a pharmaceutically acceptable salt of any of the foregoing; and the one or more KRAS inhibitors are selected from the group consisting of:

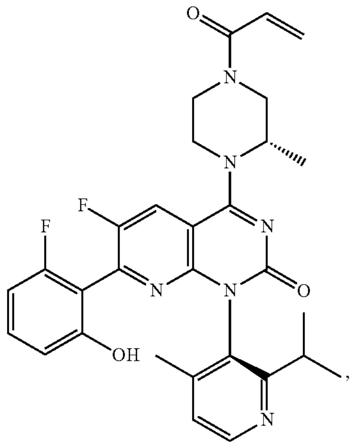

-continued

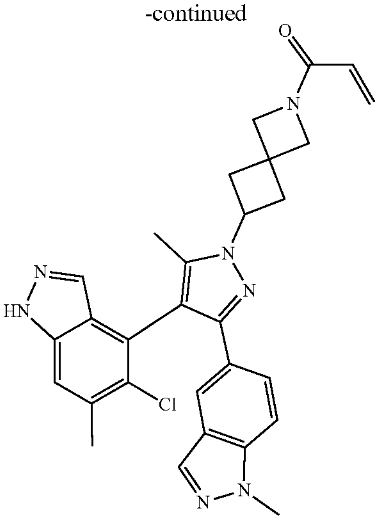

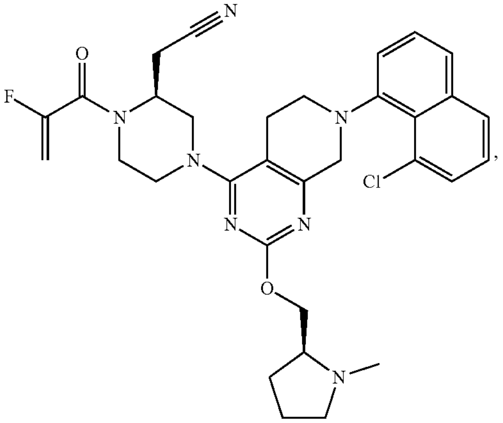

and

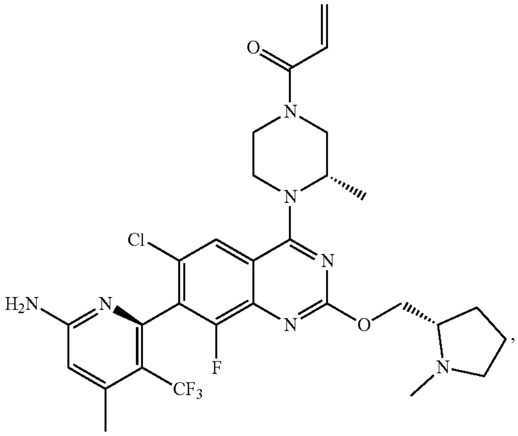

or a stereoisomer or tautomer thereof, or a pharmaceutically acceptable salt of any of the foregoing.

In some embodiments, provided herein are methods of treating cancer in a subject in need thereof, comprising administering to the subject an effective amount of a combination, comprising one or more TEAD inhibitors (e.g., any one of the TEAD inhibitors described herein, including but not limited to, any one of compounds of formula (I-AB), (AB), (AB'), (A), (I-A), (A-1), (I-A-1), (B), (I-B), (B-1), or (I-B-1), or any variations or embodiments thereof) and one or more KRAS inhibitors (e.g., any one of compounds of formula (K-I), (K-II), (K-III), or (K-IV), or any variations or embodiments thereof). In some embodiments, the KRAS inhibitor is a G12C KRAS inhibitor.

In some aspects, provided herein is a method of treating a disease or condition mediated by KRAS activity in a subject in need thereof, comprising administering to the subject an effective amount of a combination, comprising: i) one or more TEAD inhibitors; and (ii) one or more KRAS inhibitors. In some embodiments, the disease or condition mediated by KRAS activity is cancer.

In some aspects, provided herein is a method of treating a disease or condition mediated by TEAD activity in a subject in need thereof, comprising administering to the subject an effective amount of a combination, comprising: i) one or more TEAD inhibitors; and (ii) one or more KRAS inhibitors. In some embodiments, the disease or condition mediated by TEAD activity is cancer.

In another aspect, provided herein is a method of reducing resistance of a subject to treatment comprising one or more KRAS inhibitors (e.g., any one of compounds of formula (K-I), (K-II), (K-III), or (K-IV), or any variations or embodiments thereof), wherein the method comprises administering to the subject a therapeutically effective amount of one or more TEAD inhibitors (e.g., any one of the TEAD inhibitors described herein, including but not limited to, any one of compounds of formula (I-AB), (AB), (AB'), (A), (I-A), (A-1), (I-A-1), (B), (I-B), (B-1), or (I-B-1), or any variations or embodiments thereof).

In some embodiments, provided herein are kits, comprising (i) one or more TEAD inhibitors (e.g., any one of the TEAD inhibitors described herein, including but not limited to, any one of compounds of formula (I-AB), (AB), (AB'), (A), (I-A), (A-1), (I-A-1), (B), (I-B), (B-1), or (I-B-1), or any variations or embodiments thereof); (ii) one or more KRAS inhibitors (e.g., any one of compounds of formula (K-I), (K-II), (K-III), or (K-IV), or any variations or embodiments thereof); and (iii) instructions for administering the combination to treat cancer in a subject in need thereof. In some embodiments, the KRAS inhibitor is a G12C KRAS inhibitor.

Enumerated Embodiments

In one aspect, provided herein are the following embodiments, enumerated below:

Embodiment 1. A compound of formula (A) or (B):

(A)

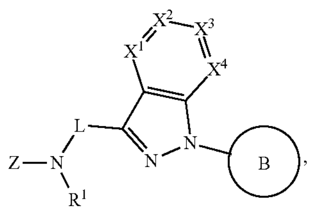

(B)

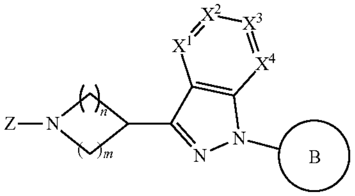

or a stereoisomer or tautomer thereof, or a pharmaceutically acceptable salt thereof, wherein:

$R^1$ is H or $C_{1-6}$ alkyl;

$X^1$ is N or $CR^s$, wherein $R^s$ is selected from H, —CN, halo, $C_{1-15}$alkyl, $C_{6-20}$aryl, 5 to 15 membered heteroaryl, $C_{3-20}$cycloalkyl, 3 to 15 membered heterocyclyl, —OH, $C_{1-15}$alkoxy, $—NR^dCOR^e$, $—CONR^dR^e$, $—SO_2R^d$, $—SO_2NR^dR^e$, $—NR^dSO_2R^e$, and $—NR^dR^e$, wherein $R^d$ and $R^e$ each independently H or $C_{1-6}$alkyl, and the $C_{1-6}$alkyl of $R^d$ or $R^e$ is optionally substituted with one or more halo, oxo, —OH, or —CN;

wherein the $C_{1-15}$alkyl and $C_{1-15}$alkoxy of $R^s$ are each independently optionally substituted with one or more $R^t$, wherein $R^t$ is independently, at each occurrence, selected from halo, oxo, —OH, —CN and $—NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^t$, wherein $R^t$ is independently, at each occurrence, selected from halo, —OH, —CN, and $C_{1-6}$alkyl;

$X^2$, $X^3$, and $X^4$ are each independently N or CH, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is $—C(O)R^x$, wherein $R^x$ is $C_{2-6}$alkenyl, optionally substituted with one or more substituents selected from $C_{1-6}$alkyl and halo; or wherein $R^x$ is $C_{1-6}$alkyl, optionally substituted with one or more halo;

L is methylene, optionally substituted with one or more $C_{1-6}$alkyl; and n and m are each independently 1 or 2.

Embodiment 2. A compound of embodiment 1, or a stereoisomer or tautomer thereof, or a pharmaceutically acceptable salt thereof, wherein $R^1$ is H.

Embodiment 3. A compound of embodiment 1 or 2, or a stereoisomer or tautomer thereof, or a pharmaceutically acceptable salt thereof, wherein the compound is a compound of formula (I-A) or (I-B):

(I-A)

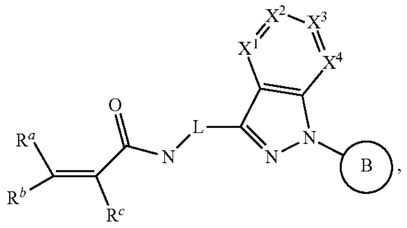

(I-B)

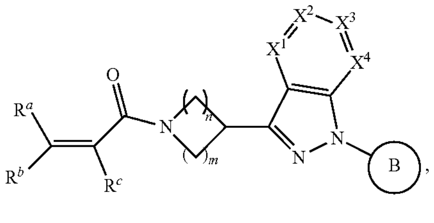

or a stereoisomer or tautomer thereof, or a pharmaceutically acceptable salt thereof, wherein $R^a$, $R^b$, and $R^c$ are each independently H, halo, or $C_{1-5}$alkyl.

Embodiment 4. The compound of embodiment 1 or 2, or a stereoisomer or tautomer thereof, or a pharmaceutically acceptable salt thereof, wherein Z is —C(O)$R^x$ and $R^x$ is $C_{1-6}$alkyl optionally substituted with one or more halo.

Embodiment 5. The compound of embodiment 4, or a stereoisomer or tautomer thereof, or a pharmaceutically acceptable salt thereof, wherein $R^x$ is ethyl, optionally substituted with one or more Cl.

Embodiment 6. The compound of embodiment 3, or a stereoisomer or tautomer thereof, or a pharmaceutically acceptable salt thereof, wherein one of $R^a$, $R^b$, and $R^c$ is H.

Embodiment 7. The compound of embodiment 3, or a stereoisomer or tautomer thereof, or a pharmaceutically acceptable salt thereof, wherein $R^a$, $R^b$, and $R^c$ are each H.

Embodiment 8. The compound of any one of embodiments 1-7, or a stereoisomer or tautomer thereof, or a pharmaceutically acceptable salt thereof, wherein $X^1$ is $CR^s$; and $X^2$, $X^3$, and $X^4$ are CH.

Embodiment 9. The compound of any one of embodiments 1-7, or a stereoisomer or tautomer thereof, or a pharmaceutically acceptable salt thereof, wherein $X^1$ is $CR^s$; $X^2$ is N; and $X^3$ and $X^4$ are CH.

Embodiment 10. The compound of any one of embodiments 1-7, or a stereoisomer or tautomer thereof, or a pharmaceutically acceptable salt thereof, wherein $X^1$ is $CR^s$; $X^3$ is N; and $X^2$ and $X^4$ are CH.

Embodiment 11. The compound of any one of embodiments 1-7, or a stereoisomer or tautomer thereof, or a pharmaceutically acceptable salt thereof, wherein $X^1$ is $CR^s$; $X^2$ and $X^3$ are CH; and $X^4$ are N.

Embodiment 12. The compound of any one of embodiments 1-11, or a stereoisomer or tautomer thereof, or a pharmaceutically acceptable salt thereof, wherein $R^s$ is H or —CN.

Embodiment 13. The compound of any one of embodiments 1-11, or a stereoisomer or tautomer thereof, or a pharmaceutically acceptable salt thereof, wherein $R^s$ is $C_{1-15}$alkyl or $C_{1-15}$alkoxy, wherein the $C_{1-15}$alkyl or $C_{1-15}$alkoxy of $R^s$ are each independently optionally substituted with one or more $R^t$, wherein $R^t$ is independently, at each occurrence, selected from halo, oxo, —OH, —CN and —$NR^dR^e$, wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN.

Embodiment 14. The compound of any one of embodiments 1-11, or a stereoisomer or tautomer thereof, or a pharmaceutically acceptable salt thereof, wherein $R^s$ is $C_{1-6}$ alkyl optionally substituted with one or more —OH.

Embodiment 15. The compound of any one of embodiments 1-11, or a stereoisomer or tautomer thereof, or a pharmaceutically acceptable salt thereof, wherein $R^s$ is $C_{6-20}$aryl, 5 to 15 membered heteroaryl, $C_{3-20}$cycloalkyl, or 3 to 15 membered heterocyclyl, wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^t$, wherein $R^t$ is independently, at each occurrence, selected from halo, —OH, —CN, and $C_{1-6}$alkyl.

Embodiment 16. The compound of any one of embodiments 1-7, or a stereoisomer or tautomer thereof, or a pharmaceutically acceptable salt thereof, wherein $X^1$ is N; and $X^2$, $X^3$, and $X^4$ are each CH.

Embodiment 17. The compound of embodiment 1 or 2, or a stereoisomer or tautomer thereof, or a pharmaceutically acceptable salt thereof, wherein the compound is a compound of formula (A-1) or (B-1):

(A-1)

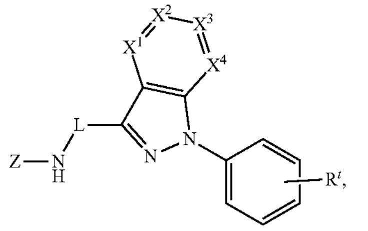

(B-1)

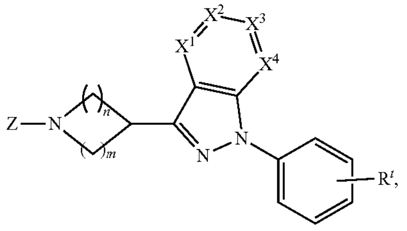

or a stereoisomer or tautomer thereof, or a pharmaceutically acceptable salt thereof.

Embodiment 18. The compound of embodiment 17, or a stereoisomer or tautomer thereof, or a pharmaceutically acceptable salt thereof, wherein the compound is selected from the group consisting of:

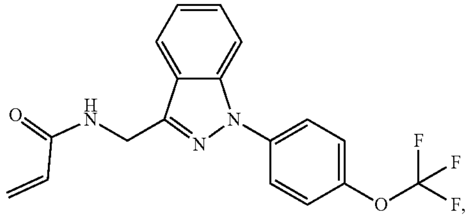

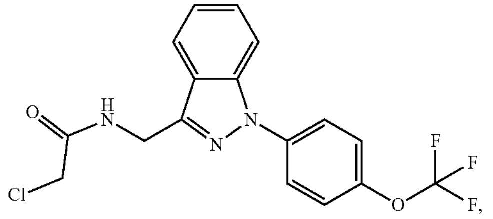

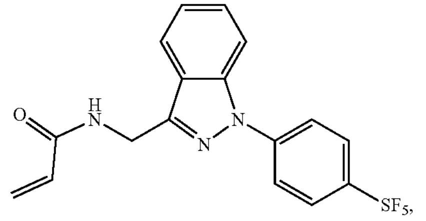

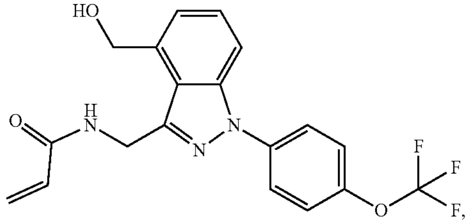

-continued

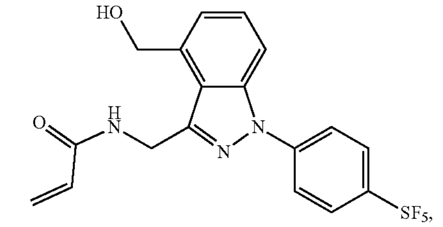

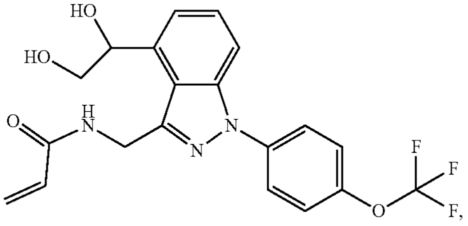

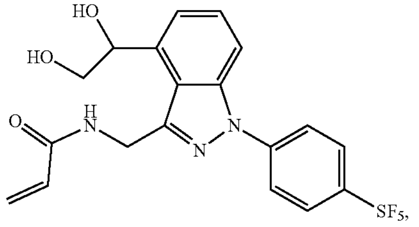

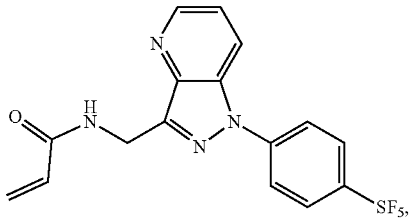

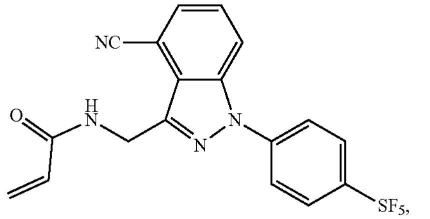

and

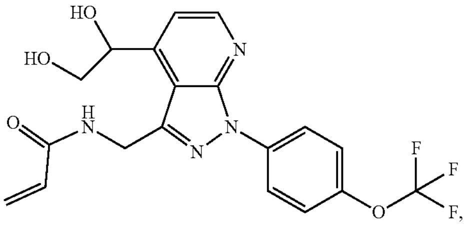

or a stereoisomer or tautomer thereof, or a pharmaceutically acceptable salt thereof.

Embodiment 19. The compound of any one of embodiments 1-3, or 17, or a stereoisomer or tautomer thereof, or a pharmaceutically acceptable salt thereof, wherein the compound is a compound of formula (I-A-1) or (I-B-1):

(I-A-1)

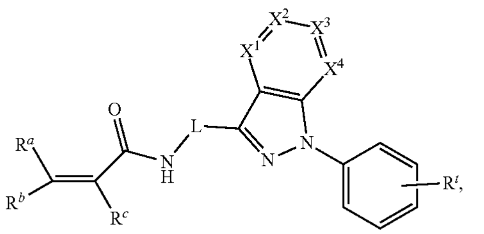

(I-B-1)

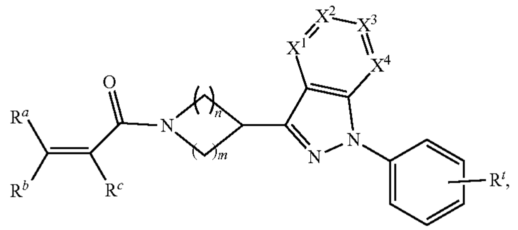

or a stereoisomer or tautomer thereof, or a pharmaceutically acceptable salt thereof, wherein:

$R^a$, $R^b$, and $R^c$ are each independently H, halo, or $C_{1-5}$alkyl; and $R^t$ is selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo.

Embodiment 20. The compound of embodiment 19, or a stereoisomer or tautomer thereof, or a pharmaceutically acceptable salt thereof, wherein the compound is selected from the group consisting of:

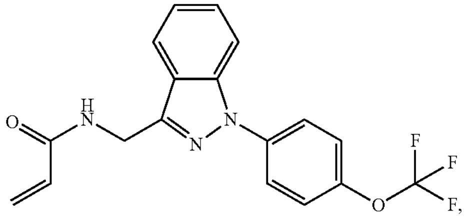

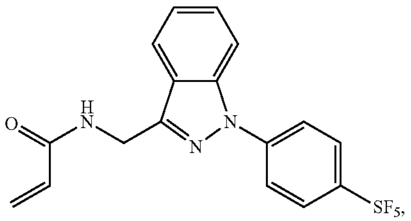

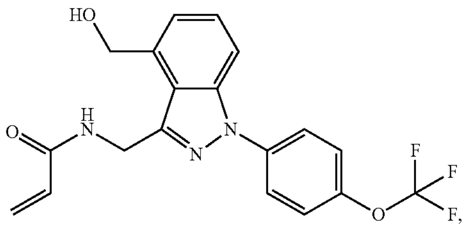

-continued

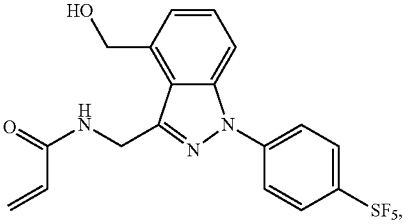

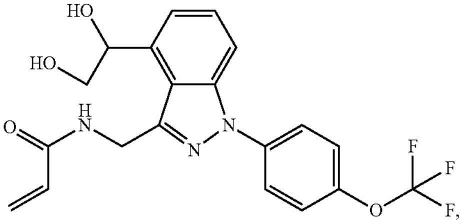

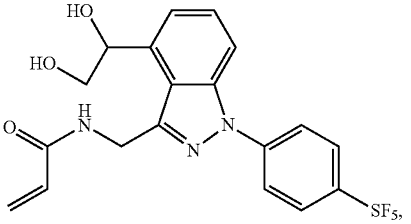

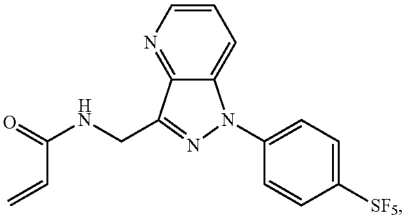

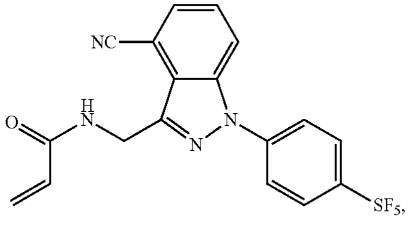

and

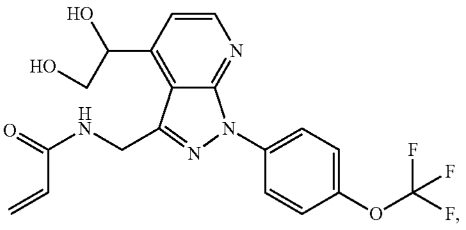

or a stereoisomer or tautomer thereof, or a pharmaceutically acceptable salt thereof.

Embodiment 21. The compound of any one of embodiments 17-20, or a pharmaceutically acceptable salt thereof, wherein the compound is selected from the group consisting of:

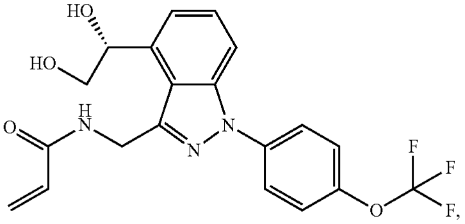

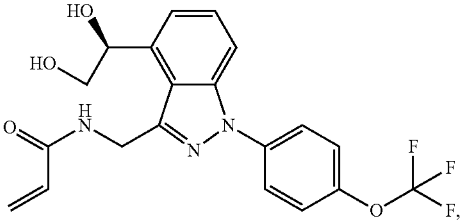

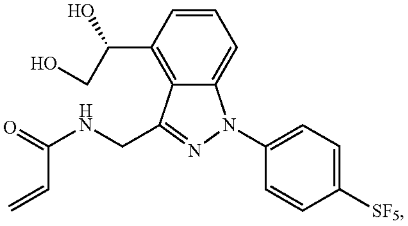

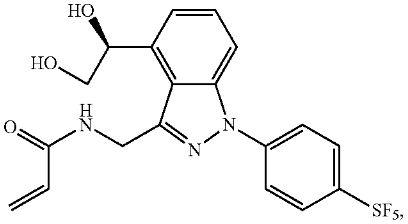

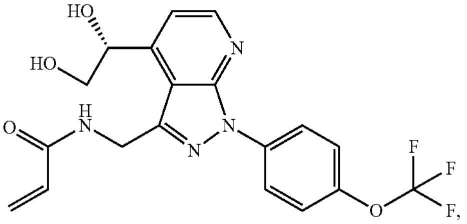

and

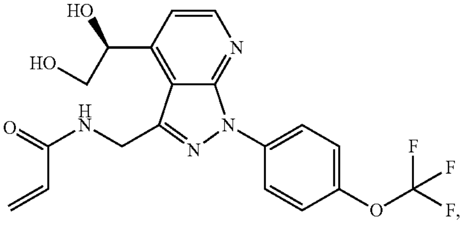

or a pharmaceutically acceptable salt thereof.

Embodiment 22. The compound of any one of embodiments 1 to 3, or a stereoisomer or tautomer thereof, or a pharmaceutically acceptable salt thereof, wherein the compound is a compound of formula (I-A-5) or (I-B-5), (I-A-5)

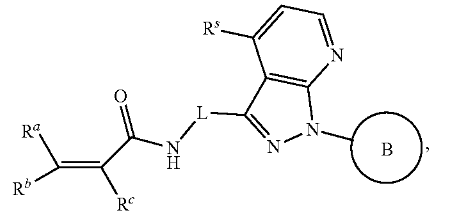

(I-B-5)

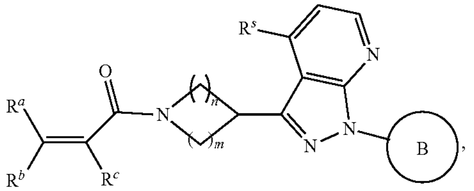

or a stereoisomer or tautomer thereof, or a pharmaceutically acceptable salt thereof.

Embodiment 23. The compound of embodiment 22, or a stereoisomer or tautomer thereof, or a pharmaceutically acceptable salt thereof, wherein the compound is

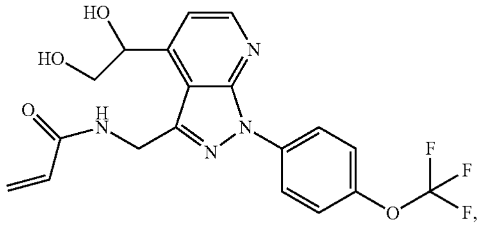 [SMILES: C=CC(=O)NCc1nn(-c2ccc(OC(F)(F)F)cc2)c2nccc(C(O)CO)c12]

or a stereoisomer or tautomer thereof, or a pharmaceutically acceptable salt thereof.

Embodiment 24. The compound of embodiment 23, or a pharmaceutically acceptable salt thereof, wherein the compound is

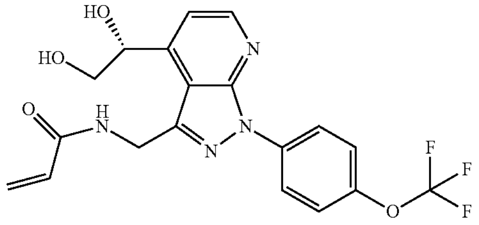

or

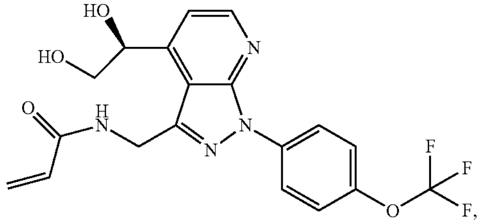

or a pharmaceutically acceptable salt thereof.

Embodiment 25. The compound of any one of embodiments 1 to 3, or a stereoisomer or tautomer thereof, or a pharmaceutically acceptable salt thereof, wherein the compound is a compound of formula (I-A-9) or (I-B-9), (I-A-9)

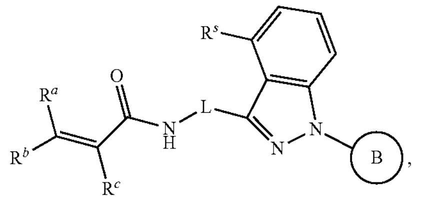

(I-B-9)

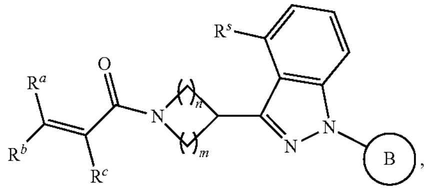

or a stereoisomer or tautomer thereof, or a pharmaceutically acceptable salt thereof.

Embodiment 26. The compound of embodiment 25, or a stereoisomer or tautomer thereof, or a pharmaceutically acceptable salt thereof, wherein the compound is selected from the group consisting of:

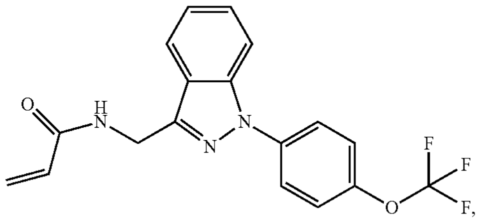

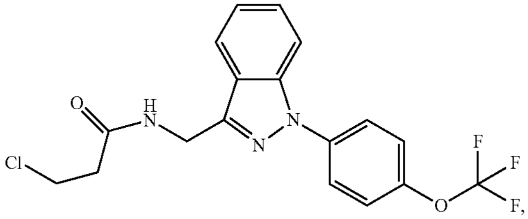

and

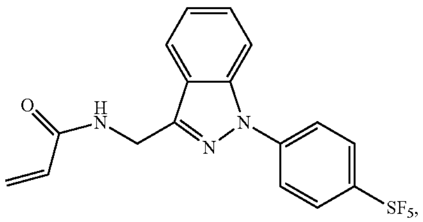

or a stereoisomer or tautomer thereof, or a pharmaceutically acceptable salt thereof.

Embodiment 27. The compound of embodiment 25, or a stereoisomer or tautomer thereof, or a pharmaceutically acceptable salt thereof, wherein $R^s$ is —CN or $C_{1-6}$alkyl optionally substituted with one or more —OH.

Embodiment 28. The compound of embodiment 27, or a stereoisomer or tautomer thereof, or a pharmaceutically acceptable salt thereof, wherein the compound is selected from the group consisting of:

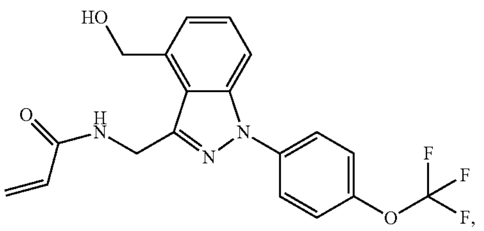

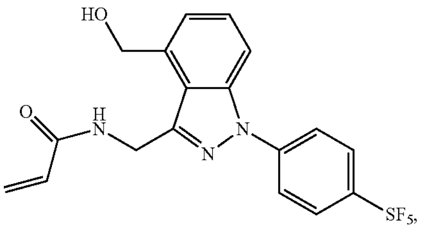

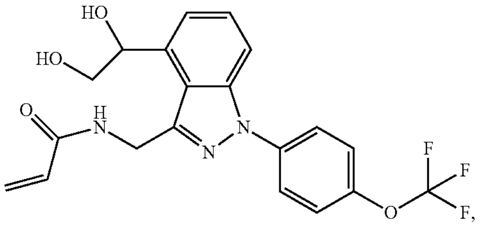

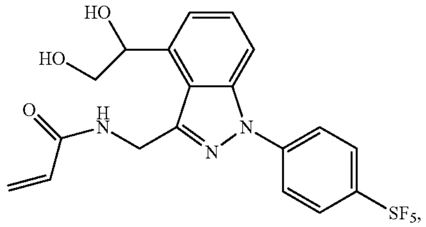

and

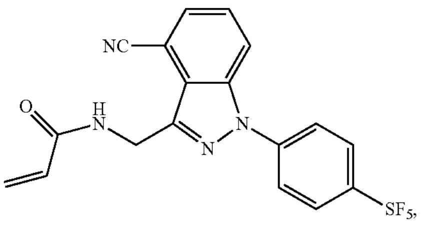

or a stereoisomer or tautomer thereof, or a pharmaceutically acceptable salt thereof.

Embodiment 29. The compound of embodiment 28, or a pharmaceutically acceptable salt thereof, wherein the compound is selected from the group consisting of:

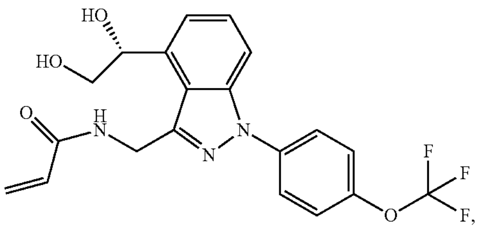

-continued

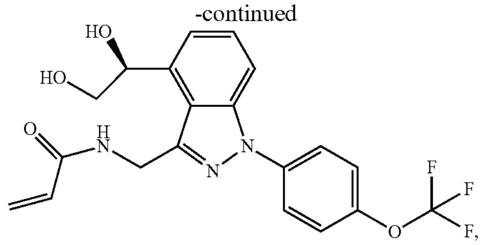

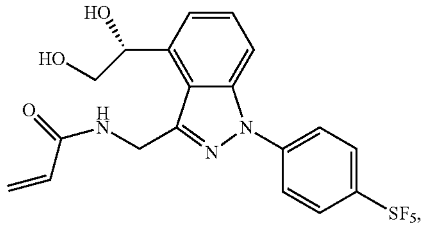

and

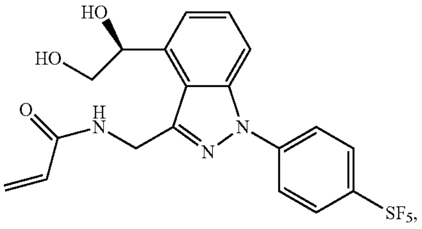

or a pharmaceutically acceptable salt thereof.

Embodiment 30. A pharmaceutical composition, comprising (i) a compound as described in any one of embodiments 1-29, or a stereoisomer, tautomer, or pharmaceutically acceptable salt thereof, and (ii) a pharmaceutically acceptable carrier, diluent, or excipient.

Embodiment 31. A compound as described in any one of embodiments 1-29, or a stereoisomer, tautomer, or pharmaceutically acceptable salt thereof, for use in medical therapy.

Embodiment 32. A compound as described in any one of embodiments 1-29, or a stereoisomer, tautomer, or pharmaceutically acceptable salt thereof, for use in the treatment and/or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 33. A method for treating cancer in a mammal, comprising administering a compound as described in any one of embodiments 1-29, or a stereoisomer, tautomer, or pharmaceutically acceptable salt thereof, to the mammal.

Embodiment 34. A compound as described in any one of embodiments 1-29, or a stereoisomer, tautomer, or pharmaceutically acceptable salt thereof, for use in modulating TEAD activity.

Embodiment 35. A compound as described in any one of embodiments 1-29, or a stereoisomer, tautomer, or pharmaceutically acceptable salt thereof, for use in the treatment and/or prophylaxis of a disease or condition mediated by TEAD activity.

Embodiment 36. The compound for the use of embodiment 35, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 37. The use of a compound as described in any one of embodiments 1-29, or a stereoisomer, tautomer, or pharmaceutically acceptable salt thereof, for the preparation of a medicament for the treatment of prophylaxis of a disease or condition that is mediated by TEAD activity.

Embodiment 38. The use of embodiment 33, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 39. A method for modulating TEAD activity, comprising contacting TEAD with a compound as described in any one of embodiments 1-29, or a stereoisomer, tautomer, or pharmaceutically acceptable salt thereof.

Embodiment 40. A method for treating a disease or condition mediated by TEAD activity in a mammal, comprising administering a compound as described in any one of embodiments 1-29, or a pharmaceutically acceptable salt thereof, to the mammal.

Embodiment 41. The method of embodiment 40, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic)

leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 42. The use of a compound as described in any one of embodiments 1-29, or a stereoisomer, tautomer, or pharmaceutically acceptable salt thereof, for modulating TEAD activity.

Embodiment 43. The use of a compound as described in any one of embodiments 1-29, or a stereoisomer, tautomer, or pharmaceutically acceptable salt thereof, for the treatment and/or prophylaxis of a disease or condition mediated by TEAD activity.

Embodiment 44. The use of embodiment 43, wherein the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 1A. A compound of formula (AB):

(AB)

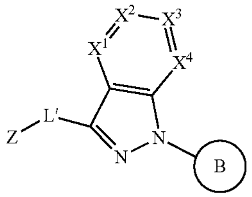

or a stereoisomer or tautomer thereof, or a pharmaceutically acceptable salt thereof, wherein:

L' is selected from the group consisting of *—N($R^1$)-L-** and

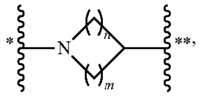

wherein * denotes the point of attachment to Z, and ** denotes the point of attachment to

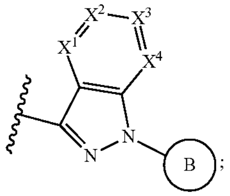

$R^1$ is H or $C_{1-6}$ alkyl;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^dCOR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —CN, —$NR^dR^e$, and 3 to 15 membered heterocyclyl optionally substituted with one or more —OH; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, and $C_{1-6}$alkyl; wherein the $C_{1-6}$alkyl of $R^{t2}$ is optionally substituted with one or more —OH or —$NR^dR^e$; wherein $R^d$ and $R^e$ are each independently H, —$C(O)CH_3$, —$C(O)C_{1-6}$alkyl, or $C_{1-6}$alkyl;

$X^2$, $X^3$, and V are each independently N, CH, or CD, provided that only one of $X^1$, $X^2$, $X^3$, and $X^4$ is N;

B is phenyl or 5 to 6 membered heteroaryl, wherein the phenyl or 5 to 6 membered heteroaryl of B are each independently optionally substituted with one or more $R^t$, wherein $R^t$ is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —$C(O)R^x$, wherein $R^x$ is $C_{2-6}$ alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl;

L is methylene, optionally substituted with one or more $C_{1-6}$alkyl; and n and m are each 1; or n and m are each 2.

Embodiment 2A. A compound of embodiment 1A, or a stereoisomer or tautomer thereof, or a pharmaceutically acceptable salt thereof, wherein the compound is a compound of formula (A):

(A)

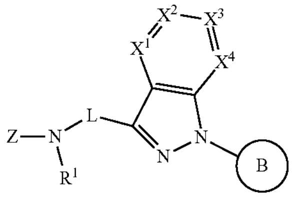

or a stereoisomer or tautomer thereof, or a pharmaceutically acceptable salt thereof.

Embodiment 3A. A compound of embodiment 1A or 2A, or a stereoisomer or tautomer thereof, or a pharmaceutically acceptable salt thereof, wherein the compound is a compound of formula (I-A):

(I-A)

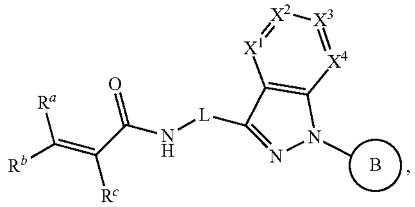

or a stereoisomer or tautomer thereof, or a pharmaceutically acceptable salt thereof, wherein $R^a$, $R^b$, and $R^c$ are each independently H, deuterium, —OH, $C_{1-6}$alkoxyl, halo, or $C_{1-5}$alkyl.

Embodiment 4A. The compound of embodiment 1A or 2A, or a stereoisomer or tautomer thereof, or a pharmaceutically acceptable salt thereof, wherein the compound is a compound of formula (A-1):

(A-1)

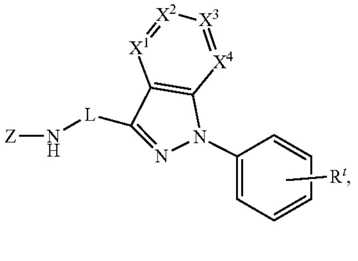

or a stereoisomer or tautomer thereof, or a pharmaceutically acceptable salt thereof.

Embodiment 5A. The compound of any one of embodiments 1A-4A, or a stereoisomer or tautomer thereof, or a pharmaceutically acceptable salt thereof, wherein the compound is a compound of formula (I-A-1):

(I-A-1)

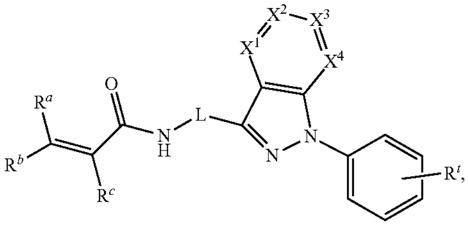

or a stereoisomer or tautomer thereof, or a pharmaceutically acceptable salt thereof, wherein:

$R^a$, $R^b$, and $R^c$ are each independently H, halo, deuterium, —OH, $C_{1-6}$alkoxyl, or $C_{1-5}$alkyl; and $R^t$ is selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo.

Embodiment 6A. The compound of any one of embodiments 1A-3A, or a stereoisomer or tautomer thereof, or a pharmaceutically acceptable salt thereof, wherein the compound is a compound of formula (I-A-5):

(I-A-5)

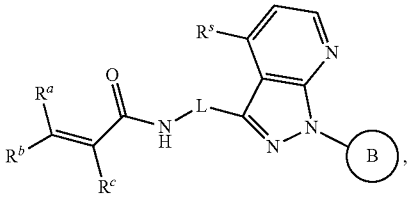

or a stereoisomer or tautomer thereof, or a pharmaceutically acceptable salt thereof.

Embodiment 7A. The compound of any one of embodiments 1A-6A, or a stereoisomer or tautomer thereof, or a pharmaceutically acceptable salt thereof, wherein the compound is a compound of formula (I-A-12):

(I-A-12)

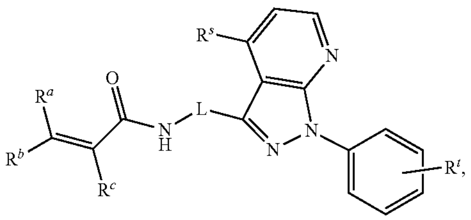

or a stereoisomer or tautomer thereof, or a pharmaceutically acceptable salt thereof.

Embodiment 8A. The compound of any one of embodiments 1A-7A, or a stereoisomer or tautomer thereof, or a pharmaceutically acceptable salt thereof, wherein the compound is a compound of formula (I-A-13):

(I-A-13)

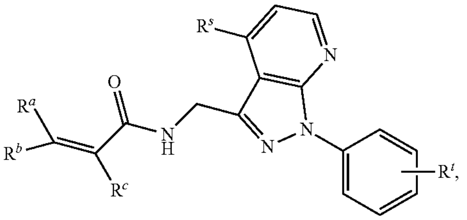

or a stereoisomer or tautomer thereof, or a pharmaceutically acceptable salt thereof.

Embodiment 9A. A compound of embodiment 1A, or a stereoisomer or tautomer thereof, or a pharmaceutically acceptable salt thereof, wherein the compound is a compound of formula (B):

(B)

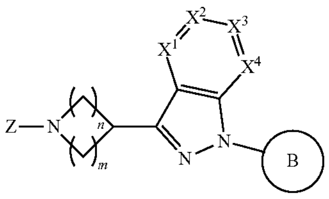

or a stereoisomer or tautomer thereof, or a pharmaceutically acceptable salt thereof.

Embodiment 10A. A compound of embodiment 1A or 9A, or a stereoisomer or tautomer thereof, or a pharmaceutically acceptable salt thereof, wherein the compound is a compound of formula (I-B):

(I-B)

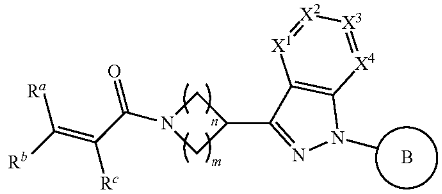

, or a stereoisomer or tautomer thereof, or a pharmaceutically acceptable salt thereof, wherein $R^a$, $R^b$, and $R^c$ are each independently H, deuterium, —OH, $C_{1-6}$alkoxyl, halo, or $C_{1-5}$alkyl.

Embodiment 11A. The compound of embodiment 1A or 9A, or a stereoisomer or tautomer thereof, or a pharmaceutically acceptable salt thereof, wherein the compound is a compound of formula (B-1):

(B-1)

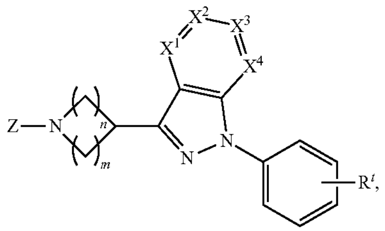

or a stereoisomer or tautomer thereof, or a pharmaceutically acceptable salt thereof.

Embodiment 12A. The compound of any one of embodiments 1A or 9A-11A, or a stereoisomer or tautomer thereof, or a pharmaceutically acceptable salt thereof, wherein the compound is a compound of formula (I-B-1):

(I-B-1)

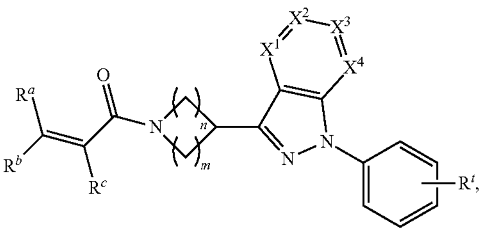

or a stereoisomer or tautomer thereof, or a pharmaceutically acceptable salt thereof, wherein:

$R^a$, $R^b$, and $R^c$ are each independently H, halo, deuterium, —OH, $C_{1-6}$alkoxyl, or $C_{1-5}$alkyl; and $R^t$ is selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo.

Embodiment 13A. The compound of any one of embodiments 1A or 9A-10A, or a stereoisomer or tautomer thereof, or a pharmaceutically acceptable salt thereof, wherein the compound is a compound of formula (I-B-5):

(I-B-5)

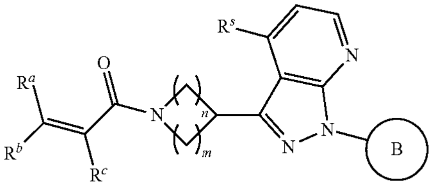

, or a stereoisomer or tautomer thereof, or a pharmaceutically acceptable salt thereof.

Embodiment 14A. The compound of any one of embodiments 1A or 9A-13A, or a stereoisomer or tautomer thereof, or a pharmaceutically acceptable salt thereof, wherein the compound is a compound of formula (X-B):

(I-B-10)

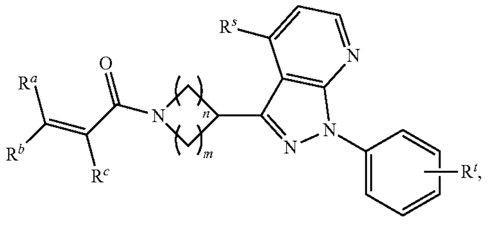

or a stereoisomer or tautomer thereof, or a pharmaceutically acceptable salt thereof.

Embodiment 15A. The compound of embodiment 14A, or a stereoisomer or tautomer thereof, or a pharmaceutically acceptable salt thereof, wherein the compound is a compound of formula (I-B-11):

(I-B-11)

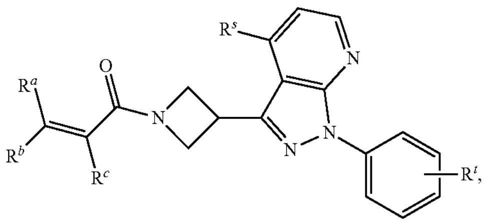

or a stereoisomer or tautomer thereof, or a pharmaceutically acceptable salt thereof.

Embodiment 16A. The compound of any one of embodiments 1A-15A, or a stereoisomer or tautomer thereof, or a pharmaceutically acceptable salt thereof, wherein the $R^t$ of B is —$SF_5$, —O—$CHF_2$, or —O—$CF_3$.

Embodiment 17A. The compound of any one of embodiment 1A-2A, 4A, 9A, or 11A or a stereoisomer or tautomer thereof, or a pharmaceutically acceptable salt thereof, wherein Z is —C(O)$R^x$ and $R^x$ is $C_{1-6}$alkyl optionally substituted with one or more halo.

Embodiment 18A. The compound of any one of embodiment 1A-2A, 4A, 9A, or 11A, or a stereoisomer or tautomer thereof, or a pharmaceutically acceptable salt thereof, wherein $R^x$ is ethyl, optionally substituted with one or more Cl.

Embodiment 19A. The compound of any one of embodiments 1A-15A, or a stereoisomer or tautomer thereof, or a pharmaceutically acceptable salt thereof, wherein two of $R^a$, $R^b$, and $R^c$ are H.

Embodiment 20A. The compound of any one of embodiments 1A-15A, or a stereoisomer or tautomer thereof, or a pharmaceutically acceptable salt thereof, wherein $R^a$, $R^b$, and $R^c$ are each H.

Embodiment 21A. The compound of any one of embodiments 1A-5A or 9A-12A, or a stereoisomer or tautomer thereof, or a pharmaceutically acceptable salt thereof, wherein $X^1$ is $CR^s$; and $X^2$, $X^3$, and $X^4$ are CH.

Embodiment 22A. The compound of any one of embodiments 1A-5A or 9A-12A, or a stereoisomer or tautomer thereof, or a pharmaceutically acceptable salt thereof, wherein $X^1$ is $CR^s$; $X^2$ is N; and $X^3$ and $X^4$ are CH.

Embodiment 23A. The compound of any one of embodiments 1A-5A or 9A-12A, or a stereoisomer or tautomer thereof, or a pharmaceutically acceptable salt thereof, wherein $X^1$ is $CR^s$; $X^3$ is N; and $X^2$ and $X^4$ are CH.

Embodiment 24A. The compound of any one of embodiments 1A-5A or 9A-12A, or a stereoisomer or tautomer thereof, or a pharmaceutically acceptable salt thereof, wherein $X^1$ is $CR^s$; $X^2$ and $X^3$ are CH; and $X^4$ are N.

Embodiment 25A. The compound of any one of embodiments 1A-5A or 9A-12A, or a stereoisomer or tautomer thereof, or a pharmaceutically acceptable salt thereof, wherein $X^1$ is N; and $X^2$, $X^3$, and $X^4$ are each CH.

Embodiment 26A. The compound of any one of embodiments 1A-25A, or a stereoisomer or tautomer thereof, or a pharmaceutically acceptable salt thereof, wherein $R^s$ is H, halo, or —CN.

Embodiment 27A. The compound of any one of embodiments 1A-25A, or a stereoisomer or tautomer thereof, or a pharmaceutically acceptable salt thereof, wherein $R^s$ is —$OR^f$, wherein $R^f$ is $C_{3-20}$cycloalkyl optionally substituted with one or more —OH.

Embodiment 28A. The compound of any one of embodiments 1A-25A, or a stereoisomer or tautomer thereof, or a pharmaceutically acceptable salt thereof, wherein $R^s$ is $C_{1-15}$alkyl or $C_{1-15}$alkoxy, wherein the $C_{1-15}$alkyl or $C_{1-15}$alkoxy of $R^s$ are each independently optionally substituted with one or more $R^{t1}$, wherein $R^{t1}$ is independently, at each occurrence, selected from halo, oxo, —OH, —CN, —$NR^dR^e$, and 3 to 15 membered heterocyclyl optionally substituted with one or more —OH; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN.

Embodiment 29A. The compound of any one of embodiments 1A-25A, or a stereoisomer or tautomer thereof, or a pharmaceutically acceptable salt thereof, wherein $R^s$ is —$NR^dR^e$, wherein $R^d$ and $R^e$ are each independently selected from the group consisting of H, $C_{1-6}$alkyl, $C_{3-20}$cycloalkyl, —C(O)$R^t$, wherein $R^t$ is $C_{1-6}$alkyl, wherein each of $C_{1-6}$alkyl, $C_{3-20}$cycloalkyl are optionally substituted with one or more —OH.

Embodiment 30A. The compound of any one of embodiments 1A-25A, or a stereoisomer or tautomer thereof, or a pharmaceutically acceptable salt thereof, wherein $R^s$ is —C(O)$NR^dR^e$, wherein $R^d$ and $R^e$ are each independently selected from the group consisting of H and $C_{1-6}$alkyl, wherein $C_{1-6}$alkyl is optionally substituted with one or more —OH.

Embodiment 31A. The compound of any one of embodiments 1A-25A, or a stereoisomer or tautomer thereof, or a pharmaceutically acceptable salt thereof, wherein $R^s$ is $C_{1-6}$alkyl optionally substituted with one or more —OH.

Embodiment 32A. The compound of any one of embodiments 1A-25A or a stereoisomer or tautomer thereof, or a pharmaceutically acceptable salt thereof, wherein $R^s$ is $C_{1-2}$ alkyl substituted with one or more —OH.

Embodiment 33A. The compound of any one of embodiments 1A-25A or a stereoisomer or tautomer thereof, or a pharmaceutically acceptable salt thereof, wherein $R^s$ is selected from the group consisting of

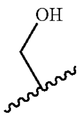
and
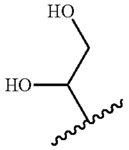
.

Embodiment 34A. The compound of any one of embodiments 1A-25A, or a stereoisomer or tautomer thereof, or a pharmaceutically acceptable salt thereof, wherein $R^s$ is $C_{6-20}$aryl, 5 to 15 membered heteroaryl, $C_{3-20}$cycloalkyl, or 3 to 15 membered heterocyclyl, wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$NR^dR^e$, —$C(O)NR^dR^e$, $C_{1-6}$alkoxyl, and $C_{1-6}$alkyl; wherein the $C_{1-6}$alkyl of $R^e$ is optionally substituted with one or more —OH or —$NR^dR^e$; wherein $R^d$ and $R^e$ are each independently H, —$C(O)C_{1-6}$alkyl, or $C_{1-6}$alkyl.

Embodiment 35A. A pharmaceutical composition, comprising (i) a compound as described in any one of embodiments 1A-34A, or a stereoisomer, tautomer, or pharmaceutically acceptable salt thereof, and (ii) a pharmaceutically acceptable carrier, diluent, or excipient.

Embodiment 36A. A compound as described in any one of embodiments 1A-34A, or a stereoisomer, tautomer, or pharmaceutically acceptable salt thereof, for use in medical therapy.

Embodiment 37A. A compound as described in any one of embodiments 1A-34A, or a stereoisomer, tautomer, or pharmaceutically acceptable salt thereof, for use in the treatment and/or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 38A. A compound as described in any one of embodiments 1A-34A, or a stereoisomer, tautomer, or pharmaceutically acceptable salt thereof, for use in modulating TEAD activity.

Embodiment 39A. A compound as described in any one of embodiments 1A-34A, or a stereoisomer, tautomer, or pharmaceutically acceptable salt thereof, for use in the treatment and/or prophylaxis of a disease or condition mediated by TEAD activity.

Embodiment 40A. The compound for the use of embodiment 39A, wherein the disease or condition mediated by TEAD activity is cancer.

Embodiment 41A. The use of a compound as described in any one of embodiments 1A-34A, or a stereoisomer, tautomer, or pharmaceutically acceptable salt thereof, for the preparation of a medicament for the treatment of prophylaxis of a disease or condition that is mediated by TEAD activity.

Embodiment 42A. The use of embodiment 41A, wherein the disease or condition mediated by TEAD activity is cancer.

Embodiment 43A. A method for treating cancer in a mammal, comprising administering a compound as described in any one of embodiments 1A-34A, or a stereoisomer, tautomer, or pharmaceutically acceptable salt thereof, to the mammal.

Embodiment 44A. A method for modulating TEAD activity, comprising contacting TEAD with a compound as described in any one of embodiments 1A-34A, or a stereoisomer, tautomer, or pharmaceutically acceptable salt thereof.

Embodiment 45A. A method for treating a disease or condition mediated by TEAD activity in a mammal, comprising administering a compound as described in any one of embodiments 1A-34A, or a pharmaceutically acceptable salt thereof, to the mammal.

Embodiment 46A. The use of a compound as described in any one of embodiments 1A-34A, or a stereoisomer, tautomer, or pharmaceutically acceptable salt thereof, for modulating TEAD activity.

Embodiment 47A. The use of a compound as described in any one of embodiments 1A-34A, or a stereoisomer, tautomer, or pharmaceutically acceptable salt thereof, for the treatment and/or prophylaxis of a disease or condition mediated by TEAD activity.

Embodiment 48A. The use of embodiment 47A, wherein the disease or condition mediated by TEAD activity is cancer.

Preparation of Compounds

The following synthetic reaction schemes detailed in the General Schemes and Examples are merely illustrative of some of the methods by which the compounds of the present disclosure (or an embodiment or aspect thereof) can be synthesized. Various modifications to these synthetic reaction schemes can be made and will be suggested to one skilled in the art having referred to the disclosure contained in this Application.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C.

Although certain exemplary embodiments are depicted and described herein, the compounds of the present disclosure (or an embodiment or aspect thereof) can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography, and/or by Preparative Thin Layer Chromatography (Prep TLC).

Mass spectrometry (MS) was performed using a (1) Sciex 15 mass spectrometer in ES+ mode, or (2) Shimadzu liquid chromatography-mass spectrometry (LCMS) 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) was performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

The following generalized schemes are used to prepare the disclosed compounds, intermediates, and pharmaceutically acceptable salts thereof. Disclosed compounds and intermediates may be prepared using standard organic synthetic techniques and from comerically available starting materials and reagents. It will be appreciated that synthetic procedures employed in the preparation of disclosed compounds and intermediates will depend on the particular substituents present in the compound or intermediate and that various protection, deprotection, and conversion steps that are standard in organic synthesis may be required, but may not be illustrated in the following general schemes. It is also to be understood that any of the steps shown in any of the following general schemes may be used in any combination and in any order that is chemically feasible to achieve a desired intermediate or disclosed compound.

Synthetic Procedures

General Procedure a for Chan-Lam Coupling:

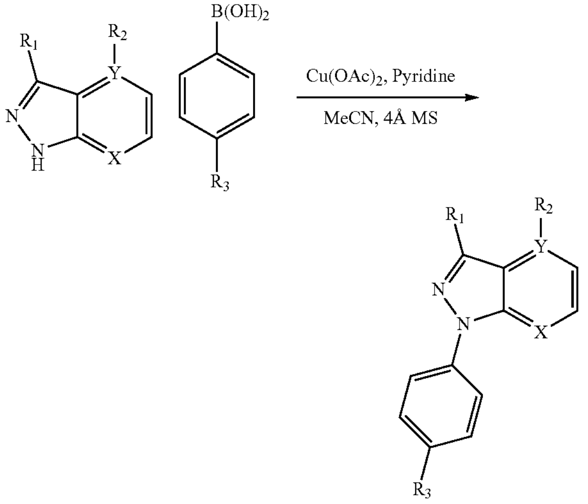

A flask containing the N-heterocycle (1 equiv.) was charged with Copper(II) Acetate (1.5 equiv.), aryl boronic acid (1.5-3 equiv.), activated 4 Å mol sieves and acetonitrile, followed by pyridine (4 equiv.). The reaction was stirred at room temp or 50° C. exposed to the ambient atmosphere until the starting material was consumed as indicated by LC-MS analysis. At which time the reaction mixture was filtered. The filtrate was diluted with iPrOAc and washed with sat. aq. NaHCO3, 0.5M aq. $NH_4OH$, and brine. The aqueous layer was back extracted with DCM, the organic layers were combined, dried over $Na_2SO_4$, filtered, and concentrated. Purification via column chromatography (0 to 100% iPrOAc/heptane) gives the desired product.

General Procedure 1 for Chan-Lam Coupling:

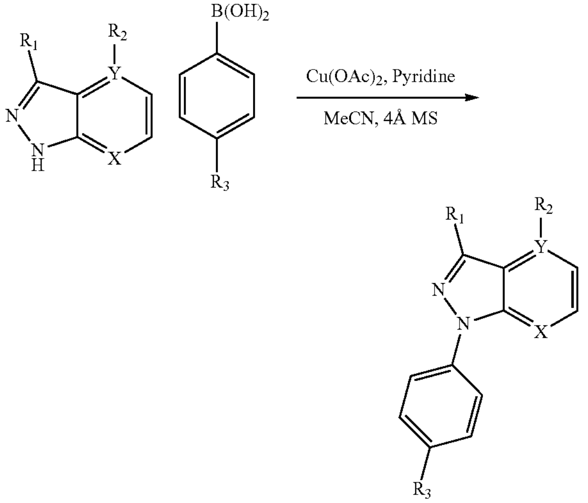

A flask containing the N-heterocycle (1 equiv.) was charged with copper(II) acetate (1.5 equiv.), aryl boronic acid (1.5-3 equiv.), activated 4A mol sieves and acetonitrile, followed by pyridine (4 equiv.). The reaction was stirred at room temp or 50° C. exposed to the ambient atmosphere until the starting material was consumed as indicated by LC-MS analysis, at which time the reaction mixture was filtered. The filtrate was diluted with iPrOAc and washed with sat. aq. $NaHCO_3$, 1M EDTA (tetrasodium salt) solution (aq.), and brine. The aqueous layer was back extracted with DCM, the organic layers were combined, dried over $Na_2SO_4$, filtered, and concentrated. Purification via column chromatography (0 to 100% iPrOAc/heptane) gives the desired product.

General Procedure 2 for Telescoped Nitrile Reduction, Acetonide Deprotection, and Acylation:

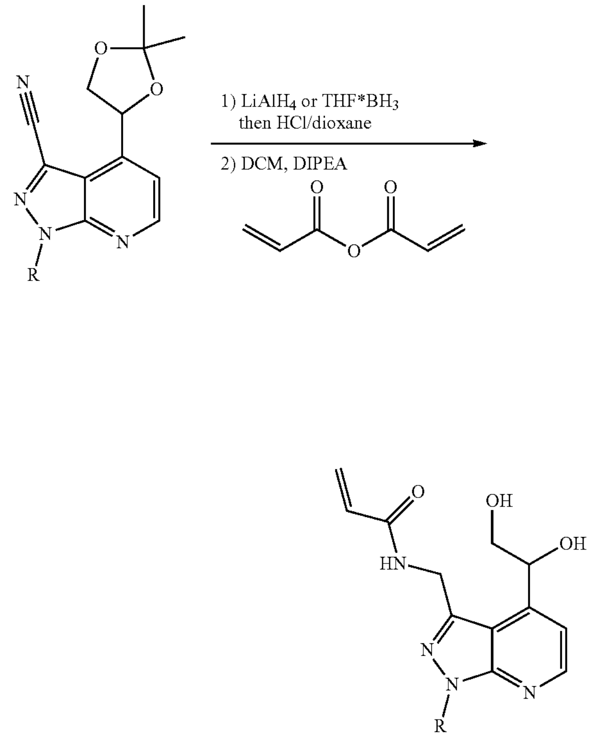

In an 8 mL vial equipped with a stir bar prepare either a suspension lithium aluminum hydride (4.0 equiv.) in THF (1 mL) or a solution of borane (4.0 equiv., 1M soln.) in THF and cool to 0° C. Then add a solution of the indicated nitrile (1.0 equiv.) in THF (2 mL). Stir at 0° C. for 30 minutes, then allow to warm to room temperature. Stir until complete consumption of the starting materials is confirmed by LCMS analysis. Quench the reaction with methanol, then follow one of the protocols below.

- if using LAH: add sat. aq. Rochelle's salt solution and stir until precipitation occurs. Dilute the mixture with iPrOAc and filter the mixture through celite, washing the filter with copious DCM. Concentrate the filtrate directly, then suspend in DCM (10 mL) and add HCl in 1,4-dioxane (4 M, 1-2 mL). Stir until complete deprotection of the acetonide is observed by LCMS, then concentrate the mixture. Take up the crude amine in DCM (10 mL) and add DIPEA (5.0 equiv.). Cool the solution to −40° C., then add a solution of acrylic anhydride (1.0 equiv.) in DCM (2 mL) slowly dropwise. Stir at this temperature until complete conversion of the amine is observed by LCMS.
- if using borane: Following the methanol quench, add HCl in 1,4-dioxane (4 M, 1-2 mL) to the reaction mixture. Stir until complete deprotection of the acetonide is observed by LCMS, then concentrate the mixture. Take up the crude amine in DCM (10 mL) and add DIPEA (5.0 equiv.). Cool the solution to −40° C., then add a solution of acrylic anhydride (1.0 equiv.) in DCM (2 mL) slowly dropwise. Stir at this temperature until complete conversion of the amine is observed by LCMS.

Purification and subsequent separation of the enantiomers via chiral SFC as described gives the desired compounds.

General Procedure 3 for HATU Coupling:

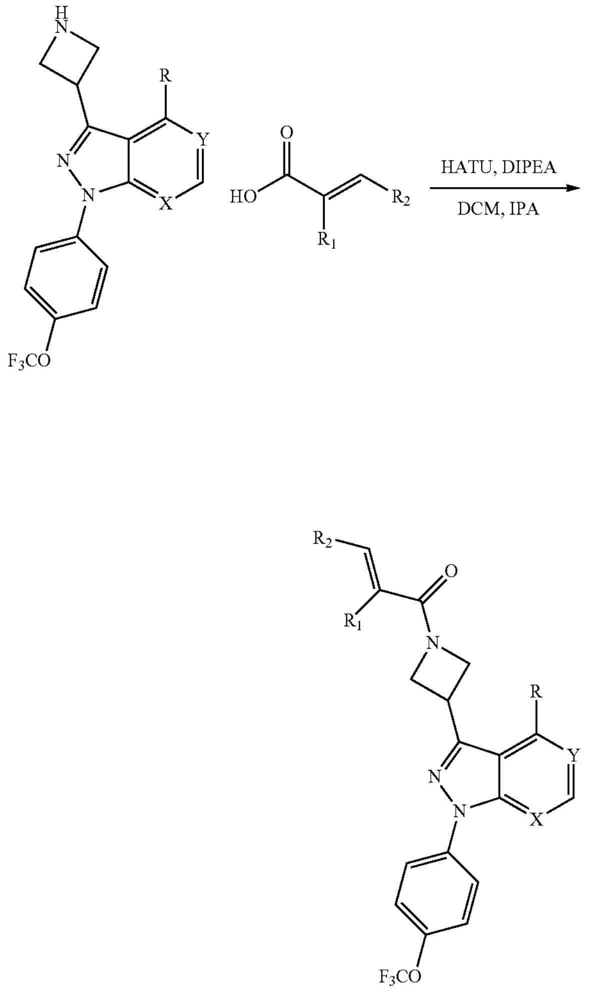

In an 8 mL vial equipped with a stir bar, suspend the indicated carboxylic acid (1.1 equiv.) and HATU (1.1 equiv.) in dichloromethane (2 mL), and add N,N-diisopropylethylamine (2.1 equiv.). Then take up the indicated amine (1.0 equiv.) in dichloromethane (2 mL) and 2-propanol (1 mL), and then add this solution to the solution of activated acid and stir the reaction at room temperature for 1 hour. On completion, as determined by LCMS analysis, the reaction mixture was diluted with iPrOAc and washed once with sat. aq. $NH_4Cl$ and once with sat. aq. $NaHCO_3$. The organic layer was dried over $Na_2SO_4$, filtered, and concentrated. Purification as indicated gives the desired compound.

General Procedure 4:

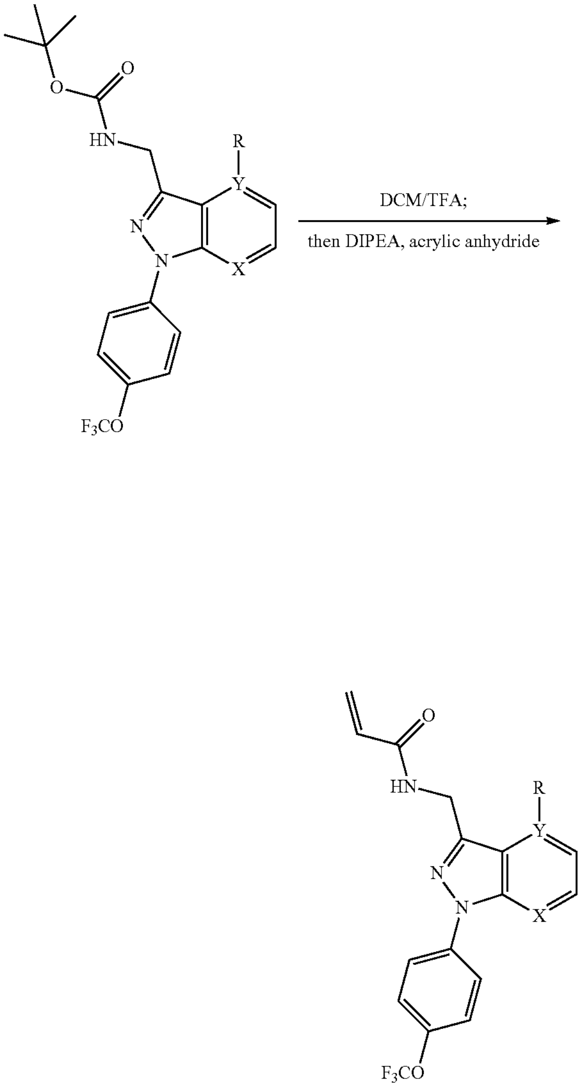

To a vial equipped with a stir bar add the appropriate Boc-protected amine (1.00 equiv.), DCM (5 mL) and TFA (1 mL). Stir the mixture until complete consumption of the starting material is confirmed by LC-MS analysis. At this time, quench the reaction mixture with saturated $NaHCO_3$ (aq) and dilute with iPrOAc. Add 1 M NaOH (aq) until pH 12 is reached, then wash the mixture three times with brine. Dry the organic fraction over $MgSO_4$, filter, and concentrate. The obtained crude amine is then taken up in DCM (5 mL) and cooled to −40° C. while stirring with a stir bar. To this solution is added DIPEA (1.1 equiv.) in one portion and a solution of acrylic anhydride (1.1 equiv.) in DCM (1 mL) slowly drop-wise. Stir at this temperature until complete consumption of the amine is confirmed by LCMS analysis. On completion, concentrate the mixture directly. Column chromatography (0 to 10% MeOH in DCM) gives the desired compound.

Preparation of Common Intermediates

Intermediate A

4-Chloro-3-iodo-1-(4-(trifluoromethoxy)phenyl)-1H-pyrazolo[3,4-b]pyridine

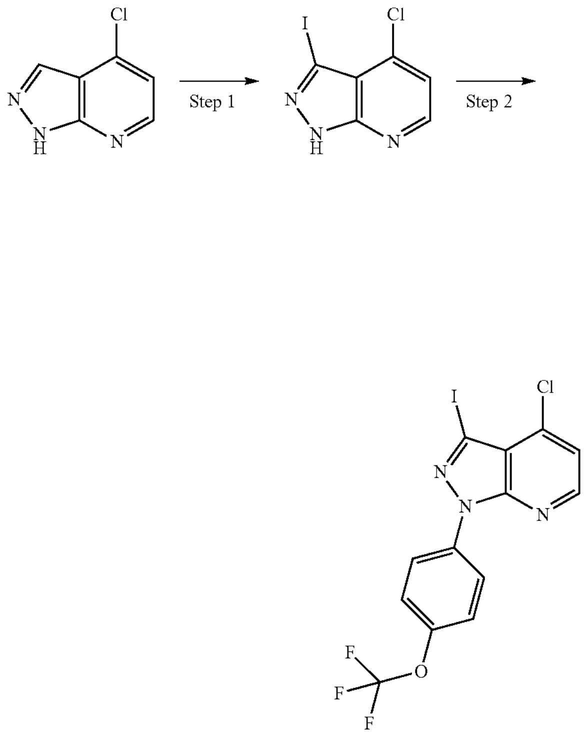

Intermediate A

Step 1: 4-chloro-3-iodo-1H-pyrazolo[3,4-b]pyridine

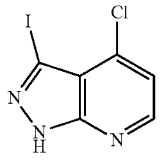 [SMILES: Clc1ccnc2[nH]nc(I)c12]

To a mixture of 4-chloro-1H-pyrazolo[3,4-b]pyridine (9.5 g, 61.9 mmol) and KOH (10.4 g, 185.6 mmol) in DMF (95 mL) was added $I_2$ (28.3 g, 111.4 mmol) at room temperature, the resulting mixture was stirred at 50° C. for 15 h under atmosphere. The mixture was diluted with water (300 mL) and extracted with ethyl acetate (500 mL×3). The organics were combined and washed with brine (500 mL×5), dried over sodium sulfate and concentrated in vacuo to afford the title compound (15.0 g, 87%) as a yellow solid. $^1H$ NMR (400 MHz, DMSO-$d_6$): δ 8.48 (d, J=5.2 Hz, 1H), 7.34 (d, J=5.2 Hz, 1H); LCMS (ESI): m/z 280.0 $(M+H)^+$.

Step 2: 4-chloro-3-iodo-1-(4-(trifluoromethoxy) phenyl)-1H-pyrazolo[3,4-b]pyridine

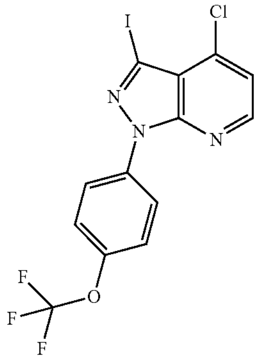 [SMILES: FC(F)(F)Oc1ccc(-n2nc(I)c3c(Cl)ccnc32)cc1]

A mixture of 4-chloro-3-iodo-1H-pyrazolo[3,4-b]pyridine (2.0 g, 7.2 mmol), Cu(OAc$_2$ (2.0 g, 10.7 mmol), (4-(trifluoromethoxy)phenyl)boronic acid (2.2 g, 10.7 mmol), pyridine (2.3 mL, 28.6 mmol) in MeCN (40 mL) under $O_2$ (15 psi) was stirred at room temperature for 16 h. The reaction mixture was filtered, the filtrate was diluted with water (100 mL) and extracted with DCM (100 mL×3). The combined organics were washed with brine (50 mL×2), dried over sodium sulfate and concentrated. The residue was purified by flash chromatography on silica gel (0-1% ethyl acetate in petroleum ether) to afford the title compound (2.55 g, 81%) as a white solid. $^1$H NMR (400 MHz, DMSO-d$_6$): δ 8.61 (d, J=5.2 Hz, 1H), 8.24 (d, J=8.4 Hz, 2H), 7.58 (d, J=8.4 Hz, 2H), 7.52 (d, J=5.2 Hz, 1H); LCMS (ESI): m/z 439.9 (M+H)$^+$.

Intermediate B tert-Butyl ((4-chloro-1-(4-(trifluoromethoxy)phenyl)-1H-pyrazolo[3,4-b]pyridin-3-yl)methyl)carbamate

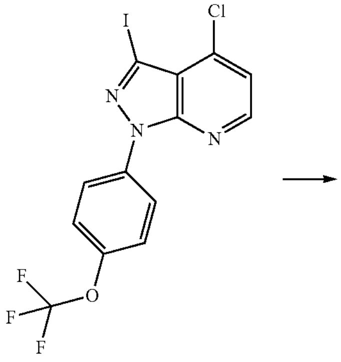

Intermediate A

-continued

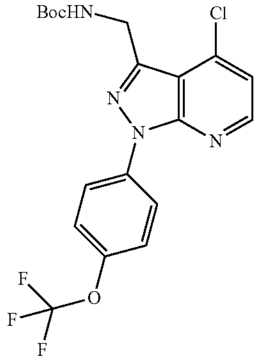

Intermediate B

A mixture of 4-chloro-3-iodo-1-(4-(trifluoromethoxy) phenyl)-1H-pyrazolo[3,4-b]pyridine (2.55 g, 5.8 mmol), CATACXIUM A Pd $G_2$ (526 mg, 0.8 mmol), potassium (((tert-butoxycarbonyl)amino)methyl)trifluoroborate (1.68 g, 7.0 mmol) and $Cs_2CO_3$ (5.7 g, 17.4 mmol) at room temperature in toluene (20 mL) and $H_2O$ (2 mL) was purged with $N_2$ for 3 min. The mixture was heated to 100° C. for 4 h under $N_2$ atmosphere. The mixture was quenched with water (50 mL) and extracted with ethyl acetate (50 mL×3), the combined organic layers were washed with brine (50 mL), dried over $Na_2SO_4$ and concentrated in vacuo. The residue was purified by flash chromatography on silica gel (0-10% ethyl acetate in petroleum ether) to afford the title compound (1.15 g, 44%) as a white solid. $^1$H NMR (400 MHz, DMSO-d$_6$): δ 8.62 (d, J=5.2 Hz, 1H), 8.35 (d, J=8.8 Hz, 2H), 7.62 (d, J=8.8 Hz, 2H), 7.54 (d, J=5.2 Hz, 1H), 7.40 (t, J=5.2 Hz, 1H), 4.70 (d, J=5.2 Hz, 2H), 1.42 (s, 9H).

Intermediate C tert-Butyl ((1-(4-(trifluoromethoxy)phenyl)-4-vinyl-1H-pyrazolo[3,4-b]pyridin-3-yl)methyl)carbamate

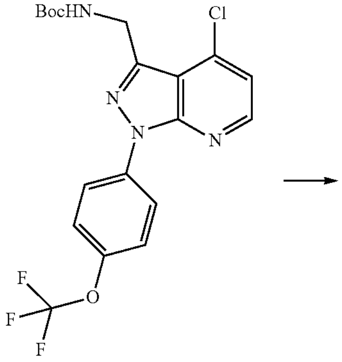

Intermediate B

-continued

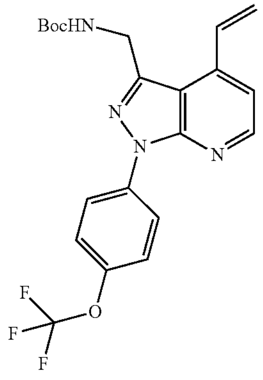

Intermediate C

A mixture of Xphos (65 mg, 0.14 mmol), Xphos Pd $G_2$ (107 mg, 0.14 mmol), KOAc (400 mg, 4.1 mmol), tert-butyl ((4-chloro-1-(4-(trifluoromethoxy)phenyl)-1H-pyrazolo[3,4-b]pyridin-3-yl)methyl)carbamate (600 mg, 1.4 mmol) and 4,4,5,5-tetramethyl-2-vinyl-1,3,2-dioxaborolane (417 mg, 2.7 mmol) in 1,4-dioxane (10 mL) and $H_2O$ (1 mL) was stirred at 100° C. for 2 h under N2 atmosphere. The mixture was diluted with water (50 mL) and extracted with ethyl acetate (50 mL×3). The combined organic layers were washed with brine (50 mL×3), dried over anhydrous sodium sulfate and concentrated under vacuum. The residue was purified by flash chromatography on silica gel (0-8% ethyl acetate in petroleum ether) to afford the title compound (440 mg, 75%) as a yellow solid. $^1H$ NMR (400 MHz, DMSO-$d_6$): δ 8.62 (d, J=4.8 Hz, 1H), 8.40 (d, J=9.2 Hz, 2H), 7.62-7.57 (m, 3H), 7.50-7.42 (m, 1H), 7.32 (dd, J=17.2, 11.2 Hz, 1H), 6.27 (d, J=17.2 Hz, 1H), 5.70 (d, J=11.2 Hz, 1H), 4.65 (d, J=5.2 Hz, 2H), 1.41 (s, 9H); LCMS (ESI): m/z 435.1 $(M+H)^+$.

Intermediate D

1-(3-(Aminomethyl)-1-(4-(trifluoromethoxy)phenyl)-1H-pyrazolo[3,4-b]pyridin-4-yl)ethane-1,2-diol

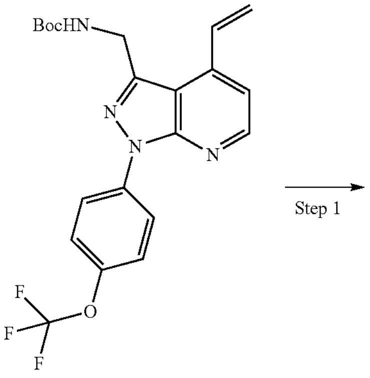

Intermediate C

-continued

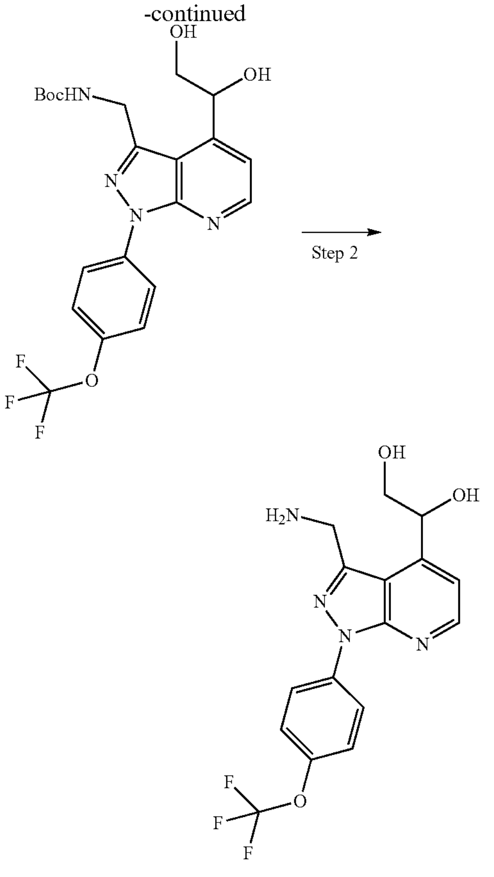

Intermediate D

Step 1: tert-butyl 04-(1,2-dihydroxyethyl)-1-(4-(trifluoromethoxy)phenyl)-1H-pyrazolo[3,4-b]pyridin-3-yl)methyl)carbamate

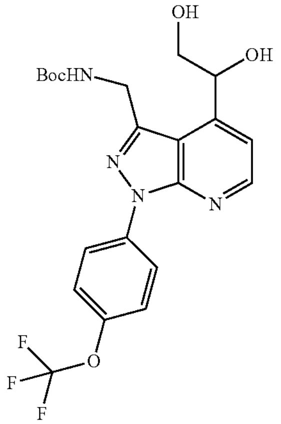 [SMILES: CC(C)(C)OC(=O)NCc1nn(-c2ccc(OC(F)(F)F)cc2)c2nccc(C(O)CO)c12]

To a solution of $K_2OsO_4·2H_2O$ (47.0 mg, 0.13 mmol) and tert-butyl 41-(4-(trifluoromethoxy)phenyl)-4-vinyl-1H-pyrazolo[3,4-b]pyridin-3-yl)methyl)carbamate (550 mg, 1.3 mmol) in THF (9 mL) and $H_2O$ (3 mL) was added NMO (740 mg, 6.3 mmol) at 0° C. The resulting mixture was stirred at room temperature for 16 h. The mixture was diluted with water (50 mL) and extracted with ethyl acetate (50 mL×3). The combined organic layers were washed with saturated $Na_2SO_3$ (50 mL), dried over anhydrous sodium sulfate and concentrated under vacuum. The residue was purified by flash chromatography on silica gel (0-50% ethyl acetate in petroleum ether) to afford the title compound (440 mg, 74%) as a yellow solid. $^1$H NMR (400 MHz, DMSO-$d_6$): δ 8.61 (d, J=4.8 Hz, 1H), 8.39 (d, J=8.8 Hz, 2H), 7.58 (d, J=8.4 Hz, 2H), 7.43 (d, J=4.8 Hz, 1H), 7.37 (t, J=4.8 Hz, 1H), 5.81 (d, J=4.4 Hz, 1H), 5.16-5.13 (m, 1H), 5.00 (t, J=5.6 Hz, 1H), 4.75-4.59 (m, 2H), 3.64-3.53 (m, 2H), 1.41 (s, 9H); LCMS (ESI): m/z 469.2 $(M+H)^+$.

Step 2: 1-(3-(aminomethyl)-1-(4-(trifluoromethoxy) phenyl)-1H-pyrazolo[3,4-b]pyridin-4-yl)ethane-1,2-diol

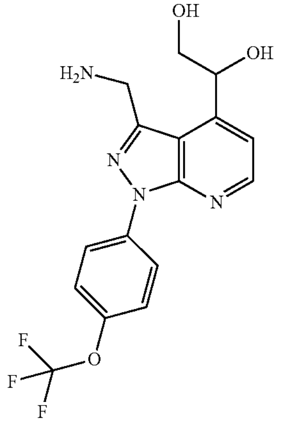 [SMILES: NCc1nn(-c2ccc(OC(F)(F)F)cc2)c2nccc(C(O)CO)c12]

To a mixture of tert-butyl ((4-(1,2-dihydroxyethyl)-1-(4-(trifluoromethoxy)phenyl)-1H-pyrazolo[3,4-b]pyridin-3-yl) methyl)carbamate (440 mg, 0.9 mmol) in DCM (5 mL) was added TFA (0.8 mL, 10.4 mmol) slowly at 0° C. The mixture was stirred at 0° C. for 2 h under nitrogen atmosphere. The reaction was quenched by water (40 mL). The reaction mixture was adjusted to pH=7 with sat. $NaHCO_3$. The resulting mixture was extracted with ethyl acetate (100 mL). The organic was washed with brine (100 mL), dried over anhydrous sodium sulfate and concentrated under reduced pressure to afford the title compound (200 mg, 58%) as a white solid. The crude product would be directly used for the next step without purification. $^1$H NMR (400 MHz, DMSO-$d_6$): δ 8.63 (d, J=4.8 Hz, 1H), 8.42 (d, J=8.8 Hz, 2H), 7.58 (d, J=8.8 Hz, 2H), 7.42 (d, J=4.8 Hz, 1H), 5.33 (t, J=6.4 Hz, 1H), 4.21 (s, 2H), 3.76-3.56 (m, 2H); LCMS (ESI): m/z 369.1 $(M+H)^+$.

Intermediate E

1-(4-(Trifluoromethoxy)phenyl)-4-vinyl-1H-pyrazolo[3,4-b]pyridine-3-carbonitrile

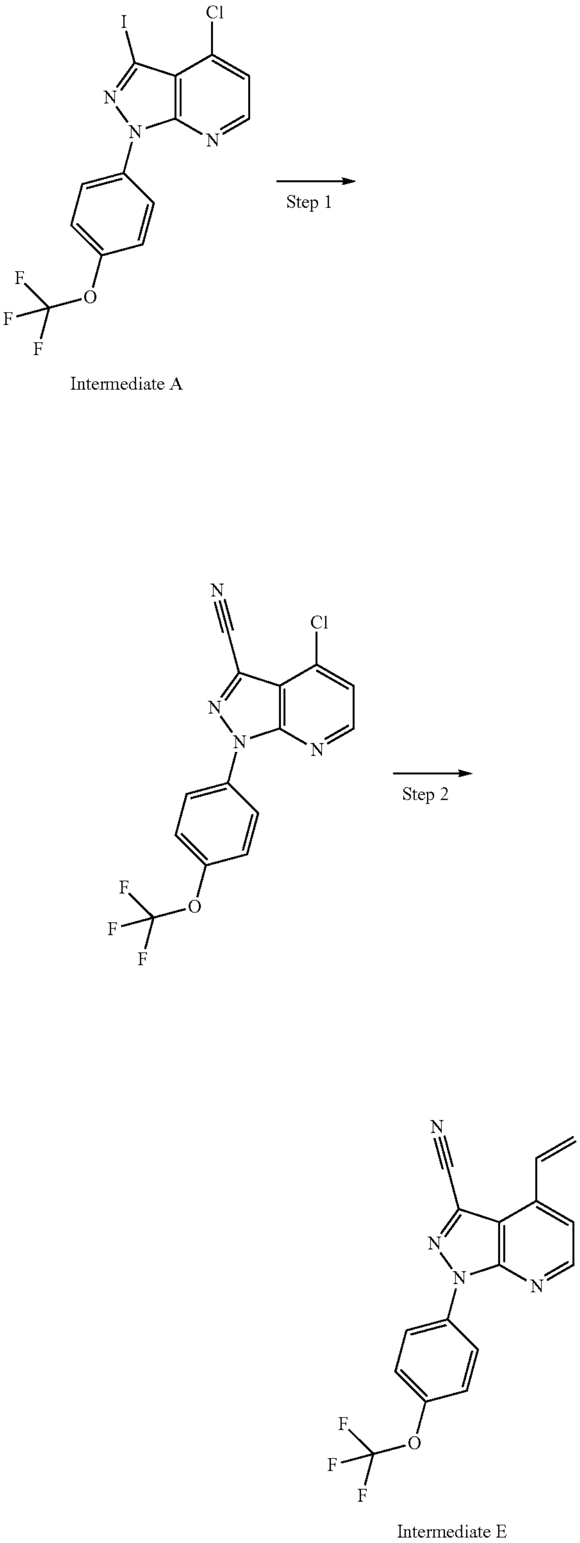

Step 1: 4-chloro-1-(4-(trifluoromethoxy)phenyl)-1H-pyrazolo[3,4-b]pyridine-3-carbonitrile

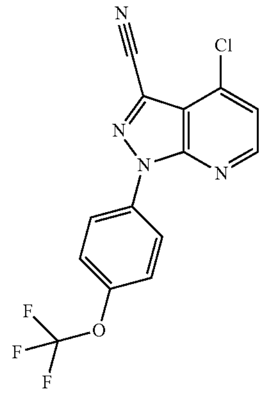 [SMILES: N#Cc1nn(-c2ccc(OC(F)(F)F)cc2)c2nccc(Cl)c12]

To a solution of 4-chloro-3-iodo-1-(4-(trifluoromethoxy)phenyl)-1H-pyrazolo[3,4-b]pyridine (5.0 g, 11.38 mmol) in DMF (25 mL) was added CuCN (1.1 g, 11.94 mmol). The mixture was stirred at 160° C. for 5 h. The reaction mixture was diluted with ethyl acetate (100 mL), washed with brine (100 mL×3), dried over $Na_2SO_4$ and concentrated to dryness. The residue was purified by flash column chromatography on silica gel (0-10% ethyl acetate in petroleum ether) to afford the title compound (3.08 g, 82%) as a white solid. $^1$H NMR (400 MHz, DMSO-$d_6$): δ 8.79 (d, J=5.2 Hz, 1H), 8.29 (d, J=8.8 Hz, 2H), 7.81 (d, J=5.2 Hz, 1H), 7.67 (d, J=8.8 Hz, 2H); LCMS (ESI): m/z 339.0 $(M+H)^+$.

Step 2: 1-(4-(trifluoromethoxy)phenyl)-4-vinyl-1H-pyrazolo[3,4-b]pyridine-3-carbonitrile

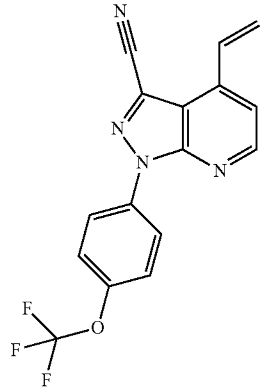 [SMILES: C=Cc1ccnc2c1c(C#N)nn2-c1ccc(OC(F)(F)F)cc1]

To a solution of 4-chloro-1-(4-(trifluoromethoxy)phenyl)-1H-pyrazolo[3,4-b]pyridine-3-carbonitrile (3.0 g, 8.86 mmol) and KOAc (1.7 g, 17.72 mmol) in 1,4-dioxane (30 mL) and water (3 mL) was added 4,4,5,5-tetramethyl-2-vinyl-1,3,2-dioxaborolane (1.8 g, 11.51 mmol), Xphos Pd $G_2$ (0.7 g, 0.88 mmol) and Xphos (0.4 g, 0.88 mmol) at room temperature. The mixture was stirred at 100° C. for 5 h under $N_2$ atmosphere. The reaction mixture was diluted with ethyl acetate (100 mL), washed with brine (90 mL×3), dried over $Na_2SO_4$ and concentrated to dryness. The residue was purified by flash column chromatography on silica gel (0-10% ethyl acetate in petroleum ether) to afford the title compound (1.8 g, 61%) as a white solid. $^1$H NMR (400 MHz, $CDCl_3$): 8.69 (d, J=4.8 Hz, 1H), 8.35 (d, J=8.4 Hz, 2H), 7.55 (dd, J=17.2, 10.8 Hz, 1H), 7.52 (d, J=4.8 Hz, 1H), 7.43 (d, J=8.4 Hz, 2H), 6.26 (d, J=17.6 Hz, 1H), 5.88 (d, J=10.8 Hz, 1H); LCMS (ESI): m/z 330.9 $(M+H)^+$.

Intermediate F (3-(Aminomethyl)-1-(4-(trifluoromethoxy)phenyl)-1H-pyrazolo[3,4-b]pyridin-4-yl)methanol

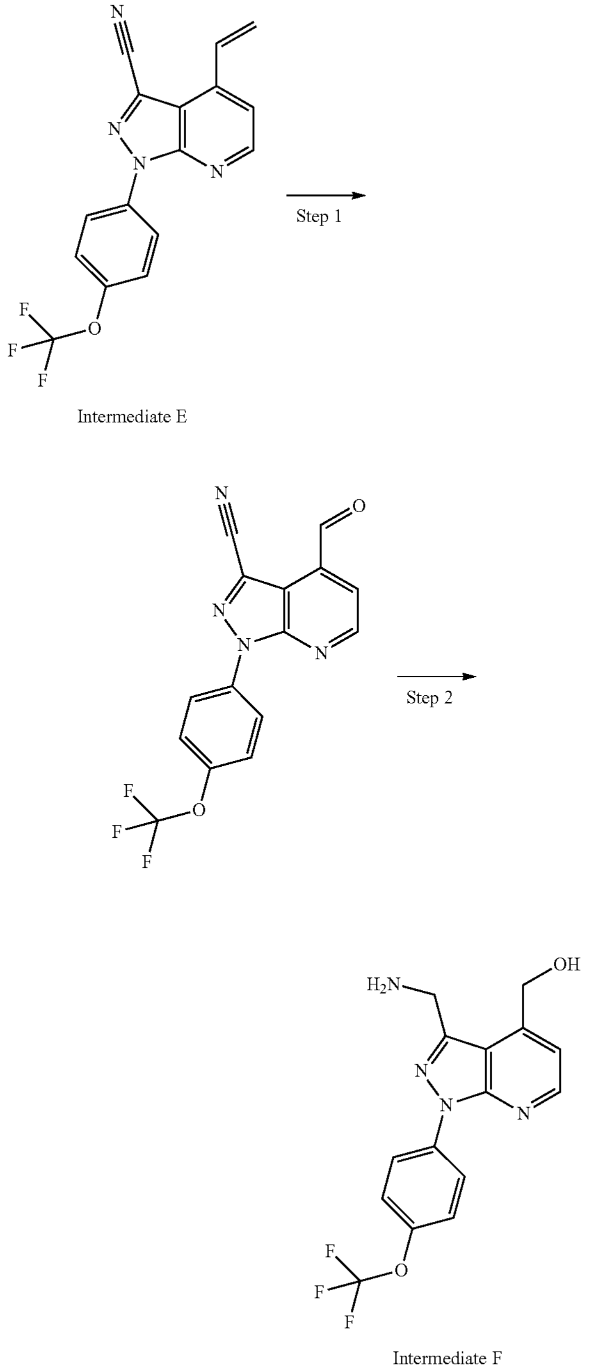

Step 1: 4-formyl-1-(4-(trifluoromethoxy)phenyl)-1H-pyrazolo[3,4-b]pyridine-3-carbonitrile

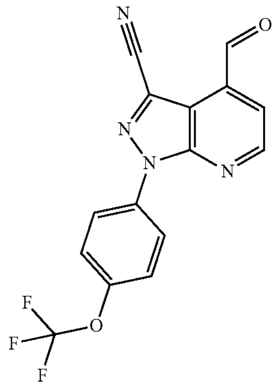 [SMILES: N#Cc1nn(-c2ccc(OC(F)(F)F)cc2)c2nccc(C=O)c12]

To a solution of 1-(4-(trifluoromethoxy)phenyl)-4-vinyl-1H-pyrazolo[3,4-b]pyridine-3-carbonitrile (1.8 g, 5.45 mmol) and $NaIO_4$ (5.8 g, 27.25 mmol) in THF (10 mL) and water (1 mL) was added potassium osmate (VI) dehydrate (200 mg, 0.55 mmol) at 0° C. The mixture was stirred at room temperature with 16 h. The reaction mixture was quenched with sat. $Na_2SO_3$ (30 mL). The reaction mixture was diluted with ethyl acetate (100 mL×2), washed with brine (60 mL×3), dried over $Na_2SO_4$ and concentrated to dryness. The residue was purified by flash column chromatography on silica gel (0-25% ethyl acetate in petroleum ether) to afford the title compound (1.3 g, 72%) as a white solid. $^1$H NMR (400 MHz, $CDCl_3$): δ 10.65 (s, 1H), 9.02 (d, J=4.4 Hz, 1H), 8.35 (d, J=8.8 Hz, 2H), 7.90 (d, J=4.4 Hz, 1H), 7.46 (d, J=8.8 Hz, 2H).

Step 2: (3-(aminomethyl)-1-(4-(trifluoromethoxy)phenyl)-1H-pyrazolo[3,4-b]pyridin-4-yl)methanol

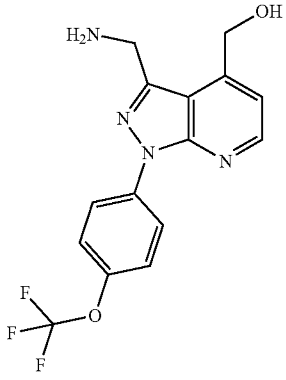 [SMILES: NCc1nn(-c2ccc(OC(F)(F)F)cc2)c2nccc(CO)c12]

To a solution of 4-formyl-1-(4-(trifluoromethoxy)phenyl)-1H-pyrazolo[3,4-b]pyridine-3-carbonitrile (1.3 g, 3.91 mmol) in MeOH (10 mL) was added $NiCl_2 \cdot 6H_2O$ (100 mg, 0.39 mmol). Then $NaBH_4$ (0.6 g, 17.04 mmol) was added to the mixture at 0° C. The reaction mixture was stirred at room temperature for 1 h. The reaction mixture was quenched by addition of sat. $NH_4Cl$ (30 mL), extracted with ethyl acetate (30 mL×3), washed with water (100 mL×3), dried over $Na_2SO_4$ and concentrated to dryness. After filtration, the filtrate was concentrated. The residue was purified by reverse phase chromatography (Welch Xtimate C18 150*25 mm*5 um, acetonitrile 40-70%/water ($NH_4HCO_3$)-CAN) to afford the title compound (500 mg, 38%) as a white solid. $^1$H NMR (400 MHz, $CDCl_3$): δ 8.59 (d, J=4.8 Hz, 1H), 8.32 (d, J=8.8 Hz, 2H), 7.40 (d, J=8.8 Hz, 2H), 7.16 (d, J=4.8 Hz, 1H), 4.94 (s, 2H), 4.50 (s, 2H).

Intermediate G tert-Butyl ((4-formyl-1-(4-(trifluoromethoxy)phenyl)-1H-pyrazolo[3,4-b]pyridin-3-yl)methyl)carbamate

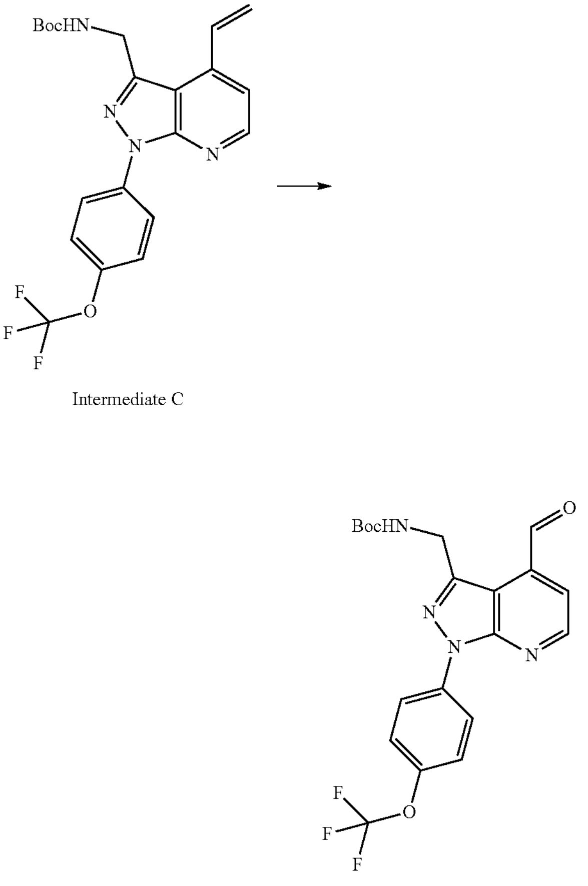

Intermediate C

Intermediate G

To a solution of tert-butyl 41-(4-(trifluoromethoxy)phenyl)-4-vinyl-1H-pyrazolo[3,4-b]pyridin-3-yl)methyl)carbamate (26.0 g, 56.47 mmol) and potassiumosmate(vi) dihydrate (2.08 g, 5.65 mmol) in THF (300 mL) and water (50 mL) was added $NaIO_4$ (48.31 g, 225.87 mmol) at 0° C. The resulting mixture was stirred at room temperature for 16 h. The mixture was quenched with aq.$Na_2SO_3$ solution (200 mL), extracted with ethyl acetate (500 mL), washed with water (300 mL×3). The organic was dried over $Na_2SO_4$ and concentrated to afford the title compound (26.0 g, 99%) as a white solid. $^1$H NMR (400 MHz, $CDCl_3$): δ 10.26 (s, 1H), 8.91 (d, J=4.4 Hz, 1H), 8.38 (d, J=8.8 Hz, 2H), 7.63 (d, J=4.4 Hz, 1H), 7.41 (d, J=8.8 Hz, 2H), 4.64-4.56 (m, 1H), 4.48-4.41 (m, 4H), 1.47 (s, 9H).

Intermediate H

3-Iodo-1-(4-(trifluoromethoxy)phenyl)-1H-pyrazolo[3,4-b]pyridine-4-carboxylic acid

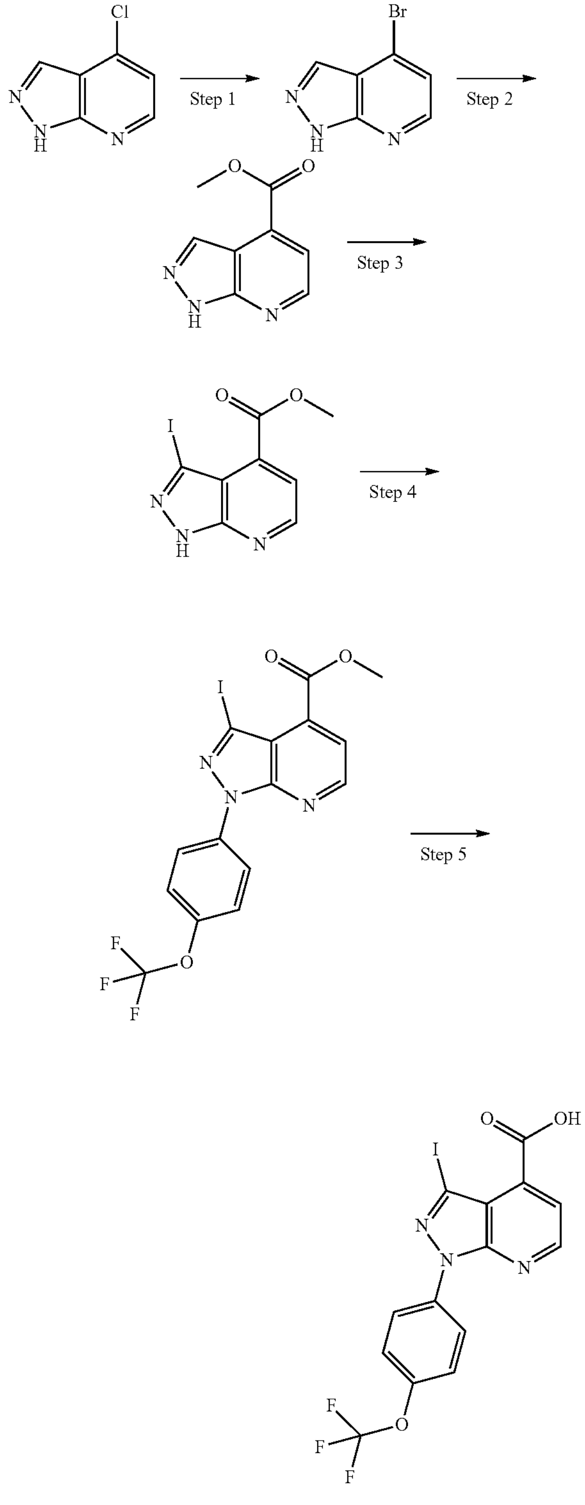

Intermediate H

Step 1: 4-bromo-1H-pyrazolo[3,4-b]pyridine

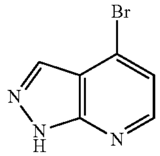

A solution of 33% HBr in acetic acid (22 mL, 29 mmol) and 4-chloro-1H-pyrazolo[3,4-b]pyridine (3.0 g, 19.5 mmol) was stirred at 60° C. for 3 h. The mixture was diluted with $NaHCO_3$ (1 L) and extracted with ethyl acetate (1 L×3). The combined organics were washed with brine (1 L), dried over sodium sulfate and concentrated to dryness. The residue was purified by flash chromatography on silica gel (0-30% ethyl acetate in petroleum ether) to afford the title compound (3.4 g, 88%) as a yellow solid. $^1H$ NMR (400 MHz, $CDCl_3$): δ 13.20 (s, 1H), 8.44 (d, J=5.2 Hz, 1H), 8.15 (s, 1H), 7.39 (d, J=5.2 Hz, 1H).

Step 2: methyl 1H-pyrazolo[3,4-b]pyridine-4-carboxylate

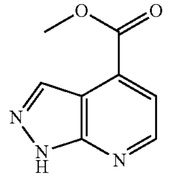

A solution of $Na_2CO_3$ (3.21 g, 30.3 mmol), 4-bromo-1H-pyrazolo[3,4-b]pyridine (3.0 g, 15.2 mmol), $Pd(OAc)_2$ (1.02 g, 4.54 mmol) and Xantphos (877 mg, 1.5 mmol) in DMF (15 mL) and methyl alcohol (6 mL) was stirred at 100° C. for 4 h under CO balloon. The reaction was diluted with water (100 mL) and extracted with ethyl acetate (200 mL×3) and the organic layers were combine. The organic layer was dried over anhydrous sodium sulfate and concentrated under vacuum. The residue was purified by flash chromatography on silica gel (0-36% ethyl acetate in petroleum ether) to afford the title compound (500 mg, 19%) as a yellow solid. $^1H$ NMR (400 MHz, $CDCl_3$): δ 12.27 (s, 1H), 8.71 (d, J=4.8 Hz, 1H), 8.48 (s, 1H), 7.74 (d, J=4.8 Hz, 1H), 4.02 (s, 3H).

Step 3: methyl 3-iodo-1H-pyrazolo[3,4-b]pyridine-4-carboxylate

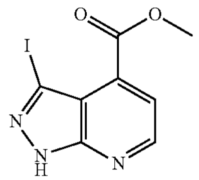

A solution of methyl 1H-pyrazolo[3,4-b]pyridine-4-carboxylate (550 mg, 3.1 mmol) and KOH (349 mg, 6.2 mmol) in DMF (5 mL) was stirred at room temperature for 30 min, then I2 (2.4 g, 9.3 mmol) was added into it at 0° C. The reaction solution was stirred at room temperature for 16 h under $N_2$ atmosphere. The mixture was diluted with water (100 mL) and extracted with ethyl acetate (100 mL×3). The organics were washed with brine (100 mL×3), dried over sodium sulfate. The residue was purified by flash chromatography on silica gel (0-36% ethyl acetate in petroleum ether) to afford the title compound (820 mg, 87%) as a yellow solid. $^1H$ NMR (400 MHz, $CDCl_3$): δ 12.85 (m, 1H), 8.74 (d, J=4.8 Hz, 1H), 7.57 (d, J=4.8 Hz, 1H), 4.10 (s, 3H); LCMS (ESI): m/z 303.9 $[M+H]^+$.

Step 4: methyl 3-iodo-1-(4-(trifluoromethoxy)phenyl)-1H-pyrazolo[3,4-b]pyridine-4-carboxylate

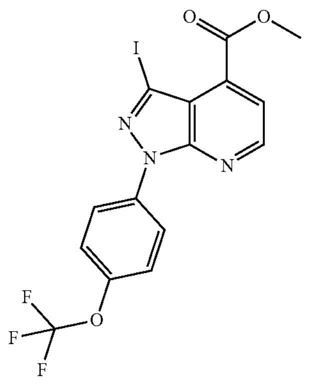 [SMILES: COC(=O)c1ccnc2c1c(I)nn2-c1ccc(OC(F)(F)F)cc1]

A mixture of (4-(trifluoromethoxy)phenyl)boronic acid (1.0 g, 6.5 mmol), methyl 3-iodo-1H-pyrazolo[3,4-b]pyridine-4-carboxylate (750 mg, 2.47 mmol), $Cu(OAC)_2$ (1.17 g, 6.5 mmol), pyridine (1.0 mL, 13.0 mmol) in MeCN (15 mL) under $O_2$ (15 psi) was stirred at room temperature for 16 h. The reaction mixture was filtered, the filtrate was diluted with water (30 mL) and extracted with DCM (50 mL×3). The combined organics were washed with brine (50 mL×2), dried over sodium sulfate, filtered and concentrated. The residue was purified by flash chromatography on silica gel (0-1% ethyl acetate in petroleum ether) to afford the title compound (735 mg, 64%) as a white solid. $^1H$ NMR (400 MHz, $CDCl_3$): δ 8.74 (d, J=4.8 Hz, 1H), 8.27 (d, J=8.8 Hz, 2H), 7.58 (d, J=4.8 Hz, 1H), 7.40 (d, J=8.4 Hz, 2H), 4.12 (s, 3H).

Step 5: 3-iodo-1-(4-(trifluoromethoxy)phenyl)-1H-pyrazolo[3,4-b]pyridine-4-carboxylic acid

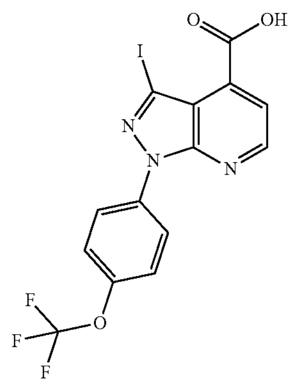 [SMILES: O=C(O)c1ccnc2c1c(I)nn2-c1ccc(OC(F)(F)F)cc1]

A mixture of methyl 3-iodo-1-(4-(trifluoromethoxy)phenyl)-1H-pyrazolo[3,4-b]pyridine-4-carboxylate (1.7 g, 3.7 mmol) and lithium hydroxide monohydrate (770 mg, 18.4 mmol) in THF (10 mL) and methyl alcohol (10 mL) was stirred at room temperature for 2 h. The reaction was quenched with water (100 mL). The resulting solution was extracted with ethyl acetate (100 mL×3) and the organic layers were combined. The organic layer was dried over anhydrous sodium sulfate. The organic layer was concentrated under vacuum to afford the title compound (1.6 g, 97%) as a yellow solid. $^1H$ NMR (400 MHz, $CDCl_3$): δ 8.77 (d, J=4.4 Hz, 1H), 8.25 (d, J=8.8 Hz, 2H), 7.68 (d, J=4.4 Hz, 1H), 7.39 (d, J=8.8 Hz, 2H).

Intermediate I 1-(3-(Piperazin-1-yl)-1-(4-(trifluoromethoxy)phenyl)-1H-pyrazolo[3,4-b]pyridin-4-yl)ethane-1,2-diol

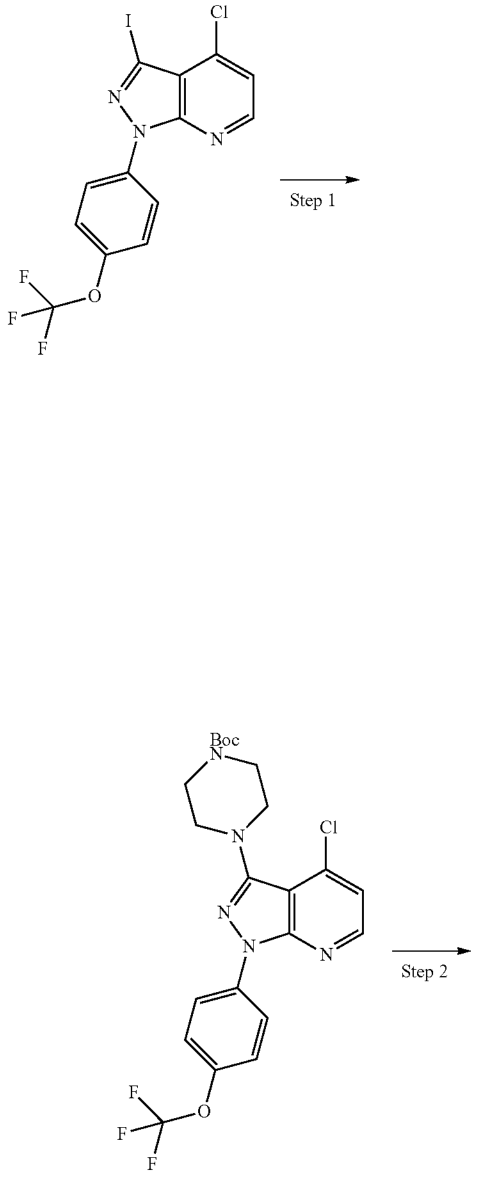

-continued

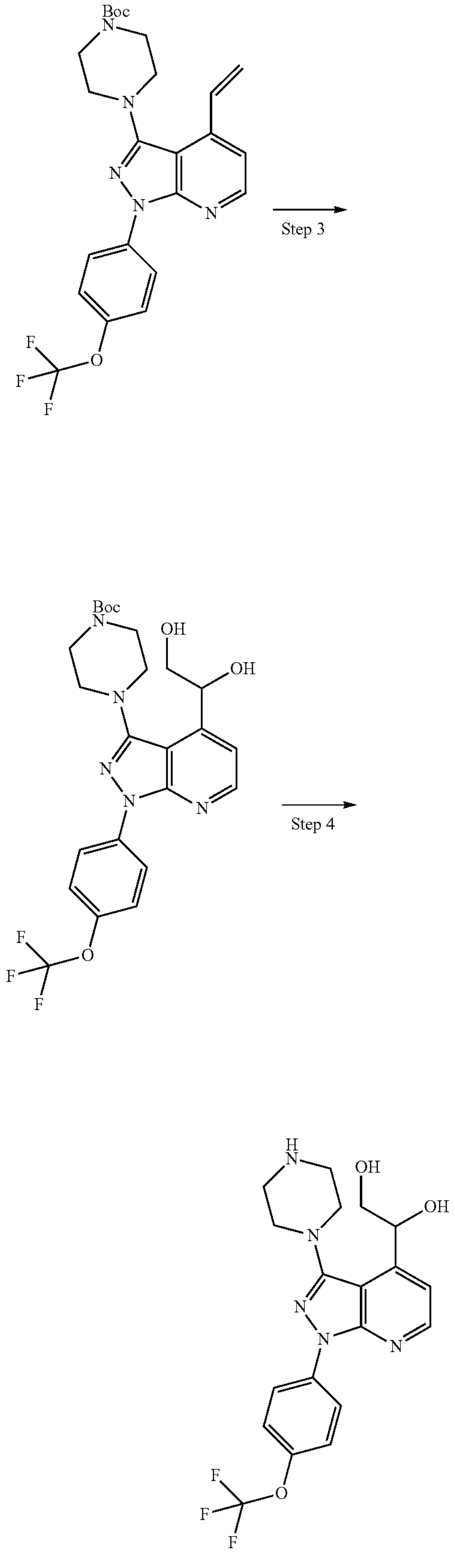

Intermediate I

Step 1: tert-butyl 4-(4-chloro-1-(4-(trifluoromethoxy)phenyl)-1H-pyrazolo[3,4-b]pyridin-3-yl) piperazine-1-carboxylate

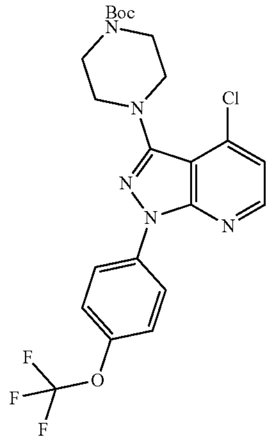 [SMILES: CC(C)(C)OC(=O)N1CCN(c2nn(-c3ccc(OC(F)(F)F)cc3)c3nccc(Cl)c23)CC1]

A solution of 4-chloro-3-iodo-1-(4-(trifluoromethoxy) phenyl)-1H-pyrazolo[3,4-b]pyridine (1.0 g, 2.28 mmol), tert-butyl piperazine-1-carboxylate (400 mg, 2.28 mmol), $Pd_2(dba)_3$ (100 mg, 0.11 mmol), Xantphos (200 mg, 0.34 mmol) and $Cs_2CO_3$ (1.5 g, 4.56 mmol) in 1,4-dioxane (25 mL) was stirred at 120° C. for 16 h under $N_2$ atmosphere. The mixture was quenched with water (100 mL) and extracted with ethyl acetate (100 mL×3). The organic layers was combined and washed with brine (50 mL×3), then dried with $Na_2SO_4$ and concentrated under vacuum. The residue was purified by column chromatography on silica gel (0-6% ethyl acetate in petroleum ether) to afford the title compound (700 mg, 62%) as a yellow solid. $^1H$ NMR (400 MHz, $CDCl_3$): 8.42 (d, J=4.8 Hz, 1H), 8.29 (d, J=8.8 Hz, 2H), 7.35 (d, J=8.8 Hz, 2H), 7.17 (d, J=4.8 Hz, 1H), 3.68 (d, J=4.8 Hz, 4H), 3.39 (d, J=4.8 Hz, 4H), 1.51 (s, 9H); LCMS (ESI): m/z 498.3 $(M+H)^+$.

Step 2: tert-butyl 4-(1-(4-(trifluoromethoxy)phenyl)-4-vinyl-1H-pyrazolo[3,4-b]pyridin-3-yl)piperazine-1-carboxylate

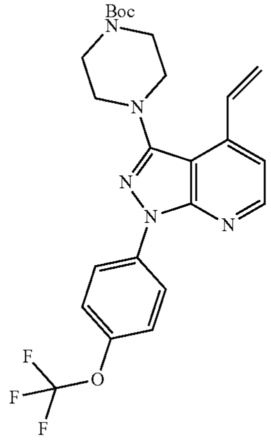 [SMILES: C=Cc1ccnc2c1c(N1CCN(C(=O)OC(C)(C)C)CC1)nn2-c1ccc(OC(F)(F)F)cc1]

A solution of tert-butyl 4-(4-chloro-1-(4-(trifluoromethoxy)phenyl)-1H-pyrazolo[3,4-b]pyridin-3-yl)piperazine-1-carboxylate (660 mg, 1.33 mmol), 4,4,5,5-tetramethyl-2-vinyl-1,3,2-dioxaborolane (408 mg, 2.65 mmol), Xphos Pd $G_2$ (104 mg, 0.13 mmol), Xphos (63 mg, 0.13 mmol) and KOAc (0.17 mL, 2.65 mmol) in 1,4-dioxane (10 mL) and water (2.5 mL) was stirred at 100° C. for 16 h under $N_2$ atmosphere. The mixture was quenched with water (20 mL) and extracted with ethyl acetate (20 mL×3). The combined organic layers were washed with brine (50 mL×3), dried with $Na_2SO_4$ and concentrated under vacuum. The residue was purified by column chromatography on silica gel (0-6% ethyl acetate in petroleum ether) to afford the title compound (700 mg, 100%) as a yellow solid. $^1H$ NMR (400 MHz, $CDCl_3$): δ 8.52 (d, J=4.8 Hz, 1H), 8.33 (d, J=8.8 Hz, 2H), 7.43 (dd, J=17.6 Hz, 10.8 Hz, 1H), 7.34 (d, J=8.8 Hz, 2H), 7.23 (d, J=4.8 Hz, 1H), 6.14 (d, J=17.6 Hz, 1H), 5.69 (d, J=10.8 Hz, 1H), 3.66 (d, J=4.8 Hz, 4H), 3.28 (d, J=4.8 Hz, 4H), 1.51 (s, 9H); LCMS (ESI): m/z 490.1 $(M+H)^+$.

Step 3: tert-butyl 4-(4-(1,2-dihydroxyethyl)-1-(4-(trifluoromethoxy)phenyl)-1H-pyrazolo[3,4-b]pyridin-3-yl)piperazine-1-carboxylate

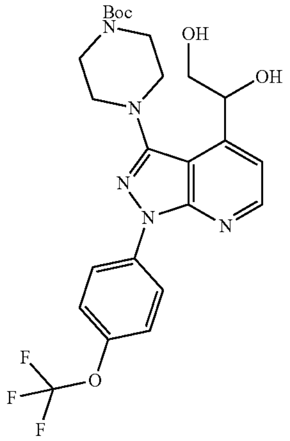 [SMILES: CC(C)(C)OC(=O)N1CCN(c2nn(-c3ccc(OC(F)(F)F)cc3)c3nccc(C(O)CO)c23)CC1]

A solution of tert-butyl 4-(1-(4-(trifluoromethoxy)phenyl)-4-vinyl-1H-pyrazolo[3,4-b]pyridin-3-yl)piperazine-1-carboxylate (400 mg, 0.82 mmol) in THF (6 mL) and water (0.60 mL) was added $K_2OsO_4 \cdot 2H_2O$ (30 mg, 0.08 mmol) and NMO (0.34 mL, 3.27 mmol) at 0° C. The resulting mixture was stirred at room temperature for 16 h. The reaction was quenched with sat. $Na_2SO_3$ (3 mL). The reaction mixture was diluted with water (20 mL) and extracted with ethyl acetate (20 mL×3). The combined organic layers were washed with brine (50 mL×3), dried over $Na_2SO_4$ and concentrated under vacuum. The residue was purified by chromatography on silica gel (0-50% ethyl acetate in petroleum ether) to afford the title compound (350 mg, 82%) as a yellow oil. $^1H$ NMR (400 MHz, DMSO-$d_6$): δ 8.61 (d, J=4.8 Hz, 1H), 8.37 (d, J=9.2 Hz, 2H), 7.55 (d, J=9.2 Hz, 2H), 7.44 (d, J=4.8 Hz, 1H), 5.69 (d, J=4.8 Hz, 1H), 5.30-5.28 (m, 1H), 4.95-4.92 (m, 1H), 3.75-3.74 (m, 2H), 3.60-3.56 (m, 4H), 3.24-3.18 (m, 4H), 1.44 (s, 9H); LCMS (ESI): m/z 524.2 $(M+H)^+$.

Step 4: 1-(3-(piperazin-1-yl)-1-(4-(trifluoromethoxy)phenyl)-1H-pyrazolo[3,4-b]pyridin-4-yl)ethane-1,2-diol

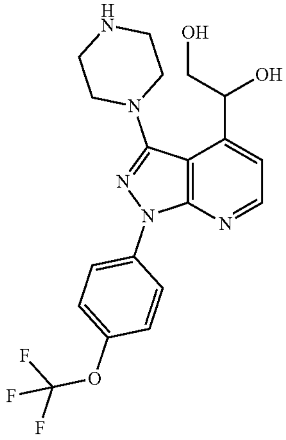 [SMILES: OCC(O)c1ccnc2c1c(N1CCNCC1)nn2-c1ccc(OC(F)(F)F)cc1]

A solution of tert-butyl 4-(4-(1,2-dihydroxyethyl)-1-(4-(trifluoromethoxy)phenyl)-1H-pyrazolo[3,4-b]pyridin-3-yl)piperazine-1-carboxylate (350 mg, 0.67 mmol) in 5% TFA HFIP (25 mL) was stirred at room temperature for 3 h. The solution was concentrated. The residue was added sat. $NaHCO_3$ (40 mL) and extracted with ethyl acetate (40 mL×3). The combined organic layers were washed with water (80 mL×3), dried over $Na_2SO_4$ and concentrated under vacuum to afford the title compound (360 mg, 99%) as a yellow oil. The crude product would be used in the next step directly; LCMS (ESI): m/z 424.0 $(M+H)^+$.

Intermediate J tert-Butyl 3-(4-chloro-1-(4-(trifluoromethoxy)phenyl)-1H-pyrazolo[3,4-b]pyridin-3-yl)azetidine-1-carboxylate

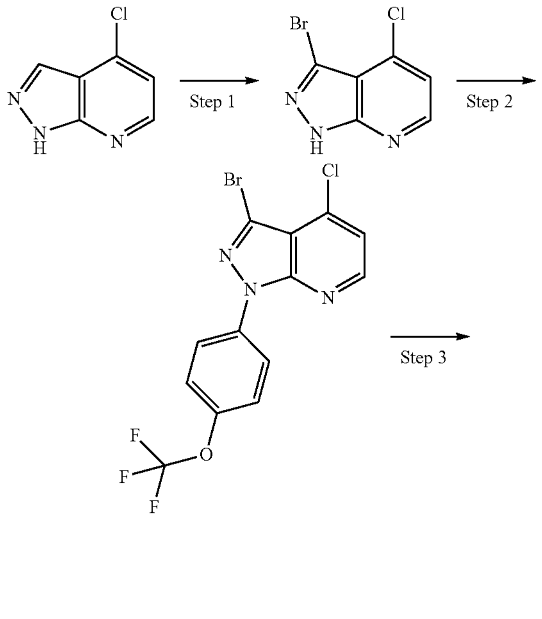

-continued

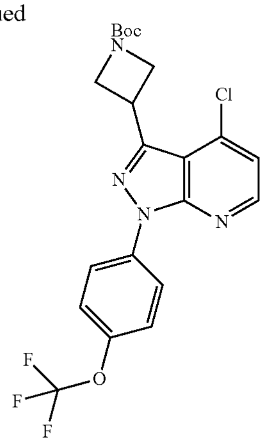

Intermediate J

Step 1: 3-bromo-4-chloro-1H-pyrazolo[3,4-b]pyridine

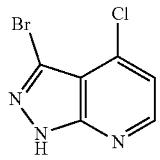 [SMILES: Clc1ccnc2[nH]nc(Br)c12]

To a solution of 4-chloro-1H-pyrazolo[3,4-b]pyridine (10.0 g, 65.1 mmol) in HOAc (100 mL) was added NBS (23.1 g, 130.2 mmol) at 0° C. The solution was stirred at room temperature for 2 h. The mixture was quenched with aq. $NaHSO_3$ solution (500 mL), adjusted pH to 8 with aq. $NaHCO_3$ solution. The residue was diluted with ethyl acetate (1 L) and washed with water (1 L×3). The organic was dried over $Na_2SO_4$, filtered, and concentrated. The residue was purified by chromatography on silica gel (0-5% ethyl acetate in petroleum ether) to afford the title compound (13.8 g, 91%) as a white solid. LCMS (ESI): m/z 232.0 $(M+H)^+$.

Step 2:3-bromo-4-chloro-1-(4-(trifluoromethoxy)phenyl)-1H-pyrazolo[3,4-b]pyridine

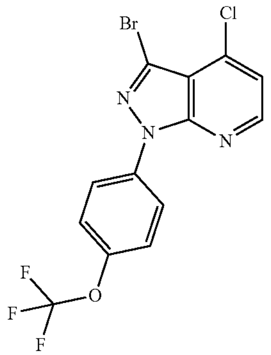 [SMILES: FC(F)(F)Oc1ccc(-n2nc(Br)c3c(Cl)ccnc32)cc1]

A mixture of (4-(trifluoromethoxy)phenyl)boronic acid (6.6 g, 32.2 mmol), pyridine (6.8 mL, 85.8 mmol), $Cu(OAc)_2$ (5.8 g, 32.2 mmol), 3-bromo-4-chloro-1H-pyrazolo[3,4-b]pyridine (5.0 g, 21.4 mmol) in MeCN (50 mL) under $O_2$ (15 psi) was stirred at room temperature for 16 h. The reaction mixture was filtered, the filtrate was diluted with water (500 mL) and extracted with dichloromethane (500 mL×3). The organics were combined, washed with brine (500 mL×2), dried over sodium sulfate, filtered and concentrated. The residue was purified by flash column chromatography on silica gel (0-10% ethyl acetate in petroleum ether) to afford the title compound (5.6 g, 67%) as a white solid. LCMS (ESI): m/z 394.0 $(M+H)^+$.

Step 3: tert-butyl 3-(4-chloro-1-(4-(trifluoromethoxy)phenyl)-1H-pyrazolo[3,4-b]pyridin-3-yl)azetidine-1-carboxylate

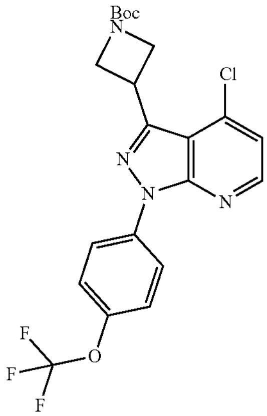 [SMILES: CC(C)(C)OC(=O)N1CC(c2nn(-c3ccc(OC(F)(F)F)cc3)c3nccc(Cl)c23)C1]

To a mixture of 3-bromo-4-chloro-1-(4-(trifluoromethoxy)phenyl)-1H-pyrazolo[3,4-b]pyridine (300 mg, 0.76 mmol) and sodium carbonate (203 mg, 1.91 mmol) in DME (10 mL) was added TTMSS (228 mg, 0.92 mmol), tert-butyl 3-bromoazetidine-1-carboxylate (271 mg, 1.15 mmol) and $Ir[dF(CF_3)ppy]_2(dtbbpy)PF_6$ (9 mg, 0.01 mmol) in a glove box. The $NiCl_2$·glyme (17 mg, 0.08 mmol) and dtbbpy (31 mg, 0.1 mmol) in DME (4 mL) was added into the mixture in the glove box at room temperature. The vial was sealed and taken out from the glove box, irradiated with 72 W Blue_LED-Strip-Light for 16 h with cooling from a fan. The reaction was quenched by water (20 mL). The resulting solution was extracted with ethyl acetate (10 mL×3) and the organic layers were combined and dried over $Na_2SO_4$. After filtration, the filtrate was concentrated under reduced pressure. The residue was purified by chromatography on silica gel (0-10% ethyl acetate in petroleum ether) to afford the title compound (183 mg, 51%) as a yellow oil. $^1H$ NMR (400 MHz, $CDCl_3$): δ 8.49 (d, J=5.2 Hz, 1H), 8.36 (d, J=8.8 Hz, 2H), 7.39 (d, J=8.8 Hz, 2H), 7.22 (d, J=5.2 Hz, 1H), 4.51-4.38 (m, 5H), 1.48 (s, 9H); LCMS (ESI): m/z 469.1 $(M+H)^+$.

Intermediate K tert-butyl 3-(1-(4-(trifluoromethoxy)phenyl)-4-vinyl-1H-pyrazolo[3,4-b]pyridin-3-yl)azetidine-1-carboxylate

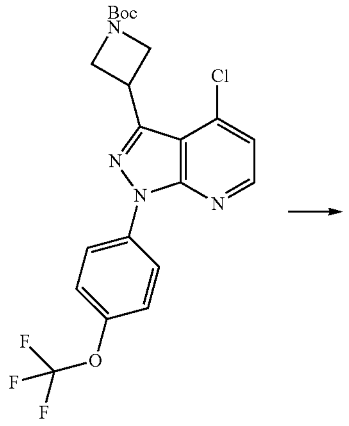

Intermediate J

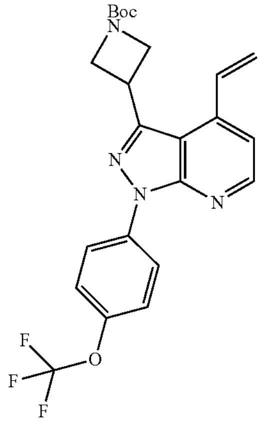

Intermediate K

A solution of ter t-butyl 3-(4-chloro-1-(4-(trifluoromethoxy)phenyl)-1H-pyrazolo[3,4-b]pyridin-3-yl)azetidine-1-carboxylate (320 mg, 0.68 mmol), Xphos (33 mg, 0.07 mmol), Xphos Pd $G_2$ (54 mg, 0.07 mmol) and 4,4,5,5-tetramethyl-2-vinyl-1,3,2-dioxaborolane (211 mg, 1.4 mmol) in 1,4-dioxane (10 mL) and water (1 mL) was stirred at 100° C. for 6 h. The solution was diluted with water (500 mL), the resulting solution was extracted with ethyl acetate (50 mL×3) and the organic layers were combined. The organic layers were dried over $Na_2SO_4$ and filtered. After filtration, the filtrate was concentrated under reduced pressure. The residue was purified by chromatography on silica gel (0-10% ethyl acetate in petroleum ether) to afford the title compound (260 mg, 82%) as a colorless oil. $^1H$ NMR (400 MHz, $CDCl_3$): δ 8.57 (d, J=4.8 Hz, 1H), 8.38 (d, J=8.8 Hz, 2H), 7.39 (d, J=8.8 Hz, 2H), 7.29 (d, J=4.8 Hz, 1H), 7.06 (dd, J=17.6, 11.2 Hz, 1H), 6.05 (d, J=17.6 Hz, 1H), 5.71 (d, J=11.2 Hz, 1H), 4.54-4.36 (m, 4H), 4.35-4.22 (m, 1H), 1.47 (s, 9H); LCMS (ESI): m/z 461.3 $(M+H)^+$.

Intermediate L (3-(Azetidin-3-yl)-1-(4-(trifluoromethoxy)phenyl)-1H-pyrazolo[3,4-b]pyridin-4-yl)methanol

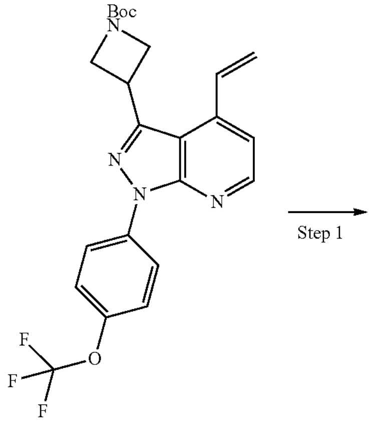

Intermediate K

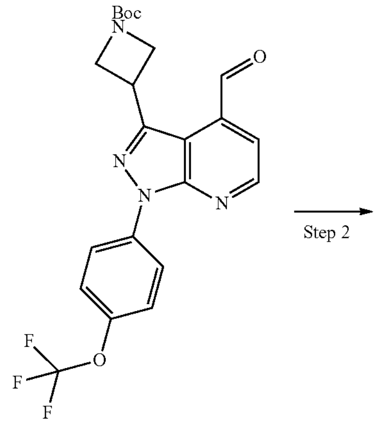

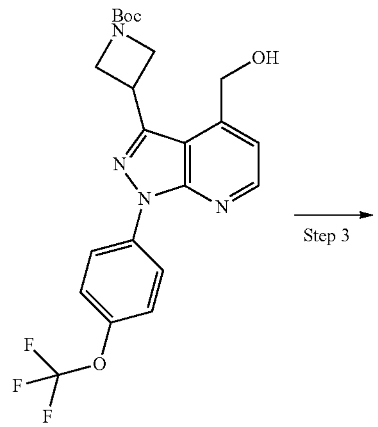

-continued

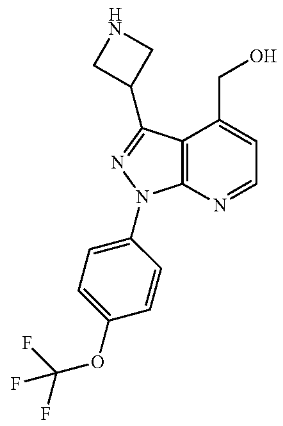

Intermediate L

Step 1: tert-butyl 3-(4-formyl-1-(4-(trifluoromethoxy)phenyl)-1H-pyrazolo[3,4-b]pyridin-3-yl) azetidine-1-carboxylate

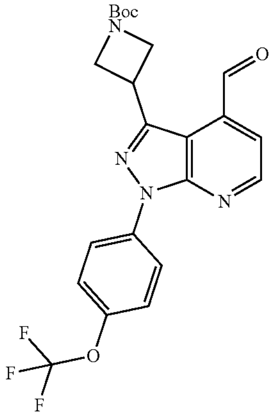 [SMILES: CC(C)(C)OC(=O)N1CC(c2nn(-c3ccc(OC(F)(F)F)cc3)c3nccc(C=O)c23)C1]

To a solution of tert-butyl 3-(1-(4-(trifluoromethoxy)phenyl)-4-vinyl-1H-pyrazolo[3,4-b]pyridin-3-yl)azetidine-1-carboxylate (360 mg, 0.78 mmol) in THF (6 mL) and water (2 mL) at 0° C. was added potassium osmate(VI) dihydrate (29 mg, 0.08 mmol) and $NaIO_4$ (700 mg, 3.3 mmol). The reaction mixture was stirred at room temperature for 12 h. The reaction mixture was quenched with saturated aqueous $Na_2SO_3$ (30 mL). The resulting solution was extracted with ethyl acetate (30 mL×3). The combined organic layers were dried over $Na_2SO_4$, filtered and concentrated to afford the title compound (350 mg, 96%) as a yellow solid. $^1H$ NMR (400 MHz, $CDCl_3$): δ 10.26 (s, 1H), 8.91 (d, J=4.4 Hz, 1H), 8.38 (d, J=8.8 Hz, 2H), 7.63 (d, J=4.4 Hz, 1H), 7.41 (d, J=8.8 Hz, 2H), 4.67-4.55 (m, 1H), 4.49-4.34 (m, 4H), 1.47 (s, 9H); LCMS (ESI): m/z 407.1 $(M-56+H)^+$.

Step 2: tert-butyl 3-(4-(hydroxymethyl)-1-(4-(trifluoromethoxy)phenyl)-1H-pyrazolo[3,4-b]pyridin-3-yl)azetidine-1-carboxylate

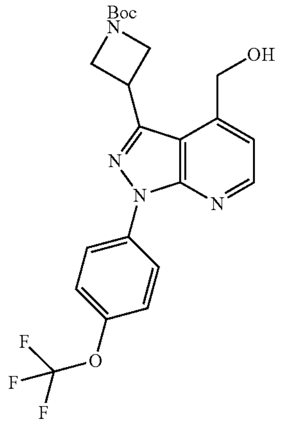 [SMILES: CC(C)(C)OC(=O)N1CC(c2nn(-c3ccc(OC(F)(F)F)cc3)c3nccc(CO)c23)C1]

To a solution of tert-butyl 3-(4-formyl-1-(4-(trifluoromethoxy)phenyl)-1H-pyrazolo[3,4-b]pyridin-3-yl)azetidine-1-carboxylate (350 mg, 0.76 mmol) in MeOH (10 mL) was added $NaBH_4$ (65.0 mg, 1.7 mmol) at 0° C. The solution was stirred at 0° C. for 1 h. The mixture was quenched with sat. $NH_4Cl$ (20 mL). The solution was extracted with ethyl acetate (100 mL), the organic layer was separated and washed with water (30 mL×3). The organic was dried over $Na_2SO_4$, filtered, and concentrated to dryness. The residue was purified by column chromatography on silica gel (0-20% ethyl acetate in petroleum ether) to afford the title compound (300 mg, 85%) as a white solid. $^1H$ NMR (400 MHz, $CDCl_3$): δ 8.60 (d, J=4.4 Hz, 1H), 8.39 (d, J=8.8 Hz, 2H), 7.39 (d, J=8.8 Hz, 2H), 7.29 (d, J=4.4 Hz, 1H), 5.01 (s, 2H), 4.49-4.43 (m, 2H), 4.40-4.38 (m, 2H), 4.35-4.27 (m, 1H), 1.48 (s, 9H).

Step 3: (3-(azetidin-3-yl)-1-(4-(trifluoromethoxy) phenyl)-1H-pyrazolo[3,4-b]pyridin-4-yl)methanol

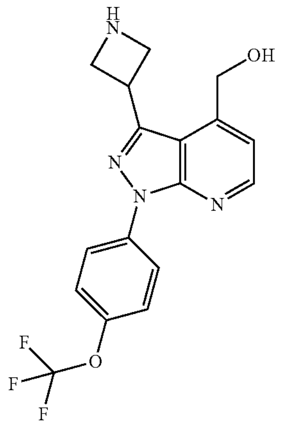

A mixture of tert-butyl 3-(4-(hydroxymethyl)-1-(4-(trifluoromethoxy)phenyl)-1H-pyrazolo[3,4-b]pyridin-3-yl)azetidine-1-carboxylate (250 mg, 0.54 mmol) and TFA (5%, HFIP, 20 mL) was stirred at 0° C. for 2 h under nitrogen atmosphere. The reaction was concentrated under vacuum. The residue was neutralized with saturated aqueous $NaHCO_3$ to pH=8. The resulting solution was extracted with ethyl acetate (50 mL×3). The organic layer was dried over anhydrous sodium sulfate, filtered, and concentrated under vacuum to afford the title compound (196 mg, 99%) as a yellow oil. LCMS (ESI): m/z 365.2 $(M+H)^+$.

Intermediate M 1-(3-(Azetidin-3-yl)-1-(4-(trifluoromethoxy)phenyl)-1H-pyrazolo[3,4-b]pyridin-4-yl)ethane-1,2-diol

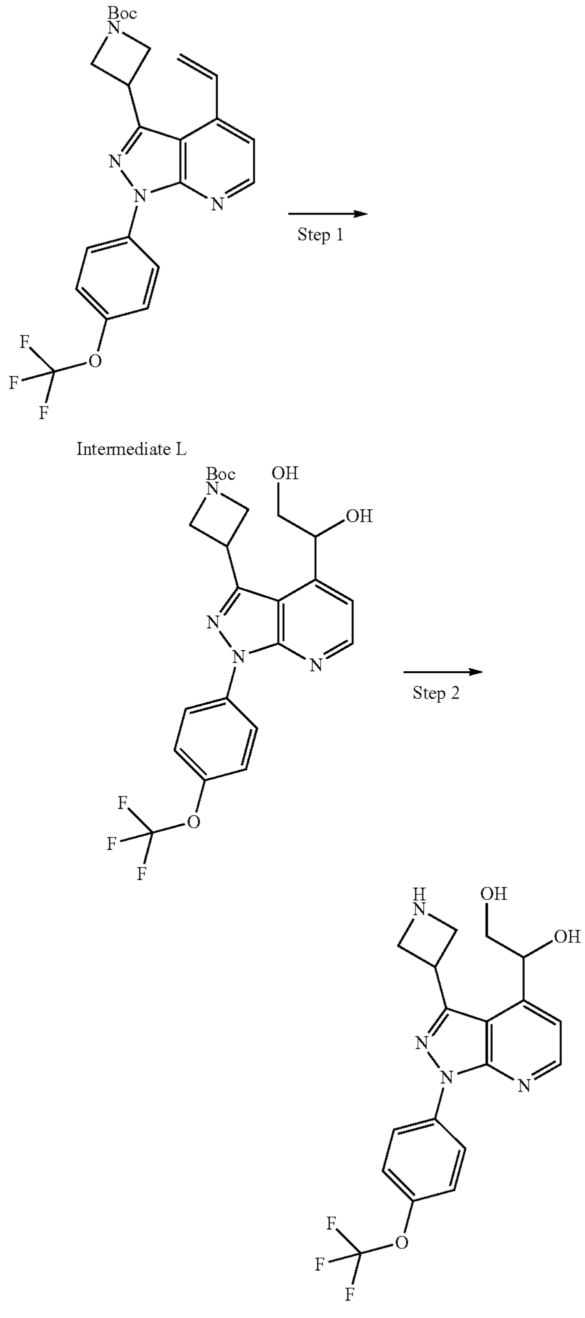

Intermediate M

Step 1: tert-butyl 3-(4-(1,2-dihydroxyethyl)-1-(4-(trifluoromethoxy)phenyl)-1H-pyrazolo[3,4-b]pyridin-3-yl)azetidine-1-carboxylate

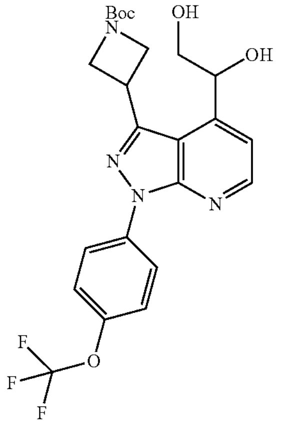 [SMILES: CC(C)(C)OC(=O)N1CC(c2nn(-c3ccc(OC(F)(F)F)cc3)c3nccc(C(O)CO)c23)C1]

To a solution of NMO (191 mg, 1.63 mmol) and potassium osmate (VI) dehydrate (22 mg, 0.06 mmol) in THF (6 mL) and water (1.2 mL) was added tert-butyl 3-(1-(4-(trifluoromethoxy)phenyl)-4-vinyl-1H-pyrazolo[3,4-b]pyridin-3-yl)azetidine-1-carboxylate (250 mg, 0.54 mmol) at room temperature. The resulting mixture was stirred at room temperature for 16 h. The reaction was quenched with sat. $Na_2SO_3$ (20 mL). The resulting solution was extracted with ethyl acetate (20 mL×3) and the organic layers were combined. The organic layer was dried over anhydrous sodium sulfate. After filtration, the filtrate was concentrated under reduced pressure. The residue was purified by flash chromatography on silica gel (0-60% ethyl acetate in petroleum ether) to afford the title compound (246 mg, 92%) as a white solid. $^1H$ NMR (400 MHz, DMSO-$d_6$): δ 8.63 (d, J=4.8 Hz, 1H), 8.45 (d, J=8.8 Hz, 2H), 7.59 (d, J=8.8 Hz, 2H), 7.43 (d, J=4.8 Hz, 1H), 5.80 (d, J=4.4 Hz, 1H), 5.04-4.95 (m, 2H), 4.55-4.46 (m, 1H), 4.37-4.26 (m, 3H), 4.26-4.19 (m, 1H), 3.63-3.49 (m, 2H), 1.41 (s, 9H).

Step 2: 1-(3-(azetidin-3-yl)-1-(4-(trifluoromethoxy)phenyl)-1H-pyrazolo[3,4-b]pyridin-4-yl)ethane-1,2-diol 2,2,2-trifluoroacetate

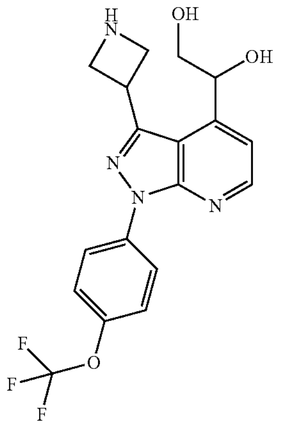 [SMILES: OCC(O)c1ccnc2c1c(C1CNC1)nn2-c1ccc(OC(F)(F)F)cc1]

A mixture of tert-butyl 3-(4-(1,2-dihydroxyethyl)-1-(4-(trifluoromethoxy)phenyl)-1H-pyrazolo[3,4-b]pyridin-3-yl) azetidine-1-carboxylate (226 mg, 0.46 mmol) in 5% TFA/HFIP (6 mL) was stirred at room temperature for 1 h. The mixture was concentrated to afford the title compound (200 mg, 100%) as a yellow solid. The crude would be used in the next step directly. LCMS (ESI): m/z 395 $(M+H)^+$.

Intermediate N tert-Butyl 3-(4-iodo-1-(4-(trifluoromethoxy)phenyl)-1H-pyrazolo[3,4-b]pyridin-3-yl)azetidine-1-carboxylate

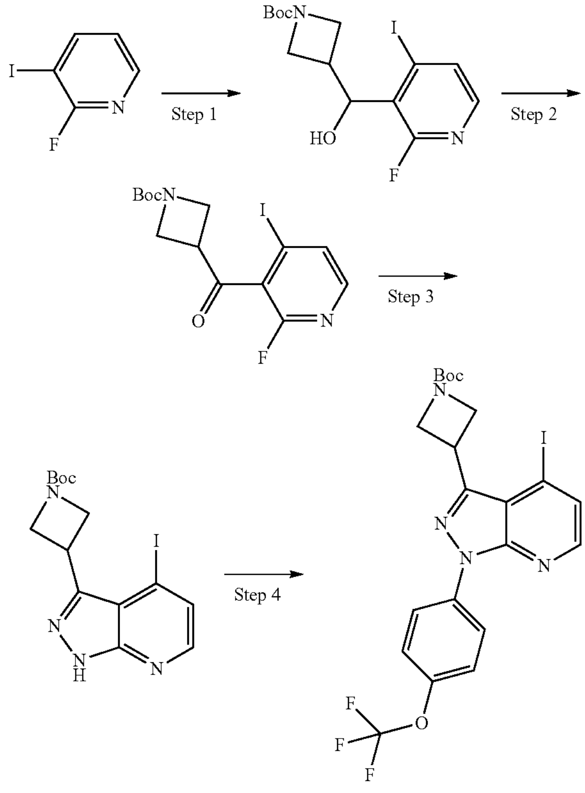

Intermediate N

Step 1: tert-butyl 3-((2-fluoro-4-iodopyridin-3-yl)(hydroxy)methyl)azetidine-1-carboxylate

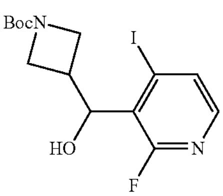 [SMILES: CC(C)(C)OC(=O)N1CC(C(O)c2c(I)ccnc2F)C1]

To a solution of 2-fluoro-3-iodopyridine (40 g, 179.38 mmol) in THF (400 mL) was added LDA (89.7 mL, 179.38 mmol) slowly at −78° C. Then the mixture was stirred at −78° C. for 1 h. Then a solution of tert-butyl 3-formylazetidine-1-carboxylate (30.0 g, 161.44 mmol) in THF (30 mL) was added slowly at −78° C. The reaction mixture was stirred at −78° C. for 1 h. The reaction mixture was quenched with water (400 mL), extracted with ethyl acetate (400 mL×3). Combined organic layers were dried over $Na_2SO_4$, filtered and concentrated under vacuum. The residue was purified by column chromatography on silica gel (0-45% ethyl acetate in petroleum ether) to afford the title compound (48.0 g, 66%) as a white solid. $^1H$ NMR (400 MHz, $CDCl_3$): δ 7.77 (d, J=4.8 Hz, 1H), 7.69 (d, J=5.6 Hz, 1H), 5.23 (t, J=8.8 Hz, 1H), 4.18-4.10 (m, 1H), 4.07-3.99 (m, 1H), 3.88-3.82 (m, 1H), 3.67-3.59 (m, 1H), 2.65-2.55 (m, 1H), 1.45 (s, 9H); LCMS (ESI): m/z 352.9 $(M-56+H)^+$.

Step 2: tert-butyl 3-(2-fluoro-4-iodonicotinoyl)azetidine-1-carboxylate

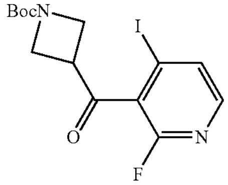 [SMILES: CC(C)(C)OC(=O)N1CC(C(=O)c2c(I)ccnc2F)C1]

To a solution of tert-butyl 3-((2-fluoro-4-iodopyridin-3-yl)(hydroxy)methyl)azetidine-1-carboxylate (48.0 g, 117.59 mmol) in DCM (500 mL) was added DMP (54.9 g, 129.35 mmol) at 0° C. The solution was stirred at room temperature for 16 h. The reaction mixture was quenched with 1M NaOH (800 mL) and extracted with ethyl acetate (400 mL×3). Combined organic layers were dried over $Na_2SO_4$, filtered and concentrated under vacuum to afford the crude title compound (47.0 g, 99%) as a white solid. The crude product was used for next step without further purification. $^1H$ NMR (400 MHz, $CDCl_3$): δ 7.92 (d, J=5.2 Hz, 1H), 7.76 (d, J=5.2 Hz, 1H), 4.26-4.20 (m, 2H), 4.14-4.09 (m, 2H), 4.03-3.91 (m, 1H), 1.44 (s, 9H); LCMS (ESI): m/z 351.0 $(M-56+H)^+$.

Step 3: tert-butyl 3-(4-iodo-1H-pyrazolo[3,4-b]pyridin-3-yl)azetidine-1-carboxylate & tert-butyl 3-(4-fluoro-1H-pyrazolo[4,3-e]pyridin-3-yl)azetidine-1-carboxylate

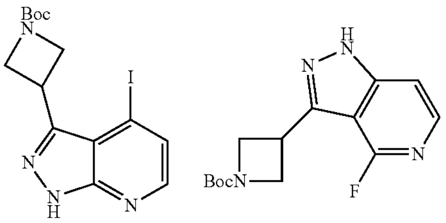 [SMILES: CC(C)(C)OC(=O)N1CC(c2n[nH]c3nccc(I)c23)C1 ; CC(C)(C)OC(=O)N1CC(c2n[nH]c3ccnc(F)c23)C1]

To a solution of tert-butyl 3-(2-fluoro-4-iodonicotinoyl)azetidine-1-carboxylate (47.0 g, 115.71 mmol) in 1,4-dioxane (500 mL) was added $N_2H_4 \cdot H_2O$ (26.41 mL, 462.84 mmol) at room temperature. The solution was stirred at room temperature for 16 h. The reaction mixture was quenched with sat. $NH_4Cl$ (500 mL), extracted with DCM (400 mL×3). The combined organic layers were dried over $Na_2SO_4$, filtered and concentrated under vacuum. The residue was purified by column chromatography on silica gel (0-40% ethyl acetate in petroleum ether) to afford the first compound tert-butyl 3-(4-iodo-1H-pyrazolo[3,4-b]pyridin-3-yl)azetidine-1-carboxylate (20.0 g, 43%) as a white solid and (0-45% ethyl acetate in petroleum ether) to afford the second compound ter t-butyl 3-(4-fluoro-1H-pyrazolo[4,3-c]pyridin-3-yl)azetidine-1-carboxylate (12.0 g, 36%) as a white solid.

tert-butyl 3-(4-iodo-1H-pyrazolo[3,4-b]pyridin-3-yl)azetidine-1-carboxylate: $^1$H NMR (400 MHz, $CDCl_3$): δ 12.43 (s, 1H), 7.17 (d, J=4.8 Hz, 1H), 7.64 (d, J=4.8 Hz, 1H), 4.58-4.50 (m, 1H), 4.47-4.39 (m, 4H), 1.47 (s, 9H); LCMS (ESI): m/z 401.1 $(M+H)^+$.

tert-Butyl 3-(4-fluoro-1H-pyrazolo[4,3-c]pyridin-3-yl) azetidine-1-carboxylate: $^1$H NMR (400 MHz, $CDCl_3$): δ 12.08 (s, 1H), 7.88 (d, J=5.2 Hz, 1H), 7.38 (dd, J=6.0, 4.0 Hz, 1H), 4.71-4.57 (m, 1H), 4.38-4.36 (m, 2H), 4.28-4.12 (m, 2H), 1.46 (s, 9H); LCMS (ESI): m/z 293.2 $(M+H)^+$.

Step 4: tert-butyl 3-(4-iodo-1-(4-(trifluoromethoxy) phenyl)-1H-pyrazolo[3,4-b]pyridin-3-yl)azetidine-1-carboxylate

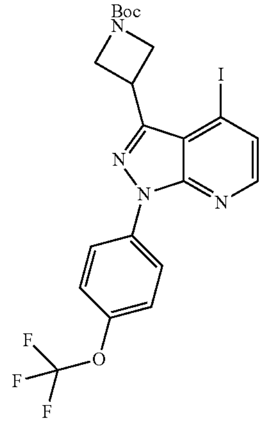 [SMILES: CC(C)(C)OC(=O)N1CC(c2nn(-c3ccc(OC(F)(F)F)cc3)c3nccc(I)c23)C1]

A solution of tert-butyl 3-(4-iodo-1H-pyrazolo[3,4-b] pyridin-3-yl)azetidine-1-carboxylate (12.0 g, 29.98 mmol) and $Cu(OAc)_2$ (8.2 g, 44.98 mmol), (4-(trifluoromethoxy) phenyl)boronic acid (9.3 g, 44.98 mmol) and pyridine (9.5 mL, 119.94 mmol) in MeCN (150 mL) was stirred at room temperature for 3 days under $O_2$ balloon atmosphere. The mixture is filtered over diatomite, diluted with ethyl acetate (800 mL), the combined organic layers were washed with water (400 mL×2), dried over $Na_2SO_4$ and concentrated. The residue was purified by column chromatography on silica gel (0-7% ethyl acetate in petroleum ether) to afford the title compound (13.0 g, 77%) as a white solid. $^1$H NMR (400 MHz, $CDCl_3$): δ 8.35 (d, J=8.8 Hz, 2H), 8.17 (d, J=4.8 Hz, 1H), 7.69 (d, J=4.8 Hz, 1H), 7.39 (d, J=8.4 Hz, 2H), 4.64-4.55 (m, 1H), 4.53-4.42 (m, 4H), 1.48 (s, 9H); LCMS (ESI): m/z 560.9 $(M+H)^+$.

Intermediate O tert-Butyl 3-(7-chloro-3-iodo-1H-pyrazolo[4,3-b] pyridin-1-yl)azetidine-1-carboxylate

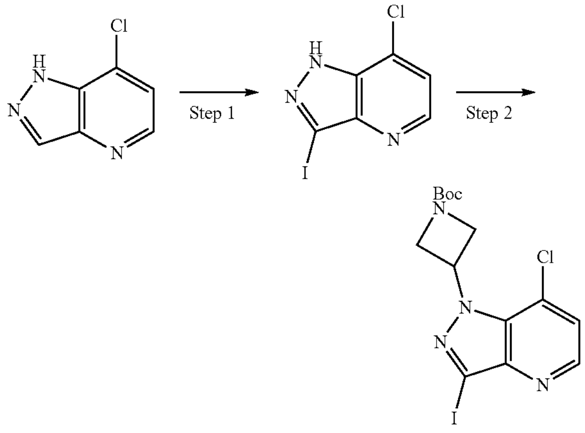

Intermediate O

Step 1: 7-chloro-3-iodo-1H-pyrazolo[4,3-b]pyridine

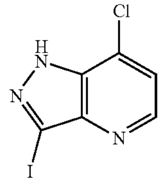 [SMILES: Clc1ccnc2c(I)n[nH]c12]

A mixture of 7-chloro-1H-pyrazolo[4,3-b]pyridine (1.6 g, 10.42 mmol) and KOH (2.9 g, 52.09 mmol) in DMF (15 mL) was added 12 (5.3 g, 20.84 mmol) at room temperature. The solution was stirred at room temperature for 15 h. The mixture was diluted with water (100 mL) and extracted with ethyl acetate (100 mL×3). The organics were washed with brine (100 mL×5), dried over $Na_2SO_4$, and filtered. The residue was purified by flash chromatography on silica gel (0-30% ethyl acetate in petroleum ether) to afford the title compound (2.8 g, 96%) as a yellow solid. $^1$H NMR (400 MHz, DMSO-$d_6$): δ 10.53 (s, 1H), 8.59 (d, J=4.8 Hz, 1H), 7.45 (d, J=4.8 Hz, 1H).

Step 2: tert-butyl 3-(7-chloro-3-iodo-1H-pyrazolo[4, 3-b]pyridin-1-yl)azetidine-1-carboxylate

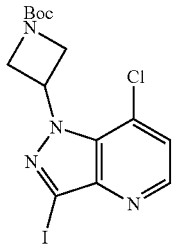 [SMILES: CC(C)(C)OC(=O)N1CC(n2nc(I)c3nccc(Cl)c32)C1]

To a solution of 7-chloro-3-iodo-1H-pyrazolo[4,3-b]pyridine (1.5 g, 5.37 mmol) in DMF (20 mL) was added NaH (0.6 g, 16.10 mmol, 60% in mineral oil) at 0° C. Then tert-butyl 3-bromoazetidine-1-carboxylate (2.5 g, 10.73 mmol) was added into the mixture. The mixture was stirred at 80° C. for 16 h. The reaction mixture was quenched by addition of sat. $NH_4Cl$ (100 mL). The reaction mixture was diluted with ethyl acetate (100 mL×3), washed with brine (90 mL), dried over $Na_2SO_4$, filtered, and concentrated to dryness. The residue was purified by column chromatography on silica gel (10-20% ethyl acetate in petroleum ether) to afford the title compound (630 mg, 27%) as a white solid. $^1H$ NMR (400 MHz, $CDCl_3$): δ 8.52 (d, J=4.8 Hz, 1H), 7.40 (d, J=4.8 Hz, 1H), 6.03-5.99 (m, 1H), 4.61-4.58 (m, 2H), 4.45-4.40 (m, 2H), 1.49 (s, 9H).

Intermediate P tert-Butyl 3-(3-(4-(trifluoromethoxy)phenyl)-7-vinyl-1H-pyrazolo[4,3-b]pyridin-1-yl)azetidine-1-carboxylate

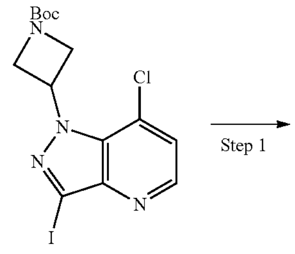

Intermediate O

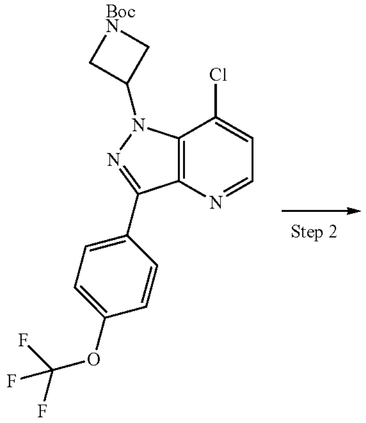

-continued

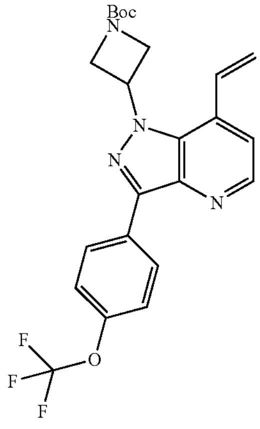

Intermediate P

Step 1: tert-butyl 3-(7-chloro-3-(4-(trifluoromethoxy)phenyl)-1H-pyrazolo[4,3-b]pyridin-1-yl) azetidine-1-carboxylate

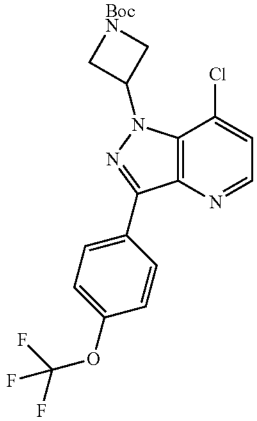 [SMILES: CC(C)(C)OC(=O)N1CC(n2nc(-c3ccc(OC(F)(F)F)cc3)c3nccc(Cl)c32)C1]

A solution of tert-butyl 3-(7-chloro-3-iodo-1H-pyrazolo[4,3-b]pyridin-1-yl)azetidine-1-carboxylate (630 mg, 1.45 mmol), $K_3PO_4$ (615 mg, 2.90 mmol), $Pd(PPh_3)_2Cl_2$ (101 mg, 0.14 mmol) and (4-(trifluoromethoxy)phenyl)boronic acid (298 mg, 1.45 mmol) in 1,4-dioxane (15 mL) and water (1.5 mL) was stirred at 80° C. for 4 h under $N_2$ atmosphere. The reaction mixture was diluted with ethyl acetate (150 mL×2), washed with brine (90 mL×3), dried over $Na_2SO_4$ and concentrated to dryness. The residue was purified by column chromatography on silica gel (8-15% ethyl acetate in petroleum ether) to afford the title compound (450 mg, 66%) as a white solid. $^1H$ NMR (400 MHz, $CDCl_3$): δ 8.50 (d, J=8.8 Hz, 2H), 8.46 (d, J=4.8 Hz, 1H), 7.30-7.27 (m, 3H), 6.03-5.99 (m, 1H), 4.61-4.58 (m, 2H), 4.41-4.37 (m, 2H), 1.42 (s, 9H); LCMS (ESI): m/z 469.0 $(M+H)^+$.

Step 2: tert-butyl 3-(3-(4-(trifluoromethoxy)phenyl)-7-vinyl-1H-pyrazolo[4,3-b]pyridin-1-yl)azetidine-1-carboxylate

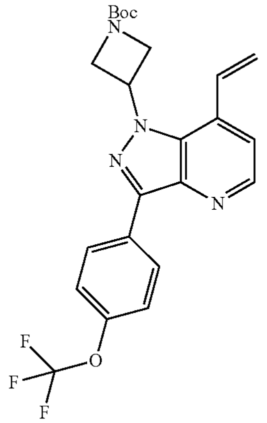 [SMILES: C=Cc1ccnc2c(-c3ccc(OC(F)(F)F)cc3)nn(C3CN(C(=O)OC(C)(C)C)C3)c12]

A mixture of tert-butyl 3-(7-chloro-3-(4-(trifluoromethoxy)phenyl)-1H-pyrazolo[4,3-b]pyridin-1-yl)azetidine-1-carboxylate (450 mg, 0.96 mmol), 4,4,5,5-tetramethyl-2-vinyl-1,3,2-dioxaborolane (192 mg, 1.2 mmol), KOAc (188 mg, 1.92 mmol), Xphos (46 mg, 0.096 mmol) and Xphos Pd $G_2$ (75 mg, 0.096 mmol) in 1,4-dioxane (20 mL) and water (2 mL) was stirred at 100° C. for 5 h under N2 atmosphere. The reaction mixture was diluted with ethyl acetate (100 mL×2), washed with brine (100 mL×3), dried over $Na_2SO_4$ and concentrated to dryness The residue was purified by column chromatography on silica gel (0-7% ethyl acetate in petroleum ether) to afford the title compound (390 mg, 88%) as a white solid. $^1$H NMR (400 MHz, $CDCl_3$): δ 8.63 (d, J=4.8 Hz, 1H), 8.60 (d, J=8.8 Hz, 2H), 7.36 (d, J=8.4 Hz, 2H), 7.28-7.27 (m, 1H), 7.16 (dd, J=17.2, 10.8 Hz, 1H), 5.91 (d, J=17.2 Hz, 1H), 5.73 (d, J=10.8 Hz, 1H), 5.66-5.59 (m, 1H), 4.69-4.65 (m, 2H), 4.44-4.40 (m, 2H), 1.50 (s, 9H); LCMS (ESI): m/z 461.0 $(M+H)^+$.

Intermediate Q 4-(2,2-dimethyl-1,3-dioxolan-4-yl)-1H-pyrazolo[3,4-b]pyridine-3-carbonitrile

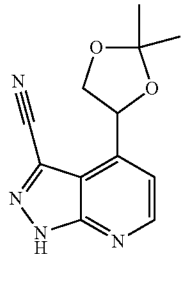 [SMILES: CC1(C)OCC(c2ccnc3[nH]nc(C#N)c23)O1]

Step 1: 4-chloro-3-iodo-1-((2-(trimethylsilyl)ethoxy)methyl)-1H-pyrazolo[3,4-b]pyridine

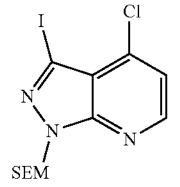 [SMILES: C[Si](C)(C)CCOCn1nc(I)c2c(Cl)ccnc21]

In a RBF equipped with a stir bar dissolve 4-chloro-3-iodo-1H-pyrazolo[3,4-b]pyridine (8000 mg, 28.626 mmol, 1 equiv.) and tetrabutylammonium bromide (93 mg, 0.01 equiv.) in DCM (100 mL). Add a solution of KOH in water (45 mass % KOH, 20 mL) and stir vigorously while cooling to 0° C. Add 2-(trimethylsilyl)ethoxymethyl chloride (5.6 mL, 1.1 equiv., 31.488 mmol) dropwise and stir overnight without removing from ice bath, allowing reaction to warm gradually. On complete consumption of the starting material, as indicated by LCMS analysis, partition the layers in a separatory funnel, then add DCM and wash the mixture with brine. Dry the organic layer over $MgSO_4$, filter, and concentrate. This gave 10.8 g of an orange solid which was taken forward in the next step without further purification (92% yield).

LCMS (ESI) $[M+H]^+$=410.050

Step 2: 4-chloro-1-((2-(trimethylsilyl)ethoxy)methyl)-1H-pyrazolo[3,4-b]pyridine-3-carbonitrile

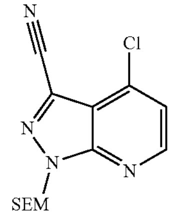 [SMILES: C[Si](C)(C)CCOCn1nc(C#N)c2c(Cl)ccnc21]

In a sealed tube equipped with a stir bar, dissolve 2-[(4-chloro-3-iodo-pyrazolo[3,4-b]pyridin-1-yl)methoxy]ethyl-trimethyl-silane (10.8 g, 26.4 mmol, 1 equiv.) and copper(I) cyanide (4.7 g, 2.0 equiv., 52.7 mmol) in DMF (50 mL). Heat to 90° C. and let stir until complete consumption of the starting material is confirmed by LCMS. At this time, pour the reaction mixture into a mixture of sat. aq. $NaHCO_3$ and brine, then dilute with iPrOAc. Wash the mixture with 0.5M $NH_4OH$ (aq), followed by 1M EDTA solution (aq). Next, wash the mixture 3 times with 10% LiCl solution (aq), then several times with brine. Dry the organic layer with $MgSO_4$, then filter and concentrate. This gave a green semi-solid which was used in the next step without purification (6.3 g, 77% yield).

LCMS (ESI) $[M+H]^+$=309.100

Step 3: 1-((2-(trimethylsilyl)ethoxy)methyl)-4-vinyl-1H-pyrazolo[3,4-b]pyridine-3-carbonitrile

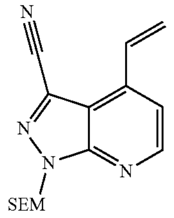 [SMILES: C=Cc1ccnc2c1c(C#N)nn2COCC[Si](C)(C)C]

To a RBF equipped with a stir bar was added XPHOS Pd-G3 (863.4 mg, 1.020 mmol, 0.05000 equiv.), potassium phosphate tribasic (11160 mg, 51.00 mmol, 2.500 equiv.), and 4-chloro-1-(2-trimethylsilylethoxymethyl)pyrazolo[3,4-b]pyridine-3-carbonitrile (6300 mg, 20.40 mmol, 1.000 equiv.). Then add 1,4-dioxane (40.80 mL) and 4,4,5,5-tetramethyl-2-vinyl-1,3,2-dioxaborolane (3770 mg, 4.15 mL, 24.48 mmol, 1.200 equiv.). The reaction mixture was degassed by bubbling nitrogen for 10 minutes, and the reaction was placed in a 50° C. heating block and allowed to stir until complete consumption of the starting materials was confirmed by LCMS. At this time, the reaction mixture is allowed to cool to room temperature, after which it is filtered through celite into a RBF containing 20 g of celite. The mixture is concentrated directly, and is then dry-loaded onto a silica column. Chromatography (0 to 100% iPrOAc/heptane) gives 2.6 g of 1-(2-trimethylsilylethoxymethyl)-4-vinyl-pyrazolo[3,4-b]pyridine-3-carbonitrile as a yellow solid (42% yield).

LCMS (ESI) $[M+H]^+$=301.200

Step 4: 4-(2,2-dimethyl-1,3-dioxolan-4-yl)-1-((2-(trimethylsilyl)ethoxy)methyl)-1H-pyrazolo[3,4-b]pyridine-3-carbonitrile

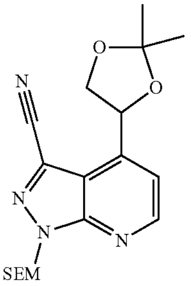 [SMILES: CC1(C)OCC(c2ccnc3c2c(C#N)nn3COCC[Si](C)(C)C)O1]

In a RBF equipped with a stir bar dissolve 1-(2-trimethylsilylethoxymethyl)-4-vinyl-pyrazolo[3,4-b]pyridine-3-carbonitrile (2600 mg, 8.655 mmol, 1 equiv.) and 4-methylmorpholine N-oxide (1150 mg, 1.1 equiv., 9.521 mmol) in DCM (35 mL). Add a solution of potassium osmate(VI) dihydrate (29 mg, 0.01 equiv., 0.08655 mmol) in water (5 mL). Stir vigorously until complete consumption of the starting material is confirmed by LCMS. On completion, add sat. aq. $Na_2S_2O_3$ to quench the reaction and stir for 20 min. Separate the layers in separatory funnel and extract the aqueous layer 3 times with 9:1 DCM:MeOH. Combine the organic layers, dry over $MgSO_4$, filter, and concentrate. This gave an orange oil which was dissolved in acetone (10 mL), and then p-TSA (151 mg, 0.1 equiv.) was added. The reaction was stirred at room temperature until completion was confirmed by LCMS, after which time it was diluted with iPrOAc and washed with sat. aq. $NaHCO_3$. The organic layer was then dried over $Na_2SO_4$, filtered, and concentrated. Purification via column (0 to 100% iPrOAc/heptane) gave 4-(2,2-dimethyl-1,3-dioxolan-4-yl)-1-(2-trimethylsilylethoxymethyl)pyrazolo[3,4-b]pyridine-3-carbonitrile (2.3 g, 71% yield) as a clear oil.

LCMS (ESI) $[M+H]^+$=375.150

Step 5: 4-(2,2-dimethyl-1,3-dioxolan-4-yl)-1H-pyrazolo[3,4-b]pyridine-3-carbonitrile

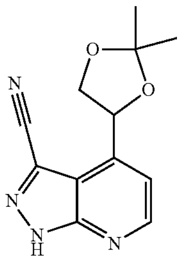 [SMILES: CC1(C)OCC(c2ccnc3[nH]nc(C#N)c23)O1]

In a RBF equipped with a stir bar dissolve 4-(2,2-dimethyl-1,3-dioxolan-4-yl)-1-(2-trimethylsilylethoxymethyl)pyrazolo[3,4-b]pyridine-3-carbonitrile (2000 mg, 5.340 mmol, 1 equiv.) in DCM (10 mL) and add TFA (10 mL). Stir at room temperature until the complete deprotection is confirmed by LCMS, then concentrate the reaction mixture directly. Add potassium carbonate (5000 mg, 36.2 mmol, 7 equiv) and acetone (40 mL) to the flask and stir until the complete disappearance of the indazole-formaldehyde adduct is confirmed by LCMS. Filter off the solids and rinse with copious acetone. Add 2,2-dimethoxypropane (10 mL, 81.1 mmol, 15 equiv.) and p-TSA (5000 mg, 28.7451 mmol, 5.4 equiv.) to the filtrate and stir until the LCMS shows complete protection of the diol. Add sat. aq. $NaHCO_3$ (aq) followed by enough solid $Na_2CO_3$ to reach pH 10 and stir for 5 minutes. Pour the mixture into a separatory funnel, then extract the mixture five times with 9:1 DCM:MeOH. Dry the combined organic fractions over $MgSO_4$, then filter and concentrate. The crude material was taken up in MeOH (5 mL) and $K_2CO_3$ (740 mg, 5.3 mmol, 1 equiv.) was added, along with ethylenediamine (0.36 mL, 1 equiv., 5.340 mmol). After stirring for 10 minutes, the LCMS trace showed complete conversion to the desired compound. The mixture was diluted with iPrOAc and filtered, then the filtrate was washed with sat. aq. $NH_4Cl$. The organic layer was dried over $MgSO_4$, filtered, and concentrated. This yielded 1000 mg of 4-(2,2-dimethyl-1,3-dioxolan-4-yl)-1H-pyrazolo[3,4-b]pyridine-3-carbonitrile as a white solid which was used without purification. LCMS (ESI) $[M+H]^+$=245.150

Intermediates R and S

Intermediate R

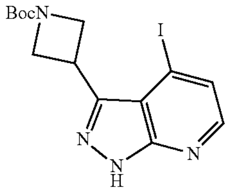

Intermediate S

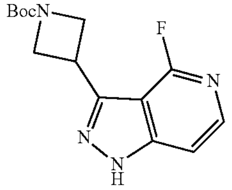

Step 1: tert-butyl 3-((2-fluoro-4-iodopyridin-3-yl)(hydroxy)methyl)azetidine-1-carboxylate

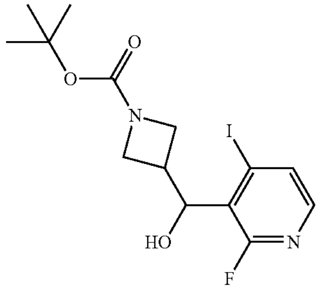 [SMILES: CC(C)(C)OC(=O)N1CC(C(O)c2c(I)ccnc2F)C1]

In a 250 mL RBF equipped with a stir bar, dissolve 2-fluoro-3-iodo-pyridine (5000 mg, 22 mmol, 1.0 equiv.) in THF (45 mL) and cool to −78° C. To this solution, add LDA (2.0 M in THF/heptane, 11.2 mL, 22 mmol, 1.0 equiv.) slowly dropwise. Stir the mixture at this temperature for 1 hr. At this time, add a solution of tert-butyl 3-formylazetidine-1-carboxylate (4153.1 mg, 22 mmol, 1.0 equiv.) in THF (6 mL) slowly dropwise. Stir at −78° C. for an hour. Then, allow the reactions to slowly warm to room temperature. On complete consumption of the starting materials, as determined by LCMS analysis, cool the reaction to 0° C. and quench with water (20 mL) followed by sat. aq. $NH_4Cl$ (20 mL). Dilute with iPrOAc, then wash with sat. aq. $NH_4Cl$ and brine. Dry the organic layer over $Na_2SO_4$, filter, and concentrate. This gives tert-butyl 3-[(2-fluoro-4-iodo-3-pyridyl)-hydroxy-methyl]azetidine-1-carboxylate (8000 mg, 87.40% Crude Yield) as a yellow semi-solid, which was used in the next step without purification.

LCMS (ESI) $[M-tBu+MeCN+H]^+$=393.700

Step 2: tert-butyl 3-(2-fluoro-4-iodonicotinoyl)azetidine-1-carboxylate

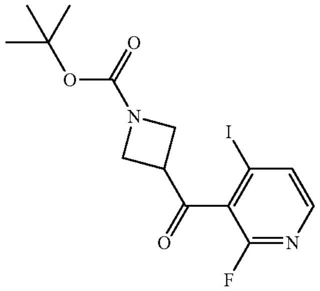 [SMILES: CC(C)(C)OC(=O)N1CC(C(=O)c2c(I)ccnc2F)C1]

In a RBF equipped with a stir bar, dissolve tert-butyl 3-[(2-fluoro-4-iodo-3-pyridyl)-hydroxy-methyl]azetidine-1-carboxylate (8000 mg, 19.60 mmol, 1 equiv.) in DCM (80 mL) and cool the solution to 0° C. Then add Dess-Martin periodinane (10461 mg, 24.665 mmol, 1.24 equiv.) portion-wise, allowing the reaction to warm to room temperature slowly after complete addition. Stir until complete consumption of the starting materials is confirmed by LCMS. At this time, dilute the reaction with iPrOAc, then wash 3× with 1M NaOH (aq), followed by brine. Dry the organic fraction over $MgSO_4$, filter, and concentrate. Column chromatography (0 to 40% iPrOAc in heptane) gives tert-butyl 3-(2-fluoro-4-iodo-pyridine-3-carbonyl)azetidine-1-carboxylate (5500 mg, 63% Yield over two steps) as a yellow oil.

LCMS (ESI) $[M-tBu+H]^+$=351.008

Step 3: tert-butyl 3-(4-iodo-1H-pyrazolo[3,4-b]pyridin-3-yl)azetidine-1-carboxylate (Common Intermediate R), and tert-butyl 3-(4-fluoro-1H-pyrazolo[4,3-c]pyridin-3-yl)azetidine-1-carboxylate (Common Intermediate S)

Intermediate R

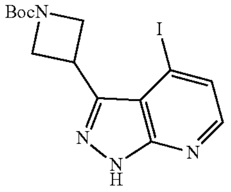

Intermediate S

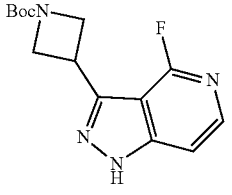

In a RBF equipped with a stir bar, dissolve tert-butyl 3-(2-fluoro-4-iodo-pyridine-3-carbonyl)azetidine-1-carboxylate (2750 mg, 6.8 mmol, 1.0 equiv.) in 1,4-dioxane (12 mL) and then add hydrazine monohydrate (1017 mg, 1.0 mL, 20.3 mmol, 3.0 equiv.). Stir at 50° C. for 15 minutes. On completion, as determined by LCMS analysis, partition the reaction mixture between DCM and sat. aq. $NH_4Cl$. Extract the aqueous layer 3× with DCM, then wash the combined organic layers with brine. Dry over $Na_2SO_4$, filter, and concentrate. Column chromatography (0 to 10% MeOH in DCM) gives tert-butyl 3-(4-iodo-1H-pyrazolo[3,4-b]pyridin-3-yl)azetidine-1-carboxylate (1440 mg, 53.1% Yield) and tert-butyl 3-(4-fluoro-1H-pyrazolo[4,3-c]pyridin-3-yl) azetidine-1-carboxylate (940 mg, 47.50% Yield), both as white solids.

LCMS (ESI) $[M+H]^+$=401.100 (Common INT R)

LCMS (ESI) $[M+H]^+$=293.15 (Common INT S)

Intermediate T

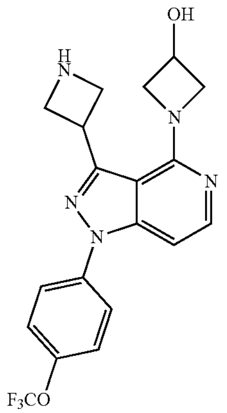

Step 1: tert-butyl 3-(4-fluoro-1-(4-(trifluoromethoxy)phenyl)-1H-pyrazolo[4,3-c]pyridin-3-yl) azetidine-1-carboxylate

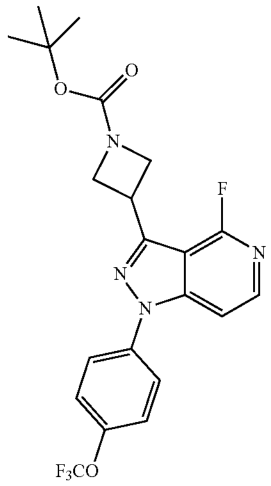 [SMILES: CC(C)(C)OC(=O)N1CC(c2nn(-c3ccc(OC(F)(F)F)cc3)c3ccnc(F)c23)C1]

Following General Procedure 1 at room temperature, 160 mg of tert-butyl 3-[4-fluoro-1-[4-(trifluoromethoxy)phenyl] pyrazolo[4,3-c]pyridin-3-yl]azetidine-1-carboxylate was isolated as a clear oil (65% yield) from Common INT C (160 mg, 0.55 mmol) and [4-(trifluoromethoxy)phenyl]boronic acid (169 mg, 0.82 mmol, 1.5 equiv).

LCMS (ESI) $[M+H]^+$=453.179

Step 2: tert-butyl 3-(4-(3-hydroxyazetidin-1-yl)-1-(4-(trifluoromethoxy)phenyl)-1H-pyrazolo[4,3-c] pyridin-3-yl)azetidine-1-carboxylate

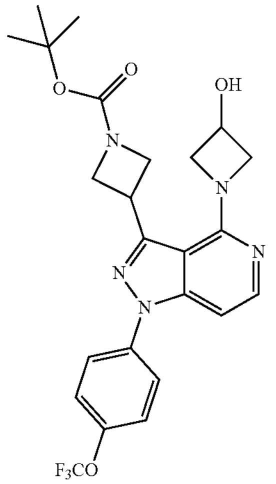 [SMILES: CC(C)(C)OC(=O)N1CC(c2nn(-c3ccc(OC(F)(F)F)cc3)c3ccnc(N4CC(O)C4)c23)C1]

In an 8 mL vial equipped with a stir bar, take up tert-butyl 3-[4-fluoro-1-[4-(trifluoromethoxy)phenyl]pyrazolo[4,3-c] pyridin-3-yl]azetidine-1-carboxylate (159 mg, 0.3515 mmol, 1.000 equiv.), azetidin-3-ol (77.06 mg, 1.054 mmol, 3.000 equiv.), and cesium carbonate (114.5 mg, 0.02781 mL, 0.3515 mmol, 1.000 equiv.) in DMSO (4 mL). Heat the reaction to 50° C. and stir at this temperature for 30 minutes, until complete conversion of the starting material is confirmed by LCMS analysis. At this time, the reaction mixture was diluted with iPrOAc and washed once with sat. aq. $NH_4Cl$, then three times with brine. The organic layer was dried over $Na_2SO_4$, filtered, and concentrated. This gave tert-butyl 3-[4-(3-hydroxyazetidin-1-yl)-1-[4-(trifluoromethoxy)phenyl]pyrazolo[4,3-c]pyridin-3-yl]azetidine-1-carboxylate (170 mg, 0.3363 mmol, 95.69% Yield) as an oil, which was used without further purification.

LCMS (ESI) $[M+H]^+$=506.250

Step 3: 1-(3-(azetidin-3-yl)-1-(4-(trifluoromethoxy) phenyl)-1H-pyrazolo[4,3-c]pyridin-4-yl)azetidin-3-ol, Common Intermediate T

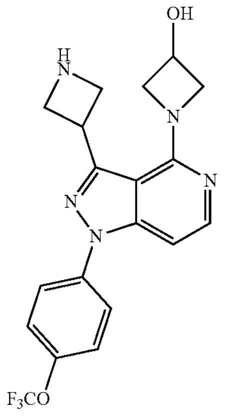 [SMILES: OC1CN(c2nccc3c2c(C2CNC2)nn3-c2ccc(OC(F)(F)F)cc2)C1]

In a RBF equipped with a stir bar dissolve tert-butyl 3-[4-(3-hydroxyazetidin-1-yl)-1-[4-(trifluoromethoxy)phenyl]pyrazolo[4,3-c]pyridin-3-yl]azetidine-1-carboxylate (170 mg, 0.3363 mmol, 1.000 equiv.) in DCM (2 mL) and then add TFA (0.2 mL, 2.645 mmol, 8 equiv.). Stir at room temperature until complete consumption of starting materials is confirmed by LCMS analysis. On completion, quench the reaction with sat. aq. $NaHCO_3$ then basify to pH 12 with 1M NaOH. Extract this mixture several times with iPrOAc, then several more times with 5:1 chloroform:isopropanol. Dry the combined organic fractions over $MgSO_4$, filter, and concentrate. This gives 1-[3-(azetidin-3-yl)-1-[4-(trifluoromethoxy)phenyl]pyrazolo[4,3-c]pyridin-4-yl]azetidin-3-ol (105 mg, 0.2590 mmol, 77.02% Yield) as a white solid, which was used without purification. LCMS (ESI) $[M+H]^+$=405.950

Intermediate U

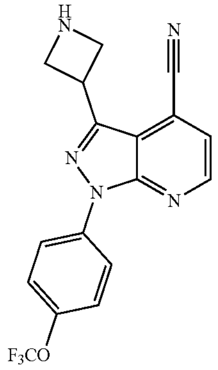

Step 1: tert-butyl 3-(4-iodo-1-(4-(trifluoromethoxy)phenyl)-1H-pyrazolo[3,4-b]pyridin-3-yl)azetidine-1-carboxylate

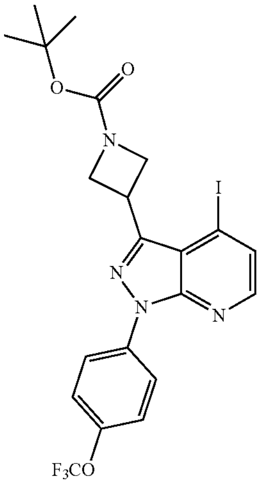 [SMILES: CC(C)(C)OC(=O)N1CC(c2nn(-c3ccc(OC(F)(F)F)cc3)c3nccc(I)c23)C1]

Following General Procedure 1 at room temperature, 200 mg of the title compound was isolated as a clear oil (50% yield) from intermediate R (285 mg, 0.71 mmol) and [4-(trifluoromethoxy)phenyl]boronic acid (220 mg, 1.07 mmol, 1.5 equiv).

LCMS (ESI) $[M+H]^+$=561.150

Step 2: tert-butyl 3-(4-cyano-1-(4-(trifluoromethoxy)phenyl)-1H-pyrazolo[3,4-b]pyridin-3-yl)azetidine-1-carboxylate

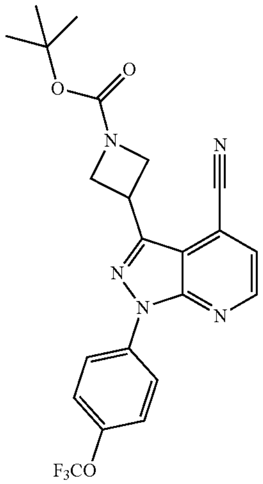 [SMILES: CC(C)(C)OC(=O)N1CC(c2nn(-c3ccc(OC(F)(F)F)cc3)c3nccc(C#N)c23)C1]

In a vial equipped with a stir bar dissolve tert-butyl 3-[4-iodo-1-[4-(trifluoromethoxy)phenyl]pyrazolo[3,4-b]pyridin-3-yl]azetidine-1-carboxylate (180 mg, 0.3213 mmol, 1.000 equiv.) and copper(I) cyanide (31.65 mg, 0.3534 mmol, 1.100 equiv.) in DMA (1.5 mL). Heat to 120° C. and stir until complete consumption of the starting materials was confirmed by LCMS analysis. The reaction was then cooled to room temperature and diluted with iPrOAc, then washed 5 times with brine. Dry the organic fraction over $MgSO_4$, filter, and concentrate. Column chromatography (silica gel, 0-100% iPrOAc in DCM) yields tert-butyl 3-[4-cyano-1-[4-(trifluoromethoxy)phenyl]pyrazolo[3,4-b]pyridin-3-yl]azetidine-1-carboxylate (103 mg, 0.22 mmol, 70% Yield) as a white solid.

LCMS (ESI) $[M-Boc+H]^+$=360.200

Step 3: 3-(azetidin-3-yl)-1-(4-(trifluoromethoxy)phenyl)-1H-pyrazolo[3,4-b]pyridine-4-carbonitrile

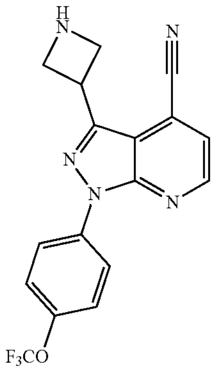 [SMILES: N#Cc1ccnc2c1c(C1CNC1)nn2-c1ccc(OC(F)(F)F)cc1]

In a RBF equipped with a stir bar, dissolve tert-butyl 3-[4-cyano-1-[4-(trifluoromethoxy)phenyl]pyrazolo[3,4-b]pyridin-3-yl]azetidine-1-carboxylate (103 mg, 0.2242 mmol, 1.000 equiv.) in DCM (2 mL), then add TFA (0.2 mL, 3 mmol, 10 equiv.). The mixture was stirred at room temperature until complete consumption of the starting materials was confirmed by LCMS analysis. At this time, the reaction was quenched with sat. aq. $NaHCO_3$, then extracted 5× with DCM, and once with 5:1 $CHCl_3$:iPrOH. The combined organic layers were dried over $MgSO_4$, filtered, and concentrated. This afforded the title compound (63 mg, 0.18 mmol, 78% Yield) as a yellow semi-solid which was used without further purification.

LCMS (ESI) $[M+H]^+$=360.150

Intermediate V ethyl 3-(((tert-butoxycarbonyl)amino)methyl)-1H-pyrazolo[3,4-b]pyridine-4-carboxylate

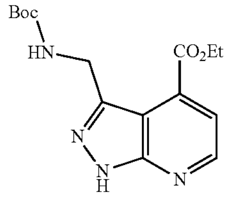 [SMILES: CCOC(=O)c1ccnc2[nH]nc(CNC(=O)OC(C)(C)C)c12]

Step 1: ethyl 6-oxo-6,7-dihydro-1H-pyrazolo[3,4-b] pyridine-4-carboxylate

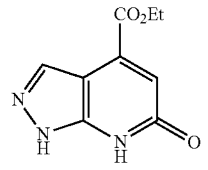

To solution of 1H-pyrazol-5-amine (2.7 kg, 32.5 mol, 1.0 eq) in $H_2O$ (27.8 L, 10.3 V) was added sodium diethyl oxalacetate (6.83 kg, 32.5 mol, 1.0 eq) at 25° C., and then AcOH (9.72 L, 3.6 V) was added at 20-30° C. The mixture was heated to an internal temperature of 85° C. and stirred for 18 hours. The reaction was monitored by HPLC until the desired product was more than 35%. The mixture was cooled to 20-25° C., and stirred for 1 hour. 2 batches (2.7 kg, and 0.83 kg) were combined, and the mixture was filtered. The filter cake was wash with $H_2O$ (2 V×2) and dried to obtain the desired product (2.2 kg, 97.3% purity, 25.0% yield) as a grey solid. $^1H$ NMR: (400 MHz, DMSO-$d_6$) δ13.34 (br, 1H), 12.12 (br, 1H), 8.16 (s, 1H), 6.67 (s, 1H), 4.36 (q, 2H), 1.36 (t, 3H).

Step 2: ethyl 6-chloro-1H-pyrazolo[3,4-b]pyridine-4-carboxylate

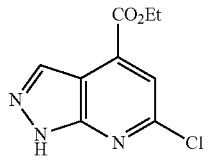 [SMILES: CCOC(=O)c1cc(Cl)nc2[nH]ncc12]

To a solution of $POCl_3$ (564 mL, 1.2 V) in MeCN (4.7 L, 10 V) was added ethyl 6-oxo-6,7-dihydro-1H-pyrazolo[3,4-b]pyridine-4-carboxylate (470 g, 2.27 mol, 1.0 eq) at 25° C., and the mixture was heated to an internal temperature between 75-80° C. and stirred for 16 hours. The reaction was monitored by HPLC until no more than 1% of starting material remained. The mixture was cooled to 40° C. and concentrated. Then iPrOAc (10 V) was added into the residue, and the mixture was added into $H_2O$ (15 V) at 20±5° C. and stirred for 1 h. The mixture was filtered through a pad of celite, and the filter cake was washed with iPrOAc (4 V). The filtrate was separated, and the aqueous layer was extracted with iPrOAc (5 V×3). 5 batches (470 g×4, and 400 g×1) were combined, and the combined organic layers were washed with brine (5 V×4), dried over $Na_2SO_4$, filtered and concentrated to obtain the desired product (2.15 kg, 96.1% purity, 86.8% yield) as a grey solid. $^1H$ NMR: (400 MHz, DMSO-$d_6$) δ 14.21 (s, 1H), 8.40 (s, 1H), 7.65 (s, 1H), 4.45 (q, 2H), 1.41 (t, 3H).

Step 3: ethyl 1H-pyrazolo[3,4-b]pyridine-4-carboxylate

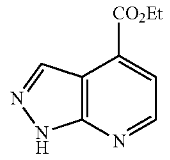

To solution of ethyl 6-chloro-1H-pyrazolo[3,4-b]pyridine-4-carboxylate (500.0 g, 2.22 mol, 1.0 eq) in THF (5.0 L, 10 V) was added TEA (246.7 kg, 2.44 mol, 1.1 eq) and Pd/C (100.0 g, 0.2 wt) at 25° C., and then the reaction was evacuated and flushed with $N_2$ followed by $H_2$ (3 times). The mixture was warmed to 40° C. and stirred for 48 hours. The reaction was monitored by HPLC until no more than 1% of starting material remained. The mixture was cooled to 25° C. and filtered, and the filter cake was washed with EtOAc (5V). 4 batches (500.0 g×4) were combined, and the combined filtrate was concentrated. Then EtOAc (20 V) was added into the residue, and the mixture was washed saturated $NaHCO_3$ aqueous (3 V×2) and brine (5 V), dried over $Na_2SO_4$, filtered and concentrated to obtain the desired product (1.38 kg, 96.4% purity, 81.4% yield) as a yellow solid. $^1H$ NMR: (400 MHz, DMSO-$d_6$) δ14.04 (br, 1H), 8.72 (d, 1H), 8.39 (s, 1H), 7.68 (s, 1H), 4.44 (q, 2H), 1.41 (t, 3H).

Step 4: ethyl 3-iodo-1H-pyrazolo[3,4-b]pyridine-4-carboxylate

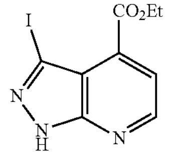 [SMILES: CCOC(=O)c1ccnc2[nH]nc(I)c12]

To solution of ethyl 1H-pyrazolo[3,4-b]pyridine-4-carboxylate (400.0 g, 2.1 mol, 1.0 eq) in DMF (8 L, 10 V) was added NIS (517.8 g, 2.3 mol, 1.1 eq) at 15° C., and the mixture was heated to 25° C. and stirred for 16 hours. The reaction was monitored by HPLC, and additional NIS (94.1 g, 0.42 mol, 0.2 eq) was added in batches (4 in total) every 16 hours until no more than 1% of the starting material remained. Once complete, the mixture was poured into ice-water (40 V), stirred for 0.5 hours and filtered. The filtrate was extracted with MTBE (5 V×3), and the filter cake was dissolved in EA (20 V). 3 batches (400.0 g×2 and 60.0 g) were combined, and the combined organic layers were washed with water (5 V×3) and brine (5 V), dried over $Na_2SO_4$, filtered and concentrated to obtain 6 (1.10 kg, 96.8% purity, 77.1% yield) as a yellow solid. $^1H$ NMR: (400 MHz, DMSO-$d_6$) δ14.45 (s, 1H) 8.68 (d, 1H), 7.44 (d, 1H), 4.46 (q, 2H), 1.40 (t, 3H).

Step 5: ethyl 3-iodo-1-((2-(trimethylsilyl)ethoxy) methyl)-1H-pyrazolo[3,4-b]pyridine-4-carboxylate

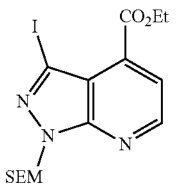 [SMILES: CCOC(=O)c1ccnc2c1c(I)nn2COCC[Si](C)(C)C]

Dissolve ethyl 3-iodo-1H-pyrazolo[3,4-b]pyridine-4-carboxylate (20000 mg, 63.08 mmol, 1.0 equiv.) and tetrabutylammonium bromide (610.0 mg, 1.892 mmol, 0.03 equiv.) in DCM (250 mL) in a 500 mL RBF equipped with a stir bar. Add KOH (45 mass %) in $H_2O$ (41.12 mL) and stir vigorously while cooling to 0° C. 2-(trimethylsilyl) ethoxymethyl chloride (11.570 g, 12 mL, 69.38 mmol, 1.10 equiv.) was then added dropwise and reaction was to gradually warmed to room temperature. The reaction was monitored by LCMS until no starting material remained.

The reaction was then transferred to a separatory funned and washed with brine. The organic layer was then dried with $Na_2SO_4$, filtered, and concentrated. Purification via column chromatography (silica gel, 0-20% iPrOAc/heptane) to give 7.26 grams of ethyl 3-iodo-1-(2-trimethylsilylethoxymethyl)pyrazolo[3,4-b]pyridine-4-carboxylate as a yellow oil (26% Yield). LCMS (ESI) $[M+H]^+$=447.900.

Step 6: ethyl 3-(((tert-butoxycarbonyl)amino) methyl)-1-((2-(trimethylsilyl)ethoxy)methyl)-1H-pyrazolo[3,4-b]pyridine-4-carboxylate

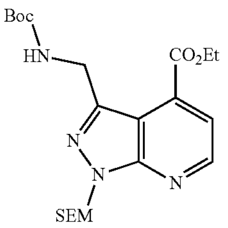 [SMILES: CCOC(=O)c1ccnc2c1c(CNC(=O)OC(C)(C)C)nn2COCC[Si](C)(C)C]

8 reactions were set up in parallel. To a 4 dram vial was added ethyl 3-iodo-1-(2-trimethylsilylethoxymethyl)pyrazolo[3,4-b]pyridine-4-carboxylate (900 mg, 2.012 mmol, 1.0 equiv.), Potassium (((tert-butoxycarbonyl)amino) methyl)trifluoroborate (1.105 grams, 4.427 mmol, 2.2 equiv.), CATACXIUM A Pd $G_2$ (137 mg, 0.2012 mmol, 0.1 equiv.), silver carbonate (277 mg, 1.006 mmol, 0.50 equiv.) and cesium carbonate (1.640 grams, 5.030 mmol, 2.5 equiv.). Tol (12 mL) and $H_2O$ (1.341 mL) were then added. The reactions were purged with $N_2$ for 10 minutes then heated to 90° C. overnight. The reactions were then cooled to room temperature, diluted with iPrOAc and combined in a separatory funnel. Organics were then washed with $H_2O$, and the aqueous phase was back extracted with iPrOAc (2×). The organic layers were combined, dried, filtered, and concentrated. Purification via column chromatography (silica gel, 0-30% iPrOAc/heptane) to give 2.61 grams of ethyl 3-[(tert-butoxycarbonylamino)methyl]-1-(2-trimethylsilylethoxymethyl)pyrazolo[3,4-b]pyridine-4-carboxylate (36%) as a yellow solid. LCMS (ESI) $[M+H]^+$=451.100.

Step 6: ethyl 3-(((tert-butoxycarbonyl)amino) methyl)-1H-pyrazolo[3,4-b]pyridine-4-carboxylate

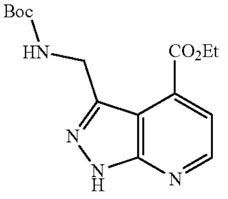 [SMILES: CCOC(=O)c1ccnc2[nH]nc(CNC(=O)OC(C)(C)C)c12]

To the 200 mL RBF equipped with a stir bar, dissolve ethyl 3-[(tert-butoxycarbonylamino)methyl]-1-(2-trimethylsilylethoxymethyl)pyrazolo[3,4-b]pyridine-4-carboxylate (2.610 grams, 5.792 mmol, 1.0 equiv.) in Hydrochloric acid (4 M in 1,4-Dioxane, 29 mL, 115.8 mmol, 20.0 equiv.). Stir until complete consumption of starting material is observed by LCMS analysis. Diluted reaction with heptane and filtered solid, which was washed with addition heptanes, collected, and dried under reduced vacuum to give intermediate ethyl 3-(aminomethyl)-1H-pyrazolo[3,4-b]pyridine-4-carboxylate as a yellow solid which was used without further purification. LCMS (ESI) $[M+H]^+$=220.950.

To a 4 dram vial containing ethyl 3-(aminomethyl)-1H-pyrazolo[3,4-b]pyridine-4-carboxylate was added anhydrous DCM (58 mL), DIPEA (4.0 mL, 23.2 mmol, 4.0 equiv.), and then Di-tert-butyl Dicarbonate (1.92 mL, 8.69 mmol, 1.50 equiv.). Reaction stirred at room temperature until complete conversion as observed by LCMS. Reaction was then concentrated under reduced pressure and purified via column chromatography (silica gel, 0-70% iPrOAc/heptane) to give 636 mg of the desired product as a white solid (34% yield over 2 steps). LCMS (ESI) $[M+H]^+$=320.950.

Intermediate W (4-bromo-1-(4-(trifluoromethoxy)phenyl)-1H-pyrazolo[3,4-b]pyridin-3-yl)methanamine

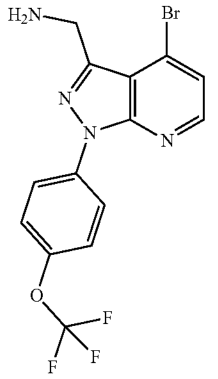 [SMILES: NCc1nn(-c2ccc(OC(F)(F)F)cc2)c2nccc(Br)c12]

To a 2 dram vial containing tert-butyl N-[[4-chloro-1-[4-(trifluoromethoxy)phenyl]pyrazolo[3,4-b]pyridin-3-yl]methyl]carbamate (450 mg, 1.016 mmol, 1.0 equiv.) was added hydrobromic acid (33 wt % in acetic acid, 1.70 mL). The reaction was heated to 60° C. and stirred until complete conversion by LCMS. Reaction then cooled to room temperature and basified with 3M NaOH. Pale yellow solid crashed out of solution, which was then collected by filtration. Washed with additional $H_2O$ and dried under reduced pressure to give (4-bromo-1-(4-(trifluoromethoxy)phenyl)-1H-pyrazolo[3,4-b]pyridin-3-yl)methanamine (387 mg, 98% Yield) as a yellow solid. LCMS (ESI) $[M+MeCN+H]^+$=427.900/429.85.

Intermediate X

4-Nitrophenyl bicyclo[1.1.0]butane-1-carboxylate

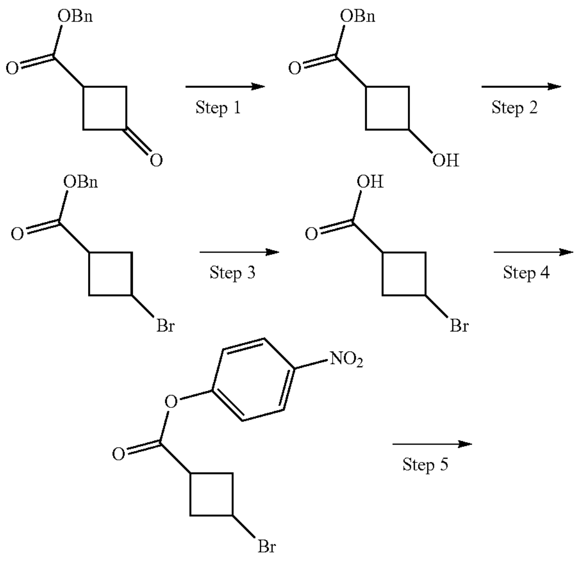

-continued

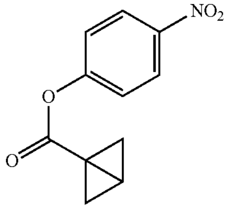

Step 1: benzyl 3-hydroxycyclobutanecarboxylate

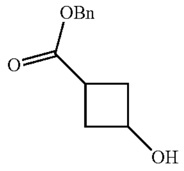 [SMILES: O=C(OCc1ccccc1)C1CC(O)C1]

To a solution of benzyl 3-oxocyclobutanecarboxylate (1.0 g, 4.9 mmol) in THF (10 mL) was added $NaBH_4$ (140 mg, 3.7 mmol) at 0° C. The mixture was stirred at 0° C. for 1 hour. The mixture was quenched with water (20 mL), extracted with ethyl acetate (20 mL×2), the organic layer was washed with brine (20 mL), dried over $Na_2SO_4$, concentrated and the residue was purified by flash chromatography on silica gel (0-20% ethyl acetate in petroleum ether) to afford the title compound (900 mg, 89%) as a yellow oil. $^1H$ NMR (400 MHz, $CDCl_3$): δ 7.40-7.29 (m, 5H), 5.13 (s, 2H), 4.25-4.15 (m, 1H), 2.76-2.60 (m, 3H), 2.30-2.08 (m, 2H).

Step 2: benzyl 3-bromocyclobutanecarboxylate

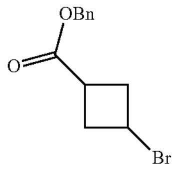 [SMILES: O=C(OCc1ccccc1)C1CC(Br)C1]

To a stirred suspension of $PPh_3$ (1.07 g, 4.09 mmol), LiBr (187 mg, 2.15 mmol) and benzyl 3-hydroxycyclobutanecarboxylate (800 mg, 3.88 mmol) in THF (15 mL) was added $CBr_4$ (1.29 g, 3.88 mmol) at 0° C. The resulting clear solution was stirred at 50° C. for 12 hours to give a cream suspension. The reaction mixture was diluted with MTBE (10 mL) and solid materials were removed by filtration through a pad of Celite®. The filtrate was washed with water (10 mL) and brine (10 mL), dried over $Na_2SO_4$ and concentrated in vacuo. The residue was purified by flash column chromatography on silica gel (0-5% ethyl acetate in petroleum ether) to afford the title compound (600 mg, 58%) as a colorless oil. $^1H$ NMR (400 MHz, $CDCl_3$): δ 7.30-7.19 (m, 5H), 5.08 (m, 2H), 4.60-4.52 (m, 1H), 3.35-3.31 (m, 1H), 2.90-2.83 (m, 2H), 2.65-2.59 (m, 2H).

Step 3: 3-bromocyclobutanecarboxylic acid

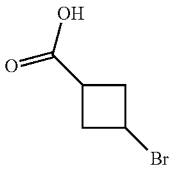

To a stirred solution of benzyl 3-bromocyclobutanecarboxylate (320 mg, 1.19 mmol) in THF (10 mL) was added 5M aq. NaOH (0.24 mL, 1.19 mmol). The solution was stirred at 50° C. for 6 hours, the mixture was then cooled to ambient temperature and further stirred at room temperature for 13 hours. The reaction mixture was concentrated in vacuo to afford the title compound (212 mg, crude) as a white solid, which was used in the next step without further purification.

Step 4: 4-nitrophenyl 3-bromocyclobutanecarboxylate

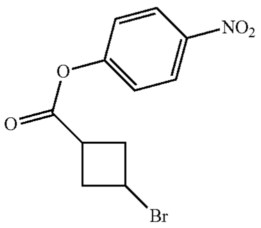 [SMILES: O=C(Oc1ccc([N+](=O)[O-])cc1)C1CC(Br)C1]

To a stirred solution of 3-bromocyclobutanecarboxylic acid (212 mg, 1.18 mmol) and EDCI (295 mg, 1.54 mmol) in DCM (5 mL) was added 4-nitrophenol (329 mg, 2.37 mmol) and DMAP (29 mg, 0.24 mmol) at room temperature. The reaction solution was stirred at room temperature for 15 hours. The reaction mixture was diluted with sat. aq. $NaHCO_3$ (10 mL) and the aqueous phase was extracted with ethyl acetate (10 mL×2). The combined organic layers were washed with brine (10 mL), dried over $Na_2SO_4$ and concentrated in vacuo. The residue was purified by flash column chromatography on silica gel (0-10% ethyl acetate in petroleum ether) to afford the title compound (200 mg, 56%) as a colorless oil. $^1H$ NMR (400 MHz, $CDCl_3$): δ 8.23-8.20 (m, 2H), 7.24-7.18 (m, 2H), 4.68-4.62 (m, 1H), 3.66-3.59 (m, 1H), 3.06-2.97 (m, 2H), 2.81-2.76 (m, 2H).

Step 5: 4-nitrophenyl bicyclo[1.1.0]butane-1-carboxylate

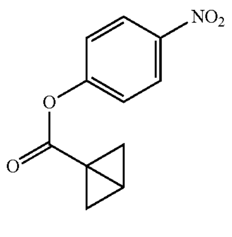 [SMILES: O=C(Oc1ccc([N+](=O)[O-])cc1)C12CC1C2]

To a stirred solution of 4-nitrophenyl 3-bromocyclobutanecarboxylate (200 mg, 0.67 mmol) in toluene (5 mL) was added LiHMDS (0.87 mL, 0.87 mmol, 1M/L in THF) at 0° C. The solution was stirred at 0° C. for 1 hour. The reaction mixture was quenched with sat. aq. $NH_4Cl$ (10 mL) and the aqueous phase was extracted with ethyl acetate (10 mL×3). The combined organic layers were washed with brine (10 mL), dried over $Na_2SO_4$ and concentrated in vacuo. The residue was purified by flash column chromatography on silica gel (0-10% ethyl acetate in petroleum ether) to afford the title compound (100 mg, 69%) as a yellow oil. $^1H$ NMR (400 MHz, $CDCl_3$): δ 8.22-8.17 (m, 2H), 7.27-7.19 (m, 2H), 2.48-2.45 (m, 2H), 2.41-2.35 (m, 1H), 1.31-1.28 (m, 2H).

Example 1

N-((1-(4-(trifluoromethoxy)phenyl)-1H-indazol-3-yl)methyl)acrylamide (Compound 1)

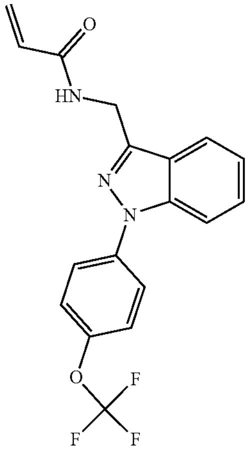 [SMILES: C=CC(=O)NCc1nn(-c2ccc(OC(F)(F)F)cc2)c2ccccc12]

Step 1: tert-butyl ((1-(4-(trifluoromethoxy)phenyl)-1H-indazol-3-yl)methyl)carbamate

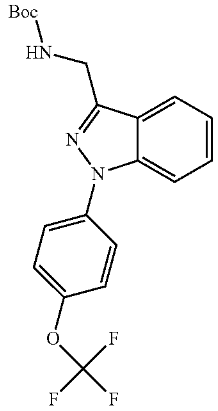

Following General Procedure A: A flask containing tert-butyl N-(1H-indazol-3-ylmethyl)carbamate (500 mg, 2.0 mmol) was charged with copper(II) acetate (550 mg, 3.0 mmol, 1.5 equiv), [4-(trifluoromethoxy)phenyl]boronic acid (832 mg, 4.0 mmol, 2.0 equiv.), activated 4 Å mol sieves (300 mg) and acetonitrile (25 mL), followed by pyridine (650 µL, 8.0 mmol, 4 equiv.). The reaction was stirred at room temp for 36 hours, after which time it was filtered through Celite® and concentrated. Purification via column chromatography (silica gel, 0 to 100% iPrOAc/Heptane) gave 750 mg of the desired product as a yellow semi-solid (91% yield). LCMS (ESI) $[M+H]^+$=407.950

Step 2: (1-(4-(trifluoromethoxy)phenyl)-1H-indazol-3-yl)methanamine) hydrochloric acid salt

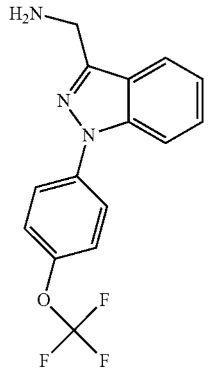 [SMILES: NCc1nn(-c2ccc(OC(F)(F)F)cc2)c2ccccc12]

Dissolve tert-butyl N-[[1-[4-(trifluoromethoxy)phenyl]indazol-3-yl]methyl]carbamate (130 mg, 0.32 mmol) in 1,4-Dioxane (1 mL) and cool the reaction mixture to 0° C. Add hydrochloric acid in 1,4-dioxane (1 mL, 4 M) and warm to room temp overnight while stirring. Concentrate directly to obtain [1-[4-(trifluoromethoxy)phenyl]indazol-3-yl]methylamine as the HCl salt (110 mg, 100% yield). LCMS (ESI) $[M+H]^+$=308.100

Step 3: N-((1-(4-(trifluoromethoxy)phenyl)-1H-indazol-3-yl)methyl)acrylamide

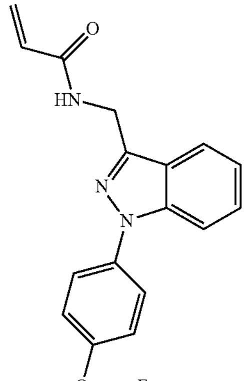

In a vial equipped with a stir bar, dissolve [1-[4-(trifluoromethoxy)phenyl]indazol-3-yl]methylammonium chloride (50 mg, 0.15 mmol) in dichloromethane (1.5 mL) and add TEA (43 µL, 0.31 mmol, 2.1 equiv). Cool to 0° C. Slowly add prop-2-enoyl chloride (12.9 µL, 0.16 mmol, 1.1 equiv). Gradually warm to room temperature while stirring. After 30 minutes, reaction was diluted with iPrOAc and washed with water, brine, and sat. aq. $NH_4Cl$. The crude mixture was purified by preparative HPLC (XSelect CSH Prep C18, 30-70% MeCN/water, 0.1% FA modifier) to yield 16.2 mg of the desired compound as a white solid (30% yield). $^1H$ NMR (400 MHz, DMSO-$d_6$) δ 8.78 (t, J=5.9 Hz, 1H), 7.96-7.86 (m, 3H), 7.91-7.83 (m, 1H), 7.59 (d, J=8.5 Hz, 2H), 7.53 (ddd, J=8.3, 6.9, 1.2 Hz, 1H), 7.34-7.24 (m, 1H), 6.28 (dd, J=17.1, 9.9 Hz, 1H), 6.17 (dd, J=17.1, 2.4 Hz, 1H), 5.64 (dd, J=9.9, 2.4 Hz, 1H), 4.79 (d, J=5.9 Hz, 2H). LCMS (ESI) $[M+H]^+$=362.000

Example 2

2-chloro-N-((1-(4-(trifluoromethoxy)phenyl)-1H-indazol-3-yl)methyl)acetamide (Compound 2)

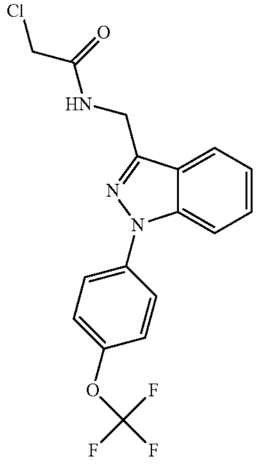 [SMILES: O=C(CCl)NCc1nn(-c2ccc(OC(F)(F)F)cc2)c2ccccc12]

In a vial equipped with a stir bar, dissolve [1-[4-(trifluoromethoxy)phenyl]indazol-3-yl]methylammonium chloride (50 mg, 0.15 mmol) in dichloromethane (1.5 mL) and add TEA (43 µL, 0.31 mmol, 2.1 equiv). Cool the reaction mixture to 0° C. and slowly add 2-chloroacetyl chloride (12.7 µL, 0.16 mmol, 1.1 equiv.) Gradually warm the reaction mixture to room temperature while stirring. After 30 minutes, the reaction mixture was put directly on a silica column (0 to 10% MeOH/DCM gradient). The isolated material was further purified by preparative HPLC (Gemini-NX C18, 5-85% MeCN/water) to give the desired compound as a white solid (38 mg, 67% yield). $^1H$ NMR (400 MHz, DMSO-$d_6$) δ 8.92 (t, J=5.8 Hz, 1H), 7.97-7.83 (m, 4H), 7.64-7.55 (m, 2H), 7.53 (ddd, J=8.3, 6.9, 1.2 Hz, 1H), 7.35-7.25 (m, 1H), 4.74 (d, J=5.8 Hz, 2H), 4.13 (s, 2H). LCMS (ESI) $[M+H]^+$=384.000

Example 3

N-((1-(4-(pentafluoro-λ$^6$-sulfanyl)phenyl)-1H-indazol-3-yl)methyl)acrylamide (Compound 3)

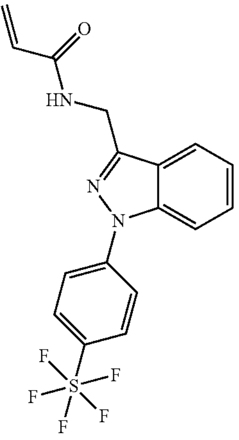 [SMILES: C=CC(=O)NCc1nn(-c2ccc(S(F)(F)(F)(F)F)cc2)c2ccccc12]

Step 1: tert-butyl ((1-(4-(pentafluoro-λ$^6$-sulfanyl) phenyl)-1H-indazol-3-yl)methyl)carbamate

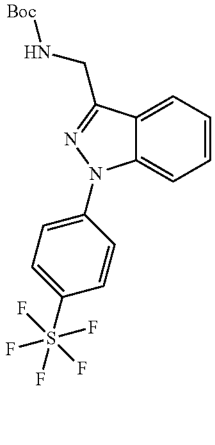 [SMILES: CC(C)(C)OC(=O)NCc1nn(-c2ccc(S(F)(F)(F)(F)F)cc2)c2ccccc12]

Following General Procedure A (except that Bpin was used instead of boronic acid): A flask containing tert-butyl N-(1H-indazol-3-ylmethyl)carbamate (250 mg, 1.0 mmol) was charged with copper(II) acetate (275 mg, 1.5 mmol, 1.5 equiv), 4,4,5,5-tetramethyl-2-(4-(pentafluoro-λ$^6$-sulfanyl) phenyl)-1,3,2-dioxaborolane (660 mg, 2.0 mmol, 2.0 equiv), activated 4 Å mol sieves (150 mg) and acetonitrile (12 mL), followed by pyridine (325 μL, 4.0 mmol, 4 equiv). The reaction mixture was stirred at room temperature for seven days, after which time it was filtered through Celite® and concentrated. Purification via column (silica gel, 0 to 100% iPrOAc/heptane) gave 245 mg of tert-butyl N-[[1-[4-(pentafluoro-λ$^6$-sulfanyl)phenyl]indazol-3-yl]methyl]carbamate as a white solid (54% yield). LCMS (ESI) $[M+H]^+$=450.150

Step 2: N-((1-(4-(pentafluoro-λ$^6$-sulfanyl)phenyl)-1H-indazol-3-yl)methyl)acrylamide

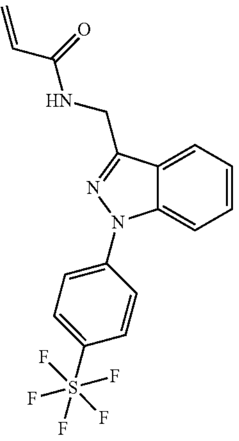 [SMILES: C=CC(=O)NCc1nn(-c2ccc(S(F)(F)(F)(F)F)cc2)c2ccccc12]

In a vial equipped with a stir bar, dissolve tert-butyl N-[[1-[4-(pentafluoro-λ$^6$-sulfanyl)phenyl]indazol-3-yl] methyl]carbamate (56 mg, 0.12 mmol) in dichloromethane (1 mL). Add trifluoroacetic acid (250 μL, 3.3 mmol) and stir until all starting material has been consumed as indicated by LCMS analysis of the reaction mixture. Concentrate the reaction mixture directly then dissolve the crude amine in DCM (1 mL) and cool to 0° C. Add DIPEA (5.0 equiv., 0.108 mL, 0.62 mmol) and acryloyl chloride (1.0 equiv, 10 μL, 0.12 mmol). Then warm the reaction mixture to room temperature. Upon consumption of the starting materials as indicated by LCMS analysis of the reaction mixture, concentrate the reaction and then purify via column chromatography (silica gel, 0 to 10% MeOH in DCM). 26 mg N-[[1-[4-(pentafluoro-λ$^6$-sulfanyl)phenyl]indazol-3-yl] methyl]prop-2-enamide was obtained as a white solid (52% yield). $^1$H NMR (400 MHz, DMSO) δ 8.84 (t, J=5.8 Hz, 1H), 8.16-8.08 (m, 2H), 8.08-7.98 (m, 3H), 7.98-7.90 (m, 1H), 7.59 (ddd, J=8.4, 7.0, 1.2 Hz, 1H), 7.39-7.30 (m, 1H), 6.28 (dd, J=17.1, 9.9 Hz, 1H), 6.17 (dd, J=17.1, 2.4 Hz, 1H), 5.65 (dd, J=9.9, 2.4 Hz, 1H), 4.80 (d, J=5.9 Hz, 2H). LCMS (ESI) $[M+H]^+$=404.000

Example 4

N-((4-(hydroxymethyl)-1-(4-(trifluoromethoxy)phenyl)-1H-indazol-3-yl)methyl)acrylamide (Compound 4)

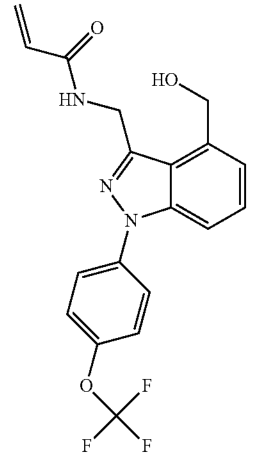 [SMILES: C=CC(=O)NCc1nn(-c2ccc(OC(F)(F)F)cc2)c2cccc(CO)c12]

Step 1: methyl 3-bromo-1-(4-(trifluoromethoxy) phenyl)-1H-indazole-4-carboxylate

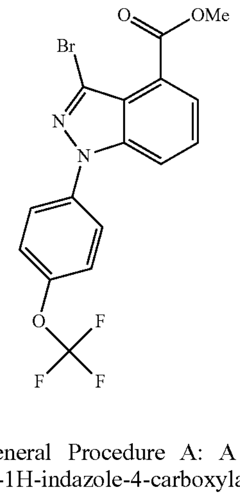

Following General Procedure A: A flask containing methyl 3-bromo-1H-indazole-4-carboxylate (500 mg, 1.96 mmol) was charged with copper(II) acetate (540 mg, 2.94 mmol, 1.5 equiv), [4-(trifluoromethoxy)phenyl]boronic acid (815 mg, 3.9 mmol, 2.0 equiv), activated 4 Å mol sieves (300 mg) and acetonitrile (25 mL) followed by pyridine (640 μL, 7.8 mmol, 4 equiv). The reaction was stirred at room temp overnight, after which time it was filtered through Celite® and concentrated. Purification via silica gel chromatography (0 to 100% iPrOAc/heptane) gave 650 mg of product as a white solid (78% yield). LCMS (ESI) $[M+4]^+$=455.750

Step 2: (3-bromo-1-(4-(trifluoromethoxy)phenyl)-1H-indazol-4-yl)methanol

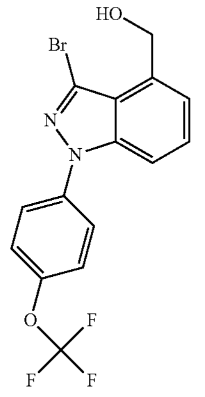 [SMILES: OCc1cccc2c1c(Br)nn2-c1ccc(OC(F)(F)F)cc1]

In an oven-dried vial, suspend methyl 3-bromo-1-[4-(trifluoromethoxy)phenyl]indazole-4-carboxylate (350 mg, 0.90 mmol) in THF (3 mL) and cool to 0° C. Then lithium aluminum hydride (51 mg, 1.4 mmol, 1.5 equiv) was suspended in 3 mL of THF and added dropwise to the solution of the ester. Stir at 0° C. until consumption of the starting materials as indicated by LCMS analysis of the reaction mixture. The reaction is then quenched with EtOH by dropwise addition at 0° C. and then sat. aq. Rochelle's salt is added to the mixture. The reaction is then filtered and washed with iPrOAc. The biphasic filtrate is poured into a separatory funnel and washed with brine. Dry organic layer over $Na_2SO_4$, filter, and concentrate. Obtained 220 mg of yellow/white solid, which was used without further purification (67% yield). LCMS (ESI) $[M+H]^+$=386.900

Step 3: 4-(hydroxymethyl)-1-(4-(trifluoromethoxy) phenyl)-1H-indazole-3-carbonitrile

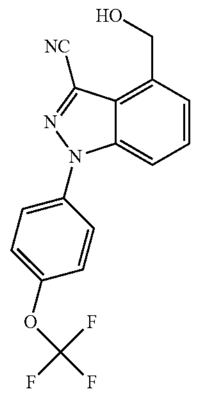 [SMILES: N#Cc1nn(-c2ccc(OC(F)(F)F)cc2)c2cccc(CO)c12]

Weigh [3-bromo-1-[4-(trifluoromethoxy)phenyl]indazol-4-yl]methanol (156 mg, 0.4 mmol), tBuXphos Pd G3 (34 mg, 0.1 equiv., 0.04029 mmol, 95 mass %), and zinc cyanide (297 mg, 0.81 mmol. 0 equiv) into a microwave vial equipped with a stir bar. Add N,N-dimethylacetamide (1.5 mL) and degas the mixture by bubbling nitrogen for 10 minutes. Seal the vial and heat the reaction mixture to 100° C. in a microwave reactor for 12 hours. The reaction mixture was diluted with iPrOAc and washed with water and brine.

The organic layer was dried over $Na_2SO_4$, filtered, and concentrated. Purification via column chromatography (silica gel, 0 to 100% iPrOAc/heptane) gave 50 mg of 4-(hydroxymethyl)-1-[4-(trifluoromethoxy)phenyl]indazole-3-carbonitrile and the dehalogenated byproduct as a mixture (~2.5:1 DP:BP) as an off-white solid. This material was taken forward without further purification (27% yield corrected for purity). LCMS (ESI) $[M+H]^+$=334.100

Step 4: N-((4-(hydroxymethyl)-1-(4-(trifluoromethoxy)phenyl)-1H-indazol-3-yl)methyl)acrylamide

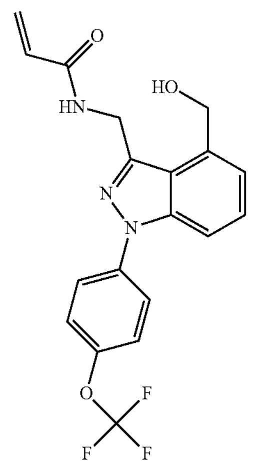 [SMILES: C=CC(=O)NCc1nn(-c2ccc(OC(F)(F)F)cc2)c2cccc(CO)c12]

In an oven-dried vial equipped with a stir bar, suspend lithium aluminum hydride (6 mg, 0.15 mmol, 1 equiv) in THF (1 mL) and cool the mixture to 0° C. Then dissolve 4-(hydroxymethyl)-1-[4-(trifluoromethoxy)phenyl]indazole-3-carbonitrile (50 mg, 0.15 mmol) in THF (1 mL) and add dropwise to reaction vial. Stir at 0° C., adding more LAH portionwise until the reaction goes to completion (6 equiv in total required for reaction completion). Upon consumption of the starting materials, as indicated by LCMS analysis of the reaction mixture, quench the cooled reaction with EtOH and then add sat. aq. $NH_4Cl$ followed by sat. aq. Rochelle salt (final pH between 9-10). Add iPrOAc (5 mL) to the mixture and stir vigorously. Let the emulsion settle and then separate the organic layer. Add more iPrOAc (5 mL) and repeat the procedure. Combine the organic layers, dry over $Na_2SO_4$ and filter into a RBF. Add triethylamine to the reaction mixture (21 µL, 0.15 mmol, 1 equiv), cool to 0° C. and then add acryloyl chloride (13.5 µL, 0.165 mmol, 1.1 equiv) slowly. Stir at 0° C. until consumption of the starting materials as indicated by LCMS analysis of the reaction mixture. Concentrate the mixture directly and then purify via column chromatography (silica gel, 0 to 10% MeOH/DCM) to give 17 mg of N-[[4-(hydroxymethyl)-1-[4-trifluoromethoxyphenyl]indazol-3-yl]methyl]prop-2-enamide as an off-white solid (40% yield over two steps, accounting for starting material impurity). 1H NMR (400 MHz, DMSO) δ 8.62 (t, J=5.1 Hz, 1H), 7.88 (d, J=8.9 Hz, 2H), 7.74 (d, J=8.5 Hz, 1H), 7.60 (d, J=8.5 Hz, 2H), 7.48 (t, J=7.8 Hz, 1H), 7.31 (d, J=7.1 Hz, 1H), 6.32 (dd, J=17.3, 10.2 Hz, 1H), 6.15 (dd, J=17.3, 1.9 Hz, 1H), 5.70-5.57 (m, 1H), 5.45 (t, J=5.3 Hz, 1H), 4.91 (d, J=5.4 Hz, 2H), 4.87 (d, J=5.1 Hz, 2H). LCMS (ESI) $[M+H]^+$=392.150

Example 5

N-((4-(hydroxymethyl)-1-(4-(pentafluoro-$\lambda^6$-sulfanyl)phenyl)-1H-indazol-3-yl)methyl)acrylamide (Compound 5)

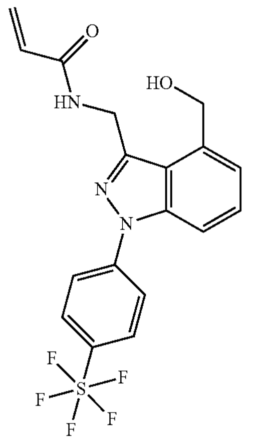 [SMILES: C=CC(=O)NCc1nn(-c2ccc(S(F)(F)(F)(F)F)cc2)c2cccc(CO)c12]

For this example the same sequence of steps was followed as for Example 4, except that [4-(pentafluoro-$\lambda^6$-sulfanyl)phenyl]boronic acid was used in the first step instead of [4-(trifluoromethoxy)phenyl]boronic acid.

Step 1: methyl 3-bromo-1-(4-(pentafluoro-$\lambda^6$-sulfanyl)phenyl)-1H-indazole-4-carboxylate

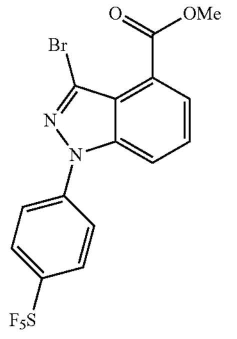

500 mg of methyl 3-bromo-1-[4-(pentafluoro-$\lambda^6$-sulfanyl)phenyl]indazole-4-carboxylate was obtained (93% yield). LCMS (ESI) $[M+H]^+$=456.996

Step 2: (3-bromo-1-(4-(pentafluoro-λ$^6$-sulfanyl)phenyl)-1H-indazol-4-yl)methanol

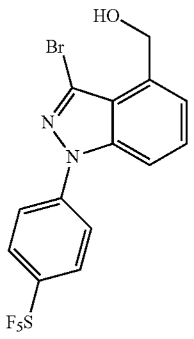

450 mg of [3-bromo-1-[4-(pentafluoro-λ$^6$-sulfanyl)phenyl]indazol-4-yl]methanol was obtained as a yellow oil (96% yield, crude). LCMS (ESI) $[M+H]^+$=429.000

Step 3: 4-(hydroxymethyl)-1-(4-(pentafluoro-λ$^6$-sulfanyl)phenyl)-1H-indazole-3-carbonitrile

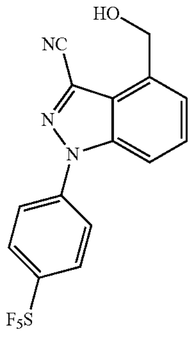

175 mg of 4-(hydroxymethyl)-1-[4-(pentafluoro-λ$^6$-sulfanyl)phenyl]indazole-3-carbonitrile was obtained as an off-white solid (45% yield). LCMS (ESI) $[M+H]^+$=375.900

Step 4: N-((4-(hydroxymethyl)-1-(4-(pentafluoro-λ$^6$-sulfanyl)phenyl)-1H-indazol-3-yl)methyl)acrylamide

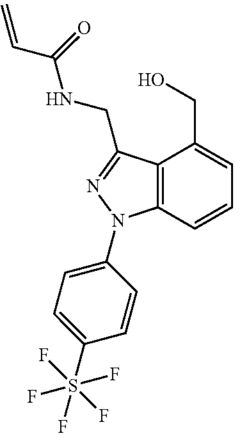 [SMILES: C=CC(=O)NCc1nn(-c2ccc(S(F)(F)(F)(F)F)cc2)c2cccc(CO)c12]

22 mg of N-[[4-(hydroxymethyl)-1-[4-(pentafluoro-λ$^6$-sulfanyl)phenyl]indazol-3-yl]methyl]prop-2-enamide was obtained as a white solid following preparative HPLC (XSelect CSH Prep C18, 20-60% MeCN/water, 0.1% formic acid modifier) (16% yield). $^1$H NMR (400 MHz, DMSO-$d_6$) δ 8.63 (t, J=5.2 Hz, 1H), 8.15-8.06 (m, 2H), 8.02 (d, J=8.9 Hz, 2H), 7.88 (d, J=8.5 Hz, 1H), 7.54 (dd, J=8.6, 7.1 Hz, 1H), 7.35 (d, J=7.1 Hz, 1H), 6.32 (dd, J=17.1, 10.1 Hz, 1H), 6.15 (dd, J=17.1, 2.2 Hz, 1H), 5.63 (dd, J=10.1, 2.3 Hz, 1H), 5.46 (t, J=5.3 Hz, 1H), 4.92 (d, J=5.1 Hz, 2H), 4.88 (d, J=5.1 Hz, 2H). LCMS (ESI) $[M+H]^+$=434.000

Example 6

N-((4-(1,2-dihydroxyethyl)-1-(4-(trifluoromethoxy)phenyl)-1H-indazol-3-yl)methyl)acrylamide (Compounds 6-8)

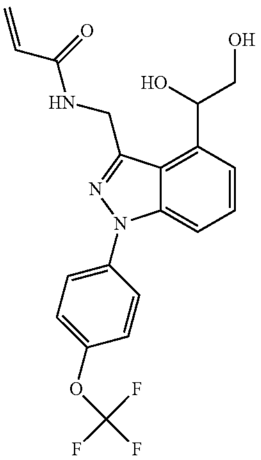 [SMILES: C=CC(=O)NCc1nn(-c2ccc(OC(F)(F)F)cc2)c2cccc(C(O)CO)c12]

Step 1: 4-bromo-1-((2-(trimethylsilyl)ethoxy)methyl)-1H-indazole-3-carbonitrile

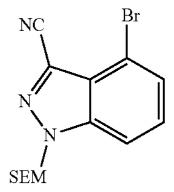 [SMILES: C[Si](C)(C)CCOCn1nc(C#N)c2c(Br)cccc21]

In a vial equipped with a stir bar, dissolve 4-bromo-1H-indazole-3-carbonitrile (1000 mg, 4.5 mmol) and tetrabutylammonium bromide (14.5 mg, 0.045 mmol, 0.01 equiv) in dichloromethane (20 mL). Add potassium hydroxide in water (45 mass % KOH, 4 mL) and stir vigorously while cooling to 0° C. Add 2-(trimethylsilyl)ethoxymethyl chloride (0.88 mL, 4.95 mmol, 1.1 equiv) dropwise and stir overnight allowing reaction to warm gradually to room temperature. Partition the layers in a separatory funnel, then extract the aqueous layer with DCM and wash the combined organic layers with brine. Dry the organic layer over $MgSO_4$, filter, and concentrate. Purification via column chromatography (silica gel, 0 to 100% iPrOAc/heptane) gave a mixture of regioisomers as a red oil (1.3 g total, ~2:1 r.r., 82% yield). LCMS (ESI) $[M+H]^+$=324.06

Step 2: 1-((2-(trimethylsilyl)ethoxy)methyl)-4-vinyl-1H-indazole-3-carbonitrile

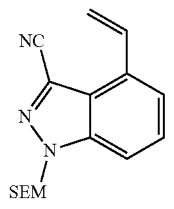 [SMILES: C=Cc1cccc2c1c(C#N)nn2COCC[Si](C)(C)C]

To a vial equipped with a stir bar was added X-Phos Pd G3 (94 mg, 0.11 mmol, 0.05 equiv.), potassium phosphate tribasic (2019 mg, 9.23 mmol, 2.5 equiv.), and 4-bromo-1-(2-trimethylsilylethoxymethyl)indazole-3-carbonitrile (1300 mg, 3.7 mmol). Then add 1,4-dioxane (7.4 mL), 4,4,5,5-tetramethyl-2-vinyl-1,3,2-dioxaborolane (751 µL, 4.4 mmol, 1.2 equiv), and water (2 mL). The reaction mixture was degassed by bubbling nitrogen for 10 minutes, the reaction was placed in a 50° C. heating block and allowed to stir overnight. Upon consumption of the starting materials as indicated by LCMS analysis of the reaction mixture, dilute with iPrOAc, filter through Celite® and concentrate. Column chromatography (silica gel, 0 to 100% iPrOAc/heptane) gave 1000 mg of red oil which was a mixture of regioisomers (90% yield). LCMS (ESI) $[M+H]^+$=300.208

Steps 3: 4-(2,2-dimethyl-1,3-dioxolan-4-yl)-14 (2-(trimethylsilyl)ethoxy)methyl)-1H-indazole-3-carbonitrile

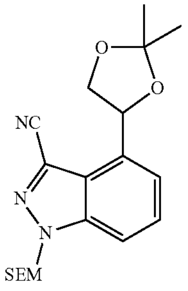 [SMILES: CC1(C)OCC(c2cccc3c2c(C#N)nn3COCC[Si](C)(C)C)O1]

Dissolve 1-(2-trimethylsilylethoxymethyl)-4-vinyl-indazole-3-carbonitrile (1000 mg, 3.3 mmol) and 3-chloroperoxybenzoic acid (922 mg, 4.0 mmol, 1.2 equiv, 75 mass %) in dichloromethane (10.0 mL) in a RBF equipped with a stir bar. Stir at room temperature until consumption of the starting materials as indicated by LCMS analysis of the reaction mixture is visualized. Upon completion, dilute with iPrOAc and wash 1× with sat. aq. $Na_2S_2O_3$, 3× with sat. aq. $NaHCO_3$, then 1× with brine. Dry the organic layer over $Na_2SO_4$, filter, and concentrate. This gave 540 mg of a red oil which was used directly. Dissolve crude epoxide in acetone (2 mL). Then add p-toluenesulfonic acid (86 mg, 0.5 mmol, 0.15 equiv) and stir for 90 minutes. At this point the reaction mixture was concentrated. Purification via column chromatography (0 to 100% iPrOAc/Heptane) gave 440 mg of 4-(2,2-dimethyl-1,3-dioxolan-4-yl)-1-(2-trimethylsilylethoxymethyl)indazole-3-carbonitrile as a yellow oil (35% yield over two steps). LCMS (ESI) $[M+H]^+$=373.997

Step 4: 4-(2,2-dimethyl-1,3-dioxolan-4-yl)-1H-indazole-3-carbonitrile

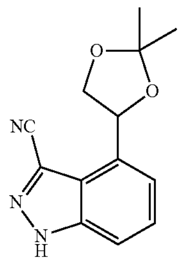 [SMILES: CC1(C)OCC(c2cccc3[nH]nc(C#N)c23)O1]

In a RBF equipped with a stir bar, dissolve 4-(2,2-dimethyl-1,3-dioxolan-4-yl)-1-(2-trimethylsilylethoxymethyl)indazole-3-carbonitrile (430 mg, 1.2 mmol) in THF (5 mL) and add TBAF solution (5 equiv, 5.8 mmol, 5.8 mL, 1M in THF). Stir the reaction mixture at 35° C. overnight. Then the reaction was heated to 60° C. for a further 3 hours. Upon consumption of the starting materials as indicated by LCMS analysis of the reaction mixture, the reaction was cooled to room temperature and diluted with iPrOAc. The organic phase was washed 3× with a water/brine mixture (1:1). The organic layer was dried over $MgSO_4$, filtered, and concentrated. Obtained 300 mg of yellow oil which was used without purification in the next step (100% yield). LCMS (ESI) $[M+H]^+$=244.325

Step 5: 4-(2,2-dimethyl-1,3-dioxolan-4-yl)-1-(4-(trifluoromethoxy)phenyl)-1H-indazole-3-carbonitrile

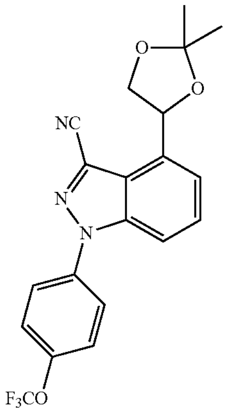 [SMILES: CC1(C)OCC(c2cccc3c2c(C#N)nn3-c2ccc(OC(F)(F)F)cc2)O1]

Following general procedure A, 90 mg of 4-(2,2-dimethyl-1,3-dioxolan-4-yl)-1-[4-(trifluoromethoxy)phenyl]indazole-3-carbonitrile was obtained as a white solid (48% yield). LCMS (ESI) $[M+H+MeCN]^+$=445.171

Step 6: N-((4-(1,2-dihydroxyethyl)-1-(4-(trifluoromethoxy)phenyl)-1H-indazol-3-yl)methyl)acrylamide

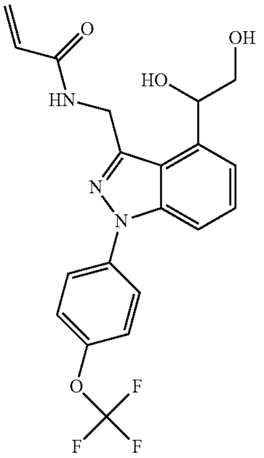 [SMILES: C=CC(=O)NCc1nn(-c2ccc(OC(F)(F)F)cc2)c2cccc(C(O)CO)c12]

In a vial equipped with a stir bar, dissolve 4-(2,2-dimethyl-1,3-dioxolan-4-yl)-1-[4-(trifluoromethoxy)phenyl]indazole-3-carbonitrile (90 mg, 0.22 mmol) in THF (0.3 mL, 0.75 M wrt nitrile) and cool to 0° C. Then add borane-tetrahydrofuran complex (1M) in THF (890 μL, 0.89 mmol, 4.0 equiv.) dropwise. Warm the reaction to 40° C. Upon consumption of the starting materials, as indicated by LCMS analysis of the reaction mixture, cool the reaction to 0° C., and add ethanol (17 equiv.) followed by hydrochloric acid in methanol (500 μL, 0.5 mmol, 1M) to quench the reaction. Stir for 10 min at 0° C., then concentrate the mixture directly. Dilute the crude amine in DCM (1 mL) and add N,N-diisopropylethylamine (195 μL, 1.1 mmol, 5 equiv) to the reaction vessel. Cool the solution to 0° C. and then add acryloyl chloride (18 μL, 0.22 mmol, 1 equiv) dropwise. Upon consumption of the starting materials, as indicated by LCMS analysis of the reaction mixture, the solution was directly concentrated. The crude amide was then diluted in methanol (2 mL) and aq. 2M hydrochloric acid (2 mL) was added to the reaction mixture. The reaction was then stirred for 2 hours at room temperature to give the unprotected diol. The solution was diluted with DCM, extracted 5× with DCM, the combined organic layers where dried over $MgSO_4$, filtered, and concentrated. Purification via column chromatography (0 to 10% MeOH/DCM) gave 30 mg of N-[[4-(1,2-dihydroxyethyl)-1-[4-(trifluoromethoxy)phenyl]indazol-3-yl]methyl]prop-2-enamide as a white solid (32% yield) as a racemate. This was combined with further 22 mg of the racemate and the enantiomers were then separated by chiral SFC (Chiralpak IC column, 0.1% $NH_4OH$ in Ethanol, 20% isocratic gradient. 20 mg [77% yield] of the fast-eluting enantiomer and 18 mg [69%] of the slow-eluting enantiomer were obtained). $^1H$ NMR (400 MHz, DMSO) δ 8.62 (t, J=5.3 Hz, 1H), 7.92-7.82 (m, 2H), 7.72 (dd, J=8.4, 0.9 Hz, 1H), 7.64-7.54 (m, 2H), 7.49 (dd, J=8.4, 7.2 Hz, 1H), 7.39 (d, J=7.2 Hz, 1H), 6.34 (dd, J=17.1, 10.2 Hz, 1H), 6.15 (dd, J=17.1, 2.2 Hz, 1H), 5.62 (dd, J=10.1, 2.3 Hz, 1H), 5.48 (d, J=4.3 Hz, 1H), 5.17 (q, broad, J=5.5 Hz, 1H), 4.96 (dd, J=15.6, 5.6 Hz, 1H), 4.91-4.79 (m, 2H), 3.61 (m, 2H). LCMS (ESI) $[M+H]^+$=422.100.

Example 7

N-((4-(1,2-dihydroxyethyl)-1-(4-(pentafluoro-$\lambda^6$-sulfanyl)phenyl)-1H-indazol-3-yl)methyl)acrylamide (Compounds 9-11)

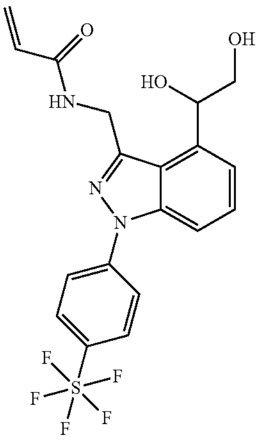 [SMILES: C=CC(=O)NCc1nn(-c2ccc(S(F)(F)(F)(F)F)cc2)c2cccc(C(O)CO)c12]

For this example the same sequence of steps was followed as for Example 6, except that [4-(pentafluoro-$\lambda^6$-sulfanyl)phenyl]boronic acid was used in step 5 instead of [4-(trifluoromethoxy)phenyl]boronic acid.

Step 5: 4-(2,2-dimethyl-1,3-dioxolan-4-yl)-1-(4-(pentafluoro-λ$^6$-sulfanyl)phenyl)-1H-indazole-3-carbonitrile

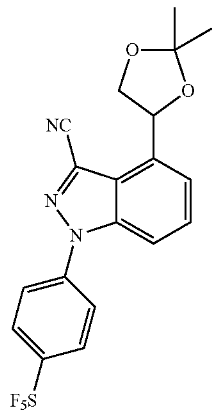

Following General procedure A, 70 mg of 4-(2,2-dimethyl-1,3-dioxolan-4-yl)-1-[4-(pentafluoro-λ$^6$-sulfanyl)phenyl]indazole-3-carbonitrile was obtained as a white solid (34% yield). LCMS (ESI) $[M+H+MeCN]^+$=483.100

Steps 6: N-((4-(1,2-dihydroxyethyl)-1-(4-(pentafluoro-λ$^6$-sulfanyl)phenyl)-1H-indazol-3-yl)methyl)acrylamide

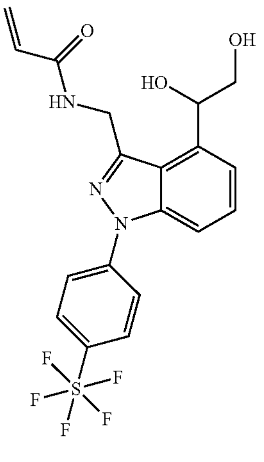 [SMILES: C=CC(=O)NCc1nn(-c2ccc(S(F)(F)(F)(F)F)cc2)c2cccc(C(O)CO)c12]

Following Step 6 for Example 6, 30 mg of racemic N-[[4-(1,2-dihydroxyethyl)-1-[4-(pentafluoro-λ$^6$-sulfanyl)phenyl]indazol-3-yl]methyl]prop-2-enamide was obtained as a white solid (42% yield). The enantiomers were then separated by chiral SFC (Chiralpak IC column, 0.1% $NH_4OH$ in Ethanol, 20% isocratic gradient. 11.5 mg [76% yield] of the fast eluting enantiomer and 12 mg [80% yield] of the slow-eluting enantiomer were obtained) $^1H$ NMR (400 MHz, DMSO-$d_6$) δ 8.66 (t, J=5.1 Hz, 1H), 8.16-8.06 (m, 2H), 8.01 (d, J=8.8 Hz, 2H), 7.91-7.83 (m, 1H), 7.55 (dd, J=8.5, 7.3 Hz, 1H), 7.44 (d, J=7.3 Hz, 1H), 6.35 (dd, J=17.1, 10.2 Hz, 1H), 6.15 (dd, J=17.1, 2.2 Hz, 1H), 5.63 (dd, J=10.2, 2.2 Hz, 1H), 5.52 (d, J=4.3 Hz, 1H), 5.17 (q, J=5.6 Hz, 1H), 4.98 (dd, J=15.7, 5.6 Hz, 1H), 4.92-4.80 (m, 2H), 3.61 (t, J=5.7 Hz, 2H). LCMS (ESI) $[M+H]^+$=464.000.

Example 8

N-((1-(4-(pentafluoro-λ$^6$-sulfanyl)phenyl)-1H-pyrazolo[4,3-b]pyridin-3-yl)methyl)acrylamide (Compound 12)

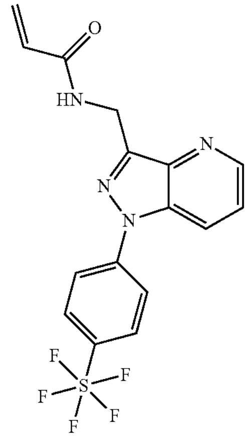 [SMILES: C=CC(=O)NCc1nn(-c2ccc(S(F)(F)(F)(F)F)cc2)c2cccnc12]

Step 1: 1-(4-(pentafluoro-λ$^6$-sulfanyl)phenyl)-1H-pyrazolo[4,3-b]pyridine-3-carbonitrile

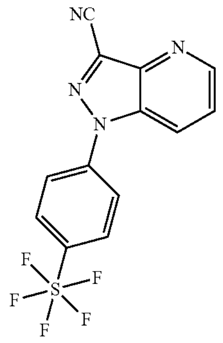 [SMILES: N#Cc1nn(-c2ccc(S(F)(F)(F)(F)F)cc2)c2cccnc12]

Following general procedure A, 250 mg of 1-[4-(pentafluoro-λ$^6$-sulfanyl)phenyl]pyrazolo[4,3-b]pyridine-3-carbonitrile was obtained as an off-white solid (quantitative yield). $[M+H+MeCN]^+$=487.800

Step 2: N-((1-(4-(pentafluoro-λ[6]-sulfanyl)phenyl)-1H-pyrazolo[4,3-b]pyridin-3-yl)methyl)acrylamide

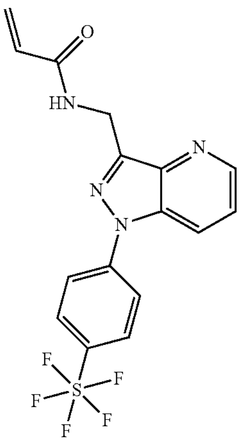 [SMILES: C=CC(=O)NCc1nn(-c2ccc(S(F)(F)(F)(F)F)cc2)c2cccnc12]

In an oven-dried vial, suspend lithium aluminum hydride (28 mg, 0.74 mmol, 1.5 equiv) in THF (2 mL), and cool to 0° C. Then dissolve 1-[4-(pentafluoro-λ[6]-sulfanyl)phenyl]pyrazolo[4,3-b]pyridine-3-carbonitrile (170 mg, 0.49 mmol) in THF (2 mL) and add dropwise to the cooled suspension. Stir at 0° C. and add more LAH portionwise (93 mg, 5 equiv of LAH used in total) until reaction is complete. Upon consumption of the starting materials, as indicated by LCMS analysis of the reaction mixture, quench with MeOH followed by sat. aq. $NH_4Cl$. Then add sat. aq. Rochelle's salt solution and iPrOAc. Filter off the gray solid, and rinse with iPrOAc and DCM. Partition the filtrate in a separatory funnel with DCM and brine/sat. aq. $NaHCO_3$ (1:1) mixture. Extract the aqueous layer 3× with DCM. Dry the combined organic layers over $Na_2SO_4$, filter, and concentrate. A dark brown oil was obtained and used directly. Dissolve the crude amine in DCM (2 mL) and add N,N-diisopropylethylamine (107 μL, 0.6 mmol, 1.1 equiv), then cool to 0° C. Then add acryloyl chloride (23 μL, 0.27 mmol, 0.5 equiv) dropwise and stir the reaction mixture for 45 minutes. At this time LCMS analysis shows full consumption of the amine and the reaction was concentrated directly. The crude material was then purified via column chromatography (0 to 10% MeOH in DCM). This gave 72 mg of a red foam which was further purified by preparative HPLC (XSelect CSH Prep C18, 20-60% MeCN/water, 0.1% $NH_4OH$ modifier) to give 26 mg as a white solid (14% yield). $^1H$ NMR (400 MHz, DMSO) δ 8.79-8.67 (m, 2H), 8.50 (dd, J=8.7, 1.2 Hz, 1H), 8.26-8.03 (m, 4H), 7.62 (dd, J=8.7, 4.4 Hz, 1H), 6.32 (dd, J=17.1, 10.2 Hz, 1H), 6.13 (dd, J=17.1, 2.2 Hz, 1H), 5.62 (dd, J=10.1, 2.2 Hz, 1H), 4.87 (d, J=5.5 Hz, 2H). LCMS (ESI) $[M+H]^+$=405.000

Example 9

N-((1-(4-(pentafluoro-λ[6]-sulfanyl)phenyl)-1H-pyrazolo[3,4-b]pyridin-3-yl)methyl)acrylamide (Compound 13)

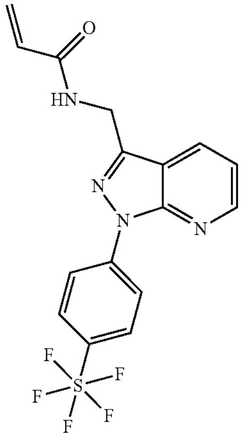 [SMILES: C=CC(=O)NCc1nn(-c2ccc(S(F)(F)(F)(F)F)cc2)c2ncccc12]

Step 1: tert-butyl ((1H-pyrazolo[3,4-b]pyridin-3-yl)methyl)carbamate

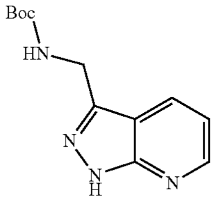 [SMILES: CC(C)(C)OC(=O)NCc1n[nH]c2ncccc12]

To a 20 mL vial equipped with a stir bar was added 1H-pyrazolo[3,4-b]pyridin-3-ylmethanamine (250 mg, 1.69 mmol), triethylamine (945 μL, 6.75 mmol, 4 equiv), and methanol (6.75 mL, 0.25 M wrt amine). Di-tert-butyl dicarbonate (380 mg, 1.7 mmol, 1 equiv) was then added and the reaction was allowed to stir at room temperature overnight. Upon consumption of the starting materials, as indicated by LCMS analysis of the reaction mixture, the mixture was concentrated. The material was suspended in iPrOAc and filtered. The filtrate was concentrated to give 170 mg of tert-butyl N-(1H-pyrazolo[3,4-b]pyridin-3-ylmethyl)carbamate as a white solid (40% yield). $^1H$ NMR (400 MHz, $CDCl_3$) δ 11.07 (s, broad, 1H), 8.58 (dd, J=4.6, 1.6 Hz, 1H), 8.25 (d, J=8.0 Hz, 1H), 7.17 (dd, J=8.1, 4.6 Hz, 1H), 5.22 (s, broad, 1H), 4.70 (d, J=6.1 Hz, 2H), 1.47 (s, 9H).

Step 2: tert-butyl ((1-(4-(pentafluoro-$\lambda^6$-sulfanyl)phenyl)-1H-pyrazolo[3,4-b]pyridin-3-yl)methyl) carbamate

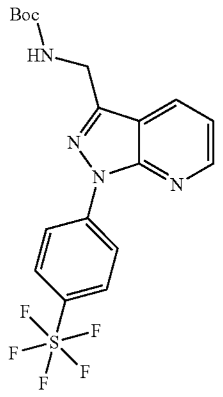 [SMILES: CC(C)(C)OC(=O)NCc1nn(-c2ccc(S(F)(F)(F)(F)F)cc2)c2ncccc12]

Following General procedure A, 160 mg of tert-butyl N-[[1-[4-(pentafluoro-$\lambda^6$-sulfanyl)phenyl]pyrazolo[3,4-b]pyridin-3-yl]methyl]carbamate was obtained as a white solid (52% yield). LCMS (ESI) $[M+H]^+$=451.150

Step 3: (1-(4-(pentafluoro-$\lambda^6$-sulfanyl)phenyl)-1H-pyrazolo[3,4-b]pyridin-3-yl)methanamine trifluoroacetate salt

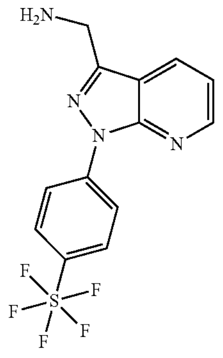 [SMILES: NCc1nn(-c2ccc(S(F)(F)(F)(F)F)cc2)c2ncccc12]

In a vial equipped with a stir bar, dissolve tert-butyl N-[[1-[4-(pentafluoro-$\lambda^6$-sulfanyl)phenyl]pyrazolo[3,4-b]pyridin-3-yl]methyl]carbamate (100 mg, 0.22 mmol) in DCM (2 mL). Add trifluoroacetic acid (250 μL) and stir until consumption of the starting materials, as indicated by LCMS analysis of the reaction mixture. Concentrate directly and use in next step.

Step 4: N-((1-(4-(pentafluoro-$\lambda^6$-sulfanyl)phenyl)-1H-pyrazolo[3,4-b]pyridin-3-yl)methyl)acrylamide

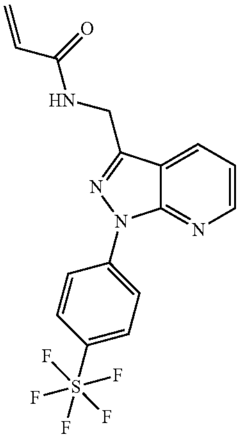 [SMILES: C=CC(=O)NCc1nn(-c2ccc(S(F)(F)(F)(F)F)cc2)c2ncccc12]

Dissolve the crude amine in DCM and cool to 0° C. Add DIPEA (388 μL, 2.2 mmol, 10 equiv.) followed by acryloyl chloride (18 μL, 0.22 mmol, 1 equiv) and warm the reaction mixture to room temperature. Upon consumption of the starting materials, as indicated by LCMS analysis of the reaction mixture, concentrate the reaction mixture and then purify via preparative HPLC (Phenomenex Gemini-NX C18, 30-70% MeCN/H2O [0.1% FA]). Subsequent purification via normal phase column chromatography (silica gel, 0 to 10% MeOH/DCM) gave 17 mg of N-[[1-[4-(pentafluoro-$\lambda^6$-sulfanyl)phenyl]pyrazolo[3,4-b]pyridin-3-yl]methyl]prop-2-enamide as a white solid (17% yield over 2 steps). $^1$H NMR (400 MHz, DMSO-$d_6$) δ 8.89 (t, J=5.9 Hz, 1H), 8.74 (dd, J=4.6, 1.6 Hz, 1H), 8.61 (d, J=9.1 Hz, 2H), 8.42 (dd, J=8.0, 1.6 Hz, 1H), 8.18-8.09 (m, 2H), 7.46 (dd, J=8.1, 4.6 Hz, 1H), 6.28 (dd, J=17.1, 9.9 Hz, 1H), 6.17 (dd, J=17.1, 2.4 Hz, 1H), 5.66 (dd, J=9.9, 2.4 Hz, 1H), 4.80 (d, J=6.0 Hz, 2H). LCMS (ESI) $[M+H]^+$=405.000

Example 10

N-((4-cyano-1-(4-(pentafluoro-$\lambda^6$-sulfanyl)phenyl)-1H-indazol-3-yl)methyl)acrylamide (Compound 14)

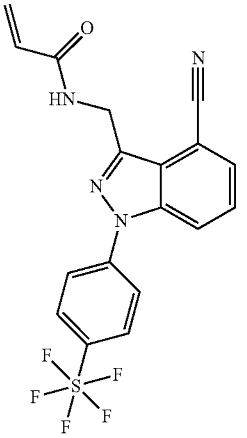 [SMILES: C=CC(=O)NCc1nn(-c2ccc(S(F)(F)(F)(F)F)cc2)c2cccc(C#N)c12]

Step 1: 4-bromo-1-(4-methoxybenzyl)-1H-indazole-3-carbonitrile

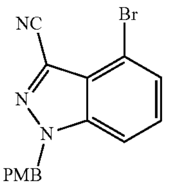

In a RBF equipped with a stir bar, dissolve 4-bromo-1H-indazole-3-carbonitrile (1000 mg, 4.5 mmol) in DMF (10 mL) along with potassium carbonate (1.25 g, 9 mmol, 2 equiv). Add 4-methoxybenzyl chloride (594 μL, 4.5 mmol, 1 equiv) and stir the mixture overnight. Dilute the reaction mixture with iPrOAc, transfer to a separation funnel and wash the organic layer three times with brine. Dry the organic layer over $MgSO_4$, filter, and concentrate. Purify via column chromatography (silica gel, 0 to 100% iPrOAc/heptane). This produced 800 mg of 4-bromo-1-[(4-methoxyphenyl)methyl]indazole-3-carbonitrile as a gray-brown solid (52% yield). LCMS (ESI) $[M+H]^+$=342.050

Step 2: tert-butyl ((4-bromo-1H-indazol-3-yl)methyl)carbamate

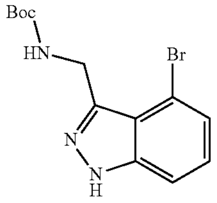 [SMILES: CC(C)(C)OC(=O)NCc1n[nH]c2cccc(Br)c12]

In a vial equipped with a stir bar, dissolve 4-bromo-1-[(4-methoxyphenyl)methyl]indazole-3-carbonitrile (370 mg, 1.081 mmol) in tetrahydrofuran (0.75 M) and cool to 0° C. Then add borane-tetrahydrofuran complex in tetrahydrofuran (3.5 mL, 3.5 mmol, 3.25 equiv, 1M) dropwise. Warm the reaction mixture to room temperature and then gradually heat to reflux. Upon consumption of the starting materials, as indicated by LCMS analysis of the reaction mixture, cool to the reaction to 0° C., add ethanol (17 equiv., 18.38 mmol) followed by 1M hydrochloric acid in methanol to fully quench the reaction. The reaction mixture was then concentrated. Dissolve the crude amine in acetic acid (10 mL) and add conc. aq. HCl (13 M, 20 mL) and heat to 90° C. in a sealed vessel until the reaction stalls, as indicated by LCMS analysis of the reaction mixture. On cooling, the liquid portion was decanted off and concentrated directly. This material was then taken up in a mixture of DCM/MeCN/MeOH (50 mL total, 2:2:1) and DIPEA (1 mL) was added. Then di-tert-butyl dicarbonate (243 mg, 1.1 mmol, 1 equiv) was added in one portion. After stirring for 1 hour, the reaction mixture was concentrated and purified via column chromatography (0 to 10% MeOH/DCM). Obtained 130 mg of tert-butyl ((4-bromo-1H-indazol-3-yl)methyl)carbamate as a white solid (37% yield). LCMS (ESI) $[M+H]^+$=325.850

Step 3: ter t-butyl ((4-bromo-1-(4-(pentafluoro-λ$^{6}$-sulfanyl)phenyl)-1H-indazol-3-yl)methyl)carbamate

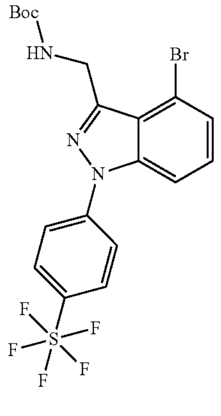 [SMILES: CC(C)(C)OC(=O)NCc1nn(-c2ccc(S(F)(F)(F)(F)F)cc2)c2cccc(Br)c12]

Following General Procedure A, 280 mg of tert-butyl N-[[4-bromo-1-[4-(pentafluoro-λ$^{6}$-sulfanyl)phenyl]indazol-3-yl]methyl]carbamate was obtained as an oil (115% yield, contained a significant impurity). LCMS (ESI) $[M+H]^+$=528.050

Step 4: ter t-butyl ((4-cyano-1-(4-(pentafluoro-)$^{6}$-sulfanyl)phenyl)-1H-indazol-3-yl)methyl)carbamate

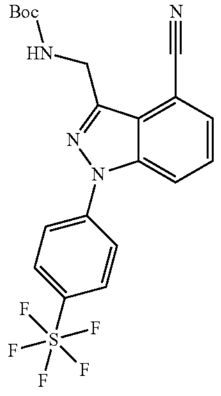 [SMILES: CC(C)(C)OC(=O)NCc1nn(-c2ccc(S(F)(F)(F)(F)F)cc2)c2cccc(C#N)c12]

To a vial equipped with a stir bar, add tert-butyl N-[[4-bromo-1-[4-(pentafluoro-λ$^{6}$-sulfanyl)phenyl]carbamate (100 mg, 0.19 mmol), tBuX-Phos PD G3 (16 mg, 0.019 mmol, 0.1 equiv.) and zinc cyanide (45 mg, 0.38 mmol, 2.0 equiv). Add N,N-dimethylacetamide (1.0 mL) and degas the solution by bubbling nitrogen for 5 minutes. Heat the reaction mixture to 100° C. and stir overnight. The reaction mixture was diluted with iPrOAc, washed with water and then brine. The organic layer was dried over $Na_2SO_4$, filtered, and concentrated. Purification via column chromatography (silica gel, 0 to 100% iPrOAc/heptane) gave 30 mg of tert-butyl N-[[4-cyano-1-[4-(pentafluoro-λ$^{6}$-sulfanyl)phenyl]indazol-3-yl]methyl]carbamate as an off white solid (33% yield). LCMS (ESI) $[M+H]^+$=475.150

Steps 5: N-((4-cyano-1-(4-(pentafluoro-$\lambda^6$-sulfanyl)phenyl)-1H-indazol-3-yl)methyl)acrylamide

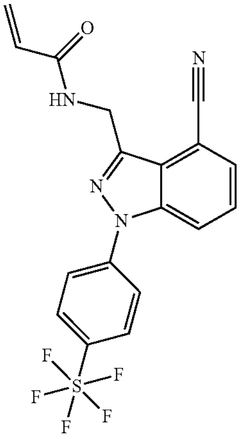 [SMILES: C=CC(=O)NCc1nn(-c2ccc(S(F)(F)(F)(F)F)cc2)c2cccc(C#N)c12]

Dissolve tert-butyl N-[[4-cyano-1-[4-(pentafluoro-$\lambda^6$-sulfanyl)phenyl]indazol-3-yl]methyl]carbamate (42 mg, 0.09 mmol) in DCM (1 mL). Add trifluoroacetic acid (250 μL) and stir until the starting materials are consumed, as indicated by LCMS analysis of the reaction mixture. Concentrate the reaction directly and use in next step. Dissolve the crude amine in DCM (1 mL) and cool to 0° C. Add DIPEA (80 μL, 0.45 mmol, 5 equiv) and acryloyl chloride (7 μL, 0.09 mmol, 1 equiv), then warm the reaction mixture to room temperature. Upon consumption of the starting materials, as indicated by LCMS analysis of the reaction mixture, dilute with iPrOAc, wash with 0.5M aq. HCl and brine. Combine the aqueous layers and extract with DCM. Combine the organic layers and dry over $Na_2SO_4$, filter, and concentrate. Obtained 37 mg of white solid which was purified by preparative HPLC (XSelect CSH Prep C18, 5-85% MeCN/water, 0.1% FA modifier). $^1$H NMR (400 MHz, DMSO-$d_6$) δ 8.72 (t, J=5.1 Hz, 1H), 8.34 (dd, J=8.7, 0.7 Hz, 1H), 8.19-8.10 (m, 2H), 8.08-8.00 (m, 2H), 7.94 (dd, J=7.3, 0.7 Hz, 1H), 7.74 (dd, J=8.7, 7.2 Hz, 1H), 6.32 (dd, J=17.1, 10.2 Hz, 1H), 6.14 (dd, J=17.1, 2.2 Hz, 1H), 5.63 (dd, J=10.2, 2.2 Hz, 1H), 4.94 (d, J=5.1 Hz, 2H). LCMS (ESI) $[M+H]^+$=429.000.

Example 11

N-((4-(1,2-dihydroxyethyl)-1-(4-(trifluoromethoxy)phenyl)-1H-pyrazolo[3,4-b]pyridin-3-yl)methyl)acrylamide (Compounds 15-17)

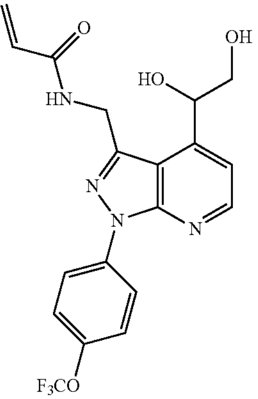 [SMILES: C=CC(=O)NCc1nn(-c2ccc(OC(F)(F)F)cc2)c2nccc(C(O)CO)c12]

Step 1: 4-Chloro-3-iodo-1H-pyrazolo[3,4-b]pyridine

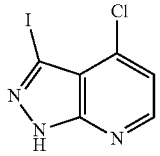 [SMILES: Clc1ccnc2[nH]nc(I)c12]

To a mixture of 4-chloro-1H-pyrazolo[3,4-b]pyridine (9.5 g, 61.9 mmol) and KOH (10.4 g, 185.6 mmol) in DMF (95 mL) was added 12 (28.3 g, 111.4 mmol) at 25° C., and the resulting mixture was stirred at 50° C. for 15 hours under a nitrogen atmosphere. TLC (30% EtOAc in petroleum ether, $R_f$=0.4) showed a new spot. The mixture was diluted with water (100 mL) and extracted with ethyl acetate (500 mL×3). The organics were washed with brine (500 mL×5), dried over sodium sulfate and concentrated in vacuo to afford the title compound (15.0 g, 87%) as a yellow solid. $^1$H NMR (400 MHz, DMSO-$d_6$): δ14.90-13.73 (m, 1H), 8.48 (d, J=5.2 Hz, 1H), 7.34 (d, J=5.2 Hz, 1H); LCMS (ESI): m/z 280.0 $(M+H)^+$.

Step 2: 4-Chloro-3-iodo-1-(4-(trifluoromethoxy) phenyl)-1H-pyrazolo[3,4-b]pyridine

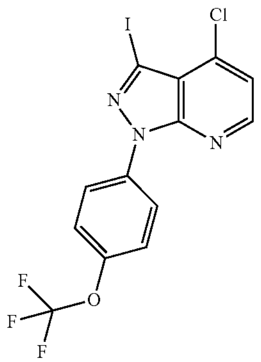 [SMILES: FC(F)(F)Oc1ccc(-n2nc(I)c3c(Cl)ccnc32)cc1]

A mixture of 4-chloro-3-iodo-1H-pyrazolo[3,4-b]pyridine (2.0 g, 7.2 mmol), Cu(OAc$_2$) (2.0 g, 10.7 mmol), (4-(trifluoromethoxy)phenyl)boronic acid (2.2 g, 10.7 mmol), and pyridine (2.3 mL, 28.6 mmol) in MeCN (40 mL) under Oxygen atmosphere (15 psi) was stirred at 25° C. for 16 hours. TLC (10% ethyl acetate in petroleum ether, $R_f$=0.7) indicated the reaction was completed. The reaction mixture was filtered, the filtrate was diluted with water (30 mL) and extracted with DCM (50 mL×3). The combined organics were washed with brine (50 mL×2), dried over sodium sulfate and concentrated in vacuo. The residue was purified by flash chromatography on silica gel (0-1% ethyl acetate in petroleum ether) to afford the title compound (2.55 g, 81%) as a white solid. $^1$H NMR (400 MHz, DMSO-d$_6$): δ 8.61 (d, J=5.2 Hz, 1H), 8.24 (d, J=9.2 Hz, 2H), 7.58 (d, J=8.4 Hz, 2H), 7.52 (d, J=5.2 Hz, 1H); LCMS (ESI): m/z 439.9 (M+H)$^+$.

Step 3: tert-Butyl ((4-chloro-1-(4-(trifluoromethoxy) phenyl)-1H-pyrazolo[3,4-b]pyridin-3-yl)methyl) carbamate

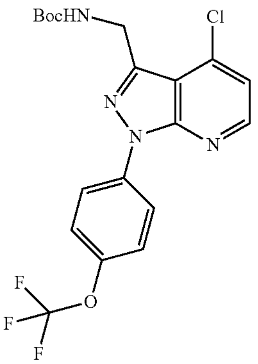 [SMILES: CC(C)(C)OC(=O)NCc1nn(-c2ccc(OC(F)(F)F)cc2)c2nccc(Cl)c12]

A mixture of 4-chloro-3-iodo-1-(4-(trifluoromethoxy) phenyl)-1H-pyrazolo[3,4-b]pyridine (2.55 g, 5.8 mmol), CATACXIUM A Pd G$_2$ (526 mg, 0.8 mmol), potassium (((tert-butoxy carbonyl)amino)methyl)trifluoroborate (1657 mg, 7.0 mmol) and $Cs_2CO_3$ (5.7 g, 17.4 mmol) at 20° C. in toluene (20 mL) and $H_2O$ (2 mL) was purged with $N_2$ for 3 minutes. The mixture was then heated to 100° C. and stirred for 4 hours under a nitrogen atmosphere. TLC (16% ethyl acetate in petroleum ether, $R_f$=0.5) indicated the reaction was completed. The mixture was quenched with water (50 mL) and extracted with ethyl acetate (50 mL×3), the combined organic layers were washed with brine (50 mL), dried over $Na_2SO_4$ and concentrated in vacuo. The residue was purified by flash chromatography on silica gel (0-10% ethyl acetate in petroleum ether) to afford the title compound (1.15 g, 44%) as a white solid. $^1$H NMR (400 MHz, DMSO-d$_6$): δ 8.62 (d, J=5.2 Hz, 1H), 8.35 (d, J=8.8 Hz, 2H), 7.62 (d, J=8.8 Hz, 2H), 7.54 (d, J=5.2 Hz, 1H), 7.40 (t, J=5.2 Hz, 1H), 4.70 (d, J=5.2 Hz, 2H), 1.42 (s, 9H).

Step 4: tert-Butyl ((1-(4-(trifluoromethoxy)phenyl)-4-vinyl-1H-pyrazolo[3,4-b]pyridin-3-yl)methyl)carbamate

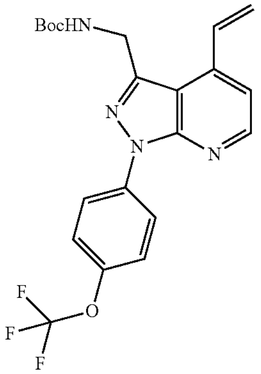 [SMILES: C=Cc1ccnc2c1c(CNC(=O)OC(C)(C)C)nn2-c1ccc(OC(F)(F)F)cc1]

A mixture of Xphos (65 mg, 0.14 mmol), tert-butyl ((4-chloro-1-(4-(trifluoromethoxy)phenyl)-1H-pyrazolo[3,4-b]pyridin-3-yl)methyl)carbamate (600 mg, 1.4 mmol), 4,4,5,5-tetramethyl-2-vinyl-1,3,2-dioxaborolane (417 mg, 2.7 mmol), Xphos Pd G$_2$ (107 mg, 0.14 mmol), KOAc (400 mg, 4.1 mmol) in 1,4-dioxane (10 mL) and $H_2O$ (1 mL) was stirred at 100° C. for 2 hours under nitrogen atmosphere. TLC (10% EtOAc in petroleum ether, $R_f$=0.3) showed a new spot. The mixture was diluted with water (50 mL) and extracted with ethyl acetate (50 mL×3). The combined organic layers were washed with brine (50 mL×3), dried over anhydrous sodium sulfate and concentrated under vacuum. The residue was purified by flash chromatography on silica gel (0-8% EtOAc in petroleum ether) to afford the title compound (440 mg, 75%) as a yellow solid. $^1$H NMR (400 MHz, DMSO-d$_6$): δ 8.62 (d, J=4.8 Hz, 1H), 8.40 (d, J=9.2 Hz, 2H), 7.62-7.57 (m, 3H), 7.50-7.42 (m, 1H), 7.32 (dd, J=17.2, 11.2 Hz, 1H), 6.27 (d, J=17.2 Hz, 1H), 5.70 (d, J=11.2 Hz, 1H), 4.65 (d, J=5.2 Hz, 2H), 1.41 (s, 9H); LCMS (ESI): m/z 435.1 (M+H)$^+$.

Step 5: tert-Butyl ((4-(1,2-dihydroxyethyl)-1-(4-(trifluoromethoxy)phenyl)-1H-pyrazolo[3,4-b]pyridin-3-yl)methyl)carbamate

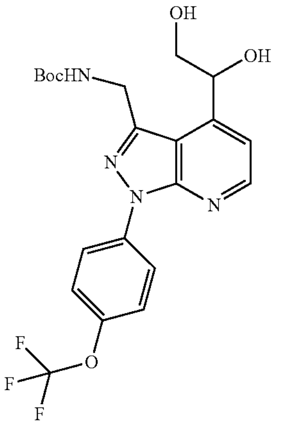 [SMILES: CC(C)(C)OC(=O)NCc1nn(-c2ccc(OC(F)(F)F)cc2)c2nccc(C(O)CO)c12]

To a solution of $K_2OsO_4 \cdot 2(H_2O)$ (47 mg, 0.13 mmol) and tert-butyl 41-(4-(trifluoromethoxy)phenyl)-4-vinyl-1H-pyrazolo[3,4-b]pyridin-3-yl)methyl)carbamate (550 mg, 1.3 mmol) in THF (9 mL) and $H_2O$ (3 mL) was added NMO (740 mg, 6.3 mmol) at 0° C. The resulting mixture was stirred at 20° C. for 16 hours. TLC (67% EtOAc in petroleum ether) showed a new spot. The mixture was diluted with water (50 mL) and extracted with ethyl acetate (50 mL×3). The combined organic layers were washed with saturated $Na_2SO_3$ (50 mL), dried over anhydrous sodium sulfate and concentrated under vacuum. The residue was purified by flash chromatography on silica gel (0-50% EtOAc in petroleum ether) to afford the title compound (440 mg, 74%) as a yellow solid. $^1H$ NMR (400 MHz, DMSO-$d_6$): δ 8.61 (d, J=4.8 Hz, 1H), 8.39 (d, J=8.8 Hz, 2H), 7.58 (d, J=8.4 Hz, 2H), 7.43 (d, J=4.8 Hz, 1H), 7.37 (t, J=4.8 Hz, 1H), 5.81 (d, J=4.4 Hz, 1H), 5.15 (q, J=5.6 Hz, 1H), 5.00 (t, J=5.6 Hz, 1H), 4.75-4.59 (m, 2H), 3.74-3.53 (m, 2H), 1.41 (s, 9H); LCMS (ESI): m/z 469.1 $(M+H)^+$.

Step 6: 1-(3-(Aminomethyl)-1-(4-(trifluoromethoxy)phenyl)-1H-pyrazolo[3,4-b]pyridin-4-yl)ethane-1,2-diol

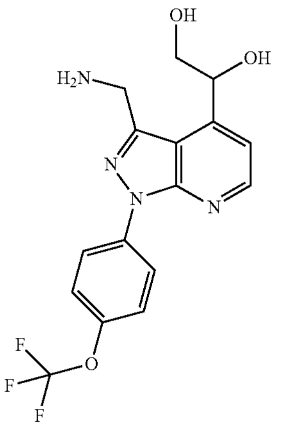 [SMILES: NCc1nn(-c2ccc(OC(F)(F)F)cc2)c2nccc(C(O)CO)c12]

To a mixture of tert-butyl ((4-(1,2-dihydroxyethyl)-1-(4-(trifluoromethoxy)phenyl)-1H-pyrazolo[3,4-b]pyridin-3-yl)methyl)carbamate (440 mg, 0.9 mmol) in DCM (5 mL), TFA (0.8 mL, 10.4 mmol) was added slowly at 0° C. The mixture was stirred at 0° C. for 2 hours under a nitrogen atmosphere. The reaction was quenched by water (40 mL). The reaction mixture was adjusted to pH=7 with sat. aq. $NaHCO_3$. The resulting mixture was extracted with EtOAc (100 mL). The organic was washed with brine (100 mL), dried over anhydrous sodium sulfate and concentrated under reduced pressure to afford the title compound (200 mg, 58%) as a white solid. The crude product was directly used for the next step without purification. $^1H$ NMR (400 MHz, DMSO-$d_6$): δ 8.63 (d, J=4.8 Hz, 1H), 8.42 (d, J=9.2 Hz, 2H), 7.58 (d, J=8.5 Hz, 2H), 7.42 (d, J=4.8 Hz, 1H), 5.33 (t, J=6.4 Hz, 1H), 4.21 (s, 2H), 3.76-3.56 (m, 2H); LCMS (ESI): m/z 369.1 $(M+H)^+$.

Step 7: N-((4-(1,2-Dihydroxyethyl)-1-(4-(trifluoromethoxy)phenyl)-1H-pyrazolo[3,4-b]pyridin-3-yl)methyl)acrylamide

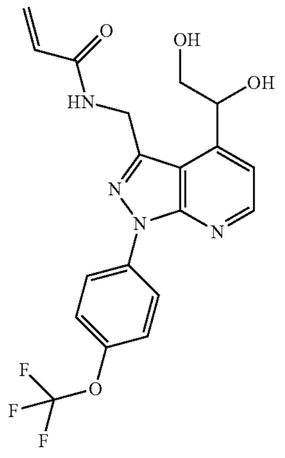 [SMILES: C=CC(=O)NCc1nn(-c2ccc(OC(F)(F)F)cc2)c2nccc(C(O)CO)c12]

To a solution of 1-(3-(aminomethyl)-1-(4-(trifluoromethoxy)phenyl)-1H-pyrazolo[3,4-b]pyridin-4-yl)ethane-1,2-diol (150 mg, 0.4 mmol) and sat. aq. $NaHCO_3$ (2 mL) in THF (6 mL) was added acryloyl chloride (41 mg, 0.45 mmol) at 0° C. The mixture was stirred at 0° C. for 1.5 hour. The mixture was diluted with water (20 mL), and extracted with EtOAc (20 mL×3). The combined organic layers were dried over anhydrous sodium sulfate and concentrated under vacuum. The resulting residue was purified by reverse phase chromatography (Boston Green ODS 150*30 mm*5 um/acetonitrile 35%-35%/water(FA)-CAN) to afford the title compound (102 mg, 59%) as a white solid, which was racemic. LCMS (ESI): m/z 423.1 $(M+H)^+$.

The enantiomers were then separated by SFC [DAICEL CHIRALPAK AD (250 mm*30 mm, 10 um)/40%-40%/Neu-ETOH] to afford the fast-eluting enantiomer (Compound 17) (23 mg, 45% recovery) as a white solid and the slow-eluting enantiomer (Compound 16) (28 mg, 55% recovery) as a white solid.

Peak1: $^1H$ NMR (400 MHz, DMSO-$d_6$): δ 8.69 (t, J=5.2 Hz, 1H), 8.64 (d, J=4.8 Hz, 1H), 8.40 (d, J=9.2 Hz, 2H), 7.59 (d, J=8.8 Hz, 2H), 7.47 (d, J=4.8 Hz, 1H), 6.34 (dd, J=17.2, 10.4 Hz, 1H), 6.18 (dd, J=17.2, 2.0 Hz, 1H), 5.79 (d, J=4.4 Hz, 1H), 5.64 (dd, J=10.0, 2.0 Hz, 1H), 5.18 (q, J=5.6 Hz, 1H), 5.03-4.93 (m, 2H), 4.81 (dd, J=16.0, 4.8 Hz, 1H), 3.68-3.57 (m, 2H); LCMS (ESI): m/z 423.0 $(M+H)^+$.

Peak 2: $^1H$ NMR (400 MHz, DMSO-$d_6$): δ 8.69 (t, J=5.2 Hz, 1H), 8.64 (d, J=4.8 Hz, 1H), 8.40 (d, J=9.2 Hz, 2H), 7.59 (d, J=8.8 Hz, 2H), 7.47 (d, J=4.8 Hz, 1H), 6.34 (dd, J=17.2, 10.0 Hz, 1H), 6.18 (dd, J=17.2, 2.0 Hz, 1H), 5.79 (d, J=4.4 Hz, 1H), 5.64 (dd, J=10.0, 2.0 Hz, 1H), 5.18 (q, J=5.6 Hz, 1H), 5.03-4.94 (m, 2H), 4.81 (dd, J=16.0, 4.8 Hz, 1H), 3.70-3.55 (m, 2H); LCMS (ESI): m/z 423.0 $(M+H)^+$.

Example 12

N-methyl-N-((1-(4-(trifluoromethoxy)phenyl)-1H-indazol-3-yl)methyl)acrylamide (Compound 18)

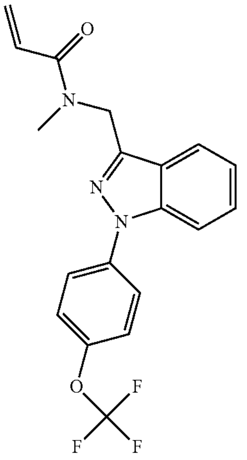 [SMILES: C=CC(=O)N(C)Cc1nn(-c2ccc(OC(F)(F)F)cc2)c2ccccc12]

Step 1: tert-butyl methyl((1-(4-(trifluoromethoxy)phenyl)-1H-indazol-3-yl)methyl)carbamate

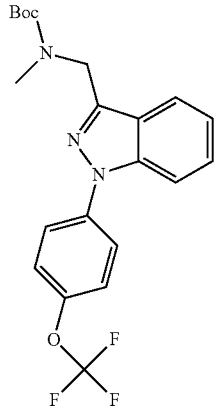 [SMILES: CN(Cc1nn(-c2ccc(OC(F)(F)F)cc2)c2ccccc12)C(=O)OC(C)(C)C]

A vial equipped with a stir bar was charged with tert-butyl N-[[1-[4-(trifluoromethoxy)phenyl]indazol-3-yl]methyl]carbamate (300 mg, 0.74 mmol) and THF (10 mL), followed by sodium hydride (60 mass %) in mineral oil (32.4 mg, 0.81 mmol, 1.1 equiv). Then add iodomethane (46 μL, 0.74 mmol, 1 equiv) and stir overnight. At this time, the reaction was diluted with iPrOAc and washed with sat. aq. $NH_4Cl$ solution followed by brine. Dry the organic layer over $MgSO_4$, filter, and concentrate. Purification via column chromatography (silica gel, 0 to 100% iPrOAc/Heptane) gave 70 mg of tert-butyl N-methyl-N-[[1-[4-(trifluoromethoxy)phenyl]indazol-3-yl]methyl]carbamate (23% yield) as a white solid. LCMS (ESI) $[M+H]^+$=421.950

Step 2: N-methyl-1-(1-(4-(trifluoromethoxy)phenyl)-1H-indazol-3-yl)methanamine

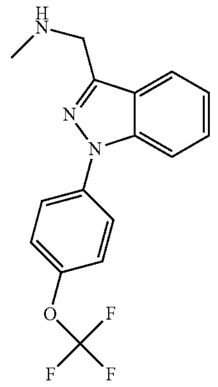 [SMILES: CNCc1nn(-c2ccc(OC(F)(F)F)cc2)c2ccccc12]

In a vial equipped with a stir bar, dissolve tert-butyl N-methyl-N-[[1-[4-(trifluoromethoxy)phenyl]indazol-3-yl]methyl]carbamate (70 mg, 0.17 mmol) in 1,4-dioxane (1 mL) and cool to 0° C. Add hydrochloric acid in 1,4-dioxane (1 mL, 4M) and warm to room temp overnight while stirring. Concentrate directly to obtain methyl-[[1-[4-(trifluoromethoxy)phenyl]indazol-3-yl]methyl]amine as the HCl salt (66 mg, 111% yield). LCMS (ESI) $[M+H]^+$=322.100

Step 3: N-methyl-N-((1-(4-(trifluoromethoxy)phenyl)-1H-indazol-3-yl)methyl)acrylamide

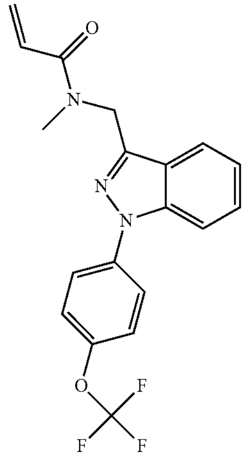 [SMILES: C=CC(=O)N(C)Cc1nn(-c2ccc(OC(F)(F)F)cc2)c2ccccc12]

In a vial equipped with a stir bar, dissolve methyl-[[1-[4-(trifluoromethoxy)phenyl]indazol-3-yl]methyl]ammonium chloride (33 mg, 0.09 mmol) in dichloromethane (1.0 mL) and add triethylamine (26 μL, 0.19 mmol, 2.1 equiv). Cool the reaction mixture to 0° C. and slowly add prop-2-enoyl chloride (8.2 μL, 0.1 mmol, 1.1 equiv). Gradually warm the reaction mixture to room temperature while stirring. After 30 minutes, the reaction mixture was put directly on a column (silica gel, 0 to 10% MeOH/DCM gradient). This isolated material was further purified via preparative HPLC (XSelect CSH Prep C18, 30-70% MeCN/water, 0.1% FA) to give 18 mg of the title compound as a white solid (51% yield). $^1$H NMR (400 MHz, DMSO-$d_6$, mixture of rotamers with the minor rotamer in brackets [ ]) δ 7.91 (dd, J=9.6, 2.8 Hz, 2H), 7.92-7.80 (m, 2H), 7.63-7.55 (m, 2H), 7.59-7.48 (m, 1H), 7.30 (dt, J=12.4, 7.6 Hz, 1H), [7.07 (m, 0.33H)], 6.82 (dd, J=16.7, 10.4 Hz, 0.67H), 6.22 (ddd, J=15.5, 13.0, 2.5 Hz, 1H), 5.73 (td, J=10.5, 2.4 Hz, 1H), 5.12 (s, 0.7H), 4.99 (s, 1.3H), 3.08 (s, 2H), 2.99 (s, 1H). LCMS (ESI) $[M+H]^+$=376.000.

Example 13

2-chloro-N-methyl-N-((1-(4-(trifluoromethoxy)phenyl)-1H-indazol-3-yl)methyl)acetamide (Compound 19)

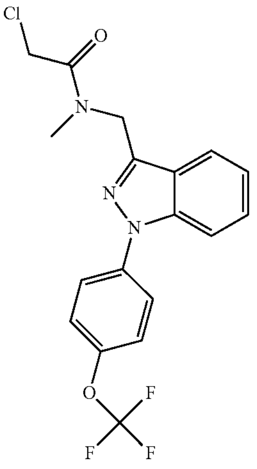 [SMILES: CN(Cc1nn(-c2ccc(OC(F)(F)F)cc2)c2ccccc12)C(=O)CCl]

In a vial equipped with a stir bar, dissolve methyl-[[1-[4-(trifluoromethoxy)phenyl]indazol-3-yl]methyl]ammonium chloride (33 mg, 0.09 mmol) in dichloromethane (1.0 mL) and add TEA (26 μL, 0.19 mmol, 2.1 equiv). Cool the reaction mixture to 0° C. and slowly add 2-chloroacetyl chloride (7.9 μL, 0.1 mmol, 1.1 equiv). Gradually warm the reaction mixture to room temperature while stirring. After 30 minutes the reaction mixture was put directly on a column (silica gel, 0 to 10% MeOH/DCM gradient). This isolated material was further purified via preparative HPLC (Gemini-NX C18, 5-85% MeCN/water) to give 22 mg of the title compound as a white solid (59% yield). $^1$H NMR (400 MHz, DMSO-$d_6$, mixture of rotamers with the minor rotamer in brackets [ ]) δ 7.97-7.83 (m, 4H), 7.63-7.49 (m, 3H), 7.39-7.26 (m, 1H), [5.06 (s, 0.5H)], 4.94 (s, 1.4H), [4.63 (s, 0.5H)], 4.48 (s, 1.5H), 3.03 (s, 2.2H), [2.96 (s, 0.7H)]. LCMS (ESI) $[M+H]^+$=398.000/400.000 (3:1).

Examples 14 & 15 (Compounds 139 and 93)

(S)-N-((4-(1,2-Dihydroxyethyl)-1-(4-(trifluoromethoxy)phenyl)-1H-pyrazolo[3,4-b]pyridin-3-yl)methyl)-N-methylacrylamide & (R)-N-((4-(1,2-dihydroxyethyl)-1-(4-(trifluoromethoxy)phenyl)-1H-pyrazolo[3,4-b]pyridin-3-yl)methyl)-N-methylacrylamide

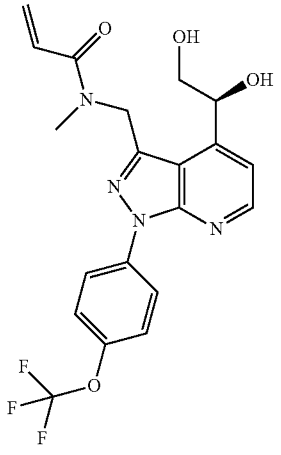

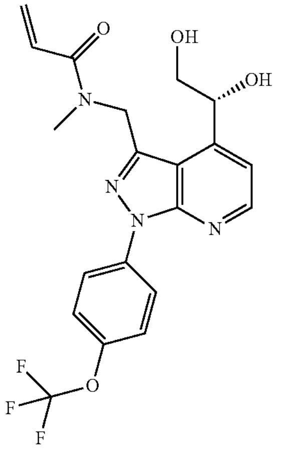

Step 1: 1-(3-((methylamino)methyl)-1-(4-(trifluoromethoxy)phenyl)-1H-pyrazolo[3,4-b]pyridin-4-yl)ethane-1,2-diol

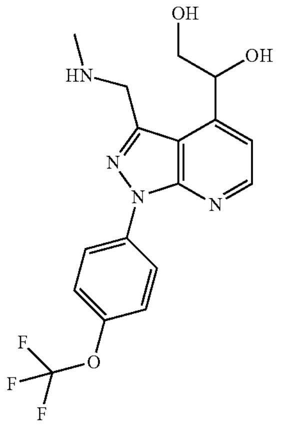

To a mixture of TEA (0.07 mL, 0.49 mmol) and MeOTf (0.83 mL, 0.73 mmol) in HFIP (5 mL) was added 1-(3-(aminomethyl)-1-(4-(trifluoromethoxy)phenyl)-1H-pyrazolo[3,4-b]pyridin-4-yl)ethane-1,2-diol (180 mg, 0.49 mmol) at 0° C., the solution was stirred at 0° C. for 2 h. The reaction was quenched with water (50 mL). The resulting solution was extracted with ethyl acetate (50 mL×3) and the organic layers were combined. The organic layer was dried over anhydrous sodium sulfate and concentrated under vacuum to afford the title compound (185 mg, 60% purity) as a yellow solid. The crude product was used directly without other purification. LCMS (ESI): m/z 382.8 $(M+H)^+$.

Step 2: N-((4-(1,2-dihydroxyethyl)-1-(4-(trifluoromethoxy)phenyl)-1H-pyrazolo[3,4-b]pyridin-3-yl)methyl)-N-methylacrylamide

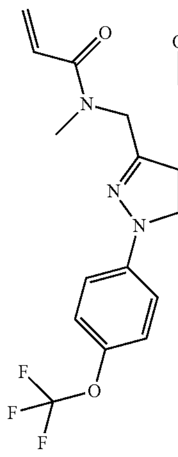

To a solution of 1-(3-((methylamino)methyl)-1-(4-(trifluoromethoxy)phenyl)-1H-pyrazolo[3,4-b]pyridin-4-yl)ethane-1,2-diol (187 mg, 0.49 mmol), sat. $NaHCO_3$ (1 mL) in THF (3 mL) was added acryloyl chloride (0.04 mL, 0.5 mmol) at 0° C., the solution was stirred at 0° C. for 2 h. The resulting solution was quenched with water (20 mL), extracted with ethyl acetate (50 mL×3) and the organic layers were combined. The organic layer was washed with brine (50 mL). The organic layer was dried over anhydrous sodium sulfate and concentrated under vacuum. The resulting residue was purified by reverse phase chromatography (Boston Green ODS 150*30 mm*5 um, 40-70%, water (FA)-CAN) to afford the title compound (70 mg, 33%) as a white solid. LCMS (ESI): m/z 436.8 $(M+H)^+$.

Step 3: (S)-N-((4-(1,2-dihydroxyethyl)-1-(4-(trifluoromethoxy)phenyl)-1H-pyrazolo[3,4-b]pyridin-3-yl)methyl)-N-methylacrylamide & (R)-N-((4-(1,2-dihydroxyethyl)-1-(4-(trifluoromethoxy)phenyl)-1H-pyrazolo[3,4-b]pyridin-3-yl)methyl)-N-methylacrylamide

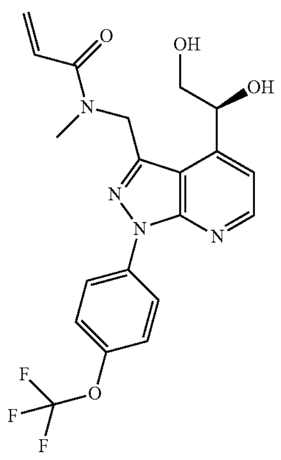 [SMILES: C=CC(=O)N(C)Cc1nn(-c2ccc(OC(F)(F)F)cc2)c2nccc(C(O)CO)c12]

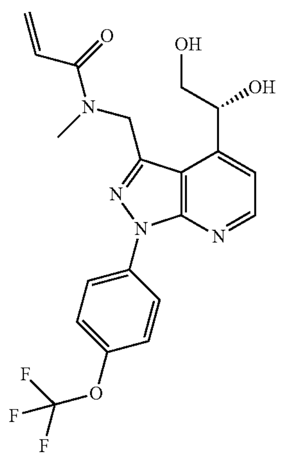

N-((4-(1,2-dihydroxyethyl)-1-(4-(trifluoromethoxy)phenyl)-1H-pyrazolo[3,4-b]pyridin-3-yl)methyl)-N-methylacrylamide (70 mg, 0.16 mmol) was separated by Chiral SFC (Instrument: SFC-12; Column: OD (DAICEL CHIRALPAK AD (250 mm*30 mm, 10 um)); Condition: Neu-EtOH; Begin B: 20%, end B: 20%; Flow Rate (14 mL/min): 14) to afford the first peak (S)-N-((4-(1,2-dihydroxyethyl)-1-(4-(trifluoromethoxy)phenyl)-1H-pyrazolo[3,4-b]pyridin-3-yl)methyl)-N-methylacrylamide (19.1 mg, 27%) and the second peak (R)-N-((4-(1,2-dihydroxyethyl)-1-(4-(trifluoromethoxy)phenyl)-1H-pyrazolo[3,4-b]pyridin-3-yl)methyl)-N-methylacrylamide (19.9 mg, 27%) both as a white solid.

The first peak: $^1H$ NMR (400 MHz, DMSO-$d_6$): δ 8.65-8.62 (m, 1H), 8.37-8.30 (m, 2H), 7.58 (d, J=8.8 Hz, 2H), 7.45-7.43 (m, 1H), 6.94-6.68 (m, 1H), 6.22-6.13 (m, 1H), 5.89-5.56 (m, 2H), 5.36-5.16 (m, 2H), 5.12-4.92 (m, 2H), 3.72-3.60 (m, 2H), 3.24, 3.06 (s, 3H total); LCMS (ESI): m/z 437.0 $(M+H)^+$.

The second peak: $^1H$ NMR (400 MHz, DMSO-$d_6$): δ 8.65-8.62 (m, 1H), 8.37-8.30 (m, 2H), 7.58 (d, J=8.8 Hz, 2H), 7.45-7.43 (m, 1H), 6.94-6.68 (m, 1H), 6.22-6.13 (m, 1H), 5.89-5.56 (m, 2H), 5.36-5.16 (m, 2H), 5.12-4.92 (m, 2H), 3.72-3.60 (m, 2H), 3.24, 3.06 (s, 3H total); LCMS (ESI): m/z 437.0 $(M+H)^+$.

Example 16 & 17 (Compounds 53 and 26)

(S,Z)-3-chloro-N-((4-(1,2-dihydroxyethyl)-1-(4-(trifluoromethoxy)phenyl)-1H-pyrazolo[3,4-b]pyridin-3-yl)methyl)acrylamide & (R,Z)-3-chloro-N-((4-(1,2-dihydroxyethyl)-1-(4-(trifluoromethoxy)phenyl)-1H-pyrazolo[3,4-b]pyridin-3-yl)methyl)acrylamide

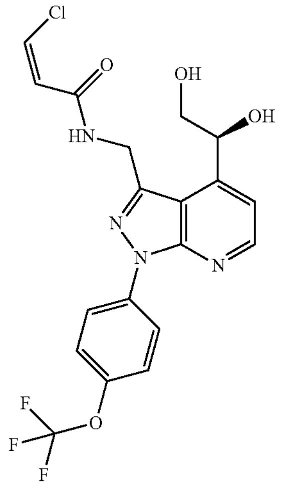

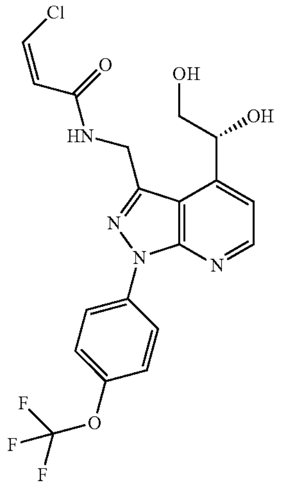

Step 1: 4-(1,2-dihydroxyethyl)-1-(4-(trifluoromethoxy)phenyl)-1H-pyrazolo[3,4-b]pyridine-3-carbonitrile

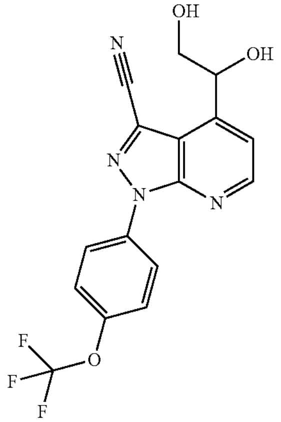 [SMILES: N#Cc1nn(-c2ccc(OC(F)(F)F)cc2)c2nccc(C(O)CO)c12]

To a solution of 1-(4-(trifluoromethoxy)phenyl)-4-vinyl-1H-pyrazolo[3,4-b]pyridine-3-carbonitrile (1.0 g, 3.03 mmol) and $K_2OsO_4 \cdot 2H_2O$ (121 mg, 0.33 mmol) in THF (6.0 mL) and water (0.6 mL) was added NMO (1.0 g, 9.08 mmol) at room temperature. The resulting mixture was stirred at room temperature for 16 h. The reaction was quenched by aqueous solution of sodium sulfite (50 mL). The resulting solution was extracted with ethyl acetate (80 mL×3) and the combined organic layers were dried over anhydrous sodium sulfate. After filtration, the filtrate was concentrated under reduced pressure. The residue was purified by flash chromatography (0-50% ethyl acetate in petroleum ether) to afford the title compound (700 mg, 64%) as a yellow solid. $^1H$ NMR (400 MHz, $CDCl_3$): δ 8.73 (d, J=4.8 Hz, 1H), 8.32 (d, J=9.2 Hz, 2H), 7.62 (d, J=4.8 Hz, 1H), 7.43 (d, J=8.8 Hz, 2H), 5.63 (dd, J=7.6, 3.6 Hz, 1H), 4.17 (dd, J=11.6, 3.6 Hz, 1H), 3.86 (dd, J=11.6, 7.6 Hz, 1H); LCMS (ESI): m/z 365.1 $(M+H)^+$.

Step 2: 1-(3-(aminomethyl)-1-(4-(trifluoromethoxy)phenyl)-1H-pyrazolo[3,4-b]pyridin-4-yl)ethane-1,2-diol

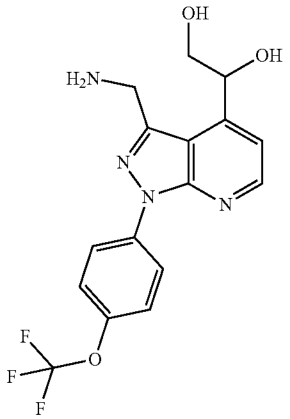 [SMILES: NCc1nn(-c2ccc(OC(F)(F)F)cc2)c2nccc(C(O)CO)c12]

A solution of 4-(1,2-dihydroxyethyl)-1-(4-(trifluoromethoxy)phenyl)-1H-pyrazolo[3,4-b]pyridine-3-carbonitrile (700 mg, 1.92 mmol) and $NiCl_2$ $6H_2O$ (46.0 mg, 0.19 mmol) in MeOH (8 mL) was stirred at 25° C. Then $NaBH_4$ (240 mg, 6.34 mmol) was added and stirred at room temperature for 3 h. The reaction was quenched with 2M HCl (10 mL). The reaction mixture was adjusted to pH=8 with sat. $NaHCO_3$ and extracted with ethyl acetate (60 mL×3). After filtration, the filtrate was concentrated under reduced pressure. The mixture was purified by flash chromatography (0-50% ethyl acetate in petroleum ether) to afford (700 mg, 99%) as white solid. LCMS (ESI): m/z 369.2 $(M+H)^+$.

Step 3: (Z)-3-chloro-N-((4-(1,2-dihydroxyethyl)-1-(4-(trifluoromethoxy)phenyl)-1H-pyrazolo[3,4-b]pyridin-3-yl)methyl)acrylamide

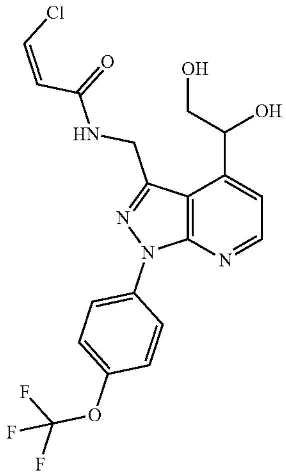

To a solution of 1-(3-(aminomethyl)-1-(4-(trifluoromethoxy)phenyl)-1H-pyrazolo[3,4-b]pyridin-4-yl)ethane-1,2-diol (700 mg, 1.90 mmol) and (Z)-3-chloroacrylic acid (243 mg, 2.28 mmol) in DCM (10 mL) was added EEDQ (1.40 g, 5.70 mmol) at 0° C., the resulting solution was stirred at room temperature with 16 h. The reaction was quenched by water (100 mL). The resulting solution was extracted with ethyl acetate (80 mL×3), the combined organic layers were dried over anhydrous sodium sulfate. After filtration, the filtrate was concentrated under reduced pressure. The residue was purified by reverse phase chromatography (Boston Green ODS 150*30 mm*5 um, acetonitrile 43-73%/water (FA)-ACN) to afford the title compound (250 mg, 29%). LCMS (ESI): m/z 457.1 $(M+H)^+$.

Step 4: (S,Z)-3-chloro-N-((4-(1,2-dihydroxyethyl)-1-(4-(trifluoromethoxy)phenyl)-1H-pyrazolo[3,4-b]pyridin-3-yl)methyl)acrylamide & (R,Z)-3-chloro-N-((4-(1,2-dihydroxyethyl)-1-(4-(trifluoromethoxy)phenyl)-1H-pyrazolo[3,4-b]pyridin-3-yl)methyl)acrylamide

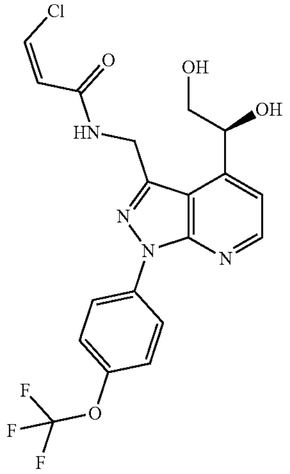

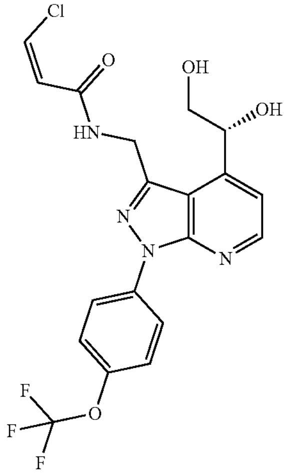 [SMILES: O=C(/C=C\Cl)NCc1nn(-c2ccc(OC(F)(F)F)cc2)c2nccc(C(O)CO)c12]

(Z)-3-chloro-N-((4-(1,2-dihydroxyethyl)-1-(4-(trifluoromethoxy)phenyl)-1H-pyrazolo[3,4-b]pyridin-3-yl)methyl)acrylamide (250 mg, 0.57 mmol) was separated by Chiral SFC (Instrument: SFC—22; Column: DAICEL CHIRALPAK AD (250 mm*30 mm, 10 um); Condition: Neu-EtOH; Flow Rate (mL/min): 80) to afford the first peak (S,Z)-3-chloro-N-((4-(1,2-dihydroxyethyl)-1-(4-(trifluoromethoxy)phenyl)-1H-pyrazolo[3,4-b]pyridin-3-yl)methyl)acrylamide (96.6 mg, 39%) and the second peak (R,Z)-3-chloro-N-((4-(1,2-dihydroxyethyl)-1-(4-(trifluoromethoxy)phenyl)-1H-pyrazolo[3,4-b]pyridin-3-yl)methyl)acrylamide (105 mg, 42%) both as a white solid.

The first peak: $^1$H NMR (400 MHz, DMSO-$d_6$): δ 8.73 (t, J=5.2 Hz, 1H), 8.65 (d, J=4.8 Hz, 1H), 8.42 (d, J=8.8 Hz, 2H), 7.60 (d, J=8.8 Hz, 2H), 7.47 (d, J=4.8 Hz, 1H), 6.81 (d, J=8.0 Hz, 1H), 6.45 (d, J=8.0 Hz, 1H), 5.82 (d, J=4.4 Hz, 1H), 5.18 (dd, J=10.4, 5.6 Hz, 1H), 5.01 (t, J=5.6 Hz, 1H), 4.95 (dd, J=15.6, 5.6 Hz, 1H), 4.81 (dd, J=16.0, 4.8 Hz, 1H), 3.70-3.58 (m, 2H); LCMS (ESI): m/z 456.9 $(M+H)^+$.

The second peak: $^1$H NMR (400 MHz, DMSO-$d_6$): δ 8.73 (t, J=5.2 Hz, 1H), 8.65 (d, J=4.8 Hz, 1H), 8.42 (d, J=8.8 Hz, 2H), 7.60 (d, J=8.8 Hz, 2H), 7.47 (d, J=4.8 Hz, 1H), 6.81 (d, J=8.0 Hz, 1H), 6.45 (d, J=8.0 Hz, 1H), 5.82 (d, J=4.4 Hz, 1H), 5.18 (dd, J=10.4, 5.6 Hz, 1H), 5.01 (t, J=5.6 Hz, 1H), 4.95 (dd, J=15.6, 5.6 Hz, 1H), 4.81 (dd, J=16.0, 4.8 Hz, 1H), 3.70-3.58 (m, 2H); LCMS (ESI): m/z 456.9 $(M+H)^+$.

Example 18 (Compound 32)

N-((4-(Hydroxymethyl)-1-(4-(trifluoromethoxy)phenyl)-1H-pyrazolo[3,4-b]pyridin-3-yl)methyl)acrylamide

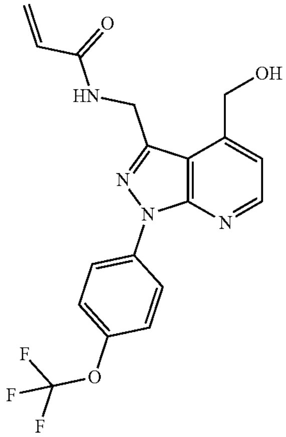 [SMILES: C=CC(=O)NCc1nn(-c2ccc(OC(F)(F)F)cc2)c2nccc(CO)c12]

To a solution of (3-(aminomethyl)-1-(4-(trifluoromethoxy)phenyl)-1H-pyrazolo[3,4-b]pyridin-4-yl)methanol (100 mg, 0.30 mmol) in THF (5 mL) was added sat. $NaHCO_3$ (1 mL, 1.48 mmol) and acryloyl chloride (29 mg, 0.33 mmol). The mixture was stirred at 0° C. for 1 h. The mixture was diluted with water (10 mL) and extracted with ethyl acetate (30 mL×3). The organics were washed with brine (20 mL×2), dried over $Na_2SO_4$, filtered and concentrated. The residue was purified by reverse phase chromatography (Welch Xtimate C18 150*30 mm*5 um, acetonitrile 45-75%/water (0.225% FA)-ACN) to afford the title compound (53.4 mg, 46%) as a white solid. $^1$H NMR (400 MHz, DMSO-$d_6$): δ 8.71-8.62 (m, 2H), 8.40 (d, J=8.8 Hz, 2H), 7.59 (d, J=8.8 Hz, 2H), 7.45 (d, J=4.8 Hz, 1H), 6.32 (dd, J=17.2, 10.0 Hz, 1H), 6.16 (dd, J=17.2, 2.0 Hz, 1H), 5.72 (t, J=5.6 Hz, 1H), 5.65 (dd, J=10.0, 2.0 Hz, 1H), 4.99 (d, J=5.2 Hz, 2H), 4.81 (d, J=5.2 Hz, 2H); LCMS (ESI): m/z 393.0 $(M+H)^+$.

Example 19 (Compound 55)

N-((4-(Hydroxymethyl)-1-(4-(trifluoromethoxy)phenyl)-1H-pyrazolo[3,4-b]pyridin-3-yl)methyl)-N-methylacrylamide

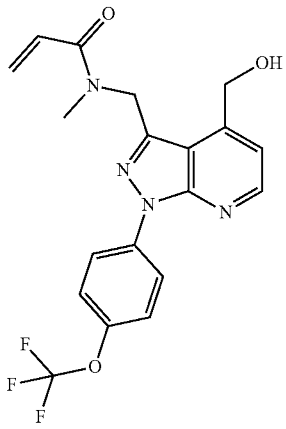 [SMILES: C=CC(=O)N(C)Cc1nn(-c2ccc(OC(F)(F)F)cc2)c2nccc(CO)c12]

Step 1: (3-((methylamino)methyl)-1-(4-(trifluoromethoxy)phenyl)-1H-pyrazolo[3,4-b]pyridin-4-yl)methanol

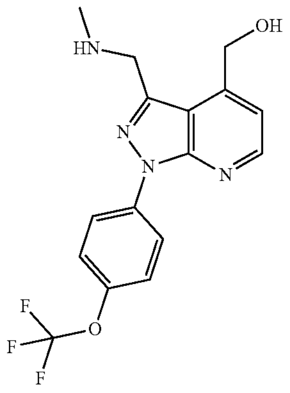 [SMILES: CNCc1nn(-c2ccc(OC(F)(F)F)cc2)c2nccc(CO)c12]

To a solution of (3-(aminomethyl)-1-(4-(trifluoromethoxy)phenyl)-1H-pyrazolo[3,4-b]pyridin-4-yl)methanol (50.0 mg, 0.15 mmol) in HFIP (2.0 mL) was added MeOTf (0.02 mL, 0.15 mmol). The reaction mixture was stirred at room temperature for 16 h. The reaction mixture was diluted with ethyl acetate (30 mL), washed with brine (40 mL×2), dried over $Na_2SO_4$ and concentrated to dryness to afford the title compound (60.0 mg, 99%) as a brown solid. LCMS (ESI): m/z 352.9 $(M+H)^+$.

Step 2: N-((4-(hydroxymethyl)-1-(4-(trifluoromethoxy)phenyl)-1H-pyrazolo[3,4-b]pyridin-3-yl)methyl)-N-methylacrylamide

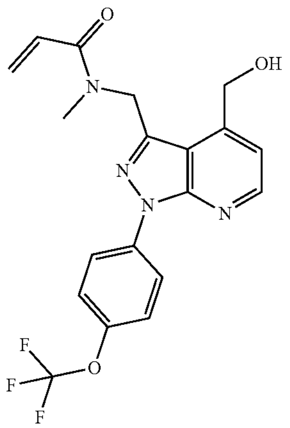 [SMILES: C=CC(=O)N(C)Cc1nn(-c2ccc(OC(F)(F)F)cc2)c2nccc(CO)c12]

To a solution of (3-((methylamino)methyl)-1-(4-(trifluoromethoxy)phenyl)-1H-pyrazolo[3,4-b]pyridin-4-yl)methanol (60.0 mg, 0.17 mmol) in THF (2 mL) and saturated $NaHCO_3$ (0.5 mL) was added acryloyl chloride (22.0 mg, 0.07 mmol) at 0° C. The reaction mixture was stirred at 0° C. for 2 h. The reaction mixture was diluted with ethyl acetate (50 mL), washed with brine (60 mL×3), dried over $Na_2SO_4$ and concentrated to dryness. After filtration, the filtrate was concentrated and purified by reverse phase chromatography (Welch Xtimate C18 150*30 mm*5 um, acetonitrile 49-79%/water (0.225% FA)-ACN) to afford the title compound (16.8 mg, 24%) as a white solid. $^1H$ NMR (400 MHz, DMSO-$d_6$): δ 8.64 (d, J=4.0 Hz, 1H), 8.37, 8.31 (d, J=8.8 Hz, 2H total), 7.58 (d, J=8.8 Hz, 2H), 6.86-6.82 (m, 1H), 6.20 (d, J=16.4 Hz, 1H), 5.72-5.59 (m, 2H), 5.24, 5.06 (s, 2H total), 5.00 (d, J=5.2 Hz, 2H), 3.18, 3.04 (s, 3H total); LCMS (ESI): m/z 407.0 $(M+H)^+$.

Example 20 (Compound 86)

N-((4-(Hydroxymethyl)-1-(4-(trifluoromethoxy)phenyl)-1H-pyrazolo[3,4-b]pyridin-3-yl)methyl)propiolamide

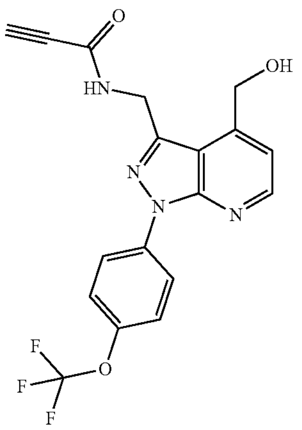 [SMILES: C#CC(=O)NCc1nn(-c2ccc(OC(F)(F)F)cc2)c2nccc(CO)c12]

To a solution of (3-(aminomethyl)-1-(4-(trifluoromethoxy)phenyl)-1H-pyrazolo[3,4-b]pyridin-4-yl)methanol (80.0 mg, 0.24 mmol), propiolic acid (0.02 mL, 0.35 mmol) in DCM (10 mL) was added EEDQ (117 mg, 0.47 mmol) at 0° C. The resulting solution was stirred at 0° C. for 16 h. The reaction was diluted with water (100 mL) and extracted with ethyl acetate (50 mL×3). The combined organic layers were dried over sodium sulfate and concentrated under reduced pressure. After filtration, the filtrate was concentrated and purified by reverse phase chromatography (Welch Xtimate C18 150*30 mm*5 um, acetonitrile 47-77%/water (0.225% FA)-ACN) to afford the title compound (35.5 mg, 39%) as a white solid. $^1$H NMR (400 MHz, DMSO-$d_6$) δ 9.38-9.30 (m, 1H), 8.65 (d, J=4.8 Hz, 1H), 8.40 (d, J=8.8 Hz, 2H), 7.60 (d, J=8.8 Hz, 2H), 7.44 (d, J=4.8 Hz, 1H), 5.78-5.69 (m, 1H), 4.99 (d, J=5.2 Hz, 2H), 4.78 (d, J=5.6 Hz, 2H), 4.21 (s, 1H); LCMS (ESI): m/z 390.9 $(M+H)^+$.

Example 21 (Compound 98)

N-((4-(Hydroxymethyl)-1-(4-(trifluoromethoxy)phenyl)-1H-pyrazolo[3,4-b]pyridin-3-yl)methyl)but-2-ynamide

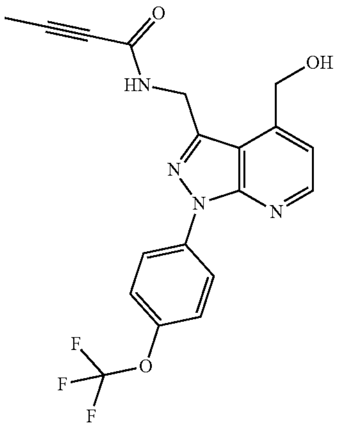 [SMILES: CC#CC(=O)NCc1nn(-c2ccc(OC(F)(F)F)cc2)c2nccc(CO)c12]

To a solution of (3-(aminomethyl)-1-(4-(trifluoromethoxy)phenyl)-1H-pyrazolo[3,4-b]pyridin-4-yl)methanol (80.0 mg, 0.24 mmol) and but-2-ynoic acid (30.0 mg, 0.35 mmol) in DCM (6.0 mL) was added EEDQ (117 mg, 0.47 mmol) at 0° C. The resulting solution was stirred at 0° C. for 16 h. The mixture was added water (100 mL) and extracted with ethyl acetate (50 mL×3). The combined organic layers were dried over anhydrous sodium sulfate and concentrated to dryness. The residue was purified by preparative HPLC (Welch Xtimate C18 150*30 mm*5 um, acetonitrile, 50%-80%/water (0.225% FA)-ACN) to afford the title compound (44.0 mg, 46%) as a white solid. $^1$H NMR (400 MHz, DMSO-$d_6$): δ 9.11-9.04 (m, 1H), 8.64 (d, J=4.8 Hz, 1H), 8.35 (d, J=9.2 Hz, 2H), 7.60 (d, J=9.2 Hz, 2H), 7.28 (d, J=4.8 Hz, 1H), 5.72 (t, J=5.6 Hz, 1H), 4.98 (d, J=5.6 Hz, 2H), 7.75 (d, J=5.2 Hz, 2H), 1.96 (s, 3H); LCMS (ESI): m/z 404.9 $(M+H)^+$.

Example 22 (Compound 128)

4-Hydroxy-N-((4-(hydroxymethyl)-1-(4-(trifluoromethoxy)phenyl)-1H-pyrazolo[3,4-b]pyridin-3-yl)methyl)but-2-ynamide

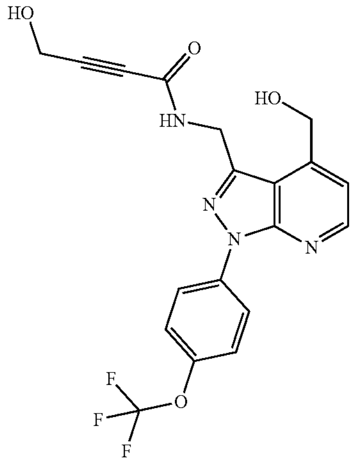 [SMILES: O=C(C#CCO)NCc1nn(-c2ccc(OC(F)(F)F)cc2)c2nccc(CO)c12]

To a solution of 4-hydroxybut-2-ynoic acid (36 mg, 0.35 mmol), (3-(aminomethyl)-1-(4-(trifluoromethoxy)phenyl)-1H-pyrazolo[3,4-b]pyridin-4-yl)methanol (100 mg, 0.30 mmol) in DCM (3 mL) was added EEDQ (219 mg, 0.89 mmol) at −78° C. The reaction was stirred with 16 h from −78° C. to room temperature. The reaction mixture was diluted with ethyl acetate (30 mL), washed with water (30 mL×3), dried over $Na_2SO_4$ and concentrated to dryness. After filtration, the filtrate was concentrated and purified by reverse phase chromatography (Welch Xtimate C18 150*30 mm*5 um, acetonitrile 53-83%/water (0.225% FA)-ACN) to afford the title compound (65 mg, 52%) as a white solid. $^1$H NMR (400 MHz, DMSO-$d_6$): δ 9.23-9.20 (m, 1H), 8.64 (d, J=4.4 Hz, 1H), 8.39 (d, J=8.8 Hz, 2H), 7.59 (d, J=8.8 Hz, 2H), 7.43 (d, J=4.4 Hz, 1H), 5.73 (t, J=4.8 Hz, 1H), 5.46 (t, J=5.6 Hz, 1H), 4.98 (d, J=4.8 Hz, 2H), 4.77 (d, J=4.8 Hz, 2H), 4.21 (d, J=5.6 Hz, 2H); LCMS (ESI): m/z 421.0 $(M+H)^+$.

Example 23 (Compound 61)

(E)-N-((4-(Hydroxymethyl)-1-(4-(trifluoromethoxy)phenyl)-1H-pyrazolo[3,4-b]pyridin-3-yl)methyl)but-2-enamide

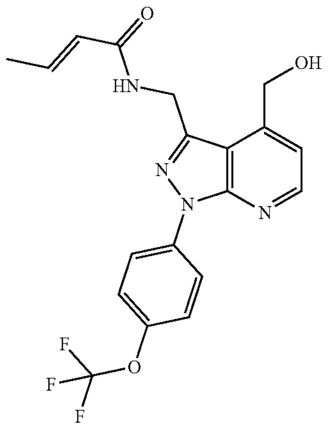 [SMILES: C/C=C/C(=O)NCc1nn(-c2ccc(OC(F)(F)F)cc2)c2nccc(CO)c12]

To a solution of (3-(aminomethyl)-1-(4-(trifluoromethoxy)phenyl)-1H-pyrazolo[3,4-b]pyridin-4-yl)methanol (50 mg, 0.15 mmol) in THF (3 mL) and saturated $NaHCO_3$ solution (1 mL) was added (E)-but-2-enoyl chloride (15 mg, 0.15 mmol) at 0° C. The reaction was stirred at 0° C. for 2 h. The reaction mixture was diluted with ethyl acetate (30 mL), washed with water (30 mL×3), dried over $Na_2SO_4$ and concentrated to dryness. After filtration, the filtrate was concentrated to dryness. The residue was purified by reverse phase chromatography (Welch Xtimate C18 150*30 mm*5 um, acetonitrile 47-77%/water (0.225% FA)-ACN) to afford the title compound (35.9 mg, 60%) as a white solid. $^1H$ NMR (400 MHz, DMSO-$d_6$): δ 8.65 (d, J=4.8 Hz, 1H), 8.46 (t, J=5.2 Hz, 1H), 8.40 (d, J=8.8 Hz, 2H), 7.59 (d, J=8.8 Hz, 2H), 7.44 (d, J=4.8 Hz, 1H), 6.74-6.68 (m, 1H), 5.98 (dd, J=15.6, 2.0 Hz, 1H), 5.70 (t, J=5.2 Hz, 1H), 4.98 (d, J=5.2 Hz, 2H), 4.77 (d, J=5.6 Hz, 2H), 1.79 (dd, J=6.8, 1.6 Hz, 3H); LCMS (ESI): m/z 407.0 $(M+H)^+$.

Example 24 (Compound 37)

(E)-3-Chloro-N-((4-(hydroxymethyl)-1-(4-(trifluoromethoxy)phenyl)-1H-pyrazolo[3,4-b]pyridin-3-yl)methyl)acrylamide

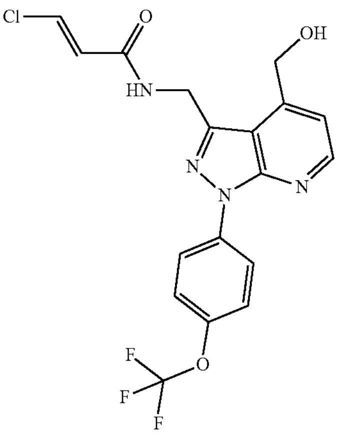 [SMILES: O=C(/C=C/Cl)NCc1nn(-c2ccc(OC(F)(F)F)cc2)c2nccc(CO)c12]

To a solution of (E)-3-chloroacrylic acid (28 mg, 0.26 mmol), (3-(aminomethyl)-1-(4-(trifluoromethoxy)phenyl)-1H-pyrazolo[3,4-b]pyridin-4-yl)methanol (80 mg, 0.24 mmol) in DCM (3 mL) was added EEDQ (175 mg, 0.71 mmol) at −78° C. The solution was stirred at room temperature for 16 h. The reaction mixture was diluted with ethyl acetate (30 mL), washed with water (30 mL×3), dried over $Na_2SO_4$ and concentrated to dryness. After filtration, the filtrate was concentrated. The residue was purified by reverse phase chromatography (Welch Xtimate C18 150*30 mm*5 um, acetonitrile 42-72%/water (0.225% FA)-ACN) to afford the title compound (34.3 mg, 30%) as a white solid. $^1H$ NMR (400 MHz, DMSO-$d_6$): δ 8.75 (t, J=5.2 Hz, 1H), 8.65 (d, J=4.8 Hz, 1H), 8.41 (d, J=9.2 Hz, 2H), 7.59 (d, J=8.0 Hz, 2H), 7.45 (d, J=4.8 Hz, 1H), 7.32 (d, J=13.2 Hz, 1H), 6.52 (d, J=13.2 Hz, 1H), 5.71 (t, J=5.2 Hz, 1H), 4.99 (d, J=5.2 Hz, 2H), 4.81 (d, J=5.2 Hz, 2H); LCMS (ESI): m/z 427.0 $(M+H)^+$.

Example 25 (Compound 99)

(Z)-3-Chloro-N-((4-(hydroxymethyl)-1-(4-(trifluoromethoxy)phenyl)-1H-pyrazolo[3,4-b]pyridin-3-yl)methyl)acrylamide

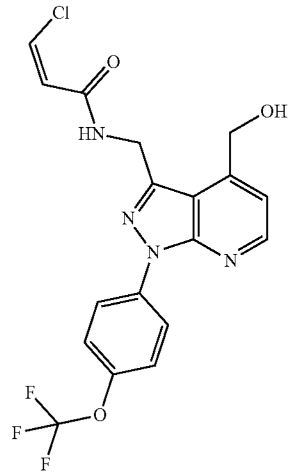 [SMILES: O=C(/C=C\Cl)NCc1nn(-c2ccc(OC(F)(F)F)cc2)c2nccc(CO)c12]

To a solution of (Z)-3-chloroacrylic acid (38 mg, 0.35 mmol), (3-(aminomethyl)-1-(4-(trifluoromethoxy)phenyl)-1H-pyrazolo[3,4-b]pyridin-4-yl)methanol (100 mg, 0.30 mmol) in DCM (3 mL) was added EEDQ (219 mg, 0.89 mmol) at −78° C. The solution was stirred at room temperature for 16 h. The reaction mixture was diluted with ethyl acetate (30 mL), washed with water (30 mL×3), dried over $Na_2SO_4$ and concentrated to dryness. After filtration, the filtrate was concentrated. The residue was purified by reverse phase chromatography (Welch Xtimate C18 150*30 mm*5 um, acetonitrile 50-80%/water (0.225% FA)-ACN) to afford the title compound (40.5 mg, 32%) as a white solid. $^1H$ NMR (400 MHz, DMSO-$d_6$): δ 8.70 (t, J=4.8 Hz, 1H), 8.65 (d, J=4.4 Hz, 1H), 8.41 (d, J=8.8 Hz, 2H), 7.59 (d, J=8.8 Hz, 2H), 7.45 (d, J=4.8 Hz, 1H), 6.79 (d, J=8.0 Hz, 1H), 6.41 (d, J=8.0 Hz, 1H), 5.72 (t, J=5.2 Hz, 1H), 5.01 (d, J=5.2 Hz, 2H), 4.78 (d, J=5.2 Hz, 2H); LCMS (ESI): m/z 448.9 $(M+Na)^+$.

Example 26 (Compound 49)

2-Chloro-N-((4-(hydroxymethyl)-1-(4-(trifluoromethoxy)phenyl)-1H-pyrazolo[3,4-b]pyridin-3-yl)methyl)acrylamide

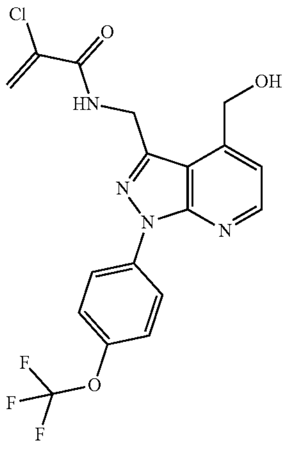 [SMILES: C=C(Cl)C(=O)NCc1nn(-c2ccc(OC(F)(F)F)cc2)c2nccc(CO)c12]

To a solution of 2-chloroacrylic acid (38 mg, 0.35 mmol), (3-(aminomethyl)-1-(4-(trifluoromethoxy)phenyl)-1H-pyrazolo[3,4-b]pyridin-4-yl)methanol (100 mg, 0.30 mmol) in DCM (3 mL) was added EEDQ (219 mg, 0.89 mmol) at −78° C. The solution was stirred at room temperature for 16 h. The reaction mixture was diluted with ethyl acetate (30 mL), washed with water (30 mL×3), dried over $Na_2SO_4$ and concentrated to dryness. After filtration, the filtrate was concentrated. The residue was purified by reverse phase chromatography (Welch Xtimate C18 150*30 mm*5 um, acetonitrile 52-82%/water (0.225% FA)-ACN) to afford the title compound (61.7 mg, 49%) as a white solid. $^1H$ NMR (400 MHz, DMSO-$d_6$): δ 9.01 (s, 1H), 8.65 (d, J=3.6 Hz, 1H), 8.38 (d, J=7.2 Hz, 2H), 7.59 (d, J=8.0 Hz, 2H), 7.43 (d, J=4.0 Hz, 1H), 6.38 (s, 1H), 5.96 (s, 1H), 5.79 (t, J=4.4 Hz, 1H), 4.99 (d, J=4.4 Hz, 2H), 4.84 (d, J=4.4 Hz, 2H); LCMS (ESI): m/z 426.9 $(M+H)^+$.

Example 27 (Compound 68)

2-Fluoro-N-((4-(hydroxymethyl)-1-(4-(trifluoromethoxy)phenyl)-1H-pyrazolo[3,4-b]pyridin-3-yl)methyl)acrylamide

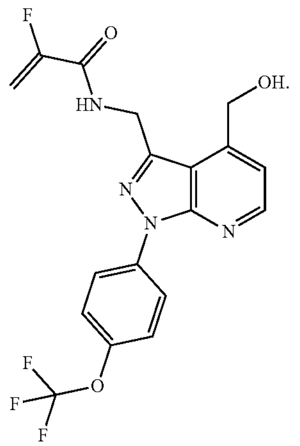 [SMILES: C=C(F)C(=O)NCc1nn(-c2ccc(OC(F)(F)F)cc2)c2nccc(CO)c12]

To a solution of 2-fluoroacrylic acid (32 mg, 0.35 mmol), (3-(aminomethyl)-1-(4-(trifluoromethoxy)phenyl)-1H-pyrazolo[3,4-b]pyridin-4-yl)methanol (100 mg, 0.30 mmol) in DCM (3 mL) was added EEDQ (219 mg, 0.89 mmol) at −78° C. The reaction was stirred at room temperature for 16 h. The reaction mixture was diluted with ethyl acetate (30 mL), washed with water (30 mL×3), dried over $Na_2SO_4$ and concentrated to dryness. After filtration, the filtrate was concentrated. The residue was purified by reverse phase chromatography (Welch Xtimate C18 150*30 mm*5 um, acetonitrile 53-83%/water (0.225% FA)-ACN) to afford the title compound (9.0 mg, 7%) as a white solid. $^1H$ NMR (400 MHz, DMSO-$d_6$): δ 9.11 (t, J=4.8 Hz, 1H), 8.64 (d, J=4.4 Hz, 1H), 8.38 (d, J=8.8 Hz, 2H), 7.59 (d, J=8.8 Hz, 2H), 7.43 (d, J=4.8 Hz, 1H), 5.76 (t, J=5.6 Hz, 1H), 5.60 (dd, J=48.0, 3.6 Hz, 1H), 5.32 (d, J=15.6, 3.6 Hz, 1H), 4.99 (d, J=5.2 Hz, 2H), 4.84 (d, J=5.6 Hz, 2H); LCMS (ESI): m/z 411.0 $(M+H)^+$.

Example 28 (Compound 132)

(E)-4,4,4-Trifluoro-N-((4-(hydroxymethyl)-1-(4-(trifluoromethoxy)phenyl)-1H-pyrazolo[3,4-b]pyridin-3-yl)methyl)but-2-enamide

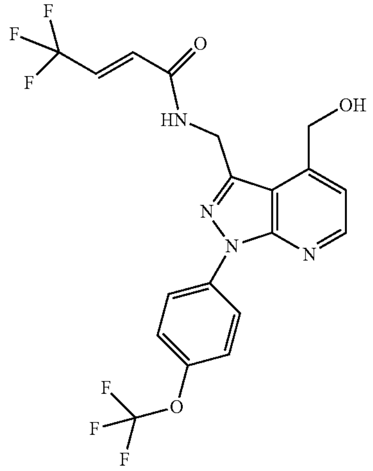 [SMILES: O=C(/C=C/C(F)(F)F)NCc1nn(-c2ccc(OC(F)(F)F)cc2)c2nccc(CO)c12]

To a solution of (E)-4,4,4-trifluorobut-2-enoic acid (36 mg, 0.26 mmol), (3-(aminomethyl)-1-(4-(trifluoromethoxy)phenyl)-1H-pyrazolo[3,4-b]pyridin-4-yl)methanol (80 mg, 0.24 mmol) in DCM (3 mL) was added EEDQ (175 mg, 0.71 mmol) at −78° C. The solution was stirred at room temperature for 16 h. The reaction mixture was diluted with ethyl acetate (30 mL), washed with water (30 mL×3), dried over $Na_2SO_4$ and concentrated to dryness. After filtration, the filtrate was concentrated. The residue was purified by reverse phase chromatography (Welch Xtimate C18 150*30 mm*5 um, acetonitrile 46-76%/water (0.225% FA)-ACN) to afford the title compound (36.3 mg, 33%) as a white solid. $^1H$ NMR (400 MHz, DMSO-$d_6$): δ 9.13 (t, J=4.8 Hz, 1H), 8.65 (d, J=4.8 Hz, 1H), 8.40 (d, J=8.8 Hz, 2H), 7.59 (d, J=8.4 Hz, 2H), 7.45 (d, J=4.8 Hz, 1H), 6.96-6.78 (m, 2H), 5.74 (s, 1H), 4.99 (s, 2H), 4.87 (d, J=5.2 Hz, 2H); LCMS (ESI): m/z 461.0 $(M+H)^+$.

Example 29 (Compound 69)

(E)-4,4-Difluoro-N-((4-(hydroxymethyl)-1-(4-(trifluoromethoxy)phenyl)-1H-pyrazolo[3,4-b]pyridin-3-yl)methyl)but-2-enamide

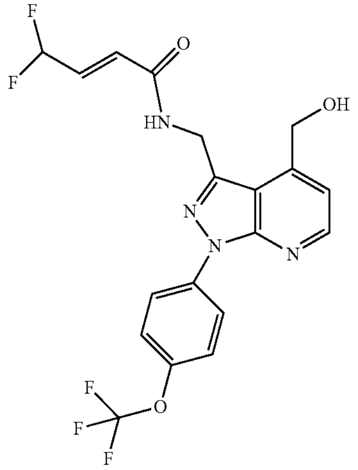 [SMILES: O=C(/C=C/C(F)F)NCc1nn(-c2ccc(OC(F)(F)F)cc2)c2nccc(CO)c12]

To a solution of (3-(azetidin-3-yl)-1-(4-(trifluoromethoxy)phenyl)-1H-pyrazolo[3,4-b]pyridin-4-yl)methanol (100 mg, 0.27 mmol) in dichloromethane (8 mL) was added (E)-4,4-difluorobut-2-enoic acid (44 mg, 0.41 mmol) and ethyl 2-ethoxyquinoline-1 (2H)-carboxylate (136 mg, 0.55 mmol) at room temperature. The solution was stirred at room temperature for 16 h. The residue was quenched with water (10 mL), extracted by DCM (10 mL×3). The organic layer was dried over $Na_2SO_4$ and concentrated. The residue was purified by reverse phase chromatography (Welch Xtimate C18 150*30 mm*5 um, acetonitrile 50-80%/water (0.225% FA)-ACN) to afford the title compound (62.0 mg, 52%) as a white solid. $^1H$ NMR (400 MHz, DMSO-$d_6$): 9.00 (t, J=5.6 Hz, 1H), 8.66 (d, J=4.8 Hz, 1H), 8.40 (d, J=9.2 Hz, 2H), 7.59 (d, J=8.4 Hz, 2H), 7.45 (d, J=4.8 Hz, 1H), 6.79-6.50 (m, 3H), 5.71 (t, J=5.2 Hz, 1H), 4.99 (d, J=5.6 Hz, 2H), 4.85 (d, J=5.2 Hz, 2H); LCMS (ESI): m/z 443.0 $(M+H)^+$.

Example 30 (Compound 121)

(E)-4-Fluoro-N-((4-(hydroxymethyl)-1-(4-(trifluoromethoxy)phenyl)-1H-pyrazolo[3,4-b]pyridin-3-yl)methyl)but-2-enamide

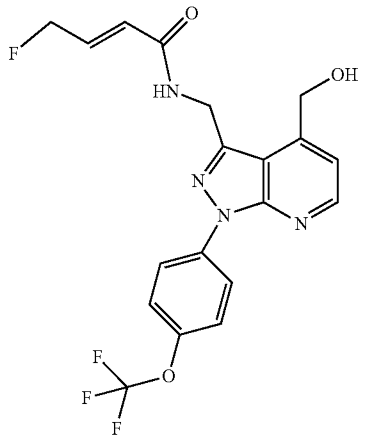 [SMILES: O=C(/C=C/CF)NCc1nn(-c2ccc(OC(F)(F)F)cc2)c2nccc(CO)c12]

Step 1: (E)-ethyl 4-fluorobut-2-enoate

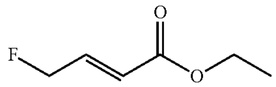

A solution of silver(I) fluoride (1.97 g, 15.54 mmol) and (E)-ethyl 4-bromobut-2-enoate (650 mg, 4.92 mmol) in acetonitrile (30 mL) was stirred at room temperature for 16 h. The reaction solution was quenched with water (100 mL), extracted with dichloromethane (100 mL×3). The organic layer was dried over $Na_2SO_4$ and concentrated at low temperature to afford the title compound (650 mg, 95%) as a brown oil. $^1H$ NMR (400 MHz, DMSO-$d_6$): δ 7.05-6.89 (m, 1H), 6.08-5.98 (m, 1H), 5.20 (dd, J=4.0, 2.0 Hz, 1H), 5.08 (dd, J=4.0, 2.0 Hz, 1H), 4.15 (q, J=7.2 Hz, 2H), 1.22 (t, J=7.2 Hz, 3H).

Step 2: (E)-4-fluorobut-2-enoic acid

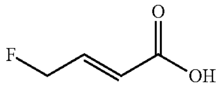

A solution of (E)-ethyl 4-fluorobut-2-enoate (650 mg, 4.92 mmol) and lithium hydroxide hydrate (619 mg, 14.76 mmol) in THF (8 mL) and water (8 mL) was stirred at room temperature for 2.5 h. The reaction was diluted with water (30 mL) and extracted with ethyl acetate (30 mL×2). The aqueous layer was quenched with 2 M HCl to pH 5. The organic layer was washed with brine (60 mL×2), dried over sodium sulfate, filtered and concentrated to afford the title compound (130 mg, 25%). $^1H$ NMR (400 MHz, DMSO-$d_6$): δ 12.35 (s, 1H), 6.93-6.83 (m, 1H), 5.98-5.93 (m, 1H), 5.18 (dd, J=4.0, 2.0 Hz, 1H), 5.07 (dd, J=4.0, 2.0 Hz, 1H).

Step 3: (E)-4-fluoro-N-((4-(hydroxymethyl)-1-(4-(trifluoromethoxy)phenyl)-1H-pyrazolo[3,4-b]pyridin-3-yl)methyl)but-2-enamide

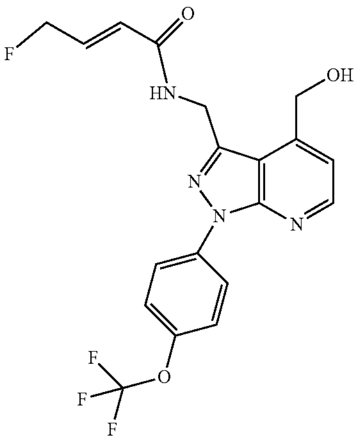 [SMILES: O=C(/C=C/CF)NCc1nn(-c2ccc(OC(F)(F)F)cc2)c2nccc(CO)c12]

To a solution of (3-(aminomethyl)-1-(4-(trifluoromethoxy)phenyl)-1H-pyrazolo[3,4-b]pyridin-4-yl)methanol (200 mg, 0.59 mmol), (E)-4-fluorobut-2-enoic acid (92 mg, 0.89 mmol) in dichloromethane (8 mL) was added ethyl 2-ethoxyquinoline-1 (2H)-carboxylate (292 mg, 1.18 mmol) at room temperature. The solution was stirred at room temperature for 16 h. The reaction was quenched with water (10 mL). The solution was extracted with dichloromethane (20 mL×3). The combined organic layers were washed with brine (30 mL), dried over sodium sulfate and concentrated under reduced pressure. The residue was purified by reverse phase chromatography (Welch Xtimate C18 150*30 mm*5 um, acetonitrile 38-68%/water (0.225% FA)-ACN) to afford the title compound (82.0 mg, 33%) as a white solid. $^1$H NMR (400 MHz, DMSO-$d_6$): δ 8.72 (t, J=5.2 Hz, 1H), 8.65 (d, J=4.8 Hz, 1H), 8.40 (d, J=8.8 Hz, 2H), 7.59 (d, J=8.8 Hz, 2H), 7.44 (d, J=4.8 Hz, 1H), 6.83-6.73 (m, 1H), 6.24 (dd, J=15.6, 2.0 Hz, 1H), 5.71 (t, J=5.2 Hz, 1H), 5.22-5.03 (m, 2H), 4.99 (d, J=5.6 Hz, 2H), 4.82 (d, J=5.2 Hz, 2H); LCMS (ESI): m/z 447.0 $(M+Na)^+$.

Example 31 (Compound 111)

2,3,3-Trideuterio-N-[[4-(hydroxymethyl)-1-[4-(trifluoromethoxy)phenyl]pyrazolo[3,4-b]pyridin-3-yl]methyl]prop-2-enamide

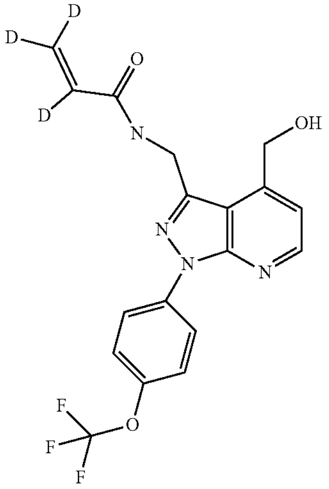 [SMILES: [2H]C([2H])=C([2H])C(=O)NCc1nn(-c2ccc(OC(F)(F)F)cc2)c2nccc(CO)c12]

To a solution of 2,3,3-trideuterioprop-2-enoic acid (26 mg, 0.35 mmol), (3-(aminomethyl)-1-(4-(trifluoromethoxy)phenyl)-1H-pyrazolo[3,4-b]pyridin-4-yl)methanol (100 mg, 0.30 mmol) in DCM (3 mL) was added EEDQ (219 mg, 0.89 mmol) at −78° C. The reaction was stirred at room temperature for 16 h. The reaction mixture was diluted with ethyl acetate (30 mL), washed with water (30 mL×3), dried over $Na_2SO_4$ and concentrated to dryness. The residue was purified by reverse phase chromatography (Welch Xtimate C18 150*30 mm*5 um, acetonitrile 36-66%/water (0.225% FA)-ACN) to afford the title compound (26.9 mg, 23%) as a white solid. $^1$H NMR (400 MHz, DMSO-$d_6$): δ 8.69 (t, J=4.8 Hz, 1H), 8.65 (d, J=4.8 Hz, 1H), 8.40 (d, J=9.2 Hz, 2H), 7.59 (d, J=8.4 Hz, 2H), 7.45 (d, J=4.8 Hz, 1H), 5.75 (s, 1H), 4.99 (s, 2H), 4.81 (d, J=4.8 Hz, 2H). LCMS (ESI): m/z 396.1 $(M+H)^+$.

Example 32 (Compound 54)

N-((4-((3-Hydroxyazetidin-1-yl)methyl)-1-(4-(trifluoromethoxy)phenyl)-1H-pyrazolo[3,4-b]pyridin-3-yl)methyl)acrylamide

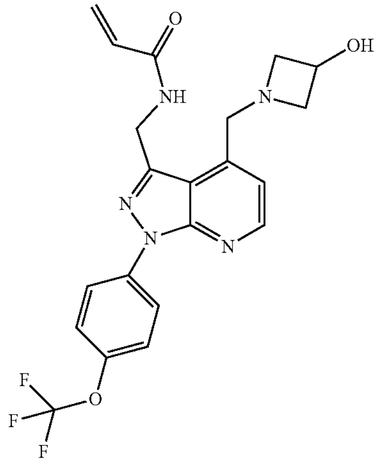 [SMILES: C=CC(=O)NCc1nn(-c2ccc(OC(F)(F)F)cc2)c2nccc(CN3CC(O)C3)c12]

Step 1: tert-butyl ((4-((3-hydroxyazetidin-1-yl)methyl)-1-(4-(trifluoromethoxy)phenyl)-1H-pyrazolo[3,4-b]pyridin-3-yl)methyl)carbamate

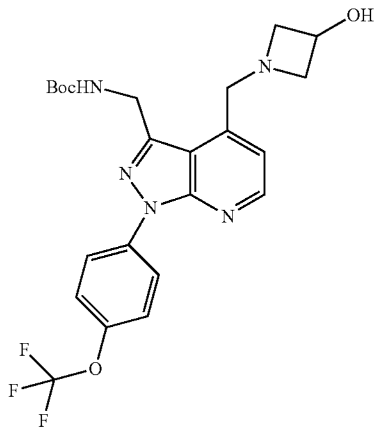 [SMILES: CC(C)(C)OC(=O)NCc1nn(-c2ccc(OC(F)(F)F)cc2)c2nccc(CN3CC(O)C3)c12]

A solution of tert-butyl ((4-formyl-1-(4-(trifluoromethoxy)phenyl)-1H-pyrazolo[3,4-b]pyridin-3-yl)methyl)carbamate (180 mg, 0.41 mmol), azetidin-3-ol (60 mg, 0.82 mmol), AcOH (0.02 ml, 0.35 mmol) in MeOH (10 mL) and DCM (10 mL) was stirred at room temperature for 12 h. Then $NaBH_3CN$ (51 mg, 0.82 mmol) was added into the reaction and the reaction solution was stirred at room temperature for 2 h. The reaction mixture was quenched with water (30 mL). The resulting mixture was extracted with ethyl acetate (30 mL×3), the organic layers were combined, dried over $Na_2SO_4$ and concentrated to dryness. The residue was purified by flash chromatography on silica gel (0-3% MeOH in DCM) to afford the title compound (90 mg, 44%) as a yellow solid. $^1H$ NMR (400 MHz, $CDCl_3$): δ 8.59 (d, J=4.0 Hz, 1H), 8.32 (d, J=9.2 Hz, 2H), 7.38 (d, J=8.4 Hz, 2H), 7.21-7.19 (m, 1H), 4.81-4.79 (m, 2H), 4.54-4.51 (m, 1H), 4.16-4.14 (m, 2H), 3.84-3.80 (m, 2H), 3.36-3.34 (m, 2H), 1.42 (s, 9H); LCMS (ESI): m/z 494.2 $(M+H)^+$.

Step 2: 1-((3-(aminomethyl)-1-(4-(trifluoromethoxy)phenyl)-1H-pyrazolo[3,4-b]pyridin-4-yl)methyl)azetidin-3-ol

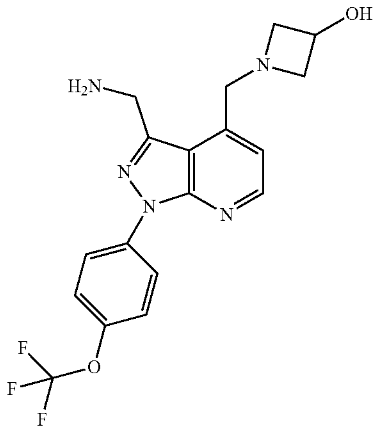 [SMILES: NCc1nn(-c2ccc(OC(F)(F)F)cc2)c2nccc(CN3CC(O)C3)c12]

A mixture of tert-butyl ((4-((3-hydroxyazetidin-1-yl)methyl)-1-(4-(trifluoromethoxy)phenyl)-1H-pyrazolo[3,4-b]pyridin-3-yl)methyl)carbamate (70 mg, 0.14 mmol) in TFA (5% in HFIP, 5 mL) was stirred at 0° C. for 2 h under nitrogen atmosphere. The reaction mixture was neutralized with saturated aqueous $NaHCO_3$ to pH=8. The resulting solution was extracted with ethyl acetate (50 mL×3). The organic layer was dried over anhydrous sodium sulfate and concentrated under vacuum to afford the title compound (55 mg, 98%) as a yellow oil. LCMS (ESI): m/z 394.2 $(M+H)^+$.

Step 3: N-((4-((3-hydroxyazetidin-1-yl)methyl)-1-(4-(trifluoromethoxy)phenyl)-1H-pyrazolo[3,4-b]pyridin-3-yl)methyl)acrylamide

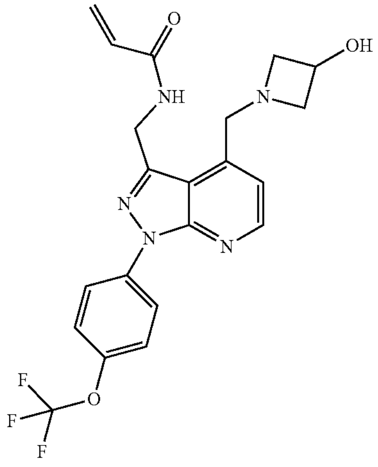 [SMILES: C=CC(=O)NCc1nn(-c2ccc(OC(F)(F)F)cc2)c2nccc(CN3CC(O)C3)c12]

To a solution of 1-((3-(aminomethyl)-1-(4-(trifluoromethoxy)phenyl)-1H-pyrazolo[3,4-b]pyridin-4-yl)methyl)azetidin-3-ol (50 mg, 0.13 mmol) in THF (5 mL) was added sat. $NaHCO_3$ (1 mL) and acrylic anhydride (30 mg, 0.24 mmol) at 0° C. The mixture was stirred at 0° C. for 1 h. The mixture was diluted with water (10 mL) and extracted with ethyl acetate (30 mL×3). The organics were combined, which washed with brine (20 mL), dried over sodium sulfate, filtered and concentrated. The residue was purified by reverse phase chromatography (Welch Xtimate C18 150*25 mm*5 um, water ($NH_4HCO_3$)-ACN, 25%-55%) to afford the title compound (16.7 mg, 28%) as a white solid. $^1H$ NMR (400 MHz, DMSO-$d_6$): δ 8.81 (s, 1H), 8.60 (d, J=4.4 Hz, 1H), 8.38 (d, J=8.4 Hz, 2H), 7.59 (d, J=8.0 Hz, 2H), 7.31 (d, J=4.4 Hz, 1H), 6.40-6.24 (m, 1H), 6.23-6.07 (m, 1H), 5.64 (d, J=9.6 Hz, 1H), 5.40 (d, J=5.2 Hz, 1H), 4.89 (d, J=4.0 Hz, 2H), 4.25-4.22 (m, 1H), 3.99 (s, 2H), 3.57-3.54 (m, 2H), 2.90-2.87 (m, 2H); LCMS (ESI): m/z 448.0 $(M+H)^+$.

Example 33 (Compound 105)

N-((4-((dimethylamino)methyl)-1-(4-(trifluoromethoxy)phenyl)-1H-pyrazolo[3,4-b]pyridin-3-yl)methyl)acrylamide

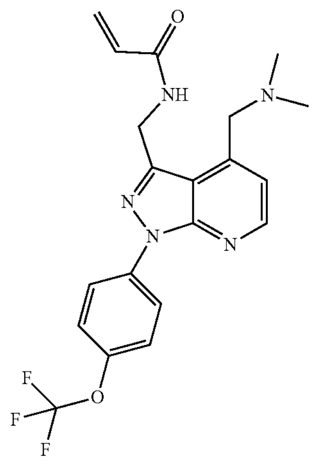 [SMILES: C=CC(=O)NCc1nn(-c2ccc(OC(F)(F)F)cc2)c2nccc(CN(C)C)c12]

Step 1: tert-butyl ((4-((dimethylamino)methyl)-1-(4-(trifluoromethoxy)phenyl)-1H-pyrazolo[3,4-b]pyridin-3-yl)methyl)carbamate

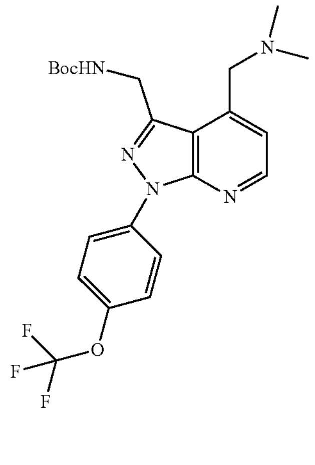 [SMILES: CN(C)Cc1ccnc2c1c(CNC(=O)OC(C)(C)C)nn2-c1ccc(OC(F)(F)F)cc1]

A solution of tert-butyl ((4-formyl-1-(4-(trifluoromethoxy)phenyl)-1H-pyrazolo[3,4-b]pyridin-3-yl)methyl)carbamate (200 mg, 0.46 mmol), dimethylamine hydrochloride (74 mg, 0.92 mmol), TEA (0.13 mL, 0.92 mmol), AcOH (0.05 mL, 0.92 mmol) in DCM (10 mL) was stirred at room temperature for 12 h. Then $NaBH_3CN$ (57 mg, 0.92 mmol) was added into the reaction. The solution was stirred at room temperature for 2 h. The reaction mixture was quenched with $H_2O$ (30 mL). The resulting solution was extracted with ethyl acetate (30 mL×3). The organics were dried over $Na_2SO_4$, filtered and concentrated. The residue was purified by flash chromatography on silica gel (0-30% MeOH in DCM) to afford the title compound (200 mg, 93%) as a yellow solid. $^1H$ NMR (400 MHz, $CDCl_3$): δ 8.54-8.53 (m, 1H), 8.33 (d, J=8.8 Hz, 2H), 7.38 (d, J=8.8 Hz, 2H), 7.13-7.11 (m, 1H), 4.85-4.83 (m, 2H), 3.77 (s, 2H), 2.32 (s, 6H), 1.49 (s, 9H); LCMS (ESI): m/z 466.2 $(M+H)^+$.

Step 2: 1-(3-(aminomethyl)-1-(4-(trifluoromethoxy)phenyl)-1H-pyrazolo[3,4-b]pyridin-4-yl)-N,N-dimethylmethanamine

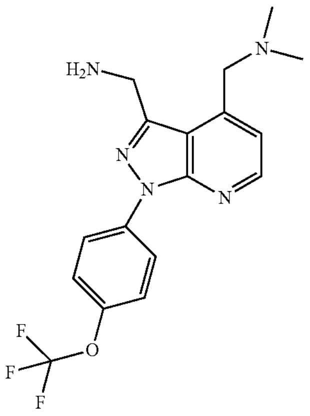 [SMILES: CN(C)Cc1ccnc2c1c(CN)nn2-c1ccc(OC(F)(F)F)cc1]

A mixture of tert-butyl ((4-((dimethylamino)methyl)-1-(4-(trifluoromethoxy)phenyl)-1H-pyrazolo[3,4-b]pyridin-3-yl)methyl)carbamate (200 mg, 0.4 mmol) in 5% TFA/HFIP (10 mL) was stirred at 0° C. for 2 h under nitrogen atmosphere. The reaction mixture was neutralized with saturated aqueous $NaHCO_3$ to pH=8. The resulting solution was extracted with ethyl acetate (50 mL×3). The organic layer was dried over anhydrous sodium sulfate and concentrated under vacuum to afford the title compound (159 mg, 99%) as a yellow oil. LCMS (ESI): m/z 366.2 $(M+H)^+$.

Step 3: N-((4-((dimethylamino)methyl)-1-(4-(trifluoromethoxy)phenyl)-1H-pyrazolo[3,4-b]pyridin-3-yl)methyl)acrylamide

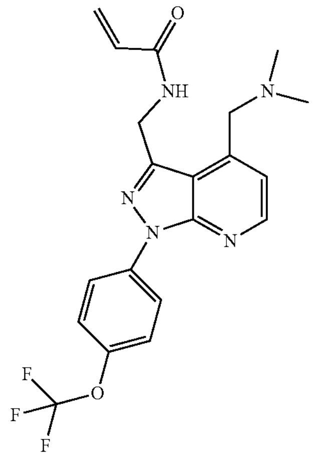 [SMILES: C=CC(=O)NCc1nn(-c2ccc(OC(F)(F)F)cc2)c2nccc(CN(C)C)c12]

To a solution of 1-(3-(aminomethyl)-1-(4-(trifluoromethoxy)phenyl)-1H-pyrazolo[3,4-b]pyridin-4-yl)-N,N-dimethylmethanamine (159 mg, 0.44 mmol) in THF (5 mL) was added sat. $NaHCO_3$ (1 mL) and acrylic anhydride (127 mg, 0.65 mmol) at 0° C. The mixture was stirred at 0° C. for 1 h. The mixture was diluted with water (10 mL) and extracted with ethyl acetate (30 mL×3). The organics were combined, washed with brine (20 mL), dried over sodium sulfate, filtered and concentrated. The residue was purified by reverse phase chromatography (Welch Xtimate C18 150*25 mm*5 um, water ($NH_4HCO_3$)-ACN, 43%-73%) to afford the title compound (62.1 mg, 33%) as a white solid. $^1$H NMR (400 MHz, DMSO-$d_6$): δ 8.78 (t, J=5.2 Hz, 1H), 8.62 (d, J=4.4 Hz, 1H), 8.40 (d, J=8.8 Hz, 2H), 7.60 (d, J=8.8 Hz, 2H), 7.34 (d, J=4.4 Hz, 1H), 6.31 (d, J=17.2, 10.0 Hz, 1H), 6.16 (dd, J=17.2, 2.0 Hz, 1H), 5.64 (dd, J=10.0, 2.0 Hz, 1H), 4.92 (d, J=5.2 Hz, 1H), 3.78 (s, 2H), 2.22 (s, 6H); LCMS (ESI): m/z 420.0 $(M+H)^+$.

Example 34 (Compound 134)

N-((4-(1H-Pyrazol-4-yl)-1-(4-(trifluoromethoxy)phenyl)-1H-pyrazolo[3,4-b]pyridin-3-yl)methyl)acrylamide

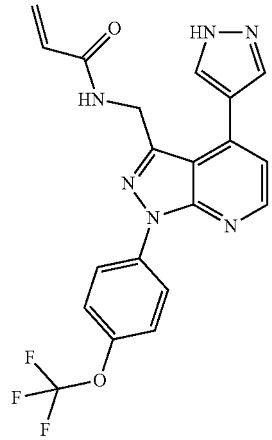 [SMILES: C=CC(=O)NCc1nn(-c2ccc(OC(F)(F)F)cc2)c2nccc(-c3cn[nH]c3)c12]

Step 1: tert-butyl ((4-(1H-pyrazol-4-yl)-1-(4-(trifluoromethoxy)phenyl)-1H-pyrazolo[3,4-b]pyridin-3-yl)methyl)carbamate

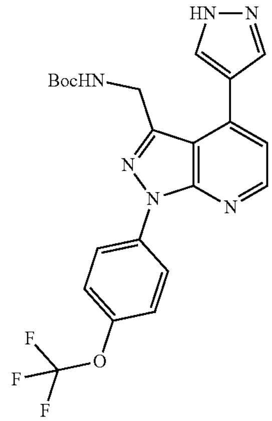 [SMILES: CC(C)(C)OC(=O)NCc1nn(-c2ccc(OC(F)(F)F)cc2)c2nccc(-c3cn[nH]c3)c12]

A solution of tert-butyl ((4-chloro-1-(4-(trifluoromethoxy)phenyl)-1H-pyrazolo[3,4-b]pyridin-3-yl)methyl)carbamate (100 mg, 0.23 mmol), Xphos Pd $G_2$ (18 mg, 0.02 mmol), KOAc (44 mg, 0.45 mmol), Xphos (10 mg, 0.02 mmol), 4-(4,4,5,5-tetramethyl-1,3,2-dioxaborolan-2-yl)-1H-pyrazole (65 mg, 0.34 mmol) in 1,4-dioxane (5 mL) and water (0.5 mL) was stirred at 100° C. under $N_2$ atmosphere for 16 h. The mixture was diluted with ethyl acetate (20 mL) and washed with water (10 mL×3). The organic layer was dried over anhydrous $Na_2SO_4$ and concentrated. The residue was purified by column chromatography on silica gel (0-20% ethyl acetate in petroleum ether) to afford the title compound (65 mg, 61%) as a white solid. LCMS (ESI): m/z 475.1 $(M+H)^+$.

Step 2: (4-(1H-pyrazol-4-yl)-1-(4-(trifluoromethoxy)phenyl)-1H-pyrazolo[3,4-b]pyridin-3-yl) methanamine 2,2,2-trifluoroacetate

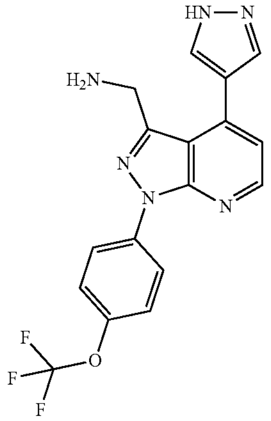 [SMILES: NCc1nn(-c2ccc(OC(F)(F)F)cc2)c2nccc(-c3cn[nH]c3)c12]

A mixture of tert-butyl ((4-(1H-pyrazol-4-yl)-1-(4-(trifluoromethoxy)phenyl)-1H-pyrazolo[3,4-b]pyridin-3-yl) methyl)carbamate (68 mg, 0.1400 mmol) in TFA (5% in HFIP, 5 mL) was stirred at room temperature for 1 h. The mixture was concentrated to afford the title compound (47 mg, 88%) as a yellow solid. LCMS (ESI): m/z 375.2 $(M+H)^+$.

Step 3: N-((4-(1H-pyrazol-4-yl)-1-(4-(trifluoromethoxy)phenyl)-1H-pyrazolo[3,4-b]pyridin-3-yl) methyl)acrylamide

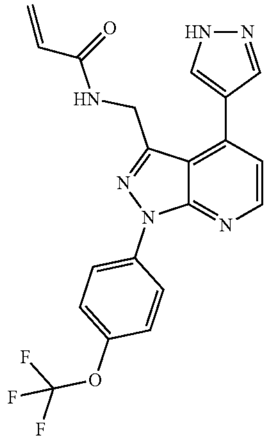 [SMILES: C=CC(=O)NCc1nn(-c2ccc(OC(F)(F)F)cc2)c2nccc(-c3cn[nH]c3)c12]

To a solution of (4-(1H-pyrazol-4-yl)-1-(4-(trifluoromethoxy)phenyl)-1H-pyrazolo[3,4-b]pyridin-3-yl)methanamine 2,2,2-trifluoroacetate (47 mg, 0.13 mmol) in THF (5 mL) was added saturated $NaHCO_3$ solution (2 mL), and acrylic anhydride (0.01 mL, 0.13 mmol) at 0° C., the solution was stirred at 0° C. for 30 mins. The solution was washed with water (10 mL) and extract with ethyl acetate (10 mL×3), the organic layer was dried with anhydrous $Na_2SO_4$ and concentrated under vacuum, the residue was purified by prep-TLC (100% ethyl acetate) to afford the title compound (28 mg, 51%) as a white solid. $^1H$ NMR (400 MHz, DMSO-$d_6$): δ 13.34 (s, 1H), 8.62 (d, J=4.8 Hz, 1H), 8.58 (s, 1H), 8.41 (d, J=8.8 Hz, 2H), 8.32 (s, 1H), 7.97 (s, 1H), 7.60 (d, J=8.8 Hz, 2H), 7.32 (d, J=4.8 Hz, 1H), 6.28 (dd, J=16.8, 10.0 Hz, 1H), 6.11 (dd, J=16.8, 2.0 Hz, 1H), 5.59 (d, J=10.0, 2.0 Hz, 1H), 4.66 (d, J=4.8 Hz, 2H), LCMS (ESI): m/z 429.1 $(M+H)^+$.

Example 35 (Compound 119)

N-((4-(1H-Imidazol-4-yl)-1-(4-(trifluoromethoxy) phenyl)-1H-pyrazolo[3,4-b]pyridin-3-yl)methyl) acrylamide

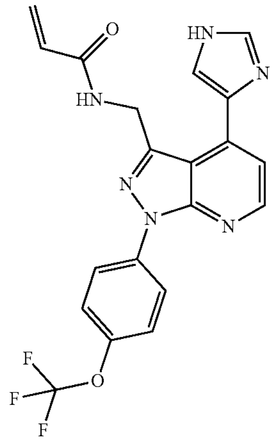 [SMILES: C=CC(=O)NCc1nn(-c2ccc(OC(F)(F)F)cc2)c2nccc(-c3c[nH]cn3)c12]

Step 1: (1-trityl-1H-imidazol-4-yl)boronic acid

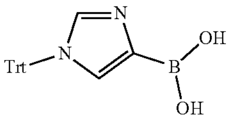

To a solution of 4-iodo-1-tritylimidazole (2.0 g, 4.58 mmol) in THF (30 mL) was added isopropylmagnesiumchloride (2M in THF, 3.44 mL, 6.88 mmol) at 0° C. The mixture was stirred at 0° C. for 10 min, then trimethylborate (2.40 g, 22.9 mmol) was added at 0° C. The mixture was stirred at 0° C. for another 10 min. The mixture was quenched with 1 M HCl (15 mL) and the mixture was stirred for 10 min at room temperature. The mixture was diluted with $H_2O$ (50 mL), extracted with ethyl acetate (50 mL×3). The combined organic layers were dried over $Na_2SO_4$, concentrated in vacuo to afford the title compound (1.40 g, 86%) as a white solid.

Step 2: tert-butyl 01-(4-(trifluoromethoxy)phenyl)-4-(1-trityl-1H-imidazol-4-yl)-1H-pyrazolo[3,4-b]pyridin-3-yl)methyl)carbamate

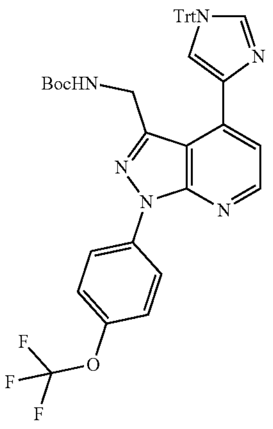

The mixture of tert-butyl ((4-chloro-1-(4-(trifluoromethoxy)phenyl)-1H-pyrazolo[3,4-b]pyridin-3-yl)methyl)carbamate (200 mg, 0.45 mmol), (1-trityl-1H-imidazol-4-yl)boronic acid (320 mg, 0.90 mmol), $K_2CO_3$ (187 mg, 1.35 mmol), $Pd(PPh_3)_2Cl_2$ (32 mg, 0.05 mmol) in 1,4-dioxane (4 mL) and water (0.4 mL) was stirred under nitrogen with MicroWave irradiation at 120° C. for 1 h. The mixture was diluted with $H_2O$ (10 mL), extracted with ethyl acetate (15 mL×3). The combined organic layers were dried over $Na_2SO_4$, filtered, and concentrated in vacuo. The residue was purified by flash column (0-20% ethyl acetate in petroleum ether) to afford the title compound (140 mg, 43%) as a white solid. LCMS (ESI): m/z 717.3 $(M+H)^+$.

Step 3: (4-(1H-imidazol-4-yl)-1-(4-(trifluoromethoxy)phenyl)-1H-pyrazolo[3,4-b]pyridin-3-yl) methanamine 2,2,2-trifluoroacetate salt

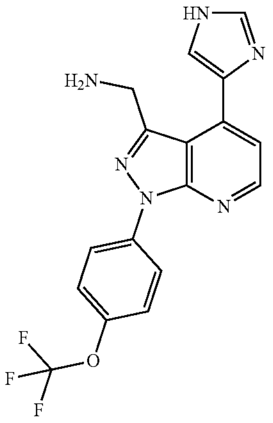 [SMILES: NCc1nn(-c2ccc(OC(F)(F)F)cc2)c2nccc(-c3c[nH]cn3)c12]

A solution of tert-butyl 41-(4-(trifluoromethoxy)phenyl)-4-(1-trityl-1H-imidazol-4-yl)-1H-pyrazolo[3,4-b]pyridin-3-yl)methyl)carbamate (140 mg, 0.20 mmol) in TFA (5% in HFIP, 9 mL) was stirred at rom temperature for 1 h. The mixture was concentrated in vacuo to afford the crude product which was used directly for next step. LCMS (ESI): m/z 375.1 $(M+H)^+$.

Step 4: N-((4-(1H-imidazol-4-yl)-1-(4-(trifluoromethoxy)phenyl)-1H-pyrazolo[3,4-b]pyridin-3-yl) methyl)acrylamide

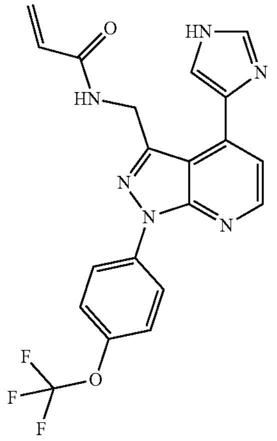 [SMILES: C=CC(=O)NCc1nn(-c2ccc(OC(F)(F)F)cc2)c2nccc(-c3c[nH]cn3)c12]

To a mixture of (4-(1H-imidazol-4-yl)-1-(4-(trifluoromethoxy)phenyl)-1H-pyrazolo[3,4-b]pyridin-3-yl)methanamine 2,2,2-trifluoroacetate salt (95 mg, 0.19 mmol) and sat.$NaHCO_3$ (1 mL) in THF (6 mL) was added acryloyl chloride (25 mg, 0.19 mmol). The mixture was stirred at 0° C. for 30 min. The mixture diluted with $H_2O$ (15 mL), extracted with ethyl acetate (15 mL×3). The organic layer was dried over $Na_2SO_4$, concentrated in vacuo. The residue was purified by flash column (0-100% ethyl acetate in petroleum ether) to afford the title compound (49.8 mg, 59%) as a white solid. $^1H$ NMR (400 MHz, DMSO-$d_6$): δ 12.67 (s, 1H), 8.70 (t, J=5.2 Hz, 1H), 8.58 (d, J=4.8 Hz, 1H), 8.42 (d, J=8.8 Hz, 2H), 7.98 (s, 2H), 7.65-7.50 (m, 3H), 6.15 (dd, J=17.2, 10.4 Hz, 1H), 6.04 (dd, J=17.2, 2.0 Hz, 1H), 5.59 (dd, J=10.4, 2.0 Hz, 1H), 5.01 (d, J=5.6 Hz, 2H); LCMS (ESI): m/z 429.0 $(M+H)^+$.

Example 36 (Compound 83)

N-((4-(1H-Pyrazol-3-yl)-1-(4-(trifluoromethoxy) phenyl)-1H-pyrazolo[3,4-b]pyridin-3-yl)methyl) acrylamide

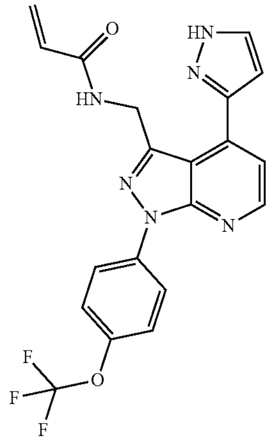 [SMILES: C=CC(=O)NCc1nn(-c2ccc(OC(F)(F)F)cc2)c2nccc(-c3cc[nH]n3)c12]

Step 1: tert-butyl ((4-(1H-pyrazol-3-yl)-1-(4-(trifluoromethoxy)phenyl)-1H-pyrazolo[3,4-b]pyridin-3-yl)methyl)carbamate

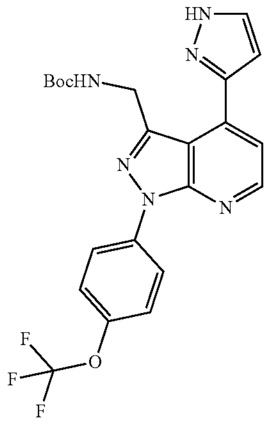 [SMILES: CC(C)(C)OC(=O)NCc1nn(-c2ccc(OC(F)(F)F)cc2)c2nccc(-c3cc[nH]n3)c12]

A solution of Xphos Pd 2 (18 mg, 0.02 mmol), KOAc (44 mg, 0.45 mmol), 3-(4,4,5,5-tetramethyl-1,3,2-dioxaborolan-2-yl)-1H-pyrazole (66 mg, 0.34 mmol), ter t-butyl ((4-chloro-1-(4-(trifluoromethoxy)phenyl)-1H-pyrazolo[3,4-b]pyridin-3-yl)methyl)carbamate (100 mg, 0.23 mmol) and Xphos (11 mg, 0.02 mmol) in 1,4-dioxane (2 mL) and water (0.25 mL) was stirred at 100° C. for 16 h. The mixture was quenched with water (20 mL) and extracted with ethyl acetate (20 mL×3). The organic was dried over $Na_2SO_4$ and concentrated. The residue was purified by flash column chromatography on silica gel (0-20% ethyl acetate in petroleum ether) to afford the title compound (60 mg, 58%) as a white solid. $^1H$ NMR (400 MHz, DMSO-$d_6$): δ 13.48 (s, 1H), 8.65 (d, J=4.4 Hz, 1H), 8.41 (d, J=8.0 Hz, 2H), 7.98 (s, 1H), 7.61-7.56 (m, 3H), 7.06 (t, J=5.2 Hz, 1H), 6.95-6.89 (m, 1H), 4.70 (d, J=6.0 Hz, 2H), 1.39 (s, 9H).

Step 2: (4-(1H-pyrazol-3-yl)-1-(4-(trifluoromethoxy)phenyl)-1H-pyrazolo[3,4-b]pyridin-3-yl)methanamine 2,2,2-trifluoroacetate salt

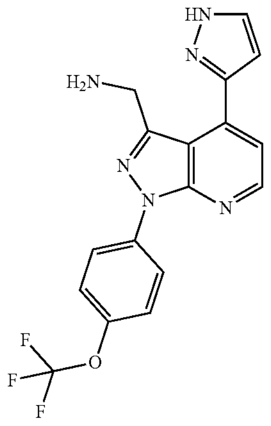 [SMILES: NCc1nn(-c2ccc(OC(F)(F)F)cc2)c2nccc(-c3cc[nH]n3)c12]

A mixture of tert-butyl ((4-(1H-pyrazol-3-yl)-1-(4-(trifluoromethoxy)phenyl)-1H-pyrazolo[3,4-b]pyridin-3-yl)methyl)carbamate (60 mg, 0.13 mmol) in TFA (5% in HFIP, 2 mL) was stirred at room temperature for 1 h. The mixture was concentrated to afford the title compound (60 mg) as a yellow solid. The crude would be used in the next step directly.

Step 3: N-((4-(1H-pyrazol-3-yl)-1-(4-(trifluoromethoxy)phenyl)-1H-pyrazolo[3,4-b]pyridin-3-yl)methyl)acrylamide

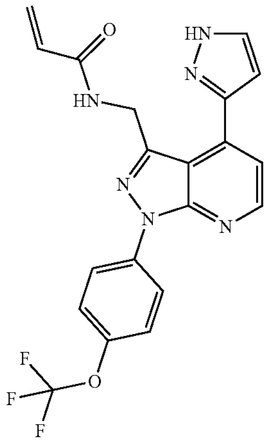 [SMILES: C=CC(=O)NCc1nn(-c2ccc(OC(F)(F)F)cc2)c2nccc(-c3cc[nH]n3)c12]

To a solution of (4-(1H-pyrazol-3-yl)-1-(4-(trifluoromethoxy)phenyl)-1H-pyrazolo[3,4-b]pyridin-3-yl)methanamine 2,2,2-trifluoroacetate salt (60 mg, 0.16 mmol) in THF (6 mL) was added sat. $NaHCO_3$ solution (2 mL) and acrylic anhydride (0.04 mL, 0.38 mmol) at 0° C. for 1 h. The mixture was quenched with water (10 mL) and extracted with ethyl acetate (30 mL×3). The organic layers were dried over anhydrous sodium sulfate and concentrated to dryness. The residue was purified by reverse phase chromatography (Welch Xtimate C18 150*30 mm*5 um, acetonitrile 54-84%/water (0.225% FA)-ACN) to afford the title compound (11.5 mg, 17%). $^1H$ NMR (400 MHz, DMSO-$d_6$): δ 13.46 (s, 1H), 8.68 (d, J=4.8 Hz, 1H), 8.46 (t, J=5.6 Hz, 1H), 8.41 (d, J=9.2 Hz, 2H), 7.97 (s, J=4.4 Hz, 1H), 7.62-7.58 (m, 3H), 6.94 (s, 1H), 6.30 (dd, J=17.2, 10.0 Hz, 1H), 6.08 (dd, J=17.2, 2.4 Hz, 1H), 5.58 (dd, J=10.0, 2.4 Hz, 1H), 4.95 (d, J=5.6 Hz, 2H); LCMS (ESI): m/z 429.0 $(M+H)^+$.

Example 37 (Compound 35)

N-((4-(1-(2-Hydroxyethyl)-1H-pyrazol-4-yl)-1-(4-(trifluoromethoxy)phenyl)-1H-pyrazolo[3,4-b]pyridin-3-yl)methyl)acrylamide

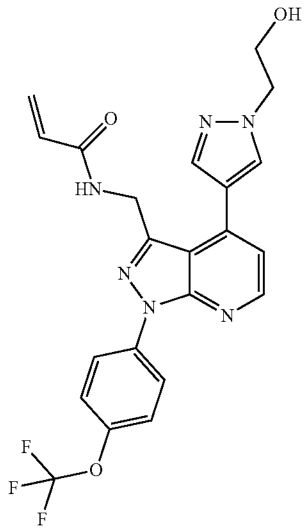 [SMILES: C=CC(=O)NCc1nn(-c2ccc(OC(F)(F)F)cc2)c2nccc(-c3cnn(CCO)c3)c12]

Step 1: tert-butyl ((4-(1-(2-hydroxyethyl)-1H-pyrazol-4-yl)-1-(4-(trifluoromethoxy)phenyl)-1H-pyrazolo[3,4-b]pyridin-3-yl)methyl)carbamate

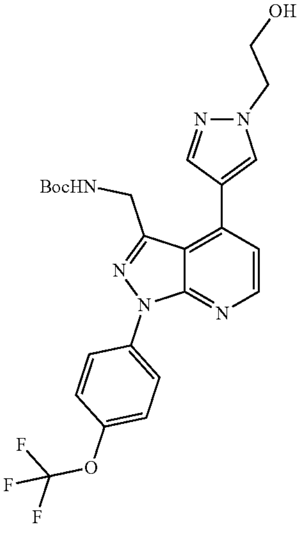 [SMILES: CC(C)(C)OC(=O)NCc1nn(-c2ccc(OC(F)(F)F)cc2)c2nccc(-c3cnn(CCO)c3)c12]

A mixture of tert-butyl ((4-chloro-1-(4-(trifluoromethoxy)phenyl)-1H-pyrazolo[3,4-b]pyridin-3-yl)methyl)carbamate (200 mg, 0.45 mmol), 2-(4-(4,4,5,5-tetramethyl-1,3,2-dioxaborolan-2-yl)-1H-pyrazol-1-yl)ethanol (215 mg, 0.90 mmol), Xphos Pd $G_2$ (36.0 mg, 0.05 mmol), Xphos (22 mg, 0.05 mmol) and $K_3PO_4$ (290 mg, 1.35 mmol) in 1,4-dioxane (10 mL) and water (1 mL) was stirred at 100° C. for 6 h under $N_2$ atmosphere. The mixture was diluted with ethyl acetate (100 mL) and washed with water (100 mL×3). The organic was dried over $Na_2SO_4$ and concentrated to dryness. The residue was purified by flash column chromatography on silica gel (0-8% ethyl acetate in petroleum ether) to afford the title compound (180 mg, 77%) as a white solid. $^1H$ NMR (400 MHz, $CDCl_3$): δ 8.59 (d, J=4.8 Hz, 1H), 8.34 (d, J=8.8 Hz, 2H), 7.88 (s, 1H), 7.73 (d, J=5.6 Hz, 1H), 7.39 (d, J=8.4 Hz, 2H), 7.15 (d, J=4.8 Hz, 1H), 5.35 (d, J=2.4 Hz, 1H), 4.57 (d, J=4.8 Hz, 2H), 4.39-4.37 (m, 2H), 4.27-2.25 (m, 1H), 4.06 (s, 2H), 1.43 (s, 9H).

Step 2: 2-(4-(3-(aminomethyl)-1-(4-(trifluoromethoxy)phenyl)-1H-pyrazolo[3,4-b]pyridin-4-yl)-1H-pyrazol-1-yl)ethanol

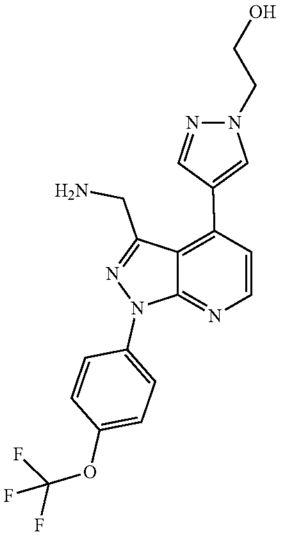 [SMILES: NCc1nn(-c2ccc(OC(F)(F)F)cc2)c2nccc(-c3cnn(CCO)c3)c12]

A mixture of tert-butyl ((4-(1-(2-hydroxyethyl)-1H-pyrazol-4-yl)-1-(4-(trifluoromethoxy)phenyl)-1H-pyrazolo[3,4-b]pyridin-3-yl)methyl)carbamate (150 mg, 0.29 mmol) in TFA (5% in HFIP, 5 mL) was stirred at room temperature with 2 h. The reaction mixture was diluted with water (60 mL) and adjusted to pH=8 with sat. $NaHCO_3$. The mixture was diluted with ethyl acetate (30 mL×2), the combined organic layers were washed with brine (60 mL×2), dried over $Na_2SO_4$ and concentrated to afford the title compound (90 mg, 74%) as a yellow oil. LCMS (ESI): m/z 419.0 $(M+H)^+$.

Step 3: N-((4-(1-(2-hydroxyethyl)-1H-pyrazol-4-yl)-1-(4-(trifluoromethoxy)phenyl)-1H-pyrazolo[3,4-b]pyridin-3-yl)methyl)acrylamide

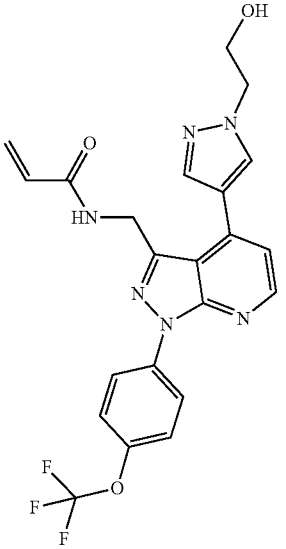

To a solution of 2-(4-(3-(aminomethyl)-1-(4-(trifluoromethoxy)phenyl)-1H-pyrazolo[3,4-b]pyridin-4-yl)-1H-pyrazol-1-yl)ethanol (90.0 mg, 0.22 mmol) and saturated $NaHCO_3$ (2 mL) in THF (6 mL) was added acryloyl chloride (20.0 uL, 0.22 mmol) at 0° C. The reaction mixture was stirred at 0° C. with 1 h. The reaction mixture was diluted with ethyl acetate (30 mL), washed with brine (30 mL×3), dried over $Na_2SO_4$ and concentrated to dryness. The resulting residue was purified by reverse phase chromatography (Welch Xtimate C18 150*30 mm*5 um, acetonitrile 46-76%/water (0.225% FA)-ACN) to afford the title compound (61.0 mg, 60%) as a white solid. $^1$H NMR (400 MHz, DMSO-$d_6$): δ 8.62 (d, J=4.8 Hz, 1H), 8.54 (t, J=4.8 Hz, 1H), 8.41 (d, J=8.8 Hz, 2H), 8.25 (s, 1H), 7.91 (s, 1H), 7.61 (d, J=8.8 Hz, 2H), 7.30 (d, J=4.8 Hz, 1H), 6.22 (dd, J=17.2, 10.4 Hz, 1H), 6.06 (dd, J=17.2, 2.0 Hz, 1H), 5.58 (dd, J=10.4, 2.0 Hz, 1H), 5.00 (t, J=5.2 Hz, 1H), 4.69 (d, J=4.8 Hz, 2H), 4.22 (t, J=5.6 Hz, 2H), 3.80 (q, J=5.2 Hz, 2H); LCMS (ESI): m/z 473.0 $(M+H)^+$.

Example 38 (Compound 51)

N-((4-(1H-1,2,3-Triazol-4-yl)-1-(4-(trifluoromethoxy)phenyl)-1H-pyrazolo[3,4-b]pyridin-3-yl)methyl)acrylamide

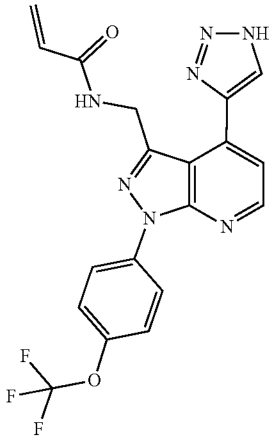 [SMILES: C=CC(=O)NCc1nn(-c2ccc(OC(F)(F)F)cc2)c2nccc(-c3c[nH]nn3)c12]

Step 1: tert-butyl 04-(2-(tetrahydro-2H-pyran-2-yl)-2H-1,2,3-triazol-4-yl)-1-(4-(trifluoromethoxy)phenyl)-1H-pyrazolo[3,4-b]pyridin-3-yl)methyl)carbamate

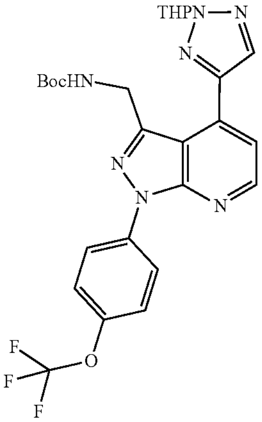

A solution of tert-butyl ((4-chloro-1-(4-(trifluoromethoxy)phenyl)-1H-pyrazolo[3,4-b]pyridin-3-yl)methyl)carbamate (100 mg, 0.23 mmol), $Pd(PPh_3)_4$ (26.0 mg, 0.02 mmol), KOAc (94.0 mg, 0.68 mmol) and 2-(tetrahydro-2H-pyran-2-yl)-4-(4,4,5,5-tetramethyl-1,3,2-dioxaborolan-2-yl)-2H-1,2,3-triazole (63.0 mg, 0.23 mmol) in 1,4-dioxane (2.0 mL) and water (0.1 mL) was stirred at 80° C. for 2 h under $N_2$ atmosphere. The reaction was quenched by water (30 mL). The resulting solution was extracted with ethyl acetate (15 mL×3) and the organic layers were combined. The organic layer was dried over $Na_2SO_4$. After filtration, the filtrate was concentrated under reduced pressure. The residue was purified by chromatography on silica gel (0-25% ethyl acetate in petroleum ether) to afford the title compound (100 mg, 79%) as a yellow solid. $^1$H NMR (400 MHz, $CDCl_3$): δ 8.66 (d, J=4.8 Hz, 1H), 8.37 (d, J=8.8

Hz, 2H), 8.09 (s, 1H), 7.43-7.40 (s, 1H), 7.39-7.36 (m, 2H), 5.87 (dd, J=9.2, 2.8 Hz, 1H), 5.79-5.73 (m, 1H), 4.91-4.78 (m, 2H), 3.87-3.80 (m, 1H), 2.59-2.48 (m, 1H), 2.35-2.23 (m, 1H), 2.19-2.13 (m, 1H), 1.86-1.78 (m, 2H), 1.78-1.67 (m, 2H), 1.46 (s, 9H); LCMS (ESI): m/z 559.9 $(M+H)^+$.

Step 2: (4-(1H-1,2,3-triazol-4-yl)-1-(4-(trifluoromethoxy)phenyl)-1H-pyrazolo[3,4-b]pyridin-3-yl) methanamine 2,2,2-trifluoroacetate salt

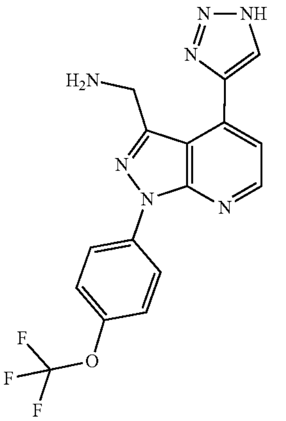 [SMILES: NCc1nn(-c2ccc(OC(F)(F)F)cc2)c2nccc(-c3c[nH]nn3)c12]

A mixture of tert-butyl ((4-(2-(tetrahydro-2H-pyran-2-yl)-2H-1,2,3-triazol-4-yl)-1-(4-(trifluoromethoxy)phenyl)-1H-pyrazolo[3,4-b]pyridin-3-yl)methyl)carbamate (100 mg, 0.2 mmol) in TFA (5% in HFIP, 2.0 mL) was stirred at room temperature for 1 h. The reaction was concentrated under reduced pressure to afford the title compound (100 mg) as a yellow solid. The crude would be used in the next step directly. LCMS (ESI): m/z 376.2 $(M+H)^+$.

Step 3: N-((4-(1H-1,2,3-triazol-4-yl)-1-(4-(trifluoromethoxy)phenyl)-1H-pyrazolo[3,4-b]pyridin-3-yl) methyl)acrylamide

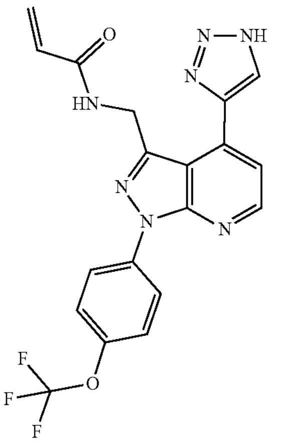 [SMILES: C=CC(=O)NCc1nn(-c2ccc(OC(F)(F)F)cc2)c2nccc(-c3c[nH]nn3)c12]

To a solution of saturated $NaHCO_3$ (1.0 mL) and (4-(1H-1,2,3-triazol-4-yl)-1-(4-(trifluoromethoxy)phenyl)-1H-pyrazolo[3,4-b]pyridin-3-yl)methanamine 2,2,2-trifluoroacetate salt (100 mg, 0.27 mmol) in THF (5.0 mL) was added acrylic anhydride (37.0 mg, 0.29 mmol) at 0° C. Then the reaction was stirred at room temperature for 2 h. The mixture was dilute with water (20 mL) and extracted with ethyl acetate (20 mL×3) and washed with brine (20 mL). The combined organic layers were dried over $Na_2SO_4$ and concentrated under reduced pressure. The residue was purified by column (Boston Green ODS 150*30 mm*5 um, acetonitrile 55-85%/water (0.225% FA)-ACN) to afford the title compound (3.3 mg, 3%) as a white solid. $^1H$ NMR (400 MHz, DMSO-$d_6$): δ 8.73 (d, J=4.8 Hz, 1H), 8.60 (s, 1H), 8.48 (t, J=5.2 Hz, 1H), 8.41 (d, J=9.2 Hz, 2H), 7.66-7.58 (m, 3H), 6.24 (dd, J=17.2, 10.0 Hz, 1H), 6.07 (dd, J=17.2, 2.0 Hz, 1H), 5.58 (dd, J=10.0, 2.0 Hz, 1H), 4.91 (d, J=5.2 Hz, 2H); LCMS (ESI): m/z 430.0 $(M+H)^+$.

Example 39 (Compound 67)

N-((4-(trans-3-Hydroxy cyclobutoxy)-1-(4-(trifluoromethoxy)phenyl)-1H-pyrazolo[3,4-b]pyridin-3-yl) methyl)acrylamide

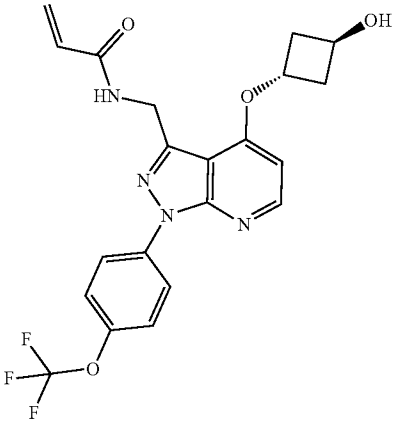

Step 1: tert-butyl 04-(trans-3-((tert-butyldimethylsilyl)oxy)cyclobutoxy)-1-(4-(trifluoromethoxy)phenyl)-1H-pyrazolo[3,4-b]pyridin-3-yl)methyl)carbamate

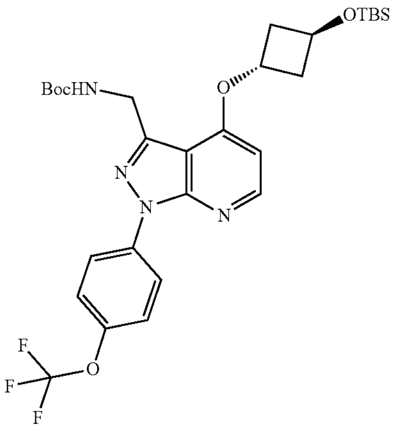 [SMILES: CC(C)(C)OC(=O)NCc1nn(-c2ccc(OC(F)(F)F)cc2)c2nccc(O[C@H]3C[C@H](O[Si](C)(C)C(C)(C)C)C3)c12]

To a solution of trans-3-((tert-butyldimethylsilyl)cyclobutanol (109 mg, 0.54 mmol) in THF (10 mL) was added NaH (89 mg, 0.9 mmol, 60% in mineral oil) slowly at 0° C. under $N_2$, then the reaction mixture was stirred at 0° C. for 1 h under $N_2$. tert-butyl ((4-chloro-1-(4-(trifluoromethoxy)phenyl)-1H-pyrazolo[3,4-b]pyridin-3-yl)methyl)carbamate (80 mg, 0.18 mmol) in THF (1 ml) was added into the reaction at 0° C. The mixture was stirred at room temperature for 2 h. The reaction mixture was quenched with saturated aqueous solution of $NH_4Cl$ (30 mL), diluted with water (30 mL) and extracted with ethyl acetate (50 mL×3), the combined organic layers were concentrated under reduced pressure, the resulting residue was purified by column chromatography on silica gel (0-5% ethyl acetate in petroleum ether) to afford the title compound (79 mg, 72%) as an orange oil. LCMS (ESI): m/z 609.4 $(M+H)^+$.

Step 2: tert-butyl 04-(trans-3-hydroxycyclobutoxy)-1-(4-(trifluoromethoxy)phenyl)-1H-pyrazolo[3,4-b]pyridin-3-yl)methyl)carbamate

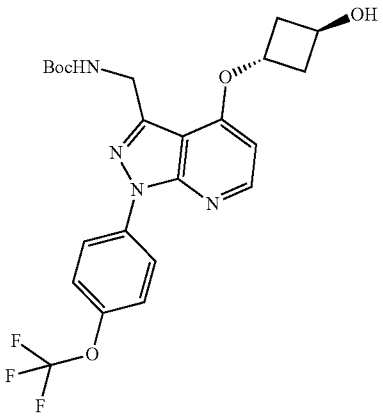

A mixture of tert-butyl ((4-(trans-3-((tert-butyldimethylsilyl)oxy)cyclobutoxy)-1-(4-(trifluoromethoxy)phenyl)-1H-pyrazolo[3,4-b]pyridin-3-yl)methyl)carbamate (79 mg, 0.13 mmol) and TBAF (0.26 mL, 0.26 mmol, 1.0 mol/L in THF) in THF (2 mL) was stirred at room temperature for 2 h under $N_2$ atmosphere. The mixture was diluted with water (30 mL) and extracted with ethyl acetate (50 mL×3), the combined organic layers were concentrated under reduced pressure to afford the title compound (60 mg, 92%). The reaction was used directly without further purification. LCMS (ESI): m/z 495.2 $(M+H)^+$.

Step 3: trans-3-((3-(aminomethyl)-1-(4-(trifluoromethoxy)phenyl)-1H-pyrazolo[3,4-b]pyridin-4-yl)oxy)cyclobutanol

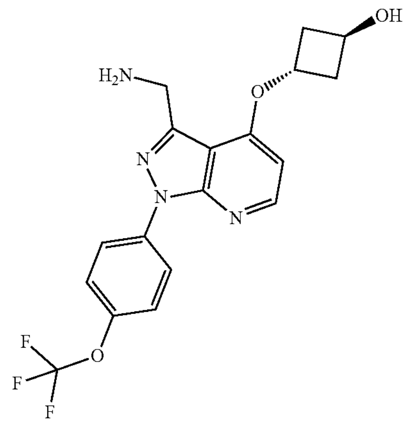

To a stirred solution of tert-butyl ((4-(trans-3-hydroxycyclobutoxy)-1-(4-(trifluoromethoxy)phenyl)-1H-pyrazolo[3,4-b]pyridin-3-yl)methyl)carbamate (60 mg, 0.10 mmol) in DCM (3 mL) was added TFA (0.13 mL, 1.72 mmol) at 0° C. The mixture was stirred at room temperature for 2 h. The reaction was quenched with aq. $NaHCO_3$ (30 mL) and diluted with water (30 mL) and extracted with ethyl acetate (50 mL×3). The combined organic layers were concentrated under reduced pressure to afford the title compound (50 mg, 99%). The reaction was used directly without further purification.

Step 4: N-((4-(trans-3-hydroxycyclobutoxy)-1-(4-(trifluoromethoxy)phenyl)-1H-pyrazolo[3,4-b]pyridin-3-yl)methyl)acrylamide

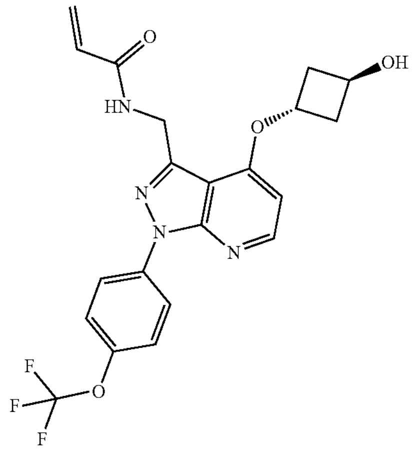

To a solution of trans-3-((3-(aminomethyl)-1-(4-(trifluoromethoxy)phenyl)-1H-pyrazolo[3,4-b]pyridin-4-yl)oxy)cyclobutanol (50 mg, 0.13 mmol) in THF (5 mL) was added sat.$NaHCO_3$ (0.5 ml) and acrylic anhydride (18 mg, 0.14 mmol) at 0° C. The mixture was stirred at 0° C. for 1 h. The reaction mixture was quenched with water (20 mL), extracted with ethyl acetate (20 mL×3). The organic layer was dried over $Na_2SO_4$ and concentrated. The residue was purified by reverse phase chromatography (Welch Xtimate C18 150*30 mm*5 um, water (0.225% FA)-ACN, 46-76%) to afford the title compound (17.0 mg, 29%) as a white solid. $^1$H NMR (400 MHz, DMSO-$d_6$): δ 8.55 (s, 1H), 8.48 (d, J=5.6 Hz, 1H), 8.39 (d, J=8.8 Hz, 2H), 7.58 (d, J=8.8 Hz, 2H), 6.68 (d, J=5.6 Hz, 1H), 6.32 (dd, J=17.2, 10.0 Hz, 1H), 6.17 (dd, J=17.2, 2.4 Hz, 1H), 5.63 (dd, J=10.0, 2.4 Hz, 1H), 5.24 (d, J=5.6 Hz, 1H), 5.16-5.05 (m, 1H), 4.78 (d, J=5.2 Hz, 2H), 4.45-4.33 (m, 1H), 2.45-2.40 (m, 2H), 2.36-2.33 (m, 2H); LCMS (ESI): m/z 448.9 $(M+H)^+$.

Example 40 (Compound 34)

N-((4-(cis-3-Hydroxycyclobutoxy)-1-(4-(trifluoromethoxy)phenyl)-1H-pyrazolo[3,4-b]pyridin-3-yl)methyl)acrylamide

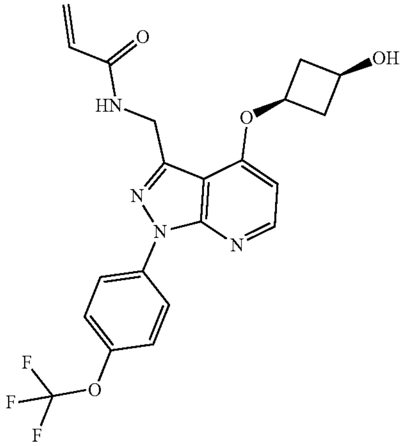 [SMILES: C=CC(=O)NCc1nn(-c2ccc(OC(F)(F)F)cc2)c2nccc(O[C@H]3C[C@@H](O)C3)c12]

Step 1: tert-butyl 04-(cis-3-((tert-butyldimethylsilyl)oxy)cyclobutoxy)-1-(4-(trifluoromethoxy)phenyl)-1H-pyrazolo[3,4-b]pyridin-3-yl)methyl)carbamate

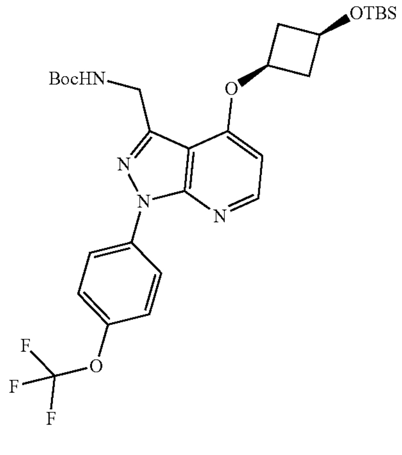

To a solution of cis-3-((tert-butyldimethylsilyl)oxy)cyclobutanol (274 mg, 1.35 mmol) in THF (10 mL) was added NaH (60% in mineral oil, 90 mg, 2.26 mmol) slowly at 0° C. under $N_2$, then the reaction mixture was stirred at 0° C. for 1 h under $N_2$ atmosphere, and then tert-butyl ((4-chloro-1-(4-(trifluoromethoxy)phenyl)-1H-pyrazolo[3,4-b]pyridin-3-yl)methyl)carbamate (200 mg, 0.45 mmol) in THF (1 ml) was added into the reaction at 0° C. The mixture was stirred at room temperature for 2 h. The reaction mixture was quenched with saturated aqueous solution of $NH_4Cl$ (30 mL), diluted with water (30 mL), and extracted with ethyl acetate (50 mL×3), the combined organic layers were concentrated under reduced pressure, the resulting residue was purified by column chromatography on silica gel (0-5% ethyl acetate in petroleum ether) to afford the title compound (200 mg, 73%) as an orange oil. $^1$H NMR (400 MHz, $CDCl_3$): δ 8.41 (d, J=5.2 Hz, 1H), 8.32 (d, J=8.8 Hz, 2H), 7.36 (d, J=8.8 Hz, 2H), 6.42 (d, J=5.2 Hz, 1H), 5.54-5.52 (m, 1H), 4.81-4.79 (m, 2H), 4.52-4.43 (m, 1H), 4.16-4.08 (m, 1H), 3.01-2.98 (m 2H), 2.35-2.28 (m, 2H), 1.51 (s, 9H), 0.91 (s, 9H), 0.09 (s, 6H); LCMS (ESI): m/z 609.3 $(M+H)^+$.

Step 2: tert-butyl ((4-(cis-3-hydroxycyclobutoxy)-1-(4-(trifluoromethoxy)phenyl)-1H-pyrazolo[3,4-b]pyridin-3-yl)methyl)carbamate

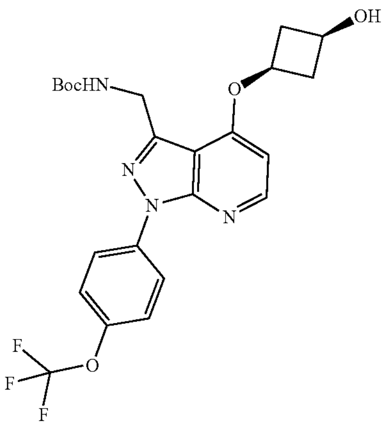 [SMILES: CC(C)(C)OC(=O)NCc1nn(-c2ccc(OC(F)(F)F)cc2)c2nccc(O[C@H]3C[C@@H](O)C3)c12]

A mixture of tert-butyl ((4-(cis-3-((tert-butyldimethylsilyl)oxy)cyclobutoxy)-1-(4-(trifluoromethoxy)phenyl)-1H-pyrazolo[3,4-b]pyridin-3-yl)methyl)carbamate (200 mg, 0.4 mmol) and TBAF (0.81 mL, 0.81 mmol, 1 mol/L in THF) was stirred at room temperature for 2 h under $N_2$ atmosphere. The mixture was diluted with water (30 mL) and extracted with ethyl acetate (50 mL×3), the combined organic layers were concentrated under reduced pressure to afford the title compound (170 mg, 96%). The reaction was used directly without further purification. LCMS (ESI): m/z 495.2 $(M+H)^+$.

Step 3: cis-3-((3-(aminomethyl)-1-(4-(trifluoromethoxy)phenyl)-1H-pyrazolo[3,4-b]pyridin-4-yl)oxy)cyclobutanol

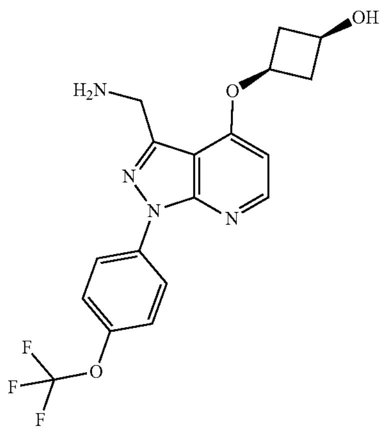 [SMILES: NCc1nn(-c2ccc(OC(F)(F)F)cc2)c2nccc(O[C@H]3C[C@@H](O)C3)c12]

To a stirred solution of tert-butyl ((4-(cis-3-hydroxycyclobutoxy)-1-(4-(trifluoromethoxy)phenyl)-1H-pyrazolo[3,4-b]pyridin-3-yl)methyl)carbamate (170 mg, 0.34 mmol) in DCM (3 mL) was added TFA (0.13 mL, 1.72 mmol) at 0° C. The mixture was stirred at room temperature for 2 h. The reaction was quenched with aq.$NaHCO_3$ (30 mL) and diluted with water (30 mL) and extracted with ethyl acetate (50 mL×3), the combined organic layers were concentrated under reduced pressure to afford the title compound (130 mg, 96%). The reaction was used directly without further purification. LCMS (ESI): m/z 395.2 $(M+H)^+$.

Step 4: N-((4-(cis-3-hydroxycyclobutoxy)-1-(4-(trifluoromethoxy)phenyl)-1H-pyrazolo[3,4-b]pyridin-3-yl)methyl)acrylamide

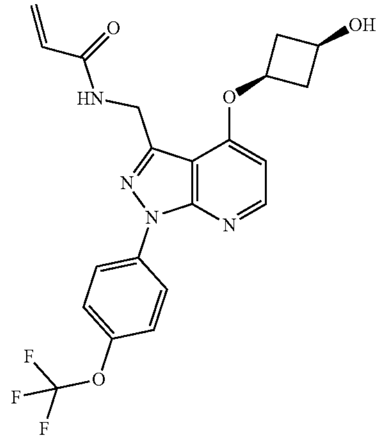 [SMILES: C=CC(=O)NCc1nn(-c2ccc(OC(F)(F)F)cc2)c2nccc(O[C@H]3C[C@@H](O)C3)c12]

To a solution of cis-3-((3-(aminomethyl)-1-(4-(trifluoromethoxy)phenyl)-1H-pyrazolo[3,4-b]pyridin-4-yl)oxy)cyclobutanol (110 mg, 0.28 mmol) in THF (5 mL) was added sat. $NaHCO_3$ (0.5 mL) at 0° C. Then acrylic anhydride (70 mg, 0.56 mmol) was added at 0° C. The mixture was stirred at 0° C. for 1 h. The reaction mixture was quenched with water (20 mL), extracted with ethyl acetate (20 mL×3). The organic layer was dried over $Na_2SO_4$ and concentrated. The residue was purified by reverse phase chromatography (Boston Green ODS 150*30 mm*5 um, water (FA)-ACN, 50-80%) to afford the title compound (100.0 mg, 79%) as a white solid. $^1H$ NMR (400 MHz, DMSO-$d_6$): δ 8.55 (t, J=5.2 Hz, 1H), 8.47 (d, J=5.6 Hz, 1H), 8.39 (d, J=8.8 Hz, 2H), 7.57 (d, J=8.8 Hz, 2H), 6.75 (d, J=5.6 Hz, 1H), 6.32 (dd, J=17.2, 10.0 Hz 1H), 6.15 (dd, J=17.2, 2.0 Hz 1H), 5.62 (dd, J=10.0, 2.0 Hz, 1H), 5.27 (d, J=6.0 Hz, 1H), 4.79 (d, J=5.2 Hz, 2H), 4.58-4.52 (m, 1H), 3.91-3.86 (m, 1H), 2.91-2.85 (m, 2H), 2.07-2.02 (m, 2H); LCMS (ESI): m/z 449.2 $(M+H)^+$.

Example 41 (Compound 126)

N-((4-(2-Hydroxyethoxy)-1-(4-(trifluoromethoxy)phenyl)-1H-pyrazolo[3,4-b]pyridin-3-yl)methyl)acrylamide

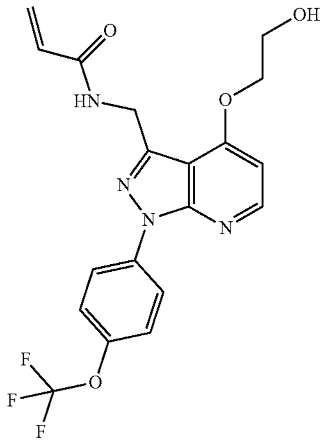

Step 1: tert-butyl 04-(2-((tert-butyldimethylsilyl)oxy)ethoxy)-1-(4-(trifluoromethoxy)phenyl)-1H-pyrazolo[3,4-b]pyridin-3-yl)methyl)carbamate

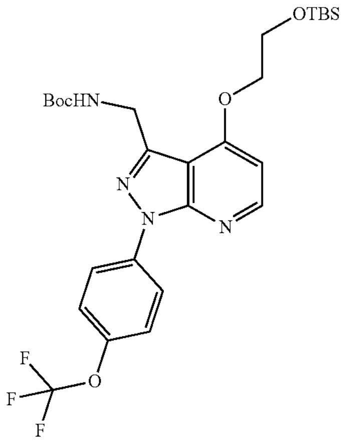

To a solution of 2-((tert-butyldimethylsilyl)oxy)ethanol (298 mg, 1.69 mmol) in THF (3 mL) was added NaH (60% in mineral oil, 68 mg, 1.69 mmol) slowly at 0° C. under $N_2$ atmosphere, then the reaction mixture was stirred at 0° C. for 1 h under $N_2$, and then tert-butyl ((4-chloro-1-(4-(trifluoromethoxy)phenyl)-1H-pyrazolo[3,4-b]pyridin-3-yl)methyl)carbamate (150 mg, 0.34 mmol) in THF (1 ml) was added into the reaction at 0° C. The mixture was stirred at room temperature for 2 h. The reaction mixture was quenched with the addition of saturated aqueous solution of $NH_4Cl$ (30 mL), diluted with water (30 mL), and extracted with ethyl acetate (50 mL×3), the combined organic layers were concentrated under reduced pressure, the resulting residue was purified by column chromatography on silica gel (0-5% ethyl acetate in petroleum ether) to afford the title compound (150 mg, 76%) as an orange oil. $^1$H NMR (400 MHz, $CDCl_3$): δ 8.45 (d, J=5.6 Hz, 1H), 8.33 (d, J=9.2 Hz, 2H), 7.36 (d, J=8.8 Hz, 2H), 6.64 (d, J=5.6 Hz, 1H), 5.55 (s, 1H), 4.77 (d, J=4.4 Hz, 2H), 4.33 (t, J=5.2 Hz, 2H), 4.09 (t, J=5.2 Hz, 2H), 1.48 (s, 9H), 0.92 (s, 9H), 0.12 (s, 6H); LCMS (ESI): m/z 583.3 $(M+H)^+$.

Step 2: 2-((3-(aminomethyl)-1-(4-(trifluoromethoxy)phenyl)-1H-pyrazolo[3,4-b]pyridin-4-yl)oxy)ethanol4-yl)oxy)ethanol

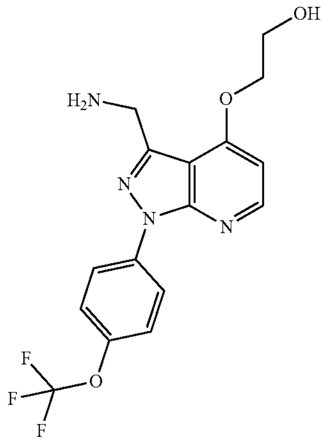

To a stirred solution of tert-butyl ((4-(2-((tert-butyldimethylsilyl)oxy)ethoxy)-1-(4-(trifluoromethoxy)phenyl)-1H-pyrazolo[3,4-b]pyridin-3-yl)methyl)carbamate (150 mg, 0.25 mmol) in DCM (3 mL) was added TFA (0.9 ml) at 0° C. The mixture was stirred at 0° C. for 2 h. The reaction was diluted with aq. $NaHCO_3$ (30 mL), extracted by ethyl acetate (25 mL×3) and concentrated under reduced pressure to afford the title compound (90 mg, 95%) as a yellow oil. The crude product would be directly used in the next step without purification. LCMS (ESI): m/z 369.2 $(M+H)^+$.

Step 3: N-((4-(2-hydroxyethoxy)-1-(4-(trifluoromethoxy)phenyl)-1H-pyrazolo[3,4-b]pyridin-3-yl)methyl)acrylamide

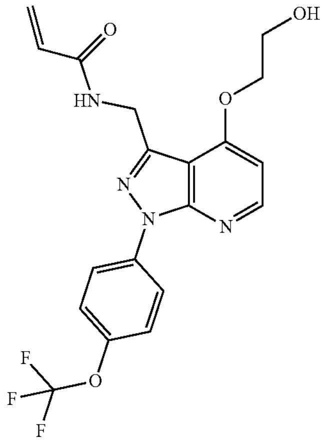

To a solution of 2-((3-(aminomethyl)-1-(4-(trifluoromethoxy)phenyl)-1H-pyrazolo[3,4-b]pyridin-4-yl)oxy)ethanol (90 mg, 0.24 mmol) in THF (5 mL) was added sat.$NaHCO_3$ (0.5 ml) and acrylic anhydride (61 mg, 0.49 mmol) at 0° C. The mixture was stirred at 0° C. for 1 h. After filtration, the filtrate was diluted with water (20 mL), then was extracted with ethyl acetate (40 mL×2), dried over $Na_2SO_4$ and concentrated. The crude was purified by reverse phase chromatography (Welch Xtimate C18 150*30 mm*5 um, water (0.225% FA)-CAN, 46%-76%) to afford the title compound (66.9 mg, 63%) as a white solid. $^1$H NMR (400 MHz, DMSO-$d_6$): δ 8.57 (t, J=5.2 Hz, 1H), 8.51 (d, J=5.6 Hz, 1H), 8.40 (d, J=8.0 Hz, 2H), 7.43 (d, J=8.0 Hz, 2H), 6.94 (d, J=5.6 Hz, 1H), 6.30 (dd, J=17.2, 10.0 Hz, 1H), 6.15 (dd, J=17.2, 2.4 Hz, 1H), 5.64 (dd, J=10.0, 2.4 Hz, 1H), 5.11 (t, J=5.2 Hz, 1H), 4.82 (d, J=5.2 Hz, 2H), 4.29 (t, J=4.8 Hz, 2H), 3.84-3.80 (m, 2H); LCMS (ESI): m/z 423.0 $(M+H)^+$.

Example 42 (Compound 24)

N-((4-(2-Hydroxyacetamido)-1-(4-(trifluoromethoxy)phenyl)-1H-pyrazolo[3,4-b]pyridin-3-yl)methyl)acrylamide

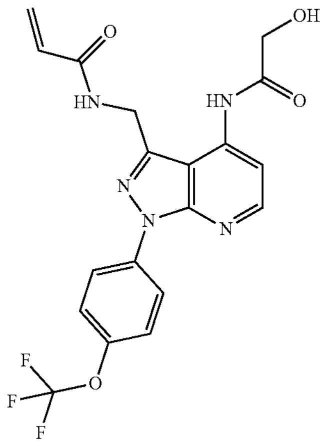 [SMILES: C=CC(=O)NCc1nn(-c2ccc(OC(F)(F)F)cc2)c2nccc(NC(=O)CO)c12]

Step 1: tert-butyl 04-(2-hydroxyacetamido)-1-(4-(trifluoromethoxy)phenyl)-1H-pyrazolo[3,4-b]pyridin-3-yl)methyl)carbamate

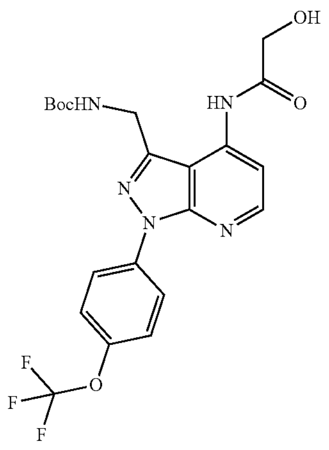 [SMILES: CC(C)(C)OC(=O)NCc1nn(-c2ccc(OC(F)(F)F)cc2)c2nccc(NC(=O)CO)c12]

To a solution of tert-butyl ((4-chloro-1-(4-(trifluoromethoxy)phenyl)-1H-pyrazolo[3,4-b]pyridin-3-yl)methyl)carbamate (150 mg, 0.34 mmol) in DMSO (5 mL) were added BTMPO (14 mg, 0.03 mmol), CuI (4 mg, 0.03 mmol), $K_3PO_4$ (270 mg, 1.0 mmol) and 2-((tert-butyldimethylsilyl)oxy)acetamide (128 mg, 0.68 mmol). The solution was stirred at 120° C. for 3 h under $N_2$ atmosphere. The reaction was diluted with water (30 mL), extracted with ethyl acetate (20 mL×3) and the organics was dried over $Na_2SO_4$ and concentrated. The residue was purified by flash column chromatography on silica gel (0-30% ethyl acetate in petroleum ether) to afford the title compound (30 mg, 16%) as a yellow oil. $^1$H NMR (400 MHz, DMSO-$d_6$): δ 10.31 (s, 1H), 8.56 (d, J=5.6 Hz, 1H), 8.39 (d, J=8.8 Hz, 2H), 7.95 (d, J=5.6 Hz, 1H), 7.59 (d, J=8.8 Hz, 2H), 5.92 (s, 1H), 4.60 (d, J=5.6 Hz, 2H), 4.17 (d, J=5.6 Hz, 2H), 1.39 (s, 9H); LCMS (ESI): m/z 482.2 $(M+H)^+$.

Step 2: N-(3-(aminomethyl)-1-(4-(trifluoromethoxy)phenyl)-1H-pyrazolo[3,4-b]pyridin-4-yl)-2-hydroxyacetamide

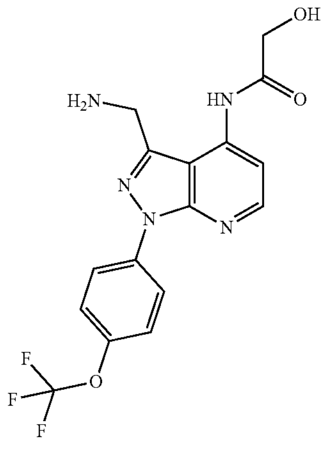 [SMILES: NCc1nn(-c2ccc(OC(F)(F)F)cc2)c2nccc(NC(=O)CO)c12]

To a stirred solution of tert-butyl ((4-(2-hydroxyacetamido)-1-(4-(trifluoromethoxy)phenyl)-1H-pyrazolo[3,4-b]pyridin-3-yl)methyl)carbamate (40 mg, 0.08 mmol) in DCM (3 mL) was added TFA (0.03 mL, 0.4 mmol) at 0° C. The mixture was stirred at 0° C. for 2 h. The reaction was diluted with aq. $NaHCO_3$ (30 mL), extracted by ethyl acetate (25 mL×3) and concentrated under reduced pressure to afford the title compound (20 mg, 61%) as a yellow oil. The crude product would be directly used in the next step without purification.

Step 3: N-((4-(2-hydroxyacetamido)-1-(4-(trifluoromethoxy)phenyl)-1H-pyrazolo[3,4-b]pyridin-3-yl)methyl)acrylamide

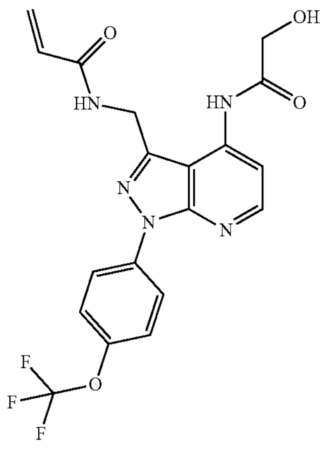 [SMILES: C=CC(=O)NCc1nn(-c2ccc(OC(F)(F)F)cc2)c2nccc(NC(=O)CO)c12]

To a solution of N-(3-(aminomethyl)-1-(4-(trifluoromethoxy)phenyl)-1H-pyrazolo[3,4-b]pyridin-4-yl)-2-hydroxyacetamide (10 mg, 0.03 mmol) in THF (5 mL) was added sat. $NaHCO_3$ (0.5 mL) and acrylic anhydride (3.64 mg, 0.03 mmol) at 0° C. The mixture was stirred at 0° C. for 1 h. After filtration, the filtrate was diluted with water (20 mL), then was extracted with ethyl acetate (40 mL×2), dried over $Na_2SO_4$ and concentrated. The residue was purified by reverse phase chromatography (Boston Green ODS 150*30 mm*5 um, water (0.225% FA)-CAN, 40%-70%) to afford the title compound (8.2 mg, 70%) as a white solid. $^1$H NMR (400 MHz, DMSO-$d_6$): δ 10.77 (s, 1H), 9.15 (s, 1H), 8.57 (d, J=5.6 Hz, 1H), 8.38 (d, J=8.8 Hz, 2H), 7.97 (d, J=5.6 Hz, 1H), 7.60 (d, J=8.8 Hz, 2H), 6.28 (dd, J=17.2, 10.0 Hz, 1H), 6.16 (dd, J=17.2, 2.0 Hz, 1H), 5.85-5.76 (m, 1H), 5.67 (dd, J=10.0, 2.0 Hz, 1H), 4.80 (d, J=5.2 Hz, 2H), 4.20 (d, J=4.8 Hz, 2H); LCMS (ESI): m/z 435.9 $(M+H)^+$.

Example 43 (Compound 36)

N-((4-((2-Hydroxyethyl)amino)-1-(4-(trifluoromethoxy)phenyl)-1H-pyrazolo[3,4-b]pyridin-3-yl)methyl)acrylamide

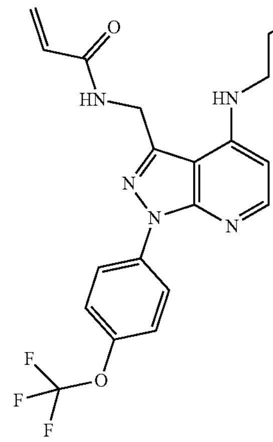

Step 1: tert-butyl ((4-((2-hydroxyethyl)amino)-1-(4-(trifluoromethoxy)phenyl)-1H-pyrazolo[3,4-b]pyridin-3-yl)methyl)carbamate

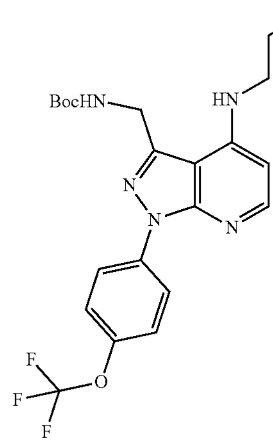

A solution of tert-butyl ((4-chloro-1-(4-(trifluoromethoxy)phenyl)-1H-pyrazolo[3,4-b]pyridin-3-yl)methyl)carbamate (100 mg, 0.23 mmol) in 2-aminoethanol (3 mL) was stirred at 120° C. for 1 h with microwave. The mixture was diluted with water (10 mL), the precipitate was filtered and washed with water (5 mL), the filter cake was dried under vacuo to afford the title compound (100 mg, 95%) as a white solid. $^1H$ NMR (400 MHz, $CDCl_3$): δ 8.20-8.11 (m, 3H), 7.27 (d, J=8.8 Hz, 2H), 6.93-6.83 (m, 1H), 6.18 (d, J=5.6 Hz, 1H), 5.27 (t, J=6.8 Hz, 1H), 4.65 (d, J=6.8 Hz, 2H), 3.97-3.89 (m, 2H), 3.41-3.35 (m, 2H), 1.39 (s, 9H); LCMS (ESI): m/z 468.1 $(M+H)^+$.

Step 2: 2-((3-(aminomethyl)-1-(4-(trifluoromethoxy)phenyl)-1H-pyrazolo[3,4-b]pyridin-4-yl)amino)ethanol

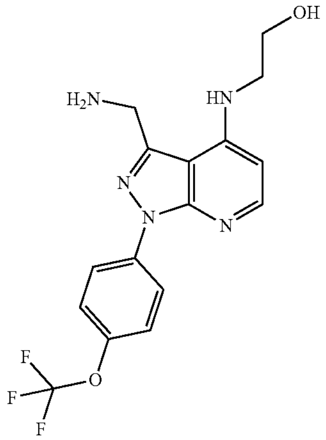

A solution of ter t-butyl ((4-((2-hydroxyethyl)amino)-1-(4-(trifluoromethoxy)phenyl)-1H-pyrazolo[3,4-b]pyridin-3-yl)methyl)carbamate (80 mg, 0.17 mmol) in TFA (5% in HFIP, 5 mL) was stirred at room temperature for 2 h. The mixture was concentrated in vacuo to afford the title compound (82 mg, crude) and used directly.

Step 3: N-((4-((2-hydroxyethyl)amino)-1-(4-(trifluoromethoxy)phenyl)-1H-pyrazolo[3,4-b]pyridin-3-yl)methyl)acrylamide

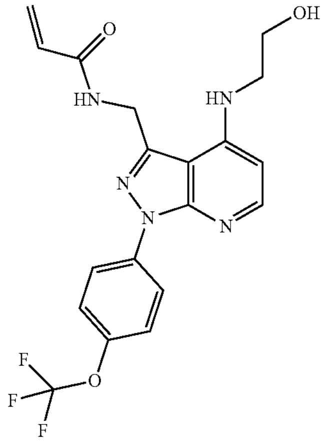

To a solution of 2-((3-(aminomethyl)-1-(4-(trifluoromethoxy)phenyl)-1H-pyrazolo[3,4-b]pyridin-4-yl)amino)ethanol (82 mg, 0.17 mmol) and sat. $NaHCO_3$ (2 mL) in THF (5 mL) was added acrylic anhydride (24 mg, 0.19 mmol) at 0° C. The mixture was stirred at 0° C. for 1 h. The reaction was diluted with water (30 mL) and extracted with ethyl acetate (30 mL×3), the combined organic layers were dried over $Na_2SO_4$ and concentrated in vacuo and purified by prep-TLC (5% MeOH in DCM) to afford the crude product, which was purified by reverse phase chromatography (Xtimate C18 100*30 mm*3 um, acetonitrile 18-58%/0.225% FA in water) to afford the title compound (35.0 mg, 49%) as a white solid. $^1H$ NMR (400 MHz, DMSO-$d_6$): δ 9.15 (t, J=5.6 Hz, 1H), 8.43 (d, J=8.8 Hz, 2H), 8.15 (d, J=5.6 Hz, 1H), 7.55 (d, J=8.8 Hz, 2H), 7.20 (t, J=5.2 Hz, 1H), 6.29 (dd, J=17.2, 10.0 Hz, 1H), 6.21 (dd, J=17.2, 2.0 Hz, 1H), 5.71 (dd, J=10.0, 2.0 Hz, 1H), 4.85-4.79 (m, 3H), 3.66 (t, J=5.6 Hz, 2H), 3.37-3.35 (m, 2H); LCMS (ESI): m/z 422.0 $(M+H)^+$.

Example 44 (Compound 84)

N-((4-(3-Fluoroazetidin-1-yl)-1-(4-(trifluoromethoxy)phenyl)-1H-pyrazolo[3,4-b]pyridin-3-yl)methyl)acrylamide

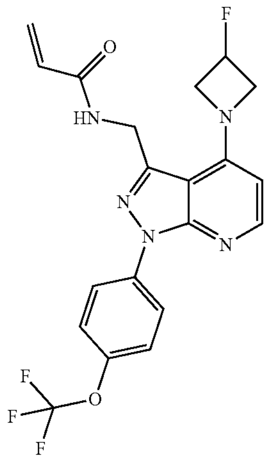

Step 1: tert-butyl ((4-(3-fluoroazetidin-1-yl)-1-(4-(trifluoromethoxy)phenyl)-1H-pyrazolo[3,4-b]pyridin-3-yl)methyl)carbamate

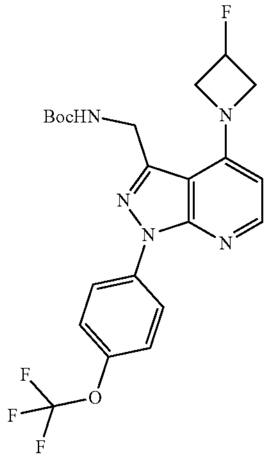

A mixture of $K_2CO_3$ (312 mg, 2.26 mmol), tert-butyl ((4-chloro-1-(4-(trifluoromethoxy)phenyl)-1H-pyrazolo[3,4-b]pyridin-3-yl)methyl)carbamate (200 mg, 0.46 mmol) and 3-fluoroazetidine hydrochloride (101 mg, 0.90 mmol) in DMF (4 mL) was stirred at 80° C. with 2 h under nitrogen. The reaction mixture was diluted with water (50 mL) and extracted with ethyl acetate (50 mL×3), the combined organic layers were washed with brine (50 mL×3). The organic layer was dried over $Na_2SO_4$ and concentrated in vacuo. The residue was purified by flash column chromatography on silica gel (0-15% ethyl acetate in petroleum ether) to afford the title compound (150 mg, 69%) as a yellow oil. $^1H$ NMR (400 MHz, DMSO-$d_6$): δ 8.41 (d, J=8.8 Hz 2H), 8.19 (d, J=5.6 Hz, 1H), 7.55 (d, J=8.8 Hz, 2H), 7.40-7.27 (m, 1H), 6.22 (d, J=5.2 Hz, 1H), 5.69-5.38 (m, 1H), 4.69-4.54 (m, 2H), 4.54-4.49 (m, 2H), 4.46-4.32 (m, 2H), 1.24 (s, 9H).

Step 2: (4-(3-fluoroazetidin-1-yl)-1-(4-(trifluoromethoxy)phenyl)-1H-pyrazolo[3,4-b]pyridin-3-yl)methanamine

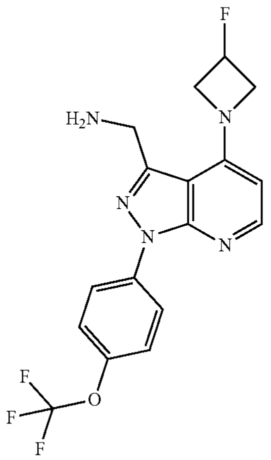 [SMILES: NCc1nn(-c2ccc(OC(F)(F)F)cc2)c2nccc(N3CC(F)C3)c12]

A solution of tert-butyl ((4-(3-fluoroazetidin-1-yl)-1-(4-(trifluoromethoxy)phenyl)-1H-pyrazolo[3,4-b]pyridin-3-yl)methyl)carbamate (150 mg, 0.31 mmol) and TFA (5% in HFIP, 5 mL) was stirred at room temperature for 2 h. The reaction mixture was diluted with water (30 mL) and adjusted to pH=8 by sat. $NaHCO_3$, the mixture was extracted with ethyl acetate (30 mL×3), the combined organic layers were washed with brine (30 mL×3). The organic layer was dried over $Na_2SO_4$ and concentrated in vacuo to afford the title compound (100 mg, 84%) as a yellow oil. LCMS (ESI): m/z 382.1 $(M+H)^+$.

Step 3: N-((4-(3-fluoroazetidin-1-yl)-1-(4-(trifluoromethoxy)phenyl)-1H-pyrazolo[3,4-b]pyridin-3-yl)methyl)acrylamide

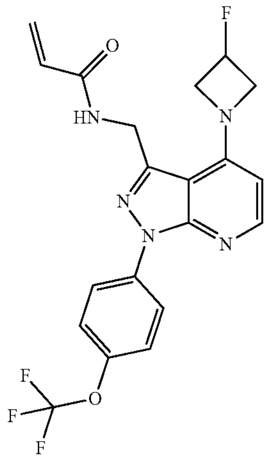 [SMILES: C=CC(=O)NCc1nn(-c2ccc(OC(F)(F)F)cc2)c2nccc(N3CC(F)C3)c12]

To a solution of (4-(3-fluoroazetidin-1-yl)-1-(4-(trifluoromethoxy)phenyl)-1H-pyrazolo[3,4-b]pyridin-3-yl)methanamine (80 mg, 0.21 mmol) and sat. $NaHCO_3$ (2 mL) in THF (4 mL) was added acryloyl chloride (0.02 mL, 0.23 mmol) at 0° C., the reaction was stirred at room temperature for 2 h. The reaction mixture was diluted with water (30 mL) and extracted with ethyl acetate (30 mL×3), the combined organic layers were washed with brine (30 mL×3). The organic layer was dried over $Na_2SO_4$ and concentrated in vacuo. The resulting residue was purified by reverse phase chromatography (Boston Green ODS 150*30 mm*5 um/water (FA)-CAN/50%-80%) to afford the title compound (22.3 mg, 24%) as a white solid. $^1H$ NMR (400 MHz, DMSO-$d_6$): 8.61 (t, J=4.8 Hz, 1H), 8.40 (d, J=8.8 Hz, 2H), 8.19 (d, J=5.6 Hz, 1H), 7.53 (d, J=8.8 Hz, 2H), 6.35 (dd, J=17.2, 10.0 Hz, 1H), 6.22 (d, J=5.6 Hz, 1H), 6.16 (dd, J=17.2, 2.0 Hz, 1H), 5.65-5.61 (m, 1H), 5.60-5.40 (m, 1H), 4.72 (d, J=4.8 Hz, 2H), 4.65-4.54 (m, 2H), 4.41-4.30 (m, 2H); LCMS (ESI): m/z 436.0 $(M+H)^+$.

Example 45 (Compound 52)

N-((4-(3-Cyanoazetidin-1-yl)-1-(4-(trifluoromethoxy)phenyl)-1H-pyrazolo[3,4-b]pyridin-3-yl)methyl)acrylamide

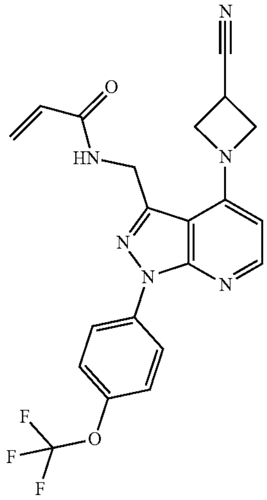 [SMILES: C=CC(=O)NCc1nn(-c2ccc(OC(F)(F)F)cc2)c2nccc(N3CC(C#N)C3)c12]

Step 1: tert-butyl ((4-(3-cyanoazetidin-1-yl)-1-(4-(trifluoromethoxy)phenyl)-1H-pyrazolo[3,4-b]pyridin-3-yl)methyl)carbamate

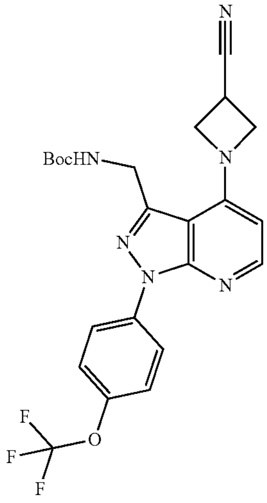 [SMILES: CC(C)(C)OC(=O)NCc1nn(-c2ccc(OC(F)(F)F)cc2)c2nccc(N3CC(C#N)C3)c12]

To a solution of tert-butyl ((4-chloro-1-(4-(trifluoromethoxy)phenyl)-1H-pyrazolo[3,4-b]pyridin-3-yl)methyl)carbamate (300 mg, 0.68 mmol) in DMF (2.0 mL) was added $K_2CO_3$ (281 mg, 2.03 mmol) and azetidine-3-carbonitrile hydrochloride (240 mg, 2.03 mmol) at room temperature. The resulting solution was stirred at 80° C. for 12 h. The mixture was quenched with water (30 mL) and extracted with ethyl acetate (60 mL×3). The combined organic layers were washed with brine (30 mL). The organic layers were dried over $Na_2SO_4$ and concentrated to dryness. The residue was purified by chromatography on silica gel (0-30% ethyl acetate in petroleum ether) to afford the title compound (60.0 mg, 18%) as a white solid. $^1$H NMR (400 MHz, $CDCl_3$): δ 8.30 (d, J=5.6 Hz, 1H), 8.26 (d, J=9.2 Hz, 2H), 7.37 (d, J=8.8 Hz, 2H), 6.09 (d, J=5.6 Hz, 1H), 4.70 (d, J=4.8 Hz, 2H), 4.66-4.60 (m, 2H), 4.54-4.49 (m, 2H), 3.36-3.30 (m, 1H), 1.52 (s, 9H); LCMS (ESI): m/z 489.2 $(M+H)^+$.

Step 2: 1-(3-(aminomethyl)-1-(4-(trifluoromethoxy)phenyl)-1H-pyrazolo[3,4-b]pyridin-4-yl)azetidine-3-carbonitrile

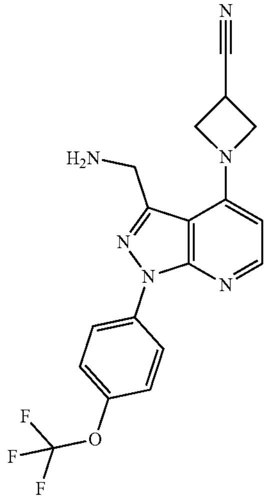 [SMILES: N#CC1CN(c2ccnc3c2c(CN)nn3-c2ccc(OC(F)(F)F)cc2)C1]

To a mixture of tert-butyl ((4-(3-cyanoazetidin-1-yl)-1-(4-(trifluoromethoxy)phenyl)-1H-pyrazolo[3,4-b]pyridin-3-yl)methyl)carbamate (50 mg, 0.10 mmol) and 2,6-lutidine (40 uL, 0.3 mmol) in DCM (3 mL) was added TMSOTf (0.11 mL, 0.61 mmol) at 0° C. The solution was stirred at room temperature for 1 h. The mixture was concentrated to afford the title compound (39 mg, 98%) as a yellow solid. The crude would be used in the next step directly. LCMS (ESI): m/z 389 $(M+H)^+$.

Step 3: N-((4-(3-cyanoazetidin-1-yl)-1-(4-(trifluoromethoxy)phenyl)-1H-pyrazolo[3,4-b]pyridin-3-yl)methyl)acrylamide

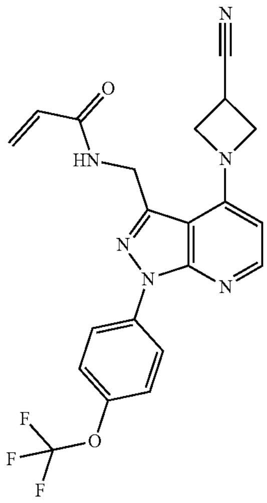 [SMILES: C=CC(=O)NCc1nn(-c2ccc(OC(F)(F)F)cc2)c2nccc(N3CC(C#N)C3)c12]

To a solution of saturated $NaHCO_3$ (1.0 mL) and 1-(3-(aminomethyl)-1-(4-(trifluoromethoxy)phenyl)-1H-pyrazolo[3,4-b]pyridin-4-yl)azetidine-3-carbonitrile (39.0 mg, 0.10 mmol) in THF (1.0 mL) was added acrylic anhydride (14.0 mg, 0.11 mmol) at 0° C. The solution was stirred at 0° C. for 1 h. The mixture was added water (20 mL) and extracted with ethyl acetate (20 mL×3) and washed with brine (30 mL). The organic layers were dried over anhydrous sodium sulfate and concentrated under reduced. The resulting residue was purified by reverse phase chromatography (Welch Xtimate C18 150*30 mm*5 um, acetonitrile 34-64%/water (0.225% FA)-ACN) to afford the title compound (30.6 mg, 69%) as a white solid. $^1$H NMR (400 MHz, DMSO-$d_6$): δ 8.64 (t, J=4.8 Hz, 1H), 8.39 (d, J=9.2 Hz, 2H), 8.23 (d, J=5.6 Hz, 1H), 7.56 (d, J=8.8 Hz, 2H), 6.36 (dd, J=16.8, 10.0 Hz, 1H), 6.24 (d, J=5.6 Hz, 1H), 6.17 (dd, J=16.8, 2.4 Hz, 1H), 5.65 (dd, J=10.4, 2.4 Hz, 1H), 4.72 (d, J=4.8 Hz, 2H), 4.60-4.54 (m, 2H), 4.50-4.44 (m, 2H), 4.02-3.95 (m, 1H). LCMS (ESI): m/z 443 $(M+H)^+$.

Example 46 (Compound 25)

3-(Acrylamidomethyl)-N-(2-hydroxyethyl)-1-(4-(trifluoromethoxy)phenyl)-1H-pyrazolo[3,4-b]pyridine-4-carboxamide

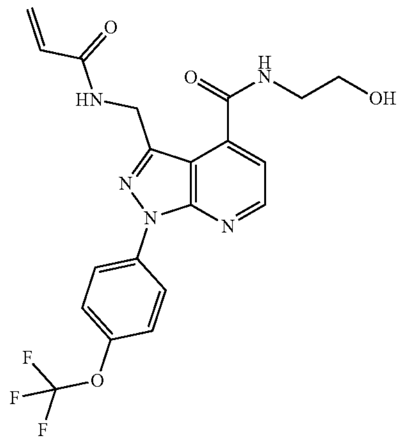 [SMILES: C=CC(=O)NCc1nn(-c2ccc(OC(F)(F)F)cc2)c2nccc(C(=O)NCCO)c12]

Step 1: N-(2-hydroxyethyl)-3-iodo-1-(4-(trifluoromethoxy)phenyl)-1H-pyrazolo[3,4-b]pyridine-4-carboxamide

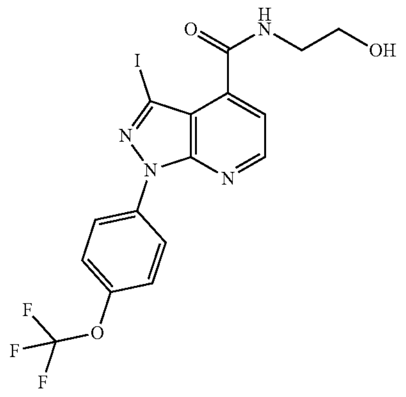 [SMILES: O=C(NCCO)c1ccnc2c1c(I)nn2-c1ccc(OC(F)(F)F)cc1]

To a solution of 3-iodo-1-(4-(trifluoromethoxy)phenyl)-1H-pyrazolo[3,4-b]pyridine-4-carboxylic acid (800 mg, 1.78 mmol), HATU (677 mg, 1.78 mmol) and 2-aminoethanol (1.3 g, 2.14 mmol) in DMF (5 mL) was added DIPEA (0.88 mL, 5.34 mmol) at room temperature, the mixture was stirred at room temperature for 12 h. The reaction was diluted with water (50 mL) and extracted with ethyl acetate (100 mL×3) and the organic layer were combined. The organic layer was washed with brine (50 mL×3). The organic layer was dried over anhydrous sodium sulfate and concentrated under vacuum. The residue was purified flash chromatography on silica gel (0-10% methyl alcohol in dichloromethane) to afford the title compound (500 mg, 61%) as a yellow solid. $^1$H NMR (400 MHz, $CDCl_3$): δ 8.67 (d, J=4.4 Hz, 1H), 8.27 (d, J=8.8 Hz, 2H), 7.38 (d, J=8.8 Hz, 2H), 7.31 (d, J=4.4 Hz, 1H), 6.70 (s, 1H), 3.99-3.95 (m, 2H), 3.80-3.76 (m, 2H).

Step 2: tert-butyl 04-((2-hydroxyethyl)carbamoyl)-1-(4-(trifluoromethoxy)phenyl)-1H-pyrazolo[3,4-b]pyridin-3-yl)methyl)carbamate

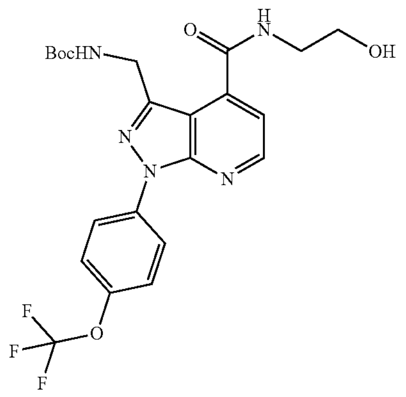 [SMILES: CC(C)(C)OC(=O)NCc1nn(-c2ccc(OC(F)(F)F)cc2)c2nccc(C(=O)NCCO)c12]

A mixture of N-(2-hydroxyethyl)-3-iodo-1-(4-(trifluoromethoxy)phenyl)-1H-pyrazolo[3,4-b]pyridine-4-carboxamide (470 mg, 0.95 mmol), CATACXIUM A Pd $G_2$ (96 mg, 0.14 mmol), potassium (((tert-butoxycarbonyl)amino)methyl)trifluoroborate (682 mg, 2.86 mmol), $Ag_2CO_3$ (132 mg, 0.14 mmol) and $Cs_2CO_3$ (934 mg, 2.86 mmol) in 1,4-dioxane (15 mL) and water (1.5 mL) was purged with $N_2$ for 3 min. The mixture was stirred at 100° C. for 16 h under $N_2$. The reaction was diluted with water (100 mL) and extracted with ethyl acetate (100 mL×3) and the organic layers were combined. The organic layer was washed with brine (50 mL×3). The organic layer was dried over anhydrous sodium sulfate and concentrated under vacuum. The residue was purified flash chromatography on silica gel (0-10% methyl alcohol in dichloromethane) to afford crude product, then the reside was purified by reverse phase chromatography (Boston Gress ODS 150*30 mm*5 um, water (FA)-ACN 50-80%) to afford the title compound (30 mg, 6%) as a white solid. LCMS (ESI): m/z 396.2 $(M+H-100)^+$.

Step 3: 3-(aminomethyl)-N-(2-hydroxyethyl)-1-(4-(trifluoromethoxy)phenyl)-1H-pyrazolo[3,4-b]pyridine-4-carboxamide 2,2,2-trifluoroacetate salt

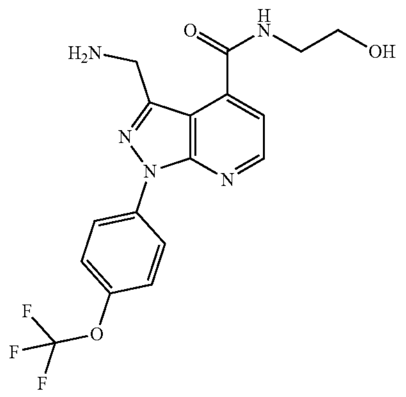 [SMILES: NCc1nn(-c2ccc(OC(F)(F)F)cc2)c2nccc(C(=O)NCCO)c12]

A mixture of tert-butyl ((4-((2-hydroxyethyl)carbamoyl)-1-(4-(trifluoromethoxy)phenyl)-1H-pyrazolo[3,4-b]pyridin- 3-yl)methyl)carbamate (30 mg, 0.06 mmol) and TFA (5% in HFIP, 3 mL) was stirred at 0° C. for 1.5 h. The reaction was directly concentrated under vacuum to afford the title compound (30 mg, 97%) as a brown oil. The crude product would be directly used in the next step without purification. LCMS (ESI): m/z 396.2 $(M+H)^+$.

Step 4: 3-(acrylamidomethyl)-N-(2-hydroxyethyl)-1-(4-(trifluoromethoxy)phenyl)-1H-pyrazolo[3,4-b]pyridine-4-carboxamide

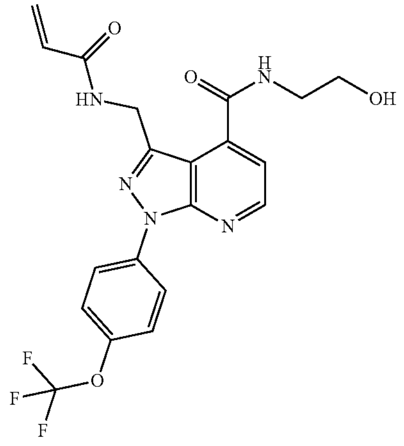 [SMILES: C=CC(=O)NCc1nn(-c2ccc(OC(F)(F)F)cc2)c2nccc(C(=O)NCCO)c12]

To a solution of 3-(aminomethyl)-N-(2-hydroxyethyl)-1-(4-(trifluoromethoxy)phenyl)-1H-pyrazolo[3,4-b]pyridine-4-carboxamide 2,2,2-trifluoroacetate (30 mg, 0.06 mmol) and sat. $NaHCO_3$ (1 mL) in THF (3 mL) was added acrylic anhydride (9 mg, 0.07 mmol) at 0° C. The reaction was stirred at 0° C. for 1.5 h. The reaction was diluted with water (10 mL) and extracted with ethyl acetate (30 mL×3) and the organic layers were combined. The organic layer was dried over anhydrous sodium sulfate and concentrated under vacuum. The resulting residue was purified by reverse phase chromatography (Welch Xtimate C18 150*30 mm*5 um, 42-72% in water (0.225% FA)-ACN) to afford the title compound (13.4 mg, 49%) as a white solid. $^1H$ NMR (400 MHz, DMSO-$d_6$): δ 8.91 (t, J=5.6 Hz, 1H), 8.77 (d, J=4.8 Hz, 1H), 8.52 (t, J=5.2 Hz, 1H), 8.38 (d, J=8.8 Hz, 2H), 7.62 (d, J=8.4 Hz, 2H), 7.47 (d, J=4.8 Hz, 1H), 6.32 (dd, J=17.2, 10.4 Hz, 1H), 6.11 (dd, J=17.2, 2.0 Hz, 1H), 5.62 (dd, J=10.4, 2.0 Hz, 1H), 4.87 (t, J=5.6 Hz, 1H), 4.77 (d, J=5.2 Hz, 2H), 3.60-3.56 (m, 2H), 3.41-3.39 (m, 2H); LCMS (ESI): m/z 450.0 $(M+H)^+$.

Example 47 (Compound 30)

3-(Acrylamidomethyl)-N-methyl-1-(4-(trifluoromethoxy)phenyl)-1H-pyrazolo[3,4-b]pyridine-4-carboxamide

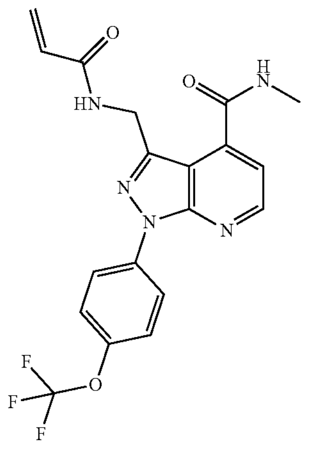 [SMILES: C=CC(=O)NCc1nn(-c2ccc(OC(F)(F)F)cc2)c2nccc(C(=O)NC)c12]

Step 1: 3-iodo-N-methyl-1-(4-(trifluoromethoxy)phenyl)-1H-pyrazolo[3,4-b]pyridine-4-carboxamide

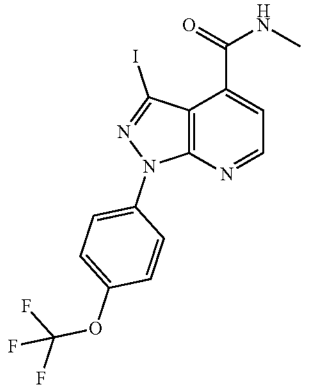 [SMILES: CNC(=O)c1ccnc2c1c(I)nn2-c1ccc(OC(F)(F)F)cc1]

To a solution of 3-iodo-1-(4-(trifluoromethoxy)phenyl)-1H-pyrazolo[3,4-b]pyridine-4-carboxylic acid (500 mg, 1.11 mmol), HATU (423 mg, 1.11 mmol) and DIPEA (0.92 mL, 5.57 mmol) in DMF (5 mL) was added methylamine hydrochloride (90 mg, 1.34 mmol) at room temperature, the mixture was stirred at room temperature for 2 h. The reaction was diluted with water (50 mL) and extracted with ethyl acetate (50 mL×3) and the organic layer were combined. The organic layer was washed with brine (50 mL×3). The organic layer was dried over anhydrous sodium sulfate and concentrated under vacuum. The reside was purified flash chromatography on silica gel (0-66% ethyl acetate in petroleum ether) to afford the title compound (250 mg, 49%) as a yellow solid. $^1H$ NMR (400 MHz, $CDCl_3$): δ 8.67 (d, J=4.4 Hz, 1H), 8.27 (d, J=9.2 Hz, 2H), 7.38 (d, J=8.8 Hz, 2H), 7.30 (d, J=4.4 Hz, 1H), 6.08-6.07 (m, 1H), 3.16 (d, J=4.8 Hz, 3H); LCMS (ESI): m/z 463.0 $(M+H)^+$.

Step 2: tert-butyl ((4-(methylcarbamoyl)-1-(4-(trifluoromethoxy)phenyl)-1H-pyrazolo[3,4-b]pyridin-3-yl)methyl)carbamate

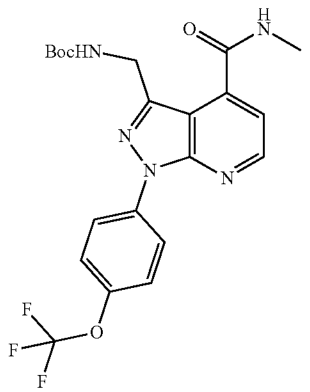 [SMILES: CNC(=O)c1ccnc2c1c(CNC(=O)OC(C)(C)C)nn2-c1ccc(OC(F)(F)F)cc1]

A mixture of $Cs_2CO_3$ (402 mg, 1.23 mmol), 3-iodo-N-methyl-1-(4-(trifluoromethoxy)phenyl)-1H-pyrazolo[3,4-b]pyridine-4-carboxamide (190 mg, 0.4 mmol), CATACXIUM A Pd $G_2$ (39 mg, 0.06 mmol) and potassium (((tert-butoxycarbonyl)amino)methyl)trifluoroborate (276 mg, 1.16 mmol) in 1,4-dioxane (15 mL) and water (1.5 mL) was purged with $N_2$ for 3 min. The mixture was stirred at 100° C. for 16 h under $N_2$ atmosphere. The reaction was diluted with water (50 mL) and extracted with ethyl acetate (50 mL×3), and the organic layers were combined. The organic layer was dried over anhydrous sodium sulfate and concentrated under vacuum. The residue was purified by flash chromatography on silica gel (0-28% ethyl acetate in petroleum ether) to afford the title compound (140 mg, 73%) as a yellow solid. $^1H$ NMR (400 MHz, DMSO-$d_6$) δ 8.88-8.82 (m, 1H), 8.76 (d, J=4.8 Hz, 1H), 8.38-8.36 (m, 2H), 7.61 (d, J=8.8 Hz, 2H), 7.43 (d, J=4.8 Hz, 1H), 7.13-7.04 (m, 1H), 4.53 (d, J=5.6 Hz, 2H), 2.87 (d, J=4.4 Hz, 3H), 1.40 (s, 9H); LCMS (ESI): m/z 465.9 $(M+H)^+$.

Step 3: 3-(aminomethyl)-N-methyl-1-(4-(trifluoromethoxy)phenyl)-1H-pyrazolo[3,4-b]pyridine-4-carboxamide 2,2,2-trifluoroacetate salt

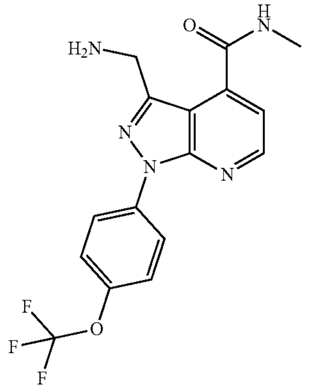 [SMILES: CNC(=O)c1ccnc2c1c(CN)nn2-c1ccc(OC(F)(F)F)cc1]

A mixture of tert-butyl ((4-(methylcarbamoyl)-1-(4-(trifluoromethoxy)phenyl)-1H-pyrazolo[3,4-b]pyridin-3-yl)methyl)carbamate (120 mg, 0.26 mmol) and 5% TFA in HFIP (12 mL) was stirred at 0° C. for 1.5 h. The reaction was directly concentrated under vacuum. The crude product would be directly used in the next step without purification. LCMS (ESI): m/z 366.2 $(M+H)^+$.

Step 4: 3-(acrylamidomethyl)-N-methyl-1-(4-(trifluoromethoxy)phenyl)-1H-pyrazolo[3,4-b]pyridine-4-carboxamide

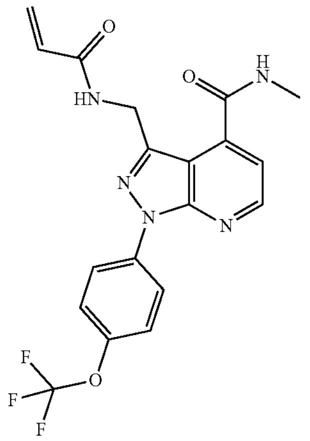 [SMILES: C=CC(=O)NCc1nn(-c2ccc(OC(F)(F)F)cc2)c2nccc(C(=O)NC)c12]

To a solution of 3-(aminomethyl)-N-methyl-1-(4-(trifluoromethoxy)phenyl)-1H-pyrazolo[3,4-b]pyridine-4-carboxamide 2,2,2-trifluoroacetate (120 mg, 0.25 mmol), sat. $NaHCO_3$ (1 mL) in THF (3 mL) was added acrylic anhydride at 0° C., the solution was stirred at 0° C. for 1.5 h. The reaction was diluted with water (10 mL) and extracted with ethyl acetate (30 mL×3) and the organic layers were combined and concentrated under reduced pressure. The resulting residue was purified by reverse phase chromatography (Boston Green ODS 150*30 mm*5 um, 50-80%, water(FA)-CAN) to afford the title compound (22.6 mg, 21%) as a white solid. $^1H$ NMR (400 MHz, DMSO-$d_6$): δ 8.83 (d, J=4.8 Hz, 1H), 8.77 (d, J=4.8 Hz, 1H), 8.49 (t, J=5.2 Hz, 1H), 8.37 (d, J=9.2 Hz, 2H), 7.61 (d, J=8.4 Hz, 2H), 7.44 (d, J=4.8 Hz, 1H), 6.30 (dd, J=17.2, 10.4 Hz, 1H), 6.12 (dd, J=17.2, 2.4 Hz, 1H), 5.62 (dd, J=10.4, 2.4 Hz, 1H), 4.75 (d, J=5.2 Hz, 2H), 2.84 (d, J=4.8 Hz, 3H); LCMS (ESI): m/z 442.0 $(M+Na)^+$.

Example 48 (Compound 44)

N-((4-(1H-1,2,4-Triazol-3-yl)-1-(4-(trifluoromethoxy)phenyl)-1H-pyrazolo[3,4-b]pyridin-3-yl)methyl)acrylamide

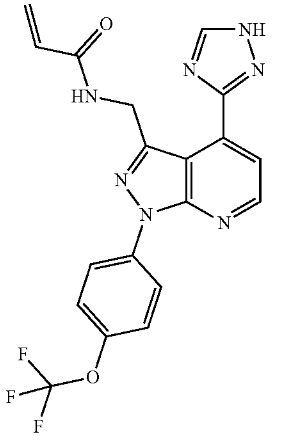 [SMILES: C=CC(=O)NCc1nn(-c2ccc(OC(F)(F)F)cc2)c2nccc(-c3nc[nH]n3)c12]

Step 1: 3-iodo-1-(4-(trifluoromethoxy)phenyl)-1H-pyrazolo[3,4-b]pyridine-4-carboxamide

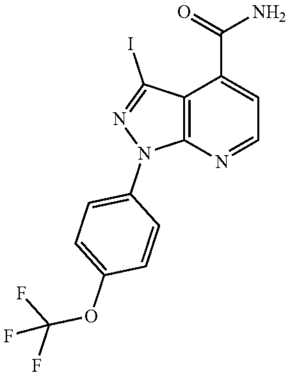 [SMILES: NC(=O)c1ccnc2c1c(I)nn2-c1ccc(OC(F)(F)F)cc1]

To a mixture of 3-iodo-1-(4-(trifluoromethoxy)phenyl)-1H-pyrazolo[3,4-b]pyridine-4-carboxylic acid (2.0 g, 4.45 mmol), DIPEA (3.1 mL, 17.8 mmol), HATU (1.80 g, 4.90 mmol) in DCM (30.0 mL) was added $NH_4Cl$ (2.40 g, 44.5 mmol) at 0° C. The mixture was stirred at room temperature for 4 h. The solution was diluted with water (100 mL) and extracted with DCM (100 mL×3), the combined organic layers were dried with $Na_2SO_4$, filtered and concentrated under vacuum, the residue was purified by column chromatography on silica gel (0-50% ethyl acetate in petroleum ether) to afford the title compound (1.7 g, 85%) as white solid. $^1$H NMR (400 MHz, DMSO-$d_6$): δ 8.76 (d, J=4.4 Hz, 1H), 8.32 (d, J=9.2 Hz, 2H), 8.24 (s, 1H), 8.05 (s, 1H), 7.61 (d, J=8.8 Hz, 2H), 7.38 (d, J=4.4 Hz, 1H); LCMS (ESI): m/z 448.8 $(M+H)^+$.

Step 2: (E)-N-((dimethylamino)methylene)-3-iodo-1-(4-(trifluoromethoxy)phenyl)-1H-pyrazolo[3,4-b]pyridine-4-carboxamide

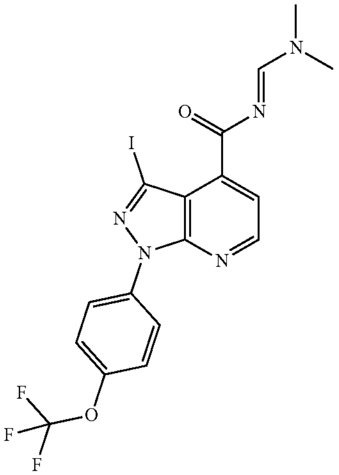 [SMILES: CN(C)/C=N/C(=O)c1ccnc2c1c(I)nn2-c1ccc(OC(F)(F)F)cc1]

A solution of 3-iodo-1-(4-(trifluoromethoxy)phenyl)-1H-pyrazolo[3,4-b]pyridine-4-carboxamide (1.7 g, 3.79 mmol) in DMF-DMA (17.0 mL, 128 mmol) was stirred at 100° C. for 16 h. The mixture was diluted with ethyl acetate (100 mL) and washed with water (100 mL×3), the organic layer was dried with $Na_2SO_4$, filtered and concentrated, the residue was purified by flash chromatography on silica gel (0-50% ethyl acetate in petroleum ether) to afford the title compound (1.6 g, 84%) as yellow solid. $^1$H NMR (400 MHz, $CDCl_3$): δ 8.80 (s, 1H), 8.70 (d, J=4.4 Hz, 1H), 8.29 (d, J=9.2 Hz, 2H), 7.58 (d, J=4.4 Hz, 1H), 7.39 (d, J=8.4 Hz, 2H), 3.32 (s, 3H), 3.28 (s, 3H); LCMS (ESI): m/z 503.9 $(M+H)^+$.

Step 3: 3-iodo-4-(1H-1,2,4-triazol-3-yl)-1-(4-(trifluoromethoxy)phenyl)-1H-pyrazolo[3,4-b]pyridine

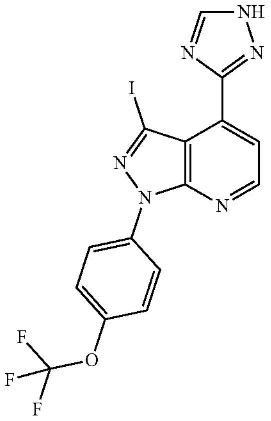 [SMILES: FC(F)(F)Oc1ccc(-n2nc(I)c3c(-c4nc[nH]n4)ccnc32)cc1]

To a solution of (E)-N-((dimethylamino)methylene)-3-iodo-1-(4-(trifluoromethoxy)phenyl)-1H-pyrazolo[3,4-b]pyridine-4-carboxamide (1.5 g, 2.98 mmol) in AcOH (16.0 mL) was added hydrazine hydrate (85% wt, 5.0 mL), the solution was purged with $N_2$ and stirred at 90° C. for 2 h. The solution cooled to room temperature and diluted with ice water (50 mL), after filtration the filter cake was collected and dried under vacuum to give the title compound (1.2 g, 85%) as yellow solid. LCMS (ESI): m/z 473.2 $(M+H)^+$.

Step 4: 4-(1H-1,2,4-triazol-3-yl)-1-(4-(trifluoromethoxy)phenyl)-1H-pyrazolo[3,4-b]pyridine-3-carbonitrile

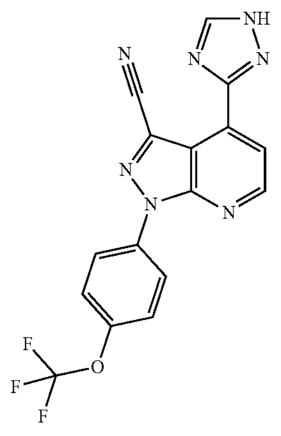 [SMILES: N#Cc1nn(-c2ccc(OC(F)(F)F)cc2)c2nccc(-c3nc[nH]n3)c12]

A solution of CuCN (208 mg, 2.33 mmol) and 3-iodo-4-(1H-1,2,4-triazol-3-yl)-1-(4-(trifluoromethoxy)phenyl)-1H-pyrazolo[3,4-b]pyridine (1.0 g, 2.12 mmol) in DMF (10 mL) was stirred for 2 h at 120° C. The mixture was diluted with ethyl acetate (100 mL) and washed with water (100 mL×3). The organic was dried over $Na_2SO_4$ and concentrated. The residue was purified by flash chromatography on silica gel (0-60% ethyl acetate in petroleum ether) to afford the title compound (350 mg, 44%) as a white solid. LCMS (ESI): m/z 372.1 $(M+H)^+$.

Step 5: (4-(1H-1,2,4-triazol-3-yl)-1-(4-(trifluoromethoxy)phenyl)-1H-pyrazolo[3,4-b]pyridin-3-yl)methanamine

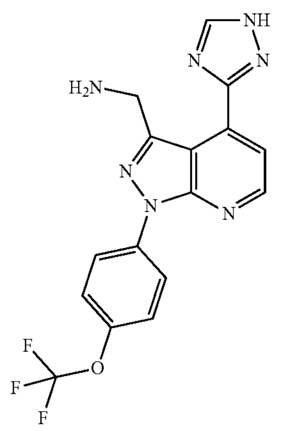 [SMILES: NCc1nn(-c2ccc(OC(F)(F)F)cc2)c2nccc(-c3nc[nH]n3)c12]

To a solution of 4-(1H-1,2,4-triazol-3-yl)-1-(4-(trifluoromethoxy)phenyl)-1H-pyrazolo[3,4-b]pyridine-3-carbonitrile (140 mg, 0.38 mmol) and $NiCl_2·6H_2O$ (9.0 mg, 0.04 mmol) in THF (5 mL) and MeOH (5 mL) was added $NaBH_4$ (57.0 mg, 1.51 mmol) at 0° C. Then the reaction was stirred at 0° C. for 30 min. The mixture was quenched with $NH_4Cl$ solution (5.0 mL) and aq.HCl (2M, 5.0 mL), then adjusted to pH=8 with aq.$NaHCO_3$ solution and diluted with ethyl acetate (100 mL) and washed with water (100 mL×3). The organic was dried over $Na_2SO_4$ and concentrated to afford the title compound (140 mg, 99%) as a yellow oil. LCMS (ESI): m/z 376.1 $(M+H)^+$.

Step 6: N-((4-(1H-1,2,4-triazol-3-yl)-1-(4-(trifluoromethoxy)phenyl)-1H-pyrazolo[3,4-b]pyridin-3-yl)methyl)acrylamide

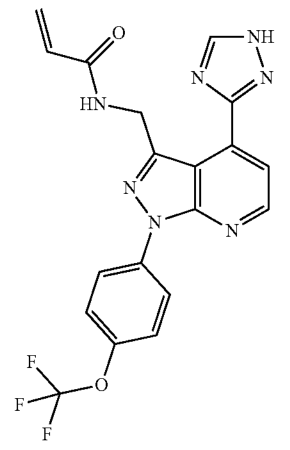 [SMILES: C=CC(=O)NCc1nn(-c2ccc(OC(F)(F)F)cc2)c2nccc(-c3nc[nH]n3)c12]

To a solution of (4-(1H-1,2,4-triazol-3-yl)-1-(4-(trifluoromethoxy)phenyl)-1H-pyrazolo[3,4-b]pyridin-3-yl)methanamine (250 mg, 0.67 mmol) and aq.$NaHCO_3$ (1.0 mL) in THF (5.0 mL) was added acryloyl chloride (0.05 mL, 0.67 mmol) at 0° C. The resulting mixture was stirred at 0° C. f or 1 h. The mixture was diluted with ethyl acetate (100 mL) and washed with water (100 mL×3). The organic was dried over $Na_2SO_4$ and concentrated. The residue was purified by prep-TLC (DCM:Ethyl acetate:EtOH=8:3:1) and reverse phase chromatography (Welch Xtimate C18 150*30 mm*5 um, water (FA)-ACN, 48-78%) to afford the title compound (8.90 mg, 3%) as a white solid. $^1H$ NMR (400 MHz, DMSO-$d_6$): δ 14.64 (s, 1H), 8.80 (s, 1H), 8.77 (d, J=4.8 Hz, 1H), 8.50-8.45 (m, 1H), 8.41 (d, J=8.8 Hz, 2H), 7.89 (d, J=4.8 Hz, 1H), 7.62 (d, J=8.8 Hz, 2H), 6.27 (dd, J=16.8, 10.0 Hz, 1H), 6.08 (dd, J=16.8, 2.0 Hz, 1H), 5.58 (dd, J=10.0, 2.0 Hz, 1H), 5.08 (d, J=5.6 Hz, 2H); LCMS (ESI): m/z 429.9 $(M+H)^+$.

Example 49 (Compound 104)

3-(Acrylamidomethyl)-1-(4-(trifluoromethoxy)phenyl)-1H-pyrazolo[3,4-b]pyridine-4-carboxamide

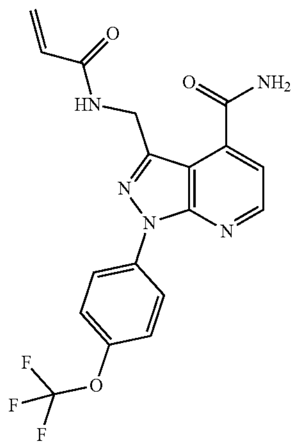 [SMILES: C=CC(=O)NCc1nn(-c2ccc(OC(F)(F)F)cc2)c2nccc(C(N)=O)c12]

Step 1: 3-(((tert-butoxycarbonyl)amino)methyl)-1-(4-(trifluoromethoxy)phenyl)-1H-pyrazolo[3,4-b]pyridine-4-carboxylic acid

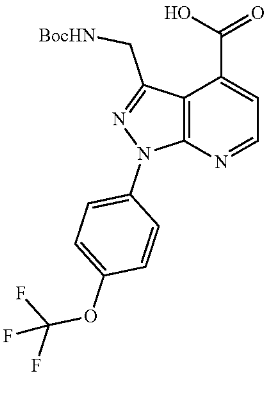 [SMILES: CC(C)(C)OC(=O)NCc1nn(-c2ccc(OC(F)(F)F)cc2)c2nccc(C(=O)O)c12]

To a solution of ethyl 3-iodo-1-(4-(trifluoromethoxy)phenyl)-1H-pyrazolo[3,4-b]pyridine-4-carboxylate (300 mg, 0.63 mmol) in 1,4-dioxane (20 mL) and water (2 mL), was added $Cs_2CO_3$ (614 mg, 1.89 mmol), CATACXIUM A Pd $G_2$ (42 mg, 0.06 mmol) and potassium (((tert-butoxycarbonyl)amino)methyl)trifluoroborate (224 mg, 0.94 mmol), the solution was purged with N2 atmosphere for 1 min. And then the solution was stirred at 100° C. for 12 h, the solution was diluted with water (50 mL) and extracted with ethyl acetate (50 mL×3), the organic layer was dried over anhydrous $Na_2SO_4$ and concentrated under vacuo, the residue was purified by column chromatography on silica gel (0-50% ethyl acetate in petroleum ether) to afford the title compound (130 mg, 46%) as a white solid, LCMS (ESI): m/z 475.0 $(M+Na)^+$.

Step 2: tert-butyl ((4-carbamoyl-1-(4-(trifluoromethoxy)phenyl)-1H-pyrazolo[3,4-b]pyridin-3-yl)methyl)carbamate

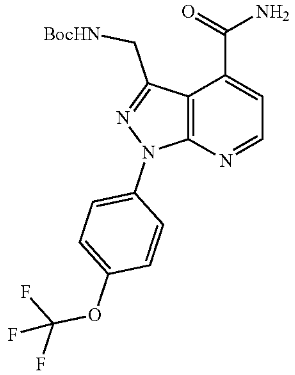 [SMILES: CC(C)(C)OC(=O)NCc1nn(-c2ccc(OC(F)(F)F)cc2)c2nccc(C(N)=O)c12]

To a mixture of 3-(((tert-butoxycarbonyl)amino)methyl)-1-(4-(trifluoromethoxy)phenyl)-1H-pyrazolo[3,4-b]pyridine-4-carboxylic acid (130 mg, 0.29 mmol) in DMF (10 mL) was added DIEA (0.2 mL, 1.15 mmol) and HATU (120 mg, 0.32 mmol), then $NH_4Cl$ (154 mg, 2.87 mmol) was added into it. The mixture was stirred at room temperature for 16. The solution was quenched with water (20 mL) and extracted with DCM (20 mL×3), the organic layer was dried with anhydrous $Na_2SO_4$ and concentrated under vacuo, the residue was purified by column chromatography on silica gel (0-40% ethyl acetate in petroleum ether) to afford the title compound (80 mg, 62%) as a yellow solid. LCMS (ESI): m/z 452.1 $(M+H)^+$.

Step 3: 3-(aminomethyl)-1-(4-(trifluoromethoxy)phenyl)-1H-pyrazolo[3,4-b]pyridine-4-carboxamide 2,2,2-trifluoroacetate

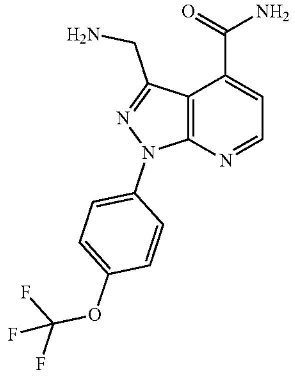 [SMILES: NCc1nn(-c2ccc(OC(F)(F)F)cc2)c2nccc(C(N)=O)c12]

A solution of tert-butyl ((4-carbamoyl-1-(4-(trifluoromethoxy)phenyl)-1H-pyrazolo[3,4-b]pyridin-3-yl)methyl)carbamate (80 mg, 0.18 mmol) in TFA (5% in HFIP, 3 mL) was stirred at room temperature for 2 h, the solution was concentrated under vacuo to afford the title compound (60 mg, 96%). LCMS (ESI): m/z 352.1 $(M+H)^+$.

Step 4: 3-(acrylamidomethyl)-1-(4-(trifluoromethoxy)phenyl)-1H-pyrazolo[3,4-b]pyridine-4-carboxamide

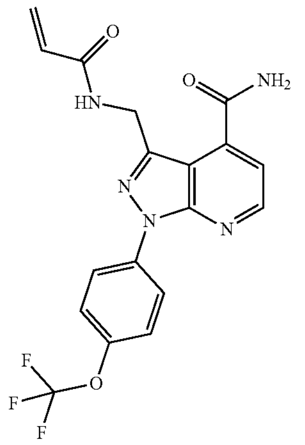 [SMILES: C=CC(=O)NCc1nn(-c2ccc(OC(F)(F)F)cc2)c2nccc(C(N)=O)c12]

To a solution of 3-(aminomethyl)-1-(4-(trifluoromethoxy) phenyl)-1H-pyrazolo[3,4-b]pyridine-4-carboxamide 2,2,2-trifluoroacetate (60 mg, 0.17 mmol) in THF (5 mL) was added sat. $NaHCO_3$ solution (2 mL) and acryloyl chloride (0.02 mL, 0.19 mmol) at 0° C., the solution was stirred at 0° C. for 30 mins, the solution was quenched with water (10 mL) and extracted with ethyl acetate (10 mL×3), the organic layer was dried with anhydrous $Na_2SO_4$ and concentrated under vacuo, the residue was purified by prep-TLC (100% ethyl acetate) to afford the title compound (22.5 mg, 33%) as a white solid. $^1H$ NMR (400 MHz, DMSO-$d_6$): δ 8.77 (d, J=4.8 Hz, 1H), 8.54 (s, 1H), 8.38-8.35 (m, 3H), 7.99 (s, 1H), 7.61 (d, J=8.8 Hz, 2H), 7.49 (d, J=4.8 Hz, 1H), 6.33 (dd, J=17.2, 10.0 Hz, 1H), 6.12 (dd, J=17.2, 2.0 Hz, 1H), 5.63 (dd, J=10.0, 2.0 Hz, 1H), 4.81 (d, J=5.6 Hz, 2H); LCMS (ESI): m/z 405.9 $(M+H)^+$, Example 50 (Compound 135)

N-((4-(2-Hydroxypropan-2-yl)-1-(4-(trifluoromethoxy)phenyl)-1H-pyrazolo[3,4-b]pyridin-3-yl) methyl)acrylamide

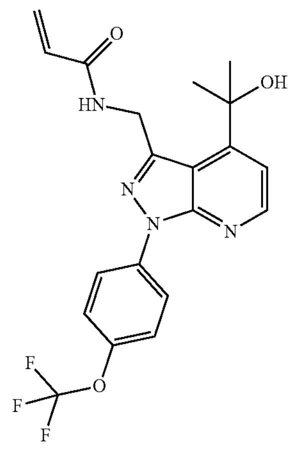 [SMILES: C=CC(=O)NCc1nn(-c2ccc(OC(F)(F)F)cc2)c2nccc(C(C)(C)O)c12]

Step 1: ethyl 3-bromo-1-(4-(trifluoromethoxy)phenyl)-1H-pyrazolo[3,4-b]pyridine-4-carboxylate

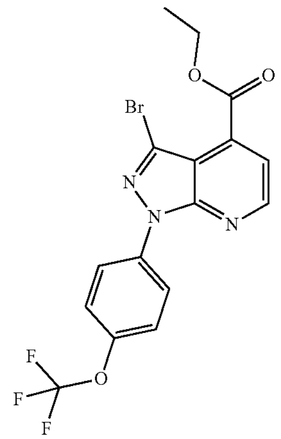 [SMILES: CCOC(=O)c1ccnc2c1c(Br)nn2-c1ccc(OC(F)(F)F)cc1]

A solution of ethyl 3-bromo-1H-pyrazolo[3,4-b]pyridine-4-carboxylate (3.0 g, 11.11 mmol), (4-(trifluoromethoxy) phenyl)boronic acid (4.5 g, 22.22 mmol), $Cu(OAc)_2$ (4.0 g, 22.22 mmol), pyridine (3.7 mL, 44.43 mmol) in acetonitrile (50 mL) was stirred at room temperature under $O_2$ balloon for 16 h. The solution was filtered, washed with water (150 mL), and extracted with ethyl acetate (150 mL×3), the organic layer was dried over anhydrous $Na_2SO_4$ and concentrated under vacuo, the residue was purified by column chromatography on silica gel (0-5% ethyl acetate in petroleum ether) to afford the title compound (3.5 g, 73%) as a yellow solid. $^1H$ NMR (400 MHz, DMSO-$d_6$): δ 8.87 (d, J=4.8 Hz, 1H), 8.27 (d, J=8.8 Hz, 2H), 7.69 (d, J=4.8 Hz, 1H), 7.61 (d, J=8.8 Hz, 2H), 4.48 (q, t=6.8 Hz, 2H), 1.41 (t, J=6.8 Hz, 3H); LCMS (ESI): m/z 430.7 $(M+H)^+$.

Step 2: 2-(3-bromo-1-(4-(trifluoromethoxy)phenyl)-1H-pyrazolo[3,4-b]pyridin-4-yl)propan-2-ol

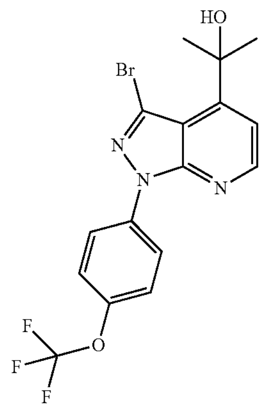 [SMILES: CC(C)(O)c1ccnc2c1c(Br)nn2-c1ccc(OC(F)(F)F)cc1]

To a solution of ethyl 3-bromo-1-(4-(trifluoromethoxy) phenyl)-1H-pyrazolo[3,4-b]pyridine-4-carboxylate (1.2 g, 2.79 mmol) in THF (20 mL) was added methylmagnesium bromide (5.58 mL, 16.74 mmol, 3.0 mol/L in THF) at 0° C., the reaction solution was stirred at 0° C. for 4 h, the solution was quenched with saturated $NH_4Cl$ solution (50 mL) and extracted with ethyl acetate (50 mL×3), the organic layer was dried with anhydrous $Na_2SO_4$ and concentrated under vacuum, the residue was purified by column chromatography on silica gel (0-5% ethyl acetate in petroleum ether) to afford the title compound (530 mg, 46%) as a yellow solid. $^1H$ NMR (400 MHz, DMSO-$d_6$): δ 8.67 (d, J=4.8 Hz, 1H), 8.27 (d, J=8.8 Hz, 2H), 7.62-7.59 (m, 3H), 5.58 (s, 1H), 1.77 (s, 6H). LCMS (ESI): m/z 416.0 $(M+H)^+$.

Step 3: 4-(2-hydroxypropan-2-yl)-1-(4-(trifluoromethoxy)phenyl)-1H-pyrazolo[3,4-b]pyridine-3-carbonitrile

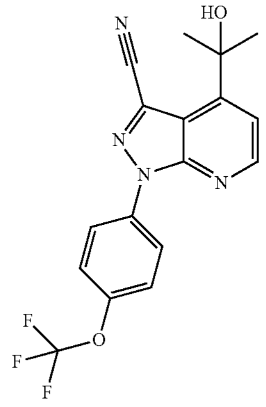 [SMILES: CC(C)(O)c1ccnc2c1c(C#N)nn2-c1ccc(OC(F)(F)F)cc1]

A solution of 2-(3-bromo-1-(4-(trifluoromethoxy)phenyl)-1H-pyrazolo[3,4-b]pyridin-4-yl)propan-2-ol (100 mg, 0.24 mmol) CuCN (86 mg, 0.96 mmol) in DMF (5 mL) was stirred at 120° C. for 4 h under $N_2$ atmosphere. The mixture was diluted with water (50 mL) and extracted with ethyl acetate (50 mL×3). The organic layer was dried with anhydrous $Na_2SO_4$ and concentrated under vacuum. The residue was purified by flash chromatography on silica gel (10-20% ethyl acetate in petroleum ether) to afford the title compound (70 mg, 80%) as a yellow solid. LCMS (ESI): m/z 362.8 $(M+H)^+$.

Step 4: 2-(3-(aminomethyl)-1-(4-(trifluoromethoxy)phenyl)-1H-pyrazolo[3,4-b]pyridin-4-yl)propan-2-ol

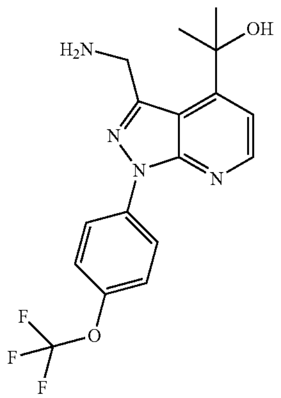 [SMILES: CC(C)(O)c1ccnc2c1c(CN)nn2-c1ccc(OC(F)(F)F)cc1]

To a solution of 4-(2-hydroxypropan-2-yl)-1-(4-(trifluoromethoxy)phenyl)-1H-pyrazolo[3,4-b]pyridine-3-carbonitrile (70 mg, 0.19 mmol) in methyl alcohol (5 mL) was added $NiCl_2 \cdot 6H_2O$ (8 mg, 0.04 mmol), $NaBH_4$ (81 mg, 0.97 mmol) at 0° C., the mixture was stirred at room temperature for 12 h, the solution was quenched with saturated $NH_4Cl$ solution (50 mL) and extracted with ethyl acetate (50 mL×3), the organic layer was dried with anhydrous $Na_2SO_4$ and concentrated under vacuum to afford the title compound (35 mg, 49%). LCMS (ESI): m/z 367.0 $(M+H)^+$.

Step 5: N-((4-(2-hydroxypropan-2-yl)-1-(4-(trifluoromethoxy)phenyl)-1H-pyrazolo[3,4-b]pyridin-3-yl)methyl)acrylamide

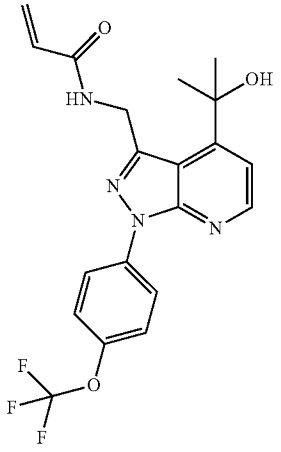 [SMILES: C=CC(=O)NCc1nn(-c2ccc(OC(F)(F)F)cc2)c2nccc(C(C)(C)O)c12]

To a solution of 2-(3-(aminomethyl)-1-(4-(trifluoromethoxy)phenyl)-1H-pyrazolo[3,4-b]pyridin-4-yl)propan-2-ol (35 mg, 0.10 mmol) in THF (3 mL) was added acryloyl chloride (0.01 mL, 0.11 mmol) and saturated $NaHCO_3$ solution (2 mL) at 0° C. Then the reaction was stirred at 0° C. for 30 mins. The reaction was diluted with water (20 mL) and extracted with ethyl acetate (50 mL×3). The combined organic layers were washed with brine (20 mL×2), dried over anhydrous $Na_2SO_4$, filtered and concentrated. The residue was purified by prep-TLC (50% ethyl acetate in petroleum ether) to afford the title compound (20.0 mg, 48%) as a white solid. $^1H$ NMR (400 MHz, DMSO-$d_6$): δ 8.58 (d, J=4.8 Hz, 1H), 8.51 (t, J=5.2 Hz, 1H), 8.38 (d, J=8.8 Hz, 2H), 7.59 (d, J=8.8 Hz, 2H), 7.30 (d, J=4.8 Hz, 1H), 6.41 (dd, J=16.8, 10.4 Hz, 1H), 6.14 (dd, J=16.8, 2.0 Hz, 1H), 5.72 (s, 1H), 5.63 (dd, J=10.4, 2.0 Hz, 1H), 5.03 (d, J=5.2 Hz, 2H), 1.64 (s, 6H); LCMS (ESI): m/z 421.0 $(M+H)^+$.

Example 51 (Compound 38)

N-((4-(cis-3-Hydroxycyclobutyl)-1-(4-(trifluoromethoxy)phenyl)-1H-pyrazolo[3,4-b]pyridin-3-yl)methyl)acrylamide

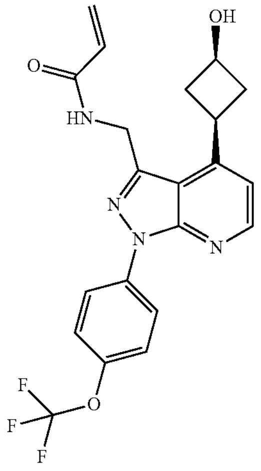 [SMILES: C=CC(=O)NCc1nn(-c2ccc(OC(F)(F)F)cc2)c2nccc([C@H]3C[C@@H](O)C3)c12]

Step 1: 4-bromo-1-(4-(trifluoromethoxy)phenyl)-1H-pyrazolo[3,4-b]pyridine-3-carboxamide

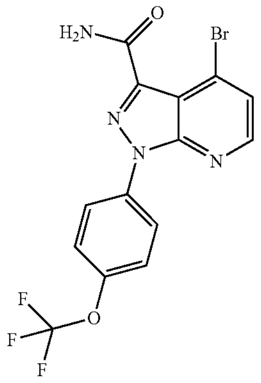 [SMILES: NC(=O)c1nn(-c2ccc(OC(F)(F)F)cc2)c2nccc(Br)c12]

A solution of 4-chloro-1-(4-(trifluoromethoxy)phenyl)-1H-pyrazolo[3,4-b]pyridine-3-carbonitrile (5.5 g, 16.2 mmol) in HBr (33% in AcOH, 50 mL) was stirred at 80° C. for 1 h. The reaction mixture was concentrated to dryness under reduced pressure. The residue was diluted with DCM (50 mL) the mixture was filtered and washed with DCM (40 mL), the filter cake was collected and dried in vacuo to afford the title compound (6.0 g, 92%) as a yellow solid. $^1H$ NMR (400 MHz, DMSO-$d_6$): δ 8.55 (d, J=4.8 Hz, 1H), 8.36 (d, J=8.8 Hz, 2H), 8.24 (s, 1H), 7.86 (s, 1H), 7.78 (d, J=4.8 Hz, 1H), 7.64 (d, J=8.8 Hz, 2H).

Step 2: 4-bromo-1-(4-(trifluoromethoxy)phenyl)-1H-pyrazolo[3,4-b]pyridine-3-carbonitrile

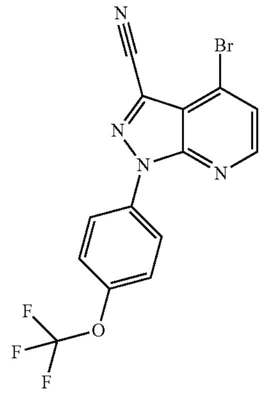 [SMILES: N#Cc1nn(-c2ccc(OC(F)(F)F)cc2)c2nccc(Br)c12]

To a solution of 4-bromo-1-(4-(trifluoromethoxy)phenyl)-1H-pyrazolo[3,4-b]pyridine-3-carboxamide (4.5 g, 11.1 mmol) and TEA (15.5 mL, 111 mmol) in DCM (60 mL) was added TMSOTf (9.4 mL, 55.6 mmol) at 0° C. The reaction mixture was stirred at room temperature for 16 h. The reaction was quenched with water (200 mL) and extracted with ethyl acetate (200 mL×3), the combined organic layers were washed with water (100 mL×3), dried over $Na_2SO_4$, filtered and concentrated. The residue was purified by column chromatography on silica gel (0-4% ethyl acetate in petroleum ether) to afford the title compound (2.4 g, 55%) as a yellow solid. $^1H$ NMR (400 MHz, DMSO-$d_6$): δ 8.67 (d, J=4.8 Hz, 1H), 8.29 (d, J=9.2 Hz, 2H), 7.95 (d, J=5.2 Hz, 1H), 7.66 (d, J=8.8 Hz, 2H); LCMS (ESI): m/z 383.0 $(M+H)^+$.

Step 3: 4-(5,8-dioxaspiro[3.4]octan-2-yl)-1-(4-(trifluoromethoxy)phenyl)-1H-pyrazolo[3,4-b]pyridine-3-carbonitrile

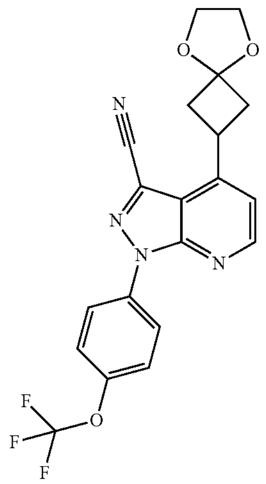 [SMILES: N#Cc1nn(-c2ccc(OC(F)(F)F)cc2)c2nccc(C3CC4(C3)OCCO4)c12]

In glove box, to a dry glass bottle was added a mixture of 4-bromo-1-(4-(trifluoromethoxy)phenyl)-1H-pyrazolo[3,4-b]pyridine-3-carbonitrile (100 mg, 0.26 mmol), $Na_2CO_3$ (69 mg, 0.65 mmol) in DME (1 mL), 2-bromo-5,8-dioxaspiro

[3.4]octane (76 mg, 0.39 mmol), TTMSS (78 mg, 0.31 mmol) and $Ir[dF(CF_3)ppy]_2(dtbbpy)PF_6$ (2.9 mg, 0.03 mmol), $NiCl_2$·glyme (5.7 mg, 0.03 mmol) and dtbbpy (11 mg, 0.04 mmol) in DME (2 mL) at room temperature. The vial was sealed and taken out from glove box, irradiated with 72W Blue_LED-Strip-Light for 16 h with cooling from a fan. (24 batches of the same scale (total 2.4 g of starting material) were carried out in parallel and combined together for work up). The reaction mixture was diluted with water (200 mL) and extracted with ethyl acetate (200 mL×3). The combined organic layers were washed with water (100 mL×3), dried over $Na_2SO_4$, filtered and concentrated. The residue was purified by chromatography on silica gel (0-14% ethyl acetate in petroleum ether) to afford the title compound (730 mg, 28%) as a yellow solid. $^1$H NMR (400 MHz, $CDCl_3$): δ 8.70 (d, J=4.8 Hz, 1H), 8.34 (d, J=9.2 Hz, 2H), 7.44-7.41 (m, 3H), 4.16-4.08 (m, 1H), 4.05-3.95 (m, 2H), 3.97-3.93 (m, 2H), 3.11-3.05 (m, 2H), 2.71-2.66 (m, 2H).

Step 4: 4-(3-oxocyclobutyl)-1-(4-(trifluoromethoxy)phenyl)-1H-pyrazolo[3,4-b]pyridine-3-carbonitrile

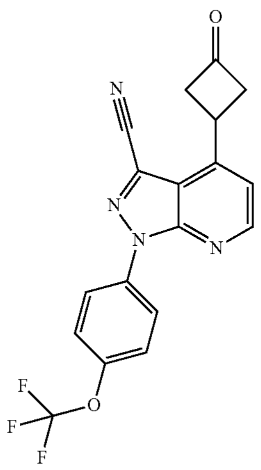 [SMILES: N#Cc1nn(-c2ccc(OC(F)(F)F)cc2)c2nccc(C3CC(=O)C3)c12]

To a solution of 4-(5,8-dioxaspiro[3.4]octan-2-yl)-1-(4-(trifluoromethoxy)phenyl)-1H-pyrazolo[3,4-b]pyridine-3-carbonitrile (650 mg, 1.56 mmol) in THF (10 mL) was added conc. HCl (3.0 mL). Then the reaction was stirred at 70° C. for 16 h. The mixture was diluted with ethyl acetate (200 mL) and washed with water (100 mL×3). The organic was dried over $Na_2SO_4$ and concentrated to afford the title compound (550 mg, 94%) as a brown solid. LCMS (ESI): m/z 373.1 $(M+H)^+$.

Step 5: 4-(3-hydroxycyclobutyl)-1-(4-(trifluoromethoxy)phenyl)-1H-pyrazolo[3,4-b]pyridine-3-carbonitrile

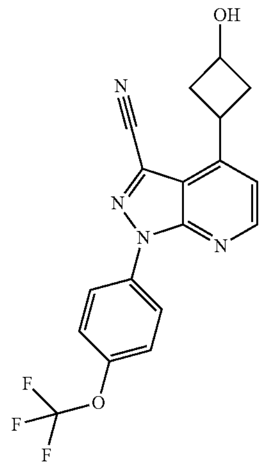 [SMILES: N#Cc1nn(-c2ccc(OC(F)(F)F)cc2)c2nccc(C3CC(O)C3)c12]

To a mixture of 4-(3-oxocyclobutyl)-1-(4-(trifluoromethoxy)phenyl)-1H-pyrazolo[3,4-b]pyridine-3-carbonitrile (500 mg, 1.34 mmol) in THF (5.0 mL) was added $NaBH_4$ (102 mg, 2.69 mmol) at 0° C. Then the reaction was stirred at 0° C. for 20 min. The reaction mixture was diluted with ice water (100 mL) and extracted with ethyl acetate (200 mL×3). The combined organic layers were dried over $Na_2SO_4$ and concentrated to dryness. The residue was purified by flash chromatography on silica gel (0-50% ethyl acetate in petroleum ether) to afford the title compound (400 mg, 80%) as a white solid. LCMS (ESI): m/z 375.1 $(M+H)^+$.

Step 6: 4-(trans-3-hydroxycyclobutyl)-1-(4-(trifluoromethoxy)phenyl)-1H-pyrazolo[3,4-b]pyridine-3-carbonitrile & 4-((cis-3-hydroxycyclobutyl)-1-(4-(trifluoromethoxy)phenyl)-1H-pyrazolo[3,4-b]pyridine-3-carbonitrile

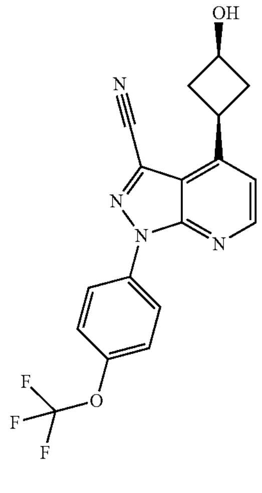

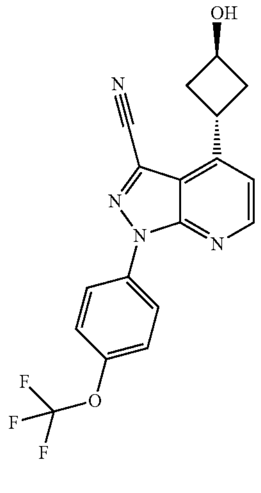

4-(3-Hydroxycyclobutyl)-1-(4-(trifluoromethoxy)phenyl)-1H-pyrazolo[3,4-b]pyridine-3-carbonitrile (400 mg, 1.07 mmol) was purified with SFC (DAICEL CHIRALPAK IG (250 mm*30 mm, 10 um), 0.1% $NH_3{\cdot}H_2O$/MeOH, 35-35%) to afford the first peak 4-((cis-3-hydroxycyclobutyl)-1-(4-(trifluoromethoxy)phenyl)-1H-pyrazolo[3,4-b]pyridine-3-carbonitrile (270 mg, 67%) and the second peak 4-(trans-3-Hydroxycyclobutyl)-1-(4-(trifluoromethoxy)phenyl)-1H-pyrazolo[3,4-b]pyridine-3-carbonitrile (80 mg, 20%) both as a white solid. 2D NMR was used to confirm the structures.

The first peak: $^1$H NMR (400 MHz, $CDCl_3$): δ 8.69 (d, J=4.8 Hz, 1H), 8.34 (d, J=9.2 Hz, 2H), 7.43 (d, J=8.8 Hz, 2H), 7.34 (d, J=4.8 Hz, 1H), 4.60-4.50 (m, 1H), 3.81-3.68 (m, 1H), 3.11-2.97 (m, 2H), 2.35-2.17 (m, 2H), 2.04-1.84 (m, 1H).

The second peak: $^1$H NMR (400 MHz, $CDCl_3$): δ 8.69 (d, J=4.8 Hz, 1H), 8.34 (d, J=8.8 Hz, 2H), 7.43 (d, J=8.8 Hz, 2H), 7.36 (d, J=4.8 Hz, 1H), 4.64-4.54 (m, 1H), 4.38-4.27 (m, 1H), 2.80-2.66 (m, 4H), 1.95-1.86 (m, 1H).

Step 7: cis-3-(3-(aminomethyl)-1-(4-(trifluoromethoxy)phenyl)-1H-pyrazolo[3,4-b]pyridin-4-yl) cyclobutanol

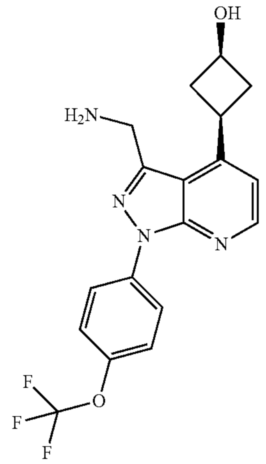 [SMILES: NCc1nn(-c2ccc(OC(F)(F)F)cc2)c2nccc([C@H]3C[C@@H](O)C3)c12]

To a solution of 4-((cis-3-hydroxycyclobutyl)-1-(4-(trifluoromethoxy)phenyl)-1H-pyrazolo[3,4-b]pyridine-3-carbonitrile (220 mg, 0.59 mmol) and $NiCl_2$ $6H_2O$ (14 mg, 0.06 mmol) in MeOH (5 mL) was added $NaBH_4$ (89 mg, 2.35 mmol) at 0° C. Then the reaction was stirred at 0° C. for 30 min. The mixture was quenched with $NH_4Cl$ solution (5.0 mL) and 2 M HCl solution (5.0 mL), then adjusted to pH=8 with aq.$NaHCO_3$ solution and extracted with ethyl acetate (100 mL) and washed with water (100 mL×3). The organic was dried over $Na_2SO_4$ and concentrated to afford the title compound (220 mg, 99%) as a yellow oil. LCMS (ESI): m/z 362.2 $(M-NH_2)^+$.

Step 8: N-((4-(cis-3-hydroxycyclobutyl)-1-(4-(trifluoromethoxy)phenyl)-1H-pyrazolo[3,4-b]pyridin-3-yl)methyl)acrylamide

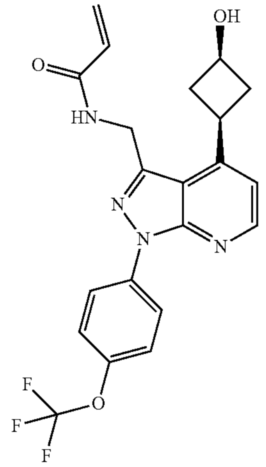 [SMILES: C=CC(=O)NCc1nn(-c2ccc(OC(F)(F)F)cc2)c2nccc([C@H]3C[C@@H](O)C3)c12]

To a solution of cis-3-(3-(aminomethyl)-1-(4-(trifluoromethoxy)phenyl)-1H-pyrazolo[3,4-b]pyridin-4-yl)cyclobutanol (220 mg, 0.58 mmol) and aq.$NaHCO_3$ (1 mL) in THF (5 mL) was added acryloyl chloride (0.05 mL, 0.58 mmol) at 0° C. The resulting mixture was stirred at 0° C. for 1 h. The mixture was diluted with ethyl acetate (30 mL) and washed with water (30 mL×3). The organic layer was dried over $Na_2SO_4$ and concentrated. The residue was purified by reverse phase chromatography (Boston Green ODS 150*30 mm*5 um, water (FA)-ACN, 41-71%) to afford the title compound (203 mg, 80%) as a white solid. $^1$H NMR (400 MHz, DMSO-$d_6$): δ 8.74-8.68 (m, 1H), 8.64 (d, J=4.8 Hz, 1H), 8.39 (d, J=8.8 Hz, 2H), 7.59 (d, J=8.8 Hz, 2H), 7.38 (d, J=4.8 Hz, 1H), 6.31 (dd, J=16.8, 10.0 Hz, 1H), 6.19 (dd, J=16.8, 2.4 Hz, 1H), 5.66 (dd, J=10.0, 2.4 Hz, 1H), 5.26 (d, J=6.8 Hz, 1H), 4.85 (d, J=4.8 Hz, 2H), 4.15-4.03 (m, 1H), 3.51-3.40 (m, 1H), 2.68-2.60 (m, 2H), 2.11-1.99 (m, 2H); LCMS (ESI): m/z 433.0 $(M+H)^+$.

Example 52 (Compound 56)

N-((4-(trans-3-hydroxycyclobutyl)-1-(4-(trifluoromethoxy)phenyl)-1H-pyrazolo[3,4-b]pyridin-3-yl)methyl)acrylamide

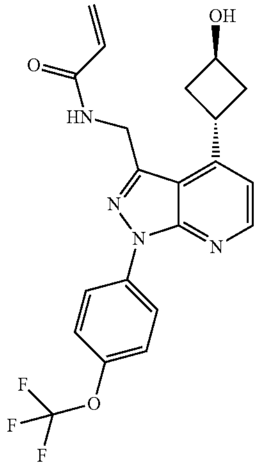 [SMILES: C=CC(=O)NCc1nn(-c2ccc(OC(F)(F)F)cc2)c2nccc([C@H]3C[C@H](O)C3)c12]

Step 1: trans-3-(3-(aminomethyl)-1-(4-(trifluoromethoxy)phenyl)-1H-pyrazolo[3,4-b]pyridin-4-yl)cyclobutanol

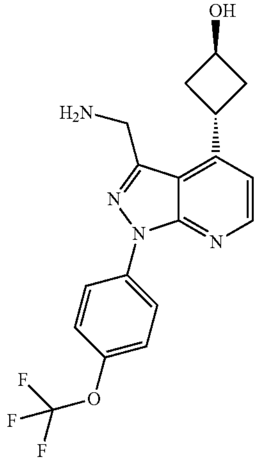 [SMILES: NCc1nn(-c2ccc(OC(F)(F)F)cc2)c2nccc([C@H]3C[C@H](O)C3)c12]

To a solution of 4-((trans-3-hydroxycyclobutyl)-1-(4-(trifluoromethoxy)phenyl)-1H-pyrazolo[3,4-b]pyridine-3-carbonitrile from example 51-step 6 (80 mg, 0.24 mmol) and $NiCl_2$ $6H_2O$ (5 mg, 0.02 mmol) in MeOH (5.0 mL) was added $NaBH_4$ (27 mg, 0.72 mmol) at 0° C. Then the reaction was stirred at 0° C. for 30 min. The mixture was quenched with $NH_4Cl$ solution (5.0 mL) and 2M HCl solution (5.0 mL), then adjusted to pH=8 with aq.$NaHCO_3$ solution and extracted with ethyl acetate (100 mL) and washed with water (100 mL×3). The organic was dried over $Na_2SO_4$ and concentrated to afford the title compound (80 mg, crude) as a yellow oil. LCMS (ESI): m/z 379.2 $(M+H)^+$.

Step 2: N-((4-(trans-3-hydroxycyclobutyl)-1-(4-(trifluoromethoxy)phenyl)-1H-pyrazolo[3,4-b]pyridin-3-yl)methyl)acrylamide

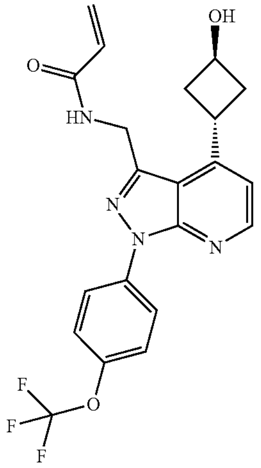 [SMILES: C=CC(=O)NCc1nn(-c2ccc(OC(F)(F)F)cc2)c2nccc([C@H]3C[C@H](O)C3)c12]

To a solution of trans-3-(3-(aminomethyl)-1-(4-(trifluoromethoxy)phenyl)-1H-pyrazolo[3,4-b]pyridin-4-yl)cyclobutanol (80 mg, 0.21 mmol) and aq.$NaHCO_3$ (1.0 mL) in THF (5 mL) was added acryloyl chloride (0.02 mL, 0.21 mmol) at 0° C. The resulting mixture was stirred at 0° C. for 1 h. The mixture was diluted with ethyl acetate (100 mL) and washed with water (100 mL×3). The organic was dried over $Na_2SO_4$ and concentrated. The residue was purified by reverse phase chromatography (Boston Green ODS 150*30 mm*5 um, water (FA)-ACN, 48-78%) to afford the title compound (25.7 mg, 28%) as a white solid. $^1H$ NMR (400 MHz, DMSO-$d_6$): δ 8.67-8.63 (m, 1H), 8.62 (d, J=4.8 Hz, 1H), 8.39 (d, J=9.2 Hz, 2H), 7.59 (d, J=8.4 Hz, 2H), 7.42 (d, J=4.8 Hz, 1H), 6.30 (dd, J=16.8, 10.0 Hz, 1H), 6.18 (dd, J=16.8, 2.4 Hz, 1H), 5.65 (dd, J=10.0, 2.4 Hz, 1H), 5.25 (d, J=6.4 Hz, 1H), 4.77 (d, J=4.8 Hz, 2H), 4.40-4.30 (m, 1H), 4.00-3.90 (m, 1H), 2.47-2.35 (m, 4H); LCMS (ESI): m/z 433.0 $(M+H)^+$.

Example 53 & 54 (Compounds 62 and 63)

(R)-N-((4-(1-Hydroxyethyl)-1-(4-(trifluoromethoxy)phenyl)-1H-pyrazolo[3,4-b]pyridin-3-yl)methyl)acrylamide & (S)-N-((4-(1-hydroxyethyl)-1-(4-(trifluoromethoxy)phenyl)-1H-pyrazolo[3,4-b]pyridin-3-yl)methyl)acrylamide

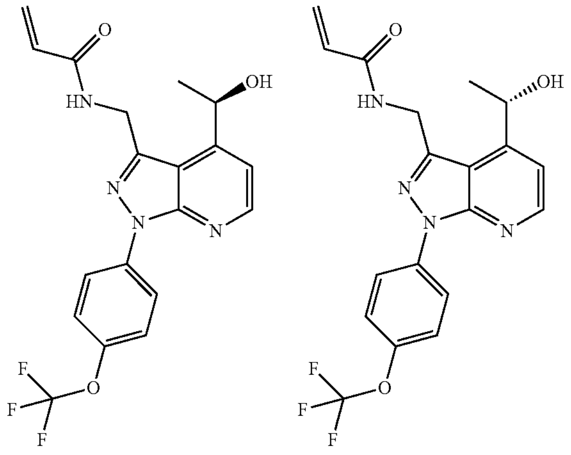 [SMILES: C=CC(=O)NCc1nn(-c2ccc(OC(F)(F)F)cc2)c2nccc([C@@H](C)O)c12 ; C=CC(=O)NCc1nn(-c2ccc(OC(F)(F)F)cc2)c2nccc([C@H](C)O)c12]

Step 1: 4-(1-ethoxyvinyl)-1-(4-(trifluoromethoxy)phenyl)-1H-pyrazolo[3,4-b]pyridine-3-carboxamide

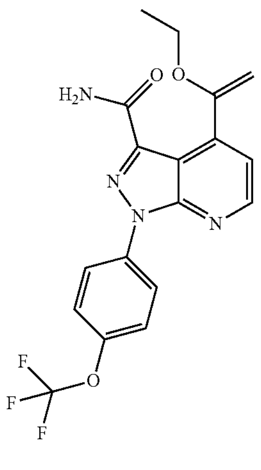 [SMILES: C=C(OCC)c1ccnc2c1c(C(N)=O)nn2-c1ccc(OC(F)(F)F)cc1]

A solution of 4-bromo-1-(4-(trifluoromethoxy)phenyl)-1H-pyrazolo[3,4-b]pyridine-3-carboxamide (880 mg, 2.19 mmol), $Pd(PPh_3)_4$ (507 mg, 0.44 mmol), CsF (666 mg, 4.39 mmol), tributyl(1-ethoxyvinyl)stannane (1.5 mL, 4.39 mmol) in 1,4-dioxane (10 mL) was stirred at 100° C. for 16 h under $N_2$ atmosphere, the solution was washed with saturated KF solution (25 mL) and extracted with ethyl acetate (25 mL×3), the organic layer was dried with anhydrous $Na_2SO_4$ and concentrated under vacuum, the residue was purified by column chromatography on silica gel (0-50% ethyl acetate in petroleum ether) to afford the title compound (420 mg, 49%) as a white solid. LCMS (ESI): m/z 393.1 $(M+H)^+$.

Step 2: 4-acetyl-1-(4-(trifluoromethoxy)phenyl)-1H-pyrazolo[3,4-b]pyridine-3-carboxamide

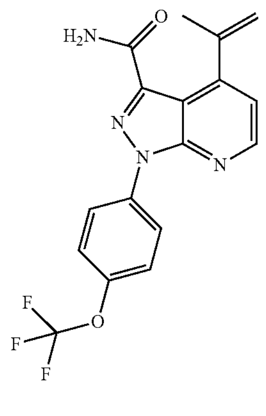 [SMILES: C=C(C)c1ccnc2c1c(C(N)=O)nn2-c1ccc(OC(F)(F)F)cc1]

To a solution of 4-(1-ethoxyvinyl)-1-(4-(trifluoromethoxy)phenyl)-1H-pyrazolo[3,4-b]pyridine-3-carboxamide (420 mg, 1.07 mmol) in THF (2 mL) was added 1M HCl (2 mL) at room temperature, the mixture was stirred at room temperature for 2 h, the solution was washed with sat. $NaHCO_3$ (30 mL) and extracted with ethyl acetate (30 mL×3), the combined organic layers were dried with anhydrous $Na_2SO_4$ and concentrated under vacuum to afford the title compound (380 mg, 97%) as a white solid. LCMS (ESI): m/z 386.9 $(M+Na)^+$.

Step 3: 4-acetyl-1-(4-(trifluoromethoxy)phenyl)-1H-pyrazolo[3,4-b]pyridine-3-carbonitrile

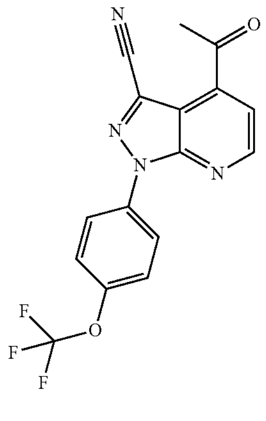 [SMILES: CC(=O)c1ccnc2c1c(C#N)nn2-c1ccc(OC(F)(F)F)cc1]

To a solution of 4-acetyl-1-(4-(trifluoromethoxy)phenyl)-1H-pyrazolo[3,4-b]pyridine-3-carboxamide (100 mg, 0.27 mmol) in 1,2-dichloroethane (10 mL), triethylamine (0.08 mL, 0.55 mmol) was added trifluoromethanesulfonic anhydride (0.11 mL, 0.63 mmol) at 0° C., the solution was stirred at room temperature for 16 h, the solution was quenched with water (10 mL) and extracted with DCM (10 mL×3), the organic layer was dried with $Na_2SO_4$ and concentrated under vacuum, the residue was purified by column chromatography on silica gel (0-5% ethyl acetate in petroleum ether) to afford the title compound (60 mg, 63%) as a white solid. $^1H$ NMR (400 MHz, DMSO-$d_6$): δ 9.07 (d, J=4.8 Hz, 1H), 8.30 (d, J=8.8 Hz, 2H), 8.16 (d, J=4.8 Hz, 1H), 7.68 (d, J=8.8 Hz, 2H), 2.80 (s, 3H); LCMS (ESI): m/z 346.9 $(M+H)^+$.

Step 4: 1-(3-(aminomethyl)-1-(4-(trifluoromethoxy)phenyl)-1H-pyrazolo[3,4-b]pyridin-4-yl)ethanol

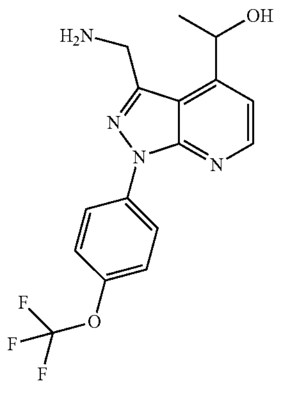 [SMILES: CC(O)c1ccnc2c1c(CN)nn2-c1ccc(OC(F)(F)F)cc1]

To a solution of 4-acetyl-1-(4-(trifluoromethoxy)phenyl)-1H-pyrazolo[3,4-b]pyridine-3-carbonitrile (71 mg, 0.21 mmol) in methyl alcohol (5 mL) was added $NiCl_2 \cdot 6H_2O$ (8 mg, 0.04 mmol) and $NaBH_4$ (38 mg, 1.03 mmol) at 0° C., the reaction was stirred at room temperature for 6 h. The solution was quenched with sat. $NH_4Cl$ solution (10 mL) and extracted with ethyl acetate (10 mL×3). The organic layer was dried with $Na_2SO_4$ and concentrated under vacuum to afford the title compound (60 mg, 83%). LCMS (ESI): m/z 335.9 $(M-NH_2)^+$.

Step 5: N-((4-(1-hydroxyethyl)-1-(4-(trifluoromethoxy)phenyl)-1H-pyrazolo[3,4-b]pyridin-3-yl)methyl)acrylamide

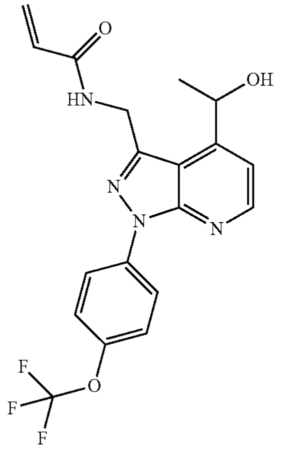

To a solution of 1-(3-(aminomethyl)-1-(4-(trifluoromethoxy)phenyl)-1H-pyrazolo[3,4-b]pyridin-4-yl)ethanol (60 mg, 0.17 mmol) in THF (3 mL) was added acryloyl chloride (0.02 mL, 0.20 mmol) and saturated $NaHCO_3$ solution (2 mL) at 0° C., then the reaction was stirred at 0° C. for 30 mins. The reaction was quenched with water (20 mL) and extracted with ethyl acetate (20 mL×3). The organic layer was dried over anhydrous $Na_2SO_4$, filtered and concentrated. The residue was purified by prep-TLC (50% ethyl acetate in petroleum ether) to afford the title compound (35 mg, 51%) as a white solid. LCMS (ESI): m/z 429.0 $(M+Na)^+$.

Step 6: (R)-N-((4-(1-hydroxyethyl)-1-(4-(trifluoromethoxy)phenyl)-1H-pyrazolo[3,4-b]pyridin-3-yl)methyl)acrylamide & (S)-N-((4-(1-hydroxyethyl)-1-(4-(trifluoromethoxy)phenyl)-1H-pyrazolo[3,4-b]pyridin-3-yl)methyl)acrylamide

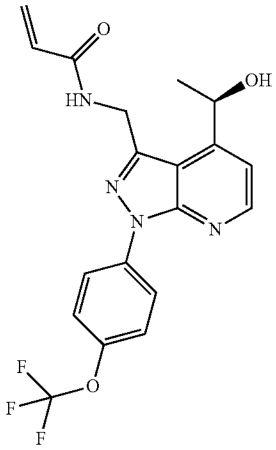

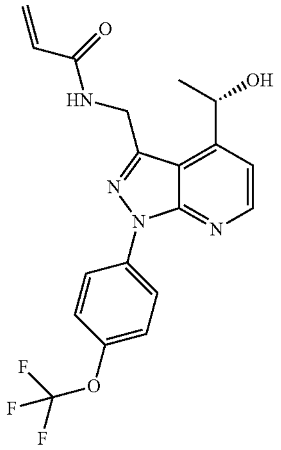 [SMILES: C=CC(=O)NCc1nn(-c2ccc(OC(F)(F)F)cc2)c2nccc(C(C)O)c12]

N-((4-(1-hydroxyethyl)-1-(4-(trifluoromethoxy)phenyl)-1H-pyrazolo[3,4-b]pyridin-3-yl)methyl)acrylamide (30 mg, 0.09 mmol) was separated by Chiral SFC (Instrument: SFC-25; Column: DAICEL CHIRALPAK AD (250 mm*30 mm, 10 um); Condition: Neu-MeOH; Begin B: 35%; Flow Rate (mL/min): 80) to afford the first peak (R)-N-((4-(1-hydroxyethyl)-1-(4-(trifluoromethoxy)phenyl)-1H-pyrazolo[3,4-b]pyridin-3-yl)methyl)acrylamide (5.9 mg, 16%) and the second peak (S)-N-((4-(1-hydroxyethyl)-1-(4-(trifluoromethoxy)phenyl)-1H-pyrazolo[3,4-b]pyridin-3-yl)methyl)acrylamide (18.6 mg, 52%) both as a white solid.

The first peak: $^1H$ NMR (400 MHz, DMSO-$d_6$): δ 8.70 (t, J=4.8 Hz, 1H), 8.62 (d, J=4.8 Hz, 1H), 8.40 (d, J=9.2 Hz, 2H), 7.60 (d, J=8.8 Hz, 2H), 7.48 (d, J=5.2 Hz, 1H), 6.30 (dd, J=17.2, 10.0 Hz, 1H), 6.17 (dd, J=17.2, 2.0 Hz, 1H), 5.67-5.63 (m, 2H), 5.32-5.28 (m, 1H), 4.92-4.80 (m, 2H), 1.43 (d, J=6.4 Hz, 3H); LCMS (ESI): m/z 406.9 $(M+H)^+$.

The second peak: $^1H$ NMR (400 MHz, DMSO-$d_6$): δ 8.70 (t, J=4.8 Hz, 1H), 8.62 (d, J=4.8 Hz, 1H), 8.40 (d, J=9.2 Hz, 2H), 7.60 (d, J=8.8 Hz, 2H), 7.48 (d, J=5.2 Hz, 1H), 6.30 (dd, J=17.2, 10.0 Hz, 1H), 6.17 (dd, J=17.2, 2.0 Hz, 1H), 5.67-5.63 (m, 2H), 5.32-5.28 (m, 1H), 4.92-4.80 (m, 2H), 1.43 (d, J=6.4 Hz, 3H); LCMS (ESI): m/z 407.0 $(M+H)^+$.

Example 55 (Compound 87)

N-((4-(Hydroxymethyl)-1-(4-(pentafluoro-λ$^6$-sulfanyl)phenyl)-1H-pyrazolo[3,4-b]pyridin-3-yl)methyl) acrylamide

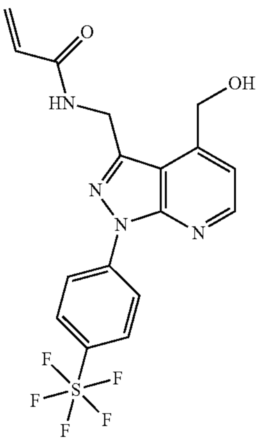 [SMILES: C=CC(=O)NCc1nn(-c2ccc(S(F)(F)(F)(F)F)cc2)c2nccc(CO)c12]

Step 1: 4-chloro-3-iodo-1-(4-(pentafluoro-l6-sulfanyl)phenyl)-1H-pyrazolo[3,4-b]pyridine

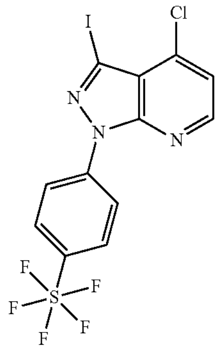 [SMILES: FS(F)(F)(F)(F)c1ccc(-n2nc(I)c3c(Cl)ccnc32)cc1]

A mixture of 4-chloro-3-iodo-1H-pyrazolo[3,4-b]pyridine (600 mg, 2.16 mmol), (4-(pentafluoro-16-sulfanyl) phenyl)boronic acid (798 mg, 3.21 mmol), $Cu(OAc)_2$ (585 mg, 3.21 mmol) and pyridine (0.60 mL, 8.58 mmol) in MeCN (10 mL) was stirred at room temperature for 16 h under $O_2$ (15 psi). The resulting solution was diluted with ethyl acetate (100 mL), after filtration, the filtrate was washed with water (50 mL×3), the organic layer was dried over anhydrous sodium sulfate and concentrated under vacuum. The residue was purified by flash chromatography on silica gel eluting with petroleum ether (100%) to afford the title compound (439 mg, 42%) as a white solid. $^1$H NMR (400 MHz, DMSO-$d_6$): δ 8.69 (d, J=5.2 Hz, 1H), 8.48 (d, J=9.2 Hz, 2H), 8.14 (d, J=9.2 Hz, 2H), 7.60 (d, J=5.2 Hz, 1H).

Step 2: tert-butyl ((4-chloro-1-(4-(pentafluoro-16-sulfanyl)phenyl)-1H-pyrazolo[3,4-b]pyridin-3-yl) methyl)carbamate

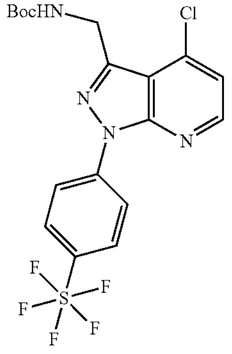 [SMILES: CC(C)(C)OC(=O)NCc1nn(-c2ccc(S(F)(F)(F)(F)F)cc2)c2nccc(Cl)c12]

A mixture of 4-chloro-3-iodo-1-(4-(pentafluoro-16-sulfanyl)phenyl)-1H-pyrazolo[3,4-b]pyridine (439 mg, 0.91 mmol), $Cs_2CO_3$ (891 mg, 2.73 mmol), potassium (((tert-butoxycarbonyl)amino)methyl)trifluoroborate (282 mg, 1.18 mmol) and CATACXIUM A Pd $G_2$ (91 mg, 0.14 mmol) in toluene (15 mL) and water (2 mL) was stirred at 100° C. for 16 h under $N_2$ atmosphere. The reaction was diluted with water (50 mL), and extracted with ethyl acetate (50 mL×3), the combined organic layers were dried over anhydrous sodium sulfate and concentrated under vacuum. The residue was purified by flash chromatography on silica gel (0-28% ethyl acetate in petroleum ether) to afford the title compound (50 mg, 11%) as a yellow solid. $^1$H NMR (400 MHz, DMSO-$d_6$): δ 8.67 (d, J=5.2 Hz, 1H), 8.54 (d, J=9.2 Hz, 2H), 8.16 (d, J=9.2 Hz, 2H), 7.58 (d, J=5.2 Hz, 1H), 7.44 (t, J=5.2 Hz, 1H), 4.71 (d, J=5.2 Hz, 2H), 1.42 (s, 9H).

Step 3: tert-butyl 01-(4-(pentafluoro-16-sulfanyl) phenyl)-4-vinyl-1H-pyrazolo[3,4-b]pyridin-3-yl) methyl)carbamate

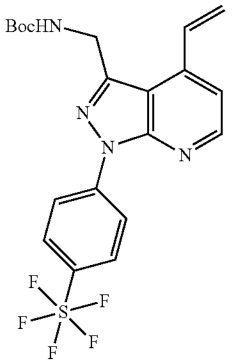 [SMILES: C=Cc1ccnc2c1c(CNC(=O)OC(C)(C)C)nn2-c1ccc(S(F)(F)(F)(F)F)cc1]

A mixture of Xphos Pd $G_2$ (8 mg, 0.01 mmol), Xphos (5 mg, 0.01 mmol), tert-butyl ((4-chloro-1-(4-(pentafluoro-16-sulfanyl)phenyl)-1H-pyrazolo[3,4-b]pyridin-3-yl)methyl) carbamate (50 mg, 0.10 mmol), 4,4,5,5-tetramethyl-2-vinyl-1,3,2-dioxaborolane (0.03 mL, 0.21 mmol) and KOAc (30 mg, 0.31 mmol) in 1,4-dioxane (5 mL) and water (0.5 mL) was stirred at 90° C. for 5 h under $N_2$ atmosphere. The mixture was added water (50 mL) and extracted with ethyl acetate (50 mL×3), the combined organic layers were washed with brine (50 mL). The organic layer was dried over anhydrous sodium sulfate and concentrated to dryness. The residue was purified by column chromatography on silica gel (0-10% ethyl acetate in petroleum ether) to afford the title compound (38 mg, 77%) as yellow solid. $^{1}H$ NMR (400 MHz, $CDCl_3$): δ 8.59 (d, J=5.2 Hz, 1H), 8.53 (d, J=8.8 Hz, 2H), 7.90 (d, J=9.2 Hz, 2H), 7.36 (d, J=4.8 Hz, 1H), 7.33-7.28 (m, 1H), 6.09 (d, J=17.2 Hz, 1H), 5.72 (d, J=11.2 Hz, 1H), 5.44-5.33 (m, 1H), 4.87 (d, J=5.2 Hz, 2H), 1.52 (s, 9H).

Step 4: tert-butyl ((4-formyl-1-(4-(pentafluoro-16-sulfanyl)phenyl)-1H-pyrazolo[3,4-b]pyridin-3-yl)methyl)carbamate

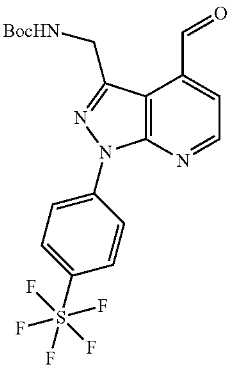 [SMILES: CC(C)(C)OC(=O)NCc1nn(-c2ccc(S(F)(F)(F)(F)F)cc2)c2nccc(C=O)c12]

To a solution of tert-butyl 41-(4-(pentafluoro-16-sulfanyl)phenyl)-4-vinyl-1H-pyrazolo[3,4-b]pyridin-3-yl)methyl) carbamate (38 mg, 0.08 mmol) in THF (6 mL) and water (2 mL) was added $K_2OsO_4 \cdot 2H_2O$ (3 mg, 0.008 mmol) and $NaIO_4$ (68 mg, 0.32 mmol) at 0° C., the reaction mixture was stirred at room temperature for 12 h. The reaction mixture was quenched with aq. $Na_2SO_3$ (5 mL) and diluted with water (30 mL). The resulting mixture was extracted with ethyl acetate (30 mL×3), the combined organic layers were dried over $Na_2SO_4$, filtered and concentrated to dryness. The residue was purified by prep-TLC (50% ethyl acetate in petroleum ether) to afford the title compound (21.0 mg, 55%) as a yellow solid. $^{1}H$ NMR (400 MHz, $CDCl_3$): δ 10.36 (s, 1H), 8.93 (d, J=4.4 Hz, 1H), 8.53 (d, J=8.8 Hz, 2H), 7.92 (d, J=8.8 Hz, 2H), 7.69 (d, J=4.4 Hz, 1H), 5.57-5.49 (m, 1H), 4.97 (d, J=5.2 Hz, 2H), 1.48 (s, 9H).

Step 5: tert-butyl 04-(hydroxymethyl)-1-(4-(pentafluoro-16-sulfanyl)phenyl)-1H-pyrazolo[3,4-b]pyridin-3-yl)methyl)carbamate

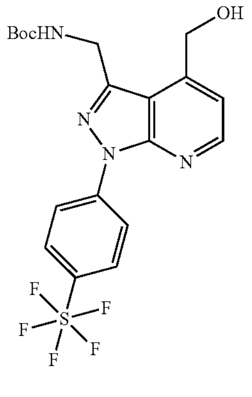

To a solution of ter t-butyl ((4-formyl-1-(4-(pentafluoro-16-sulfanyl)phenyl)-1H-pyrazolo[3,4-b]pyridin-3-yl)methyl)carbamate (21 mg, 0.04 mmol) in THF (2 mL) and MeOH (1 mL) was added and $NaBH_4$ (5 mg, 0.13 mmol) at 0° C., the reaction mixture was stirred at 0° C. for 2.5 h. The reaction mixture was quenched with sat. $NH_4Cl$ (20 mL). The resulting mixture was extracted with ethyl acetate (30 mL×3), the combined organic layers were dried over $Na_2SO_4$, filtered and concentrated to afford the title compound (21 mg, 99%) as a yellow solid. LCMS (ESI): m/z 481.1 $(M+H)^+$.

Step 6: (3-(aminomethyl)-1-(4-(pentafluoro-16-sulfanyl)phenyl)-1H-pyrazolo[3,4-b]pyridin-4-yl)methanol

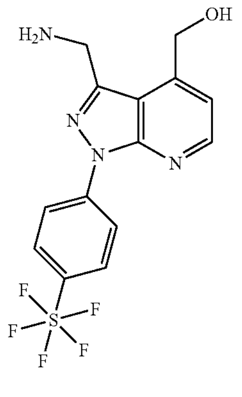 [SMILES: NCc1nn(-c2ccc(S(F)(F)(F)(F)F)cc2)c2nccc(CO)c12]

A solution of tert-butyl ((4-(hydroxymethyl)-1-(4-(pentafluoro-16-sulfanyl)phenyl)-1H-pyrazolo[3,4-b]pyridin-3-yl)methyl)carbamate (20 mg, 0.05 mmol) in TFA (5% in HFIP, 5 mL) was stirred at room temperature for 2 h. The reaction was diluted with water (30 mL) and adjusted to pH=8 with sat.$NaHCO_3$. The mixture was extracted with ethyl acetate (50 mL×3), the combined organic layers were dried over $Na_2SO_4$ and concentrated under vacuum to afford the title compound (16 mg, crude) as a brown oil. The crude was used for next step without further purification.

Step 7: N-((4-(hydroxymethyl)-1-(4-(pentafluoro-16-sulfanyl)phenyl)-1H-pyrazolo[3,4-b]pyridin-3-yl)methyl)acrylamide

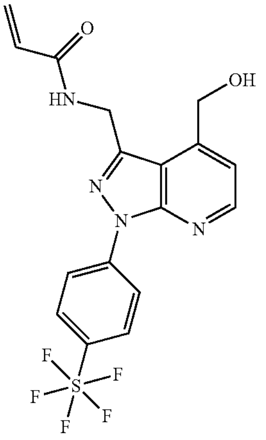 [SMILES: C=CC(=O)NCc1nn(-c2ccc(S(F)(F)(F)(F)F)cc2)c2nccc(CO)c12]

To a mixture of (3-(aminomethyl)-1-(4-(pentafluoro-16-sulfanyl)phenyl)-1H-pyrazolo[3,4-b]pyridin-4-yl)methanol (16.0 mg, 0.04 mmol) and sat. $NaHCO_3$ (1 mL) in THF (2 mL) was added acryloyl chloride (0.01 mL, 0.06 mmol) at 0° C. The solution was stirred at 0° C. for 1 h. The reaction was diluted with water (20 mL) and extracted with ethyl acetate (30 mL×3), the combined organic layers were dried over anhydrous sodium sulfate and concentrated under vacuum. The resulting residue was purified by reverse phase chromatography (welch xtimate C18 150*25 mm*5 um, water ($NH_4HCO_3$)-ACN, 40-70%) to afford the title compound (1.38 mg, 8%) as a white solid. $^1H$ NMR (400 MHz, DMSO-$d_6$): δ 8.75-8.67 (m, 2H), 8.60 (d, J=8.8 Hz, 2H), 8.13 (d, J=9.2 Hz, 2H), 7.49 (d, J=4.8 Hz, 1H), 6.31 (dd, J=17.2, 10.0 Hz, 1H), 6.16 (dd, J=17.2, 2.0 Hz, 1H), 5.85-5.71 (m, 1H), 5.66 (dd, J=10.0, 2.0 Hz, 1H), 4.99 (s, 2H), 4.82 (d, J=5.2 Hz, 2H); LCMS (ESI): m/z 435.0 $(M+H)^+$.

Example 56 (Compound 112)

1-(3-(4-(Hydroxymethyl)-1-(4-(trifluoromethoxy)phenyl)-1H-pyrazolo[3,4-b]pyridin-3-yl)azetidin-1-yl)prop-2-en-1-one

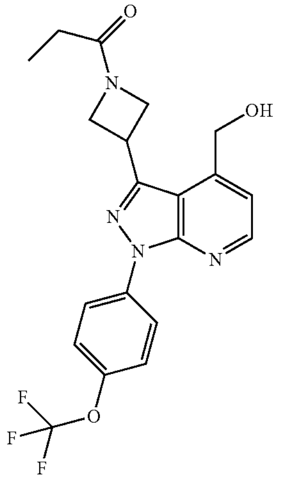 [SMILES: CCC(=O)N1CC(c2nn(-c3ccc(OC(F)(F)F)cc3)c3nccc(CO)c23)C1]

To a solution of (3-(azetidin-3-yl)-1-(4-(trifluoromethoxy)phenyl)-1H-pyrazolo[3,4-b]pyridin-4-yl)methanol 2,2,2-trifluoroacetate salt (120 mg, 0.25 mmol) and aq $NaHCO_3$ (2 mL) in THF (5 mL) was added acryloyl chloride (0.03 mL, 0.3800 mmol) at 0° C. The resulting mixture was stirred at 0° C. for 1 h. The mixture was diluted with ethyl acetate (100 mL) and washed with water (100 mL×3). The organic layer was dried over $Na_2SO_4$, filtered, and concentrated. The residue was purified by reverse phase chromatography (Welch Xtimate C18 150*30 mm*5 um, water (FA)-ACN, 50-80%) to afford the title compound (55.3 mg, 52%) as a white solid. $^1H$ NMR (400 MHz, DMSO-$d_6$): δ 8.64 (d, J=4.8 Hz, 1H), 8.44 (d, J=8.8 Hz, 2H), 7.58 (d, J=8.8 Hz, 2H), 7.41 (d, J=4.8 Hz, 1H), 6.39 (dd, J=17.2, 10.4 Hz, 1H), 6.14 (dd, J=17.2, 2.0 Hz, 1H), 5.74 (t, J=5.6 Hz, 1H), 5.70 (dd, J=10.4, 2.0 Hz, 1H), 4.90 (d, J=5.2 Hz, 2H), 4.73-4.67 (m, 1H), 4.67-4.60 (m, 1H), 4.55-4.45 (m, 1H), 4.43-4.30 (m, 2H); LCMS (ESI): m/z 419.0 $(M+H)^+$.

Example 57 (Compound 20)

2-Fluoro-1-(3-(4-(hydroxymethyl)-1-(4-(trifluoromethoxy)phenyl)-1H-pyrazolo[3,4-b]pyridin-3-yl)azetidin-1-yl)prop-2-en-1-one

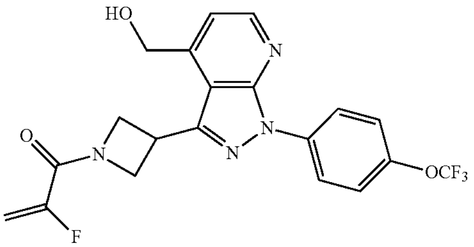 [SMILES: C=C(F)C(=O)N1CC(c2nn(-c3ccc(OC(F)(F)F)cc3)c3nccc(CO)c23)C1]

To a solution of (3-(azetidin-3-yl)-1-(4-(trifluoromethoxy)phenyl)-1H-pyrazolo[3,4-b]pyridin-4-yl)methanol (780 mg, 2.14 mmol) and EEDQ (794 mg, 3.21 mmol) in MeOH (2 mL) and DCM (10 mL) was added 2-fluoroacrylic acid (289 mg, 3.21 mmol) at 0° C. The mixture was stirred at room temperature for 16 h. The reaction mixture was quenched with $H_2O$ (20 mL), and extracted with ethyl acetate (20 mL×3), the combined organic layers were washed with water (20 mL×3), dried over $Na_2SO_4$, filtered, and concentrated under vacuum. The residue was purified by reverse phase chromatography (Welch Xtimate C18 150*30 mm*5 um, water (FA)-ACN, 45-75%) to afford the title compound (378.10 mg, 40%) as a white solid. $^1$H NMR (400 MHz, DMSO-$d_6$): δ 8.65 (d, J=4.8 Hz, 1H), 8.47 (d, J=9.2 Hz, 2H), 7.59 (d, J=8.4 Hz, 2H), 7.41 (d, J=4.8 Hz, 1H), 5.72 (t, J=5.6 Hz, 1H), 5.52 (dd, J=48.4, 3.6 Hz, 1H), 5.33 (dd, J=16.8, 3.6 Hz, 1H), 4.90 (d, J=5.6 Hz, 2H), 4.86-4.81 (m, 1H), 4.79-4.71 (m, 1H), 4.56-4.38 (m, 3H); LCMS (ESI): m/z 437.0 $(M+H)^+$.

Example 58 (Compound 22)

1-(3-(4-(Hydroxymethyl)-1-(4-(trifluoromethoxy)phenyl)-1H-pyrazolo[3,4-b]pyridin-3-yl)azetidin-1-yl)-2-methylprop-2-en-1-one

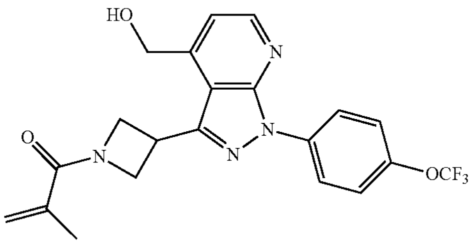 [SMILES: C=C(C)C(=O)N1CC(c2nn(-c3ccc(OC(F)(F)F)cc3)c3nccc(CO)c23)C1]

To a solution of (3-(azetidin-3-yl)-1-(4-(trifluoromethoxy)phenyl)-1H-pyrazolo[3,4-b]pyridin-4-yl)methanol (100 mg, 0.27 mmol) and sat. $NaHCO_3$ (1 mL) in THF (3 mL) was added methacryloyl chloride (0.03 mL, 0.27 mmol) at 0° C. The mixture was stirred at room temperature for 1 h. The reaction was diluted with water (40 mL) and extracted with ethyl acetate (30 mL×3). The organics were combined, washed with brine (30 mL×2), dried over sodium sulfate, filtered and concentrated. The resulting residue was purified by reverse phase chromatography (Welch Xtimate C18 150*30 mm*5 um, acetonitrile 51-81%/water (FA)-ACN) to afford the title compound (15 mg, 13%) as a white solid. $^1$H NMR (400 MHz, DMSO-$d_6$): δ 8.64 (d, J=4.4 Hz, 1H), 8.46 (d, J=8.4 Hz, 2H), 7.59 (d, J=8.4 Hz, 2H), 7.41 (d, J=4.4 Hz, 1H), 5.70 (t, J=5.6 Hz, 1H), 5.46 (s, 1H), 5.41 (s, 1H), 4.89 (d, J=5.6 Hz, 2H), 4.73-4.36 (m, 5H), 1.84 (s, 3H); LCMS (ESI): m/z 433.0 $(M+H)^+$.

Example 59 (Compound 40)

(E)-1-(3-(4-(Hydroxymethyl)-1-(4-(trifluoromethoxy)phenyl)-1H-pyrazolo[3,4-b]pyridin-3-yl)azetidin-1-yl)-4-methoxybut-2-en-1-one

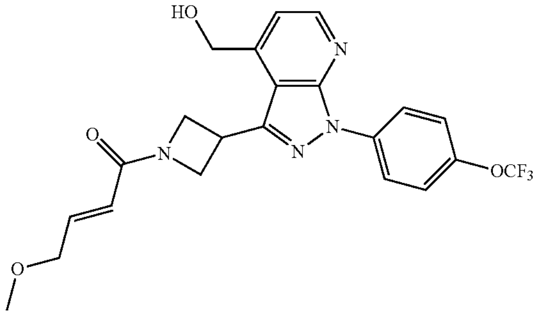 [SMILES: COC/C=C/C(=O)N1CC(c2nn(-c3ccc(OC(F)(F)F)cc3)c3nccc(CO)c23)C1]

To a solution of (3-(azetidin-3-yl)-1-(4-(trifluoromethoxy)phenyl)-1H-pyrazolo[3,4-b]pyridin-4-yl)methanol (100 mg, 0.3 mmol), (E)-4-methoxybut-2-enoic acid (51 mg, 0.44 mmol) in DCM (3 mL) and MeOH (1 mL) was added EEDQ (146 mg, 0.59 mmol) at 0° C. The mixture was stirred at room temperature for 16 h. The reaction mixture was quenched with water (10 mL). The solution was extracted with ethyl acetate (10 mL×3). The combined organic layers were washed with brine (30 mL×2), dried over sodium sulfate and concentrated under reduced pressure. The resulting residue was purified by reverse phase chromatography (Welch Xtimate C18 150*30 mm*5 um, acetonitrile 49-79%/water (FA)-ACN) to afford the title compound (16.3 mg, 13%) as a white solid. $^1$H NMR (400 MHz, DMSO-$d_6$): δ 8.65 (d, J=4.8 Hz, 1H), 8.46 (d, J=8.8 Hz, 2H), 7.58 (d, J=8.8 Hz, 2H), 7.41 (d, J=4.8 Hz, 1H), 6.70-6.65 (m, 1H), 6.20 (d, J=15.6 Hz, 1H), 5.72 (t, J=5.2 Hz, 1H), 4.90 (d, J=5.6 Hz, 2H), 4.75-4.57 (m, 2H), 4.53-4.26 (m, 3H), 4.07-4.05 (m, 2H), 3.29 (s, 3H); LCMS (ESI): m/z 463.0 $(M+H)^+$.

Example 60 (Compound 94)

(E)-4-Hydroxy-1-(3-(4-(hydroxymethyl)-1-(4-(trifluoromethoxy)phenyl)-1H-pyrazolo[3,4-b]pyridin-3-yl)azetidin-1-yl)but-2-en-1-one

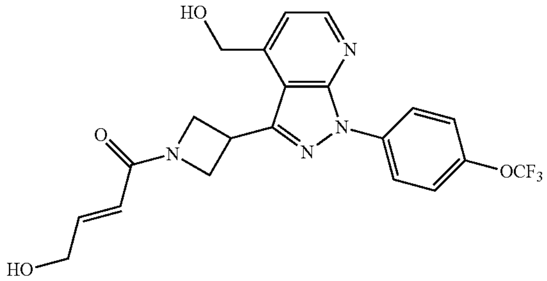 [SMILES: O=C(/C=C/CO)N1CC(c2nn(-c3ccc(OC(F)(F)F)cc3)c3nccc(CO)c23)C1]

To a mixture of (3-(azetidin-3-yl)-1-(4-(trifluoromethoxy)phenyl)-1H-pyrazolo[3,4-b]pyridin-4-yl)methanol (100 mg, 0.27 mmol),) and EEDQ (204 mg, 0.82 mmol) in DCM (3 mL) and MeOH (1 mL) at 0° C. was added (E)-4-hydroxybut-2-enoic acid (56 mg, 0.55 mmol). Then the reaction was stirred at room temperature for 16 h. The mixture was diluted with ethyl acetate (100 mL) and washed with water (100 mL×3). The organic was dried over $Na_2SO_4$, filtered, and concentrated. The residue was purified by reverse phase chromatography (Welch Xtimate C18 150*30 mm*5 um, water (0.2% FA)-ACN, 37-67%) to afford the title compound (58.9 mg, 47%) as a white solid. $^1$H NMR (400 MHz, DMSO-$d_6$): δ 8.65 (d, J=4.8 Hz, 1H), 8.44 (d, J=8.4 Hz, 2H), 7.58 (d, J=8.4 Hz, 2H), 7.41 (d, J=4.8 Hz, 1H), 6.76 (dt, J=17.2, 4.0 Hz, 1H), 6.20 (dt, J=17.2, 2.0 Hz, 1H), 5.72 (t, J=5.6 Hz, 1H), 5.05 (t, J=5.2 Hz, 1H), 4.90 (d, J=5.6 Hz, 2H), 4.71-4.59 (m, 2H), 4.54-4.44 (m, 1H), 4.42-4.29 (m, 2H), 4.17-4.08 (m, 2H); LCMS (ESI): m/z 449.1 $(M+H)^+$.

Example 61 & 62 (Compound 66 & 97)

(R,E)-4-Hydroxy-1-(3-(4-(hydroxymethyl)-1-(4-(trifluoromethoxy)phenyl)-1H-pyrazolo[3,4-b]pyridin-3-yl)azetidin-1-yl)pent-2-en-1-one & (S,E)-4-hydroxy-1-(3-(4-(hydroxymethyl)-1-(4-(trifluoromethoxy)phenyl)-1H-pyrazolo[3,4-b]pyridin-3-yl)azetidin-1-yl)pent-2-en-1-one

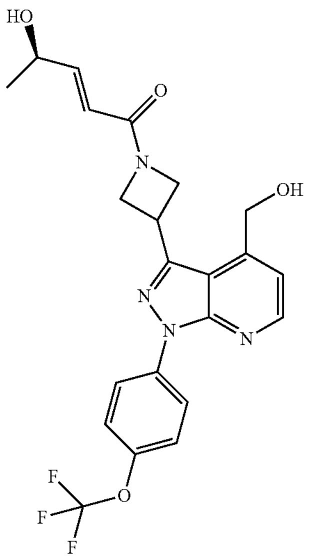

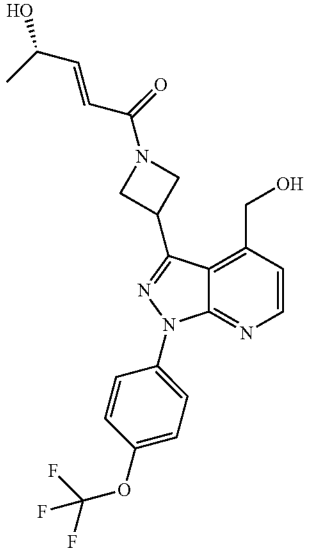

Step 1: (E)-methyl 4-hydroxypent-2-enoate

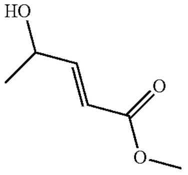

To a solution of (E)-methyl 4-oxopent-2-enoate (900 mg, 7.0 mmol) in MeOH (10 mL) was added $NaBH_4$ (80 mg, 2.1 mmol) at 0° C. The reaction solution was stirred at 0° C. for 1 h. The mixture was quenched with $NH_4Cl$ (30 mL). The solution was extracted with ethyl acetate (100 mL) and washed with water (30 mL×3). The organic was dried over $Na_2SO_4$, filtered, and concentrated. The residue was purified by column chromatography on silica gel (0-15% ethyl acetate in petroleum ether) to afford the title compound (850 mg, 93%) as a colorless oil. $^1$H NMR (400 MHz, DMSO-$d_6$): δ 6.89 (dd, J=15.6, 4.4 Hz, 1H), 5.93 (dd, J=15.6, 1.6 Hz, 1H), 5.11 (d, J=4.4 Hz, 1H), 4.33-4.30 (m, 1H), 3.65 (s, 3H), 1.16 (d, J=6.8 Hz, 3H).

Step 2: (E)-4-hydroxypent-2-enoic acid

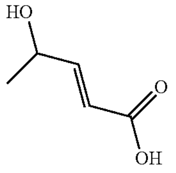

To a solution of (E)-methyl 4-hydroxypent-2-enoate (400 mg, 3.1 mmol) in THF (5 mL), MeOH (5 mL) and water (3 mL) was added lithium hydroxide monohydrate (516 mg, 12.3 mmol) at room temperature. The resulting mixture was stirred at room temperature for 16 h. The reaction was concentrated to dryness and the residue was acidified by 1 M HCl to pH=5. The resulting solution was extracted with ethyl acetate (100 mL×3). The combined organic layers were dried over $Na_2SO_4$, filtered, and concentrated to dryness to afford the title compound (350 mg, 98%) as a colorless oil. $^1$H NMR (400 MHz, DMSO-$d_6$): δ 12.15 (s, 1H), 6.80 (dd, J=15.6, 4.4 Hz, 1H), 5.84 (dd, J=15.6, 1.6 Hz, 1H), 5.05 (s, 1H), 4.36-4.26 (m, 1H), 1.16 (d, J=6.8 Hz, 3H).

Step 3: (E)-4-hydroxy-1-(3-(4-(hydroxymethyl)-1-(4-(trifluoromethoxy)phenyl)-1H-pyrazolo[3,4-b]pyridin-3-yl)azetidin-1-yl)pent-2-en-1-one

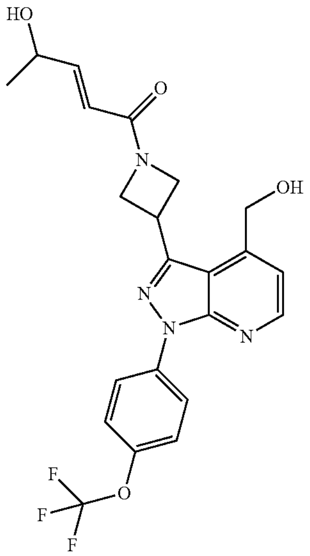 [SMILES: CC(O)/C=C/C(=O)N1CC(c2nn(-c3ccc(OC(F)(F)F)cc3)c3nccc(CO)c23)C1]

To a mixture of (E)-4-hydroxypent-2-enoic acid (95 mg, 0.82 mmol) in DMF (3 mL) was added DIEA (0.17 mL, 1.04 mmol) and HATU (238 mg, 0.63 mmol) at room temperature. The solution was stirred at room temperature for 5 min. Then (3-(azetidin-3-yl)-1-(4-(trifluoromethoxy)phenyl)-1H-pyrazolo[3,4-b]pyridin-4-yl)methanol (190 mg, 0.52 mmol) in DMF (1 mL) was added into it. The solution was stirred at room temperature for 3 h. The reaction mixture was diluted with water (100 mL) and extracted with ethyl acetate (30 mL×2). The organic layer was washed with brine (30 mL×2), dried over $Na_2SO_4$, filtered, and concentrated in vacuo. The residue was purified by column chromatography on silica gel (0-8% MeOH in DCM) to afford the title compound (180 mg, 74%) as a white solid. LCMS (ESI): m/z 462.8 $(M+H)^+$.

Step 4: (R,E)-4-hydroxy-1-(3-(4-(hydroxymethyl)-1-(4-(trifluoromethoxy)phenyl)-1H-pyrazolo[3,4-b]pyridin-3-yl)azetidin-1-yl)pent-2-en-1-one & (S,E)-4-hydroxy-1-(3-(4-(hydroxymethyl)-1-(4-(trifluoromethoxy)phenyl)-1H-pyrazolo[3,4-b]pyridin-3-yl)azetidin-1-yl)pent-2-en-1-one

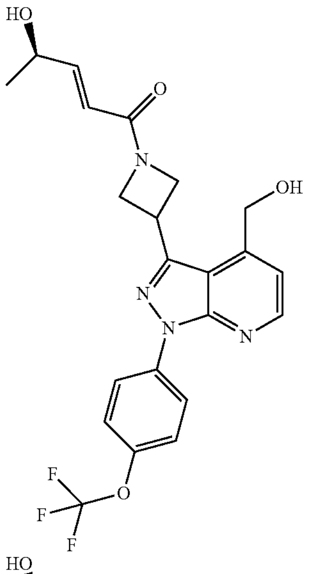

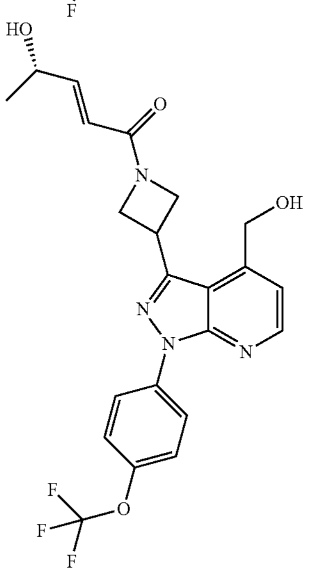

(E)-4-hydroxy-1-(3-(4-(hydroxymethyl)-1-(4-(trifluoromethoxy)phenyl)-1H-pyrazolo[3,4-b]pyridin-3-yl)azetidin-1-yl)pent-2-en-1-one (180 mg, 0.39 mmol) was separated by Chiral SFC (Instrument: SFC-13; Column: Phenomenex-Cellulose-2 (250 mm*30 mm, 10 um); Condition: Neu-EtOH; Begin B: 35%; Flow Rate (mL/min): 80) to afford the first peak, compound 66 (49.0 mg, 26%) and the second peak, compound 97 (63.0 mg, 34%) both as a white solid.

The first peak: $^1H$ NMR (400 MHz, DMSO-$d_6$): δ 8.64 (d, J=4.8 Hz, 1H), 8.45 (d, J=8.8 Hz, 2H), 7.58 (d, J=8.8 Hz, 2H), 7.41 (d, J=4.8 Hz, 1H), 6.69 (dd, J=15.2, 4.4 Hz, 1H), 6.13 (dd, J=15.2, 1.6 Hz, 1H), 5.71 (s, 1H), 5.02 (s, 1H), 4.90 (s, 2H), 4.73-4.58 (m, 2H), 4.53-4.43 (m, 1H), 4.42-4.25 (m, 3H), 1.17 (d, J=6.8 Hz, 3H); LCMS (ESI): m/z 463.0 $(M+H)^+$.

The first peak: $^1$H NMR (400 MHz, DMSO-$d_6$): δ 8.64 (d, J=4.8 Hz, 1H), 8.45 (d, J=8.8 Hz, 2H), 7.58 (d, J=8.8 Hz, 2H), 7.41 (d, J=4.8 Hz, 1H), 6.69 (dd, J=15.2, 4.4 Hz, 1H), 6.13 (dd, J=15.2, 1.6 Hz, 1H), 5.71 (s, 1H), 5.02 (s, 1H), 4.90 (s, 2H), 4.73-4.58 (m, 2H), 4.53-4.43 (m, 1H), 4.42-4.25 (m, 3H), 1.17 (d, J=6.8 Hz, 3H); LCMS (ESI): m/z 463.0 $(M+H)^+$.

Example 63 (Compound 120)

(E)-1-(3-(4-(Hydroxymethyl)-1-(4-(trifluoromethoxy)phenyl)-1H-pyrazolo[3,4-b]pyridin-3-yl)azetidin-1-yl)but-2-en-1-one

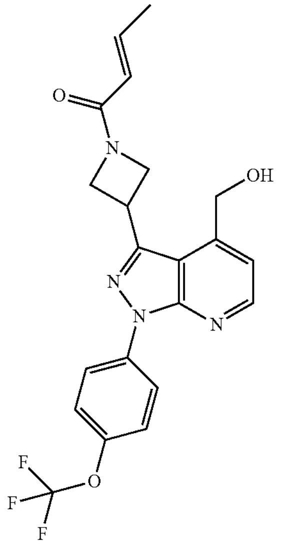 [SMILES: C/C=C/C(=O)N1CC(c2nn(-c3ccc(OC(F)(F)F)cc3)c3nccc(CO)c23)C1]

To a mixture of (3-(azetidin-3-yl)-1-(4-(trifluoromethoxy)phenyl)-1H-pyrazolo[3,4-b]pyridin-4-yl)methanol (100 mg, 0.27 mmol) and sat. $NaHCO_3$ (2 mL) in THF (5 mL) was added (E)-but-2-enoyl chloride (29.0 mg, 0.27 mmol) at 0° C. The mixture was stirred at 0° C. for 1 h. The reaction was quenched with water (50 mL) and extracted with ethyl acetate (50 mL×3). The combined organic layers were dried over sodium sulfate and concentrated under reduced pressure. After filtration, the filtrate was concentrated. The residue was purified by reverse phase chromatography (Welch Xtimate C18 150*30 mm*5 um, acetonitrile 44-74%/water (FA)-ACN) to afford the title compound (53 mg, 45%) as a white solid. $^1$H NMR (400 MHz, DMSO-$d_6$): δ 8.45 (d, J=4.8 Hz, 1H), 8.44 (d, J=8.8 Hz, 2H), 7.57 (d, J=8.8 Hz, 2H), 7.41 (d, J=4.8 Hz, 1H), 6.75-6.59 (m, 1H), 6.12-6.02 (m, 1H), 5.71 (t, J=5.2 Hz, 1H), 4.90 (d, J=5.2 Hz, 2H), 4.72-4.26 (m, 5H), 1.84 (d, J=8.4 Hz, 3H); LCMS (ESI): m/z 433.0 $(M+H)^+$.

Example 64 Compound 102

(E)-3-Chloro-1-(3-(4-(hydroxymethyl)-1-(4-(trifluoromethoxy)phenyl)-1H-pyrazolo[3,4-b]pyridin-3-yl)azetidin-1-yl)prop-2-en-1-one

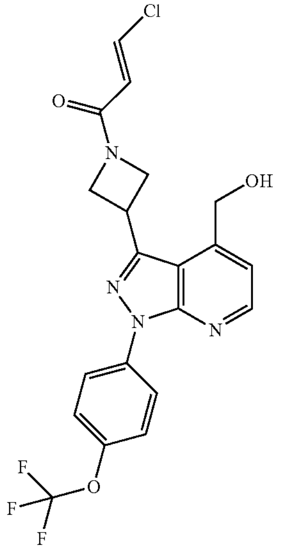 [SMILES: O=C(/C=C/Cl)N1CC(c2nn(-c3ccc(OC(F)(F)F)cc3)c3nccc(CO)c23)C1]

To a solution of (3-(azetidin-3-yl)-1-(4-(trifluoromethoxy)phenyl)-1H-pyrazolo[3,4-b]pyridin-4-yl)methanol (110 mg, 0.30 mmol), (E)-3-chloroacrylic acid (48.0 mg, 0.45 mmol) in DCM (8.0 mL) was added EEDQ (149 mg, 0.60 mmol) at room temperature. The resulting solution was stirred for 16 h at room temperature. The reaction was quenched with water (50 mL) and extracted with ethyl acetate (50 mL×3). The combined organic layers were dried over sodium sulfate and concentrated under reduced pressure. The residue was purified by reverse phase chromatography (Welch Xtimate C18 150*30 mm*5 um, acetonitrile 51-81%/water (FA)-ACN) to afford the title compound (31.0 mg, 23%) as a white solid. $^1$H NMR (400 MHz, DMSO-d6): δ 8.65 (d, J=4.8 Hz, 1H), 8.46 (d, J=8.8 Hz, 2H), 7.60 (d, J=8.8 Hz, 2H), 7.42 (d, J=4.8 Hz, 1H), 7.27 (s, 1H), 6.70-6.60 (m, 1H), 5.76-5.68 (m, 1H), 4.90 (d, J=5.2 Hz, 2H), 4.76-4.29 (m, 5H); LCMS (ESI): m/z 452.9 $(M+H)^+$.

Example 65 Compound 89

Cyclobut-1-en-1-yl(3-(4-(hydroxymethyl)-1-(4-(trifluoromethoxy)phenyl)-1H-pyrazolo[3,4-b]pyridin-3-yl)azetidin-1-yl)methanone

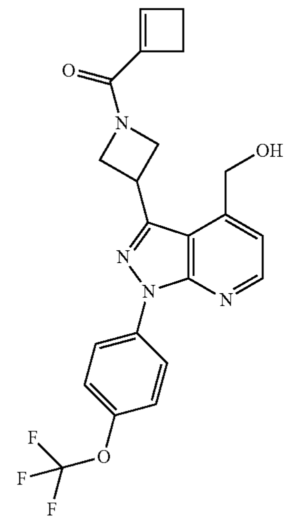 [SMILES: O=C(C1=CCC1)N1CC(c2nn(-c3ccc(OC(F)(F)F)cc3)c3nccc(CO)c23)C1]

A mixture of (3-(azetidin-3-yl)-1-(4-(trifluoromethoxy)phenyl)-1H-pyrazolo[3,4-b]pyridin-4-yl)methanol (150 mg, 0.41 mmol), EEDQ (153 mg, 0.62 mmol) and cyclobut-1-ene-1-carboxylic acid (61.0 mg, 0.62 mmol) in DCM (1.5 mL) and MeOH (0.3 mL) was stirred at room temperature for 16 h. The reaction mixture was quenched with $H_2O$ (10 mL) and extracted with ethyl acetate (10 mL×3), the combined organic layers were washed with water (10 mL×3), dried over $Na_2SO_4$, filtered, and concentrated to dryness. The residue was purified by reverse phase chromatography (Welch Xtimate C18 150*30 mm*5 um, water (FA)-ACN, 48%-78%) to afford the title compound (63.0 mg, 34.0%) as a white solid. $^1H$ NMR (400 MHz, DMSO-$d_6$): 8.64 (d, J=4.8 Hz, 1H), 8.45 (d, J=9.2 Hz, 2H), 7.59 (d, J=8.8 Hz, 2H), 7.41 (d, J=4.8 Hz, 1H), 6.54 (s, 1H), 5.72 (t, J=4.8 Hz, 1H), 4.90 (d, J=4.0 Hz, 2H), 4.76-4.75 (m, 1H), 4.72-4.62 (m, 1H), 4.58-4.47 (m, 1H), 4.43-4.32 (m, 2H), 2.67-2.65 (m, 2H), 2.44-2.40 (m, 2H); LCMS (ESI): m/z 445.0 $(M+H)^+$.

Example 66 & 67 (Compound 113 & 114)

(S)-1-(3-(4-(1,2-Dihydroxyethyl)-1-(4-(trifluoromethoxy)phenyl)-1H-pyrazolo[3,4-b]pyridin-3-yl)azetidin-1-yl)prop-2-en-1-one & (R)-1-(3-(4-(1,2-Dihydroxyethyl)-1-(4-(trifluoromethoxy)phenyl)-1H-pyrazolo[3,4-b]pyridin-3-yl)azetidin-1-yl)prop-2-en-1-one

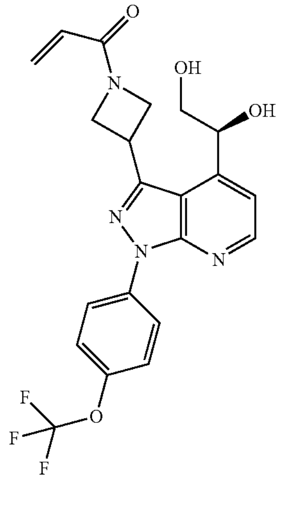

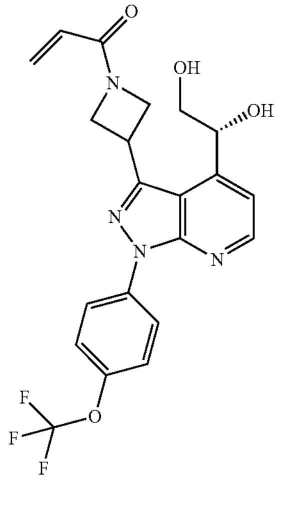

Step 1: 1-(3-(4-(1,2-dihydroxyethyl)-1-(4-(trifluoromethoxy)phenyl)-1H-pyrazolo[3,4-b]pyridin-3-yl)azetidin-1-yl)prop-2-en-1-one

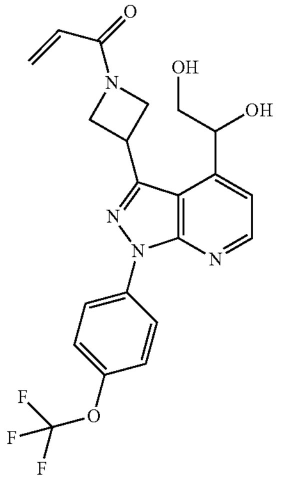

To a solution of 1-(3-(azetidin-3-yl)-1-(4-(trifluoromethoxy)phenyl)-1H-pyrazolo[3,4-b]pyridin-4-yl)ethane-1,2-diol (200 mg, 0.51 mmol) and saturated $NaHCO_3$ (3 mL) in THF (3 mL) was added acrylic anhydride (0.14 mL, 1.22 mmol) at 0° C. The solution was stirred at 0° C. for 2 h. The mixture was quenched with water (30 mL) and extracted with ethyl acetate (60 mL×3) and washed with brine (60 mL). The organic layers were dried over anhydrous sodium sulfate, filtered, and concentrated under reduced. The residue was purified by reverse phase chromatography (Boston Green ODS 150*30 mm*5 um, acetonitrile 40-70%/water (FA)-ACN) to afford the title compound (100 mg, 46%). LCMS (ESI): m/z 449 $(M+H)^+$.

Step 2: (S)-1-(3-(4-(1,2-Dihy dr oxy ethyl)-1-(4-(trifluoromethoxy)phenyl)-1H-pyrazolo[3,4-b]pyridin-3-yl)azetidin-1-yl)prop-2-en-1-one & (R)-1-(3-(4-(1,2-dihydroxyethyl)-1-(4-(trifluoromethoxy) phenyl)-1H-pyrazolo[3,4-b]pyridin-3-yl)azetidin-1-yl)prop-2-en-1-one

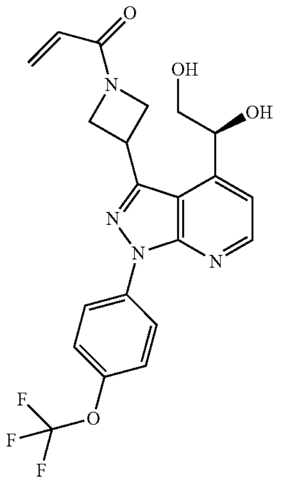

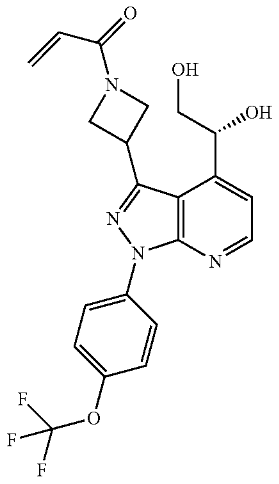 [SMILES: C=CC(=O)N1CC(c2nn(-c3ccc(OC(F)(F)F)cc3)c3nccc(C(O)CO)c23)C1]

1-(3-(4-(1,2-Dihydroxyethyl)-1-(4-(trifluoromethoxy) phenyl)-1H-pyrazolo[3,4-b]pyridin-3-yl)azetidin-1-yl)prop-2-en-1-one (100 mg, 0.23 mmol) was separated by Chiral SFC (Instrument: SFC—22; Column: DAICEL CHIRALPAK AD (250 mm*30 mm, 10 um); Condition: 0.1% $NH_3H_2O$ IPA; Flow Rate (mL/min): 60) to afford the first peak, compound 113 (38.0 mg, 38%) and the second peak, compound 114 (38.1 mg, 38%) both as a white solid.

The first peak: $^1H$ NMR (400 MHz, DMSO-$d_6$): δ 8.64 (d, J=4.8 Hz, 1H), 8.45 (d, J=8.8 Hz, 2H), 7.59 (d, J=8.8 Hz, 2H), 7.44 (d, J=4.8 Hz, 1H), 6.45-6.35 (m, 1H), 6.14 (dd, J=17.2, 2.0 Hz, 1H), 5.83 (d, J=4.4 Hz, 1H), 5.71 (dt, J=10.4, 2.0 Hz, 1H), 5.06-4.99 (m, 2H), 4.72-4.57 (m, 3H), 4.45-4.28 (m, 2H), 3.64-3.52 (m, 2H); LCMS (ESI): m/z 449 $(M+H)^+$.

The second peak: $^1H$ NMR (400 MHz, DMSO-$d_6$): δ 8.64 (d, J=4.8 Hz, 1H), 8.45 (d, J=8.8 Hz, 2H), 7.59 (d, J=8.8 Hz, 2H), 7.44 (d, J=4.8 Hz, 1H), 6.45-6.35 (m, 1H), 6.14 (dd, J=17.2, 2.0 Hz, 1H), 5.84 (d, J=4.4 Hz, 1H), 5.71 (dt, J=10.4, 2.0 Hz, 1H), 5.06-4.99 (m, 2H), 4.72-4.57 (m, 3H), 4.45-4.28 (m, 2H), 3.64-3.52 (m, 2H); LCMS (ESI): m/z 449 $(M+H)^+$.

Example 68 & 69 (Compound 31 & 21)

(S)-1-(3-(4-(1,2-Dihy dr oxy ethyl)-1-(4-(trifluoromethoxy)phenyl)-1H-pyrazolo[3,4-b]pyridin-3-yl) azetidin-1-yl)-2-fluoroprop-2-en-1-one & (R)-1-(3-(4-(1,2-dihydroxyethyl)-1-(4-(trifluoromethoxy) phenyl)-1H-pyrazolo[3,4-b]pyridin-3-yl)azetidin-1-yl)-2-fluoroprop-2-en-1-one

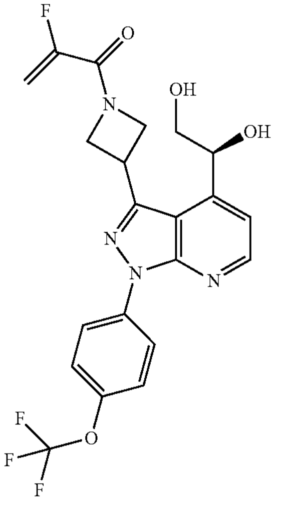

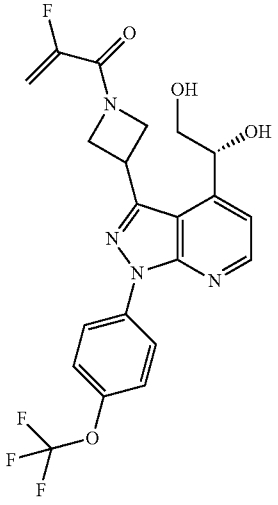

Step 1: 1-(3-(4-(1,2-dihydroxyethyl)-1-(4-(trifluoromethoxy)phenyl)-1H-pyrazolo[3,4-b]pyridin-3-yl) azetidin-1-yl)-2-fluoroprop-2-en-1-one

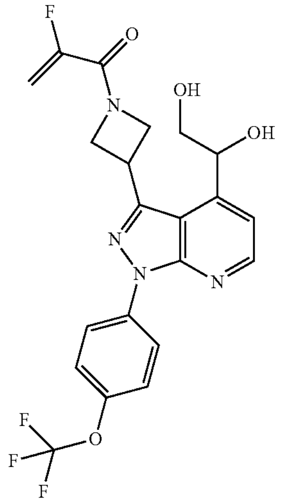

To a mixture of 1-(3-(azetidin-3-yl)-1-(4-(trifluoromethoxy)phenyl)-1H-pyrazolo[3,4-b]pyridin-4-yl)ethane-1,2-diol (150 mg, 0.38 mmol) and EEDQ (141 mg, 0.57 mmol) in DCM (5 mL) and MeOH (1 mL) was added 2-fluoroacrylic acid (51 mg, 0.57 mmol) at 0° C. Then the reaction was stirred at room temperature for 16 h. The mixture was diluted with ethyl acetate (100 mL) and washed with water (100 mL×3). The organic was dried over $Na_2SO_4$, filtered, and concentrated. The residue was purified by reverse phase chromatography (Welch Xtimate C18 150*30 mm*5 um, water (0.2% FA)-ACN, 42-72%) to afford the title compound (50 mg, 28%) as a white solid. LCMS (ESI): m/z 467.0 $(M+H)^+$.

Step 2: (S)-1-(3-(4-(1,2-dihydroxyethyl)-1-(4-(trifluoromethoxy)phenyl)-1H-pyrazolo[3,4-b]pyridin-3-yl)azetidin-1-yl)-2-fluoroprop-2-en-1-one & (R)-1-(3-(4-(1,2-dihydroxyethyl)-1-(4-(trifluoromethoxy)phenyl)-1H-pyrazolo[3,4-b]pyridin-3-yl)azetidin-1-yl)-2-fluoroprop-2-en-1-one

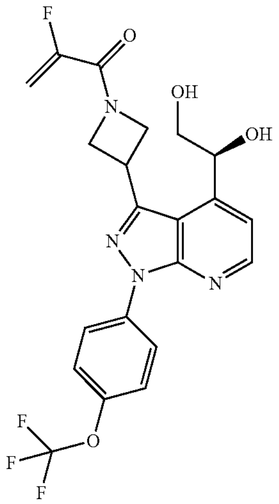

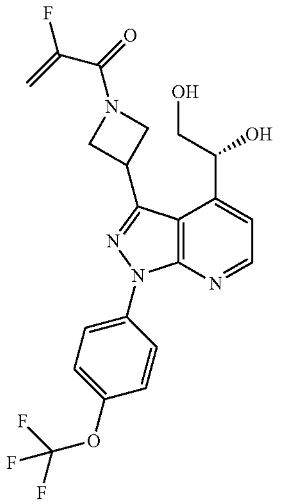

1-(3-(4-(1,2-dihydroxyethyl)-1-(4-(trifluoromethoxy)phenyl)-1H-pyrazolo[3,4-b]pyridin-3-yl)azetidin-1-yl)-2-fluoroprop-2-en-1-one (50 mg, 0.11 mmol) was separated by Chiral SFC (DAICEL CHIRALPAK AD (250 mm*30 mm, 10 urn), 0.1% $NH_3H_2O$ EtOH, 20-20%) to afford the first peak, compound 31 (16.6 mg, 33%) and the second peak, compound 21 (21.2 mg, 42%) as a white solid.

The first peak: $^1H$ NMR (400 MHz, DMSO-$d_6$): δ 8.64 (d, J=4.8 Hz, 1H), 8.45 (d, J=8.8 Hz, 2H), 7.59 (d, J=8.8 Hz, 2H), 7.43 (d, J=4.8 Hz, 1H), 5.83 (d, J=4.0 Hz, 1H), 5.51 (dd, J=48.4, 3.2 Hz, 1H), 5.33 (dd, J=16.4, 3.2 Hz, 1H), 5.05-4.95 (m, 2H), 4.89-4.72 (m, 2H), 4.70-4.61 (m, 1H), 4.51-4.36 (m, 2H), 3.66-3.50 (m, 2H); LCMS (ESI): m/z 467.0 $(M+H)^+$.

The second peak: $^1H$ NMR (400 MHz, DMSO-$d_6$): δ 8.64 (d, J=4.8 Hz, 1H), 8.45 (d, J=8.8 Hz, 2H), 7.59 (d, J=8.8 Hz, 2H), 7.43 (d, J=4.8 Hz, 1H), 5.83 (d, J=4.0 Hz, 1H), 5.51 (dd, J=48.4, 3.2 Hz, 1H), 5.33 (dd, J=16.4, 3.2 Hz, 1H), 5.05-4.95 (m, 2H), 4.89-4.72 (m, 2H), 4.70-4.61 (m, 1H), 4.51-4.36 (m, 2H), 3.66-3.50 (m, 2H); LCMS (ESI): m/z 467.0 $(M+H)^+$.

Example 70 & 71 (Compound 108 & 95)

(S,E)-1-(3-(4-(1,2-Dihydroxyethyl)-1-(4-(trifluoromethoxy)phenyl)-1H-pyrazolo[3,4-b]pyridin-3-yl)azetidin-1-yl)-4-hydroxybut-2-en-1-one & (R,E)-1-(3-(4-(1,2-dihydroxyethyl)-1-(4-(trifluoromethoxy)phenyl)-1H-pyrazolo[3,4-b]pyridin-3-yl)azetidin-1-yl)-4-hydroxybut-2-en-1-one

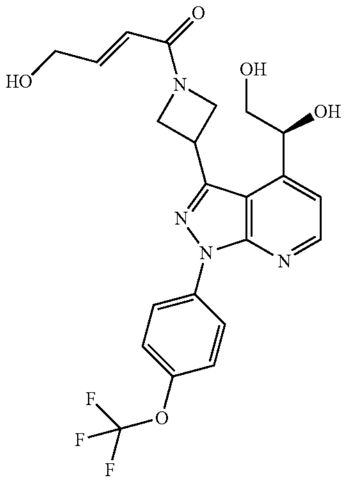

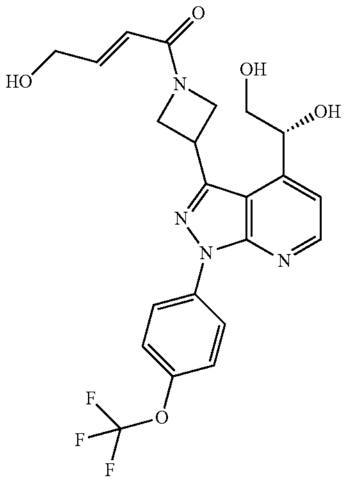

Step 1: (E)-1-(3-(4-(1,2-dihydroxyethyl)-1-(4-(trifluoromethoxy)phenyl)-1H-pyrazolo[3,4-b]pyridin-3-yl)azetidin-1-yl)-4-hydroxybut-2-en-1-one

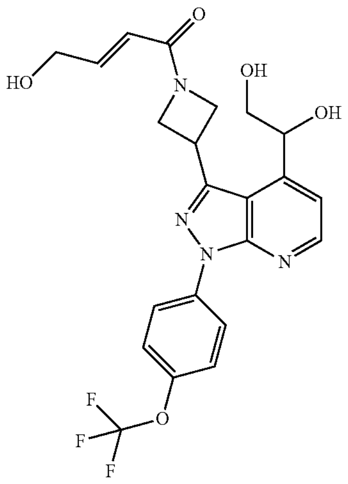 [SMILES: O=C(/C=C/CO)N1CC(c2nn(-c3ccc(OC(F)(F)F)cc3)c3nccc(C(O)CO)c23)C1]

To a mixture of 1-(3-(azetidin-3-yl)-1-(4-(trifluoromethoxy)phenyl)-1H-pyrazolo[3,4-b]pyridin-4-yl)ethane-1,2-diol (150 mg, 0.38 mmol) and EEDQ (283 mg, 1.14 mmol) in DCM (5 mL) and MeOH (1 mL) was added (E)-4-hydroxybut-2-enoic acid (78 mg, 0.76 mmol) at 0° C. The reaction was stirred at room temperature for 16 h. The mixture was diluted with ethyl acetate (100 mL) and washed with water (100 mL×3). The organic was dried over $Na_2SO_4$, filtered, and concentrated. The residue was purified by reverse phase chromatography (Welch Xtimate C18 150*30 mm*5 um, water (0.2% FA)-ACN, 34-64%) to afford the title compound (40 mg, 22%) as a white solid. LCMS (ESI): m/z 479.0 $(M+H)^+$.

Step 2: (S,E)-1-(3-(4-(1,2-dihydroxyethyl)-1-(4-(trifluoromethoxy)phenyl)-1H-pyrazolo[3,4-b]pyridin-3-yl)azetidin-1-yl)-4-hydroxybut-2-en-1-one & (R,E)-1-(3-(4-(1,2-dihydroxyethyl)-1-(4-(trifluoromethoxy)phenyl)-1H-pyrazolo[3,4-b]pyridin-3-yl)azetidin-1-yl)-4-hydroxybut-2-en-1-one

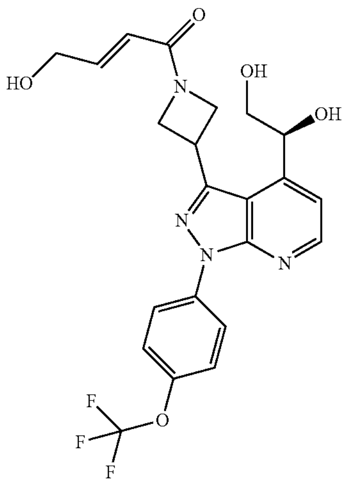

-continued

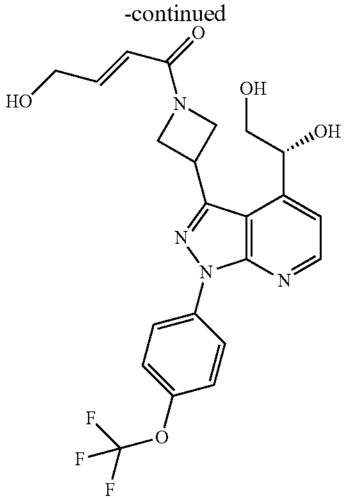

(E)-1-(3-(4-(1,2-Dihydroxyethyl)-1-(4-(trifluoromethoxy)phenyl)-1H-pyrazolo[3,4-b]pyridin-3-yl)azetidin-1-yl)-4-hydroxybut-2-en-1-one (40 mg, 0.08 mmol) was separated by Chiral SFC (DAICEL CHIRALPAK AD (250 mm*30 mm, 10 um), Neu-IPA, 25-25%) to afford the first peak, compound 108 (7.7 mg, 19%) and the second peak, compound 95 (8.8 mg, 22%) as a white solid.

The first peak: $^1$H NMR (400 MHz, DMSO-$d_6$): δ 8.64 (d, J=4.8 Hz, 1H), 8.45 (d, J=8.8 Hz, 2H), 7.59 (d, J=8.8 Hz, 2H), 7.44 (d, J=4.8 Hz, 1H), 6.82-6.73 (m, 1H), 6.21 (d, J=15.2 Hz, 1H), 5.83 (d, J=4.0 Hz, 1H), 5.09-4.99 (m, 3H), 4.70-4.55 (m, 3H), 4.44-4.24 (m, 2H), 4.17-4.12 (m, 2H), 3.65-3.51 (m, 2H); LCMS (ESI): m/z 479.0 $(M+H)^+$.

The second peak: $^1$H NMR (400 MHz, DMSO-$d_6$): δ 8.64 (d, J=4.8 Hz, 1H), 8.45 (d, J=8.8 Hz, 2H), 7.59 (d, J=8.8 Hz, 2H), 7.44 (d, J=4.8 Hz, 1H), 6.82-6.73 (m, 1H), 6.21 (d, J=15.2 Hz, 1H), 5.83 (d, J=4.0 Hz, 1H), 5.09-4.99 (m, 3H), 4.71-4.54 (m, 3H), 4.44-4.25 (m, 2H), 4.17-4.12 (m, 2H), 3.64-3.51 (m, 2H); LCMS (ESI): m/z 479.0 $(M+H)^+$.

Example 72 & 73 (Compound 109 & 110)

(S)-2-Chloro-1-(3-(4-(1,2-dihydroxyethyl)-1-(4-(trifluoromethoxy)phenyl)-1H-pyrazolo[3,4-b]pyridin-3-yl)azetidin-1-yl)prop-2-en-1-one & (R)-2-chloro-1-(3-(4-(1,2-dihydroxyethyl)-1-(4-(trifluoromethoxy)phenyl)-1H-pyrazolo[3,4-b]pyridin-3-yl)azetidin-1-yl)prop-2-en-1-one

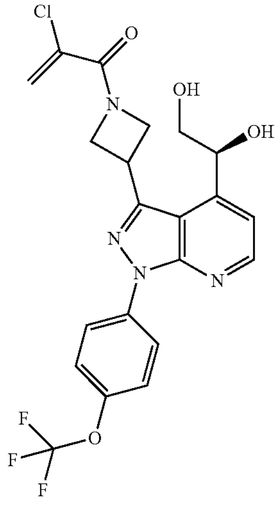

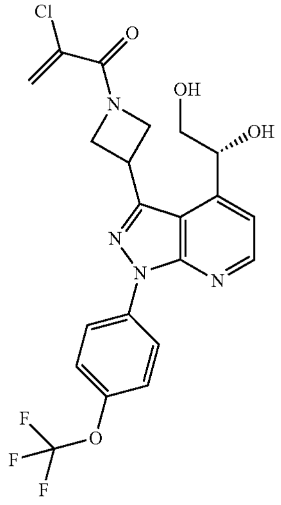

Step 1: 2-chloro-1-(3-(4-(1,2-dihydroxyethyl)-1-(4-(trifluoromethoxy)phenyl)-1H-pyrazolo[3,4-b]pyridin-3-yl)azetidin-1-yl)prop-2-en-1-one

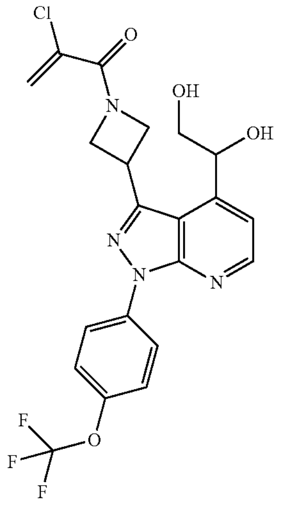

To a mixture of 1-(3-(azetidin-3-yl)-1-(4-(trifluoromethoxy)phenyl)-1H-pyrazolo[3,4-b]pyridin-4-yl)ethane-1,2-diol (110 mg, 0.28 mmol) and EEDQ (103 mg, 0.42 mmol) in DCM (5 mL) and MeOH (1 mL) was added 2-chloroacrylic acid (39 mg, 0.28 mmol) 0° C. The reaction was stirred at room temperature for 16 h. The mixture was diluted with ethyl acetate (100 mL) and washed with water (100 mL×3). The organic was dried over $Na_2SO_4$, filtered, and concentrated. The residue was purified by reverse phase chromatography (Welch Xtimate C18 150*30 mm*5 um, water (0.2% FA)-ACN, 43-73%) to afford the title compound (50 mg, 37%) as a white solid. LCMS (ESI): m/z 483.0 $(M+H)^+$.

Step 2: (S)-2-chloro-1-(3-(4-(1,2-dihydroxyethyl)-1-(4-(trifluoromethoxy)phenyl)-1H-pyrazolo[3,4-b]pyridin-3-yl)azetidin-1-yl)prop-2-en-1-one& (R)-2-chloro-1-(3-(4-(1,2-dihydroxyethyl)-1-(4-(trifluoromethoxy)phenyl)-1H-pyrazolo[3,4-b]pyridin-3-yl)azetidin-1-yl)prop-2-en-1-one

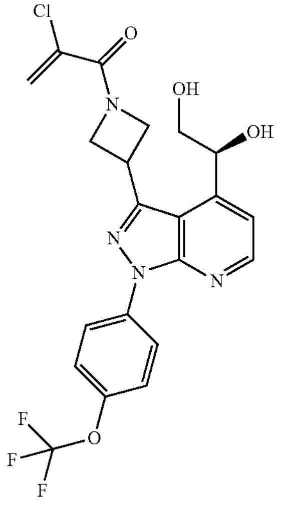

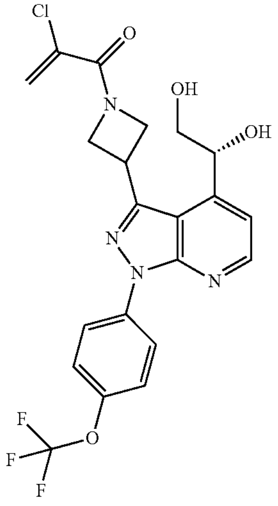 [SMILES: C=C(Cl)C(=O)N1CC(c2nn(-c3ccc(OC(F)(F)F)cc3)c3nccc(C(O)CO)c23)C1]

2-Chloro-1-(3-(4-(1,2-dihydroxyethyl)-1-(4-(trifluoromethoxy)phenyl)-1H-pyrazolo[3,4-b]pyridin-3-yl)azetidin-1-yl)prop-2-en-1-one (50 mg, 0.10 mmol) was separated by Chiral SFC (DAICEL CHIRALPAK AD (250 mm*30 mm, 10 urn), 0.1% $NH_3H_2O$ EtOH, 20-20%) to afford the first peak, compound 109 (23.1 mg, 42%) and the second peak, compound 110 (17.5 mg, 35%) as a white solid.

The first peak: $^1H$ NMR (400 MHz, DMSO-$d_6$): δ 8.64 (d, J=4.8 Hz, 1H), 8.46 (d, J=8.8 Hz, 2H), 7.59 (d, J=8.4 Hz, 2H), 7.43 (d, J=4.8 Hz, 1H), 6.13 (d, J=2.4 Hz, 1H), 6.00 (s, 1H), 5.83 (s, 1H), 5.05-4.95 (m, 2H), 4.86-4.70 (m, 2H), 4.69-4.59 (m, 1H), 4.51-4.36 (m, 2H), 3.66-3.50 (m, 2H); LCMS (ESI): m/z 483.0 $(M+H)^+$.

The second peak: $^1H$ NMR (400 MHz, DMSO-$d_6$): δ 8.64 (d, J=4.8 Hz, 1H), 8.46 (d, J=8.8 Hz, 2H), 7.59 (d, J=8.8 Hz, 2H), 7.43 (d, J=4.8 Hz, 1H), 6.13 (d, J=2.4 Hz, 1H), 6.00 (s, 1H), 5.83 (s, 1H), 5.05-4.95 (m, 2H), 4.87-4.70 (m, 2H), 4.69-4.59 (m, 1H), 4.51-4.35 (m, 2H), 3.66-3.51 (m, 2H); LCMS (ESI): m/z 482.9 $(M+H)^+$.

Example 74 & 75 (Compound 72 &115)

(S)-Cyclobut-1-en-1-yl(3-(4-(1,2-dihydroxyethyl)-1-(4-(trifluoromethoxy)phenyl)-1H-pyrazolo[3,4-b]pyridin-3-yl)azetidin-1-yl)methanone & (R)-cyclobut-1-en-1-yl(3-(4-(1,2-dihydroxyethyl)-1-(4-(trifluoromethoxy)phenyl)-1H-pyrazolo[3,4-b]pyridin-3-yl)azetidin-1-yl)methanone

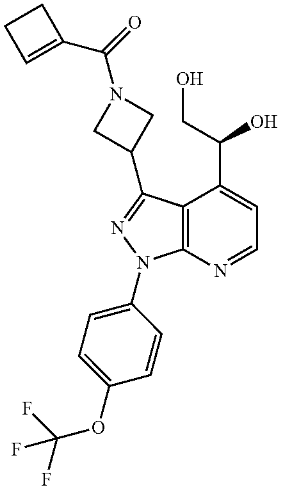

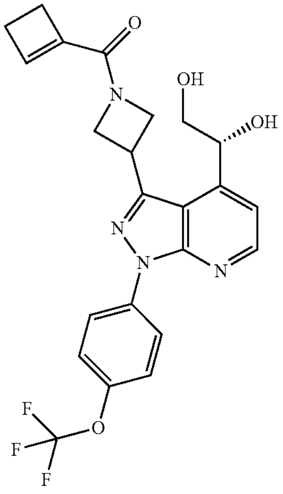

Step 1: cyclobut-1-en-1-yl(3-(4-(1,2-dihydroxyethyl)-1-(4-(trifluoromethoxy)phenyl)-1H-pyrazolo[3,4-b]pyridin-3-yl)azetidin-1-yl)methanone

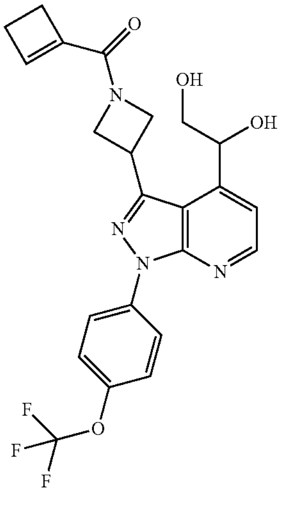 [SMILES: O=C(C1=CCC1)N1CC(c2nn(-c3ccc(OC(F)(F)F)cc3)c3nccc(C(O)CO)c23)C1]

To a solution of 1-(3-(azetidin-3-yl)-1-(4-(trifluoromethoxy)phenyl)-1H-pyrazolo[3,4-b]pyridin-4-yl)ethane-1,2-diol (350 mg, 0.89 mmol) in MeOH (1 mL) and DCM (5 mL) was added EEDQ (329 mg, 1.33 mmol) and cyclobut-1-enecarboxylic acid (174 mg, 1.78 mmol) at 0° C. The mixture was stirred at room temperature for 16 h. The reaction mixture was quenched with $H_2O$ (20 mL), and extracted with ethyl acetate (20 mL×3), the combined organic layers were washed with water (10 mL×3), dried over $Na_2SO_4$ and concentrated. The residue was purified by reverse phase chromatography (Welch Xtimate C18 150*30 mm*5 um, water (FA)-ACN, 42-72%) to afford the title compound (300 mg, 71%) as a white solid. $^1$H NMR (400 MHz, DMSO-$d_6$): 8.65 (d, J=4.8 Hz, 1H), 8.46 (d, J=8.4 Hz, 2H), 7.60 (d, J=8.4 Hz, 2H), 7.45 (d, J=5.2 Hz, 1H), 6.54 (s, 1H), 5.84-5.81 (m, 1H), 5.10-4.94 (m, 2H), 4.82-4.59 (m, 3H), 4.48-4.26 (m, 2H), 3.66-3.48 (m, 2H), 2.68-2.66 (m, 2H), 2.46-2.43 (m, 2H); LCMS (ESI): m/z 475.0 $(M+H)^+$.

Step 2: (S)-cyclobut-1-en-1-yl(3-(4-(1,2-dihydroxyethyl)-1-(4-(trifluoromethoxy)phenyl)-1H-pyrazolo[3,4-b]pyridin-3-yl)azetidin-1-yl)methanone & (R)-cyclobut-1-en-1-yl(3-(4-(1,2-dihydroxyethyl)-1-(4-(trifluoromethoxy)phenyl)-1H-pyrazolo[3,4-b]pyridin-3-yl)azetidin-1-yl)methanone

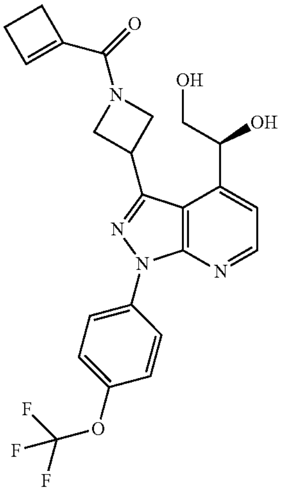

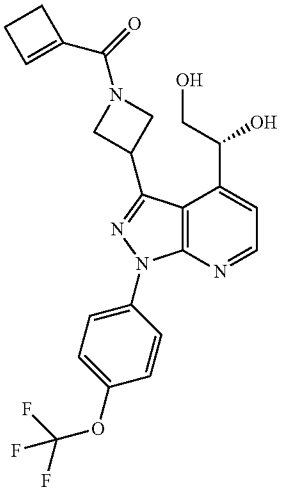

Cyclobut-1-en-1-yl(3-(4-(1,2-dihydroxyethyl)-1-(4-(trifluoromethoxy)phenyl)-1H-pyrazolo[3,4-b]pyridin-3-yl)azetidin-1-yl)methanone (300 mg, 0.63 mmol) was separated by Chiral SFC (DAICEL CHIRALPAK AD (250 mm*30 mm, 10 um)); Condition: Neu-EtOH; Begin B: 30%; Flow Rate (mL/min): 70) to afford the first peak, compound 72 (41.3 mg, 14%) and the second peak, compound 115 (40.5 mg, 14%) both as white solid.

The first peak: $^1$H NMR (400 MHz, DMSO-$d_6$): δ 8.65 (d, J=4.8 Hz, 1H), 8.46 (d, J=8.8 Hz, 2H), 7.60 (d, J=8.0 Hz, 2H), 7.44 (d, J=4.8 Hz, 1H), 6.54 (s, 1H), 5.84-5.81 (m, 1H), 5.08-4.99 (m, 2H), 4.81-4.54 (m, 3H), 4.48-4.16 (m, 2H), 3.69-3.46 (m, 2H), 2.69-2.64 (m, 2H), 2.46-2.40 (m, 2H); LCMS (ESI): m/z 475.0 $(M+H)^+$.

The second peak: $^1$H NMR (400 MHz, DMSO-$d_6$): δ 8.65 (d, J=4.8 Hz, 1H), 8.46 (d, J=8.8 Hz, 2H), 7.60 (d, J=8.0 Hz, 2H), 7.44 (d, J=4.8 Hz, 1H), 6.54 (s, 1H), 5.84-5.81 (m, 1H), 5.08-4.99 (m, 2H), 4.81-4.54 (m, 3H), 4.48-4.16 (m, 2H), 3.69-3.46 (m, 2H), 2.69-2.64 (m, 2H), 2.46-2.40 (m, 2H); LCMS (ESI): m/z 475.0 $(M+H)^+$.

Example 76 & 77 (Compound 129 & 71)

(S)-1-(3-(4-(1,2-Dihydroxyethyl)-1-(4-(trifluoromethoxy)phenyl)-1H-pyrazolo[3,4-b]pyridin-3-yl)azetidin-1-yl)but-2-yn-1-one & (R)-1-(3-(4-(1,2-dihydroxyethyl)-1-(4-(trifluoromethoxy)phenyl)-1H-pyrazolo[3,4-b]pyridin-3-yl)azetidin-1-yl)but-2-yn-1-one

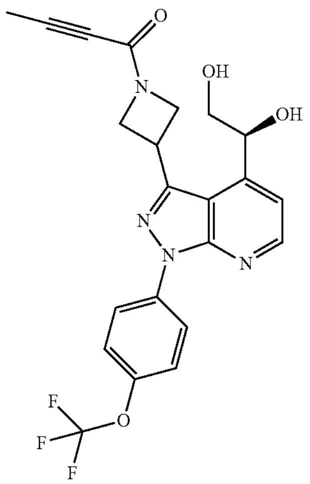

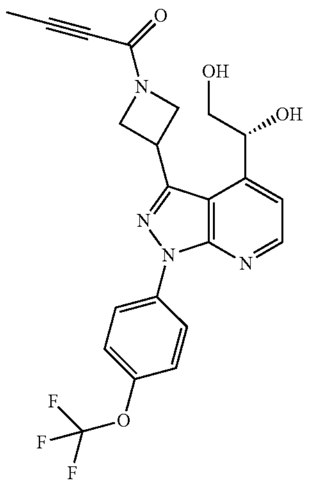

Step 1: 1-(3-(4-(1,2-dihydroxyethyl)-1-(4-(trifluoromethoxy)phenyl)-1H-pyrazolo[3,4-b]pyridin-3-yl)azetidin-1-yl)but-2-yn-1-one

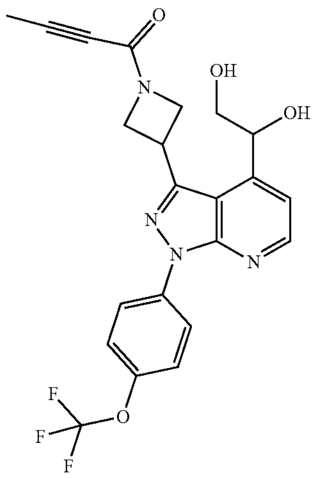 [SMILES: CC#CC(=O)N1CC(c2nn(-c3ccc(OC(F)(F)F)cc3)c3nccc(C(O)CO)c23)C1]

To a solution of 1-(3-(azetidin-3-yl)-1-(4-(trifluoromethoxy)phenyl)-1H-pyrazolo[3,4-b]pyridin-4-yl)ethane-1,2-diol (500 mg, 1.27 mmol) in MeOH (2 mL) and DCM (10 mL) was added EEDQ (470 mg, 1.90 mmol) and but-2-ynoic acid (160 mg, 1.90 mmol) at 0° C. The mixture was stirred at room temperature for 16 h. The reaction mixture was quenched with $H_2O$ (20 mL), and extracted with ethyl acetate (20 mL×3), the combined organic layers were washed with water (10 mL×3), dried over $Na_2SO_4$, filtered, and concentrated. The residue was purified by reverse phase chromatography (Welch Xtimate C18 150*30 mm*5 um, water (FA)-ACN, 43-73%) to afford the title compound (400 mg, 68%) as a white solid. $^1$H NMR (400 MHz, DMSO-$d_6$): 8.63 (d, J=4.8 Hz, 1H), 8.44 (d, J=8.8 Hz, 2H), 7.59 (d, J=8.8 Hz, 2H), 7.43 (d, J=4.8 Hz, 1H), 5.88-5.78 (m, 1H), 5.08-4.93 (m, 2H), 4.65-4.52 (m, 3H), 4.41-4.24 (m, 2H), 3.66-3.49 (m, 2H), 2.02 (s, 3H); LCMS (ESI): m/z 461.2 $(M+H)^+$.

Step 2: (S)-1-(3-(4-(1,2-dihydroxyethyl)-1-(4-(trifluoromethoxy)phenyl)-1H-pyrazolo[3,4-b]pyridin-3-yl)azetidin-1-yl)but-2-yn-1-one & (R)-1-(3-(4-(1,2-dihydroxyethyl)-1-(4-(trifluoromethoxy)phenyl)-1H-pyrazolo[3,4-b]pyridin-3-yl)azetidin-1-yl)but-2-yn-1-one

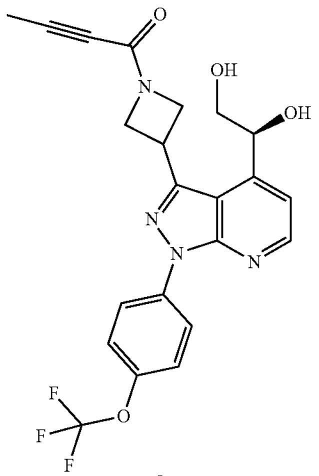

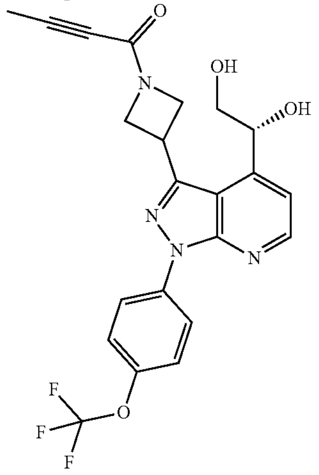

1-(3-(4-(1,2-Dihydroxyethyl)-1-(4-(trifluoromethoxy)phenyl)-1H-pyrazolo[3,4-b]pyridin-3-yl)azetidin-1-yl)but-2-yn-1-one (400 mg, 0.87 mmol) was separated by Chiral SFC (DAICEL CHIRALPAK IG (250 mm*30 mm, 10 um)); Condition: Neu-IPA; Begin B: 30%; Flow Rate (mL/min): 80) to afford the first peak, compound 129 (108.6 mg, 27%) and the second peak, compound 71 (127.1 mg, 32%) both as yellow solid.

The first peak: $^{1}$H NMR (400 MHz, DMSO-$d_6$): δ 8.63 (d, J=4.8 Hz, 1H), 8.44 (d, J=8.8 Hz, 2H), 7.59 (d, J=8.8 Hz, 2H), 7.43 (d, J=4.8 Hz, 1H), 5.84-5.82 (m, 1H), 5.05-4.97 (m, 2H), 4.66-4.50 (m, 3H), 4.43-4.24 (m, 2H), 3.66-3.50 (m, 2H), 2.02 (s, 3H); LCMS (ESI): m/z 461.0 $(M+H)^+$.

The second peak: $^{1}$H NMR (400 MHz, DMSO-$d_6$): δ 8.63 (d, J=4.8 Hz, 1H), 8.44 (d, J=8.8 Hz, 2H), 7.59 (d, J=8.8 Hz, 2H), 7.43 (d, J=4.8 Hz, 1H), 5.84-5.82 (m, 1H), 5.05-4.97 (m, 2H), 4.66-4.50 (m, 3H), 4.43-4.24 (m, 2H), 3.66-3.50 (m, 2H), 2.02 (s, 3H); LCMS (ESI): m/z 461.0 $(M+H)^+$.

Example 78 (Compound 96)

(E)-4-Hydroxy-1-(3-(4-methyl-1-(4-(trifluoromethoxy)phenyl)-1H-pyrazolo[3,4-b]pyridin-3-yl)azetidin-1-yl)but-2-en-1-one

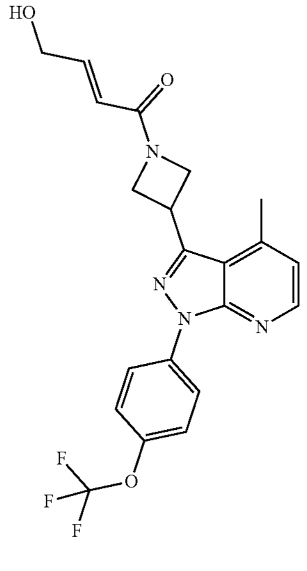 [SMILES: Cc1ccnc2c1c(C1CN(C(=O)/C=C/CO)C1)nn2-c1ccc(OC(F)(F)F)cc1]

Step 1: tert-butyl 3-(4-methyl-1-(4-(trifluoromethoxy) phenyl)-1H-pyrazolo[3,4-b]pyridin-3-yl)azetidine-1-carboxylate

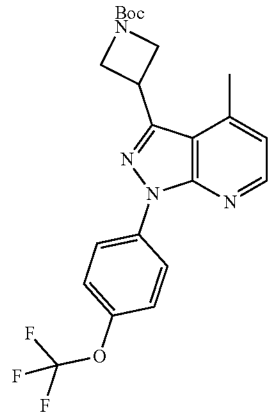 [SMILES: Cc1ccnc2c1c(C1CN(C(=O)OC(C)(C)C)C1)nn2-c1ccc(OC(F)(F)F)cc1]

A solution of tert-butyl 3-(4-chloro-1-(4-(trifluoromethoxy)phenyl)-1H-pyrazolo[3,4-b]pyridin-3-yl)azetidine-1-carboxylate (200 mg, 0.43 mmol), $Pd(PPh_3)_4$ (50 mg, 0.04 mmol), $K_2CO_3$ (177 mg, 1.28 mmol) and 2,4,6-trimethyl-1,3,5,2,4,6-trioxatriborinane (0.6 mL, 2.13 mmol) in 1,4-dioxane (4 mL) and water (0.4 mL) was stirred at 80° C. for 2 h under $N_2$ atmosphere. The reaction was quenched with water (20 mL). The resulting solution was extracted with ethyl acetate (20 mL×3) and the organic layers were combined. The organic layer was dried over anhydrous sodium sulfate. After filtration, the filtrate was concentrated under reduced pressure. The residue was purified by chromatography on silica gel (0-10% ethyl acetate in petroleum ether) to afford the title compound (130 mg, 68%) as a yellow oil. $^1$H NMR (400 MHz, $CDCl_3$): δ 8.46 (d, J=3.6 Hz, 1H), 8.38 (d, J=9.2 Hz, 2H), 7.37 (d, J=8.4 Hz, 2H), 6.97 (d, J=3.6 Hz, 1H), 4.50-4.46 (m, 2H), 4.41-4.37 (m, 2H), 4.32-4.25 (m, 1H), 2.62 (s, 3H), 1.47 (s, 9H); LCMS (ESI): m/z 449.2 $(M+H)^+$.

Step 2: 3-(azetidin-3-yl)-4-methyl-1-(4-(trifluoromethoxy)phenyl)-1H-pyrazolo[3,4-b]pyridine

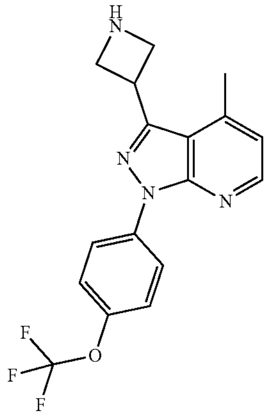 [SMILES: Cc1ccnc2c1c(C1CNC1)nn2-c1ccc(OC(F)(F)F)cc1]

A mixture of tert-butyl 3-(4-methyl-1-(4-(trifluoromethoxy) phenyl)-1H-pyrazolo[3,4-b]pyridin-3-yl)azetidine-1-carboxylate (120 mg, 0.27 mmol) and 5% TFA in HFIP (2 mL) was stirred at room temperature for 1 h. The reaction was quenched with saturated $NaHCO_3$ (7 mL) and extracted it with ethyl acetate (20 mL×3), dried over sodium sulfate and filtered. The filtrate was concentrated under reduced pressure. The mixture was concentrated to afford the title compound (90 mg, 96%) as a yellow solid. The crude product would be used in the next step directly. LCMS (ESI): m/z 349.2 $(M+H)^+$.

Step 3: (E)-4-hydroxy-1-(3-(4-methyl-1-(4-(trifluoromethoxy)phenyl)-1H-pyrazolo[3,4-b]pyridin-3-yl) azetidin-1-yl)but-2-en-1-one

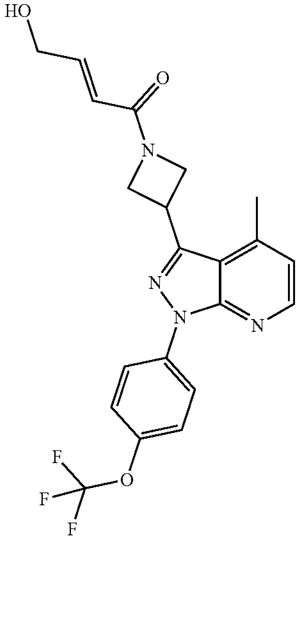 [SMILES: Cc1ccnc2c1c(C1CN(C(=O)/C=C/CO)C1)nn2-c1ccc(OC(F)(F)F)cc1]

A mixture of (E)-4-hydroxybut-2-enoic acid (43 mg, 0.41 mmol), HATU (197 mg, 0.52 mmol) and DIPEA (0.11 mL, 0.69 mmol) in DMF (2 mL) was stirred at 0° C. for 5 min. Then 3-(azetidin-3-yl)-4-methyl-1-(4-(trifluoromethoxy) phenyl)-1H-pyrazolo[3,4-b]pyridine (120 mg, 0.34 mmol) was added into it. The solution was stirred at room temperature for 3 h. After filtration, the filtrate was purified by reverse phase chromatography (Boston Green ODS 150*30 mm*5 um, acetonitrile 53-83%/water (0.2% FA)-ACN) to afford the title compound (37.4 mg, 25%) as white solid. $^1$H NMR (400 MHz, DMSO-$d_6$): δ 8.52 (d, J=4.8 Hz, 1H), 8.46 (d, J=8.8 Hz, 2H), 7.57 (d, J=8.8 Hz, 2H), 7.19 (d, J=4.8 Hz, 1H), 6.77 (dt, J=15.6, 4.0 Hz, 1H), 6.20 (d, J=15.6 Hz, 1H), 5.05 (t, J=5.2 Hz, 1H), 4.74-4.62 (m, 2H), 4.58-4.49 (m, 1H), 4.45-4.31 (m, 2H), 4.17-4.09 (m, 2H), 2.64 (s, 3H); LCMS (ESI): m/z 433.0 $(M+H)^+$.

Example 79 (Compound 127)

(E)-1-(3-(4-Chloro-1-(4-(trifluoromethoxy)phenyl)-1H-pyrazolo[3,4-b]pyridin-3-yl)azetidin-1-yl)-4-hydroxybut-2-en-1-one

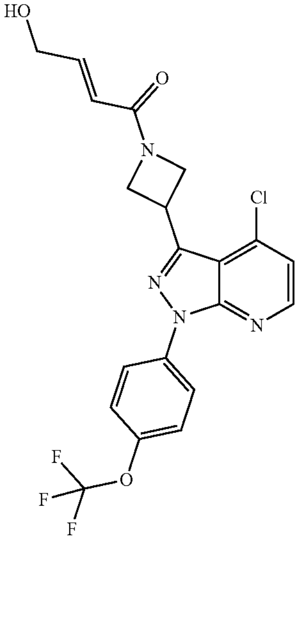 [SMILES: O=C(/C=C/CO)N1CC(c2nn(-c3ccc(OC(F)(F)F)cc3)c3nccc(Cl)c23)C1]

Step 1: 3-(azetidin-3-yl)-4-chloro-1-(4-(trifluoromethoxy)phenyl)-1H-pyrazolo[3,4-b]pyridine

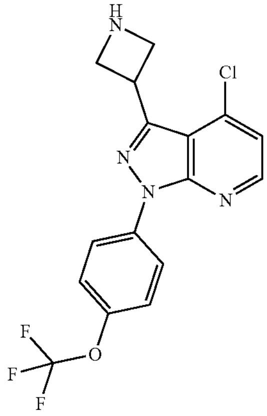 [SMILES: FC(F)(F)Oc1ccc(-n2nc(C3CNC3)c3c(Cl)ccnc32)cc1]

A mixture of tert-butyl 3-(4-chloro-1-(4-(trifluoromethoxy)phenyl)-1H-pyrazolo[3,4-b]pyridin-3-yl)azetidine-1-carboxylate (100 mg, 0.21 mmol) and 5% TFA in HFIP (2 mL) was stirred at room temperature for 3 h. The reaction was quenched with saturated sodium bicarbonate (20 mL), extracted with ethyl acetate (10 mL×3), dried over sodium sulfate, filtered, and concentrated under reduced pressure to afford the title compound (75 mg, 95%) as a yellow solid. The crude product was used for the next step directly. LCMS (ESI): m/z 369.1 $(M+H)^+$.

Step 2: (E)-1-(3-(4-chloro-1-(4-(trifluoromethoxy)phenyl)-1H-pyrazolo[3,4-b]pyridin-3-yl)azetidin-1-yl)-4-hydroxybut-2-en-1-one

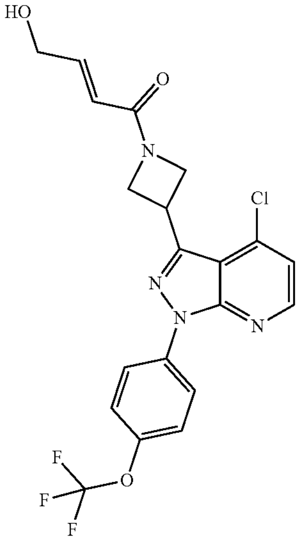 [SMILES: O=C(/C=C/CO)N1CC(c2nn(-c3ccc(OC(F)(F)F)cc3)c3nccc(Cl)c23)C1]

A mixture of 3-(azetidin-3-yl)-4-chloro-1-(4-(trifluoromethoxy)phenyl)-1H-pyrazolo[3,4-b]pyridine (60 mg, 0.16 mmol), (E)-4-hydroxybut-2-enoic acid (20 mg, 0.20 mmol) and DIPEA (0.05 mL, 0.33 mmol) in DMF (2 mL) was stirred at 0° C. for 5 min. Then HATU (93 mg, 0.24 mmol) was added into it. The solution was stirred at room temperature for 3 h. The resulting solution was purified by reverse phase chromatography (Boston Green ODS 150*30 mm*5 um acetonitrile 47-77%/water (0.2% FA)-ACN) to afford the title compound (24.5 mg, 33%) as a white solid. $^1H$ NMR (400 MHz, DMSO-$d_6$): δ 8.63 (d, J=5.2 Hz, 1H), 8.40 (d, J=8.8 Hz, 2H), 7.60 (d, J=8.8 Hz, 2H), 7.54 (d, J=4.8 Hz, 1H), 6.76 (dt, J=15.2, 4.0 Hz, 1H), 6.19 (d, J=15.2 Hz, 1H), 5.05 (t, J=5.2 Hz, 1H), 4.75-4.69 (m, 1H), 4.68-4.62 (m, 1H), 4.58-4.48 (m, 1H), 4.46-4.33 (m, 2H), 4.17-4.10 (m, 2H); LCMS (ESI): m/z 452.9 $(M+H)^+$.

Example 80 (Compound 48)

1-(3-(4-Ethynyl-1-(4-(trifluoromethoxy)phenyl)-1H-pyrazolo[3,4-b]pyridin-3-yl)azetidin-1-yl)prop-2-en-1-one

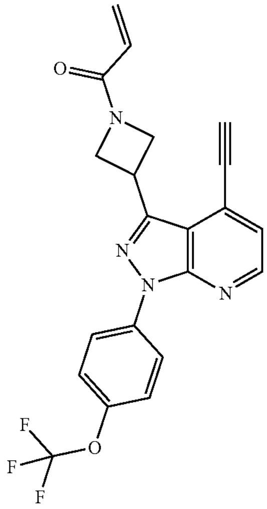 [SMILES: C#Cc1ccnc2c1c(C1CN(C(=O)C=C)C1)nn2-c1ccc(OC(F)(F)F)cc1]

Step 1: tert-butyl 3-(1-(4-(trifluoromethoxy)phenyl)-4-((triisopropylsilyl)ethynyl)-1H-pyrazolo[3,4-b]pyridin-3-yl)azetidine-1-carboxylate

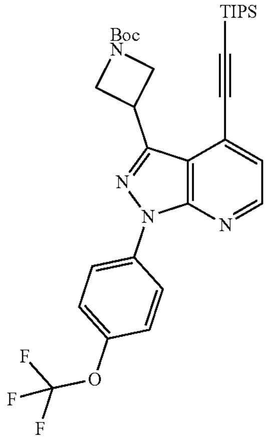

To a solution of tert-butyl 3-(4-chloro-1-(4-(trifluoromethoxy)phenyl)-1H-pyrazolo[3,4-b]pyridin-3-yl)azetidine-1-carboxylate (400 mg, 0.85 mmol) and $Pd(PPh_3)_2Cl_2$ (120 mg, 0.17 mmol), CuI (65 mg, 0.34 mmol) in DMF (5 mL) was added TEA (0.5 mL, 3.41 mmol) and ethynyltriisopropylsilane (1.0 mL, 4.27 mmol). The resulting solution was stirred at 100° C. for 16 h under $N_2$ atmosphere. The mixture was quenched with water (60 mL) and extracted with ethyl acetate (60 mL×3) and washed with brine (30 mL). The organic layers were dried over anhydrous sodium sulfate, filtered, and concentrated under reduced pressure. The residue was purified by chromatography on silica gel (0-10% ethyl acetate in petroleum ether) to afford the title compound (270 mg, 52%). $^1$H NMR (400 MHz, $CDCl_3$): δ 8.55 (d, J=4.8 Hz, 1H), 8.37 (d, J=8.8 Hz, 2H), 7.39 (d, J=8.8 Hz, 2H), 7.28-7.27 (m, 1H), 4.64-4.56 (m, 1H), 4.49-4.37 (m, 4H), 1.48 (s, 9H), 1.27-1.24 (m, 3H), 1.22-1.19 (m, 18H); LCMS (ESI): m/z 615.3 $(M+H)^+$.

Step 2: tert-butyl 3-(4-ethynyl-1-(4-(trifluoromethoxy)phenyl)-1H-pyrazolo[3,4-b]pyridin-3-yl)azetidine-1-carboxylate

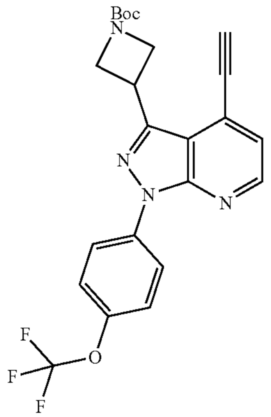 [SMILES: C#Cc1ccnc2c1c(C1CN(C(=O)OC(C)(C)C)C1)nn2-c1ccc(OC(F)(F)F)cc1]

A mixture of tert-butyl 3-(1-(4-(trifluoromethoxy)phenyl)-4-((triisopropylsilyl)ethynyl)-1H-pyrazolo[3,4-b]pyridin-3-yl)azetidine-1-carboxylate (300 mg, 0.5 mmol) and TBAF (0.35 mL, 0.35 mmol, 1M in THF) in THF (4 mL) was stirred at room temperature for 2 h. The mixture was diluted with $NaHCO_3$ (30 mL). The resulting solution was extracted with ethyl acetate (20 mL×3). The combined organic layers were dried over $Na_2SO_4$. After filtration, the filtrate was concentrated under reduced pressure. The residue was purified by chromatography on silica gel (0-20% ethyl acetate in petroleum ether) to afford the title compound (150 mg, 67%) as a yellow solid. $^1$H NMR (400 MHz, $CDCl_3$): δ 8.59 (d, J=4.8 Hz, 1H), 8.37 (d, J=8.8 Hz, 2H), 7.39 (d, J=8.8 Hz, 2H), 7.30 (d, J=4.8 Hz, 1H), 4.50-4.45 (m, 3H), 4.44-4.38 (m, 2H), 3.66 (s, 1H), 1.48 (s, 9H); LCMS (ESI): m/z 459.1 $(M+H)^+$.

Step 3: 3-(azetidin-3-yl)-4-ethynyl-1-(4-(trifluoromethoxy)phenyl)-1H-pyrazolo[3,4-b]pyridine 2,2,2-trifluoroacetate salt

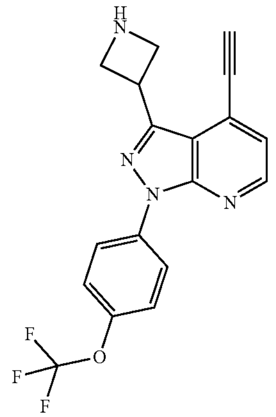 [SMILES: C#Cc1ccnc2c1c(C1CNC1)nn2-c1ccc(OC(F)(F)F)cc1]

A mixture of tert-butyl 3-(4-ethynyl-1-(4-(trifluoromethoxy)phenyl)-1H-pyrazolo[3,4-b]pyridin-3-yl)azetidine-1-carboxylate (150 mg, 0.33 mmol) and TFA (1 mL, 13 mmol) in DCM (3 mL) was stirred at room temperature for 2 h. The mixture was concentrated under reduced pressure to afford the title compound (150 mg, crude) as a yellow solid. The crude product would be used in the next step directly. LCMS (ESI): m/z 359.1 $(M+H)^+$.

Step 4: 1-(3-(4-ethynyl-1-(4-(trifluoromethoxy)phenyl)-1H-pyrazolo[3,4-b]pyridin-3-yl)azetidin-1-yl)prop-2-en-1-one

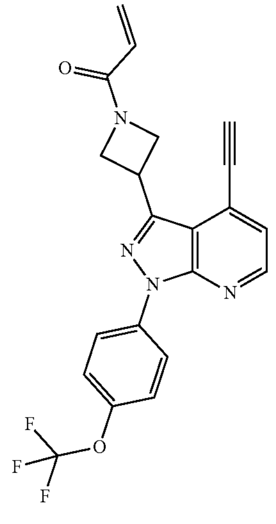 [SMILES: C#Cc1ccnc2c1c(C1CN(C(=O)C=C)C1)nn2-c1ccc(OC(F)(F)F)cc1]

To a solution of saturated sodium bicarbonate (1 mL, 0.42 mmol) and 3-(azetidin-3-yl)-4-ethynyl-1-(4-(trifluoromethoxy)phenyl)-1H-pyrazolo[3,4-b]pyridine 2,2,2-trifluoroacetate salt (150 mg, 0.42 mmol) in THF (3 mL) was added acrylic anhydride (53 mg, 0.42 mmol) at 0° C. The solution was stirred at 0° C. for 2 h. The mixture was quenched with water (20 mL) and extracted with ethyl acetate (30 mL) and washed with brine (30 mL). The organic layers were dried over anhydrous sodium sulfate, filtered, and concentrated under reduced pressure. The residue was purified by reverse phase chromatography (Welch Xtimate C18 150*30 mm*5 um, acetonitrile 56-86%/water (FA)-ACN) to afford the title compound (90.2 mg, 52%). $^1$H NMR (400 MHz, DMSO-$d_6$): δ 8.68 (d, J=4.8 Hz, 1H), 8.40 (d, J=8.8 Hz, 2H), 7.59 (d, J=8.8 Hz, 2H), 7.48 (d, J=5.2 Hz, 1H), 6.39 (dd, J=17.2, 10.4 Hz, 1H), 6.13 (dd, J=17.2, 1.6 Hz, 1H), 5.70 (dd, J=10.4, 1.6 Hz, 1H), 5.10 (s, 1H), 4.75-4.64 (m, 2H), 4.59-4.50 (m, 1H), 4.46-4.33 (m, 2H); LCMS (ESI): m/z 413.0 $(M+H)^+$.

Example 81 (Compound 70)

(E)-4-Hydroxy-1-(3-(4-(3-hydroxyazetidin-1-yl)-1-(4-(trifluoromethoxy)phenyl)-1H-pyrazolo[3,4-b]pyridin-3-yl)azetidin-1-yl)but-2-en-1-one

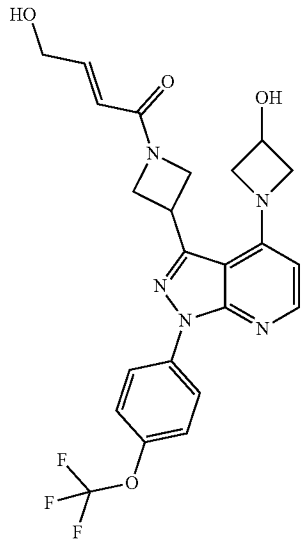 [SMILES: O=C(/C=C/CO)N1CC(c2nn(-c3ccc(OC(F)(F)F)cc3)c3nccc(N4CC(O)C4)c23)C1]

Step 1: tert-butyl 3-(4-(3-hydroxyazetidin-1-yl)-1-(4-(trifluoromethoxy)phenyl)-1H-pyrazolo[3,4-b]pyridin-3-yl)azetidine-1-carboxylate

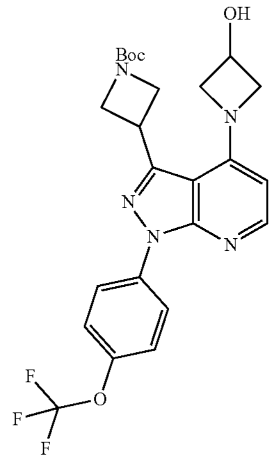 [SMILES: CC(C)(C)OC(=O)N1CC(c2nn(-c3ccc(OC(F)(F)F)cc3)c3nccc(N4CC(O)C4)c23)C1]

A mixture of azetidin-3-ol hydrochloride (140 mg, 1.28 mmol), $Cs_2CO_3$ (625 mg, 1.92 mmol), tert-butyl 3-(4-chloro-1-(4-(trifluoromethoxy)phenyl)-1H-pyrazolo[3,4-b]pyridin-3-yl)azetidine-1-carboxylate (300 mg, 0.64 mmol) in DMF (5.0 mL) was stirred at 80° C. for 2 h. The reaction mixture was diluted with water (50 mL) and extracted with ethyl acetate (50 mL×3), the combined organic layers were washed with brine (50 mL×3). The organic layer was dried over anhydrous sodium sulfate, filtered, and concentrated under vacuum. The residue was purified by flash chromatography on silica gel (0-6% MeOH in DCM) to afford the title compound (260 mg, 80%) as a yellow solid.

Step 2: 1-(3-(azetidin-3-yl)-1-(4-(trifluoromethoxy)phenyl)-1H-pyrazolo[3,4-b]pyridin-4-yl)azetidin-3-ol

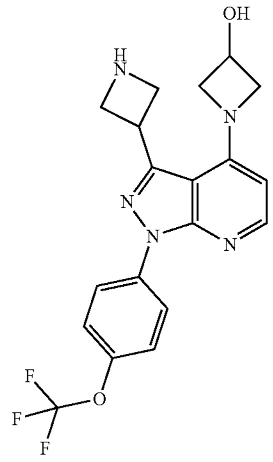 [SMILES: OC1CN(c2ccnc3c2c(C2CNC2)nn3-c2ccc(OC(F)(F)F)cc2)C1]

A solution of tert-butyl 3-(4-(3-hydroxyazetidin-1-yl)-1-(4-(trifluoromethoxy)phenyl)-1H-pyrazolo[3,4-b]pyridin-3-yl)azetidine-1-carboxylate (260 mg, 0.52 mmol) and TFA (5% in HFIP, 10.0 mL) was stirred at room temperature for 2 h. The reaction was diluted with water (50 mL) and adjusted to pH=8 with sat. $NaHCO_3$, extracted with ethyl acetate (50 mL×3). The combined organic layers were dried over $Na_2SO_4$ and concentrated to afford the title compound (210 mg, 100%). The crude was used for next step without further purification.

Step 3: (E)-4-hydroxy-1-(3-(4-(3-hydroxyazetidin-1-yl)-1-(4-(trifluoromethoxy)phenyl)-1H-pyrazolo[3,4-b]pyridin-3-yl)azetidin-1-yl)but-2-en-1-one

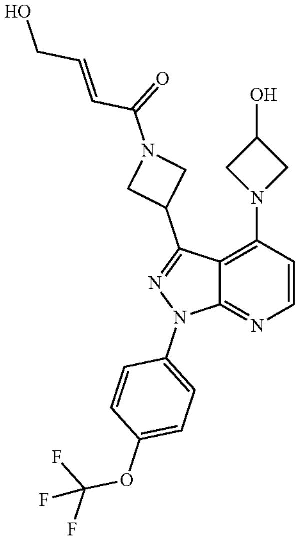 [SMILES: O=C(/C=C/CO)N1CC(c2nn(-c3ccc(OC(F)(F)F)cc3)c3nccc(N4CC(O)C4)c23)C1]

To a mixture of 1-(3-(azetidin-3-yl)-1-(4-(trifluoromethoxy)phenyl)-1H-pyrazolo[3,4-b]pyridin-4-yl)azetidin-3-ol (100 mg, 0.25 mmol) in DCM (5.0 mL) and MeOH (1.0 mL) was added (E)-4-hydroxybut-2-enoic acid (50 mg, 0.49 mmol) and EEDQ (183 mg, 0.74 mmol). Then the reaction was stirred at room temperature for 16 h. The mixture was diluted with ethyl acetate (100 mL) and washed with water (100 mL×3). The organic was dried over $Na_2SO_4$, filtered, and concentrated. The residue was purified by reverse phase chromatography (Welch Xtimate C18 150*30 mm*5 um, water (0.2% FA)-ACN, 15-45%) to afford the title compound (28.0 mg, 23%) as a white solid. $^1H$ NMR (400 MHz, DMSO-$d_6$): δ 8.44 (d, J=8.8 Hz, 2H), 8.16 (d, J=5.6 Hz, 1H), 7.54 (d, J=8.8 Hz, 2H), 6.75 (dt, J=15.6, 4.0 Hz, 1H), 6.22-6.14 (m, 2H), 5.85 (d, J=6.0 Hz, 1H), 5.04 (t, J=5.6 Hz, 1H), 4.69-4.54 (m, 3H), 4.48-4.42 (m, 2H), 4.40-4.34 (m, 1H), 4.33-4.26 (m, 2H), 4.16-4.10 (m, 2H), 3.99-3.93 (m, 2H); LCMS (ESI): m/z 490.0 $(M+H)^+$.

Example 82 (Compound 81)

2-Fluoro-1-(3-(4-(3-hydroxyazetidin-1-yl)-1-(4-(trifluoromethoxy)phenyl)-1H-pyrazolo[3,4-b]pyridin-3-yl)azetidin-1-yl)prop-2-en-1-one

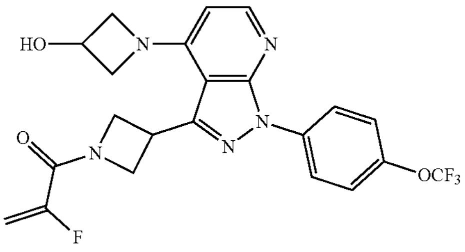 [SMILES: C=C(F)C(=O)N1CC(c2nn(-c3ccc(OC(F)(F)F)cc3)c3nccc(N4CC(O)C4)c23)C1]

A mixture of 1-(3-(azetidin-3-yl)-1-(4-(trifluoromethoxy)phenyl)-1H-pyrazolo[3,4-b]pyridin-4-yl)azetidin-3-ol (96.0 mg, 0.24 mmol), 2-fluoroacrylic acid (43.0 mg, 0.47 mmol) and EEDQ (176 mg, 0.71 mmol) in DCM (2 mL) and methanol (0.5 mL) was stirred at room temperature for 16 h. The reaction was diluted with water (2 mL) and extracted with ethyl acetate (20 mL×3). The organics were washed with brine (10 mL×2), dried over sodium sulfate, filtered and concentrated to dryness. The resulting residue was purified by reverse phase chromatography (Welch Xtimate C18 150*30 mm*5 um, acetonitrile 35-65%/water (FA)-ACN) to afford the title compound (100 mg, 88%) as a white solid. $^1H$ NMR (400 MHz, DMSO-$d_6$): δ 8.45 (d, J=8.8 Hz, 2H), 8.16 (d, J=5.6 Hz, 1H), 7.54 (d, J=8.8 Hz, 2H), 6.19 (d, J=5.6 Hz, 1H), 5.86 (d, J=6.0 Hz, 1H), 5.51 (dd, J=48.8, 3.6 Hz, 1H), 5.32 (dd, J=16.8, 3.6 Hz, 1H), 4.87-4.78 (m, 1H), 4.74-4.60 (m, 2H), 4.50-4.39 (m, 4H), 4.39-4.32 (m, 1H), 4.00-3.90 (m, 2H); LCMS (ESI): m/z 478.1 $(M+H)^+$.

Example 83 (Compound 39)

2-Fluoro-1-(3-(4-(3-fluoro-3-(hydroxymethyl)azetidin-1-yl)-1-(4-(trifluoromethoxy)phenyl)-1H-pyrazolo[3,4-b]pyridin-3-yl)azetidin-1-yl)prop-2-en-1-one

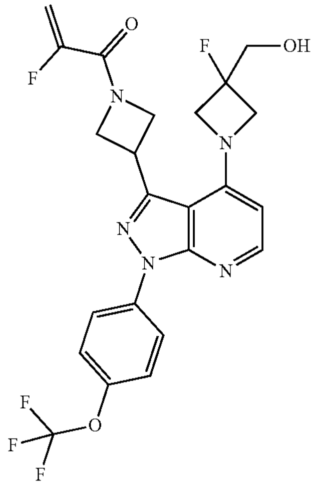 [SMILES: C=C(F)C(=O)N1CC(c2nn(-c3ccc(OC(F)(F)F)cc3)c3nccc(N4CC(F)(CO)C4)c23)C1]

Step 1: (3-fluoroazetidin-3-yl)methanol 2,2,2-trifluoroacetate salt

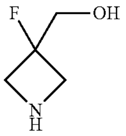

The mixture of tert-butyl 3-fluoro-3-(hydroxymethyl)azetidine-1-carboxylate (100 mg, 0.49 mmol) in TFA (5% in HFIP, 5 mL) was stirred at 0° C. for 16 h under nitrogen atmosphere. The reaction was concentrated under vacuum to afford the title compound (30.0 mg, 58%) as an oil. $^1H$ NMR (400 MHz, DMSO-$d_6$): δ 4.12 (d, J=18.0 Hz, 4H), 3.67 (d, J=19.6 Hz, 2H).

Step 2: tert-butyl 3-(4-(3-fluoro-3-(hydroxymethyl) azetidin-1-yl)-1-(4-(trifluoromethoxy)phenyl)-1H-pyrazolo[3,4-b]pyridin-3-yl)azetidine-1-carboxylate

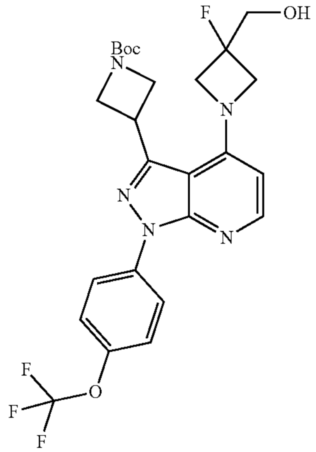 [SMILES: CC(C)(C)OC(=O)N1CC(c2nn(-c3ccc(OC(F)(F)F)cc3)c3nccc(N4CC(F)(CO)C4)c23)C1]

A solution of tert-butyl 3-(4-chloro-1-(4-(trifluoromethoxy)phenyl)-1H-pyrazolo[3,4-b]pyridin-3-yl)azetidine-1-carboxylate (32.0 mg, 0.07 mmol), $Cs_2CO_3$ (89.0 mg, 0.27 mmol), (3-fluoroazetidin-3-yl)methanol 2,2,2-trifluoroacetate salt (30.0 mg, 0.14 mmol) in DMF (1 mL) was stirred at 100° C. under $N_2$ atmosphere for 16 h. The reaction mixture was diluted with water (5 mL) and extracted with Ethyl acetate (10 mL×3), the combined organic layers were washed with brine (10 mL×5). The organic layer was dried over $Na_2SO_4$, filtered, and concentrated to dryness. The residue was purified by prep-TLC (75% ethyl acetate in petroleum ether) to afford the title compound (15 mg, 41%) as a white solid. $^1H$ NMR (400 MHz, $CDCl_3$): δ 8.32 (d, J=8.8 Hz, 2H), 8.26 (d, J=5.2 Hz, 1H), 7.36 (d, J=8.8 Hz, 2H), 6.13 (d, J=5.6 Hz, 1H), 4.49-4.41 (m, 2H), 4.38-4.24 (m, 6H), 4.13-4.05 (m, 1H), 3.99 (d, J=20.0 Hz, 2H), 1.47 (s, 9H).

Step 3: (1-(3-(azetidin-3-yl)-1-(4-(trifluoromethoxy) phenyl)-1H-pyrazolo[3,4-b]pyridin-4-yl)-3-fluoroazetidin-3-yl)methanol

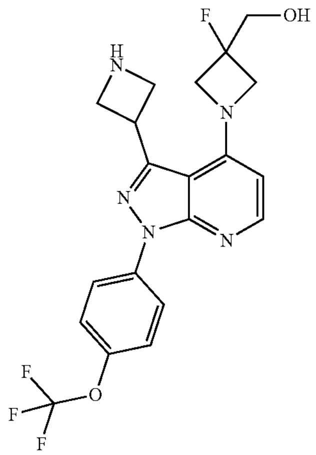 [SMILES: OCC1(F)CN(c2ccnc3c2c(C2CNC2)nn3-c2ccc(OC(F)(F)F)cc2)C1]

The mixture of tert-butyl 3-(4-(3-fluoro-3-(hydroxymethyl)azetidin-1-yl)-1-(4-(trifluoromethoxy)phenyl)-1H-pyrazolo[3,4-b]pyridin-3-yl)azetidine-1-carboxylate (130 mg, 0.24 mmol) in TFA (5% in HFIP, 5 mL) was stirred at 0° C. for 16 h under nitrogen atmosphere. The reaction was concentrated under vacuum. The residue was neutralized with saturated aqueous $NaHCO_3$ to pH=8. The resulting solution was extracted with ethyl acetate (30 mL×3). The combined organic layers were dried over anhydrous sodium sulfate, filtered, and concentrated under vacuum to afford the title compound (39.0 mg, 37%) as a white solid. LCMS (ESI): m/z 438.0 $(M+H)^+$.

Step 3: 2-fluoro-1-(3-(4-(3-fluoro-3-(hydroxymethyl)azetidin-1-yl)-1-(4-(trifluoromethoxy)phenyl)-1H-pyrazolo[3,4-b]pyridin-3-yl)azetidin-1-yl)prop-2-en-1-one

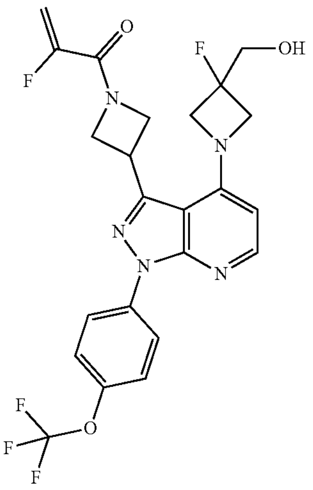 [SMILES: C=C(F)C(=O)N1CC(c2nn(-c3ccc(OC(F)(F)F)cc3)c3nccc(N4CC(F)(CO)C4)c23)C1]

A mixture of (1-(3-(azetidin-3-yl)-1-(4-(trifluoromethoxy)phenyl)-1H-pyrazolo[3,4-b]pyridin-4-yl)-3-fluoroazetidin-3-yl)methanol (100 mg, 0.23 mmol), EEDQ (85.0 mg, 0.34 mmol) and 2-fluoroacrylic acid (31.0 mg, 0.34 mmol) in DCM (1 mL) and MeOH (0.20 mL) was stirred at 0° C. for 16 h. The reaction mixture was quenched with $H_2O$ (20 mL) and extracted with ethyl acetate (50 mL×3), the combined organic layers were washed with water (50 mL×3), dried over $Na_2SO_4$ and concentrated. The residue was purified by prep-TLC (petroleum ether:ethyl acetate:EtOH=8:3:1) to afford the title compound (16.0 mg, 14%) as a white solid. $^1H$ NMR (400 MHz, DMSO-$d_6$): δ 8.44 (d, J=9.2 Hz, 2H), 8.22 (d, J=5.6 Hz, 1H), 7.55 (d, J=9.2 Hz, 2H), 6.30 (d, J=5.6 Hz, 1H), 5.51 (dd, J=48.8, 3.6 Hz, 1H), 5.40 (t, J=5.2 Hz, 1H), 5.32 (dd, J=16.4, 3.6 Hz, 1H), 4.75-7.65 (m, 2H), 4.46-4.45 (m, 1H), 4.38-4.30 (m, 6H), 3.78-3.72 (m, 2H); LCMS (ESI): m/z 509.9 $(M+H)^+$.

Example 84 & 85 (Compound 58 & 141)

(R)-1-(3-(4-(3-(1,2-Dihydroxyethyl)azetidin-1-yl)-1-(4-(trifluoromethoxy)phenyl)-1H-pyrazolo[3,4-b]pyridin-3-yl)azetidin-1-yl)-2-fluoroprop-2-en-1-one & (S)-1-(3-(4-(3-(1,2-dihydroxyethyl)azetidin-1-yl)-1-(4-(trifluoromethoxy)phenyl)-1H-pyrazolo[3,4-b]pyridin-3-yl)azetidin-1-yl)-2-fluoroprop-2-en-1-one

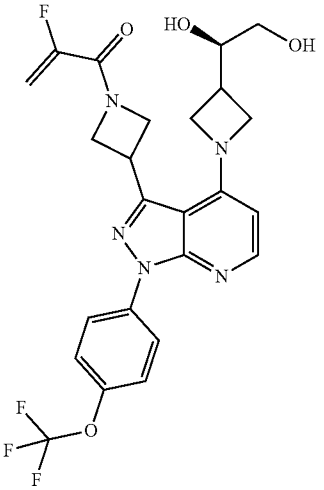

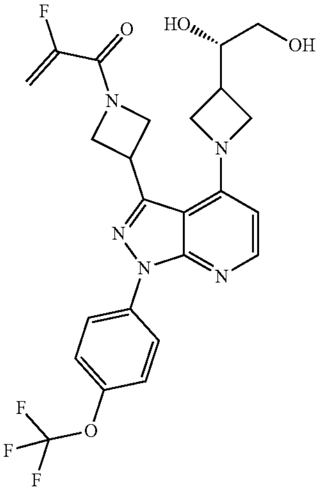

Step 1: tert-butyl 3-vinylazetidine-1-carboxylate

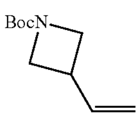

To a solution of methyltriphenylphosphonium bromide (4.8 g, 13.5 mmol) in THF (50 mL) was added n-BuLi (5.4 mL, 13.5 mmol, 2.5 M in hexane) at 0° C. The solution was stirred at 0° C. for 10 min. Then a solution of tert-butyl 3-formylazetidine-1-carboxylate (500 mg, 2.7 mmol) in THF (5 mL) was added at 0° C., and the mixture was stirred at room temperature for 16 h. The reaction was quenched with sat. $NH_4Cl$ (200 mL) and extract with ethyl acetate (200 mL×3), the combined organic layers were dried over anhydrous sodium sulfate, filtered, and concentrated under vacuum. The residue was purified by flash chromatography on silica gel (0-15% ethyl acetate in petroleum ether) to afford the title compound (500 mg, 96%) as a colorless liquid. $^1H$ NMR (400 MHz, $CDCl_3$): δ 6.12-5.88 (m, 1H), 5.11 (d, J=6.4 Hz, 1H), 5.07 (s, 1H), 4.09 (t, J=8.4 Hz, 2H), 3.75 (dd, J=8.4, 6.0 Hz, 2H), 3.25-3.11 (m, 1H), 1.45 (s, 9H).

Step 3: 3-vinylazetidine 2,2,2-trifluoroacetate salt

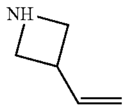

A mixture of tert-butyl 3-formylazetidine-1-carboxylate (500 mg, 2.73 mmol) and TFA (5% in HFIP, 10 mL) was stirred at room temperature for 16 h. The reaction mixture was concentrated under vacuum to afford the title compound (530 mg) as brown oil. The crude was used for next step without further purification. $^1H$ NMR (400 MHz, $CDCl_3$): δ 6.01-5.89 (m, 1H), 5.27-5.17 (m, 2H), 4.29-4.18 (m, 2H), 4.10-4.00 (m, 2H), 3.73-3.64 (m, 1H).

Step 3: tert-butyl 3-(1-(4-(trifluoromethoxy)phenyl)-4-(3-vinylazetidin-1-yl)-1H-pyrazolo[3,4-b]pyridin-3-yl)azetidine-1-carboxylate

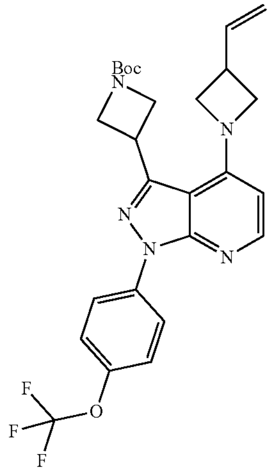 [SMILES: C=CC1CN(c2ccnc3c2c(C2CN(C(=O)OC(C)(C)C)C2)nn3-c2ccc(OC(F)(F)F)cc2)C1]

A mixture of tert-butyl 3-(4-chloro-1-(4-(trifluoromethoxy)phenyl)-1H-pyrazolo[3,4-b]pyridin-3-yl)azetidine-1-carboxylate (900 mg, 1.92 mmol), 3-vinylazetidine 2,2,2-trifluoroacetate salt (492 mg, 2.50 mmol) and $Cs_2CO_3$ (1.90 g, 5.76 mmol) in DMF (10.0 mL) was stirred at 100° C. for 16 h. The reaction was quenched with water (100 mL) and extracted with ethyl acetate (100 mL×3), the combined organic layers were washed with brine (100 mL×3) and dried over anhydrous sodium sulfate. After filtration, the filtrate was concentrated under reduced pressure. The residue was purified by chromatography on silica gel (0-14% ethyl acetate in petroleum ether) to afford the title compound (700 mg, 71%) as a yellow oil. $^1H$ NMR (400 MHz, $CDCl_3$):

δ 8.34 (d, J=9.2 Hz, 2H), 8.22 (d, J=5.6 Hz, 1H), 7.36 (d, J=8.8 Hz, 2H), 6.15-6.07 (m, 1H), 6.05 (d, J=5.6 Hz, 1H), 5.22 (d, J=10.8 Hz, 1H), 5.20-5.17 (m, 1H), 4.50-4.43 (m, 2H), 4.45-4.40 (m, 2H), 4.38-4.34 (m, 2H), 4.16-4.07 (m, 1H), 4.03-3.96 (m, 2H), 3.53-3.46 (m, 1H), 1.47 (s, 9H); LCMS(ESI): m/z 516.2 $(M+H)^+$.

Step 4: tert-butyl 3-(4-(3-(1,2-dihydroxyethyl)azetidin-1-yl)-1-(4-(trifluoromethoxy)phenyl)-1H-pyrazolo[3,4-b]pyridin-3-yl)azetidine-1-carboxylate

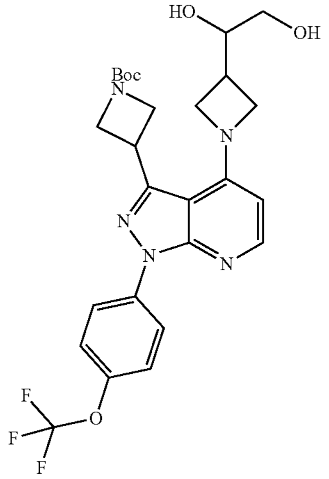 [SMILES: CC(C)(C)OC(=O)N1CC(c2nn(-c3ccc(OC(F)(F)F)cc3)c3nccc(N4CC(C(O)CO)C4)c23)C1]

To a solution of tert-butyl 3-(1-(4-(trifluoromethoxy)phenyl)-4-(3-vinylazetidin-1-yl)-1H-pyrazolo[3,4-b]pyridin-3-yl)azetidine-1-carboxylate (350 mg, 0.68 mmol) and $K_2OsO_4 \cdot 2H_2O$ (25 mg, 0.07 mmol) in THF (5.0 mL) and water (1.0 mL) was added NMO (119 mg, 1.02 mmol) at 0° C. The resulting mixture was stirred at room temperature 16 h. The reaction mixture was diluted with ethyl acetate (100 mL), washed with water (100 mL×2) and brine (100 mL×2). The organic was dried over $Na_2SO_4$, filtered, and concentrated to afford the title compound (300 mg, 80%) as a brown liquid. LCMS (ESI): m/z 550.2 $(M+H)^+$.

Step 5: 1-(1-(3-(azetidin-3-yl)-1-(4-(trifluoromethoxy)phenyl)-1H-pyrazolo[3,4-b]pyridin-4-yl)azetidin-3-yl)ethane-1,2-diol

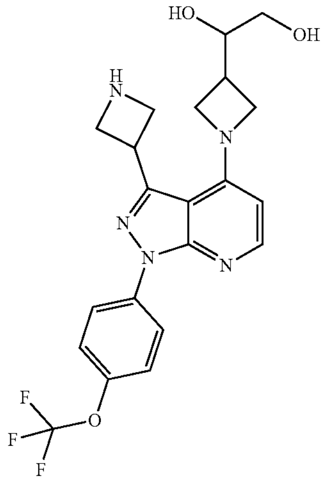 [SMILES: OCC(O)C1CN(c2ccnc3c2c(C2CNC2)nn3-c2ccc(OC(F)(F)F)cc2)C1]

A solution of tert-butyl 3-(4-(3-(1,2-dihydroxyethyl)azetidin-1-yl)-1-(4-(trifluoromethoxy)phenyl)-1H-pyrazolo[3,4-b]pyridin-3-yl)azetidine-1-carboxylate (325 mg, 0.59 mmol) in TFA (5% in HFIP, 5.0 mL) was stirred at room temperature for 2 h. The mixture was quenched with water (20 mL) then adjusted to pH=8 with aq. $NaHCO_3$ solution and diluted with ethyl acetate (100 mL) and washed with water (100 mL×3). The organic was dried over $Na_2SO_4$, filtered, and concentrated to afford the title compound (200 mg, 75%) as a brown oil. LCMS (ESI): m/z 450.2 $(M+H)^+$.

Step 5: 1-(3-(4-(3-(1,2-dihydroxyethyl)azetidin-1-yl)-1-(4-(trifluoromethoxy)phenyl)-1H-pyrazolo[3,4-b]pyridin-3-yl)azetidin-1-yl)-2-fluoroprop-2-en-1-one

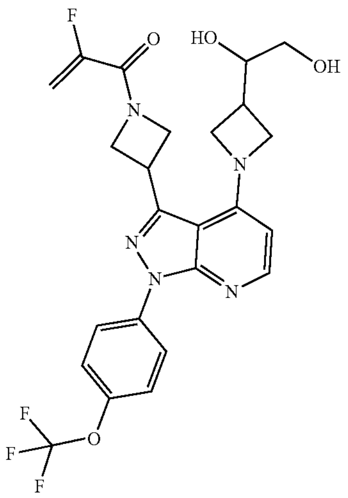 [SMILES: C=C(F)C(=O)N1CC(c2nn(-c3ccc(OC(F)(F)F)cc3)c3nccc(N4CC(C(O)CO)C4)c23)C1]

To a mixture of 1-(1-(3-(azetidin-3-yl)-1-(4-(trifluoromethoxy)phenyl)-1H-pyrazolo[3,4-b]pyridin-4-yl)azetidin-3-yl)ethane-1,2-diol (200 mg, 0.45 mmol) in DCM (5.0 mL) and MeOH (1.0 mL) was added 2-fluoroacrylic acid (48.0 mg, 0.53 mmol) and EEDQ (165 mg, 0.67 mmol) at 0° C. The reaction was stirred at room temperature for 16 h. The mixture was diluted with ethyl acetate (100 mL) and washed with water (100 mL×3). The organic was dried over $Na_2SO_4$ and concentrated to dryness. The residue was purified by reverse phase chromatography (Welch Xtimate C18 150*30 mm*5 um, water (0.2% FA)-ACN, 29-59%) to afford the title compound (80.0 mg, 35%) as a white solid. LCMS (ESI): m/z 522.1 $(M+H)^+$.

Step 6: (R)-1-(3-(4-(3-(1,2-dihydroxyethyl)azetidin-1-yl)-1-(4-(trifluoromethoxy)phenyl)-1H-pyrazolo[3,4-b]pyridin-3-yl)azetidin-1-yl)-2-fluoroprop-2-en-1-one & (S)-1-(3-(4-(3-(1,2-dihydroxyethyl)azetidin-1-yl)-1-(4-(trifluoromethoxy)phenyl)-1H-pyrazolo[3,4-b]pyridin-3-yl)azetidin-1-yl)-2-fluoroprop-2-en-1-one

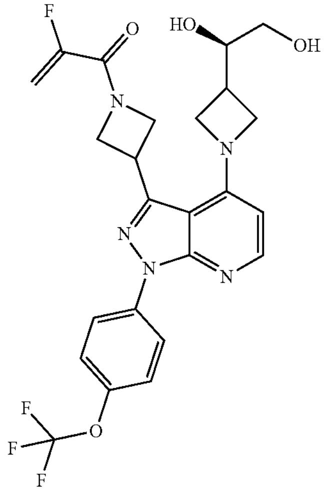

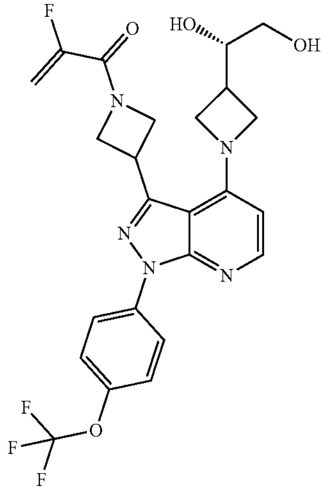

1-(3-(4-(3-(1,2-Dihydroxyethyl)azetidin-1-yl)-1-(4-(trifluoromethoxy)phenyl)-1H-pyrazolo[3,4-b]pyridin-3-yl)azetidin-1-yl)-2-fluoroprop-2-en-1-one (80 mg, 0.15 mmol) was separated by Chiral SFC (DAICEL CHIRALPAK AD (250 mm*30 mm, 10 um), Neu-EtOH, 30-30%) to afford the first peak, compound 58 (27.0 mg, 33%) and the second peak, compound 141 (26.7 mg, 33%) both as a white solid.

The first peak: $^1$H NMR (400 MHz, DMSO-$d_6$): δ 8.45 (d, J=8.8 Hz, 2H), 8.14 (d, J=5.6 Hz, 1H), 7.54 (d, J=8.8 Hz, 2H), 6.15 (d, J=5.6 Hz, 1H), 5.50 (dd, J=48.4, 3.6 Hz, 1H), 5.32 (dd, J=16.8, 3.6 Hz, 1H), 4.96 (d, J=5.2 Hz, 1H), 4.85-4.72 (m, 2H), 4.62 (t, J=5.6 Hz, 1H), 4.48-4.34 (m, 3H), 4.30-4.17 (m, 2H), 4.16-4.08 (m, 1H), 4.08-4.00 (m, 1H), 3.68-3.62 (m, 1H), 3.43-3.35 (m, 1H), 3.31-3.26 (m, 1H), 2.95-2.85 (m, 1H); LCMS (ESI): m/z 522.2 $(M+H)^+$.

The second peak: $^1$H NMR (400 MHz, DMSO-$d_6$): δ 8.45 (d, J=8.8 Hz, 2H), 8.14 (d, J=5.6 Hz, 1H), 7.54 (d, J=8.8 Hz, 2H), 6.15 (d, J=5.6 Hz, 1H), 5.50 (dd, J=48.4, 3.6 Hz, 1H), 5.32 (dd, J=16.4, 3.6 Hz, 1H), 4.96 (d, J=5.2 Hz, 1H), 4.86-4.72 (m, 2H), 4.63 (t, J=5.6 Hz, 1H), 4.50-4.34 (m, 3H), 4.30-4.17 (m, 2H), 4.16-4.09 (m, 1H), 4.07-3.99 (m, 1H), 3.69-3.61 (m, 1H), 3.43-3.36 (m, 1H), 3.31-3.26 (m, 1H), 2.95-2.85 (m, 1H); LCMS (ESI): m/z 522.1 $(M+H)^+$.

Example 86 (Compound 142)

1-(3-(4-(3,3-Bis(hydroxymethyl)azetidin-1-yl)-1-(4-(trifluoromethoxy)phenyl)-1H-pyrazolo[3,4-b]pyridin-3-yl)azetidin-1-yl)-2-fluoroprop-2-en-1-one

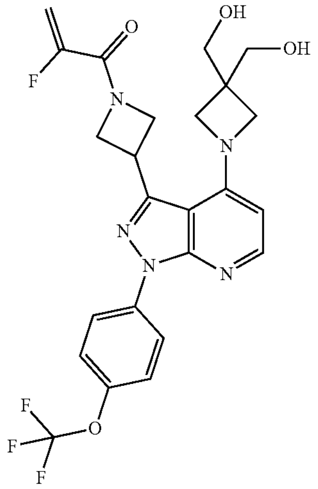 [SMILES: C=C(F)C(=O)N1CC(c2nn(-c3ccc(OC(F)(F)F)cc3)c3nccc(N4CC(CO)(CO)C4)c23)C1]

Step1: tert-butyl 3-(4-(3,3-bis(hydroxymethyl)azetidin-1-yl)-1-(4-(trifluoromethoxy) phenyl)-1H-pyrazolo[3,4-b]pyridin-3-yl)azetidine-1-carboxylate

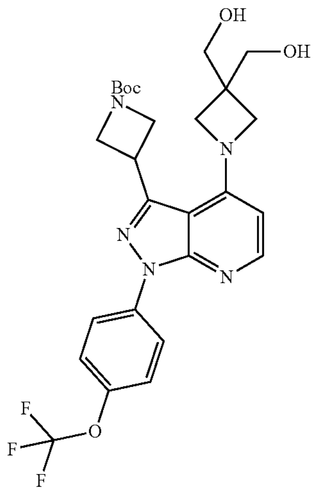 [SMILES: CC(C)(C)OC(=O)N1CC(c2nn(-c3ccc(OC(F)(F)F)cc3)c3nccc(N4CC(CO)(CO)C4)c23)C1]

A solution of tert-butyl 3-(4-chloro-1-(4-(trifluoromethoxy)phenyl)-1H-pyrazolo[3,4-b]pyridin-3-yl)azetidine-1-carboxylate (50 mg, 0.11 mmol), $Cs_2CO_3$ (139 mg, 0.43 mmol), azetidine-3,3-diyldimethanol hydrochloride (33.0 mg, 0.21 mmol) in DMF (5.0 mL) was stirred at 100° C. under $N_2$ atmosphere for 16 h. The reaction mixture was diluted with water (50 mL) and extracted with ethyl acetate (30 mL×3), and the combined organic layers were washed with brine (30 mL×3). The organic layer was dried over $Na_2SO_4$, filtered, and concentrated. The residue was purified by flash column chromatography on silica gel (0-80% ethyl acetate in petroleum ether) to afford the title compound (30.0 mg, 52%) as a yellow solid. $^1H$ NMR (400 MHz, $CDCl_3$): δ 8.29 (d, J=8.8 Hz, 2H), 8.17 (d, J=5.6 Hz, 1H), 7.35 (d, J=8.8 Hz, 2H), 6.02 (d, J=5.6 Hz, 1H), 4.75-4.46 (m, 1H), 4.35-4.33 (m, 2H), 4.18-4.04 (m, 2H), 3.96-3.93 (m, 8H), 3.79-3.25 (m, 2H), 1.46 (s, 9H).

Step 2: (1-(3-(azetidin-3-yl)-1-(4-(trifluoromethoxy)phenyl)-1H-pyrazolo[3,4-b]pyridin-4-yl)azetidine-3,3-diyl)dimethanol

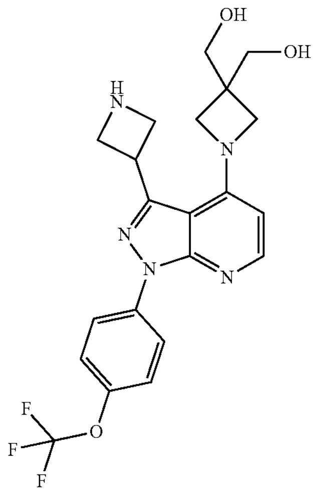 [SMILES: OCC1(CO)CN(c2ccnc3c2c(C2CNC2)nn3-c2ccc(OC(F)(F)F)cc2)C1]

A mixture of tert-butyl 3-(4-(3,3-bis(hydroxymethyl)azetidin-1-yl)-1-(4-(trifluoromethoxy)phenyl)-1H-pyrazolo[3,4-b]pyridin-3-yl)azetidine-1-carboxylate (30 mg, 0.05 mmol) in TFA (5% in HFIP, 5 mL) was stirred at room temperature for 16 h. The reaction mixture was quenched with sat. $NaHCO_3$ to pH=8 and extracted with ethyl acetate (30 mL×3), the combined organic layers were washed with water (20 mL×2), dried over $Na_2SO_4$, filtered, and concentrated to afford the title compound (24 mg, 98%) as a yellow solid. LCMS (ESI): m/z 450.0 $(M+H)^+$.

Step 3: 1-(3-(4-(3,3-bis(hydroxymethyl)azetidin-1-yl)-1-(4-(trifluoromethoxy)phenyl)-1H-pyrazolo[3,4-b]pyridin-3-yl)azetidin-1-yl)-2-fluoroprop-2-en-1-one

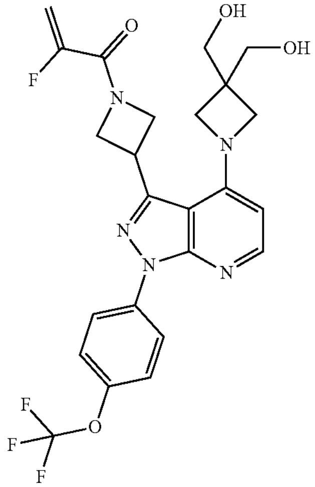 [SMILES: C=C(F)C(=O)N1CC(c2nn(-c3ccc(OC(F)(F)F)cc3)c3nccc(N4CC(CO)(CO)C4)c23)C1]

A mixture of (1-(3-(azetidin-3-yl)-1-(4-(trifluoromethoxy)phenyl)-1H-pyrazolo[3,4-b]pyridin-4-yl)azetidine-3,3-diyl)dimethanol (50 mg, 0.22 mmol), EEDQ (82.0 mg, 0.33 mmol) and 2-fluoroacrylic acid (30 mg, 0.33 mmol) in DCM (1 mL) and methanol (0.20 mL) was stirred at room temperature for 16 h. The reaction mixture was quenched with $H_2O$ (10 mL), and extracted with ethyl acetate (50 mL×3), the combined organic layers were washed with water (50 mL×3), dried over $Na_2SO_4$, filtered and concentrated to dryness. The residue was purified by reverse phase chromatography (Welch Xtimate C18 150*30 mm*5 um, water (0.2% FA)-CAN, 52-82%) to afford the title compound (20.0 mg, 17%) as a white solid. $^1H$ NMR (400 MHz, DMSO-$d_6$): 8.45 (d, J=8.8 Hz, 2H), 8.15 (d, J=5.6 Hz, 1H), 7.54 (d, J=8.8 Hz, 2H), 6.18 (d, J=5.6 Hz, 1H), 5.46 (dd, J=48.4, 3.6 Hz, 1H) 5.35 (dd, J=16.8, 3.6 Hz, 1H), 4.95-4.93 (m, 2H) 4.92-4.91 (m, 2H), 4.50-4.37 (m, 3H), 3.97 (s, 4H), 3.59-3.57 (m, 4H); LCMS (ESI): m/z 522.0 $(M+H)^+$.

Example 87 (Compound 57)

3-Fluoro-1-(3-(1-(2-fluoroacryloyl)azetidin-3-yl)-1-(4-(trifluoromethoxy)phenyl)-1H-pyrazolo[3,4-b]pyridin-4-yl)azetidine-3-carboxamide

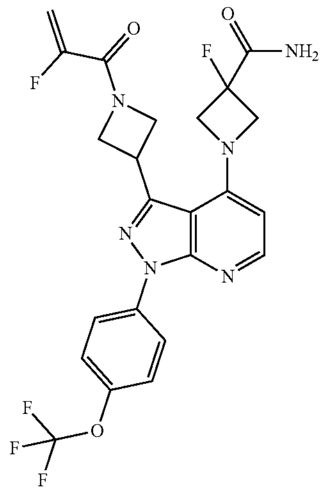 [SMILES: C=C(F)C(=O)N1CC(c2nn(-c3ccc(OC(F)(F)F)cc3)c3nccc(N4CC(F)(C(N)=O)C4)c23)C1]

Step 1: tert-butyl 3-carbamoyl-3-fluoroazetidine-1-carboxylate

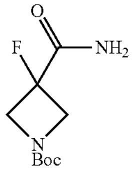

To the solution of 1-tert-butoxycarbonyl-3-fluoro-azetidine-3-carboxylic acid (1.0 g, 4.56 mmol) and one drop of DMF in DCM (30 mL) was added oxalyl dichloride (0.48 mL, 5.70 mmol). The reaction mixture was stirred at 0° C. for 2 h. Then $NH_3{\cdot}H_2O$ (2.50 mL, 22.8 mmol) was added at 0° C., the resulting solution was stirred at 0° C. for 30 min. The reaction was allowed to warm to room temperature. After stirring for 1 h, the mixture was diluted with water (50 mL) and extracted with DCM (50 mL×3). The combined organic layers were dried over anhydrous sodium sulfate, filtered, and concentrated to afford the title compound (680 mg, 68%) as a white solid. The crude would be used in the next step directly. $^1$H NMR (400 MHz, DMSO-$d_6$) δ 7.86 (s, 1H), 7.73 (s, 1H), 4.23-4.16 (m, 2H), 4.06-3.95 (m, 2H), 1.39 (s, 9H).

Step 2: 3-fluoroazetidine-3-carboxamide 2,2,2-trifluoroacetate salt

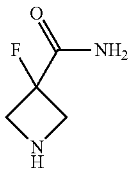

A solution of tert-butyl 3-carbamoyl-3-fluoroazetidine-1-carboxylate (480 mg, 2.20 mmol) in TFA (5% in HFIP, 10 mL) was stirred at room temperature for 1 h. The reaction was concentrated to afford the title compound (480 mg) as a yellow oil. The crude was used for next step directly.

Step 3: tert-butyl 3-(4-(3-carbamoyl-3-fluoroazetidin-1-yl)-1-(4-(trifluoromethoxy)phenyl)-1H-pyrazolo[3,4-b]pyridin-3-yl)azetidine-1-carboxylate

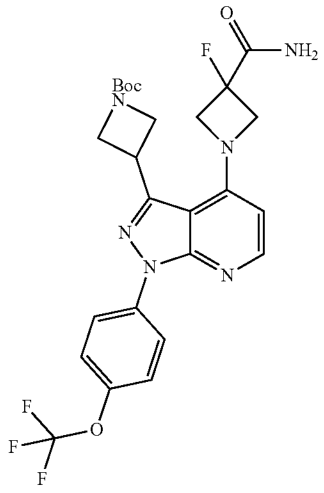 [SMILES: CC(C)(C)OC(=O)N1CC(c2nn(-c3ccc(OC(F)(F)F)cc3)c3nccc(N4CC(F)(C(N)=O)C4)c23)C1]

A solution of tert-butyl 3-(4-chloro-1-(4-(trifluoromethoxy)phenyl)-1H-pyrazolo[3,4-b]pyridin-3-yl)azetidine-1-carboxylate (200 mg, 0.43 mmol), $Cs_2CO_3$ (560 mg, 1.71 mmol), 3-fluoroazetidine-3-carboxamide 2,2,2-trifluoroacetate salt (198 mg, 0.85 mmol) in DMF (10 mL) was stirred at 100° C. under $N_2$ atmosphere for 16 h. The reaction mixture was diluted with water (100 mL) and extracted with ethyl acetate (50 mL×3), the combined organic layers were washed with brine (50 mL×3). The organic layer was dried over $Na_2SO_4$, filtered, and concentrated in vacuo. The residue was purified by prep-TLC (50% ethyl acetate in petroleum ether) to afford the title compound (80.0 mg, 34%) as a yellow oil. LCMS (ESI): m/z 495.2 (M−56+H)

Step 4: 1-(3-(azetidin-3-yl)-1-(4-(trifluoromethoxy) phenyl)-1H-pyrazolo[3,4-b]pyridin-4-yl)-3-fluoro-azetidine-3-carboxamide

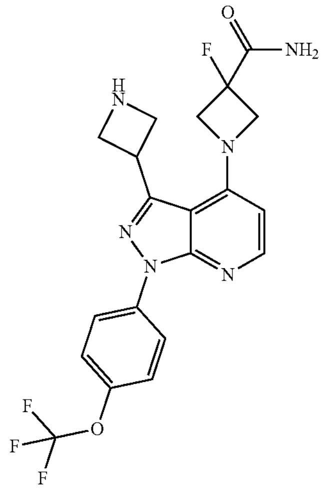 [SMILES: NC(=O)C1(F)CN(c2ccnc3c2c(C2CNC2)nn3-c2ccc(OC(F)(F)F)cc2)C1]

A solution of tert-butyl 3-(4-(3-carbamoyl-3-fluoro azetidin-1-yl)-1-(4-(trifluoromethoxy)phenyl)-1H-pyrazolo[3,4-b]pyridin-3-yl)azetidine-1-carboxylate (80.0 mg, 0.15 mmol) in TFA (5% in HFIP, 5 mL) was stirred at room temperature for 2 h. The reaction was diluted with water (30 mL) and adjusted to pH=8 with sat. $NaHCO_3$, the mixture was extracted with ethyl acetate (20 mL×3). The combined organic layers were dried over $Na_2SO_4$, filtered, and concentrated to afford the title compound (98 mg, crude) as a yellow oil. The crude was used for next step directly.

Step 5: 3-fluoro-1-(3-(1-(2-fluoroacryloyl)azetidin-3-yl)-1-(4-(trifluoromethoxy)phenyl)-1H-pyrazolo[3,4-b]pyridin-4-yl)azetidine-3-carboxamide

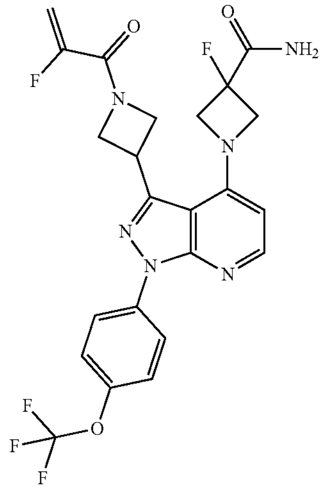 [SMILES: C=C(F)C(=O)N1CC(c2nn(-c3ccc(OC(F)(F)F)cc3)c3nccc(N4CC(F)(C(N)=O)C4)c23)C1]

To a solution of 1-(3-(azetidin-3-yl)-1-(4-(trifluoromethoxy)phenyl)-1H-pyrazolo[3,4-b]pyridin-4-yl)-3-fluoroazetidine-3-carboxamide (97.0 mg, 0.22 mmol) and 2-fluoroacrylic acid (29.0 mg, 0.32 mmol) in DCM (5 mL) was added EEDQ (107 mg, 0.43 mmol) at 0° C., the resulting solution was stirred at 0° C. for 1 h. The mixture was diluted with water (20 mL) and extracted with DCM (15 mL×3). The combined organic layers were dried over anhydrous sodium sulfate, filtered, and concentrated. The residue was purified by reverse phase chromatography (Welch Xtimate C18 150*30 mm*5 um, water (0.2% FA)-ACN, 54-84%) to afford the title compound (25.0 mg, 22%) as a white solid. $^1H$ NMR (400 MHz, DMSO-$d_6$): δ 8.44 (d, J=9.2 Hz, 2H), 8.25 (d, J=5.6 Hz, 1H), 7.98 (s, 1H), 7.83 (s, 1H), 7.56 (d, J=8.4 Hz, 2H), 6.34 (d, J=5.6 Hz, 1H), 5.50 (dd, J=48.8, 3.6 Hz, 1H), 5.31 (dd, J=16.8, 3.6 Hz, 1H), 4.88-4.81 (m, 1H), 4.74-4.53 (m, 4H), 4.50-4.30 (m, 4H); LCMS (ESI): m/z 523.1 $(M+H)^+$.

Example 88 (Compound 64)

1-(3-(4-(1H-Imidazol-1-yl)-1-(4-(trifluoromethoxy) phenyl)-1H-pyrazolo[3,4-b]pyridin-3-yl)azetidin-1-yl)-2-fluoroprop-2-en-1-one

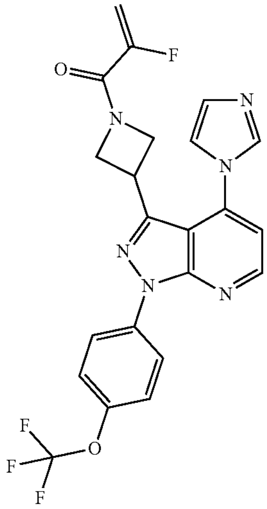 [SMILES: C=C(F)C(=O)N1CC(c2nn(-c3ccc(OC(F)(F)F)cc3)c3nccc(-n4ccnc4)c23)C1]

Step 1: tert-butyl 3-(4-(1H-imidazol-1-yl)-1-(4-(trifluoromethoxy)phenyl)-1H-pyrazolo[3,4-b]pyridin-3-yl)azetidine-1-carboxylate

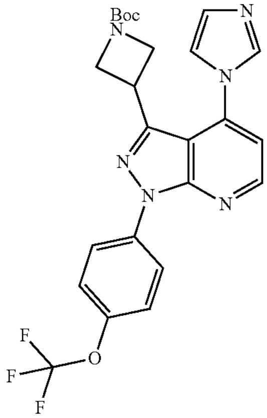 [SMILES: CC(C)(C)OC(=O)N1CC(c2nn(-c3ccc(OC(F)(F)F)cc3)c3nccc(-n4ccnc4)c23)C1]

To a solution of tert-butyl 3-(4-chloro-1-(4-(trifluoromethoxy)phenyl)-1H-pyrazolo[3,4-b]pyridin-3-yl)azetidine-1-carboxylate (200 mg, 0.43 mmol) in DMF (2 mL) was added CuO (17.0 mg, 0.21 mmol), imidazole (44.0 mg, 0.64 mmol) and $K_2CO_3$ (147 mg, 1.07 mmol) at room temperature. The resulting solution was stirred at 120° C. for 20 h under $N_2$ atmosphere. The reaction was quenched by water (80 mL). The mixture was extracted with ethyl acetate (60 mL×3) and washed with brine (80 mL). The organic layers were dried over $Na_2SO_4$, filtered, and concentrated to dryness. The residue was purified by column chromatography on silica gel (0-10% methyl alcohol in dichloromethane) to afford the title compound (175 mg, 84%) as a white solid. $^1H$ NMR (400 MHz, $CDCl_3$): δ 8.72 (d, J=4.8 Hz, 1H), 8.39 (d, J=9.2 Hz, 2H), 7.78 (s, 1H), 7.42 (d, J=8.8 Hz, 2H), 7.38 (s, 1H), 7.25 (s, 1H), 7.17 (d, J=4.8 Hz, 1H), 4.25-4.18 (m, 2H), 4.05-4.01 (m, 2H), 3.83-3.75 (m, 1H), 1.43 (s, 9H).

Step 2: 3-(azetidin-3-yl)-4-(1H-imidazol-1-yl)-1-(4-(trifluoromethoxy)phenyl)-1H-pyrazolo[3,4-b]pyridine

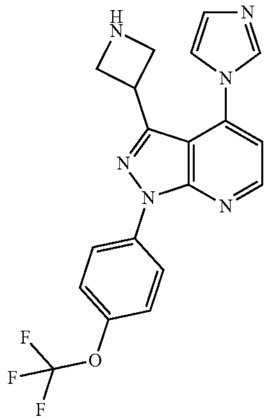

A mixture of tert-butyl 3-(4-(1H-imidazol-1-yl)-1-(4-(trifluoromethoxy)phenyl)-1H-pyrazolo[3,4-b]pyridin-3-yl) azetidine-1-carboxylate (150 mg, 0.30 mmol) in TFA (5% in HFIP, 2.0 mL) was stirred at room temperature for 1 h. Then TFA (0.1 mL) was added into the mixture and the solution was stirred at room temperature for 1 h. The reaction mixture was adjusted to pH=8 with sat. $NaHCO_3$. The resulting solution was extracted with ethyl acetate (30 mL×3). The combined organic layers were dried over $Na_2SO_4$. After filtration, the mixture was concentrated to afford the title compound (115 mg, 96%) as a yellow solid. LCMS (ESI): m/z 401.2 $(M+H)^+$.

Step 3: 1-(3-(4-(1H-imidazol-1-yl)-1-(4-(trifluoromethoxy)phenyl)-1H-pyrazolo[3,4-b]pyridin-3-yl) azetidin-1-yl)-2-fluoroprop-2-en-1-one

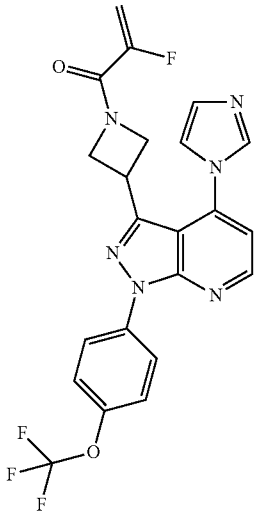 [SMILES: C=C(F)C(=O)N1CC(c2nn(-c3ccc(OC(F)(F)F)cc3)c3nccc(-n4ccnc4)c23)C1]

To a solution of 2-fluoroacrylic acid (31.0 mg, 0.34 mmol), 3-(azetidin-3-yl)-4-(1H-imidazol-1-yl)-1-(4-(trifluoromethoxy)phenyl)-1H-pyrazolo[3,4-b]pyridine (115 mg, 0.29 mmol) in DCM (4 mL) and MeOH (1 mL) was added EEDQ (142 mg, 0.57 mmol) at 0° C. and the solution was stirred at room temperature with 16 h. The reaction was quenched by water (30 mL). The resulting solution was extracted with ethyl acetate (30 mL×3), the organic layers were combined and dried over $Na_2SO_4$. After filtration, the filtrate was concentrated under reduced pressure. The resulting residue was purified by reverse phase chromatography (Welch Xtimate C18 150*30 mm*5 um, acetonitrile 44-74%/water (FA)-ACN) to afford the title compound (60.9 mg, 45%) as a white solid. $^1H$ NMR (400 MHz, DMSO-$d_6$): δ 8.82 (d, J=4.8 Hz, 1H), 8.43 (d, J=8.8 Hz, 2H), 8.20 (s, 1H), 7.76 (s, 1H), 7.63 (d, J=8.8 Hz, 2H), 7.49 (d, J=4.8 Hz, 1H), 7.29 (s, 1H), 5.43 (dd, J=48.8, 3.6 Hz, 1H), 5.26 (dd, J=16.4, 3.6 Hz, 1H), 4.62-4.55 (m, 1H), 4.44-4.37 (m, 1H), 4.16-4.07 (m, 2H), 3.98-3.90 (m, 1H); LCMS (ESI): m/z 473.0 $(M+H)^+$ Example 89 (Compound 50)

(E)-1-(3-(4-(1H-Pyrazol-4-yl)-1-(4-(trifluoromethoxy)phenyl)-1H-pyrazolo[3,4-b]pyridin-3-yl)azetidin-1-yl)-4-hydroxybut-2-en-1-one

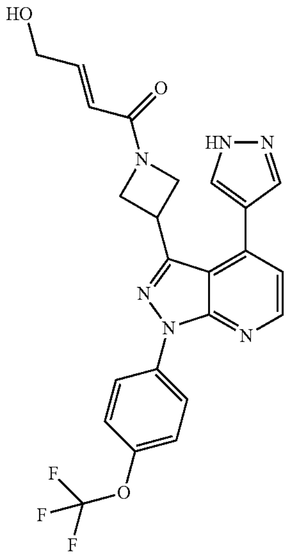 [SMILES: O=C(/C=C/CO)N1CC(c2nn(-c3ccc(OC(F)(F)F)cc3)c3nccc(-c4cn[nH]c4)c23)C1]

Step 1: tert-butyl 3-(4-(1H-pyrazol-4-yl)-1-(4-(trifluoromethoxy)phenyl)-1H-pyrazolo[3,4-b]pyridin-3-yl)azetidine-1-carboxylate

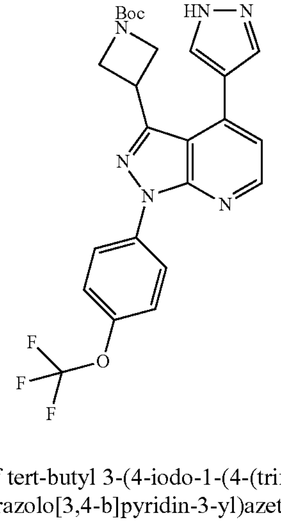

A mixture of tert-butyl 3-(4-iodo-1-(4-(trifluoromethoxy)phenyl)-1H-pyrazolo[3,4-b]pyridin-3-yl)azetidine-1-carboxylate (500 mg, 0.89 mmol), $Na_2CO_3$ (189 mg, 1.78 mmol), 4-(4,4,5,5-tetramethyl-1,3,2-dioxaborolan-2-yl)-1H-pyrazole (346 mg, 1.78 mmol) and Pd (dppf)$Cl_2$ (131 mg, 0.18 mmol) in 1,4-dioxane (10 mL) and water (1 mL) was stirred at 80° C. for 3 h under N2 atmosphere. The reaction was diluted with water (100 mL) and extracted with ethyl acetate (100 mL×3). The combined organic layers were dried over $Na_2SO_4$, filtered, and concentrated in vacuo. The residue was purified by column chromatography on silica gel (0-60% ethyl acetate in petroleum ether) to afford the title compound (370 mg, 83%) as a yellow oil. $^1$H NMR (400 MHz, DMSO-$d_6$): δ 13.37 (s, 1H), 8.62 (d, J=4.8 Hz, 1H), 8.46 (d, J=9.2 Hz, 2H), 8.24 (s, 1H), 7.89 (s, 1H), 7.60 (d, J=8.4 Hz, 2H), 7.28 (d, J=4.8 Hz, 1H), 4.33-4.21 (m, 1H), 3.95-3.93 (m, 2H), 3.92-3.75 (m, 2H), 1.34 (s, 9H).

Step 2: 3-(azetidin-3-yl)-4-(1H-pyrazol-4-yl)-1-(4-(trifluoromethoxy)phenyl)-1H-pyrazolo[3,4-b]pyridine

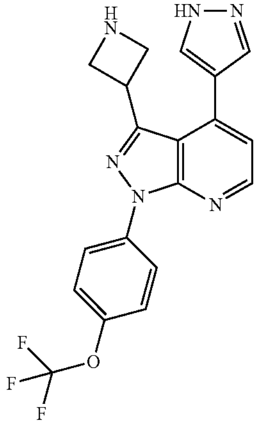 [SMILES: FC(F)(F)Oc1ccc(-n2nc(C3CNC3)c3c(-c4cn[nH]c4)ccnc32)cc1]

A solution of tert-butyl 3-(4-(1H-pyrazol-4-yl)-1-(4-(trifluoromethoxy)phenyl)-1H-pyrazolo[3,4-b]pyridin-3-yl)azetidine-1-carboxylate (350 mg, 0.70 mmol) in TFA (5% in HFIP, 10.0 mL) was stirred at room temperature for 1 h. The mixture was quenched with water (5.0 mL), then adjusted to pH=8 with aq.$NaHCO_3$ solution and diluted with ethyl acetate (100 mL) and washed with water (100 mL×3). The organic was dried over $Na_2SO_4$, filtered, and concentrated to afford the title compound (200 mg, 71%) as a white solid. LCMS (ESI): m/z 401.2 $(M+H)^+$.

Step 3: (E)-1-(3-(4-(1H-pyrazol-4-yl)-1-(4-(trifluoromethoxy)phenyl)-1H-pyrazolo[3,4-b]pyridin-3-yl)azetidin-1-yl)-4-hydroxybut-2-en-1-one

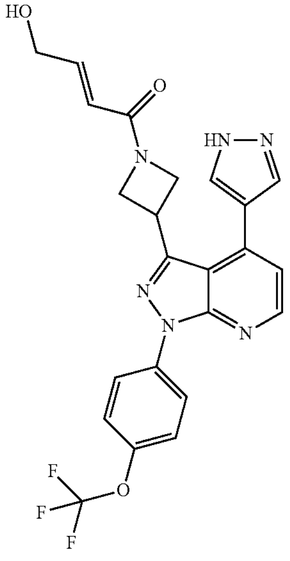 [SMILES: O=C(/C=C/CO)N1CC(c2nn(-c3ccc(OC(F)(F)F)cc3)c3nccc(-c4cn[nH]c4)c23)C1]

To a mixture of 3-(azetidin-3-yl)-4-(1H-pyrazol-4-yl)-1-(4-(trifluoromethoxy)phenyl)-1H-pyrazolo[3,4-b]pyridine (200 mg, 0.50 mmol) in DCM (5.0 mL) and MeOH (1.0 mL) was added (E)-4-hydroxybut-2-enoic acid (102 mg, 1.0 mmol) and EEDQ (371 mg, 1.5 mmol) at 0° C. Then the reaction was stirred at room temperature for 16 h. The mixture was diluted with ethyl acetate (100 mL) and washed with water (100 mL×3). The organic was dried over $Na_2SO_4$, filtered, and concentrated. The residue was purified by column chromatography on silica gel (Welch Xtimate C18 150*30 mm*5 um, water (0.2% FA)-ACN, 41-71%) to afford the title compound (58.7 mg, 24%) as a white solid. $^1H$ NMR (400 MHz, DMSO-$d_6$): δ 13.39 (s, 1H), 8.63 (d, J=4.8 Hz, 1H), 8.46 (d, J=8.8 Hz, 2H), 8.26 (s, 1H), 7.92 (s, 1H), 7.60 (d, J=8.8 Hz, 2H), 7.29 (d, J=4.8 Hz, 1H), 6.74-6.64 (m, 1H), 6.07 (d, J=15.2 Hz, 1H), 5.02 (t, J=5.6 Hz, 1H), 4.50-4.43 (m, 1H), 4.40-4.22 (m, 2H), 4.12-4.07 (m, 2H), 4.03-3.97 (m, 1H), 3.92-3.82 (m, 1H); LCMS (ESI): m/z 485.0 $(M+H)^+$.

Example 90 (Compound 45)

1-(3-(4-(1-(2-(Dimethylamino)ethyl)-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one

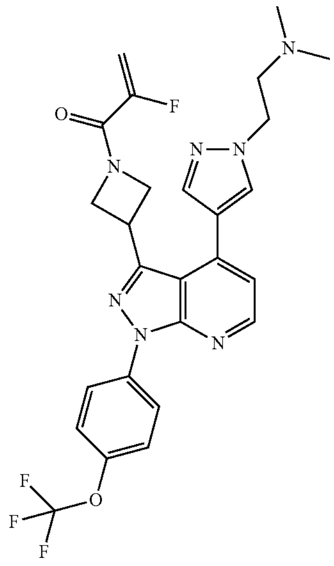 [SMILES: C=C(F)C(=O)N1CC(c2nn(-c3ccc(OC(F)(F)F)cc3)c3nccc(-c4cnn(CCN(C)C)c4)c23)C1]

Step1: N,N-dimethyl-2-(4-(4,4,5,5-tetramethyl-1,3,2-dioxaborolan-2-yl)-1H-pyrazol-1-yl)ethan-1-amine

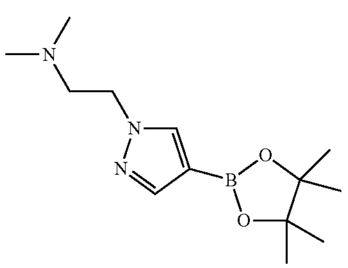

4-(4,4,5,5-Tetramethyl-1,3,2-dioxaborolan-2-yl)-1H-pyrazole (1.00 g, 5.15 mmol), $Cs_2CO_3$ (3.36 g, 10.31 mmol) and 2-chloro-N,N-dimethylethanamine hydrochloride (1.11 g, 7.73 mmol) were suspended in acetonitrile (15 mL) and the mixture was heated at reflux for 5 h. The reaction mixture was cooled to room temperature, diluted with ethyl acetate (100 mL) and filtered. The filtrate was concentrated in vacuo to afford the crude title compound (1.37 g, 100%) as an amber oil which was used in the next step without further purification.

$^1H$ NMR (400 MHz, DMSO-$d_6$): δ 7.93 (s, 1H), 7.55 (s, 1H), 4.18 (t, J=6.0 Hz, 2H), 2.60 (t, J=6.0 Hz, 2H), 2.13 (s, 6H), 1.24 (s, 12H).

Step 2: tert-butyl 3-(4-(1-(2-(dimethylamino)ethyl)-1H-pyrazol-4-yl)-1-(4-(trifluoromethoxy)phenyl)-1H-pyrazolo[3,4-b]pyridin-3-yl)azetidine-1-carboxylate

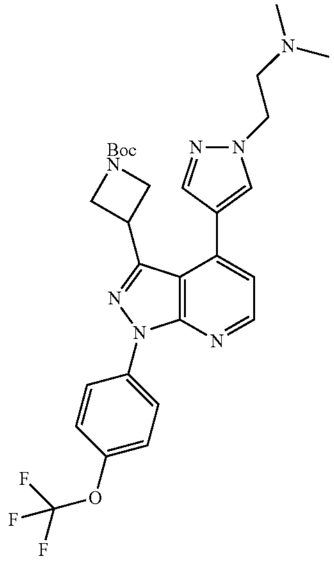 [SMILES: CN(C)CCn1cc(-c2ccnc3c2c(C2CN(C(=O)OC(C)(C)C)C2)nn3-c2ccc(OC(F)(F)F)cc2)cn1]

A mixture of $K_3PO_4$ (379 mg, 1.78 mmol), tert-butyl 3-(4-iodo-1-(4-(trifluoromethoxy)phenyl)-1H-pyrazolo[3,4-b]pyridin-3-yl)azetidine-1-carboxylate (500 mg, 0.89 mmol), N,N-dimethyl-4-(4,4,5,5-tetramethyl-1,3,2-dioxaborolan-2-yl)-1H-pyrazole-1-ethanamine (473 mg, 1.78 mmol) and Pd(dppf)$Cl_2$ (65.0 mg, 0.09 mmol) in 1,4-dioxane (10 mL) and water (2 mL) was stirred at 100° C. for 2 h under $N_2$ atmosphere. The mixture was quenched with water (100 mL) and extracted with ethyl acetate (100 mL×2). The organic was dried over $Na_2SO_4$, filtered, and concentrated. The residue was purified by column chromatography on silica gel (0-15% MeOH in DCM) to afford the title compound (440 mg, 86%) as a white solid. $^1H$ NMR (400 MHz, DMSO-$d_6$): δ 8.62 (d, J=4.8 Hz, 1H), 8.47 (d, J=8.8 Hz, 2H), 8.21 (s, 1H), 7.84 (s, 1H), 7.60 (d, J=8.8 Hz, 2H), 7.26 (d, J=4.8 Hz, 1H), 4.35-4.30 (m, 3H), 4.05-3.96 (m, 4H), 2.50-2.47 (m, 2H), 2.24 (s, 6H), 1.34 (s, 9H).

Step 3: 2-(4-(3-(azetidin-3-yl)-1-(4-(trifluoromethoxy)phenyl)-1H-pyrazolo[3,4-b]pyridin-4-yl)-1H-pyrazol-1-yl)-N,N-dimethylethan-1-amine

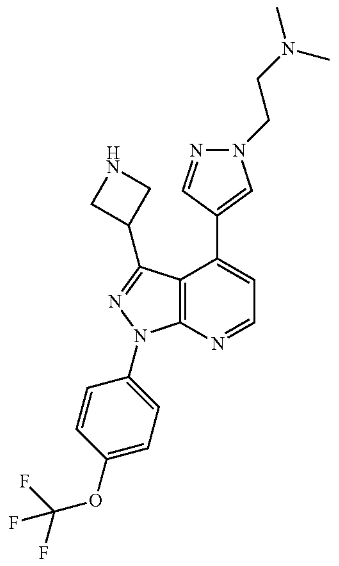 [SMILES: CN(C)CCn1cc(-c2ccnc3c2c(C2CNC2)nn3-c2ccc(OC(F)(F)F)cc2)cn1]

The mixture of ter t-butyl 3-(4-(1-(2-(dimethyl amino) ethyl)-1H-pyrazol-4-yl)-1-(4-(trifluoromethoxy)phenyl)-1H-pyrazolo[3,4-b]pyridin-3-yl)azetidine-1-carboxylate (500 mg, 0.87 mmol) in TFA (5% in HFIP 10 mL) was stirred at room temperature for 16 h. The mixture was quenched with sat. $NaHCO_3$ solution to pH=8, extracted with ethyl acetate (200 mL) and washed with water (100 mL×3). The organic was dried over $Na_2SO_4$, filtered, and concentrated to afford the title compound (400 mg, 97%) as a yellow oil. LCMS (ESI): m/z 472.1 $(M+H)^+$.

Step4: 1-(3-(4-(1-(2-(dimethylamino)ethyl)-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one

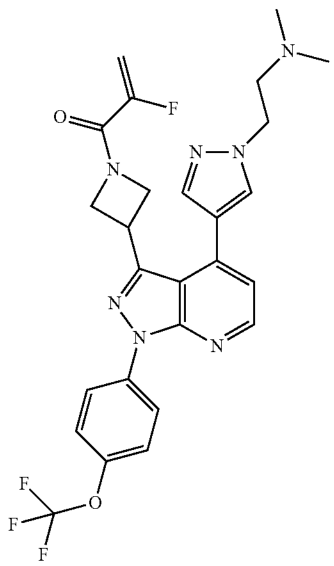 [SMILES: C=C(F)C(=O)N1CC(c2nn(-c3ccc(OC(F)(F)F)cc3)c3nccc(-c4cnn(CCN(C)C)c4)c23)C1]

To the mixture of 2-fluoroacrylic acid (109 mg, 1.21 mmol) and EEDQ (299 mg, 1.21 mmol) in DCM (4.0 mL) and MeOH (1.0 mL) was added 2-(4-(3-(azetidin-3-yl)-1-(4-(trifluoromethoxy)phenyl)-1H-pyrazolo[3,4-b]pyridin-4-yl)-1H-pyrazol-1-yl)-N,N-dimethylethan-1-amine (380 mg, 0.81 mmol) was added at 0° C. The mixture was stirred at room temperature for 16 h. The mixture was diluted with ethyl acetate (50 mL) and washed with water (50 mL×3). The organic was dried over $Na_2SO_4$, filtered, and concentrated to dryness. The residue was purified by reverse phase chromatography (Boston Green ODS 150*30 mm*5 um, water (0.2% FA)-ACN, 30-60%) to afford the title compound (41.0 mg, 9%) as a white solid. $^1H$ NMR (400 MHz, DMSO-$d_6$): δ 8.64 (d, J=4.8 Hz, 1H), 8.49-8.44 (m, 2H), 8.24 (s, 1H), 7.84 (s, 1H), 7.60 (d, J=8.4 Hz, 2H), 7.28 (d, J=4.8 Hz, 1H), 5.42 (dd, J=48.8, 3.6 Hz, 1H), 5.26 (dd, J=16.8, 3.6 Hz, 1H), 4.54-4.52 (m, 1H), 4.50-4.43 (m, 2H), 4.33 (t, J=6.0 Hz, 2H), 4.17-4.10 (m, 2H), 2.73 (t, J=6.0 Hz, 2H), 2.22 (s, 6H); LCMS (ESI): m/z 544.0 $(M+H)^+$.

Example 91 (Compound 28)

2-Fluoro-1-(3-(4-(1-(2-hydroxyethyl)-1H-pyrazol-4-yl)-1-(4-(trifluoromethoxy)phenyl)-1H-pyrazolo[3,4-b]pyridin-3-yl)azetidin-1-yl)prop-2-en-1-one

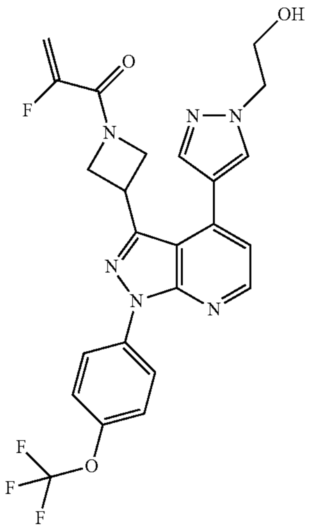 [SMILES: C=C(F)C(=O)N1CC(c2nn(-c3ccc(OC(F)(F)F)cc3)c3nccc(-c4cnn(CCO)c4)c23)C1]

Step 1: 2-(4-(4,4,5,5-tetramethyl-1,3,2-dioxaborolan-2-yl)-1H-pyrazol-1-yl)ethanol

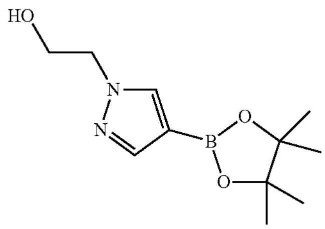 [SMILES: CC1(C)OB(c2cnn(CCO)c2)OC1(C)C]

A mixture of 4-(4,4,5,5-Tetramethyl-1,3,2-dioxaborolan-2-yl)-1H-pyrazole (1.0 g, 5.15 mmol), $Cs_2CO_3$ (5.0 g, 15.5 mmol) and 2-bromoethanol (0.73 mL, 10.3 mmol) in DMF (10 mL) was stirred at 70° C. with 16 h. The reaction mixture was diluted with ethyl acetate (100 mL), washed with brine (300 mL×3), dried over $Na_2SO_4$, filtered, and concentrated to dryness to afford the title compound (650 mg, 53%) as a colorless oil. $^1H$ NMR (400 MHz, $CDCl_3$): δ 7.81 (s, 1H), 7.74 (s, 1H), 4.27-4.25 (m, 2H), 4.00-3.98 (m, 2H), 1.32 (s, 12H).

Step 2: tert-butyl 3-(4-(1-(2-hydroxyethyl)-1H-pyrazol-4-yl)-1-(4-(trifluoromethoxy)phenyl)-1H-pyrazolo[3,4-b]pyridin-3-yl)azetidine-1-carboxylate

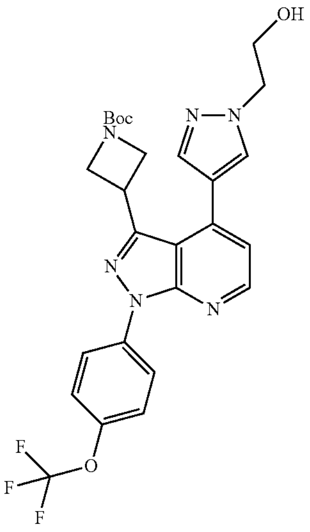 [SMILES: CC(C)(C)OC(=O)N1CC(c2nn(-c3ccc(OC(F)(F)F)cc3)c3nccc(-c4cnn(CCO)c4)c23)C1]

A mixture of tert-butyl 3-(4-iodo-1-(4-(trifluoromethoxy)phenyl)-1H-pyrazolo[3,4-b]pyridin-3-yl)azetidine-1-carboxylate (100 mg, 0.18 mmol), 2-(4-(4,4,5,5-tetramethyl-1,3,2-dioxaborolan-2-yl)-1H-pyrazol-1-yl)ethanol (85.0 mg, 0.36 mmol), Pd(dppf)$Cl_2$ (13.0 mg, 0.02 mmol) and $K_3PO_4$ (113 mg, 0.54 mmol) in 1,4-dioxane (2 mL) and water (0.2 mL) was stirred at 100° C. for 5 h under $N_2$ atmosphere. The reaction mixture was diluted with ethyl acetate (50 mL), washed with brine (60 mL×3), dried over $Na_2SO_4$, filtered, and concentrated to dryness. The residue was purified by prep-TLC (50% ethyl acetate in petroleum ether) to afford the title compound (30.0 mg, 31%) as a white solid. LCMS (ESI): m/z 545.3 $(M+H)^+$.

Step 3: 2-(4-(3-(azetidin-3-yl)-1-(4-(trifluoromethoxy)phenyl)-1H-pyrazolo[3,4-b]pyridin-4-yl)-1H-pyrazol-1-yl)ethanol

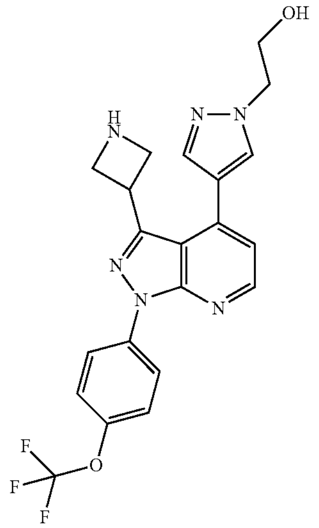 [SMILES: OCCn1cc(-c2ccnc3c2c(C2CNC2)nn3-c2ccc(OC(F)(F)F)cc2)cn1]

A mixture of tert-butyl 3-(4-(1-(2-hydroxyethyl)-1H-pyrazol-4-yl)-1-(4-(trifluoromethoxy)phenyl)-1H-pyrazolo[3,4-b]pyridin-3-yl)azetidine-1-carboxylate (30.0 mg, 0.06 mmol) in TFA (5% in HFIP, 2 mL) was stirred at room temperature for 16 h. The reaction mixture was diluted with water (60 mL) and adjusted to pH=8 by sat. $NaHCO_3$. The reaction mixture was extracted with ethyl acetate (30 mL×2). The combined organic layers were washed with brine (60 mL×2), dried over $Na_2SO_4$, filtered, and concentrated to dryness to afford the title compound (20.0 mg, 82%). The crude product would be directly used in the next step without purification. LCMS (ESI): m/z 445.1 $(M+H)^+$.

Step 4: 2-fluoro-1-(3-(4-(1-(2-hydroxyethyl)-1H-pyrazol-4-yl)-1-(4-(trifluoromethoxy)phenyl)-1H-pyrazolo[3,4-b]pyridin-3-yl)azetidin-1-yl)prop-2-en-1-one

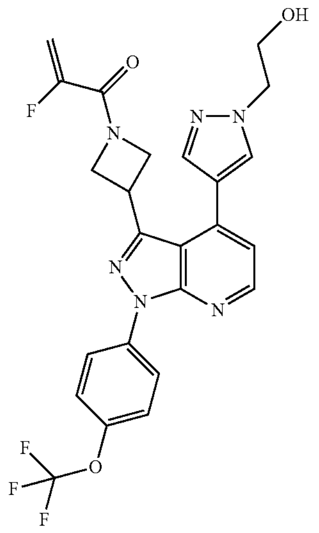 [SMILES: C=C(F)C(=O)N1CC(c2nn(-c3ccc(OC(F)(F)F)cc3)c3nccc(-c4cnn(CCO)c4)c23)C1]

To a solution of 2-(4-(3-(azetidin-3-yl)-1-(4-(trifluoromethoxy)phenyl)-1H-pyrazolo[3,4-b]pyridin-4-yl)-1H-pyrazol-1-yl)ethanol (80.0 mg, 0.18 mmol) and 2-fluoroacrylic acid (25.0 mg, 0.27 mmol) in DCM (3 mL) was added EEDQ (89.0 mg, 0.36 mmol) at 0° C. The resulting solution was stirred at room temperature for 16 h. The reaction mixture was diluted with ethyl acetate (50 mL), washed with brine (60 mL×3), dried over $Na_2SO_4$. After filtration, the filtrate was concentrated to dryness and purified by reverse phase chromatography (Welch Xtimate C18 150*30 mm*5 um, acetonitrile 49-79%/water (0.225% FA)-ACN) to afford the title compound (37.6 mg, 40%) as a white solid. $^1H$ NMR (400 MHz, DMSO-$d_6$): δ 8.62 (d, J=4.8 Hz, 1H), 8.46 (d, J=8.8 Hz, 2H), 8.19 (s, 1H), 7.87 (s, 1H), 7.60 (d, J=8.8 Hz, 2H), 7.27 (d, J=4.8 Hz, 1H), 5.42 (dd, J=48.4, 3.2 Hz, 1H), 5.26 (dd, J=16.4, 3.2 Hz, 1H), 5.04 (t, J=4.8 Hz, 1H), 4.57-4.47 (m, 2H), 4.45-4.40 (m, 1H), 4.29 (t, J=5.6 Hz, 2H), 4.18-4.07 (m, 2H), 3.83 (q, J=5.2 Hz, 2H); LCMS (ESI): m/z 517.0 $(M+H)^+$.

Example 92 (Compound 130)

1-(3-(4-(1H-Imidazol-4-yl)-1-(4-(trifluoromethoxy)phenyl)-1H-pyrazolo[3,4-b]pyridin-3-yl)azetidin-1-yl)-2-fluoroprop-2-en-1-one

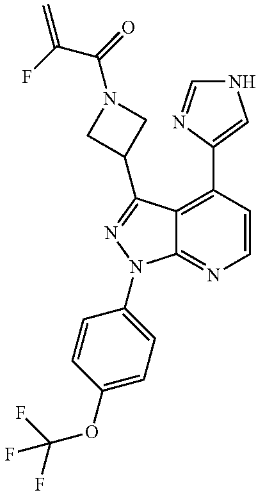 [SMILES: C=C(F)C(=O)N1CC(c2nn(-c3ccc(OC(F)(F)F)cc3)c3nccc(-c4c[nH]cn4)c23)C1]

Step 1: tert-butyl 3-(1-(4-(trifluoromethoxy)phenyl)-4-(1-trityl-1H-imidazol-4-yl)-1H-pyrazolo[3,4-b]pyridin-3-yl)azetidine-1-carboxylate

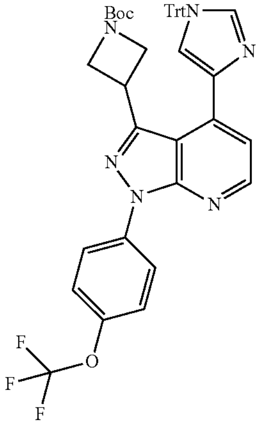

A solution of ter-butyl 3-(4-iodo-1-(4-(trifluoromethoxy)phenyl)-1H-pyrazolo[3,4-b]pyridin-3-yl)azetidine-1-carboxylate (100 mg, 0.18 mmol), KOAc (35.0 mg, 0.36 mmol), (1-trityl-1H-imidazol-4-yl)boronic acid (190 mg, 0.54 mmol) and Pd(dppf)$Cl_2$ (13.0 mg, 0.02 mmol) in 1,4-dioxane (10 mL) and water (1 mL) was stirred at 100° C. for 16 h under $N_2$ atmosphere. The reaction mixture diluted with water (20 mL), extracted with ethyl acetate (20 mL×2). The combined organics were concentrated to dryness. The residue was purified by flash chromatography on silica gel (0-100% ethyl acetate in petroleum ether) to afford the title compound (100 mg, 75%) as a brown solid. LCMS (ESI): m/z 743.4 $(M+H)^+$.

Step 2: 3-(azetidin-3-yl)-4-(1H-imidazol-4-yl)-1-(4-(trifluoromethoxy)phenyl)-1H-pyrazolo[3,4-b]pyridine 2,2,2-trifluoroacetate salt

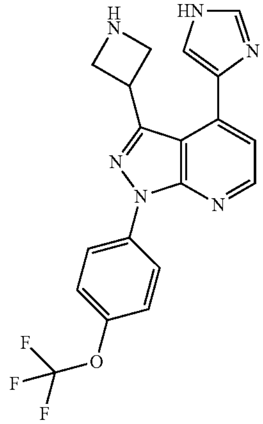 [SMILES: FC(F)(F)Oc1ccc(-n2nc(C3CNC3)c3c(-c4c[nH]cn4)ccnc32)cc1]

A mixture of tert-butyl 3-(1-(4-(trifluoromethoxy)phenyl)-4-(1-trityl-1H-imidazol-4-yl)-1H-pyrazolo[3,4-b]pyridin-3-yl)azetidine-1-carboxylate (50.0 mg, 0.10 mmol) in TFA (5% in HFIP 5 mL) was stirred at room temperature for 1 h. The mixture was concentrated to afford the title compound (50.0 mg, 100%) as a yellow oil. The crude would be used in the next step directly.

Step 3: 1-(3-(4-(1H-imidazol-4-yl)-1-(4-(trifluoromethoxy)phenyl)-1H-pyrazolo[3,4-b]pyridin-3-yl)azetidin-1-yl)-2-fluoroprop-2-en-1-one

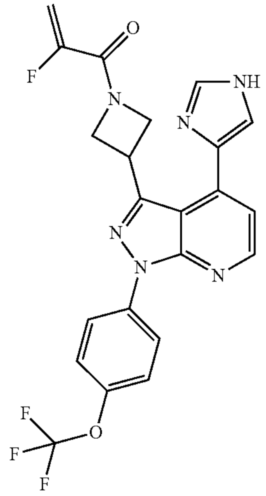 [SMILES: C=C(F)C(=O)N1CC(c2nn(-c3ccc(OC(F)(F)F)cc3)c3nccc(-c4c[nH]cn4)c23)C1]

The solution of 2-fluoroacrylic acid (113 mg, 1.26 mmol) in anhydrous DMF (15 mL) was added DIPEA (0.624 mL, 3.77 mmol) and HATU (670 mg, 1.76 mmol). The resulted mixture was stirred at room temperature for 5 min, then 3-(azetidin-3-yl)-4-(1H-imidazol-4-yl)-1-(4-(trifluoromethoxy)phenyl)-1H-pyrazolo[3,4-b]pyridine 2,2,2-trifluoroacetate salt (250 mg, 0.62 mmol) was added into it. The mixture was stirred at room temperature for 16 h. The mixture was purified by reverse phase chromatography (Welch Xtimate C18 100*40 mm*3 um/water (0.075% TFA)-ACN/63%-93%) to afford the title compound (11.0 mg, 4%) as a white solid. $^1$H NMR (400 MHz, DMSO-$d_6$): δ 12.8 (s, 1H), 8.60 (d, J=5.2 Hz, 1H), 8.49 (d, J=9.2 Hz, 2H), 8.06 (s, 1H), 7.97 (s, 1H), 7.59 (d, J=9.2 Hz, 2H), 7.50 (d, J=5.2 Hz, 1H), 5.46 (dd, J=48.8, 3.6 Hz, 1H), 5.28 (dd, J=16.4, 3.6 Hz, 1H), 4.89-4.86 (m, 1H), 4.67-4.65 (m, 2H), 4.26-4.24 (m, 2H); LCMS (ESI): m/z 473.0 $(M+H)^+$.

Example 93 (Compound 133)

1-(3-(4-(Azetidin-3-yl)-1-(4-(trifluoromethoxy)phenyl)-1H-pyrazolo[3,4-b]pyridin-3-yl)azetidin-1-yl)-2-fluoroprop-2-en-1-one

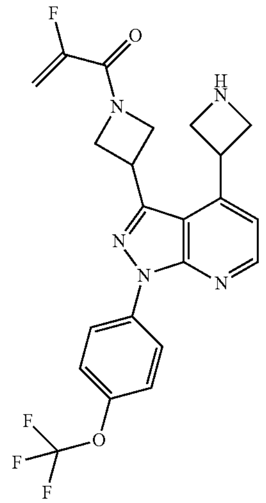 [SMILES: C=C(F)C(=O)N1CC(c2nn(-c3ccc(OC(F)(F)F)cc3)c3nccc(C4CNC4)c23)C1]

Step 1: 3-(azetidin-3-yl)-4-iodo-1-(4-(trifluoromethoxy)phenyl)-1H-pyrazolo[3,4-b]pyridine

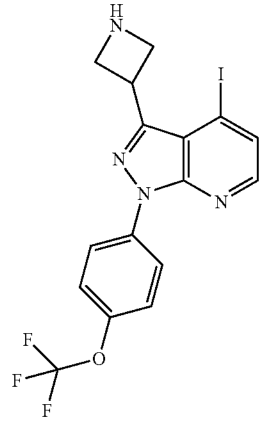 [SMILES: FC(F)(F)Oc1ccc(-n2nc(C3CNC3)c3c(I)ccnc32)cc1]

A mixture of tert-butyl 3-(4-iodo-1-(4-(trifluoromethoxy)phenyl)-1H-pyrazolo[3,4-b]pyridin-3-yl)azetidine-1-carboxylate (700 mg, 1.13 mmol) and TFA (5% in HFIP, 10 mL) was stirred at room temperature for 4 h. The reaction mixture was quenched with saturated aqueous $NaHCO_3$ until pH=8. The resulting solution was extracted with ethyl acetate (50 mL×3). The combined organic layers were dried over anhydrous sodium sulfate, filtered, and concentrated under vacuum to afford the title compound (550 mg, crude) as a yellow oil. LCMS (ESI): m/z 460.9 $(M+H)^+$ Step 2: benzyl 3-(4-iodo-1-(4-(trifluoromethoxy)phenyl)-1H-pyrazolo[3,4-b]pyridin-3-yl)azetidine-1-carboxylate

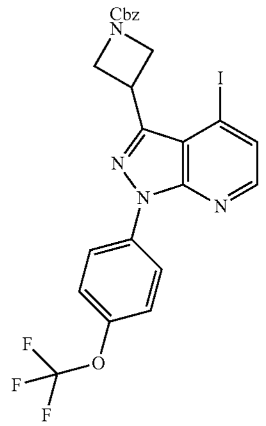 [SMILES: O=C(OCc1ccccc1)N1CC(c2nn(-c3ccc(OC(F)(F)F)cc3)c3nccc(I)c23)C1]

A mixture of 3-(azetidin-3-yl)-4-iodo-1-(4-(trifluoromethoxy)phenyl)-1H-pyrazolo[3,4-b]pyridine (550 mg, 1.21 mmol), $Na_2CO_3$ (201 mg, 2.39 mmol), benzyl carbonochloridate (0.2 mL, 1.44 mmol) in THF (15 mL) was stirred at room temperature for 16 h. The reaction mixture was quenched with water (120 mL), extracted with ethyl acetate (100 mL×2). Combined organic layers were dried over $Na_2SO_4$, filtered and concentrated to dryness. The residue was purified by column chromatography on silica gel (0-10% ethyl acetate in petroleum ether) to afford the title compound (400 mg, 54%) as a white solid. $^1$H NMR (400 MHz, DMSO-$d_6$): δ 8.32 (d, J=9.2 Hz, 2H), 8.20 (d, J=4.8 Hz, 1H), 7.83 (d, J=4.8 Hz, 1H), 7.53 (d, J=9.2 Hz, 2H), 7.31-7.29 (m, 3H), 7.26-7.23 (m, 2H), 5.01 (s, 2H), 4.64-4.53 (m, 1H), 4.48-4.35 (m, 4H); LCMS (ESI): m/z 595.0 $(M+H)^+$.

Step 3: benzyl 3-(4-(1-(tert-butoxycarbonyl)azetidin-3-yl)-1-(4-(trifluoromethoxy)phenyl)-1H-pyrazolo[3,4-b]pyridin-3-yl)azetidine-1-carboxylate

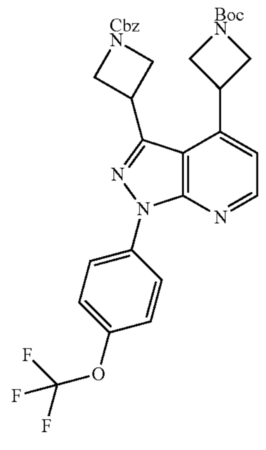 [SMILES: CC(C)(C)OC(=O)N1CC(c2ccnc3c2c(C2CN(C(=O)OCc4ccccc4)C2)nn3-c2ccc(OC(F)(F)F)cc2)C1]

In glove box, to a glass bottle was added a mixture of benzyl 3-(4-iodo-1-(4-(trifluoromethoxy)phenyl)-1H-pyrazolo[3,4-b]pyridin-3-yl)azetidine-1-carboxylate (400 mg, 1.60 mmol), $Na_2CO_3$ (404 mg, 3.80 mmol), $NiCl_2$·glyme (33.0 mg, 0.14 mmol), tert-butyl 3-bromoazetidine-1-carboxylate (542 mg, 2.20 mmol), dtbbpy (62.0 mg, 0.30 mmol), Ir[dF($CF_3$)ppy]2(dtbbpy)$PF_6$ (17.2 mg, 0.02 mmol) and TTMSS (456 mg, 1.82 mmol) in DME (10 mL). The vial was sealed and taken out from glove box, irradiated with 72W Blue_LED-Strip-Light for 16 h with cooling from a fan at room temperature. The reaction mixture was quenched with water (40 mL), extracted with ethyl acetate (50 mL×3). The combined organic layers were dried over $Na_2SO_4$, filtered and concentrated to dryness. The residue was purified by column chromatography on silica gel (0-25% ethyl acetate in petroleum ether) to afford the title compound (250 mg, 25%) as a white solid. $^1$H NMR (400 MHz, DMSO-$d_6$): δ 8.67 (d, J=4.8 Hz, 1H), 8.43 (d, J=8.8 Hz, 2H), 7.58 (d, J=8.8 Hz, 2H), 7.54 (d, J=4.8 Hz, 1H), 7.40-7.28 (m, 5H), 5.08 (s, 2H), 4.60-4.32 (m, 7H), 4.26-4.13 (m, 1H), 4.01-3.94 (m, 2H), 1.41 (s, 9H); LCMS (ESI): m/z 624.1 (M+H)$^+$.

Step 4: tert-butyl 3-(3-(azetidin-3-yl)-1-(4-(trifluoromethoxy)phenyl)-1H-pyrazolo[3,4-b]pyridin-4-yl)azetidine-1-carboxylate

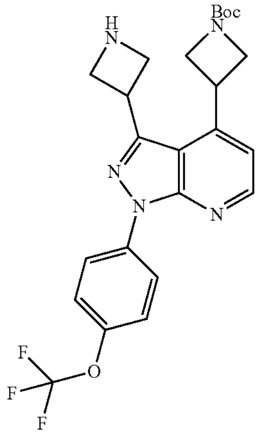 [SMILES: CC(C)(C)OC(=O)N1CC(c2ccnc3c2c(C2CNC2)nn3-c2ccc(OC(F)(F)F)cc2)C1]

To a solution of benzyl 3-(4-(1-(tert-butoxycarbonyl)azetidin-3-yl)-1-(4-(trifluoromethoxy)phenyl)-1H-pyrazolo[3,4-b]pyridin-3-yl)azetidine-1-carboxylate (250 mg, 0.40 mmol) in ethyl acetate (10 mL) was added 10% Pd/C (25 mg) at room temperature. The mixture was stirred under $H_2$ (15 psi) at room temperature for 12 h. The reaction mixture was filtered, and the filtrate was concentrated. The resulting residue was purified by reverse phase chromatography (Welch Xtimate C18 150*30 mm*5 um, acetonitrile 40-70%/water (0.225% FA)-ACN) to afford the title compound (150 mg, 76%) as a white solid. LCMS (ESI): m/z 490.2 (M+H)$^+$.

Step 5: tert-butyl 3-(3-(1-(2-fluoroacryloyl)azetidin-3-yl)-1-(4-(trifluoromethoxy)phenyl)-1H-pyrazolo[3,4-b]pyridin-4-yl)azetidine-1-carboxylate

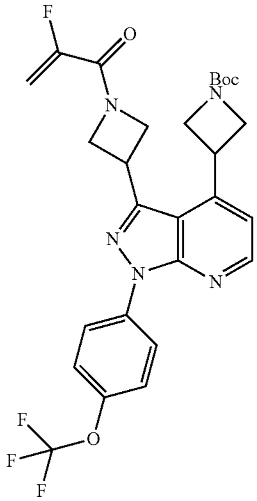 [SMILES: C=C(F)C(=O)N1CC(c2nn(-c3ccc(OC(F)(F)F)cc3)c3nccc(C4CN(C(=O)OC(C)(C)C)C4)c23)C1]

A mixture of 2-fluoroacrylic acid (55 mg, 0.61 mmol), DIPEA (0.1 mL, 0.61 mmol) and HATU (140 mg, 0.37 mmol) in DMF (5 mL) was stirred at room temperature for 30 min. Then the tert-butyl 3-(3-(azetidin-3-yl)-1-(4-(trifluoromethoxy)phenyl)-1H-pyrazolo[3,4-b]pyridin-4-yl)azetidine-1-carboxylate (150 mg, 0.31 mmol) was added into the above mixture. Then the reaction solution was stirred at room temperature for 1 h. The reaction mixture was quenched with water (50 mL) and extracted with ethyl acetate (50 mL×3). The combined organic layers were washed with brine (50 mL×3), the organic was dried over $Na_2SO_4$, filtered, and concentrated to afford the title compound (140 mg, 85%) as a yellow solid. LCMS (ESI): m/z 584.1 (M+Na)$^+$.

Step 6: 1-(3-(4-(azetidin-3-yl)-1-(4-(trifluoromethoxy)phenyl)-1H-pyrazolo[3,4-b]pyridin-3-yl)azetidin-1-yl)-2-fluoroprop-2-en-1-one 2,2,2-trifluoroacetate salt

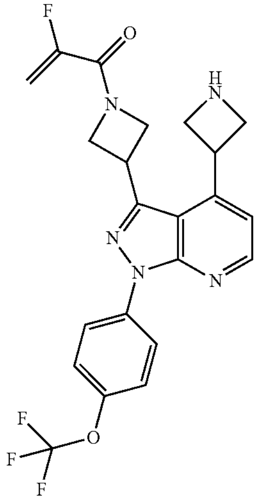 [SMILES: C=C(F)C(=O)N1CC(c2nn(-c3ccc(OC(F)(F)F)cc3)c3nccc(C4CNC4)c23)C1]

A mixture of tert-butyl 3-(3-(1-(2-fluoroacryloyl)azetidin-3-yl)-1-(4-(trifluoromethoxy)phenyl)-1H-pyrazolo[3,4-b]pyridin-4-yl)azetidine-1-carboxylate (140 mg, 0.29 mmol) and TFA (5% in HFIP 5 mL) was stirred for 4 h at room temperature. The reaction was concentrated under vacuum. The resulting residue was purified by reverse phase chromatography (Welch Xtimate C18 100*40 mm*3 um, acetonitrile 40-70%/water (0.225% FA)-ACN) to afford the title compound (33.0 mg, 30%) as a white solid. $^1$H NMR (400 MHz, DMSO-$d_6$): 8.94-8.80 (m, 2H), 8.78 (d, J=4.8 Hz, 1H), 8.44 (d, J=9.2 Hz, 2H), 7.66-7.55 (m, 3H), 5.53 (dd, J=48.4, 3.6 Hz, 1H), 5.35 (dd, J=16.8, 3.6 Hz, 1H), 4.98-4.80 (m, 2H), 4.57-4.55 (m, 1H), 4.50-4.37 (m, 5H), 4.28-4.25 (m, 2H); LCMS (ESI): m/z 462.0 $(M+H)^+$.

Example 94 (Compound 42)

N-(3-(1-(2-Fluoroacryloyl)azetidin-3-yl)-1-(4-(trifluoromethoxy)phenyl)-1H-pyrazolo[3,4-b]pyridin-4-yl)-2-hydroxyacetamide

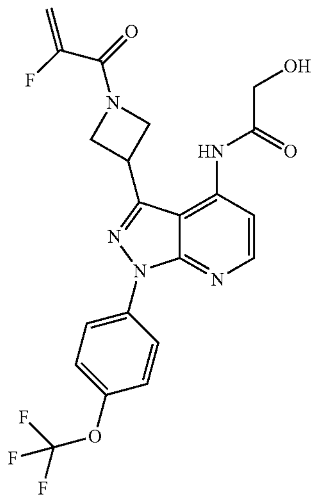 [SMILES: C=C(F)C(=O)N1CC(c2nn(-c3ccc(OC(F)(F)F)cc3)c3nccc(NC(=O)CO)c23)C1]

Step 1: tert-butyl 3-(4-(2-((tert-butyldimethylsilyl)oxy)acetamido)-1-(4-(trifluoromethoxy)phenyl)-1H-pyrazolo[3,4-b]pyridin-3-yl)azetidine-1-carboxylate

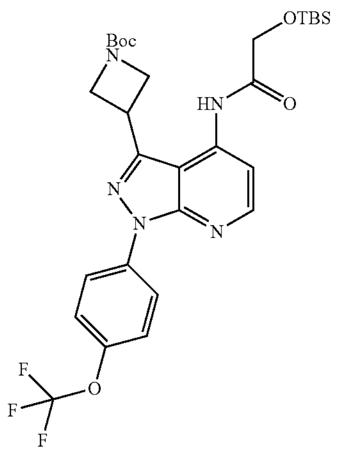 [SMILES: CC(C)(C)OC(=O)N1CC(c2nn(-c3ccc(OC(F)(F)F)cc3)c3nccc(NC(=O)CO[Si](C)(C)C(C)(C)C)c23)C1]

A solution of tert-butyl 3-(4-(2-((ter t-butyldimethylsilyl)oxy)acetamido)-1-(4-(trifluoromethoxy)phenyl)-1H-pyrazolo[3,4-b]pyridin-3-yl)azetidine-1-carboxylate (500 mg, 0.89 mmol), Xantphos (52 mg, 0.09 mmol), $Cs_2CO_3$ (872 mg, 2.68 mmol), $Pd_2(dba)_3$ (82 mg, 0.09 mmol) and 2-((tert-butyldimethylsilyl)oxy)acetamide (337 mg, 1.78 mmol) in 1,4-dioxane (10 mL) was stirred at 100° C. for 16 h under $N_2$ atmosphere. The mixture was diluted with ethyl acetate (100 mL) and washed with water (100 mL×3). The combined organics were dried over $Na_2SO_4$ and concentrated. The residue was purified by column chromatography on silica gel (0-30% ethyl acetate in petroleum ether) to afford the title compound (400 mg, 72%) as a colorless liquid. $^1$H NMR (400 MHz, $CDCl_3$): δ 9.06 (s, 1H), 8.55 (d, J=5.2 Hz, 1H), 8.40 (d, J=9.2 Hz, 2H), 8.17 (d, J=5.2 Hz, 1H), 7.39 (d, J=8.8 Hz, 2H), 4.64-4.40 (m, 4H), 4.38 (s, 2H), 4.28-4.18 (m, 1H), 1.46 (s, 9H), 1.04 (s, 9H), 0.31 (s, 6H).

Step 2: tert-butyl 3-(4-(2-hydroxyacetamido)-1-(4-(trifluoromethoxy)phenyl)-1H-pyrazolo[3,4-b]pyridin-3-yl)azetidine-1-carboxylate

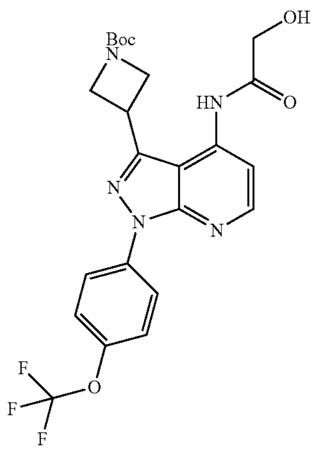 [SMILES: CC(C)(C)OC(=O)N1CC(c2nn(-c3ccc(OC(F)(F)F)cc3)c3nccc(NC(=O)CO)c23)C1]

To a solution of ter t-butyl 3-(4-(2-((tert-butyldimethylsilyl)oxy)acetamido)-1-(4-(trifluoromethoxy)phenyl)-1H-pyrazolo[3,4-b]pyridin-3-yl)azetidine-1-carboxylate (400 mg, 0.64 mmol) in THF (5 mL) at 0° C. was added TBAF (1.30 mL, 1.29 mmol. 1.0 mol/L in THF). The reaction was stirred at 0° C. for 1 h. The mixture was diluted with ethyl acetate (200 mL) and washed with water (200 mL×3). The organic was dried over $Na_2SO_4$ and concentrated to afford the title compound (300 mg, 92%) as a brown liquid. LCMS (ESI): m/z 508.2 $(M+H)^+$.

Step 3: N-(3-(azetidin-3-yl)-1-(4-(trifluoromethoxy)phenyl)-1H-pyrazolo[3,4-b]pyridin-4-yl)-2-hydroxyacetamide

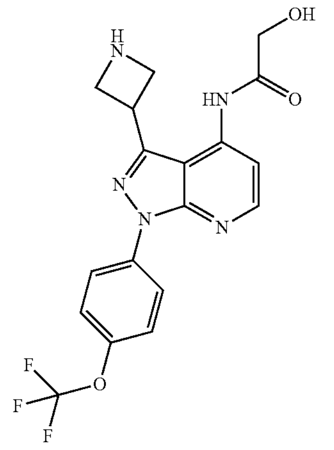 [SMILES: O=C(CO)Nc1ccnc2c1c(C1CNC1)nn2-c1ccc(OC(F)(F)F)cc1]

A solution of tert-butyl 3-(4-(2-hydroxyacetamido)-1-(4-(trifluoromethoxy)phenyl)-1H-pyrazolo[3,4-b]pyridin-3-yl)azetidine-1-carboxylate (300 mg, 0.59 mmol) in TFA (5% in HFIP, 5.0 mL) was stirred at room temperature for 16 h. The mixture was quenched with water (5 mL) then adjusted to pH=8 with aq.$NaHCO_3$ solution and diluted with ethyl acetate (100 mL) and washed with water (100 mL×3). The organic was dried over $Na_2SO_4$, filtered, and concentrated to afford the title compound (200 mg, 83%) as a brown solid. LCMS (ESI): m/z 408.2 $(M+H)^+$.

Step 4: N-(3-(1-(2-fluoroacryloyl)azetidin-3-yl)-1-(4-(trifluoromethoxy)phenyl)-1H-pyrazolo[3,4-b]pyridin-4-yl)-2-hydroxyacetamide

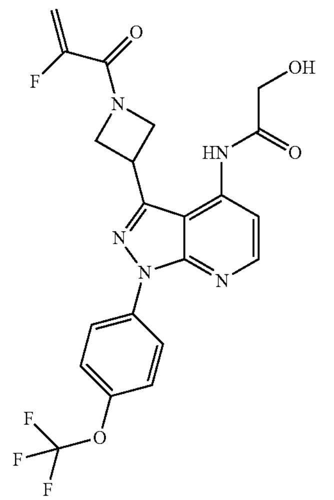 [SMILES: C=C(F)C(=O)N1CC(c2nn(-c3ccc(OC(F)(F)F)cc3)c3nccc(NC(=O)CO)c23)C1]

To a mixture of N-(3-(azetidin-3-yl)-1-(4-(trifluoromethoxy)phenyl)-1H-pyrazolo[3,4-b]pyridin-4-yl)-2-hydroxyacetamide (200 mg, 0.49 mmol) in DCM (5.0 mL) and MeOH (1 mL) was added 2-fluoroacrylic acid (88.0 mg, 0.98 mmol) and EEDQ (243 mg, 0.98 mmol) at 0° C. The reaction was stirred at room temperature for 16 h. The mixture was diluted with ethyl acetate (100 mL) and washed with water (100 mL×3). The organic was dried over $Na_2SO_4$, filtered, and concentrated. The residue was purified by reverse phase chromatography (Welch Xtimate C18 150*30 mm*5 um, water (0.2% FA)-ACN, 44-74%) to afford the title compound (76 mg, 32%) as a white solid. $^1H$ NMR (400 MHz, DMSO-$d_6$): δ 9.73 (s, 1H), 8.59 (d, J=5.2 Hz, 1H), 8.45 (d, J=9.2 Hz, 2H), 7.81 (d, J=5.2 Hz, 1H), 7.59 (d, J=8.4 Hz, 2H), 6.38-6.36 (m, 1H), 5.50 (dd, J=48.4, 3.6 Hz, 1H), 5.32 (dd, J=16.4, 3.6 Hz, 1H), 4.92-4.83 (m, 1H), 4.83-4.77 (m, 1H), 4.62-4.48 (m, 2H), 4.44-4.37 (m, 1H), 4.17 (s, 2H); LCMS (ESI): m/z 480.1 $(M+H)^+$.

Example 95 (Compound 29)

1-(3-(4-(4H-1,2,4-Triazol-4-yl)-1-(4-(trifluoromethoxy)phenyl)-1H-pyrazolo[3,4-b]pyridin-3-yl)azetidin-1-yl)-2-fluoroprop-2-en-1-one

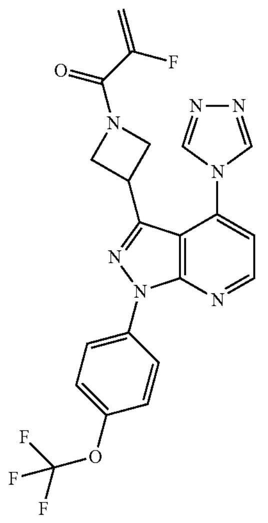

Step 1: tert-butyl 3-(4-amino-1-(4-(trifluoromethoxy)phenyl)-1H-pyrazolo[3,4-b]pyridin-3-yl)azetidine-1-carboxylate

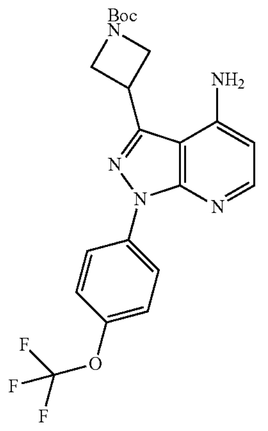 [SMILES: CC(C)(C)OC(=O)N1CC(c2nn(-c3ccc(OC(F)(F)F)cc3)c3nccc(N)c23)C1]

To a solution of tert-butyl 3-(4-iodo-1-(4-(trifluoromethoxy)phenyl)-1H-pyrazolo[3,4-b]pyridin-3-yl)azetidine-1-carboxylate (500 mg, 0.89 mmol) in DMSO (4 mL) was added BPMPO (37 mg, 0.09 mmol), $K_3PO_4$ (568 mg, 2.68 mmol), $NH_3 \cdot H_2O$ (1 mL) and CuI (17 mg, 0.09 mmol), the mixture was stirred at 100° C. for 16 h under $N_2$ atmosphere. The solution was diluted with water (50 mL) and extracted with ethyl acetate (30 mL×3). The combined organic layers were dried over anhydrous $Na_2SO_4$, filtered and concentrated under vacuum. The residue was purified by column chromatography on silica gel (0-35% ethyl acetate in petroleum ether) to afford the title compound (200 mg, 50%) as a white solid. $^1$H NMR (400 MHz, DMSO-$d_6$): δ 8.46 (d, J=8.8 Hz, 2H), 8.04 (d, J=5.2 Hz, 1H), 7.52 (d, J=8.8 Hz, 2H), 6.60 (s, 2H), 6.37 (d, J=5.2 Hz, 1H), 4.42-4.42 (m, 1H), 4.40-4.03 (m, 2H), 4.20-4.17 (m, 2H), 1.39 (s, 9H); LCMS (ESI): m/z 450.0 $(M+H)^+$.

Step 2: (E)-tert-butyl 3-(4-(((dimethylamino)methylene)amino)-1-(4-(trifluoromethoxy)phenyl)-1H-pyrazolo[3,4-b]pyridin-3-yl)azetidine-1-carboxylate

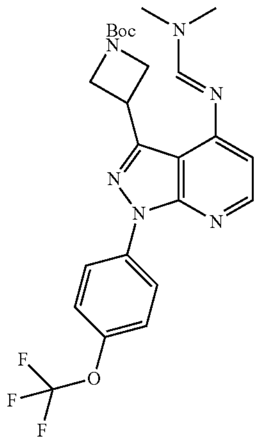 [SMILES: CN(C)/C=N/c1ccnc2c1c(C1CN(C(=O)OC(C)(C)C)C1)nn2-c1ccc(OC(F)(F)F)cc1]

A mixture of tert-butyl 3-(4-amino-1-(4-(trifluoromethoxy)phenyl)-1H-pyrazolo[3,4-b]pyridin-3-yl)azetidine-1-carboxylate (100 mg, 0.22 mmol) in DMF-DMA (10 mL, 75 mmol) was stirred at 100° C. for 1 h in Microwave. The reaction was diluted with water (50 mL) and extracted with ethyl acetate (50 mL×3), the combined organic layers were washed with brine (50 mL×3) and dried with anhydrous $Na_2SO_4$. After filtration, filtrate was concentrated to afford the title compound (110 mg, 98%). LCMS (ESI): m/z 449.2 $(M-56+H)^+$.

Step 3: tert-butyl 3-(4-(4H-1,2,4-triazol-4-yl)-1-(4-(trifluoromethoxy)phenyl)-1H-pyrazolo[3,4-b]pyridin-3-yl)azetidine-1-carboxylate

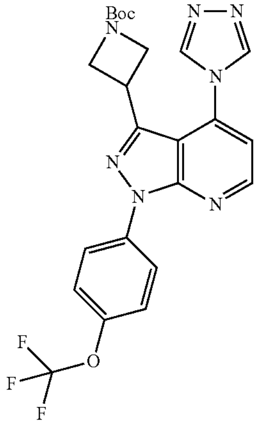 [SMILES: CC(C)(C)OC(=O)N1CC(c2nn(-c3ccc(OC(F)(F)F)cc3)c3nccc(-n4cnnc4)c23)C1]

To a solution of (E)-tert-butyl 3-(4-(((dimethylamino)methylene)amino)-1-(4-(trifluoromethoxy)phenyl)-1H-pyrazolo[3,4-b]pyridin-3-yl)azetidine-1-carboxylate (110 mg, 0.22 mmol) in AcOH (3 mL), was added formohydrazide (52 mg, 0.87 mmol), the solution was stirred at 60° C. for 1 h in Microwave. The reaction was diluted with water (50 mL) and adjusted to pH=8 by sat. $NaHCO_3$, the mixture was extracted with ethyl acetate (50 mL), the combined organic layers were dried over $Na_2SO_4$ and concentrated. The residue was purified by column chromatography on silica gel (0-100% ethyl acetate in petroleum ether) to afford the title compound (80.0 mg, 73%) as white solid. $^1$H NMR (400 MHz, DMSO-$d_6$): δ 9.10 (s, 2H), 8.88 (d, J=4.8 Hz, 1H), 8.42 (d, J=9.2 Hz, 2H), 7.63 (d, J=8.4 Hz, 2H), 7.59 (d, J=5.2 Hz, 1H), 4.05-4.03 (m, 2H), 3.93-3.86 (m, 1H), 3.81-3.79 (m, 2H), 1.35 (s, 9H); LCMS (ESI): m/z 502.0 $(M+H)^+$.

Step 4: 3-(azetidin-3-yl)-4-(4H-1,2,4-triazol-4-yl)-1-(4-(trifluoromethoxy)phenyl)-1H-pyrazolo[3,4-b]pyridine

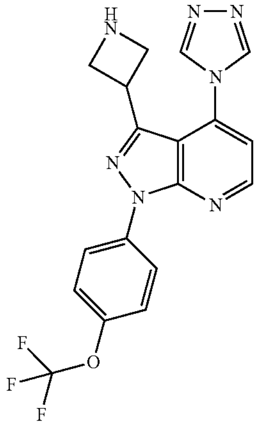 [SMILES: FC(F)(F)Oc1ccc(-n2nc(C3CNC3)c3c(-n4cnnc4)ccnc32)cc1]

A mixture of tert-butyl 3-(4-(4H-1,2,4-triazol-4-yl)-1-(4-(trifluoromethoxy)phenyl)-1H-pyrazolo[3,4-b]pyridin-3-yl)azetidine-1-carboxylate (80.0 mg, 0.16 mmol) in TFA (5% in HFIP, 3 mL) was stirred at room temperature for 16 h. The reaction was diluted with water (50 mL) and adjusted to pH=8 by sat. $NaHCO_3$, the mixture was extracted with ethyl acetate (50 mL×3), the combined organic layers were dried over $Na_2SO_4$, filtered, and concentrated under vacuum to afford the title compound (60 mg, 94%). The crude was used for next step without further purification. LCMS (ESI): m/z 402.1 $(M+H)^+$.

Step 5: 1-(3-(4-(4H-1,2,4-triazol-4-yl)-1-(4-(trifluoromethoxy)phenyl)-1H-pyrazolo[3,4-b]pyridin-3-yl)azetidin-1-yl)-2-fluoroprop-2-en-1-one

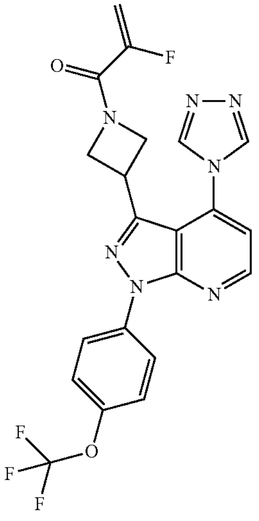

A mixture of 3-(azetidin-3-yl)-4-(4H-1,2,4-triazol-4-yl)-1-(4-(trifluoromethoxy)phenyl)-1H-pyrazolo[3,4-b]pyridine (67 mg, 0.17 mmol), 2-fluoroacrylic acid (30 mg, 0.33 mmol) and EEDQ (123 mg, 0.50 mmol) in DCM (5 mL) and MeOH (1 mL) was stirred at room temperature for 2 h. The solution was diluted with water (50 mL) and extracted with DCM (30 mL×3), the combined organic layers were dried over anhydrous $Na_2SO_4$, filtered and concentrated under vacuum. The residue was purified by reverse phase chromatography (Boston Green ODS 150*30 mm*5 um, water (FA)-CAN, 60%-90%) to afford the title compound (23.9 mg, 30%) as a white solid. $^1H$ NMR (400 MHz, DMSO-$d_6$): δ 9.12 (s, 2H), 8.89 (d, J=4.8 Hz, 1H), 8.43 (d, J=9.2 Hz, 2H), 7.64 (d, J=8.8 Hz, 2H), 7.61 (d, J=4.8 Hz, 1H), 5.43 (dd, J=48.8, 3.6 Hz, 1H), 5.27 (dd, J=16.4, 3.6 Hz, 1H), 4.66-4.56 (m, 1H), 4.40-4.36 (m, 1H), 4.15-4.11 (m, 1H), 4.07-4.00 (m, 1H), 3.93-3.88 (m, 1H); LCMS (ESI): m/z 473.9 $(M+H)^+$.

Example 96 (Compound 41)

1-(3-(4-(2,6-Diazaspiro[3.3]heptan-2-yl)-1-(4-(trifluoromethoxy)phenyl)-1H-pyrazolo[3,4-b]pyridin-3-yl)azetidin-1-yl)-2-fluoroprop-2-en-1-one formate

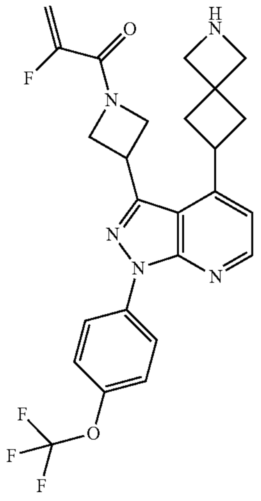 [SMILES: C=C(F)C(=O)N1CC(c2nn(-c3ccc(OC(F)(F)F)cc3)c3nccc(C4CC5(CNC5)C4)c23)C1]

Step 1: 3-(azetidin-3-yl)-4-iodo-1-(4-(trifluoromethoxy)phenyl)-1H-pyrazolo[3,4-b]pyridine

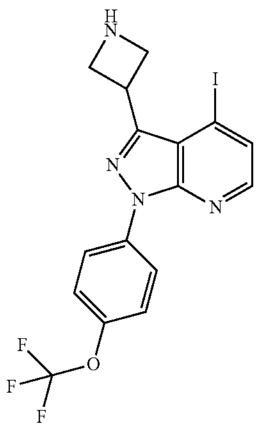 [SMILES: FC(F)(F)Oc1ccc(-n2nc(C3CNC3)c3c(I)ccnc32)cc1]

A mixture of tert-butyl 3-(4-iodo-1-(4-(trifluoromethoxy)phenyl)-1H-pyrazolo[3,4-b]pyridin-3-yl)azetidine-1-carboxylate (300 mg, 0.54 mmol) in TFA (5% in HFIP, 2.0 mL) was stirred at room temperature for 2 h. The reaction mixture was adjusted to pH=8 with sat. $NaHCO_3$. The resulting solution was extracted with ethyl acetate (30 mL×3), the organic layers were combined and dried over $Na_2SO_4$. After filtration, the filtrate was concentrated to afford the title compound (240 mg, 97%) as a yellow solid. The crude would be used in the next step directly. LCMS (ESI): m/z 461.1 $(M+H)^+$.

Step 2: 2-fluoro-1-(3-(4-iodo-1-(4-(trifluoromethoxy)phenyl)-1H-pyrazolo[3,4-b]pyridin-3-yl)azetidin-1-yl)prop-2-en-1-one

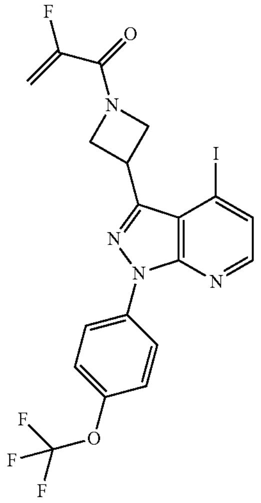 [SMILES: C=C(F)C(=O)N1CC(c2nn(-c3ccc(OC(F)(F)F)cc3)c3nccc(I)c23)C1]

To a solution of 2-fluoroacrylic acid (71.0 mg, 0.78 mmol), 3-(azetidin-3-yl)-4-iodo-1-(4-(trifluoromethoxy)phenyl)-1H-pyrazolo[3,4-b]pyridine (240 mg, 0.65 mmol) in DCM (4 mL) and MeOH (1 mL) was added EEDQ (322 mg, 1.30 mmol) at 0° C. and the resulting was stirred at room temperature with 16 h. The reaction was quenched by water (30 mL). The resulting solution was extracted with ethyl acetate (30 mL×3), the organic layers were combined and dried over $Na_2SO_4$. After filtration, the filtrate was concentrated under reduced pressure. The residue was purified by column chromatography on silica gel (0-25% ethyl acetate in petroleum ether) to afford the title compound (180 mg, 52%) as a white solid. $^1$H NMR (400 MHz, $CDCl_3$): δ 8.34 (d, J=9.2 Hz, 2H), 8.19 (d, J=4.8 Hz, 1H), 7.71 (d, J=4.8 Hz, 1H), 7.40 (d, J=9.6 Hz, 2H), 5.65 (dd, J=46.4, 2.8 Hz 1H), 5.13 (dd, J=15.6, 2.8 Hz, 1H), 5.01-4.90 (m, 2H), 4.79-4.72 (m, 1H), 4.69-4.63 (m, 2H); LCMS (ESI): m/z 533 $(M+H)^+$.

Step 3: tert-butyl 6-(3-(1-(2-fluoroacryloyl)azetidin-3-yl)-1-(4-(trifluoromethoxy)phenyl)-1H-pyrazolo[3,4-b]pyridin-4-yl)-2,6-diazaspiro[3.3]heptane-2-carboxylate

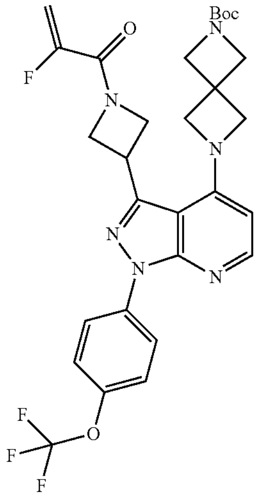 [SMILES: C=C(F)C(=O)N1CC(c2nn(-c3ccc(OC(F)(F)F)cc3)c3nccc(N4CC5(CN(C(=O)OC(C)(C)C)C5)C4)c23)C1]

To a solution of 2-fluoro-1-(3-(4-iodo-1-(4-(trifluoromethoxy)phenyl)-1H-pyrazolo[3,4-b]pyridin-3-yl)azetidin-1-yl)prop-2-en-1-one (140 mg, 0.26 mmol) in 1,4-dioxane (4.0 mL) was added tert-butyl 2,6-diazaspiro[3.3]heptane-2-carboxylate (78.0 mg, 0.39 mmol), $K_2CO_3$ (109 mg, 0.79 mmol), Ruphos (19.0 mg, 0.04 mmol) and Ruphos Pd G3 (11 mg, 0.01 mmol) at room temperature. The mixture was stirred at 120° C. for 4 h under $N_2$ atmosphere. The reaction was quenched by water (20 mL). The resulting solution was extracted with ethyl acetate (20 mL×3), the organic layers were combined and dried over $Na_2SO_4$. After filtration, the filtrate was concentrated under reduced pressure. The residue was purified by chromatography on silica gel (0-50% ethyl acetate in petroleum ether) to afford the title compound (70.0 mg, 44%) as a white solid. $^1$H NMR (400 MHz, $CDCl_3$): δ 8.30 (d, J=8.4 Hz, 2H), 8.26 (d, J=5.2 Hz, 1H), 7.37 (d, J=8.8 Hz, 2H), 6.08 (d, J=5.6 Hz, 1H), 5.67 (dd, J=46.8, 2.8 Hz, 1H), 5.13 (dd, J=14.8, 2.8 Hz, 1H), 5.06-4.97 (m, 1H), 4.86-4.78 (m, 1H), 4.57-4.55 (m, 2H), 4.33 (s, 4H), 4.28-4.21 (m, 1H), 4.18 (s, 4H), 1.47 (s, 9H); LCMS (ESI): m/z 603.3 $(M+H)^+$.

Step 4: 1-(3-(4-(2,6-diazaspiro[3.3]heptan-2-yl)-1-(4-(trifluoromethoxy)phenyl)-1H-pyrazolo[3,4-b]pyridin-3-yl)azetidin-1-yl)-2-fluoroprop-2-en-1-one formate salt

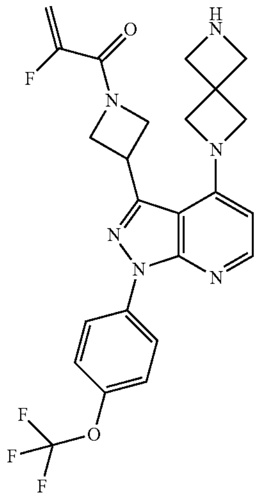 [SMILES: C=C(F)C(=O)N1CC(c2nn(-c3ccc(OC(F)(F)F)cc3)c3nccc(N4CC5(CNC5)C4)c23)C1]

A mixture of tert-butyl 6-(3-(1-(2-fluoroacryloyl)azetidin-3-yl)-1-(4-(trifluoromethoxy)phenyl)-1H-pyrazolo[3,4-b]pyridin-4-yl)-2,6-diazaspiro[3.3]heptane-2-carboxylate (70.0 mg, 0.12 mmol) in TFA (5% in HFIP, 6.0 mL) was stirred at room temperature for 4 h. The reaction mixture was adjusted to pH=7 with sat. $NaHCO_3$. The resulting solution was extracted with ethyl acetate (20 mL×3), the organic layers were combined and dried over $Na_2SO_4$. After filtration, the filtrate was concentrated under reduced pressure. The resulting residue was purified by reverse phase chromatography (Welch Xtimate C18 150*30 mm*5 um, acetonitrile 19-49%/water (FA)-ACN) to afford the title compound (32.7 mg, 56%) as a white solid. $^1H$ NMR (400 MHz, DMSO-$d_6$): δ 8.44 (d, J=8.8 Hz, 2H), 8.31 (s, 1H), 8.18 (d, J=5.6 Hz, 1H), 7.55 (d, J=8.8 Hz, 2H), 6.19 (d, J=5.6 Hz, 1H), 5.53 (dd, J=48.4, 3.6 1H), 5.34 (dd, J=16.8, 3.6 Hz, 1H), 4.90-4.82 (m, 1H), 4.81-4.74 (m, 1H), 4.55-4.47 (m, 1H), 4.43-4.05 (m, 6H), 4.00 (s, 4H); LCMS (ESI): m/z 525 $(M+Na)^+$.

Example 97 (Compound 75)

2-Fluoro-1-(3-(4-(3-hydroxy-3-(hydroxymethyl)azetidin-1-yl)-1-(4-(trifluoromethoxy)phenyl)-1H-pyrazolo[3,4-b]pyridin-3-yl)azetidin-1-yl)prop-2-en-1-one

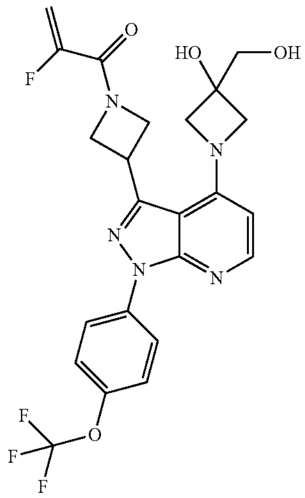 [SMILES: C=C(F)C(=O)N1CC(c2nn(-c3ccc(OC(F)(F)F)cc3)c3nccc(N4CC(O)(CO)C4)c23)C1]

Step 1: tert-butyl 3-(4-chloro-1-(4-(trifluoromethoxy)phenyl)-1H-pyrazolo[3,4-b]pyridin-3-yl)azetidine-1-carboxylate

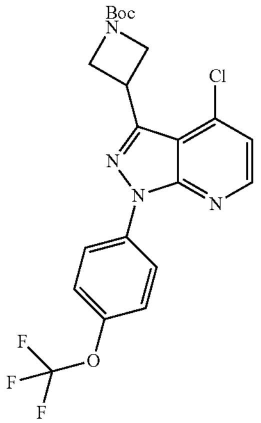 [SMILES: CC(C)(C)OC(=O)N1CC(c2nn(-c3ccc(OC(F)(F)F)cc3)c3nccc(Cl)c23)C1]

To a solution of tert-butyl 3-(4-iodo-1-(4-(trifluoromethoxy)phenyl)-1H-pyrazolo[3,4-b]pyridin-3-yl)azetidine-1-carboxylate (500 mg, 0.89 mmol) in THF (4 mL) was added isobutylmagnesium chloride (0.54 mL, 1.07 mmol, 2 M in THF,) slowly at 0° C. The solution was stirred at the same temperature for 45 min under $N_2$ atmosphere. NCS (143 mg, 1.07 mmol) was added to the mixture at 0° C. The solution was stirred at 0° C. for 45 min under $N_2$ atmosphere. The reaction was quenched by sat. $NH_4Cl$ (30 mL) and extracted with ethyl acetate (50 mL×3). The organic layers were dried over anhydrous sodium sulfate. After filtration, the filtrate was concentrated under reduced pressure. The residue was purified by chromatography on silica gel (0-25% ethyl acetate in petroleum ether) to afford the title compound (350 mg, 84%) as a colorless oil. $^1$H NMR (400 MHz, $CDCl_3$): δ 8.49 (d, J=5.2 Hz, 1H), 8.36 (d, J=9.2 Hz, 2H), 7.39 (d, J=9.2 Hz, 2H), 7.22 (d, J=5.2 Hz, 1H), 4.48-4.41 (m, 5H), 1.48 (s, 9H).

Step 2: tert-butyl 3-(4-(3-methyleneazetidin-1-yl)-1-(4-(trifluoromethoxy)phenyl)-1H-pyrazolo[3,4-b]pyridin-3-yl)azetidine-1-carboxylate

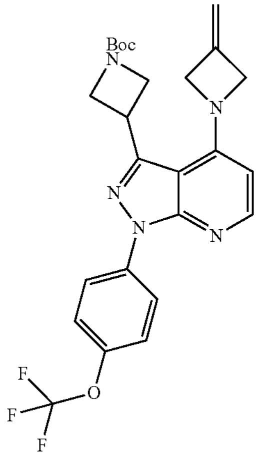 [SMILES: C=C1CN(c2ccnc3c2c(C2CN(C(=O)OC(C)(C)C)C2)nn3-c2ccc(OC(F)(F)F)cc2)C1]

A mixture of 3-methyleneazetidine 2,2,2-trifluoroacetate salt (195 mg, 1.07 mmol), $Cs_2CO_3$ (869 mg, 2.67 mmol) and tert-butyl 3-(4-chloro-1-(4-(trifluoromethoxy)phenyl)-1H-pyrazolo[3,4-b]pyridin-3-yl)azetidine-1-carboxylate (250 mg, 0.53 mmol) in DMF (2 mL) was stirred at 120° C. for 20 h under $N_2$ atmosphere. The reaction was quenched by water (80 mL) and extracted with ethyl acetate (60 mL×3). The combined organic layers were washed with brine (80 mL). The organic layers were dried over anhydrous sodium sulfate, filtered, and concentrated under reduced. The residue was purified by column chromatography on silica gel (0-10% methanol in dichloromethane) to afford the title compound (140 mg, 52%) as a white solid. $^1$H NMR (400 MHz, $CDCl_3$): δ 8.34 (d, J=9.2 Hz, 2H), 8.24 (d, J=5.2 Hz, 1H), 7.36 (d, J=8.8 Hz, 2H), 6.09 (d, J=5.6 Hz, 1H), 5.15-5.13 (m, 2H), 4.80-7.78 (m, 4H), 4.50-4.45 (m, 2H), 4.40-4.34 (m, 2H), 4.16-4.08 (m, 1H), 1.47 (s, 9H); LCMS (ESI): m/z 502.2 (M+H)$^+$.

Step 3: tert-butyl 3-(4-(3-hydroxy-3-(hydroxymethyl)azetidin-1-yl)-1-(4-(trifluoromethoxy)phenyl)-1H-pyrazolo[3,4-b]pyridin-3-yl)azetidine-1-carboxylate

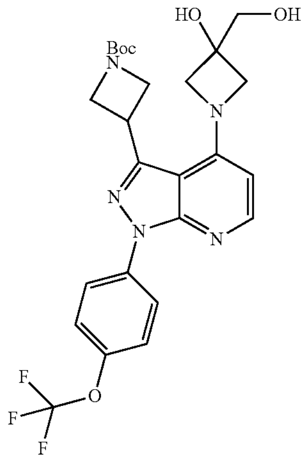 [SMILES: CC(C)(C)OC(=O)N1CC(c2nn(-c3ccc(OC(F)(F)F)cc3)c3nccc(N4CC(O)(CO)C4)c23)C1]

A mixture of tert-butyl 3-(4-(3-methyleneazetidin-1-yl)-1-(4-(trifluoromethoxy)phenyl)-1H-pyrazolo[3,4-b]pyridin-3-yl)azetidine-1-carboxylate (140 mg, 0.28 mmol), NMO (98 mg, 0.84 mmol) and $K_2Os_4 \cdot 2H_2O$ (11 mg, 0.03 mmol) in THF (10 mL) and water (1 mL) was stirred at room temperature for 16 h. The reaction was quenched by sat.$Na_2SO_3$ (50 mL). The mixture was extracted with ethyl acetate (50 mL×3). The combined organic layers were dried over $Na_2SO_4$ and concentrated under vacuo. The residue was purified by flash chromatography on silica gel (0-10% methyl alcohol in dichloromethane) to afford the title compound (60 mg, 40%) as a white solid. $^1$H NMR (400 MHz, $CDCl_3$): δ 8.29 (d, J=8.8 Hz, 2H), 8.21 (d, J=5.2 Hz, 1H), 7.36 (d, J=8.8 Hz, 2H), 6.08 (d, J=5.2 Hz, 1H), 4.46-4.38 (m, 1H), 4.34-4.30 (m, 2H), 4.20-4.15 (m, 2H), 4.14-4.09 (m, 1H), 4.08-4.05 (m, 2H), 3.93-3.87 (m, 2H), 3.74-3.62 (m, 1H), 1.47 (s, 9H); LCMS (ESI): m/z 536.2 (M+H)$^+$.

Step 4: 1-(3-(azetidin-3-yl)-1-(4-(trifluoromethoxy)phenyl)-1H-pyrazolo[3,4-b]pyridin-4-yl)-3-(hydroxymethyl)azetidin-3-ol

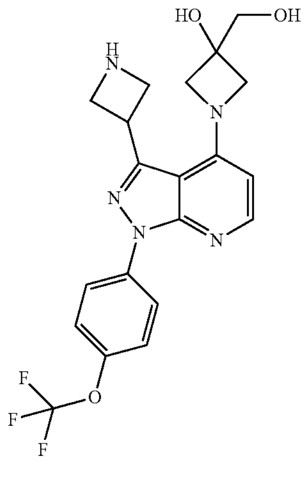 [SMILES: OCC1(O)CN(c2ccnc3c2c(C2CNC2)nn3-c2ccc(OC(F)(F)F)cc2)C1]

A solution of tert-butyl 3-(4-(3-hydroxy-3-(hydroxymethyl)azetidin-1-yl)-1-(4-(trifluoromethoxy)phenyl)-1H-pyrazolo[3,4-b]pyridin-3-yl)azetidine-1-carboxylate (60.0 mg, 0.11 mmol) in TFA (5% in HFIP, 5 mL) was stirred at room temperature for 2 h. The reaction mixture was diluted with water (50 mL) and adjusted to pH=8 with sat. $NaHCO_3$. The mixture was extracted with ethyl acetate (50 mL×3) and the organic layers were combined. The organic layer was dried over anhydrous sodium sulfate. After filtration, The mixture was concentrated to afford the title compound (40 mg, 82%) as a white solid. The crude would be used in the next step directly. LCMS (ESI): m/z 436.2 $(M+H)^+$.

Step 5: 2-fluoro-1-(3-(4-(3-hydroxy-3-(hydroxymethyl)azetidin-1-yl)-1-(4-(trifluoromethoxy)phenyl)-1H-pyrazolo[3,4-b]pyridin-3-yl)azetidin-1-yl)prop-2-en-1-one

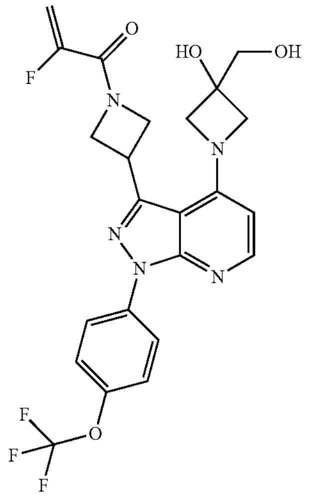 [SMILES: C=C(F)C(=O)N1CC(c2nn(-c3ccc(OC(F)(F)F)cc3)c3nccc(N4CC(O)(CO)C4)c23)C1]

To a solution of 2-fluoroacrylic acid (11 mg, 0.12 mmol), 1-(3-(azetidin-3-yl)-1-(4-(trifluoromethoxy)phenyl)-1H-pyrazolo[3,4-b]pyridin-4-yl)-3-(hydroxymethyl)azetidin-3-ol (40.0 mg, 0.10 mmol) in DCM (5 mL) and MeOH (1 mL) was added EEDQ (49.0 mg, 0.20 mmol) at 0° C., the resulting solution was stirred at room temperature with 16 h. The reaction was quenched by water (30 mL) and extracted with ethyl acetate (30 mL×3) and the organic layers were combined. The organic layer was dried over anhydrous sodium sulfate. After filtration, the filtrate was concentrated under reduced pressure. The residue was purified by chromatography on silica gel (0-25% ethyl acetate in petroleum ether) to afford the title compound (8.0 mg, 17%) as a white solid. $^1H$ NMR (400 MHz, DMSO-$d_6$): δ 8.45 (d, J=9.2 Hz, 2H), 8.16 (d, J=5.6 Hz, 1H), 7.54 (d, J=8.8 Hz, 2H), 6.21 (d, J=5.6 Hz, 1H), 5.84 (s, 1H), 5.50 (dd, J=48.4, 3.6 Hz, 1H), 5.32 (dd, J=16.8, 3.6 Hz, 1H), 5.07 (t, J=6.0 Hz, 1H), 4.90-4.75 (m, 1H), 4.77-4.71 (m, 1H), 4.50-4.42 (m, 1H), 4.41-4.33 (m, 2H), 4.30-4.20 (m, 2H), 3.98-3.96 (m, 2H), 3.47 (d, J=5.6 Hz, 2H); LCMS (ESI): m/z 508.0 $(M+H)^+$.

Example 98 & 99 (Compound 59 & 60)

(S)-1-(3-(4-(1,2-dihydroxyethyl)-1-(4-(pentafluoro-$\lambda^6$-sulfanyl)phenyl)-1H-pyrazolo[3,4-b]pyridin-3-yl)azetidin-1-yl)-2-fluoroprop-2-en-1-one & (R)-1-(3-(4-(1,2-dihydroxyethyl)-1-(4-(pentafluoro-16-sulfanyl)phenyl)-1H-pyrazolo[3,4-b]pyridin-3-yl)azetidin-1-yl)-2-fluoroprop-2-en-1-one

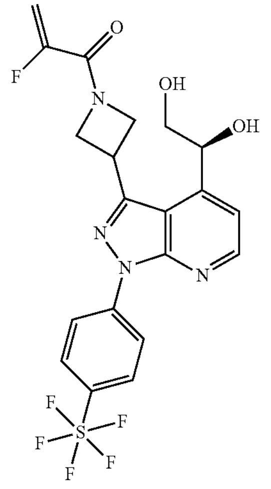

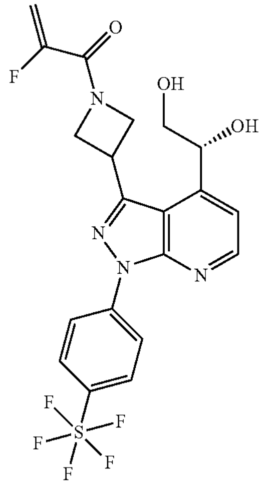

Step 1: tert-butyl 3-(4-iodo-1-(4-(pentafluoro-16-sulfanyl)phenyl)-1H-pyrazolo[3,4-b]pyridin-3-yl)azetidine-1-carboxylate

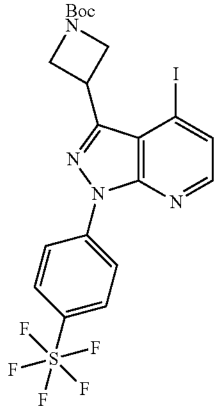 [SMILES: CC(C)(C)OC(=O)N1CC(c2nn(-c3ccc(S(F)(F)(F)(F)F)cc3)c3nccc(I)c23)C1]

A mixture of tert-butyl 3-(4-iodo-1H-pyrazolo[3,4-b]pyridin-3-yl)azetidine-1-carboxylate (900 mg, 2.25 mmol), $Cu(OAc)_2$, (613 mg, 3.37 mmol), (4-(pentafluoro-16-sulfanyl)phenyl)boronic acid (837 mg, 3.37 mmol), pyridine (0.71 mL, 9.50 mmol) in MeCN (10 mL) under $O_2$ (15 psi) was stirred at room temperature for 16 h. The reaction mixture was filtered, the filtrate was diluted with water (100 mL) and extracted with ethyl acetate (100 mL×3). The organics were washed with brine (100 mL×2), dried over sodium sulfate, filtered and concentrated to dryness. The residue was purified by flash chromatography on silica gel (0-1% ethyl acetate in petroleum ether) to afford the title compound (800 mg, 59%) as a white solid. $^1$H NMR (400 MHz, $CDCl_3$): δ 8.55 (d, J=8.8 Hz, 2H), 8.20 (d, J=4.8 Hz, 1H), 7.91 (d, J=8.8 Hz, 2H), 7.73 (d, J=4.8 Hz, 1H), 4.64-4.55 (m, 1H), 4.53-4.44 (m, 4H), 1.49 (s, 9H).

Step 2: tert-butyl 3-(1-(4-(pentafluoro-16-sulfanyl) phenyl)-4-vinyl-1H-pyrazolo[3,4-b]pyridin-3-yl) azetidine-1-carboxylate

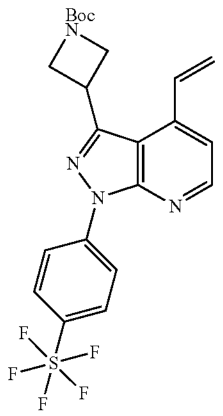 [SMILES: C=Cc1ccnc2c1c(C1CN(C(=O)OC(C)(C)C)C1)nn2-c1ccc(S(F)(F)(F)(F)F)cc1]

A mixture of tert-butyl 3-(4-iodo-1-(4-(pentafluoro-16-sulfanyl)phenyl)-1H-pyrazolo[3,4-b]pyridin-3-yl)azetidine-1-carboxylate (800 mg, 1.57 mmol), Xphos (75.0 mg, 0.15 mmol), Xphos Pd $G_2$ (123 mg, 0.15 mmol), $K_3PO_4$ (952 mg, 4.48 mmol), 4,4,5,5-tetramethyl-2-vinyl-1,3,2-dioxaborolane (299 mg, 1.94 mmol) in 1,4-dioxane (10 mL) and water (1 ml) was stirred at 100° C. for 5 h under $N_2$ atmosphere. The reaction mixture was diluted with water (50 mL) and extracted with ethyl acetate (50 mL×3), the combined organic layers were washed with brine (50 mL×3). The organic layer was dried over $Na_2SO_4$, filtered, and concentrated to dryness. The residue was purified by flash column chromatography on silica gel (0-5% ethyl acetate in petroleum ether) to afford the title compound (700 mg, crude) as a white solid. $^1$H NMR (400 MHz, $CDCl_3$): δ 8.62-8.55 (m, 3H), 7.91 (d, J=9.2 Hz, 2H), 7.31 (d, J=4.8 Hz, 1H), 7.05 (dd, J=17.2, 11.2 Hz, 1H), 6.07 (d, J=17.2 Hz, 1H), 5.73 (d, J=11.2 Hz, 1H), 4.52-4.36 (m, 4H), 4.33-4.24 (m, 1H), 1.48 (s, 9H).

Step 3: tert-butyl 3-(4-(1,2-dihydroxyethyl)-1-(4-(pentafluoro-16-sulfanyl)phenyl)-1H-pyrazolo[3,4-b]pyridin-3-yl)azetidine-1-carboxylate

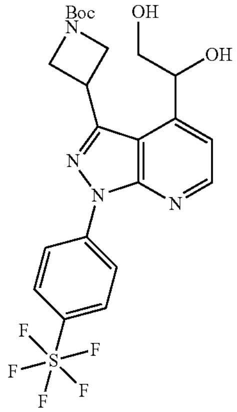 [SMILES: CC(C)(C)OC(=O)N1CC(c2nn(-c3ccc(S(F)(F)(F)(F)F)cc3)c3nccc(C(O)CO)c23)C1]

To a solution of tert-butyl 3-(1-(4-(pentafluoro-16-sulfanyl)phenyl)-4-vinyl-1H-pyrazolo[3,4-b]pyridin-3-yl)azetidine-1-carboxylate (800 mg, 1.59 mmol) in THF (10 mL) and water (1 mL) was added NMO (759 mg, 6.37 mmol) and $K_2OsO_4{\cdot}2H_2O$ (56 mg, 0.16 mmol) at room temperature. The resulting mixture was stirred at room temperature for 16 h. The reaction was quenched with aq. $Na_2SO_3$ (50 mL), diluted with ethyl acetate (50 mL) and washed with water (50 mL×3). The organic was dried over $Na_2SO_4$, filtered, and concentrated. The residue was purified by flash column chromatography on silica gel (0-5% MeOH in DCM) to afford to afford the title compound (700 mg, 82%) as a white solid. $^1$H NMR (400 MHz, $CDCl_3$): δ 8.64 (d, J=4.8 Hz, 1H), 8.58 (d, J=8.8 Hz, 2H), 7.91 (d, J=9.2 Hz, 2H), 7.42 (d, J=4.4 Hz, 1H), 5.24-5.28 (m, 1H), 4.58-4.51 (m, 1H), 4.45-4.38 (m, 3H), 4.36-4.29 (m, 1H), 3.90-3.85 (m, 1H), 3.80-3.73 (m, 1H), 1.49 (s, 9H).

Step 5: 1-(3-(azetidin-3-yl)-1-(4-(pentafluoro-16-sulfanyl)phenyl)-1H-pyrazolo[3,4-b]pyridin-4-yl) ethane-1,2-diol

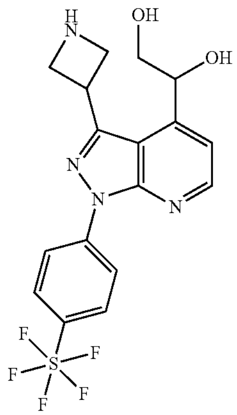 [SMILES: OCC(O)c1ccnc2c1c(C1CNC1)nn2-c1ccc(S(F)(F)(F)(F)F)cc1]

To a mixture of tert-butyl 3-(4-(1,2-dihydroxyethyl)-1-(4-(pentafluoro-16-sulfanyl)phenyl)-1H-pyrazolo[3,4-b]pyridin-3-yl)azetidine-1-carboxylate (700 mg, 1.30 mmol) and 2,6-lutidine (0.46 mL, 3.91 mmol) in DCM (5 mL) was added TMSOTf (1.40 mL, 7.82 mmol) at 0° C., then the reaction was stirred at 0° C. for 2 h under $N_2$ atmosphere. The reaction mixture was diluted with water (50 mL) and extracted with ethyl acetate (50 mL×3), the combined organic layers were washed with brine (50 mL×3). The organic layer was dried over $Na_2SO_4$, filtered, and concentrated to afford the title compound (450 mg, 80%) as a pale oil. The crude was used directly for the next step without purification.

Step 6: 1-(3-(4-(1,2-dihydroxyethyl)-1-(4-(pentafluoro-16-sulfanyl)phenyl)-1H-pyrazolo[3,4-b]pyridin-3-yl)azetidin-1-yl)-2-fluoroprop-2-en-1-one

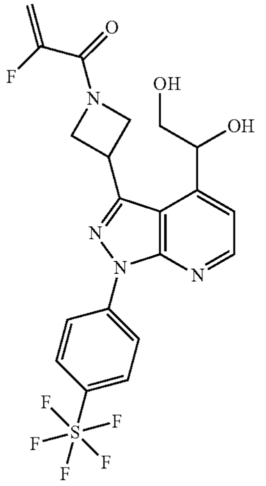

To a mixture of 1-(3-(azetidin-3-yl)-1-(4-(pentafluoro-16-sulfanyl)phenyl)-1H-pyrazolo[3,4-b]pyridin-4-yl)ethane-1,2-diol (600 mg, 1.37 mmol), 2-fluoroacrylic acid (371 mg, 4.12 mmol) in DCM (5 mL) and MeOH (1 mL) was added EEDQ (850 mg, 3.44 mmol). The solution was stirred at room temperature for 1 h. The mixture was diluted with ethyl acetate (50 mL) and washed with water (50 mL×3). The organic was dried over $Na_2SO_4$ and concentrated. The residue was purified by flash column chromatography on silica gel (0-5% MeOH in DCM) to afford the title compound (100 mg, 14%) as a white solid.

Step 7: (S)-1-(3-(4-(1,2-dihydroxyethyl)-1-(4-(pentafluoro-16-sulfanyl)phenyl)-1H-pyrazolo[3,4-b]pyridin-3-yl)azetidin-1-yl)-2-fluoroprop-2-en-1-one & (R)-1-(3-(4-(1,2-dihydroxyethyl)-1-(4-(pentafluoro-16-sulfanyl)phenyl)-1H-pyrazolo[3,4-b]pyridin-3-yl)azetidin-1-yl)-2-fluoroprop-2-en-1-one

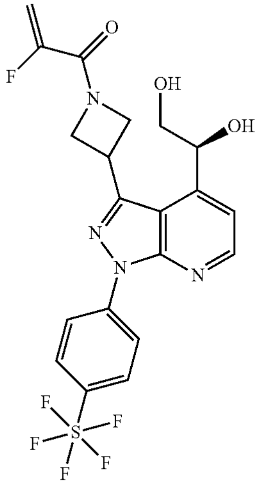

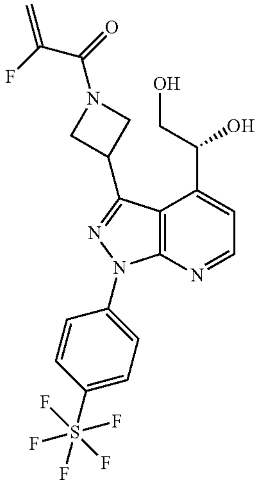 [SMILES: C=C(F)C(=O)N1CC(c2nn(-c3ccc(S(F)(F)(F)(F)F)cc3)c3nccc(C(O)CO)c23)C1]

1-(3-(4-(1,2-Dihydroxyethyl)-1-(4-(pentafluoro-16-sulfanyl)phenyl)-1H-pyrazolo[3,4-b]pyridin-3-yl)azetidin-1-yl)-2-fluoroprop-2-en-1-one (100 mg, 0.20 mmol) was separated by Chiral SFC (Instrument: SFC-13; Column: OD (250 mm*30 mm, 10 um); Condition: Neu-EtOH; Begin B:35%; Flow Rate (mL/min): 80) to afford the first peak, compound 59 (35 mg, 35%) and the second peak, compound 60 (37 mg, 37%) both as a white solid.

The first peak: $^1H$ NMR (400 MHz, DMSO-$d_6$): δ 8.76-8.56 (m, 3H), 8.12 (d, J=8.8 Hz, 2H), 7.48 (d, J=4.4 Hz, 1H), 5.85 (d, J=3.6 Hz, 1H), 5.53 (dd, J=48.8, 3.2 Hz, 1H), 5.34 (dd, J=16.8, 2.4 Hz, 1H), 5.08-4.94 (m, 2H), 4.92-4.73 (m, 2H), 4.72-4.60 (m, 1H), 4.48-4.41 (m, 2H), 3.70-3.58 (m, 2H); LCMS (ESI): m/z 509.0 $(M+H)^+$.

The second peak: $^1H$ NMR (400 MHz, DMSO-$d_6$): δ 8.71-8.63 (m, 3H), 8.13 (d, J=9.2 Hz, 2H), 7.48 (d, J=4.8 Hz, 1H), 5.86 (d, J=4.2 Hz, 1H), 5.53 (dd, J=48.4, 3.2 Hz, 1H), 5.34 (dd, J=16.8, 3.2 Hz, 1H), 5.08-4.96 (m, 2H), 4.91-4.74 (m, 2H), 4.72-4.60 (m, 1H), 4.51-4.39 (m, 2H), 3.72-3.54 (m, 2H); LCMS (ESI): m/z 509.0 $(M+H)^+$ Example 100 & 101: N-((4-(1,2-dihydroxyethyl)-1-(4-(trifluoromethyl)phenyl)-1H-pyrazolo[3,4-b]pyridin-3-yl)methyl)acrylamide, (Compounds 88 & 100)

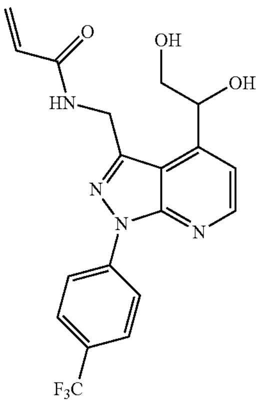 [SMILES: C=CC(=O)NCc1nn(-c2ccc(C(F)(F)F)cc2)c2nccc(C(O)CO)c12]

Step 1: 4-(2,2-dimethyl-1,3-dioxolan-4-yl)-1-(4-(trifluoromethyl)phenyl)-1H-pyrazolo[3,4-b]pyridine-3-carbonitrile

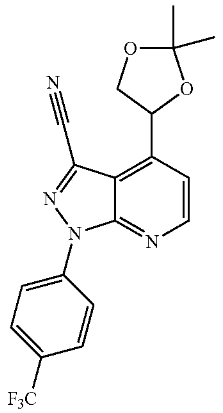 [SMILES: CC1(C)OCC(c2ccnc3c2c(C#N)nn3-c2ccc(C(F)(F)F)cc2)O1]

Following General Procedure 1 at 50° C., 96 mg of 4-(2,2-dimethyl-1,3-dioxolan-4-yl)-1-(4-(trifluoromethyl)phenyl)-1H-pyrazolo[3,4-b]pyridine-3-carbonitrile was isolated as a white solid (60% yield) from Intermediate Q (100 mg, 0.41 mmol) and [4-(trifluoromethyl)phenyl]boronic acid (117 mg, 0.61 mmol, 1.5 equiv).

LCMS (ESI) $[M+H]^+$=389.150

Steps 2-4: N-((4-(1,2-dihydroxyethyl)-1-(4-(trifluoromethyl)phenyl)-1H-pyrazolo[3,4-b]pyridin-3-yl)methyl)acrylamide

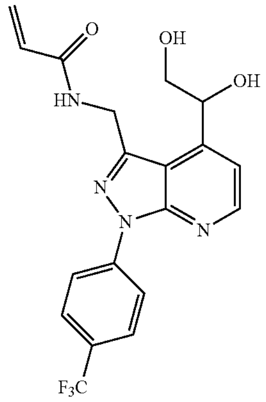 [SMILES: C=CC(=O)NCc1nn(-c2ccc(C(F)(F)F)cc2)c2nccc(C(O)CO)c12]

Following General Procedure 2 (borane protocol), 67 mg of the above compound was isolated as an off-white solid (40% yield) following chromatography (0 to 10% MeOH gradient in DCM). Chiral resolution (SFC, Chiralpak IG column, 0.1% $NH_4OH$ in Methanol, 20% isocratic gradient) gave 21.8 mg of the fast-eluting enantiomer (Compound 88, 66% separation yield) and 21.3 mg of the slow-eluting enantiomer (Compound 100, 65% separation yield).

$^1H$ NMR (400 MHz, DMSO) δ 8.71 (t, J=5.3 Hz, 1H), 8.68 (d, J=4.9 Hz, 1H), 8.60 (d, J=8.4 Hz, 2H), 7.95 (d, J=8.6 Hz, 2H), 7.50 (d, J=5.5 Hz, 1H), 6.36 (dd, J=17.1, 10.2 Hz, 1H), 6.16 (dd, J=17.1, 2.1 Hz, 1H), 5.82 (bs, 1H), 5.65 (dd, J=10.2, 2.2 Hz, 1H), 5.19 (t, J=5.6 Hz, 1H), 5.02-4.94 (m, 2H), 4.83 (dd, J=15.9, 4.9 Hz, 1H), 3.63-3.50 (m, 2H). LCMS (ESI) $[M+H]^+$=407.100

Example 102 & 103: N-((4-(1,2-dihydroxyethyl)-1-(3-(trifluoromethoxy)phenyl)-1H-pyrazolo[3,4-b]pyridin-3-yl)methyl)acrylamide, (Compound 131 & 73)

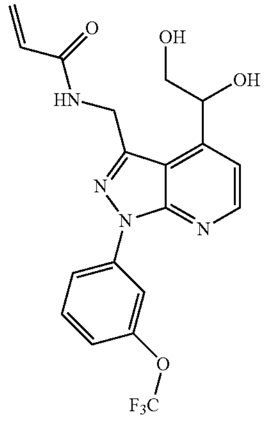 [SMILES: C=CC(=O)NCc1nn(-c2cccc(OC(F)(F)F)c2)c2nccc(C(O)CO)c12]

Step 1: 4-(2,2-dimethyl-1,3-dioxolan-4-yl)-1-(3-(trifluoromethoxy)phenyl)-1H-pyrazolo[3,4-b]pyridine-3-carbonitrile

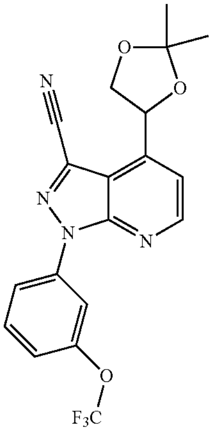 [SMILES: CC1(C)OCC(c2ccnc3c2c(C#N)nn3-c2cccc(OC(F)(F)F)c2)O1]

Following General Procedure 1 at 50° C., 90 mg of 4-(2,2-dimethyl-1,3-dioxolan-4-yl)-1-(3-(trifluoromethoxy)phenyl)-1H-pyrazolo[3,4-b]pyridine-3-carbonitrile was isolated as a clear oil (54% yield) from Intermediate Q (100 mg, 0.41 mmol) and [3-(trifluoromethoxy)phenyl]boronic acid (127 mg, 0.61 mmol, 1.5 equiv).

LCMS (ESI) $[M+H]^+$=405.150

Steps 2-4: N-((4-(1,2-dihydroxyethyl)-1-(3-(trifluoromethoxy)phenyl)-1H-pyrazolo[3,4-b]pyridin-3-yl)methyl)acrylamide

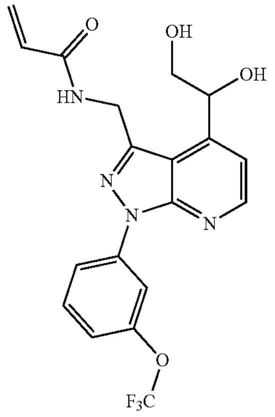 [SMILES: C=CC(=O)NCc1nn(-c2cccc(OC(F)(F)F)c2)c2nccc(C(O)CO)c12]

Following General Procedure 2 (borane protocol), 57 mg of the above compound was isolated as an off-white solid (60% yield) following chromatography (0 to 10% MeOH gradient in DCM). Chiral resolution (SFC, 2 columns used in tandem in this order: Cellulose-3 then Chiralcel OJ, 0.1% $NH_4OH$ in Methanol, 10% isocratic gradient) gave 21.6 mg of the fast-eluting enantiomer (Compound 131, 76% separation yield) and 24.2 mg of the slow-eluting enantiomer (Compound 73, 85% separation yield).

$^1$H NMR (400 MHz, DMSO) δ 8.70-8.65 (m, 2H), 8.42 (d, J=8.5 Hz, 1H), 8.36 (s, 1H), 7.71 (t, J=8.3 Hz, 1H), 7.48 (d, J=4.9 Hz, 1H), 7.33 (d, J=8.3 Hz, 1H), 6.36 (dd, J=17.4, 10.3 Hz, 1H), 6.16 (dd, J=16.9, 2.1 Hz, 1H), 5.80 (d, J=4.4 Hz, 1H), 5.65 (dd, J=10.1, 2.1 Hz, 1H), 5.22-5.13 (m, 1H), 5.03-4.92 (m, 2H), 4.82 (dd, J=15.9, 4.9 Hz, 1H), 3.68-3.55 (m, 2H). LCMS (ESI) $[M+H]^+$=423.100

Example 104 and 105: N-((4-(1,2-dihydroxyethyl)-1-(4-(pentafluoro-$\lambda^6$-sulfanyl)phenyl)-1H-pyrazolo[3,4-b]pyridin-3-yl)methyl)acrylamide, (Compounds 23 & 27)

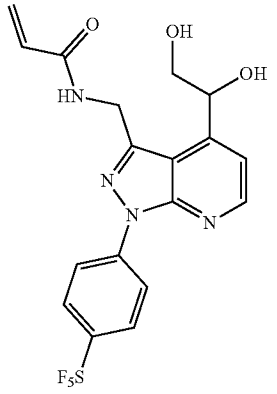

Step 1: 4-(2,2-dimethyl-1,3-dioxolan-4-yl)-1-(4-(pentafluoro-$\lambda^6$-sulfanyl)phenyl)-1H-pyrazolo[3,4-b]pyridine-3-carbonitrile

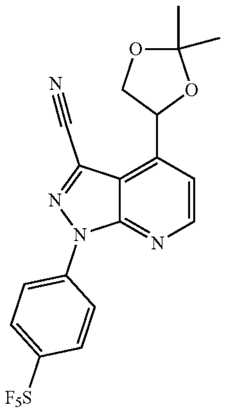

Following General Procedure 1 at 50° C., 122 mg of 4-(2,2-dimethyl-1,3-dioxolan-4-yl)-1-(4-(pentafluoro-$\lambda^6$-sulfanyl)phenyl)-1H-pyrazolo[3,4-b]pyridine-3-carbonitrile was isolated as a clear oil (39% yield) from Intermediate Q (170 mg, 0.70 mmol) and [4-(pentafluoro-$\lambda^6$-sulfanyl)phenyl]boronic acid (260 mg, 1.04 mmol, 1.5 equiv).

LCMS (ESI) $[M+H]^+$=447.150

Steps 2-4: N-((4-(1,2-dihydroxyethyl)-1-(4-(pentafluoro-λ6-sulfanyl)phenyl)-1H-pyrazolo[3,4-b]pyridin-3-yl)methyl)acrylamide

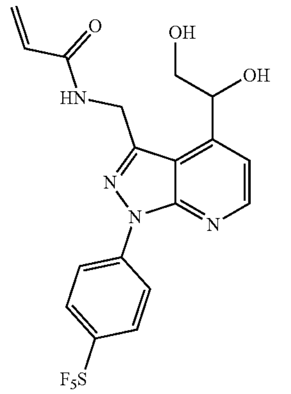

Following General Procedure 2 (borane protocol), 60 mg of the above compound was isolated as a white solid (52% yield) following chromatography (0 to 10% MeOH gradient in DCM). Chiral resolution (SFC, Chiralpak IA column, 0.1% $NH_4OH$ in Ethanol, 25% isocratic gradient) gave 19.5 mg of the fast-eluting enantiomer (Compound 23, 65% separation yield) and 20.9 mg of the slow-eluting enantiomer (Compound 27, 67% separation yield).

$^1$H NMR (400 MHz, DMSO) δ 8.72 (t, J=5.2 Hz, 1H), 8.69 (d, J=4.9 Hz, 1H), 8.61 (d, J=9.4 Hz, 2H), 8.13 (d, J=9.4 Hz, 2H), 7.51 (d, J=4.9 Hz, 1H), 6.35 (dd, J=17.1, 10.1 Hz, 1H), 6.16 (dd, J=17.1, 2.3 Hz, 1H), 5.83 (d, J=4.3 Hz, 1H), 5.65 (dd, J=10.1, 2.3 Hz, 1H), 5.22-5.13 (m, 1H), 5.05-4.92 (m, 2H), 4.83 (dd, J=15.8, 4.9 Hz, 1H), 3.71-3.51 (m, 2H). LCMS (ESI) $[M+H]^+$=465.000

Example 106: 2-fluoro-1-(3-(4-(3-hydroxyazetidin-1-yl)-1-(4-(trifluoromethoxy)phenyl)-1H-pyrazolo[4,3-c]pyridin-3-yl)azetidin-1-yl)prop-2-en-1-one, (Compound 78)

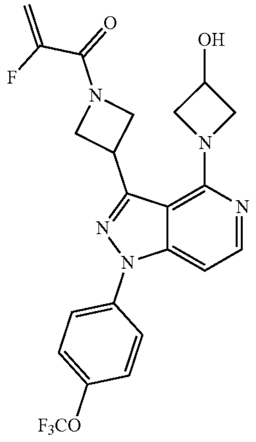 [SMILES: C=C(F)C(=O)N1CC(c2nn(-c3ccc(OC(F)(F)F)cc3)c3ccnc(N4CC(O)C4)c23)C1]

Following General Procedure 3, 19 mg of the title compound (46% yield) was prepared from 35 mg of common intermediate T and 8.5 mg of 2-fluoroprop-2-enoic acid (1.1 equiv), following purification via preparative HPLC (Mobile phase: 0.1% Ammonium Hydroxide in Water/MeCN; 30-70% MeCN gradient).

$^1$H NMR (400 MHz, DMSO) δ 7.97 (d, J=6.0 Hz, 1H), 7.89 (d, J=9.0 Hz, 2H), 7.59 (d, J=8.3 Hz, 2H), 7.12 (d, J=6.0 Hz, 1H), 5.69 (d, J=6.1 Hz, 1H), 5.49 (dd, J=48.5, 3.5 Hz, 1H), 5.31 (dd, J=16.6, 3.6 Hz, 1H), 4.86 (td, J=8.6, 3.9 Hz, 1H), 4.72-4.64 (m, 1H), 4.63-4.55 (m, 1H), 4.52-4.28 (m, 5H), 4.03-3.91 (m, 2H). LCMS (ESI) $[M+H]^+$=478.100

Example 107: (E)-4-hydroxy-1-(3-(4-(3-hydroxyazetidin-1-yl)-1-(4-(trifluoromethoxy)phenyl)-1H-pyrazolo[4,3-c]pyridin-3-yl)azetidin-1-yl)but-2-en-1-one, (Compound 103)

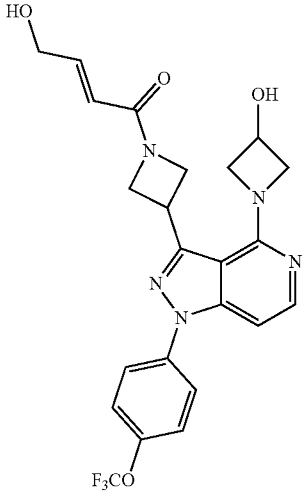 [SMILES: O=C(/C=C/CO)N1CC(c2nn(-c3ccc(OC(F)(F)F)cc3)c3ccnc(N4CC(O)C4)c23)C1]

Following General Procedure 3, 18 mg of the title compound (42% yield) was prepared from 35 mg of common intermediate T and 9.7 mg of (E)-4-hydroxybut-2-enoic acid (1.1 equiv), following purification via preparative HPLC (XSelect CSH Prep C18 column; Mobile phase: 0.1% Ammonium Hydroxide in Water/MeCN; 20-60% MeCN gradient).

$^1$H NMR (400 MHz, DMSO) δ 7.97 (d, J=6.0 Hz, 1H), 7.92-7.84 (m, 2H), 7.59 (d, J=8.5 Hz, 2H), 7.11 (d, J=6.0 Hz, 1H), 6.74 (dt, J=15.3, 3.9 Hz, 1H), 6.17 (dt, J=15.3, 2.1 Hz, 1H), 5.69 (d, J=6.2 Hz, 1H), 5.02 (t, J=5.3 Hz, 1H), 4.69 (t, J=8.1 Hz, 1H), 4.63-4.55 (m, 1H), 4.52 (dd, J=8.1, 5.1 Hz, 1H), 4.47-4.37 (m, 3H), 4.34-4.22 (m, 2H), 4.16-4.09 (m, 2H), 3.97 (dd, J=9.0, 4.7 Hz, 2H). LCMS (ESI) $[M+H]^+$=490.100

Example 108: (E)-4-fluoro-1-(3-(4-(3-hydroxyazetidin-1-yl)-1-(4-(trifluoromethoxy)phenyl)-1H-pyrazolo[4,3-c]pyridin-3-yl)azetidin-1-yl)but-2-en-1-one, (Compound 137)

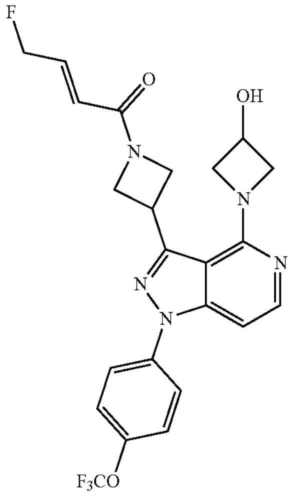 [SMILES: O=C(/C=C/CF)N1CC(c2nn(-c3ccc(OC(F)(F)F)cc3)c3ccnc(N4CC(O)C4)c23)C1]

Following General Procedure 3, 12 mg of the title compound (29% yield) was prepared from 35 mg of common intermediate T and 9.9 mg of (E)-4-fluorobut-2-enoic acid acid (1.1 equiv), following purification via preparative HPLC (XSelect CSH Prep C18 column; Mobile phase: 0.1% Ammonium Hydroxide in Water/MeCN; 20-60% MeCN gradient).

$^1$H NMR (400 MHz, DMSO) δ 7.97 (d, J=6.0 Hz, 1H), 7.88 (d, J=8.9 Hz, 2H), 7.59 (d, J=8.0 Hz, 2H), 7.11 (d, J=6.0 Hz, 1H), 6.74 (ddt, J=22.0, 15.6, 4.1 Hz, 1H), 6.27 (dq, J=15.4, 2.1 Hz, 1H), 5.69 (d, J=6.1 Hz, 1H), 5.12 (ddd, J=46.4, 4.2, 2.0 Hz, 2H), 4.73 (t, J=8.2 Hz, 1H), 4.63-4.50 (m, 2H), 4.46-4.38 (m, 3H), 4.39-4.26 (m, 2H), 3.97 (dt, J=8.7, 4.2 Hz, 2H). LCMS (ESI) $[M+H]^+$=492.100

Common Intermediate U

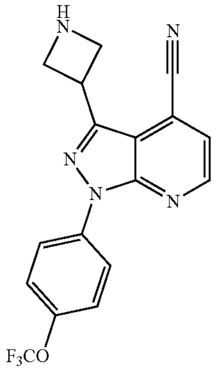 [SMILES: N#Cc1ccnc2c1c(C1CNC1)nn2-c1ccc(OC(F)(F)F)cc1]

Step 1: tert-butyl 3-(4-iodo-1-(4-(trifluoromethoxy)phenyl)-1H-pyrazolo[3,4-b]pyridin-3-yl)azetidine-1-carboxylate

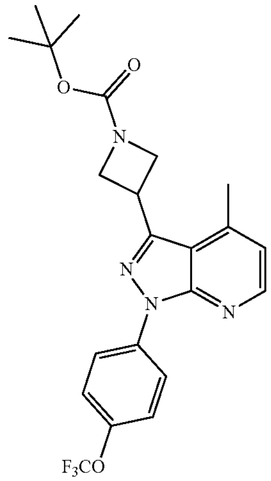 [SMILES: Cc1ccnc2c1c(C1CN(C(=O)OC(C)(C)C)C1)nn2-c1ccc(OC(F)(F)F)cc1]

Following General Procedure 1 at room temperature, 200 mg of the title compound was isolated as a clear oil (50% yield) from intermediate R (285 mg, 0.71 mmol) and [4-(trifluoromethoxy)phenyl]boronic acid (220 mg, 1.07 mmol, 1.5 equiv).

LCMS (ESI) $[M+H]^+$=561.150

Step 2: tert-butyl 3-(4-cyano-1-(4-(trifluoromethoxy)phenyl)-1H-pyrazolo[3,4-b]pyridin-3-yl)azetidine-1-carboxylate

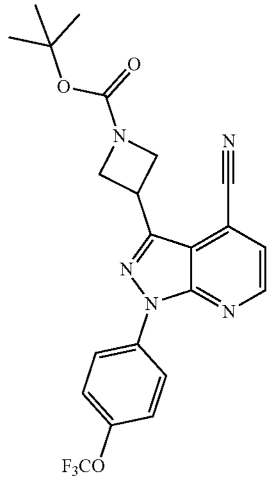 [SMILES: CC(C)(C)OC(=O)N1CC(c2nn(-c3ccc(OC(F)(F)F)cc3)c3nccc(C#N)c23)C1]

In a vial equipped with a stir bar dissolve tert-butyl 3-[4-iodo-1-[4-(trifluoromethoxy)phenyl]pyrazolo[3,4-b]pyridin-3-yl]azetidine-1-carboxylate (180 mg, 0.3213 mmol, 1.000 equiv.) and copper(I) cyanide (31.65 mg, 0.3534 mmol, 1.100 equiv.) in DMA (1.5 mL). Heat to 120° C. and stir until complete consumption of the starting materials was confirmed by LCMS analysis. The reaction was then cooled to room temperature and diluted with iPrOAc, then washed 5 times with brine. Dry the organic fraction over $MgSO_4$, filter, and concentrate. Column chromatography (silica gel, 0-100% iPrOAc in DCM) yields tert-butyl 3-[4-cyano-1-[4-(trifluoromethoxy)phenyl]pyrazolo[3,4-b]pyridin-3-yl]azetidine-1-carboxylate (103 mg, 0.22 mmol, 70% Yield) as a white solid.

LCMS (ESI) $[M-Boc+H]^+=360.200$

Step 3: 3-(azetidin-3-yl)-1-(4-(trifluoromethoxy)phenyl)-1H-pyrazolo[3,4-b]pyridine-4-carbonitrile

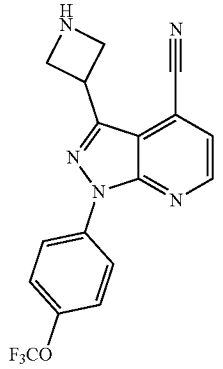 [SMILES: N#Cc1ccnc2c1c(C1CNC1)nn2-c1ccc(OC(F)(F)F)cc1]

In a RBF equipped with a stir bar, dissolve tert-butyl 3-[4-cyano-1-[4-(trifluoromethoxy)phenyl]pyrazolo[3,4-b]pyridin-3-yl]azetidine-1-carboxylate (103 mg, 0.2242 mmol, 1.000 equiv.) in DCM (2 mL), then add TFA (0.2 mL, 3 mmol, 10 equiv.). The mixture was stirred at room temperature until complete consumption of the starting materials was confirmed by LCMS analysis. At this time, the reaction was quenched with sat. aq. $NaHCO_3$, then extracted 5× with DCM, and once with 5:1 CHCl3:iPrOH. The combined organic layers were dried over $MgSO_4$, filtered, and concentrated. This afforded the title compound (63 mg, 0.18 mmol, 78% Yield) as a yellow semi-solid which was used without further purification.

LCMS (ESI) $[M+H]^+=360.150$

Example 109: 3-(1-(2-fluoroacryloyl)azetidin-3-yl)-1-(4-(trifluoromethoxy)phenyl)-1H-pyrazolo[3,4-b]pyridine-4-carbonitrile, (Compound 80)

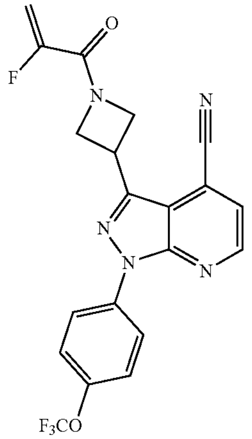 [SMILES: C=C(F)C(=O)N1CC(c2nn(-c3ccc(OC(F)(F)F)cc3)c3nccc(C#N)c23)C1]

Following General Procedure 3-9 mg of the title compound (27% yield) was prepared from 31 mg of intermediate U and 8.5 mg of 2-fluoroprop-2-enoic acid (1.1 equiv), following purification via preparative HPLC (triart C18 column; Mobile phase: 0.1% Formic Acid in Water/MeCN; 40-80% MeCN gradient).

$^1H$ NMR (400 MHz, DMSO) δ 8.93 (d, J=4.7 Hz, 1H), 8.38 (d, J=9.1 Hz, 2H), 7.97 (d, J=4.7 Hz, 1H), 7.63 (d, J=10.3 Hz, 2H), 5.51 (dd, J=48.5, 3.5 Hz, 1H), 5.32 (dd, J=16.6, 3.6 Hz, 1H), 4.92 (td, J=8.9, 3.6 Hz, 1H), 4.88-4.79 (m, 1H), 4.69-4.39 (m, 3H). LCMS (ESI) $[M+H]^+=432.100$

Example 110: 3-(1-(2-fluoroacryloyl)azetidin-3-yl)-1-(4-(trifluoromethoxy)phenyl)-1H-pyrazolo[3,4-b]pyridine-4-carbonitrile (Compound 79)

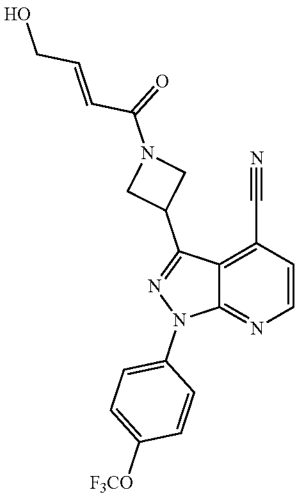 [SMILES: N#Cc1ccnc2c1c(C1CN(C(=O)/C=C/CO)C1)nn2-c1ccc(OC(F)(F)F)cc1]

Following General Procedure 3 11.2 mg of the title compound (29% yield) was prepared from 31 mg of intermediate U and 9.7 mg of (E)-4-hydroxybut-2-enoic acid (1.1 equiv), following purification via preparative HPLC (triart C18 column; Mobile phase: 0.1% Formic Acid in Water/MeCN; 30-70% MeCN gradient).

$^1H$ NMR (400 MHz, DMSO) δ 8.93 (d, J=4.7 Hz, 1H), 8.42-8.34 (m, 2H), 7.96 (d, J=4.7 Hz, 1H), 7.67-7.58 (m, 2H), 6.77 (dt, J=15.3, 3.8 Hz, 1H), 6.20 (dt, J=15.2, 2.1 Hz, 1H), 5.04 (t, J=5.3 Hz, 1H), 4.79-4.66 (m, 2H), 4.54 (tt, J=8.4, 5.8 Hz, 1H), 4.49-4.36 (m, 2H), 4.14 (ddd, J=5.6, 3.9, 2.1 Hz, 2H). LCMS (ESI) $[M+H]^+=444.200$ Example 111 (Compound 124)

N-((4-(3-hydroxy-3-(hydroxymethyl)azetidin-1-yl)-1-(4-(trifluoromethoxy)phenyl)-1H-pyrazolo[3,4-b]pyridin-3-yl)methyl)acrylamide

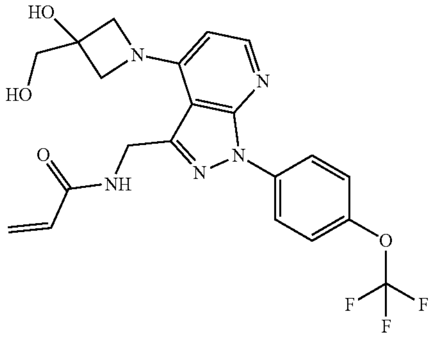 [SMILES: C=CC(=O)NCc1nn(-c2ccc(OC(F)(F)F)cc2)c2nccc(N3CC(O)(CO)C3)c12]

4-chloro-1-[4-(trifluoromethoxy)phenyl]pyrazolo[3,4-b]pyridine-3-carbonitrile (300 mg, 0.89 mmol, See Step 2 of Intermediate E for preparation), 3-(hydroxymethyl)azetidin-3-ol oxalic acid salt (131 mg, 0.44 mmol) and triethylamine (0.37 mL, 2.66 mmol) were dissolved in NMP (3 mL) and heated to 100° C. Water (5 mL) was added and extracted with EtOAc (3×20 mL). The combined organic phases were washed with brine (10 mL), dried over sodium sulfate, filtered and concentrated to yield 4-[3-hydroxy-3-(hydroxymethyl)azetidin-1-yl]-1-[4-(trifluoromethoxy)phenyl]pyrazolo[3,4-b]pyridine-3-carbonitrile (359 mg) as a brown solid. LCMS (ESI): m/z 406.2 $(M+H)^+$.

To this brown solid in methanol (3.0 mL) at 0° C. was added nickel(II) chloride hexahydrate (32 mg, 0.13 mmol) followed by sodium borohydride (134 mg, 3.54 mmol). The reaction was stirred for 30 min and more sodium borohydride (134 mg, 3.54 mmol) was added and stirred again for 30 min. Then acrylic anhydride (0.12 mL, 1.06 mmol) was added, stirred for 5 min and the reaction was quenched with saturated aqueous $Na_2CO_3$ solution (3 mL). The solution was extracted with EtOAc (3×20 mL), combined organic phases were washed with brine (5 mL), dried over sodium sulfate, filtered and concentrated. The crude was purified by flash column chromatography (silica, C18, 5-80% MeCN/10 mM ammonium formate) to yield the title compound (17.4 mg, 4% yield) as a white solid. LCMS (ESI): m/z 464.3 $(M+H)^+$. $^1H$ NMR (400 MHz, $CD_3OD$) δ 6.69 (d, J=9.0 Hz, 2H), 6.56 (s, 1H), 5.86 (d, J=8.6 Hz, 2H), 4.85 (dd, J=17.1, 9.8 Hz, 1H), 4.77 (dd, J=17.1, 2.1 Hz, 1H), 4.63 (d, J=5.6 Hz, 1H), 4.18 (dd, J=9.8, 2.1 Hz, 1H), 3.30 (s, 2H), 2.83 (d, J=8.7 Hz, 2H), 2.56 (d, J=8.5 Hz, 2H), 2.15 (s, 2H).

Example 112 (Compound 140)

N-((1-(4-(difluoromethoxy)phenyl)-4-(hydroxymethyl)-1H-pyrazolo[3,4-b]pyridin-3-yl)methyl)acrylamide

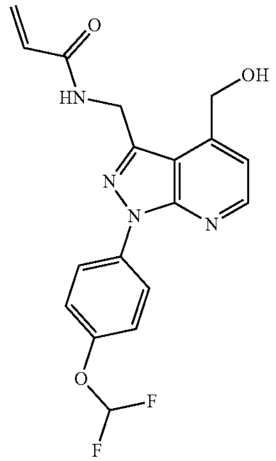 [SMILES: C=CC(=O)NCc1nn(-c2ccc(OC(F)F)cc2)c2nccc(CO)c12]

Step 1: ethyl 3-(((tert-butoxycarbonyl)amino)methyl)-1-(4-(difluoromethoxy)phenyl)-1H-pyrazolo[3,4-b]pyridine-4-carboxylate

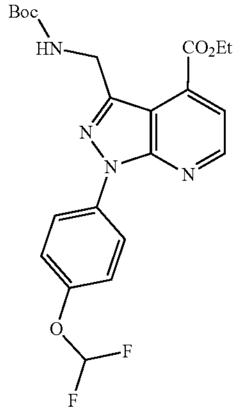 [SMILES: CCOC(=O)c1ccnc2c1c(CNC(=O)OC(C)(C)C)nn2-c1ccc(OC(F)F)cc1]

A 2 dram containing ethyl 3-[(tert-butoxycarbonylamino)methyl]-1H-pyrazolo[3,4-b]pyridine-4-carboxylate (60 mg, 0.1873 mmol, 1.0 equiv.) and a stir bar was charged with Copper(II) Acetate (51 mg, 0.2810 mmol, 1.5 equiv.) (4-(Difluoromethoxy)Phenyl)Boronic Acid (92.6 mg, 0.468 mmol, 2.5 equiv.), and MeCN (0.75 mL), followed by Pyridine (0.06 mL, 0.75 mmol, 4.0 equiv.). The reaction was stirred at 40° C. while open to air until complete conversion observed by LCMS. Reaction filtered through celite, concentrated and purified via column chromatography (silica gel, 0-30% iPrOAc/heptane). Gave 60 mg of ethyl 3-[(tert-butoxy carbonylamino)methyl]-1-[4-(difluoromethoxy)phenyl]pyrazolo[3,4-b]pyridine-4-carboxylate (69% Yield) as a white solid. LCMS (ESI) $[M+H]^+$=463.00

Step 2: tert-butyl ((1-(4-(difluoromethoxy)phenyl)-4-(hydroxymethyl)-1H-pyrazolo[3,4-b]pyridin-3-yl)methyl)carbamate

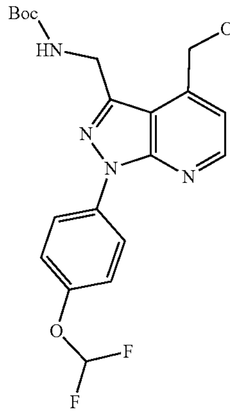

To a 2 dram vial containing ethyl 3-[(tert-butoxycarbonylamino)methyl]-1-[4-(difluoromethoxy)phenyl]pyrazolo[3,4-b]pyridine-4-carboxylate (60 mg, 0.1298 mmol, 1.0 equiv.) in THF (0.87 mL) under $N_2$ at 0° C. was added Lithium aluminum hydride (2.3 M) in 2-MethylTetrahydrofuran (0.062 mL, 0.143 mmol, 1.1 equiv.) dropwise. The reaction was then stirred at 0° C. and monitored by LCMS until full consumption of starting material observed. Sodium Sulfate Dodecahydrate slowly added to the stirring reaction until gas evolution stopped. Reaction was then filtered through celite, washed with iPrOAc, concentrated and purified by column chromatography (silica 0-55% iPrOAc/heptane). Gave 27 mg of tert-butyl N-[[1-[4-(difluoromethoxy)phenyl]-4-(hydroxymethyl)pyrazolo[3,4-b]pyridin-3-yl]methyl]carbamate (50% Yield) as a yellow solid. LCMS (ESI) $[M+H]^+$=420.950.

Step 3: N-((1-(4-(difluoromethoxy)phenyl)-4-(hydroxymethyl)-1H-pyrazolo[3,4-b]pyridin-3-yl)methyl)acrylamide

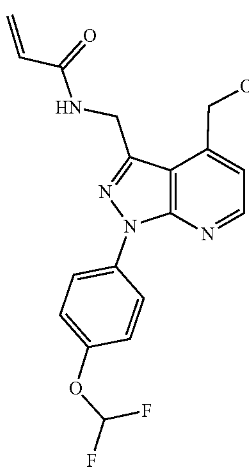

To a 2 dram vial containing tert-butyl N-[[1-[4-(difluoromethoxy)phenyl]-4-(hydroxymethyl)pyrazolo[3,4-b]pyridin-3-yl]methyl]carbamate (27 mg, 0.064 mmol, 1.0 equiv.) was added DCM (0.22 mL) and Hydrochloric acid (4 M in 1,4-Dioxane, 0.16 mL, 0.6422 mmol, 10.0 equiv.). The reaction was stirred at room temperature overnight until no starting material remaining as monitored by LCMS. Reaction concentrated under reduced pressure to give the crude amine [3-(aminomethyl)-1-[4-(difluoromethoxy)phenyl]pyrazolo[3,4-b]pyridin-4-yl]methanol, which was then dissolved in DCM (0.32 mL). DIPEA (0.22 mL, 1.284 mmol, 20.0 equiv.) was added, reaction was cooled to −40° C., and a solution of acrylic anhydride (0.008 mL, 0.071 mmol, 1.10 equiv.) in DCM (0.32 mL) was then added dropwise. Reaction was stirred at −40° C. until full conversion to the desired product was observed by LCMS. Saturated aqueous $NH_4Cl$ was added at −40° C. and mixture was allowed to warm to room temperature. Reaction transferred to a separatory funnel extracted with iPrOAc. Organic layer was washed with saturated aqueous $NaHCO_3$, then combined aqueous layers were back extracted (2× iPrOAc and 1×DCM). Organics were combined, dried, filtered, and concentrated. The resulting residue was purified by preparative HPLC (Triart C18, 20-60% MeCN/water, 0.1% $NH_4OH$ modifier). Afforded the title compound (10.74 mg, 45% yield over 2 steps) as a white solid. $^1H$ NMR (400 MHz, DMSO) δ 8.65 (dd, J=8.7, 4.9 Hz, 2H), 8.33-8.25 (m, 2H), 7.49-7.35 (m, 3H), 7.29 (s, 1H), 6.31 (dd, J=17.1, 10.1 Hz, 1H), 6.16 (dd, J=17.1, 2.3 Hz, 1H), 5.72-5.60 (m, 2H), 4.99 (d, J=5.1 Hz, 2H), 4.80 (d, J=5.2 Hz, 2H). LCMS (ESI) $[M+H]^+$=375.100

Example 113 (Compound 101)

N-((4-((2-hydroxyethyl)(methyl)amino)-1-(4-(trifluoromethoxy)phenyl)-1H-pyrazolo[3,4-b]pyridin-3-yl)methyl)acrylamide

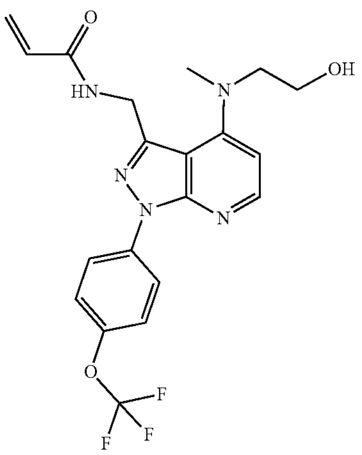 [SMILES: C=CC(=O)NCc1nn(-c2ccc(OC(F)(F)F)cc2)c2nccc(N(C)CCO)c12]

Step 1: tert-butyl ((4-((2-hydroxyethyl)(methyl) amino)-1-(4-(trifluoromethoxy)phenyl)-1H-pyrazolo [3,4-b]pyridin-3-yl)methyl)carbamate

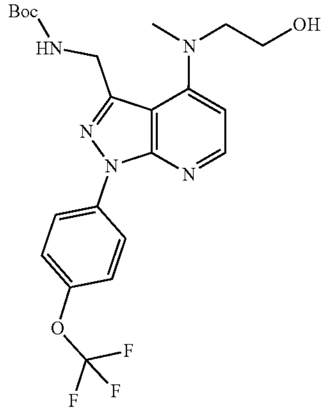 [SMILES: CN(CCO)c1ccnc2c1c(CNC(=O)OC(C)(C)C)nn2-c1ccc(OC(F)(F)F)cc1]

To a 2 dram vial containing tert-butyl N-[[4-chloro-1-[4-(trifluoromethoxy)phenyl]pyrazolo[3,4-b]pyridin-3-yl] methyl]carbamate (Intermediate B, 40 mg, 0.09033 mmol, 1.0 equiv.) and 2-(methylamino)ethanol (14 mg, 0.1807 mmol, 2.0 equiv.) was added NMP (0.60 mL) and DIPEA (0.06 mL, 0.3613 mmol, 4.0 equiv.). The reaction was then heated to 100° C. until no starting material remained as observed by LCMS. The reaction was cooled and directly purified by column chromatography (silica 0-50% iPrOAc/heptane). Gave 200 mg of tert-butyl ((4-((2-hydroxyethyl)(methyl)amino)-1-(4-(trifluoromethoxy)phenyl)-1H-pyrazolo[3,4-b]pyridin-3-yl)methyl)carbamate contaminated with NMP was obtained; wet product used directly. LCMS (ESI) $[M+H]^+$=482.100.

Step 2: N-((4-((2-hydroxyethyl)(methyl)amino)-1-(4-(trifluoromethoxy)phenyl)-1H-pyrazolo[3,4-b] pyridin-3-yl)methyl)acrylamide

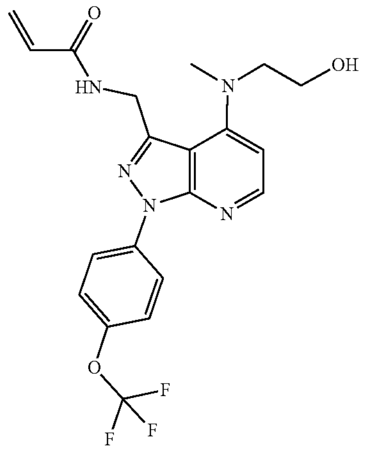 [SMILES: C=CC(=O)NCc1nn(-c2ccc(OC(F)(F)F)cc2)c2nccc(N(C)CCO)c12]

To a 2 dram vial containing impure tert-butyl ((4-((2-hydroxyethyl)(methyl)amino)-1-(4-(trifluoromethoxy)phenyl)-1H-pyrazolo[3,4-b]pyridin-3-yl)methyl)carbamate (0.09 mmol, 1.0 equiv.) was added DCM (0.30 mL) and Hydrochloric acid (4 M in 1,4-Dioxane, 0.34 mL, 1.40 mmol, 15.0 equiv.). The reaction was stirred at room temperature and additional HCl was added until no starting material remained as monitored by LCMS. Reaction concentrated under reduced pressure to give the crude amine 2-[[3-(aminomethyl)-1-[4-(trifluoromethoxy)phenyl]pyrazolo[3,4-b]pyridin-4-yl]-methyl-amino]ethanol, which was then dissolved in DCM (0.45 mL). DIPEA (0.78 mL, 4.5 mmol, 50.0 equiv.) was added, reaction was cooled to −40° C., and a solution of acrylic anhydride (0.011 mL, 0.099 mmol, 1.1 equiv.) in DCM (0.45 mL) was then added dropwise. Reaction was stirred at −40° C. until full conversion to the desired product was observed by LCMS. Saturated aqueous $NH_4Cl$ was added at −40° C. and mixture was allowed to warm to room temperature. Reaction transferred to a separatory funnel extracted with iPrOAc. Organic layer was washed with saturated aqueous $NaHCO_3$, then combined aqueous layers were back extracted (2× iPrOAc and 1×DCM). Organics were combined, dried, filtered, and concentrated. The resulting residue was purified by preparative HPLC (Triart C18 column, 20-60% MeCN/water, 0.1% $NH_4OH$ modifier) to afford 23.2 mg of N-((4-((2-hydroxyethyl)(methyl)amino)-1-(4-(trifluoromethoxy)phenyl)-1H-pyrazolo[3,4-b]pyridin-3-yl)methyl)acrylamide as a white solid (59% yield over 3 steps). $^1H$ NMR (400 MHz, DMSO) δ 8.52 (t, J=5.2 Hz, 1H), 8.43-8.35 (m, 2H), 8.27 (d, J=5.5 Hz, 1H), 7.55 (d, J=8.7 Hz, 2H), 6.71 (d, J=5.6 Hz, 1H), 6.35 (dd, J=17.1, 10.1 Hz, 1H), 6.13 (dd, J=17.1, 2.2 Hz, 1H), 5.62 (dd, J=10.2, 2.2 Hz, 1H), 4.82 (d, J=5.2 Hz, 2H), 4.71 (t, J=5.3 Hz, 1H), 3.65 (q, J=5.6 Hz, 2H), 3.45 (t, J=5.7 Hz, 2H), 3.06 (s, 3H). LCMS (ESI) $[M+H]^+$=436.100.

Example 114 and 115 (Compound 85 & 143)

N-((4-((3-hydroxycyclobutyl)amino)-1-(4-(trifluoromethoxy)phenyl)-1H-pyrazolo[3,4-b]pyridin-3-yl) methyl)acrylamide

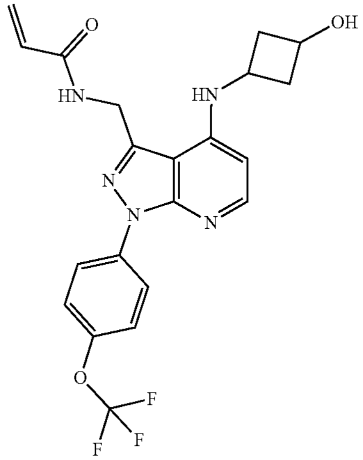 [SMILES: C=CC(=O)NCc1nn(-c2ccc(OC(F)(F)F)cc2)c2nccc(NC3CC(O)C3)c12]

For this example, the same sequence of steps was followed as for Example 113, except that 3-aminocyclobutanol hydrochloride was used in the first step instead of 2-(methylamino) ethanol.

Step 1: tert-butyl ((4-((3-hydroxycyclobutyl)amino)-1-(4-(trifluoromethoxy)phenyl)-1H-pyrazolo[3,4-b]pyridin-3-yl)methyl)carbamate

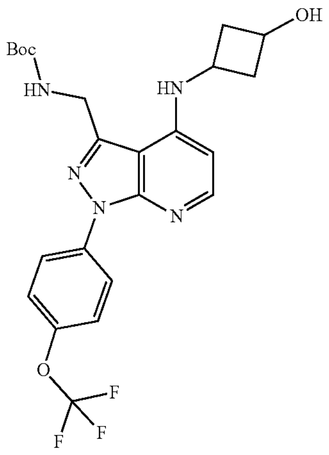 [SMILES: CC(C)(C)OC(=O)NCc1nn(-c2ccc(OC(F)(F)F)cc2)c2nccc(NC3CC(O)C3)c12]

Reaction was run on a 0.2033 mmol scale with Intermediate B. 150 mg of tert-butyl N-[[4-[(3-hydroxycyclobutyl)amino]-1-[4-(trifluoromethoxy)phenyl]pyrazolo[3,4-b]pyridin-3-yl]methyl]carbamate contaminated with NMP was obtained. LCMS (ESI) $[M+H]^+$=494.100.

Step 2: N-((4-((3-hydroxycyclobutyl)amino)-1-(4-(trifluoromethoxy)phenyl)-1H-pyrazolo[3,4-b]pyridin-3-yl)methyl)acrylamide

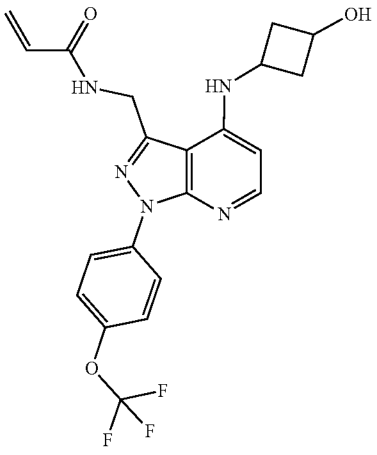 [SMILES: C=CC(=O)NCc1nn(-c2ccc(OC(F)(F)F)cc2)c2nccc(NC3CC(O)C3)c12]

After deprotection and acylation, 32 mg of N-((4-((3-hydroxycyclobutyl)amino)-1-(4-(trifluoromethoxy)phenyl)-1H-pyrazolo[3,4-b]pyridin-3-yl)methyl)acrylamide was obtained as a white solid (35% yield over 3 steps) following preparative HPLC (Triart C18 column, 20-60% MeCN/water, 0.1% formic acid modifier). The mixture of diastereomers were further separated by chiral SFC (Regis I-Amylose-A column, 0.1% $NH_4OH$ in MeOH, 20% isocratic gradient. 1.76 mg [2% yield] of the fast eluting isomer and 15.55 mg [17%] of the slow-eluting isomer were obtained.)

$^1H$ NMR Fast eluting isomer was not obtained; $^1H$ NMR Slower eluting isomer (400 MHz, DMSO) δ 9.16 (t, J=6.2 Hz, 1H), 8.46-8.37 (m, 2H), 8.13 (d, J=5.6 Hz, 1H), 7.58-7.50 (m, 2H), 7.29 (d, J=6.0 Hz, 1H), 6.35-6.21 (m, 3H), 5.73 (dd, J=7.5, 4.7 Hz, 1H), 5.15 (d, J=5.7 Hz, 1H), 4.80 (d, J=6.2 Hz, 2H), 3.93 (h, J=7.1 Hz, 1H), 3.55 (tt, J=14.8, 6.8 Hz, 1H), 2.74 (tq, J=6.9, 3.0 Hz, 2H), 1.94 (qt, J=8.5, 2.8 Hz, 2H).

LCMS (ESI) $[M+H]^+$ (both isomers)=448.100.

Example 116 and 117 (Compound 90 & 117)

N-((4-((3-hydroxycyclobutyl)(methyl)amino)-1-(4-(trifluoromethoxy)phenyl)-1H-pyrazolo[3,4-b]pyridin-3-yl)methyl)acrylamide

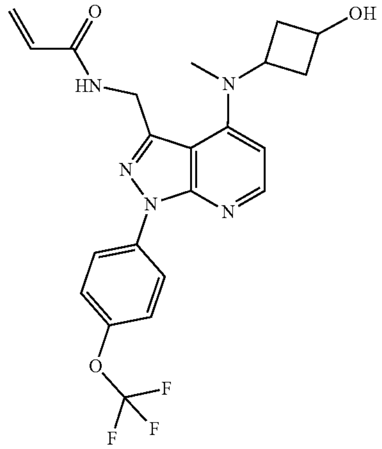 [SMILES: C=CC(=O)NCc1nn(-c2ccc(OC(F)(F)F)cc2)c2nccc(N(C)C3CC(O)C3)c12]

For this example, the same sequence of steps was followed as for Example 113, except that 3-(methylamino)cyclobutanol hydrochloride was used in the first step instead of 2-(methylamino) ethanol.

Step 1: tert-butyl 04-((3-hydroxycyclobutyl)(methyl)amino)-1-(4-(trifluoromethoxy)phenyl)-1H-pyrazolo[3,4-b]pyridin-3-yl)methyl)carbamate

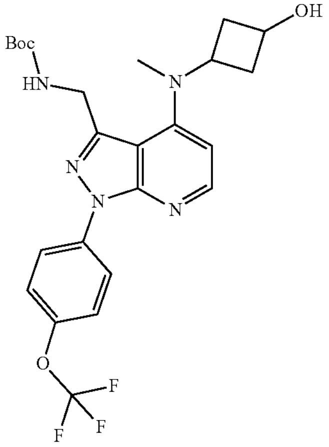 [SMILES: CN(c1ccnc2c1c(CNC(=O)OC(C)(C)C)nn2-c1ccc(OC(F)(F)F)cc1)C1CC(O)C1]

Reaction was run on a 0.2033 mmol scale with Intermediate B. 700 mg of tert-butyl ((4-((3-hydroxycyclobutyl)(methyl)amino)-1-(4-(trifluoromethoxy)phenyl)-1H-pyrazolo[3,4-b]pyridin-3-yl)methyl)carbamate contaminated with NMP was obtained. LCMS (ESI) $[M+H]^+$=508.150.

Step 2: N-((4-((3-hydroxycyclobutyl)(methyl) amino)-1-(4-(trifluoromethoxy)phenyl)-1H-pyrazolo [3,4-b]pyridin-3-yl)methyl)acrylamide

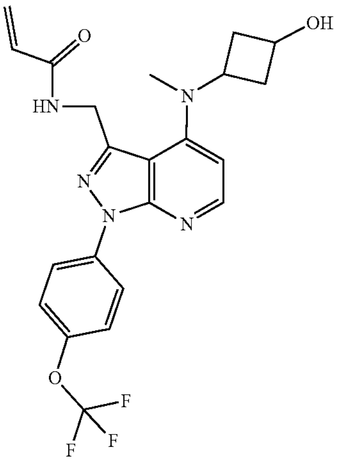 [SMILES: C=CC(=O)NCc1nn(-c2ccc(OC(F)(F)F)cc2)c2nccc(N(C)C3CC(O)C3)c12]

After deprotection and acylation, 53.8 mg of N-((4-((3-hydroxycyclobutyl)(methyl)amino)-1-(4-(trifluoromethoxy) phenyl)-1H-pyrazolo[3,4-b]pyridin-3-yl)methyl)acrylamide was obtained as a white solid (57% yield over 3 steps) following preparative HPLC (Triart C18 column, 30-70% MeCN/water, 0.1% formic acid modifier). The mixture of diastereomers were further separated by chiral SFC (Lux Amylose-3 column, 0.1% $NH_4OH$ in MeOH, 20% isocratic gradient. 3.7 mg [4% yield] of the fast eluting isomer and 36.22 mg [39%] of the slow-eluting isomer were obtained.)

$^1H$ NMR Fast eluting isomer (400 MHz, DMSO) δ 8.52 (t, J=5.0 Hz, 1H), 8.43-8.34 (m, 2H), 8.32 (d, J=5.3 Hz, 1H), 7.56 (d, J=8.7 Hz, 2H), 6.51 (d, J=5.4 Hz, 1H), 6.33 (dd, J=17.1, 10.1 Hz, 1H), 6.15 (dd, J=17.1, 2.3 Hz, 1H), 5.63 (dd, J=10.1, 2.3 Hz, 1H), 5.05 (d, J=5.0 Hz, 1H), 4.82 (d, J=5.0 Hz, 2H), 4.23-4.14 (m, 1H), 4.15-4.04 (m, 1H), 2.92 (s, 3H), 2.27 (dt, J=12.7, 6.9 Hz, 2H), 2.18-2.08 (m, 2H).

$^1H$ NMR Slower eluting isomer (400 MHz, DMSO) δ 8.57 (t, J=4.9 Hz, 1H), 8.43-8.34 (m, 2H), 8.30 (d, J=5.3 Hz, 1H), 7.60-7.52 (m, 2H), 6.61 (d, J=5.5 Hz, 1H), 6.36 (dd, J=17.1, 10.2 Hz, 1H), 6.16 (dd, J=17.1, 2.2 Hz, 1H), 5.63 (dd, J=10.1, 2.2 Hz, 1H), 5.09 (d, J=6.3 Hz, 1H), 4.79 (d, J=5.0 Hz, 2H), 3.86 (h, J=7.1 Hz, 1H), 3.60-3.44 (m, 1H), 2.93 (s, 3H), 2.57 (ddt, J=8.1, 6.1, 3.3 Hz, 2H), 1.89 (qd, J=8.5, 2.7 Hz, 2H).

LCMS (ESI) $[M+H]^+$ (both isomers)=462.100.

Example 118 (Compound 74)

N-((4-(3-hydroxy-3-methylazetidin-1-yl)-1-(4-(trifluoromethoxy)phenyl)-1H-pyrazolo[3,4-b]pyridin-3-yl)methyl)acrylamide

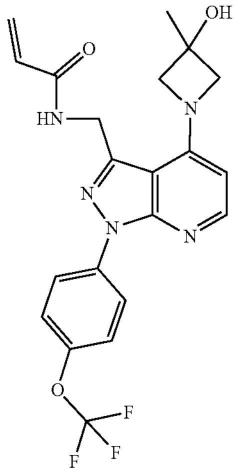 [SMILES: C=CC(=O)NCc1nn(-c2ccc(OC(F)(F)F)cc2)c2nccc(N3CC(C)(O)C3)c12]

For this example, the same sequence of steps was followed as for Example 113, except that 3-methylazetidin-3-ol hydrochloride was used in the first step instead of 2-(methylamino) ethanol.

Step 1: tert-butyl ((4-(3-hydroxy-3-methylazetidin-1-yl)-1-(4-(trifluoromethoxy)phenyl)-1H-pyrazolo[3,4-b]pyridin-3-yl)methyl)carbamate

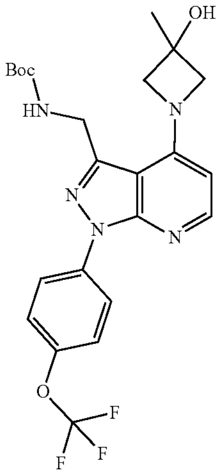 [SMILES: CC1(O)CN(c2ccnc3c2c(CNC(=O)OC(C)(C)C)nn3-c2ccc(OC(F)(F)F)cc2)C1]

Reaction was run on a 0.09033 mmol scale with Intermediate B. 120 mg of tert-butyl ((4-(3-hydroxy-3-methylazetidin-1-yl)-1-(4-(trifluoromethoxy)phenyl)-1H-pyrazolo [3,4-b]pyridin-3-yl)methyl)carbamate contaminated with NMP was obtained. LCMS (ESI) $[M+H]^+$=494.100.

Step 2: N-((4-(3-hydroxy-3-methylazetidin-1-yl)-1-(4-(trifluoromethoxy)phenyl)-1H-pyrazolo[3,4-b]pyridin-3-yl)methyl)acrylamide

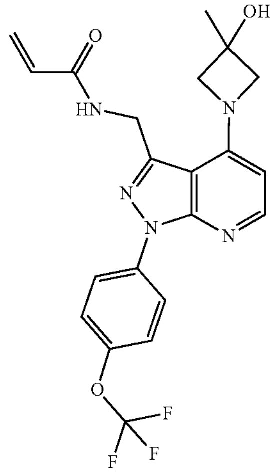 [SMILES: C=CC(=O)NCc1nn(-c2ccc(OC(F)(F)F)cc2)c2nccc(N3CC(C)(O)C3)c12]

After deprotection and acylation, 28.4 mg of N-((4-(3-hydroxy-3-methylazetidin-1-yl)-1-(4-(trifluoromethoxy)phenyl)-1H-pyrazolo[3,4-b]pyridin-3-yl)methyl)acrylamide was obtained as a white solid (71% yield over 3 steps) following preparative HPLC (XSelect CSH Prep C18 column, 30-70% MeCN/water, 0.1% $NH_4OH$ modifier). $^1H$ NMR (400 MHz, DMSO) δ 8.59 (t, J=4.9 Hz, 1H), 8.46-8.38 (m, 2H), 8.16 (d, J=5.6 Hz, 1H), 7.54 (d, J=8.8 Hz, 2H), 6.37 (dd, J=17.1, 10.2 Hz, 1H), 6.21-6.12 (m, 2H), 5.73 (s, 1H), 5.64 (dd, J=10.1, 2.3 Hz, 1H), 4.71 (d, J=4.8 Hz, 2H), 4.16 (d, J=8.3 Hz, 2H), 4.09 (d, J=8.3 Hz, 2H), 1.44 (s, 3H). LCMS (ESI) $[M+H]^+$=448.100.

Example 119 (Compound 116)

N-((4-(3-acetamidoazetidin-1-yl)-1-(4-(trifluoromethoxy)phenyl)-1H-pyrazolo[3,4-b]pyridin-3-yl)methyl)acrylamide

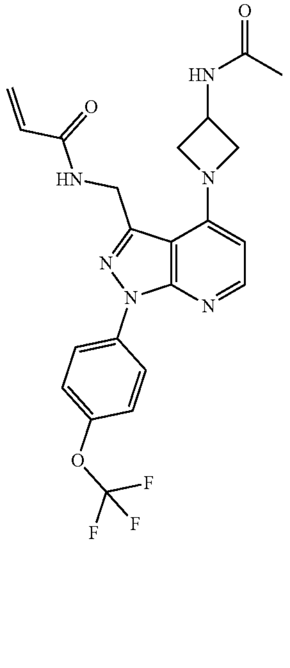 [SMILES: C=CC(=O)NCc1nn(-c2ccc(OC(F)(F)F)cc2)c2nccc(N3CC(NC(C)=O)C3)c12]

For this example, the same sequence of steps was followed as for Example 113, except that N-(azetidin-3-yl)acetamide hydrochloride was used in the first step instead of 2-(methylamino) ethanol.

Step 1: tert-butyl ((4-(3-acetamidoazetidin-1-yl)-1-(4-(trifluoromethoxy)phenyl)-1H-pyrazolo[3,4-b]pyridin-3-yl)methyl)carbamate

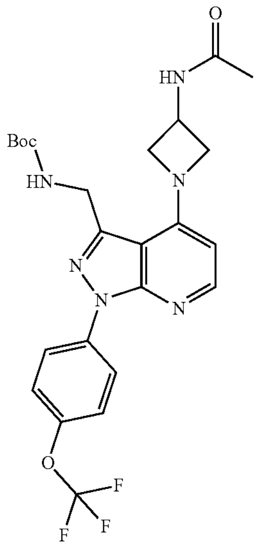 [SMILES: CC(=O)NC1CN(c2ccnc3c2c(CNC(=O)OC(C)(C)C)nn3-c2ccc(OC(F)(F)F)cc2)C1]

Reaction was run on a 0.09033 mmol scale with Intermediate B. 170 mg of tert-butyl ((4-(3-acetamidoazetidin-1-yl)-1-(4-(trifluoromethoxy)phenyl)-1H-pyrazolo[3,4-b]pyridin-3-yl)methyl)carbamate contaminated with NMP was obtained. LCMS (ESI) $[M+H]^+$=521.100.

Step 2: N-((4-(3-acetamidoazetidin-1-yl)-1-(4-(trifluoromethoxy)phenyl)-1H-pyrazolo[3,4-b]pyridin-3-yl)methyl)acrylamide

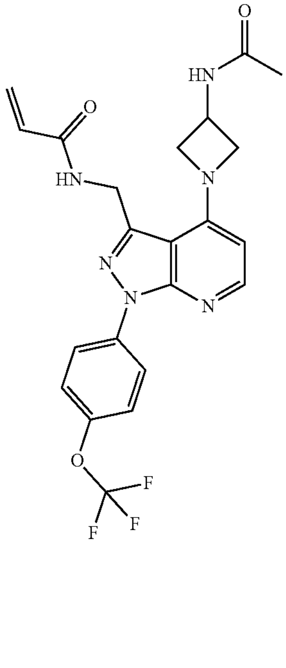 [SMILES: C=CC(=O)NCc1nn(-c2ccc(OC(F)(F)F)cc2)c2nccc(N3CC(NC(C)=O)C3)c12]

After deprotection and acylation, 19.8 mg of N-((4-(3-acetamidoazetidin-1-yl)-1-(4-(trifluoromethoxy)phenyl)-1H-pyrazolo[3,4-b]pyridin-3-yl)methyl)acrylamide was obtained as a white solid (46% yield over 3 steps) following preparative HPLC (Triart C18 column, 20-60% MeCN/water). $^1$H NMR (400 MHz, DMSO) δ 8.64-8.57 (m, 2H), 8.46-8.37 (m, 2H), 8.18 (d, J=5.6 Hz, 1H), 7.58-7.51 (m, 2H), 6.38 (dd, J=17.1, 10.2 Hz, 1H), 6.26-6.09 (m, 2H), 5.64 (dd, J=10.2, 2.2 Hz, 1H), 4.72 (d, J=5.0 Hz, 2H), 4.63 (dt, J=11.2, 6.7 Hz, 1H), 4.55 (t, J=8.0 Hz, 2H), 4.09 (dd, J=8.6, 4.9 Hz, 2H), 1.85 (s, 3H). LCMS (ESI) $[M+H]^+$=475.100.

Example 120 and 121 (Compound 33 & 65)

N-((4-(3-hydroxypiperidin-1-yl)-1-(4-(trifluoromethoxy)phenyl)-1H-pyrazolo[3,4-b]pyridin-3-yl)methyl)acrylamide

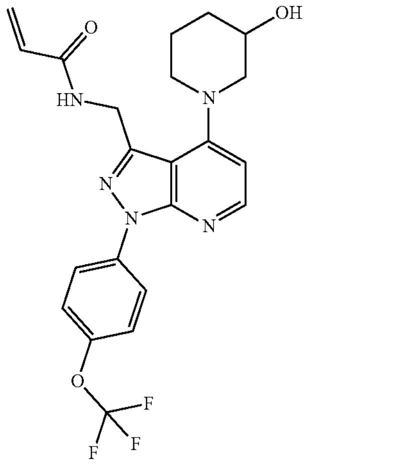 [SMILES: C=CC(=O)NCc1nn(-c2ccc(OC(F)(F)F)cc2)c2nccc(N3CCCC(O)C3)c12]

For this example, the same sequence of steps was followed as for Example 113, except that piperidin-3-ol was used in the first step instead of 2-(methylamino)ethanol.

Step 1: tert-butyl 04-(3-hydroxypiperidin-1-yl)-1-(4-(trifluoromethoxy)phenyl)-1H-pyrazolo[3,4-b]pyridin-3-yl)methyl)carbamate

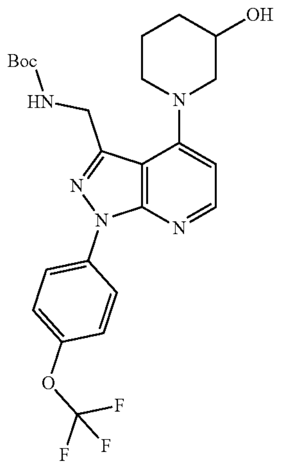 [SMILES: CC(C)(C)OC(=O)NCc1nn(-c2ccc(OC(F)(F)F)cc2)c2nccc(N3CCCC(O)C3)c12]

Reaction was run on a 0.2033 mmol scale with Intermediate B. 600 mg of tert-butyl ((4-(3-hydroxypiperidin-1-yl)-1-(4-(trifluoromethoxy)phenyl)-1H-pyrazolo[3,4-b]pyridin-3-yl)methyl)carbamate contaminated with NMP was obtained. LCMS (ESI) $[M+H]^+$=508.100.

Step 2: N-((4-(3-hydroxypiperidin-1-yl)-1-(4-(trifluoromethoxy)phenyl)-1H-pyrazolo[3,4-b]pyridin-3-yl)methyl)acrylamide

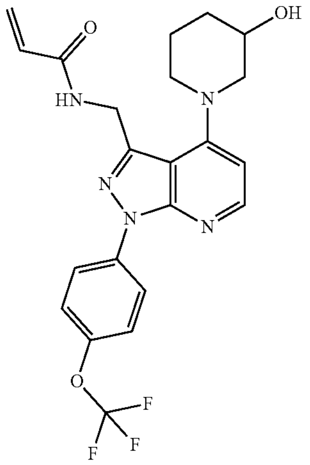 [SMILES: C=CC(=O)NCc1nn(-c2ccc(OC(F)(F)F)cc2)c2nccc(N3CCCC(O)C3)c12]

After deprotection and acylation, 57.95 mg of N-((4-(3-hydroxypiperidin-1-yl)-1-(4-(trifluoromethoxy)phenyl)-1H-pyrazolo[3,4-b]pyridin-3-yl)methyl)acrylamide was obtained as a white solid (62% yield over 3 steps) following preparative HPLC (Triart C18 column, 30-70% MeCN/water, 0.1% $NH_4OH$ modifier). The enantiomers were further separated by chiral SFC (Chiralpak IH column, 0.1% $NH_4OH$ in MeOH, 20% isocratic gradient. 24.5 mg [26% yield] of the fast eluting isomer and 26.4 mg [28%] of the slow-eluting isomer were obtained.)

$^1$H NMR (400 MHz, DMSO) δ 8.58 (t, J=5.1 Hz, 1H), 8.43-8.34 (m, 3H), 7.56 (d, J=8.7 Hz, 2H), 6.80 (d, J=5.4 Hz, 1H), 6.36 (dd, J=17.1, 10.2 Hz, 1H), 6.14 (dd, J=17.1, 2.2 Hz, 1H), 5.63 (dd, J=10.2, 2.2 Hz, 1H), 5.00 (d, J=4.2 Hz, 1H), 4.88-4.73 (m, 2H), 3.78 (tt, J=8.6, 4.1 Hz, 1H), 3.47 (dd, J=11.6, 3.7 Hz, 1H), 3.43-3.33 (m, 1H), 2.98-2.88 (m, 1H), 2.77 (dd, J=11.7, 8.6 Hz, 1H), 1.97-1.82 (m, 1H), 1.72-1.62 (m, 1H), 1.46-1.32 (m, 1H). LCMS (ESI) $[M+H]^+$=462.39.

Example 122 and 123 (Compound 123 & 138)

N-((4-(3-(1-hydroxyethyl)azetidin-1-yl)-1-(4-(trifluoromethoxy)phenyl)-1H-pyrazolo[3,4-b]pyridin-3-yl)methyl)acrylamide

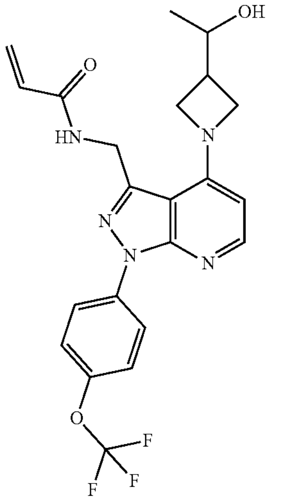 [SMILES: C=CC(=O)NCc1nn(-c2ccc(OC(F)(F)F)cc2)c2nccc(N3CC(C(C)O)C3)c12]

For this example, the same sequence of steps was followed as for Example 113, except that 1-(azetidin-3-yl) ethan-1-ol hydrochloride was used in the first step instead of 2-(methylamino) ethanol.

Step 1: tert-butyl ((4-(3-(1-hydroxyethyl)azetidin-1-yl)-1-(4-(trifluoromethoxy)phenyl)-1H-pyrazolo[3,4-b]pyridin-3-yl)methyl)carbamate

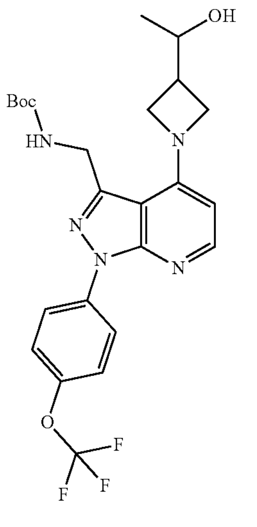 [SMILES: CC(O)C1CN(c2ccnc3c2c(CNC(=O)OC(C)(C)C)nn3-c2ccc(OC(F)(F)F)cc2)C1]

Reaction was run on a 0.2033 mmol scale with Intermediate B. 500 mg of tert-butyl ((4-(3-(1-hydroxyethyl)azetidin-1-yl)-1-(4-(trifluoromethoxy)phenyl)-1H-pyrazolo[3,4-b]pyridin-3-yl)methyl)carbamate contaminated with NMP was obtained. LCMS (ESI) $[M+H]^+$=508.100.

Step 2: N-((4-(3-(1-hydroxyethyl)azetidin-1-yl)-1-(4-(trifluoromethoxy)phenyl)-1H-pyrazolo[3,4-b]pyridin-3-yl)methyl)acrylamide

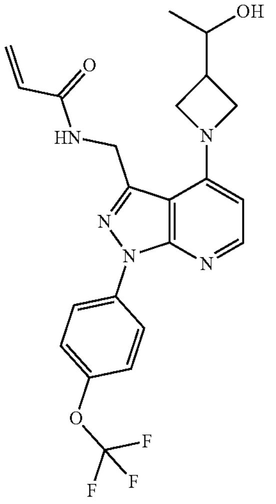 [SMILES: C=CC(=O)NCc1nn(-c2ccc(OC(F)(F)F)cc2)c2nccc(N3CC(C(C)O)C3)c12]

After deprotection and acylation, 59.72 mg of N-((4-(3-(1-hydroxyethyl)azetidin-1-yl)-1-(4-(trifluoromethoxy)phenyl)-1H-pyrazolo[3,4-b]pyridin-3-yl)methyl)acrylamide was obtained as a white solid (64% yield over 3 steps) following preparative HPLC (Triart C18 column, 30-70% MeCN/water, 0.1% $NH_4OH$ modifier). The enantiomers were further separated by chiral SFC (Chiralpak IG column, 0.1% $NH_4OH$ in MeOH, 25% isocratic gradient. 26.9 mg [26% yield] of the fast eluting isomer and 26.4 mg [28%] of the slow-eluting isomer were obtained.) $^1H$ NMR (400 MHz, DMSO) δ 8.60 (t, J=4.9 Hz, 1H), 8.46-8.37 (m, 2H), 8.14 (d, J=5.6 Hz, 1H), 7.54 (d, J=8.7 Hz, 2H), 6.37 (dd, J=17.1, 10.2 Hz, 1H), 6.20-6.10 (m, 2H), 5.64 (dd, J=10.2, 2.2 Hz, 1H), 4.82 (d, J=4.9 Hz, 1H), 4.80-4.67 (m, 2H), 4.26 (q, J=8.1 Hz, 2H), 4.12 (dd, J=8.3, 5.6 Hz, 1H), 4.01 (dd, J=8.3, 5.7 Hz, 1H), 3.78 (h, J=6.1 Hz, 1H), 2.73-2.60 (m, 1H), 1.05 (d, J=6.2 Hz, 3H). LCMS (ESI) $[M+H]^+$=462.100.

Example 124 (Compound 91)

N-((4-(4-hydroxypiperidin-1-yl)-1-(4-(trifluoromethoxy)phenyl)-1H-pyrazolo[3,4-b]pyridin-3-yl)methyl)acrylamide

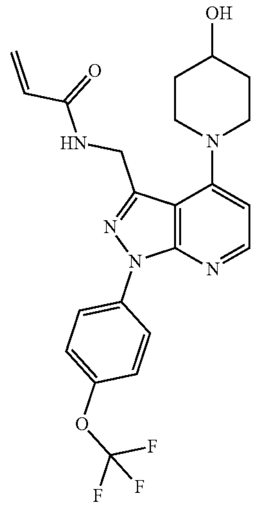 [SMILES: C=CC(=O)NCc1nn(-c2ccc(OC(F)(F)F)cc2)c2nccc(N3CCC(O)CC3)c12]

For this example, the same sequence of steps was followed as for Example 131, except that piperidin-4-ol was used in the first step instead of 2-(methylamino)ethanol.

Step 1: tert-butyl 04-(4-hydroxypiperidin-1-yl)-1-(4-(trifluoromethoxy)phenyl)-1H-pyrazolo[3,4-b]pyridin-3-yl)methyl)carbamate

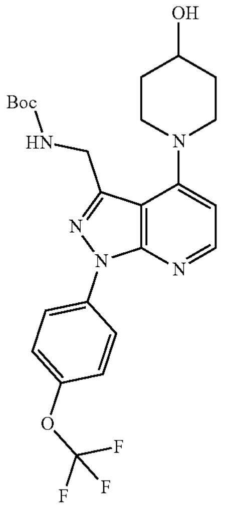 [SMILES: CC(C)(C)OC(=O)NCc1nn(-c2ccc(OC(F)(F)F)cc2)c2nccc(N3CCC(O)CC3)c12]

Reaction was run on a 0.09033 mmol scale with Intermediate B. 160 mg of tert-butyl ((4-(4-hydroxypiperidin-1-yl)-1-(4-(trifluoromethoxy)phenyl)-1H-pyrazolo[3,4-b]pyridin-3-yl)methyl)carbamate contaminated with NMP was obtained. LCMS (ESI) $[M+H]^+$=508.100.

Step 2: N-((4-(4-hydroxypiperidin-1-yl)-1-(4-(trifluoromethoxy)phenyl)-1H-pyrazolo[3,4-b]pyridin-3-yl)methyl)acrylamide

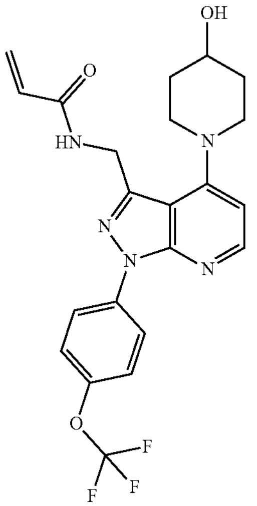 [SMILES: C=CC(=O)NCc1nn(-c2ccc(OC(F)(F)F)cc2)c2nccc(N3CCC(O)CC3)c12]

After deprotection and acylation, 29.63 mg of N-((4-(4-hydroxypiperidin-1-yl)-1-(4-(trifluoromethoxy)phenyl)-1H-pyrazolo[3,4-b]pyridin-3-yl)methyl)acrylamide was obtained as a white solid (71% yield over 3 steps) following preparative HPLC (Triart C18 column, 30-70% MeCN/water, 0.1% formic acid modifier). $^1H$ NMR (400 MHz, DMSO) δ 8.59 (t, J=4.9 Hz, 1H), 8.43-8.35 (m, 3H), 7.61-7.52 (m, 2H), 6.80 (d, J=5.4 Hz, 1H), 6.37 (dd, J=17.1, 10.2 Hz, 1H), 6.15 (dd, J=17.1, 2.2 Hz, 1H), 5.63 (dd, J=10.2, 2.2 Hz, 1H), 4.79 (dd, J=4.5, 1.9 Hz, 3H), 3.73 (dq, J=8.4, 4.2 Hz, 1H), 3.46 (dt, J=11.0, 4.6 Hz, 2H), 3.02 (ddd, J=12.5, 9.4, 2.9 Hz, 2H), 1.91 (dt, J=10.1, 3.7 Hz, 2H), 1.63 (ddt, J=13.5, 9.1, 4.5 Hz, 2H). LCMS (ESI) $[M+H]^+$=462.100.

Example 125 (Compound 136)

N-((4-(3-(2-hydroxypropan-2-yl)azetidin-1-yl)-1-(4-(trifluoromethoxy)phenyl)-1H-pyrazolo[3,4-b]pyridin-3-yl)methyl)acrylamide

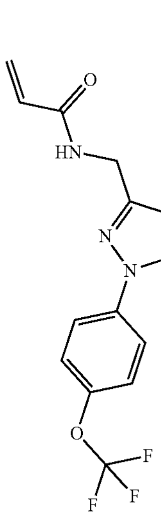

For this example, the same sequence of steps was followed as for Example 113, except that 2-(azetidin-3-yl) propan-2-ol hydrochloride was used in the first step instead of 2-(methylamino) ethanol.

Step 1: tert-butyl 04-(3-(2-hydroxypropan-2-yl)azetidin-1-yl)-1-(4-(trifluoromethoxy)phenyl)-1H-pyrazolo[3,4-b]pyridin-3-yl)methyl)carbamate

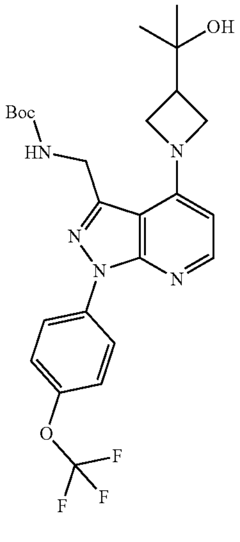 [SMILES: CC(C)(C)OC(=O)NCc1nn(-c2ccc(OC(F)(F)F)cc2)c2nccc(N3CC(C(C)(C)O)C3)c12]

Reaction was run on a 0.09033 mmol scale with Intermediate B. 160 mg of tert-butyl ((4-(3-(2-hydroxypropan-2-yl)azetidin-1-yl)-1-(4-(trifluoromethoxy)phenyl)-1H-pyrazolo[3,4-b]pyridin-3-yl)methyl)carbamate contaminated with NMP was obtained. LCMS (ESI) $[M+H]^+$=522.100.

Step 2: N-((4-(3-(2-hydroxypropan-2-yl)azetidin-1-yl)-1-(4-(trifluoromethoxy)phenyl)-1H-pyrazolo[3,4-b]pyridin-3-yl)methyl)acrylamide

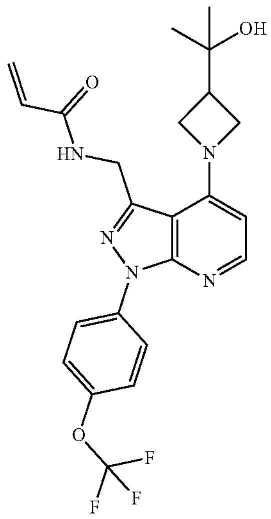 [SMILES: C=CC(=O)NCc1nn(-c2ccc(OC(F)(F)F)cc2)c2nccc(N3CC(C(C)(C)O)C3)c12]

After deprotection and acylation, 21.2 mg of N-((4-(3-(2-hydroxypropan-2-yl)azetidin-1-yl)-1-(4-(trifluoromethoxy) phenyl)-1H-pyrazolo[3,4-b]pyridin-3-yl)methyl)acrylamide was obtained as a white solid (49% yield over 3 steps) following preparative HPLC (Triart C18 column, 20-60% MeCN/water, 0.1% formic acid modifier). $^1$H NMR (400 MHz, DMSO) δ 8.60 (t, J=4.9 Hz, 1H), 8.46-8.37 (m, 2H), 8.13 (d, J=5.6 Hz, 1H), 7.58-7.50 (m, 2H), 6.37 (dd, J=17.1, 10.2 Hz, 1H), 6.20-6.10 (m, 2H), 5.63 (dd, J=10.2, 2.3 Hz, 1H), 4.75 (d, J=4.8 Hz, 2H), 4.53 (s, 1H), 4.26-4.11 (m, 4H), 2.74 (tt, J=8.6, 6.0 Hz, 1H), 1.08 (s, 6H). LCMS (ESI) $[M+H]^+$=476.100.

Example 126 (Compound 77)

N-((4-morpholino-1-(4-(trifluoromethoxy)phenyl)-1H-pyrazolo[3,4-b]pyridin-3-yl)methyl)acrylamide

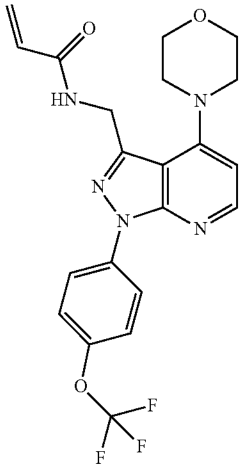 [SMILES: C=CC(=O)NCc1nn(-c2ccc(OC(F)(F)F)cc2)c2nccc(N3CCOCC3)c12]

For this example, the same sequence of steps was followed as for Example 113, except that morpholine was used in the first step instead of 2-(methylamino)ethanol.

Step 1: tert-butyl ((4-morpholino-1-(4-(trifluoromethoxy)phenyl)-1H-pyrazolo[3,4-b]pyridin-3-yl) methyl)carbamate

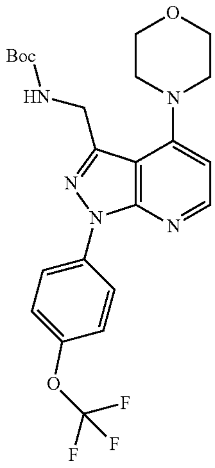 [SMILES: CC(C)(C)OC(=O)NCc1nn(-c2ccc(OC(F)(F)F)cc2)c2nccc(N3CCOCC3)c12]

Reaction was run on a 0.0669 mmol scale with Intermediate B. 33 mg of tert-butyl ((4-morpholino-1-(4-(trifluoromethoxy)phenyl)-1H-pyrazolo[3,4-b]pyridin-3-yl) methyl)carbamate contaminated with NMP was obtained. LCMS (ESI) $[M+H]^+$=494.100.

Step 2: N-((4-morpholino-1-(4-(trifluoromethoxy) phenyl)-1H-pyrazolo[3,4-b]pyridin-3-yl)methyl) acrylamide

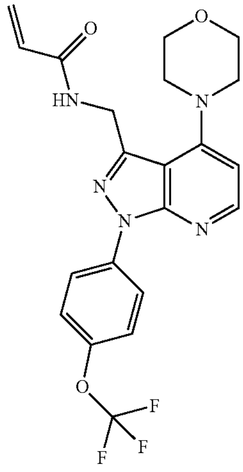 [SMILES: C=CC(=O)NCc1nn(-c2ccc(OC(F)(F)F)cc2)c2nccc(N3CCOCC3)c12]

After deprotection and acylation, 13.88 mg of N-((4-morpholino-1-(4-(trifluoromethoxy)phenyl)-1H-pyrazolo [3,4-b]pyridin-3-yl)methyl)acrylamide was obtained as a white solid (46% yield over 3 steps) following preparative HPLC (XSelect CSH Prep C18 column, 30-70% MeCN/ water, 0.1% $NH_4OH$ modifier). $^1H$ NMR (400 MHz, DMSO) δ 8.61 (t, J=5.0 Hz, 1H), 8.45 (d, J=5.3 Hz, 1H), 8.42-8.34 (m, 2H), 7.62-7.54 (m, 2H), 6.85 (d, J=5.4 Hz, 1H), 6.36 (dd, J=17.1, 10.1 Hz, 1H), 6.15 (dd, J=17.1, 2.2 Hz, 1H), 5.64 (dd, J=10.2, 2.2 Hz, 1H), 4.79 (d, J=5.0 Hz, 2H), 3.80 (t, J=4.5 Hz, 4H), 3.23 (t, J=4.6 Hz, 4H). LCMS (ESI) $[M+H]^+$=448.100

Example 127 (Compound 106)

N-((4-(3-hydroxyazetidin-1-yl)-1-(4-(trifluoromethoxy)phenyl)-1H-pyrazolo[3,4-b]pyridin-3-yl) methyl)acrylamide

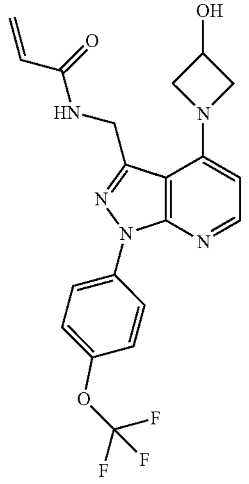 [SMILES: C=CC(=O)NCc1nn(-c2ccc(OC(F)(F)F)cc2)c2nccc(N3CC(O)C3)c12]

For this example, the same sequence of steps was followed as for Example 113, except that 3-[(Tert-butyldimethylsilanyl)oxy]azetidine was used in the first step instead of 2-(methylamino) ethanol.

Step 1: tert-butyl 04-(3-((tert-butyldimethylsilyl) oxy)azetidin-1-yl)-1-(4-(trifluoromethoxy)phenyl)-1H-pyrazolo[3,4-b]pyridin-3-yl)methyl)carbamate

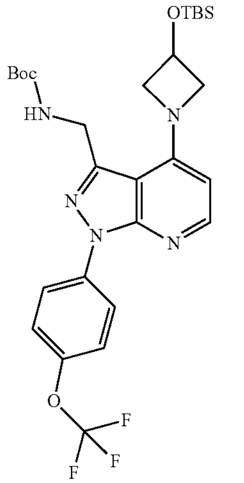 [SMILES: CC(C)(C)OC(=O)NCc1nn(-c2ccc(OC(F)(F)F)cc2)c2nccc(N3CC(O[Si](C)(C)C(C)(C)C)C3)c12]

Reaction was run on a 0.3388 mmol scale with Intermediate B. 265 mg of tert-butyl ((4-(3-((tert-butyldimethylsilyl)oxy)azetidin-1-yl)-1-(4-(trifluoromethoxy)phenyl)-1H- pyrazolo[3,4-b]pyridin-3-yl)methyl)carbamate contaminated with NMP was obtained. LCMS (ESI) $[M+H]^+$=594.100.

Step 2: N-((4-(3-hydroxyazetidin-1-yl)-1-(4-(trifluoromethoxy)phenyl)-1H-pyrazolo[3,4-b]pyridin-3-yl)methyl)acrylamide

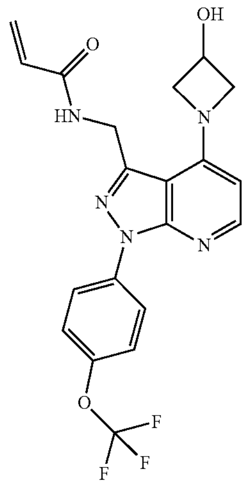 [SMILES: C=CC(=O)NCc1nn(-c2ccc(OC(F)(F)F)cc2)c2nccc(N3CC(O)C3)c12]

After HCl deprotection (which deprotected both NBoc and OTBS protecting groups) and acylation, 69.34 mg of N-((4-(3-hydroxyazetidin-1-yl)-1-(4-(trifluoromethoxy)phenyl)-1H-pyrazolo[3,4-b]pyridin-3-yl)methyl)acrylamide was obtained as a white solid (47% yield over 3 steps) following preparative HPLC (Triart C18 column, 20-60% MeCN/water, 0.1% formic acid modifier). $^1$H NMR (400 MHz, DMSO) δ 8.59 (t, J=4.8 Hz, 1H), 8.46-8.37 (m, 2H), 8.15 (d, J=5.6 Hz, 1H), 7.58-7.51 (m, 2H), 6.37 (dd, J=17.1, 10.2 Hz, 1H), 6.21-6.11 (m, 2H), 5.84 (d, J=5.9 Hz, 1H), 5.64 (dd, J=10.2, 2.2 Hz, 1H), 4.71 (d, J=4.8 Hz, 2H), 4.60 (dd, J=8.5, 3.9 Hz, 1H), 4.53-4.45 (m, 2H), 4.01 (dd, J=9.1, 4.3 Hz, 2H). LCMS (ESI) $[M+H]^+$=434.100

Example 128 (Compound 43)

N-((4-(3-(hydroxymethyl)azetidin-1-yl)-1-(4-(trifluoromethoxy)phenyl)-1H-pyrazolo[3,4-b]pyridin-3-yl)methyl)acrylamide

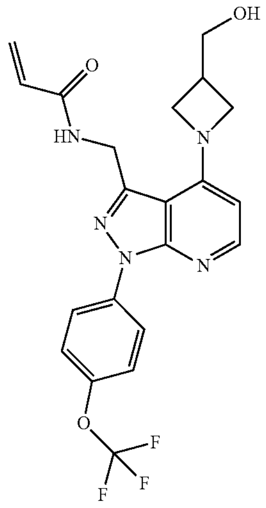 [SMILES: C=CC(=O)NCc1nn(-c2ccc(OC(F)(F)F)cc2)c2nccc(N3CC(CO)C3)c12]

For this example, the same sequence of steps was followed as for Example 113, except that azetidin-3-ylmethanol hydrochloride was used in the first step instead of 2-(methylamino) ethanol.

Step 1: tert-butyl 04-(3-(hydroxymethyl)azetidin-1-yl)-1-(4-(trifluoromethoxy)phenyl)-1H-pyrazolo[3,4-b]pyridin-3-yl)methyl)carbamate

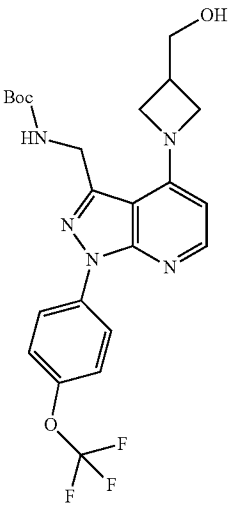 [SMILES: CC(C)(C)OC(=O)NCc1nn(-c2ccc(OC(F)(F)F)cc2)c2nccc(N3CC(CO)C3)c12]

Reaction was run on a 0.3388 mmol scale with Intermediate B. 700 mg of tert-butyl ((4-(3-(hydroxymethyl)azetidin-1-yl)-1-(4-(trifluoromethoxy)phenyl)-1H-pyrazolo[3,4-b]pyridin-3-yl)methyl)carbamate contaminated with NMP was obtained. LCMS (ESI) $[M+H]^+$=494.100.

Step 2: N-((4-(3-(hydroxymethyl)azetidin-1-yl)-1-(4-(trifluoromethoxy)phenyl)-1H-pyrazolo[3,4-b]pyridin-3-yl)methyl)acrylamide

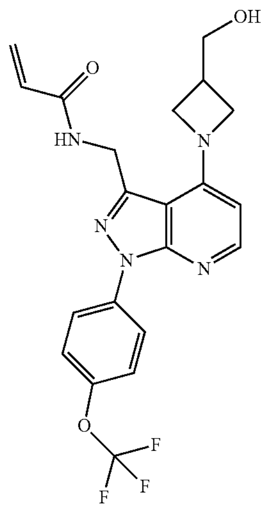 [SMILES: C=CC(=O)NCc1nn(-c2ccc(OC(F)(F)F)cc2)c2nccc(N3CC(CO)C3)c12]

After deprotection and acylation, 83.9 mg of N-((4-(3-(hydroxymethyl)azetidin-1-yl)-1-(4-(trifluoromethoxy)phenyl)-1H-pyrazolo[3,4-b]pyridin-3-yl)methyl)acrylamide was obtained as a white solid (55% yield over 3 steps) following preparative HPLC (Triart C18 column, 5-50% MeCN/water, 0.1% formic acid modifier). $^{1}H$ NMR (400 MHz, DMSO) δ 8.59 (t, J=4.9 Hz, 1H), 8.46-8.37 (m, 2H), 8.14 (d, J=5.6 Hz, 1H), 7.54 (d, J=8.7 Hz, 2H), 6.38 (dd, J=17.1, 10.2 Hz, 1H), 6.21-6.10 (m, 2H), 5.64 (dd, J=10.2, 2.2 Hz, 1H), 4.85 (t, J=5.3 Hz, 1H), 4.74 (d, J=4.9 Hz, 2H), 4.30 (t, J=8.3 Hz, 2H), 4.02 (dd, J=8.3, 5.4 Hz, 2H), 3.60 (t, J=5.6 Hz, 2H), 2.86 (tt, J=8.1, 5.6 Hz, 1H). LCMS (ESI) $[M+H]^{+}$=448.100

Example 129 (Compound 107)

N-((4-(3-(dimethylamino)azetidin-1-yl)-1-(4-(trifluoromethoxy)phenyl)-1H-pyrazolo[3,4-b]pyridin-3-yl)methyl)acrylamide

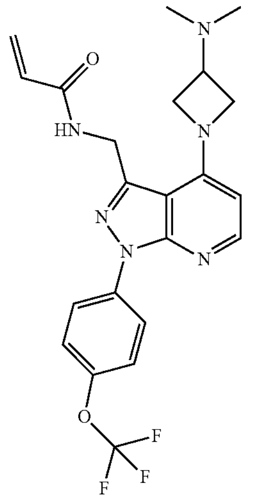 [SMILES: C=CC(=O)NCc1nn(-c2ccc(OC(F)(F)F)cc2)c2nccc(N3CC(N(C)C)C3)c12]

For this example, the same sequence of steps was followed as for Example 113, except that N,N-dimethylazetidin-3-amine dihydrochloride was used in the first step instead of 2-(methylamino) ethanol.

Step 1: tert-butyl ((4-(3-(dimethylamino)azetidin-1-yl)-1-(4-(trifluoromethoxy)phenyl)-1H-pyrazolo[3,4-b]pyridin-3-yl)methyl)carbamate

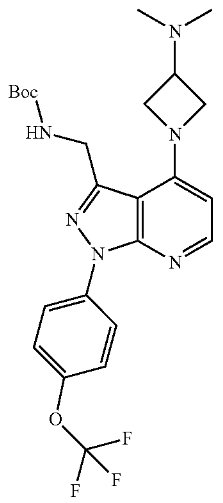 [SMILES: CN(C)C1CN(c2ccnc3c2c(CNC(=O)OC(C)(C)C)nn3-c2ccc(OC(F)(F)F)cc2)C1]

Reaction was run on a 0.0678 mmol scale with Intermediate B. 115 mg of tert-butyl ((4-(3-(dimethylamino)azetidin-1-yl)-1-(4-(trifluoromethoxy)phenyl)-1H-pyrazolo[3,4-b]pyridin-3-yl)methyl)carbamate contaminated with NMP was obtained. LCMS (ESI) $[M+H]^{+}$=507.200.

Step 2: N-((4-(3-(dimethylamino)azetidin-1-yl)-1-(4-(trifluoromethoxy)phenyl)-1H-pyrazolo[3,4-b]pyridin-3-yl)methyl)acrylamide

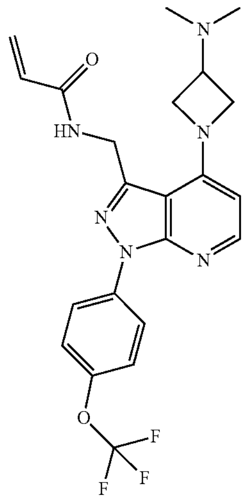 [SMILES: C=CC(=O)NCc1nn(-c2ccc(OC(F)(F)F)cc2)c2nccc(N3CC(N(C)C)C3)c12]

After deprotection and acylation, 12.15 mg of N-((4-(3-(dimethylamino)azetidin-1-yl)-1-(4-(trifluoromethoxy)phenyl)-1H-pyrazolo[3,4-b]pyridin-3-yl)methyl)acrylamide was obtained as a white solid (39% yield over 3 steps)

following preparative HPLC (Triart C18 column, 30-70% MeCN/water, 0.1% $NH_4OH$ modifier). $^1H$ NMR (400 MHz, DMSO) δ 8.61 (t, J=4.8 Hz, 1H), 8.46-8.37 (m, 2H), 8.16 (d, J=5.6 Hz, 1H), 7.58-7.51 (m, 2H), 6.35 (dd, J=17.1, 10.2 Hz, 1H), 6.20-6.11 (m, 2H), 5.63 (dd, J=10.1, 2.3 Hz, 1H), 4.73 (d, J=4.8 Hz, 2H), 4.30 (t, J=7.9 Hz, 2H), 4.06 (dd, J=8.7, 4.9 Hz, 2H), 3.26-3.11 (m, 1H), 2.12 (s, 6H) LCMS (ESI) $[M+H]^+$=461.100

Example 130 (Compound 118)

N-((4-(3-methoxyazetidin-1-yl)-1-(4-(trifluoromethoxy)phenyl)-1H-pyrazolo[3,4-b]pyridin-3-yl)methyl)acrylamide

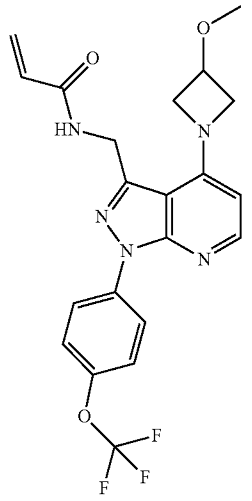 [SMILES: C=CC(=O)NCc1nn(-c2ccc(OC(F)(F)F)cc2)c2nccc(N3CC(OC)C3)c12]

For this example, the same sequence of steps was followed as for Example 113, except that 3-methoxyazetidine hydrochloride was used in the first step instead of 2-(methylamino) ethanol.

Step 1: tert-butyl 04-(3-methoxyazetidin-1-yl)-1-(4-(trifluoromethoxy)phenyl)-1H-pyrazolo[3,4-b]pyridin-3-yl)methyl)carbamate

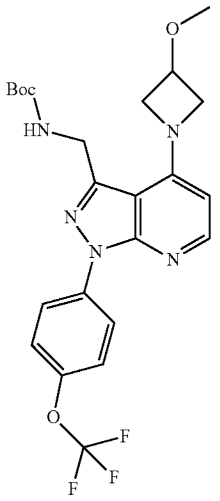 [SMILES: COC1CN(c2ccnc3c2c(CNC(=O)OC(C)(C)C)nn3-c2ccc(OC(F)(F)F)cc2)C1]

Reaction was run on a 0.0567 mmol scale with Intermediate B. 28 mg of tert-butyl ((4-(3-methoxyazetidin-1-yl)-1-(4-(trifluoromethoxy)phenyl)-1H-pyrazolo[3,4-b]pyridin-3-yl)methyl)carbamate contaminated with NMP was obtained. LCMS (ESI) $[M+H]^+$=494.200.

Step 2: N-((4-(3-methoxyazetidin-1-yl)-1-(4-(trifluoromethoxy)phenyl)-1H-pyrazolo[3,4-b]pyridin-3-yl)methyl)acrylamide

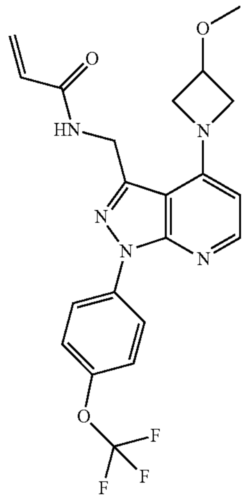 [SMILES: C=CC(=O)NCc1nn(-c2ccc(OC(F)(F)F)cc2)c2nccc(N3CC(OC)C3)c12]

After deprotection and acylation, 15.37 mg of N-((4-(3-methoxyazetidin-1-yl)-1-(4-(trifluoromethoxy)phenyl)-1H-pyrazolo[3,4-b]pyridin-3-yl)methyl)acrylamide was obtained as a white solid (61% yield over 3 steps) following preparative HPLC (Triart C18 column, 20-60% MeCN/water, 0.1% $NH_4OH$ modifier). $^1H$ NMR (400 MHz, DMSO) δ 8.60 (t, J=4.8 Hz, 1H), 8.45-8.37 (m, 2H), 8.17 (d, J=5.6 Hz, 1H), 7.59-7.50 (m, 2H), 6.36 (dd, J=17.1, 10.2 Hz, 1H), 6.21-6.11 (m, 2H), 5.64 (dd, J=10.2, 2.3 Hz, 1H), 4.72 (d, J=4.9 Hz, 2H), 4.47 (ddd, J=9.1, 6.3, 1.2 Hz, 2H), 4.35 (tt, J=6.7, 3.7 Hz, 1H), 4.14-4.07 (m, 2H), 3.27 (s, 3H). LCMS (ESI) $[M+H]^+$=448.100

Example 131 (Compound 76)

N-((4-(6-hydroxy-2-azaspiro[3.3]heptan-2-yl)-1-(4-(trifluoromethoxy)phenyl)-1H-pyrazolo[3,4-b]pyridin-3-yl)methyl)acrylamide

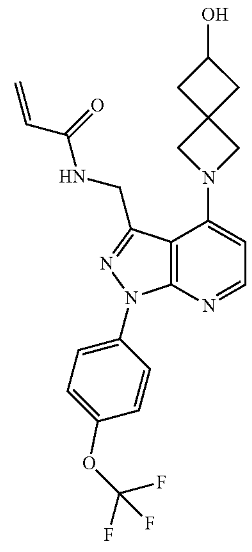 [SMILES: C=CC(=O)NCc1nn(-c2ccc(OC(F)(F)F)cc2)c2nccc(N3CC4(CC(O)C4)C3)c12]

Step 1: tert-butyl ((4-(6-((tert-butyldiphenylsilyl)oxy)-2-azaspiro[3.3]heptan-2-yl)-1-(4-(trifluoromethoxy)phenyl)-1H-pyrazolo[3,4-b]pyridin-3-yl)methyl)carbamate

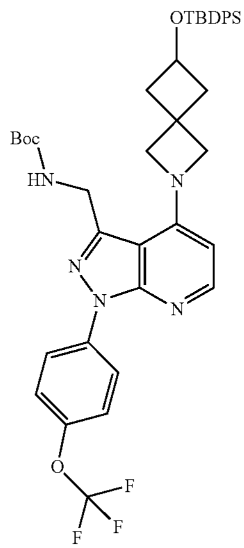

To a 2 dram vial containing tert-butyl N-[[4-chloro-1-[4-(trifluoromethoxy)phenyl]pyrazolo[3,4-b]pyridin-3-yl]methyl]carbamate (Intermediate B, 50 mg, 0.1129 mmol, 1.0 equiv.) and 2-azaspiro[3.3]heptan-6-yloxy-tert-butyl-diphenyl-silane (119 mg, 0.3388 mmol, 3.0 equiv.) was added NMP (0.75 mL) and DIPEA (0.10 mL, 0.5646 mmol, 5.0 equiv.). The reaction was then heated to 100° C. and stirred until no starting material remained as observed by LCMS. The reaction was directly purified by column chromatography (silica 0-5% iPrOAc/heptane). Gave 45 mg (53%) of tert-butyl ((4-(6-((tert-butyldiphenylsilyl)oxy)-2-azaspiro[3.3]heptan-2-yl)-1-(4-(trifluoromethoxy)phenyl)-1H-pyrazolo[3,4-b]pyridin-3-yl)methyl)carbamate. LCMS (ESI) $[M+H]^+$=758.350.

Step 2: tert-butyl 04-(6-hydroxy-2-azaspiro[3.3]heptan-2-yl)-1-(4-(trifluoromethoxy)phenyl)-1H-pyrazolo[3,4-b]pyridin-3-yl)methyl)carbamate

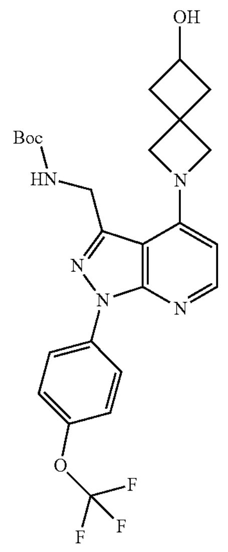 [SMILES: CC(C)(C)OC(=O)NCc1nn(-c2ccc(OC(F)(F)F)cc2)c2nccc(N3CC4(CC(O)C4)C3)c12]

To a 2 dram vial containing tert-butyl N-[[4-[6-[tert-butyl)diphenyl)silyl]oxy-2-azaspiro[3.3]heptan-2-yl]-1-[4-(trifluoromethoxy)phenyl]pyrazolo[3,4-b]pyridin-3-yl]methyl]carbamate (43 mg, 0.05674 mmol, 1.0 equiv.) under nitrogen was added anhydrous THF (0.52 mL) followed by tetrabutylammonium fluoride (1.0 M in THF, 0.08 mL, 0.079 mmol, 1.4 equiv.). The reaction was stirred at room temperature until no starting material remained as monitored by LCMS. The reaction was quenched by the addition of sat $NaHCO_3$ and extracted with iPrOAc (3×). Organics were then combined, washed with brine, dried, filtered and concentrated to give tert-butyl N-[[4-(6-hydroxy-2-azaspiro[3.3]heptan-2-yl)-1-[4-(trifluoromethoxy)phenyl]pyrazolo[3,4-b]pyridin-3-yl]methyl]carbamate which was used directly without further purification. LCMS (ESI) $[M+H]^+$=520.25

Step 3: N-((4-(6-hydroxy-2-azaspiro[3.3]heptan-2-yl)-1-(4-(trifluoromethoxy)phenyl)-1H-pyrazolo[3,4-b]pyridin-3-yl)methyl)acrylamide

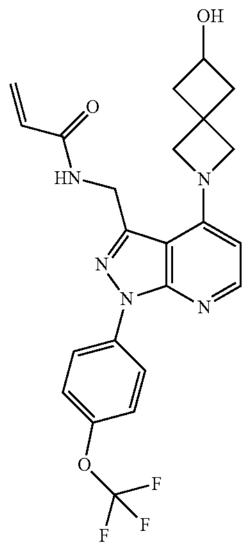 [SMILES: C=CC(=O)NCc1nn(-c2ccc(OC(F)(F)F)cc2)c2nccc(N3CC4(CC(O)C4)C3)c12]

To a 2 dram vial containing crude tert-butyl ((4-(6-hydroxy-2-azaspiro[3.3]heptan-2-yl)-1-(4-(trifluoromethoxy)phenyl)-1H-pyrazolo[3,4-b]pyridin-3-yl)methyl)carbamate (42 mg, 1.0 equiv.) was added DCM (0.20 mL) and Hydrochloric acid (4 M in 1,4-Dioxane, 0.06 mL, 0.2425 mmol, 3.0 equiv.). The reaction was stirred at room temperature until no starting material remained as monitored by LCMS. Reaction concentrated under reduced pressure to give the crude amine 2-[3-(aminomethyl)-1-[4-(trifluoromethoxy)phenyl]pyrazolo[3,4-b]pyridin-4-yl]-2-azaspiro[3.3]heptan-6-ol, which was then dissolved in DCM (0.40 mL). DIPEA (0.14 mL, 0.8085 mmol, 10.0 equiv.) was added, reaction was cooled to −40° C., and a solution of acrylic anhydride (0.01 mL, 0.0889 mmol, 1.1 equiv.) in DCM (0.27 mL) was then added dropwise. Reaction was stirred at −40° C. until full conversion to the desired product was observed by LCMS. Saturated aqueous $NH_4Cl$ was added at −40° C. and mixture was allowed to warm to room temperature. Reaction transferred to a separatory funnel and extracted with iPrOAc. Organic layer was washed with saturated aqueous $NaHCO_3$, then combined aqueous layers were back extracted (2× iPrOAc and 1×DCM). Organics were combined, dried, filtered, and concentrated. The resulting residue was purified by preparative HPLC (Triart C18 column, 20-60% MeCN/water, 0.1% formic acid modifier). Afford the title compound (15.53 mg of a white solid, 58% yield over 3 steps). $^1H$ NMR (400 MHz, DMSO) δ 8.59 (t, J=4.9 Hz, 1H), 8.45-8.36 (m, 2H), 8.14 (d, J=5.6 Hz, 1H), 7.53 (d, J=8.8 Hz, 2H), 6.37 (dd, J=17.1, 10.2 Hz, 1H), 6.17 (dd, J=17.1, 2.3 Hz, 1H), 6.10 (d, J=5.6 Hz, 1H), 5.64 (dd, J=10.1, 2.3 Hz, 1H), 5.08 (d, J=6.2 Hz, 1H), 4.72 (d, J=4.9 Hz, 2H), 4.25 (s, 2H), 4.20 (s, 2H), 4.01 (h, J=7.1 Hz, 1H), 2.54 (s, 1H), 2.50-2.44 (m, 1H), 2.09-1.99 (m, 2H). LCMS (ESI) $[M+H]^+$=474.100.

Example 132 (Compound 46)

(S)-N-((4-(3-hydroxypyrrolidin-1-yl)-1-(4-(trifluoromethoxy)phenyl)-1H-pyrazolo[3,4-b]pyridin-3-yl)methyl)acrylamide

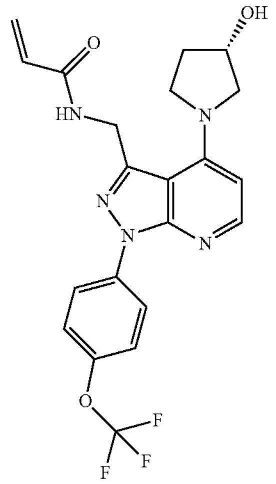 [SMILES: C=CC(=O)NCc1nn(-c2ccc(OC(F)(F)F)cc2)c2nccc(N3CC[C@H](O)C3)c12]

For this example, the same sequence of steps was followed as for Example 148, except that tert-butyl-diphenyl-[(3S)-pyrrolidin-3-yl]oxy-silane was used in the first step instead of 2-azaspiro[3.3]heptan-6-yloxy-tert-butyl-diphenyl-silane.

Step 1: tert-butyl (S)-((4-(3-((tert-butyldiphenylsilyl)oxy)pyrrolidin-1-yl)-1-(4-(trifluoromethoxy)phenyl)-1H-pyrazolo[3,4-b]pyridin-3-yl)methyl)carbamate

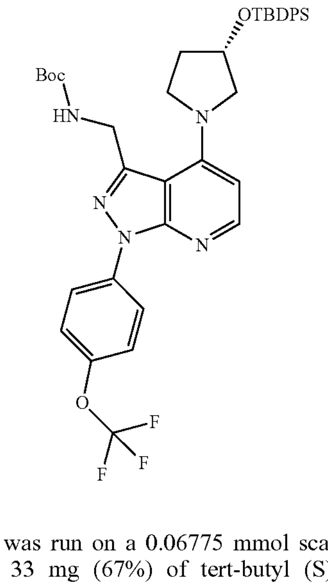

Reaction was run on a 0.06775 mmol scale with Intermediate B. 33 mg (67%) of tert-butyl (S)-((4-(3-((tert-butyldiphenylsilyl)oxy)pyrrolidin-1-yl)-1-(4-(trifluoromethoxy)phenyl)-1H-pyrazolo[3,4-b]pyridin-3-yl)methyl)carbamate was obtained. LCMS (ESI) $[M+H]^+$=732.200.

Step 2: tert-butyl (S)-44-(3-hydroxypyrrolidin-1-yl)-1-(4-(trifluoromethoxy)phenyl)-1H-pyrazolo[3,4-b]pyridin-3-yl)methyl)carbamate

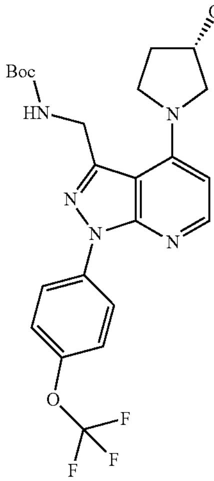

32 mg of crude tert-butyl (S)-((4-(3-hydroxypyrrolidin-1-yl)-1-(4-(trifluoromethoxy)phenyl)-1H-pyrazolo[3,4-b]pyridin-3-yl)methyl)carbamate was obtained as an oil and was used directly without purification. LCMS (ESI) $[M+H]^+$=494.050.

Step 3: (S)-N-((4-(3-hydroxypyrrolidin-1-yl)-1-(4-(trifluoromethoxy)phenyl)-1H-pyrazolo[3,4-b]pyridin-3-yl)methyl)acrylamide

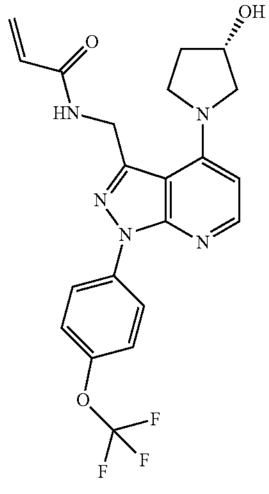 [SMILES: C=CC(=O)NCc1nn(-c2ccc(OC(F)(F)F)cc2)c2nccc(N3CC[C@H](O)C3)c12]

After deprotection and acylation, 10.98 mg of (S)-N-((4-(3-hydroxypyrrolidin-1-yl)-1-(4-(trifluoromethoxy)phenyl)-1H-pyrazolo[3,4-b]pyridin-3-yl)methyl)acrylamide was obtained as a white solid (54% yield over 3 steps) following preparative HPLC (XSelect CSH Prep C18 column, 20-60% MeCN/water, 0.1% $NH_4OH$ modifier). $^1H$ NMR (400 MHz, DMSO) δ 8.60 (t, J=5.1 Hz, 1H), 8.47-8.38 (m, 2H), 8.12 (d, J=5.7 Hz, 1H), 7.58-7.51 (m, 2H), 6.43-6.31 (m, 2H), 6.14 (dd, J=17.1, 2.2 Hz, 1H), 5.63 (dd, J=10.2, 2.2 Hz, 1H), 5.07 (d, J=3.3 Hz, 1H), 4.90-4.75 (m, 2H), 4.42 (s, 1H), 3.82-3.68 (m, 2H), 3.59 (td, J=8.7, 2.9 Hz, 1H), 3.41 (d, J=10.4 Hz, 1H), 2.08-1.97 (m, 1H), 1.95 (s, 1H). LCMS (ESI) $[M+H]^+$=448.100

Example 133 (Compound 47)

(R)-N-((4-(3-hydroxypyrrolidin-1-yl)-1-(4-(trifluoromethoxy)phenyl)-1H-pyrazolo[3,4-b]pyridin-3-yl)methyl)acrylamide

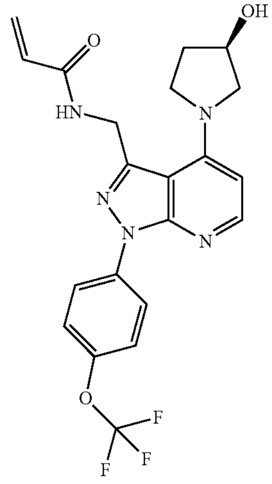 [SMILES: C=CC(=O)NCc1nn(-c2ccc(OC(F)(F)F)cc2)c2nccc(N3CC[C@@H](O)C3)c12]

For this example, the same sequence of steps was followed as for Example 131, except that tert-butyl-diphenyl-[(3R)-pyrrolidin-3-yl]oxy-silane was used in the first step instead of 2-azaspiro[3.3]heptan-6-yloxy-tert-butyl-diphenyl-silane.

Step 1: tert-butyl (R)-04-(3-((tert-butyldiphenylsilyl)oxy)pyrrolidin-1-yl)-1-(4-(trifluoromethoxy)phenyl)-1H-pyrazolo[3,4-b]pyridin-3-yl)methyl)carbamate

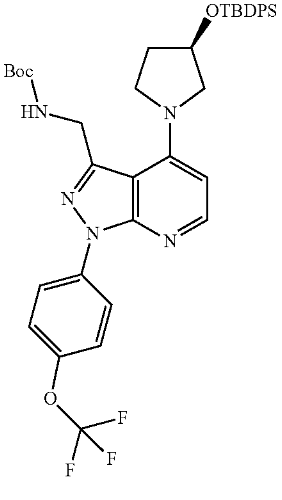

Reaction was run on a 0.06775 mmol scale with Intermediate B. 27 mg (54%) of tert-butyl (R)-((4-(3-((tert-butyldiphenylsilyl)oxy)pyrrolidin-1-yl)-1-(4-(trifluoromethoxy)phenyl)-1H-pyrazolo[3,4-b]pyridin-3-yl) methyl)carbamate was obtained. LCMS (ESI) $[M+H]^+$=732.200.

Step 2: tert-butyl (R)-04-(3-hydroxypyrrolidin-1-yl)-1-(4-(trifluoromethoxy)phenyl)-1H-pyrazolo[3,4-b]pyridin-3-yl)methyl)carbamate

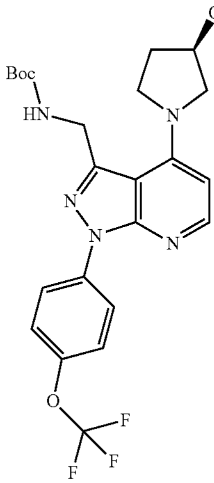

27 mg of crude ter t-butyl (R)-((4-(3-hydroxypyrrolidin-1-yl)-1-(4-(trifluoromethoxy)phenyl)-1H-pyrazolo[3,4-b] pyridin-3-yl)methyl)carbamate was obtained as an oil and was used directly without purification. LCMS (ESI) $[M+H]^+$=494.050.

Step 3: (R)-N-((4-(3-hydroxypyrrolidin-1-yl)-1-(4-(trifluoromethoxy)phenyl)-1H-pyrazolo[3,4-b]pyridin-3-yl)methyl)acrylamide

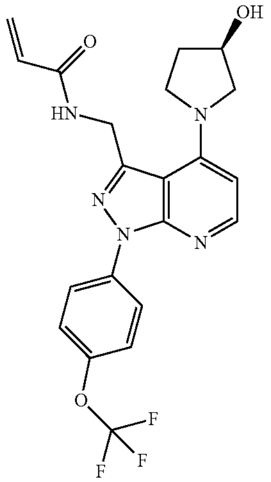 [SMILES: C=CC(=O)NCc1nn(-c2ccc(OC(F)(F)F)cc2)c2nccc(N3CC[C@@H](O)C3)c12]

After deprotection and acylation, 10.84 mg of (R)-N-((4-(3-hydroxypyrrolidin-1-yl)-1-(4-(trifluoromethoxy)phenyl)-1H-pyrazolo[3,4-b]pyridin-3-yl)methyl)acrylamide was obtained as a white solid (66% yield over 3 steps) following preparative HPLC (XSelect CSH Prep C18 column, 20-60% MeCN/water, 0.1% $NH_4OH$ modifier). $^1H$ NMR (400 MHz, DMSO) δ 8.60 (t, J=4.9 Hz, 1H), 8.47-8.38 (m, 2H), 8.12 (d, J=5.7 Hz, 1H), 7.59-7.51 (m, 2H), 6.43-6.31 (m, 2H), 6.14 (dd, J=17.1, 2.2 Hz, 1H), 5.63 (dd, J=10.2, 2.2 Hz, 1H), 5.07 (d, J=3.3 Hz, 1H), 4.90-4.75 (m, 2H), 4.42 (s, 1H), 3.82-3.68 (m, 2H), 3.59 (ddd, J=9.8, 8.1, 3.0 Hz, 1H), 3.41 (d, J=10.3 Hz, 1H), 2.09-1.93 (m, 1H), 1.94 (s, 1H). LCMS (ESI) $[M+H]^+$=448.100

Example 134 (Compound 92)

N-((4-(3-aminoazetidin-1-yl)-1-(4-(trifluoromethoxy)phenyl)-1H-pyrazolo[3,4-b]pyridin-3-yl) methyl)acrylamide

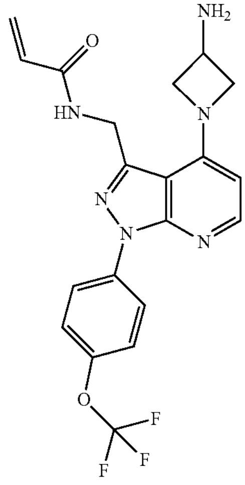 [SMILES: C=CC(=O)NCc1nn(-c2ccc(OC(F)(F)F)cc2)c2nccc(N3CC(N)C3)c12]

Step 1: tert-butyl (1-(3-(aminomethyl)-1-(4-(trifluoromethoxy)phenyl)-1H-pyrazolo[3,4-b]pyridin-4-yl) azetidin-3-yl)carbamate

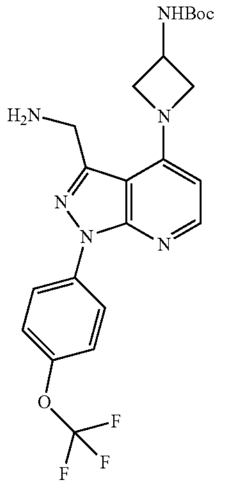 [SMILES: CC(C)(C)OC(=O)NC1CN(c2ccnc3c2c(CN)nn3-c2ccc(OC(F)(F)F)cc2)C1]

To a 2 dram vial containing [4-bromo-1-[4-(trifluoromethoxy)phenyl]pyrazolo[3,4-b]pyridin-3-yl]methanamine (Intermediate W, 40 mg, 0.1033 mmol, 1.0 equiv.) and tert-butyl N-(azetidin-3-yl)carbamate (36 mg, 0.2066 mmol, 2.0 equiv.) was added NMP (0.69 mL) and DIPEA (0.07 mL, 0.4132 mmol, 4.0 equiv.). The reaction was then heated to 100° C. and stirred until no starting material remained as observed by LCMS. The reaction was directly purified by column chromatography (silica 0-20% MeOH/DCM). Gave 30 mg (61%) of tert-butyl (1-(3-(aminomethyl)-1-(4-(trifluoromethoxy)phenyl)-1H-pyrazolo[3,4-b]pyridin-4-yl)azetidin-3-yl)carbamate. LCMS (ESI) $[M+H]^+$=479.000.

Step 2: N-((4-(3-aminoazetidin-1-yl)-1-(4-(trifluoromethoxy)phenyl)-1H-pyrazolo[3,4-b]pyridin-3-yl)methyl)acrylamide

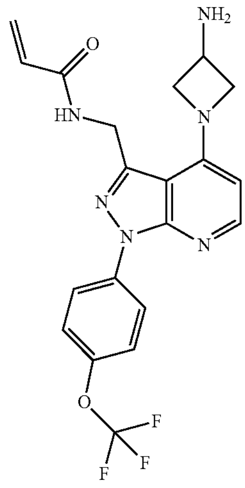 [SMILES: C=CC(=O)NCc1nn(-c2ccc(OC(F)(F)F)cc2)c2nccc(N3CC(N)C3)c12]

To a 2 dram vial containing tert-butyl N-[1-[3-(aminomethyl)-1-[4-(trifluoromethoxy)phenyl]pyrazolo[3,4-b]pyridin-4-yl]azetidin-3-yl]carbamate (30 mg, 0.06270 mmol, 1.0 equiv.) dissolved in DCM (0.63 mL) was added DIPEA (0.05 mL, 0.3135 mmol, 5.0 equiv.). The reaction was cooled to −40° C. and a solution of acrylic anhydride (0.0080 mL, 0.06897 mmol, 1.10 equiv.) in DCM (0.31 mL) added dropwise. Reaction was stirred at −40° C. until full conversion to the desired product was observed by LCMS. Saturated aqueous $NH_4Cl$ was added at −40° C. and mixture was allowed to warm to room temperature. Reaction transferred to a separatory funnel extracted with iPrOAc. Organic layer was washed with saturated aqueous $NaHCO_3$, then combined aqueous layers were back extracted (2× iPrOAc and 1×DCM). Organics were combined, dried, filtered, and concentrated. The crude product was then dissolved in DCM (0.42 mL) and trifluoroacetic acid (0.047 mL, 0.627 mmol, 10.0 equiv.) was added at 0° C. The reaction was gradually allowed to warm to room temperature and monitored by LCMS. Once complete, reaction was concentrated under reduced pressure and purified by preparative HPLC (XSelect CSH Prep C18 column, 20-60% MeCN/water, 0.1% $NH_4OH$ modifier). Gave 5.5 mgs (20% yield over 2 steps, 92% purity) of N-[[4-[(3-aminoazetidin-1-yl)-1-[4-(trifluoromethoxy)phenyl]pyrazolo[3,4-b]pyridin-3-yl]methyl]prop-2-enamide as a white solid. $^1H$ NMR (400 MHz, DMSO) δ 8.62-8.55 (m, 1H), 8.46-8.38 (m, 2H), 8.14 (d, J=5.6 Hz, 1H), 7.57-7.50 (m, 2H), 6.38 (dd, J=17.1, 10.2 Hz, 1H), 6.21-6.08 (m, 2H), 5.64 (dd, J=10.2, 2.2 Hz, 1H), 4.72 (d, J=4.9 Hz, 2H), 4.45 (dt, J=7.7, 4.7 Hz, 2H), 3.86 (q, J=5.5 Hz, 3H), 2.36 (d, J=13.2 Hz, 1H). LCMS (M+H)+=433.100

Example 135 (Compound 122)

N-((4-(3-(methylamino)azetidin-1-yl)-1-(4-(trifluoromethoxy)phenyl)-1H-pyrazolo[3,4-b]pyridin-3-yl)methyl)acrylamide

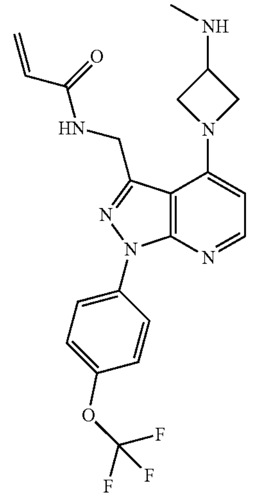 [SMILES: C=CC(=O)NCc1nn(-c2ccc(OC(F)(F)F)cc2)c2nccc(N3CC(NC)C3)c12]

For this example, the same sequence of steps was followed as for Example 134, except that tert-butyl azetidin-3-yl(methyl)carbamate hydrochloride was used in the first step instead of tert-butyl N-(azetidin-3-yl)carbamate.

Step 1: tert-butyl (1-(3-(aminomethyl)-1-(4-(trifluoromethoxy)phenyl)-1H-pyrazolo[3,4-b]pyridin-4-yl)azetidin-3-yl)(methyl)carbamate

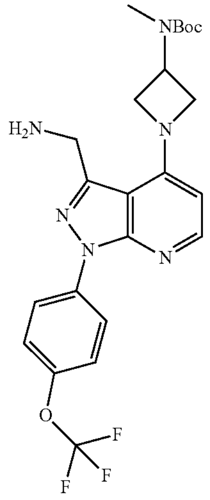 [SMILES: CN(C(=O)OC(C)(C)C)C1CN(c2ccnc3c2c(CN)nn3-c2ccc(OC(F)(F)F)cc2)C1]

Reaction was ran on a 0.103 mmol scale with Intermediate W. 40 mg (79% yield) of tert-butyl (1-(3-(aminomethyl)-1-(4-(trifluoromethoxy)phenyl)-1H-pyrazolo[3,4-b]pyridin-4-yl)azetidin-3-yl)(methyl)carbamate was obtained as an oil. LCMS (ESI) $[M+H]^+$=493.100.

Step 2: N-((4-(3-(methylamino)azetidin-1-yl)-1-(4-(trifluoromethoxy)phenyl)-1H-pyrazolo[3,4-b]pyridin-3-yl)methyl)acrylamide

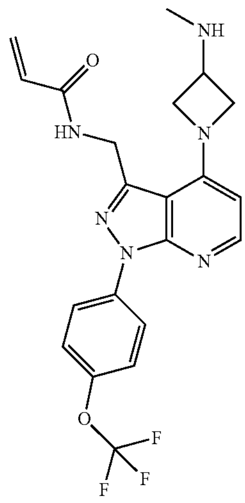 [SMILES: C=CC(=O)NCc1nn(-c2ccc(OC(F)(F)F)cc2)c2nccc(N3CC(NC)C3)c12]

After Acylation and deprotection, 14.68 mg of N-((4-(3-(methylamino)azetidin-1-yl)-1-(4-(trifluoromethoxy)phenyl)-1H-pyrazolo[3,4-b]pyridin-3-yl)methyl)acrylamide was obtained as a white solid (40% yield over 2 steps) following preparative HPLC (XSelect CSH Prep C18 column, 20-60% MeCN/water, 0.1% $NH_4OH$ modifier). $^1H$ NMR (400 MHz, DMSO) δ 8.60 (t, J=4.9 Hz, 1H), 8.47-8.38 (m, 2H), 8.14 (d, J=5.6 Hz, 1H), 7.58-7.50 (m, 2H), 6.37 (dd, J=17.1, 10.2 Hz, 1H), 6.21-6.10 (m, 2H), 5.64 (dd, J=10.2, 2.2 Hz, 1H), 4.73 (d, J=4.9 Hz, 2H), 4.40 (t, J=7.8 Hz, 2H), 3.95 (dd, J=8.6, 5.0 Hz, 2H), 3.62 (tt, J=7.2, 4.9 Hz, 1H), 2.25 (s, 3H). LCMS (ESI) $[M+H]^+$=447.100

Example 136 (Compound 144)

(S)-N-((4-(2-Oxo-1,3-dioxolan-4-yl)-1-(4-(trifluoromethoxy)phenyl)-1H-pyrazolo[3,4-b]pyridin-3-yl)methyl)acrylamide

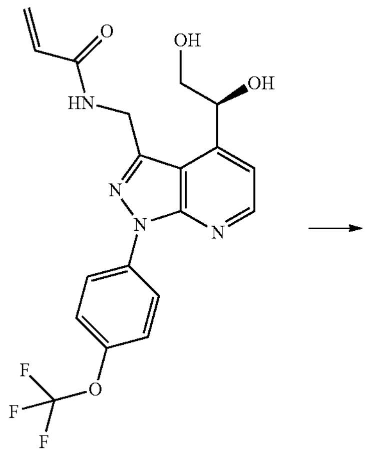

-continued

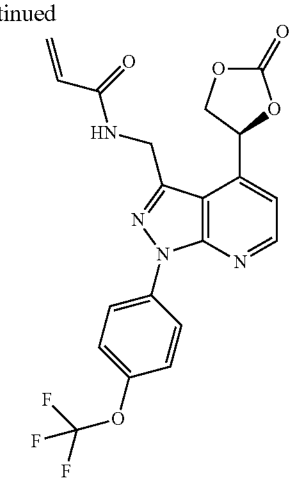

To a solution of (S)-N-((4-(1,2-dihydroxyethyl)-1-(4-(trifluoromethoxy)phenyl)-1H-pyrazolo[3,4-b]pyridin-3-yl)methyl)acrylamide (100 mg, 0.236 mmol) in THF (2 mL) was added TEA (0.947 mmol, 0.131 mL) and CDI (77 mg, 0.473 mmol) at 0° C. The mixture was stirred at room temperature for 12 hours under a $N_2$ atmosphere. The reaction mixture was quenched with $H_2O$ (2 mL) and extracted with ethyl acetate (5 mL×3). The combined organic layers were washed with brine (2 mL), dried over $Na_2SO_4$, filtered and concentrated under reduced pressure to give the crude product. The organic material was purified by reverse phase chromatography (Waters Xbridge Prep OBD C18 150*40 mm*10 um/water ($NH_4HCO_3$)-CAN/40%-70%) to afford the title compound (51.7 mg, 48%) as a yellow solid. $^1H$ NMR (400 MHz, DMSO-$d_6$): δ 8.82-8.76 (m, 2H), 8.39-8.33 (m, 2H), 7.61 (d, J=8.8 Hz, 2H), 7.51 (d, J=4.8 Hz, 1H), 6.58 (dd, J=8.4, 6.8 Hz, 1H), 6.31 (dd, J=17.2, 10.0 Hz, 1H), 6.17 (dd, J=17.2, 2.0 Hz, 1H), 5.66 (dd, J=10.0, 2.0 Hz, 1H), 5.06 (t, J=8.4 Hz, 1H), 4.80-4.78 (m, 2H), 4.62 (dd, J=8.4, 6.8 Hz, 1H); LCMS (ESI): m/z 449.0 $(M+H)^+$.

Example 137 (Compound 145)

(S)-2-(3-(Acrylamidomethyl)-1-(4-(trifluoromethoxy)phenyl)-1H-pyrazolo[3,4-b]pyridin-4-yl)-2-hydroxyethyl 2-aminoacetate formate

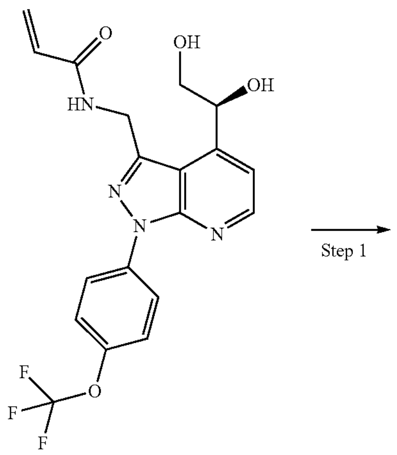

-continued

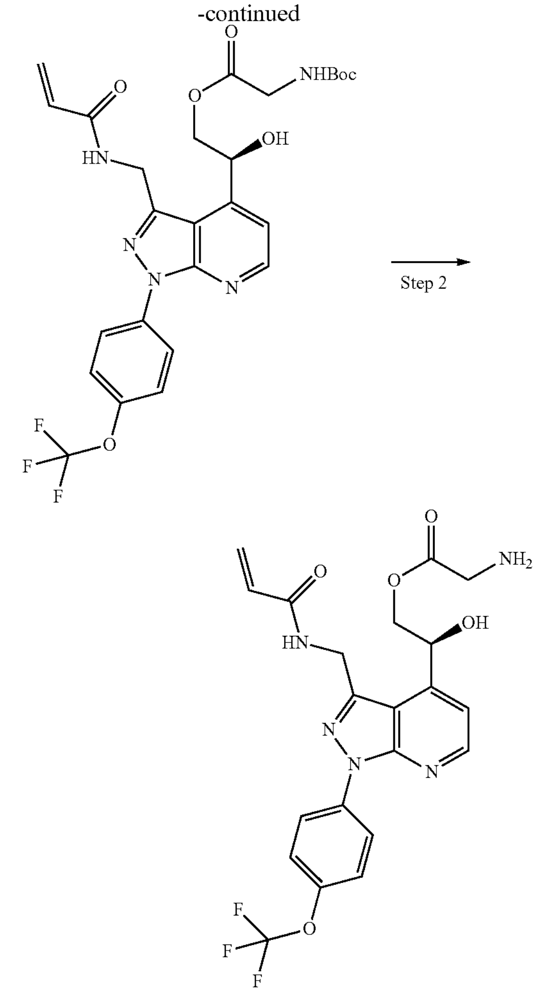

Step 1: (S)-2-(3-(acrylamidomethyl)-1-(4-(trifluoromethoxy)phenyl)-1H-pyrazolo[3,4-b]pyridin-4-yl)-2-hydroxyethyl 2-((tert-butoxycarbonyl)amino) acetate

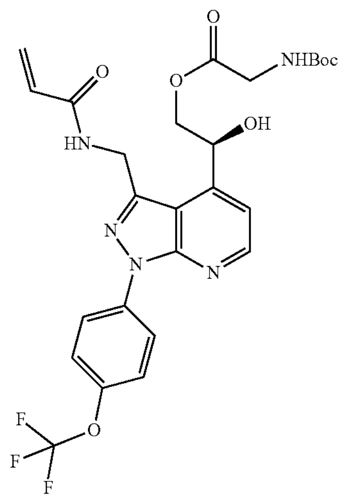 [SMILES: C=CC(=O)NCc1nn(-c2ccc(OC(F)(F)F)cc2)c2nccc([C@H](O)COC(=O)CNC(=O)OC(C)(C)C)c12]

To a solution of (S)-N-((4-(1,2-dihydroxyethyl)-1-(4-(trifluoromethoxy)phenyl)-1H-pyrazolo[3,4-b]pyridin-3-yl) methyl)acrylamide (300 mg, 0.71 mmol) and EDCI (204 mg, 1.07 mmol) in DCM (4 mL) was added 2-((tert-butoxycarbonyl)amino)acetic acid (149 mg, 0.85 mmol) and DMAP (173 mg, 1.42 mmol) at 0° C. The mixture was stirred at room temperature for 12 hours under a $N_2$ atmosphere. The reaction mixture was diluted with $H_2O$ (8 mL) and extracted with DCM (4 mL×3). The combined organic layers were dried over $Na_2SO_4$, filtered and concentrated under reduced pressure to give a residue. The residue was purified by reverse phase chromatography (Phenomenex C18 75*30 mm*3 um/water (0.225% FA)-ACN/35%-75%) to afford the title compound (80 mg, 19%) as a white solid. $^1$H NMR (400 MHz, $CDCl_3$): δ 8.61 (d, J=4.8 Hz, 1H), 8.28 (d, J=8.8 Hz, 2H), 7.39-7.37 (m, 3H), 6.76-6.74 (m, 1H), 6.34 (dd, J=16.8, 1.6 Hz, 1H), 6.20 (dd, J=16.8, 10.0 Hz, 1H), 5.70 (dd, J=10.0, 1.6 Hz, 1H), 5.60-5.58 (m, 1H), 5.20-5.19 (m, 1H), 5.07-5.01 (m, 2H), 4.53-4.50 (m, 1H), 4.44-4.41 (m, 1H), 4.34-4.32 (m, 1H), 3.96-3.91 (m, 2H), 1.44 (s, 9H).

Step 2: (S)-2-(3-(acrylamidomethyl)-1-(4-(trifluoromethoxy)phenyl)-1H-pyrazolo[3,4-b]pyridin-4-yl)-2-hydroxyethyl 2-aminoacetate formate

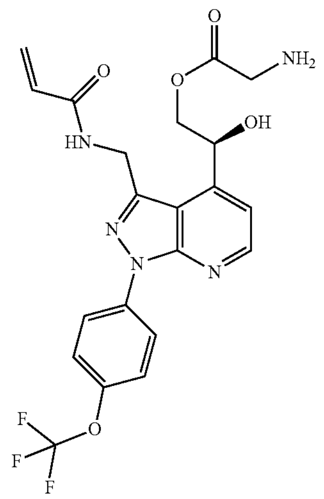 [SMILES: C=CC(=O)NCc1nn(-c2ccc(OC(F)(F)F)cc2)c2nccc([C@H](O)COC(=O)CN)c12]

To a solution of (S)-2-(3-(acrylamidomethyl)-1-(4-(trifluoromethoxy)phenyl)-1H-pyrazolo[3,4-b]pyridin-4-yl)-2-hydroxyethyl 2-((tert-butoxycarbonyl)amino)acetate (80 mg, 0.13 mmol) in dioxane (1 mL) was added 4M HCl/dioxane (1 mL) at 0° C. The mixture was stirred at room temperature for 2 hours under a $N_2$ atmosphere. The solution was filtered and evaporated to give the crude product. The organic material was purified by reverse phase chromatography (Phenomenex C18 75*30 mm*3 um/water (0.225% FA)-ACN/10%-40%) to afford the title compound (32.1 mg, 48%) as a white solid. $^1$H NMR (400 MHz, DMSO-$d_6$): δ 8.73 (t, J=5.2 Hz, 1H), 8.68 (d, J=4.8 Hz, 1H), 8.40 (d, J=9.2 Hz, 2H), 8.22 (s, 1H), 7.60 (d, J=8.4 Hz, 2H), 7.51 (d, J=4.8 Hz, 1H), 6.31 (dd, J=17.2, 10.4 Hz, 1H), 6.16 (dd, J=17.2, 2.4 Hz, 1H), 5.65 (dd, J=10.4, 2.4 Hz, 1H), 5.42 (dd, J=6.8, 4.4 Hz, 1H), 4.89-4.87 (m, 2H), 4.30-4.26 (m, 1H), 4.26-4.23 (m, 1H), 3.30-3.28 (m, 2H); LCMS (ESI): m/z 480.1 $(M+H)^+$.

Example 138 (Compound 146)

(S)-2-(3-(Acrylamidomethyl)-1-(4-(trifluoromethoxy)phenyl)-1H-pyrazolo[3,4-b]pyridin-4-yl)-2-hydroxyethyl acetate

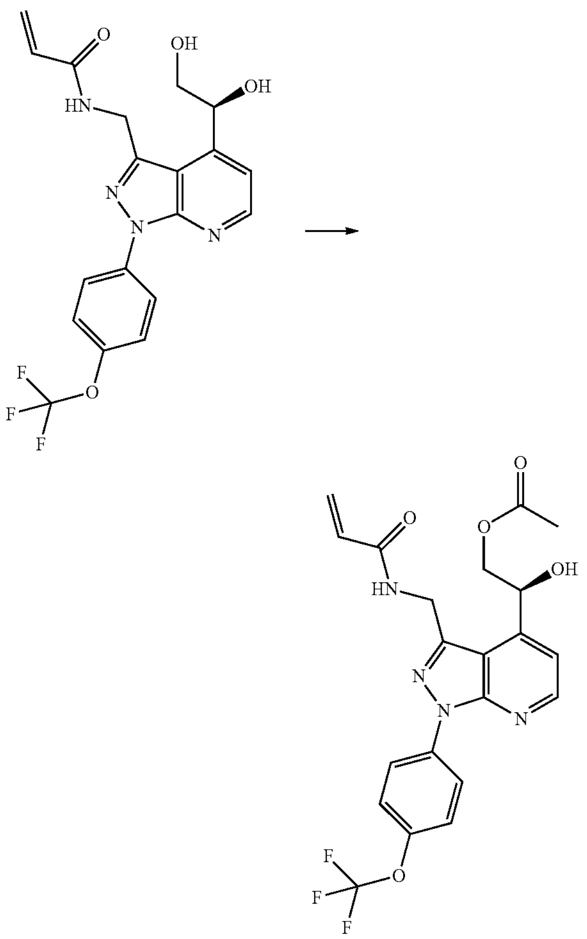

To a solution of (S)-N-((4-(1,2-dihydroxyethyl)-1-(4-(trifluoromethoxy)phenyl)-1H-pyrazolo[3,4-b]pyridin-3-yl)methyl)acrylamide (100 mg, 0.236 mmol) in DCM (2 mL) was added TEA (48 mg, 0.473 mmol) and acetyl chloride (24 mg, 0.307 mmol) at 0° C. The mixture was stirred at room temperature for 12 hours. The reaction mixture was diluted with $H_2O$ (5 mL) and extracted with DCM (5 mL×3). The combined organic layers were washed with brine (5 mL), dried over $Na_2SO_4$, filtered and concentrated under reduced pressure to give the crude product. The organic material was purified by reverse phase chromatography (Waters Xbridge Prep OBD C18 150*40 mm*10 um/water ($NH_4HCO_3$)-CAN, 40%-70%) and further purified by SFC DAICEL CHIRALPAK AD (250 mm*30 mm, 10 um)/45%-45%/Neu-ETOH to afford the title compound (13.7 mg, 12%) as a white solid. $^1H$ NMR (400 MHz, DMSO-$d_6$): δ 8.72-8.69 (m, 2H), 8.41 (d, J=8.8 Hz, 2H), 7.61 (d, J=9.2 Hz, 2H), 7.52 (d, J=5.2 Hz, 1H), 6.32 (dd, J=16.8, 10.0 Hz, 1H), 6.19-6.13 (m, 2H), 5.65 (dd, J=10.0, 1.6 Hz, 1H), 5.42-5.38 (m, 1H), 4.89 (t, J=5.2 Hz, 2H), 4.24-4.21 (m, 2H), 1.98 (s, 3H); LCMS(ESI): m/z 465.1 $(M+H)^+$.

Example 139 (Compound 147)

(S)-2-(3-(Acrylamidomethyl)-1-(4-(trifluoromethoxy)phenyl)-1H-pyrazolo[3,4-b]pyridin-4-yl)-2-hydroxyethyl dihydrogen phosphate

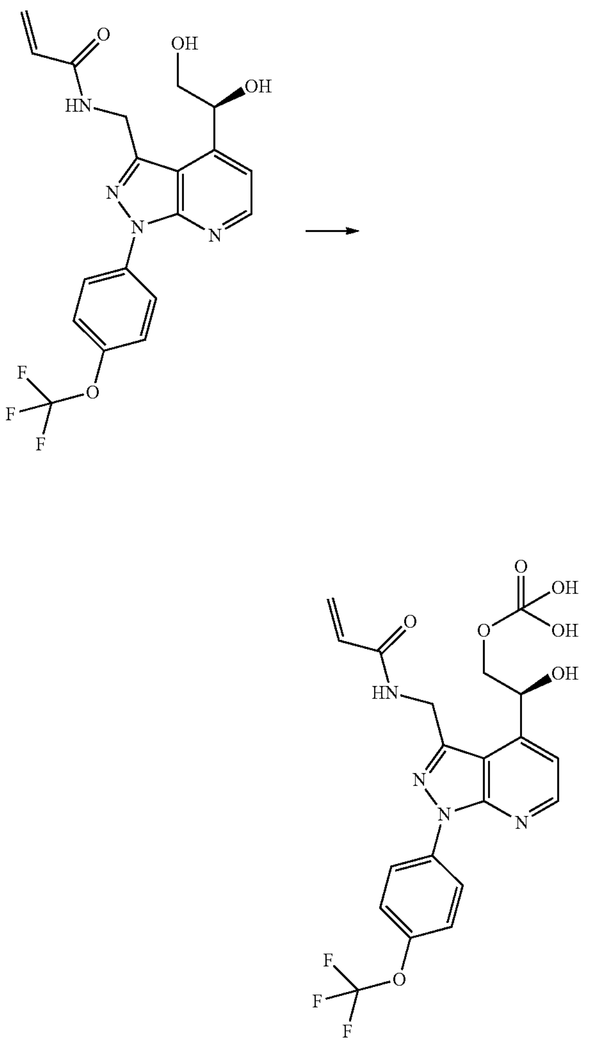

To the mixture of (S)-N-((4-(1,2-dihydroxyethyl)-1-(4-(trifluoromethoxy)phenyl)-1H-pyrazolo[3,4-b]pyridin-3-yl)methyl)acrylamide (300 mg, 0.71 mmol) and TEA (72 mg, 0.71 mmol) in THF (10 mL) was added $POCl_3$ (109 mg, 0.71 mmol) at 0° C. The resulting mixture was stirred at room temperature for 1 hour. The mixture was quenched with water (3 mL) and concentrated. The residue was purified by reverse phase chromatography (Welch Xtimate C18 150*30 mm*5 um, water (0.225% FA)-CAN, 20-50%) to afford the title compound (35.4 mg, 14%) as a light yellow solid. $^1H$ NMR (400 MHz, DMSO-$d_6$): δ 9.87 (s, 1H), 8.60 (d, J=4.8 Hz, 1H), 8.37 (d, J=9.2 Hz, 2H), 7.58 (d, J=8.4 Hz, 2H), 7.37 (d, J=4.8 Hz, 1H), 6.45 (dd, J=17.2, 10.4 Hz, 1H), 6.09 (dd, J=17.2, 2.4 Hz, 1H), 5.55-5.51 (m, 2H), 5.00-4.97 (m, 1H), 4.87-4.79 (m, 1H), 3.87-3.84 (m, 1H), 3.69-3.60 (m, 2H), 1.82-1.71 (m, 1H), 1.62-1.55 (m, 1H); LCMS(ESI): m/z 503.0 $(M+H)^+$.

Example 140 (Compound 148)

N-((4-(Hydroxymethyl)-1-(4-(trifluoromethoxy) phenyl)-1H-pyrazolo[3,4-b]pyridin-3-yl)methyl) cyclobut-1-enecarboxamide

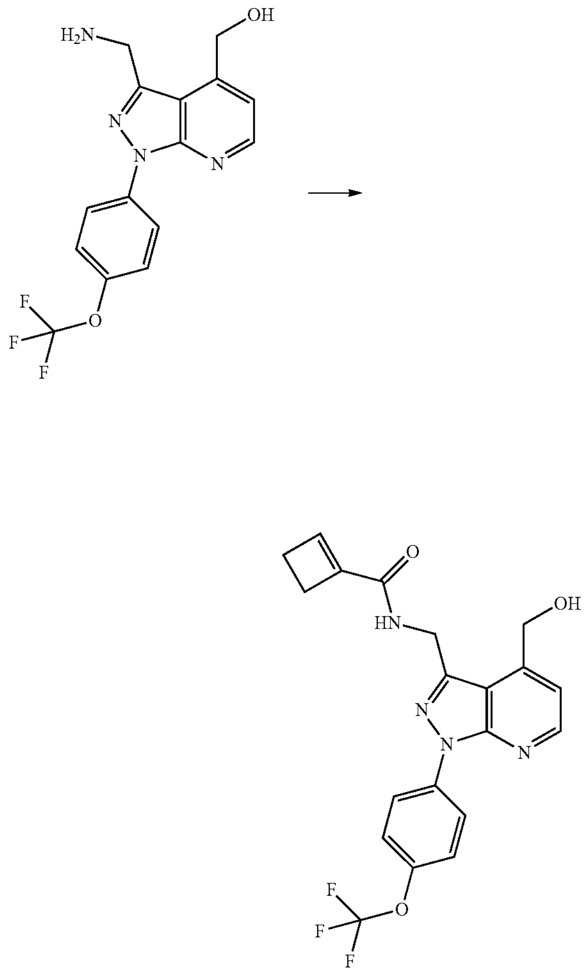

To a solution of (3-(aminomethyl)-1-(4-(trifluoromethoxy)phenyl)-1H-pyrazolo[3,4-b]pyridin-4-yl)methanol (100 mg, 0.30 mmol) in dichloromethane (10 mL) was added cyclobut-1-enecarboxylic acid (35 mg, 0.35 mmol) and ethyl 2-ethoxyquinoline-1 (2H)-carboxylate (220 mg, 0.89 mmol) at 0° C. The mixture was stirred at room temperature for 16 hours. The reaction mixture was diluted with ethyl acetate (50 mL), washed with brine (100 mL), dried over $Na_2SO_4$ and concentrated to dryness. The residue was purified by reverse phase chromatography (Boston Green ODS 150*30 mm*5 um, acetonitrile 50%-80%/water (0.225% FA)-ACN) to afford the title compound (38.1 mg, 31%) as a white solid. $^1$H NMR (400 MHz, DMSO-$d_6$): δ 8.65 (d, J=4.8 Hz, 1H), 8.51 (t, J=4.8 Hz, 1H), 8.40 (d, J=9.2 Hz, 2H), 7.59 (d, J=8.4 Hz, 2H), 7.44 (d, J=4.8 Hz, 1H), 6.61 (s, 1H), 5.72 (t, J=5.2 Hz, 1H), 4.98 (d, J=5.2 Hz, 2H), 4.76 (d, J=4.8 Hz, 2H), 2.63-2.60 (m, 2H), 2.37-2.35 (m, 2H); LCMS (ESI): m/z 419.0 $(M+H)^+$.

Example 141 (Compound 149)

N-((4-(Hydroxymethyl)-1-(4-(trifluoromethoxy) phenyl)-1H-pyrazolo[3,4-b]pyridin-3-yl)methyl)-2, 5-dihydrofuran-3-carboxamide

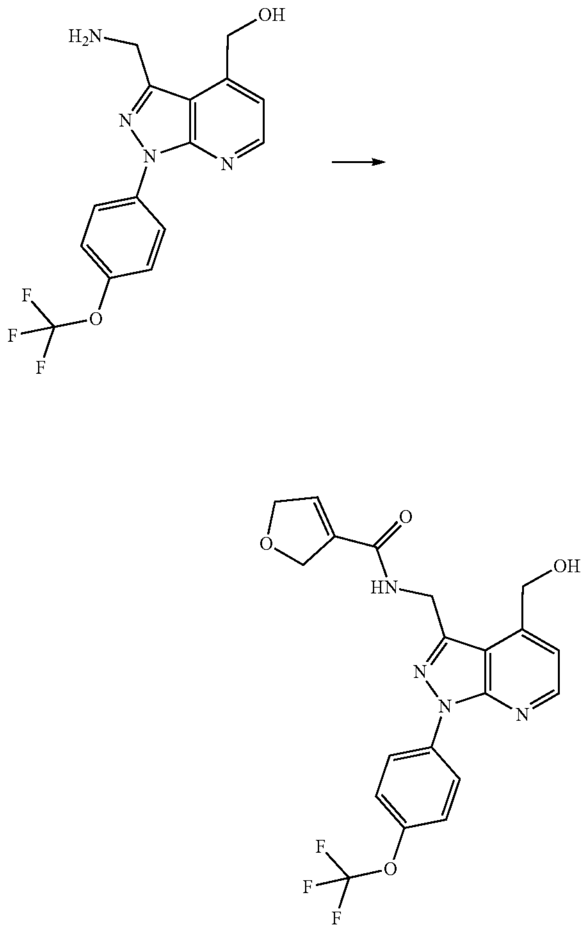

To a solution of (3-(aminomethyl)-1-(4-(trifluoromethoxy)phenyl)-1H-pyrazolo[3,4-b]pyridin-4-yl)methanol (105 mg, 0.31 mmol) in dichloromethane (8 mL) was added 2,5-dihydrofuran-3-carboxylic acid (54 mg, 0.47 mmol) and ethyl 2-ethoxyquinoline-1 (2H)-carboxylate (192 mg, 0.78 mmol) at 0° C. The reaction was stirred at room temperature for 16 hours. The reaction mixture was quenched with water (20 mL), extracted with ethyl acetate (20 mL×3). The organic phase was washed with brine (50 mL), dried over anhydrous sodium sulfate, filtered and concentrated. The residue was purified by column chromatography on silica gel (0-100% ethyl acetate in petroleum ether) to give the residue, then the residue was purified by reverse phase chromatography (Welch Xtimate C18 150*30 mm*5 um, acetonitrile 42-72%/water (0.225% FA)-ACN) to afford the title compound (47.5 mg, 35%) as a white solid. $^1$H NMR (400 MHz, DMSO-$d_6$): δ 8.71 (t, J=4.8 Hz, 1H), 8.65 (d, J=4.8 Hz, 1H), 8.41 (d, J=8.8 Hz, 2H), 7.60 (d, J=8.8 Hz, 2H), 7.45 (d, J=4.8 Hz, 1H), 6.76 (s, 1H), 5.72 (t, J=5.2 Hz, 1H), 4.99 (d, J=5.2 Hz, 2H), 4.80 (d, J=4.8 Hz, 2H), 4.71-4.69 (m, 4H); LCMS (ESI): m/z 435.0 $(M+H)^+$.

Example 142 (Compound 150)

Cyclopent-1-en-1-yl(3-(4-(hydroxymethyl)-1-(4-(trifluoromethoxy)phenyl)-1H-pyrazolo[3,4-b]pyridin-3-yl)azetidin-1-yl)methanone

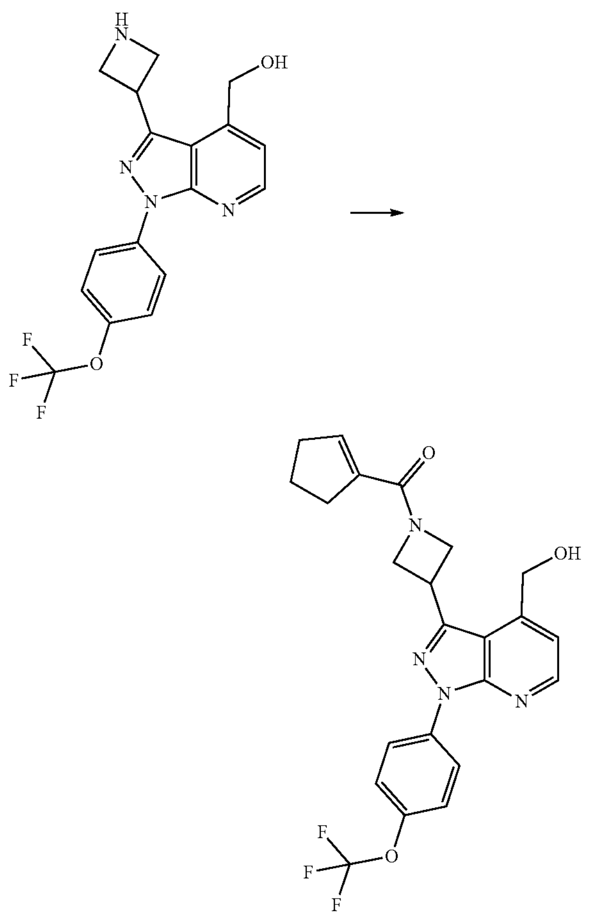

To a solution of (3-(azetidin-3-yl)-1-(4-(trifluoromethoxy)phenyl)-1H-pyrazolo[3,4-b]pyridin-4-yl)methanol (70 mg, 0.19 mmol) in dichloromethane (10 mL)/methanol (2 mL) was added cyclopent-1-enecarboxylic acid (33 mg, 0.29 mmol) and ethyl 2-ethoxyquinoline-1 (2H)-carboxylate (119 mg, 0.48 mmol) at 0° C. The reaction solution was stirred at room temperature for 16 hours. The reaction mixture was quenched with $H_2O$ (5 mL), and extracted with ethyl acetate (20 mL×3), the combined organic layers were washed with water (30 mL×3), dried over $Na_2SO_4$ and concentrated to dryness. The residue was purified by reverse phase chromatography (Boston Green ODS 150*30 mm*5 um, acetonitrile 57%-87%/water (0.225% FA)-ACN) and prep-TLC (100% ethyl acetate in petroleum ether) to afford the title compound (17.3 mg, 19%) as a white solid. $^1H$ NMR (400 MHz, DMSO-$d_6$): δ 8.64 (d, J=4.8 Hz, 1H), 8.50-8.42 (m, 2H), 7.58 (d, J=8.4 Hz, 2H), 7.41 (d, J=4.8 Hz, 1H), 6.36-6.35 (m, 1H), 5.71 (t, J=5.6 Hz, 1H), 4.90 (d, J=5.6 Hz, 2H), 4.74-4.63 (m, 2H), 4.54-4.31 (m, 3H), 2.53-2.51 (m, 2H), 2.48-2.44 (m, 2H), 1.86-1.77 (m, 2H); LCMS (ESI): m/z 459.0 $(M+H)^+$.

Example 143 (Compound 151)

(E)-1-(3-(4-(Hydroxymethyl)-1-(4-(trifluoromethoxy)phenyl)-1H-pyrazolo[3,4-b]pyridin-3-yl)azetidin-1-yl)-2-methylbut-2-en-1-one

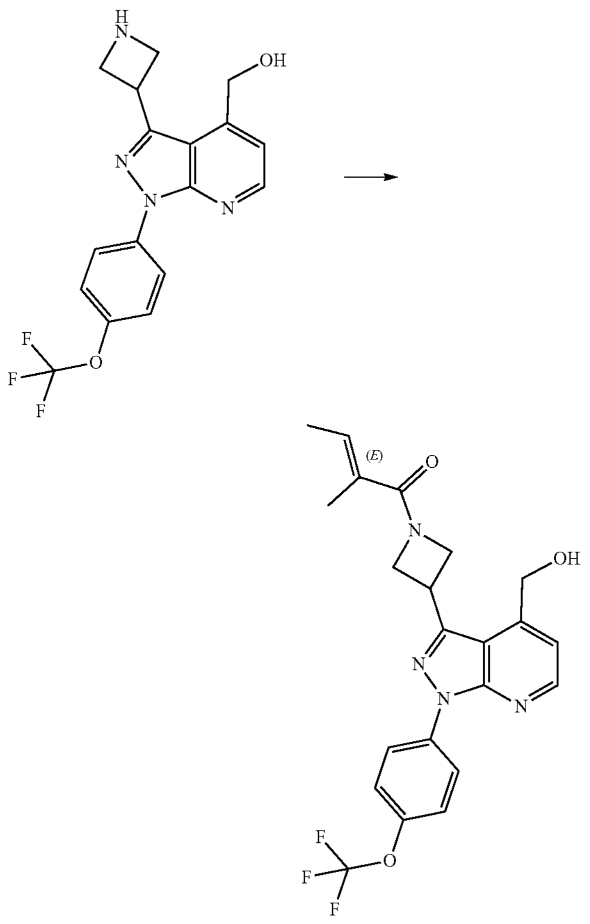

To a solution of (3-(azetidin-3-yl)-1-(4-(trifluoromethoxy)phenyl)-1H-pyrazolo[3,4-b]pyridin-4-yl)methanol (150 mg, 0.41 mmol) in dichloromethane (5 mL)/methanol (1 mL) was added (E)-2-methylbut-2-enoic acid (62 mg, 0.62 mmol) and ethyl 2-ethoxyquinoline-1 (2H)-carboxylate (255 mg, 1.03 mmol) at 0° C. The reaction solution was stirred at room temperature for 16 hours. The reaction mixture was quenched with $H_2O$ (5 mL), and extracted with ethyl acetate (10 mL×3), the combined organic layers were washed with water (10 mL×3), dried over $Na_2SO_4$ and concentrated. The residue was purified by reverse phase chromatography (Boston Green ODS 150*30 mm*5 um, acetonitrile 55-85%/water (0.225% FA)-ACN) to afford the title compound (15.4 mg, 8%) as a white solid. $^1H$ NMR (400 MHz, DMSO-$d_6$): δ 8.63 (d, J=4.8 Hz, 1H), 8.44 (d, J=8.8 Hz, 2H), 7.58 (d, J=8.8 Hz, 2H), 7.40 (d, J=4.8 Hz, 1H), 6.07-6.03 (m, 1H), 5.73-5.72 (m, 1H), 4.88 (d, J=4.0 Hz, 2H), 4.73-4.35 (m, 5H), 1.73-1.68 (m, 6H); LCMS (ESI): m/z 447.0 $(M+H)^+$.

Example 144 (Compound 152)

(2,5-Dihydrofuran-3-yl)(3-(4-(hydroxymethyl)-1-(4-(trifluoromethoxy)phenyl)-1H-pyrazolo[3,4-b]pyridin-3-yl)azetidin-1-yl)methanone

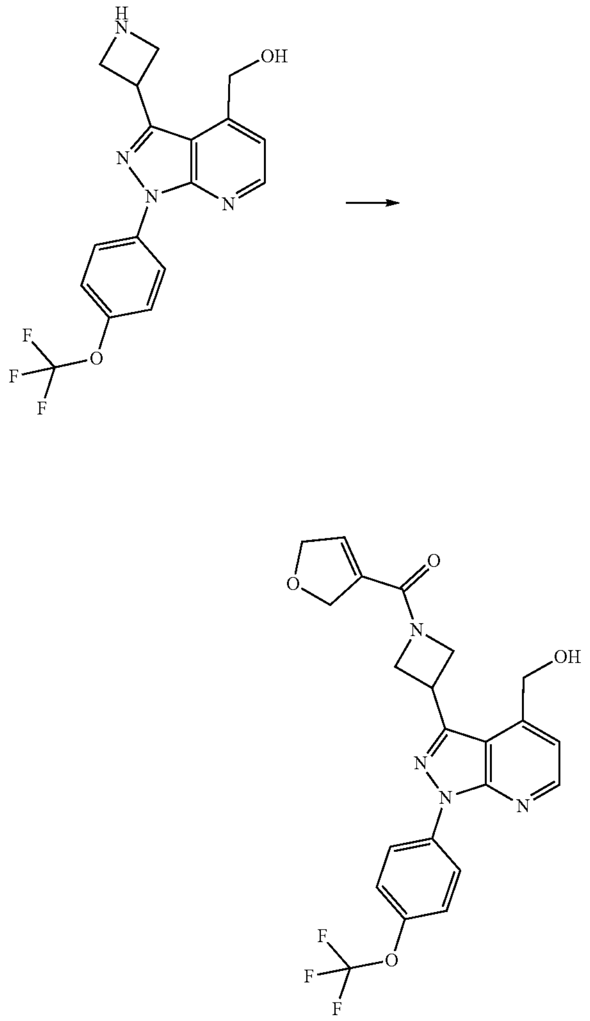

To a solution of (3-(azetidin-3-yl)-1-(4-(trifluoromethoxy)phenyl)-1H-pyrazolo[3,4-b]pyridin-4-yl)methanol (70 mg, 0.19 mmol) in dichloromethane (10 mL)/methanol (2 mL) was added 2,5-dihydrofuran-3-carboxylic acid (33 mg, 0.29 mmol) and ethyl 2-ethoxyquinoline-1(2H)-carboxylate (72 mg, 0.29 mmol) at 0° C. The reaction was stirred at room temperature for 16 hours. The reaction mixture was diluted with water (5 mL), and extracted with ethyl acetate (10 mL×3), the combined organic layers were washed with water (10 mL×3), dried over $Na_2SO_4$ and concentrated. The residue was purified by reverse phase chromatography (Boston Green ODS 150*30 mm*5 um, acetonitrile 20%-80%/water (0.225% FA)-ACN) to afford the title compound (29.2 mg, 34%) as a white solid. $^1H$ NMR (400 MHz, DMSO-$d_6$): δ 8.65 (d, J=4.8 Hz, 1H), 8.52-8.41 (m, 2H), 7.59 (d, J=8.4 Hz, 2H), 7.41 (d, J=4.8 Hz, 1H), 6.59 (s, 1H), 5.72 (t, J=5.2 Hz, 1H), 4.91-4.88 (m, 2H), 4.85-4.80 (m, 1H), 4.76-4.66 (m, 5H), 4.56-4.48 (m, 1H), 4.42-4.37 (m, 2H); LCMS (ESI): m/z 461.0 $(M+H)^+$.

Example 145 (Compound 153)

Bicyclo[1.1.0]butan-1-yl(3-(4-(hydroxymethyl)-1-(4-(trifluoromethoxy)phenyl)-1H-pyrazolo[3,4-b]pyridin-3-yl)azetidin-1-yl)methanone

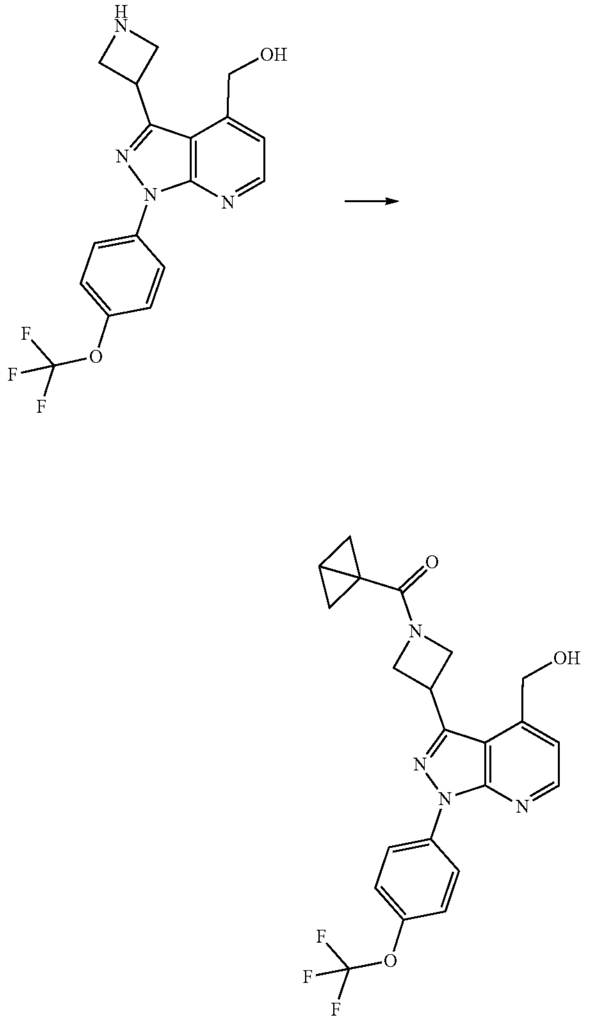

To a solution of (3-(azetidin-3-yl)-1-(4-(trifluoromethoxy)phenyl)-1H-pyrazolo[3,4-b]pyridin-4-yl)methanol (150 mg, 0.41 mmol) in THF (8 mL) was added N-ethyl-N-isopropylpropan-2-amine (0.18 mL, 1.03 mmol) and 4-nitrophenyl bicyclo[1.1.0]butane-1-carboxylate (109 mg, 0.49 mmol) at 0° C., the mixture was stirred at room temperature for 12 hours. The reaction mixture was quenched with water (5 mL). The solution was concentrated and the residue was purified by column chromatography on silica gel (0-100% ethyl acetate in petroleum ether) and then prep-TLC (75% ethyl acetate in petroleum ether) to afford the title compound (97.8 mg, 53%) as a white solid. $^1H$ NMR (400 MHz, DMSO-$d_6$): δ 8.64 (d, J=4.4 Hz, 1H), 8.46 (d, J=8.8 Hz, 2H), 7.59 (d, J=8.8 Hz, 2H), 7.41 (d, J=4.8 Hz, 1H), 5.71 (t, J=5.6 Hz, 1H), 4.90 (d, J=5.6 Hz, 2H), 4.73-4.58 (m, 2H), 4.52-4.44 (m, 1H), 4.37-4.35 (m, 2H), 2.22-2.15 (m, 3H), 1.03-1.01 (m, 2H); LCMS (ESI): m/z 445.0 $(M+H)^+$.

Example 146 (Compound 154)

(S)-N-((4-(1,2-Dihydroxyethyl)-1-(4-(trifluoromethoxy)phenyl)-1H-pyrazolo[3,4-b]pyridin-3-yl)methyl)acrylamide-2,3,3-$d_3$

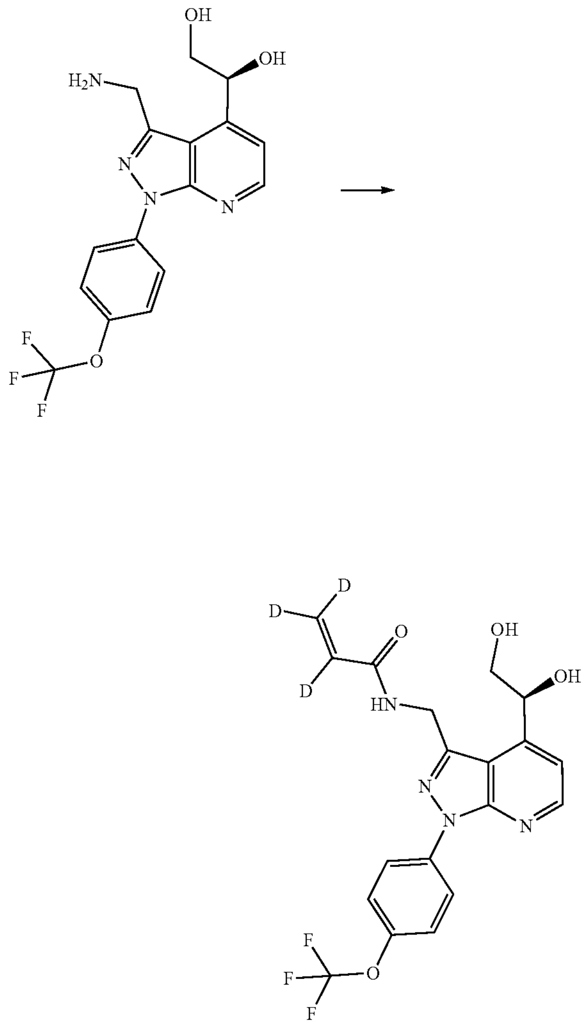

To a mixture of (S)-1-(3-(aminomethyl)-1-(4-(trifluoromethoxy)phenyl)-1H-pyrazolo[3,4-b]pyridin-4-yl)ethane-1,2-diol (100 mg, 0.27 mmol) and 2,3,3-trideuterioprop-2-enoic acid (24 mg, 0.33 mmol) in DCM (5 mL) was added ethyl 2-ethoxyquinoline-1 (2H)-carboxylate (168 mg, 0.68 mmol) at 0° C., the resulting mixture was stirred at 0° C. for 1 hour. The mixture was diluted with water (10 mL) and extracted with ethyl acetate (10 mL×3), the combined organic layers were dried over $Na_2SO_4$ and concentrated. The resulting residue was purified by prep-TLC (10% methanol in DCM) to afford the title compound (21.5 mg, 19%) as a white solid. $^1H$ NMR (400 MHz, DMSO-$d_6$): δ 8.68 (t, J=5.2 Hz, 1H), 8.64 (d, J=4.8 Hz, 1H), 8.43-8.36 (m, 2H), 7.59 (d, J=8.8 Hz, 2H), 7.47 (d, J=4.8 Hz, 1H), 5.79 (d, J=4.8 Hz, 1H), 5.19-5.16 (m, 1H), 5.00-4.94 (m, 2H), 4.83-4.78 (m, 1H), 3.68-3.57 (m, 2H); LCMS (ESI): m/z 425.9 $(M+H)^+$.

Example 147 (Compound 155)

(S)-N-((4-(1,2-Dihydroxyethyl)-1-(4-(trifluoromethoxy)phenyl)-1H-pyrazolo[3,4-b]pyridin-3-yl)methyl)-2-fluoroacrylamide

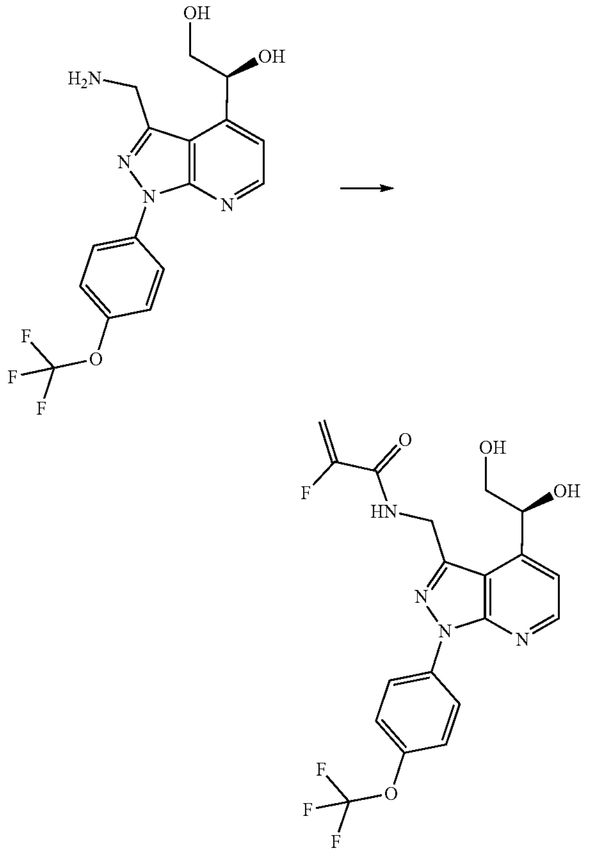

To a solution of (S)-1-(3-(aminomethyl)-1-(4-(trifluoromethoxy)phenyl)-1H-pyrazolo[3,4-b]pyridin-4-yl)ethane-1,2-diol (130 mg, 0.35 mmol) and 2-fluoroacrylic acid (39 mg, 0.42 mmol) in dichloromethane (10 mL) was added ethyl 2-ethoxyquinoline-1 (2H)-carboxylate (219 mg, 0.88 mmol) at 0° C. The mixture was stirred at room temperature for 16 hours. The reaction mixture was diluted with ethyl acetate (50 mL), washed with brine (100 mL), dried over $Na_2SO_4$ and concentrated to dryness. The residue was purified by column chromatography on silica gel (0-60% ethyl acetate in petroleum ether) to give the crude, then the crude was purified by reverse phase chromatography (Welch Xtimate C18 150*30 mm*5 um, acetonitrile 43-73%/water (0.225% FA)-ACN) to afford the title compound (48.2 mg, 31%) as a white solid. $^1H$ NMR (400 MHz, DMSO-$d_6$): δ 9.08 (t, J=5.2 Hz, 1H), 8.64 (d, J=4.8 Hz, 1H), 8.40-8.34 (m, 2H), 7.59 (d, J=8.4 Hz, 2H), 7.45 (d, J=4.8 Hz, 1H), 5.86 (d, J=4.4 Hz, 1H), 5.60 (dd, J=48.0, 3.6 Hz, 1H), 5.31 (dd, J=15.6, 3.6 Hz, 1H), 5.19-5.12 (m, 1H), 5.03-4.94 (m, 2H), 4.92-4.82 (m, 1H), 3.68-3.57 (m, 2H); LCMS (ESI): m/z 440.9 $(M+H)^+$.

Example 148 (Compound 156)

(S)-N-((4-(1,2-Dihydroxyethyl)-1-(4-(trifluoromethoxy)phenyl)-1H-pyrazolo[3,4-b]pyridin-3-yl)methyl)cyclobut-1-enecarboxamide

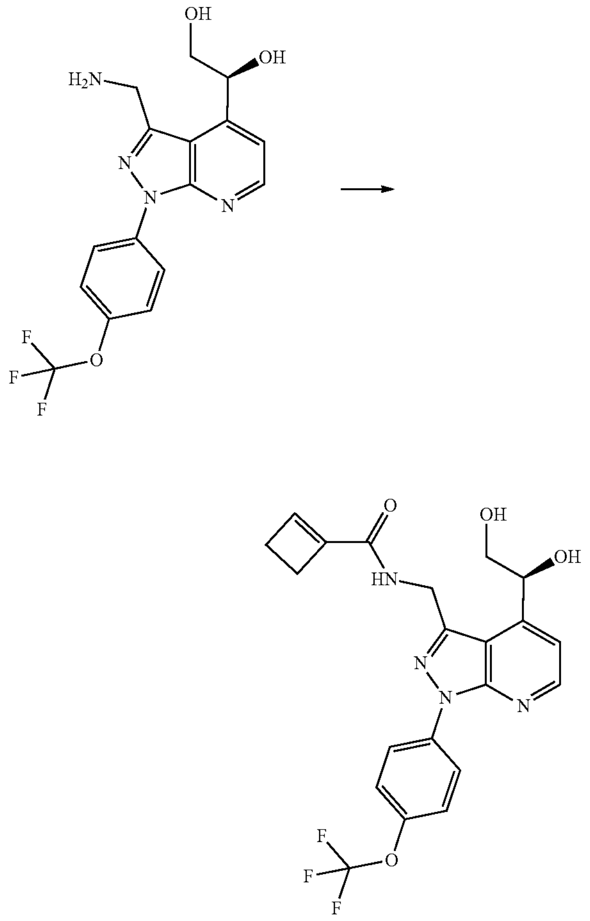

To a solution of (S)-1-(3-(aminomethyl)-1-(4-(trifluoromethoxy)phenyl)-1H-pyrazolo[3,4-b]pyridin-4-yl)ethane-1,2-diol (130 mg, 0.35 mmol) and cyclobut-1-enecarboxylic acid (42 mg, 0.42 mmol) in dichloromethane (10 mL) was added ethyl 2-ethoxyquinoline-1 (2H)-carboxylate (219 mg, 0.88 mmol) at 0° C. The mixture was stirred at room temperature for 16 hours. The reaction mixture was diluted with ethyl acetate (30 mL), washed with brine (30 mL), dried over $Na_2SO_4$ and concentrated to dryness. The residue was purified by column chromatography on silica gel (0-70% ethyl acetate in petroleum ether) to give the crude, then the crude was purified by reverse phase chromatography (Welch Xtimate C18 150*30 mm*5 um, acetonitrile 45-75%/water (0.225% FA)-ACN) to afford the title compound (32.4 mg, 20%) as a white solid. $^1H$ NMR (400 MHz, DMSO-$d_6$): δ 8.63 (d, J=4.8 Hz, 1H), 8.50 (t, J=4.4 Hz, 1H), 8.39 (d, J=8.8 Hz, 2H), 7.59 (d, J=8.8 Hz, 2H), 7.46 (d, J=4.8 Hz, 1H), 6.61 (s, 1H), 5.81 (d, J=4.0 Hz, 1H), 5.24-5.19 (m, 1H), 5.00-4.89 (m, 2H), 4.78-4.73 (m, 1H), 3.67-3.57 (m, 2H), 2.65-2.60 (m, 2H), 2.38-2.35 (m, 2H); LCMS (ESI): m/z 449.0 $(M+H)^+$.

Example 149 (Compound 157)

(R)-Cyclobut-1-en-1-yl(3-(4-(1,2-dihydroxyethyl)-1-(4-(trifluoromethoxy)phenyl)-1H-pyrazolo[3,4-b]pyridin-3-yl)azetidin-1-yl)methanone

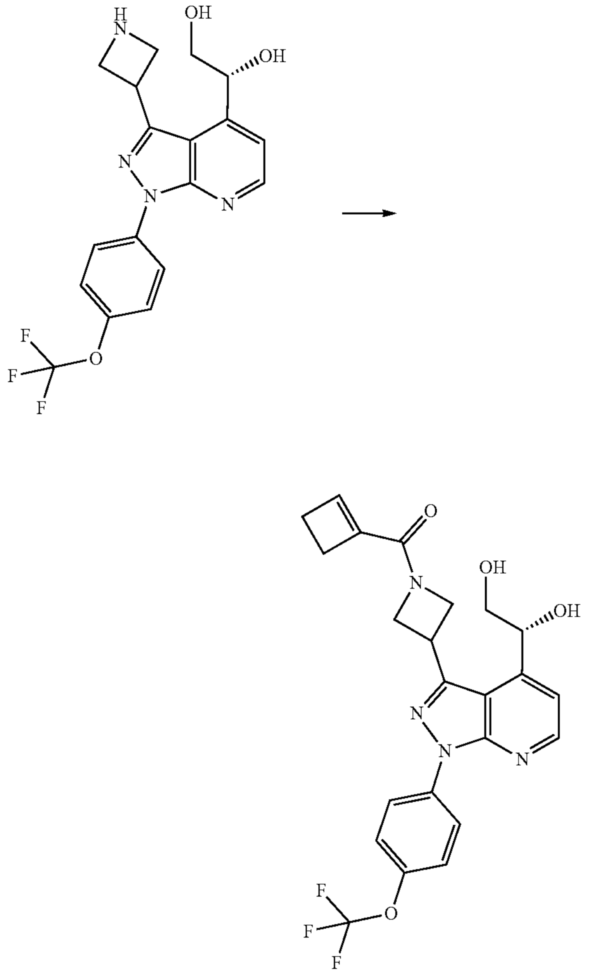

To a solution of (R)-1-(3-(azetidin-3-yl)-1-(4-(trifluoromethoxy)phenyl)-1H-pyrazolo[3,4-b]pyridin-4-yl)ethane-1,2-diol (300 mg, 0.76 mmol) in dichloromethane (5 mL)/methanol (1 mL) was added cyclobut-1-enecarboxylic acid (90 mg, 0.91 mmol) and ethyl 2-ethoxyquinoline-1 (2H)-carboxylate (283 mg, 1.14 mmol) at 0° C. The resulting mixture was stirred at room temperature for 2 hours. The reaction was diluted with water (20 mL) and extracted with ethyl acetate (20 mL×3), the combined organic layers were dried over $Na_2SO_4$ and concentrated in vacuo. The resulting residue was purified by reverse phase chromatography (Welch Xtimate C18 150*30 mm*5 um, acetonitrile 45-75%/water (0.225% FA)-ACN) to afford the title compound (29.7 mg, 8%) as a white solid. $^1H$ NMR (400 MHz, DMSO-$d_6$): δ 8.64 (d, J=4.8 Hz, 1H), 8.45 (d, J=8.8 Hz, 2H), 7.59 (d, J=8.8 Hz, 2H), 7.44 (d, J=4.8 Hz, 1H), 6.53 (s, 1H), 5.83 (d, J=4.0 Hz, 1H), 5.03-5.00 (m, 2H), 4.75-4.59 (m, 3H), 4.42-4.27 (m, 2H), 3.61-3.53 (m, 2H), 2.69-2.66 (m, 2H), 2.45-2.43 (m, 2H); LCMS (ESI): m/z 475.1 $(M+H)^+$.

Example 150 (Compound 158)

2-Fluoro-1-(3-(4-(1-methyl-1H-pyrazol-4-yl)-1-(4-(trifluoromethoxy)phenyl)-1H-pyrazolo[3,4-b]pyridin-3-yl)azetidin-1-yl)prop-2-en-1-one

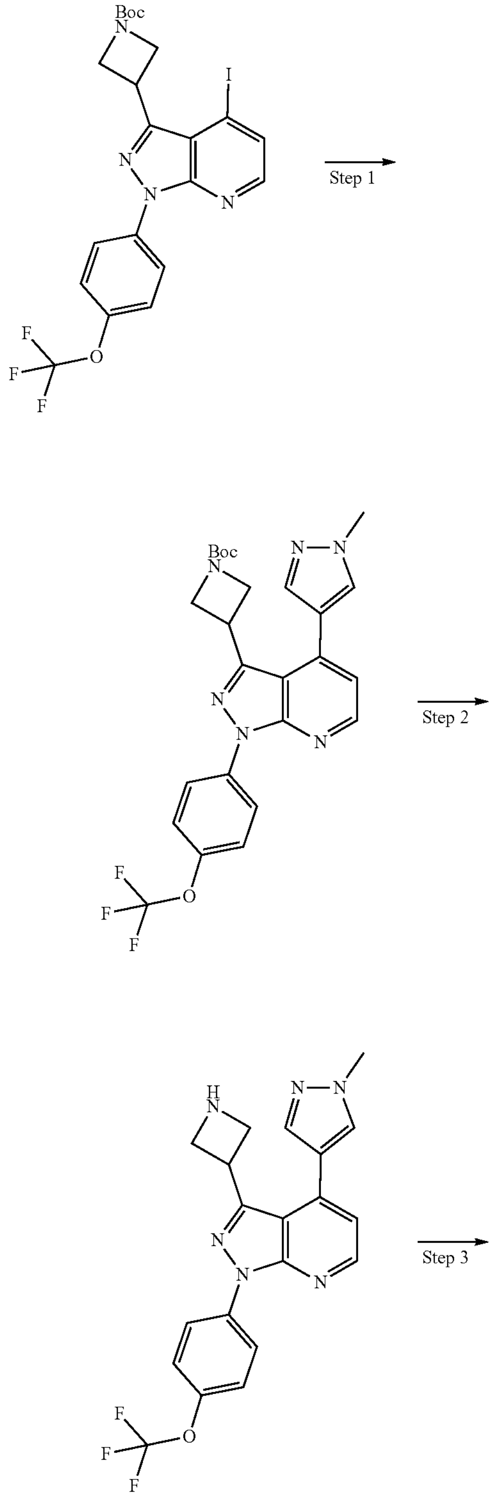

-continued

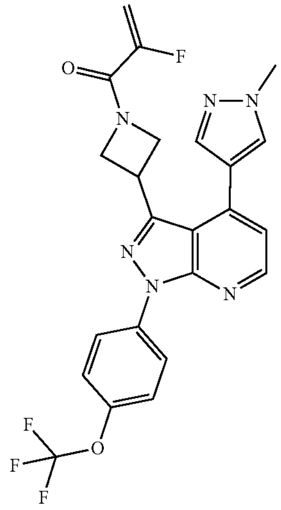

Step 1: tert-butyl 3-(4-(1-methyl-1H-pyrazol-4-yl)-1-(4-(trifluoromethoxy)phenyl)-1H-pyrazolo[3,4-b]pyridin-3-yl)azetidine-1-carboxylate

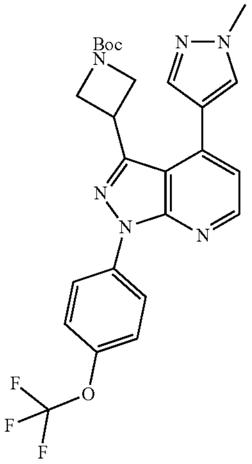 [SMILES: Cn1cc(-c2ccnc3c2c(C2CN(C(=O)OC(C)(C)C)C2)nn3-c2ccc(OC(F)(F)F)cc2)cn1]

A solution of tert-butyl 3-(4-iodo-1-(4-(trifluoromethoxy)phenyl)-1H-pyrazolo[3,4-b]pyridin-3-yl)azetidine-1-carboxylate (500 mg, 0.89 mmol), $K_3PO_4$ (379 mg, 1.78 mmol), 1-methyl-4-(4,4,5,5-tetramethyl-1,3,2-dioxaborolan-2-yl)-1H-pyrazole (371 mg, 1.78 mmol) and Pd(dppf)$Cl_2$ (66 mg, 0.09 mmol) in 1,4-dioxane (10 mL) and water (1 mL) was stirred at 90° C. for 3 hours under a N2 atmosphere. The mixture was diluted with ethyl acetate (100 mL) and washed with water (100 mL×3). The organic layer was dried over $Na_2SO_4$ and concentrated. The residue was purified by chromatography on silica gel (0-35% ethyl acetate in petroleum ether) to afford the title compound (300 mg, 65%) as a white solid. LCMS (ESI): m/z 515.2 $(M+H)^+$.

Step 2: 3-(azetidin-3-yl)-4-(1-methyl-1H-pyrazol-4-yl)-1-(4-(trifluoromethoxy)phenyl)-1H-pyrazolo[3,4-b]pyridine

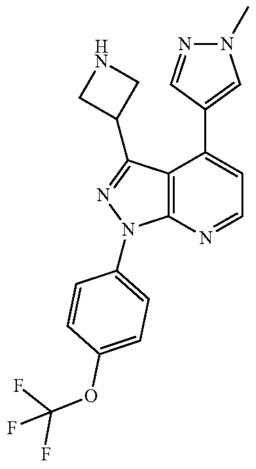 [SMILES: Cn1cc(-c2ccnc3c2c(C2CNC2)nn3-c2ccc(OC(F)(F)F)cc2)cn1]

A solution of tert-butyl 3-(4-(1-methyl-1H-pyrazol-4-yl)-1-(4-(trifluoromethoxy)phenyl)-1H-pyrazolo[3,4-b]pyridin-3-yl)azetidine-1-carboxylate (450 mg, 1.04 mmol) in 5% TFA in HFIP (10 mL) was stirred at room temperature for 2 hours. The mixture was quenched with water (100 mL), then the solution was adjusted to pH 8 with sat. aq. $NaHCO_3$ solution. The solution was extracted with ethyl acetate (200 mL) and washed with water (100 mL×3). The organic layer was dried over $Na_2SO_4$ and concentrated to afford the title compound (300 mg, crude) as a brown solid. LCMS (ESI): m/z 415.2 $(M+H)^+$.

Step 3: 2-fluoro-1-(3-(4-(1-methyl-1H-pyrazol-4-yl)-1-(4-(trifluoromethoxy)phenyl)-1H-pyrazolo[3,4-b]pyridin-3-yl)azetidin-1-yl)prop-2-en-1-one

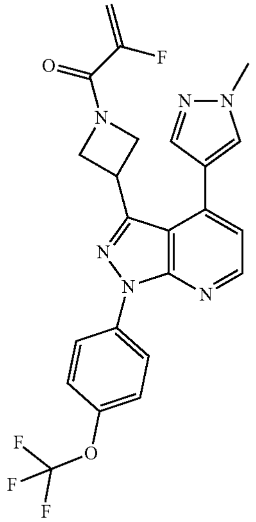 [SMILES: C=C(F)C(=O)N1CC(c2nn(-c3ccc(OC(F)(F)F)cc3)c3nccc(-c4cnn(C)c4)c23)C1]

To a mixture of 3-(azetidin-3-yl)-4-(1-methyl-1H-pyrazol-4-yl)-1-(4-(trifluoromethoxy)phenyl)-1H-pyrazolo[3,4-b]pyridine (300 mg, 0.72 mmol), 2-fluoroacrylic acid (78 mg, 0.87 mmol) in DCM (5 mL)/methanol (1 mL) was added ethyl 2-ethoxyquinoline-1 (2H)-carboxylate (269 mg, 1.09 mmol) at 0° C. The solution was stirred at room temperature for 16 hours. The mixture was diluted with ethyl acetate (100 mL) and washed with water (100 mL×3). The organic layer was dried over $Na_2SO_4$ and concentrated. The resulting residue was purified by reverse phase chromatography (Welch Xtimate C18 150*30 mm*5 um, water (0.225% FA)-ACN, 59%-89%) to afford the title compound (164.84 mg, 46%) as a white solid. $^1H$ NMR (400 MHz, DMSO-$d_6$): δ 8.63 (d, J=4.8 Hz, 1H), 8.47-8.42 (m, 2H), 8.19 (s, 1H), 7.85 (s, 1H), 7.60 (d, J=8.4 Hz, 2H), 7.27 (d, J=4.8 Hz, 1H), 5.44 (dd, J=48.4, 3.6 Hz, 1H), 5.27 (dd, J=16.8, 3.6 Hz, 1H), 4.62-4.57 (m, 1H), 4.54-4.37 (m, 2H), 4.17-4.02 (m, 2H), 3.99 (s, 3H); LCMS (ESI): m/z 487.0 $(M+H)^+$.

Example 151 & 152 (Compounds 159 & 160)

(S)-1-(3-(1-(Prop-1-en-2-ylsulfonyl)azetidin-3-yl)-1-(4-(trifluoromethoxy)phenyl)-1H-pyrazolo[3,4-b]pyridin-4-yl)ethane-1,2-diol & (R)-1-(3-(1-(prop-1-en-2-ylsulfonyl)azetidin-3-yl)-1-(4-(trifluoromethoxy)phenyl)-1H-pyrazolo[3,4-b]pyridin-4-yl)ethane-1,2-diol

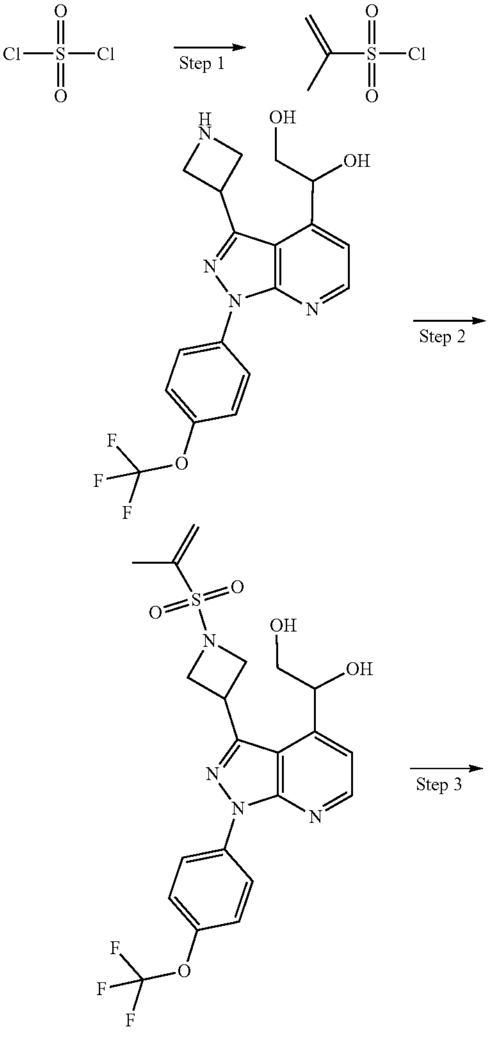

-continued

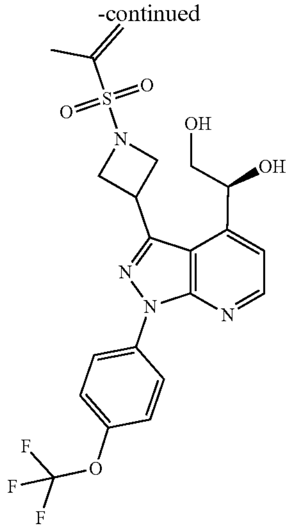

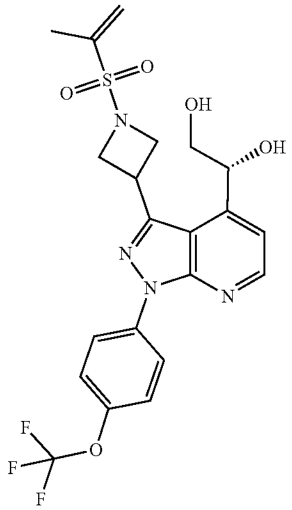 [SMILES: C=C(C)S(=O)(=O)N1CC(c2nn(-c3ccc(OC(F)(F)F)cc3)c3nccc([C@@H](O)CO)c23)C1]

Step 1: prop-1-ene-2-sulfonyl chloride

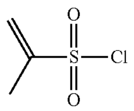

A mixture of sulfuryl dichloride (2.0 g, 14.82 mmol) in THF (20 mL) was added prop-1-en-2-ylmagnesium bromide (20 mL, 10 mmol, 0.50 mol/L in THF) at 0° C. slowly. The reaction mixture was stirred at room temperature for 16 hours. The reaction mixture was quenched with water (40 mL). The reaction mixture was then diluted with ethyl acetate (60 mL×3), washed with brine (60 mL×3), dried over $Na_2SO_4$ and concentrated to dryness. The residue was purified by chromatography on silica gel (0-5% methanol in dichloromethane) to afford the title compound (400 mg, 19%) as a yellow oil.

Step 2: 1-(3-(1-(prop-1-en-2-ylsulfonyl)azetidin-3-yl)-1-(4-(trifluoromethoxy)phenyl)-1H-pyrazolo[3,4-b]pyridin-4-yl)ethane-1,2-diol

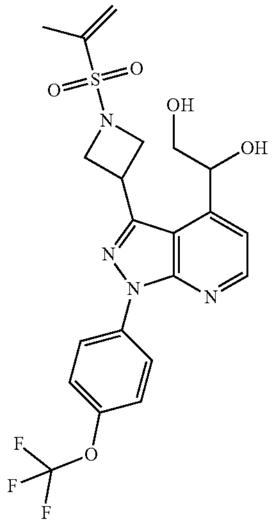 [SMILES: C=C(C)S(=O)(=O)N1CC(c2nn(-c3ccc(OC(F)(F)F)cc3)c3nccc(C(O)CO)c23)C1]

A solution of 1-(3-(azetidin-3-yl)-1-(4-(trifluoromethoxy)phenyl)-1H-pyrazolo[3,4-b]pyridin-4-yl)ethane-1,2-diol (300 mg, 0.76 mmol) and prop-1-ene-2-sulfonyl chloride (107 mg, 0.76 mmol) in DCM (10 mL) was stirred at 0° C. for 0.5 hour. Then TEA (0.11 mL, 0.76 mmol) was added into the mixture and the reaction solution was stirred at room temperature for 16 hours. The reaction mixture was diluted with ethyl acetate (100 mL×3), washed with brine (90 mL×5), dried over $Na_2SO_4$ and concentrated to dryness. After filtration, the filtrate was concentrated and the residue was purified by reverse phase chromatography (Welch Xtimate C18 150 mm*30 mm, 5 um; acetonitrile 48-78%/0.225% formic acid in water) to afford the title compound (45 mg, 12%) as a white solid. LCMS (ESI): m/z 499.0 $(M+H)^+$.

Step 3: (S)-1-(3-(1-(prop-1-en-2-ylsulfonyl)azetidin-3-yl)-1-(4-(trifluoromethoxy)phenyl)-1H-pyrazolo[3,4-b]pyridin-4-yl)ethane-1,2-diol & (R)-1-(3-(1-(prop-1-en-2-ylsulfonyl)azetidin-3-yl)-1-(4-(trifluoromethoxy)phenyl)-1H-pyrazolo[3,4-b]pyridin-4-yl)ethane-1,2-diol

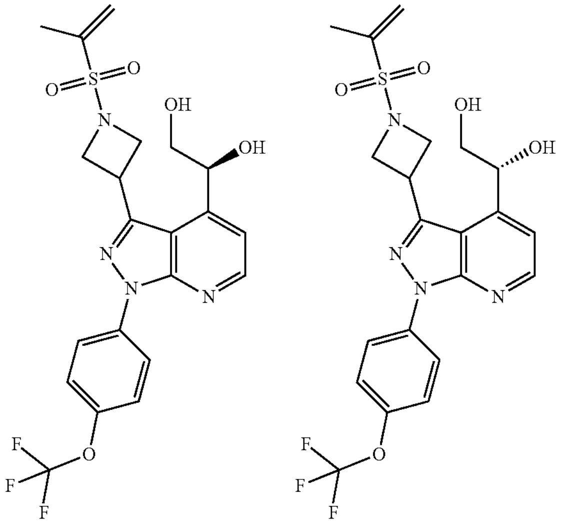 [SMILES: C=C(C)S(=O)(=O)N1CC(c2nn(-c3ccc(OC(F)(F)F)cc3)c3nccc([C@H](O)CO)c23)C1 ; C=C(C)S(=O)(=O)N1CC(c2nn(-c3ccc(OC(F)(F)F)cc3)c3nccc([C@@H](O)CO)c23)C1]

1-(3-(1-(Prop-1-en-2-yl sulfonyl)azetidin-3-yl)-1-(4-(trifluoromethoxy)phenyl)-1H-pyrazolo[3,4-b]pyridin-4-yl)ethane-1,2-diol (45 mg, 0.09 mmol) was separated by Chiral SFC (Instrument: SFC-22; Column: Phenomenex-Cellulose-2 (250 mm*30 mm, 10 um); Condition: Neu-MEOH; Begin B:45%; Flow Rate (mL/min): 80) to afford the first peak (S)-1-(3-(1-(prop-1-en-2-ylsulfonyl)azetidin-3-yl)-1-(4-(trifluoromethoxy)phenyl)-1H-pyrazolo[3,4-b]pyridin-4-yl)ethane-1,2-diol (12.8 mg, 28%) and the second peak (R)-1-(3-(1-(prop-1-en-2-ylsulfonyl)azetidin-3-yl)-1-(4-(trifluoromethoxy)phenyl)-1H-pyrazolo[3,4-b]pyridin-4-yl) ethane-1,2-diol (10.4 mg, 23%) both as white solid.

The first peak: $^1$H NMR (400 MHz, DMSO-$d_6$): δ 8.63 (d, J=4.8 Hz, 1H), 8.44 (d, J=8.8 Hz, 2H), 7.62 (d, J=8.8 Hz, 2H), 7.42 (d, J=4.8 Hz, 1H), 5.97-5.93 (m, 2H), 5.82 (d, J=4.0 Hz, 1H), 5.04-4.96 (m, 2H), 4.62-4.54 (m, 1H), 4.38-4.33 (m, 2H), 4.31-4.23 (m, 2H), 3.62-3.51 (m, 2H), 2.15 (s, 3H); LCMS (ESI): m/z 499.0 $(M+H)^+$.

The second peak: $^1$H NMR (400 MHz, DMSO-$d_6$): δ 8.63 (d, J=4.8 Hz, 1H), 8.44 (d, J=8.8 Hz, 2H), 7.62 (d, J=8.8 Hz, 2H), 7.42 (d, J=4.8 Hz, 1H), 5.97-5.93 (m, 2H), 5.82 (d, J=4.0 Hz, 1H), 5.04-4.96 (m, 2H), 4.62-4.54 (m, 1H), 4.38-4.33 (m, 2H), 4.31-4.23 (m, 2H), 3.62-3.51 (m, 2H), 2.15 (s, 3H); LCMS (ESI): m/z 499.0 $(M+H)^+$.

Example 153 & 154 (Compounds 161 & 162)

(S,E)-1-(3-(1-(Prop-1-en-1-ylsulfonyl)azetidin-3-yl)-1-(4-(trifluoromethoxy)phenyl)-1H-pyrazolo[3,4-b]pyridin-4-yl)ethane-1,2-diol & (R,E)-1-(3-(1-(prop-1-en-1-ylsulfonyl)azetidin-3-yl)-1-(4-(trifluoromethoxy)phenyl)-1H-pyrazolo[3,4-b]pyridin-4-yl)ethane-1,2-diol

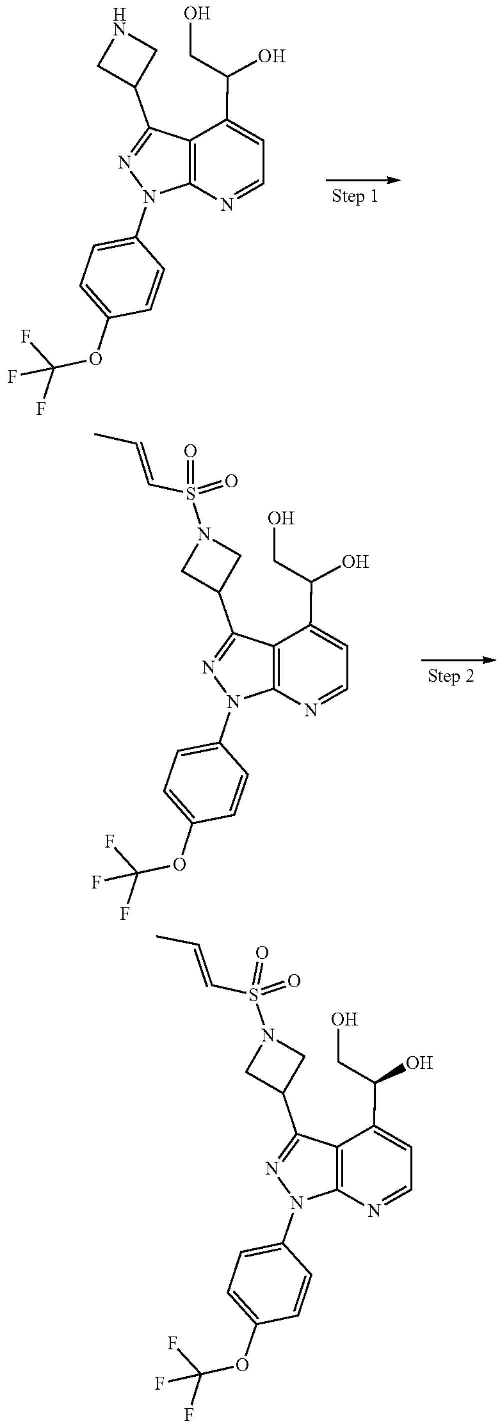

-continued

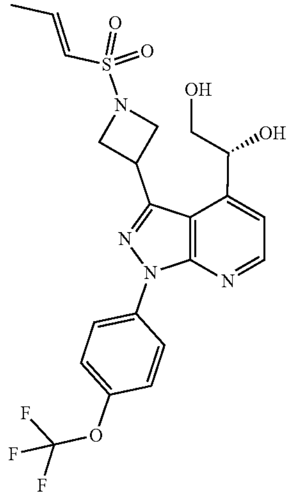 [SMILES: C/C=C/S(=O)(=O)N1CC(c2nn(-c3ccc(OC(F)(F)F)cc3)c3nccc([C@@H](O)CO)c23)C1]

Step 1: (E)-1-(3-(1-(prop-1-en-1-ylsulfonyl)azetidin-3-yl)-1-(4-(trifluoromethoxy)phenyl)-1H-pyrazolo[3,4-b]pyridin-4-yl)ethane-1,2-diol

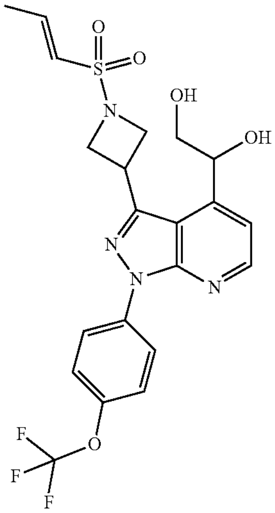

To a mixture of 1-(3-(azetidin-3-yl)-1-(4-(trifluoromethoxy)phenyl)-1H-pyrazolo[3,4-b]pyridin-4-yl)ethane-1,2-diol (200 mg, 0.51 mmol) in dichloromethane (5 mL) was added (E)-prop-1-ene-1-sulfonyl chloride (86 mg, 0.61 mmol) and TEA (0.14 mL, 1.01 mmol) at 0° C., the resulting mixture was stirred at room temperature for 1 hour. The reaction mixture was quenched with $H_2O$ (5 mL), extracted with ethyl acetate (50 mL×3), and the combined organic layers were washed with water (50 mL×3), dried over $Na_2SO_4$ then concentrated. The residue was purified by chromatography on silica gel (45-55% ethyl acetate in petroleum ether) to afford the title compound (110 mg, 44%) as a white solid. LCMS (ESI): m/z 499.1 $(M+H)^+$.

Step 2: (S,E)-1-(3-(1-(prop-1-en-1-ylsulfonyl)azetidin-3-yl)-1-(4-(trifluoromethoxy)phenyl)-1H-pyrazolo[3,4-b]pyridin-4-yl)ethane-1,2-diol & (R,E)-1-(3-(1-(prop-1-en-1-ylsulfonyl)azetidin-3-yl)-1-(4-(trifluoromethoxy)phenyl)-1H-pyrazolo[3,4-b]pyridin-4-yl)ethane-1,2-diol

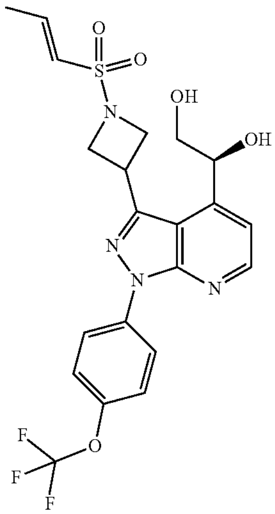

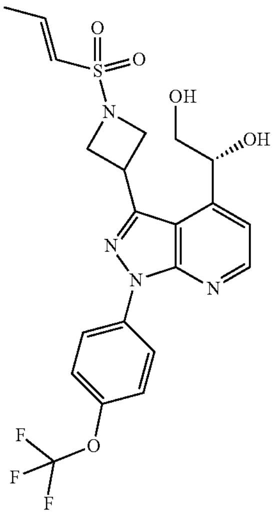 [SMILES: C/C=C/S(=O)(=O)N1CC(c2nn(-c3ccc(OC(F)(F)F)cc3)c3nccc(C(O)CO)c23)C1]

(E)-1-(3-(1-(Prop-1-en-1-ylsulfonyl)azetidin-3-yl)-1-(4-(trifluoromethoxy)phenyl)-1H-pyrazolo[3,4-b]pyridin-4-yl)ethane-1,2-diol (110 mg, 0.26 mmol) was separated by Chiral SFC (Instrument: SFC-17; Column:Phenomenex-Cellulose-2 (250 mm*30 mm, 10 um) to afford the first peak (S,E)-1-(3-(1-(prop-1-en-1-ylsulfonyl)azetidin-3-yl)-1-(4-(trifluoromethoxy)phenyl)-1H-pyrazolo[3,4-b]pyridin-4-yl)ethane-1,2-diol (18.82 mg, 17%) and the second peak (R,E)-1-(3-(1-(prop-1-en-1-ylsulfonyl)azetidin-3-yl)-1-(4-(trifluoromethoxy)phenyl)-1H-pyrazolo[3,4-b]pyridin-4-yl)ethane-1,2-diol (18.46 mg, 17%) as both white solid.

The first peak: $^1$H NMR (400 MHz, DMSO-$d_6$): δ 8.63 (d, J=4.8 Hz, 1H), 8.49-8.44 (m, 2H), 7.61 (d, J=8.4 Hz, 2H), 7.42 (d, J=4.8 Hz, 1H), 6.84-6.75 (m, 2H), 5.82 (d, J=4.4 Hz, 1H), 5.05-5.01 (m, 1H), 4.99-4.95 (m, 1H), 4.59-4.48 (m, 1H), 4.30-4.20 (m, 4H), 3.64-3.48 (m, 2H), 1.91 (d, J=5.2 Hz, 3H); LCMS (ESI): m/z 499.0 $(M+H)^+$.

The second peak: $^1$H NMR (400 MHz, DMSO-$d_6$): δ 8.63 (d, J=4.8 Hz, 1H), 8.49-8.44 (m, 2H), 7.61 (d, J=8.4 Hz, 2H), 7.42 (d, J=4.8 Hz, 1H), 6.84-6.75 (m, 2H), 5.82 (d, J=4.4 Hz, 1H), 5.05-5.01 (m, 1H), 4.99-4.95 (m, 1H), 4.59-4.48 (m, 1H), 4.30-4.20 (m, 4H), 3.64-3.48 (m, 2H), 1.91 (d, J=5.2 Hz, 3H); LCMS (ESI): m/z 499.0 $(M+H)^+$.

Example 155 (Compound 163)

Cyclobut-1-en-1-yl(3-(1-(4-(trifluoromethoxy)phenyl)-1H-pyrazolo[3,4-b]pyrazin-3-yl)azetidin-1-yl)methanone

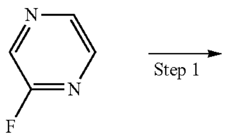

-continued

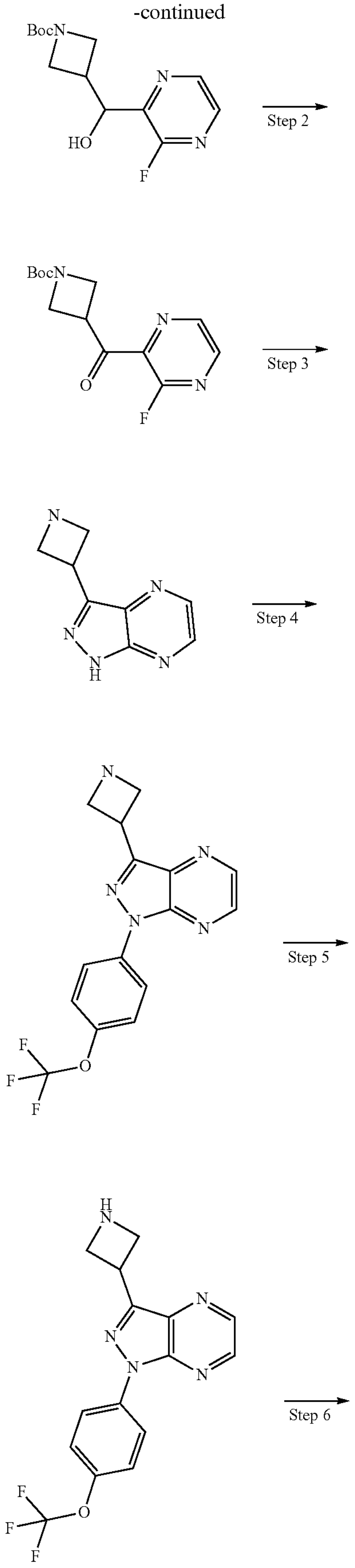

-continued

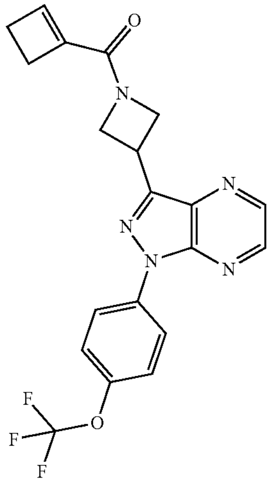 [SMILES: O=C(C1=CCC1)N1CC(c2nn(-c3ccc(OC(F)(F)F)cc3)c3nccnc23)C1]

Step 1: tert-butyl 3-((3-fluoropyrazin-2-yl)(hydroxy) methyl)azetidine-1-carboxylate

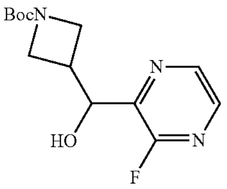 [SMILES: CC(C)(C)OC(=O)N1CC(C(O)c2nccnc2F)C1]

To a solution of 2-fluoropyrazine (3.1 mL, 40.78 mmol) in THF (200 mL) was added LDA (24.5 mL, 48.94 mmol, 2.0 mol/L in THF/hexane) dropwise at −78° C. under a $N_2$ atmosphere and after stirring for 30 minutes tert-butyl 3-formylazetidine-1-carboxylate (7.55 g, 40.78 mmol) in THF (40 mL) was added into it dropwise at −78° C. The reaction solution was stirred at −78° C. for 1 hour. The solution was quenched with saturated sat. aq. $NH_4Cl$ (100 mL), extracted with ethyl acetate (100 mL×2). The combined organic layer was dried over anhydrous $Na_2SO_4$, filtered and concentrated under in vacuo. The crude residue was purified by column chromatography on silica gel (0-30% ethyl acetate in petroleum ether) to afford the title compound (4.77 g, 41%) as a brown oil. LCMS (ESI): m/z 284.1 $(M+H)^+$.

Step 2: tert-butyl 3-(3-fluoropyrazine-2-carbonyl) azetidine-1-carboxylate

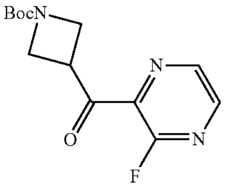 [SMILES: CC(C)(C)OC(=O)N1CC(C(=O)c2nccnc2F)C1]

To a solution of tert-butyl 3-((3-fluoropyrazin-2-yl)(hydroxy)methyl)azetidine-1-carboxylate (3.77 g, 13.31 mmol) in dichloromethane (100 mL) was added DMP (5.93 g, 13.97 mmol) at 0° C., the mixture was stirred at room temperature for 16 hours. The mixture was quenched with sat. aq. $Na_2S_2O_3$ solution (50 mL) and extracted with ethyl acetate (100 mL×2). The combined organic layer was dried with anhydrous $Na_2SO_4$, filtered and concentrated under in vacuo to afford the title compound (3.7 g, 99%) as a yellow solid. $^1H$ NMR (400 MHz, $CDCl_3$): δ 8.59-8.57 (m, 1H), 8.48-8.44 (m, 1H), 4.45-4.36 (m, 1H), 4.21 (d, J=7.6 Hz, 4H), 1.45 (s, 9H).

Step 3: tert-butyl 3-(1H-pyrazolo[3,4-b]pyrazin-3-yl)azetidine-1-carboxylate

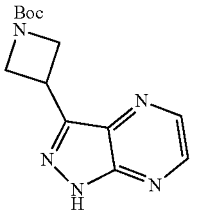 [SMILES: c1cnc2c(C3CNC3)n[nH]c2n1]

To a solution of tert-butyl 3-(3-fluoropyrazine-2-carbonyl)azetidine-1-carboxylate (3.7 g, 13.15 mmol) in THF (50 mL) was added 85% $N_2H_4 \cdot H_2O$ (3.9 mL, 65.97 mmol) at 0° C., the mixture was stirred at 50° C. for 2h. The reaction mixture was concentrated and the residue was purified by column chromatography on silica gel (0-50% ethyl acetate in petroleum ether) to afford the title compound (2.66 g, 74%) as a white solid. LCMS (ESI): m/z 220.1 $(M+1-56)^+$.

Step 4: tert-butyl 3-(1-(4-(trifluoromethoxy)phenyl)-1H-pyrazolo[3,4-b]pyrazin-3-yl)azetidine-1-carboxylate

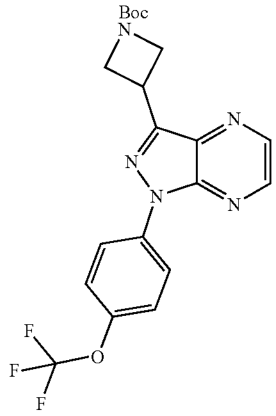 [SMILES: FC(F)(F)Oc1ccc(-n2nc(C3CNC3)c3nccnc32)cc1]

To a solution of tert-butyl 3-(1H-pyrazolo[3,4-b]pyrazin-3-yl)azetidine-1-carboxylate (2.66 g, 9.66 mmol), 4-(trifluoromethoxy)phenylboronicacid (3.98 g, 19.32 mmol) and $Cu(OAc)_2$ (3.50 g, 19.32 mmol) in acetonitrile (25 mL) under a $O_2$ atmosphere was added pyridine (1.2 mL, 14.49 mmol). The resulting mixture was stirred at room temperature for 16 hours under a $O_2$ atmosphere. The reaction mixture was diluted with water (50 mL) and extracted with ethyl acetate (50 mL×3). The combined organic layer were washed with brine (50 mL), dried over $Na_2SO_4$, filtered and concentrated in vacuo. The residue was purified by flash column chromatography on silica gel (0-25% ethyl acetate in petroleum ether) to afford the title compound (1.3 g, 31%) as a yellow solid. LCMS (ESI): m/z 380.0 $(M+H-56)^+$.

Step 5: 3-(azetidin-3-yl)-1-(4-(trifluoromethoxy)phenyl)-1H-pyrazolo[3,4-b]pyrazine

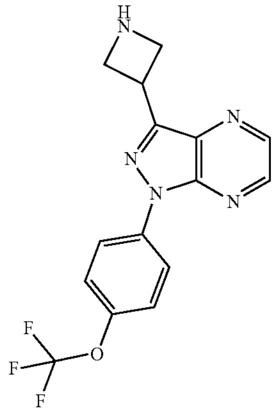 [SMILES: FC(F)(F)Oc1ccc(-n2nc(C3CNC3)c3nccnc32)cc1]

A solution of tert-butyl 3-(1-(4-(trifluoromethoxy)phenyl)-1H-pyrazolo[3,4-b]pyrazin-3-yl)azetidine-1-carboxylate (1.3 g, 2.99 mmol) in 5% TFA in HFIP (19.2 mL) was stirred at room temperature for 3 hours. The reaction mixture was quenched with sat. aq. $NaHCO_3$ solution (100 mL) and the aqueous phase was extracted with ethyl acetate (100 mL×2). The combined organic layer was washed with brine (50 mL), dried over $Na_2SO_4$ and concentrated in vacuo to afford the title compound (1.0 g, 99%) as a yellow solid. LCMS (ESI): m/z 336.1 $(M+1)^+$.

Step 6: cyclobut-1-en-1-yl(3-(1-(4-(trifluoromethoxy)phenyl)-1H-pyrazolo[3,4-b]pyrazin-3-yl)azetidin-1-yl)methanone

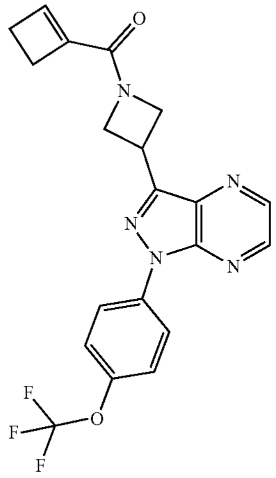 [SMILES: O=C(C1=CCC1)N1CC(c2nn(-c3ccc(OC(F)(F)F)cc3)c3nccnc23)C1]

A mixture of 3-(azetidin-3-yl)-1-(4-(trifluoromethoxy)phenyl)-1H-pyrazolo[3,4-b]pyrazine (150 mg, 0.45 mmol), ethyl 2-ethoxyquinoline-1 (2H)-carboxylate (166 mg, 0.67 mmol) and cyclobutene-1-carboxylic acid (66 mg, 0.67 mmol) in dichloromethane (2 mL)/methanol (0.4 mL) was stirred at room temperature for 2 hours. The reaction mixture was then concentrated. The residue was purified by flash chromatography on silica gel (0-3% methanol in dichloromethane) to afford the title compound (35 mg, 18%) as a yellow solid. $^1$H NMR (400 MHz, DMSO-$d_6$): 8.81-8.74 (m, 2H), 8.37 (d, J=8.8 Hz, 2H), 7.63 (d, J=8.8 Hz, 2H), 6.53 (s, 1H), 4.85-4.80 (m, 1H), 4.75-4.71 (m, 1H), 4.50-4.42 (m, 3H), 2.67-2.64 (m, 2H), 2.45-2.42 (m, 2H); LCMS (ESI): m/z 416.1 $(M+H)^+$.

Example 156 (Compound 164)

N-((4-(1-methyl-1H-pyrazol-4-yl)-1-(4-(trifluoromethoxy)phenyl)-1H-pyrazolo[3,4-b]pyridin-3-yl)methyl)acrylamide

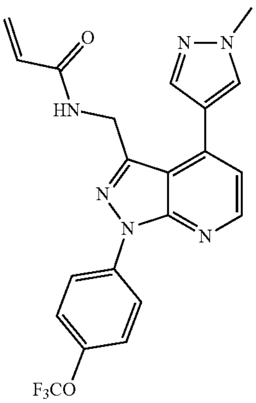 [SMILES: C=CC(=O)NCc1nn(-c2ccc(OC(F)(F)F)cc2)c2nccc(-c3cnn(C)c3)c12]

Step 1: tert-butyl ((4-((2-hydroxyethyl)(methyl)amino)-1-(4-(trifluoromethoxy)phenyl)-1H-pyrazolo[3,4-b]pyridin-3-yl)methyl)carbamate

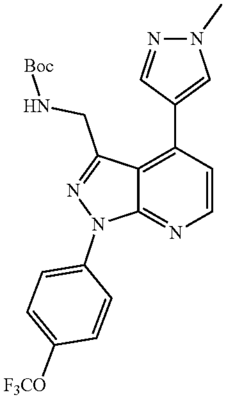 [SMILES: Cn1cc(-c2ccnc3c2c(CNC(=O)OC(C)(C)C)nn3-c2ccc(OC(F)(F)F)cc2)cn1]

To a 2 dram vial was added tert-butyl N-[[4-chloro-1-[4-(trifluoromethoxy)phenyl]pyrazolo[3,4-b]pyridin-3-yl]methyl]carbamate (50 mg, 0.1129 mmol, 1.0 equiv.), 1-methyl-4-(4,4,5,5-tetramethyl-1,3,2-dioxaborolan-2-yl)-1H-pyrazole (35 mg, 0.158 mmol, 1.4 equiv.), Pd(dppf)$Cl_2$·DCM (9 mg, 0.0113 mmol, 0.10 equiv.), and $K_3PO_4$ (62 mg, 0.282 mmol, 2.5 equiv.). 1,4-Dioxane (1.41 mL) and $H_2O$ (0.16 mL) were added, and then the reaction was sparged with $N_2$ for 10 minutes. The reaction was then stirred at 90° C. until no starting material remained as observed by LCMS. Reaction was then filtered through celite, concentrated, and purified on by column chromatography (silica, 0-60% iPrOAc/heptane). Gave tert-butyl N-[[4-(1-methylpyrazol-4-yl)-1-[4-(trifluoromethoxy)phenyl]pyrazolo[3,4-b]pyridin-3-yl]methyl]carbamate (46 mg, 83%) as a white solid. LCMS (ESI) $[M+H]^+$=489.000.

Step 2: N-((4-(1-methyl-1H-pyrazol-4-yl)-1-(4-(trifluoromethoxy)phenyl)-1H-pyrazolo[3,4-b]pyridin-3-yl)methyl)acrylamide

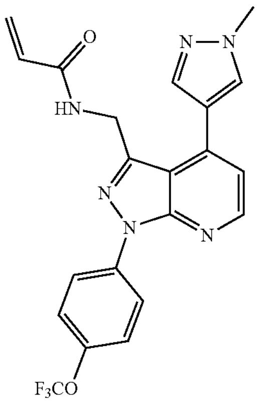 [SMILES: C=CC(=O)NCc1nn(-c2ccc(OC(F)(F)F)cc2)c2nccc(-c3cnn(C)c3)c12]

To a 2 dram vial containing tert-butyl N-[[4-(1-methylpyrazol-4-yl)-1-[4-(trifluoromethoxy)phenyl]pyrazolo[3,4-b]pyridin-3-yl]methyl]carbamate (46 mg, 0.094 mmol, 1.0 equiv.) was added DCM (0.31 mL) and Hydrochloric acid (4 M in 1,4-Dioxane, 0.24 mL, 0.94 mmol, 10.0 equiv.). The reaction was stirred at room temperature until no starting material remained as monitored by LCMS. Reaction concentrated under reduced pressure to give the crude amine [4-(1-methylpyrazol-4-yl)-1-[4-(trifluoromethoxy)phenyl]pyrazolo[3,4-b]pyridin-3-yl]methanamine, which was then dissolved in DCM (0.47 mL). DIPEA (0.33 mL, 1.88 mmol, 20.0 equiv.) was added, reaction was cooled to −40° C., and a solution of acrylic anhydride (0.012 mL, 0.104 mmol, 1.1 equiv.) in DCM (0.47 mL) was then added dropwise. Reaction was stirred at −40° C. until full conversion to the desired product was observed by LCMS. Saturated aqueous $NH_4Cl$ was added at −40° C. and mixture was allowed to warm to room temperature. Reaction transferred to a separatory funnel extracted with iPrOAc. Organic layer was washed with saturated aqueous $NaHCO_3$, then combined aqueous layers were back extracted (2× iPrOAc and 1×DCM). Organics were combined, dried with $MgSO_4$, filtered, and concentrated. The resulting residue was purified by preparative HPLC (Gemini-NX C18 column, 30-70% MeCN/water, 0.1% $NH_4OH$ modifier) to afford 34.7 mg of N-[[4-(1-methylpyrazol-4-yl)-1-[4-(trifluoromethoxy)phenyl]pyrazolo[3,4-b]pyridin-3-yl]methyl]prop-2-enamide as a white solid (83% yield over 2 steps). $^1$H NMR (400 MHz, DMSO) δ 8.62 (d, J=4.8 Hz, 1H), 8.52 (t, J=5.0 Hz, 1H), 8.45-8.37 (m, 2H), 8.20 (s, 1H), 7.88 (d, J=0.8 Hz, 1H), 7.65-7.56 (m, 2H), 7.30 (d, J=4.8 Hz, 1H), 6.22 (dd, J=17.1, 10.1 Hz, 1H), 6.07 (dd, J=17.1, 2.3 Hz, 1H), 5.58 (dd, J=10.0, 2.3 Hz, 1H), 4.69 (d, J=5.0 Hz, 2H), 3.91 (s, 3H). LCMS (ESI) $[M+H]^+$=443.100

Example 157 (Compound 165)

N-((4-(1-(2-amino-2-oxoethyl)-1H-pyrazol-4-yl)-1-(4-(trifluoromethoxy)phenyl)-1H-pyrazolo[3,4-b]pyridin-3-yl)methyl)acrylamide

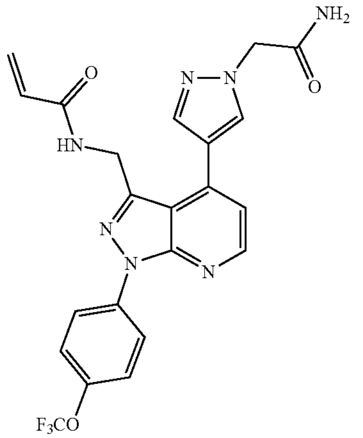 [SMILES: C=CC(=O)NCc1nn(-c2ccc(OC(F)(F)F)cc2)c2nccc(-c3cnn(CC(N)=O)c3)c12]

For this example, the same sequence of steps was followed as for example 21, except that 2-(4-(4,4,5,5-tetramethyl-1,3,2-dioxaborolan-2-yl)-1H-pyrazol-1-yl)acetamide was used in the first step instead of 1-methyl-4-(4,4,5,5-tetramethyl-1,3,2-dioxaborolan-2-yl)-1H-pyrazole and TFA was used in the second step instead of hydrochloric acid.

Step 1: tert-butyl ((4-(1-(2-amino-2-oxoethyl)-1H-pyrazol-4-yl)-1-(4-(trifluoromethoxy)phenyl)-1H-pyrazolo[3,4-b]pyridin-3-yl)methyl)carbamate

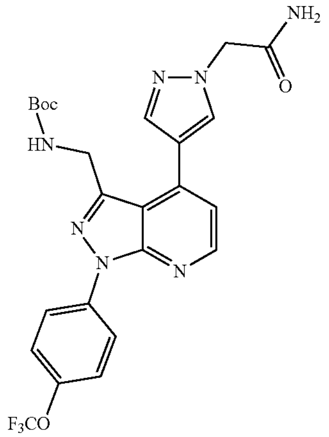 [SMILES: CC(C)(C)OC(=O)NCc1nn(-c2ccc(OC(F)(F)F)cc2)c2nccc(-c3cnn(CC(N)=O)c3)c12]

Reaction was run on a 0.113 mmol scale with tert-butyl N-[[4-chloro-1-[4-(trifluoromethoxy)phenyl]pyrazolo[3,4-b]pyridin-3-yl]methyl]carbamate. 40 mgs (67% yield) of tert-butyl N-[[4-[1-(2-amino-2-oxo-ethyl)pyrazol-4-yl]-1-[4-(trifluoromethoxy)phenyl]pyrazolo[3,4-b]pyridin-3-yl]methyl]carbamate as obtained as a beige solid. LCMS (ESI) $[M+H]^+$=532.000.

Step 2: N-((4-(1-(2-amino-2-oxoethyl)-1H-pyrazol-4-yl)-1-(4-(trifluoromethoxy)phenyl)-1H-pyrazolo[3,4-b]pyridin-3-yl)methyl)acrylamide

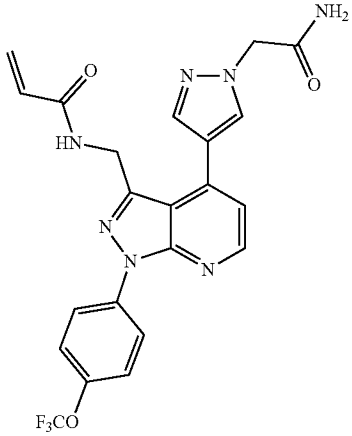 [SMILES: C=CC(=O)NCc1nn(-c2ccc(OC(F)(F)F)cc2)c2nccc(-c3cnn(CC(N)=O)c3)c12]

After deprotection and acylation, 18.1 mg of N-((4-(1-(2-amino-2-oxoethyl)-1H-pyrazol-4-yl)-1-(4-(trifluoromethoxy)phenyl)-1H-pyrazolo[3,4-b]pyridin-3-yl)methyl)acrylamide was obtained as a white solid (50% yield over 2 steps) following preparative HPLC (XSelect CSH Prep C18 column, 20-60% MeCN/water, 0.1% $NH_4OH$ modifier). $^1H$ NMR (400 MHz, DMSO) δ 8.63 (d, J=4.8 Hz, 1H), 8.41 (td, J=7.4, 3.6 Hz, 3H), 8.26 (s, 1H), 7.91 (s, 1H), 7.65 (s, 1H), 7.61 (d, J=8.4 Hz, 2H), 7.38 (s, 1H), 7.31 (d, J=4.8 Hz, 1H), 6.17 (dd, J=17.1, 10.1 Hz, 1H), 6.03 (dd, J=17.1, 2.3 Hz, 1H), 5.55 (dd, J=10.1, 2.3 Hz, 1H), 4.87 (s, 2H), 4.71 (d, J=5.3 Hz, 2H), 3.00 (s, 1H). LCMS (ESI) $[M+H]^+$=486.100.

Example 158 (Compound 166)

N-((4-(1-(2-(dimethylamino)-2-oxoethyl)-1H-pyrazol-4-yl)-1-(4-(trifluoromethoxy)phenyl)-1H-pyrazolo[3,4-b]pyridin-3-yl)methyl)acrylamide

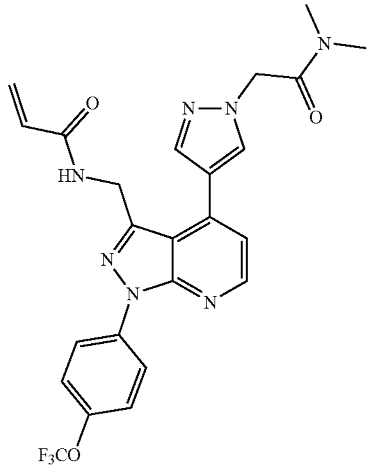 [SMILES: C=CC(=O)NCc1nn(-c2ccc(OC(F)(F)F)cc2)c2nccc(-c3cnn(CC(=O)N(C)C)c3)c12]

For this example, the same sequence of steps was followed as for example 21, except that N,N-dimethyl-2-[4-

(tetramethyl-1,3,2-dioxaborolan-2-yl)-1H-pyrazol-1-yl]acetamide was used in the first step instead of 1-methyl-4-(4,4,5,5-tetramethyl-1,3,2-dioxaborolan-2-yl)-1H-pyrazole and TFA was used in the second step instead of hydrochloric acid.

Step 1: tert-butyl 04-(1-(2-(dimethylamino)-2-oxoethyl)-1H-pyrazol-4-yl)-1-(4-(trifluoromethoxy)phenyl)-1H-pyrazolo[3,4-b]pyridin-3-yl)methyl)carbamate

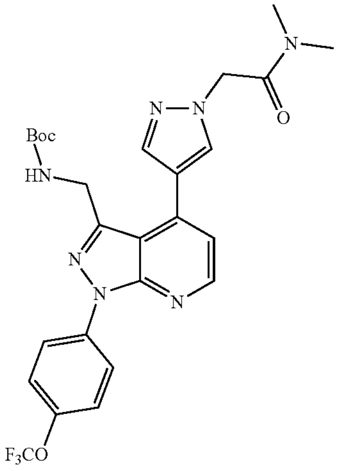 [SMILES: CN(C)C(=O)Cn1cc(-c2ccnc3c2c(CNC(=O)OC(C)(C)C)nn3-c2ccc(OC(F)(F)F)cc2)cn1]

Reaction was run on a 0.113 mmol scale with tert-butyl N-[[4-chloro-1-[4-(trifluoromethoxy)phenyl]pyrazolo[3,4-b]pyridin-3-yl]methyl]carbamate. 64 mgs (99% yield) of tert-butyl N-[[4-[1-[2-(di methyl amino)-2-oxo-ethyl]pyrazol-4-yl]-1-[4-(trifluoromethoxy)phenyl]pyrazolo[3,4-b]pyridin-3-yl]methyl]carbamate was obtained as an off-white solid. LCMS (ESI) $[M+H]^+=560.100$.

Step 2: N-((4-(1-(2-(dimethylamino)-2-oxoethyl)-1H-pyrazol-4-yl)-1-(4-(trifluoromethoxy)phenyl)-1H-pyrazolo[3,4-b]pyridin-3-yl)methyl)acrylamide

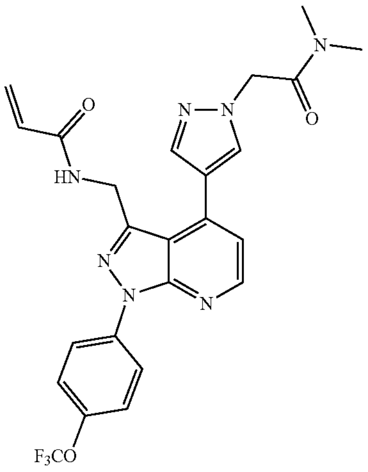 [SMILES: C=CC(=O)NCc1nn(-c2ccc(OC(F)(F)F)cc2)c2nccc(-c3cnn(CC(=O)N(C)C)c3)c12]

After deprotection and acylation, 38.23 mg of N-((4-(1-(2-(dimethylamino)-2-oxoethyl)-1H-pyrazol-4-yl)-1-(4-(trifluoromethoxy)phenyl)-1H-pyrazolo[3,4-b]pyridin-3-yl)methyl)acrylamide was obtained as an off-white solid (65% yield over 2 steps) following preparative HPLC (XSelect CSH Prep C18 column, 30-70% MeCN/water, 0.1% $NH_4OH$ modifier). $^1H$ NMR (400 MHz, DMSO) δ 8.63 (d, J=4.8 Hz, 1H), 8.46-8.35 (m, 3H), 8.22 (s, 1H), 7.90 (d, J=0.7 Hz, 1H), 7.65-7.56 (m, 2H), 7.31 (d, J=4.8 Hz, 1H), 6.19 (dd, J=17.1, 10.1 Hz, 1H), 6.03 (dd, J=17.1, 2.2 Hz, 1H), 5.56 (dd, J=10.2, 2.2 Hz, 1H), 5.24 (s, 2H), 4.69 (d, J=5.4 Hz, 2H), 3.08 (s, 3H), 2.89 (s, 3H). LCMS (ESI) $[M+H]^+=514.200$.

Example 159 (Compound 167)

N-[[4-[1-(2-methoxyethyl)pyrazol-4-yl]-1-[4-(trifluoromethoxy)phenyl]pyrazolo[3,4-b]pyridin-3-yl]methyl]prop-2-enamide

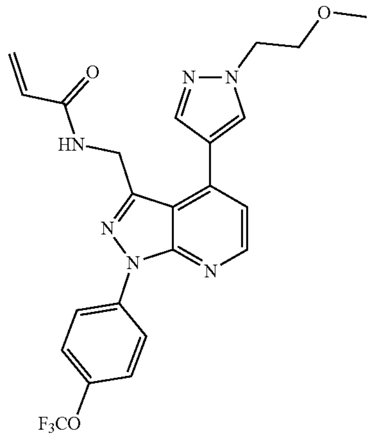 [SMILES: C=CC(=O)NCc1nn(-c2ccc(OC(F)(F)F)cc2)c2nccc(-c3cnn(CCOC)c3)c12]

For this example, the same sequence of steps was followed as for example 21, except that 1-(2-methoxyethyl)-4-(4,4,5,5-tetramethyl-1,3,2-dioxaborolan-2-yl)-1H-pyrazole was used in the first step instead of 1-methyl-4-(4,4,5,5-tetramethyl-1,3,2-dioxaborolan-2-yl)-1H-pyrazole.

Step 1: tert-butyl N-[[4-[1-(2-methoxyethyl)pyrazol-4-yl]-1-[4-(trifluoromethoxy)phenyl]pyrazolo[3,4-b]pyridin-3-yl]methyl]carbamate

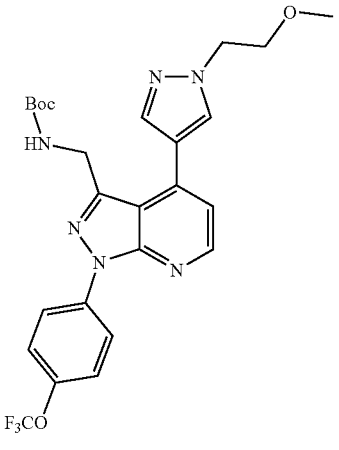 [SMILES: COCCn1cc(-c2ccnc3c2c(CNC(=O)OC(C)(C)C)nn3-c2ccc(OC(F)(F)F)cc2)cn1]

Reaction was run on a 0.113 mmol scale with tert-butyl N-[[4-chloro-1-[4-(trifluoromethoxy)phenyl]pyrazolo[3,4-b]pyridin-3-yl]methyl]carbamate. 53 mgs (88% yield) of ter t-butyl N-[[4-[1-(2-methoxyethyppyrazol-4-yl]-1-[4-(trifluoromethoxy)phenyl]pyrazolo[3,4-b]pyridin-3-yl]methyl] carbamate as obtained as a white solid. LCMS (ESI) $[M+H]^+$=533.050.

Step 2: N-[[4-[1-(2-methoxyethyl)pyrazol-4-yl]-1-[4-(trifluoromethoxy)phenyl]pyrazolo[3,4-b]pyridin-3-yl]methyl]prop-2-enamide

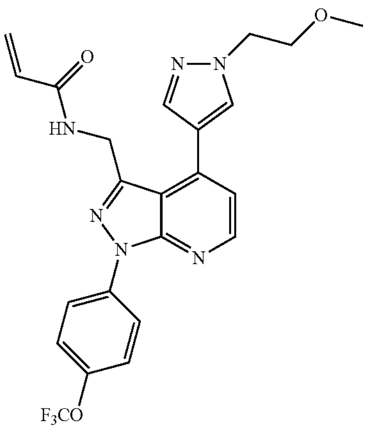 [SMILES: C=CC(=O)NCc1nn(-c2ccc(OC(F)(F)F)cc2)c2nccc(-c3cnn(CCOC)c3)c12]

After deprotection and acylation, 35.56 mg of N-[[4-[1-(2-methoxyethyl)pyrazol-4-yl]-1-[4-(trifluoromethoxy)phenyl]pyrazolo[3,4-b]pyridin-3-yl]methyl]prop-2-enamide was obtained as a white solid (76% yield over 2 steps) following preparative HPLC (Gemini-NX C18 column, 30-70% MeCN/water, 0.1% $NH_4OH$ modifier). $^1H$ NMR (400 MHz, DMSO) δ 8.63 (d, J=4.8 Hz, 1H), 8.53 (t, J=5.1 Hz, 1H), 8.45-8.37 (m, 2H), 8.26 (d, J=0.8 Hz, 1H), 7.92 (d, J=0.8 Hz, 1H), 7.65-7.56 (m, 2H), 7.32 (d, J=4.8 Hz, 1H), 6.24 (dd, J=17.1, 10.1 Hz, 1H), 6.08 (dd, J=17.1, 2.3 Hz, 1H), 5.59 (dd, J=10.1, 2.3 Hz, 1H), 4.69 (d, J=5.1 Hz, 2H), 4.34 (t, J=5.3 Hz, 2H), 3.75 (t, J=5.3 Hz, 2H), 3.25 (s, 3H). LCMS (ESI) $[M+H]^+$=487.100.

Example 160 (Compound 168)

N-((4-(1-(2-(methylsulfonyl)ethyl)-1H-pyrazol-4-yl)-1-(4-(trifluoromethoxy)phenyl)-1H-pyrazolo[3,4-b]pyridin-3-yl)methyl)acrylamide

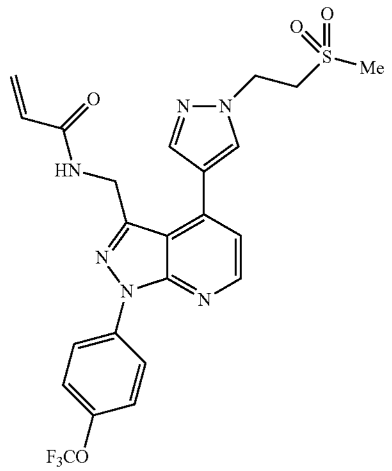 [SMILES: C=CC(=O)NCc1nn(-c2ccc(OC(F)(F)F)cc2)c2nccc(-c3cnn(CCS(C)(=O)=O)c3)c12]

For this example, the same sequence of steps was followed as for example 21, except that 1-(2-methanesulfonylethyl)-4-(tetramethyl-1,3,2-dioxaborolan-2-yl)-1h-pyrazole was used in the first step instead of 1-methyl-4-(4,4,5,5-tetramethyl-1,3,2-dioxaborolan-2-yl)-1H-pyrazole and TFA was used in the second step instead of hydrochloric acid.

Step 1: tert-butyl ((4-(1-(2-(methylsulfonyl)ethyl)-1H-pyrazol-4-yl)-1-(4-(trifluoromethoxy)phenyl)-1H-pyrazolo[3,4-b]pyridin-3-yl)methyl)carbamate

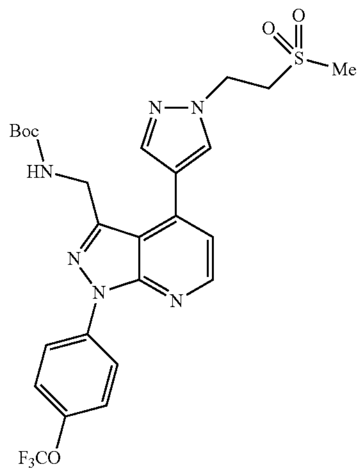 [SMILES: CC(C)(C)OC(=O)NCc1nn(-c2ccc(OC(F)(F)F)cc2)c2nccc(-c3cnn(CCS(C)(=O)=O)c3)c12]

Reaction was run on a 0.113 mmol scale with tert-butyl N-[[4-chloro-1-[4-(trifluoromethoxy)phenyl]pyrazolo[3,4-b]pyridin-3-yl]methyl]carbamate. 57 mgs (87% yield) of tert-butyl ((4-(1-(2-(methylsulfonyl)ethyl)-1H-pyrazol-4-yl)-1-(4-(trifluoromethoxy)phenyl)-1H-pyrazolo[3,4-b]pyridin-3-yl)methyl)carbamate as obtained as a yellow semi-solid. LCMS (ESI) $[M+H]^+$=581.050.

Step 2: N-((4-(1-(2-(methylsulfonyl)ethyl)-1H-pyrazol-4-yl)-1-(4-(trifluoromethoxy)phenyl)-1H-pyrazolo[3,4-b]pyridin-3-yl)methyl)acrylamide

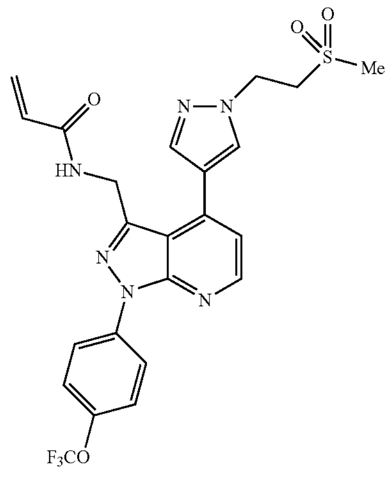 [SMILES: C=CC(=O)NCc1nn(-c2ccc(OC(F)(F)F)cc2)c2nccc(-c3cnn(CCS(C)(=O)=O)c3)c12]

After deprotection and acylation, 23.51 mg of N-((4-(1-(2-(methylsulfonyl)ethyl)-1H-pyrazol-4-yl)-1-(4-(trifluoromethoxy)phenyl)-1H-pyrazolo[3,4-b]pyridin-3-yl)methypacrylamide was obtained as a white solid (46% yield over 2 steps) following preparative HPLC (Triart C18 column, 30-70% MeCN/water, 0.1% $NH_4OH$ modifier). $^1H$ NMR (400 MHz, DMSO) δ 8.64 (d, J=4.8 Hz, 1H), 8.50 (t, J=5.0 Hz, 1H), 8.45-8.37 (m, 2H), 8.35 (s, 1H), 7.97 (s, 1H), 7.61 (d, J=8.7 Hz, 2H), 7.31 (d, J=4.8 Hz, 1H), 6.20 (dd, J=17.1, 10.0 Hz, 1H), 6.07 (dd, J=17.1, 2.3 Hz, 1H), 5.58 (dd, J=10.1, 2.3 Hz, 1H), 4.70 (d, J=5.0 Hz, 2H), 4.63 (t, J=7.0 Hz, 2H), 3.79 (t, J=7.0 Hz, 2H), 2.98 (s, 3H). LCMS (ESI) $[M+H]^+$=535.100.

Example 161 (Compound 169)

N-[[4-[1-(difluoromethyl)pyrazol-4-yl]-1-[4-(trifluoromethoxy)phenyl]pyrazolo[3,4-b]pyridin-3-yl]methyl]prop-2-enamide

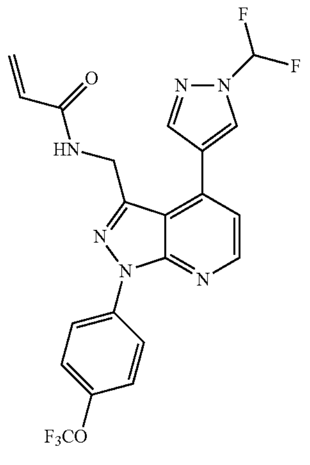 [SMILES: C=CC(=O)NCc1nn(-c2ccc(OC(F)(F)F)cc2)c2nccc(-c3cnn(C(F)F)c3)c12]

For this example, the same sequence of steps was followed as for example 21, except that 1-(difluoromethyl)-4-(4,4,5,5-tetramethyl-1,3,2-dioxaborolan-2-yl)-1H-pyrazole was used in the first step instead of 1-methyl-4-(4,4,5,5-tetramethyl-1,3,2-dioxaborolan-2-yl)-1H-pyrazole.

Step 1: tert-butyl N-[[4-[1-(difluoromethyl)pyrazol-4-yl]-1-[4-(trifluoromethoxy)phenyl]pyrazolo[3,4-b]pyridin-3-yl]methyl]carbamate

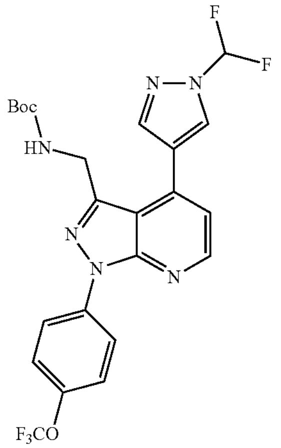 [SMILES: CC(C)(C)OC(=O)NCc1nn(-c2ccc(OC(F)(F)F)cc2)c2nccc(-c3cnn(C(F)F)c3)c12]

Reaction was run on a 0.113 mmol scale with tert-butyl N-[[4-chloro-1-[4-(trifluoromethoxy)phenyl]pyrazolo[3,4-b]pyridin-3-yl]methyl]carbamate. 50 mgs (84% yield) of tert-butyl N-[[4-[1-(difluoromethyl)pyrazol-4-yl]-1-[4-(trifluoromethoxy)phenyl]pyrazolo[3,4-b]pyridin-3-yl]methyl]carbamate as obtained as a white solid. LCMS (ESI) $[M+H]^+$=525.000.

Step 2: N-[[4-[1-(difluoromethyl)pyrazol-4-yl]-1-[4-(trifluoromethoxy)phenyl]pyrazolo[3,4-b]pyridin-3-yl]methyl]prop-2-enamide

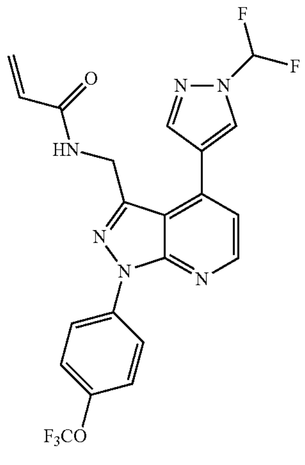 [SMILES: C=CC(=O)NCc1nn(-c2ccc(OC(F)(F)F)cc2)c2nccc(-c3cnn(C(F)F)c3)c12]

After deprotection and acylation, 36.12 mg of N-[[4-[1-(difluoromethyl)pyrazol-4-yl]-1-[4-(trifluoromethoxy)phenyl]pyrazolo[3,4-b]pyridin-3-yl]methyl]prop-2-enamide was obtained as a white solid (79% yield over 2 steps) following preparative HPLC (Gemini-NX C18 column, 30-70% MeCN/water, 0.1% $NH_4OH$ modifier). $^1H$ NMR (400 MHz, DMSO) δ 8.78 (d, J=0.7 Hz, 1H), 8.70 (d, J=4.7 Hz, 1H), 8.52 (t, J=5.1 Hz, 1H), 8.45-8.36 (m, 2H), 8.25 (d, J=0.7 Hz, 1H), 8.09-7.71 (m, 1H), 7.66-7.57 (m, 2H), 7.40 (d, J=4.8 Hz, 1H), 6.21 (dd, J=17.1, 10.1 Hz, 1H), 6.06 (dd, J=17.1, 2.3 Hz, 1H), 5.57 (dd, J=10.1, 2.3 Hz, 1H), 4.64 (d, J=5.1 Hz, 2H). LCMS (ESI) $[M+H]^+$=479.100.

Example 162 (Compound 170)

N-[[4-(1-isopropylpyrazol-4-yl)-1-[4-(trifluoromethoxy)phenyl]pyrazolo[3,4-b]pyridin-3-yl]methyl]prop-2-enamide

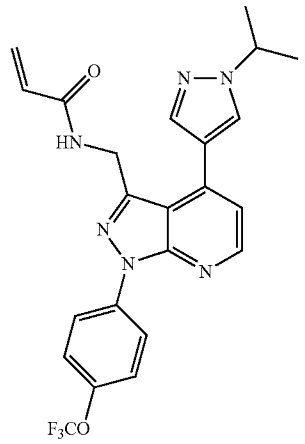 [SMILES: C=CC(=O)NCc1nn(-c2ccc(OC(F)(F)F)cc2)c2nccc(-c3cnn(C(C)C)c3)c12]

For this example, the same sequence of steps was followed as for example 21, except that 1-isopropyl-4-(4,4,5,5-tetramethyl-1,3,2-dioxaborolan-2-yl)-1H-pyrazole was used in the first step instead of 1-methyl-4-(4,4,5,5-tetramethyl-1,3,2-dioxaborolan-2-yl)-1H-pyrazole.

Step 1: tert-butyl N-[[4-(1-isopropylpyrazol-4-yl)-1-[4-(trifluoromethoxy)phenyl]pyrazolo[3,4-b]pyridin-3-yl]methyl]carbamate

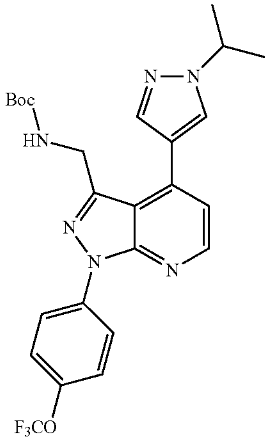 [SMILES: CC(C)n1cc(-c2ccnc3c2c(CNC(=O)OC(C)(C)C)nn3-c2ccc(OC(F)(F)F)cc2)cn1]

Reaction was run on a 0.113 mmol scale with tert-butyl N-[[4-chloro-1-[4-(trifluoromethoxy)phenyl]pyrazolo[3,4-b]pyridin-3-yl]methyl]carbamate. 55 mgs (94% yield) of tert-butyl N-[[4-(1-isopropylpyrazol-4-yl)-1-[4-(trifluoromethoxy)phenyl]pyrazolo[3,4-b]pyridin-3-yl]methyl]carbamate as obtained as a white solid. LCMS (ESI) $[M+H]^+$=517.000.

Step 2: N-[[4-(1-isopropylpyrazol-4-yl)-1-[4-(trifluoromethoxy)phenyl]pyrazolo[3,4-b]pyridin-3-yl]methyl]prop-2-enamide

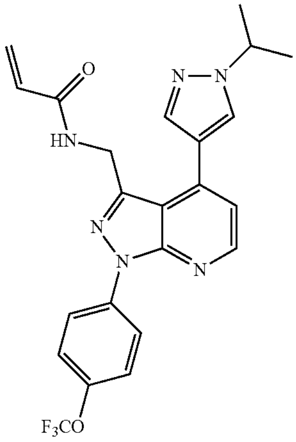 [SMILES: C=CC(=O)NCc1nn(-c2ccc(OC(F)(F)F)cc2)c2nccc(-c3cnn(C(C)C)c3)c12]

After deprotection and acylation, 37.82 mg of N-[[4-(1-isopropylpyrazol-4-yl)-1-[4-(trifluoromethoxy)phenyl]pyrazolo[3,4-b]pyridin-3-yl]methyl]prop-2-enamide was obtained as a white solid (76% yield over 2 steps) following preparative HPLC (Gemini-NX C18 column, 30-70% MeCN/water, 0.1% $NH_4OH$ modifier). $^1H$ NMR (400 MHz, DMSO) δ 8.62 (d, J=4.8 Hz, 1H), 8.52 (t, J=4.9 Hz, 1H), 8.47-8.38 (m, 2H), 8.31 (s, 1H), 7.90 (d, J=0.8 Hz, 1H), 7.65-7.57 (m, 2H), 7.33 (d, J=4.8 Hz, 1H), 6.24 (dd, J=17.1, 10.1 Hz, 1H), 6.07 (dd, J=17.1, 2.3 Hz, 1H), 5.58 (dd, J=10.1, 2.3 Hz, 1H), 4.68 (d, J=4.9 Hz, 2H), 4.56 (hept, J=6.6 Hz, 1H), 1.48 (d, J=6.6 Hz, 6H). LCMS (ESI) $[M+H]^+$=471.100.

Example 163 (Compound 171)

N-[[4-[1-(oxetan-3-yl)pyrazol-4-yl]-1-[4-(trifluoromethoxy)phenyl]pyrazolo[3,4-b]pyridin-3-yl]methyl]prop-2-enamide

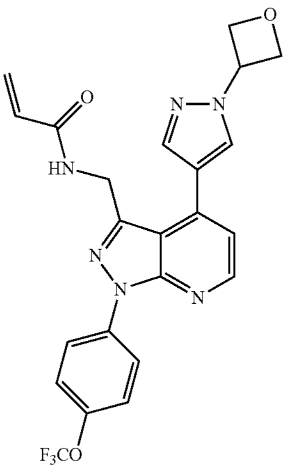 [SMILES: C=CC(=O)NCc1nn(-c2ccc(OC(F)(F)F)cc2)c2nccc(-c3cnn(C4COC4)c3)c12]

For this example, the same sequence of steps was followed as for example 21, except that 1-(oxetan-3-yl)-4-(4,4,5,5-tetramethyl-1,3,2-dioxaborolan-2-yl)-1H-pyrazole was used in the first step instead of 1-methyl-4-(4,4,5,5-tetramethyl-1,3,2-dioxaborolan-2-yl)-1H-pyrazole and TFA was used in the second step instead of hydrochloric acid.

Step 1: tert-butyl N-[[4-(1-isopropylpyrazol-4-yl)-1-[4-(trifluoromethoxy)phenyl]pyrazolo[3,4-b]pyridin-3-yl]methyl]carbamate

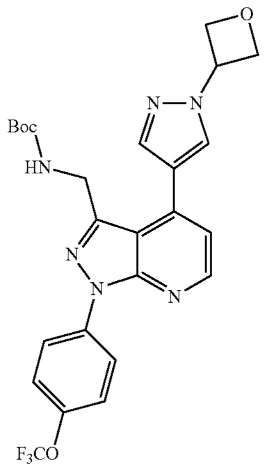 [SMILES: CC(C)(C)OC(=O)NCc1nn(-c2ccc(OC(F)(F)F)cc2)c2nccc(-c3cnn(C4COC4)c3)c12]

Reaction was run on a 0.113 mmol scale with tert-butyl N-[[4-chloro-1-[4-(trifluoromethoxy)phenyl]pyrazolo[3,4-b]pyridin-3-yl]methyl]carbamate. 61 mgs (100% yield) of tert-butyl N-[[4-(1-isopropylpyrazol-4-yl)-1-[4-(trifluoromethoxy)phenyl]pyrazolo[3,4-b]pyridin-3-yl]methyl]carbamate as obtained as a clear semi-solid. LCMS (ESI) $[M+H]^+$=531.100.

Step 2: N-[[4-[1-(oxetan-3-yl)pyrazol-4-yl]-1-[4-(trifluoromethoxy)phenyl]pyrazolo[3,4-b]pyridin-3-yl]methyl]prop-2-enamide

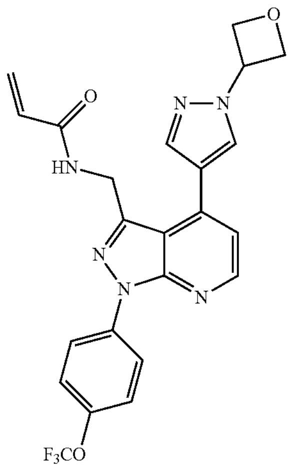 [SMILES: C=CC(=O)NCc1nn(-c2ccc(OC(F)(F)F)cc2)c2nccc(-c3cnn(C4COC4)c3)c12]

After deprotection and acylation, 15.63 mg of N-[[4-[1-(oxetan-3-yl)pyrazol-4-yl]-1-[4-(trifluoromethoxy)phenyl]pyrazolo[3,4-b]pyridin-3-yl]methyl]prop-2-enamide was obtained as a white solid (31% yield over 2 steps) following first preparative HPLC (Gemini-NX C18 column, 30-70% MeCN/neat water) then achiral SFC (Torus Diol column, 10-50% MeOH/Carbon Dioxide). $^1$H NMR (400 MHz, DMSO) δ 8.65 (d, J=4.8 Hz, 1H), 8.47-8.37 (m, 4H), 8.02 (s, 1H), 7.65-7.57 (m, 2H), 7.33 (d, J=4.8 Hz, 1H), 6.14 (dd, J=17.1, 10.0 Hz, 1H), 6.02 (dd, J=17.1, 2.4 Hz, 1H), 5.68-5.51 (m, 2H), 4.96 (d, J=7.0 Hz, 4H), 4.69 (d, J=4.9 Hz, 2H). LCMS (ESI) $[M+H]^+$=485.100.

Example 164 (Compound 172)

N-[[4-[1-[2-(dimethylamino)ethyl]pyrazol-4-yl]-1-[4-(trifluoromethoxy)phenyl]pyrazolo[3,4-b]pyridin-3-yl]methyl]prop-2-enamide

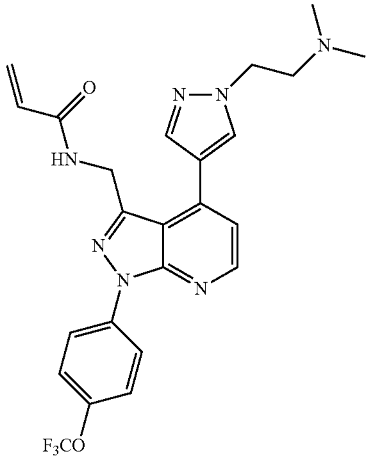 [SMILES: C=CC(=O)NCc1nn(-c2ccc(OC(F)(F)F)cc2)c2nccc(-c3cnn(CCN(C)C)c3)c12]

For this example, the same sequence of steps was followed as for example 21, except that N,N-dimethyl-2-(4-(4,4,5,5-tetramethyl-1,3,2-dioxaborolan-2-yl)-1H-pyrazol-1-yl)ethanamine was used in the first step instead of 1-methyl-4-(4,4,5,5-tetramethyl-1,3,2-dioxaborolan-2-yl)-1H-pyrazole and TFA was used in the second step instead of hydrochloric acid.

Step 1: tert-butyl N-[[4-[1-[2-(dimethylamino)ethyl]pyrazol-4-yl]-1-[4-(trifluoromethoxy)phenyl]pyrazolo[3,4-b]pyridin-3-yl]methyl]carbamate

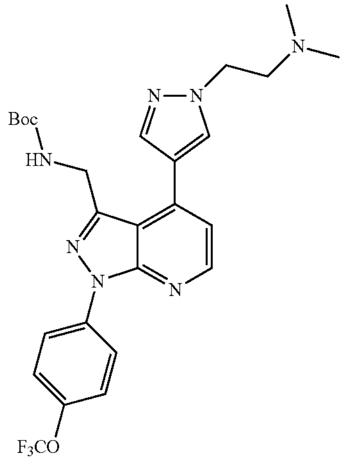 [SMILES: CN(C)CCn1cc(-c2ccnc3c2c(CNC(=O)OC(C)(C)C)nn3-c2ccc(OC(F)(F)F)cc2)cn1]

Reaction was run on a 0.113 mmol scale with tert-butyl N-[[4-chloro-1-[4-(trifluoromethoxy)phenyl]pyrazolo[3,4-b]pyridin-3-yl]methyl]carbamate. 48 mgs (78% yield) of tert-butyl N-[[4-[1-[2-(dimethylamino)ethyl]pyrazol-4-yl]-1-[4-(trifluoromethoxy)phenyl]pyrazolo[3,4-b]pyridin-3-yl]methyl]carbamate was obtained as a brown oil. LCMS (ESI) $[M+H]^+$=546.100.

Step 2: N-[[4-[1-[2-(dimethylamino)ethyl]pyrazol-4-yl]-1-[4-(trifluoromethoxy)phenyl]pyrazolo[3,4-b]pyridin-3-yl]methyl]prop-2-enamide

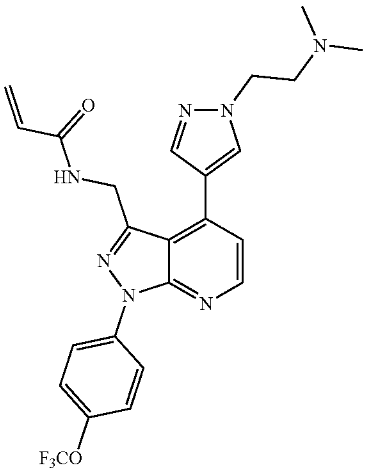 [SMILES: C=CC(=O)NCc1nn(-c2ccc(OC(F)(F)F)cc2)c2nccc(-c3cnn(CCN(C)C)c3)c12]

After deprotection and acylation, 32.17 mg of N-[[4-[1-[2-(dimethylamino)ethyl]pyrazol-4-yl]-1-[4-(trifluoromethoxy)phenyl]pyrazolo[3,4-b]pyridin-3-yl]methyl]prop-2-enamide was obtained as an brown solid (64% yield over 2 steps) following preparative HPLC (XSelect CSH Prep C18 column, 30-70% MeCN/water, 0.1% $NH_4OH$ modifier). $^1$H NMR (400 MHz, DMSO) δ 8.62 (d, J=4.8 Hz, 1H), 8.49 (t, J=5.1 Hz, 1H), 8.45-8.38 (m, 2H), 8.29 (s, 1H), 7.89 (s, 1H), 7.60 (d, J=8.6 Hz, 2H), 7.31 (d, J=4.8 Hz, 1H), 6.22 (dd, J=17.1, 10.1 Hz, 1H), 6.07 (dd, J=17.2, 2.3 Hz, 1H), 5.58 (dd, J=10.0, 2.3 Hz, 1H), 4.70 (d, J=5.1 Hz, 2H), 4.27 (t, J=6.4 Hz, 2H), 2.70 (t, J=6.4 Hz, 2H), 2.19 (s, 6H). LCMS (ESI) $[M+H]^+$=500.200.

Example 165 (Compound 173)

N-((4-(1-cyclopropyl-1H-pyrazol-4-yl)-1-(4-(trifluoromethoxy)phenyl)-1H-pyrazolo[3,4-b]pyridin-3-yl)methyl)acrylamide

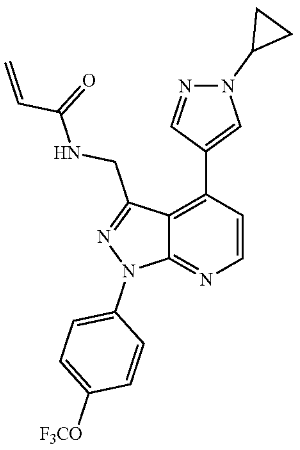 [SMILES: C=CC(=O)NCc1nn(-c2ccc(OC(F)(F)F)cc2)c2nccc(-c3cnn(C4CC4)c3)c12]

For this example, the same sequence of steps was followed as for example 21, except that 1-cyclopropyl-4-(4,4,5,5-tetramethyl-1,3,2-dioxaborolan-2-yl)-1h-pyrazole was used in the first step instead of 1-methyl-4-(4,4,5,5-tetramethyl-1,3,2-dioxaborolan-2-yl)-1H-pyrazole.

Step 1: tert-butyl 04-(1-cyclopropyl-1H-pyrazol-4-yl)-1-(4-(trifluoromethoxy)phenyl)-1H-pyrazolo[3,4-b]pyridin-3-yl)methyl)carbamate

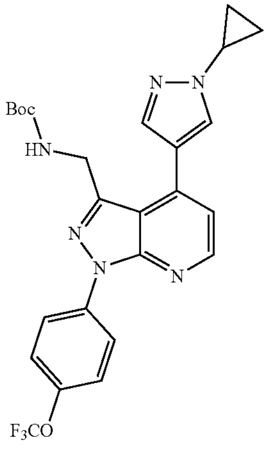 [SMILES: CC(C)(C)OC(=O)NCc1nn(-c2ccc(OC(F)(F)F)cc2)c2nccc(-c3cnn(C4CC4)c3)c12]

Reaction was run on a 0.113 mmol scale with tert-butyl N-[[4-chloro-1-[4-(trifluoromethoxy)phenyl]pyrazolo[3,4-b]pyridin-3-yl]methyl]carbamate. 60 mgs (100% yield) of ter t-butyl ((4-(1-cyclopropyl-1H-pyrazol-4-yl)-1-(4-(trifluoromethoxy)phenyl)-1H-pyrazolo[3,4-b]pyridin-3-yl)methyl)carbamate as obtained as a yellow solid. LCMS (ESI) $[M+H]^+$=515.000.

Step 2: N-((4-(1-cyclopropyl-1H-pyrazol-4-yl)-1-(4-(trifluoromethoxy)phenyl)-1H-pyrazolo[3,4-b]pyridin-3-yl)methyl)acrylamide

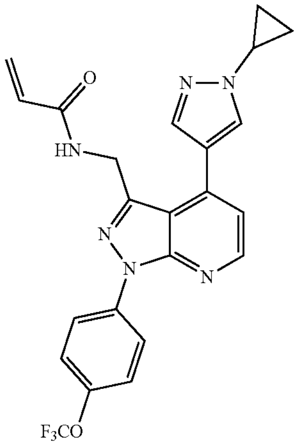 [SMILES: C=CC(=O)NCc1nn(-c2ccc(OC(F)(F)F)cc2)c2nccc(-c3cnn(C4CC4)c3)c12]

After deprotection and acylation, 25.63 mg of N-((4-(1-cyclopropyl-1H-pyrazol-4-yl)-1-(4-(trifluoromethoxy)phenyl)-1H-pyrazolo[3,4-b]pyridin-3-yl)methyl)acrylamide was obtained as a white solid (47% yield over 2 steps) following preparative HPLC (Gemini-NX C18 column, 30-70% MeCN/water, 0.1% $NH_4OH$ modifier). $^1H$ NMR (400 MHz, DMSO) δ 8.62 (d, J=4.8 Hz, 1H), 8.50 (t, J=4.9 Hz, 1H), 8.46-8.37 (m, 2H), 8.31 (d, J=0.8 Hz, 1H), 7.87 (d, J=0.8 Hz, 1H), 7.65-7.56 (m, 2H), 7.31 (d, J=4.8 Hz, 1H), 6.22 (dd, J=17.1, 10.1 Hz, 1H), 6.07 (dd, J=17.1, 2.3 Hz, 1H), 5.58 (dd, J=10.0, 2.4 Hz, 1H), 4.67 (d, J=4.9 Hz, 2H), 3.79 (tt, J=7.4, 3.8 Hz, 1H), 1.18-1.05 (m, 2H), 1.09-0.94 (m, 2H). LCMS (ESI) $[M+H]^+$=469.100.

Example 166 (Compound 174)

1-(3-(4-(1-(difluoromethyl)-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one

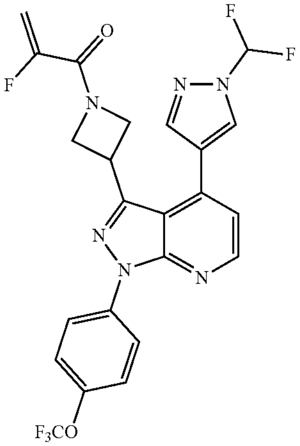 [SMILES: C=C(F)C(=O)N1CC(c2nn(-c3ccc(OC(F)(F)F)cc3)c3nccc(-c4cnn(C(F)F)c4)c23)C1]

Step 1: tert-butyl 3-(4-(1-(difluoromethyl)-1H-pyrazol-4-yl)-1-(4-(trifluoromethoxy)phenyl)-1H-pyrazolo[3,4-b]pyridin-3-yl)azetidine-1-carboxylate

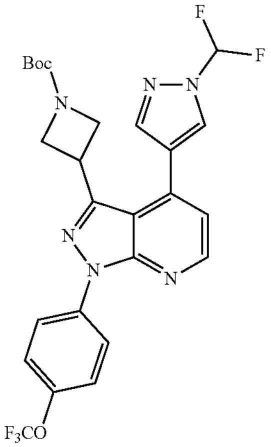 [SMILES: CC(C)(C)OC(=O)N1CC(c2nn(-c3ccc(OC(F)(F)F)cc3)c3nccc(-c4cnn(C(F)F)c4)c23)C1]

To a 2 dram vial was added tert-butyl 3-[4-iodo-1-[4-(trifluoromethoxy)phenyl]pyrazolo[3,4-b]pyridin-3-yl]azetidine-1-carboxylate (50 mg, 0.09 mmol, 1.0 equiv.), 1-(difluoromethyl)-4-(4,4,5,5-tetramethyl-1,3,2-dioxaborolan-2-yl)-1h-pyrazole (32 mg, 0.125 mmol, 1.4 equiv.), Pd(dppf)$Cl_2$·DCM (7 mg, 0.009 mmol, 0.10 equiv.), and $K_3PO_4$ (49 mg, 0.223 mmol, 2.5 equiv.). 1,4-Dioxane (1.12 mL) and water (0.12 ml) were added and then the reaction was sparged with $N_2$ for 10 minutes. The reaction was then stirred at 90° C. until no starting material remained as observed by LCMS. Reaction was then filtered through celite, concentrated, and purified on by column chromatography (silica, 0-40% iPrOAc/heptane). Gave tert-butyl 3-(4-(1-(difluoromethyl)-1H-pyrazol-4-yl)-1-(4-(trifluoromethoxy)phenyl)-1H-pyrazolo[3,4-b]pyridin-3-yl)azetidine-1-carboxylate (50 mgs, 100%) as obtained as an off-white solid. LCMS (ESI) $[M-tBu+MeCN+H]^+$=536.000.

Step 2: 1-(3-(4-(1-(difluoromethyl)-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one

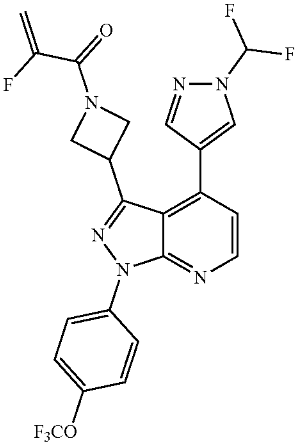 [SMILES: C=C(F)C(=O)N1CC(c2nn(-c3ccc(OC(F)(F)F)cc3)c3nccc(-c4cnn(C(F)F)c4)c23)C1]

To a 2 dram vial containing tert-butyl 3-[4-[1-(difluoromethyl)pyrazol-4-yl]-1-[4-(trifluoromethoxy)phenyl]pyrazolo[3,4-b]pyridin-3-yl]azetidine-1-carboxylate (50 mg, 0.09 mmol, 1.0 equiv.) was added DCM (0.23 mL) followed by trifluoroacetic acid (0.07 ml, 10.0 equiv.). The reaction was stirred at room temperature until no starting material remained as monitored by LCMS. Reaction concentrated under reduced pressure to give the crude amine 3-(azetidin-3-yl)-4-[1-(difluoromethyl)pyrazol-4-yl]-1-[4-(trifluoromethoxy)phenyl]pyrazolo[3,4-b]pyridine, which was then used directly without further purification. To the vial containing the crude amine was added 2-fluoroprop-2-enoic acid (12 mg, 0.14 mmol, 1.5 equiv.) and DCM (1.1 mL). Reaction was cooled to 0° C. and then N-ethoxycarbonyl-2-ethoxy-1,2-dihydroquinoline (35 mg, 1.5 equiv., 0.14, 1.5 equiv.) was added. The reaction was then gradually allowed to warm to room temperature and monitored by LCMS until full consumption of the starting material was observed. The reaction was quenched by the addition of saturated aqueous $NH_4Cl$ and extracted with iPrOAc (3×) and DCM (1×). Organics were combined, dried with $MgSO_4$, filtered, and concentrated. 31.93 mg of 1-(3-(4-(1-(difluoromethyl)-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one was obtained as a white solid (67% yield over 2 steps) following preparative HPLC (Gemini-NX C18 column, 30-70% MeCN/water, 0.1% $NH_4OH$ modifier). $^1H$ NMR (400 MHz, DMSO) δ 8.77-8.68 (m, 2H), 8.50-8.42 (m, 2H), 8.23 (s, 1H), 8.18-7.78 (m, 1H), 7.61 (d, J=8.8 Hz, 2H), 7.37 (d, J=4.8 Hz, 1H), 5.53-5.33 (m, 1H), 5.27 (dd, J=16.6, 3.6 Hz, 1H), 4.62 (q, J=5.4 Hz, 1H), 4.47-4.28 (m, 2H), 4.15 (dd, J=10.2, 5.8 Hz, 1H), 4.00 (t, J=9.5 Hz, 1H). LCMS (ESI) $[M+H]^+$=523.100.

Example 167 (Compound 175)

2-fluoro-1-(3-(4-(1-(oxetan-3-yl)-1H-pyrazol-4-yl)-1-(4-(trifluoromethoxy)phenyl)-1H-pyrazolo[3,4-b]pyridin-3-yl)azetidin-1-yl)prop-2-en-1-one

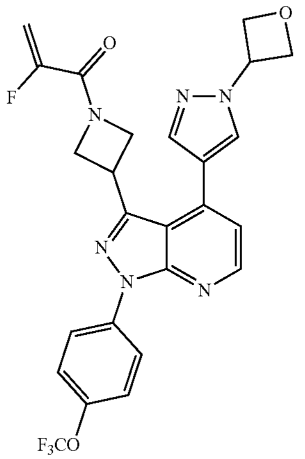 [SMILES: C=C(F)C(=O)N1CC(c2nn(-c3ccc(OC(F)(F)F)cc3)c3nccc(-c4cnn(C5COC5)c4)c23)C1]

For this example, the same sequence of steps was followed as for example 31, except that 1-(oxetan-3-yl)-4-(4,4,5,5-tetramethyl-1,3,2-dioxaborolan-2-yl)-1h-pyrazole was used in the first step instead of 1-(difluoromethyl)-4-(4,4,5,5-tetramethyl-1,3,2-dioxaborolan-2-yl)-1h-pyrazole.

Step 1: tert-butyl 3-(4-(1-(oxetan-3-yl)-1H-pyrazol-4-yl)-1-(4-(trifluoromethoxy)phenyl)-1H-pyrazolo[3,4-b]pyridin-3-yl)azetidine-1-carboxylate

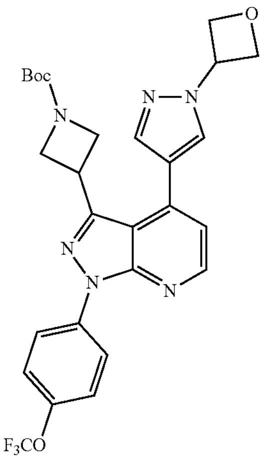 [SMILES: CC(C)(C)OC(=O)N1CC(c2nn(-c3ccc(OC(F)(F)F)cc3)c3nccc(-c4cnn(C5COC5)c4)c23)C1]

Reaction was run on a 0.09 mmol scale with tert-butyl 3-[4-iodo-1-[4-(trifluoromethoxy)phenyl]pyrazolo[3,4-b]pyridin-3-yl]azetidine-1-carboxylate. 54 mgs (100% yield) of tert-butyl 3-(4-(1-(oxetan-3-yl)-1H-pyrazol-4-yl)-1-(4-(trifluoromethoxy)phenyl)-1H-pyrazolo[3,4-b]pyridin-3-yl)azetidine-1-carboxylate as obtained as a brown solid. LCMS (ESI) $[M+H]^+$=557.100.

Step 2: 2-fluoro-1-(3-(4-(1-(oxetan-3-yl)-1H-pyrazol-4-yl)-1-(4-(trifluoromethoxy)phenyl)-1H-pyrazolo[3,4-b]pyridin-3-yl)azetidin-1-yl)prop-2-en-1-one

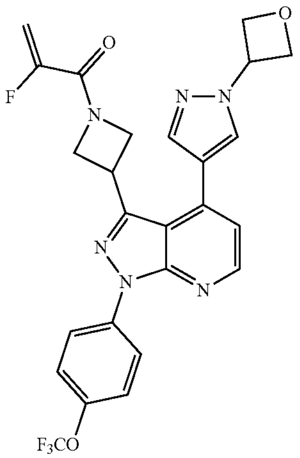 [SMILES: C=C(F)C(=O)N1CC(c2nn(-c3ccc(OC(F)(F)F)cc3)c3nccc(-c4cnn(C5COC5)c4)c23)C1]

After deprotection and acylation, 26.17 mg of 2-fluoro-1-(3-(4-(1-(oxetan-3-yl)-1H-pyrazol-4-yl)-1-(4-(trifluoromethoxy)phenyl)-1H-pyrazolo[3,4-b]pyridin-3-yl)azetidin-1-yl)prop-2-en-1-one was obtained as a white solid (51% yield over 2 steps) following preparative HPLC (Triart C18 column, 30-70% MeCN/water). $^1H$ NMR (400 MHz, DMSO) δ 8.65 (d, J=4.8 Hz, 1H), 8.50-8.42 (m, 2H), 8.37 (s, 1H), 8.02 (s, 1H), 7.64-7.57 (m, 2H), 7.30 (d, J=4.8 Hz, 1H), 5.79-5.68 (m, 1H), 5.55-5.33 (m, 1H), 5.26 (dd, J=16.7, 3.5 Hz, 1H), 5.00 (p, J=6.7 Hz, 4H), 4.62-4.55 (m, 1H), 4.49-4.35 (m, 2H), 4.15 (dd, J=10.0, 4.8 Hz, 1H), 4.04 (t, J=9.0 Hz, 1H). LCMS (ESI) $[M+H]^+$=529.100.

Example 168 (Compound 176)

2-fluoro-1-(3-(4-(1-(2-methoxyethyl)-1H-pyrazol-4-yl)-1-(4-(trifluoromethoxy)phenyl)-1H-pyrazolo[3,4-b]pyridin-3-yl)azetidin-1-yl)prop-2-en-1-one

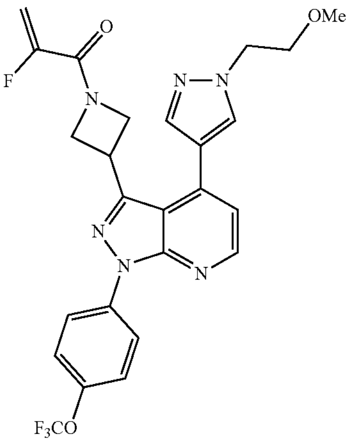 [SMILES: C=C(F)C(=O)N1CC(c2nn(-c3ccc(OC(F)(F)F)cc3)c3nccc(-c4cnn(CCOC)c4)c23)C1]

For this example, the same sequence of steps was followed as for example 31, except that 1-(2-methoxyethyl)-4-(4,4,5,5-tetramethyl-1,3,2-dioxaborolan-2-yl)-1h-pyrazole was used in the first step instead of 1-(difluoromethyl)-4-(4,4,5,5-tetramethyl-1,3,2-dioxaborolan-2-yl)-1h-pyrazole.

Step 1: tert-butyl 3-(4-(1-(2-methoxyethyl)-1H-pyrazol-4-yl)-1-(4-(trifluoromethoxy)phenyl)-1H-pyrazolo[3,4-b]pyridin-3-yl)azetidine-1-carboxylate

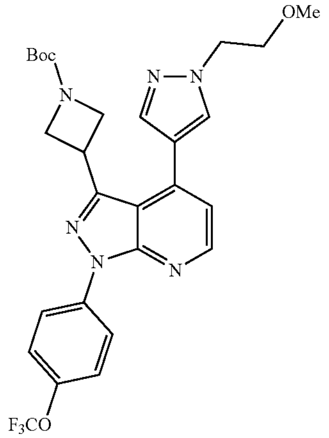 [SMILES: COCCn1cc(-c2ccnc3c2c(C2CN(C(=O)OC(C)(C)C)C2)nn3-c2ccc(OC(F)(F)F)cc2)cn1]

Reaction was run on a 0.09 mmol scale with tert-butyl 3-[4-iodo-1-[4-(trifluoromethoxy)phenyl]pyrazolo[3,4-b]pyridin-3-yl]azetidine-1-carboxylate. 50 mgs (100% yield) of ter t-butyl 3-(4-(1-(2-methoxy ethyl)-1H-pyrazol-4-yl)-1-(4-(trifluoromethoxy)phenyl)-1H-pyrazolo[3,4-b]pyridin-3-yl)azetidine-1-carboxylate as obtained as a brown oil. LCMS (ESI) $[M+H]^+$=559.100.

Step 2: 2-fluoro-1-(3-(4-(1-(2-methoxyethyl)-1H-pyrazol-4-yl)-1-(4-(trifluoromethoxy)phenyl)-1H-pyrazolo[3,4-b]pyridin-3-yl)azetidin-1-yl)prop-2-en-1-one

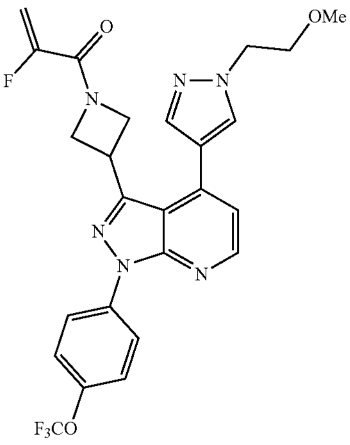 [SMILES: C=C(F)C(=O)N1CC(c2nn(-c3ccc(OC(F)(F)F)cc3)c3nccc(-c4cnn(CCOC)c4)c23)C1]

After deprotection and acylation, 29.69 mg of 2-fluoro-1-(3-(4-(1-(2-methoxyethyl)-1H-pyrazol-4-yl)-1-(4-(trifluoromethoxy)phenyl)-1H-pyrazolo[3,4-b]pyridin-3-yl)azetidin-1-yl)prop-2-en-1-one was obtained as a white semi-solid (63% yield over 2 steps) following preparative HPLC (Triart C18 column, 40-80% MeCN/water). $^1$H NMR (400 MHz, DMSO) δ 8.64 (d, J=4.8 Hz, 1H), 8.51-8.42 (m, 2H), 8.21 (s, 1H), 7.87 (d, J=0.7 Hz, 1H), 7.64-7.57 (m, 2H), 7.28 (d, J=4.8 Hz, 1H), 5.55-5.33 (m, 1H), 5.26 (dd, J=16.7, 3.5 Hz, 1H), 4.57 (s, 1H), 4.43 (dt, J=10.2, 4.4 Hz, 4H), 4.14 (dd, J=10.2, 4.8 Hz, 1H), 4.07 (t, J=9.0 Hz, 1H), 3.78 (t, J=5.1 Hz, 2H), 3.29 (s, 3H). LCMS (ESI) $[M+H]^+$=531.100.

Example 169 (Compound 177)

1-(3-(4-(1-cyclopropyl-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one

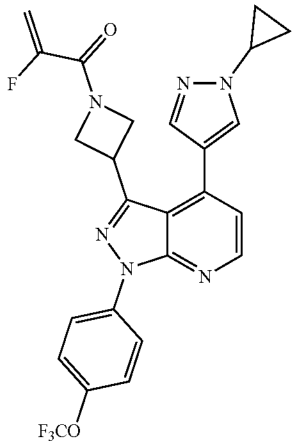 [SMILES: C=C(F)C(=O)N1CC(c2nn(-c3ccc(OC(F)(F)F)cc3)c3nccc(-c4cnn(C5CC5)c4)c23)C1]

For this example, the same sequence of steps was followed as for example 31, except that 1-cyclopropyl-4-(4,4,5,5-tetramethyl-1,3,2-dioxaborolan-2-yl)-1h-pyrazole was used in the first step instead of 1-(difluoromethyl)-4-(4,4,5,5-tetramethyl-1,3,2-dioxaborolan-2-yl)-1h-pyrazole.

Step 1: tert-butyl 3-(4-(1-cyclopropyl-1H-pyrazol-4-yl)-1-(4-(trifluoromethoxy)phenyl)-1H-pyrazolo[3,4-b]pyridin-3-yl)azetidine-1-carboxylate

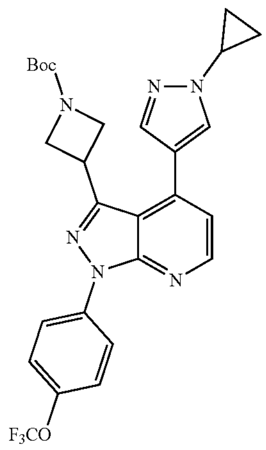 [SMILES: CC(C)(C)OC(=O)N1CC(c2nn(-c3ccc(OC(F)(F)F)cc3)c3nccc(-c4cnn(C5CC5)c4)c23)C1]

Reaction was run on a 0.09 mmol scale with tert-butyl 3-[4-iodo-1-[4-(trifluoromethoxy)phenyl]pyrazolo[3,4-b]pyridin-3-yl]azetidine-1-carboxylate. 47 mgs (97% yield) of tert-butyl 3-(4-(1-cyclopropyl-1H-pyrazol-4-yl)-1-(4-(trifluoromethoxy)phenyl)-1H-pyrazolo[3,4-b]pyridin-3-yl)azetidine-1-carboxylate as obtained as an off-white solid. LCMS (ESI) $[M+H]^+$=541.000.

Step 2: 1-(3-(4-(1-cyclopropyl-1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one

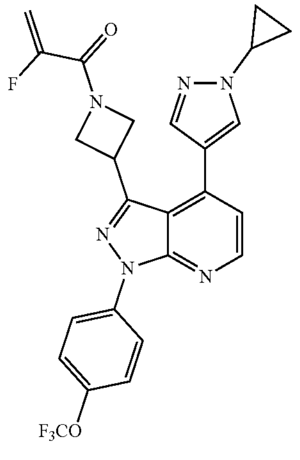 [SMILES: C=C(F)C(=O)N1CC(c2nn(-c3ccc(OC(F)(F)F)cc3)c3nccc(-c4cnn(C5CC5)c4)c23)C1]

After deprotection and acylation, 13.99 mg of 2-fluoro-1-(3-(4-(1-(2-methoxyethyl)-1H-pyrazol-4-yl)-1-(4-(trifluoromethoxy)phenyl)-1H-pyrazolo[3,4-b]pyridin-3-yl)azetidin-1-yl)prop-2-en-1-one was obtained as a white solid (31% yield over 2 steps) following preparative HPLC (Triart C18 column, 40-80% MeCN/water). $^1$H NMR (400 MHz, DMSO) δ 8.63 (d, J=4.8 Hz, 1H), 8.50-8.42 (m, 2H), 8.29 (s, 1H), 7.84 (d, J=0.9 Hz, 1H), 7.64-7.56 (m, 2H), 7.27 (d, J=4.8 Hz, 1H), 5.54-5.34 (m, 1H), 5.27 (dd, J=16.7, 3.5 Hz, 1H), 4.62-4.53 (m, 1H), 4.48-4.34 (m, 2H), 4.13 (dd, J=10.1, 4.8 Hz, 1H), 4.01 (t, J=9.0 Hz, 1H), 3.91 (tt, J=7.4, 3.8 Hz, 1H), 1.20-1.01 (m, 4H). LCMS (ESI) $[M+H]^+$=513.100.

Example 170 (Compound 178)

2-fluoro-1-(3-(4-(1-isopropyl-1H-pyrazol-4-yl)-1-(4-(trifluoromethoxy)phenyl)-1H-pyrazolo[3,4-b]pyridin-3-yl)azetidin-1-yl)prop-2-en-1-one

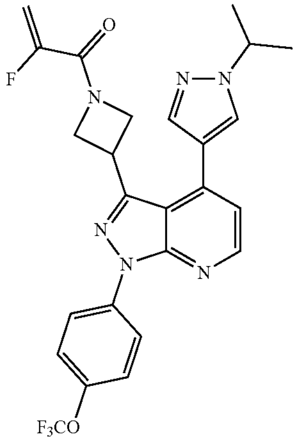 [SMILES: C=C(F)C(=O)N1CC(c2nn(-c3ccc(OC(F)(F)F)cc3)c3nccc(-c4cnn(C(C)C)c4)c23)C1]

For this example, the same sequence of steps was followed as for example 31, except that 1-isopropyl-4-(4,4,5,5-tetramethyl-1,3,2-dioxaborolan-2-yl)-1h-pyrazole was used in the first step instead of 1-(difluoromethyl)-4-(4,4,5,5-tetramethyl-1,3,2-dioxaborolan-2-yl)-1h-pyrazole.

Step 1: tert-butyl 3-(4-(1-isopropyl-1H-pyrazol-4-yl)-1-(4-(trifluoromethoxy)phenyl)-1H-pyrazolo[3,4-b]pyridin-3-yl)azetidine-1-carboxylate

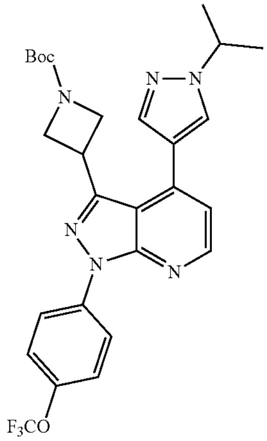 [SMILES: CC(C)n1cc(-c2ccnc3c2c(C2CN(C(=O)OC(C)(C)C)C2)nn3-c2ccc(OC(F)(F)F)cc2)cn1]

Reaction was run on a 0.09 mmol scale with tert-butyl 3-[4-iodo-1-[4-(trifluoromethoxy)phenyl]pyrazolo[3,4-b]pyridin-3-yl]azetidine-1-carboxylate. 52 mgs (100% yield)

of tert-butyl 3-(4-(1-isopropyl-1H-pyrazol-4-yl)-1-(4-(trifluoromethoxy)phenyl)-1H-pyrazolo[3,4-b]pyridin-3-yl)azetidine-1-carboxylate as obtained as a yellow solid. LCMS (ESI) $[M+H]^+$=543.150.

Step 2: 2-fluoro-1-(3-(4-(1-isopropyl-1H-pyrazol-4-yl)-1-(4-(trifluoromethoxy)phenyl)-1H-pyrazolo[3,4-b]pyridin-3-yl)azetidin-1-yl)prop-2-en-1-one

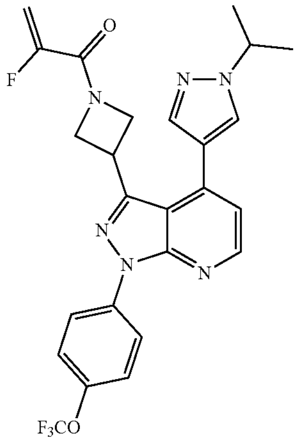 [SMILES: C=C(F)C(=O)N1CC(c2nn(-c3ccc(OC(F)(F)F)cc3)c3nccc(-c4cnn(C(C)C)c4)c23)C1]

After deprotection and acylation, 36.87 mg of 2-fluoro-1-(3-(4-(1-isopropyl-1H-pyrazol-4-yl)-1-(4-(trifluoromethoxy)phenyl)-1H-pyrazolo[3,4-b]pyridin-3-yl)azetidin-1-yl)prop-2-en-1-one was obtained as a white solid (75% yield over 2 steps) following preparative HPLC (Triart C18 column, 40-80% MeCN/water). $^1H$ NMR (400 MHz, DMSO) δ 8.63 (d, J=4.8 Hz, 1H), 8.51-8.42 (m, 2H), 8.26 (d, J=0.8 Hz, 1H), 7.86 (d, J=0.8 Hz, 1H), 7.64-7.56 (m, 2H), 7.28 (d, J=4.8 Hz, 1H), 5.52-5.32 (m, 1H), 5.25 (dd, J=16.7, 3.5 Hz, 1H), 4.66 (hept, J=6.6 Hz, 1H), 4.58-4.51 (m, 1H), 4.50-4.33 (m, 2H), 4.15 (dd, J=10.2, 5.4 Hz, 1H), 4.02 (t, J=9.2 Hz, 1H), 1.52 (d, J=6.6 Hz, 6H). LCMS (ESI) $[M+H]^+$=515.200.

Example 171 (Compound 179)

2-fluoro-1-(3-(4-(1-(2-(methylsulfonyl)ethyl)-1H-pyrazol-4-yl)-1-(4-(trifluoromethoxy)phenyl)-1H-pyrazolo[3,4-b]pyridin-3-yl)azetidin-1-yl)prop-2-en-1-one

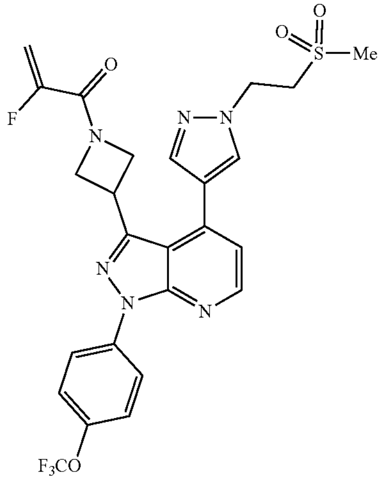 [SMILES: C=C(F)C(=O)N1CC(c2nn(-c3ccc(OC(F)(F)F)cc3)c3nccc(-c4cnn(CCS(C)(=O)=O)c4)c23)C1]

For this example, the same sequence of steps was followed as for example 31, except that 1-(2-methanesulfonylethyl)-4-(tetramethyl-1,3,2-dioxaborolan-2-yl)-1h-pyrazole was used in the first step instead of 1-(difluoromethyl)-4-(4,4,5,5-tetramethyl-1,3,2-dioxaborolan-2-yl)-1h-pyrazole.

Step 1: tert-butyl 3-(4-(1-(2-(methylsulfonyl)ethyl)-1H-pyrazol-4-yl)-1-(4-(trifluoromethoxy)phenyl)-1H-pyrazolo[3,4-b]pyridin-3-yl)azetidine-1-carboxylate

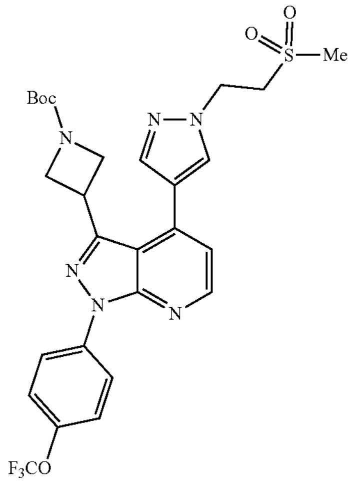 [SMILES: CC(C)(C)OC(=O)N1CC(c2nn(-c3ccc(OC(F)(F)F)cc3)c3nccc(-c4cnn(CCS(C)(=O)=O)c4)c23)C1]

Reaction was run on a 0.11 mmol scale with tert-butyl 3-[4-iodo-1-[4-(trifluoromethoxy)phenyl]pyrazolo[3,4-b]pyridin-3-yl]azetidine-1-carboxylate. 70 mgs (100% yield) of tert-butyl 3-(4-(1-(2-(methylsulfonyl)ethyl)-1H-pyrazol-4-yl)-1-(4-(trifluoromethoxy)phenyl)-1H-pyrazolo[3,4-b]

pyridin-3-yl)azetidine-1-carboxylate as obtained as a brown semi-solid. LCMS (ESI) $[M+H]^+$=607.050.

Step 2: 2-fluoro-1-(3-(4-(1-(2-(methylsulfonyl)ethyl)-1H-pyrazol-4-yl)-1-(4-(trifluoromethoxy)phenyl)-1H-pyrazolo[3,4-b]pyridin-3-yl)azetidin-1-yl)prop-2-en-1-one

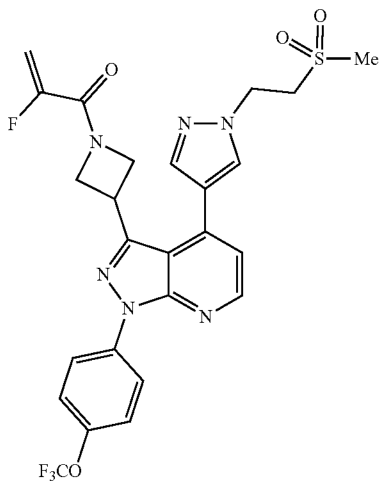 [SMILES: C=C(F)C(=O)N1CC(c2nn(-c3ccc(OC(F)(F)F)cc3)c3nccc(-c4cnn(CCS(C)(=O)=O)c4)c23)C1]

After deprotection and acylation, 48.43 mg of 2-fluoro-1-(3-(4-(1-(2-(methylsulfonyl)ethyl)-1H-pyrazol-4-yl)-1-(4-(trifluoromethoxy)phenyl)-1H-pyrazolo[3,4-b]pyridin-3-yl)azetidin-1-yl)prop-2-en-1-one was obtained as a white solid (76% yield over 2 steps) following preparative HPLC (Triart C18 column, 30-70% MeCN/water). $^1H$ NMR (400 MHz, DMSO) δ 8.65 (d, J=4.8 Hz, 1H), 8.50-8.42 (m, 2H), 8.30 (s, 1H), 7.94 (s, 1H), 7.64-7.57 (m, 2H), 7.27 (d, J=4.8 Hz, 1H), 5.54-5.35 (m, 1H), 5.27 (dd, J=16.6, 3.6 Hz, 1H), 4.72 (t, J=6.9 Hz, 2H), 4.61-4.47 (m, 2H), 4.41 (tt, J=8.7, 5.9 Hz, 1H), 4.18 (dd, J=10.2, 5.8 Hz, 1H), 4.12 (t, J=9.4 Hz, 1H), 3.82 (t, J=6.8 Hz, 2H), 3.01 (s, 3H). LCMS (ESI) $[M+H]^+$=579.100.

Example 172 (Compound 180)

2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)-N,N-dimethylacetamide

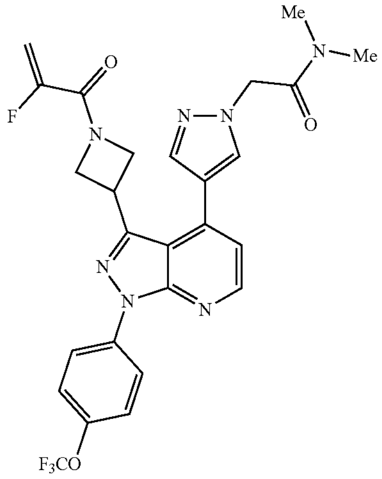 [SMILES: C=C(F)C(=O)N1CC(c2nn(-c3ccc(OC(F)(F)F)cc3)c3nccc(-c4cnn(CC(=O)N(C)C)c4)c23)C1]

For this example, the same sequence of steps was followed as for example 31, except that N,N-dimethyl-2-[4-(tetramethyl-1,3,2-dioxaborolan-2-yl)-1h-pyrazol-1-yl]acetamide was used in the first step instead of 1-(difluoromethyl)-4-(4,4,5,5-tetramethyl-1,3,2-dioxaborolan-2-yl)-1h-pyrazole.

Step 1: tert-butyl 3-(4-(1-(2-(dimethylamino)-2-oxoethyl)-1H-pyrazol-4-yl)-1-(4-(trifluoromethoxy)phenyl)-1H-pyrazolo[3,4-b]pyridin-3-yl)azetidine-1-carboxylate

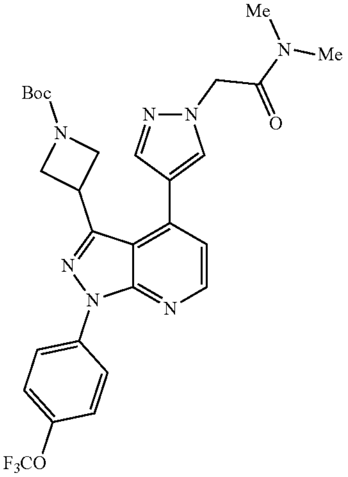 [SMILES: CN(C)C(=O)Cn1cc(-c2ccnc3c2c(C2CN(C(=O)OC(C)(C)C)C2)nn3-c2ccc(OC(F)(F)F)cc2)cn1]

Reaction was run on a 0.11 mmol scale with tert-butyl 3-[4-iodo-1-[4-(trifluoromethoxy)phenyl]pyrazolo[3,4-b]pyridin-3-yl]azetidine-1-carboxylate. 76 mgs (120% yield) of tert-butyl 3-(4-(1-(2-(dimethylamino)-2-oxoethyl)-1H-pyrazol-4-yl)-1-(4-(trifluoromethoxy)phenyl)-1H-pyrazolo

[3,4-b]pyridin-3-yl)azetidine-1-carboxylate as obtained as an brown semi-solid. LCMS (ESI) $[M+H]^+$=586.050.

Step 2: 2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)-N,N-dimethylacetamide

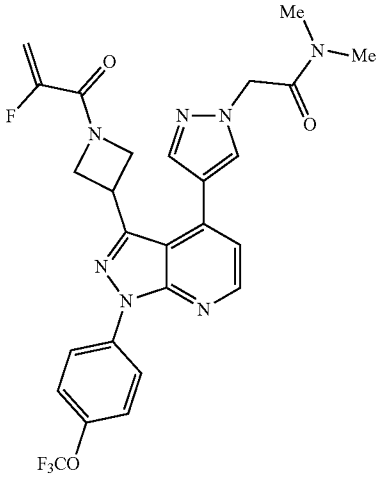 [SMILES: C=C(F)C(=O)N1CC(c2nn(-c3ccc(OC(F)(F)F)cc3)c3nccc(-c4cnn(CC(=O)N(C)C)c4)c23)C1]

After deprotection and acylation, 40.52 mg of 2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)-N,N-dimethylacetamide was obtained as a white solid (68% yield over 2 steps) following preparative HPLC (Triart C18 column, 30-70% MeCN/water). $^1$H NMR (400 MHz, DMSO) δ 8.64 (d, J=4.8 Hz, 1H), 8.51-8.43 (m, 2H), 8.14 (s, 1H), 7.86 (d, J=0.8 Hz, 1H), 7.64-7.57 (m, 2H), 7.29 (d, J=4.8 Hz, 1H), 5.54-5.34 (m, 1H), 5.31-5.21 (m, 3H), 4.57 (dq, J=16.3, 4.6 Hz, 2H), 4.43 (ddd, J=14.7, 8.5, 6.1 Hz, 1H), 4.25-4.13 (m, 2H), 3.09 (s, 3H), 2.89 (s, 3H). LCMS (ESI) $[M+H]^+$=558.100.

Example 173 (Compound 181)

2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)acetamide

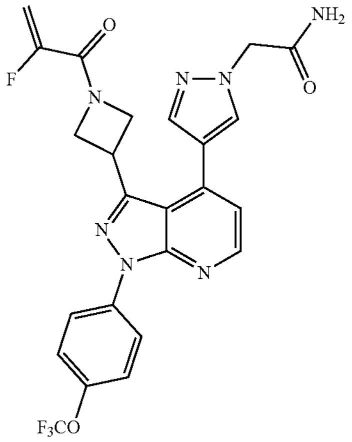 [SMILES: C=C(F)C(=O)N1CC(c2nn(-c3ccc(OC(F)(F)F)cc3)c3nccc(-c4cnn(CC(N)=O)c4)c23)C1]

For this example, the same sequence of steps was followed as for example 31, except that 2-(4-(4,4,5,5-tetramethyl-1,3,2-dioxaborolan-2-yl)-1h-pyrazol-1-yl)acetamide was used in the first step instead of 1-(difluoromethyl)-4-(4,4,5,5-tetramethyl-1,3,2-dioxaborolan-2-yl)-1h-pyrazole.

Step 1: tert-butyl 3-(4-(1-(2-amino-2-oxoethyl)-1H-pyrazol-4-yl)-1-(4-(trifluoromethoxy)phenyl)-1H-pyrazolo[3,4-b]pyridin-3-yl)azetidine-1-carboxylate

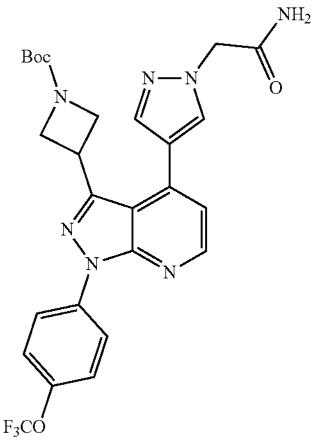 [SMILES: CC(C)(C)OC(=O)N1CC(c2nn(-c3ccc(OC(F)(F)F)cc3)c3nccc(-c4cnn(CC(N)=O)c4)c23)C1]

Reaction was run on a 0.11 mmol scale with tert-butyl 3-[4-iodo-1-[4-(trifluoromethoxy)phenyl]pyrazolo[3,4-b]pyridin-3-yl]azetidine-1-carboxylate. 52 mgs (87% yield) of tert-butyl 3-(4-(1-(2-amino-2-oxoethyl)-1H-pyrazol-4-yl)-1-(4-(trifluoromethoxy)phenyl)-1H-pyrazolo[3,4-b]pyridin-3-yl)azetidine-1-carboxylate as obtained as an brown semi-solid. LCMS (ESI) $[M+H]^+$=558.100.

Step 2: 2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)acetamide

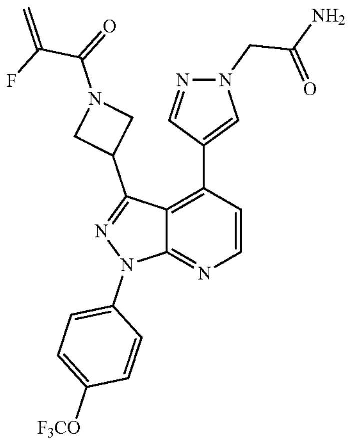 [SMILES: C=C(F)C(=O)N1CC(c2nn(-c3ccc(OC(F)(F)F)cc3)c3nccc(-c4cnn(CC(N)=O)c4)c23)C1]

After deprotection and acylation, 32.96 mg of 2-(4-(3-(1-(2-fluoroacryloyl)azetidin-3-yl)-1-(4-(trifluoromethoxy)phenyl)-1H-pyrazolo[3,4-b]pyridin-4-yl)-1H-pyrazol-1-yl)acetamide was obtained as a beige solid (67% yield over 2 steps) following preparative HPLC (Triart C18 column, 30-70% MeCN/water). $^1$H NMR (400 MHz, DMSO) δ 8.64 (d, J=4.8 Hz, 1H), 8.51-8.43 (m, 2H), 8.19 (s, 1H), 7.86 (d, J=0.8 Hz, 1H), 7.66 (s, 1H), 7.64-7.57 (m, 2H), 7.38 (s, 1H), 7.29 (d, J=4.8 Hz, 1H), 5.53-5.34 (m, 1H), 5.25 (dd, J=16.6, 3.6 Hz, 1H), 4.93 (s, 2H), 4.55 (td, J=7.8, 3.3 Hz, 2H), 4.44 (ddd, J=14.7, 8.4, 6.2 Hz, 1H), 4.22-4.13 (m, 2H). LCMS (ESI) $[M+H]^+$=530.100.

Example 174 (Compound 182)

1-(3-(4-(1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one

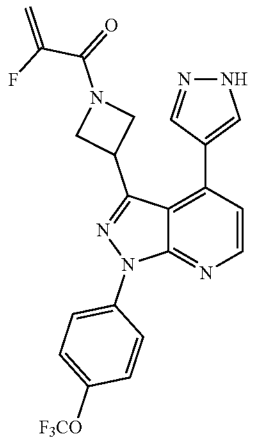 [SMILES: C=C(F)C(=O)N1CC(c2nn(-c3ccc(OC(F)(F)F)cc3)c3nccc(-c4cn[nH]c4)c23)C1]

For this example, the same sequence of steps was followed as for example 31, except that 4-(4,4,5,5-tetramethyl-1,3,2-dioxaborolan-2-yl)-1h-pyrazole was used in the first step instead of 1-(difluoromethyl)-4-(4,4,5,5-tetramethyl-1,3,2-dioxaborolan-2-yl)-1h-pyrazole.

Step 1: tert-butyl 3-(4-(1H-pyrazol-4-yl)-1-(4-(trifluoromethoxy)phenyl)-1H-pyrazolo[3,4-b]pyridin-3-yl)azetidine-1-carboxylate

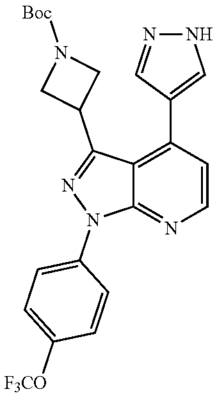 [SMILES: CC(C)(C)OC(=O)N1CC(c2nn(-c3ccc(OC(F)(F)F)cc3)c3nccc(-c4cn[nH]c4)c23)C1]

Reaction was run on a 0.11 mmol scale with tert-butyl 3-[4-iodo-1-[4-(trifluoromethoxy)phenyl]pyrazolo[3,4-b]pyridin-3-yl]azetidine-1-carboxylate. 11 mg (21% yield) of tert-butyl 3-(4-(1H-pyrazol-4-yl)-1-(4-(trifluoromethoxy)phenyl)-1H-pyrazolo[3,4-b]pyridin-3-yl)azetidine-1-carboxylate as obtained as an brown semi-solid. LCMS (ESI) $[M+H]^+$=501.000.

Step 2: 1-(3-(4-(1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one

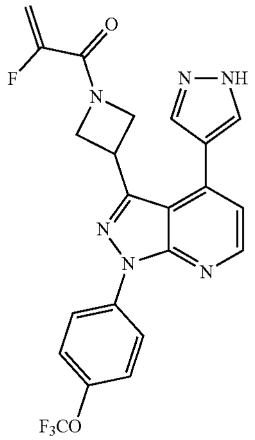 [SMILES: C=C(F)C(=O)N1CC(c2nn(-c3ccc(OC(F)(F)F)cc3)c3nccc(-c4cn[nH]c4)c23)C1]

Started with 46 mgs (0.09 mmol) of tert-butyl 3-(4-(1H-pyrazol-4-yl)-1-(4-(trifluoromethoxy)phenyl)-1H-pyrazolo[3,4-b]pyridin-3-yl)azetidine-1-carboxy late. After deprotection and acylation, 17.9 mg of 1-(3-(4-(1H-pyrazol-4-yl)-1-(4-(trifluoromethoxy)phenyl)-1H-pyrazolo[3,4-b]pyridin-3-yl)azetidin-1-yl)-2-fluoroprop-2-en-1-one was obtained as an off-white solid (41% yield over 2 steps) following preparative HPLC purifications (Triart C18 column, 30-70% MeCN/water) followed by achiral SFC (Torus Diol Column, neat MeOH, 15% isocratic gradient). $^1$H NMR (400 MHz, DMSO) δ 13.38 (s, 1H), 8.63 (d, J=4.8 Hz, 1H), 8.51-8.42 (m, 2H), 8.24 (s, 1H), 7.92 (s, 1H), 7.60 (d, J=8.7 Hz, 2H), 7.29 (d, J=4.8 Hz, 1H), 5.53-5.34 (m, 1H), 5.26 (dd, J=16.6, 3.6 Hz, 1H), 4.60 (t, J=3.7 Hz, 1H), 4.42 (qq, J=8.7, 4.5 Hz, 2H), 4.11 (dd, J=10.2, 4.7 Hz, 1H), 3.98 (t, J=9.0 Hz, 1H). LCMS (ESI) $[M+H]^+$=473.100.

Example 175 (Compound 183)

1-(3-(1-(2-chloro-4-(trifluoromethoxy)phenyl)-4-(hydroxymethyl)-1H-pyrazolo[3,4-b]pyridin-3-yl) azetidin-1-yl)-2-fluoroprop-2-en-1-one

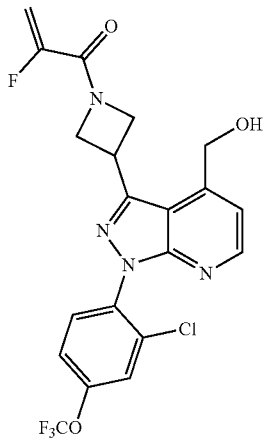 [SMILES: C=C(F)C(=O)N1CC(c2nn(-c3ccc(OC(F)(F)F)cc3Cl)c3nccc(CO)c23)C1]

Step 1: tert-butyl 3-(1-(2-chloro-4-(trifluoromethoxy)phenyl)-4-iodo-1H-pyrazolo[3,4-b]pyridin-3-yl)azetidine-1-carboxylate

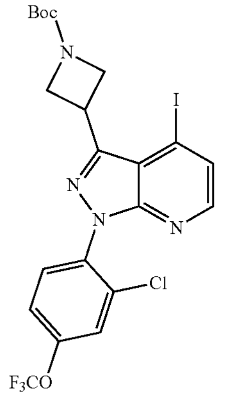 [SMILES: CC(C)(C)OC(=O)N1CC(c2nn(-c3ccc(OC(F)(F)F)cc3Cl)c3nccc(I)c23)C1]

A 2 dram vial containing ter t-butyl 3-(4-iodo-1h-pyrazolo [3,4-b]pyridin-3-yl)azetidine-1-carboxylate (350 mg, 0.875 mmol, 1.0 equiv.) was charged with Copper(II) Acetate (349 mg, 1.9 mmol, 2.2 equiv.), (2-chloro-4-(trifluoromethoxy) phenyl)boronic acid (465 mg, 1.8 mmol, 2.1 equiv.), and MeCN (3.5 mL), followed by Triethylamine (0.61 mL, 4.4 mmol, 5.0 equiv.). The reaction was stirred at 40° C. while open to air until no more consumption of starting material was observed by LCMS. Reaction diluted with iPrOAc, filtered through celite, concentrated and purified via column chromatography (silica gel, 0-25% iPrOAc/heptane). Gave 89 mg of tert-butyl 3-[1-[2-chloro-4-(trifluoromethoxy)phenyl]-4-iodo-pyrazolo[3,4-b]pyridin-3-yl]azetidine-1-carboxylate (17% Yield) as a white semi-solid. LCMS (ESI) $[M-tBu+H]^+$=538.900 (major isotope).

Step 2: tert-butyl 3-(1-(2-chloro-4-(trifluoromethoxy)phenyl)-4-vinyl-1H-pyrazolo[3,4-b]pyridin-3-yl)azetidine-1-carboxylate

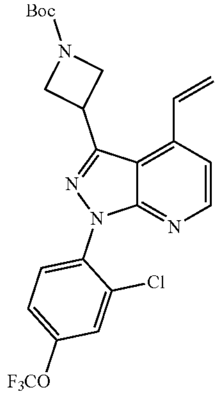 [SMILES: C=Cc1ccnc2c1c(C1CN(C(=O)OC(C)(C)C)C1)nn2-c1ccc(OC(F)(F)F)cc1Cl]

To a 2 dram vial was added tert-butyl 3-[1-[2-chloro-4-(trifluoromethoxy)phenyl]-4-iodo-pyrazolo[3,4-b]pyridin-3-yl]azetidine-1-carboxylate (106 mg, 0.18 mmol, 1.0 equiv.), potassium vinyltrifluoroborate (32 mg, 0.21 mmol, 1.2 equiv.), Pd(dppf)$Cl_2$·DCM (15 mg, 0.018 mmol, 0.10 equiv.), and $K_3PO_4$ (98 mg, 0.45 mmol, 2.5 equiv.). 1,4-Dioxane (2.23 mL) and $H_2O$ (0.25 mL) were added and the reaction was sparged with $N_2$ for 10 minutes. The reaction was then stirred at 90° C. until full consumption of the starting material was observed by LCMS. The reaction was then diluted with iPrOAc, filtered through celite, concentrated, and purified via column chromatography (silica gel, 0-30% iPrOAc/heptane). Gave 80 mg tert-butyl 3-[1-[2-chloro-4-(trifluoromethoxy)phenyl]-4-vinyl-pyrazolo[3,4-b]pyridin-3-yl]azetidine-1-carboxylate (91% Yield) as an off-white semi-solid which was used in step 3 immediately. LCMS (ESI) $[M+H]^+$=495.050.

Step 3: tert-butyl 3-(1-(2-chloro-4-(trifluoromethoxy)phenyl)-4-(hydroxymethyl)-1H-pyrazolo [3,4-b]pyridin-3-yl)azetidine-1-carboxylate

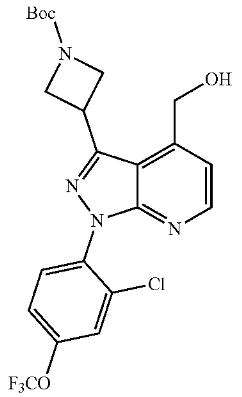 [SMILES: CC(C)(C)OC(=O)N1CC(c2nn(-c3ccc(OC(F)(F)F)cc3Cl)c3nccc(CO)c23)C1]

To a 4 dram equipped with a stir bar, Potassium Osmate (VI) Dihydrate (1.6 mg, 0.005 mmol, 0.03 equiv.) was dissolved in $H_2O$ (0.50 mL), then a solution of tert-butyl 3-[1-[2-chloro-4-(trifluoromethoxy)phenyl]-4-vinyl-pyrazolo[3,4-b]pyridin-3-yl]azetidine-1-carboxylate (80 mg, 0.1616 mmol, 1.0 equiv.) in THF (1.62 mL) was added to this solution. While stirring, sodium periodate (86 mg, 0.40 mmol, 2.5 equiv.) was added to the reaction mixture. Reaction was then allowed to stir at room temperature. Additional sodium periodate was added until complete conversion to the desired aldehyde was observed by LCMS and no intermediate diol remained. On completion, a saturated solution of sodium sulfite (4 mL) was added, and the reaction was stirred for 30 min then poured into a separatory funnel. The aqueous layer was extracted 3 times with iPrOAc. The organic layers were combined, washed once with saturated aqueous sodium sulfite solution, and then once with brine. The organics were dried with $MgSO_4$, filtered, and concentrated to obtain a yellow oil, which was used directly in the next step.

In a rbf equipped with a stir bar, the crude aldehyde was dissolved in MeOH (0.81 mL) and cooled to 0° C. Sodium borohydride (18 mg, 0.48 mmol, 3.0 equiv.) was then added slowly and the reaction was allowed to warm to room temperature until complete conversion of the starting material was observed by LCMS analysis. On completion, the reaction was quenched by the addition of saturated aqueous $NH_4Cl$ and extracted with iPrOAc (4×). Organics were combined, dried with $MgSO_4$, filtered, and concentrated. Purified via column chromatography (silica gel, 0-80% iPrOAc/heptane) to give 70 mg of tert-butyl 3-[1-[2-chloro-4-(trifluoromethoxy)phenyl]-4-(hydroxymethyl)pyrazolo[3,4-b]pyridin-3-yl]azetidine-1-carboxylate (87% Yield) as a yellow semi-solid. LCMS (ESI) $[M+H]^+$=499.000.

Step 4: 1-(3-(1-(2-chloro-4-(trifluoromethoxy)phenyl)-4-(hydroxymethyl)-1H-pyrazolo[3,4-b]pyridin-3-yl)azetidin-1-yl)-2-fluoroprop-2-en-1-one

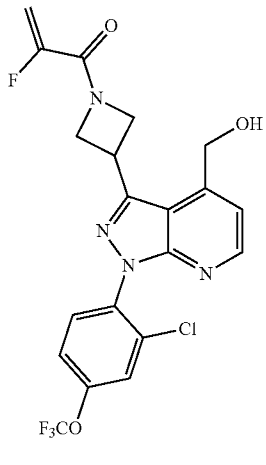

To a 2 dram vial containing tert-butyl 3-[1-[2-chloro-4-(trifluoromethoxy)phenyl]-4-(hydroxymethyl)pyrazolo[3,4-b]pyridin-3-yl]azetidine-1-carboxylate (70 mg, 0.14 mmol, 1.0 equiv.) was added DCM (0.35 mL) followed by trifluoroacetic acid (0.11 ml, 1.4 mmol, 10.0 equiv.). The reaction was stirred at room temperature until no starting material remained as monitored by LCMS. Reaction concentrated under reduced pressure to give the crude amine [3-(azetidin-3-yl)-1-[2-chloro-4-(trifluoromethoxy)phenyl]pyrazolo[3,4-b]pyridin-4-yl]methanol, which was then used directly without further purification. To the vial containing the crude amine was added 2-fluoroprop-2-enoic acid (19 mg, 0.21 mmol, 1.5 equiv.) and DCM (1.6 mL). Reaction was cooled to 0° C. and then N-ethoxycarbonyl-2-ethoxy-1,2-dihydroquinoline (53 mg, 0.21 mmol, 1.5 equiv.) was added. The reaction was then gradually allowed to warm to room temperature and monitored by LCMS until full consumption of the starting material was observed. The reaction was quenched by the addition of saturated aqueous $NH_4Cl$ and extracted with iPrOAc (3×) and DCM (1×). Organics were combined, dried with $MgSO_4$, filtered, and concentrated. 19.7 mg of 1-(3-(1-(2-chloro-4-(trifluoromethoxy)phenyl)-4-(hydroxymethyl)-1H-pyrazolo[3,4-b]pyridin-3-yl)azetidin-1-yl)-2-fluoroprop-2-en-1-one was obtained as an off-white solid (30% yield over 2 steps) following preparative HPLC (Triart C18 column, 30-70% MeCN/water). $^1H$ NMR (400 MHz, DMSO) δ 8.51 (d, J=4.7 Hz, 1H), 7.91 (d, J=2.7 Hz, 1H), 7.84 (d, J=8.8 Hz, 1H), 7.62 (ddd, J=8.8, 2.7, 1.2 Hz, 1H), 7.35 (d, J=4.7 Hz, 1H), 5.69 (t, J=5.4 Hz, 1H), 5.58-5.40 (m, 1H), 5.31 (dd, J=16.6, 3.6 Hz, 1H), 4.90 (d, J=5.1 Hz, 2H), 4.84 (td, J=9.0, 3.7 Hz, 1H), 4.69 (dt, J=9.5, 3.9 Hz, 1H), 4.55 (tt, J=8.7, 5.9 Hz, 1H), 4.46 (t, J=9.4 Hz, 1H), 4.31 (dd, J=9.9, 5.9 Hz, 1H). LCMS (ESI) $[M+H]^+$ =471.000.

Example 176 (Compound 184)

2-fluoro-1-(3-(4-(hydroxymethyl)-1-(2-methyl-4-(trifluoromethoxy)phenyl)-1H-pyrazolo[3,4-b]pyridin-3-yl)azetidin-1-yl)prop-2-en-1-one

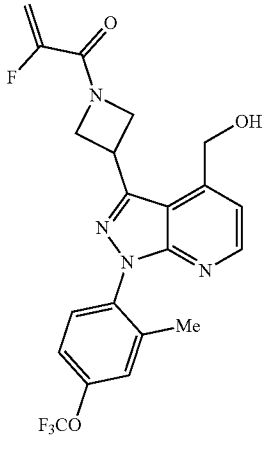 [SMILES: C=C(F)C(=O)N1CC(c2nn(-c3ccc(OC(F)(F)F)cc3Cl)c3nccc(CO)c23)C1]

For this example, the same sequence of steps was followed as for example 40, except that 2-methyl-4-(trifluoromethoxy)phenylboronic acid was used in the first step instead of (2-chloro-4-(trifluoromethoxy)phenyl)boronic acid.

Step 1: tert-butyl 3-(4-iodo-1-(2-methyl-4-(trifluoromethoxy)phenyl)-1H-pyrazolo[3,4-b]pyridin-3-yl) azetidine-1-carboxylate

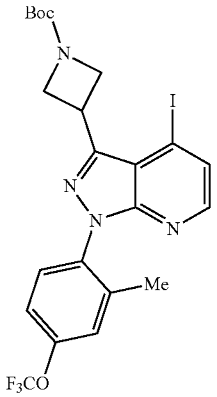 [SMILES: Cc1cc(OC(F)(F)F)ccc1-n1nc(C2CN(C(=O)OC(C)(C)C)C2)c2c(I)ccnc21]

Reaction was run on a 1.25 mmol scale with tert-butyl 3-(4-iodo-1h-pyrazolo[3,4-b]pyridin-3-yl)azetidine-1-carboxylate. 184 mgs (26% yield) of tert-butyl 3-(4-iodo-1-(2-methyl-4-(trifluoromethoxy)phenyl)-1H-pyrazolo[3,4-b] pyridin-3-yl)azetidine-1-carboxylate as obtained as an brown semi-solid. LCMS (ESI) $[M+H]^+$=575.000 (major isotope).

Step 2: tert-butyl 3-(1-(2-methyl-4-(trifluoromethoxy)phenyl)-4-vinyl-1H-pyrazolo[3,4-b]pyridin-3-yl)azetidine-1-carboxylate

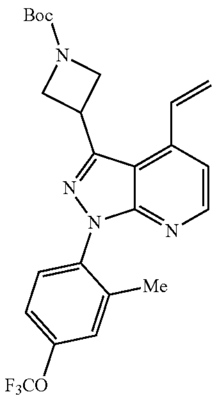 [SMILES: C=Cc1ccnc2c1c(C1CN(C(=O)OC(C)(C)C)C1)nn2-c1ccc(OC(F)(F)F)cc1C]

Reaction was run on a 0.394 mmol scale with tert-butyl 3-(4-iodo-1-(2-methyl-4-(trifluoromethoxy)phenyl)-1H-pyrazolo[3,4-b]pyridin-3-yl)azetidine-1-carboxylate. 166 mgs (89% yield) of tert-butyl 3-(1-(2-methyl-4-(trifluoromethoxy)phenyl)-4-vinyl-1H-pyrazolo[3,4-b]pyridin-3-yl)azetidine-1-carboxylate as obtained as an brown semi-solid. LCMS (ESI) $[M+H]^+$=475.100.

Step 3: tert-butyl 3-(4-(hydroxymethyl)-1-(2-methyl-4-(trifluoromethoxy)phenyl)-1H-pyrazolo[3,4-b]pyridin-3-yl)azetidine-1-carboxylate

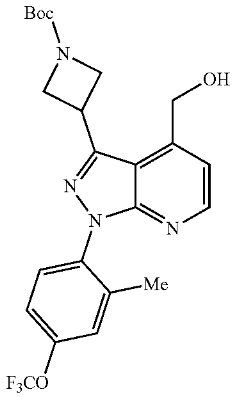 [SMILES: Cc1cc(OC(F)(F)F)ccc1-n1nc(C2CN(C(=O)OC(C)(C)C)C2)c2c(CO)ccnc21]

Reaction was run on a 0.35 mmol scale with tert-butyl 3-(1-(2-methyl-4-(trifluoromethoxy)phenyl)-4-vinyl-1H-pyrazolo[3,4-b]pyridin-3-yl)azetidine-1-carboxylate. 140 mgs (84% yield) of tert-butyl 3-(4-(hydroxymethyl)-1-(2-methyl-4-(trifluoromethoxy)phenyl)-1H-pyrazolo[3,4-b] pyridin-3-yl)azetidine-1-carboxylate was obtained as a yellow semi-solid. LCMS (ESI) $[M+H]^+$=479.100.

Step 4: 2-fluoro-1-(3-(4-(hydroxymethyl)-1-(2-methyl-4-(trifluoromethoxy)phenyl)-1H-pyrazolo[3,4-b]pyridin-3-yl)azetidin-1-yl)prop-2-en-1-one

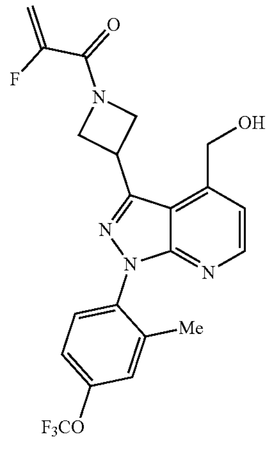

After deprotection and acylation, 55.66 mg of 2-fluoro-1-(3-(4-(hydroxymethyl)-1-(2-methyl-4-(trifluoromethoxy) phenyl)-1H-pyrazolo[3,4-b]pyridin-3-yl)azetidin-1-yl)prop-2-en-1-one was obtained as a white solid (42% yield over 2 steps) following preparative HPLC (Triart C18 column, 30-70% MeCN/water). $^1$H NMR (400 MHz, DMSO) δ 8.50 (d, J=4.7 Hz, 1H), 7.60 (d, J=8.7 Hz, 1H), 7.54-7.48 (m, 1H), 7.39 (dd, J=8.7, 2.7 Hz, 1H), 7.33 (d, J=4.7 Hz, 1H), 5.67 (t, J=5.4 Hz, 1H), 5.59-5.39 (m, 1H), 5.30 (dd, J=16.6, 3.6 Hz, 1H), 4.90 (d, J=5.1 Hz, 2H), 4.82 (dd, J=9.0, 3.7 Hz, 1H), 4.70 (dt, J=9.3, 4.1 Hz, 1H), 4.55 (ddd, J=14.6, 8.8, 6.0 Hz, 1H), 4.45 (t, J=9.3 Hz, 1H), 4.32 (dd, J=9.9, 6.0 Hz, 1H), 2.14 (s, 3H). LCMS (ESI) $[M+H]^+$=451.100.

Example 177 (Compound 185)

2-fluoro-1-[3-[1-[2-fluoro-4-(trifluoromethoxy)phenyl]-4-(hydroxymethyl)pyrazolo[3,4-b]pyridin-3-yl]azetidin-1-yl]prop-2-en-1-one

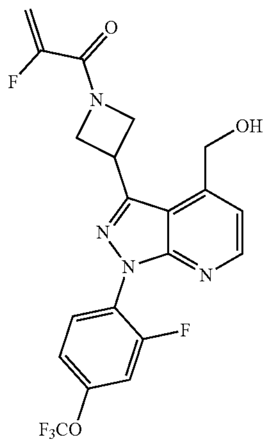 [SMILES: C=C(F)C(=O)N1CC(c2nn(-c3ccc(OC(F)(F)F)cc3F)c3nccc(CO)c23)C1]

For this example, the same sequence of steps was followed as for example 40, except that 2-fluoro-4-trifluoromethoxyphenylboronic acid was used in the first step instead of (2-chloro-4-(trifluoromethoxy)phenyl)boronic acid.

Step 1: tert-butyl 3-[1-[2-fluoro-4-(trifluoromethoxy)phenyl]-4-iodo-pyrazolo[3,4-b]pyridin-3-yl]azetidine-1-carboxylate

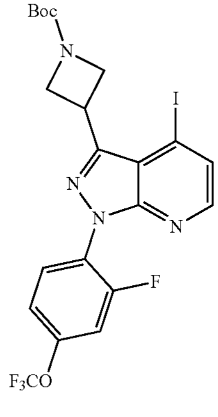 [SMILES: CC(C)(C)OC(=O)N1CC(c2nn(-c3ccc(OC(F)(F)F)cc3F)c3nccc(I)c23)C1]

Reaction was run on a 4.40 mmol scale with tert-butyl 3-(4-iodo-1h-pyrazolo[3,4-b]pyridin-3-yl)azetidine-1-carboxylate. 96 mgs (8% yield) of tert-butyl 3-[1-[2-fluoro-4-(trifluoromethoxy)phenyl]-4-iodo-pyrazolo[3,4-b]pyridin-3-yl]azetidine-1-carboxylate was obtained as a white solid. LCMS (ESI) [M−tBu+H]$^+$=522.850 (major isotope).

Step 2: tert-butyl 3-[1-[2-fluoro-4-(trifluoromethoxy)phenyl]-4-vinyl-pyrazolo[3,4-b]pyridin-3-yl]azetidine-1-carboxylate

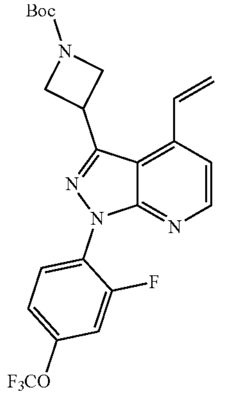 [SMILES: C=Cc1ccnc2c1c(C1CN(C(=O)OC(C)(C)C)C1)nn2-c1ccc(OC(F)(F)F)cc1F]

Reaction was run on a 0.166 mmol scale with tert-butyl 3-[1-[2-fluoro-4-(trifluoromethoxy)phenyl]-4-iodo-pyrazolo[3,4-b]pyridin-3-yl]azetidine-1-carboxylate. 82 mgs (100% yield) of tert-butyl 3-[1-[2-fluoro-4-(trifluoromethoxy)phenyl]-4-vinyl-pyrazolo[3,4-b]pyridin-3-yl]azetidine-1-carboxylate was obtained as a yellow oil. LCMS (ESI) [M+H]$^+$=479.000.

Step 3: tert-butyl 3-[1-[2-fluoro-4-(trifluoromethoxy)phenyl]-4-(hydroxymethyl)pyrazolo[3,4-b]pyridin-3-yl]azetidine-1-carboxylate

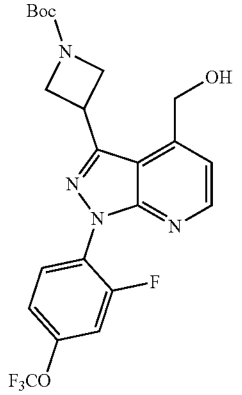 [SMILES: CC(C)(C)OC(=O)N1CC(c2nn(-c3ccc(OC(F)(F)F)cc3F)c3nccc(CO)c23)C1]

Reaction was run on a 0.17 mmol scale with tert-butyl 3-[1-[2-fluoro-4-(trifluoromethoxy)phenyl]-4-vinyl-pyrazolo[3,4-b]pyridin-3-yl]azetidine-1-carboxylate. 62 mgs (75% yield) of tert-butyl 3-[1-[2-fluoro-4-(trifluoromethoxy)phenyl]-4-(hydroxymethyl)pyrazolo[3,4-b]pyridin-3-yl]azetidine-1-carboxylate was obtained as a yellow oil. LCMS (ESI) [M+H]$^+$=483.050.

Step 4: 2-fluoro-1-[3-[1-[2-fluoro-4-(trifluoromethoxy)phenyl]-4-(hydroxymethyl)pyrazolo[3,4-b]pyridin-3-yl]azetidin-1-yl]prop-2-en-1-one

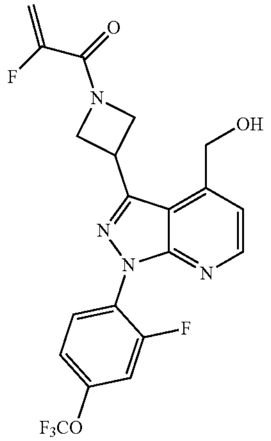 [SMILES: C=C(F)C(=O)N1CC(c2nn(-c3ccc(OC(F)(F)F)cc3F)c3nccc(CO)c23)C1]

Reaction ran with 100 mg (0.21 mmol) of tert-butyl 3-[1-[2-fluoro-4-(trifluoromethoxy)phenyl]-4-(hydroxymethyl)pyrazolo[3,4-b]pyridin-3-yl]azetidine-1-carboxylate. After deprotection and acylation, 17.27 mg of 2-fluoro-1-[3-[1-[2-fluoro-4-(trifluoromethoxy)phenyl]-4-(hydroxymethyl)pyrazolo[3,4-b]pyridin-3-yl]azetidin-1-yl]prop-2-en-1-one was obtained as a white solid (18% yield over 2 steps) following preparative HPLC (Triart C18 column, 30-70% MeCN/water) followed by achiral SFC (Princeton PPU Column, neat MeOH, 15% isocratic gradient). $^1$H NMR (400 MHz, DMSO) δ 8.54 (d, J=4.7 Hz, 1H), 7.91 (t, J=8.6 Hz, 1H), 7.76 (dd, J=10.5, 2.6 Hz, 1H), 7.52-7.44 (m, 1H), 7.37 (d, J=4.7 Hz, 1H), 5.69 (t, J=5.4 Hz, 1H), 5.59-5.38 (m, 1H), 5.31 (dd, J=16.6, 3.6 Hz, 1H), 4.90 (d, J=4.8 Hz, 2H), 4.84 (td, J=9.0, 3.7 Hz, 1H), 4.71 (dq, J=9.2, 3.7 Hz, 1H), 4.55 (tt, J=8.7, 5.9 Hz, 1H), 4.45 (t, J=9.3 Hz, 1H), 4.34 (dd, J=9.9, 6.0 Hz, 1H). LCMS (ESI) $[M+H]^+$=455.1142.

Example 178 (Compound 186)

N-((4-cyano-1-(4-(trifluoromethoxy)phenyl)-1H-indazol-3-yl)methyl)acrylamide

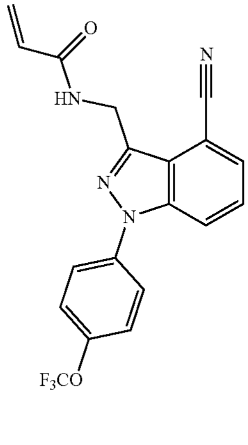 [SMILES: C=CC(=O)NCc1nn(-c2ccc(OC(F)(F)F)cc2)c2cccc(C#N)c12]

Step 1: 3-bromo-1-(4-(trifluoromethoxy)phenyl)-1H-pyrazolo[4,3-b]pyridine

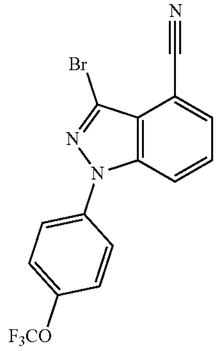 [SMILES: N#Cc1cccc2c1c(Br)nn2-c1ccc(OC(F)(F)F)cc1]

Following General Procedure 1 850 mg of the title compound was isolated as a white solid (90% yield) from 3-bromo-1H-pyrazolo[4,3-b]pyridine (500 mg, 2.5 mmol, 1.00 equiv.) and [4-(trifluoromethoxy)phenyl]boronic acid (780 mg, 3.9 mmol, 1.5 equiv). (product does not ionize well on LCMS)

Step 2: tert-butyl ((4-cyano-1-(4-(trifluoromethoxy)phenyl)-1H-indazol-3-yl)methyl)carbamate

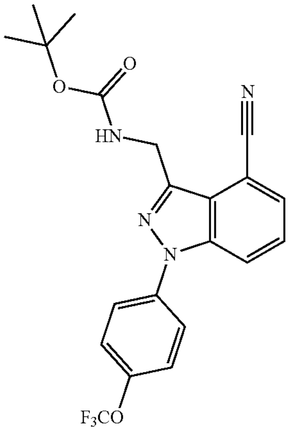 [SMILES: CC(C)(C)OC(=O)NCc1nn(-c2ccc(OC(F)(F)F)cc2)c2cccc(C#N)c12]

Into an 8 mL vial equipped with a stir bar, weigh cesium carbonate (171 mg, 0.52 mmol, 2.5 equiv.) and potassium (((tert-butoxycarbonyl)amino)methyl)trifluoroborate (105 mg, 0.42 mmol, 2.0 equiv.), along with cataCXium Pd $G_2$ (14 mg, 0.021 mmol, 0.10 equiv.). Dissolve 3-bromo-1-[4-(trifluoromethoxy)phenyl]indazole-4-carbonitrile (80 mg, 0.21 mmol, 1.0 equiv.) in toluene (1.0 mL) to make a stock solution and add to the vial, then add water (0.1 mL). Degas by bubbling nitrogen for 10 minutes, then stir at 75° C. overnight. At this time the reaction was cooled to room temperature and filtered through celite, then concentrated directly. Column chromatography (0 to 10% iPrOAc/DCM) gave the title compound (69 mg, 76.22% Yield) as a white solid.

LCMS (ESI) $[M+H]^+$=433.000

Step 3 and 4: N-((4-cyano-1-(4-(trifluoromethoxy)phenyl)-1H-indazol-3-yl)methyl)acrylamide

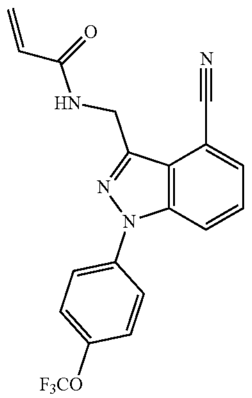 [SMILES: C=CC(=O)NCc1nn(-c2ccc(OC(F)(F)F)cc2)c2cccc(C#N)c12]

Following General Procedure 4, the title compound (46 mg, 74% yield over two steps) was obtained as a white solid from tert-butyl ((4-cyano-1-(4-(trifluoromethoxy)phenyl)-1H-indazol-3-yl)methyl)carbamate (69 mg).

$^1$H NMR (400 MHz, DMSO) δ 8.70 (t, J=5.0 Hz, 1H), 8.21 (dd, J=8.7, 0.8 Hz, 1H), 7.95-7.86 (m, 3H), 7.69 (dd, J=8.7, 7.2 Hz, 1H), 7.68-7.59 (m, 2H), 6.33 (dd, J=17.1, 10.2 Hz, 1H), 6.14 (dd, J=17.1, 2.2 Hz, 1H), 5.63 (dd, J=10.2, 2.2 Hz, 1H), 4.94 (d, J=5.0 Hz, 2H).

LCMS (ESI) $[M+H]^+$=387.050

Example 179 (Compound 187)

N-((1-(4-(trifluoromethoxy)phenyl)-1H-pyrazolo[4,3-b]pyridin-3-yl)methyl)acrylamide

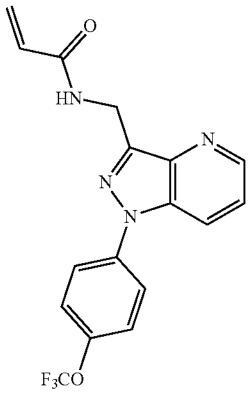 [SMILES: C=CC(=O)NCc1nn(-c2ccc(OC(F)(F)F)cc2)c2cccnc12]

Step 1: 3-bromo-1-(4-(trifluoromethoxy)phenyl)-1H-pyrazolo[4,3-b]pyridine

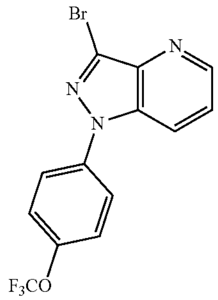 [SMILES: FC(F)(F)Oc1ccc(-n2nc(Br)c3ncccc32)cc1]

Following General Procedure 1 350 mg of the title compound was isolated as a clear oil (39% yield) from 3-bromo-1H-pyrazolo[4,3-b]pyridine (500 mg, 2.5 mmol, 1.00 equiv.) and [4-(trifluoromethoxy)phenyl]boronic acid (780 mg, 3.9 mmol, 1.5 equiv).

LCMS (ESI) $[M+H]^+$=357.900

Step 2: tert-butyl ((1-(4-(trifluoromethoxy)phenyl)-1H-pyrazolo[4,3-b]pyridin-3-yl)methyl)carbamate

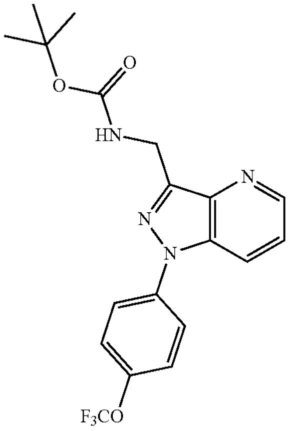 [SMILES: CC(C)(C)OC(=O)NCc1nn(-c2ccc(OC(F)(F)F)cc2)c2cccnc12]

Into three 8 mL vials equipped with stir bars, weigh cesium carbonate (182.0 mg, 0.56 mmol, 2.5 equiv.) and potassium (((tert-butoxycarbonyl)amino)methyl)trifluoroborate (111.5 mg, 0.45 mmol, 2.0 equiv.), along with cataCXium Pd $G_2$ (15 mg, 0.022 mmol, 0.10 equiv.). In a separate vial dissolve 3-bromo-1-[4-(trifluoromethoxy)phenyl]pyrazolo[4,3-b]pyridine (240 mg, 0.66 mmol, 3.0 equiv.) in toluene (3.0 mL) to make a stock solution. Add 1 mL of this solution to each of the above mentioned vials (so that each receives 1 equiv. Of the aryl bromide), and then add water (0.1 mL). Degas each vial by bubbling nitrogen for 10 minutes, then stir at 75° C. overnight. At this time the reactions were cooled to room temperature, combined, and filtered through celite, then concentrated directly. Column chromatography (0 to 10% iPrOAc/Heptane) gave tert-butyl N-[[1-[4-(trifluoromethoxy)phenyl]pyrazolo[4,3-b]pyridin-3-yl]methyl]carbamate (72 mg, 26% Yield averaged over three runs) as a white solid.

LCMS (ESI) $[M+H]^+$=409.050

Step 3 and 4: N-((1-(4-(trifluoromethoxy)phenyl)-1H-pyrazolo[4,3-b]pyridin-3-yl)methyl)acrylamide

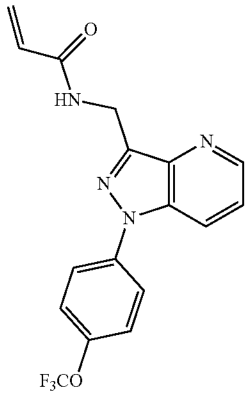 [SMILES: C=CC(=O)NCc1nn(-c2ccc(OC(F)(F)F)cc2)c2cccnc12]

Following General Procedure 4, the title compound (87 mg, 84% yield over two steps) was obtained as a white solid from tert-butyl ((1-(4-(trifluoromethoxy)phenyl)-1H-pyrazolo[4,3-b]pyridin-3-yl)methyl)carbamate (117 mg).

$^1$H NMR (400 MHz, DMSO) δ 8.74-8.62 (m, 2H), 8.38 (dd, J=8.7, 1.3 Hz, 1H), 7.98-7.90 (m, 2H), 7.65-7.51 (m, 3H), 6.32 (dd, J=17.1, 10.2 Hz, 1H), 6.13 (dd, J=17.1, 2.3 Hz, 1H), 5.61 (dd, J=10.1, 2.2 Hz, 1H), 4.86 (d, J=5.5 Hz, 2H).

LCMS (ESI) $[M+H]^+$=363.000

Example 180 (Compound 188)

N-((1-(4-(trifluoromethoxy)phenyl)-1H-pyrazolo[3,4-b]pyridin-3-yl)methyl)acrylamide

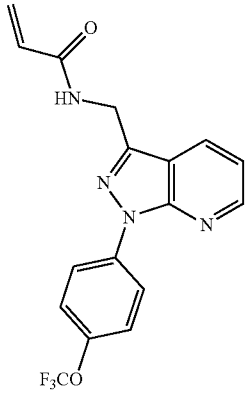 [SMILES: C=CC(=O)NCc1nn(-c2ccc(OC(F)(F)F)cc2)c2ncccc12]

Step 1: tert-butyl ((1H-pyrazolo[3,4-b]pyridin-3-yl)methyl)carbamate

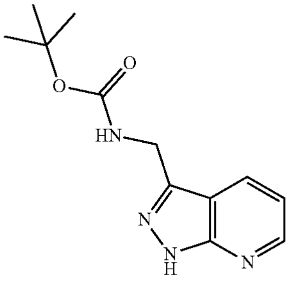 [SMILES: CC(C)(C)OC(=O)NCc1n[nH]c2ncccc12]

To a vial equipped with a stir bar add 1H-pyrazolo[3,4-b]pyridin-3-ylmethanamine (250 mg, 1.69 mmol, 1.00 equiv.) and methanol (6.7495 mL), followed by di-tert-butyl dicarbonate (380 mg, 0.37 mL, 1.69 mmol, 1.00 equiv.). The mixture was stirred until complete consumption of the starting materials was confirmed by LCMS analysis. The mixture was directly concentrated to give tert-butyl N-(1H-pyrazolo[3,4-b]pyridin-3-ylmethyl)carbamate (420 mg, 1.6 mmol, quant. Yield) as an off-white solid, which was used without purification.

LCMS (ESI) $[M+H]^+$=249.050

Step 2: tert-butyl 41-(4-(trifluoromethoxy)phenyl)-1H-pyrazolo[3,4-b]pyridin-3-yl)methyl)carbamate

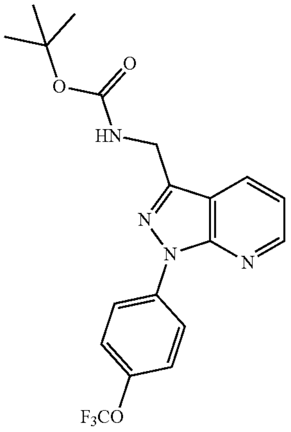 [SMILES: CC(C)(C)OC(=O)NCc1nn(-c2ccc(OC(F)(F)F)cc2)c2ncccc12]

Following General Procedure 1 150 mg of tert-butyl 41-(4-(trifluoromethoxy)phenyl)-1H-pyrazolo[3,4-b]pyridin-3-yl)methyl)carbamate was isolated as a white solid (22% yield) from tert-butyl 41H-pyrazolo[3,4-b]pyridin-3-yl)methyl)carbamate (410 mg, 1.69 mmol) and [4-(trifluoromethoxy)phenyl]boronic acid (523 mg, 2.54 mmol, 1.5 equiv).

LCMS (ESI) $[M+H]^+$=409.000

Step 3 and 4: N-((1-(4-(trifluoromethoxy)phenyl)-1H-pyrazolo[3,4-b]pyridin-3-yl)methyl)acrylamide

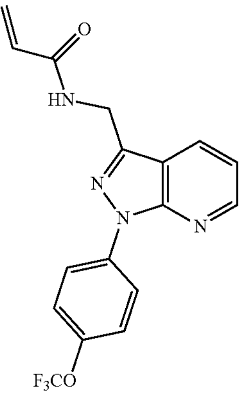 [SMILES: C=CC(=O)NCc1nn(-c2ccc(OC(F)(F)F)cc2)c2ncccc12]

Following General Procedure 4, N-((1-(4-(trifluoromethoxy)phenyl)-1H-pyrazolo[3,4-b]pyridin-3-yl)methyl)acrylamide (104 mg, 84% yield over two steps) was obtained as a white solid from tert-butyl ((1-(4-(trifluoromethoxy)phenyl)-1H-pyrazolo[3,4-b]pyridin-3-yl)methyl)carbamate (150 mg).

$^1$H NMR (400 MHz, DMSO) δ 8.86 (t, J=5.9 Hz, 1H), 8.70 (dd, J=4.6, 1.6 Hz, 1H), 8.46-8.36 (m, 3H), 7.64-7.55 (m, 2H), 7.41 (dd, J=8.0, 4.6 Hz, 1H), 6.28 (dd, J=17.1, 9.9 Hz, 1H), 6.17 (dd, J=17.1, 2.4 Hz, 1H), 5.65 (dd, J=9.9, 2.4 Hz, 1H), 4.79 (d, J=5.9 Hz, 2H).

LCMS (ESI) $[M+H]^+$=363.000

Example 181 & 182 (Compounds 82 & 125)

(R)-1-(3-(1-(2-fluoroacryloyl)azetidin-3-yl)-1-(4-(trifluoromethoxy)phenyl)-1H-pyrazolo[3,4-b]pyridin-4-yl)-3-hydroxypyrrolidin-2-one (Compound 125) & (S)-1-(3-(1-(2-fluoroacryloyl)azetidin-3-yl)-1-(4-(trifluoromethoxy)phenyl)-1H-pyrazolo[3,4-b]pyridin-4-yl)-3-hydroxypyrrolidin-2-one (Compound 82)

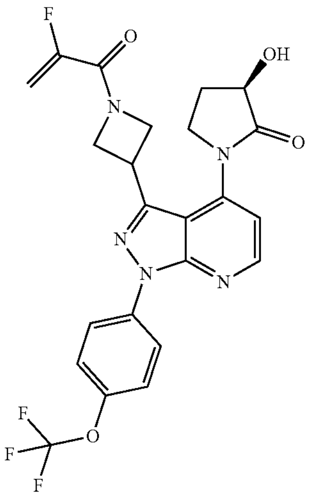

-continued

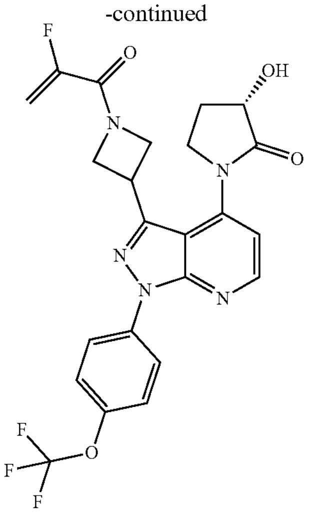

Step 1: tert-butyl (R)-3-(4-(3-hydroxy-2-oxopyrrolidin-1-yl)-1-(4-(trifluoromethoxy)phenyl)-1H-pyrazolo[3,4-b]pyridin-3-yl)azetidine-1-carboxylate & tert-butyl (S)-3-(4-(3-hydroxy-2-oxopyrrolidin-1-yl)-1-(4-(trifluoromethoxy)phenyl)-1H-pyrazolo[3,4-b]pyridin-3-yl)azetidine-1-carboxylate

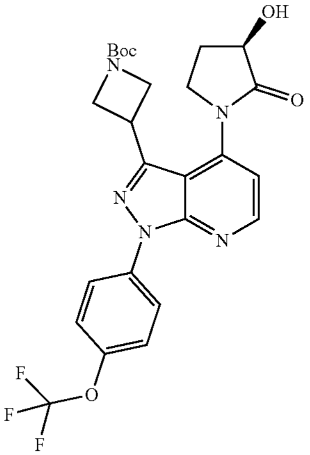

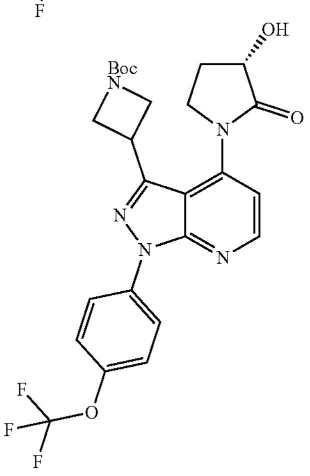

A mixture of (R)-3-hydroxypyrrolidin-2-one (135 mg, 1.34 mmol), tert-butyl 3-(4-iodo-1-(4-(trifluoromethoxy) phenyl)-1H-pyrazolo[3,4-b]pyridin-3-yl)azetidine-1-carboxylate (500 mg, 0.89 mmol), $K_2CO_3$ (370 mg, 2.68 mmol), CuI (85.0 mg, 0.45 mmol) and $N^1$,$N^2$-dimethylethane-1,2-diamine (39.0 mg, 0.45 mmol) in DMF (5 mL) was stirred at 120° C. for 2 h under $N_2$ atmosphere. The reaction mixture was diluted with water (50 mL) and extracted it with ethyl acetate (50 mL×3), the combined organic layers were washed with water (50 mL×3), dried over $Na_2SO_4$, filtered and concentrated to dryness. The residue was purified by flash chromatography on silica gel (0-35% ethyl acetate in petroleum ether) to afford the title compound tert-butyl (R)-3-(4-(3-hydroxy-2-oxopyrrolidin-1-yl)-1-(4-(trifluoromethoxy)phenyl)-1H-pyrazolo[3,4-b]pyridin-3-yl)azetidine-1-carboxylate (300 mg, 63%) as a yellow solid. $^1$H NMR (400 MHz, DMSO-$d_6$): δ 8.69 (d, J=4.8 Hz, 1H), 8.40 (d, J=8.8 Hz, 2H), 7.60 (d, J=8.8 Hz, 2H), 7.26 (d, J=4.8 Hz, 1H), 6.05 (d, J=6.0 Hz, 1H), 4.46-4.40 (m, 1H), 4.26-4.21 (m, 3H), 4.13-4.09 (m, 2H), 3.96-3.94 (m, 1H), 3.81-3.77 (m, 1H), 2.59-2.58 (m, 2H), 1.39 (s, 9H); LCMS (ESI): m/z 534.0 $(M+H)^+$.

A mixture of (S)-3-hydroxypyrrolidin-2-one (135 mg, 1.34 mmol), tert-butyl 3-(4-iodo-1-(4-(trifluoromethoxy) phenyl)-1H-pyrazolo[3,4-b]pyridin-3-yl)azetidine-1-carboxylate (500 mg, 0.89 mmol), $K_2CO_3$ (370 mg, 2.68 mmol), CuI (85.0 mg, 0.45 mmol) and $N^1$,$N^2$-dimethylethane-1,2-diamine (39.0 mg, 0.45 mmol) in DMF (5 mL) was stirred at 120° C. for 2 h under $N_2$ atmosphere. The reaction mixture was diluted with water (50 mL) and extracted it with ethyl acetate (50 mL×3), the combined organic layers were washed with water (50 mL×3), dried over $Na_2SO_4$, filtered and concentrated. The residue was purified by flash chromatography on silica gel (0-35% ethyl acetate in petroleum ether) to afford the title compound 2 (410 mg, 86%) as a yellow solid. $^1$H NMR (400 MHz, DMSO-$d_6$): δ 8.69 (d, J=4.8 Hz, 1H), 8.40 (d, J=8.8 Hz, 2H), 7.60 (d, J=8.8 Hz, 2H), 7.26 (d, J=4.8 Hz, 1H), 6.05 (d, J=6.0 Hz, 1H), 4.46-4.40 (m, 1H), 4.26-4.21 (m, 3H), 4.13-4.10 (m, 2H), 3.96-3.94 (m, 1H), 3.81-3.77 (m, 1H), 2.59-2.55 (m, 2H), 1.39 (s, 9H); LCMS (ESI): m/z 534.0 $(M+H)^+$.

Step 2: (R)-1-(3-(azetidin-3-yl)-1-(4-(trifluoromethoxy)phenyl)-1H-pyrazolo[3,4-b]pyridin-4-yl)-3-hydroxypyrrolidin-2-one & (S)-1-(3-(azetidin-3-yl)-1-(4-(trifluoromethoxy)phenyl)-1H-pyrazolo[3,4-b]pyridin-4-yl)-3-hydroxypyrrolidin-2-one

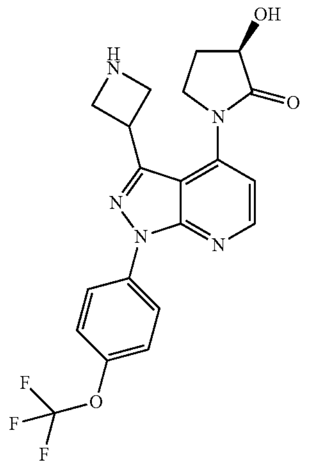

-continued

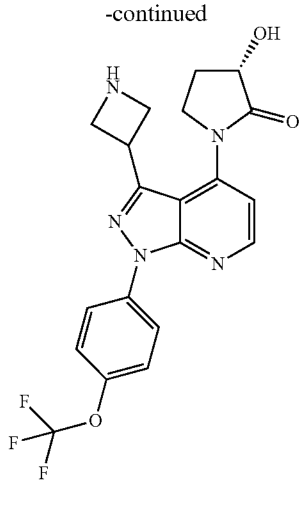

A solution of tert-butyl (R)-3-(4-(3-hydroxy-2-oxopyrrolidin-1-yl)-1-(4-(trifluoromethoxy)phenyl)-1H-pyrazolo[3,4-b]pyridin-3-yl)azetidine-1-carboxylate (300 mg, 0.56 mmol) in TFA (5% in HFIP, 15 mL) was stirred at room temperature for 1 h. The reaction was diluted with water (50 mL) and adjusted to pH=8 with sat. $NaHCO_3$, the mixture was extracted with ethyl acetate (50 mL×3), the combined organic layers were dried over $Na_2SO_4$ and concentrated under vacuum to afford the title compound (R)-1-(3-(azetidin-3-yl)-1-(4-(trifluoromethoxy)phenyl)-1H-pyrazolo[3,4-b]pyridin-4-yl)-3-hydroxypyrrolidin-2-one (155 mg, 64%) as a yellow oil. The crude would be used for the next step directly. LCMS (ESI): m/z 434.2 $(M+H)^+$.

A solution of tert-butyl (S)-3-(4-(3-hydroxy-2-oxopyrrolidin-1-yl)-1-(4-(trifluoromethoxy)phenyl)-1H-pyrazolo[3,4-b]pyridin-3-yl)azetidine-1-carboxylate (180 mg, 0.34 mmol) in TFA (5% in HFIP, 15 mL) was stirred at room temperature for 1 h. The reaction was diluted with water (50 mL) and adjusted to pH=8 with sat. $NaHCO_3$, the mixture was extracted with ethyl acetate (50 mL×3), the combined organic layers were dried over $Na_2SO_4$ and concentrated under vacuum to afford the title compound (S)-1-(3-(azetidin-3-yl)-1-(4-(trifluoromethoxy)phenyl)-1H-pyrazolo[3,4-b]pyridin-4-yl)-3-hydroxypyrrolidin-2-one (120 mg, 81%) as a yellow oil. The crude would be used in the next step directly. LCMS (ESI): m/z 434.0 $(M+H)^+$.

Step 3: (R)-1-(3-(1-(2-fluoroacryloyl)azetidin-3-yl)-1-(4-(trifluoromethoxy)phenyl)-1H-pyrazolo[3,4-b]pyridin-4-yl)-3-hydroxypyrrolidin-2-one & (S)-1-(3-(1-(2-fluoroacryloyl)azetidin-3-yl)-1-(4-(trifluoromethoxy)phenyl)-1H-pyrazolo[3,4-b]pyridin-4-yl)-3-hydroxypyrrolidin-2-one

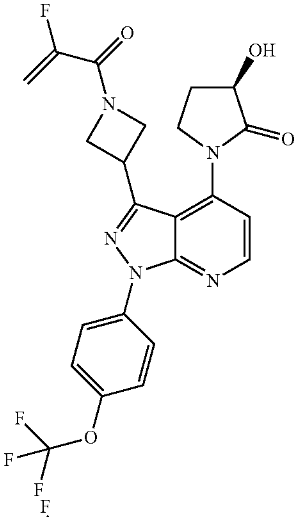

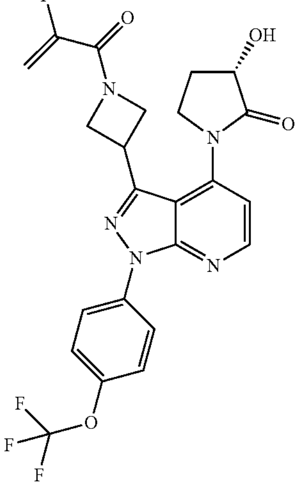

To a solution of 2-fluoroacrylic acid (64.0 mg, 0.72 mmol) in DMF (2 mL) was added DIPEA (0.12 mL, 0.72 mmol), HATU (163 mg, 0.43 mmol) and (R)-1-(3-(azetidin-3-yl)-1-(4-(trifluoromethoxy)phenyl)-1H-pyrazolo[3,4-b]pyridin-4-yl)-3-hydroxypyrrolidin-2-one (155 mg, 0.36 mmol). The mixture was stirred at room temperature for 16 h. The reaction solution was purified by reverse phase chromatography (Welch Xtimate C18 150*30 mm*5 um, water (FA)-ACN, 50%-80%, 25 mL/min) to afford the enantiomer mixture (55.0 mg, 30%) as a white solid. LCMS (ESI): m/z 506.1 $(M+H)^+$; SFC (IC_3_MeOH_DEA_40_25ML): RT=2.141 min showed 46% of peak 1 and RT=2.757 min showed 54% of peak 2.

To a solution of 2-fluoroacrylic acid (44.0 mg, 0.49 mmol) in DMF (3 mL) was added DIPEA (0.29 mL, 1.64 mmol), HATU (150 mg, 0.39 mmol) and (S)-1-(3-(azetidin-3-yl)-1-(4-(trifluoromethoxy)phenyl)-1H-pyrazolo[3,4-b]pyridin-4-yl)-3-hydroxypyrrolidin-2-one (180 mg, 0.33 mmol). The mixture was stirred at room temperature for 16 h. The reaction solution was purified by reverse phase chromatography (Welch Xtimate C18 150*30 mm*5 um, water (FA)-ACN, 49%-79%, 25 mL/min) to afford the enantiomer mixture (75 mg, 45%) as a white solid. LCMS (ESI): m/z 506.1 $(M+H)^+$; SFC (IC_3_MeOH_DEA_40_25ML): RT=2.143 min showed 60% of peak 1 and RT=2.761 min showed 40% of peak 2.

All of these enantiomer mixture (130 mg, 0.26 mmol) were separated by Chiral SFC (Instrument: SFC-1; Column: IC (250 mm*30 mm, 10 um); Condition: 0.1% $NH_3{\cdot}H_2O$-MeOH; Begin B:40%; Flow Rate (mL/min): 80) to afford the title compound (S)-1-(3-(1-(2-fluoroacryloyl)azetidin-3-yl)-1-(4-(trifluoromethoxy)phenyl)-1H-pyrazolo[3,4-b]pyridin-4-yl)-3-hydroxypyrrolidin-2-one (50.0 mg, 38%) as a white solid. $^1H$ NMR (400 MHz, DMSO-$d_6$): δ 8.70 (d, J=5.2 Hz, 1H), 8.41 (d, J=8.8 Hz, 2H), 7.60 (d, J=8.8 Hz, 2H), 7.28-7.26 (m, 1H), 6.04 (s, 1H), 5.49 (dd, J=48.4, 3.6 Hz, 1H), 5.32 (dd, J=16.8, 3.6 Hz, 1H), 4.79-4.63 (m, 2H), 4.47-4.22 (m, 4H), 3.98-3.92 (m, 1H), 3.83-3.78 (m, 1H), 2.57-2.56 (m, 1H), 2.06-1.99 (m, 1H); LCMS (ESI): m/z 506.1 $(M+H)^+$.

(R)-1-(3-(1-(2-fluoroacryloyl)azetidin-3-yl)-1-(4-(trifluoromethoxy)phenyl)-1H-pyrazolo[3,4-b]pyridin-4-yl)-3-hydroxypyrrolidin-2-one (63.3 mg, 48%) as a white solid. $^1H$ NMR (400 MHz, DMSO-$d_6$): δ 8.70 (d, J=5.2 Hz, 1H), 8.41 (d, J=8.8 Hz, 2H), 7.60 (d, J=8.8 Hz, 2H), 7.28-7.26 (m, 1H), 6.04 (s, 1H), 5.49 (dd, J=48.4, 3.6 Hz, 1H), 5.32 (dd, J=16.8, 3.6 Hz, 1H), 4.79-4.63 (m, 2H), 4.47-4.22 (m, 4H), 3.98-3.92 (m, 1H), 3.83-3.78 (m, 1H), 2.57-2.56 (m, 1H), 2.06-1.99 (m, 1H); LCMS (ESI): m/z 506.1 $(M+H)^+$.

Example 183

TR-FRET Assay

His-tagged TEAD proteins are pre-incubated with TEAD project compounds for 30 minutes or 4 hours at room temperature. Biotinylated lipid pocket probes are then added to the TEAD/Compound mixture and incubated for 60 minutes at room temperature. The lipid pocket probe competes with the test compound for the TEAD lipid pocket until equilibrium is reached. After 60 minutes, Europium labelled anti-His (Perkin Elmer #AD0110) and XL665 labelled streptavidin (CIS Bio 610SAXAC) are added to the TEAD/test compound/lipid pocket mixture and incubated for 30 minutes or 4 hours. TR-FRET values are then measured using an EnVision multi-label plate reader (Perkin Elmer Cat #2104-0010A.) If the lipid pocket probe binds to TEAD as expected, a TR-FRET signal results from the proximity of anti-His Eu and XL665. If a TEAD lipid pocket binder such as binds and displaces the lipid pocket probe, the disruption of the TEAD:probe interaction results in a decrease in TR-FRET signal. The potency of compounds as TEAD lipid pocket binders is determined by $IC_{50}$ value generated using a non-linear 4 parameter curve fit.

The $IC_{50}$ data for selected compounds are presented in Table 3 (4 hours) below. Note that the "Compound Number" in Table 3 corresponds to the "Compound Number" in Table 1.

TABLE 3

| Compound Number | Lipid HTRF TEAD1 $IC_{50}$ [uM] | Lipid HTRF TEAD2 $IC_{50}$ [uM] | Lipid HTRF TEAD3 $IC_{50}$ [uM] | Lipid HTRF TEAD4 $IC_{50}$ [uM] |
|---|---|---|---|---|
| 1 | 0.0053 | 0.11 | 0.18 | 0.0069 |
| 2 | 0.0033 | 0.027 | 0.029 | 0.0032 |

TABLE 3-continued

| Compound Number | Lipid HTRF TEAD1 $IC_{50}$ [uM] | Lipid HTRF TEAD2 $IC_{50}$ [uM] | Lipid HTRF TEAD3 $IC_{50}$ [uM] | Lipid HTRF TEAD4 $IC_{50}$ [uM] |
|---|---|---|---|---|
| 3 | 0.007 | 0.25 | 0.21 | 0.0079 |
| 4 | 0.023 | 0.14 | 0.27 | 0.059 |
| 5 | 0.017 | 0.31 | 0.27 | 0.037 |
| 7 | 0.3 | 0.11 | 1.2 | 0.12 |
| 8 | 0.042 | 0.039 | 2 | 0.037 |
| 10 | 0.1 | 0.18 | 0.56 | 0.049 |
| 11 | 0.023 | 0.086 | 1.3 | 0.017 |
| 13 | 0.01 | 0.33 | 0.23 | 0.0086 |
| 12 | 0.048 | 2.8 | 0.63 | 0.043 |
| 14 | 0.084 | 50 | 0.14 | 0.033 |
| 16 | 0.23 | 0.12 | 0.68 | 0.061 |
| 17 | 0.035 | 0.032 | 0.77 | 0.02 |
| 18 | 0.0068 | 0.066 | 0.1 | 0.0034 |
| 19 | 0.0029 | 0.0082 | 0.0035 | 0.0029 |
| 20 | 0.012 | 0.023 | 0.058 | 0.0167 |
| 21 | 0.0215 | 0.0072 | 0.0385 | 0.013 |
| 22 | 0.033 | 0.25 | 0.3 | 0.082 |
| 23 | 0.043 | 0.066 | 0.89 | 0.017 |
| 24 | 0.0185 | 0.13 | 0.405 | 0.0455 |
| 25 | 0.96 | 6 | 3.7 | 0.095 |
| 26 | 0.14 | 0.16 | 50 | 0.014 |
| 27 | 0.29 | 0.27 | 1.1 | 0.071 |
| 28 | 0.023 | 0.22 | 5.7 | 0.033 |
| 29 | 0.84 | 0.92 | 1.6 | 0.17 |
| 30 | 0.49 | 1.5 | 2.6 | 0.18 |
| 31 | 0.035 | 0.032 | 0.062 | 0.0255 |
| 32 | 0.013 | 0.057 | 0.22 | 0.025 |
| 33 | 0.025 | 0.11 | 17 | 0.011 |
| 34 | 0.023 | 0.34 | 50 | 0.039 |
| 35 | 0.017 | 0.17 | 0.64 | 0.014 |
| 36 | 0.0092 | 0.12 | 0.5 | 0.0058 |
| 37 | 0.0069 | 0.014 | 0.033 | 0.0032 |
| 38 | 0.18 | 0.1 | 50 | 0.039 |
| 39 | 0.042 | 0.019 | 0.84 | 0.0054 |
| 40 | 0.016 | 0.048 | 0.066 | 0.013 |
| 41 | 0.64 | 0.064 | 50 | 0.023 |
| 42 | 0.02 | 0.2 | 0.027 | 0.025 |
| 43 | 0.013 | 0.054 | 0.78 | 0.0046 |
| 44 | 0.22 | 0.39 | 0.45 | 0.12 |
| 45 | 0.25 | 1.5 | 50 | 0.34 |
| 46 | 0.05 | 0.15 | 2.1 | 0.013 |
| 47 | 0.033 | 0.1 | 2 | 0.011 |
| 48 | 0.0035 | 0.0023 | 0.0048 | 0.00088 |
| 49 | 0.00305 | 0.0027 | 0.00425 | 0.00215 |
| 50 | 0.024 | 0.075 | 0.2 | 0.0095 |
| 51 | 0.032 | 0.12 | 0.51 | 0.015 |
| 52 | 0.014 | 0.045 | 3.5 | 0.0034 |
| 53 | 0.045 | 0.036 | 50 | 0.0035 |
| 54 | 0.49 | 0.73 | 10 | 0.86 |
| 55 | 0.017 | 0.12 | 0.16 | 0.012 |
| 56 | 0.039 | 0.085 | 50 | 0.011 |
| 57 | 0.036 | 0.037 | 0.35 | 0.0051 |
| 58 | 0.038 | 0.07 | 50 | 0.0096 |
| 59 | 0.028 | 0.033 | 0.052 | 0.013 |
| 60 | 0.025 | 0.008 | 0.02 | 0.0084 |
| 61 | 0.9 | 2.3 | 50 | 0.94 |
| 62 | 0.058 | 0.071 | 0.86 | 0.013 |
| 63 | 0.135 | 0.1235 | 10.5 | 0.0785 |
| 64 | 0.023 | 0.17 | 1.3 | 0.021 |
| 65 | 0.15 | 0.099 | 27 | 0.031 |
| 66 | 0.044 | 0.18 | 0.34 | 0.033 |
| 67 | 0.1005 | 0.365 | 50 | 0.031 |
| 68 | 0.071 | 0.55 | 0.98 | 0.14 |
| 69 | 0.0061 | 0.014 | 0.051 | 0.0054 |
| 70 | 0.017 | 0.037 | 0.14 | 0.0036 |
| 71 | 0.032 | 0.0053 | 0.043 | 0.016 |
| 72 | 0.032 | 0.0075 | 0.019 | 0.0056 |
| 73 | 0.87 | 0.43 | 0.29 | 0.033 |
| 74 | 0.032 | 0.14 | 4.1 | 0.0048 |
| 75 | 0.045 | 0.019 | 1.1 | 0.0052 |
| 76 | 0.062 | 0.16 | 8.2 | 0.0074 |
| 77 | 0.093 | 0.04 | 5.7 | 0.065 |
| 78 | 0.18 | 2.8 | 13 | 0.15 |
| 79 | 0.019 | 0.06 | 0.02 | 0.0068 |
| 80 | 0.018 | 0.068 | 0.029 | 0.016 |
| 81 | 0.032 | 0.024 | 0.24 | 0.011 |

TABLE 3-continued

| Compound Number | Lipid HTRF TEAD1 $IC_{50}$ [uM] | Lipid HTRF TEAD2 $IC_{50}$ [uM] | Lipid HTRF TEAD3 $IC_{50}$ [uM] | Lipid HTRF TEAD4 $IC_{50}$ [uM] |
|---|---|---|---|---|
| 82 | 0.031 | 0.39 | 0.27 | 0.0048 |
| 83 | 0.12 | 0.093 | 50 | 0.047 |
| 84 | 0.023 | 0.089 | 50 | 0.0063 |
| 85 | 0.14 | 0.48 | 15 | 0.17 |
| 86 | 0.0036 | 0.0032 | 0.0097 | 0.0024 |
| 87 | 0.023 | 0.19 | 0.52 | 0.033 |
| 88 | 0.08 | 0.15 | 2.1 | 0.043 |
| 89 | 0.011 | 0.0036 | 0.0087 | 0.0029 |
| 90 | 0.19 | 0.075 | 3.7 | 0.0099 |
| 91 | 0.044 | 0.066 | 41 | 0.0285 |
| 92 | 0.11 | 0.78 | 13 | 0.052 |
| 93 | 0.17 | 0.71 | 0.57 | 0.022 |
| 94 | 0.015 | 0.029 | 0.048 | 0.011 |
| 95 | 0.052 | 0.027 | 0.092 | 0.015 |
| 96 | 0.01 | 0.03 | 0.038 | 0.0037 |
| 97 | 0.078 | 0.52 | 0.57 | 0.058 |
| 98 | 0.032 | 0.075 | 0.46 | 0.011 |
| 99 | 0.0033 | 0.028 | 0.087 | 0.005 |
| 100 | 0.48 | 0.52 | 0.72 | 0.1 |
| 101 | 0.12 | 0.036 | 7.7 | 0.022 |
| 102 | 0.01 | 0.0035 | 0.0088 | 0.0033 |
| 103 | 0.18 | 3.35 | 50 | 0.0825 |
| 104 | 0.17 | 0.6 | 0.66 | 0.054 |
| 105 | 1 | 0.62 | 50 | 0.45 |
| 106 | 0.0155 | 0.061 | 0.935 | 0.00675 |
| 107 | 0.28 | 0.96 | 50 | 0.036 |
| 108 | 0.09 | 0.12 | 0.14 | 0.031 |
| 109 | 0.023 | 0.0078 | 0.018 | 0.00515 |
| 110 | 0.019 | 0.008 | 0.017 | 0.0043 |
| 111 | 0.016 | 0.062 | 0.29 | 0.028 |
| 112 | 0.0093 | 0.0038 | 0.0089 | 0.0032 |
| 113 | 0.019 | 0.0065 | 0.02 | 0.0045 |
| 114 | 0.014 | 0.0046 | 0.016 | 0.0029 |
| 115 | 0.024 | 0.006 | 0.011 | 0.0048 |
| 116 | 0.027 | 0.075 | 14 | 0.011 |
| 117 | 0.16 | 0.044 | 16 | 0.033 |
| 118 | 0.016 | 0.097 | 50 | 0.0043 |
| 119 | 0.16 | 0.25 | 0.55 | 0.11 |
| 120 | 0.027 | 0.16 | 0.27 | 0.055 |
| 121 | 0.021 | 0.068 | 0.35 | 0.046 |
| 122 | 0.19 | 2 | 21 | 0.039 |
| 123 | 0.016 | 0.18 | 1 | 0.0042 |
| 124 | 0.041 | 0.2 | 0.93 | 0.0099 |
| 125 | 0.8 | 0.87 | 1.7 | 0.044 |
| 126 | 0.022 | 0.12 | 50 | 0.0044 |
| 127 | 0.0079 | 0.017 | 0.013 | 0.0033 |
| 128 | 0.0065 | 0.012 | 0.072 | 0.0036 |
| 129 | 0.11 | 0.02 | 0.2 | 0.043 |
| 130 | 0.38 | 1 | 5.4 | 0.54 |
| 131 | 0.29 | 0.089 | 2.9 | 0.03 |
| 132 | 0.012 | 0.01 | 0.026 | 0.0039 |
| 133 | 0.22 | 0.34 | 2.2 | 0.057 |
| 134 | 0.014 | 0.043 | 0.36 | 0.022 |
| 135 | 0.39 | 0.068 | 34 | 0.099 |
| 136 | 0.33 | 0.68 | 50 | 0.038 |
| 137 | 0.072 | 0.36 | 5.2 | 0.026 |
| 138 | 0.036 | 0.29 | 2.8 | 0.0067 |
| 139 | 0.031 | 0.026 | 0.6 | 0.012 |
| 140 | 0.23 | 0.72 | 4.4 | 0.44 |
| 141 | 0.027 | 0.054 | 2 | 0.0069 |
| 142 | 0.15 | 0.33 | 50 | 0.009 |
| 143 | 0.016 | 0.065 | 50 | 0.065 |
| 144 | 0.56 | 0.15 | 50 | 0.055 |
| 145 | 0.14 | 0.071 | 5.5 | 0.049 |
| 146 | 0.04 | 0.066 | 2.8 | 0.028 |
| 147 | 50 | 50 | 50 | 36 |
| 148 | 0.017 | 0.09 | 0.28 | 0.014 |
| 149 | 0.91 | 50 | 50 | 4.2 |
| 150 | 0.56 | 1.2 | 50 | 0.46 |
| 151 | 0.68 | 0.63 | 50 | 0.57 |
| 152 | 0.22 | 0.81 | 1.2 | 0.14 |
| 153 | 0.58 | 0.29 | 50 | 0.27 |
| 154 | 0.044 | 0.036 | 1.2 | 0.022 |
| 155 | 0.32 | 0.35 | 6.9 | 0.16 |
| 156 | 0.033 | 0.025 | 0.74 | 0.0078 |
| 157 | 0.026 | 0.0057 | 0.017 | 0.004 |

TABLE 3-continued

| Compound Number | Lipid HTRF TEAD1 $IC_{50}$ [uM] | Lipid HTRF TEAD2 $IC_{50}$ [uM] | Lipid HTRF TEAD3 $IC_{50}$ [uM] | Lipid HTRF TEAD4 $IC_{50}$ [uM] |
|---|---|---|---|---|
| 158 | 0.051 | 0.69 | 4.3 | 0.064 |
| 159 | 0.045 | 0.0057 | 0.24 | 0.0085 |
| 160 | 0.076 | 0.015 | 1.2 | 0.043 |
| 161 | 0.027 | 0.0034 | 0.15 | 0.0037 |
| 162 | 0.036 | 0.01 | 1 | 0.0069 |
| 163 | 0.011 | 0.0083 | 0.01 | 0.0053 |
| 164 | 0.04786 | 0.1289 | 2.043 | 0.032 |
| 165 | 0.12 | 0.04 | 50 | 0.1 |
| 166 | 0.31 | 0.33 | 50 | 0.32 |
| 167 | 0.057 | 0.21 | 1.7 | 0.035 |
| 168 | 0.14 | 1.1 | 50 | 0.049 |
| 169 | 0.09775 | 0.135 | 26.325 | 0.0455 |
| 170 | 0.1205 | 0.355 | 26.625 | 0.09275 |
| 171 | 0.06 | 0.33 | 0.81 | 0.029 |
| 172 | 0.47 | 0.81 | 19 | 0.15 |
| 173 | 0.086 | 0.3825 | 26.175 | 0.0525 |
| 174 | 0.065 | 0.56 | 50 | 0.1 |
| 175 | 0.062 | 0.42 | 50 | 0.045 |
| 176 | 0.046 | 0.8 | 50 | 0.077 |
| 177 | 0.086 | 0.89 | 50 | 0.12 |
| 178 | 0.087 | 0.86 | 50 | 0.2 |
| 179 | 0.032 | 0.65 | 50 | 0.017 |
| 180 | 0.043 | 0.16 | 50 | 0.11 |
| 181 | 0.024 | 0.062 | 50 | 0.037 |
| 182 | 0.025 | 0.13 | 0.44 | 0.013 |
| 183 | 0.18 | 1.8 | 1.1 | 0.11 |
| 184 | 0.14 | 2.3 | 0.79 | 0.1 |
| 185 | 0.057 | 0.12 | 0.26 | 0.031 |
| 186 | 0.27 | 0.43 | 0.255 | 0.0525 |
| 187 | 0.091 | 1.2 | 0.95 | 0.055 |
| 188 | 0.0072 | 0.084 | 0.15 | 0.0073 |

Example 183 A: Effects of Test Article on Cloned hNav1.5 Sodium Channels Expressed in Mammalian Cells Chinese hamster ovary (CHO) cells expressing cloned hNav1.5 sodium channels (hNav1.5, encoded by the human SCNSA gene) are responsible for INa sodium channel current. From a 10 mM stock solution, test article was diluted to make a 1 mM, 0.1 mM, and 0.01 mM sub stock, which were stored frozen. All chemicals used in solution preparation were purchased from Sigma-Aldrich (St. Louis, MO) and were of ACS reagent grade purity or higher. Stock solutions of the test articles and the positive control were prepared in dimethyl sulfoxide (DMSO) and stored frozen. Test article and positive control concentrations were prepared fresh daily by diluting stock solutions into a HEPES-buffered physiological saline (HB-PS) solution (composition in mM): NaCl, 137; KCl, 4.0; CaCl2, 1.8; MgCl2, 1; HEPES, 10; Glucose, 10; pH adjusted to 7.4 with NaOH (refrigerated until use). All test and control solutions contained either 0.3% DMSO (10 μM) or 1.0% DMSO (IC50 curve). Each test article formulation was sonicated (Model 2510/5510, Branson Ultrasonics, Danbury, CT) at room temperature for 20 minutes to facilitate dissolution. In preparation for the recording session, a glass-lined 96-well compound plate was loaded with the appropriate amounts of test and control solutions and placed in the plate well of the QPatch HT® (Sophion Bioscience A/S, Denmark), an automatic parallel patch clamp system. Test articles were evaluated either at 10 μM for the 2 pt assessment of NaV1.5 channel inhibitor, or at 0.01, 0.1, 1, 10, 30, and 100 μM for generation of an IC50 value. Each concentration was tested in at least two cells (n≥2). Mean % inhibition is reported. Data as shown in Table 4 indicated reduced off-target inhibition by the TEAD inhibitors.

TABLE 4

| Compound Number | $NaV_{1.5}$ (Phasic) 10 uM concentration % inhibition | $NaV_{1.5}$ (Phasic) $IC_{50}$ (uM) |
|---|---|---|
| 17 (also referred to as T1) | 32.1 | |
| 20 (also referred to as T2) | 49.1 | 42.1 |

Example 184: Synthesis of Compound K1, Compound K2, Compound K3, and Compound K4

An exemplary synthesis of Compound K1 is described in US2018/0334454A1 (see, e.g., Example 41 on pages 210-212 of US2018/0334454A1).

An exemplary synthesis of Compound K2 is described in WO2021/124222A1 (see, e.g., Method 1 Synthetic Scheme as described on pages 111 to 114 of WO2021/124222A1).

An exemplary synthesis of Compound K3 is described in US2019/0144444A1 (see, e.g., Example 478 on pages 668-669 of US2019/0144444A1).

An exemplary synthesis of Compound K4 is described in US2021/0230142A9. For example, method of making Compound K4 can be found in Example 17a & 17b on pages 130 to 135 of US2021/0230142A9.

Any references detailed in this section are incorporated herein by reference in their entirety, and specifically with respect to methods of making compounds detailed therein.

Preparation of 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2 (1H)-one (Compound K1/Example 41 of US2018/0334454A1)

Step 1: 2,6-Dichloro-5-fluoronicotinamide (Intermediate S)

To a mixture of 2,6-dichloro-5-fluoronicotinic acid (4.0 g, 19.1 mmol, AstaTech Inc., Bristol, Pa.) in dichloromethane (48 mL) was added oxalyl chloride (2M solution in DCM, 11.9 mL, 23.8 mmol), followed by a catalytic amount of DMF (0.05 mL). The reaction was stirred at room temperature overnight and then was concentrated. The residue was dissolved in 1,4-dioxane (48 mL) and cooled to 0° C. Ammonium hydroxide solution (28.0-30% NH3 basis, 3.6 mL, 28.6 mmol) was added slowly via syringe. The resulting mixture was stirred at 0° C. for 30 min and then was concentrated. The residue was diluted with a 1:1 mixture of EtOAc/Heptane and agitated for 5 min, then was filtered. The filtered solids were discarded, and the remaining mother liquor was partially concentrated to half volume and filtered. The filtered solids were washed with heptane and dried in a reduced-pressure oven (45° C.) overnight to provide 2,6-dichloro-5-fluoronicotinamide. $^1H$ NMR (400 MHz, DMSO-$d_6$) δ ppm 8.23 (d, J=7.9 Hz, 1H) 8.09 (br s, 1H) 7.93 (br s, 1H). m/z (ESI, +ve ion): 210.9 $(M+H)^+$.

Step 2: 2,6-Dichloro-5-fluoro-N-((2-isopropyl-4-methylpyridin-3-yl)carbamoyl)nicotinamide To an ice-cooled slurry of 2,6-dichloro-5-fluoronicotinamide (Intermediate S, 5.0 g, 23.9 mmol) in THF (20 mL) was added oxalyl chloride (2 M solution in DCM, 14.4 mL, 28.8 mmol) slowly via syringe. The resulting mixture was heated at 75° C. for 1 h, then heating was stopped, and the reaction was concentrated to half volume. After cooling to 0° C., THF (20 mL) was added, followed by a solution of 2-isopropyl-4-methylpyridin-3-amine (Intermediate R, 3.59 g, 23.92 mmol) in THF (10 mL), dropwise via cannula. The resulting mixture was stirred at 0° C. for 1 h and then was quenched with a 1:1 mixture of brine and saturated aqueous ammonium chloride. The mixture was extracted with EtOAc (3×) and the combined organic layers were dried over anhydrous sodium sulfate and concentrated to provide 2,6-dichloro-5-fluoro-N-((2-isopropyl-4-methylpyridin-3-yl) carbamoyl)nicotinamide. This material was used without further purification in the following step. m/z (ESI, +ve ion): 385.1 $(M+H)^+$.

Step 3: 7-Chloro-6-fluoro-1-(2-isopropyl-4-methyl-pyridin-3-yl)pyrido[2,3-d]pyrimidine-2,4 (1H,3H)-dione To an ice-cooled solution of 2,6-dichloro-5-fluoro-N-((2-isopropyl-4-methylpyridin-3-yl)carbamoyl)nicotinamide (9.2 g, 24.0 mmol) in THF (40 mL) was added KHMDS (1 M solution in THF, 50.2 mL, 50.2 mmol) slowly via syringe. The ice bath was removed and the resulting mixture was stirred for 40 min at room temperature. The reaction was quenched with saturated aqueous ammonium chloride and extracted with EtOAc (3×). The combined organic layers were dried over anhydrous sodium sulfate and concentrated. The residue was purified by silica gel chromatography (eluent: 0-50% 3:1 EtOAc-EtOH/heptane) to provide 7-chloro-6-fluoro-1-(2-isopropyl-4-methylpyridin-3-yl) pyrido[2,3-d]pyrimidine-2,4 (1H,3H)-dione. $^1$H NMR (400 MHz, DMSO-$d_6$) δ ppm 12.27 (br s, 1H), 8.48-8.55 (m, 2H), 7.29 (d, J=4.8 Hz, 1H), 2.87 (quin, J=6.6 Hz, 1H), 1.99-2.06 (m, 3H), 1.09 (d, J=6.6 Hz, 3H), 1.01 (d, J=6.6 Hz, 3H). $^1$H NMR (376 MHz, DMSO-$d_6$) δ: −126.90 (s, 1F). m/z (ESI, +ve ion): 349.1 $(M+H)^+$.

Step 4: 4,7-Dichloro-6-fluoro-1-(2-isopropyl-4-methylpyridin-3-yl)pyrido[2,3-d]pyrimidin-2 (1H)-one To a solution of 7-chloro-6-fluoro-1-(2-isopropyl-4-methylpyridin-3-yl)pyrido[2,3-d]pyrimidine-2,4 (1H,3H)-dione (4.7 g, 13.5 mmol) and DIPEA (3.5 mL, 20.2 mmol) in acetonitrile (20 mL) was added phosphorus oxychloride (1.63 mL, 17.5 mmol), dropwise via syringe. The resulting mixture was heated at 80° C. for 1 h, and then was cooled to room temperature and concentrated to provide 4,7-dichloro-6-fluoro-1-(2-isopropyl-4-methylpyridin-3-yl)pyrido [2,3-d]pyrimidin-2 (1H)-one. This material was used without further purification in the following step. m/z (ESI, +ve ion): 367.1 $(M+H)^+$.

Step 5: (5)-tert-Butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate To an ice-cooled solution of 4,7-dichloro-6-fluoro-1-(2-isopropyl-4-methylpyridin-3-yl)pyrido[2,3-d]pyrimidin-2 (1H)-one (13.5 mmol) in acetonitrile (20 mL) was added DIPEA (7.1 mL, 40.3 mmol), followed by (S)-4-N-Boc-2-methyl piperazine (3.23 g, 16.1 mmol, Combi-Blocks, Inc., San Diego, Calif., USA). The resulting mixture was warmed to room temperature and stirred for 1 h, then was diluted with cold saturated aqueous sodium bicarbonate solution (200 mL) and EtOAc (300 mL). The mixture was stirred for an additional 5 min, the layers were separated, and the aqueous layer was extracted with more EtOAc (1×). The combined organic layers were dried over anhydrous sodium sulfate and concentrated. The residue was purified by silica gel chromatography (eluent: 0-50% EtOAc/heptane) to provide (5)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate. m/z (ESI, +ve ion): 531.2 $(M+H)^+$.

Step 6: (35)-tert-Butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate A mixture of (5)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (4.3 g, 8.1 mmol), potassium trifluoro(2-fluoro-6-hydroxyphenyl) borate (Intermediate Q, 2.9 g, 10.5 mmol), potassium acetate (3.2 g, 32.4 mmol) and [1,1'-bis(diphenylphosphino)ferrocene]dichloropalladium(II), complex with dichloromethane (661 mg, 0.81 mmol) in 1,4-dioxane (80 mL) was degassed with nitrogen for 1 min. De-oxygenated water (14 mL) was added, and the resulting mixture was heated at 90° C. for 1 h. The reaction was allowed to cool to room temperature, quenched with half-saturated aqueous sodium bicarbonate, and extracted with EtOAc (2×) and DCM (1×). The combined organic layers were dried over anhydrous sodium sulfate and concentrated. The residue was purified by silica gel chromatography (eluent: 0-60% 3:1 EtOAc-EtOH/heptane) to provide (3S)-tert-butyl 4-(6-fluoro-7-(2-fluoro-6-hydroxy phenyl)-1-(2-isopropyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-$d_6$) δ ppm 10.19 (br s, 1H), 8.38 (d, J=5.0 Hz, 1H), 8.26 (dd, J=12.5, 9.2 Hz, 1H), 7.23-7.28 (m, 1H), 7.18 (d, J=5.0 Hz, 1H), 6.72 (d, J=8.0 Hz, 1H), 6.68 (t, J=8.9 Hz, 1H), 4.77-4.98 (m, 1H), 4.24 (brt, J=14.2 Hz, 1H), 3.93-4.08 (m, 1H), 3.84 (br d, J=12.9 Hz, 1H), 3.52-3.75 (m, 1H), 3.07-3.28 (m, 1H), 2.62-2.74 (m, 1H), 1.86-1.93 (m, 3H), 1.43-1.48 (m, 9H), 1.35 (dd, J=10.8, 6.8 Hz, 3H), 1.26-1.32 (m, 1H), 1.07 (dd, J=6.6, 1.7 Hz, 3H), 0.93 (dd, J=6.6, 2.1 Hz, 3H). $^1$H NMR (376 MHz, DMSO-$d_6$) δ: −115.65 (s, 1F), −128.62 (s, 1F). m/z (ESI, +ve ion): 607.3 $(M+H)^+$.

Step 7: 6-Fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyflpyrido[2,3-d] pyrimidin-2 (1H)-one Trifluoroacetic acid (25 mL, 324 mmol) was added to a solution of (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (6.3 g, 10.4 mmol) in DCM (30 mL). The resulting mixture was stirred at room temperature for 1 h and then was concentrated. The residue was dissolved in DCM (30 mL), cooled to 0° C., and sequentially treated with DIPEA (7.3 mL, 41.7 mmol) and a solution of acryloyl chloride (0.849 mL, 10.4 mmol) in DCM (3 mL; added dropwise via syringe). The reaction was stirred at 0° C. for 10 min, then was quenched with half-saturated aqueous sodium bicarbonate and extracted with DCM (2×). The combined organic layers were dried over anhydrous sodium sulfate and concentrated. The residue was purified by silica gel chromatography (eluent: 0-100% 3:1 EtOAc-EtOH/heptane) to provide 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2 (1H)-one (Compound K1). $^1$H NMR (400 MHz, DMSO-$d_6$) δ ppm 10.20 (s, 1H), 8.39 (d, J=4.8 Hz, 1H), 8.24-8.34 (m, 1H), 7.23-7.32 (m, 1H), 7.19 (d, J=5.0 Hz, 1H), 6.87 (td, J=16.3, 11.0 Hz, 1H), 6.74 (d, J=8.6 Hz, 1H), 6.69 (t, J=8.6 Hz, 1H), 6.21 (br d, J=16.2 Hz, 1H), 5.74-5.80 (m, 1H), 4.91 (br s, 1H), 4.23-4.45 (m, 2H), 3.97-4.21 (m, 1H), 3.44-3.79 (m, 2H), 3.11-3.31 (m, 1H), 2.67-2.77 (m, 1H), 1.91 (s, 3H), 1.35 (d, J=6.8 Hz, 3H), 1.08 (d, J=6.6 Hz, 3H), 0.94 (d, J=6.8 Hz, 3H). $^1$H NMR (376 MHz, DMSO-$d_6$) δ ppm −115.64 (s, 1F), −128.63 (s, 1F). m/z (ESI, +ve ion): 561.2 (M+H)$^+$.

Preparation of a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one and a(S)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one (Compound K2/Example 1 of WO2021/124222A1)

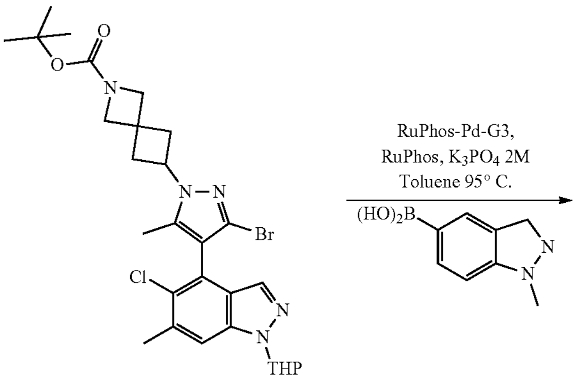

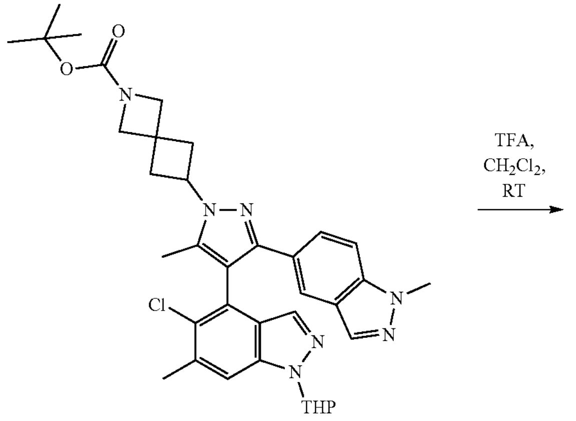

-continued

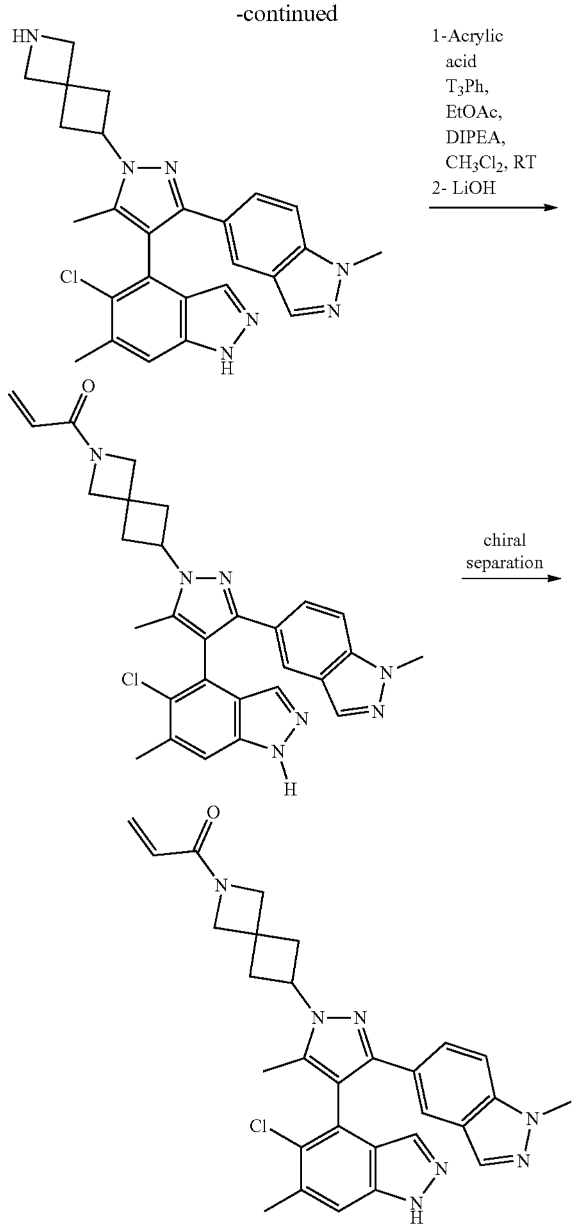

first eluting isomer + second eluting isomer

Step 1: Tert-butyl 6-(4-(5-chloro-6-methyl-1-(tetrahydro-2H-pyran-2-yl)-1H-indazol-4-yl)-5-methyl-3-(1-methyl-1H-indazol-5-yl)-1H-pyrazol-1-yl)-2-azaspiro[3.3]heptane-2-carboxylate In a 500 mL flask, tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 10 g, 16.5 mmol), (1-methyl-1H-indazol-5-yl)boronic acid (6.12 g, 33.1 mmol), RuPhos (1.16 g, 2.48 mmol) and RuPhos-Pd-G3 (1.66 g, 1.98 mmol) were suspended in toluene (165 mL) under argon. $K_3PO_4$ (2M, 24.8 mL, 49.6 mmol) was added and the reaction mixture was placed in a preheated oil bath (95° C.) and stirred for 45 min. The reaction mixture was poured into a sat. aq. $NH_4Cl$ solution and was extracted with EtOAc (×3). The combined organic layers were washed with a sat. aq.

$NaHCO_3$ solution, dried (phase separator) and concentrated under reduced pressure. The crude residue was diluted with THE (50 mL), SiliaMetS® Thiol (15.9 mmol) was added and the mixture swirled for 1 h at 40° C. The mixture was filtered, the filtrate was concentrated and the crude residue was purified by normal phase chromatography (eluent: MeOH in $CH_2Cl_2$ from 0 to 2%), the purified fractions were again purified by normal phase chromatography (eluent: MeOH in $CH_2Cl_2$ from 0 to 2%) to give the title compound as a beige foam. UPLC-MS-3: Rt=1.23 min; MS m/z $[M+H]^+$; 656.3/658.3.

Step 2: 5-Chloro-6-methyl-4-(5-methyl-3-(1-methyl-1H-indazol-5-yl)-1-(2-azaspiro[3.3]heptan-6-yl)-1H-pyrazol-4-yl)-1H-indazole TFA (19.4 mL, 251 mmol) was added to a solution of tert-butyl 6-(4-(5-chloro-6-methyl-1-(tetrahy dro-2H-pyran-2-yl)-1H-indazol-4-yl)-5-methyl-3-(1-methyl-1H-indazol-5-yl)-1H-pyrazol-1-yl)-2-azaspiro[3.3]heptane-2-carboxylate (Step 1, 7.17 g, 10.0 mmol) in $CH_2Cl_2$ (33 mL). The reaction mixture was stirred at RT under nitrogen for 1.5 h. The RM was concentrated under reduced pressure to give the title compound as a trifluoroacetate salt, which was used without purification in the next step. UPLC-MS-3: Rt=0.74 min; MS m/z $[M+H]^+$; 472.3/474.3.

Step 3: 1-(6-(4-(5-Chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one A mixture of acrylic acid (0.69 mL, 10.1 mmol), propylphosphonic anhydride (50% in EtOAc, 5.94 mL, 7.53 mmol) and DIPEA (21.6 mL, 126 mmol) in $CH_2Cl_2$ (80 mL) was stirred for 20 min at RT and then added (dropping funnel) to an ice-cooled solution of 5-chloro-6-methyl-4-(5-methyl-3-(1-methyl-1H-indazol-5-yl)-1-(2-azaspiro[3.3]heptan-6-yl)-1H-pyrazol-4-yl)-1H-indazole trifluoroacetate (Step 2, 6.30 mmol) in $CH_2Cl_2$ (40 mL). The reaction mixture was stirred at RT under nitrogen for 15 min. The RM was poured into a sat. aq. $NaHCO_3$ solution and extracted with $CH_2Cl_2$ (×3). The combined organic layers were dried (phase separator) and concentrated. The crude residue was diluted with THF (60 mL) and LiOH (2N, 15.7 mL, 31.5 mmol) was added. The mixture was stirred at RT for 30 min until disappearance (UPLC) of the side product resulting from the reaction of the acryloyl chloride with the free NH group of the indazole then was poured into a sat. aq. $NaHCO_3$ solution and extracted with $CH_2Cl_2$ (3×). The combined organic layers were dried (phase separator) and concentrated. The crude residue was purified by normal phase chromatography (eluent: MeOH in $CH_2Cl_2$ from 0 to 5%) to give the title compound. The isomers were separated by chiral SFC (C-SFC-1; mobile phase: $CO_2$/[IPA+0.1% $Et_3N$]: 69/31) to give Example 1a: a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl) prop-2-en-1-one as the second eluting peak (white powder): $^1H$ NMR (600 MHz, DMSO-$d_6$) δ 13.1 (s, 1H), 7.89 (s, 1H), 7.59 (s, 1H), 7.55 (s, 1H), 7.42 (m, 2H), 7.30 (d, 1H), 6.33 (m, 1H), 6.12 (m, 1H), 5.68 (m, 1H), 4.91 (m, 1H), 4.40 (s, 1H), 4.33 (s, 1H), 4.11 (s, 1H), 4.04 (s, 1H), 3.95 (s, 3H), 2.96-2.86 (m, 2H), 2.83-2.78 (m, 2H), 2.49 (s, 3H), 2.04 (s, 3H); UPLC-MS-4: Rt=4.22 min; MS m/z $[M+H]^+$ 526.3/528.3: C-SFC-3 (mobile phase: $CO_2$/[IPA+0.1% $Et_3N$]: 67/33): Rt=2.23 min. The compound of Example 1a of WO2021/124222A1 is also referred to as "Compound X" of WO2021/124222A1.

The other isomer Example 1b of WO2021/124222A1; a(S)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one was obtained as the first eluting peak: C-SFC-3 (mobile phase: $CO_2$/[IPA+0.1% $Et_3N$]: 67/33): Rt=1.55 min.

Preparation of 2-((S)-4-(7-(8-chloronaphthalen-1-yl)-2-(((S)-1-methylpyrrolidin-2-yl)methoxy)-5,6,7,8-tetrahy dropyrido[3,4-d]pyrimidin-4-yl)-1-(2-fluoroacryloyl)piperazin-2-yl)acetonitrile (Compound K3/Example 478 of US2019/0144444A1)

2-fluoroprop-2-enoyl chloride

To a solution of 2-fluoroprop-2-enoic acid (400 mg, 4.44 mmol, 1 eq) in DCM (4 mL) was added $(COCl)_2$ (846 mg, 6.66 mmol, 583 uL, 1.5 eq) and DMF (32.5 mg, 444 umol, 34.2 uL, 0.1 eq). The mixture was stirred at 25° C. for 2 hrs. The reaction mixture was concentrated under reduced pressure to remove a part of solvent and give a residue in DCM. Compound 2-fluoroprop-2-enoyl chloride (400 mg, crude) was obtained as a yellow liquid and used into the next step without further purification.

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, 528 umol, 1 eq, HCl) in DCM (5 mL) was added DIEA (1.73 g, 13.4 mmol, 2.33 mL, 25.4 eq) and 2-fluoroprop-2-enoyl chloride (286 mg, 2.64 mmol, 5 eq) in DCM (5 mL). The mixture was stirred at 0° C. for 1 hour. The reaction mixture was concentrated under reduced pressure to give a residue. The residue was purified by column chromatography ($Al_2O_3$, Dichloromethane/Methanol=10/1 to 10/1). The residue was purified by prep-HPLC (column: Gemini 150*25 5u; mobile phase: [water (0.05% ammonia hydroxide v/v)-ACN]; B %: 55%-85%, 12 min). The residue was purified by prep-HPLC (column: Phenomenex Synergi C18 150*30 mm*4 um; mobile phase: [water (0.225% FA)-ACN]; B %: 20%-50%, 10.5 min). The residue was concentrated under reduced pressure to remove ACN, and then lyophlization. Title compound 2-((S)-4-(7-(8-chloronaphthal en-1-yl)-2-(((S)-1-methylpyrrolidin-2-yl) methoxy)-5,6,7,8-tetrahydropyrido[3,4-d]pyrimidin-4-yl)-1-(2-fluoroacryloyl)piperazin-2-yl)acetonitrile (Compound K3/EXAMPLE 478 of US2019/0144444A1, 24.1 mg, 36.7 umol, 7% yield, 99.1% purity, FA) was obtained as a brown solid.

SFC condition: "AD—3S_3_5_40_3ML Column: Chiralpak AD—3 100×4.6 mm I.D., 3 um Mobile phase: methanol (0.05% DEA) in $CO_2$ from 5% to 40% Flow rate: 3 mL/min Wavelength: 220 nm".

$^1H$ NMR (400 MHz, Acetic) 8=7.82 (d, J=8.0 Hz, 1H), 7.69 (d, J=8.0 Hz, 1H), 7.56 (d, J=7.6 Hz, 1H), 7.49 (t, J=7.6 Hz, 1H), 7.41-7.30 (m, 2H), 5.58-5.25 (m, 2H), 5.17-4.59 (m, 4H), 4.57-4.28 (m, 3H), 4.24-3.78 (m, 4H), 3.67-3.13

(m, 7H), 3.08 (br d, J=2.4 Hz, 3H), 2.98 (br d, J=6.4 Hz, 1H), 2.83-2.61 (m, 1H), 2.45-2.29 (m, 1H), 2.24-2.08 (m, 3H).

Preparation of 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4/Example 17a&17b of US2021/0230142A9) and 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4-S)

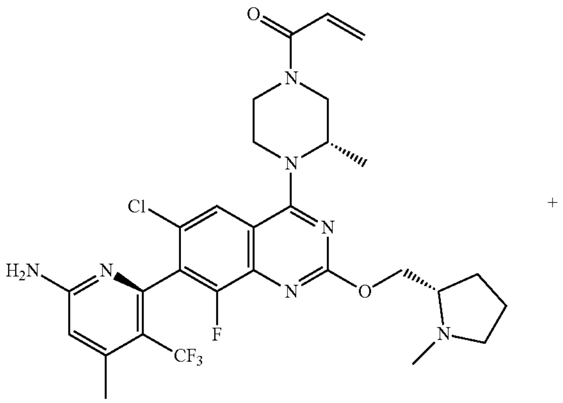

+

K4

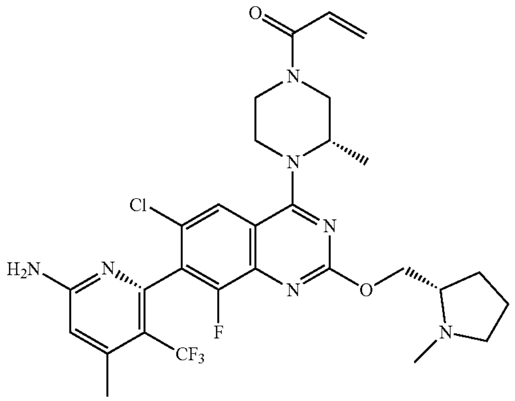

K4-S

Synthetic Route

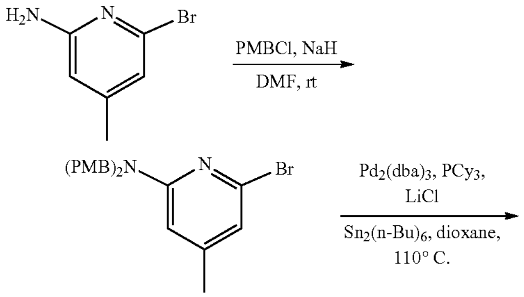

-continued

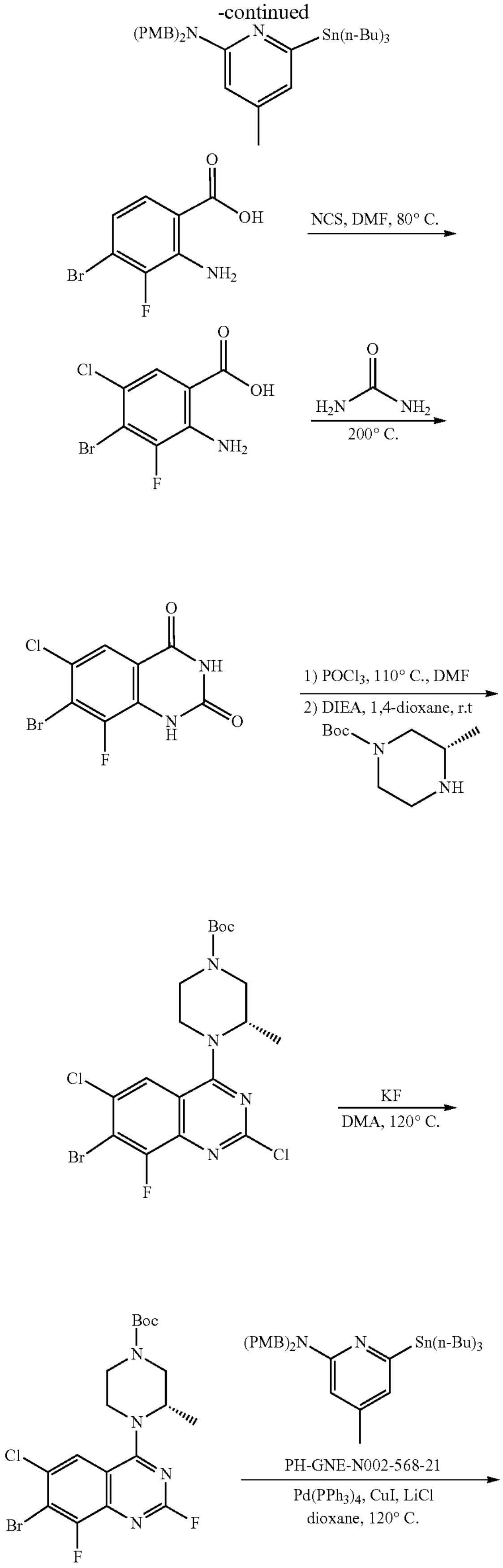

-continued

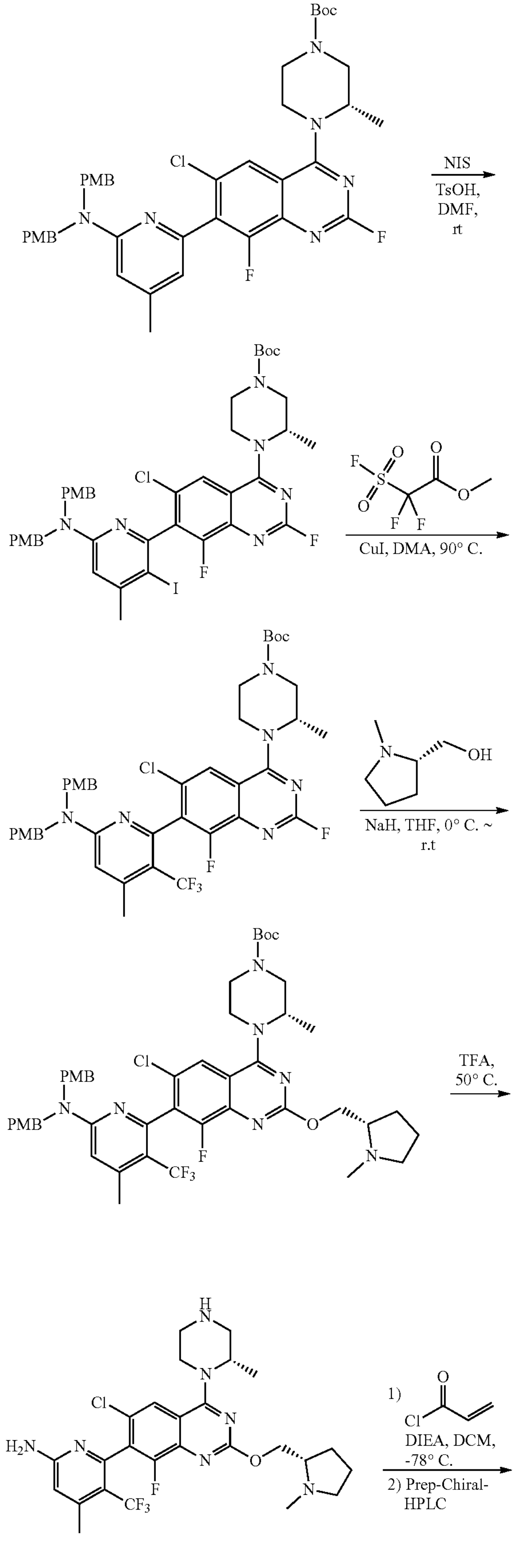

-continued

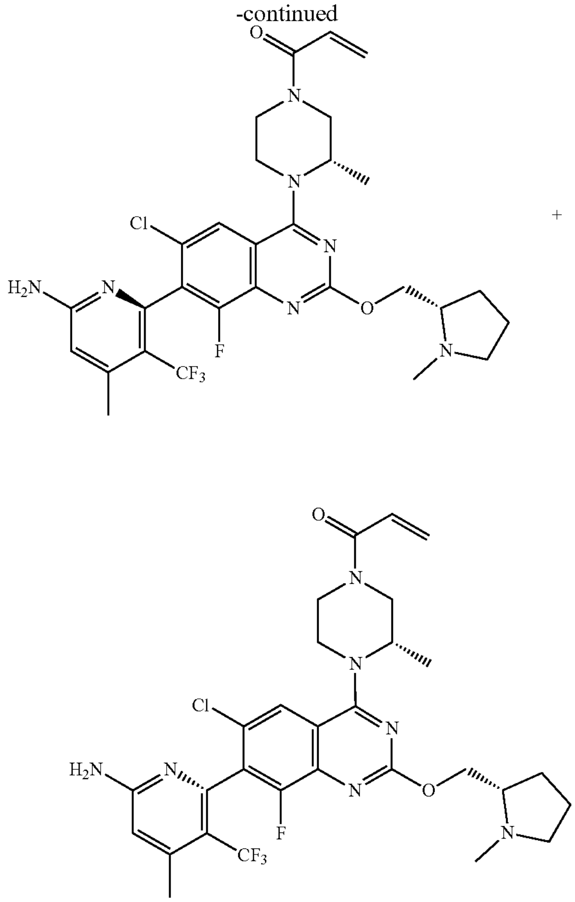

Step 1: 6-bromo-N,N-bis(4-methoxybenzyl)-4-methylpyridin-2-amine

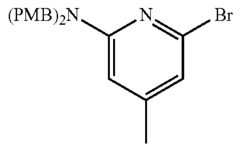

To a solution of 6-bromo-4-methylpyridin-2-amine (30.0 g, 160 mmol) in N,N-dimethylformamide (500 mL) was added slowly sodium hydride (19.0 g, 792 mmol) at 0° C. and stirred at 25° C. for 1 hour. Then 4-methoxybenzylchloride (56.0 g, 359 mmol) was added into the reaction system and stirred at 25° C. for 2 hours. After completion, the reaction system was quenched with saturated ammonium chloride solution (500 mL) and diluted with ethyl acetate (2.5 L). The mixture was washed with brine (5×500 mL) and the organic layers were combined, dried with $Na_2SO_4$, evaporated under vacuum. The residue was applied onto a silica gel column eluting with petroleum ether/ethyl acetate (15%) to afford 6-bromo-N,N-bis(4-methoxybenzyl)-4-methylpyridin-2-amine (60 g, 140 mmol, 87.5% yield) as an off-white solid. LC-MS: (ESI, m/z): 427.1 $[M+H]^+$.

Step 2: N,N-bis[(4-methoxyphenyl)methyl]-4-methyl-6-tributylstannyl-pyridin-2-amine

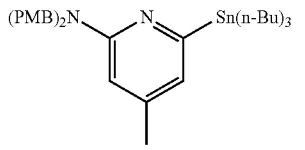

Under nitrogen, a solution of 6-bromo-N,N-bis[(4-methoxyphenyl)methyl]-4-methyl-pyridin-2-amine (35.0 g, 82 mmol), hexabutylditin (143.0 g, 247 mmol), tris(dibenzylideneacetone)dipalladium (7.53 g, 8.2 mmol), tricyclohexyl phosphine (4.6 g, 16.4 mmol) and Lithium chloride (17.3 g, 412 mmol) in 1,4-dioxane (220 mL) was stirred at 110° C. for 5 hours. After completion, the reaction system was concentrated under vacuum. The residue was purified by flash chromatography on silica gel eluting with petroleum ether/ethyl acetate (10/1) to afford N,N-bis[(4-methoxyphenyl)methyl]-4-methyl-6-tributylstarmyl-pyridin-2-amine (45 g, 71 mmol, 86.2% yield) as a red oil. LC-MS: (ESI, m/z): 639.3 $[M+H]^+$.

Step 3: 2-amino-4-bromo-5-chloro-3-fluoro-benzoic acid

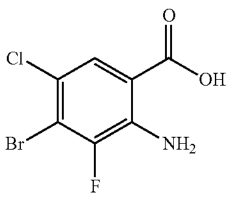 [SMILES: Nc1c(C(=O)O)cc(Cl)c(Br)c1F]

A solution of 2-amino-4-bromo-3-fluoro-benzoic acid (100.0 g, 427 mmol) and N-chlorosuccinimide (66.0 g, 494 mmol) in N,N-dimethylformamide (1 L) was stirred at 80° C. for 2 hours. After completion, the system was poured into water (2.0 L), a large amount of solids were precipitated. Then the solids were collected after filtration. The solids were washed with hot water (1 L). Then the solids were dried under infrared lamp to afford 2-amino-4-bromo-5-chloro-3-fluoro-benzoic acid (100 g, 373 mmol, 87.2% yield) as off-white solid. LC-MS: (ESI, m/z): 265.9 $[M-H]^+$.

Step 4: 7-bromo-6-chloro-8-fluoroquinazoline-2,4 (1H,3H)-dione

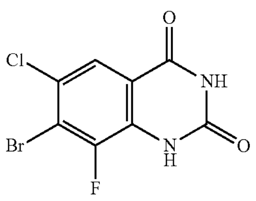 [SMILES: O=c1[nH]c(=O)c2cc(Cl)c(Br)c(F)c2[nH]1]

A solution of 2-amino-4-bromo-5-chloro-3-fluoro-benzoic acid (120.0 g, 447 mmol) in urea (806.0 g, 13.4 mol) was stirred at 200° C. for 1.5 hours. After completion, the reaction system was cooled to 80° C., and water (1.5 L) was added into the system with stirring for 20 mins. After filtration, the solids were collected and washed with hot water (1 L). Then the solids were dried under infrared lamp to afford 7-bromo-6-chloro-8-fluoroquinazoline-2,4 (1H, 3H)-dione (120 g, 409 mmol, 91.5% yield) as a light brown solid. LC-MS: (ESI, m/z): 290.9 $[M-H]^+$.

Step 5: tert-butyl (3S)-4-(7-bromo-2,6-dichloro-8-fluoroquinazolin-4-yl)-3-methylpiperazine-1-carboxylate

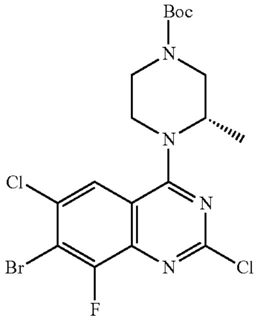 [SMILES: C[C@H]1CN(C(=O)OC(C)(C)C)CCN1c1nc(Cl)nc2c(F)c(Br)c(Cl)cc12]

A solution of 7-bromo-6-chloro-8-fluoro-quinazoline-2,4-diol (65.0 g, 222 mmol) and DMF (500.0 mg, 6.85 mmol) in $POCl_3$ (1.0 L) was stirred at 110° C. for 60 hours. After the starting material was completely, the resulting mixture was concentrated under vacuum. Then 1,4-dioxane (1.0 L), N,N-diisopropylethylamine (286.0 g, 2217 mmol) and tert-butyl (3S)-3-methyl-1-piperazinecarboxylate (90.0 g, 449 mmol) was added into the reaction system and stirred at 25° C. for 1 hours. After completion, the solvent was concentrated under vacuum. The residue was purified by flash chromatography on silica gel eluting with petroleum ether/ethyl acetate (20%) to afford tert-butyl (3S)-4-(7-bromo-2,6-dichloro-8-fluoroquinazolin-4-yl)-3-methylpiperazine-1-carboxylate (65 g, 132 mmol, 59.4% yield) as a yellow solid. LC-MS: (ESI, m/z): 493.0 $[M+H]^+$.

Step 6: tert-butyl (3S)-4-(7-bromo-6-chloro-2,8-difluoroquinazolin-4-yl)-3-methylpiperazine-1-carboxylate

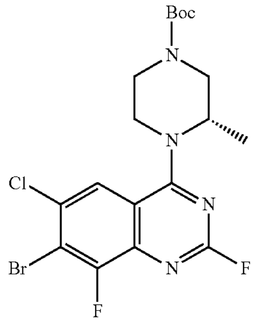 [SMILES: C[C@H]1CN(C(=O)OC(C)(C)C)CCN1c1nc(F)nc2c(F)c(Br)c(Cl)cc12]

A mixture of tert-butyl (3S)-4-(7-bromo-2,6-dichloro-8-fluoroquinazolin-4-yl)-3-methylpiperazine-1-carboxylate (30.0 g, 61 mmol) and potassium fluoride (71.0 g, 1224 mmol) in N,N-dimethylacetamide (300 mL) was stirred at 120° C. for 18 hours. After completion, the reaction system was cooled to room temperature. Then ethyl acetate (1.5 L) was added into the system and the mixture was washed with water (3×500 mL). The organic layer was dried over anhydrous sodium sulfate and concentrated under vacuum. The residue was purified by flash chromatography on silica gel eluting with petroleum ether/ethyl acetate (20%) to afford tert-butyl (3S)-4-(7-bromo-6-chloro-2,8-difluoroquinazolin-4-yl)-3-methylpiperazine-1-carboxylate (23 g, 48 mmol, 79.3% yield) as a yellow solid. LC-MS: (ESI, m/z): 477.0 $[M+H]^+$.

Step 7: tert-butyl (3S)-4-(7-(6-(bis(4-methoxybenzyl)amino)-4-methylpyridin-2-yl)-6-chloro-2,8-difluoroquinazolin-4-yl)-3-methylpiperazine-1-carboxylate

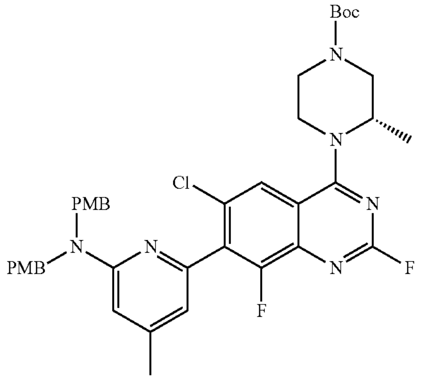

Under nitrogen, a solution of tert-butyl (3S)-4-(7-bromo-6-chloro-2,8-difluoroquinazolin-4-yl)-3-methylpiperazine-1-carboxylate (23.0 g, 48 mmol), N,N-bis[(4-methoxyphenyl)methyl]-4-methyl-6-tributylstarmyl-pyridin-2-amine (62.0 g, 97 mmol), tetrakis(triphenylphosphine)palladium (11.2 g, 9.7 mmol), cuprous iodide (2.8 g, 15 mmol) and Lithium chloride (5.0 g, 119 mmol) in 1,4-dioxane (320 mL) was stirred at 120° C. for 16 hours. After completion, the reaction system was diluted with water (100 mL) and extracted with ethyl acetate (100 mL). Then the organic layers were combined, dried over anhydrous sodium sulfate and concentrated under vacuum. The residue was purified by flash chromatography on silica gel eluting with petroleum ether/ethyl acetate (30%) to afford tert-butyl (3S)-4-(7-(6-(bis(4-methoxybenzyl)amino)-4-methylpyridin-2-yl)-6-chloro-2,8-difluoroquinazolin-4-yl)-3-methylpiperazine-1-carboxylate (18.5 g, 25 mmol, 51.6% yield) as a yellow solid. LC-MS: (ESI, m/z): 745.3 $[M+H]^+$.

Step 8: tert-butyl (3S)-4-(7-(6-(bis(4-methoxybenzyl)amino)-3-iodo-4-methylpyridin-2-yl)-6-chloro-2,8-difluoroquinazolin-4-yl)-3-methylpiperazine-1-carboxylate

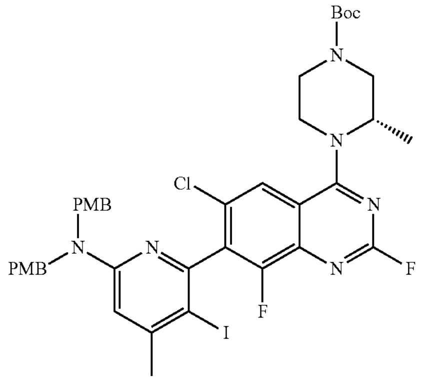

A solution of tert-butyl (3 S)-4-(7-(6-(bis(4-methoxybenzyl)amino)-4-methylpyridin-2-yl)-6-chloro-2,8-difluoro quinazolin-4-yl)-3-methylpiperazine-1-carboxylate (18.5 g, 25 mmol), p-toluenesulfonic acid (171.0 mg, 0.99 mmol) and N-iodosuccinimide (28.0 g, 125 mmol) in N,N-dimethylformamide (350 mL) was stirred at 25° C. for 5 hours. After completion, the reaction system was diluted with ethyl acetate (1.5 L) and washed with saturated sodium thiosulfate solution (4×350 mL). The organic layer was dried over anhydrous sodium sulfate and concentrated under vacuum. The residue was purified by flash chromatography on silica gel eluting with petroleum ether/ethyl acetate (25%) to afford tert-butyl (3S)-4-(7-(6-(bis(4-methoxybenzyl)amino)-3-iodo-4-methylpyridin-2-yl)-6-chloro-2,8-difluoroquinazolin-4-yl)-3-methylpiperazine-1-carboxylate (16 g, 18.4 mmol, 74% yield) as a yellow solid. LC-MS: (ESI, m/z): 871.2 $[M+H]^+$.

Step 9: tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate

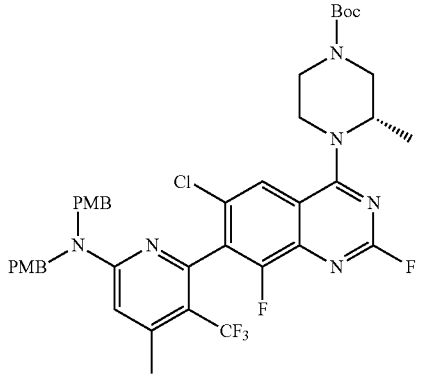

Under nitrogen, a solution of tert-butyl (3S)-4-(7-(6-(bis(4-methoxybenzyl)amino)-3-iodo-4-methylpyridin-2-yl)-6-chloro-2,8-difluoroquinazolin-4-yl)-3-methylpiperazine-1-carboxylate (16.0 g, 18.4 mmol), methyl 2,2-difluoro-2-

(fluorosulfonyl)acetate (88.3 g, 460 mmol) and cuprous iodide (42.0 g, 221 mmol) in N,N-dimethylacetamide (400 mL) was stirred at 90° C. for 18 hours. After completion, the reaction system was diluted with ethyl acetate (2.0 L) and washed with brine (4×350 mL). The organic layer was dried over anhydrous sodium sulfate and concentrated under vacuum. The residue was purified by flash chromatography on silica gel eluting with petroleum ether/ethyl acetate (30%) to afford tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate (12.2 g, 15 mmol, 81.7% yield) as a yellow solid. LC-MS: (ESI, m/z): 813.3 [M+H]+.

Step 10: tert-butyl (3S)-4-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazine-1-carboxylate

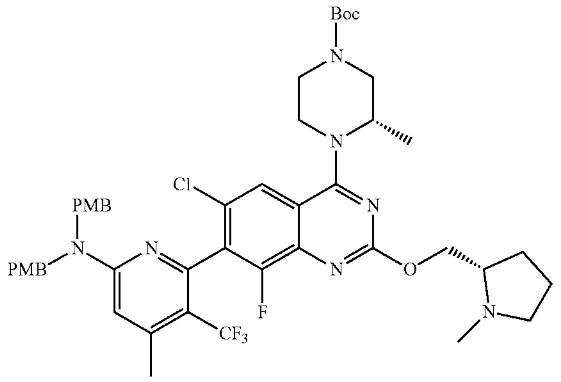

To a solution of (S)-(1-methylpyrrolidin-2-yl)methanol (4.32 g, 37.5 mmol) in tetrahydrofuran (300 mL) was added slowly sodium hydride (2.1 g, 87.5 mmol) at 0° C. and stirred for 1 h at 25° C. Then tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate (12.2 g, 15 mmol) was added into the reaction system and stirred at 25° C. for 1 hours. After completion, the reaction system was quenched with methanol (50 mL). Then the mixture was concentrated under vacuum and the residue was purified by flash chromatography on silica gel eluting with dichloromethane/methanol (6/94) to afford tert-butyl (3S)-4-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazine-1-carboxylate (8.6 g, 9.5 mmol, 63.1% yield) as a brown solid. LC-MS: (ESI, m/z): 908.4 [M+H]+.

Step 11: 6-(6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine

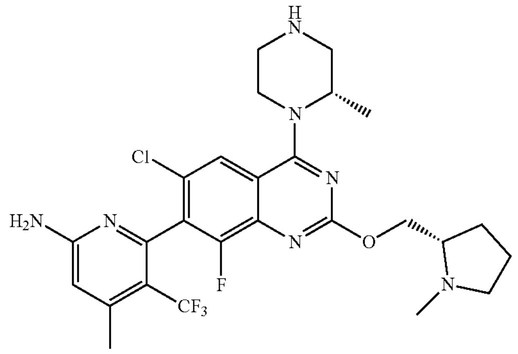 [SMILES: Cc1cc(N)nc(-c2c(Cl)cc3c(N4CCNC[C@@H]4C)nc(OC[C@@H]4CCCN4C)nc3c2F)c1C(F)(F)F]

A solution of tert-butyl (3S)-4-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazine-1-carboxylate (8.6 g, 9.5 mmol) in trifluoroacetic acid (100 mL) was stirred at 50° C. for 4 hours. After completion, the reaction system was concentrated under vacuum. The residue was dissolved with dichloromethane (50 mL) and the pH was adjusted to pH=9 with N,N-diisopropylethylamine. After concentrated under vacuum, the residue was purified by a reversed-phase chromatography directly with the following conditions: Column, C18 silica gel; mobile phase, A: water, B:ACN, B % (5%-40% in 30 min); Detector, UV 254 nm to afford 6-(6-chloro-8-fluoro-4-((S)-2-methylpiperazin-1-yl)-2-(((S)-1-methyl pyrrolidin-2-yl)methoxy)quinazolin-7-yl)-4-methyl-5-(trifluoromethyl)pyridin-2-amine (3.5 g, 6.17 mmol, 65.1% yield) as a yellow solid. LC-MS: (ESI, m/z): 568.2 [M+H]+.

Step 12: 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4) and 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4-S)

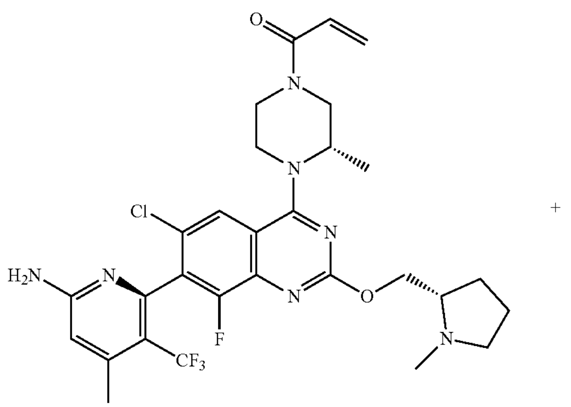

K4

+

-continued

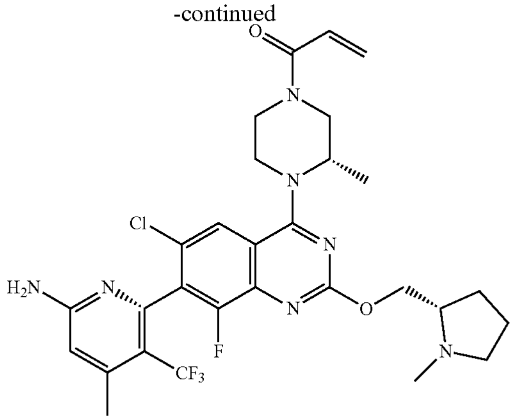

K4-S

To a solution of 6-(6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine (2.5 g, 4.4 mmol) and N,N-diisopropylethylamine (2.9 g, 22.5 mmol) in dichloromethane (120 mL) was added acryloyl chloride (359.0 mg, 3.97 mmol) at −78° C. and stirred at −78° C. for 25 mins. The reaction was quenched by water and extracted with dichloromethane. The organic layers were combined. The organic layer was dried over anhydrous sodium sulfate and concentrated under vacuum. The residue was purified by a reversed-phase chromatography directly with the following conditions: Column, C18 silica gel; mobile phase, A: water, B:ACN, B % (5%~60% in 30 min); Detector, UV 254 nm to afford 1-[(3S)-4-[7-[6-amino-4-methyl-3-(trifluoromethyl)-2-pyridyl]-6-chloro-8-fluoro-2-[[(2S)-1-methylpyrrolidin-2-yl]methoxy]quinazolin-4-yl]-3-methyl-piperazin-1-yl]prop-2-en-1-one (1.3 g, 2.09 mmol, 47.5% yield) as a brown solid. The mixture of diasteroisomer was separated by Prep-Chiral-HPLC with the following condition: Column, CHIRALPAK IC-3 0.46*5 Cm 3 um; mobile phase, (Hex:dichloromethane=3:1) (0.1% DEA): EtOH=50:50; Detector, 254 nm; Flow, 1.0 ml/min; Temperature: 25° C. to afford 657.7 mg of 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy) quinazolin-4-yl)-3-methylpiperazin-1-yl)prop-2-en-1-one (K4) as a white solid and 352.1 mg of 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (K4-S) as a white solid.

K4: LC-MS: (ESI, m/z): 622.2 $[M+H]^+$, $^1H$ NMR: (400 MHz, $CDCl_3$, ppm) δ 7.64 (s, 1H), 6.70-6.55 (m, 1H), 6.48 (s, 1H), 6.42-6.35 (m, 1H), 5.82-5.75 (m, 1H), 4.90-4.79 (m, 2H), 4.78-4.40 (m, 3H), 4.35-4.28 (m, 1H), 4.18-4.00 (m, 1H), 3.99-3.76 (m, 1H), 3.72-3.45 (m, 2H), 3.31-2.98 (m, 2H), 2.81-2.70 (m, 1H), 2.55-2.45 (m, 6H), 2.35-2.25 (m, 1H), 2.11-2.01 (m, 1H), 1.95-1.72 (m, 3H), 1.36-1.34 (m, 3H).

K4-S: LC-MS: (ESI, m/z): 622.2 $[M+H]^+$, $^1H$ NMR: (400 MHz, $CDCl_3$, ppm) δ 7.63 (s, 1H), 6.70-6.55 (m, 1H), 6.50 (s, 1H), 6.42-6.35 (m, 1H), 5.82-5.75 (m, 1H), 4.85-4.70 (m, 2H), 4.78-4.68 (m, 2H), 4.65-4.55 (m, 1H), 4.50-4.40 (m, 1H), 4.30-4.10 (m, 1H), 4.05-3.75 (m, 1H), 3.80-3.76 (m, 2H), 3.25-3.08 (m, 2H), 2.85-2.75 (m, 1H), 2.60-2.45 (m, 6H), 2.40-2.25 (m, 1H), 2.15-2.05 (m, 1H), 1.95-1.72 (m, 3H), 1.45-1.32 (m, 3H).

| Example No. | $^1H$ NMR | MS $(M + H)^+$ |
|---|---|---|
| K4 | $^1H$ NMR: (400 MHz, $CDCl_3$, ppm) δ 7.64 (s, 1H), 6.70-6.55 (m, 1H), 6.48 (s, 1H), 6.42-6.35 (m, 1H), 5.82-5.75 (m, 1H), 4.90-4.79 (m, 2H), 4.78-4.40 (m, 3H), 4.35-4.28 (m, 1H), 4.18-4.00 (m, 1H), 3.99-3.76 (m, 1H), 3.72-3.45 (m, 2H), 3.31-2.98 (m, 2H), 2.81-2.70 (m, 1H), 2.55-2.45 (m, 6H), 2.35-2.25 (m, 1H), 2.11-2.01 (m, 1H), 1.95-1.72 (m, 3H), 1.36-1.34 (m, 3H). | 622.2 |
| K4-S | $^1H$ NMR: (400 MHz, $CDCl_3$, ppm) δ 7.63 (s, 1H), 6.70-6.55 (m, 1H), 6.50 (s, 1H), 6.42-6.35 (m, 1H), 5.82-5.75 (m, 1H), 4.85-4.70 (m, 2H), 4.78-4.68 (m, 2H), 4.65-4.55 (m, 1H), 4.50-4.40 (m, 1H), 4.30-4.10 (m, 1H), 4.05-3.75 (m, 1H), 3.80-3.76 (m, 2H), 3.25-3.08 (m, 2H), 2.85-2.75 (m, 1H), 2.60-2.45 (m, 6H), 2.40-2.25 (m, 1H), 2.15-2.05 (m, 1H), 1.95-1.72 (m, 3H), 1.45-1.32 (m, 3H). | 622.2 |

Example 185: Biological Examples for Combination of One or More TEAD Inhibitors and One or More KRAS Inhibitors

Example B-1: Drug Combination Assay

Figure 2:
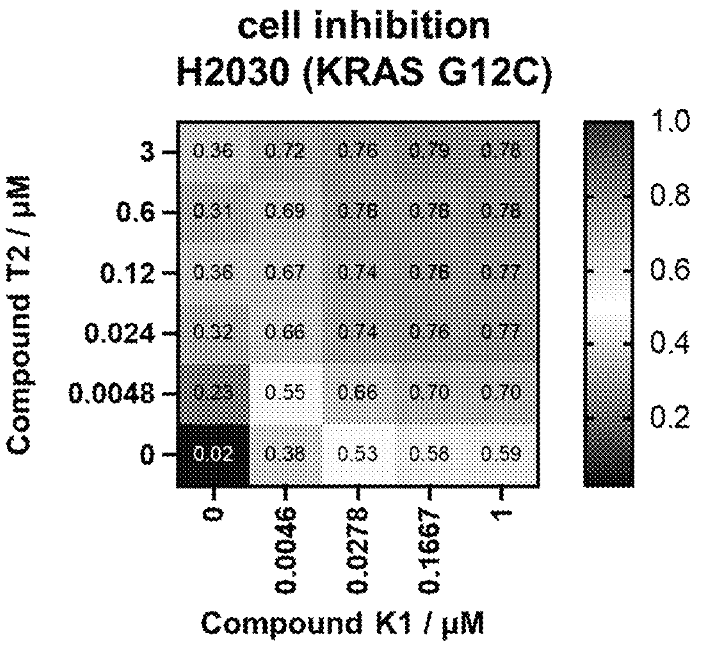
FIG. 2 depicts % inhibition of H2030 cells (KRAS G12C) following administration of a combination comprising Compound T2 (a YAP/TAZ-TEAD inhibitor) and Compound K1 (a KRAS inhibitor).
Figure 3:
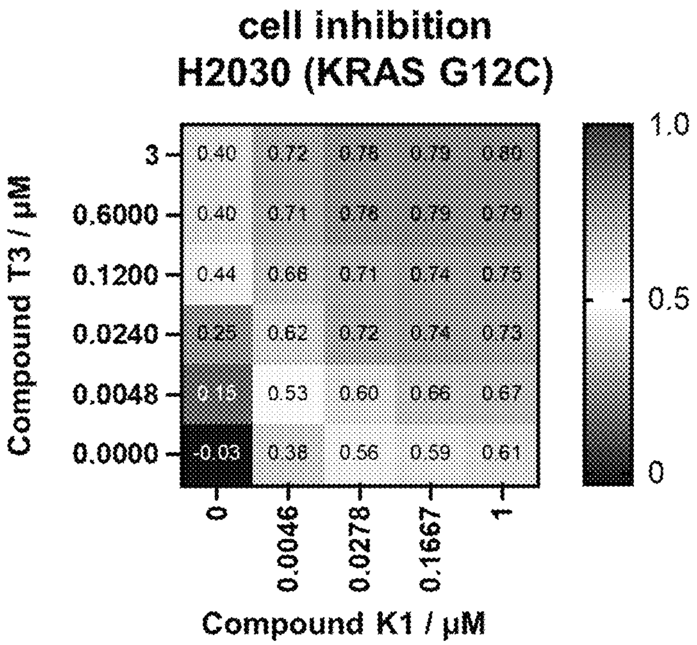
FIG. 3 depicts % inhibition of H2030 cells (KRAS G12C) following administration of a combination comprising Compound T3 (a YAP/TAZ-TEAD inhibitor) and Compound K1 (a KRAS inhibitor).
Figure 4:
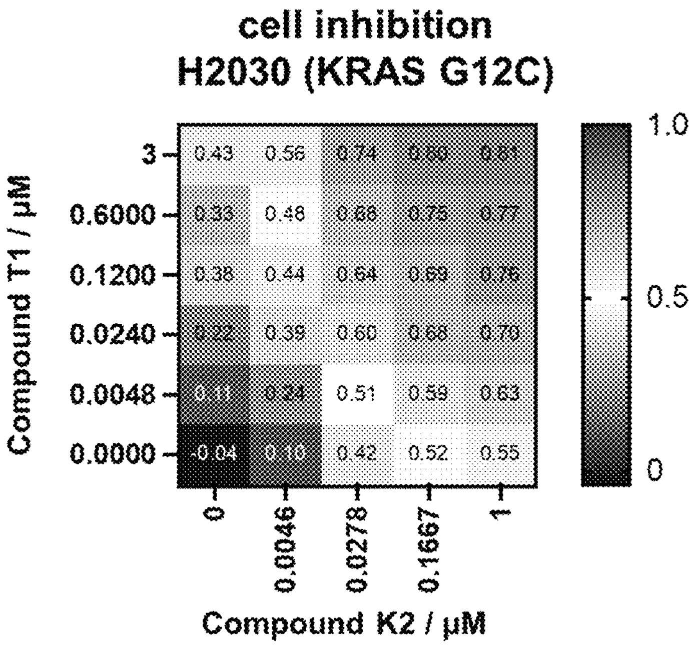
FIG. 4 depicts % inhibition of H2030 cells (KRAS G12C) following administration of a combination comprising Compound T1 (a YAP/TAZ-TEAD inhibitor) and Compound K2 (a KRAS inhibitor).
Figure 5:
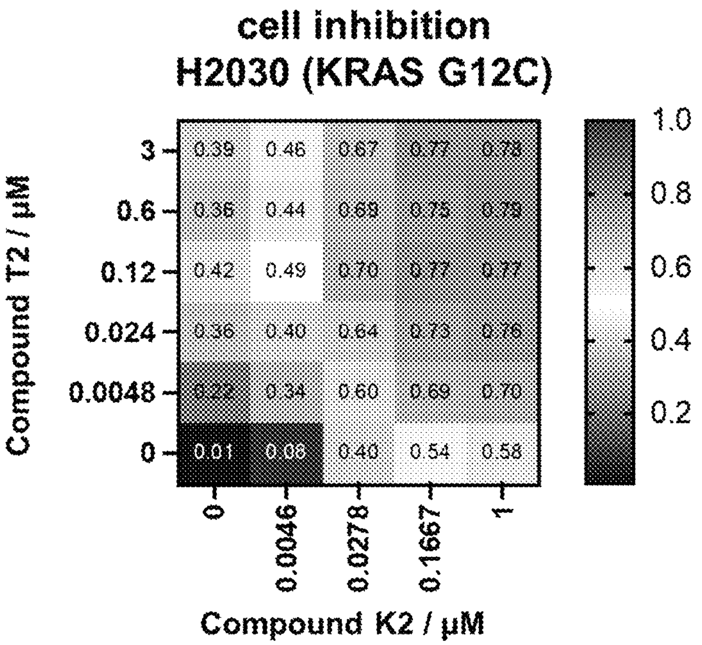
FIG. 5 depicts % inhibition of H2030 cells (KRAS G12C) following administration of a combination comprising Compound T2 (a YAP/TAZ-TEAD inhibitor) and Compound K2 (a KRAS inhibitor).
Figure 6:
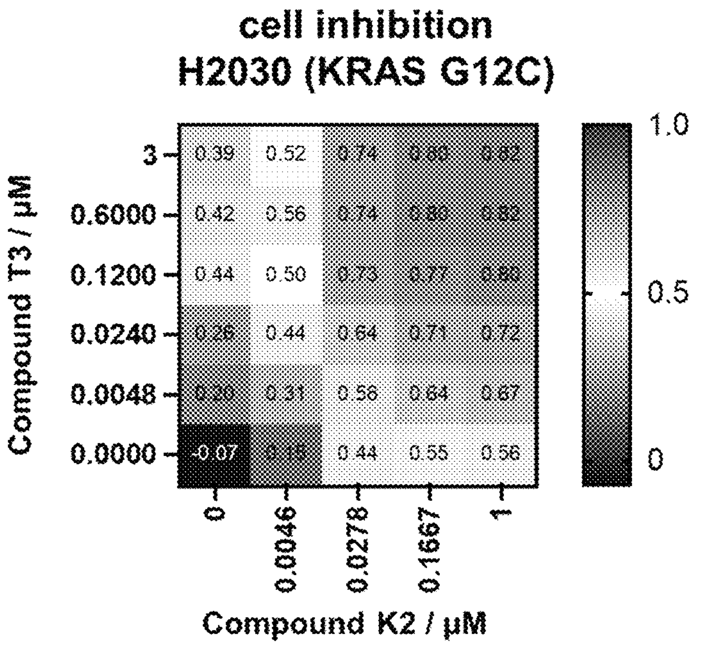
FIG. 6 depicts % inhibition of H2030 cells (KRAS G12C) following administration of a combination comprising Compound T3 (a YAP/TAZ-TEAD inhibitor) and Compound K2 (a KRAS inhibitor).
Figure 7:
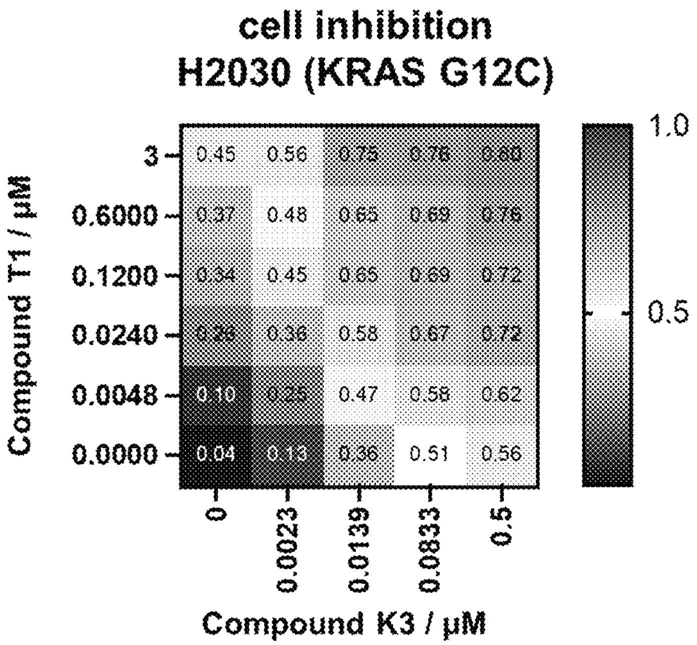
FIG. 7 depicts % inhibition of H2030 cells (KRAS G12C) following administration of a combination comprising Compound T1 (a YAP/TAZ-TEAD inhibitor) and Compound K3 (a KRAS inhibitor).
Figure 8:
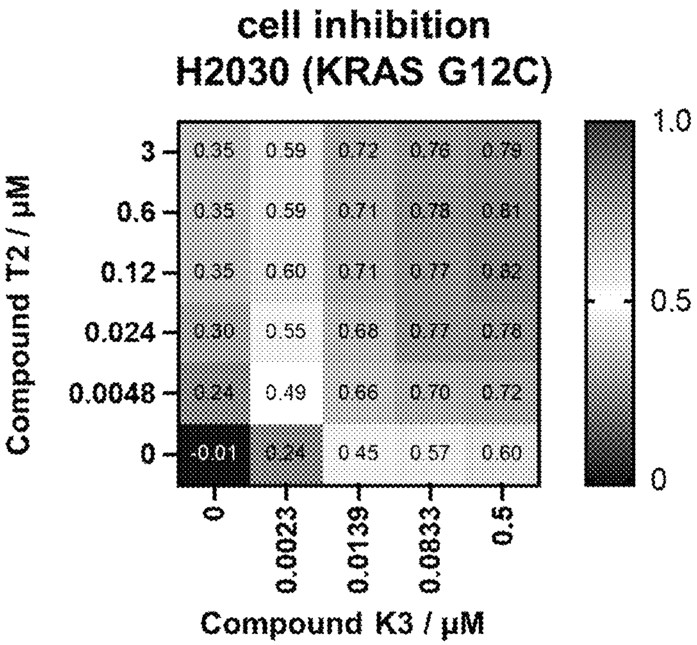
FIG. 8 depicts % inhibition of H2030 cells (KRAS G12C) following administration of a combination comprising Compound T2 (a YAP/TAZ-TEAD inhibitor) and Compound K3 (a KRAS inhibitor).
Figure 9:
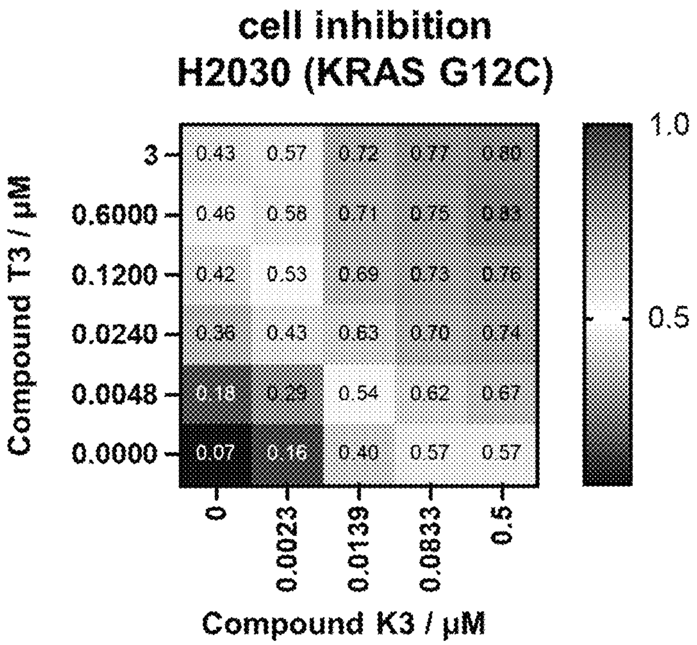
FIG. 9 depicts % inhibition of H2030 cells (KRAS G12C) following administration of a combination comprising Compound T3 (a YAP/TAZ-TEAD inhibitor) and Compound K3 (a KRAS inhibitor).
Figure 10:
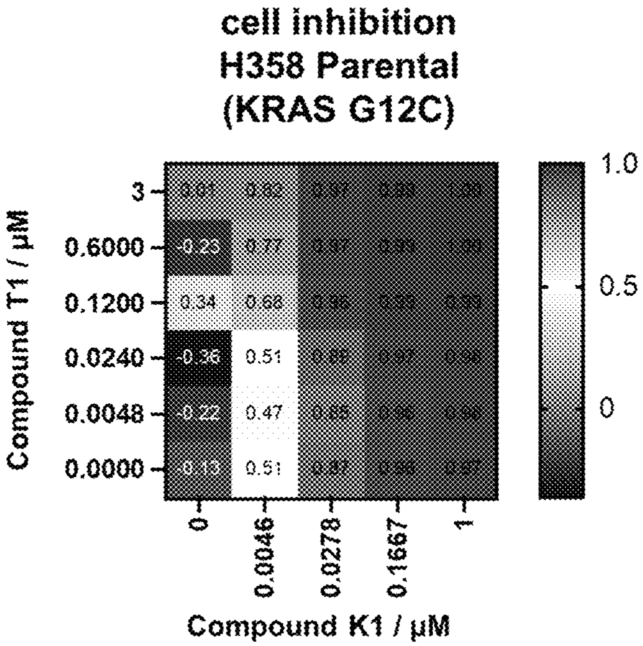
FIG. 10 depicts % inhibition of H358 parental cells (KRAS G12C) following administration of a combination comprising Compound T1 (a YAP/TAZ-TEAD inhibitor) and Compound K1 (a KRAS inhibitor).
Figure 11:
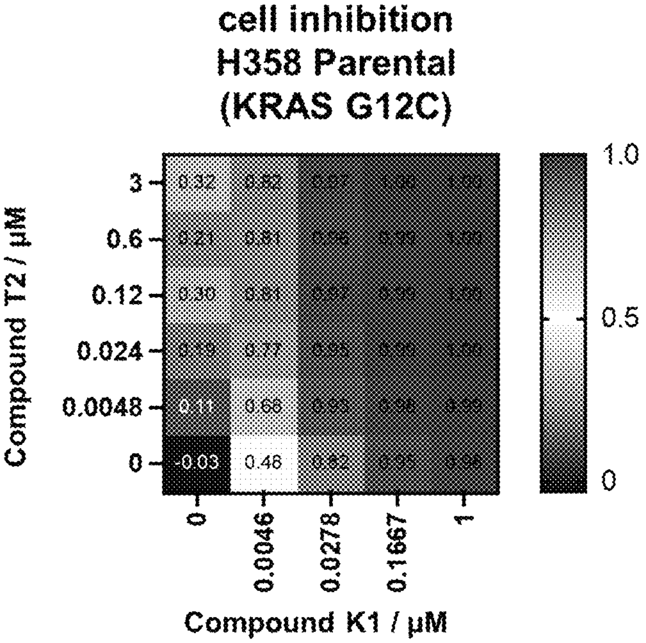
FIG. 11 depicts % inhibition of H358 parental cells (KRAS G12C) following administration of a combination comprising Compound T2 (a YAP/TAZ-TEAD inhibitor) and Compound K1 (a KRAS inhibitor).
Figure 12:
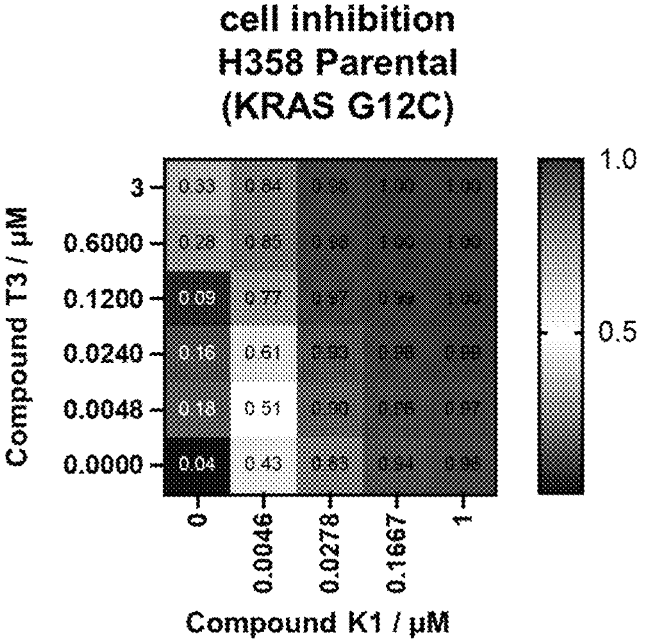
FIG. 12 depicts % inhibition of H358 parental cells (KRAS G12C) following administration of a combination comprising Compound T3 (a YAP/TAZ-TEAD inhibitor) and Compound K1 (a KRAS inhibitor).
Figure 13:
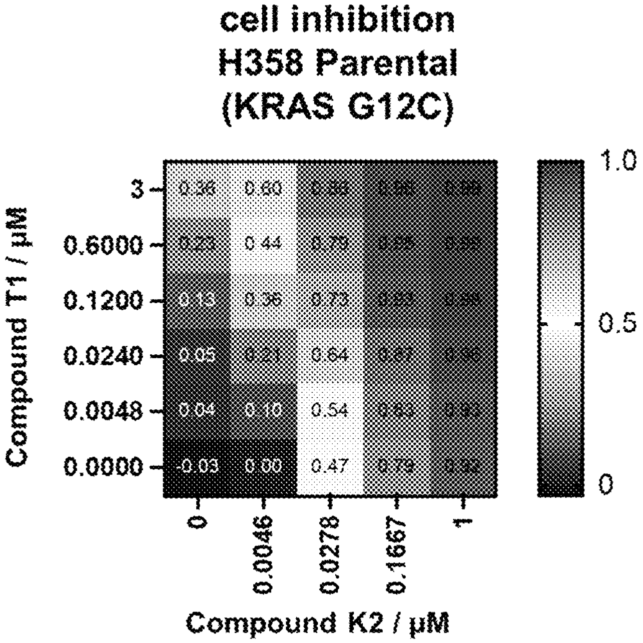
FIG. 13 depicts % inhibition of H358 parental cells (KRAS G12C) following administration of a combination comprising Compound T1 (a YAP/TAZ-TEAD inhibitor) and Compound K2 (a KRAS inhibitor).
Figure 14:
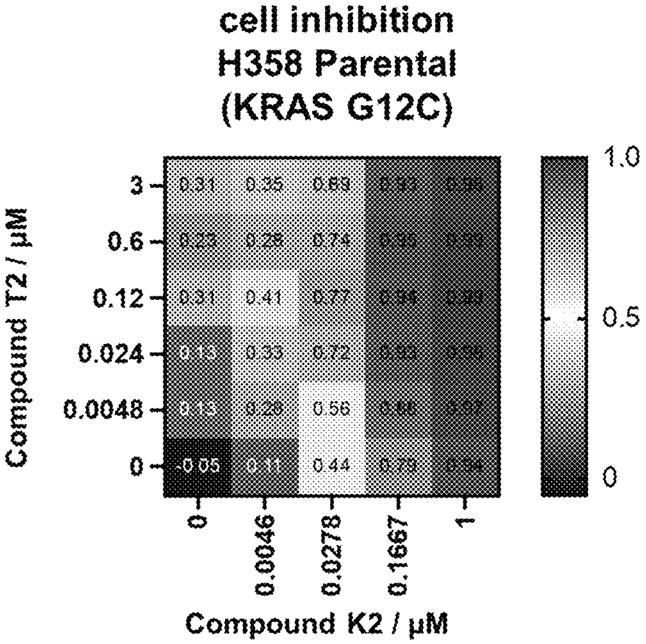
FIG. 14 depicts % inhibition of H358 parental cells (KRAS G12C) following administration of a combination comprising Compound T2 (a YAP/TAZ-TEAD inhibitor) and Compound K2 (a KRAS inhibitor).
Figure 15:
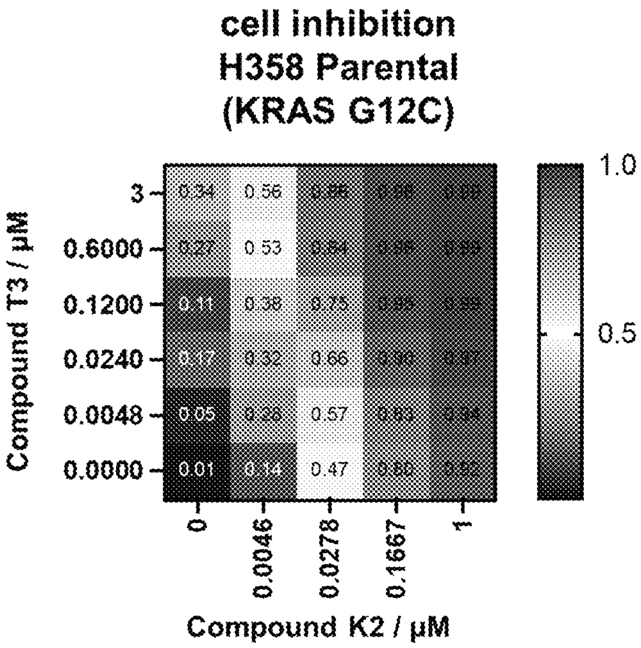
FIG. 15 depicts % inhibition of H358 parental cells (KRAS G12C) following administration of a combination comprising Compound T3 (a YAP/TAZ-TEAD inhibitor) and Compound K2 (a KRAS inhibitor).
Figure 16:
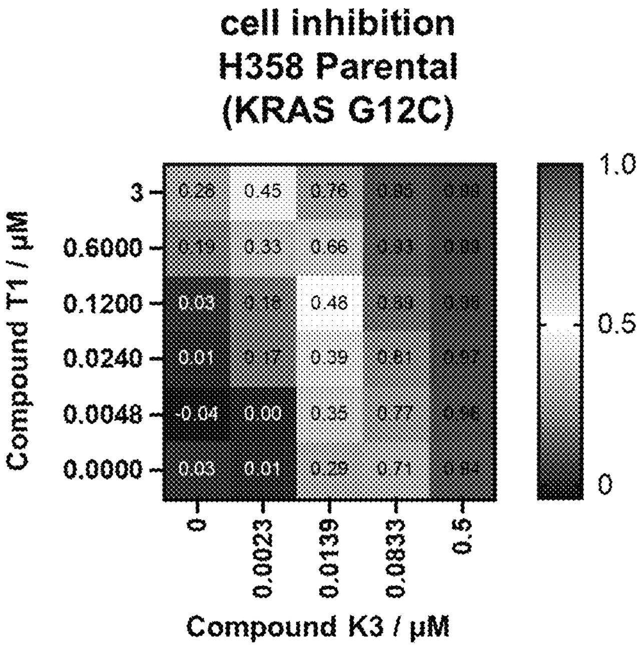
FIG. 16 depicts % inhibition of H358 parental cells (KRAS G12C) following administration of a combination comprising Compound T1 (a YAP/TAZ-TEAD inhibitor) and Compound K3 (a KRAS inhibitor).
Figure 17:
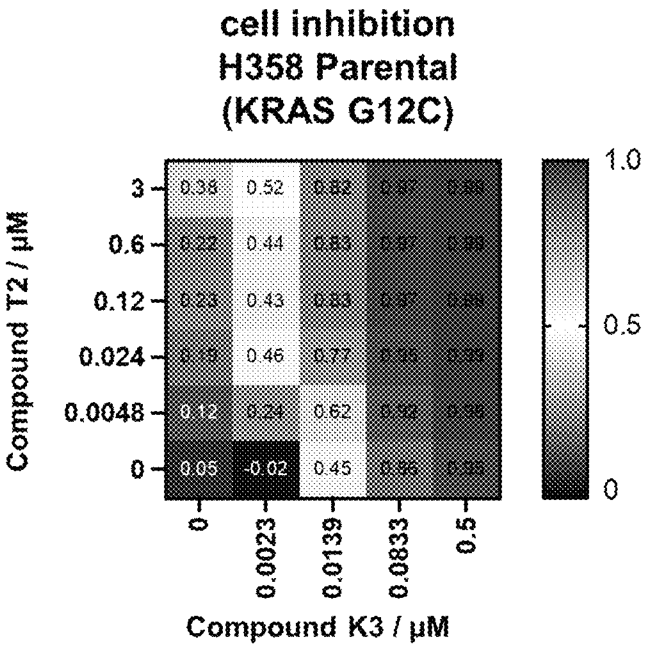
FIG. 17 depicts % inhibition of H358 parental cells (KRAS G12C) following administration of a combination comprising Compound T2 (a YAP/TAZ-TEAD inhibitor) and Compound K3 (a KRAS inhibitor).
Figure 18:
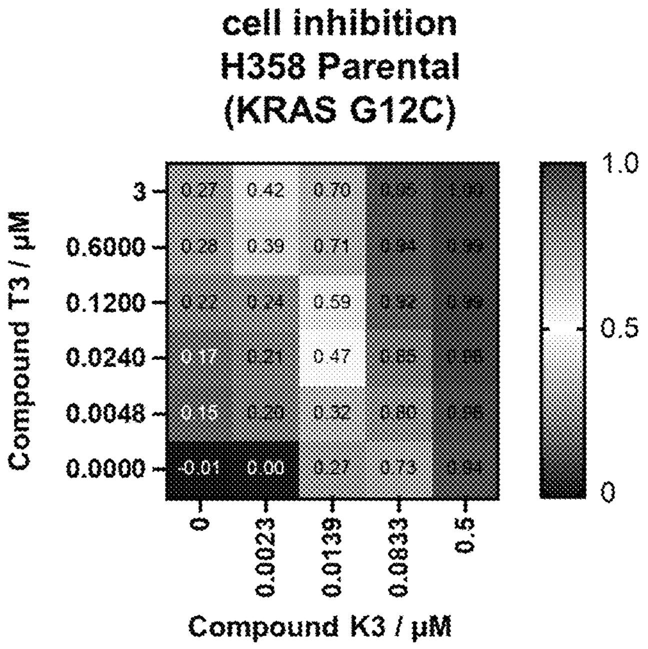
FIG. 18 depicts % inhibition of H358 parental cells (KRAS G12C) following administration of a combination comprising Compound T3 (a YAP/TAZ-TEAD inhibitor) and Compound K3 (a KRAS inhibitor).
Figure 19:
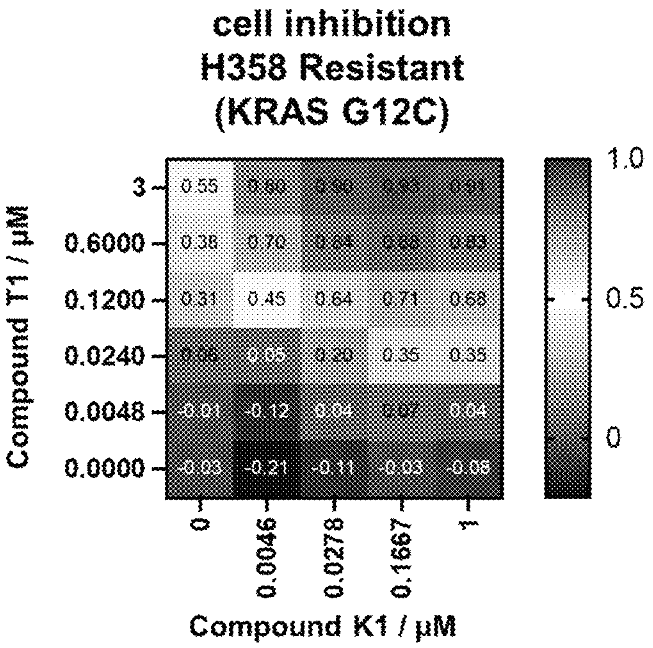
FIG. 19 depicts % inhibition of H358 resistant cells (KRAS G12C) following administration of a combination comprising Compound T1 (a YAP/TAZ-TEAD inhibitor) and Compound K1 (a KRAS inhibitor).
Figure 20:
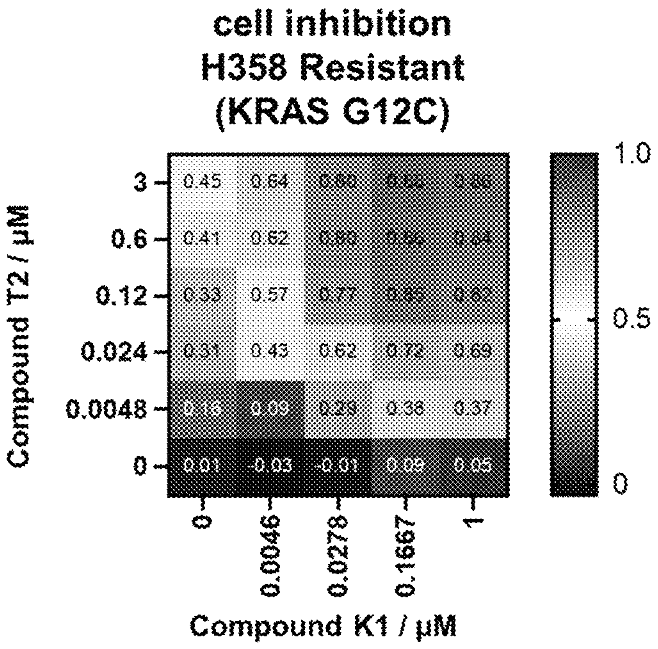
FIG. 20 depicts % inhibition of H358 resistant cells (KRAS G12C) following administration of a combination comprising Compound T2 (a YAP/TAZ-TEAD inhibitor) and Compound K1 (a KRAS inhibitor).
Figure 21:
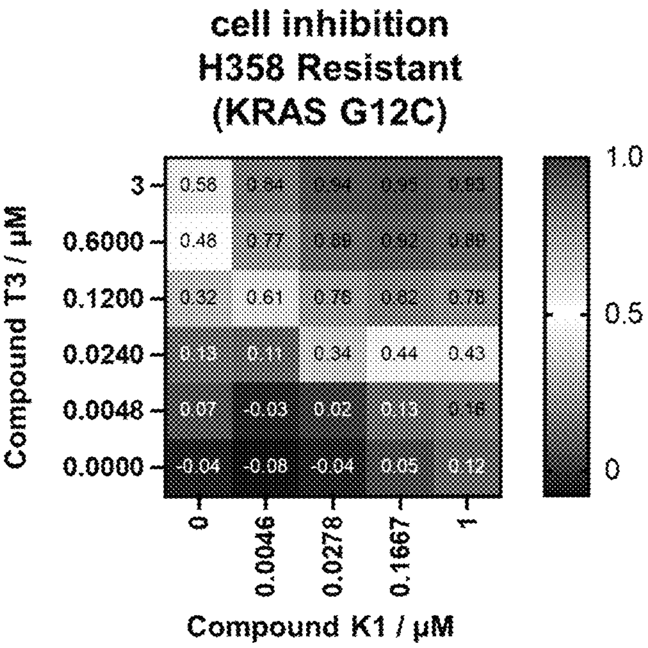
FIG. 21 depicts % inhibition of H358 resistant cells (KRAS G12C) following administration of a combination comprising Compound T3 (a YAP/TAZ-TEAD inhibitor) and Compound K1 (a KRAS inhibitor).
Figure 22:
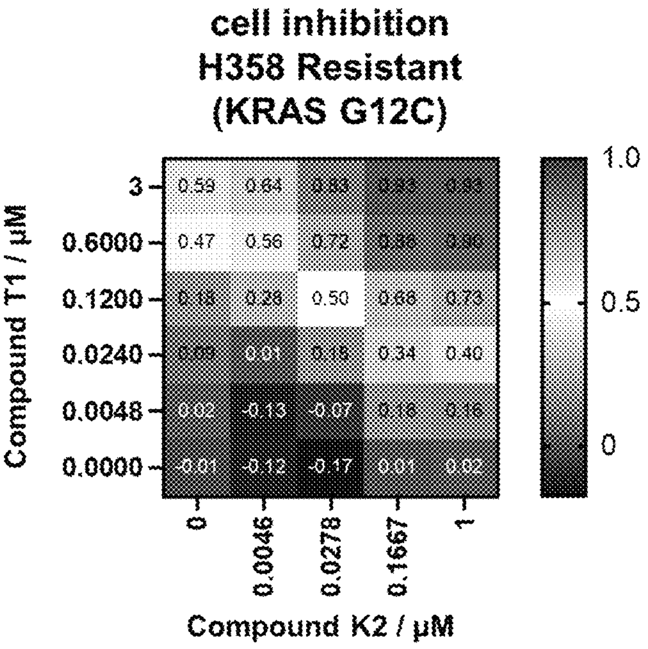
FIG. 22 depicts % inhibition of H358 resistant cells (KRAS G12C) following administration of a combination comprising Compound T1 (a YAP/TAZ-TEAD inhibitor) and Compound K2 (a KRAS inhibitor).
Figure 23:
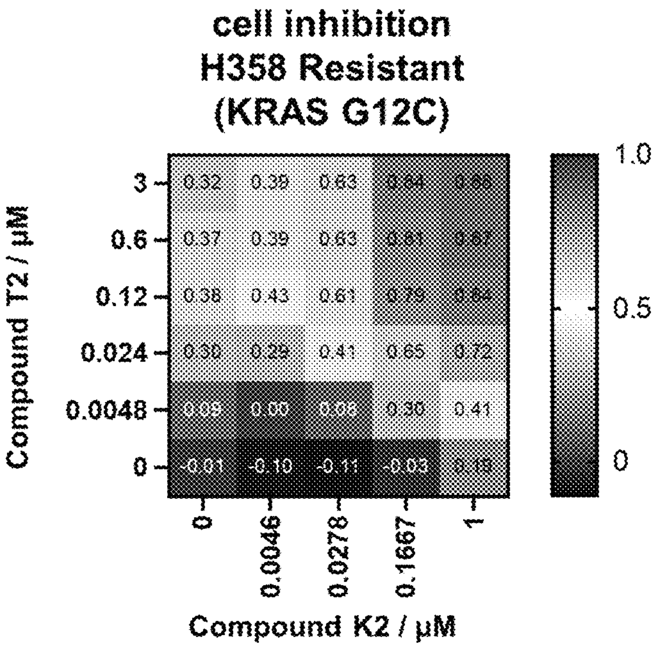
FIG. 23 depicts % inhibition of H358 resistant cells (KRAS G12C) following administration of a combination comprising Compound T2 (a YAP/TAZ-TEAD inhibitor) and Compound K2 (a KRAS inhibitor).
Figure 24:
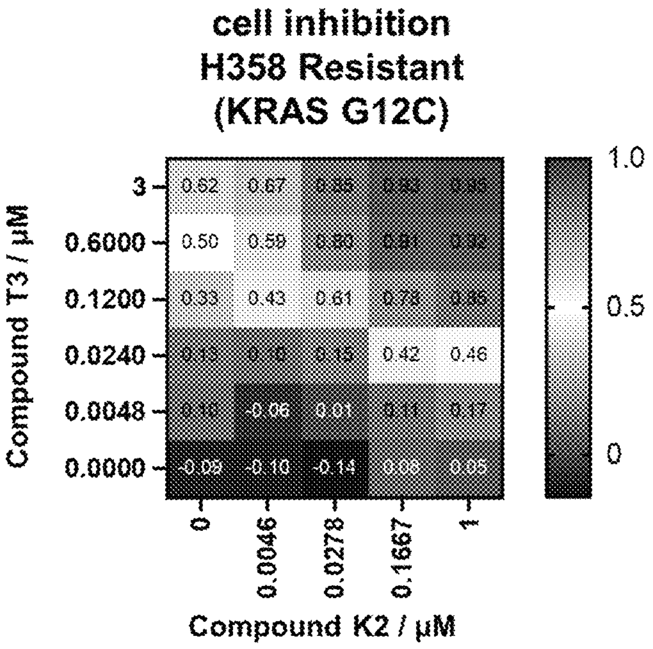
FIG. 24 depicts % inhibition of H358 resistant cells (KRAS G12C) following administration of a combination comprising Compound T3 (a YAP/TAZ-TEAD inhibitor) and Compound K2 (a KRAS inhibitor).
Figure 25:
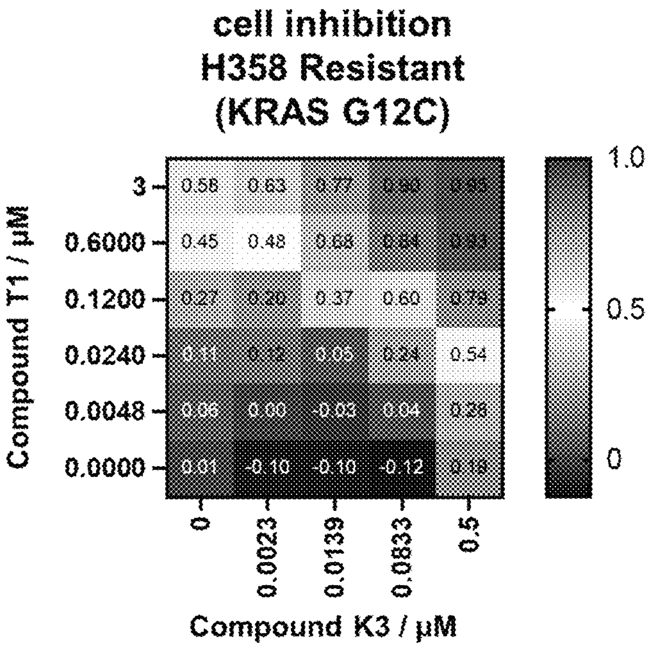
FIG. 25 depicts % inhibition of H358 resistant cells (KRAS G12C) following administration of a combination comprising Compound T1 (a YAP/TAZ-TEAD inhibitor) and Compound K3 (a KRAS inhibitor).
Figure 26:
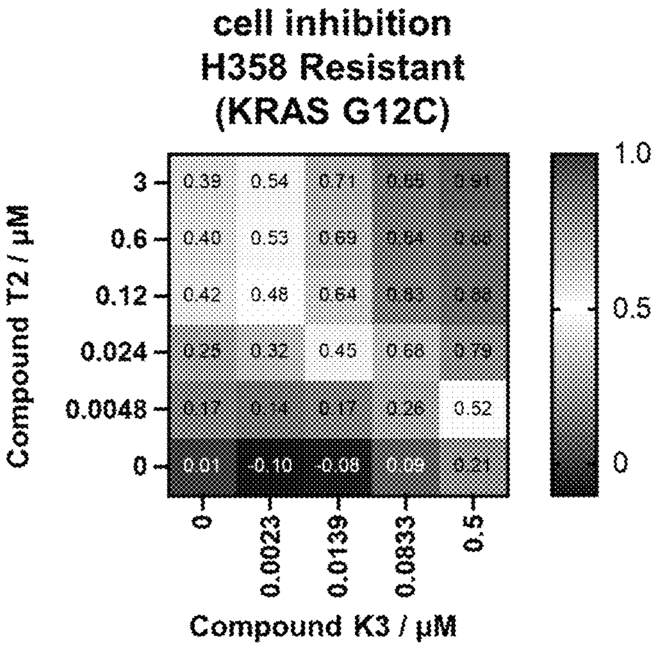
FIG. 26 depicts % inhibition of H358 resistant cells (KRAS G12C) following administration of a combination comprising Compound T2 (a YAP/TAZ-TEAD inhibitor) and Compound K3 (a KRAS inhibitor).
Figure 27:
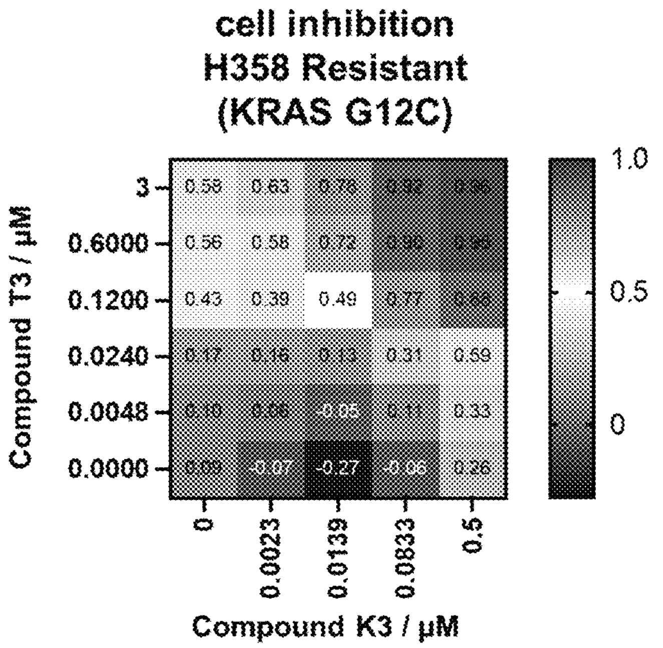
FIG. 27 depicts % inhibition of H358 resistant cells (KRAS G12C) following administration of a combination comprising Compound T3 (a YAP/TAZ-TEAD inhibitor) and Compound K3 (a KRAS inhibitor).
Figure 28:
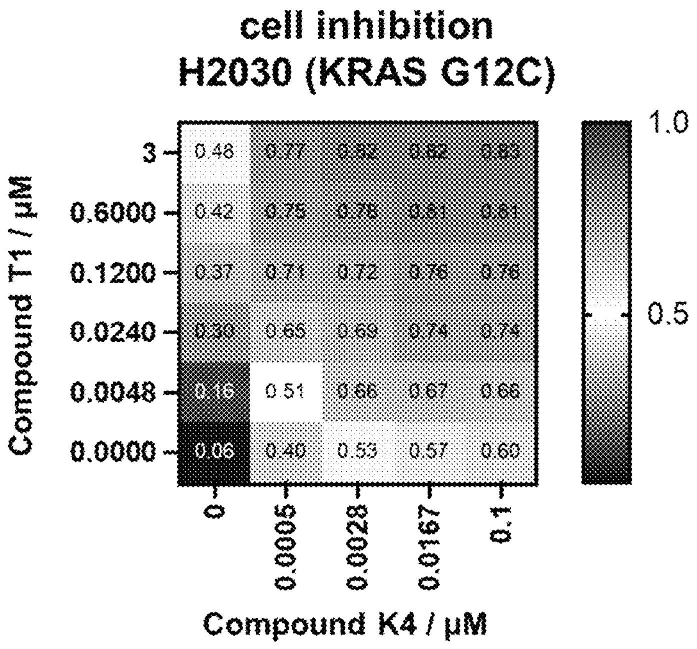
FIG. 28 depicts % inhibition of H2030 cells (KRAS G12C) following administration of a combination comprising Compound T1 (a YAP/TAZ-TEAD inhibitor) and Compound K4 (a KRAS inhibitor).
Figure 29:
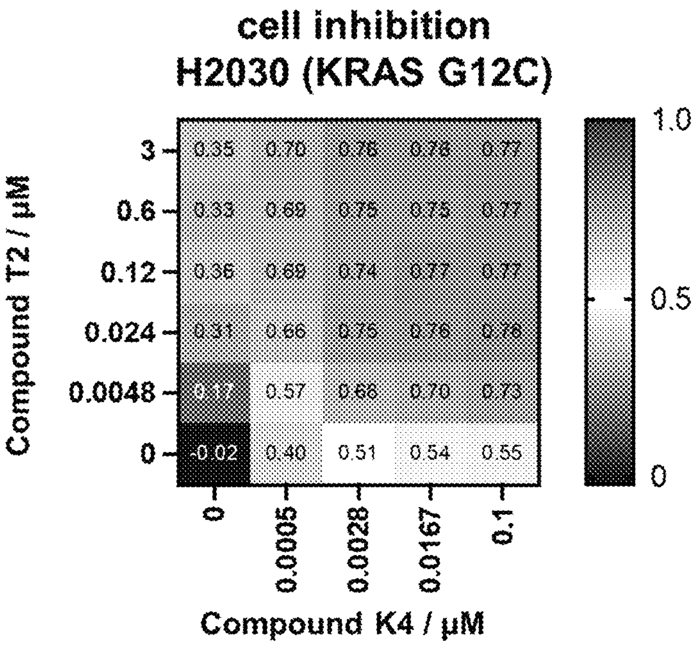
FIG. 29 depicts % inhibition of H2030 cells (KRAS G12C) following administration of a combination comprising Compound T2 (a YAP/TAZ-TEAD inhibitor) and Compound K4 (a KRAS inhibitor).
Figure 30:
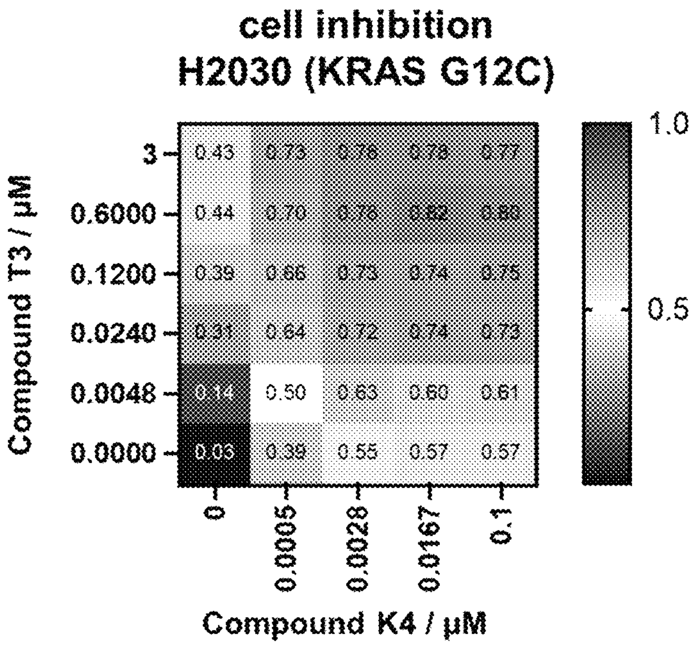
FIG. 30 depicts % inhibition of H2030 cells (KRAS G12C) following administration of a combination comprising Compound T3 (a YAP/TAZ-TEAD inhibitor) and Compound K4 (a KRAS inhibitor).
Figure 31:
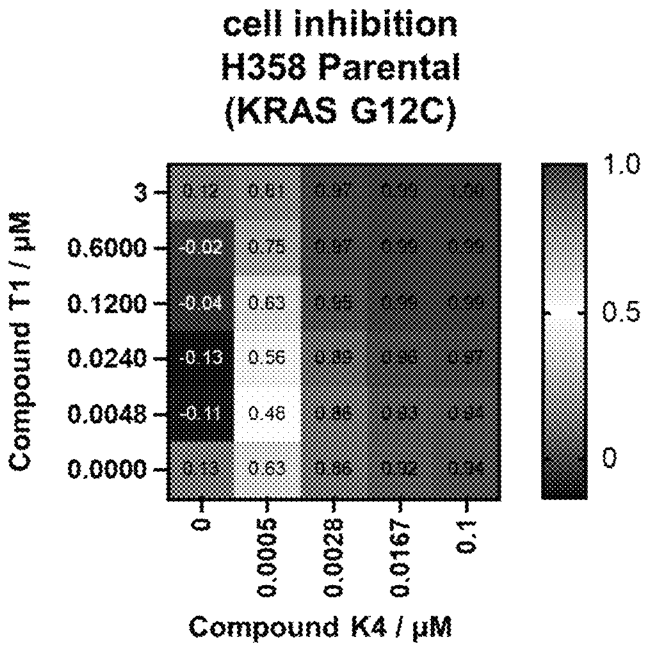
FIG. 31 depicts % inhibition of H358 parental cells (KRAS G12C) following administration of a combination comprising Compound T1 (a YAP/TAZ-TEAD inhibitor) and Compound K4 (a KRAS inhibitor).
Figure 32:
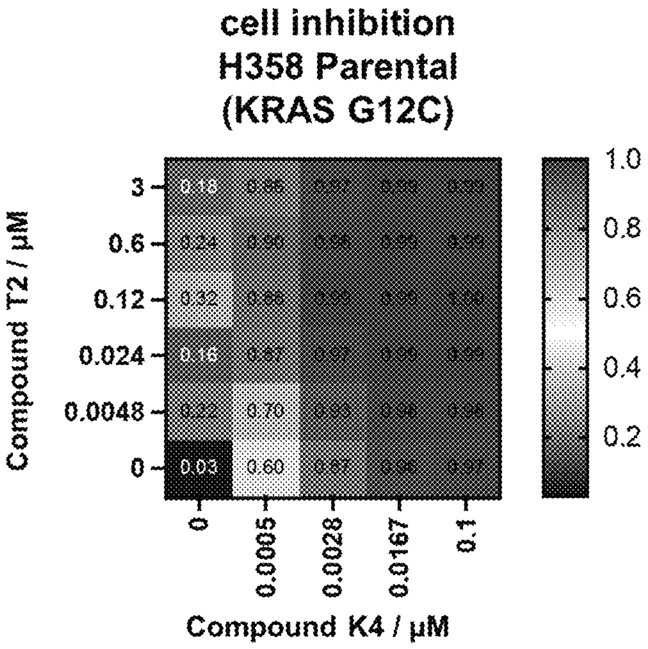
FIG. 32 depicts % inhibition of H358 parental cells (KRAS G12C) following administration of a combination comprising Compound T2 (a YAP/TAZ-TEAD inhibitor) and Compound K4 (a KRAS inhibitor).
Figure 33:
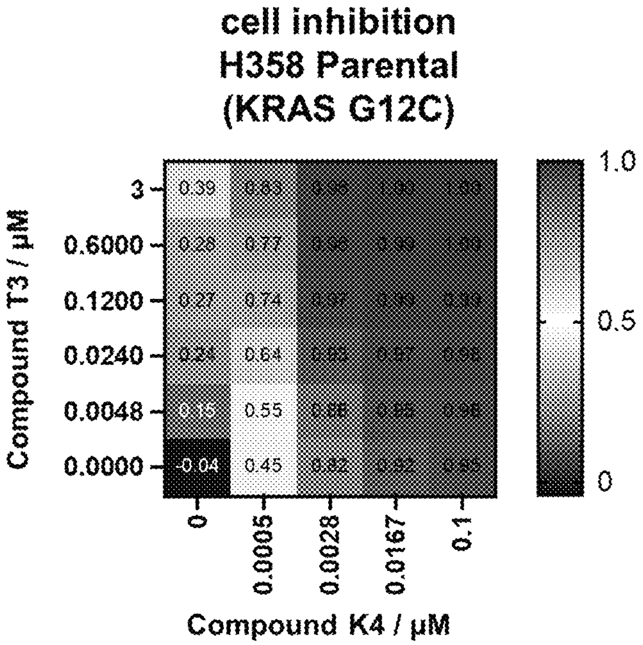
FIG. 33 depicts % inhibition of H358 parental cells (KRAS G12C) following administration of a combination comprising Compound T3 (a YAP/TAZ-TEAD inhibitor) and Compound K4 (a KRAS inhibitor).
Figure 34:
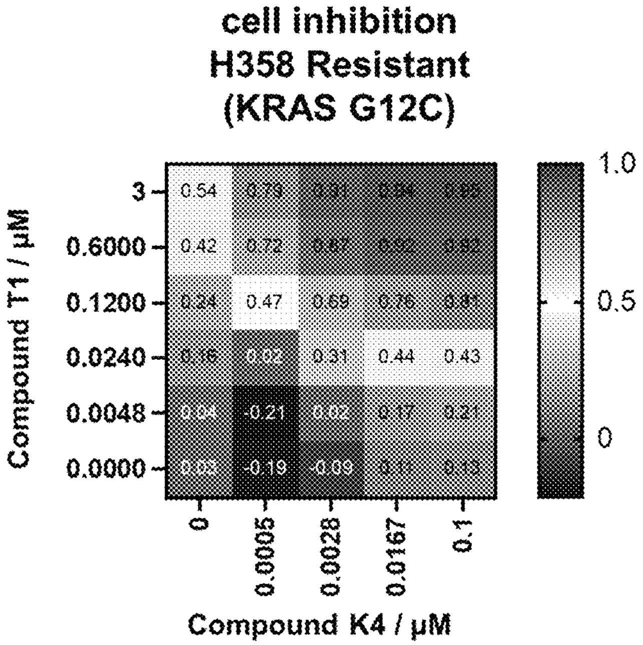
FIG. 34 depicts % inhibition of H358 resistant cells (KRAS G12C) following administration of a combination comprising Compound T1 (a YAP/TAZ-TEAD inhibitor) and Compound K4 (a KRAS inhibitor).
Figure 35:
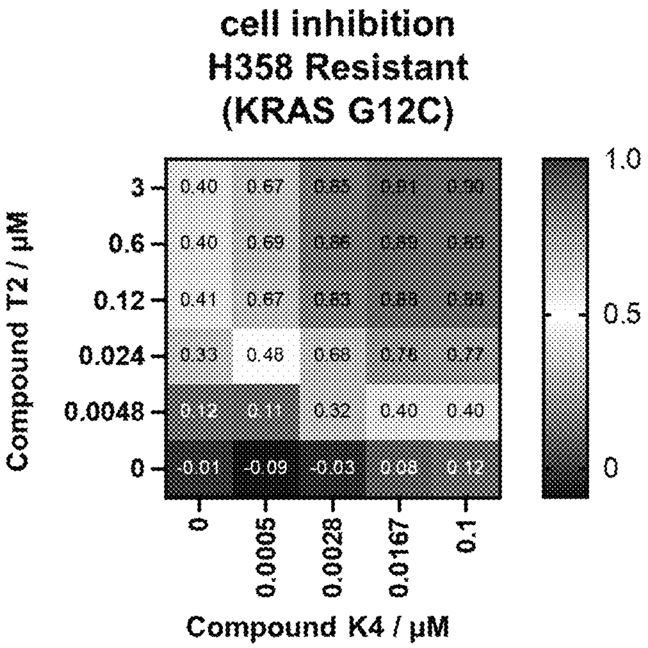
FIG. 35 depicts % inhibition of H358 resistant cells (KRAS G12C) following administration of a combination comprising Compound T2 (a YAP/TAZ-TEAD inhibitor) and Compound K4 (a KRAS inhibitor).
Figure 36:
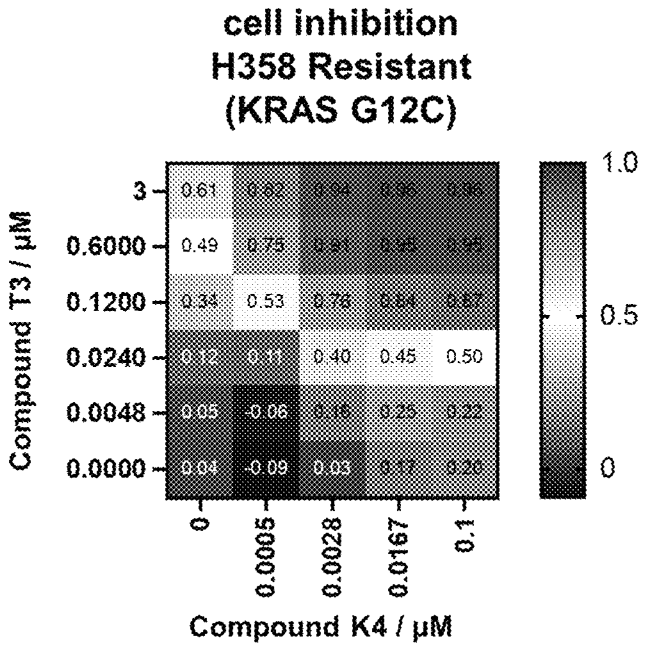
FIG. 36 depicts % inhibition of H358 resistant cells (KRAS G12C) following administration of a combination comprising Compound T3 (a YAP/TAZ-TEAD inhibitor) and Compound K4 (a KRAS inhibitor).

Cells were seeded in 96-well plates 16h before treatment at a density of 1000 cells per well. Then, cells were treated with varying concentrations of compound(s) as indicated in FIGS. 1-36, either a single agent or in combination, for six days. The relative number of viable cells was estimated using CellTiter-Glo Luminescent Cell Viability Assay (Promega, G7573) as a proportion from 0, representing no cells inhibited, to 1.0 representing all cells inhibited. Total luminescence was detected on a Wallac Multilabel Reader (Perkin-Elmer).

Example B-2: In Vivo Drug Combination Assay

Figure 37:
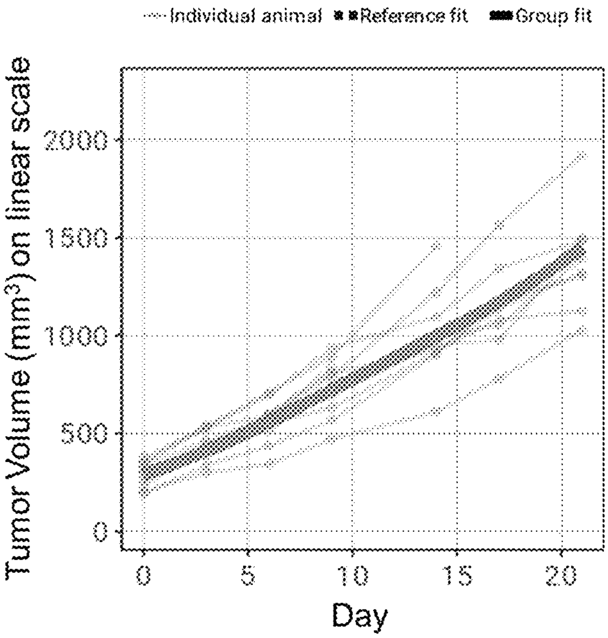
FIG. 37 depicts tumor volume over time of mice inoculated with NCI-H2122 cells; MC 0.5% PO QDx21+MCT PO BIDx21.
Figure 38:
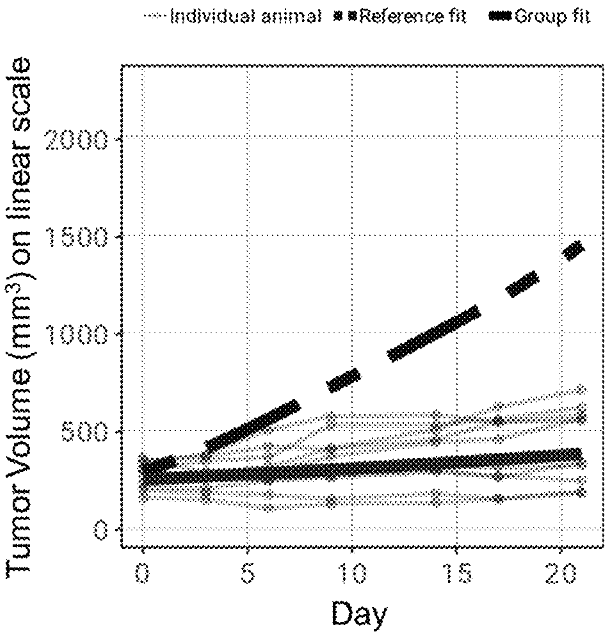
FIG. 38 depicts tumor volume over time of mice inoculated with NCI-H2122 cells; Compound K4 25 mg/kg PO QDx21.
Figure 39:
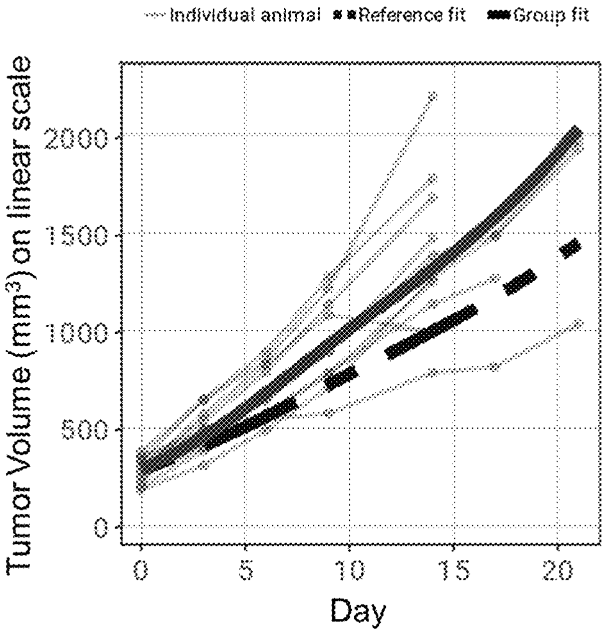
FIG. 39 depicts tumor volume over time of mice inoculated with NCI-H2122 cells; Compound T1 10 mg/kg PO BIDx21.
Figure 40:
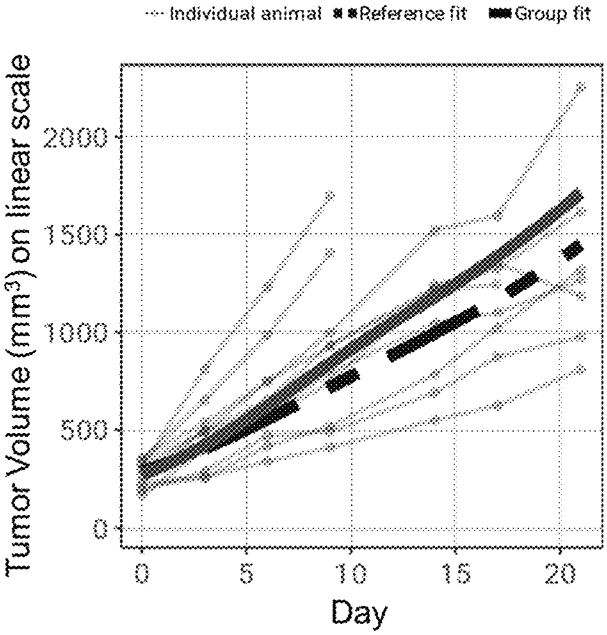
FIG. 40 depicts tumor volume over time of mice inoculated with NCI-H2122 cells; Compound T1 20 mg/kg PO QDx21
Figure 41:
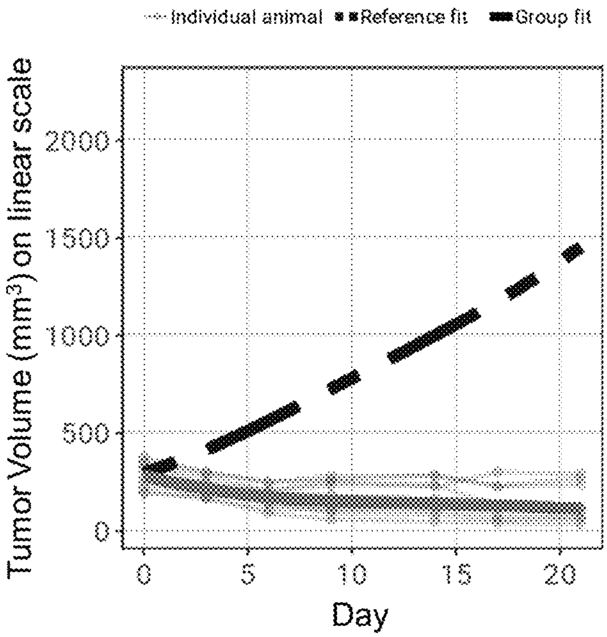
FIG. 41 depicts tumor volume over time of mice inoculated with NCI-H2122 cells; Compound K4 25 mg/kg PO QDx21 and Compound T1 10 mg/kg PO BIDx21.
Figure 42:
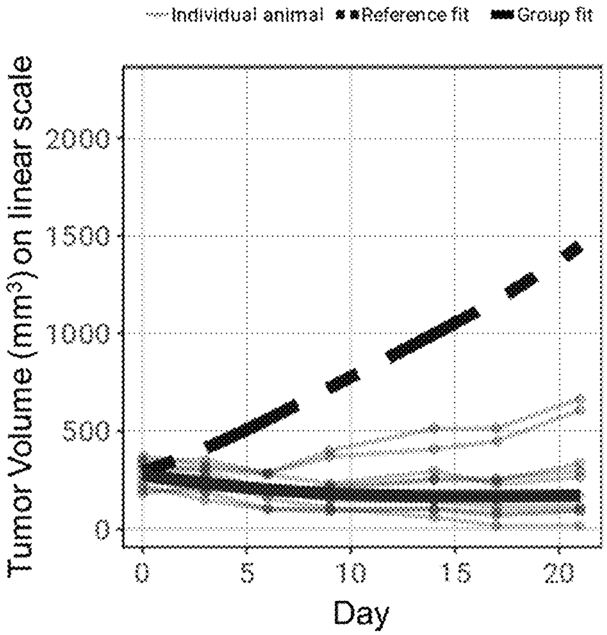
FIG. 42 depicts tumor volume over time of mice inoculated with NCI-H2122 cells; Compound K4 25 mg/kg PO QDx21 and Compound T1 20 mg/kg PO QDx21.
Figure 43:
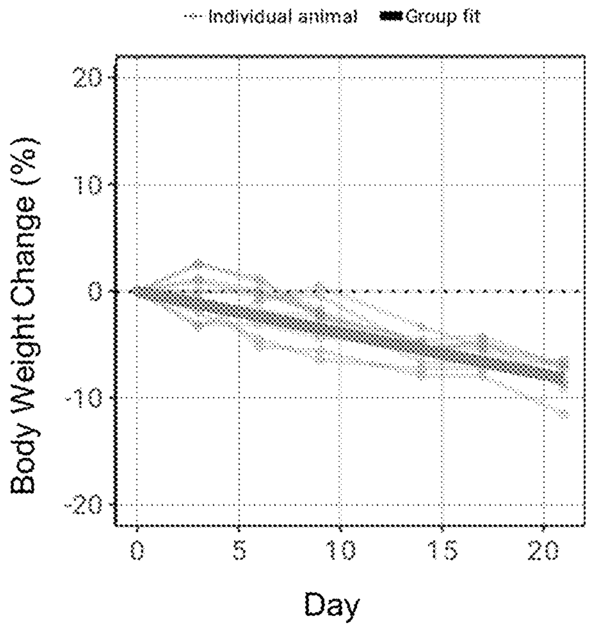
FIG. 43 depicts body weight change % over time of mice inoculated with NCI-H2122 cells; MC 0.5% PO QDx21+ MCT PO BIDx21.
Figure 44:
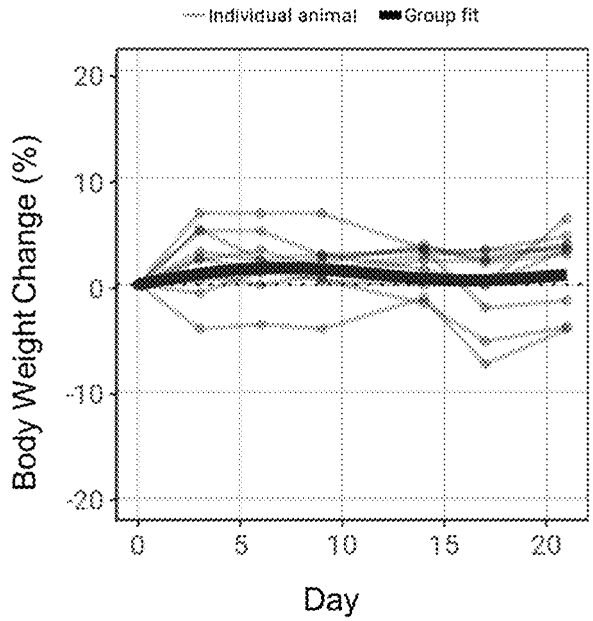
FIG. 44 depicts body weight change % over time of mice inoculated with NCI-H2122 cells; Compound K4 25 mg/kg PO QDx21.
Figure 45:
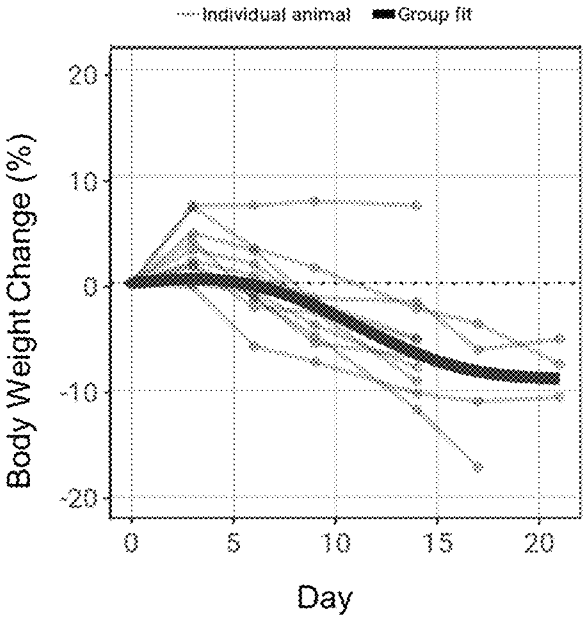
FIG. 45 depicts body weight change % over time of mice inoculated with NCI-H2122 cells; Compound T1 10 mg/kg PO BIDx21.
Figure 46:
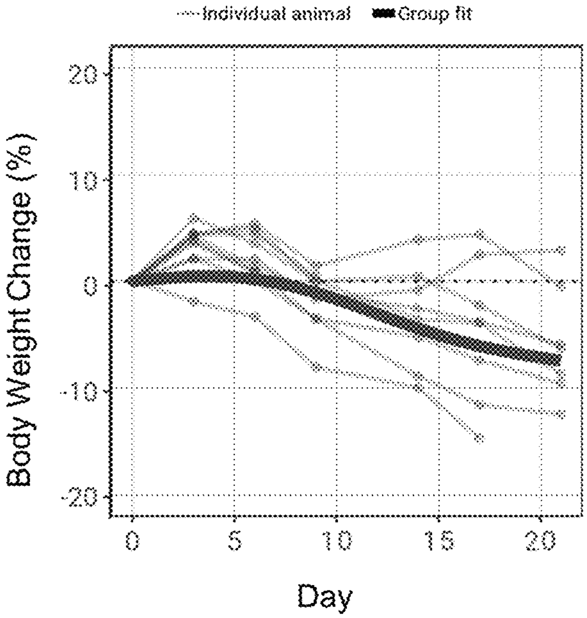
FIG. 46 depicts body weight change % over time of mice inoculated with NCI-H2122 cells; Compound T1 20 mg/kg PO QDx21.
Figure 47:
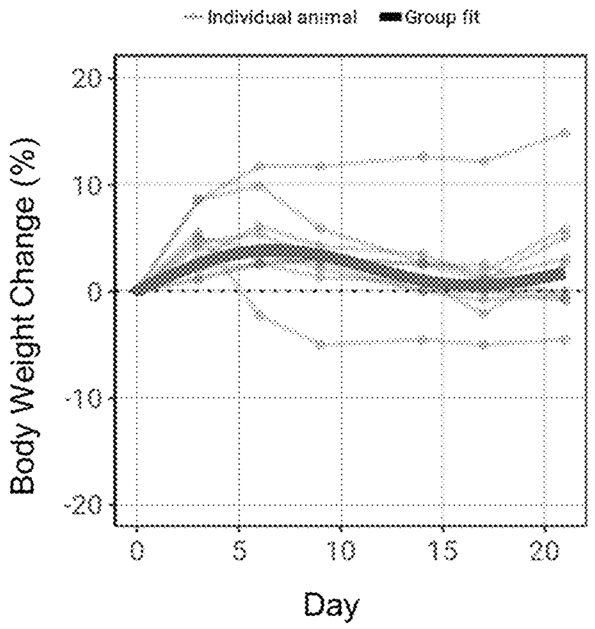
FIG. 47 depicts body weight change % over time of mice inoculated with NCI-H2122 cells; Compound K4 25 mg/kg PO QDx21 and Compound T1 10 mg/kg PO BIDx21.
Figure 48:
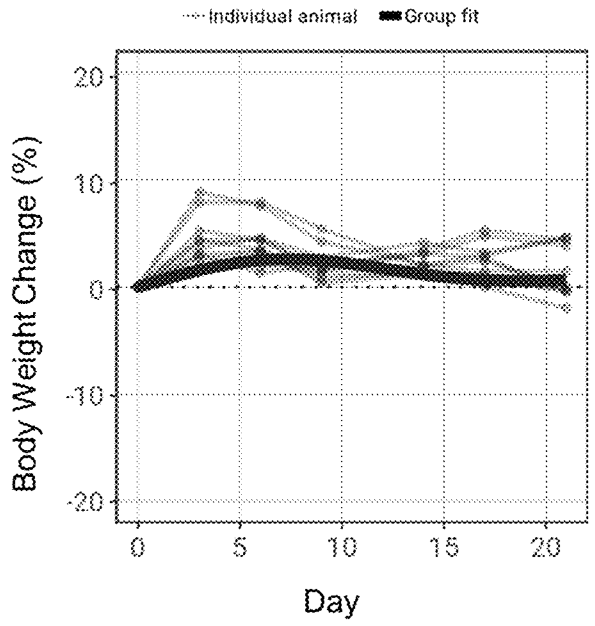
FIG. 48 depicts body weight change % over time of mice inoculated with NCI-H2122 cells; Compound K4 25 mg/kg PO QDx21 and Compound T1 20 mg/kg PO QDx21.

NCI-H2122 cells were cultured in vitro in RPMI 1640 media plus 1% L-glutamine with 10% fetal bovine serum, harvested in log-phase growth, and resuspended in Hank's Balanced Salt Solution (HBSS) containing Matrigel (BD Biosciences; San Jose, CA) at a 1:1 ratio by volume for in vivo inoculation. Immunodeficient female Nu/Nu (nude-CRL) mice were subcutaneously inoculated with 1 million cells in the right flank. Mice were dosed with K4 at 25 mg/kg qd po and with T1 at 10 mg/kg bid po or 20 mg/kg qd po alone or in combination for 21 days. Tumor size was measured with a caliper. Tumor volumes over time are depicted in FIGS. 37-42 and body weight change % over time is depicted in FIGS. 43-48.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

It is to be understood that the invention is not limited to the particular embodiments and aspects of the disclosure described above, as variations of the particular embodiments and aspects may be made and still fall within the scope of the appended claims. All documents cited to or relied upon herein are expressly incorporated by reference.

What is claimed is:

1. A compound of formula (I-AB):

(I-AB)

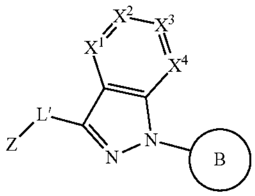

or a stereoisomer or tautomer thereof, or a pharmaceutically acceptable salt thereof, wherein:

L' is *—N($R^1$)-L-**, wherein * denotes the point of attachment to Z, and ** denotes the point of attachment to

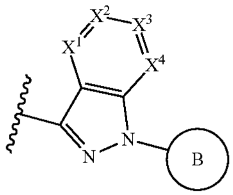

;

$R^1$ is H or $C_{1-6}$ alkyl;

$X^1$ is N or $CR^s$, wherein $R^s$ is selected from H, deuterium, —CN, halo, $C_{1-15}$alkyl, $C_{1-6}$alkynyl, $C_{6-20}$aryl, 5 to 15 membered heteroaryl, $C_{3-20}$cycloalkyl, 3 to 15 membered heterocyclyl, —OH, —$OR^f$, $C_{1-15}$alkoxy, —$NR^d$-$COR^e$, —$CONR^dR^e$, —$SO_2R^d$, —$SO_2NR^dR^e$, —$NR^dSO_2R^e$, and —$NR^dR^e$;

wherein each of $R^d$, $R^e$ and $R^f$ are independently H, $C_{1-6}$alkyl, or $C_{3-20}$cycloalkyl, wherein each of $C_{1-6}$alkyl and $C_{3-20}$cycloalkyl are independently optionally substituted with one or more halo, oxo, —OH, or —CN;

wherein the $C_{1-15}$alkyl and $C_{1-15}$alkoxy of $R^s$ are each independently optionally substituted with one or more $R^{t1}$, wherein $R^{t1}$ is independently, at each occurrence, selected from halo, oxo, —OH, —$OR^1$, —CN, —$NR^dR^e$, and 3 to 15 membered heterocyclyl optionally substituted with one or more —OH; wherein $R^{f1}$ is —$C(O)CH_2NR^dR^e$, —$C(O)C_{1-6}$alkyl, —$P(O)(OH)_2$; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN; and wherein the $C_{6-20}$aryl, 5 to 15 membered heteroaryl, $C_{3-20}$cycloalkyl, and 3 to 15 membered heterocyclyl of $R^s$ are each independently optionally substituted with one or more $R^{t2}$, wherein $R^{t2}$ is independently, at each occurrence, selected from halo, oxo, —OH, —CN, $C(O)NH_2$, —$C(O)NR^dR^e$, —$NR^dR^e$, $C_{1-6}$alkoxyl, 3 to 6 membered heterocyclyl, $C_{3-6}$cycloalkyl, and $C_{1-6}$alkyl; wherein the $C_{1-6}$alkyl of $R^{t2}$ is optionally substituted with one or more —OH, $C_{1-6}$alkoxyl, halo, oxo, —$S(O)_2CH_3$, or —$NR^dR^e$; wherein $R^d$ and $R^e$ are each independently H, —C(O)$CH_3$, —C(O)$C_{1-6}$alkyl, or $C_{1-6}$alkyl;

$X^2$, $X^3$, and $X^4$ are each independently N, CH, or CD, provided that: 1) only one of $X^1$, $X^2$, $X^3$, and $X^4$ is N; or 2) $X^1$ is N, $X^2$ is CH, $X^3$ is CH, and $X^4$ is N; or 3) $X^1$ is $CR^s$ and $X^2$, $X^3$, and $X^4$ are each independently CH or CD;

B is phenyl or 5 to 6 membered heteroaryl, wherein the phenyl or 5 to 6 membered heteroaryl of B are each independently optionally substituted with one or more R, wherein R is independently at each occurrence selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo;

Z is —C(O)$R^x$, wherein $R^x$ is $C_{2-6}$alkenyl, optionally substituted with one or more substituents selected from $C_{1-6}$alkyl, deuterium, —OH, $C_{1-6}$alkoxyl, and halo; or $R^x$ is $C_{1-6}$alkyl, optionally substituted with one or more halo; or $R^x$ is $C_{1-6}$alkynyl optionally substituted with —OH; or $R^x$ is cyclobutenyl, dihydrofuranyl, bicyclobutanyl, or cyclopentenyl; or Z is $S(O)_2R^{x1}$, wherein $R^{x1}$ is $C_{2-6}$alkenyl; and L is methylene, optionally substituted with one or more $C_{1-6}$alkyl.

2. The compound of claim 1, or a stereoisomer or tautomer thereof, or a pharmaceutically acceptable salt thereof, wherein the compound is a compound of formula (I-A):

(I-A)

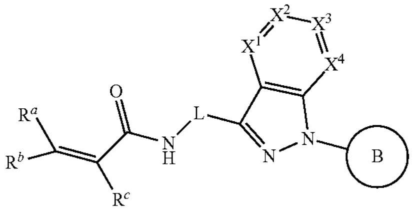

, or a stereoisomer or tautomer thereof, or a pharmaceutically acceptable salt thereof, wherein $R^a$, $R^b$, and $R^c$ are each independently H, deuterium, —OH, $C_{1-6}$alkoxyl, halo, or $C_{1-5}$alkyl.

3. The compound of claim 1, or a stereoisomer or tautomer thereof, or a pharmaceutically acceptable salt thereof, wherein the compound is a compound of formula (A-1):

(A-1)

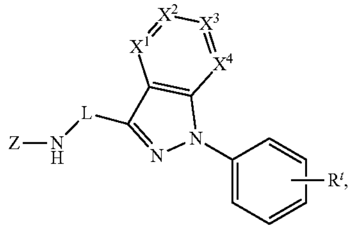

or a stereoisomer or tautomer thereof, or a pharmaceutically acceptable salt thereof.

4. The compound of claim 1, or a stereoisomer or tautomer thereof, or a pharmaceutically acceptable salt thereof, wherein the compound is a compound of formula (I-A-1):

(I-A-1)

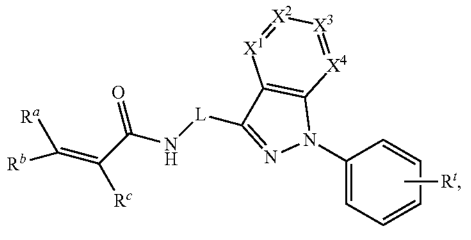

or a stereoisomer or tautomer thereof, or a pharmaceutically acceptable salt thereof, wherein:

$R^a$, $R^b$, and $R^c$ are each independently H, halo, deuterium, —OH, $C_{1-6}$alkoxyl, or $C_{1-5}$alkyl; and $R^t$ is selected from halo, $C_{1-15}$alkyl, $C_{1-6}$alkoxy, and $S(R^y)_5$, wherein each $R^y$ is halo, and wherein the $C_{1-15}$alkyl or $C_{1-6}$alkoxy of $R^t$ is optionally substituted with one or more halo.

5. The compound of claim 2, or a stereoisomer or tautomer thereof, or a pharmaceutically acceptable salt thereof, wherein the compound is a compound of formula (I-A-5):

(I-A-5)

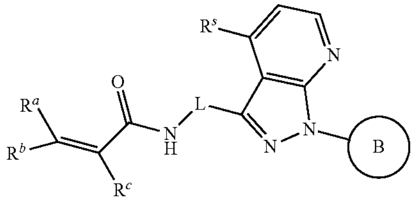

, or a stereoisomer or tautomer thereof, or a pharmaceutically acceptable salt thereof.

6. The compound of claim 5, or a stereoisomer or tautomer thereof, or a pharmaceutically acceptable salt thereof, wherein the compound is a compound of formula (I-A-12):

(I-A-12)

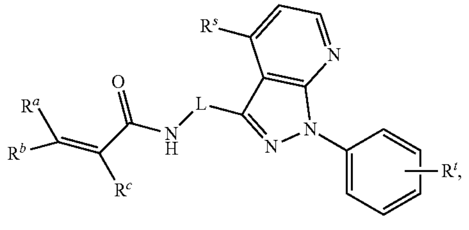

or a stereoisomer or tautomer thereof, or a pharmaceutically acceptable salt thereof.

7. The compound of claim 6, or a stereoisomer or tautomer thereof, or a pharmaceutically acceptable salt thereof, wherein the compound is a compound of formula (I-A-13):

(I-A-13)

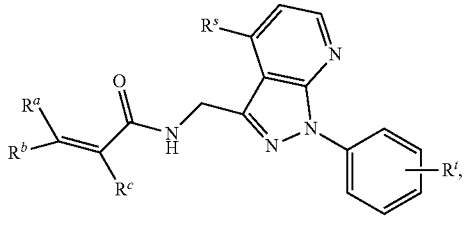

or a stereoisomer or tautomer thereof, or a pharmaceutically acceptable salt thereof.

8. The compound of claim 1, or a stereoisomer or tautomer thereof, or a pharmaceutically acceptable salt thereof, wherein the R of B is —$SF_5$, —O—$CHF_2$, or —O—$CF_3$.

9. The compound of claim 1 or a stereoisomer or tautomer thereof, or a pharmaceutically acceptable salt thereof, wherein Z is —C(O)$R^x$ and $R^x$ is $C_{2-6}$alkenyl optionally substituted with one or more substituents selected from $C_{1-6}$alkyl, deuterium, —OH, $C_{1-6}$alkoxyl, and halo; or $R^x$ is $C_{1-6}$alkyl optionally substituted with one or more halo.

10. The compound of claim 1, or a stereoisomer or tautomer thereof or a pharmaceutically acceptable salt thereof, wherein $X^1$ is $CR^s$; and $X^2$, $X^3$, and $X^4$ are CH.

11. The compound of claim 1, or a stereoisomer or tautomer thereof or a pharmaceutically acceptable salt thereof, wherein $X^1$ is $CR^s$; $X^2$ and $X^3$ are CH; and $X^4$ is N.

12. The compound of claim 1, or a stereoisomer or tautomer thereof, or a pharmaceutically acceptable salt thereof, wherein $R^s$ is H, halo, or —CN.

13. The compound of claim 1, or a stereoisomer or tautomer thereof, or a pharmaceutically acceptable salt thereof, wherein $R^s$ is —$OR^f$, wherein $R^f$ is $C_{3-20}$cycloalkyl optionally substituted with one or more —OH.

14. The compound of claim 1, or a stereoisomer or tautomer thereof, or a pharmaceutically acceptable salt thereof, wherein $R^s$ is $C_{1-15}$alkyl or $C_{1-15}$alkoxy, wherein the $C_{1-15}$alkyl or $C_{1-15}$alkoxy of $R^s$ are each independently optionally substituted with one or more $R^{t1}$, wherein $R^{t1}$ is independently, at each occurrence, selected from halo, oxo, —OH, —$OR^{f1}$, —CN, —$NR^dR^e$, and 3 to 15 membered heterocyclyl optionally substituted with one or more —OH; wherein $R^{f1}$ is —C(O)$CH_2NR^dR^e$, —C(O)$C_{1-6}$alkyl, —P(O)$(OH)_2$; wherein $R^d$ and $R^e$ are each independently H or $C_{1-6}$alkyl, and the $C_{1-6}$alkyl of $R^d$ or $R^e$ is optionally substituted with one or more halo, oxo, —OH, or —CN.

15. The compound of claim 1, or a stereoisomer or tautomer thereof, or a pharmaceutically acceptable salt thereof, wherein $R^s$ is —$NR^dR^e$, wherein $R^d$ and $R^e$ are each independently selected from the group consisting of H, $C_{1-6}$alkyl, $C_{3-20}$cycloalkyl, —C(O)$R^t$, wherein $R^t$ is $C_{1-6}$alkyl, wherein each of $C_{1-6}$alkyl, $C_{3-20}$cycloalkyl are optionally substituted with one or more —OH.

16. The compound of claim 1, or a stereoisomer or tautomer thereof, or a pharmaceutically acceptable salt thereof, wherein $R^s$ is —C(O)$NR^dR^e$, wherein $R^d$ and $R^e$ are each independently selected from the group consisting of H and $C_{1-6}$alkyl, wherein $C_{1-6}$alkyl is optionally substituted with one or more —OH.

17. The compound of claim 1, or a stereoisomer or tautomer thereof, or a pharmaceutically acceptable salt thereof, wherein $R^s$ is $C_{1-6}$alkyl optionally substituted with one or more —OH.

18. The compound of claim 1 or a stereoisomer or tautomer thereof, or a pharmaceutically acceptable salt thereof, wherein $R^s$ is selected from the group consisting of

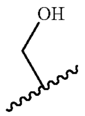 and 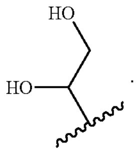.

19. The compound of claim 1 or a stereoisomer or tautomer thereof, or a pharmaceutically acceptable salt thereof, wherein the compound is selected from:

| Compound Number | Structure | Compound Name |
|---|---|---|
| 1 | 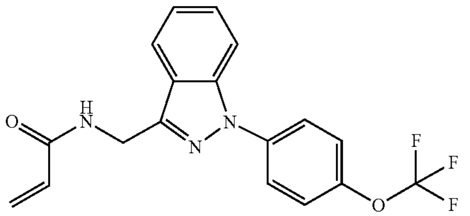 [SMILES: C=CC(=O)NCc1nn(-c2ccc(OC(F)(F)F)cc2)c2ccccc12] | N-((1-(4-(trifluoromethoxy)phenyl)-1H-indazol-3-yl)methyl)acrylamide |
| 2 | 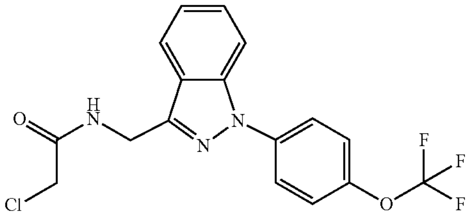 [SMILES: O=C(CCl)NCc1nn(-c2ccc(OC(F)(F)F)cc2)c2ccccc12] | 2-chloro-N-((1-(4-(trifluoromethoxy)phenyl)-1H-indazol-3-yl)methyl)acetamide |

-continued

| Compound Number | Structure | Compound Name |
|---|---|---|
| 3 | 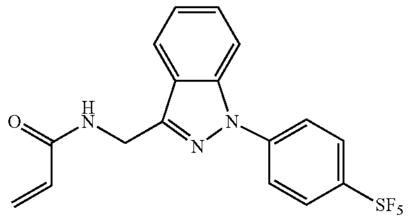 | N-((1-(4-(pentafluoro-λ6-sulfaneyl)phenyl)-1H-indazol-3-yl)methyl)acrylamide |
| 4 | 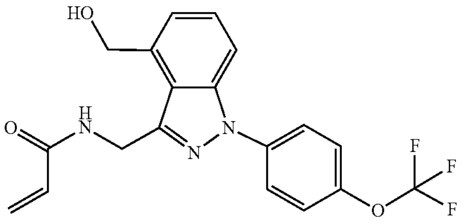 [SMILES: C=CC(=O)NCc1nn(-c2ccc(OC(F)(F)F)cc2)c2cccc(CO)c12] | N-((4-(hydroxymethyl)-1-(4-(trifluoromethoxy)phenyl)-1H-indazol-3-yl)methyl)acrylamide |
| 5 | 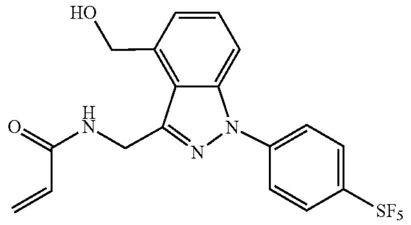 | N-((4-(hydroxymethyl)-1-(4-(pentafluoro-λ6-sulfaneyl)phenyl)-1H-indazol-3-yl)methyl)acrylamide |
| 6 | 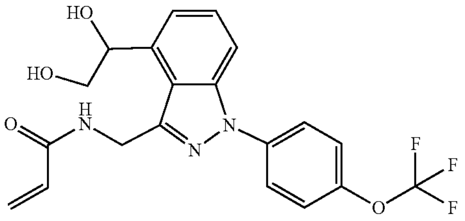 [SMILES: C=CC(=O)NCc1nn(-c2ccc(OC(F)(F)F)cc2)c2cccc(C(O)CO)c12] | N-((4-(1,2-dihydroxyethyl)-1-(4-(trifluoromethoxy)phenyl)-1H-indazol-3-yl)methyl)acrylamide |
| 7 | 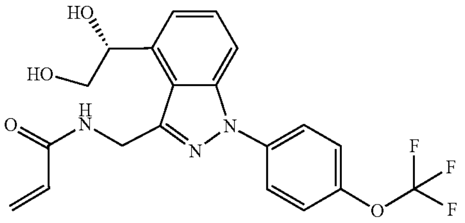 [SMILES: C=CC(=O)NCc1nn(-c2ccc(OC(F)(F)F)cc2)c2cccc([C@@H](O)CO)c12] | (R)-N-((4-(1,2-dihydroxyethyl)-1-(4-(trifluoromethoxy)phenyl)-1H-indazol-3-yl)methyl)acrylamide |
| 8 | 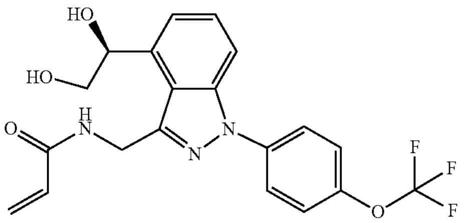 [SMILES: C=CC(=O)NCc1nn(-c2ccc(OC(F)(F)F)cc2)c2cccc([C@H](O)CO)c12] | (S)-N-((4-(1,2-dihydroxyethyl)-1-(4-(trifluoromethoxy)phenyl)-1H-indazol-3-yl)methyl)acrylamide |

-continued

| Compound Number | Structure | Compound Name |
|---|---|---|
| 9 | 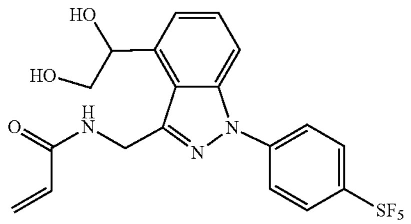 | N-((4-(1,2-dihydroxyethyl)-1-(4-(pentafluoro-λ6-sulfaneyl)phenyl)-1H-indazol-3-yl)methyl)acrylamide |
| 10 | 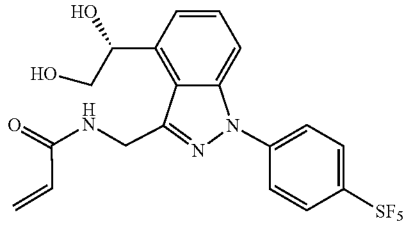 | (R)-N-((4-(1,2-dihydroxyethyl)-1-(4-(pentafluoro-λ6-sulfaneyl)phenyl)-1H-indazol-3-yl)methyl)acrylamide |
| 11 | 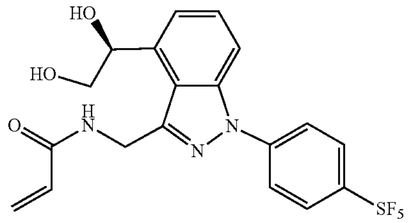 | (S)-N-((4-(1,2-dihydroxyethyl)-1-(4-(pentafluoro-λ6-sulfaneyl)phenyl)-1H-indazol-3-yl)methyl)acrylamide |
| 12 | 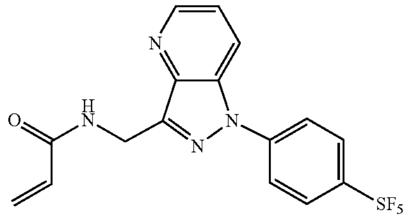 | N-((l-(4-(pentafluoro-λ6-sulfaneyl)phenyl)-1H-pyrazolo[4,3-b]pyridin-3-yl)methyl)acrylamide |
| 13 | 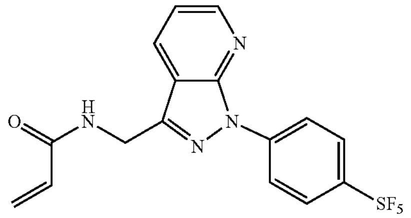 | N-((l-(4-(pentafluoro-λ6-sulfaneyl)phenyl)-1H-pyrazolo[3,4-b]pyridin-3-yl)methyl)acrylamide |
| 14 | 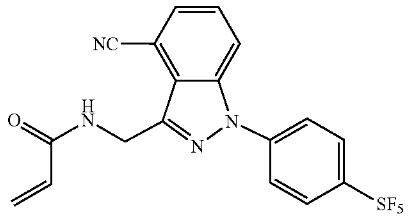 | N-((4-cyano-1-(4-(pentafluoro-λ6-sulfaneyl)phenyl)-1H-indazol-3-yl)methyl)acrylamide |

-continued

| Compound Number | Structure | Compound Name |
|---|---|---|
| 15 | 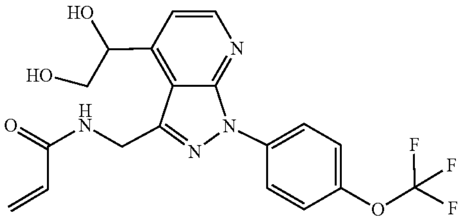 [SMILES: C=CC(=O)NCc1nn(-c2ccc(OC(F)(F)F)cc2)c2nccc(C(O)CO)c12] | N-[[4-(1,2-dihydroxyethyl)-1-(4-(trifluoromethoxy)phenyl)-1H-pyrazolo[3,4-b]pyridin-3-yl]methyl]acrylamide |
| 16 | 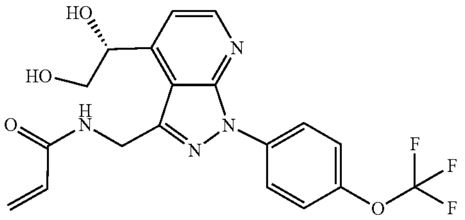 [SMILES: C=CC(=O)NCc1nn(-c2ccc(OC(F)(F)F)cc2)c2nccc([C@@H](O)CO)c12] | (R)-N-[[4-(1,2-dihydroxyethyl)-1-(4-(trifluoromethoxy)phenyl)-1H-pyrazolo[3,4-b]pyridin-3-yl]methyl]acrylamide |
| 17 | 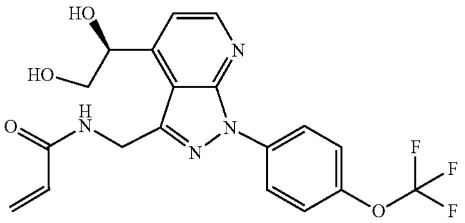 [SMILES: C=CC(=O)NCc1nn(-c2ccc(OC(F)(F)F)cc2)c2nccc([C@H](O)CO)c12] | (S)-N-[[4-(1,2-dihydroxyethyl)-1-(4-(trifluoromethoxy)phenyl)-1H-pyrazolo[3,4-b]pyridin-3-yl]methyl]acrylamide |
| 18 | 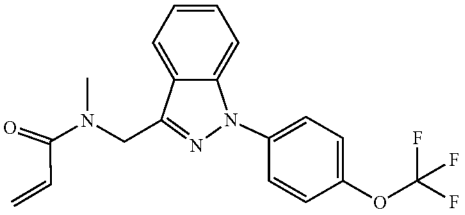 [SMILES: C=CC(=O)N(C)Cc1nn(-c2ccc(OC(F)(F)F)cc2)c2ccccc12] | N-methyl-N-((1-(4-(trifluoromethoxy)phenyl)-1H-indazol-3-yl)methyl)acrylamide |
| 19 | 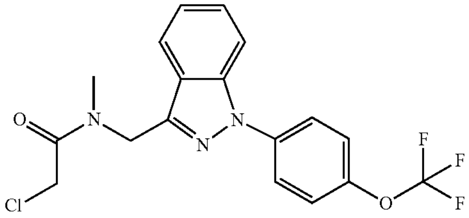 [SMILES: CN(Cc1nn(-c2ccc(OC(F)(F)F)cc2)c2ccccc12)C(=O)CCl] | 2-chloro-N-methyl-N-((1-(4-(trifluoromethoxy)phenyl)-1H-indazol-3-yl)methyl)acetamide |
| 23 | 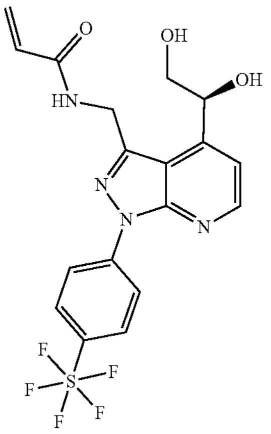 [SMILES: C=CC(=O)NCc1nn(-c2ccc(S(F)(F)(F)(F)F)cc2)c2nccc([C@H](O)CO)c12] | N-[[1-[4-(pentafluoro-lambda6-sulfanyl)phenyl]-4-[rac-(1S)-1,2-dihydroxyethyl]pyrazolo[3,4-b]pyridin-3-yl]methyl]prop-2-enamide |

-continued
| Compound Number | Structure | Compound Name |
|---|---|---|
| 24 | 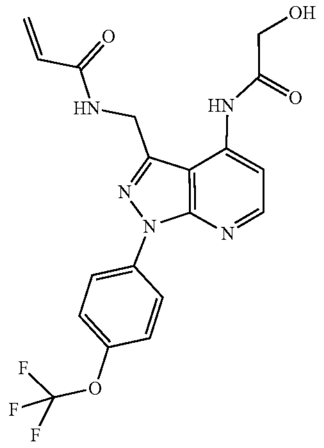 [SMILES: C=CC(=O)NCc1nn(-c2ccc(OC(F)(F)F)cc2)c2nccc(NC(=O)CO)c12] | N-[[4-[(2-hydroxyacetyl)amino]-1-[4-(trifluoromethoxy)phenyl]pyrazolo[3,4-b]pyridin-3-yl]methyl]prop-2-enamide |
| 25 | 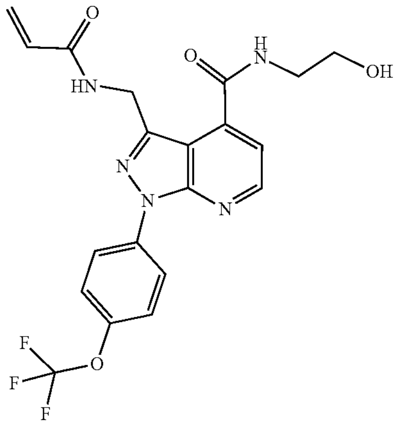 [SMILES: C=CC(=O)NCc1nn(-c2ccc(OC(F)(F)F)cc2)c2nccc(C(=O)NCCO)c12] | N-(2-hydroxyethyl)-3-[(prop-2-enoylamino)methyl]-1-[4-(trifluoromethoxy)phenyl]pyrazolo[3,4-b]pyridine-4-carboxamide |
| 26 | 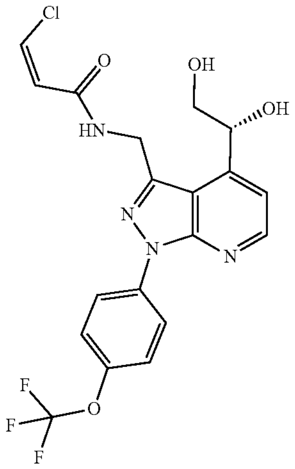 [SMILES: O=C(/C=C\Cl)NCc1nn(-c2ccc(OC(F)(F)F)cc2)c2nccc([C@@H](O)CO)c12] | (Z)-3-chloro-N-[[4-[(1R)-1,2-dihydroxyethyl]-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 27 | 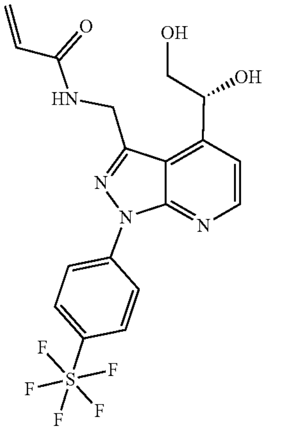 [SMILES: C=CC(=O)NCc1nn(-c2ccc(S(F)(F)(F)(F)F)cc2)c2nccc([C@@H](O)CO)c12] | N-[[1-[4-(pentafluoro-lambda6-sulfanyl)phenyl]-4-[rac-(1R)-1,2-dihydroxyethyl]pyrazolo[3,4-b]pyridin-3-yl]methyl]prop-2-enamide |
| 30 | 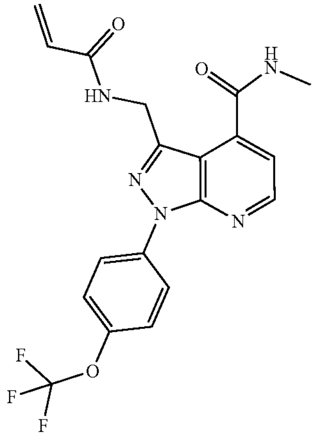 [SMILES: C=CC(=O)NCc1nn(-c2ccc(OC(F)(F)F)cc2)c2nccc(C(=O)NC)c12] | N-methyl-3-[(prop-2-enoylamino)methyl]-1-[4-(trifluoromethoxy)phenyl]pyrazolo[3,4-b]pyridine-4-carboxamide |
| 32 | 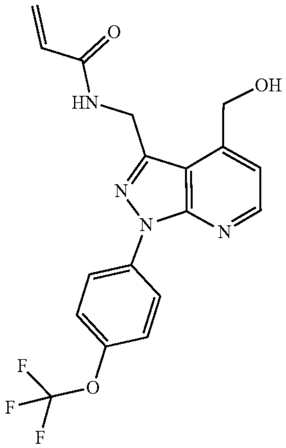 [SMILES: C=CC(=O)NCc1nn(-c2ccc(OC(F)(F)F)cc2)c2nccc(CO)c12] | N-[[4-(hydroxymethyl)-1-[4-(trifluoromethoxy)phenyl]pyrazolo[3,4-b]pyridin-3-yl]methyl]prop-2-enamide |

-continued
| Compound Number | Structure | Compound Name |
| --- | --- | --- |
| 33 | 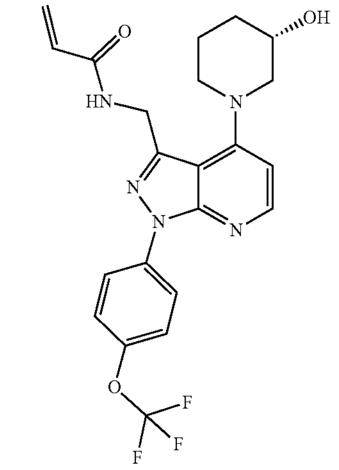 [SMILES: C=CC(=O)NCc1nn(-c2ccc(OC(F)(F)F)cc2)c2nccc(N3CCC[C@H](O)C3)c12] | N-[[4-[(3S)-3-hydroxy-1-piperidyl]-1-[4-(trifluoromethoxy)phenyl]pyrazolo[3,4-b]pyridin-3-yl]methyl]prop-2-enamide |
| 34 | 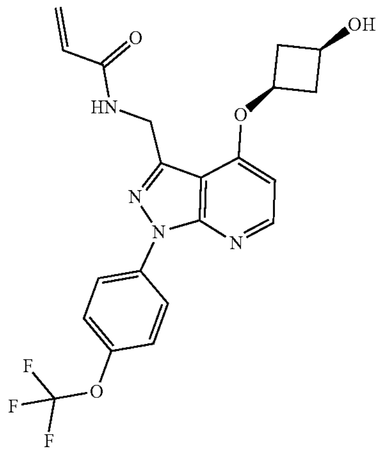 [SMILES: C=CC(=O)NCc1nn(-c2ccc(OC(F)(F)F)cc2)c2nccc(O[C@H]3C[C@@H](O)C3)c12] | N-[[4-(3-hydroxycyclobutoxy)-1-[4-(trifluoromethoxy)phenyl]pyrazolo[3,4-b]pyridin-3-yl]methyl]prop-2-enamide |
| 35 | 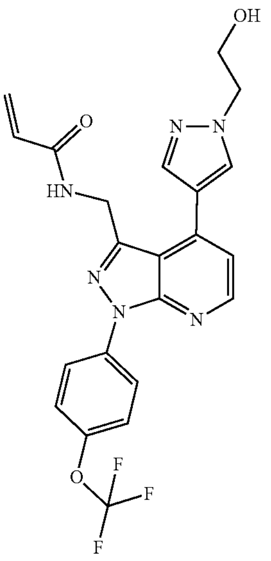 [SMILES: C=CC(=O)NCc1nn(-c2ccc(OC(F)(F)F)cc2)c2nccc(-c3cnn(CCO)c3)c12] | N-[[4-[l-(2-hydroxyethyl)pyrazol-4-yl]-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 36 | 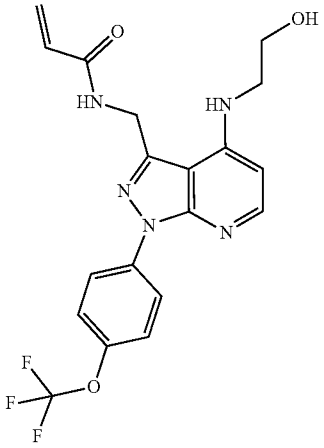 [SMILES: C=CC(=O)NCc1nn(-c2ccc(OC(F)(F)F)cc2)c2nccc(NCCO)c12] | N-[[4-(2-hydroxyethylamino)-1-[4-(trifluoromethoxy)phenyl]pyrazolo[3,4-b]pyridin-3-yl]methyl]prop-2-enamide |
| 37 | 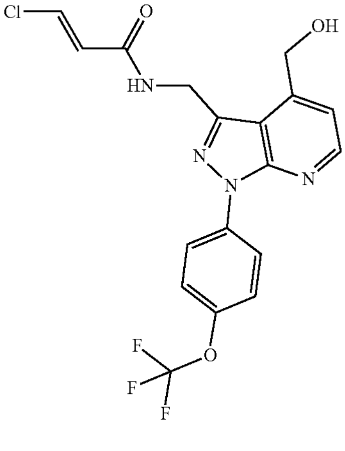 [SMILES: O=C(/C=C/Cl)NCc1nn(-c2ccc(OC(F)(F)F)cc2)c2nccc(CO)c12] | (E)-3-chloro-N-[[4-(hydroxymethyl)-1-[4-(trifluoromethoxy)phenyl]pyrazolo[3,4-b]pyridin-3-yl]methyl]prop-2-enamide |
| 38 | 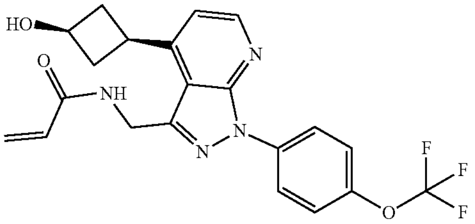 [SMILES: C=CC(=O)NCc1nn(-c2ccc(OC(F)(F)F)cc2)c2nccc([C@H]3C[C@@H](O)C3)c12] | N-[[4-(3-hydroxycyclobutyl)-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 43 | 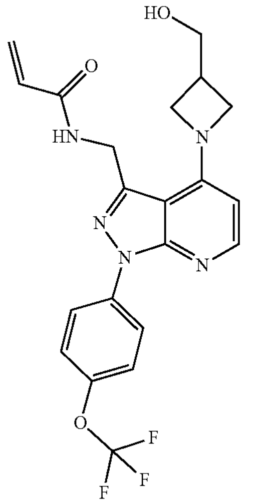 [SMILES: C=CC(=O)NCc1nn(-c2ccc(OC(F)(F)F)cc2)c2nccc(N3CC(CO)C3)c12] | N-[[4-[3-(hydroxymethyl)azetidin-1-yl]-1-[4-(trifluoromethoxy)phenyl]pyrazolo[3,4-b]pyridin-3-yl]methyl]prop-2-enamide |
| 44 | 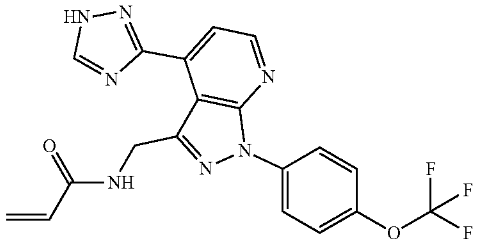 [SMILES: C=CC(=O)NCc1nn(-c2ccc(OC(F)(F)F)cc2)c2nccc(-c3nc[nH]n3)c12] | N-[[4-(1H-1,2,4-triazol-3-yl)-1-[4-(trifluoromethoxy)phenyl]pyrazolo[3,4-b]pyridin-3-yl]methyl]prop-2-enamide |
| 46 | 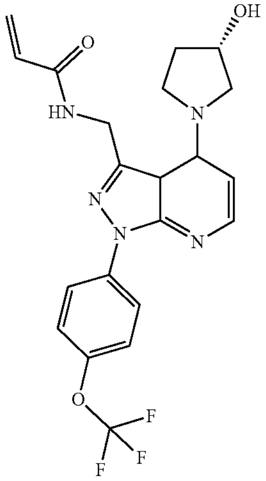 | N-[[4-[(3S)-3-hydroxypyrrolidin-1-yl]-1-4-(trifluoromethoxy)phenyl]pyrazolo[3,4-b]pyridin-3-yl]methyl]prop-2-enamide |

-continued
| Compound Number | Structure | Compound Name |
|---|---|---|
| 47 | 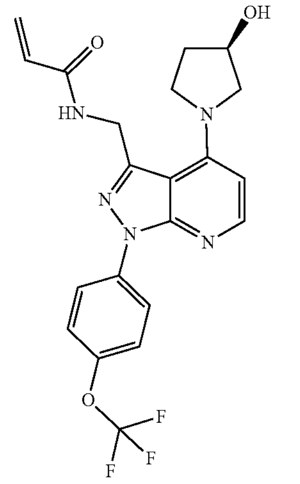 [SMILES: C=CC(=O)NCc1nn(-c2ccc(OC(F)(F)F)cc2)c2nccc(N3CC[C@@H](O)C3)c12] | N-[[4-[(3R)-3-hydroxypyrrolidin-1-yl]-1-4-(trifluoromethoxy)phenyl]pyrazolo[3,4-b]pyridin-3-yl]methyl]prop-2-enamide |
| 49 | 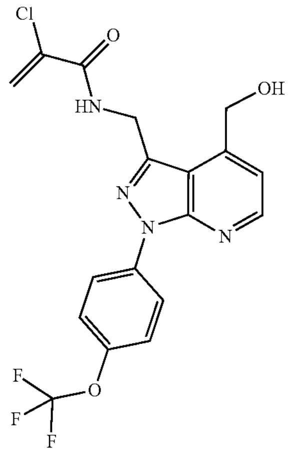 [SMILES: C=C(Cl)C(=O)NCc1nn(-c2ccc(OC(F)(F)F)cc2)c2nccc(CO)c12] | 2-chloro-N-[[4-(hydroxymethyl)-1-[4-(trifluoromethoxy)phenyl]pyrazolo[3,4-b]pyridin-3-yl]methyl]prop-2-enamide |
| 51 | 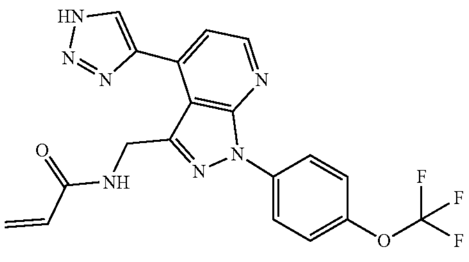 [SMILES: C=CC(=O)NCc1nn(-c2ccc(OC(F)(F)F)cc2)c2nccc(-c3c[nH]nn3)c12] | N-[[4-(1H-triazol-4-yl)-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 52 | 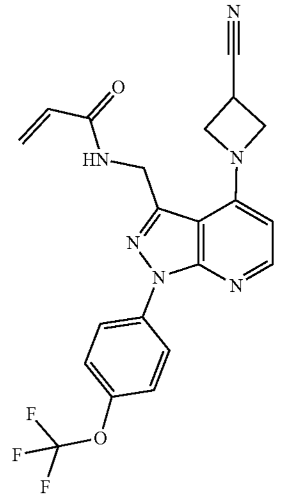 [SMILES: C=CC(=O)NCc1nn(-c2ccc(OC(F)(F)F)cc2)c2nccc(N3CC(C#N)C3)c12] | N-[[4-(3-cyanoazetidin-1-yl)-1-[4-(trifluoromethoxy)phenyl]pyrazolo[3,4-b]pyridin-3-yl]methyl]prop-2-enamide |
| 53 | 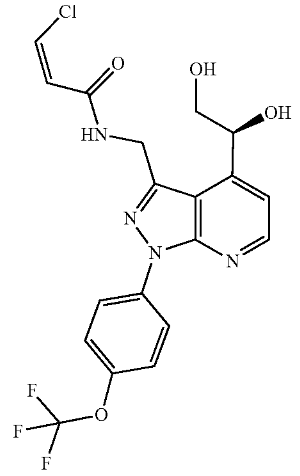 [SMILES: O=C(/C=C\Cl)NCc1nn(-c2ccc(OC(F)(F)F)cc2)c2nccc([C@H](O)CO)c12] | (Z)-3-chloro-N-[[4-[(1S)-1,2-dihydroxyethyl]-1-[4-(trifluoromethoxy)phenyl]pyrazolo[3,4-b]pyridin-3-yl]methyl]prop-2-enamide |
| 54 | 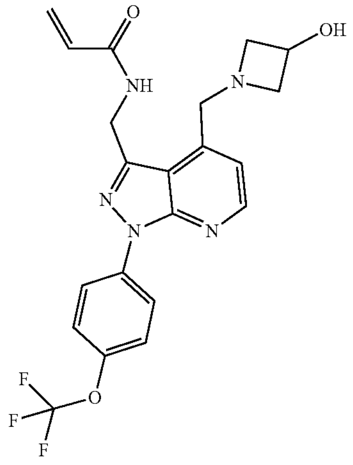 [SMILES: C=CC(=O)NCc1nn(-c2ccc(OC(F)(F)F)cc2)c2nccc(CN3CC(O)C3)c12] | N-[[4-[(3-hydroxyazetidin-1-yl)methyl]-1-[4-(trifluoromethoxy)phenyl]pyrazolo[3,4-b]pyridin-3-yl]methyl]prop-2-enamide |

-continued

| Compound Number | Structure | Compound Name |
|---|---|---|
| 55 | 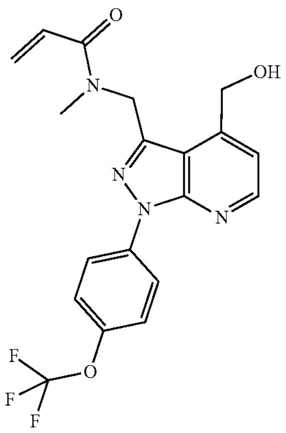 [SMILES: C=CC(=O)N(C)Cc1nn(-c2ccc(OC(F)(F)F)cc2)c2nccc(CO)c12] | N-[[4-(hydroxymethyl)-1-[4-(trifluoromethoxy)phenyl]pyrazolo[3,4-b]pyridin-3-yl]methyl]-N-methyl-prop-2-enamide |
| 56 | 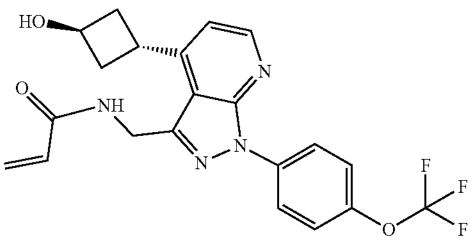 [SMILES: C=CC(=O)NCc1nn(-c2ccc(OC(F)(F)F)cc2)c2nccc([C@H]3C[C@H](O)C3)c12] | N-[[4-(3-hydroxycyclobutyl)-1-[4-(trifluoromethoxy)phenyl]pyrazolo[3,4-b]pyridin-3-yl]methyl]prop-2-enamide |
| 61 | 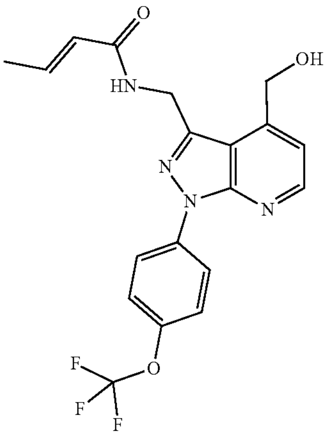 [SMILES: C/C=C/C(=O)NCc1nn(-c2ccc(OC(F)(F)F)cc2)c2nccc(CO)c12] | (E)-N-[[4-(hydroxymethyl)-1-[4-(trifluoromethoxy)phenyl]pyrazolo[3,4-b]pyridin-3-yl]methyl]but-2-enamide |
| 62 | 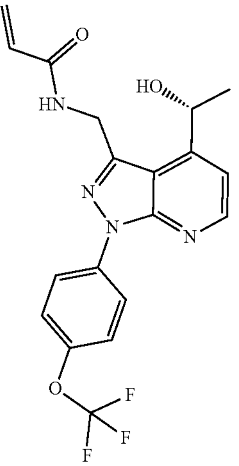 [SMILES: C=CC(=O)NCc1nn(-c2ccc(OC(F)(F)F)cc2)c2nccc([C@@H](C)O)c12] | N-[[4-[(lR)-1-hydroxyethyl]-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 63 | 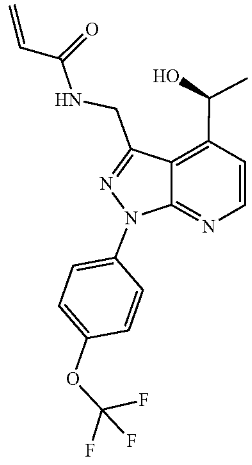 [SMILES: C=CC(=O)NCc1nn(-c2ccc(OC(F)(F)F)cc2)c2nccc([C@H](C)O)c12] | N-[[4-[(1S)-1-hydroxyethyl]-1-[4-(trifluoromethoxy)phenyl]pyrazolo[3,4-b]pyridin-3-yl]methyl]prop-2-enamide |
| 65 | 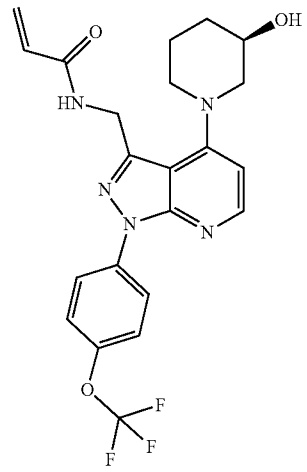 [SMILES: C=CC(=O)NCc1nn(-c2ccc(OC(F)(F)F)cc2)c2nccc(N3CCC[C@@H](O)C3)c12] | N-[[4-[(3R)-3-hydroxy-1-piperidyl]-1-[4-(trifluoromethoxy)phenyl]pyrazolo[3,4-b]pyridin-3-yl]methyl]prop-2-enamide |
| 67 | 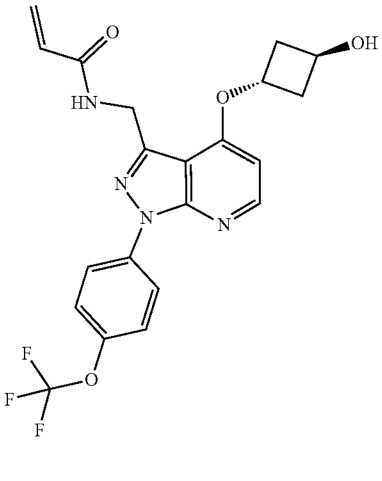 [SMILES: C=CC(=O)NCc1nn(-c2ccc(OC(F)(F)F)cc2)c2nccc(O[C@H]3C[C@H](O)C3)c12] | N-[[4-(3-hydroxycyclobutoxy)-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 68 | 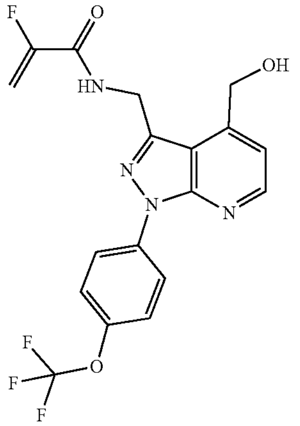 [SMILES: C=C(F)C(=O)NCc1nn(-c2ccc(OC(F)(F)F)cc2)c2nccc(CO)c12] | 2-fluoro-N-[[4-(hydroxymethyl)-1-[4-(trifluoromethoxy)phenyl]pyrazolo[3,4-b]pyridin-3-yl]methyl]prop-2-enamide |
| 69 | 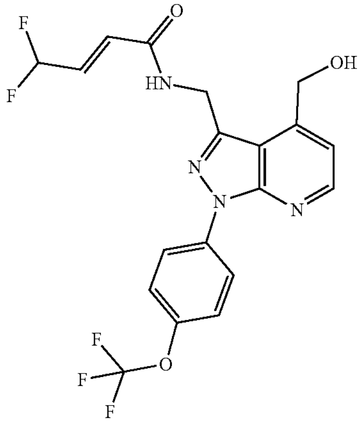 [SMILES: O=C(/C=C/C(F)F)NCc1nn(-c2ccc(OC(F)(F)F)cc2)c2nccc(CO)c12] | (E)-4,4-difluoro-N-[[4-(hydroxymethyl)-1-[4-(trifluoromethoxy)phenyl]pyrazolo[3,4-b]pyridin-3-yl]methyl]but-2-enamide |
| 73 | 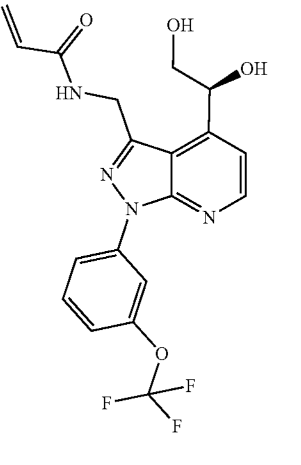 [SMILES: C=CC(=O)NCc1nn(-c2cccc(OC(F)(F)F)c2)c2nccc([C@H](O)CO)c12] | N-[[4-[rac-(1S)-1,2-dihydroxyethyl]-1-[3-(trifluoromethoxy)phenyl]pyrazolo[3,4-b]pyridin-3-yl]methyl]prop-2-enamide |

-continued
| Compound Number | Structure | Compound Name |
|---|---|---|
| 74 | 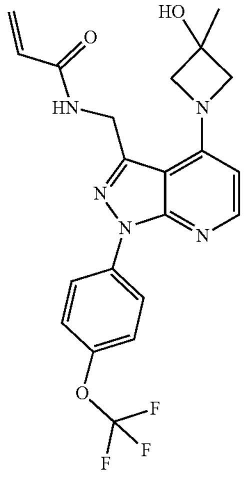 [SMILES: C=CC(=O)NCc1nn(-c2ccc(OC(F)(F)F)cc2)c2nccc(N3CC(C)(O)C3)c12] | N-[[4-(3-hydroxy-3-methyl-azetidin-1-yl)-1-[4-(trifluoromethoxy)phenyl]pyrazolo[3,4-b]pyridin-3-yl]methyl]prop-2-enamide |
| 76 | 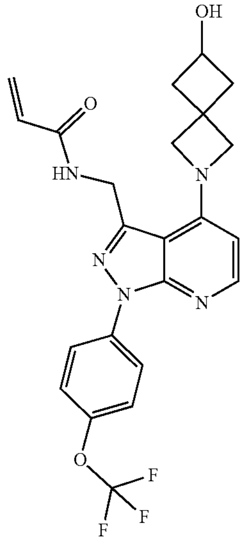 [SMILES: C=CC(=O)NCc1nn(-c2ccc(OC(F)(F)F)cc2)c2nccc(N3CC4(CC(O)C4)C3)c12] | N-[[4-(6-hydroxy-2-azaspiro[3.3]heptan-2-yl)-1-[4-(trifluoromethoxy)phenyl]pyrazolo[3,4-b]pyridin-3-yl]methyl]prop-2-enamide |
| 77 | 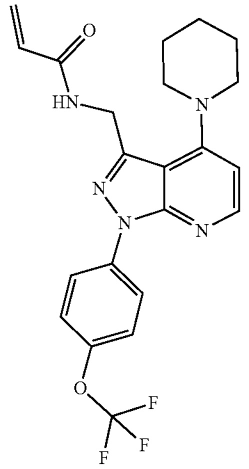 | N-[[4-morpholino-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 83 | 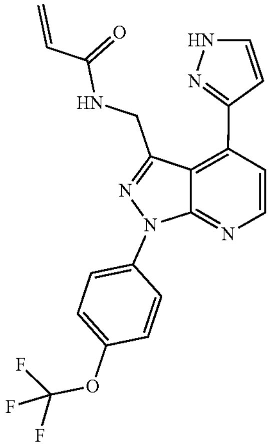 [SMILES: C=CC(=O)NCc1nn(-c2ccc(OC(F)(F)F)cc2)c2nccc(-c3cc[nH]n3)c12] | N-[[4-(1H-pyrazol-3-yl)-1-[4-(trifluoromethoxy)phenyl]pyrazolo[3,4-b]pyridin-3-yl]methyl]prop-2-enamide |
| 84 | 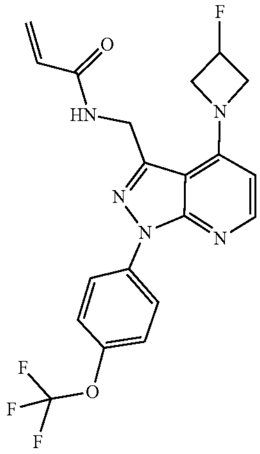 | N-[[4-(3-fluoroazetidin-1-yl)-1-[4-(trifluoromethoxy)phenyl]pyrazolo[3,4-b]pyridin-3-yl]methyl]prop-2-enamide |
| 85 | 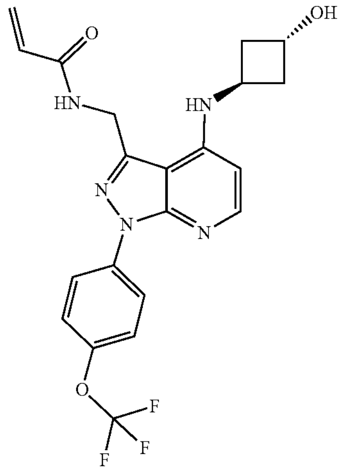 [SMILES: C=CC(=O)NCc1nn(-c2ccc(OC(F)(F)F)cc2)c2nccc(N[C@H]3C[C@H](O)C3)c12] | N-[[4-[(3-hydroxycyclobutyl)amino]-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 86 | 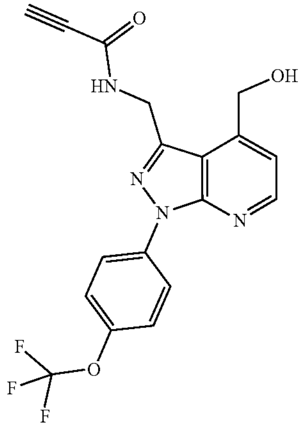 [SMILES: C#CC(=O)NCc1nn(-c2ccc(OC(F)(F)F)cc2)c2nccc(CO)c12] | N-[[4-(hydroxymethyl)-1-[4-(trifluoromethoxy)phenyl]pyrazolo[3,4-b]pyridin-3-yl]methyl]prop-2-ynamide |
| 87 | 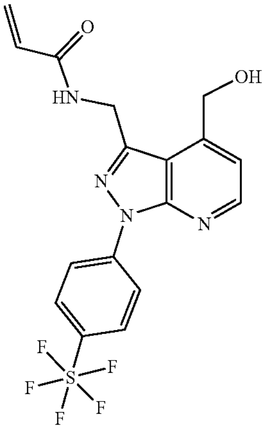 [SMILES: C=CC(=O)NCc1nn(-c2ccc(S(F)(F)(F)(F)F)cc2)c2nccc(CO)c12] | N-[[4-(hydroxymethyl)-1-[4-(pentafluoro-lambda6-sulfanyl)phenyl]pyrazolo[3,4-b]pyridin-3-yl]methyl]prop-2-enamide |
| 88 | 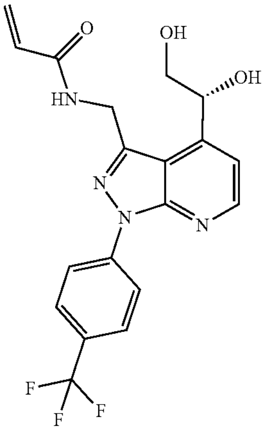 [SMILES: C=CC(=O)NCc1nn(-c2ccc(C(F)(F)F)cc2)c2nccc([C@@H](O)CO)c12] | N-[[4-[rac-(lR)-1,2-dihydroxyethyl]-1-[4-(trifluoromethyl)phenyl]pyrazolo[3,4-b]pyridin-3-yl]methyl]prop-2-enamide |

-continued
| Compound Number | Structure | Compound Name |
|---|---|---|
| 90 | 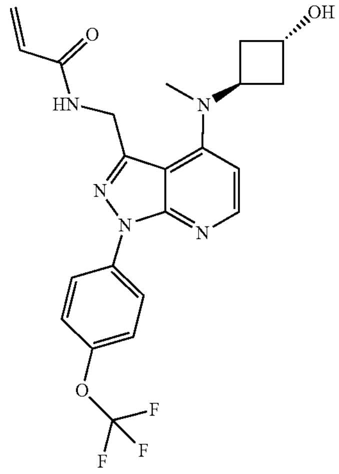 [SMILES: C=CC(=O)NCc1nn(-c2ccc(OC(F)(F)F)cc2)c2nccc(N(C)[C@H]3C[C@H](O)C3)c12] | N-[[4-[(3-hydroxycyclobutyl)-methyl-amino]-1-[4-(trifluoromethoxy)phenyl]pyrazolo[3,4-b]pyridin-3-yl]methyl]prop-2-enamide |
| 91 | 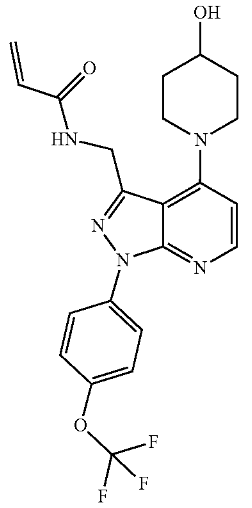 [SMILES: C=CC(=O)NCc1nn(-c2ccc(OC(F)(F)F)cc2)c2nccc(N3CCC(O)CC3)c12] | N-[[4-(4-hydroxy-1-piperidyl)-1-[4-(trifluoromethoxy)phenyl]pyrazolo[3,4-b]pyridin-3-yl]methyl]prop-2-enamide |
| 92 | 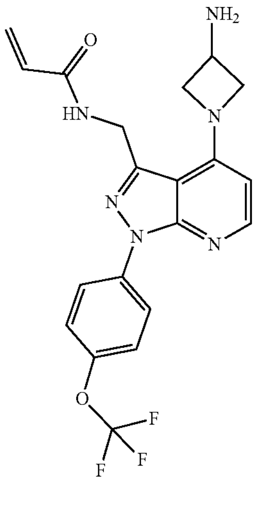 [SMILES: C=CC(=O)NCc1nn(-c2ccc(OC(F)(F)F)cc2)c2nccc(N3CC(N)C3)c12] | N-[[4-(3-aminoazetidin-1-yl)-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 93 | 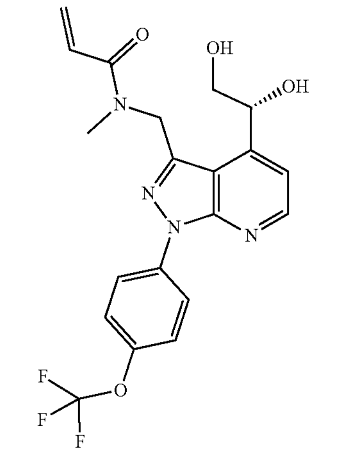 [SMILES: C=CC(=O)N(C)Cc1nn(-c2ccc(OC(F)(F)F)cc2)c2nccc([C@@H](O)CO)c12] | N-[[4-[(1R)-1,2-dihydroxyethyl]-1-[4-(trifluoromethoxy)phenyl]pyrazolo[3,4-b]pyridin-3-yl]methyl]-N-methyl-prop-2-enamide |
| 98 | 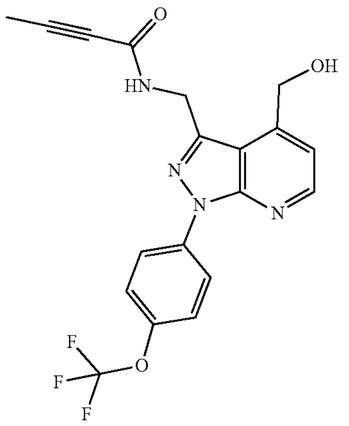 [SMILES: CC#CC(=O)NCc1nn(-c2ccc(OC(F)(F)F)cc2)c2nccc(CO)c12] | N-[[4-(hydroxymethyl)-1-[4-(trifluoromethoxy)phenyl]pyrazolo[3,4-b]pyridin-3-yl]methyl]but-2-ynamide |
| 99 | 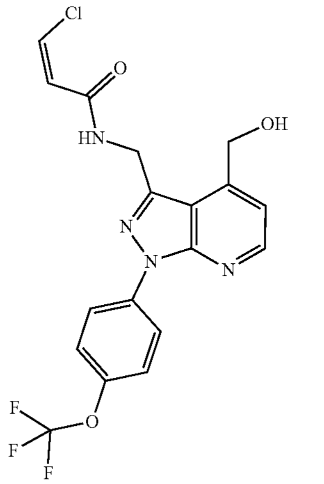 [SMILES: O=C(/C=C\Cl)NCc1nn(-c2ccc(OC(F)(F)F)cc2)c2nccc(CO)c12] | (Z)-3-chloro-N-[[4-(hydroxymethyl)-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 100 | 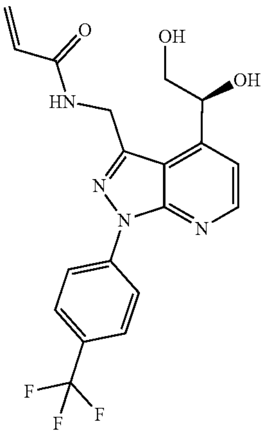 [SMILES: C=CC(=O)NCc1nn(-c2ccc(C(F)(F)F)cc2)c2nccc([C@H](O)CO)c12] | N-[[4-[rac-(1S)-1,2-dihydroxyethyl]-1-[4-(trifluoromethyl)phenyl]pyrazolo[3,4-b]pyridin-3-yl]methyl]prop-2-enamide |
| 101 | 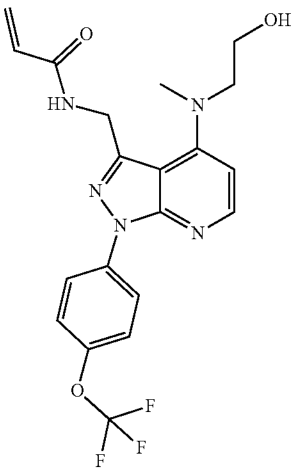 [SMILES: C=CC(=O)NCc1nn(-c2ccc(OC(F)(F)F)cc2)c2nccc(N(C)CCO)c12] | N-[[4-[2-hydroxyethyl(methyl)amino]-1-4-(trifluoromethoxy)phenyl]pyrazolo[3,4-b]pyridin-3-yl]methyl]prop-2-enamide |
| 104 | 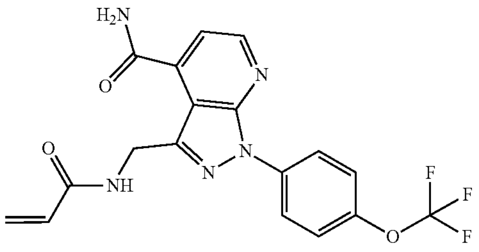 [SMILES: C=CC(=O)NCc1nn(-c2ccc(OC(F)(F)F)cc2)c2nccc(C(N)=O)c12] | 3-[(prop-2-enoylamino)methyl]-1-[4-(trifluoromethoxy)phenyl]pyrazolo[3,4-b]pyridine-4-carboxamide |

-continued
| Compound Number | Structure | Compound Name |
|---|---|---|
| 105 | 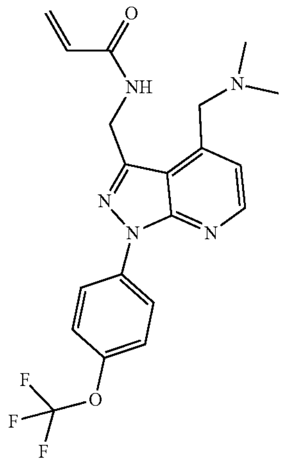 [SMILES: C=CC(=O)NCc1nn(-c2ccc(OC(F)(F)F)cc2)c2nccc(CN(C)C)c12] | N-[[4-[(dimethylamino)methyl]-1-[4-(trifluoromethoxy)phenyl]pyrazolo[3,4-b]pyridin-3-yl]methyl]prop-2-enamide |
| 106 | 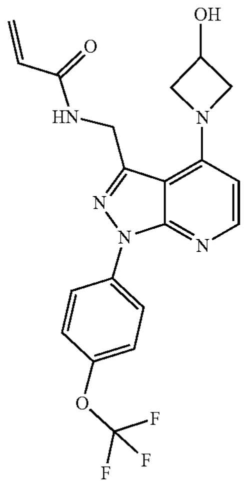 [SMILES: C=CC(=O)NCc1nn(-c2ccc(OC(F)(F)F)cc2)c2nccc(N3CC(O)C3)c12] | N-[[4-(3-hydroxyazetidin-1-yl)-1-[4-(trifluoromethoxy)phenyl]pyrazolo[3,4-b]pyridin-3-yl]methyl]prop-2-enamide |
| 107 | 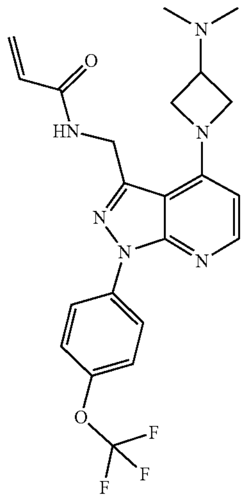 | N-[[4-[3-(dimethylamino)azetidin-1-yl]-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 111 | 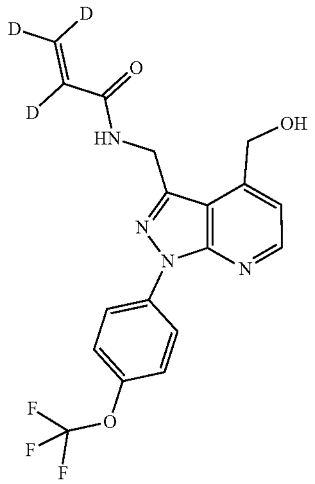 [SMILES: [2H]C([2H])=C([2H])C(=O)NCc1nn(-c2ccc(OC(F)(F)F)cc2)c2nccc(CO)c12] | 2,3,3-trideuterio-N-[[4-(hydroxymethyl)-1-[4-(trifluoromethoxy)phenyl]pyrazolo[3,4-b]pyridin-3-yl]methyl]prop-2-enamide |
| 116 | 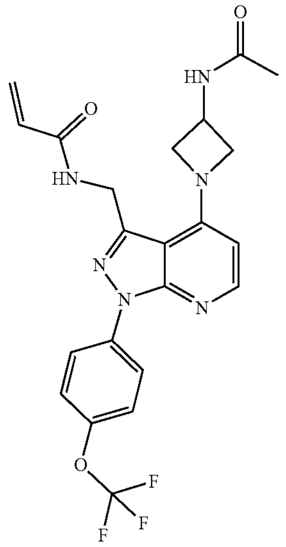 [SMILES: C=CC(=O)NCc1nn(-c2ccc(OC(F)(F)F)cc2)c2nccc(N3CC(NC(C)=O)C3)c12] | N-[[4-(3-acetamidoazetidin-1-yl)-1-[4-(trifluoromethoxy)phenyl]pyrazolo[3,4-b]pyridin-3-yl]methyl]prop-2-enamide |
| 117 | 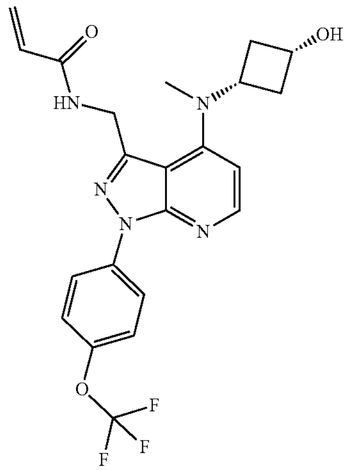 [SMILES: C=CC(=O)NCc1nn(-c2ccc(OC(F)(F)F)cc2)c2nccc(N(C)[C@H]3C[C@@H](O)C3)c12] | N-[[4-[(3-hydroxycyclobutyl)-methyl-amino]-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 118 | 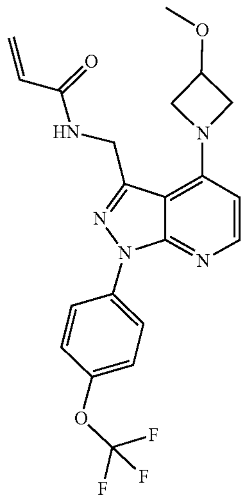 | N-[[4-(3-methoxyazetidin-1-yl)-1-[4-(trifluoromethoxy)phenyl]pyrazolo[3,4-b]pyridin-3-yl]methyl]prop-2-enamide |
| 119 | 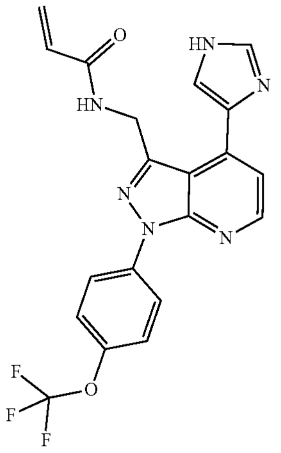 [SMILES: C=CC(=O)NCc1nn(-c2ccc(OC(F)(F)F)cc2)c2nccc(-c3c[nH]cn3)c12] | N-[[4-(IH-imidazol-4-yl)-1-[4-(trifluoromethoxy)phenyl]pyrazolo[3,4-b]pyridin-3-yl]methyl]prop-2-enamide |
| 121 | 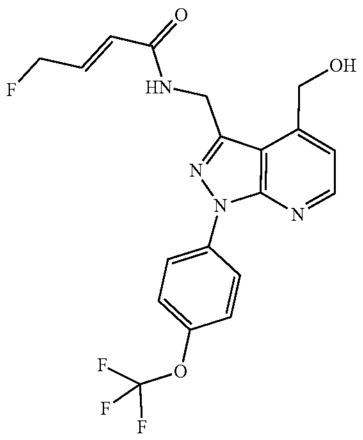 [SMILES: O=C(/C=C/CF)NCc1nn(-c2ccc(OC(F)(F)F)cc2)c2nccc(CO)c12] | (E)-4-fluoro-N-[[4-(hydroxymethyl)-1-[4-(trifluoromethoxy)phenyl]pyrazolo[3,4-b]pyridin-3-yl]methyl]but-2-enamide |

-continued
| Compound Number | Structure | Compound Name |
|---|---|---|
| 122 | 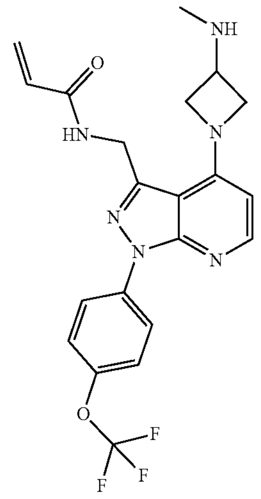 [SMILES: C=CC(=O)NCc1nn(-c2ccc(OC(F)(F)F)cc2)c2nccc(N3CC(NC)C3)c12] | N-[[4-[3-(methylamino)azetidin-1-yl]-1-4-(trifluoromethoxy)phenyl]pyrazolo[3,4-b]pyridin-3-yl]methyl]prop-2-enamide |
| 123 | 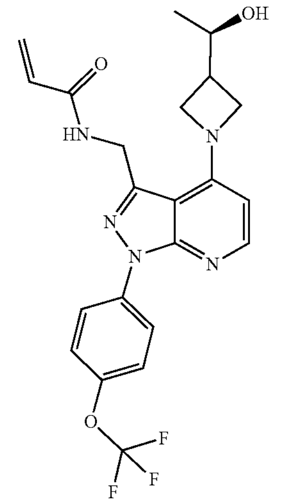 [SMILES: C=CC(=O)NCc1nn(-c2ccc(OC(F)(F)F)cc2)c2nccc(N3CC([C@@H](C)O)C3)c12] | N-[[4-[3-[(1R)-1-hydroxyethyl]azetidin-1-yl]-1-[4-(trifluoromethoxy)phenyl]pyrazolo[3,4-b]pyridin-3-yl]methyl]prop-2-enamide |
| 124 | 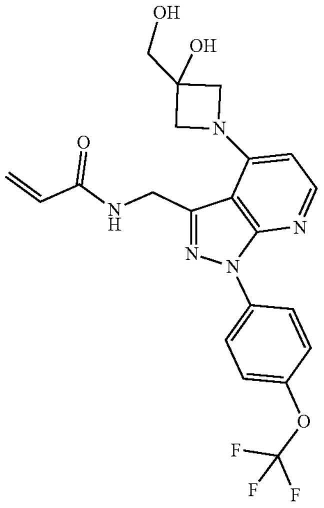 [SMILES: C=CC(=O)NCc1nn(-c2ccc(OC(F)(F)F)cc2)c2nccc(N3CC(O)(CO)C3)c12] | N-[[4-[3-hydroxy-3-(hydroxymethyl)azetidin-1-yl]-1-[4-(trifluoromethoxy)phenyl]pyrazolo[3,4-b]pyridin-3-yl]methyl]prop-2-enamide |

-continued

| Compound Number | Structure | Compound Name |
|---|---|---|
| 126 | 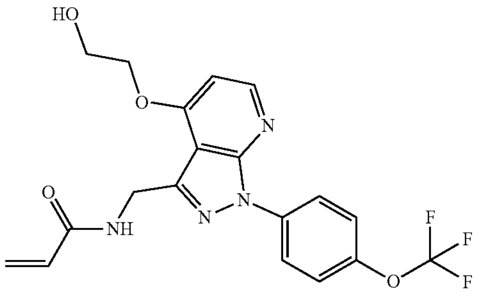 [SMILES: C=CC(=O)NCc1nn(-c2ccc(OC(F)(F)F)cc2)c2nccc(OCCO)c12] | N-[[4-(2-hydroxyethoxy)-1-[4-(trifluoromethoxy)phenyl]pyrazolo[3,4-b]pyridin-3-yl]methyl]prop-2-enamide |
| 128 | 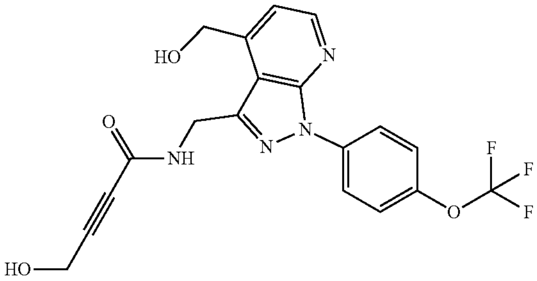 [SMILES: O=C(C#CCO)NCc1nn(-c2ccc(OC(F)(F)F)cc2)c2nccc(CO)c12] | 4-hydroxy-N-[[4-(hydroxymethyl)-1-[4-(trifluoromethoxy)phenyl]pyrazolo[3,4-b]pyridin-3-yl]methyl]but-2-ynamide |
| 131 | 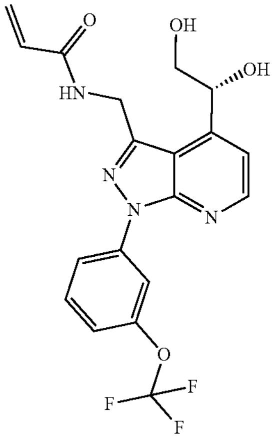 [SMILES: C=CC(=O)NCc1nn(-c2cccc(OC(F)(F)F)c2)c2nccc([C@@H](O)CO)c12] | N-[[4-[rac-(lR)-1,2-dihydroxyethyl]-1-3-(trifluoromethoxy)phenyl]pyrazolo[3,4-b]pyridin-3-yl]methyl]prop-2-enamide |
| 132 | 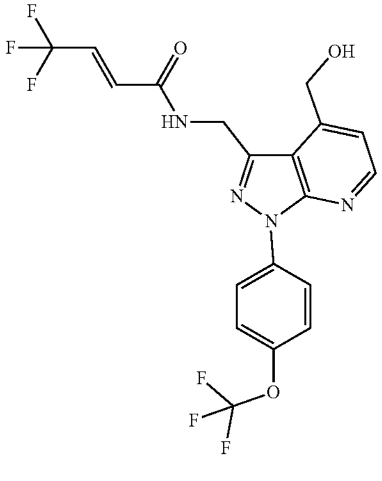 [SMILES: O=C(/C=C/C(F)(F)F)NCc1nn(-c2ccc(OC(F)(F)F)cc2)c2nccc(CO)c12] | (E)-4,4,4-trifluoro-N-[[4-(hydroxymethyl)-1-[4-(trifluoromethoxy)phenyl]pyrazolo[3,4-b]pyridin-3-yl]methyl]but-2-enamide |

-continued
| Compound Number | Structure | Compound Name |
|---|---|---|
| 134 | 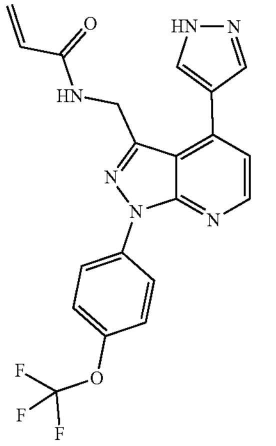 [SMILES: C=CC(=O)NCc1nn(-c2ccc(OC(F)(F)F)cc2)c2nccc(-c3cn[nH]c3)c12] | N-[[4-(1H-pyrazol-4-yl)-1-[4-(trifluoromethoxy)phenyl]pyrazolo[3,4-b]pyridin-3-yl]methyl]prop-2-enamide |
| 135 | 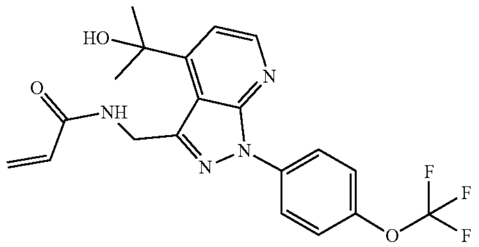 [SMILES: C=CC(=O)NCc1nn(-c2ccc(OC(F)(F)F)cc2)c2nccc(C(C)(C)O)c12] | N-[[4-(1-hydroxy-1-methyl-ethyl)-1-[4-(trifluoromethoxy)phenyl]pyrazolo[3,4-b]pyridin-3-yl]methyl]prop-2-enamide |
| 136 | 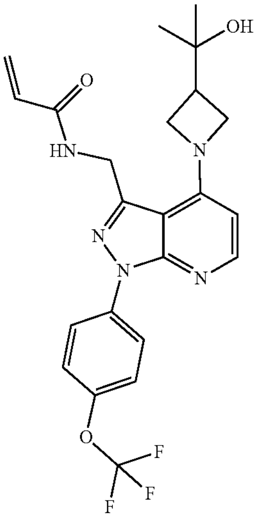 [SMILES: C=CC(=O)NCc1nn(-c2ccc(OC(F)(F)F)cc2)c2nccc(N3CC(C(C)(C)O)C3)c12] | N-[[4-[3-(1-hydroxy-1-methyl-ethyl)azetidin-1-yl]-1-[4-(trifluoromethoxy)phenyl]pyrazolo[3,4-b]pyridin-3-yl]methyl]prop-2-enamide |

-continued
| Compound Number | Structure | Compound Name |
|---|---|---|
| 138 | 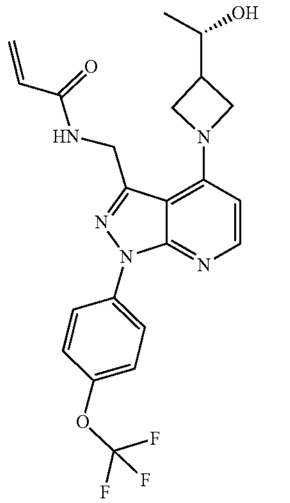 [SMILES: C=CC(=O)NCc1nn(-c2ccc(OC(F)(F)F)cc2)c2nccc(N3CC([C@H](C)O)C3)c12] | N-[[4-[3-[(1S)-1-hydroxyethyl]azetidin-1-yl]-1-[4-(trifluoromethoxy)phenyl]pyrazolo[3,4-b]pyridin-3-yl]methyl]prop-2-enamide |
| 139 | 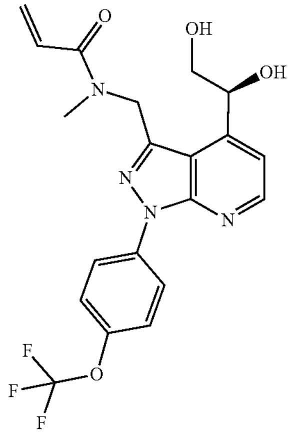 [SMILES: C=CC(=O)N(C)Cc1nn(-c2ccc(OC(F)(F)F)cc2)c2nccc([C@H](O)CO)c12] | N-[[4-[(1S)-1,2-dihydroxyethyl]-1-[4-(trifluoromethoxy)phenyl]pyrazolo[3,4-b]pyridin-3-yl]methyl]-N-methyl-prop-2-enamide |
| 140 | 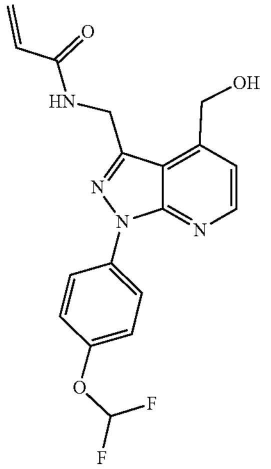 [SMILES: C=CC(=O)NCc1nn(-c2ccc(OC(F)F)cc2)c2nccc(CO)c12] | N-[[l-[4-(difluoromethoxy)phenyl]-4-(hydroxymethyl)pyrazolo[3,4-b]pyridin-3-yl]methyl]prop-2-enamide |

-continued
| Compound Number | Structure | Compound Name |
| --- | --- | --- |
| 143 | 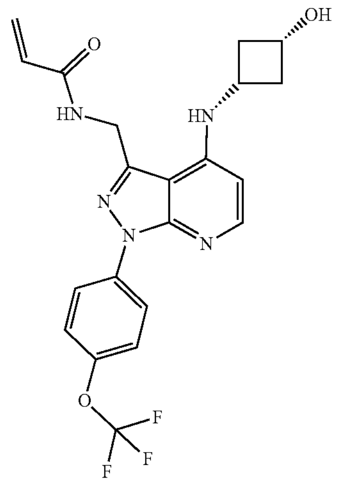 | N-[[4-[(3-hydroxycyclobutyl)amino]-1-[4-(trifluoromethoxy)phenyl]pyrazolo[3,4-b]pyridin-3-yl]methyl]prop-2-enamide |
| 144 | 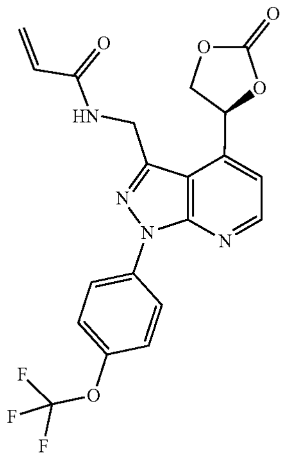 [SMILES: C=CC(=O)NCc1nn(-c2ccc(OC(F)(F)F)cc2)c2nccc([C@H]3COC(=O)O3)c12] | (S)-N-((4-(2-Oxo-1,3-dioxolan-4-yl)-1-(4-(trifluoromethoxy)phenyl)-1H-pyrazolo[3,4-b]pyridin-3-yl)methyl)acrylamide |
| 145 | 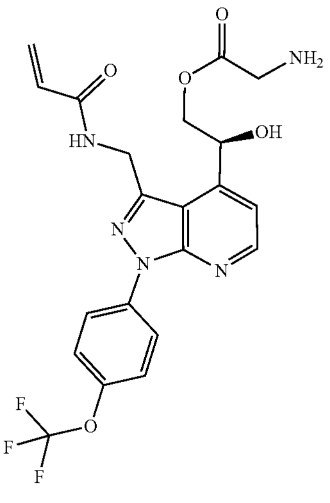 [SMILES: C=CC(=O)NCc1nn(-c2ccc(OC(F)(F)F)cc2)c2nccc([C@H](O)COC(=O)CN)c12] | (S)-2-(3-(Acrylamidomethyl)-1-(4-(trifluoromethoxy)phenyl)-1H-pyrazolo[3,4-b]pyridin-4-yl)-2-hydroxyethyl2-aminoacetateformate |

-continued
| Compound Number | Structure | Compound Name |
|---|---|---|
| 146 | 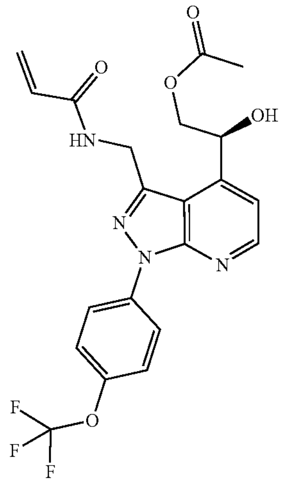 [SMILES: C=CC(=O)NCc1nn(-c2ccc(OC(F)(F)F)cc2)c2nccc([C@H](O)COC(C)=O)c12] | (S)-2-(3-(Acrylamidomethyl)-1-(4-(trifluoromethoxy)phenyl)-1H-pyrazolo[3,4-b]pyridin-4-yl)-2-hydroxyethylacetate |
| 147 | 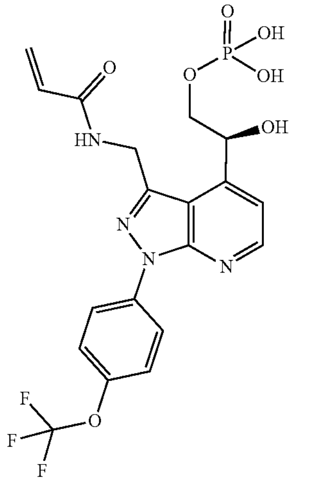 [SMILES: C=CC(=O)NCc1nn(-c2ccc(OC(F)(F)F)cc2)c2nccc([C@H](O)COP(=O)(O)O)c12] | (S)-2-(3-(Acrylamidomethyl)-1-(4-(trifluoromethoxy)phenyl)-1H-pyrazolo[3,4-b]pyridin-4-yl)-2-hydroxyethyldihydrogenphosphate |
| 148 | 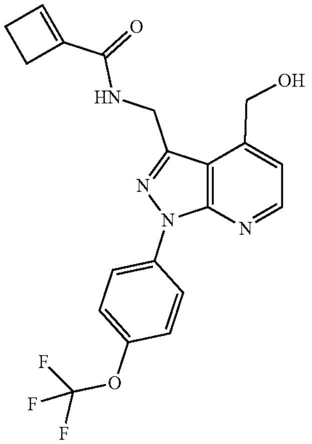 [SMILES: O=C(NCc1nn(-c2ccc(OC(F)(F)F)cc2)c2nccc(CO)c12)C1=CCC1] | N-((4-(Hydroxymethyl)-1-(4-(trifluoromethoxy)phenyl)-1H-pyrazolo[3,4-b]pyridin-3-yl)methyl)cyclobut-1-enecarboxamide |

-continued
| Compound Number | Structure | Compound Name |
|---|---|---|
| 149 | 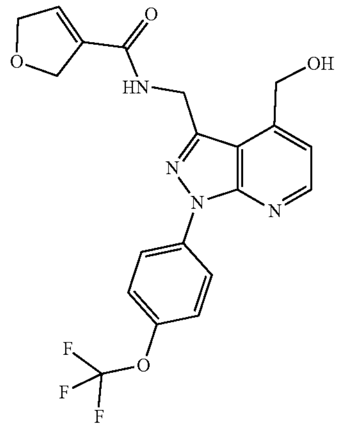 [SMILES: O=C(NCc1nn(-c2ccc(OC(F)(F)F)cc2)c2nccc(CO)c12)C1=CCOC1] | N-((4-(Hydroxymethyl)-1-(4-(trifluoromethoxy)phenyl)-1H-pyrazolo[3,4-b]pyridin-3-yl)methyl)-2,5-dihydrofuran-3-carboxamide |
| 154 | 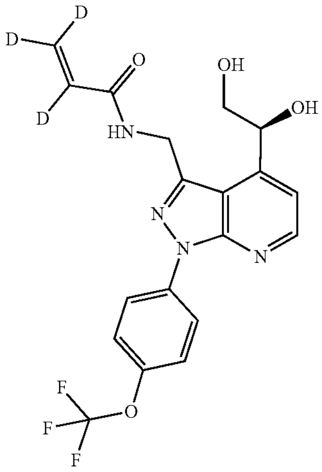 [SMILES: [2H]C([2H])=C([2H])C(=O)NCc1nn(-c2ccc(OC(F)(F)F)cc2)c2nccc([C@H](O)CO)c12] | (S)-N-((4-(1,2-Dihydroxyethyl)-1-(4-(trifluoromethoxy)phenyl)-1H-pyrazolo[3,4-b]pyridin-3-yl)methyl)acrylamide-2,3,3-d3 |
| 155 | 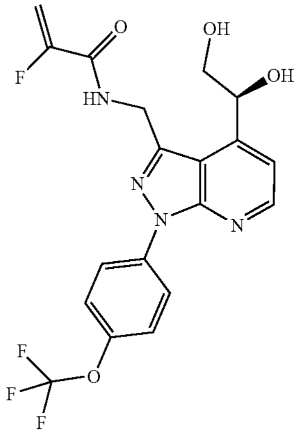 | (S)-N-((4-(1,2-Dihydroxyethyl)-1-(4-(trifluoromethoxy)phenyl)-1H-pyrazolo[3,4-b]pyridin-3-yl)methyl)-2-fluoroacrylamide |

-continued

| Compound Number | Structure | Compound Name |
|---|---|---|
| 156 | 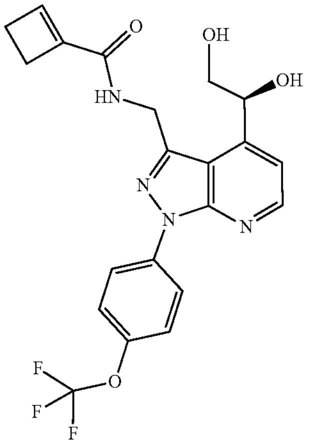 [SMILES: O=C(NCc1nn(-c2ccc(OC(F)(F)F)cc2)c2nccc([C@H](O)CO)c12)C1=CCC1] | (S)-N-((4-(1,2-Dihydroxyethyl)-1-(4-(trifluoromethoxy)phenyl)-1H-pyrazolo[3,4-b]pyridin-3-yl)methyl)cyclobut-1-enecarboxamide |
| 164 | 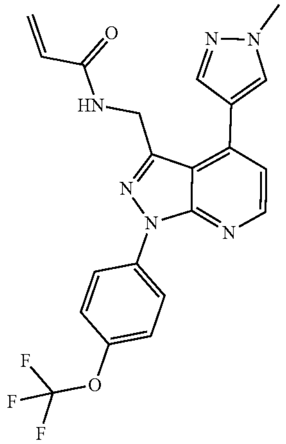 [SMILES: C=CC(=O)NCc1nn(-c2ccc(OC(F)(F)F)cc2)c2nccc(-c3cnn(C)c3)c12] | N-((4-(l-Methyl-IH-pyrazol-4-yl)-1-(4-(trifluoromethoxy)phenyl)-1H-pyrazolo[3,4-b]pyridin-3-yl)methyl)acrylamide |
| 165 | 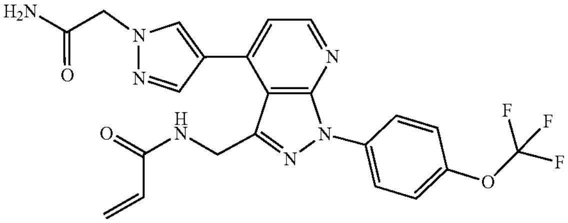 [SMILES: C=CC(=O)NCc1nn(-c2ccc(OC(F)(F)F)cc2)c2nccc(-c3cnn(CC(N)=O)c3)c12] | N-((4-(1-(2-amino-2-oxoethyl)-1H-pyrazol-4-yl)-1-(4-(trifluoromethoxy)phenyl)-1H-pyrazolo[3,4-b]pyridin-3-yl)methyl)acrylamide |
| 166 | 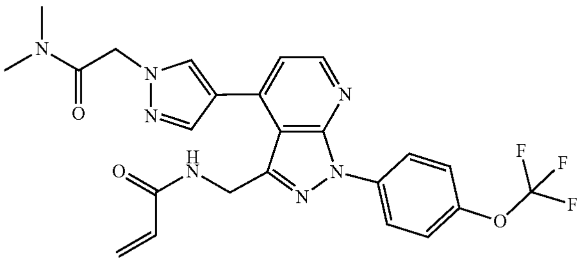 [SMILES: C=CC(=O)NCc1nn(-c2ccc(OC(F)(F)F)cc2)c2nccc(-c3cnn(CC(=O)N(C)C)c3)c12] | N-((4-(1-(2-(dimethylamino)-2-oxoethyl)-1H-pyrazol-4-yl)-1-(4-(trifluoromethoxy)phenyl)-1H-pyrazolo[3,4-b]pyridin-3-yl)methyl)acrylamide |

-continued

| Compound Number | Structure | Compound Name |
|---|---|---|
| 167 | 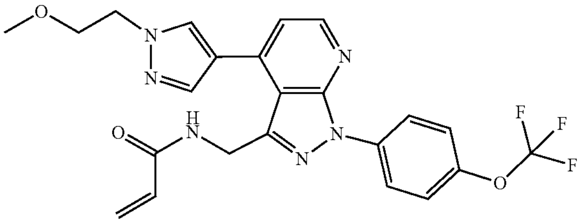 [SMILES: C=CC(=O)NCc1nn(-c2ccc(OC(F)(F)F)cc2)c2nccc(-c3cnn(CCOC)c3)c12] | N-((4-(1-(2-methoxyethyl)-1H-pyrazol-4-yl)-1-(4-(trifluoromethoxy)phenyl)-1H-pyrazolo[3,4-b]pyridin-3-yl)methyl)acrylamide |
| 168 | 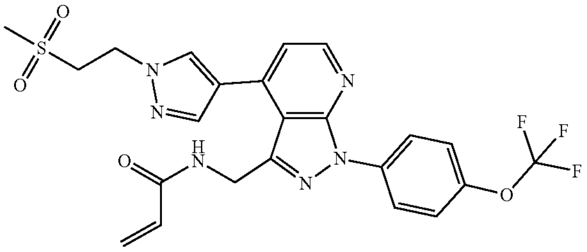 [SMILES: C=CC(=O)NCc1nn(-c2ccc(OC(F)(F)F)cc2)c2nccc(-c3cnn(CCS(C)(=O)=O)c3)c12] | N-((4-(1-(methylsulfonyl)ethyl)-1H-pyrazol-pyrazol-4-yl)-1-(4-(trifluoromethoxy)phenyl)-1H-pyrazolo[3,4-b]pyridin-3-yl)methyl)acrylamide |
| 169 | 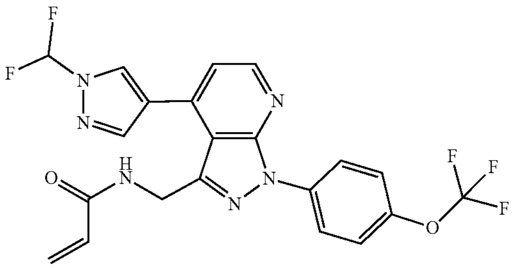 [SMILES: C=CC(=O)NCc1nn(-c2ccc(OC(F)(F)F)cc2)c2nccc(-c3cnn(C(F)F)c3)c12] | N-((4-(1-(difluoromethyl)-1H-pyrazol-4-yl)-1-(4-(trifluoromethoxy)phenyl)-1H-pyrazolo[3,4-b]pyridin-3-yl)methyl)acrylamide |
| 170 | 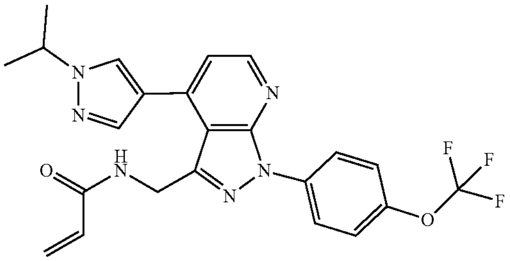 [SMILES: C=CC(=O)NCc1nn(-c2ccc(OC(F)(F)F)cc2)c2nccc(-c3cnn(C(C)C)c3)c12] | N-((4-(1-isopropyl-1H-pyrazol-4-yl)-1-(4-(trifluoromethoxy)phenyl)-1H-pyrazolo[3,4-b]pyridin-3-yl)methyl)acrylamide |
| 171 | 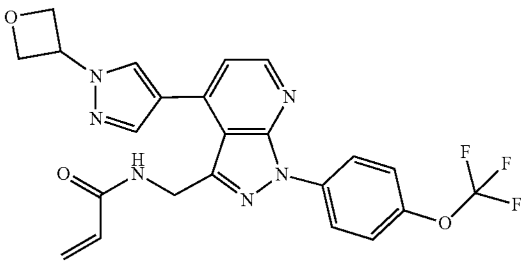 [SMILES: C=CC(=O)NCc1nn(-c2ccc(OC(F)(F)F)cc2)c2nccc(-c3cnn(C4COC4)c3)c12] | N-((4-(1-(oxetan-3-yl)-1H-pyrazol-4-yl)-1-(4-(trifluoromethoxy)phenyl)-1H-pyrazolo[3,4-b]pyridin-3-yl)methyl)acrylamide |
| 172 | 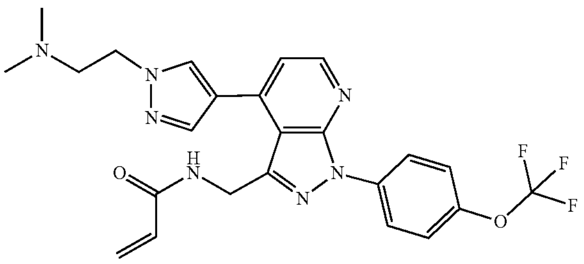 [SMILES: C=CC(=O)NCc1nn(-c2ccc(OC(F)(F)F)cc2)c2nccc(-c3cnn(CCN(C)C)c3)c12] | pyrazol-4-yl)-1-(4-(trifluoromethoxy)phenyl)-1H-pyrazolo[3,4-b]pyridin-3-yl)methyl)acrylamide |

-continued

| Compound Number | Structure | Compound Name |
|---|---|---|
| 173 | 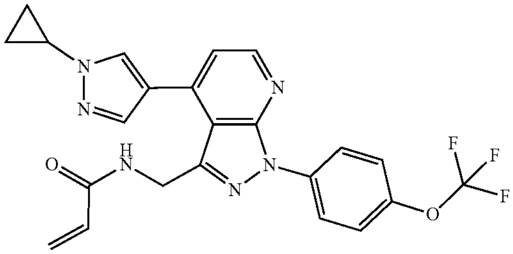 [SMILES: C=CC(=O)NCc1nn(-c2ccc(OC(F)(F)F)cc2)c2nccc(-c3cnn(C4CC4)c3)c12] | N-((4-(1-cycloprpyl-1H-pyrazol-4-yl)-1-(4-(trifluoromethoxy)phenyl)-1H-pyrazolo[3,4-b]pyridin-3-yl)methyl)acrylamide |
| 186 | 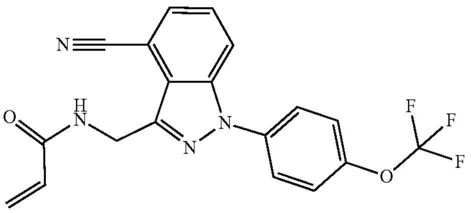 [SMILES: C=CC(=O)NCc1nn(-c2ccc(OC(F)(F)F)cc2)c2cccc(C#N)c12] | N-((4-cyano-1-(4-(trifluoromethoxy)phenyl)-1H-indazol-3-yl)methyl)acrylamide |
| 187 | 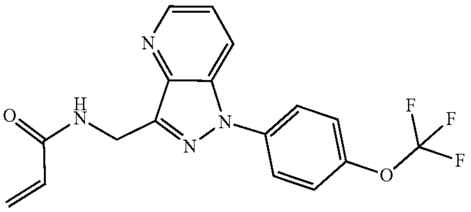 [SMILES: C=CC(=O)NCc1nn(-c2ccc(OC(F)(F)F)cc2)c2cccnc12] | N-((1-(4-(trifluoromethoxy)phenyl)-1H-pyrazolo[4,3-b]pyridin-3-yl)methyl)acrylamide |
| 188 | 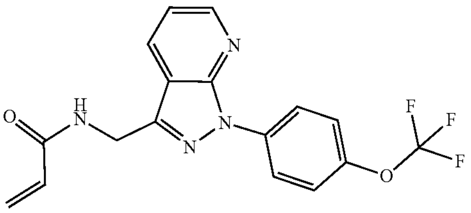 [SMILES: C=CC(=O)NCc1nn(-c2ccc(OC(F)(F)F)cc2)c2ncccc12] | N-((1-(4-(trifluoromethoxy)phenyl)-1H-pyrazolo[3,4-b]pyridin-3-yl)methyl)acrylamide |

or a pharmaceutically acceptable salt thereof.

20. A pharmaceutical composition, comprising (i) a compound of claim 1, or a stereoisomer, tautomer, or pharmaceutically acceptable salt thereof, and (ii) a pharmaceutically acceptable carrier, diluent, or excipient.

21. A method for treating cancer in a mammal, comprising administering a therapeutically effective amount of a compound of claim 1, or a stereoisomer, tautomer, or pharmaceutically acceptable salt thereof, to the mammal.

22. A method for treating a disease or condition mediated by TEAD activity in a mammal, comprising administering a therapeutically effective amount of a compound of claim 1, or a pharmaceutically acceptable salt thereof, to the mammal, wherein the disease or condition is selected from the group consisting of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

23. A composition, comprising: (i) one or more TEAD inhibitors, or a pharmaceutically acceptable salt thereof; and (ii) one or more KRAS inhibitors, or a pharmaceutically acceptable salt thereof, wherein the one or more TEAD inhibitors comprise a compound of claim 1.

24. A method of treating cancer in a subject in need thereof, comprising administering to the subject an effective amount of a combination, comprising: i) one or more TEAD inhibitors, or a pharmaceutically acceptable salt thereof; and (ii) one or more KRAS inhibitors, or a pharmaceutically acceptable salt thereof, wherein the one or more TEAD inhibitors comprise a compound of claim 1.

25. A method of reducing resistance of a subject to treatment comprising a KRAS inhibitor, wherein the method comprises administering a therapeutically effective amount of a TEAD inhibitor, or a pharmaceutically acceptable salt thereof, wherein the TEAD inhibitor is a compound of claim 1.

26. The compound of claim 19, wherein the compound is:

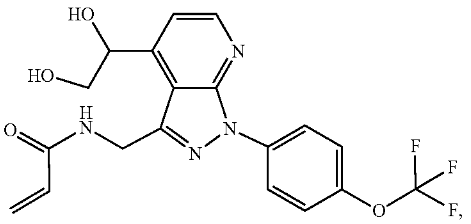 [SMILES: C=CC(=O)NCc1nn(-c2ccc(OC(F)(F)F)cc2)c2nccc(C(O)CO)c12]

or a pharmaceutically acceptable salt thereof.

27. The compound of claim 19, wherein the compound is:

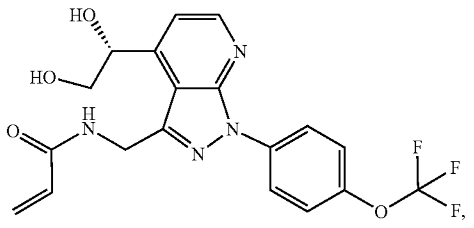

or a pharmaceutically acceptable salt thereof.

28. The compound of claim 19, wherein the compound is:

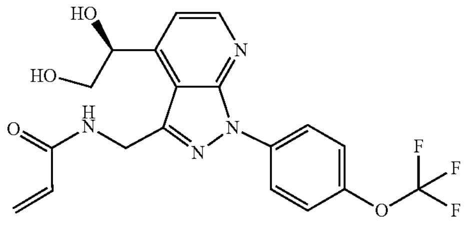 [SMILES: C=CC(=O)NCc1nn(-c2ccc(OC(F)(F)F)cc2)c2nccc([C@H](O)CO)c12]

or a pharmaceutically acceptable salt thereof.

* * * * *

SEQUENCE LISTING

```
Sequence total quantity: 18
SEQ ID NO: 1            moltype = AA  length = 440
FEATURE                 Location/Qualifiers
source                  1..440
                        mol_type = protein
                        organism = synthetic construct
SEQUENCE: 1
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                               440

SEQ ID NO: 2            moltype = AA  length = 214
FEATURE                 Location/Qualifiers
source                  1..214
                        mol_type = protein
                        organism = synthetic construct
SEQUENCE: 2
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 3            moltype = AA  length = 447
FEATURE                 Location/Qualifiers
source                  1..447
                        mol_type = protein
                        organism = synthetic construct
SEQUENCE: 3
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                       447

SEQ ID NO: 4            moltype = AA  length = 218
FEATURE                 Location/Qualifiers
source                  1..218
                        mol_type = protein
                        organism = synthetic construct
SEQUENCE: 4
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                           218

SEQ ID NO: 5            moltype = AA  length = 10
FEATURE                 Location/Qualifiers
source                  1..10
                        mol_type = protein
                        organism = synthetic construct
SEQUENCE: 5
GFTFSDSWIH                                                          10

SEQ ID NO: 6            moltype = AA  length = 18
FEATURE                 Location/Qualifiers
source                  1..18
                        mol_type = protein
                        organism = synthetic construct
SEQUENCE: 6
AWISPYGGST YYADSVKG                                                 18

SEQ ID NO: 7            moltype = AA  length = 9
FEATURE                 Location/Qualifiers
source                  1..9
                        mol_type = protein
                        organism = synthetic construct
SEQUENCE: 7
RHWPGGFDY                                                           9

SEQ ID NO: 8            moltype = AA  length = 11
```

```
FEATURE                 Location/Qualifiers
source                  1..11
                        mol_type = protein
                        organism = synthetic construct
SEQUENCE: 8
RASQDVSTAV A                                                      11

SEQ ID NO: 9            moltype = AA  length = 7
FEATURE                 Location/Qualifiers
source                  1..7
                        mol_type = protein
                        organism = synthetic construct
SEQUENCE: 9
SASFLYS                                                           7

SEQ ID NO: 10           moltype = AA  length = 9
FEATURE                 Location/Qualifiers
source                  1..9
                        mol_type = protein
                        organism = synthetic construct
SEQUENCE: 10
QQYLYHPAT                                                         9

SEQ ID NO: 11           moltype = AA  length = 118
FEATURE                 Location/Qualifiers
source                  1..118
                        mol_type = protein
                        organism = synthetic construct
SEQUENCE: 11
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSS    118

SEQ ID NO: 12           moltype = AA  length = 108
FEATURE                 Location/Qualifiers
source                  1..108
                        mol_type = protein
                        organism = synthetic construct
SEQUENCE: 12
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR              108

SEQ ID NO: 13           moltype = AA  length = 447
FEATURE                 Location/Qualifiers
source                  1..447
                        mol_type = protein
                        organism = synthetic construct
SEQUENCE: 13
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                      447

SEQ ID NO: 14           moltype = AA  length = 214
FEATURE                 Location/Qualifiers
source                  1..214
                        mol_type = protein
                        organism = synthetic construct
SEQUENCE: 14
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 15           moltype = AA  length = 449
FEATURE                 Location/Qualifiers
source                  1..449
                        mol_type = protein
                        organism = synthetic construct
SEQUENCE: 15
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
```

-continued

```
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 16          moltype = AA  length = 216
FEATURE                Location/Qualifiers
source                 1..216
                       mol_type = protein
                       organism = synthetic construct
SEQUENCE: 16
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 17          moltype = AA  length = 450
FEATURE                Location/Qualifiers
source                 1..450
                       mol_type = protein
                       organism = synthetic construct
SEQUENCE: 17
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                   450

SEQ ID NO: 18          moltype = AA  length = 215
FEATURE                Location/Qualifiers
source                 1..215
                       mol_type = protein
                       organism = synthetic construct
SEQUENCE: 18
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215
```